US011730762B2

(12) United States Patent
Wong

(10) Patent No.: US 11,730,762 B2
(45) Date of Patent: Aug. 22, 2023

(54) METHODS FOR STIMULATING PROLIFERATION OR DIFFERENTIATION OF AN IMMUNE CELL WITH A MULTI-CHAIN CHIMERIC POLYPEPTIDE

(71) Applicant: HCW Biologies, Inc., Miramar, FL (US)

(72) Inventor: Hing Wong, Miramar, FL (US)

(73) Assignee: HCW Biologics, Inc., Miramar, FL (US)

( * ) Notice: Subject to any disclaimer, the term of this patent is extended or adjusted under 35 U.S.C. 154(b) by 427 days.

(21) Appl. No.: 16/557,822

(22) Filed: Aug. 30, 2019

(65) Prior Publication Data

US 2021/0100840 A1 Apr. 8, 2021

Related U.S. Application Data

(60) Provisional application No. 62/881,088, filed on Jul. 31, 2019, provisional application No. 62/881,039, filed on Jul. 31, 2019, provisional application No. 62/817,244, filed on Mar. 12, 2019, provisional application No. 62/817,230, filed on Mar. 12, 2019, provisional application No. 62/817,241, filed on Mar. 12, 2019, provisional application No. 62/816,683, filed on Mar. 11, 2019, provisional application No. 62/749,506, filed on Oct. 23, 2018, provisional application No. 62/749,007, filed on Oct. 22, 2018, provisional application No. 62/746,832, filed on Oct. 17, 2018, provisional application No. 62/724,969, filed on Aug. 30, 2018, provisional application No. 62/725,010, filed on Aug. 30, 2018, provisional application No. 62/725,038, filed on Aug. 30, 2018, provisional application No. 62/725,043, filed on Aug. 30, 2018.

(51) Int. Cl.
| | |
|---|---|
| *C07K 14/715* | (2006.01) |
| *C07K 14/54* | (2006.01) |
| *A61K 35/17* | (2015.01) |
| *C07K 14/705* | (2006.01) |
| *C07K 16/22* | (2006.01) |
| *C07K 16/24* | (2006.01) |
| *C07K 16/28* | (2006.01) |
| *C07K 16/46* | (2006.01) |

(52) U.S. Cl.
CPC ........ *A61K 35/17* (2013.01); *C07K 14/70503* (2013.01); *C07K 14/7155* (2013.01); *C07K 16/22* (2013.01); *C07K 16/244* (2013.01); *C07K 16/2863* (2013.01); *C07K 16/468* (2013.01); *C07K 2317/24* (2013.01); *C07K 2317/52* (2013.01); *C07K 2317/569* (2013.01); *C07K 2317/622* (2013.01)

(58) Field of Classification Search
None
See application file for complete search history.

(56) References Cited

U.S. PATENT DOCUMENTS

| | | |
|---|---|---|
| 6,117,980 A | 9/2000 | Gonzalez et al. |
| 7,452,537 B2 | 11/2008 | Bauer et al. |
| 7,482,436 B2 | 1/2009 | Sugimura et al. |
| 7,488,802 B2 | 2/2009 | Collins et al. |
| 7,521,051 B2 | 4/2009 | Collins et al. |
| 7,612,181 B2 | 11/2009 | Wu et al. |
| 7,691,380 B2 | 4/2010 | Thorpe et al. |
| 7,723,482 B2 | 5/2010 | Soulillou et al. |
| 7,968,094 B2 | 6/2011 | Jiao et al. |
| 8,007,795 B2 | 8/2011 | Jiao et al. |
| 8,133,485 B2 | 3/2012 | Levi-Schaffer et al. |
| 8,217,149 B2 | 7/2012 | Irving et al. |
| 8,258,268 B2 | 9/2012 | Wu et al. |
| 8,475,792 B2 | 7/2013 | Dall'Acqua et al. |
| 8,552,156 B2 | 10/2013 | Takayanagi et al. |
| 8,586,714 B2 | 11/2013 | Ghayur et al. |
| 8,716,450 B2 | 5/2014 | Ghayur et al. |
| 8,722,855 B2 | 5/2014 | Ghayur et al. |
| 8,735,546 B2 | 5/2014 | Ghayur et al. |
| 8,741,604 B2 | 6/2014 | Campbell et al. |
| 8,753,640 B2 | 6/2014 | Wu et al. |
| 8,759,494 B2 | 6/2014 | Bachmann et al. |
| 8,822,645 B2 | 9/2014 | Ghayur et al. |
| 9,035,026 B2 | 5/2015 | Hoffmann et al. |
| 9,067,997 B2 | 6/2015 | Romagne et al. |

(Continued)

FOREIGN PATENT DOCUMENTS

| | | |
|---|---|---|
| CN | 102153653 | 8/2011 |
| EP | 1245676 A1 | 10/2002 |

(Continued)

OTHER PUBLICATIONS

PCT International Preliminary Report on Patentability in International Appln. No. PCT/US2020/038717, dated Dec. 30, 2021, 9 pages.

(Continued)

*Primary Examiner* — Christine J Saoud
*Assistant Examiner* — Jon M Lockard
(74) *Attorney, Agent, or Firm* — Fish & Richardson P.C.

(57) ABSTRACT

The present disclosure relates to the field of biotechnology, and more specifically, to single-chain and multi-chain chimeric polypeptides having a linker domain positioned between two target-binding domains that are useful for a variety of applications including, without limitation, stimulating an immune cell, inducing or increasing proliferation of an immune cell, inducing differentiation of an immune cell, or treating a subject in need thereof (e.g., a subject having cancer or an aging-related disease or condition).

28 Claims, 123 Drawing Sheets

Specification includes a Sequence Listing.

(56) References Cited

U.S. PATENT DOCUMENTS

| | | |
|---|---|---|
| 9,085,623 B2 | 7/2015 | Rother et al. |
| 9,090,684 B2 | 7/2015 | Borras et al. |
| 9,226,962 B2 | 1/2016 | Le Gall et al. |
| 9,238,084 B2 | 1/2016 | Liu et al. |
| 9,273,136 B2 | 3/2016 | Rader et al. |
| 9,371,395 B2 | 6/2016 | Takahashi et al. |
| 9,441,034 B2 | 9/2016 | Sivakumar et al. |
| 9,505,843 B2 | 11/2016 | Kim et al. |
| 9,617,345 B2 | 4/2017 | Berne et al. |
| 9,701,758 B2 | 7/2017 | Cooper et al. |
| 11,518,792 B2 | 12/2022 | Wong |
| 2001/0044427 A1 | 11/2001 | Mazel et al. |
| 2003/0219441 A1 | 11/2003 | Thorpe et al. |
| 2005/0014224 A1 | 1/2005 | Collins et al. |
| 2006/0159655 A1 | 7/2006 | Collins et al. |
| 2007/0160579 A1 | 7/2007 | Schmitz et al. |
| 2009/0148942 A1 | 6/2009 | McDonagh et al. |
| 2012/0171197 A1 | 7/2012 | Eriksson et al. |
| 2013/0274446 A1 | 10/2013 | Kumagai et al. |
| 2014/0242077 A1 | 8/2014 | Choi |
| 2015/0218274 A1 | 8/2015 | Sabatos-Peyton et al. |
| 2015/0259429 A1 | 9/2015 | Benaroch et al. |
| 2016/0175397 A1 | 6/2016 | Umana et al. |
| 2016/0340413 A1 | 11/2016 | Duerner et al. |
| 2016/0367664 A1 | 12/2016 | Wang et al. |
| 2017/0051063 A1 | 2/2017 | Baum et al. |
| 2017/0198042 A1 | 7/2017 | Williams et al. |
| 2017/0283499 A1 | 10/2017 | Delhem et al. |
| 2018/0200366 A1 | 7/2018 | Wong |
| 2020/0071374 A1 | 3/2020 | Wong |
| 2020/0190174 A1 | 6/2020 | Wong |
| 2021/0060064 A1 | 3/2021 | Wong |
| 2021/0070825 A1 | 3/2021 | Wong |
| 2021/0070826 A1 | 3/2021 | Wong |
| 2021/0137981 A1 | 5/2021 | Wong |
| 2021/0268022 A1 | 9/2021 | Wong et al. |
| 2021/0277054 A1 | 9/2021 | Wong et al. |
| 2021/0338724 A1 | 11/2021 | Wong |
| 2022/0073578 A1 | 3/2022 | Wong et al. |
| 2023/0023389 A1 | 1/2023 | Wong |
| 2023/0039157 A1 | 2/2023 | Wong |

FOREIGN PATENT DOCUMENTS

| | | |
|---|---|---|
| EP | 2537933 | 12/2012 |
| EP | 3029069 | 6/2016 |
| EP | 3348276 | 7/2018 |
| KR | 2016/0127688 | 11/2016 |
| KR | 101778439 | 9/2017 |
| WO | WO 1995/015341 | 6/1995 |
| WO | WO 2001/083755 | 11/2001 |
| WO | WO 2002/083152 | 10/2002 |
| WO | WO 2003/037911 | 5/2003 |
| WO | WO 2003/104425 | 12/2003 |
| WO | WO 2004/076488 | 9/2004 |
| WO | WO 2006/096828 | 9/2006 |
| WO | WO 2006/119897 | 11/2006 |
| WO | WO 2008/096158 | 8/2008 |
| WO | WO 2011/127324 | 10/2011 |
| WO | WO 2012/040323 | 3/2012 |
| WO | WO 2012/120125 | 9/2012 |
| WO | WO 2012/170470 | 12/2012 |
| WO | WO 2012/175222 | 12/2012 |
| WO | WO 2012/175692 | 12/2012 |
| WO | WO 2013/068946 | 5/2013 |
| WO | WO 2014/007513 | 1/2014 |
| WO | WO 2014/026054 | 2/2014 |
| WO | WO 2014/095808 | 6/2014 |
| WO | WO 2014/130635 | 8/2014 |
| WO | WO 2014/159531 | 10/2014 |
| WO | WO 2015/089881 | 6/2015 |
| WO | WO 2016/106221 | 6/2016 |
| WO | WO 2016/154585 | 9/2016 |
| WO | WO 2016/166348 | 10/2016 |
| WO | WO 2017/053748 | 3/2017 |
| WO | WO 2017/083612 | 5/2017 |
| WO | WO 2017/149538 | 9/2017 |
| WO | WO 2017/189526 | 11/2017 |
| WO | WO 2018/075989 | 4/2018 |
| WO | WO 2018/129007 | 7/2018 |
| WO | WO 2018/158350 | 9/2018 |
| WO | WO 2018/183169 | 10/2018 |
| WO | WO 2018/165208 | 12/2018 |
| WO | WO 2019/046313 | 3/2019 |
| WO | WO 2020/047299 | 3/2020 |
| WO | WO 2020/047333 | 3/2020 |
| WO | WO 2020/047462 | 3/2020 |

OTHER PUBLICATIONS

Bork, "Powers and Pitfalls in Sequence Analysis: The 70% Hurdle," Genome Research, 2000, 10:398-400.

Bowie et al., "Deciphering the Message in Protein Sequences: Tolerance to Amino Acid Substitutions," Science, 1990, 247:1306-1310.

Burgess et al., "Possible Dissociation of the Heparin-binding and Mitogenic Activities of Heparin-binding (Acidic Fibroblast) GrowthFactor-1 from Its Receptor-binding Activities by Site-directed Mutagenesis of a Single Lysine Residue," J. Cell Biol., 1990, 111:2129-2138.

Greenspan et al., "Defining epitopes: Its not as easy as it seems," Nature Biotechnology, 1999, 17:936-937.

Lazar et al., "Transforming Growth Factor Alpha: Mutation of Aspartic Acid 47 and Leucine 48 Results in Different Biological Activities," Mol. Cell. Biol., 1988, 8:1247-1252.

PCT International Search Report and Written Opinion in International Appln. No. PCT/US2021/029920, dated Oct. 6, 2021, 21 pages.

PCT International Search Report and Written Opinion in International Appln. No. PCT/US2021/035285, dated Oct. 18, 2021, 14 pages.

Abbott et al., "Genomic organization, exact localization, and tissue expression of the human CD26 (dipeptidyl peptidase IV) gene," Immunogentics, Sep. 1994, 40(5):331-338.

Abdul-Aziz et al., "Acute myeloid leukemia induces protumoral p16INK4a-driven senescence in the bone marrow microenvironment," Blood, Jan. 31, 2019, 133(5):446-456.

Aertgeerts et al., "Crystal structure of human dipeptidyl peptidase IV in complex with a decapeptide reveals details on substrate specificity and tetrahedral intermediate formation," Protein Science, Feb. 2004, 13(2):412-421.

Ait-Oufella el al., "Natural regulatory T cells control the development of atherosclerosis in mice," Nature Medicine, Feb. 5, 2006, 12:178-180.

Ali et al., "Regulatory T cells in skin," Immunology, Jul. 12, 2017, 152(3):372-381.

Angevin et al., "First-in-human phase 1 of YS110, a monoclonal antibody directed against CD26 in advanced CD26-expressing cancers," British Journal of Cancer, Mar. 14, 2017, 116(9):1126-1134.

Bennett et al., "Erratum: Killing the old: cell senescence in atherosclerosis," Nature Reviews Cardiology, Jan. 12, 2017, 14(3):132.

Bennett et al., "Killing the old: cell senescence in atherosclerosis," Nature Reviews Cardiology, Dec. 12, 2016, 14(1):8-9, 2 pages.

Bentebibel et al., "A First-in-Human Study and Biomarker Analysis of NKTR-214, a Novel IL2Rαβ Biased Cytokine, in Patients with Advanced or Metastatic Solid Tumors," Cancer Discovery, Jun. 2019, 9(6):711-721.

Bhat et al., "Astrocyte Senescence as a Component of Alzheimer's Disease," PLoS One, Sep. 12, 2012, 7(9):e45069, 10 pages.

Biran et al., "Senescent cells communicate via intercellular protein transfer," Genes & Development, Apr. 8, 2015, 29(8):791-802, 13 pages.

Borea et al., "Pharmacology of Adenosine Receptors: The State of the Art," Physiological Reviews, May 31, 2918, 98(3):1591-1625.

Boyman et al., "IL-7/Anti-IL-7 mAb Complexes Restore T Cell Development and Induce Homeostatic T Cell Expansion without Lymphopenia," The Journal of Immunology, Jun. 1, 2008, 180:7265-7275.

(56) References Cited

OTHER PUBLICATIONS

Boyman et al., "Selective Stimulation of T Cell Subsets with Antibody-Cytokine Immune Complexes," Science, Mar. 31, 2006, 311(5769):1924-1927.

Broxmeyer et al., "Modulation of Hematopoietic Chemokine Effects In Vitro and In Vivo by DPP-4/CD26," Stem Cells and Development, Mar. 4, 2016, 25(8):575-585.

Brunstein et al., "Infusion of Ex Vivo Expanded T Regulatory Cells in Adults Transplanted with Umbilical Cord Blood: Safety Profile and Detection Kinetics," Blood, Jan. 20, 2011, 117(3):1061-1070.

Brunstein et al., "Umbilical cord blood-derived T regulatory cells to prevent GVHD:Nineties, toxicity profile, and clinical effect," Blood, Feb. 25, 2016, 127(8):1044-1051.

Buhling et al., "Functional role of CD26 on human B lymphocytes," Immunology Letters, Feb. 1995, 45(1-2):47-51.

Bussian et al., "Clearance of senescent glial cells prevents tan-dependent pathology and cognitive decline," Nature, Sep. 19, 2018, 562(7728):578-582, 21 pages.

Cai et al., "Chibby suppresses aerobic glycolysis and proliferation of nasopharyngeal carcinoma via the Wnt/β-catenin-Lin28/let7-PDK1 cascade," Journal of Experimental & Clinical Cancer Research, Dec. 1, 2018, 37(1):104.

Cao, "Self-regulation and cross-regulation of pattern-recognition receptor signaling in health and disease," Nature Reviews Immunology, Dec. 29, 2015, 16(1):35-50.

Carr et al., "NK Cell-Mediated Lysis of Autologous HCMV-Infected Skin Fibroblasts Is Highly Variable among NK Cell Clones and Polyclonal NK Cell Lines," Clinical Immunology, Nov. 2002, 105(2):126-140.

Catania et al., "The tumor-targeting immunocytokine F16-IL2 in combination with doxombicin: dose escalation in patients with advanced solid tumors and expansion into patients with metastatic breast cancer," Cell Adhesion and Migration, Jan.-Apr. 2015, 9(1-2):14-21.

Cavinato et al., "Molecular mechanisms of UVB-induced senescence of dermal fibroblasts and its relevance for photoaging of the human skin," Experimental Gerontology. Aug. 2017, 94:78-82.

Chambers et al., "Can blocking inflammation enhance immunity during aging?," Journal of Allergy and Clinical Immunology, May 2020, 145(5):1323-1331.

Chance et al., "A simple and rapid assay of oxidative phosphorylation," Nature, Jun. 1955, 175(4469):1120-1121.

Chen et al., "Sterile inflammation: sensing and reacting to damage," Nature Reviews Immunology, Nov. 19, 2010, 10(12):826-837.

Childs et al., "Senescent cells: an emerging target for diseases of ageing," Nature Reviews Drug Discovery, Jul. 21, 2017, 16(10):718-735, 18 pages.

Childs et al., "Senescent intimal foam cells are deleterious at all stages of atherosclerosis," Science, Oct. 28, 2016, 354(6311):472-477.

Chong et al., "CD36 initiates the secretory phenotype during the establishment of cellular senescence," EMBO Rep., May 18, 2018, 19(6):e45274, 13 pages.

Cifaldi et al., "Boosting Natural Killer Cell-Based Immunotherapy with Anticancer Drugs: a Perspective," Trends Molecular Medicine, Dec. 2017, 23(12):1156-1175, 20 pages.

Cipriani et al., "Hippocampal Radial Glial Subtypes and Their Neurogenic Potential in Human Fetuses and Healthy and Alzheimer's Disease Adults," Cerebral Cortex, May 2, 2018, 28(7):2458-2478, 21 pages.

Collado et al., "Senescence in tumours: evidence from mice and humans," Nature Reviews Cancer, Jan. 2010, 10(1):51-57.

Conarello et al., "Mice lacking dipeptidyl peptidase IV are protected against obesity and insulin resistance," Proc. Natl. Acad. Sci. U.S.A., May 27, 2003, 100(11):6825-6830.

Conlon et al., "Abstract CT082: Phase (Ph) I/Ib study of NIZ985 with and without spartalizumab (PDR001) in patients (pts) with metastatic/unresectable solid tumors," Cancer Res. 79(13 Suppl.):CT082, Jul. 1, 2019, 2 pages.

Coppe et al., "Tumor Suppressor and Aging Biomarker p16INK4a Induces Cellular Senescence without the Associated Inflammatory Secretory Phenotype," Journal of Biological Chemistry, Oct. 21, 2011, 286(42): 36396-36403.

Crews et al., "Molecular mechanisms of neurodegeneration in Alzheimer's disease," Human Molecular Genetics, Apr. 22, 2010, 19(R1):R12-R20, 9 pages.

Da Silva et al., "Dipeptidylpeptidase 4 inhibition enhances lymphocyte trafficking, improving both naturally occurring tumor immunity and immunotherapy," Nature Immunology, Jun. 15, 2015, 16(8):850-858, 11 pages.

Dall'Era et al., "Adoptive Regulatory T Cell Therapy in a Patient with Systemic Lupus Eiythematosus," Arthritis Rheumatology, Mar. 2019, 71(3):431-440.

De Stefano et al., "Establishing pathological cut-offs of brain atrophy rates in multiple sclerosis," Journal of Neurology, Neurosurgery, and Psychiatry, Jan. 2016, 87(1):93-99.

Deacon, "Physiology and Pharmacology of DPP-4 in Glucose Homeostasis and the Treatment of Type 2 Diabetes," Frontiers in Endocrinology, Feb. 2019, 10:80, 14 pages.

Deaglio et al., "Adenosine generation catalyzed by CD39 and CD73 expressed on regulatory T cells mediates immune suppression," Journal of Experimental Medicine, May 14, 2007, 204(6):1257-1265.

Demaria et al., "An Essential Role for Senescent Cellsin Optimal Wound Healingthrough Secretion of PDGF-AA," Developmental Cell, Dec. 22, 2014, 31(6):722-733.

Di Ianni et al., "Tregs prevent GVHD and promote immune reconstitution inHLA-haploidentical transplantation," Blood, Apr. 7, 2011, 117(14):3921-3928.

Dietel et al., "Decreased numbers of regulatory T cells are associated with human atherosclerotic lesion vulnerability and inversely correlate with infiltrated mature dendritic cells," Atherosclerosis, Sep. 2013, 230:92-99.

Dikov et al., "New fluorescent method for the histochemical detection of tripeptidyl peptidase I using glycyl-1-prolyl-1-met-2-anthraquinonyl hydrazide as substrate," Cellular and Molecular Biology, Jan. 1, 2004, 50 Online Pub: OL565-568, 1 page (Abstract Only).

Dimri et al., "A biomarker that identifies senescent human cells in culture and in aging skin in vivo," Proceedings of the National Academy of Sciences, Sep. 29, 1995, 92(20):9363-9367.

Dinarello, "Interleukin 1 and interleukin 18 as mediators of inflammation and the aging process," The American Journal of Clinical Nutrition, Feb. 1, 2006, 83(2):447S-455S.

Dong et al., "Characterization of adenosine deaminase binding to human CD26 on T cells and its biologic role in immune response," Journal of Immunology, Feb. 15, 1996, 156(4):1349-1355.

Dong et al., "Determination of adenosine deaminase binding domain on CD26 and its immunoregulatory effect on T cell activation," Journal of Immunology, Dec. 15, 1997, 159(12):6070-6076.

Dong et al., "Loss of methylation at theIFNGpromoter and CNS-1 is associated with the development of functional IFN-γ memory in human CD4+T lymphocytes," European Journal of Immunology, 2013, 43(3), 793-804.

Dou et al., "Cytoplasmic chromatin triggers inflammation in senescence and cancer," Nature, Oct. 4, 2017, 550(7676):402-406, 21 pages.

Dubois et al., "Preassociation of IL-15 with IL-15Rα-IgG1-Fc Enhances Its Activity on Proliferation of NK and CD8+/CD44high T Cells and Its Antitumor Action," The Journal of Immunology, Feb. 15, 2008, 180:2099-2106.

Eisenhut et al., "Ion Channels in Inflammation," Pflugers Archive, Jan. 29, 2011, 461(4):401-421.

Elpek et al., "Mature natural killer cells with phenotypic and functional alterations accumulate upon sustained stimulation with IL-15/IL-15Rα complexes," Proceedings of the National Academy of Science, Dec. 14, 2010, 107: 21647-21652.

Engel et al., "The crystal structure of dipeptidyl peptidase IV (CD26) reveals its functional regulation and enzymatic mechanism," Proc. Natl. Acad. Sci. U.S.A., Apr. 29, 2003, 100(9):5063-5068.

(56) References Cited

OTHER PUBLICATIONS

Epardaud et al., "Interleukin-15/Interleukin-15RA Complexes Promote Destruction of Established Tumors by Reviving Tumor-Resident CD8+ T Cells," Cancer Research 68: Apr. 15, 2008, 2972-2983.
Esensten et al., "Regulatory T-cell therapy for autoimmune and autoinflammatory diseases: The next frontier," The Journal of Allergy and Clinical Immunology, Dec. 1, 2018, 142(6):1710-1718.
Fehniger et al., "A Phase 1 Trial of CNDO-109—Activated Natural Killer Cells in Patients with High-Risk Acute Myeloid Leukemia," Biology of Blood and Marrow Transplantation, Aug. 2018, 24(8):1581-1589.
Feng et al., "The yin and yang functions of extracellular ATP and adenosine in tumor immunity," Cancer Cell International, Apr. 7, 2020, 20:110, 11 pages.
Ferreira et al., "Next-generation regulatory T cell therapy," Nature Reviews Drug Discovery, Sep. 20, 2019, 18(10):749-769, 21 pages.
Ferrucci et al., "The origins of age-related proinflammatory state," Blood, Mar. 15, 2005, 105(6):2294-2299.
Finkelman et al., "Anti-cytokine antibodies as carrier proteins. Prolongation of in vivo effects of exogenous cytokines by injection of cytokine-anti-cytokine antibody complexes," The Journal of Immunology, Aug. 1, 1993, 151:1235-1244.
Finkelstein et al., "Obesity and Severe Obesity Forecasts Through 2030," American Journal of Preventative Medicine, Jun. 2012, 42(6):563-570.
Ford et al., "TREM and TREM-like receptors in inflammation and disease," Current Opinion in Immunology, Feb. 21, 2009, 21(1):38-46.
Franceschi et al., "Inflamm-aging. An evolutionary perspective on immunosenescence," Annals of the New York Academy of Sciences, Jun. 2000, 908:244-254.
Frutoso et al., "Emergence of NK Cell Hyporesponsiveness after Two IL-15 Stimulation Cycles," Journal of Immunology, May 30, 2018, 201: 493-506.
Ganesh et al., "TGF-β Inhibition and Immunotherapy: Checkmate," Immunity, Apr. 17, 2018, 48(4):626-628.
Georgilis et al., "PTBP1-Mediated Alternative Splicing Regulates the Inflammatory Secretome and the Pro-tumorigenic Effects of Senescent Cells," Cancer Cell, Jul. 9, 2018, 34(1):85-102.
Ghosh et al., "The Senescence-Associated Secretory Phenotype: Critical Effector in SkinCancer and Aging," Journal of Investigative Dermatology, Nov. 2016, 136(11):2133-2139.
Gong et al., "DAMP-sensing receptors in sterile inflammation and inflammatory diseases," Nature Reviews Immunology, Sep. 26, 2019, 20(2):95-112.
Gorrell et al., "Expression of the rat CD26 Antigen (dipeptidyl peptidase IV) on subpopulations of rat lymphocytes," Cellular Immunology, Apr. 15, 1991, 134(1):205-215.
Grupp et al., "Chimeric Antigen Receptor-Modified T Cells for Acute Lymphoid Leukemia," The New England Journal of Medicine, Apr. 18, 2013, 368(16):1509-1518.
Gu et al., "Human CD39hi regulatory T cells present stronger stability and function under inflammatory conditions," Cellular and Molecular Immunology, Jul. 4, 2016, 14(6):521-528.
Gutschmidt et al., "A quantitative histochemical study of dipeptidyl peptidase IV (DPP IV)," Histochemistry, 1981, 73(2):285-304.
Hayflick et al., "The serial cultivation of human diploid cell strains," Experimental Cell Research, Dec. 1961, 25:585-621.
He et al., "Senescence in Health and Disease," Cell, Jun. 1, 2017, 169(6):1000-1011.
Heneka et al., "Inflammasome signaling in brain function and neurodegenerative disease," Nature Reviews Neuroscience, Sep. 11, 2018, 19(10):610-621.
Heneka et al., "NLRP3 is activated in Alzheimer's disease and contributes to pathology in APP/PS1 mice," Nature, Jan. 31, 2013, 493(7434):674-678, 8 pages.
Heng et al., "G Protein-Coupled Receptors Revisited: Therapeutic Applications Inspired by Synthetic Biology," Annual Review of Pharmacology and Toxicology, Jan. 2014, 54:227-249.
Highfill et al., "Overcoming Challenges in Process Development of Cellular Therapies," Current Hematologic Malignancy Reports, Jul. 6, 2019, 14(4):269-277, 9 pages.
Hoare et al., "The Power Behind the Throne: Senescence and the Hallmarks of Cancer," Annual Review of Cancer Biology, 2018, 2:175-194.
Hoffmann et al., "Large-scale in vitro expansion of polyclonal human CD4+CD25high regulatory T Cells," Blood, Aug. 2004, 104(3):895-903.
Hollande et al., "Inhibition of the dipeptidyl peptidase DPP4 (CD26) reveals IL-33-dependent eosinophil-mediated control of tumor growth," Nature Immunology, Feb. 18, 2019, 20(3):257-264.
Hudson et al., "Targeting RAGE Signaling in Inflammatory Disease," Annual Review of Medicine, Jan. 2018, 69:349-364, 16 pages.
Huell et al., "Interleukin-6 is present in early stages of plaque formation and is restricted to the brains of Alzheimer's disease patients," Acta Neuropathologica, Nov. 1995, 89(6):544-551.
Hynes et al., "In vitro analysis of cell metabolism using a long-decay pH-sensitive lanthanide probe and extracellular acidification assay," Analytical biochemistry, Jul. 1, 2009, 390(1):21-28.
Iihoshi et al., "Aclarubicin, an anthracycline anti-cancer drug, fluorescently contrasts mitochondria and reduces the oxygen consumption rate in living human cells," Toxicology Letters, Aug. 5, 2017, 277:109-114, 22 pages.
Inzucchi et al., "New Drugs for the Treatment of Diabetes, Part II: Incretin-Based Therapy and Beyond," Circulation, Jan. 29, 2008, 117(4):574-584, 21 pages.
Jain et al., "Mitochondrial Reactive Oxygen Species Regulate Transforming Growth Factor-β Signaling," Journal of Biological Chemistry, Jan. 11, 2013, 288(2):770-777.
Janeway, "Approaching the Asymptote? Evolution and Revolution in Immunology," Cold Spring Harbor Symposia on Quantitative Biology, 1989, 54 Pt 1:1-13.
Jin et al., "Novel Insights Into the NLRP3 Inflammasome in Atherosclerosis," Journal of the American Heart Association, Jun. 11, 2019, 8(12):e012219, 12 pages.
Justice et al., "Senolytics in idiopathic pulmonary fibrosis: Results from a first-in-human, open-label, pilot study," EBioMedicine, Feb. 2019, 40:554-563.
Karin et al., "Senescent cell turnover slows with age providing an explanation for the Gompertz law," Nature Communications, 10:5495, 9 pages.
Karkera et al., "The anti-interleukin-6 antibody siltuximab down-regulates genes implicated in tumorigenesis in prostate cancer patients from a phase I study," The Prostate, Feb. 14, 2011, 71(13):1455-1465.
Katsuumi et al., "Vascular Senescence in Cardiovascular and Metabolic Diseases," Frontiers in Cardiovascular Medicine, 5:18, 13 pages.
Kim et al., "Identification of senescent cell surface targetable protein DPP4," Genes & Development, 2017, 31(15):1529-1534.
Kim et al., "SCAMP4 enhances the senescent cell secretome," Genes & Development, 2018, 32(13-14):909-914.
Kirkland et al., "Cellular Senescence: A Translational Perspective," EBioMedicine, Jul. 2017, 21:21-28.
Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology, 2017 6(3):e1277306, 15 pages.
Klemann et al., "Cut to the chase: a review of CD26/dipeptidyl peptidase-4's (DPP4) entanglement in the immune system," Clinical and Experimental Immunology, Feb. 25, 2016, 185(1):1-21.
Klingenberg et al., "Depletion of FOXP3+ regulatory T cells promotes hypercholesterolemia and atherosclerosis," The Journal of Clinical Investigation, Feb. 15, 2013, 123:1323-1334.
Kritsilis et al., "Ageing, Cellular Senescence and Neurodegenerative Disease," International Journal of Molecular Sciences, Sep. 27, 2018, 19(10):2937, 37 pages.
Kumagai et al., "Monitoring of glutamate-induced excitotoxicity by mitochondrial oxygen consumption," Synapse, Jan. 2019, 73(1):e22067, 24 Pages.

(56) References Cited

OTHER PUBLICATIONS

Lambeir et al., "Dipeptidyl-Peptidase IV from Bench to Bedside: An Update on Structural Properties, Functions, and Clinical Aspects of the Enzyme DPP IV," Critical Reviews in Clinical Laboratory Sciences, Sep. 29, 2003, 40(3):209-294.
Lamkanfi et al., "Mechanisms and Functions of Inflammasomes," Cell, May 22, 2014, 157(5): 1013-1022.
Lansigan et al., "DI-Leu16-IL2, an Anti-CD20-Interleukin-2 Immunocytokine, Is Safe and Active in Patients with Relapsed and Refractory B-Cell Lymphoma: A Report of Maximum Tolerated Dose, Optimal Biologic Dose, and Recommended Phase 2 Dose," Blood, Dec. 2, 2016, 128(22):620, 3 pages (Abstract Only).
Latz et al., "Activation and regulation of the inflammasomes," Nature Reviews Immunology, May 24, 2013, 13(6):397-411.
Latz et al., "NLRP3 inflammasome activation in inflammaging," Seminars in Immunology, Dec. 2018, 40:61-73, 13 pages.
Lan et al., "RNA-associated autoantigens activate B cells by combined B cell antigen receptor/Toll-like receptor 7 engagement," The Journal of Experimental Medicine, Oct. 31, 2005, 202(9):1171-1177.
Li et al., "A Novel I L2-based Irrmunotherapeutic Protein Prevents the Development of Atherosclerosis in ApoE-/mice and LDLR-/-mice," Journal of Immunology, May 1, 2020, 204(1):Supplement (Abstract Only), 2 pages.
Li et al., "Adoptive transfer of natural killer cells in combination with chemotherapy improves outcomes of patients with locally advanced colon carcinoma," Cytotherapy, Jan. 2018, 20(1):134-148, 15 pages.
Li et al., "The cGAS-cGAMP-STING pathway connects DNA damage to inflammation, senescence, and cancer," Journal of Experimental Medicine, Apr. 5, 2018, 215(5):1287-1299.
Liton et al., "Cellular senescence in the glaucomatous outflow pathway," Experimental Gerontology, Aug.-Sep. 2005, 40(8-9):745-748.
Liu et al., "Evaluation of the biological activities of the IL-15 superagonist complex, ALT-803, following intravenous versus subcutaneous administration in murine models," Cytokine, Jul. 2018, 107: 105-112, 8 pages.
Loster et al., "The Cysteine-Rich Region of Dipeptidyl Peptidase IV (CD 26) Is the Collagen Binding Site," Biochemical and Biophysical Research Communications, Dec. 5, 1995, 217(1):341-348.
Lu et al., "Molecular basis of binding between novel human coronavirus MERS-CoV and its receptor CD26," Nature, Jul. 7, 2013, 500(7461):227-231.
Lujambio et al., "Non-Cell-Autonomous Tumor Suppression by p53," Cell, Apr. 11, 2013, 153(2):449-460.
Maganto-García et al., "Dynamic Changes in Regulatory T Cells Are Linked to Levels of Diet-Induced Hypercholesterolemia," Circulation, Jun. 20, 2011, 124:185-195.
Marguet et al., "Enhanced insulin secretion and improved glucose tolerance in mice lacking CD26," Proc. Natl. Acad. Sci. U.S.A., Jun. 6, 2000, 97(12):6874-6879.
Martelli et al., "HLA-haploidentical transplantation with regulatory and conventional T-cell adoptive immunotherapy prevents acute leukemia relapse," Blood, Jul. 24, 2014, 124(4):638-644.
McHugh et al., "Senescence and aging: Causes, consequences, and therapeutic avenues," Journal of Cellular Biology, Nov. 7, 2017, 217(1):65-77.
Mehta et al., "Why do trials for Alzheimer's disease drugs keep failing? A discontinued drug perspective for 2010-2015," Expert Opinion on Investigational Drugs, May 2017, 26(6):735-739.
Mentlein et al., "Dipeptidyl-peptidase IV (CD26)-role in the inactivation of regulatory peptides," Regulatoiy Peptides, Nov. 30, 1999, 85(1):9-24.
Michelet et al., "Metabolic reprogramming of natural killer cells in obesity limits antitumor responses," Nature Immunology, Nov. 12, 2018, 19(12):1330-1340.
Milanovic et al., "Senescence-associated reprogramming promotes cancer sternness," Nature, Dec. 20, 2017, 553(7686):96-100.

Milanovic et al., "The Senescence-Sternness Alliance—A Cancer-Hijacked Regeneration Principle," Trends in Cellular Biology, Dec. 2018, 28(12):1049-1061, 13 pages.
Miller et al., "Successful adoptive transfer and in vivo expansion of human haploidentical NK cells in patients with cancer," Blood, Apr. 15, 2005, 105(8):3051-3057.
Minamino et al., "A crucial role for adipose tissue p53 in the regulation of insulin resistance," Nature Medicine, Aug. 30, 2009, 15(9):1082-1087.
Mitterberger et al., "Adipogenic Differentiation Is Impaired in Replicative Senescent Human Subcutaneous Adipose-Derived Stromal/Progenitor Cells," The Journals of Gerontology: Series A, Biological Sciences and Medical Sciences, Jan. 2014, 69(1):13-24.
Miyazaki et al., "Abstract 3265: NKTR-255, a polymer-conjugated IL-15 enhances anti-tumor NK cell responses and synergizes with monoclonal antibodies to provide long-term survival in human lymphoma model," Proceedings: AACR Annual Meeting 2019, Atlanta, GA, Mar. 29-Apr. 3, 2019, 1 page.
Moesta et al., "Targeting CD39 in cancer," Nature Reviews Immunology, Jul. 29, 2020, 20(12):739-755, 17 pages.
Moiseeva et al., "Metformin inhibits the senescence-associated secretory phenotype by interfering with IKK/NF-κB activation," Aging Cell, Mar. 23, 2013, 12(3):489-498.
Mookerjee et al., "Measurement and Analysis of Extracellular Acid Production to Determine Glycolytic Rate," Journal of Visualized Experiments : Jove, Dec. 2015, (106):e53464, 9 Pages.
Moore et al., "Macrophages in atherosclerosis: a dynamic balance," Nature Reviews Immunology, Sep. 2, 2013, 13:709-721, 13 pages.
Moreno et al., "Molecular Evidence of Adenosine Deaminase Linking Adenosine A2A Receptor and CD26 Proteins," Frontiers in Pharmacology, Feb. 15, 2018, 9:106, 18 pages.
Mulvihill et al., "Pharmacology, Physiology, and Mechanisms of Action of Dipeptidyl Peptidase-4 Inhibitors," Endocrine Reviews, Dec. 1, 2014, 35(6):992-1019.
Munoz-Espin et al., "Cellular senescence: from physiology to pathology," Nature Reviews Molecular Cellular Biology, Jun. 23, 2014, 15(7):482-496.
Munoz-Espin et al., "Programmed Cell Senescence during Mammalian Embryonic Development," Cell, Nov. 21, 2013, 155(5):1104-1118.
Musi et al., "Tau protein aggregation is associated with cellular senescence in the brain," Aging Cell, Aug. 20, 2018, 17(6):e12840, 13 pages.
Must et al., "The Disease Burden Associated with Overweight and Obesity," Endotext, Feingold et al. (eds.), South Dartmouth, MA, 2000, 35 pages.
Myung et al., "Evidence of DNA damage in Alzheimer disease: phosphorylation of histone H2AX in astrocytes," Age, Apr. 23, 2008, 30(4):209-215.
Nayyar et al., "Overcoming Resistance to Natural Killer Cell Based Immunotherapies for Solid Tumors," Frontiers in Oncology, 2019, 9: DOI:10.3389/fonc.2019.00051.
Nelson et al., "A senescent cell bystander effect: senescence-induced senescence," Aging Cell, Feb. 9, 2012, 11(2):345-349.
Nishida et al., "CD26 is a potential therapeutic target by humanized monoclonal antibody for the treatment of multiple myeloma," Blood Cancer Journal, Oct. 22, 2018, 8(11):99, 17 pages.
Oberle et al., "Rapid Suppression of Cytokine Transcription in Human CD4+CD25—T Cells by CD4+Foxp3+ Regulatory T Cells: Independence of IL-2 Consumption, TGF-β, and Various Inhibitors of TCR Signaling," The Journal of Immunology, Sep. 15, 2007, 179(6):3578-3587.
Ogrodnik et al., "Cellular senescence drives age-dependent hepatic steatosis," Nat Commun. Jun. 13, 2017;8:15691, 12 pages.
Ogrodnik et al., "Obesity-Induced Cellular Senescence Drives Anxiety and Impairs Neurogenesis," Cell Metabolism, May 2019, 29(5):1061-1077, 25 pages.
Ohnuma et al., "Blockade of CD26-mediated T cell costimulation with soluble caveolin-1-Ig fusion protein induces anergy in CD4+T cells," Biochemical and Biophysics Research Communications, Aug. 21, 2009, 386(2):327-332.

(56) References Cited

OTHER PUBLICATIONS

Ohnuma et al., "CD26 Mediates Dissociation of Tollip and IRAK-1 from Caveolin-1 and Induces Upregulation of CD86 on Antigen-Presenting Cells," Molecular and Cellular Biology, Sep. 1, 2005, 25(17):7743-7757.
Ohnuma et al., "CD26 up-regulates expression of CD86 on antigen-presenting cells by means of caveolin-1," Proc. Natl. Acad. Sci. U.S.A., Sep. 28, 2004, 101(39):14186-14191.
Ohnuma et al., "Role of CD26/dipeptidyl peptidase IV in human T cell activation and function," Frontiers in Bioscience, Jan. 1, 2008, 13:2299-2310.
Ohnuma et al., "Soluble CD26/Dipeptidyl Peptidase IV Induces T Cell Proliferation Through CD86 Up-Regulation on APCs," Journal of Immunology, Dec. 15, 2001, 167(12):6745-6755.
Owicki et al., "Biosensors based on the energy metabolism of living cells: the physical chemistry and cell biology of extracellular acidification," Biosensors and Bioelectronics, Jan. 1, 1992, 7(4):255-272.
Padutsch et al., "Superior Treg-Expanding Properties of a Novel Dual-Acting Cytokine Fusion Protein," Frontiers in Pharmacology, Dec. 18, 2019, 10:1490, 10 pages.
Palmer et al., "Cellular Senescence in Type 2 Diabetes: A Therapeutic Opportunity," Diabetes, Jul. 2015, 64(7):2289-2298.
PCT International Preliminary Report on Patentability in International Appln. No. PCT/US2019/048881, dated Mar. 11, 2021, 7 pages.
PCT International Preliminary Report on Patentability in International Appln. No. PCT/US2019/048930, dated Mar. 11, 2021, 9 pages.
PCT International Preliminary Report on Patentability in International Appln. No. PCT/US2019/049142, dated Mar. 11, 2021, 11 pages.
PCT International Preliminary Report on Patentability in International Appln. No. PCT/US2019/049158, dated Mar. 11, 2021, 8 pages.
PCT International Search Report and Written Opinion in International Appln. No. PCT/US2020/035598, dated Feb. 18, 2021, 12 pages.
PCT International Search Report and Written Opinion in International Appln. No. PCT/US2021/017620, dated Aug. 6, 2021, 22 pages.
PCT International Search Report and Written Opinion in International Appln. No. PCT/US2021/017621, dated Jun. 9, 2021, 15 pages.
PCT International Search Report and Written Opinion in International Appln. No. PCT/US2021/017714, dated Aug. 27, 2021, 22 pages.
PCT International Search Report and Written Opinion in International Appln. No. PCTUS2020/03 8717, dated Oct. 16, 2020, 17 pages.
Pittayapmek et al., "Role of Matrix Metalloproteinases in Photoaging and Photocarcinogenesis," International Journal of Molecular Sciences, 2016, 17(6):868, 20 pages.
Purohit et al., "Smad3-dependent regulation of type I collagen in human dermal fibroblasts: Impact on human skin connective tissue aging," Journal of Dermatological Science, Jul. 2016, 83(1):80-83, 4 pages.
Qin et al., "Critical Role of P2Y12 Receptor in Regulation of Th17 Differentiation and Experimental Autoimmune Encephalomyelitis Pathogenesis," The Journal of Immunology, Jul. 1, 2017, 199(1):72-81.
Rafei et al., "Off-the-shelf vims specific T-cells for therapy of adenovims disease in immunosuppressed patients," Journal of Clinical Oncology, May 26, 2019, 37(15 Suppl.):7008, 2 pages.
Raj et al., "Adenosine Deaminase Acts as a Natural Antagonist for Dipeptidyl Peptidase 4-Mediated Entry of the Middle East Respiratory Syndrome Coronavirus," Journal of Virology, Feb. 2014, 88(3):1834-1838, 7 pages.
Rao et al., "Purification and characterization of rabbit tissue factor," Thrombosis Research, Oct. 1, 1989, 56(1):109-118.
Rasmussen et al., "Crystal structure of human dipeptidyl peptidase IV/CD26 in complex with a substrate analog," Nature Structural and Molecular Biology, 2003, 10(1):19-25.
Raz et al., "Efficacy and safety of the dipeptidyl peptidase-4 inhibitor sitagliptin as monotherapy in patients with type 2 diabetes mellitus," Diabetologia, Sep. 26, 2006, 49(11):2564-2571.
Resta et al., "Ecto-enzyme and signaling functions of lymphocyte CD 7 3," Immunological Reviews, 1998, 161:95-109.
Rittie et al., "Natural and Sun-Induced Aging of Human Skin," Cold Spring Harbor Perspective in Medicine, 2015, 5(1):a015370, 15 pages.
Rocha et al., "A novel immunofluorescent assay to investigate oxidative phosphorylation deficiency in mitochondrial myopathy: understanding mechanisms and improving diagnosis," Scientific reports, Oct. 15, 2015, 5:15037, 17 Pages.
Rodier et al., "Persistent DNA damage signaling triggers senescence-associated inflammatory cytokine secretion," Nature Cell Biology, Jul. 13, 2009, 11(8): 973-979, 15 pages.
Roh et al., "Damage-Associated Molecular Patterns in Inflammatory Diseases," Immune Network, Aug. 2018, 18(4):e27, 14 pages.
Romano et al., "Past, Present, and Future of Regulatory T Cell Therapy in Transplantation and Autoimmunity," Frontiers in Immunology, Jan. 1, 2019, 10:43, 14 pages.
Romee et al., "Cytokine activation induces human memory-like NK cells," Blood, Dec. 6, 2012, 120(24):4751-4760.
Rubinstein et al., "Converting IL-15 to a superagonist by binding to soluble IL-15Rα," Proceedings of the National Academy of Sciences U.S.A., Jun. 13, 2006, 103(24):9166-9171.
Ruscetti et al., "NK cell-mediated cytotoxicity contributes to tumor control by a cytostatic drug combination," Science, Dec. 21, 2018, 362(6421):1416-1422, 8 pages.
Sakaguchi et al., "Regulatory T Cells and Human Disease," Annual Review of Immunology, Apr. 26, 2020, 38:541-566.
Sakaguchi et al., "Regulatory T Cells and Immune Tolerance," Cell, May 30, 2008, 133(5):775-787.
Sakaguchi et al., "Regulatory T cells: how do they suppress immune responses?" International Immunology, Sep. 7, 2009, 21(10):1105-1111.
Sakamoto et al., "Phase I clinical trial of autologous NK cell therapy using novel expansion method in patients with advanced digestive cancer," Journal of Translational Medicine, Aug. 25, 2015, 13:277, 13 pages.
Sakamuri et al., "Measurement of respiratory function in isolated cardiac mitochondria using Seahorse XFe24 Analyzer: applications for aging research," Geroscience, Jun. 1, 2018, 40(3):347-356.
Salminen et al., "Emerging role of NF-κB signaling in the induction of senescence-associated secretory phenotype (SASP)," Cellular Signaling, Apr. 2012, 24(4):835-845.
Sato et al., "Recombinant soluble murine IL-4 receptor can inhibit or enhance IgE responses in vivo," The Journal of Immunology, Apr. 1, 1993, 150:2717-2723.
Schafer et al., "Cellular senescence mediates fibrotic pulmonary disease," Nat Commun., Feb. 2017, 8:14532, 11 pages.
Schwoppe et al., "Tissue-factor fusion proteins induce occlusion of tumor vessels," Thrombosis Research, Apr. 1, 2010, 125:S143-S150.
Seo et al., "Positive Feedback Loop between Plasminogen Activator Inhibitor-1 and Transforming Growth Factor-Beta1 during Renal Fibrosis in Diabetes," American Journal of Nephrology, Sep. 25, 2009, 30:481-490.
Sharma et al., "Regulatory T Cells License Macrophage Pro Resolving Functions During Atherosclerosis Regression," Circulation Research, Apr. 27, 2020, 127:335-353.
Soerensen et al., "Safety, PK/PD, and anti-tumor activity of RO6874281, an engineered variant of interleukin-2 (IL-2v) targeted to tumor-associated fibroblasts via binding to fibroblast activation protein (FAP)," Journal of Clinical Oncology, Jun. 1, 2018, 36(No. 15 Suppl.):e15155, 2 pages.
Sondel et al., "Combination Therapy with Interleukin-2 and Antitumor Monoclonal Antibodies," Cancer Journal from Scientific American, Jan. 1, 1997, 3(Suppl. 1):S121-S127.

(56) References Cited

OTHER PUBLICATIONS

Sone et al., "Pancreatic beta cell senescence contributes to the pathogenesis of type 2 diabetes in high-fat diet-induced diabetic mice," Diabetologia, 2005, 48(1):58-67.

Song et al., "IL-12/IL-18-preactivated donor NK cells enhance GVL effects and mitigate GvHD after allogeneic hematopoietic stem cell transplantation," European Journal of Immunology, Apr. 2018, 48(4):670-682.

Stoklasek et al., "Combined IL-15/IL-15Rα Immunotherapy Maximizes IL-15 Activity In Vivo," The Journal of Immunology, Nov. 1, 2006, 177(9):6072-6080.

Storer et al., "Senescence Is a Developmental Mechanism that Contributes to Embryonic Growth and Patterning," Cell, Nov. 21, 2013, 155(5):1119-1130.

Stryer, Biochemistry Fourth Edition, W. H. Freeman and Company, New York, 1995, pp. 18-23, 8 pages.

Swanson et al., "The NLRP3 inflammasome: molecular activation and regulation to therapeutics," Nature Reviews Immunology, Apr. 29, 2019, 19(8):477-489, 13 pages.

Takahashi et al., "Downregulation of cytoplasmic DNases is implicated in cytoplasmic DNA accumulation and SASP in senescent cells," Nature Communications, Mar. 28, 2018, 9:1249, 12 pages.

Takahashi et al., "Simple and inexpensive technique for measuring oxygen consumption rate in adherent cultured cells," The Journal of Physiological Sciences, Nov. 2017, 67(6):731-737.

Takeda et al., "Phase I study of YS110, a recombinant humanized monoclonal antibody to CD26, in Japanese patients with advanced malignant pleural mesothelioma," Lung Cancer, Nov. 2019, 137:64-70.

Tanaka et al., "Cloning and functional expression of the T cell activation antigen CD26," Journal of Immunology, Jul. 15, 1992, 149(2):481-486.

Tang et al., "The Foxp3+ regulatory T cell: a jack of all trades, master of regulation," Nature Immunology, Feb. 19, 2008, 9(3):239-244.

Teissier et al., "The receptor for advanced glycation end-products (RAGE) is an important pattern recognition receptor (PRR) for inflammaging," Biogerontology, Apr. 9, 2019, 20(3):279-301, 23 pages.

Teng et al., "Structural assessment of the effects of amino acid substitutions on protein stability and protein proteininteraction," International journal of computational biology and drug design, Feb. 7, 2011, 3(4):334-349.

Theil et al., "Adoptive transfer of allogeneic regulatory T cells into patients with chronic graft-versus-host disease," Cytotherapy, Apr. 2015, 17(4):473-486, 14 pages.

Thonhoff et al., "Expanded autologous regulatory T-lymphocyte infusions in ALS," Neurology Neuroimmunology Neuroinflammation, May 18, 2018, 5(4):e465, 8 pages.

Tobin et al., "NK cells in childhood obesity are activated, metabolically stressed, and functionally deficient," JCI Insight, Dec. 21, 2017, 2(24):e94939, 9 pages.

Tomala et al., "In Vivo Expansion of Activated Naive CD8+ T Cells and NK Cells Driven by Complexes of IL-2 and Anti-IL-2 Monoclonal Antibody As Novel Approach of Cancer Immunotherapy," The Journal of Immunology, Oct. 15, 2009, 183:4904-4912.

Tominaga et al., "TGF-β Signaling in Cellular Senescence and Aging-Related Pathology," International Journal of Molecular Sciences, Oct. 10, 2019, 20(20):5002, 18 pages.

Trevani et al., "Extracellular acidification induces human neutrophil activation," The Journal of Immunology, Apr. 15, 1999, 162(8):4849-4857.

Tse et al., "ABT-263: A Potent and Orally Bioavailable Bcl-2 Family Inhibitor," Cancer Research, May 2008, 68(9):3421-3428.

Uryga et al., "Ageing induced vascular smooth muscle cell senescence in atherosclerosis," Journal of Physiology, Apr. 15, 2016, 594(8):2115-2124.

Vaishampayan et al., "A phase I trial of ALKS 4230, an engineered cytokine activator of NK and effector T cells, in patients with advanced solid tumors," Journal of Clinical Oncology, 2017, 35(15 Suppl.):TPS3111, 4 pages (Abstract Only).

Van Deursen, "The role of senescent cells in ageing," Nature, May 21, 2014, 509(7501):439-446.

Vankadari et al., "Emerging COVID-19 coronavirus: glycan shield and structure prediction of spike glycoprotein and its interaction with human CD26," Emerging Microbes and Infection, Mar. 17, 2020, 9(1):601-604.

Vidarsson et al., "IgG subclasses and allotypes: from structure to effector functions," Frontiers in immunology, Oct. 20, 2014, 5:520, 17 Pages.

Von Kobbe, "Cellular senescence: a view throughout organismal life," Cellular and Molecular Life Sciences, Jul. 20, 2018, 75:3553-3567, 15 pages.

Waaijer et al., "Do senescence markers correlate in vitro and in situ within individual human donors?," Aging Feb. 2018, 10(2):278-289.

Walsh et al., "Inflammasomes in the CNS," Nature Reviews Neuroscience, Jan. 8, 2014, 15(2):84-97, 14 pages.

Wang et al., "Biomarkers of Cellular Senescence and Skin Aging," Frontiers in Genetics, Aug. 23, 2018, 9:247, 14 pages.

Wang et al., "Loss of lamin B1 is a biomarker to quantify cellular senescence in photoaged skin," Scientific Reports, Nov. 15, 2017, 7(1):15678, 8 pages.

Weihermann et al., "Elastin structure and its involvement in skin photoageing," International Journal of Cosmetic Science, Jun. 2017, 39(3):241-247.

Weihofen et al., "Crystal Structure of CD26/Dipeptidyl-peptidase IV in Complex with Adenosine Deaminase Reveals a Highly Amphiphilic Interface," Journal of Biological Chemistry, Oct. 2004, 279(41):43330-43335.

Weiss et al., "Formyl-Peptide Receptors in Infection, Inflammation, and Cancer," Trends in Immunology, Oct. 2018, 39(10):815-829, 15 pages.

Wiemann et al., "Hepatocyte telomere shortening and senescence are general markers of human liver cirrhosis," The FASEB Journal, Jul. 2002, 16(9):935-942.

Wiley et al., "Mitochondrial Dysfunction Induces Senescence with a Distinct Secretory Phenotype," Cell Metabolism, Feb. 9, 2016, 23(2):303-314.

Xu et al., "JAK inhibition alleviates the cellular senescence-associated secretory phenotype and frailty in old age," Proceedings of the National Academy of Sciences U.S.A., Nov. 17, 2015, 112(46):E6301-6310, 10 pages.

Yamamoto et al., "Measurement of glucose uptake in cultured cells," Curr Protoc Pharmacol, Dec. 2011, Chapter 12:12.14.1-12.14.22.

Yamazaki et al., "Vascular Cell Senescence Contributes to Blood-Brain Barrier Breakdown," Stroke, Feb. 16, 2016, 47(4):1068-1077, 15 pages.

Yan et al., "Obesity- and aging-induced excess of central transforming growth factor-β potentiates diabetic development via an RNA stress response," Nature Medicine, Aug. 3, 2014, 20:1001-1008, 9 pages.

Yanai et al., "Cellular senescence-like features of lung fibroblasts derived from idiopathic pulmonary fibrosis patients," Aging (Albany NY), Sep. 2015, 7(9):664-672.

Yousefzadeh et al., "An aged immune system drives senescence and ageing of solid organs," Nature, May 12, 2021, 594:100-105, 34 pages.

Yu et al., "Targeting the Senescence-Overriding Cooperative Activity of Structurally Unrelated H3K9 Demethylases in Melanoma," Cancer Cell, Feb. 12, 2018, 33(2):322-336, 23 pages.

Yu et al., "The dipeptidyl peptidase IV family in cancer and cell biology," FEBS Journal, Feb. 5, 2010, 277(5):1126-1144.

Yun et al., "Recurrent turnover of senescent cells during regeneration of a complex stmeture," Elife, May 5, 2015, 4:e05505, 16 pages.

Zhang et al., "AAED1 modulates proliferation and glycolysis in gastric cancer," Oncology Reports, Aug. 1, 2018, 40(2):1156-1164.

Zhang et al., "The bone anabolic effects of irisin are through preferential stimulation of aerobic glycolysis," Bone, Sep. 1, 2018, 114:150-160.

(56) References Cited

OTHER PUBLICATIONS

Zhao et al., "Histone Deacetylase-3 Modification of MicroRNA-31 Promotes Cell Proliferation and Aerobic Glycolysis in Breast Cancer and Is Predictive of Poor Prognosis," Journal of breast cancer, Jun. 1, 2018, 21(2):112-123.
Zheng et al., "Acquisition of Suppressive Function by Activated Human CD4+CD25—T Cells Is Associated with the Expression of CTLA-4 Not FoxP3," The Journal of Immunology, Aug. 1, 2008, 181(3):1683-1691.
Zhong et al., "A Potential Role for Dendritic Cell/Macrophage-Expressing DPP4 in Obesity-Induced Visceral Inflammation," Diabetes, Jan. 2013, 62(1):149-157.
Zhou et al., "A novel chimeric antigen receptor redirecting T-cell specificity towards CD26cancer cells," Leukemia, Apr. 2020, 35(1):119-129, 11 pages.
Zhu et al., "New agents that target senescent cells: the flavone, fisetin, and the BCL-XL inhibitors, A1331852 and A1155463," Aging (Albany NY), Mar. 2017, 9(3):955-963.
Zhu et al., "Novel Human Interleukin-15 Agonists," The Journal of Immunology, Sep. 15, 2009, 183(6):3598-3607.
Zou et al., "2-NBDG as a fluorescent indicator for direct glucose uptake measurement," Journal of biochemical and biophysical methods, Sep. 30, 2005, 64(3):207-215.
U.S. Appl. No. 16/556,040, filed Aug. 29, 2019, Wong.
U.S. Appl. No. 16/557,875, filed Aug. 30, 2019, Wong.
Akbari, et al., "Design, expression and evaluation of a novel humanized single chain antibody against epidermal growth factor receptor (EGFR)," Protein Expr. Purif., 2016, 127:8-15.
Bachelet et al., "Mast Cell Costimulation by CD226/CD112 (DNAM-1/Nectin-2) A Novel Interface in the Allergic Process," Journal of Biological Chemistry, Sep. 15, 2006, 281(37):27190-6.
Baker, et al., "Clearance of p16Ink4a-positive senescent cells delays ageing-associated disorders," Nature, 2011, 479(7372): 232-236.
Borgerding et al., "B-lymphoma cells escape rituximab-triggered elimination by NK cells through increased HLA class I expression," Experimental Hematology, Mar. 1, 2010, 38(3):213-21.
Bourgeois et al., "Regulation of cellular senescence via the FOXO4-p53 axis," FEBS Lett., 2018, 592(12): 2083-2097.
Brennan et al., "Structural determination of lipid antigens captured at the CD1d-T-cell receptor interface," PNAS, 2017, 114(31):8348-8353.
Brighton et al., "Clearance of senescent decidual cells by uterine natural killer cells in cycling human endometrium," Elife, Dec. 11, 2017, 6:e31274, 23 pages.
Brooks et al., "Combined inhibition of PD1 and CD96 checkpoints improves survival in a resectable murine model of pancreatic cancer," European Journal of Cancer, Jul. 1, 2016, 61:S189, 1 page.
Cao et al., "Expression and characterization of recombinant humanized anti-HER2 single-chain antibody in Pichia pastoris for targeted cancer therapy," Biotechnology Letters, Jul. 1, 2015, 37(7):1347-54.
Chalan et al., "Expression of Lectin-Like Transcript 1, the Ligand for CD161, in Rheumatoid Arthritis," PLoS ONE, 2015, 10(7):e0132436.
Chattopadyhay et al., "Structural Basis of Inducible Costimulator Ligand Costimulatory Function: Determination of the Cell Surface Oligomeric State and Functional Mapping of the Receptor Binding Site of the Protein1," J Immunol., 2006, 3920-3929.
Chichili et al., "Linkers in the structural biology of protein-protein interactions," Protein Science, Feb. 2013, 22(2):153-67.
Chinta, et al., "Cellular senescence is induced by the environmental neurotoxin paraquat and bontributes to neuropathology linked to Parkinson's Disease," Cell Rep., 2018, 22(4): 930-940.
Ciaglia, et al., "Recognition by natural killer cells of N6-isopentenyladensoine-treated human glioma cell lines," Int. J. Cancer, 2018 142(1): 176-190.
Cichocki et al., "GSK3 inhibition drives maturation of NK cells and enhances their antitumor activity," Cancer Research, Oct. 15, 2017, 77(20):5664-75.
Clayton et al.,"Soluble T Cell Immunoglobulin Mucin Domain 3 Is Shed from CD8 T Cells by the Sheddase ADAM10, Is Increased in Plasma during Untreated HIV Infection, and Correlates with HIV Disease Progression," J Viral., 2015, 89(7):3723-3736.
Cosman et al., "ULBPs, novel MHC class I-related molecules, bind to CMV glycoprotein UL16 and stimulate NK cytotoxicity through the NKG2D receptor," Immunity, Feb. 1, 2001, 14(2):123-33.
Costa et al., "Targeting the epidermal growth factor receptor can counteract the inhibition of natural killer cell function exerted by colorectal tumor-associated fibroblasts," Frontiers in Immunology, May 29, 2018, 9:1150, 14 pages.
Cromie et al., "Nanobodies and their use in GPCR drug discovery," Current Topics in Medicinal Chemistry, Dec. 1, 2015, 15(24):2543-57.
Czaja et al., "A comprehensive analysis of the binding of anti-KIR antibodies to activating KIRs," Genes and Immunity, Jan. 2014, 15(1), 15 pages.
De Crescenzo et al., "Engineering TGF-β Traps: Artificially Dimerized Receptor Ectodomains as High-affinity Blockers of TGF-β Action," Transforming Growth Factor-β in Cancer Therapy, vol. II, 2008, Humana Press, 671-84.
De Genst et al., "Antibody repertoire development in camelids," Developmental & Comparative Immunology, Jan. 1, 2006, 30(1-2):187-98.
De Meyer et al., "Nanobody-based products as research and diagnostic tools," Trends in Biotechnology, May 1, 2014, 32(5):263-70.
Deyev et al., "Design of multivalent complexes using the bamase•barstar module," Nature Biotechnology, Dec. 2003, 21(12):1486-92.
Digiammarino et al., "Design and generation of DVD-Ig™ molecules for dual-specific targeting," Therapeutic Proteins: Methods and Protocols, Methods in Molecular Biology, 2012, Humana Press, Totowa, NJ., 899:145-516.
Docagne et al., "A soluble transforming growth factor-β (TGF-β) type I receptor mimics TGF-β responses," Journal of Biological Chemistry, Dec. 7, 2001, 276(49):46243-50.
Drees, et al., "Soluble production of a biologically active single-chain antibody against murine PD-L1 in *Escherichia coli*," Protein Express. Purif., 2014, 94:60-66.
Edwardraja et al., "Redesigning of anti-c-met single chain Fv antibody for the cytoplasmic folding and its structural analysis," Biotechnology and Bioengineering, Jun. 15, 2010, 106(3):367-75.
Elgueta et al., "Molecular mechanism and function of CD40/CD40L engagement in the immune system," Immunological Reviews, 2009, 229(1):152-172.
Farr et al., "Targeting cellular senescence prevents age-related bone loss in mice," Nat. Med., 2017, 23(9): 1072-1079.
Garber, "Bispecific antibodies rise again," Nat. Rev. Drug Discov., 2014, 13:799-801.
Gaulton et al., "Characterization of a monoclonal rat anti-mouse interleukin 2 (IL-2) receptor antibody and its use in the biochemical characterization of the murine IL-2 receptor," Clinical Immunology and Immunopathology, Jul. 1, 1985, 36(1):18-29.
Gejima et al., "Human single-chain Fv (scFv) antibody specific to human IL-6 with the inhibitory activity on IL-6-signaling," Human Antibodies, Jan. 1, 2002, 11(4):121-9.
Geng et al., "A novel anti-TNF scFv constructed with human antibody frameworks and antagonistic peptides," Immunol, Res. 62(3):377-385, 2015.
Gibbs et al., "Identification of the factor VIIa binding site on tissue factor by homologous loop swap and alanine scanning mutagenesis," Biochemistiy, Nov. 1, 1994, 33(47):14003-10.
Guo et al., "Immunobiology of the IL-15-IL-15R complex as an antitumor and antiviral agent," 2017, Cytokine & Growth Factor Reviews, 38:10-21.
Haile et al., "Soluble CD80 Restores T Cell Activation and Overcomes Tumor Cell Programmed Death Ligand 1-Mediated Immune Suppression," J, Immunol., 2013, 191(5):2829-2836.
Hebbar et al., "Detection of circulating soluble CD28 in patients with systemic lupus erythematosus, primary Sjogren's syndrome and systemic sclerosis," Clinical & Experimental Immunology, May 2004, 136(2):388-92.
Helfrich et al., "A rapid and versatile method for harnessing scFv antibody fragments with varous biological effector functions," Journal of Immunological methods, 2000, 237(1-2):131-145.

(56) References Cited

OTHER PUBLICATIONS

Heng et al., Sophea, et al. "Multiple soluble TGF-β receptors in addition to soluble endoglin are elevated in preeclamptic serum and they synergistically inhibit TGF-β signalling." Placenta, 2017 57:320 (1 page).

Hombach et al., "Generation of the single chain antibody fragment conserves the idiotypic profile of the anti-CD30 monoclonal antibody HRS3," Scandinavian Journal of Immunology, Nov. 1998, 48(5):497-501.

Hu et al., "Discovery of a novel IL-15 based protein with improved developability and efficacy for cancer immunotherapy," Scientific Reports, 2018, 8:7675, 11 pages.

Huang et al., "Substrate recognition by tissue factor-factor Vila Evidence for interaction of residues Lys165 and Lys166 of tissue factor with the 4-carboxy glutamate-rich domain of factor X," Journal of Biological Chemistiy, Sep. 6, 1996, 271(36):21752-7.

Hudak et al., "Glycocalyx engineering reveals a Siglec-based mechanism for NK cell immunoevasion," Nature Chemical Biology, Jan. 2014, 10(1), 20 pages.

Hughes, et al., "Transfer of a TCR gene derived from a patient with a marked antitumor response conveys highly active T-cell effector functions," Hum. Gene Ther., 2005, 16:457-72.

Iannello et al., "p53-dependent chemokine production by senescent tumor cells supports NKG2D-dependent tumor elimination by natural killer cells," Journal of Experimental Medicine, Sep. 23, 2013, 210(10):2057-69.

Jakob et al., Structure reveals function of the dual variable domain immunoglobulin (DVD-Ig™) molecule, Mabs, May 1, 2013,Taylor & Francis, 5(3):358-63.

Jeannin et al., "Soluble CD86 Is a Costimulatory Moleculefor Human T Lymphocytes," Immunity, 2000, 13(3):303-312.

Kain et al., "The identification of the endogenous ligands of natural killer T cells reveals the presence of mammalian α-linked glycosylceramides," Immunity, Oct. 16, 2014, 41(4):543-54.

Kellner et al., "Enhancing natural killer cell-mediated lysis of lymphoma cells by combining therapeutic antibodies with CD20-specific immunoligands engaging NKG2D or NKp30," Oncoimmunology, Jan. 2, 2016, 5(1):e1058459, 12 pages.

Kijanka et al., "Nanobody-based cancer therapy of solid tumors," Nanomedicine, Jan. 2015, 10(1):161-74.

Kim et al., "Experimental malaria infection triggers early expansion of natural killer cells," Infection and Immunity, Dec. 1, 2008, 76(12):5873-82.

Kirchhofer et al., "The tissue factor region that interacts with substrates factor IX and factor X," Biochemistry, Jun. 27, 2000, 39(25):7380-7.

Klein et al., "Design and characterization of structured protein linkers with differing flexibilities," Protein Engineering, Design & Selection, 2014, 27(10):325-30.

Kondo et al., "Requirements for the functional expression of OX40 ligand on human activated CD4+ and CD8+ T cells," Human Immunology, 2007, 68(7):563-571.

Kovaleva et al., "Shark variable new antigen receptor biologics-a novel technology platform for therapeutic drug development," Expert Opinion on Biological Therapy, Oct. 1, 2014, 14(10):1527-39.

Krah et al., "Single-domain antibodies for biomedical applications," Immunopharmacology and Immunotoxicology, Jan. 2, 2016, 38(1):21-8.

Krizhanovsky et al., "Senescence of activated stellate cells limits liver fibrosis," Cell, Aug. 22, 2008, 134(4):657-67.

Liu et al., "A Novel Fusion of ALT-803 (IL-15 Superagonist) with an Antibody Demonstrates Antigen-specific Antitumor Responses," Journal of Biological Chemistry, 2016, 291(46):23869-23881.

Maeda et al., "Original Ligand for LTβR Is LIGHT: Insight into Evolution of the LT/LTβR System," J Immunol., 2018, 201(1):202-214.

Mandelboim et al., "Recognition of haemagglutinins on virus-infected cells by NKp46 activates lysis by human NK cells," Nature, Feb. 2001, 409(6823):1055.

Masoumi et al., "The role of hypoxia as the driving force for non-erythroid production of globin chains in preeclamptic placentas," Placenta. 2017;57:320.

Menshawy et al., ""CD58; leucocyte function adhesion-3 (LFA-3) could be used as a differentiating marker between immune and non-immune thyroid disorders,"" Comparative Clinical Pathology, 2018, 27(3), 721-727.

Miah et al., "KIR2DL4 differentially signals downstream functions in human NK cells through distinct structural modules," The Journal of Immunology, Mar. 1, 2008, 180(5):2922-32.

Miller et al., "Soluble CD70: a novel immunotherapeutic agent for experimental glioblastoma," J Neurosurg., 2010, 113(2):280-285.

Molema et al., "The use of bispecific antibodies in tumor cell and tumor vasculature directed immunotherapy," Journal of Controlled Release, 2000, 64(1-3):229-239.

Molgora et al., "Regulatory role of IL-1R8 in immunity and disease," Frontiers in Immunology, Apr. 20, 2016, 7:149.

Moretta et al., "CD69-mediated pathway of lymphocyte activation: anti-CD69 monoclonal antibodies trigger the cytolytic activity of different lymphoid effector cells with the exception of cytolytic T lymphocytes expressing T cell receptor alpha/beta," Journal of Experimental Medicine, Dec. 1, 1991, 174(6):1393-8.

Mujić-Delić et al., "GPCR-targeting nanobodies: attractive research tools, diagnostics, and therapeutics," Trends in Pharmacological Sciences, May 1, 2014, 35(5):247-55.

Muller et al., "Antibody fusions with immunomodulatory proteins for cancer therapy," Pharmacology and Therapeutics, 2015, 154:57-66.

Muyldermans et al., "Recognition of antigens by single-domain antibody fragments: the superfluous luxmy of paired domains," Trends in Biochemical Sciences, Apr. 1, 2001, 26(4):230-5.

Muyldermans, "Nanobodies: natural single-domain antibodies," Annual Review of Biochemistry, Jun. 2, 2013, 82:775-97.

Muyldermans, "Single domain camel antibodies: current status," Reviews in Molecular Biotechnology, Jun. 1, 2001, 74(4):277-302.

Nag et al., "Soluble MHC II—peptide complexes induce antigen-specific apoptosis in T cells," Cellular Immunology, May 25, 1996, 170(1):25-33.

Nilsson et al., "Targeted delivery of tissue factor to the ED-B domain of fibronectin, a marker of angiogenesis, mediates the infarction of solid tumors in mice," Cancer Research, American Association for Cancer Researc, Procedings: AACR 107th Annual Meeting, 2016, Apr. 16-20, 2016, New Orleans, LA 61(2):711-716.

O'Sullivan et al., "Natural Killer Cell Memory," Immunity, 2015, 43:634-645.

Ovadya et al., "Strategies targeting cellular senescence," The Journal of Clinical Investigation, Apr. 2, 2018, 128(4):1247-54.

Parker et al., "Design, production, and characterization of a single-chain variable fragment (ScFv) derived from the prostate specific membrane antigen (PSMA) monoclonal antibody J591," Protein Expression and Purification, Jun. 1, 2013, 89(2):136-45.

PCT International Search Report and Written Opinion in International Appln. No. PCT/US2019/048881, dated Nov. 9, 2019, 16 pages.

PCT International Search Report and Written Opinion in International Appln. No. PCT/US2019/048930, dated Nov. 20, 2019, 18 pages.

PCT International Search Report and Written Opinion in International Appln. No. PCT/US2019/049158, dated Jan. 20, 2020, 18 pages.

PCT International Search Report and Written Opinion in International Appln. No. PCT/US2019/04912, dated Jun. 23, 2020, 20 pages.

Peipp et al., "HER2-specific immunoligands engaging NKp30 or NKp80 trigger NK-cell-mediated lysis of tumor cells and enhance antibody-dependent cell-mediated cytotoxicity," Oncotarget, Oct. 13, 2015, 6(31):32075.

Priyanka et al., "Linkers in the structural biology of protein-protein interactions," Protein Sci., 2013, 22(2):153-167.

Rahbarizadeh et al., "Nanobody; an old concept and new vehicle for immunotargeting," Immunological Investigations, Jan. 1, 2011, 40(3):299-338.

(56) References Cited

OTHER PUBLICATIONS

Ranganathan et al., "Pinpointing the putative heparin/sialic acid-binding residues in the 'sushi' domain 7 of factor H: a molecular modeling study," Pacific Symposium on Biocomputing 2000, 5:152-164.
Rhein et al., "Characterization of Human and Murine T-Cell Immunoglobulin Mucin Domain 4 (TIM-4) IgV Domain Residues Critical for Ebola Virus Entry," J Viral., 2016, 90(13):6097-6111.
Rippmann et al., "Fusion of the Tissue Factor Extracellular Domain to a Tumor Stromaspecific Single-Chain Fragment Variable Antibody Results in an Antigen-Specific Coagulation-Promoting Molecule," Biochemical Journal, 2000, 349(3):805-812.
Rogge et al., "Antibodies to the IL-12 receptor β2 chain mark human Th1 but not Th2 cells in vitro and in vivo," The Journal of Immunology, Apr. 1, 1999, 162(7):3926-32.
Rossi et al., "Complex and defined biostructures with the dock-and-lock method," Trends in Pharmacological Sciences, Sep. 1, 2012, 33(9):474-81.
Rossi et al., "Stably tethered multifunctional structures of defined composition made by the dock and lock method for use in cancer targeting," Proceedings of the National Academy of Sciences, May 2, 2006, 103(18):6841-6.
Ruf et al., "Cofactor residues lysine 165 and 166 are critical for protein substrate recognition by the tissue factor-factor VIIa protease complex," Journal of Biological Chemistry, Mar. 25, 1992, 267(9):6375-81.
Ruf et al., "Tissue factor residues 157-167 are required for efficient proteolytic activation of factor X and factor VII," Journal of Biological Chemistiy, Nov. 5, 1992, 267(31):22206-10.
Sagiv et al., "Granule exocytosis mediates immune surveillance of senescent cells," Oncogene, 2013, 32(15):1971-1977.
Sandusky et al., "Regulation of 2B4 (CD244)-mediated NK cell activation by ligand-induced receptor modulation," European Journal of Immunology, Dec. 2006, 36(12):3268-76.
Schullek et al., "Key ligand interface residues in tissue factor contribute independently to factor VIIa binding," Journal of Biological Chemistiy, Jul. 29, 1994, 269(30):19399-403.
Sharkey et al., "Improved Therapeutic Results by Pretargeted Radioimmunotherapy of Non-Hodgkin's Lymphoma with a New Recombinant, Trivalent, Anti-CD20, Bispecific Antibody," Cancer Research, Jul. 1, 2008, 68(13):5282-90.
Smith et al., "Antigen Nature and Complexity Influence Human Antibody Light Chain Usage and Specificity," Vaccine, 2016, 34(25): 2813-2820.
Smith et al., "Development and evaluation of an optimal human single-chain variable fragment-derived BCMA-targeted CAR T cell vector," Molecular Therapy, Jun. 6, 2018, 26(6):1447-56.
Soriani et al., "ATM-ATR—dependent up-regulation of DNAM-1 and NKG2D ligands on multiple myeloma cells by therapeutic agents results in enhanced NK-cell susceptibility and is associated with a senescent phenotype," Blood, Apr. 9, 2009, 113(15):3503-11.
Spiess et al., "Alternative molecular formats and therapeutic applications for bispecific antibodies," Molecular Immunology, Oct. 1, 2015, 67(2):95-106.
Szalay et al., "Cutting edge: anti-CD1 monoclonal antibody treatment reverses the production patterns of TGF-β2 and Th1 cytokines and ameliorates listeriosis in mice," The Journal of Immunology, Jun. 15, 1999, 162(12):6955-8.
Tahara-Hanaoka et al., "Functional characterization of DNAM-1 (CD226) interaction with its ligands PVR (CD155) and nectin-2 (PRR-2/CD112)," International Immunology, Apr. 1, 2004, 16(4):533-8.
Van Audenhove et al., "Nanobodies as versatile tools to understand, diagnose, visualize and treat cancer," EBioMedicine, Jun. 1, 2016, 8:40-8.
Van den Bergh et al., "IL-15 receptor alpha as the magic wand to boost the success of IL-15 antitumor therapies: The upswing of IL-15 transpresentation," Pharmacology and Therapeutics, 2017, 170:73-79.
Vincke et al., "Introduction to heavy chain antibodies and derived Nanobodies," Single Domain Antibodies, Humana Press, Totowa, NJ, 2012, pp. 15-26.
Wang et al., A New Recombinant Single Chain Trispecific Antibody Recruits T Lymphocytes to Kill CEA (Carcinoma Embryonic Antigen) Positive Tumor Cells In Vitro Efficiently, Journal of Biochemisty, 2004, 135(4):555-565 DOI: 10.1093/jb/mvh065.
Wang et al., "Recombinant human CD137L for cancer immunotherapy: effects of different fusions and linkers on its activity," Cancer Immunol Immunother., 2012, 61(4):489-495.
Washburn et al., "A potential role for shed soluble major histocompatibility class I molecules as modulators of neurite outgrowth," PLoS One, Mar. 31, 2011, 6(3):e18439.
Weber et al., "Specific low-affinity recognition of major histocompatibility complex plus peptide by soluble T-cell receptor," Nature, Apr. 1992, 356(6372):793.
Weiner et al., "Antibody-based immunotherapy of cancer," Cell, Mar. 16, 2012, 148(6):1081-4.
Wesolowski et al., "Single domain antibodies: promising experimental and therapeutic tools in infection and immunity," Medical Microbiology and Immunology, Aug. 1, 2009, 198(3):157-74.
Witkowsa et al., "Soluble intercellular adhesion molecule-1 (sICAM-1): an overview," Eur Cytokine Netw. 2004, 15(2):91-98.
Xiong et al., "Maternal uterine NK cell-activating receptor KIR2DS1 enhances placentation," The Journal of Clinical Investigation, Oct. 1, 2013, 123(10):4264-72.
Xu et al., "Senolytics improve physical function and increase lifespan in old age," Nature Medicine, Aug. 2018, 24(8):1246.
Xu et al., "Transplanted senescent cells induce an osteoarthritis-like condition in mice," The Journals of Gerontology: Series A, Jun. 1, 2017, 72(6):780-5.
Yigit et al., "A combination of an anti-SLAMF6 antibody and ibrutinib efficiently abrogates expansion of chronic lymphocytic leukemia cells," Oncotarget, May 3, 2016, 7(18):26346.
Yung et al., "A selective transforming growth factor-β ligand trap attenuates pulmonary hypertension," American Journal of Respiratory and Critical Care Medicine, Nov. 1, 2016, 194(9):1140-51.
Zwaagstra et al., "Engineering and therapeutic application of single-chain bivalent TGF-β family traps," Molecular Cancer Therapeutics, Jul. 1, 2012, 11(7):1477-87.
Li et al., "Transforming Growth Factor-β Regulation of Immune Responses," Annu. Rev. Immunol., 2006, 24:99-146.
McCarron et al., "TGF-β prevents T follicular helper cell accumulation and B cell autoreactivity," J Clin Invest., 2014, 124(10):4375-4386.
Voelker et al., "Anti-TGF-β1 Antibody Therapy in Patients with Diabetic Nephropathy," J Am Soc Nephrol., 2017, 28:953-962.
Wallace et al., "B lymphocytes confer immune tolerance via cell surface GARP-TGF-β complex," JCI Insight, 2018, 3(7):e99863, 19 pages.
Chandrudu et al., "Chemical methods for peptide and protein production," Molecules, 2013, 18(4):4373-4388.
Tam et al., "Methods and strategies of peptide ligation," Peptide Science: Original Research on Biomolecules, 2001, 60(3):494-205.
Baker et al., "Chronic treatment with the beta(2)-adrenoceptor agonist prodrug BRL-47672 impairs rat skeletal muscle function by inducing a comprehensive shift to a faster muscle phenotype," J Pharmacol Exp Ther., Oct. 2006, 319(1):439-446.
Baker et al., "Effects of conjugated linoleic acid (CLA) on tissue composition parameters in a murine cachexia model," The FASEB Journal, Mar. 2006, 20(4), 2 pages (Abstract Only).
Berry et al., "Cancer Anorexia and Cachexia: Screening in an Ambulatory Infusion Service and Nutrition Consultation," Clin J Oncol Nurs., 2018, 22(1):63-68.
Chang et al., "Association Between Sarcopenia and Cognitive Impairment: A Systematic Review and Meta-Analysis," J Am Med Dir Assoc., Dec. 1, 2016, 17(12):1164e7-1164e15, 9 pages.
Chen et al., "Circulating levels of resistin and risk of type 2 diabetes in men and women: results from two prospective cohorts," Diabetes Care, Feb. 2009, 32(2):329-334.
Cosgrove et al., "Usher protein functions in hair cells and photoreceptors," Int J Biochem Cell Biol., Jan. 2014, 46:80-89.

(56) References Cited

OTHER PUBLICATIONS

Helman et al., "Effects of ageing and senescence on pancreatic β-cell function," Diabetes Obes Metab., Sep. 2016, 18(Suppl. 1):58-62.
Jeon et al., "Local clearance of senescent cells attenuates the development of post-traumatic osteoarthritis and creates a pro-regenerative environment," Nat Med., Jun. 2017, 23(6):775-781.
Kim et al., "Insulin resistance, inflammation, and nonalcoholic fatty liver disease in non-obese adults without metabolic syndrome components," Hepatol Int., Jun. 2013, 7(2):586-591.
Kuyinu et al., "Animal models of osteoarthritis: classification, update, and measurement of outcomes," J Orthop Surg Res., Feb. 2, 2016, 11:19, 27 pages.
Melk et al., "Expression of p16INK4a and other cell cycle regulator and senescence associated genes in aging human kidney," Kidney Int, Feb. 2004, 65(2):510-520.
Melk et al., "Senescence of renal cells: molecular basis and clinical implications," Nephrology Dialysis Transplantation, Dec. 2003, 18(12):2474-2478.
Price et al., "Comparison of collagenase-cleaved articular cartilage collagen in mice in the naturally occurring STR/ort model of osteoarthritis and in collagen-induced arthritis," Osteoarthritis Cartilage, Mar. 2002, 10(3):172-179.
Sousa-Victor et al., "Geroconversion of aged muscle stem cells under regenerative pressure," Cell Cycle, Oct. 15, 2014, 13(20):3183-3190.
Xu et al., "Celecoxib attenuates cachectic events in mice by modulating the expression of vascular endothelial growth factor," Mol Med Rep., Jan. 2015, 11(1):289-294.
Mikayama et al., "Molecular cloning and functional expression of a cDNA encoding glycosylation-inhibiting factor," Proc. Natl. Acad. Sci. USA, Nov. 1, 1993, 90(21):10056-10060.
Voet et al., Biochemistry, John Wiley & Sons, Inc., 1990, pp. 126-128 and 228-234, 12 pages.

PCT International Preliminary Report on Patentability in International Appln. No. PCT/US2021/017620, dated Aug. 25, 2022, 12 pages.
PCT International Preliminary Report on Patentability in International Appln. No. PCT/US2021/017621, dated Aug. 25, 2022, 8 pages.
PCT International Preliminary Report on Patentability in International Appln. No. PCT/US2021/017714, dated Aug. 25, 2022, 12 pages.
Huang et al., "Targeting the vasculature of colorectal carcinoma with a fused protein of (RGD) 3-tTF" The Scientific World Journal, 2013(637086): Jan. 11, 2013.
International Preliminary Report on Patentability in International Appln. No. PCT/US2020/035598, dated Dec. 6, 2022, 7 pages.
International Preliminary Report on Patentability in International Appln. No. PCT/US2021/029920, dated Nov. 10, 2022, 11 pages.
International Preliminary Report on Patentability in International Appln. No. PCT/US2021/035285, dated Dec. 15, 2022, 7 pages.
Chan et al., "Molecular mechanisms of natural killer cell activation in response to cellular stress," Cell Death & Differentiation, Jan. 2014, 21(1):5-14.
Chang et al., "The dock and lock method: a novel platform technology for building multivalent, multifunctional structures of defined composition with retained bioactivity," Clinical cancer research, Sep. 15, 2007, 13(18):5586s-5591s.
Hui et al., "Butyrate inhibit collagen-induced arthritis via Treg/IL-10/Th17 axis," International immunopharmacology, Mar. 1, 2019, 68: Abstract 1 page.
Li et al., "Lipid metabolism fuels cancer's spread," Cell metabolism, Feb. 7, 2017, 25(2):228-230.
Wilchek et al., "Essentials of biorecognition: The (strept) avidin-biotin system as a model for protein-protein and protein-ligand interaction," Immunology letters, Feb. 28, 2006, 103(1): Abstract 2 pages.
Zhang et al., "Depletion of NK cells improves cognitive function in the Alzheimer disease mouse model," The Journal of Immunology, Jul. 15, 2020, 205(2): 10pages.

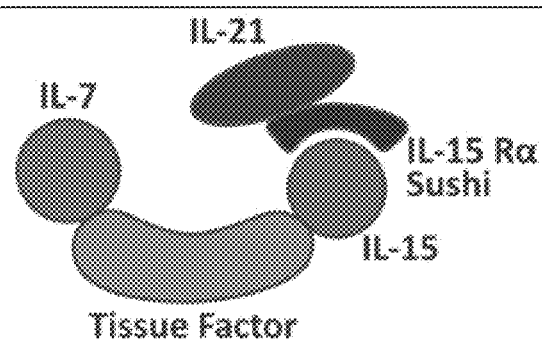
FIG. 80
FIG. 81
FIG. 82
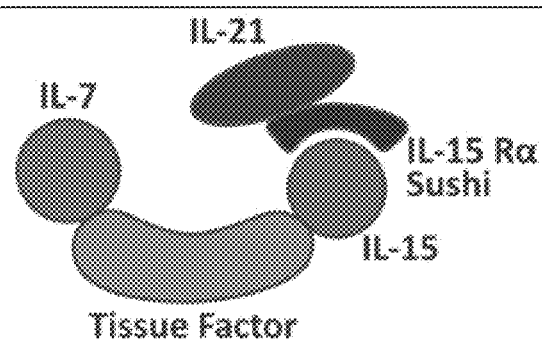
FIG. 83

METHODS FOR STIMULATING PROLIFERATION OR DIFFERENTIATION OF AN IMMUNE CELL WITH A MULTI-CHAIN CHIMERIC POLYPEPTIDE

CROSS-REFERENCE TO RELATED APPLICATIONS

This application claims priority to: U.S. Patent Application Ser. No. 62/816,683, filed Mar. 11, 2019; U.S. Patent Application Ser. No. 62/725,038, filed Aug. 30, 2018; U.S. Patent Application Ser. No. 62/817,244, filed Mar. 12, 2019; U.S. Patent Application Ser. No. 62/881,039, filed Jul. 31, 2019; U.S. Patent Application Ser. No. 62/724,969, filed Aug. 30, 2018; U.S. Patent Application Ser. No. 62/817,230, filed Mar. 12, 2019; U.S. Patent Application Ser. No. 62/725,043, filed Aug. 30, 2018; U.S. Patent Application Ser. No. 62/725,010, filed Aug. 30, 2018; U.S. Patent Application Ser. No. 62/749,007, filed Oct. 22, 2018; U.S. Patent Application Ser. No. 62/746,832, filed Oct. 17, 2018; U.S. Patent Application Ser. No. 62/749,506, filed Oct. 23, 2018; U.S. Patent Application Ser. No. 62/817,241, filed Mar. 12, 2019; and U.S. Patent Application Ser. No. 62/881,088, filed Jul. 31, 2019, each of which is incorporated hereby reference in its entirety.

TECHNICAL FIELD

The present disclosure relates to the field of biotechnology, and more specifically, to single-chain and multi-chain chimeric polypeptides having a linker domain positioned between two target-binding domains that are useful for a variety of applications.

BACKGROUND

Adoptive immunotherapy or cellular therapy requires the culture of immune cells obtained from a subject in vivo (and optionally genetic manipulation of the immune cells to express a chimeric antigen receptor or a T-cell receptor) before administration back into the subject. A sufficient number of immune cells is necessary in order to provide a therapeutic effect in the subject. In many examples, immune cells obtained from a subject need to be cultured for three or more weeks before a therapeutically effective number of immune cells can be obtained. In addition, many methods of culturing immune cells obtained from a subject in vitro require a layer of feeder cells, which requires subsequent purification or isolation of the immune cells before administration back to the subject.

SUMMARY

The present invention is based on the discovery that single-chain and multi-chain chimeric polypeptides having a linker domain positioned between two target-binding domains are effective in stimulating an immune cell, inducing or increasing proliferation of an immune cell, inducing differentiation of an immune cell, or treating a subject in need thereof (e.g., a subject having cancer or an aging-related disease or condition). The present invention is also based on the discovery that the multi-chain chimeric polypeptides described herein promote the metabolism of the immune cells by increasing their aerobic glycolysis (Warburg Effect), oxidative phosphorylation, and mitochondrial reserve respiratory capacity to support their differentiation to effector cells and to enhance their effector-cell function(s).

In some aspects, provided herein are methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, under conditions that allow for the activation and proliferation of the natural killer cell or the T cell, wherein the first target-binding domain and the second target-binding domain are each independently selected from the group consisting of: a soluble interleukin, soluble cytokine protein, or soluble cell surface protein, an antigen-binding domain, a soluble interleukin receptor, soluble cytokine receptor, or soluble cell surface receptor, and ligands of co-stimulatory molecules. In some embodiments, the first target-binding domain and the linker domain directly abut each other. In some embodiments, the single-chain chimeric polypeptide further includes a linker sequence between the first target-binding domain and the linker domain. In some embodiments, the linker domain and the second target-binding domain directly abut each other. In some embodiments, the single-chain chimeric polypeptide further includes a linker sequence between the linker domain and the second target-binding domain. In some embodiments, the first target-binding domain and the second target-binding domain directly abut each other. In some embodiments, the single-chain chimeric polypeptide further includes a linker sequence between the first target-binding domain and the second target-binding domain. In some embodiments, the second target-binding domain and the linker domain directly abut each other. In some embodiments, the single-chain chimeric polypeptide further includes a linker sequence between the second target-binding domain and the linker domain. In some embodiments, the first target-binding domain and the second target-binding domain bind specifically to the same antigen. In some embodiments, the first target-binding domain and the second target-binding domain bind specifically to the same epitope. In some embodiments, the first target-binding domain and the second target-binding domain comprise the same amino acid sequence. In some embodiments, the first target-binding domain and the second target-binding domain bind specifically to different antigens. In some embodiments, one or both of the first target-binding domain and the second target-binding domain is an antigen-binding domain. In some embodiments, the first target-binding domain and the second target-binding domain are each an antigen-binding domain. In some embodiments, antigen-binding domain comprises a scFv or a single domain antibody.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, one or both of the first target-binding domain and the second target-binding domain bind to a target selected from the group consisting of: CD16a, CD28, CD3, CD33, CD20, CD19, CD22, CD52, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, one or both of the first target-binding domain and the second target-binding domain is a soluble interleukin or cytokine protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or both of the first target-binding domain and the second target-binding domain is a soluble interleukin or cytokine receptor. In some embodiments, the soluble interleukin or cytokine receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28. In some embodiments, one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, the linker domain is a soluble tissue factor domain. In some embodiments, the soluble tissue factor domain is a soluble human tissue factor domain. In some embodiments, the soluble human tissue factor domain comprises a sequence that is at least 80% identical to SEQ ID NO: 1. In some embodiments, the soluble human tissue factor domain comprises a sequence that is at least 90% identical to SEQ ID NO: 1. In some embodiments, the soluble human tissue factor domain comprises a sequence that is at least 95% identical to SEQ ID NO: 1. In some embodiments, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding Factor VIIa. In some embodiments, the soluble tissue factor domain does not convert inactive Factor X into Factor Xa. In some embodiments, the single-chain chimeric polypeptide does not stimulate blood coagulation in a mammal.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, the IgG1 antibody construct includes at least one antigen-binding domain that binds specifically to the soluble tissue factor domain. In some embodiments, the linker domain is selected from the group consisting of: a kappa chain and a lambda chain. In some embodiments, the IgG1 antibody construct is a monoclonal IgG1 antibody, where both of the antigen-binding domains in the monoclonal IgG1 antibody bind specifically to the linker domain. In some embodiments, the IgG1 antibody construct is a bispecific IgG1 antibody, where one of the two antigen-binding domains in the bispecific IgG1 antibody binds specifically to the linker domain. In some embodiments, the single-chain chimeric polypeptide further includes one or more additional target-binding domains at its N- and/or C-terminus. In some embodiments, the single-chain chimeric polypeptide includes one or more additional target-binding domains at its N-terminus. In some embodiments, one or more additional target-binding domains directly abuts the first target-binding domain, the second target-binding domain, or the linker domain. In some embodiments, the single-chain chimeric polypeptide further includes a linker sequence between one of the at least one additional target-binding domains and the first target-binding domain, the second target-binding domain, or the linker domain. In some embodiments, the single-chain chimeric polypeptide includes one or more additional target-binding domains at its C-terminus. In some embodiments, one of the one or more additional target-binding domains directly abuts the first target-binding domain, the second target-binding domain, or the linker domain. In some embodiments, the single-chain chimeric polypeptide further includes a linker sequence between one of the at least one additional target-binding domains and the first target-binding domain, the second target-binding domain, or the linker domain. In some embodiments, the single-chain chimeric polypeptide includes one or more additional target binding domains at its N-terminus and the C-terminus. In some embodiments, one of the one or more additional target-binding domains at the N-terminus directly abuts the first target-binding domain, the second target-binding domain, or the linker domain. In some embodiments, the single-chain chimeric polypeptide further includes a linker sequence between one of the one or more additional target-binding domains at the N-terminus and the first target-binding domain, the second target-binding domain, or the linker domain. In some embodiments, one of the one or more additional target-binding domains at the C-terminus directly abuts the first target-binding domain, the second target-binding domain, or the linker domain. In some embodiments, the single-chain chimeric polypeptide further includes a linker sequence between one of the one or more additional target-binding domains at the C-terminus and the first target-binding domain, the second target-binding domain, or the linker domain.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each comprise the same amino acid sequence. In some embodiments, the first target-binding domain, the second target-binding domain, and the one or more additional target-binding domains bind specifically to different antigens. In some embodiments, one or more of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain. In some embodiments, the antigen-binding domain comprises a scFv or a single domain antibody.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or more of the first target-binding domain, the second target-binding domain, and the one or more additional target-binding domains is a soluble interleukin, soluble cytokine protein, or soluble cell surface protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, wherein one or more of the first target-binding domain, the second target-binding domain, and the one or more additional target-binding domains is a soluble interleukin or cytokine receptor. In some embodiments, the soluble interleukin or cytokine receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28. In some embodiments, one or more of the first target-binding domain, the second target-binding domain, and the one or more additional target-binding domains is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, the single-chain chimeric polypeptide further comprises a signal sequence at its N-terminal end. In some embodiments, the single-chain chimeric polypeptide lacks a signal sequence at its N-terminal end. In some embodiments, the single-chain chimeric polypeptide further comprises a peptide tag positioned at the N-terminal end or the C-terminal end of the single-chain chimeric polypeptide. In some embodiments, the single-chain chimeric polypeptide further includes a signal sequence at its N-terminal end. In some embodiments, the single-chain chimeric polypeptide lacks a signal sequence at its N-terminal end.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, the contacting step is performed for a period of about 2 hours to about 20 days. In some embodiments, the contacting step is performed for a period of about 1 day to about 15 days. In some embodiments, the liquid culture medium is a serum-free liquid culture medium. In some embodiments, the liquid culture medium is a chemically-defined liquid culture medium. In some embodiments, the liquid culture medium comprises the single-chain chimeric polypeptide and the IgG1 antibody construct at a molar ratio of about 0.5:1 to about 2:1. In some embodiments, the liquid culture medium comprises the single-chain chimeric polypeptide and the IgG1 antibody construct at a molar ratio of about 0.8:1 to about 1.2:1.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, the NK cell or T cell was previously obtained from a subject. In some embodiments, the method further includes obtaining the NK cell or T cell from the subject prior to the contacting step. In some embodiments, the NK cell or T cell has previously been genetically modified to express a chimeric antigen receptor or a recombinant T-cell receptor. In some embodiments, the method further includes, after the contacting step, introducing into the NK cell or the T cell a nucleic acid encoding a chimeric antigen-receptor or a recombinant T-cell receptor. In some embodiments, the method further includes, before the contacting step, introducing into the NK cell or the T cell a nucleic acid encoding a chimeric antigen-receptor or a recombinant T-cell receptor. In some embodiments, the method further includes, after the contacting step, isolating the NK cell or the T cell. In some embodiments, after the contacting step, the NK cell or the T cell has an increased level of expression or secretion of one or more proteins selected from the group consisting of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, the method further includes, after the contacting step, administering the NK cell or the T cell to a subject in need thereof. In some embodiments, the subject has been identified or diagnosed as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been diagnosed or identified as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

In some aspects, provided herein are activated NK cell or T cells produced by any of the methods described herein that employ single-chain chimeric polypeptides. In some aspects, provided herein are pharmaceutical compositions that include such activated NK cells or T cell. In some aspects, provided herein are kits that include such pharmaceutical compositions. In some aspects, provided herein are methods of killing a cancer cell, an infected cell, or a senescent cell in a subject in need thereof that include administering to the subject a therapeutically effective amount of the activated NK cell or the activated T cell produced by any of the methods described herein that employ single-chain chimeric polypeptides or the pharmaceutical composition that include such NK cells or T cell. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been identified or diagnosed as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments, the methods of killing a cancer cell, an infected cell, or a senescent cell in a subject in need thereof include administering to the subject a therapeutically effective amount of the activated NK cell or the activated T cell produced by any of the methods described herein that employ single-chain chimeric polypeptides or the pharmaceutical composition that includes such activated NK cells or T cells. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been identified or diagnosed as having an aging-related disease or condition. In some embodiments, the subject has been identified or diagnosed as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the subject has been diagnosed or identified as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

In some aspects, provided herein are kits that include (i) a single-chain chimeric polypeptide including a first target-binding domain, a linker domain, and a second target-binding domain, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules; and (ii) an IgG1 antibody construct including at least one antigen-binding domain that binds specifically to the linker domain. In some embodiments, the first target-binding domain and the linker domain directly abut each other. In some embodiments, the single-chain chimeric polypeptide further comprises a linker sequence between the first target-binding domain and the linker domain. In some embodiments, the linker domain and the second target-binding domain directly abut each other. In some embodiments, the single-chain chimeric polypeptide further includes a linker sequence between the linker domain and the second target-binding domain. In some embodiments, the first target-binding domain and the second target-binding domain directly abut each other. In some embodiments, the single-chain chimeric polypeptide further includes a linker sequence between the first target-binding domain and the second target-binding domain. In some embodiments, the second target-binding domain and the linker domain directly abut each other. In some embodiments, the single-chain chimeric polypeptide further includes a linker sequence between the second target-binding domain and the linker domain. In some embodiments, the first target-binding domain and the second target-binding domain bind specifically to the same antigen. In some embodiments, the first target-binding domain and the second target-binding domain bind specifically to the same epitope. In some embodiments, the first target-binding domain and the second target-binding domain comprise the same amino acid sequence. In some embodiments, the first target-binding domain and the second target-binding domain bind specifically to different antigens. In some embodiments, one or both of the first target-binding domain and the second target-binding domain is an antigen-binding domain. In some embodiments, the first target-binding domain and the second target-binding domain are each an antigen-binding domain. In some embodiments, the antigen-binding domain comprises a scFv or a single domain antibody.

In some embodiments of kits that include a single-chain chimeric polypeptide and an IgG1 antibody construct, one or both of the first target-binding domain and the second target-binding domain bind to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or both of the first target-binding domain and the second target-binding domain is a soluble interleukin, soluble cytokine protein, or soluble cell surface protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or both of the first target-binding domain and the second target-binding domain is a soluble interleukin receptor, soluble cytokine receptor, or soluble cell surface receptor. In some embodiments, the soluble interleukin receptor, soluble cytokine receptor, or soluble cell surface receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28. In some embodiments, one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of kits that include a single-chain chimeric polypeptide and an IgG1 antibody construct, the linker domain is a soluble tissue factor domain. In some embodiments, the soluble tissue factor domain is a soluble human tissue factor domain. In some embodiments, the soluble human tissue factor domain includes a sequence that is at least 80% identical to SEQ ID NO: 1. In some embodiments, the soluble human tissue factor domain includes a sequence that is at least 90% identical to SEQ ID NO: 1. In some embodiments, the soluble human tissue factor domain includes a sequence that is at least 95% identical to SEQ ID NO: 1. In some embodiments, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding Factor VIIa. In some embodiments, the soluble tissue factor domain does not convert inactive Factor X into Factor Xa. In some embodiments, the single-chain chimeric polypeptide does not stimulate blood coagulation in a mammal.

In some embodiments of kits that include a single-chain chimeric polypeptide and an IgG1 antibody construct, the IgG1 antibody construct includes at least one antigen-binding domain that binds specifically to the soluble tissue factor domain. In some embodiments, the linker domain is selected from the group consisting of: a kappa chain and a lambda chain. In some embodiments, the IgG1 antibody construct is a monoclonal IgG1 antibody, where both antigen-binding domains in the monoclonal IgG1 antibody bind specifically to the linker domain. In some embodiments, the IgG1 antibody construct is a bispecific IgG1 antibody, where one of the two antigen-binding domains in the bispecific IgG1 antibody binds specifically to the linker domain.

In some embodiments of kits that include a single-chain chimeric polypeptide and an IgG1 antibody construct, the single-chain chimeric polypeptide further includes one or more additional target-binding domains at its N- and/or C-terminus. In some embodiments, the single-chain chimeric polypeptide includes one or more additional target-binding domains at its N-terminus. In some embodiments, the one or more additional target-binding domains directly abuts the first target-binding domain, the second target-binding domain, or the linker domain. In some embodiments, the single-chain chimeric polypeptide further includes a linker sequence between one of the at least one additional target-binding domains and the first target-binding domain, the second target-binding domain, or the linker domain. In some embodiments, the single-chain chimeric polypeptide includes one or more additional target-binding domains at its C-terminus. In some embodiments, one of the one or more additional target-binding domains directly abuts the first target-binding domain, the second target-binding domain, or the linker domain. In some embodiments, the single-chain chimeric polypeptide further includes a linker sequence between one of the at least one additional target-binding domains and the first target-binding domain, the second target-binding domain, or the linker domain. In some embodiments, the single-chain chimeric polypeptide includes one or more additional target binding domains at its N-terminus and the C-terminus. In some embodiments, one of the one or more additional target-binding domains at the N-terminus directly abuts the first target-binding domain, the second target-binding domain, or the linker domain. In some embodiments, the single-chain chimeric polypeptide further includes a linker sequence between one of the one or more additional target-binding domains at the N-terminus and the first target-binding domain, the second target-binding domain, or the linker domain. In some embodiments, one of the one or more additional target-binding domains at the C-terminus directly abuts the first target-binding domain, the second target-binding domain, or the linker domain. In some embodiments, the single-chain chimeric polypeptide further includes a linker sequence between one of the one or more additional target-binding domains at the C-terminus and the first target-binding domain, the second target-binding domain, or the linker domain.

In some embodiments of kits that include a single-chain chimeric polypeptide and an IgG1 antibody construct, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence. In some embodiments, the first target-binding domain, the second target-binding domain, and the one or more additional target-binding domains bind specifically to different antigens. In some embodiments, one or more of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain. In some embodiments, the antigen-binding domain includes a scFv or a single domain antibody.

In some embodiments of kits that include a single-chain chimeric polypeptide and an IgG1 antibody construct, one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or more of the first target-binding domain, the second target-binding domain, and the one or more additional target-binding domains is a soluble interleukin, soluble cytokine protein, or soluble cell surface protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or more of the first target-binding domain, the second target-binding domain, and the one or more additional target-binding domains is a soluble interleukin receptor, soluble cytokine receptor, or soluble cell surface receptor. In some embodiments, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28. In some embodiments, one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1. In some embodiments, the single-chain chimeric polypeptide further includes a peptide tag positioned at the N-terminal end or the C-terminal end of the single-chain chimeric polypeptide. In some embodiments, the single-chain chimeric polypeptide further includes a signal sequence at its N-terminal end. In some embodiments, the single-chain chimeric polypeptide lacks a signal sequence at its N-terminal end.

In some aspects, provided herein are methods of promoting the activation and proliferation of a natural killer cell or a T cell that include contacting a natural killer cell or a T cell in a liquid culture medium including: (1) an effective amount of a multi-chain chimeric polypeptide that includes: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, wherein the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain, under conditions that allow for the activation and proliferation of the natural killer cell or the T cell. In some embodiments, the first target-binding domain and the linker domain directly abut each other in the first chimeric polypeptide. In some embodiments, the first chimeric polypeptide further includes a linker sequence between the first target-binding domain and the linker domain in the first chimeric polypeptide. In some embodiments, the linker domain and the first domain of the pair of affinity domains directly abut each other in the first chimeric polypeptide. In some embodiments, the first chimeric polypeptide further includes a linker sequence between the linker domain and the first domain of the pair of affinity domains in the first chimeric polypeptide. In some embodiments, the second domain of the pair of affinity domains and the second target-binding domain directly abut each other in the second chimeric polypeptide. In some embodiments, the second chimeric polypeptide further includes a linker sequence between the second domain of the pair of affinity domains and the second target-binding domain in the second chimeric polypeptide. In some embodiments, the first target-binding domain and the second target-binding domain bind specifically to the same antigen. In some embodiments, the first target-binding domain and the second target-binding domain bind specifically to the same epitope. In some embodiments, the first target-binding domain and the second target-binding domain include the same amino acid sequence. In some embodiments, the first target-binding domain and the second target-binding domain bind specifically to different antigens. In some embodiments, one or both of the first target-binding domain and the second target-binding domain is an antigen-binding domain. In some embodiments, the first target-binding domain and the second target-binding domain are each antigen-binding domains. In some embodiments, the antigen-binding domain includes a scFv or a single domain antibody.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or both of the first target-binding domain and the second target-binding domain is a soluble interleukin or cytokine protein. one or both of the first target-binding domain and the second target-binding domain is a soluble interleukin, soluble cytokine protein, or soluble cell surface protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or both of the first target-binding domain and the second target-binding domain is a soluble interleukin receptor, soluble cytokine receptor, or soluble cell surface receptor. In some embodiments, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28. In some embodiments, one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the first chimeric polypeptide further includes one or more additional target-binding domain(s), where at least one of the one or more target-binding domain(s) is positioned between the linker domain and the first domain of the pair of affinity domains. In some embodiments, the first chimeric polypeptide further includes a linker sequence between the linker domain and the at least one of the one or more target antigen-binding domain(s), and/or a linker sequence between the at least one of the one or more target antigen-binding domain(s) and the first domain of the pair of affinity domains. In some embodiments, the first chimeric polypeptide further includes one or more additional target-binding domains at the N-terminal and/or C-terminal end of the first chimeric polypeptide. In some embodiments, at least one of the one or more additional target-binding domains directly abuts the first domain of the pair of affinity domains in the first chimeric polypeptide. In some embodiments, the first chimeric polypeptide further includes a linker sequence between the at least one of the one or more additional target-binding domains and the first domain of the pair of affinity domains. In some embodiments, the at least one of the one or more additional target-binding domains directly abuts the first target-binding domain in the first chimeric polypeptide. In some embodiments, the first chimeric polypeptide further includes a linker sequence between the at least one of the one or more additional target-binding domains and the first target-binding domain. In some embodiments, at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide. In some embodiments, the at least one additional target-binding domain of the one or more additional target-binding domains disposed at the N-terminus directly abuts the first target-binding domain or the first domain of the pair of affinity domains in the first chimeric polypeptide. In some embodiments, the first chimeric polypeptide further includes a linker sequence disposed between the at least one additional target-binding domain and the first target-binding domain or the first domain of the pair of affinity domains in the first chimeric polypeptide. In some embodiments, the at least one additional target-binding domain of the one or more additional target-binding domains disposed at the C-terminus directly abuts the first target-binding domain or the first domain of the pair of affinity domains in the first chimeric polypeptide. In some embodiments, the first chimeric polypeptide further includes a linker sequence disposed between the at least one additional target-binding domain and the first target-binding domain or the first domain of the pair of affinity domains in the first chimeric polypeptide. In some embodiments, the at least one of the one or more additional target-binding domains positioned between the linker domain and the first domain of the pair of affinity domains, directly abuts the linker domain and/or the first domain of the pair of affinity domains. In some embodiments, the first chimeric polypeptide further includes a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the second chimeric polypeptide further includes one or more additional target-binding domains at the N-terminal end and/or the C-terminal end of the second chimeric polypeptide. In some embodiments, at least one of the one or more additional target-binding domains directly abuts the second domain of the pair of affinity domains in the second chimeric polypeptide. In some embodiments, the second chimeric polypeptide further includes a linker sequence between at least one of the one or more additional target-binding domains and the second domain of the pair of affinity domains in the second chimeric polypeptide. In some embodiments, at least one of the one or more additional target-binding domains directly abuts the second target-binding domain in the second chimeric polypeptide. In some embodiments, the second chimeric polypeptide further includes a linker sequence between at least one of the one or more additional target-binding domains and the second target-binding domain in the second chimeric polypeptide.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each comprise the same amino acid sequence. In some embodiments, first target-binding domain, the second target-binding domain, and the one or more additional target-binding domains bind specifically to different antigens. In some embodiments, one or more of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain. In some embodiments, the antigen-binding domain includes a scFv.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28. In some embodiments, one or more of the first target-binding domain, the second target-binding domain, and the one or more additional target-binding domains is a soluble interleukin, soluble cytokine protein, or soluble cell surface protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or more of the first target-binding domain, the second target-binding domain, and the one or more additional target-binding domains is a soluble interleukin receptor, soluble cytokine receptor, or soluble cell surface receptor. In some embodiments, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28. In some embodiments, the first chimeric polypeptide further comprises a peptide tag at the N-terminal end or the C-terminal end of the first chimeric polypeptide. In some one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1. In some embodiments, the first chimeric polypeptide further comprises a peptide tag at the N-terminal end or the C-terminal end of the second chimeric polypeptide. In some embodiments, the second chimeric polypeptide further comprises a peptide tag at the N-terminal end or the C-terminal end of the second chimeric polypeptide.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the linker domain is a soluble tissue factor domain. In some embodiments, the soluble tissue factor domain is a soluble human tissue factor domain. In some embodiments, the soluble human tissue factor domain includes a sequence that is at least 80% identical to SEQ ID NO: 1. In some embodiments, the soluble human tissue factor domain includes a sequence that is at least 90% identical to SEQ ID NO: 1. In some embodiments, the soluble human tissue factor domain includes a sequence that is at least 95% identical to SEQ ID NO: 1. In some embodiments, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding to Factor VIIa. In some embodiments, the soluble tissue factor domain does not convert inactive Factor X into Factor Xa. In some embodiments, the multi-chain chimeric polypeptide does not stimulate blood coagulation in a mammal.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the IgG1 antibody construct includes at least one antigen-binding domain that binds specifically to the soluble tissue factor domain. In some embodiments, the linker domain is selected from the group consisting of: a kappa chain and a lambda chain. In some embodiments, the IgG1 antibody construct is a monoclonal IgG1 antibody, where both antigen-binding domains in the monoclonal IgG1 antibody bind specifically to the linker domain. In some embodiments, the IgG1 antibody construct is a bispecific IgG1 antibody, where one of the two antigen-binding domains in the bispecific IgG1 antibody binds specifically to the linker domain.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the pair of affinity domains is a sushi domain from an alpha chain of human IL-15 receptor (IL15Rα) and a soluble IL-15. In some embodiments, the soluble IL15 has a D8N or D8A amino acid substitution. In some embodiments, the human IL15Rα is a mature full-length IL15Rα. In some embodiments, the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25. In some embodiments, the first chimeric polypeptide and/or the second chimeric polypeptide further includes a signal sequence at its N-terminal end. In some embodiments, the first chimeric polypeptide and/or the second chimeric polypeptide lacks a signal sequence at its N-terminal end.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the contacting step is performed for a period of about 2 hours to about 20 days. In some embodiments, the contacting step is performed for a period of about 1 day to about 15 days. In some embodiments, the liquid culture medium is a serum-free liquid culture medium. In some embodiments, the liquid culture medium is a chemically-defined liquid culture medium. In some embodiments, the liquid culture medium comprises the multi-chain chimeric polypeptide and the IgG1 antibody construct at a molar ratio of about 0.5:1 to about 2:1. In some embodiments, the liquid culture medium comprises the multi-chain chimeric polypeptide and the IgG1 antibody construct at a molar ratio of about 0.8:1 to about 1.2:1. In some embodiments, the NK cell or T cell was previously obtained from a subject. In some embodiments, the method further includes obtaining the NK cell or T cell from the subject prior to the contacting step. In some embodiments, the NK cell or T cell has previously been genetically modified to express a chimeric antigen receptor or a recombinant T-cell receptor. In some embodiments, the method further includes, after the contacting step, introducing into the NK cell or the T cell a nucleic acid encoding a chimeric antigen-receptor or a recombinant T-cell receptor. In some embodiments, the method further includes, before the contacting step, introducing into the NK cell or the T cell a nucleic acid encoding a chimeric antigen-receptor or a recombinant T-cell receptor. In some embodiments, the method further includes, after the contacting step, isolating the NK cell or the T cell. In some embodiments, after the contacting step, the NK cell or the T cell has an increased level of expression or secretion of one or more proteins selected from the group consisting of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step. In some embodiments, the method further includes, after the contacting step, administering the NK cell or the T cell to a subject in need thereof.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the subject has been identified or diagnosed as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been diagnosed or identified as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

In some aspects, provided herein are activated NK cell or T cells produced by any of the methods described herein that employ multi-chain chimeric polypeptides. In some aspects, provided herein are pharmaceutical compositions that include such activated NK cells or T cell. In some aspects, provided herein are kits that include such pharmaceutical compositions. In some aspects, provided herein are methods of killing a cancer cell, an infected cell, or a senescent cell in a subject in need thereof that include administering to the subject a therapeutically effective amount of the activated NK cell or the activated T cell produced by any of the methods described herein that employ multi-chain chimeric polypeptides or the pharmaceutical composition that include such NK cells or T cell. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been identified or diagnosed as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments, the methods of killing a cancer cell, an infected cell, or a senescent cell in a subject in need thereof include administering to the subject a therapeutically effective amount of the activated NK cell or the activated T cell produced by any of the methods described herein that employ multi-chain chimeric polypeptides or the pharmaceutical composition that includes such activated NK cells or T cells. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been identified or diagnosed as having an aging-related disease or condition. In some embodiments, the subject has been identified or diagnosed as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the subject has been diagnosed or identified as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

In some aspects, provided herein are kits that include: 1) a multi-chain chimeric polypeptide that includes: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, wherein the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain. In some embodiments, the first target-binding domain and the linker domain directly abut each other in the first chimeric polypeptide. In some embodiments, the first chimeric polypeptide further includes a linker sequence between the first target-binding domain and the linker domain in the first chimeric polypeptide. In some embodiments, the linker domain and the first domain of the pair of affinity domains directly abut each other in the first chimeric polypeptide. In some embodiments, the first chimeric polypeptide further includes a linker sequence between the linker domain and the first domain of the pair of affinity domains in the first chimeric polypeptide. In some embodiments, the second domain of the pair of affinity domains and the second target-binding domain directly abut each other in the second chimeric polypeptide. In some embodiments, the second chimeric polypeptide further includes a linker sequence between the second domain of the pair of affinity domains and the second target-binding domain in the second chimeric polypeptide. In some embodiments, the first target-binding domain and the second target-binding domain bind specifically to the same antigen. In some embodiments, the first target-binding domain and the second target-binding domain bind specifically to the same epitope. In some embodiments, the first target-binding domain and the second target-binding domain include the same amino acid sequence. In some embodiments, the first target-binding domain and the second target-binding domain bind specifically to different antigens. In some embodiments, one or both of the first target-binding domain and the second target-binding domain is an antigen-binding domain. In some embodiments, the first target-binding domain and the second target-binding domain are each antigen-binding domains. In some embodiments, the antigen-binding domain includes a scFv or a single domain antibody.

In some embodiments of kits that include a multi-chain chimeric polypeptide and an IgG1 antibody construct, one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or both of the first target-binding domain and the second target-binding domain is a soluble interleukin, soluble cytokine protein, or soluble cell surface protein. In some embodiments, the soluble interleukin, soluble cytokine protein, or soluble cell surface protein is selected from the group consisting of:

IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or both of the first target-binding domain and the second target-binding domain is a soluble interleukin receptor, soluble cytokine receptor, or soluble cell surface receptor. In some embodiments, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28. In some embodiments, one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of kits that include a multi-chain chimeric polypeptide and an IgG1 antibody construct, the first chimeric polypeptide further includes one or more additional target-binding domain(s), where at least one of the one or more target-binding domain(s) is positioned between the linker domain and the first domain of the pair of affinity domains. In some embodiments, the first chimeric polypeptide further includes a linker sequence between the linker domain and the at least one of the one or more target antigen-binding domain(s), and/or a linker sequence between the at least one of the one or more target antigen-binding domain(s) and the first domain of the pair of affinity domains. In some embodiments, the first chimeric polypeptide further includes one or more additional target-binding domains at the N-terminal and/or C-terminal end of the first chimeric polypeptide. In some embodiments, at least one of the one or more additional target-binding domains directly abuts the first domain of the pair of affinity domains in the first chimeric polypeptide. In some embodiments, the first chimeric polypeptide further includes a linker sequence between the at least one of the one or more additional target-binding domains and the first domain of the pair of affinity domains. In some embodiments, the at least one of the one or more additional target-binding domains directly abuts the first target-binding domain in the first chimeric polypeptide. In some embodiments, the first chimeric polypeptide further includes a linker sequence between the at least one of the one or more additional target-binding domains and the first target-binding domain. In some embodiments, at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide. In some embodiments, the at least one additional target-binding domain of the one or more additional target-binding domains disposed at the N-terminus directly abuts the first target-binding domain or the first domain of the pair of affinity domains in the first chimeric polypeptide. In some embodiments, the first chimeric polypeptide further includes a linker sequence disposed between the at least one additional target-binding domain and the first target-binding domain or the first domain of the pair of affinity domains in the first chimeric polypeptide. In some embodiments, the at least one additional target-binding domain of the one or more additional target-binding domains disposed at the C-terminus directly abuts the first target-binding domain or the first domain of the pair of affinity domains in the first chimeric polypeptide. In some embodiments, the first chimeric polypeptide further includes a linker sequence disposed between the at least one additional target-binding domain and the first target-binding domain or the first domain of the pair of affinity domains in the first chimeric polypeptide. In some embodiments, the at least one of the one or more additional target-binding domains positioned between the linker domain and the first domain of the pair of affinity domains, directly abuts the linker domain and/or the first domain of the pair of affinity domains. In some embodiments, the first chimeric polypeptide further includes a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

In some embodiments of kits that include a multi-chain chimeric polypeptide and an IgG1 antibody construct, the second chimeric polypeptide further includes one or more additional target-binding domains at the N-terminal end or the C-terminal end of the second chimeric polypeptide. In some embodiments, at least one of the one or more additional target-binding domains directly abuts the second domain of the pair of affinity domains in the second chimeric polypeptide. In some embodiments, the second chimeric polypeptide further includes a linker sequence between at least one of the one or more additional target-binding domains and the second domain of the pair of affinity domains in the second chimeric polypeptide. In some embodiments, at least one of the one or more additional target-binding domains directly abuts the second target-binding domain in the second chimeric polypeptide. In some embodiments, the second chimeric polypeptide further includes a linker sequence between at least one of the one or more additional target-binding domains and the second target-binding domain in the second chimeric polypeptide.

In some embodiments of kits that include a multi-chain chimeric polypeptide and an IgG1 antibody construct, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some two or more of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence. In some embodiments, the first target-binding domain, the second target-binding domain, and the one or more additional target-binding domains bind specifically to different antigens. In some embodiments, one or more of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain. In some embodiments, the antigen-binding domain includes a scFv.

In some embodiments of kits that include a multi-chain chimeric polypeptide and an IgG1 antibody construct, one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28. In some embodiments, one or more of the first target-binding domain, the second target-binding domain, and the one or more additional target-binding domains is a soluble interleukin, soluble cytokine protein, or soluble cell surface protein. In some embodiments, the soluble interleukin, soluble cytokine protein, or soluble cell surface receptor is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or more of the first target-binding domain, the second target-binding domain, and the one or more additional target-binding domains is a soluble interleukin receptor, soluble cytokine receptor, or soluble cell surface receptor. In some embodiments, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28. In some embodiments, one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of kits that include a multi-chain chimeric polypeptide and an IgG1 antibody construct, the linker domain is a soluble tissue factor domain. In some embodiments, the soluble tissue factor domain is a soluble human tissue factor domain. In some embodiments, the soluble human tissue factor domain includes a sequence that is at least 80% identical to SEQ ID NO: 1. In some embodiments, the soluble human tissue factor domain includes a sequence that is at least 90% identical to SEQ ID NO: 1. In some embodiments, the soluble human tissue factor domain includes a sequence that is at least 95s % identical to SEQ ID NO: 1. In some embodiments, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding to Factor VIIa. In some embodiments, the soluble tissue factor domain does not convert inactive Factor X into Factor Xa. In some embodiments, the multi-chain chimeric polypeptide does not stimulate blood coagulation in a mammal.

In some embodiments of kits that include a multi-chain chimeric polypeptide and an IgG1 antibody construct, the IgG1 antibody construct includes at least one antigen-binding domain that binds specifically to the soluble tissue factor domain. In some embodiments, the linker domain is selected from the group consisting of: a kappa chain and a lambda chain. In some embodiments, the IgG1 antibody construct is a monoclonal IgG1 antibody, where both antigen-binding domains in the monoclonal IgG1 antibody bind specifically to the linker domain. In some embodiments, the IgG1 antibody construct is a bispecific IgG1 antibody, where one of the two antigen-binding domains in the bispecific IgG1 antibody binds specifically to the linker domain.

In some embodiments of kits that include a multi-chain chimeric polypeptide and an IgG1 antibody construct, the pair of affinity domains is a sushi domain from an alpha chain of human IL-15 receptor (IL15Rα) and a soluble IL-15. In some embodiments, the soluble IL15 has a D8N or D8A amino acid substitution. In some embodiments, the human IL15Rα is a mature full-length IL15Rα. In some embodiments, the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25. In some embodiments, the first chimeric polypeptide and/or the second chimeric polypeptide further include a signal sequence at its N-terminal end. In some embodiments, the first chimeric polypeptide and/or the second chimeric polypeptide lacks a signal sequence at its N-terminal end. In some embodiments, the first chimeric polypeptide and/or the second chimeric polypeptide further include a signal sequence at its N-terminal end. In some embodiments, the first chimeric polypeptide and/or the second chimeric polypeptide lacks a signal sequence at its N-terminal end.

Also provided herein are methods of increasing the glucose consumption of an immune cell that include: contacting an immune cell in a liquid culture medium including an effective amount of (i) a single-chain chimeric polypeptide including a first target-binding domain, a linker domain, and a second target-binding domain, and optionally (ii) an IgG1 antibody construct that includes at least one antigen-binding domain that binds specifically to the linker domain, under conditions that allow for glucose consumption in the immune cell, where the first target-binding domain and the second target-binding domain are each independently selected from the group of: a soluble interleukin, soluble cytokine protein, or soluble cell surface protein, an antigen-binding domain, a soluble interleukin receptor, soluble cytokine receptor, or soluble cell surface receptor, and ligands of co-stimulatory molecules.

Also provided herein are methods of increasing the oxidative phosphorylation of an immune cell that include: contacting an immune cell in a liquid culture medium including an effective amount of (i) a single-chain chimeric polypeptide including a first target-binding domain, a linker domain, and a second target-binding domain, and optionally (ii) an IgG1 antibody construct that includes at least one antigen-binding domain that binds specifically to the linker domain, under conditions that allow for oxidative phosphorylation in the immune cell, where the first target-binding domain and the second target-binding domain are each independently selected from the group of: a soluble interleukin, soluble cytokine protein, or soluble cell surface protein, an antigen-binding domain, a soluble interleukin receptor, soluble cytokine receptor, or soluble cell surface receptor, and ligands of co-stimulatory molecules.

Also provided herein are methods of increasing the aerobic glycolysis of an immune cell that include: contacting an immune cell in a liquid culture medium including an effective amount of (i) a single-chain chimeric polypeptide including a first target-binding domain, a linker domain, and a second target-binding domain, and optionally (ii) an IgG1 antibody construct that includes at least one antigen-binding domain that binds specifically to the linker domain, under conditions that allow for aerobic glycolysis in the immune cell, where the first target-binding domain and the second target-binding domain are each independently selected from the group of: a soluble interleukin, soluble cytokine protein, or soluble cell surface protein, an antigen-binding domain, a soluble interleukin receptor, soluble cytokine receptor, or soluble cell surface receptor, and ligands of co-stimulatory molecules.

Also provided herein are methods of increasing the extracellular acidification rate (ECAR) of an immune cell that include: contacting an immune cell in a liquid culture medium including an effective amount of (i) a single-chain chimeric polypeptide including a first target-binding domain, a linker domain, and a second target-binding domain, and optionally (ii) an IgG1 antibody construct that includes at least one antigen-binding domain that binds specifically to the linker domain, under conditions that allow for extracellular acidification by the immune cell, where the first target-binding domain and the second target-binding domain are each independently selected from the group of: a soluble interleukin, soluble cytokine protein, or soluble cell surface protein, an antigen-binding domain, a soluble interleukin receptor, soluble cytokine receptor, or soluble cell surface receptor, and ligands of co-stimulatory molecules.

Also provided herein are methods of increasing the mitochondrial oxygen consumption rate of an immune cell that include: contacting an immune cell in a liquid culture medium including an effective amount of (i) a single-chain chimeric polypeptide including a first target-binding domain, a linker domain, and a second target-binding domain, and optionally (ii) an IgG1 antibody construct that includes at least one antigen-binding domain that binds specifically to the linker domain, under conditions that allow for mitochondrial oxygen consumption rate by the immune cell, where the first target-binding domain and the second target-binding domain are each independently selected from the group of: a soluble interleukin, soluble cytokine protein, or soluble cell surface protein, an antigen-binding domain, a soluble interleukin receptor, soluble cytokine receptor, or soluble cell surface receptor, and ligands of co-stimulatory molecules.

In some embodiments of any of the methods described herein, the liquid culture medium includes the single-chain chimeric polypeptide and the IgG1 antibody construct. In some embodiments of any of the methods described herein, the IgG1 antibody construct is a monoclonal IgG1 antibody, where both of the antigen-binding domains in the monoclonal IgG1 antibody bind specifically to the linker domain. In some embodiments of any of the methods described herein, the IgG1 antibody construct is a bispecific IgG1 antibody, where one of the two antigen-binding domains in the bispecific IgG1 antibody binds specifically to the linker domain.

In some embodiments of any of the methods described herein, the contacting step is performed for a period of about 2 hours to about 20 days (e.g., about 1 day to about 15 days). In some embodiments of any of the methods described herein, the liquid culture medium is a serum-free liquid culture medium. In some embodiments of any of the methods described herein, the liquid culture medium is a chemically-defined liquid culture medium. In some embodiments of any of the methods described herein, the liquid culture medium includes serum. In some embodiments of any of the methods described herein, the liquid culture medium includes the single-chain chimeric polypeptide and the IgG1 antibody construct at a molar ratio of about 0.5:1 to about 2:1 (e.g., about 0.8:1 to about 1.2:1).

In some embodiments of any of the methods described herein, the first target-binding domain and the linker domain directly abut each other. In some embodiments of any of the methods described herein, the single-chain chimeric polypeptide further comprises a linker sequence between the first target-binding domain and the linker domain. In some embodiments of any of the methods described herein, the linker domain and the second target-binding domain directly abut each other. In some embodiments of any of the methods described herein, the single-chain chimeric polypeptide further includes a linker sequence between the linker domain and the second target-binding domain. In some embodiments of any of the methods described herein, the first target-binding domain and the second target-binding domain directly abut each other.

In some embodiments of any of the methods described herein, the single-chain chimeric polypeptide further includes a linker sequence between the first target-binding domain and the second target-binding domain. In some embodiments of any of the methods described herein, the second target-binding domain and the linker domain directly abut each other. In some embodiments of any of the methods described herein, the single-chain chimeric polypeptide further includes a linker sequence between the second target-binding domain and the linker domain.

In some embodiments of any of the methods described herein, the first target-binding domain and the second target-binding domain bind specifically to the same antigen. In some embodiments of any of the methods described herein, the first target-binding domain and the second target-binding domain bind specifically to the same epitope. In some embodiments of any of the methods described herein, the first target-binding domain and the second target-binding domain include the same amino acid sequence. In some embodiments of any of the methods described herein, the first target-binding domain and the second target-binding domain bind specifically to different antigens.

In some embodiments of any of the methods described herein, one or both of the first target-binding domain and the second target-binding domain is an antigen-binding domain. In some embodiments of any of the methods described herein, the first target-binding domain and the second target-binding domain are each an antigen-binding domain. In some embodiments of any of the methods described herein, the antigen-binding domain includes a scFv or a single domain antibody.

In some embodiments of any of the methods described herein, one or both of the first target-binding domain and the second target-binding domain bind to a target selected from the group of: CD16a, CD28, CD3, CD33, CD20, CD19, CD22, CD52, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the methods described herein, one or both of the first target-binding domain and the second target-binding domain is a soluble interleukin, soluble cytokine protein, or soluble cell surface protein. In some embodiments of any of the methods described herein, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

In some embodiments of any of the methods described herein, one or both of the first target-binding domain and the second target-binding domain is a soluble interleukin receptor, soluble cytokine receptor, or soluble cell surface receptor. In some embodiments of any of the methods described herein, the soluble interleukin receptor, soluble cytokine receptor, or soluble cell surface receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

In some embodiments of any of the methods described herein, the linker domain is a soluble tissue factor domain. In some embodiments of any of the methods described herein, the soluble tissue factor domain is a soluble human tissue factor domain. In some embodiments of any of the methods described herein, the soluble human tissue factor domain comprises a sequence that is at least 80% identical, at least 90% identical, or at least 95% identical to SEQ ID NO: 1. In some embodiments of any of the methods described herein, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble tissue factor domain is not capable of binding Factor VIIa. In some embodiments of any of the methods described herein, the soluble tissue factor domain does not convert inactive Factor X into Factor Xa. In some embodiments of any of the methods described herein, the single-chain chimeric polypeptide does not stimulate blood coagulation in a mammal. In some embodiments of any of the methods described herein, the IgG1 antibody construct includes at least one antigen-binding domain that binds specifically to the soluble tissue factor domain. In some embodiments of any of the methods described herein, the linker domain is selected from the group of: a kappa chain and a lambda chain. In some embodiments of any of the methods described herein, the IgG1 antibody construct is a monoclonal IgG1 antibody, where both of the antigen-binding domains in the monoclonal IgG1 antibody bind specifically to the linker domain. In some embodiments of any of the methods described herein, the IgG1 antibody construct is a bispecific IgG1 antibody, where one of the two antigen-binding domains in the bispecific IgG1 antibody binds specifically to the linker domain.

In some embodiments of any of the methods described herein, the single-chain chimeric polypeptide further includes one or more additional target-binding domains at its N- and/or C-terminus. In some embodiments of any of the methods described herein, the single-chain chimeric polypeptide includes one or more additional target-binding domains at its N-terminus. In some embodiments of any of the methods described herein, one or more additional target-binding domains directly abuts the first target-binding domain, the second target-binding domain, or the linker domain. In some embodiments of any of the methods described herein, the single-chain chimeric polypeptide further includes a linker sequence between one of the at least one additional target-binding domains and the first target-binding domain, the second target-binding domain, or the linker domain.

In some embodiments of any of the methods described herein, the single-chain chimeric polypeptide includes one or more additional target-binding domains at its C-terminus. In some embodiments of any of the methods described herein, one of the one or more additional target-binding domains directly abuts the first target-binding domain, the second target-binding domain, or the linker domain. In some embodiments of any of the methods described herein, the single-chain chimeric polypeptide further includes a linker sequence between one of the at least one additional target-binding domains and the first target-binding domain, the second target-binding domain, or the linker domain.

In some embodiments of any of the methods described herein, the single-chain chimeric polypeptide includes one or more additional target binding domains at its N-terminus and the C-terminus. In some embodiments of any of the methods described herein, one of the one or more additional target-binding domains at the N-terminus directly abuts the first target-binding domain, the second target-binding domain, or the linker domain. In some embodiments of any of the methods described herein, the single-chain chimeric polypeptide further includes a linker sequence between one of the one or more additional target-binding domains at the N-terminus and the first target-binding domain, the second target-binding domain, or the linker domain. In some embodiments of any of the methods described herein, one of the one or more additional target-binding domains at the C-terminus directly abuts the first target-binding domain, the second target-binding domain, or the linker domain. In some embodiments of any of the methods described herein, the single-chain chimeric polypeptide further includes a linker sequence between one of the one or more additional target-binding domains at the C-terminus and the first target-binding domain, the second target-binding domain, or the linker domain.

In some embodiments of any of the methods described herein, two or more of the first target-binding domain, the second target-binding domain, and the one or more additional target-binding domains bind specifically to the same antigen. In some embodiments of any of the methods described herein, two or more of the first target-binding domain, the second target-binding domain, and the one or more additional target-binding domains bind specifically to the same epitope. In some embodiments of any of the methods described herein, two or more of the first target-binding domain, the second target-binding domain, and the one or more additional target-binding domains include the same amino acid sequence. In some embodiments of any of the methods described herein, the first target-binding domain, the second target-binding domain, and the one or more additional target-binding domains each bind specifically to the same antigen. In some embodiments of any of the methods described herein, the first target-binding domain, the second target-binding domain, and the one or more additional target-binding domains each bind specifically to the same epitope. In some embodiments of any of the methods described herein, the first target-binding domain, the second target-binding domain, and the one or more additional target-binding domains each include the same amino acid sequence. In some embodiments of any of the methods described herein, the first target-binding domain, the second target-binding domain, and the one or more additional target-binding domains bind specifically to different antigens.

In some embodiments of any of the methods described herein, one or more of the first target-binding domain, the second target-binding domain, and the one or more target-binding domains is an antigen-binding domain. In some embodiments of any of the methods described herein, the first target-binding domain, the second target-binding domain, and the one or more additional target-binding domains are each an antigen-binding domain. In some embodiments of any of the methods described herein, the antigen-binding domain includes a scFv or a single domain antibody.

In some embodiments of any of the methods described herein, one or more of the first target-binding domain, the second target-binding domain, and the one or more target-binding domains bind specifically to a target selected from the group of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the methods described herein, one or more of the first target-binding domain, the second target-binding domain, and the one or more additional target-binding domains is a soluble interleukin, soluble cytokine protein, or soluble cell surface protein. In some embodiments of any of the methods described herein, the soluble interleukin, soluble cytokine protein, or soluble cell surface protein is selected from the group of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

In some embodiments of any of the methods described herein, one or more of the first target-binding domain, the second target-binding domain, and the one or more additional target-binding domains is a soluble interleukin receptor, soluble cytokine receptor, or soluble cell surface receptor. In some embodiments of any of the methods described herein, the soluble interleukin, soluble cytokine receptor, or soluble cell surface receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

In some embodiments of any of the methods described herein, one or more of the first target-binding domain, the second target-binding domain, and the one or more additional target-binding domains is a ligand of a co-stimulatory molecule. In some embodiments of any of the methods described herein, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of any of the methods described herein, the single-chain chimeric polypeptide further includes a peptide tag positioned at the N-terminal end or the C-terminal end of the single-chain chimeric polypeptide. In some embodiments of any of the methods described herein, the immune cell was previously obtained from a subject. Some embodiments of any of the methods described herein further include obtaining the immune cell from the subject prior to the contacting step. In some embodiments of any of the methods described herein, the immune cell has previously been genetically modified to express a chimeric antigen receptor or a recombinant T-cell receptor. Some embodiments of any of the methods described herein further include, after the contacting step, introducing into the immune cell a nucleic acid encoding a chimeric antigen-receptor or a recombinant T-cell receptor. Some embodiments of any of the methods described herein further include, before the contacting step, introducing into the immune cell a nucleic acid encoding a chimeric antigen-receptor or a recombinant T-cell receptor. Some embodiments of any of the methods described herein further include, after the contacting step, isolating the immune cell. In some embodiments of any of the methods described herein, after the contacting step, the immune cell has an increased level of expression or secretion of one or more proteins selected from the group of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step. administering the immune cell to a subject in need thereof.

In some embodiments of any of the methods described herein, the subject has been identified or diagnosed as having an age-related disease or condition. In some embodiments of any of the methods described herein, the age-related disease or condition is selected from the group of: Alzheimer's disease, aneurysm, cysticfibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been diagnosed or identified as having an infectious disease. In some embodiments of any of the methods described herein, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Also provided herein are activated immune cells produced by any of the methods described herein. Also provided herein are pharmaceutical compositions that include any of the activated immune cells produced by any of the methods described herein. Also provided herein are kits that include a pharmaceutical composition including any of the activated immune cells described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein. In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been identified or diagnosed as having an aging-related disease or condition. In some embodiments of any of the methods described herein, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Also provided herein are methods of treating a subject in need thereof that include administering to the subject a therapeutically effective amount of any of the activated immune cells described herein produced by any of the methods described herein or any of the pharmaceutical compositions described herein. In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been identified or diagnosed as having an aging-related disease or condition. In some embodiments of any of the methods described herein, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments of any of the methods described herein, the subject has been diagnosed or identified as having an infectious disease. In some embodiments of any of the methods described herein, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Also provided herein are methods of increasing the glucose consumption of an immune cell that include: contacting an immune cell in a liquid culture medium including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain, under conditions that allow for glucose consumption in the immune cell.

Also provided herein are methods of increasing the oxidative phosphorylation of an immune cell that include: contacting an immune cell in a liquid culture medium including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain, under conditions that allow for oxidative phosphorylation in the immune cell.

Also provided herein are methods of increasing the aerobic glycolysis of an immune cell that include: contacting an immune cell in a liquid culture medium including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain, under conditions that allow for aerobic glycolysis in the immune cell.

Also provided herein are methods of increasing the extracellular acidification rate (ECAR) of an immune cell that include: contacting an immune cell in a liquid culture medium including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain, under conditions that allow for extracellular acidification by the immune cell.

Also provided herein are methods of increasing the mitochondrial oxygen consumption rate of an immune cell that include: contacting an immune cell in a liquid culture medium including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain, under conditions that allow for mitochondrial oxygen consumption rate by the immune cell.

In some embodiments of any of the methods described herein, the liquid culture medium includes the single-chain chimeric polypeptide and the IgG1 antibody construct. In some embodiments of any of the methods described herein, the IgG1 antibody construct is a monoclonal IgG1 antibody, where both of the antigen-binding domains in the monoclonal IgG1 antibody bind specifically to the linker domain. In some embodiments of any of the methods described herein, the IgG1 antibody construct is a bispecific IgG1 antibody, where one of the two antigen-binding domains in the bispecific IgG1 antibody binds specifically to the linker domain. In some embodiments of any of the methods described herein, the contacting step is performed for a period of about 2 hours to about 20 days (e.g., about 1 day to about 15 days).

In some embodiments of any of the methods described herein, the liquid culture medium is a serum-free liquid culture medium. In some embodiments of any of the methods described herein, the liquid culture medium is a chemically-defined liquid culture medium. In some embodiments of any of the methods described herein, the liquid culture medium includes serum. In some embodiments of any of the methods described herein, the liquid culture medium includes the single-chain chimeric polypeptide and the IgG1 antibody construct at a molar ratio of about 0.5:1 to about 2:1 (e.g., about 0.8:1 to about 1.2:1).

In some embodiments of any of the methods described herein, the first target-binding domain and the linker domain directly abut each other in the first chimeric polypeptide. In some embodiments of any of the methods described herein, the first chimeric polypeptide further includes a linker sequence between the first target-binding domain and the linker domain in the first chimeric polypeptide. In some embodiments of any of the methods described herein, the linker domain and the first domain of the pair of affinity domains directly abut each other in the first chimeric polypeptide. In some embodiments of any of the methods described herein, the first chimeric polypeptide further comprises a linker sequence between the linker domain and the first domain of the pair of affinity domains in the first chimeric polypeptide. In some embodiments of any of the methods described herein, the second domain of the pair of affinity domains and the second target-binding domain directly abut each other in the second chimeric polypeptide. In some embodiments of any of the methods described herein, the second chimeric polypeptide further includes a linker sequence between the second domain of the pair of affinity domains and the second target-binding domain in the second chimeric polypeptide.

In some embodiments of any of the methods described herein, the first target-binding domain and the second target-binding domain bind specifically to the same antigen. In some embodiments of any of the methods described herein, the first target-binding domain and the second target-binding domain bind specifically to the same epitope. In some embodiments of any of the methods described herein, the first target-binding domain and the second target-binding domain include the same amino acid sequence. In some embodiments of any of the methods described herein, the first target-binding domain and the second target-binding domain bind specifically to different antigens.

In some embodiments of any of the methods described herein, one or both of the first target-binding domain and the second target-binding domain is an antigen-binding domain. In some embodiments of any of the methods described herein, the first target-binding domain and the second target-binding domain are each antigen-binding domains. In some embodiments of any of the methods described herein, the antigen-binding domain comprises a scFv or a single domain antibody. In some embodiments of any of the methods described herein, one or both of the first target-binding domain and the second target-binding domain bind specifically to a target selected from the group of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the methods described herein, one or both of the first target-binding domain and the second target-binding domain is a soluble interleukin, soluble cytokine protein, or soluble cell surface protein. In some embodiments of any of the methods described herein, the soluble interleukin, soluble cytokine protein, or soluble cell surface protein is selected from the group of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

In some embodiments of any of the methods described herein, one or both of the first target-binding domain and the second target-binding domain is a soluble interleukin receptor, soluble cytokine receptor, or soluble cell surface receptor. In some embodiments of any of the methods described herein, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

In some embodiments of any of the methods described herein, the first chimeric polypeptide further includes one or more additional target-binding domain(s), where at least one of the one or more target-binding domain(s) is positioned between the linker domain and the first domain of the pair of affinity domains. In some embodiments of any of the methods described herein, the first chimeric polypeptide further includes a linker sequence between the linker domain and the at least one of the one or more target antigen-binding domain(s), and/or a linker sequence between the at least one of the one or more target antigen-binding domain(s) and the first domain of the pair of affinity domains.

In some embodiments of any of the methods described herein, the first chimeric polypeptide further comprises one or more additional target-binding domains at the N-terminal and/or C-terminal end of the first chimeric polypeptide. In some embodiments of any of the methods described herein, at least one of the one or more additional target-binding domains directly abuts the first domain of the pair of affinity domains in the first chimeric polypeptide. In some embodiments of any of the methods described herein, the first chimeric polypeptide further includes a linker sequence between the at least one of the one or more additional target-binding domains and the first domain of the pair of affinity domains. In some embodiments of any of the methods described herein, the at least one of the one or more additional target-binding domains directly abuts the first target-binding domain in the first chimeric polypeptide. In some embodiments of any of the methods described herein, the first chimeric polypeptide further includes a linker sequence between the at least one of the one or more additional target-binding domains and the first target-binding domain. In some embodiments of any of the methods described herein, at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide. In some embodiments of any of the methods described herein, the at least one additional target-binding domain of the one or more additional target-binding domains disposed at the N-terminus directly abuts the first target-binding domain or the first domain of the pair of affinity domains in the first chimeric polypeptide. In some embodiments of any of the methods described herein, the first chimeric polypeptide further includes a linker sequence disposed between the at least one additional target-binding domain and the first target-binding domain or the first domain of the pair of affinity domains in the first chimeric polypeptide. In some embodiments of any of the methods described herein, the at least one additional target-binding domain of the one or more additional target-binding domains disposed at the C-terminus directly abuts the first target-binding domain or the first domain of the pair of affinity domains in the first chimeric polypeptide. In some embodiments of any of the methods described herein, the first chimeric polypeptide further includes a linker sequence disposed between the at least one additional target-binding domain and the first target-binding domain or the first domain of the pair of affinity domains in the first chimeric polypeptide. In some embodiments of any of the methods described herein, the at least one of the one or more additional target-binding domains positioned between the linker domain and the first domain of the pair of affinity domains, directly abuts the linker domain and/or the first domain of the pair of affinity domains. In some embodiments of any of the methods described herein, the first chimeric polypeptide further includes a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

In some embodiments of any of the methods described herein, the second chimeric polypeptide further includes one or more additional target-binding domains at the N-terminal end and/or the C-terminal end of the second chimeric polypeptide. In some embodiments of any of the methods described herein, at least one of the one or more additional target-binding domains directly abuts the second domain of the pair of affinity domains in the second chimeric polypeptide. In some embodiments of any of the methods described herein, the second chimeric polypeptide further includes a linker sequence between at least one of the one or more additional target-binding domains and the second domain of the pair of affinity domains in the second chimeric polypeptide. In some embodiments of any of the methods described herein, at least one of the one or more additional target-binding domains directly abuts the second target-binding domain in the second chimeric polypeptide. In some embodiments of any of the methods described herein, the second chimeric polypeptide further includes a linker sequence between at least one of the one or more additional target-binding domains and the second target-binding domain in the second chimeric polypeptide.

In some embodiments of any of the methods described herein, two or more of the first target-binding domain, the second target-binding domain, and the one or more additional target-binding domains bind specifically to the same antigen. In some embodiments of any of the methods described herein, two or more of the first target-binding domain, the second target-binding domain, and the one or more additional target-binding domains bind specifically to the same epitope. In some embodiments of any of the methods described herein, two or more of the first target-binding domain, the second target-binding domain, and the one or more additional target-binding domains include the same amino acid sequence. In some embodiments of any of the methods described herein, the first target-binding domain, the second target-binding domain, and the one or more additional target-binding domains each bind specifically to the same antigen. In some embodiments of any of the methods described herein, the first target-binding domain, the second target-binding domain, and the one or more additional target-binding domains each bind specifically to the same epitope. In some embodiments of any of the methods described herein, the first target-binding domain, the second target-binding domain, and the one or more additional target-binding domains each include the same amino acid sequence. In some embodiments of any of the methods described herein, the first target-binding domain, the second target-binding domain, and the one or more additional target-binding domains bind specifically to different antigens.

In some embodiments of any of the methods described herein, one or more of the first target-binding domain, the second target-binding domain, and the one or more target-binding domains is an antigen-binding domain. In some embodiments of any of the methods described herein, the first target-binding domain, the second target-binding domain, and the one or more additional target-binding domains are each an antigen-binding domain. In some embodiments of any of the methods described herein, the antigen-binding domain comprises a scFv.

In some embodiments of any of the methods described herein, one or more of the first target-binding domain, the second target-binding domain, and the one or more target-binding domains bind specifically to a target selected from the group of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

In some embodiments of any of the methods described herein, one or more of the first target-binding domain, the second target-binding domain, and the one or more additional target-binding domains is a soluble interleukin, soluble cytokine protein, or soluble cell surface protein. In some embodiments of any of the methods described herein, the soluble interleukin, soluble cytokine protein, or soluble cell surface protein is selected from the group of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

In some embodiments of any of the methods described herein, one or more of the first target-binding domain, the second target-binding domain, and the one or more additional target-binding domains is a soluble interleukin receptor, soluble cytokine receptor, or soluble cell surface receptor. In some embodiments of any of the methods described herein, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

In some embodiments of any of the methods described herein, the first chimeric polypeptide further includes a peptide tag at the N-terminal end or the C-terminal end of the first chimeric polypeptide. In some embodiments of any of the methods described herein, the second chimeric polypeptide further includes a peptide tag at the N-terminal end or the C-terminal end of the second chimeric polypeptide.

In some embodiments of any of the methods described herein, the linker domain is a soluble tissue factor domain. In some embodiments of any of the methods described herein, the soluble tissue factor domain is a soluble human tissue factor domain. In some embodiments of any of the methods described herein, the soluble human tissue factor domain includes a sequence that is at least 80% identical, at least 90% identical, or at least 95% identical to SEQ ID NO: 1. In some embodiments of any of the methods described herein, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods described herein, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods described herein, the soluble tissue factor domain is not capable of binding to Factor VIIa. In some embodiments of any of the methods described herein, the soluble tissue factor domain does not convert inactive Factor X into Factor Xa. In some embodiments of any of the methods described herein, the multi-chain chimeric polypeptide does not stimulate blood coagulation in a mammal. In some embodiments of any of the methods described herein, the IgG1 antibody construct includes at least one antigen-binding domain that binds specifically to the soluble tissue factor domain. In some embodiments of any of the methods described herein, the linker domain is selected from the group of: a kappa chain and a lambda chain. In some embodiments of any of the methods described herein, the IgG1 antibody construct is a monoclonal IgG1 antibody, where both antigen-binding domains in the monoclonal IgG1 antibody bind specifically to the linker domain. In some embodiments of any of the methods described herein, the IgG1 antibody construct is a bispecific IgG1 antibody, where one of the two antigen-binding domains in the bispecific IgG1 antibody binds specifically to the linker domain.

In some embodiments of any of the methods described herein, the pair of affinity domains is a sushi domain from an alpha chain of human IL-15 receptor (IL15Rα) and a soluble IL-15. In some embodiments of any of the methods described herein, the soluble IL15 has a D8N or D8A amino acid substitution. In some embodiments of any of the methods described herein, the human IL15Rα is a mature full-length IL15Rα. In some embodiments of any of the methods described herein, the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

In some embodiments of any of the methods described herein, the first chimeric polypeptide and/or the second chimeric polypeptide further includes a signal sequence at its N-terminal end. In some embodiments of any of the methods described herein, the first chimeric polypeptide and/or the second chimeric polypeptide lacks a signal sequence at its N-terminal end.

In some embodiments of any of the methods described herein, the immune cell was previously obtained from a subject. Some embodiments of any of the methods described herein further include obtaining the immune cell from the subject prior to the contacting step. In some embodiments of any of the methods described herein, the immune cell has previously been genetically modified to express a chimeric antigen receptor or a recombinant T-cell receptor. Some embodiments of any of the methods described herein further include, after the contacting step, introducing into the immune cell a nucleic acid encoding a chimeric antigen-receptor or a recombinant T-cell receptor. Some embodiments of any of the methods described herein further include, before the contacting step, introducing into the immune cell a nucleic acid encoding a chimeric antigen-receptor or a recombinant T-cell receptor. Some embodiments of any of the methods described herein further include, after the contacting step, isolating the immune cell. In some embodiments of any of the methods described herein, after the contacting step, the immune cell has an increased level of expression or secretion of one or more proteins selected from the group of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step. Some embodiments of any of the methods described herein further include, after the contacting step, administering the immune cell to a subject in need thereof.

In some embodiments of any of the methods described herein, the subject has been identified or diagnosed as having an age-related disease or condition. In some embodiments of any of the methods described herein, the age-related disease or condition is selected from the consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been diagnosed or identified as having an infectious disease. In some embodiments of any of the methods described herein, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Also provided herein are activated immune cells produced using any of the methods described herein. Also pharmaceutical compositions that include any of the activated immune cells described herein produced by any of the methods described herein. Also provided herein are kits that include any of the pharmaceutical compositions described herein that include any of the activated immune cells described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced using any of the methods described herein or any of the pharmaceutical compositions described herein.

In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been identified or diagnosed as having an aging-related disease or condition. In some embodiments of any of the methods described herein, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Also provided herein are methods of treating a subject in need thereof that include administering to the subject a therapeutically effective amount of any of the activated immune cells described herein produced by any of the methods described herein or any of the pharmaceutical compositions described herein. In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been identified or diagnosed as having an aging-related disease or condition. In some embodiments of any of the methods described herein, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments of any of the methods described herein, the subject has been diagnosed or identified as having an infectious disease. In some embodiments of any of the methods described herein, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

In some embodiments of any of the methods or kits described herein, the soluble human tissue factor domain does not stimulate blood coagulation. In some embodiments of any of the methods or kits described herein, the soluble tissue factor domain comprises or consists of a sequence from a wildtype soluble human tissue factor (or any sequence therefrom).

Also provided herein are methods of inducing differentiation of an immune cell into a memory or memory-like immune cell that include contacting an immune cell in a liquid culture medium including: (1) an effective amount of a multi-chain chimeric polypeptide comprising: (a) a first chimeric polypeptide including: (i) a first target-binding domain; (ii) a linker domain; and (iii) a first domain of a pair of affinity domains;
(b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain.

Also provided herein are methods of inducing differentiation of an immune cell into a memory or memory-like immune cell that include contacting an immune cell in a liquid culture medium including an effective amount of (i) a single-chain chimeric polypeptide including a first target-binding domain, a linker domain, and a second target-binding domain, and (ii) an IgG1 antibody construct that includes at least one antigen-binding domain that binds specifically to the linker domain.

In some embodiments of any of the methods described herein, the immune cell was previously obtained from a subject. In some embodiments of any of the methods described herein, the immune cell is selected from the group c of: an immature thymocyte, a periperhal blood Treg cell, a Th17 cell, a Th22 cell, a Th9 cell, a Th2 cell, a Th1 cell, a Th3 cell, $\lambda\delta$ T cell, an $\alpha\beta$ T cell, a tumor-infiltrating T cell, a CD8$^+$ T cell, a CD4$^+$ T cell, a natural killer T cell, a mast cell, a macrophage, a neutrophil, a dendritic cell, a basophil, an eosinophil, and a natural killer cell. In some embodiments of any of the methods described herein, the immune cell has previously been genetically modified to express a chimeric antigen receptor or a recombinant T-cell receptor.

Some embodiments of any of the methods described herein further include, after the contacting step, introducing into the immune cell a nucleic acid encoding a chimeric antigen-receptor or a recombinant T-cell receptor. Some embodiments of any of the methods described herein further include administering to the immune cell to a subject in need thereof.

As used herein, the term "chimeric" refers to a polypeptide that includes amino acid sequences (e.g., domains) originally derived from two different sources (e.g., two different naturally-occurring proteins, e.g., from the same or different species). For example, a chimeric polypeptide can include domains from at least two different naturally occurring human proteins. In some examples, a chimeric polypeptide can include a domain that is a synthetic sequence (e.g., a scFv) and a domain that is derived from a naturally-occurring protein (e.g., a naturally-occurring human protein). In some embodiments, a chimeric polypeptide can include at least two different domains that are synthetic sequences (e.g., two different scFvs).

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art.

A "soluble tissue factor domain" refers to a polypeptide having at least 70% identity (e.g., at least 75% identity, at least 80% identity, at least 85% identity, at least 90% identity, at least 95% identity, at least 99% identity, or 100% identical) to a segment of a wildtype mammalian tissue factor protein (e.g., a wildtype human tissue factor protein) that lacks the transmembrane domain and the intracellular domain. Non-limiting examples of soluble tissue factor domains are described herein.

The term "soluble interleukin protein" is used herein to refer to a mature and secreted interleukin protein or a biologically active fragment thereof. In some examples, a soluble interleukin protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble interleukin proteins are described herein.

The term "soluble cytokine protein" is used herein to refer to a mature and secreted cytokine protein or a biologically active fragment thereof. In some examples, a soluble cytokine protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble cytokine proteins are described herein.

The term "soluble interleukin receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble interleukin receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype interleukin receptor and retains its ability to specifically bind to one or more of its natural ligands, but lacks its transmembrane domain (and optionally, further lacks its intracellular domain). Non-limiting examples of soluble interleukin receptors are described herein.

The term "soluble cytokine receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble cytokine receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype cytokine receptor and retains its ability to specifically bind to one or more of its natural ligands, but lacks its transmembrane domain (and optionally, further lacks its intracellular domain). Non-limiting examples of soluble cytokine receptors are described herein.

The term "ligand of a co-stimulatory molecule" is used herein in the broadest sense to refer to a polypeptide that is capable of binding and activating a co-stimulatory receptor molecule on an immune cell (e.g., under physiological conditions, e.g., in phosphate buffered saline at room temperature). For example, a ligand of a co-stimulatory molecule can include a sequence that is at least 70% identical (e.g., at least 75% identical, at least 80% identical, at least 85% identical, at least 90% identical, at least 95% identical, at least 99% identical, or 100% identical) to a ligand of a co-stimulatory molecule that retains its ability to specifically bind to one or more of its natural receptors. Non-limiting examples of ligands of co-stimulatory molecules are described herein.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins), antibody fragments, and multi-specific antibodies. One example of an antigen-binding domain is an antigen-binding domain formed by a VH-VL dimer. Additional examples of an antibody are described herein. Additional examples of an antibody are known in the art.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

A "single-chain polypeptide" as used herein to refers to a single protein chain.

The term "pair of affinity domains" is two different protein domain(s) that bind specifically to each other with a $K_D$ of less than of less than $1 \times 10^{-7}$ M (e.g., less than $1 \times 10^{-8}$ M, less than $1 \times 10^{-9}$ M, less than $1 \times 10^{-10}$ M, or less than $1 \times 10^{-11}$ M). In some examples, a pair of affinity domains can be a pair of naturally-occurring proteins. In some embodiments, a pair of affinity domains can be a pair of synthetic proteins. Non-limiting examples of pairs of affinity domains are described herein.

The term "epitope" means a portion of an antigen that specifically binds to an antigen-binding domain. Epitopes can, e.g., consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. Methods for identifying an epitope to which an antigen-binding domain binds are known in the art.

An "immune effector cell" refers to a cell of the immune system of a mammal that is capable, directly or indirectly, of recognizing and/or causing cytostasis or cell death of a pathogenic cell (e.g., a cancer cell) in the mammal. Non-limiting examples of immune effector cells include macrophages, natural killer cells, T-lymphocytes (e.g., cytotoxic T-lymphocytes and T-helper cells), neutrophils, monocytes, and eosinophils. Additional examples of immune effector cells are known in the art.

The term "treatment" means to ameliorate at least one symptom of a disorder. In some examples, the disorder being treated is cancer and to ameliorate at least one symptom of cancer includes reducing aberrant proliferation, gene expression, signaling, translation, and/or secretion of factors. Generally, the methods of treatment include administering a therapeutically effective amount of composition that reduces at least one symptom of a disorder to a subject who is in need of, or who has been determined to be in need of such treatment.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 80 shows a schematic diagram of an exemplary IL-21/IL-15RαSu DNA construct.

FIG. 81 shows a schematic diagram of an exemplary IL-7/TF/IL-15 DNA construct.

FIG. 82 shows a schematic diagram of the interaction between the exemplary IL-21/IL-15RαSu and IL-7/TF/IL-15 DNA constructs.

FIG. 83 shows a schematic diagram of the interaction between the exemplary IL-21/IL-15RαSu and IL-7/TF/IL-15 fusion proteins resulting in an IL-7/TF/IL-15:IL-21/IL-15RαSU complex (7t15-21s).

FIG. 94A shows binding affinity of TGFRt15-16s21 with CHO cells expressing human CD16b. FIG. 94B shows binding affinity of 7t15-21s with CHO cells expressing human CD16b.

FIG. 113A shows spleen weight in mice treated with TGFRt15-TGFRs as compared to PBS control. FIG. 113B shows the percentage of CD4$^+$ T cells, CD8$^+$ T cells, and NK cells in mice treated with TGFRt15-TGFRs as compared to PBS control.

FIG. 114A shows spleen weight of mice treated with TGFRt15-TGFRs at 16, 24, 48, 72, and 92 hours after treatment. FIG. 114B shows the percentages of immune cells in mice treated with TGFRt15-TGFRs at 16, 24, 48, 72, and 92 hours after treatment.

FIGS. 115A and 115B show Ki67 and Granzyme B expression in mice treated with TGFRt15-TGFRs over time.

FIG. 119A shows a schematic of the treatment regimen. FIG. 119B shows tumor volume over time following saline treatment, chemotherapy (DTX), or chemotherapy (DTX), TGFRt15-TGFRs and TA99 (anti-TRP1 antibody) combination treatment. FIG. 119C shows peripheral blood analysis using fluorescently labeled antibodies against NK1.1. FIG. 119D shows peripheral blood analysis using fluorescently labeled antibodies against CD8. FIG. 119E shows peripheral blood analysis using fluorescently labeled antibodies against CD4.

FIG. 121 shows an additional schematic of the 7t15-21s137L (long version) construct.

FIG. 122 is a line graph showing the chromatographic profile of 7t15-21s137L (long version) protein containing cell culture supernatant following binding and elution on anti-TF antibody resin.

FIG. 123 shows the analytical SEC profile of 7t15-21s137L (long version).

FIG. 124 shows binding of 7t15-21s137L (short version) to CD137L (4.1BBL)

FIGS. 125A-125C show detection of IL15, IL21, and IL7 in 7t15-21s137L (short version) with ELISA. FIG. 125A shows detection of IL15 in 7t15-21s137L (short version)

Figure 125A:
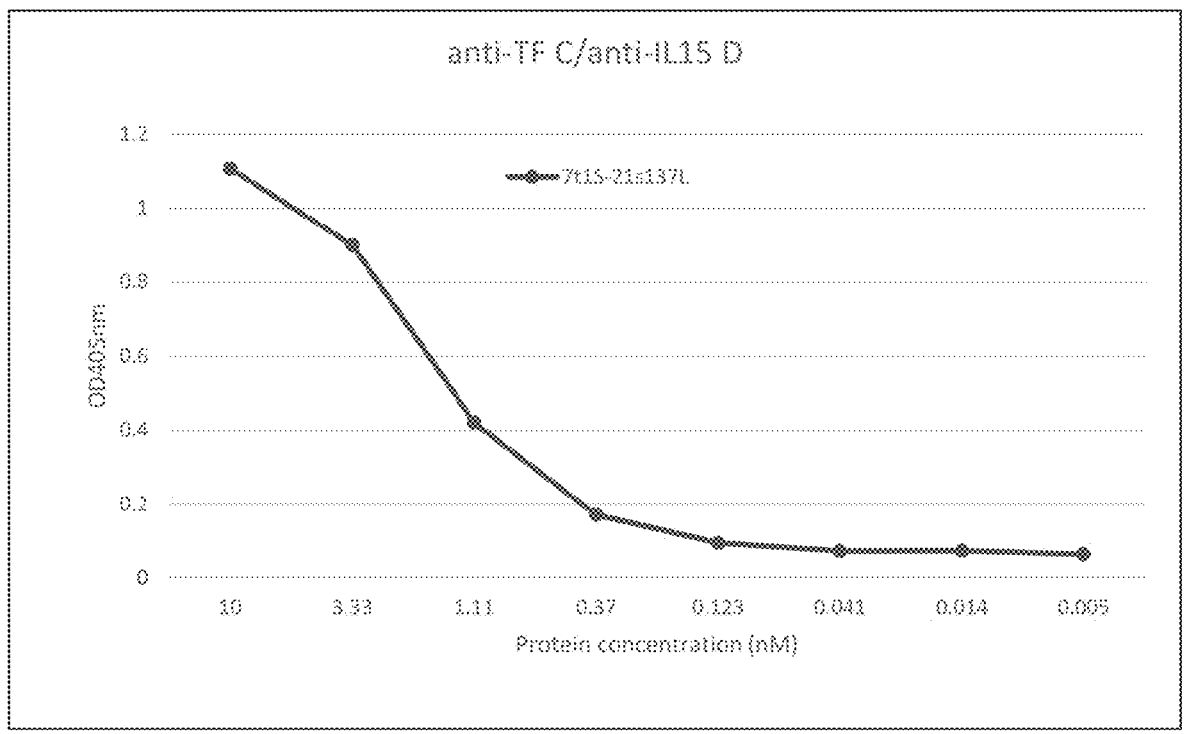
Figure 125B:
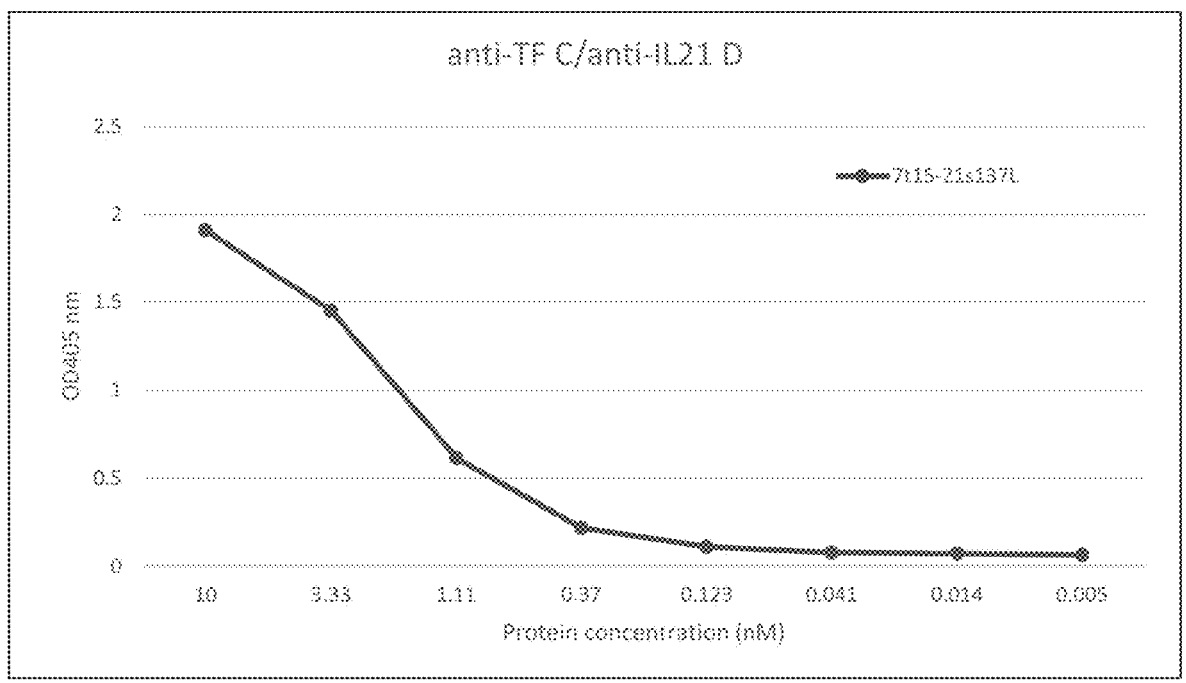
Figure 125C:
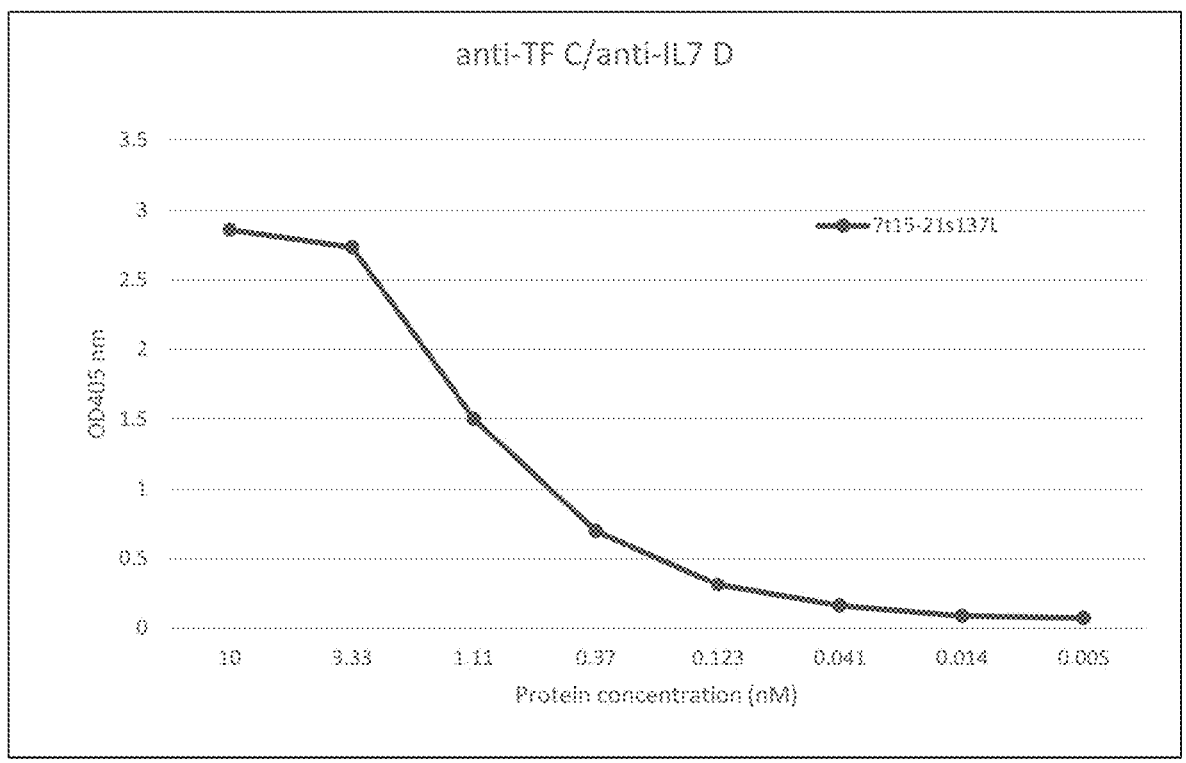

with ELISA. FIG. 125B shows detection of IL21 in 7t15-21s137L (short version) with ELISA. FIG. 125C shows detection of IL7 in 7t15-21s137L (short version) with ELISA.

Figure 126:
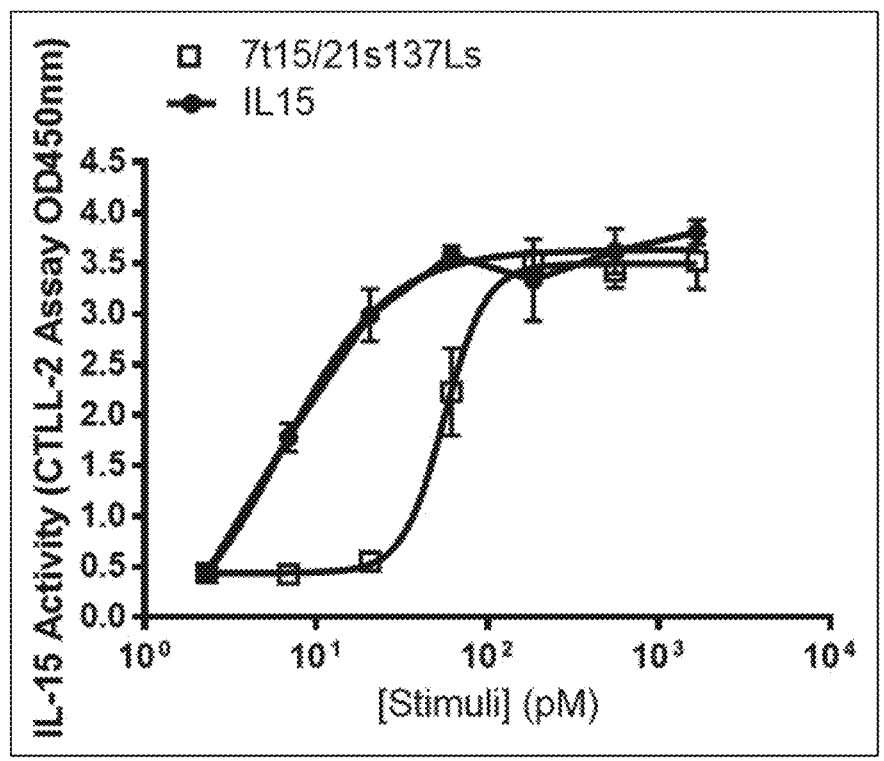

FIG. 126 shows results from a CTLL-2 cell proliferation assay.

Figure 127:
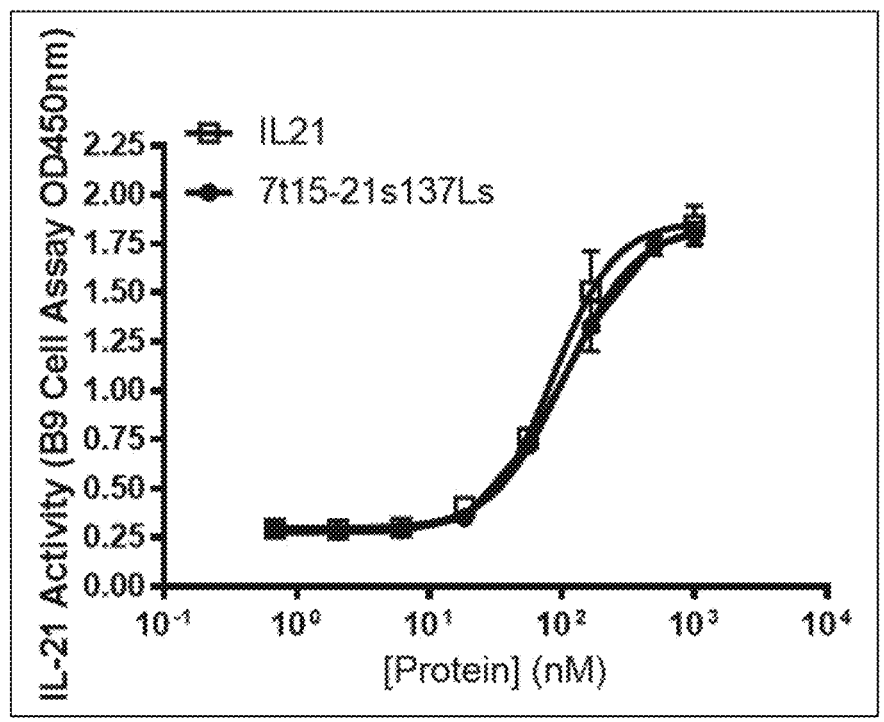

FIG. 127 shows the activity of 7t15-1s137L (short version) in promoting IL21R containing B9 cell proliferation.

Figure 128:
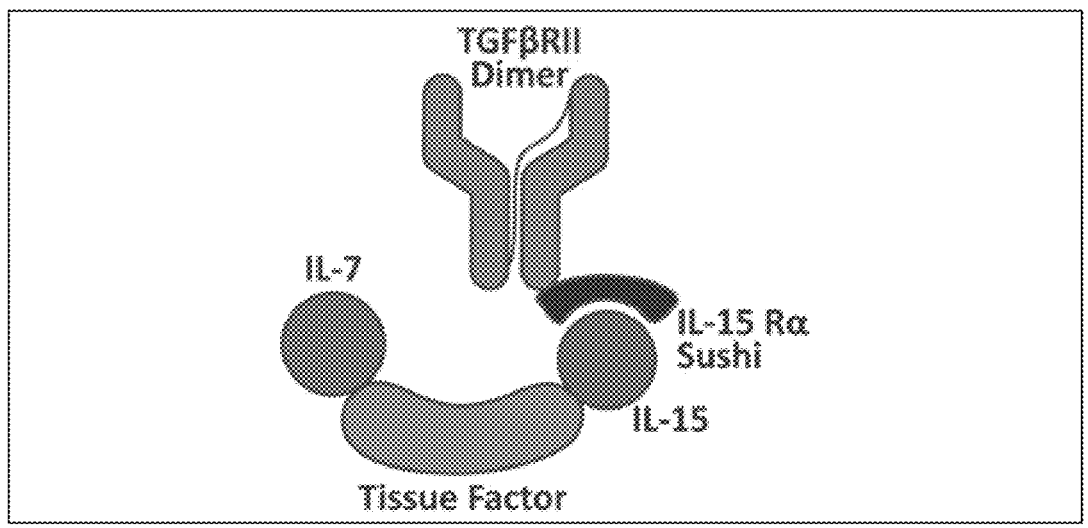

FIG. 128 shows a schematic of the 7t15-TGFRs construct.

Figure 129:
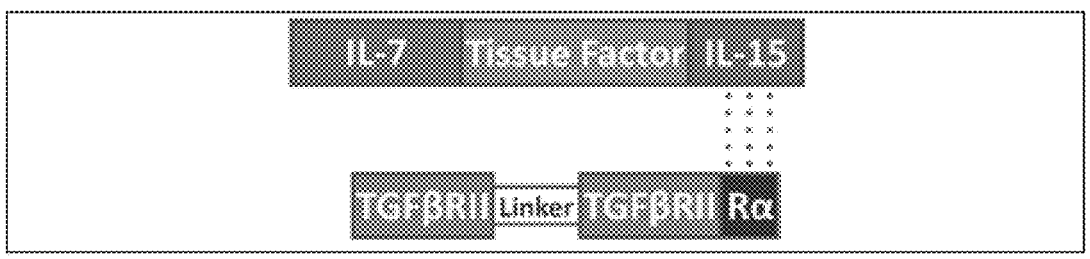

FIG. 129 shows an additional schematic of the 7t15-TGFRs construct.

Figure 130:
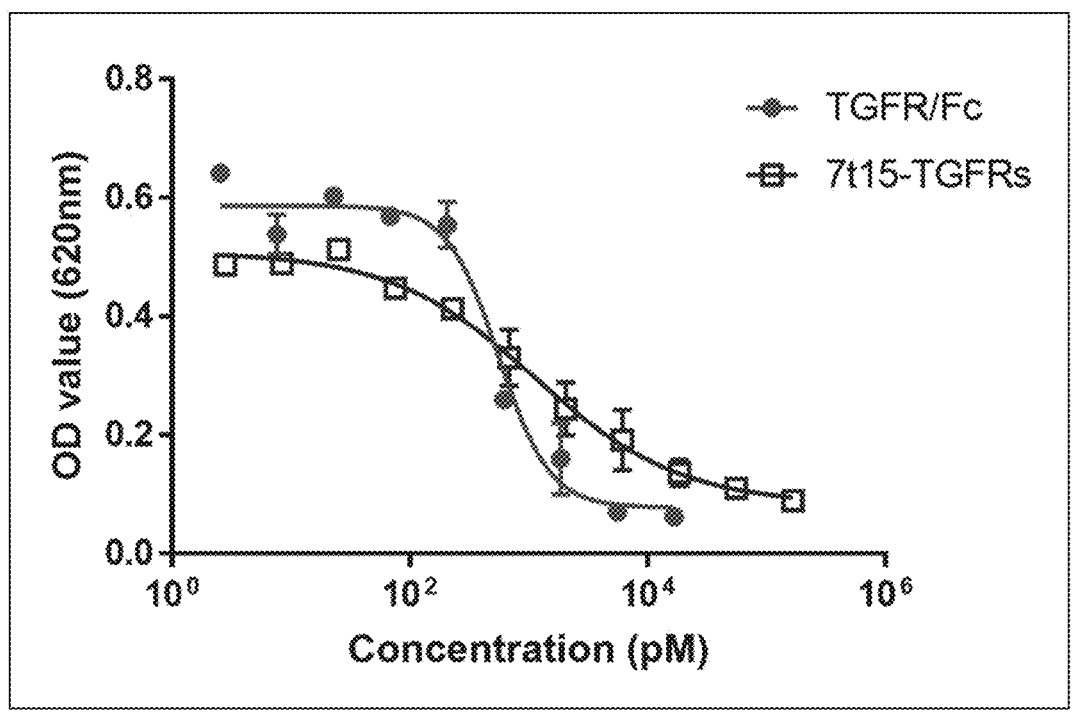

FIG. 130 shows results of TGFβ1 inhibition by 7t15-TGFRs and TGFR-Fc.

Figure 131A:
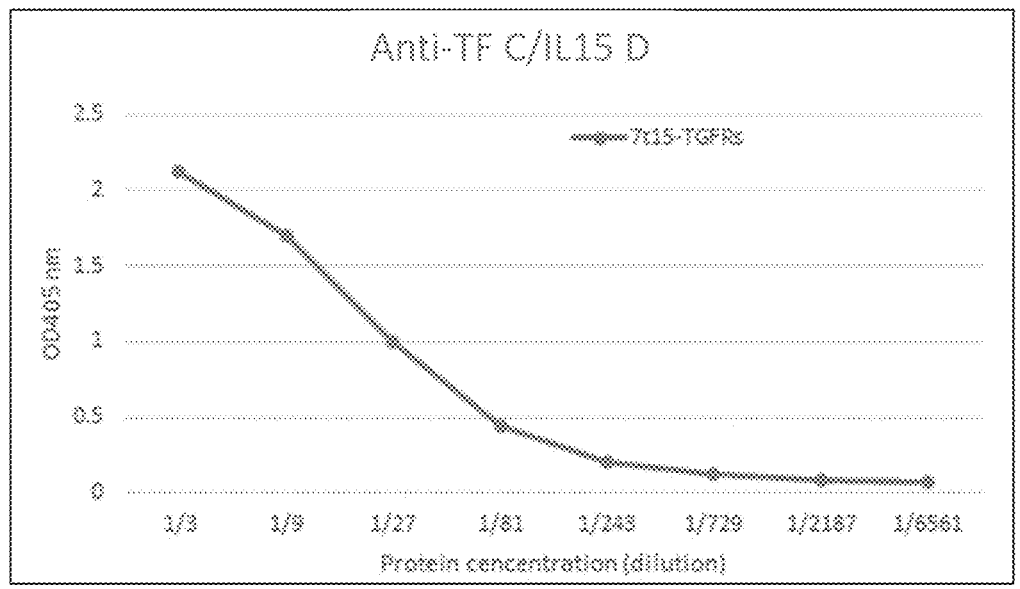
Figure 131B:
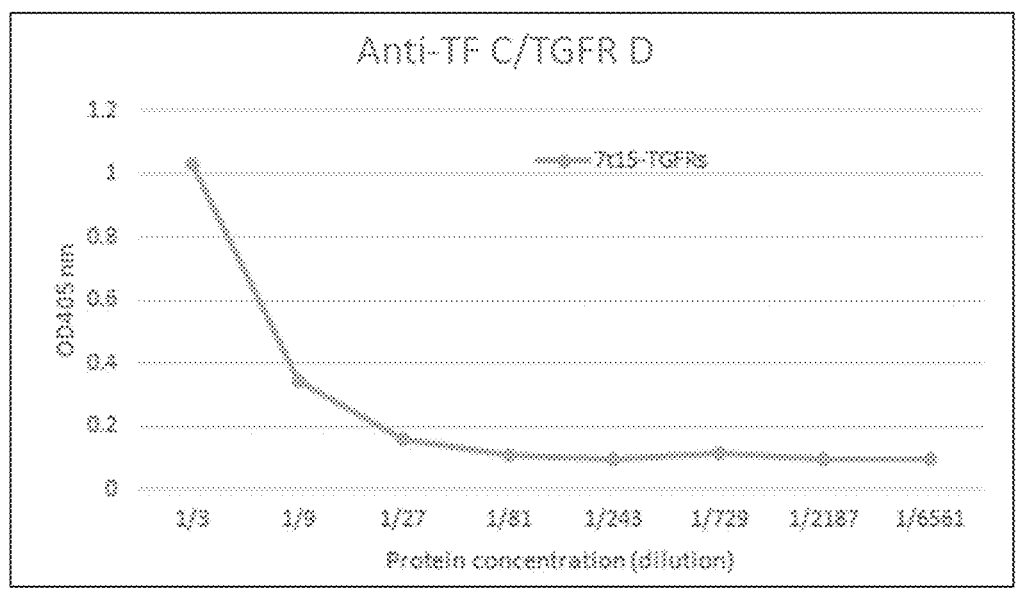
Figure 131C:
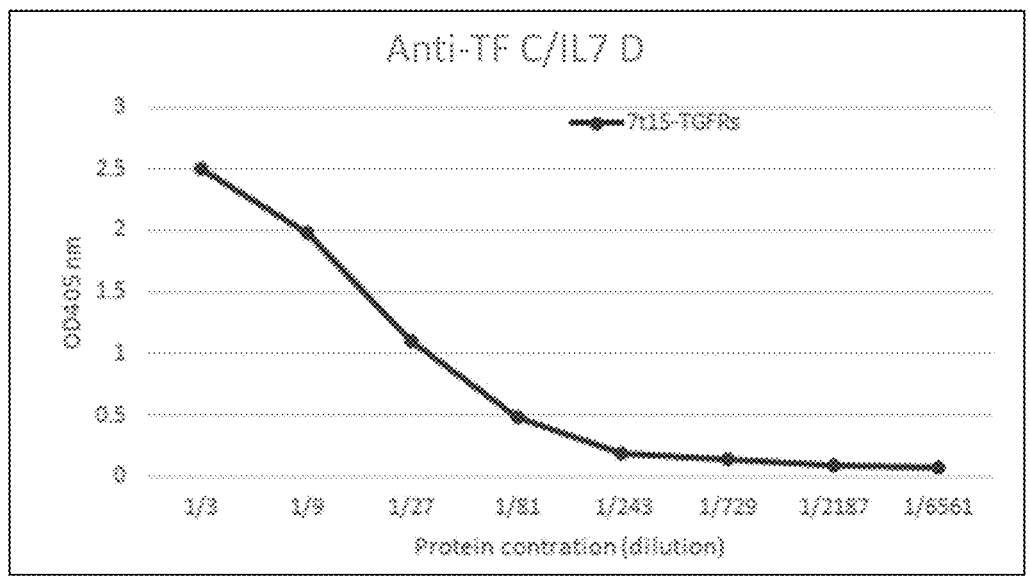

FIGS. 131A-131C show detection of IL-15, TGFβRII, and IL-7 in 7t15-TGFRs with ELISA.

Figure 132:
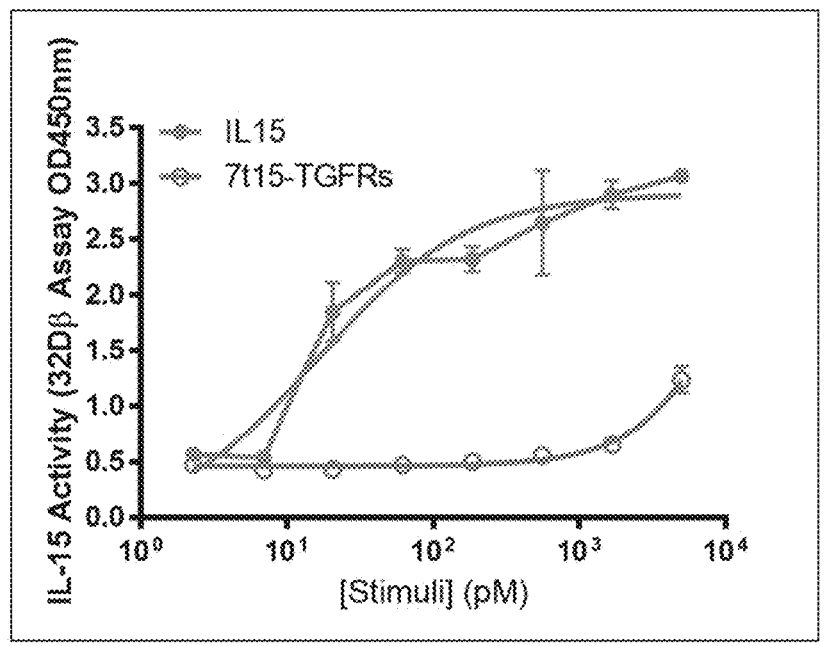

FIG. 132 shows results of 32Dβ cell proliferation assay with 7t15-TGFRs or recombinant IL-15.

Figure 133:
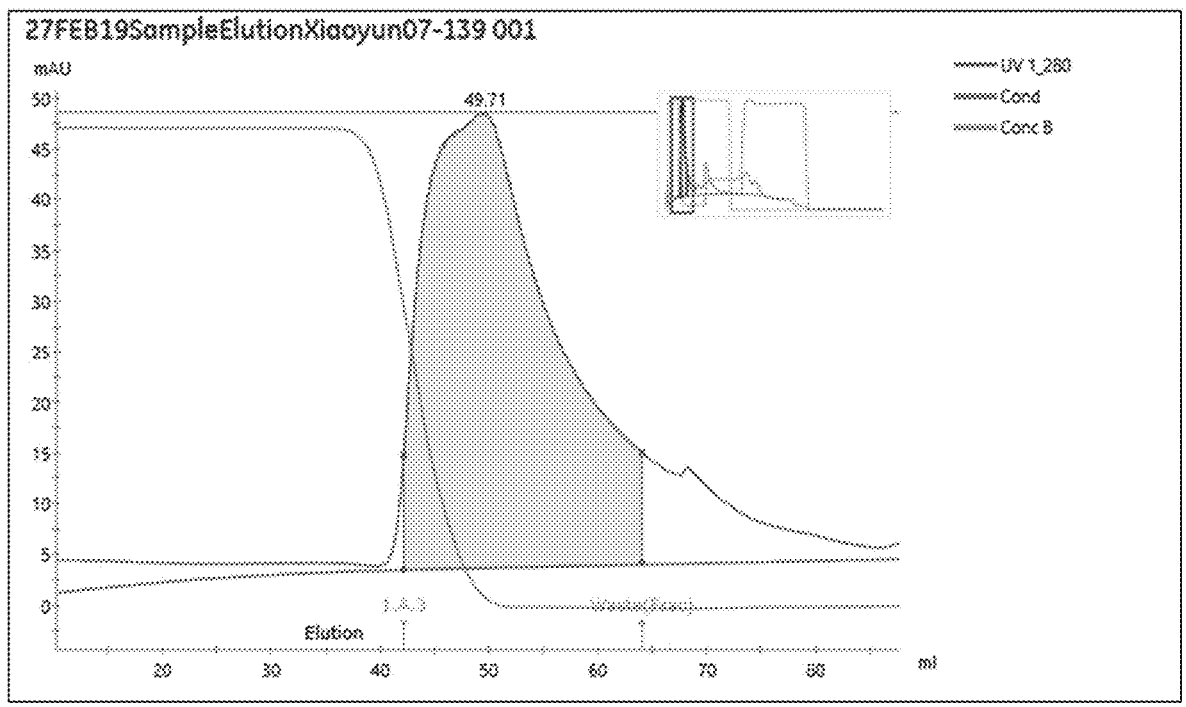

FIG. 133 is a line graph showing the chromatographic profile of 7t15-TGFRs protein containing cell culture supernatant following binding and elution on anti-TF antibody resin.

Figure 134:
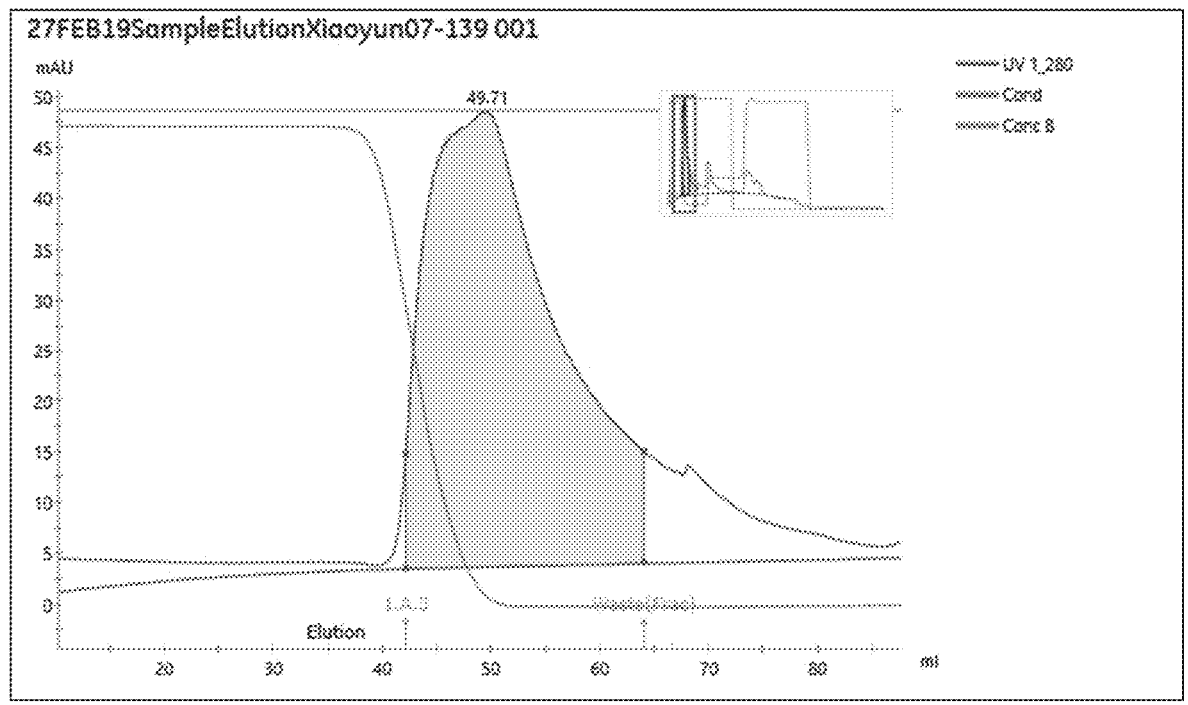

FIG. 134 shows 7t15-TGFRs before and after deglycosylation as analyzed using reduced SDS-PAGE.

Figure 135:
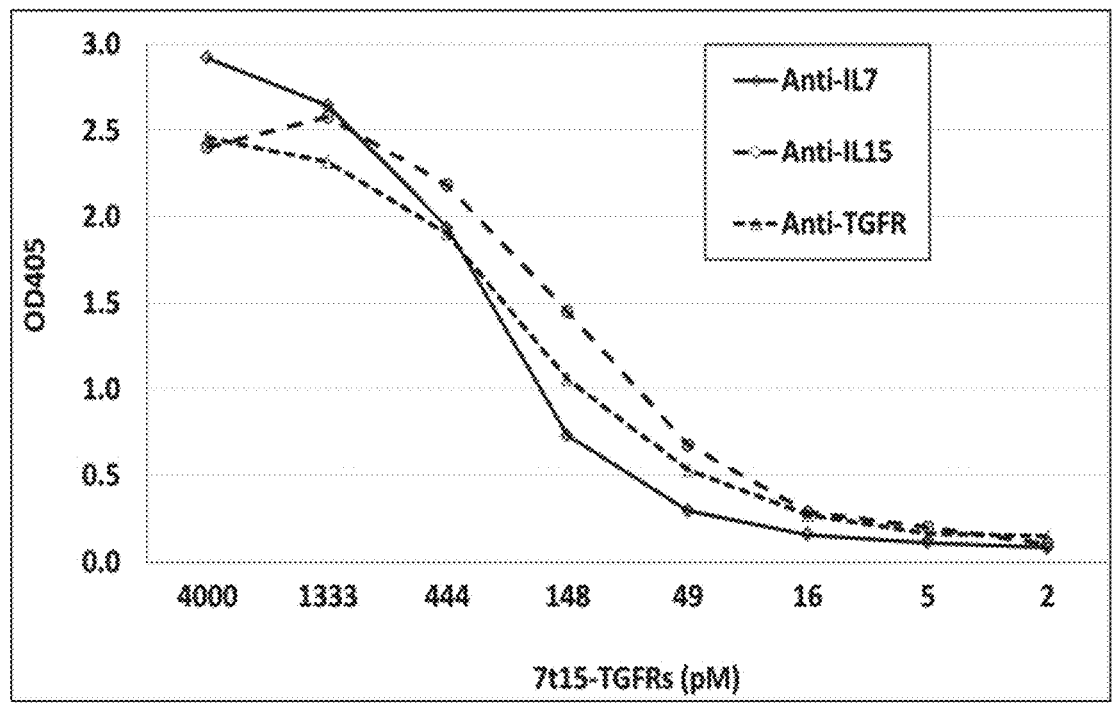

FIG. 135 shows ELISA detection of IL-7, IL-15 and TGFβRII in the 7t15-TGFRs protein.

Figure 136A:
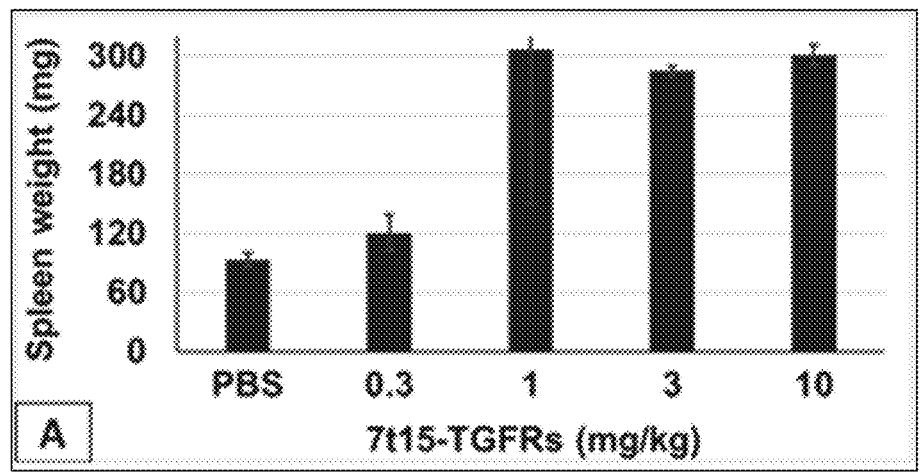
Figure 136B:
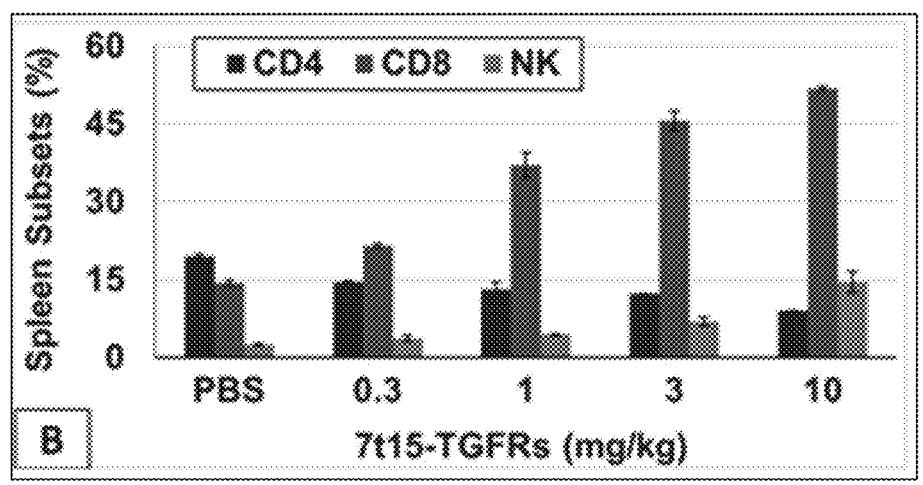

FIGS. 136A and 136B show spleen weight and the percentages of immune cell types in 7t15-TGFRs-treated and control-treated mice. FIG. 136A shows spleen weight in mice treated with 7t15-TGFRs at various dosages, as compared to PBS control. FIG. 136B shows the percentage of $CD4^+$ T cells, $CD8^+$ T cells, and NK cells in mice treated with 7t15-TGFRs at various dosages, as compared to PBS control.

Figure 137A:
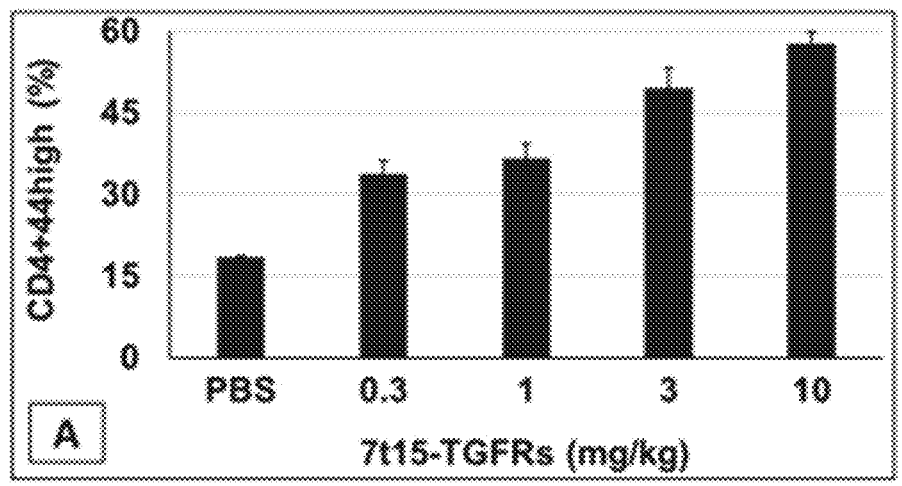
Figure 137B:
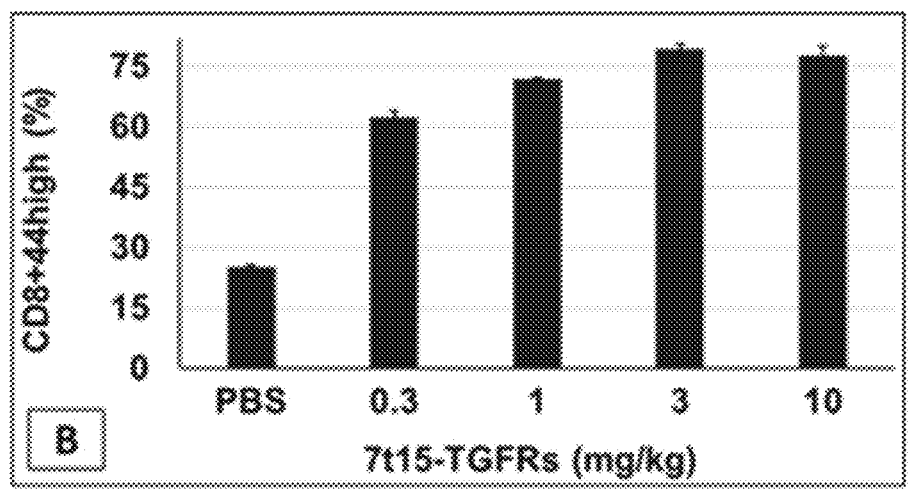

FIGS. 137A and 137B show upregulation of CD44 expression of $CD4^+$ and $CD8^+$ T cells by 7t15-TGFRs in C57BL/6 mice.

Figure 138A:
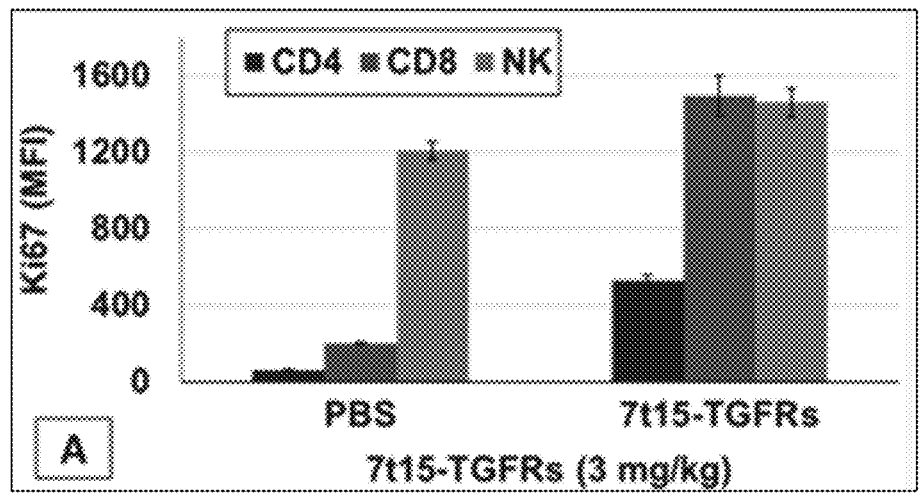
Figure 138B:
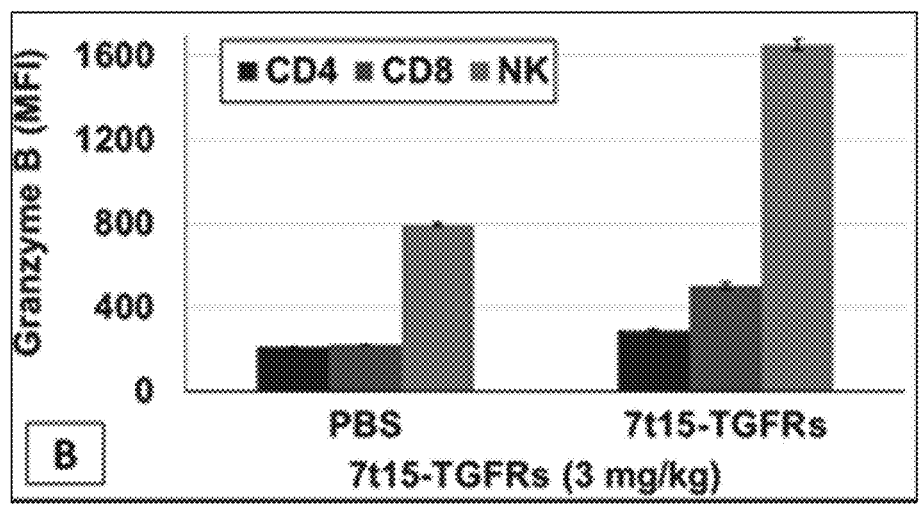

FIGS. 138A and 138B show upregulation of Ki67 expression and Granzyme B expression of $CD8^+$ T cells and NK Cells by 7t15-TGFRs in C57BL/6 mice.

Figure 139:
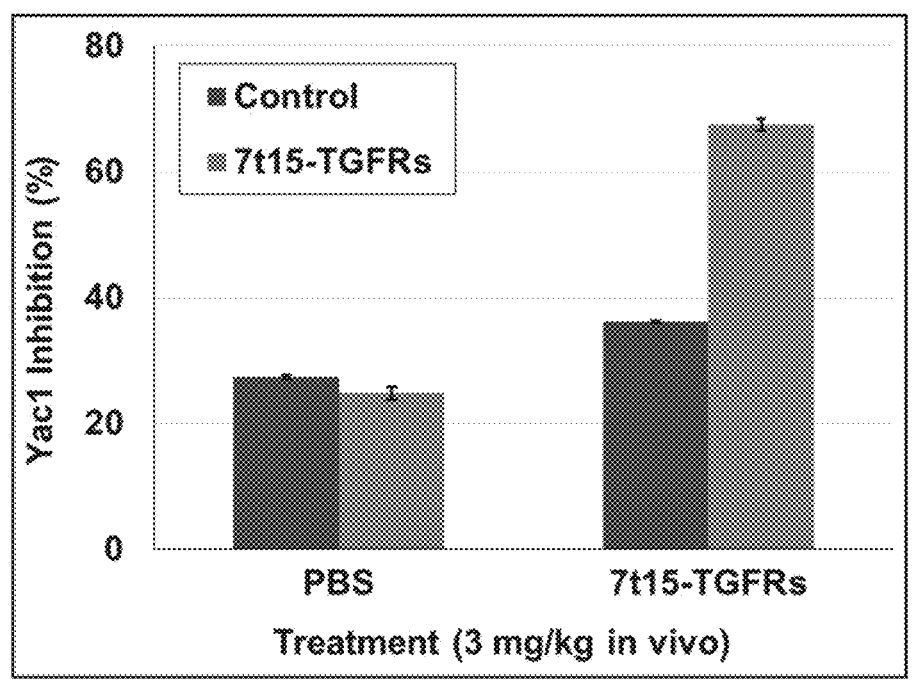

FIG. 139 shows enhancement of cytotoxicity of splenocytes by 7t15-TGFRs in C57BL/6 mice.

Figure 140:
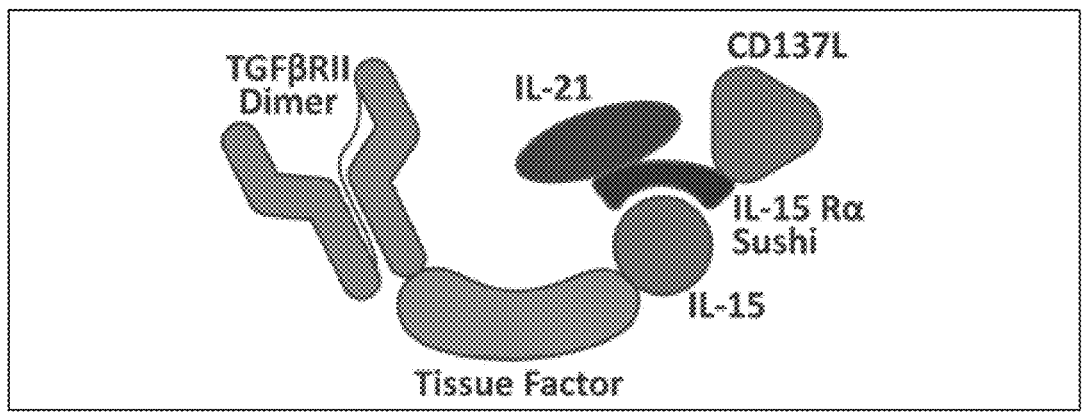

FIG. 140 shows a schematic of the TGFRt15-21s137L construct.

Figure 141:

FIG. 141 shows an additional schematic of the TGFRt15-21s137L construct.

Figure 142:
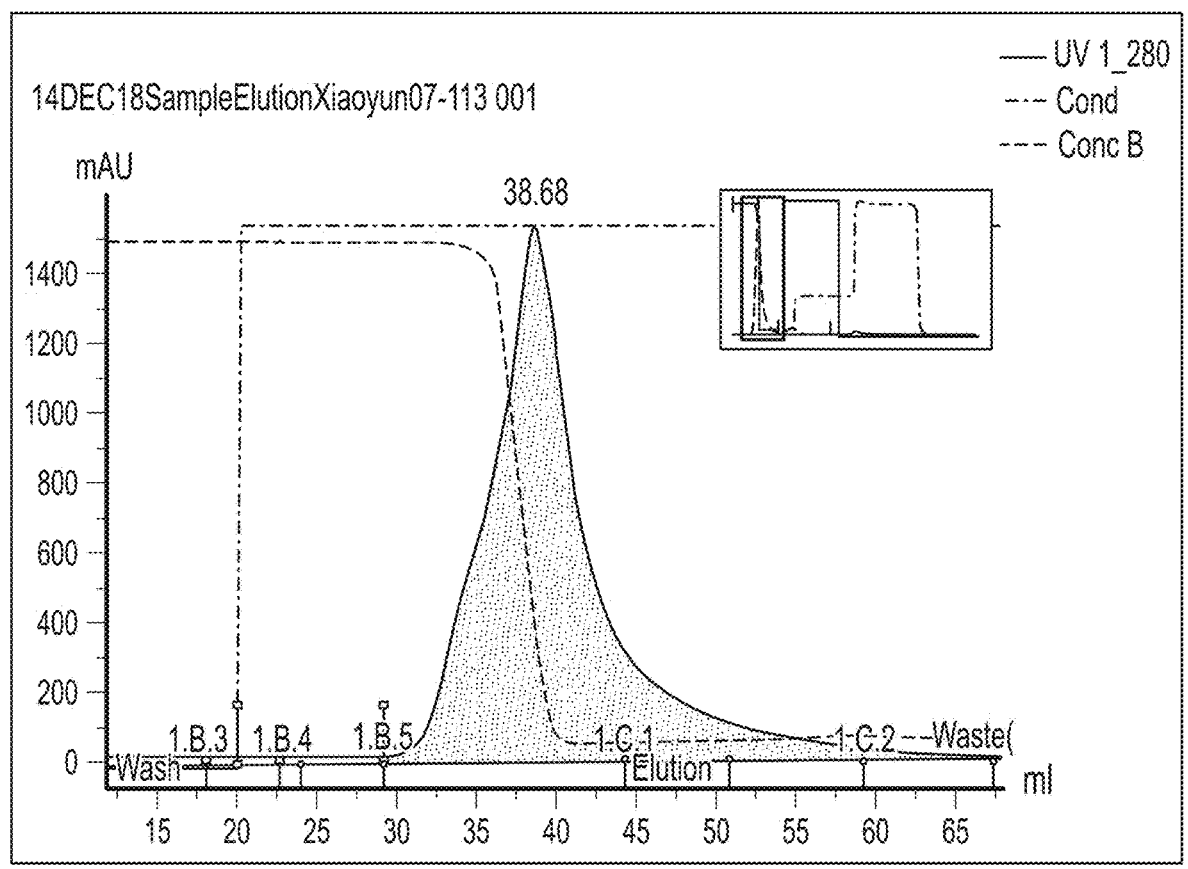

FIG. 142 is a line graph showing the chromatographic profile of TGFRt15-21s137L protein containing cell culture supernatant following binding and elution on anti-TF antibody resin.

Figure 143:
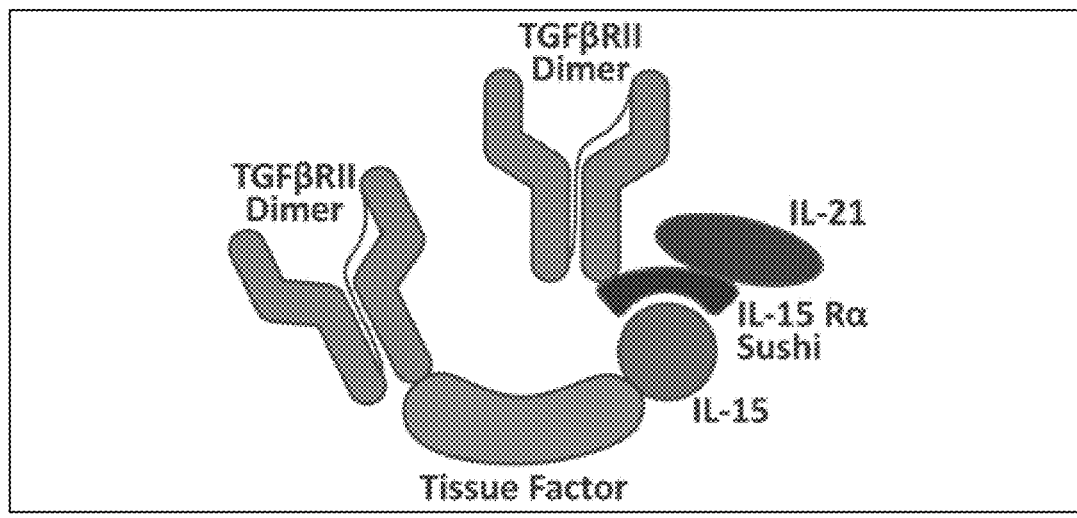

FIG. 143 shows a schematic of the TGFRt15-TGFRs21 construct.

Figure 144:
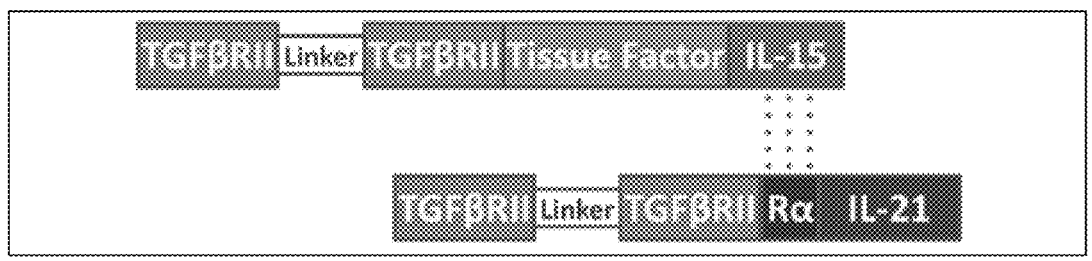

FIG. 144 shows an additional schematic of the TGFRt15-TGFRs21 construct.

Figure 145:
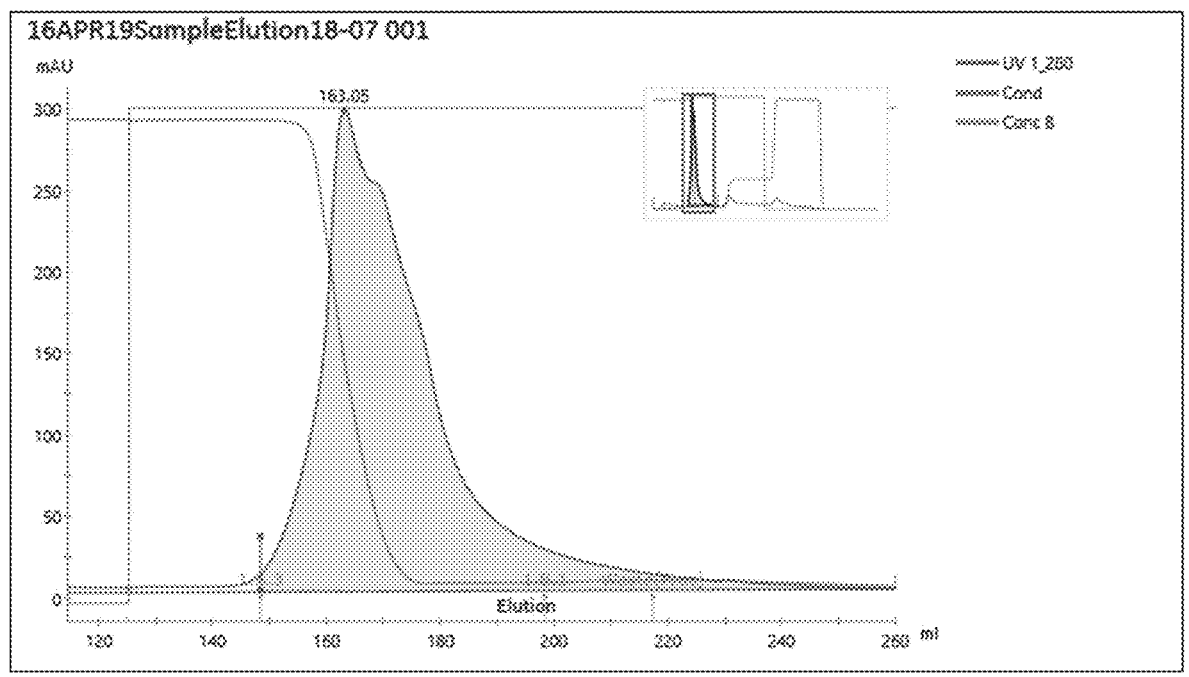

FIG. 145 is a line graph showing the chromatographic profile of TGFRt15-TGFRs21 protein containing cell culture supernatant following binding and elution on anti-TF antibody resin.

Figure 146:
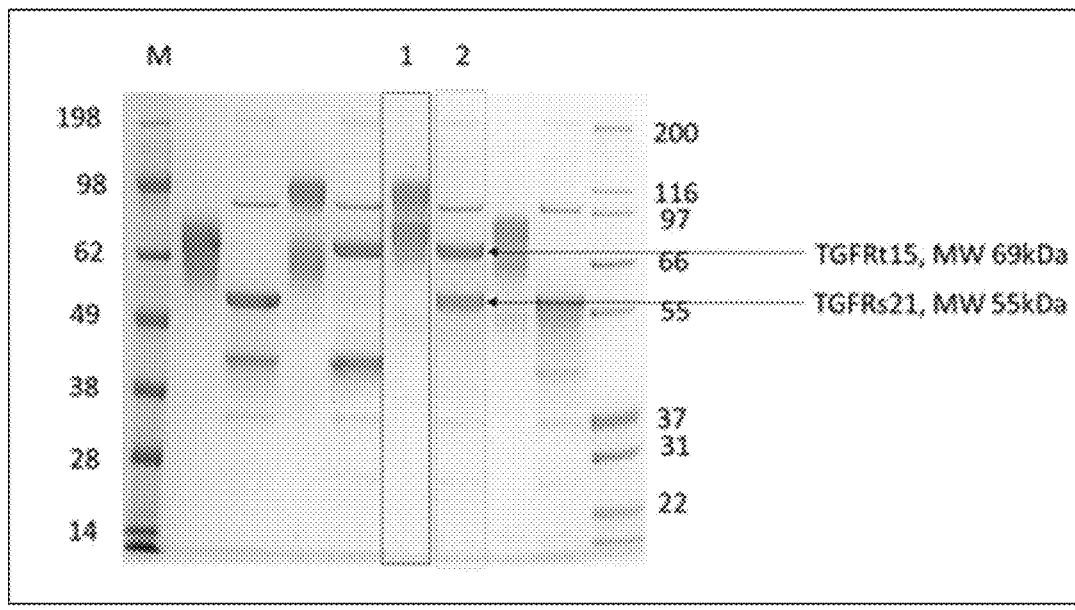

FIG. 146 shows TGFRt15-TGFRs21 before and after deglycosylation as analyzed by reduced SDS-PAGE.

Figure 147A:
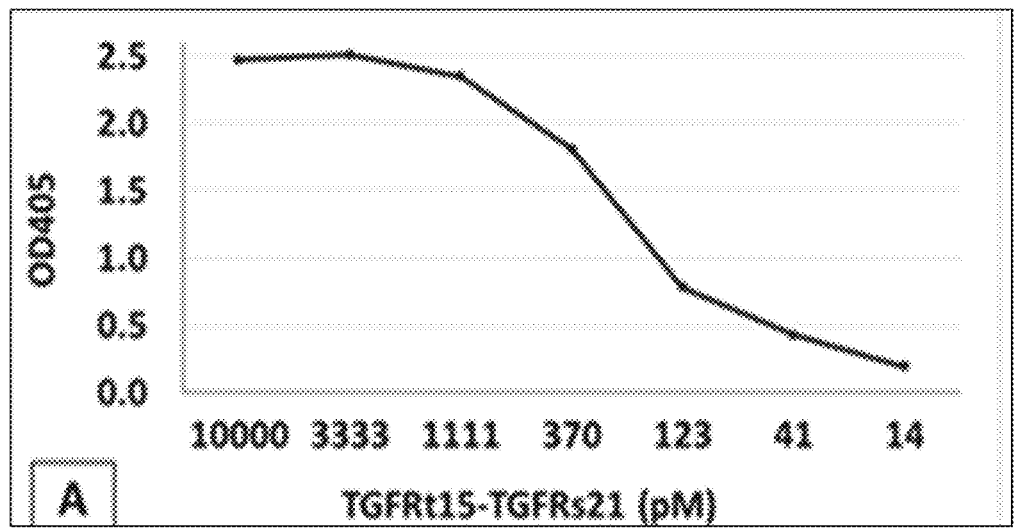
Figure 147B:
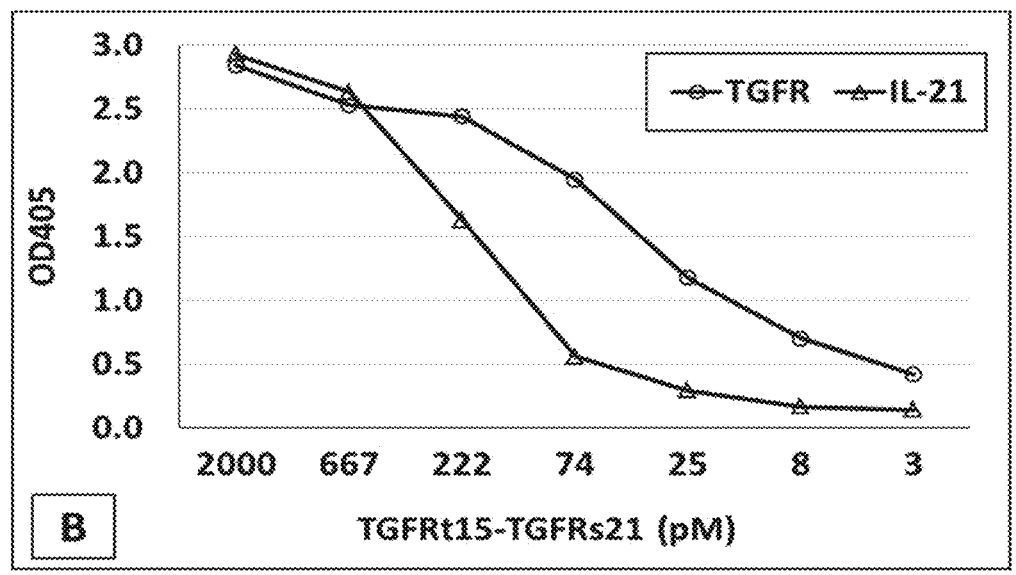

FIGS. 147A and 147B show detection of components of TGFRt15-TGFRs21 using ELISA.

Figure 148A:
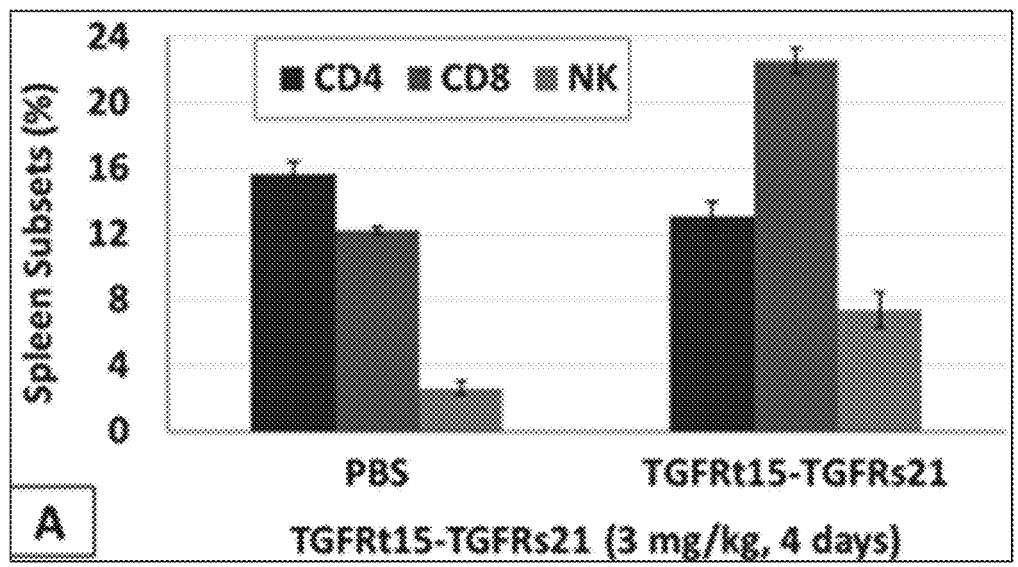
Figure 148B:
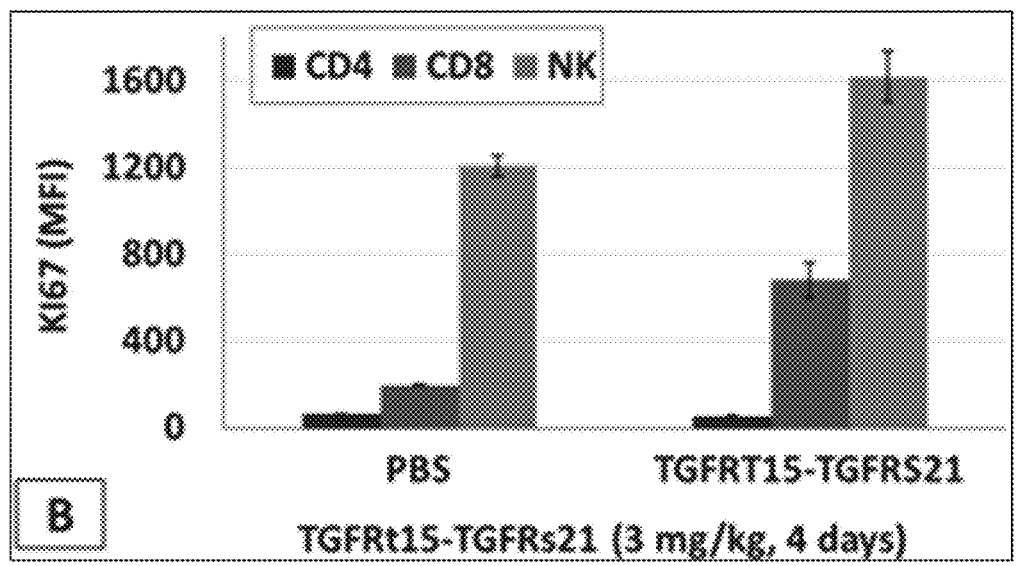

FIGS. 148A and 148B show the percentages and proliferation of $CD4^+$ T cells, $CD8^+$ T cells, and natural killer (NK) cells present in the spleen of control-treated and TGFRt15-TGFRs21-treated mice.

Figure 149:
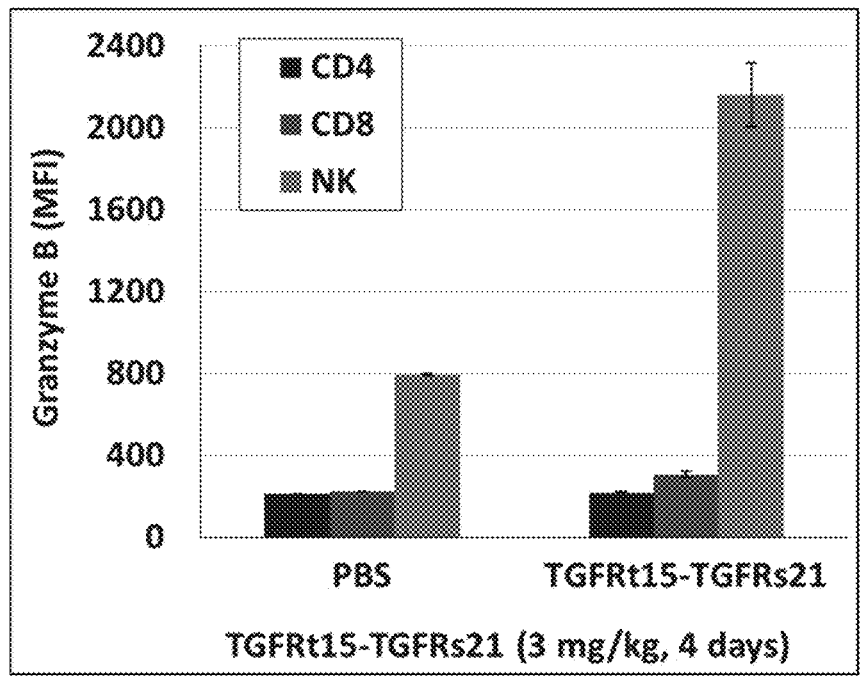

FIG. 149 shows upregulation of Granzyme B expression of splenocytes in mice treated with TGFRt15-TGFRs21.

Figure 150:
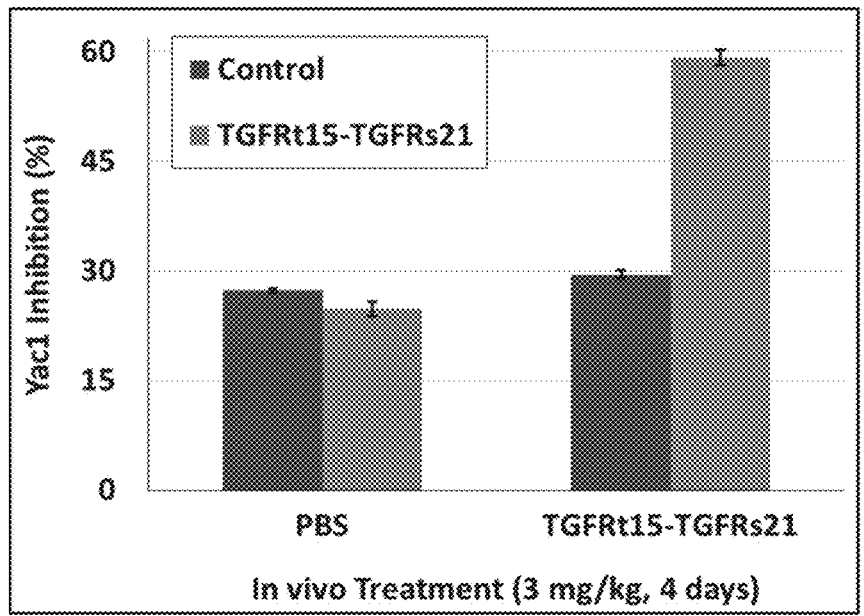

FIG. 150 shows enhancement of cytotoxicity of splenocytes by TGFRt15-TGFRs21 in C57BL/6 Mice.

Figure 151:
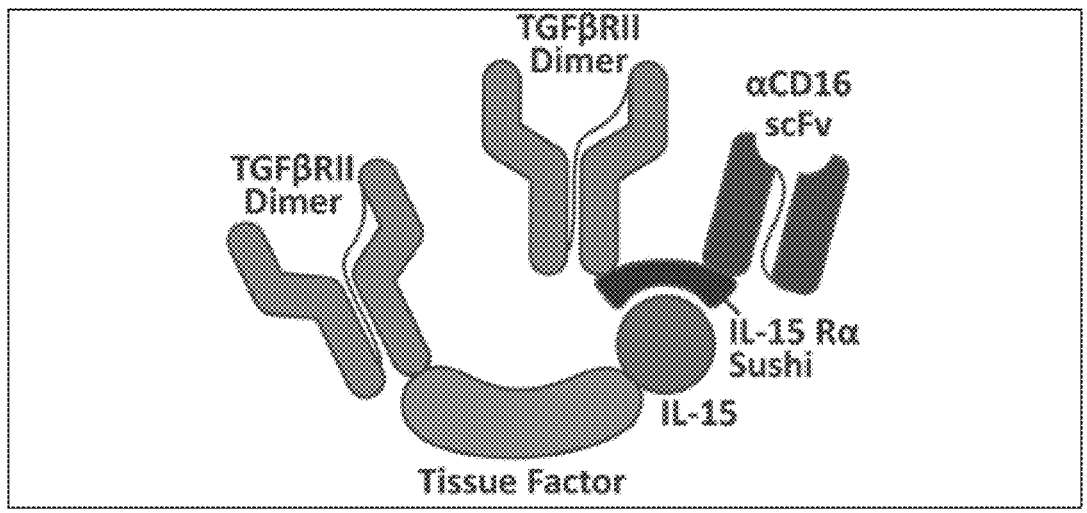

FIG. 151 shows a schematic of the TGFRt15-TGFRs16 construct.

Figure 152:
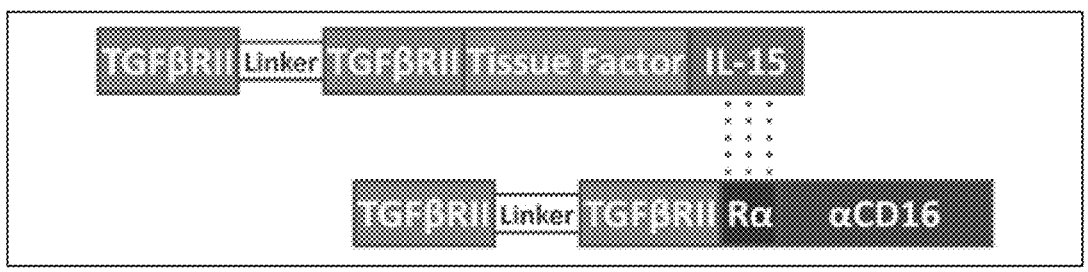

FIG. 152 shows an additional schematic of the TGFRt15-TGFRs16 construct.

Figure 153:
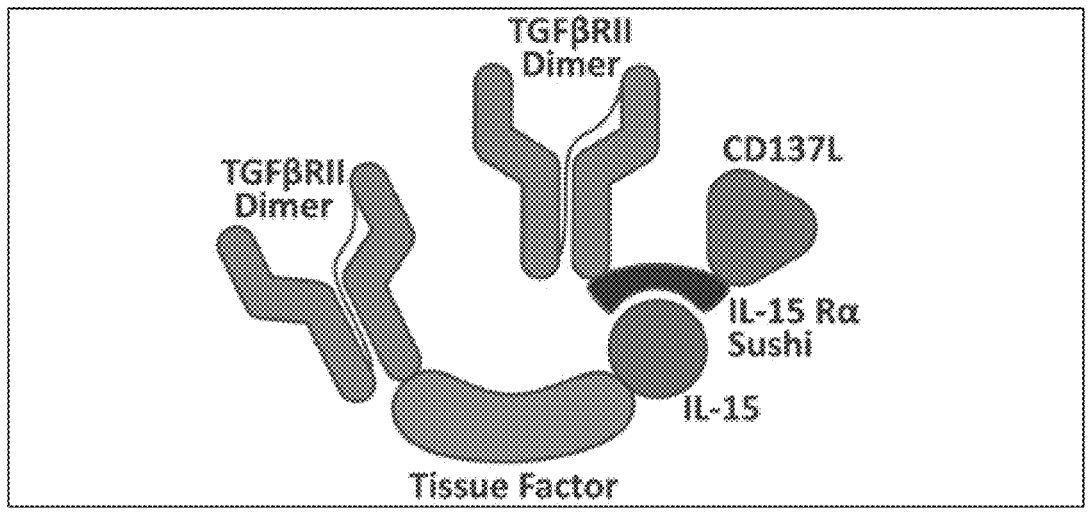

FIG. 153 shows a schematic of the TGFRt15-TGFRs137L construct.

Figure 154:
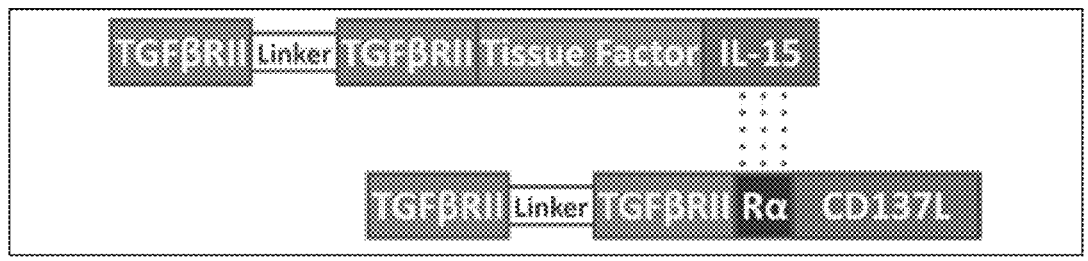

FIG. 154 shows an additional schematic of the TGFRt15-TGFRs137L construct.

Figure 155:
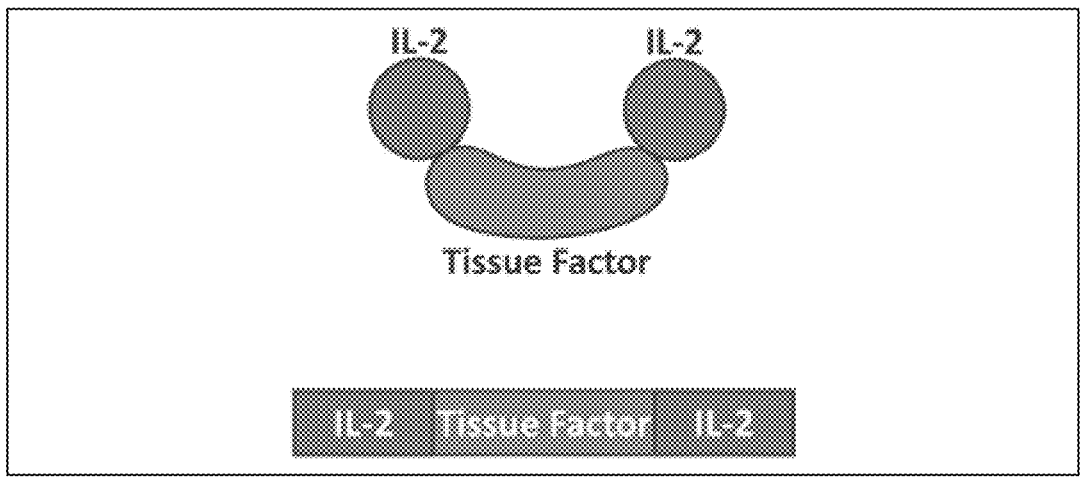

FIG. 155 are schematic diagrams of an exemplary 2t2 single-chain chimeric polypeptide.

Figure 156:
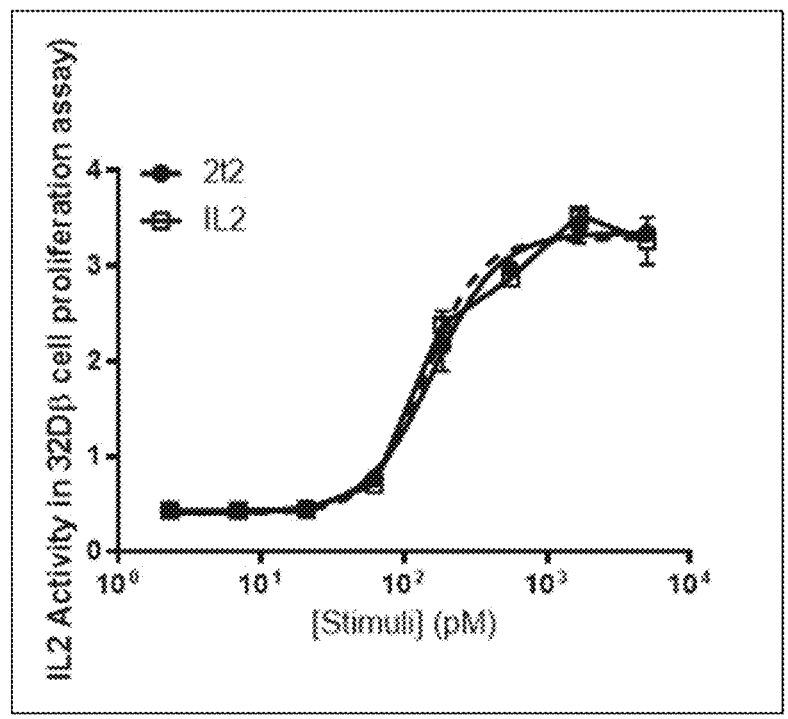

FIG. 156 shows IL-2 activity in 2t2 as compared to recombinant IL-2 using a 32Dβ cell proliferation assay.

Figure 157:
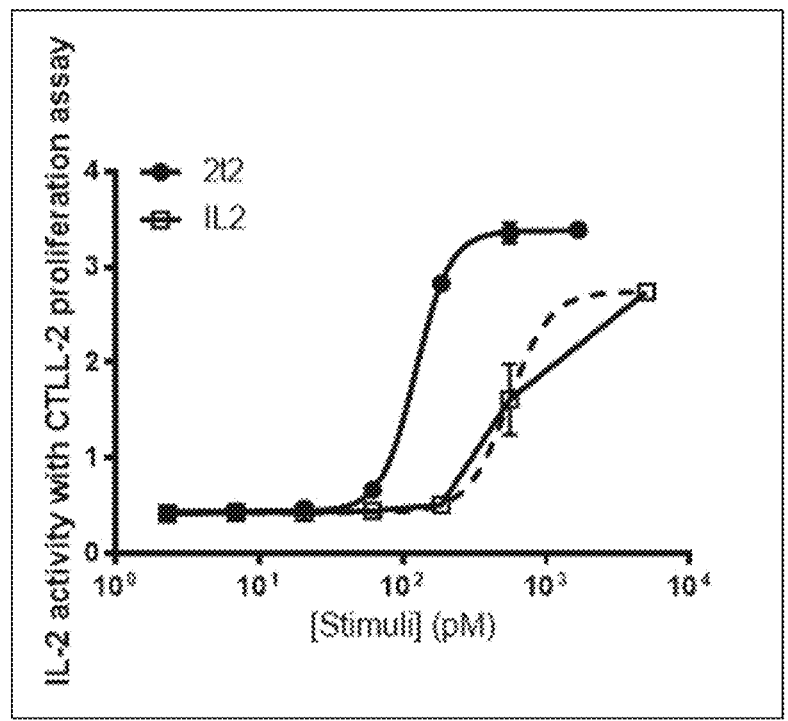

FIG. 157 shows IL-2 activity in 2t2 as compared to recombinant IL-2 using a CTLL-2 cell proliferation assay.

Figure 158:
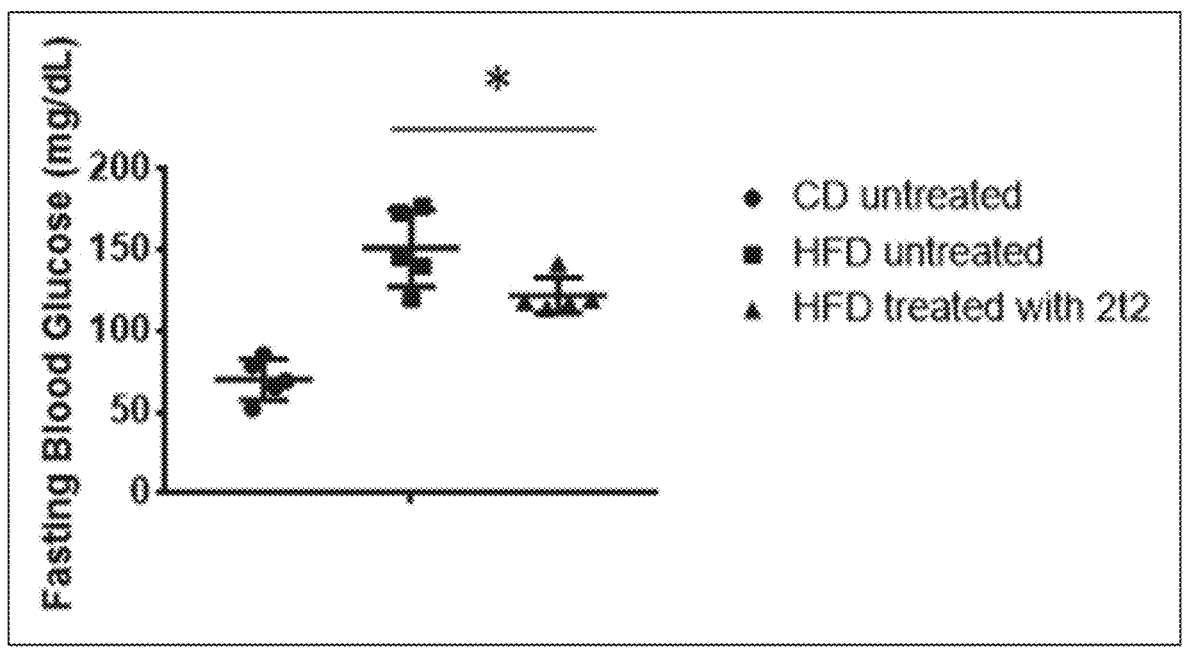

FIG. 158 shows the fasting blood glucose levels in $ApoE^{-/-}$ mice fed with standard chow or a high fat diet and treated with a PBS control (untreated) or with 2t2.

Figure 159:
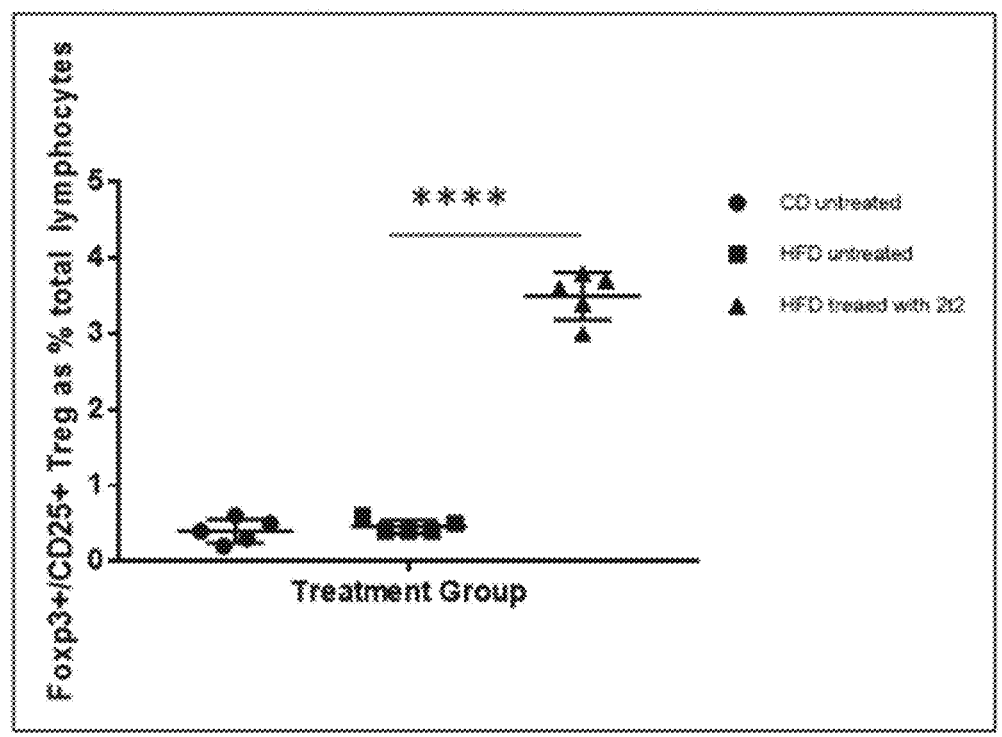

FIG. 159 shows the ratio of $CD4^+CD25^+FoxP3^+$ T regulatory cells in blood lymphocytes from $ApoE^{-/-}$ mice fed with standard chow or a high fat diet and treated with a PBS control (untreated) or with 2t2.

Figure 160:
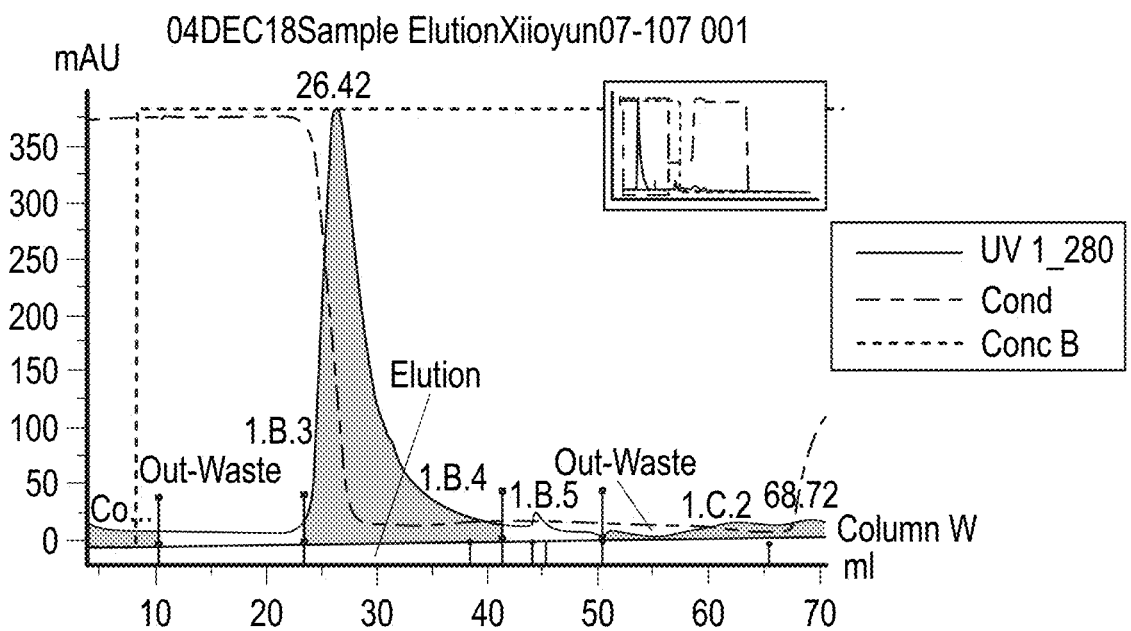

FIG. 160 is a line graph showing the chromatographic profile of 2t2 protein containing cell culture supernatant following binding and elution on anti-TF antibody resin.

Figure 161:
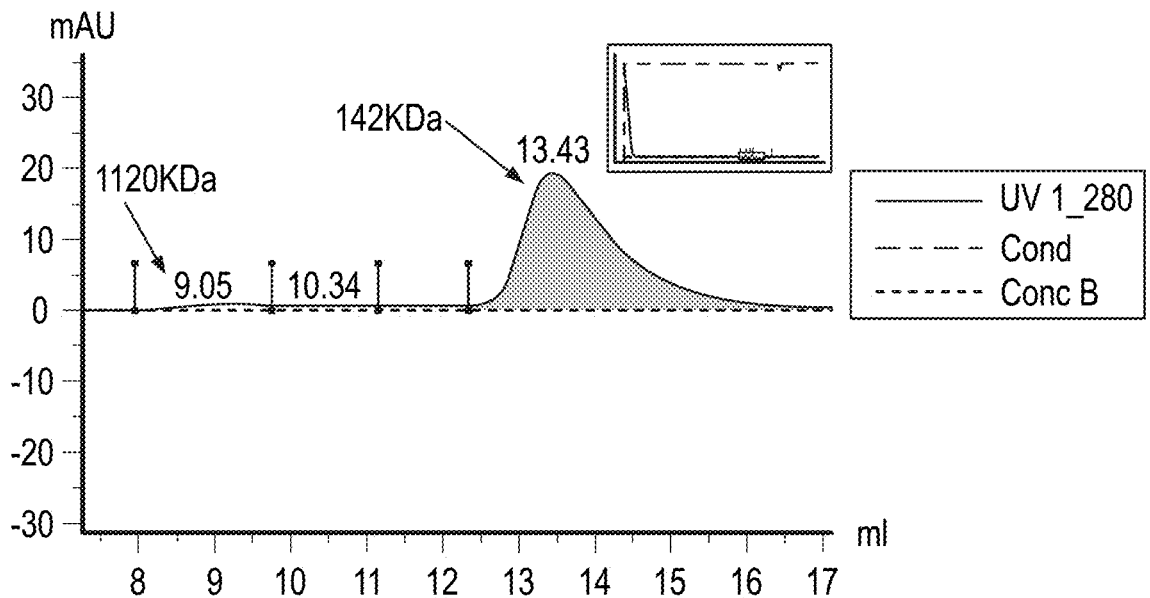

FIG. 161 shows an analytical SEC profile of 2t2.

Figure 162A:
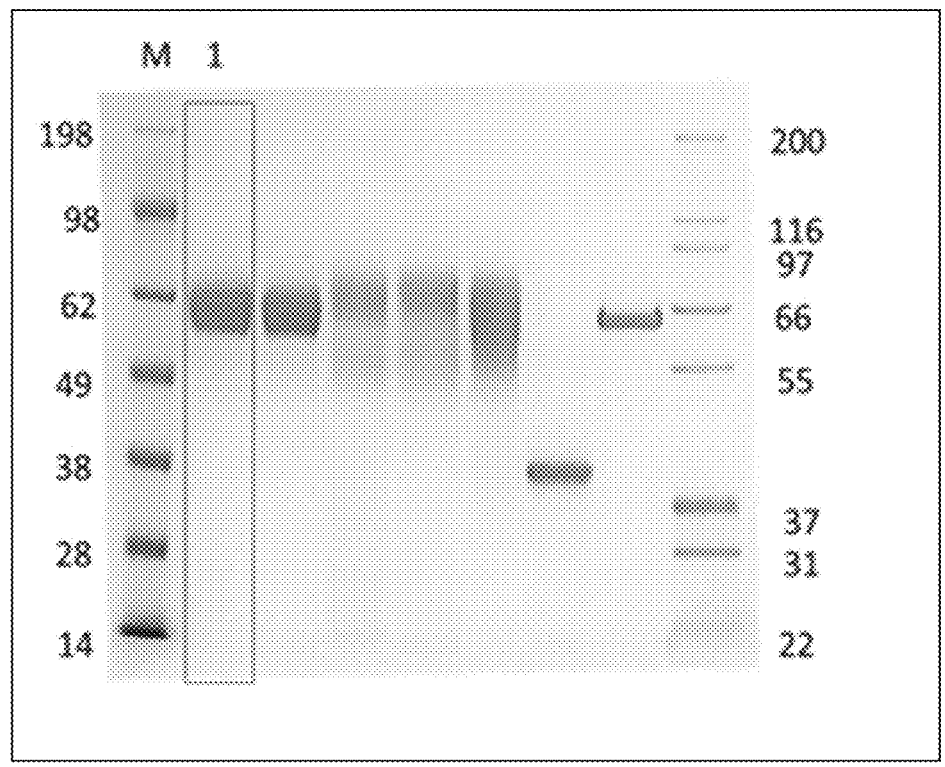
Figure 162B:
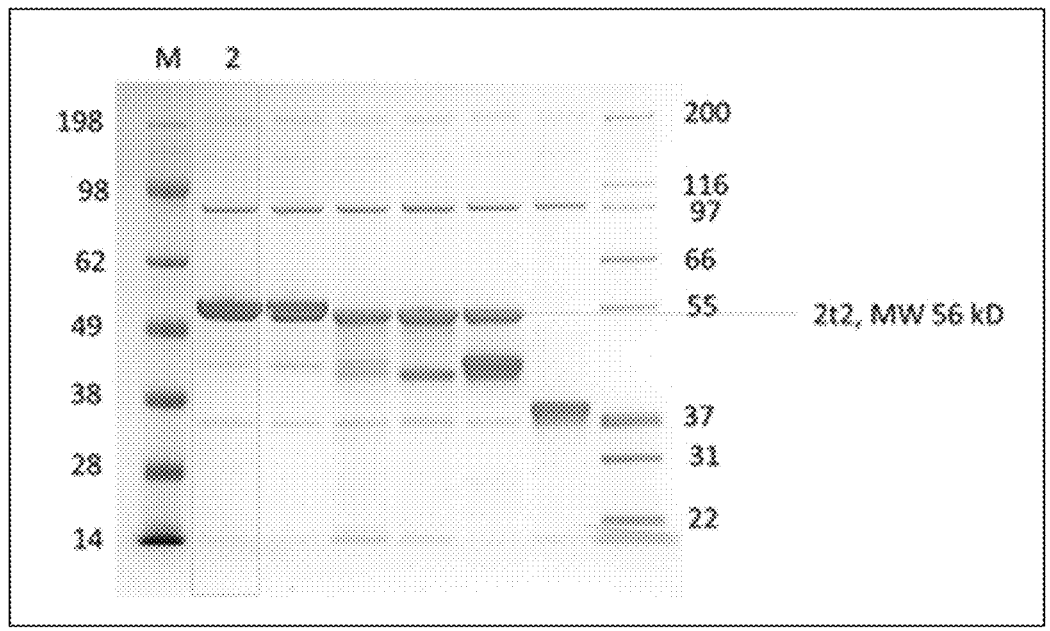

FIGS. 162A and 162B show reduced SDS-PAGE analysis of 2t2 before and after deglycosylation. FIG. 162A shows reduced SDS-PAGE analysis of 2t2 before deglycosylation. FIG. 162B shows reduced SDS-PAGE analysis of 2t2 after deglycosylation.

Figure 163A:
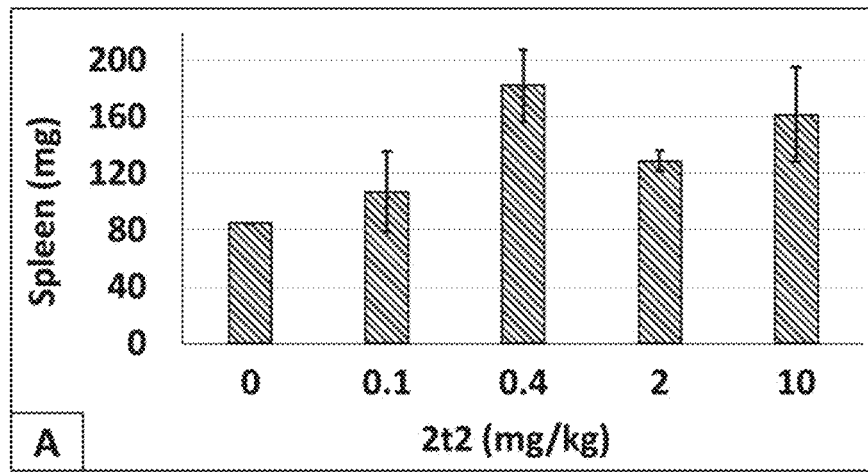
Figure 163B:
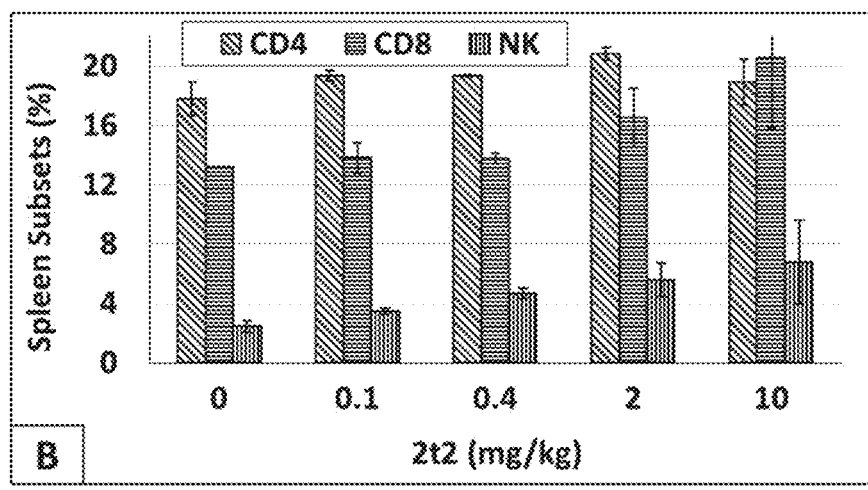

FIGS. 163A and 163B show results of immunostimulation in C57BL/6 mice using 2t2. FIG. 163A shows spleen weight following treatment with 2t2. FIG. 163B shows the percentages of immune cell types following 2t2 treatment.

Figure 164:
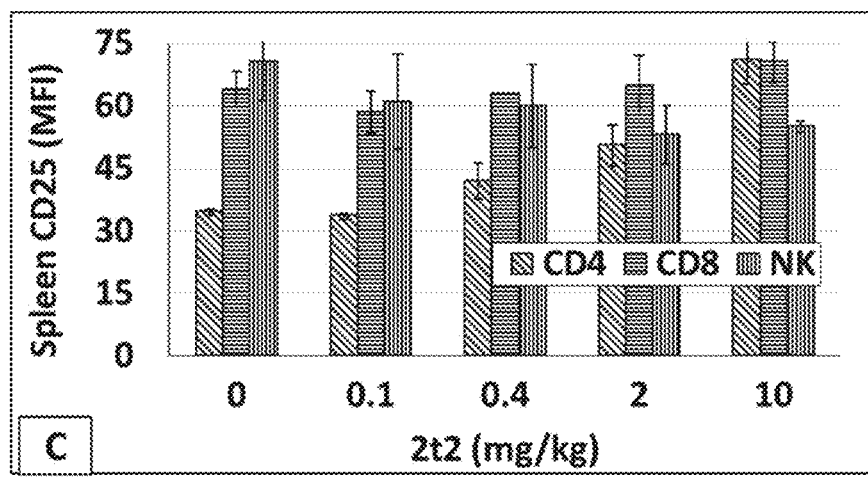

FIG. 164 shows upregulation of CD25 expression of $CD4^+$ T cells in mice treated with 2t2.

Figure 165:
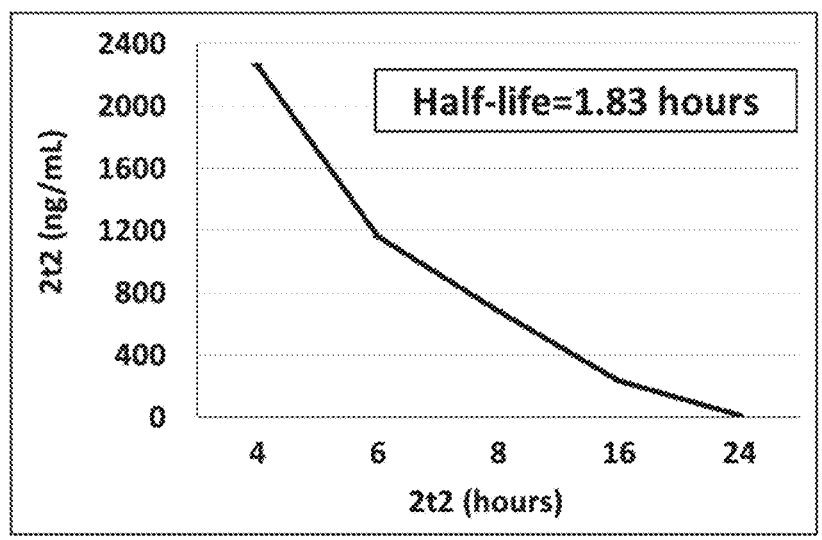

FIG. 165 shows the pharmacokinetics of 2t2 in C57BL/6 mice.

Figure 166A:
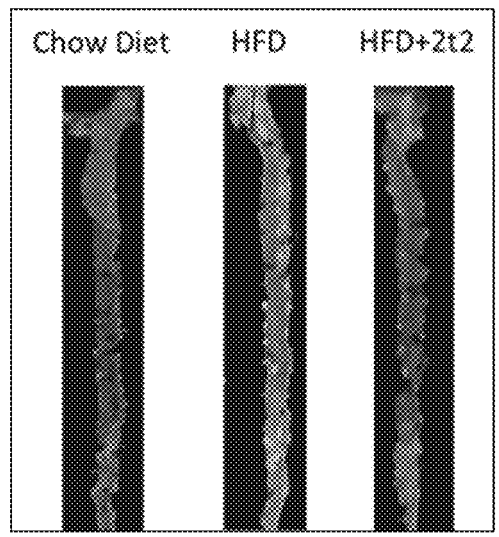
Figure 166B:
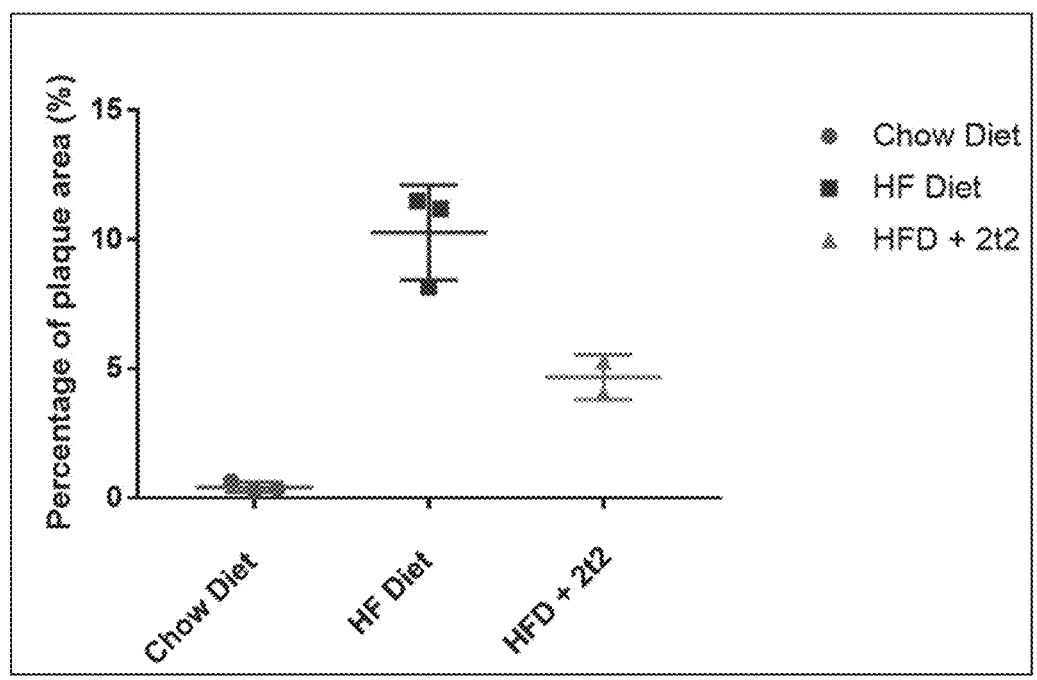

FIGS. 166A and 166B show effects of 2t2 in attenuating the formation of high fat-induced atherosclerotic plaques in $ApoE^{-/-}$ mice. FIG. 166A shows a representative view of atherosclerotic plaques from $ApoE^{-/-}$ mice fed with standard chow or a high fat diet and treated with either PBS control or 2t2. FIG. 166B shows the results of quantitative analysis of atherosclerotic plaques of each group.

Figure 167:
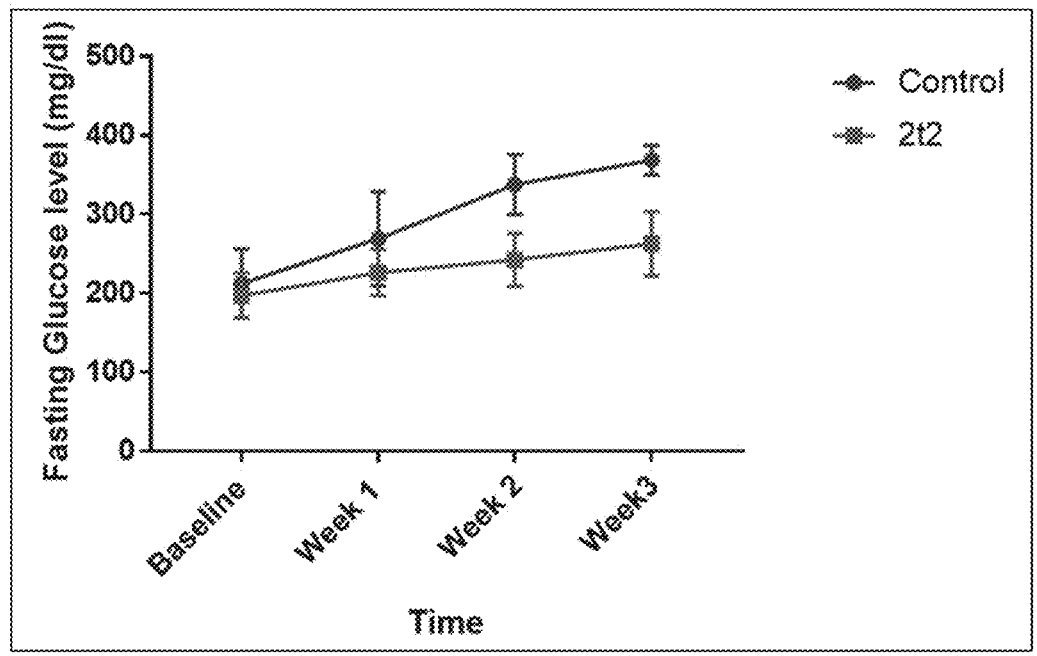

FIG. 167 shows fasting glucose levels in 2t2 treated-mice as compared to control-treated mice.

Figure 168:
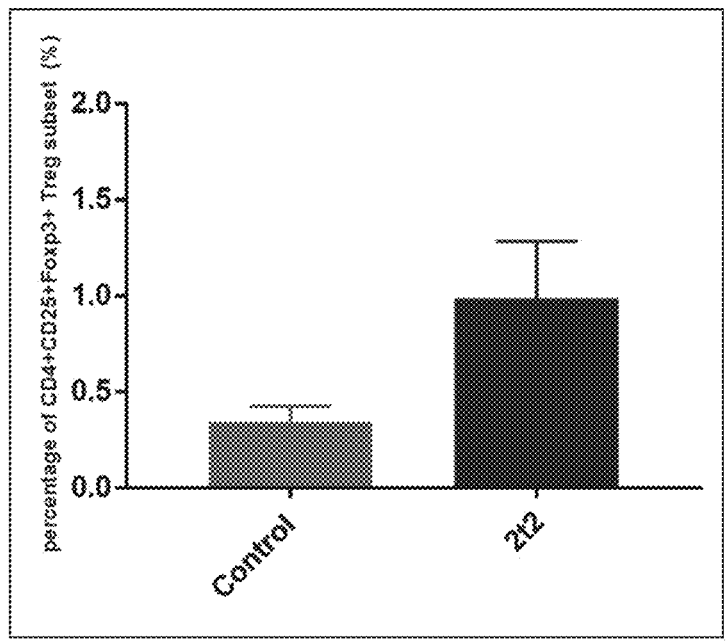

FIG. 168 shows the percentage of $CD4^+CD25^+FoxP3^+$ Tregs in blood lymphocytes from mice treated with 2t2 and control-treated mice.

Figure 169:
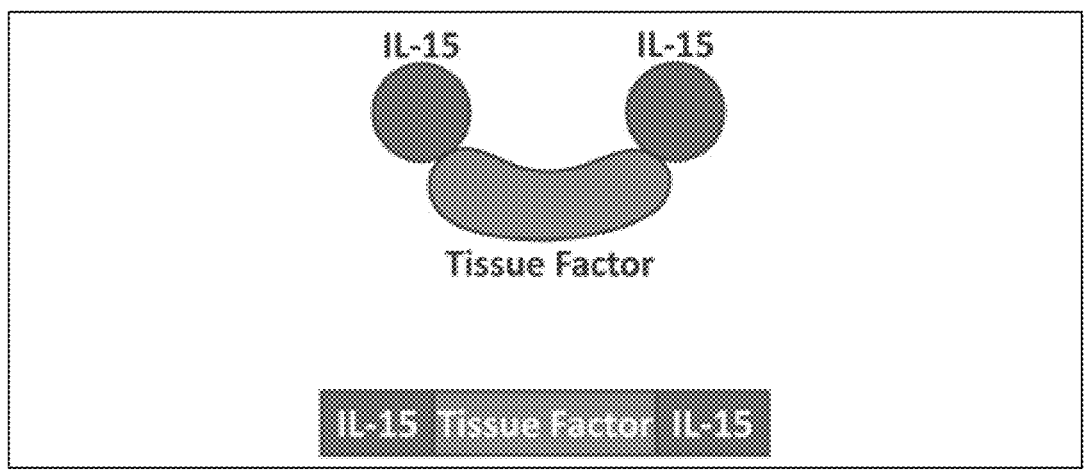

FIG. 169 are schematic diagrams of an exemplary 15t15 single-chain chimeric polypeptide.

Figure 170:
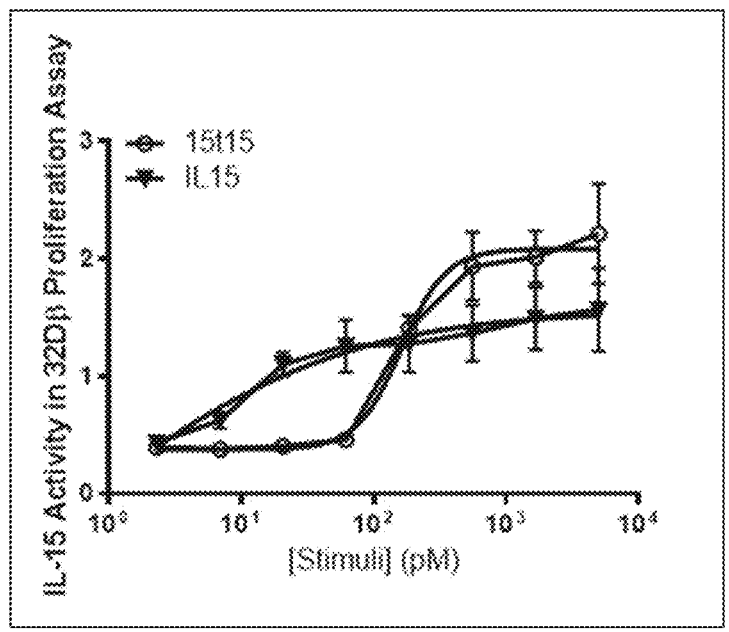

FIG. 170 shows the IL-15 activity of 15t15 as compared to recombinant IL-15 in a 32Dβ cell proliferation assay.

Figure 171:
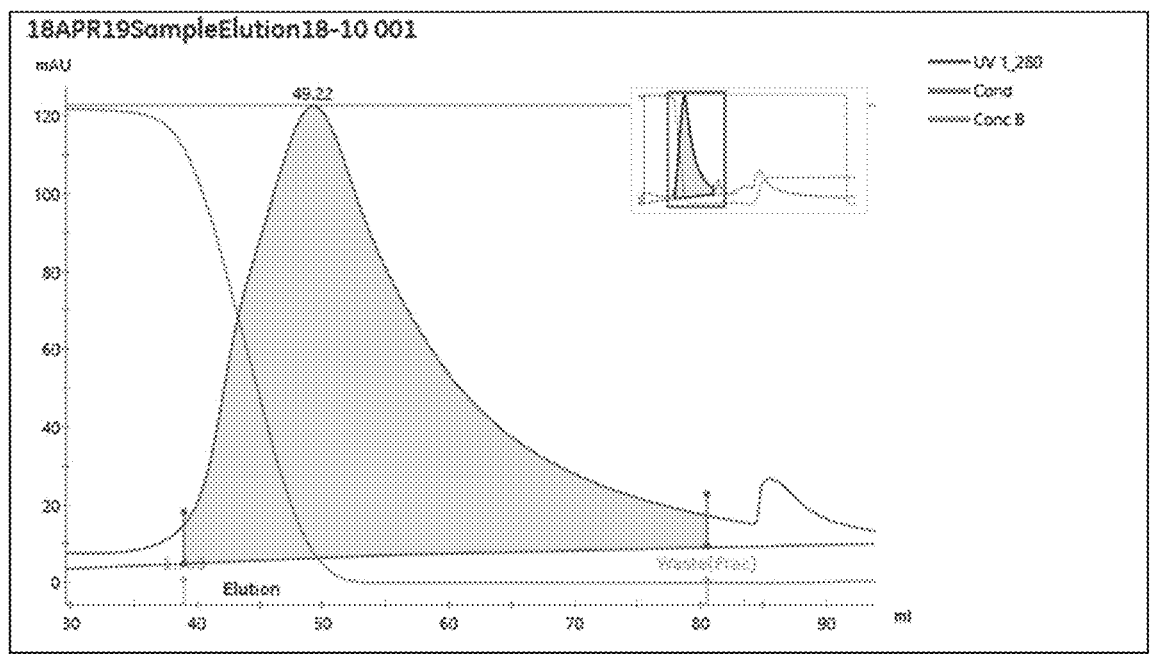

FIG. 171 is a line graph showing the chromatographic profile of 15t15 protein containing cell culture supernatant following binding and elution on anti-TF resin.

Figure 172A:
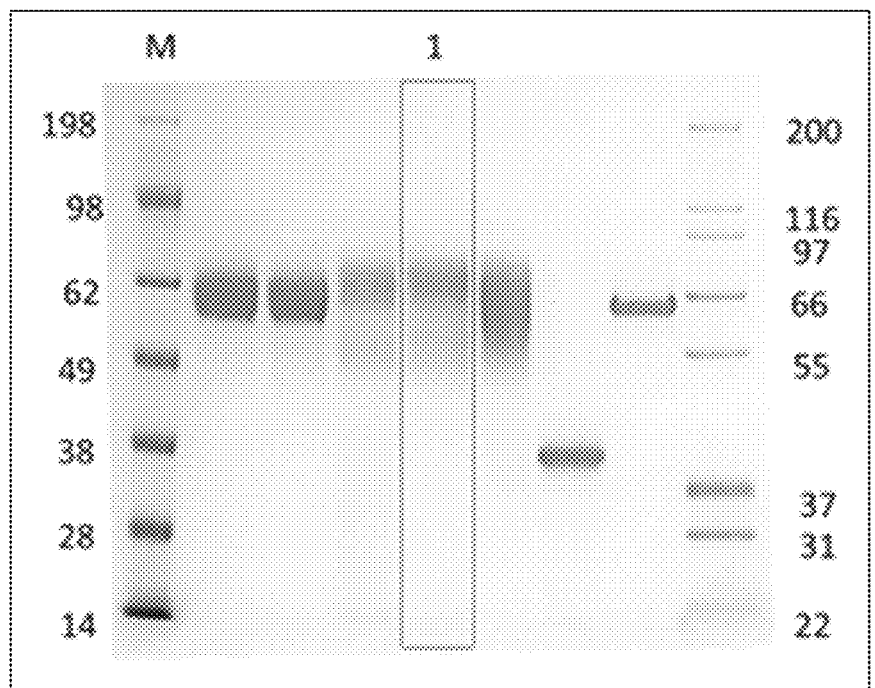
Figure 172B:
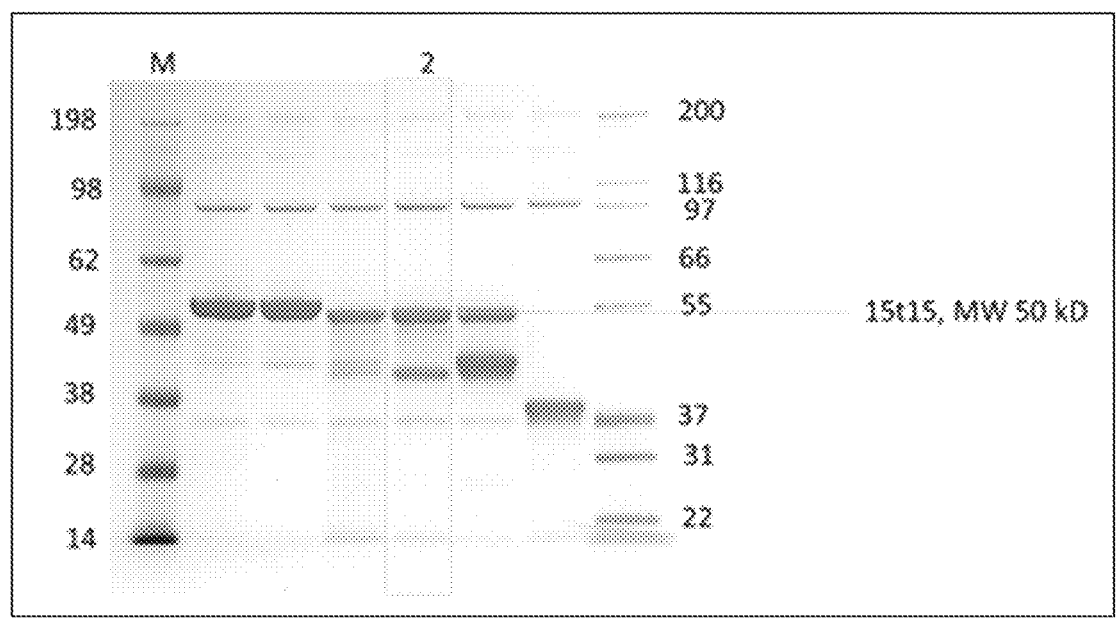

FIGS. 172A and 172B show reduced SDS-PAGE analysis of 15t15 before and after deglycosylation. FIG. 172A shows reduced SDS-PAGE analysis of 15t15 before deglycosylation. FIG. 172B shows reduced SDS-PAGE analysis of 15t15 after deglycosylation.

Figure 173:
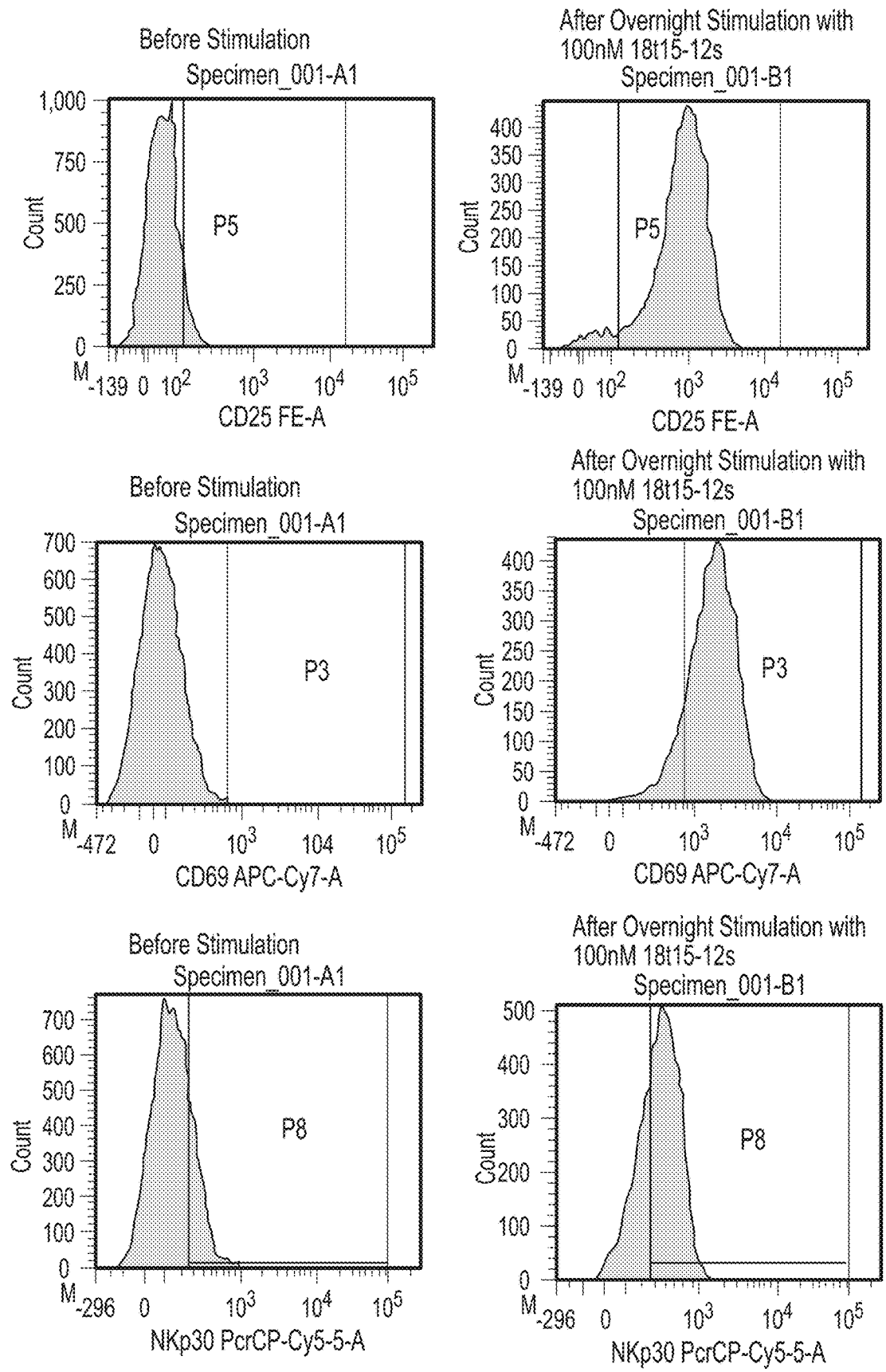
Figure 173:
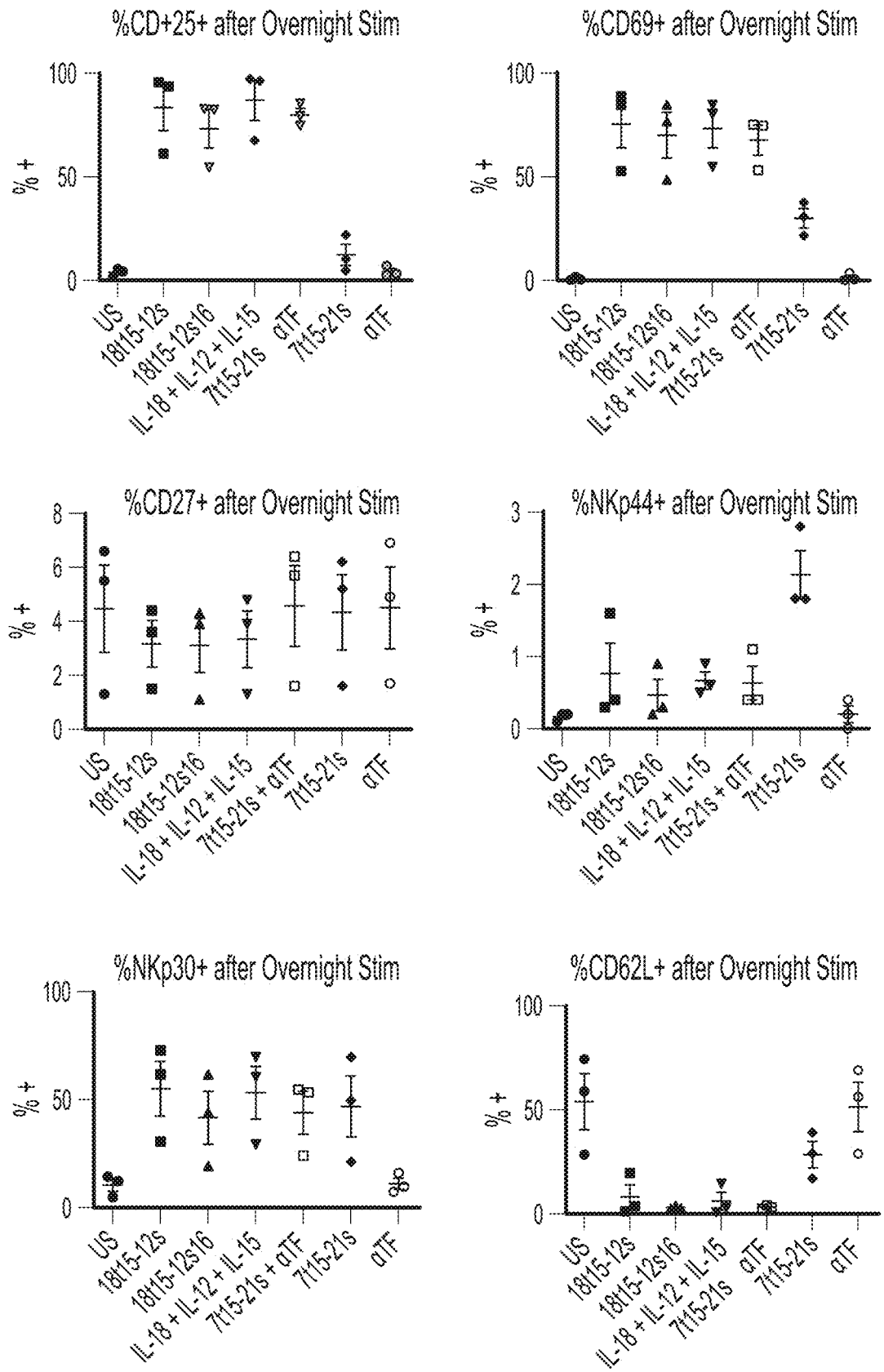

FIG. 173 is a set of histograms and a set of graphs showing the change in the surface phenotype of NK cells after stimulation with 18t15-12s, 18t15-12s16, and 7t15-21s+anti-TF antibody.

Figure 174:
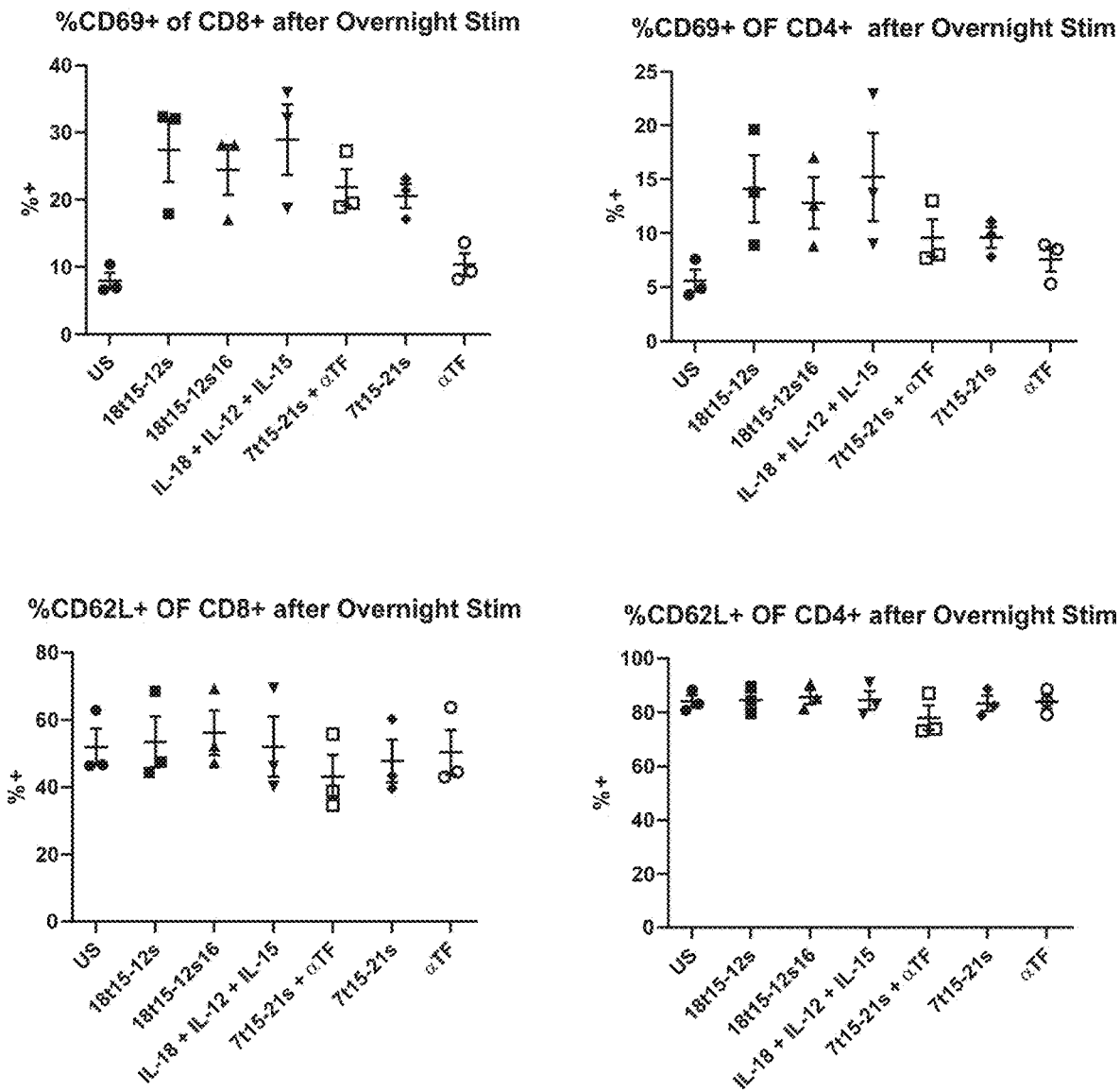

FIG. 174 is a set of graphs showing changes in the surface phenotype of lymphocyte populations after stimulation with 18t15-12s; 18t15-12s16; a mixture of single cytokines rhIL15, rhIL18, and rhIL-12; 7t15-21s+anti-TF antibody; 7t15-21s; or anti-TF antibody.

Figure 175:
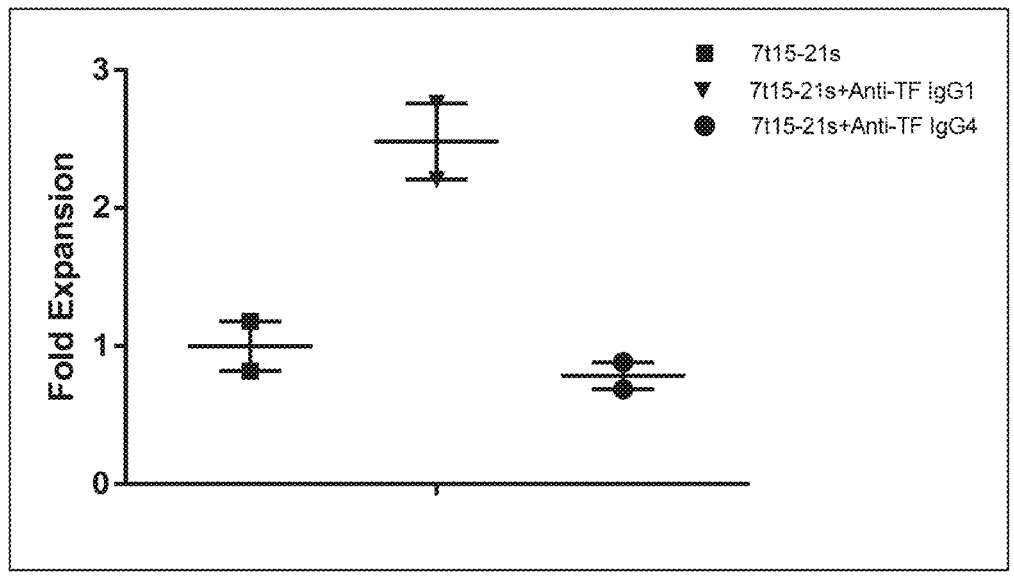

FIG. 175 is a graph of the increase in proliferation of NK cells in vitro after stimulation with a multi-chain construct alone or in the presence of anti-TF IgG1 or anti-TF IgG4.

Figure 176:
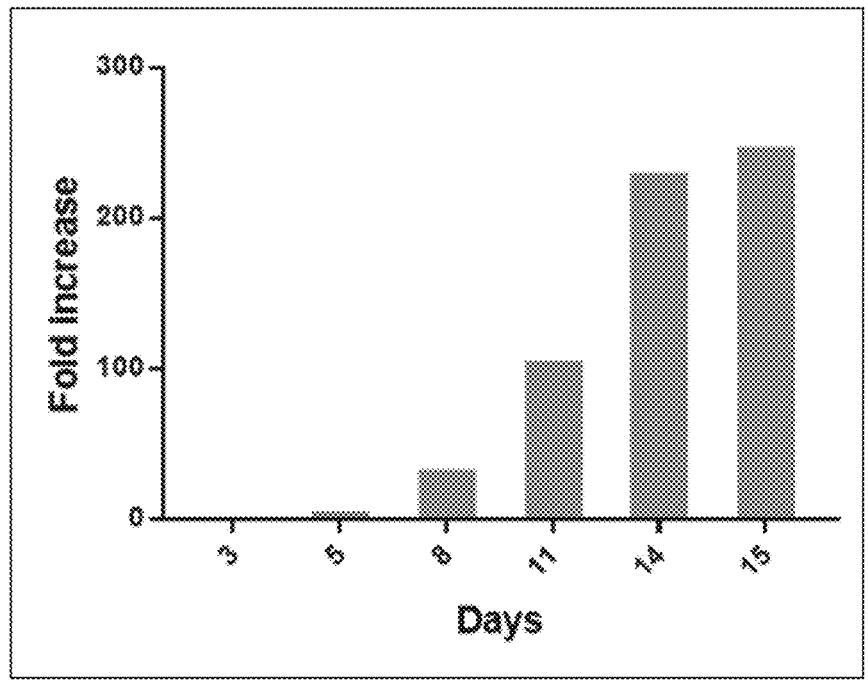

FIG. 176 is a graph of the increase in proliferation over time of NK cells in vitro after stimulation with the combination of 7t15-21s and anti-TF antibody.

Figure 177:
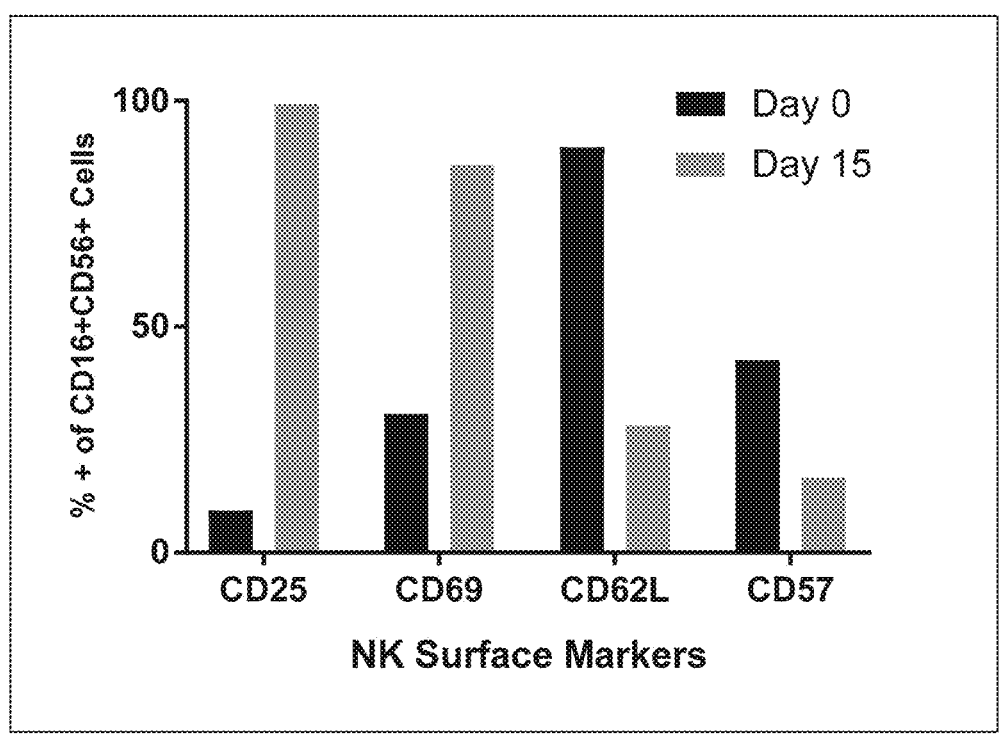

FIG. 177 is a graph of the changes in surface phenotype on 7t15-21s+anti-TF antibody-expanded NK cells.

Figure 178:
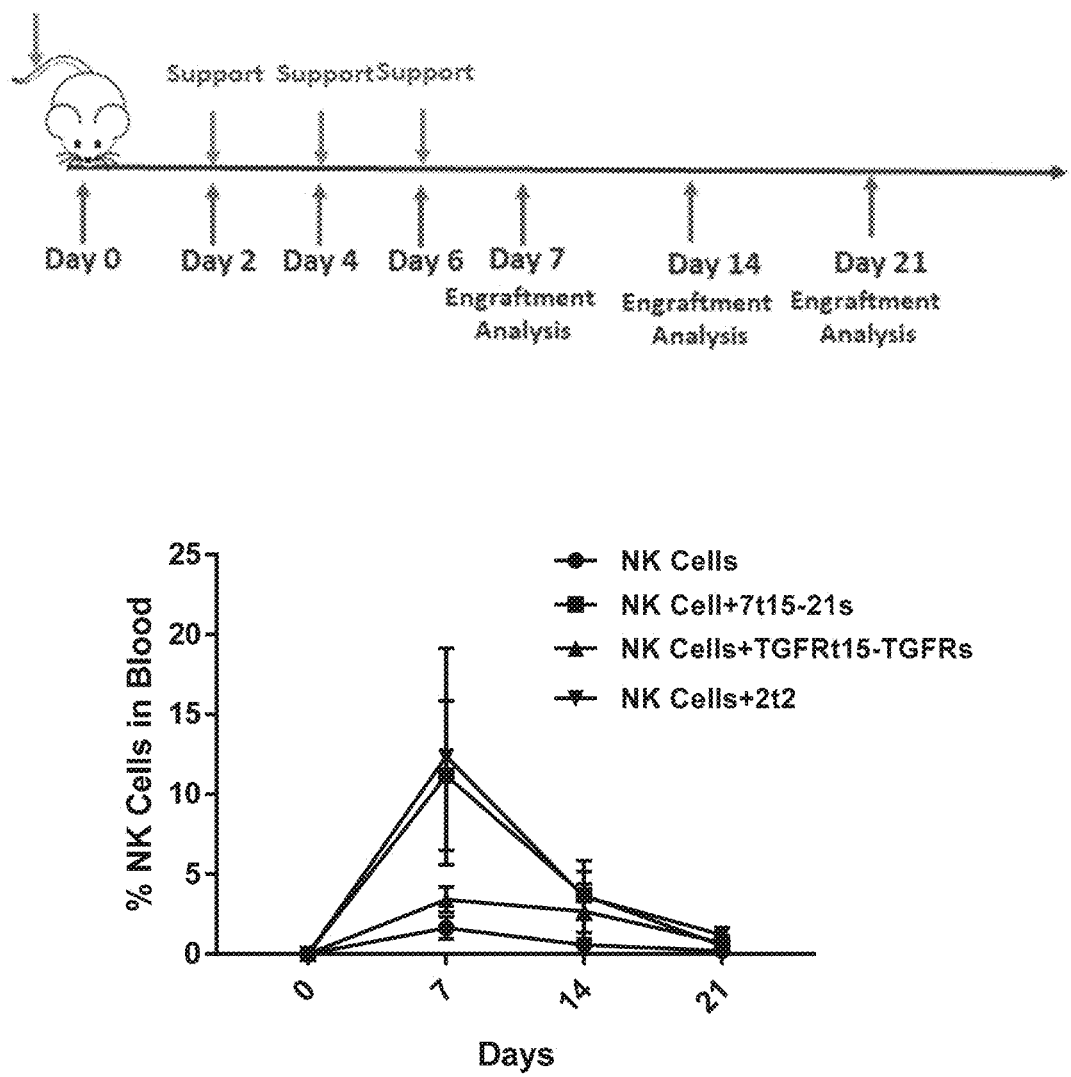

FIG. 178 is a schematic and a set of graphs showing the persistence of 7t15-21s and anti-TF antibody-expanded NK cells in NSG mice following treatment with 7t15-21, TGFRt15-TGFRs or 2t2.

Figure 179A:
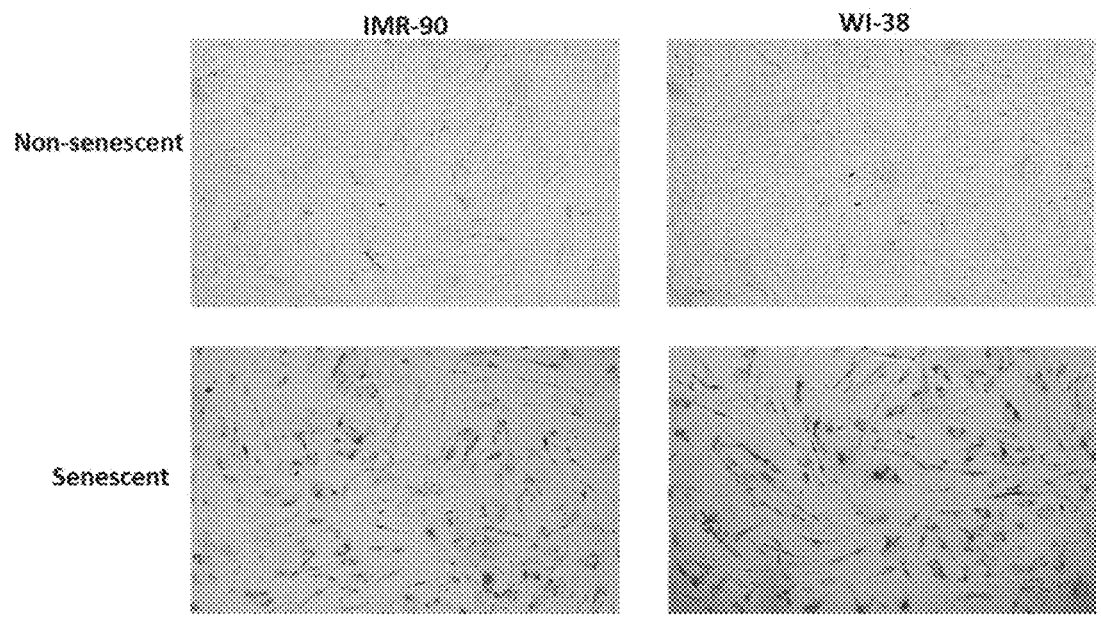
Figure 179B:
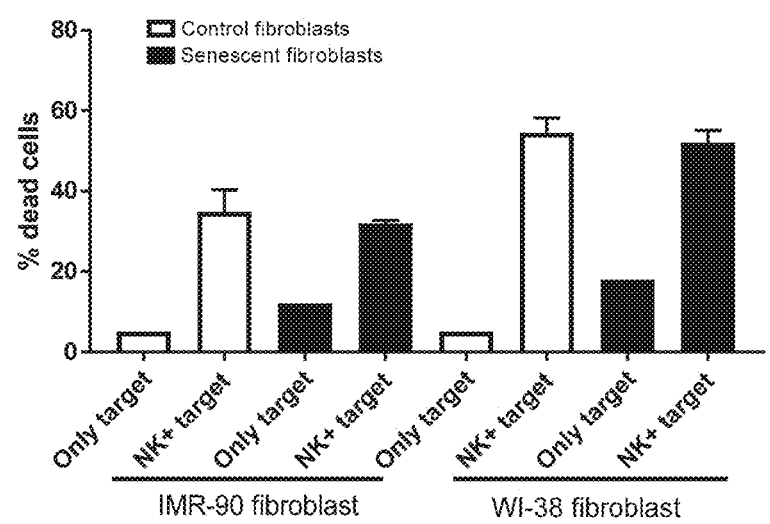

FIGS. 179A and 179B is a set of images and a set of graphs showing killing of chemically-induced senescent human fibroblasts by 7t15-21s+anti-TF antibody-expanded NK cells.

Figure 180A:
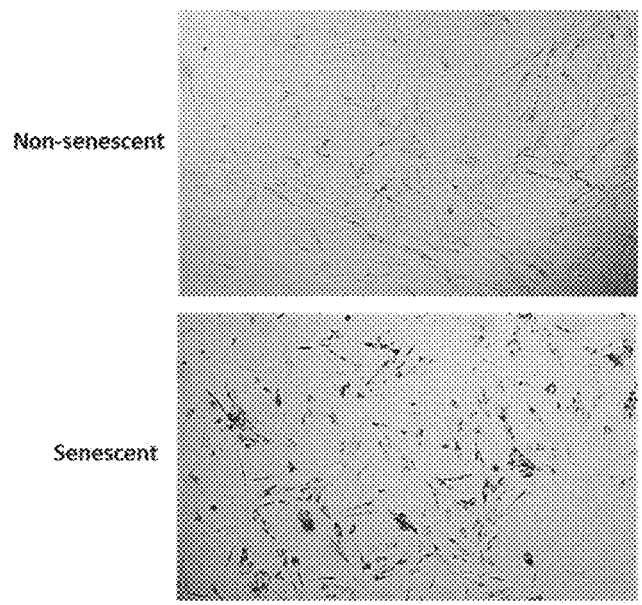
Figure 180B:
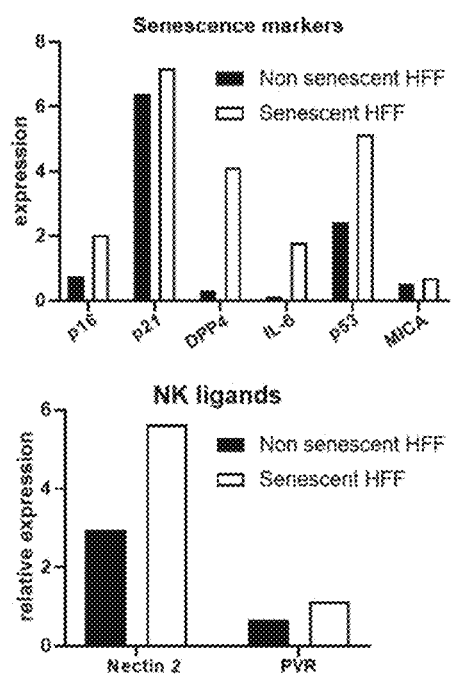
Figure 180C:
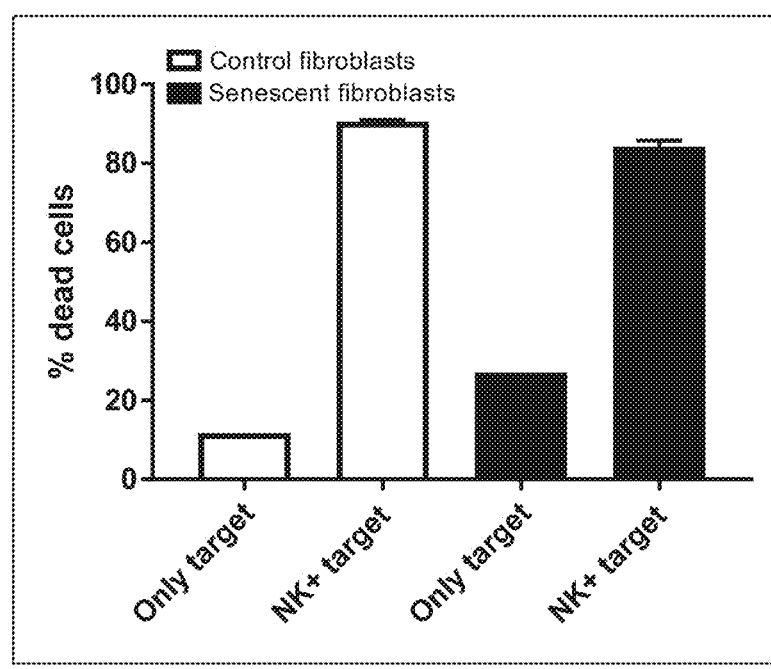

FIG. 180A-180C is a set of images and a set of graphs showing killing of UV-induced senescent human fibroblast by 7t15-21s+anti-TF antibody-expanded NK cells.

Figure 181:
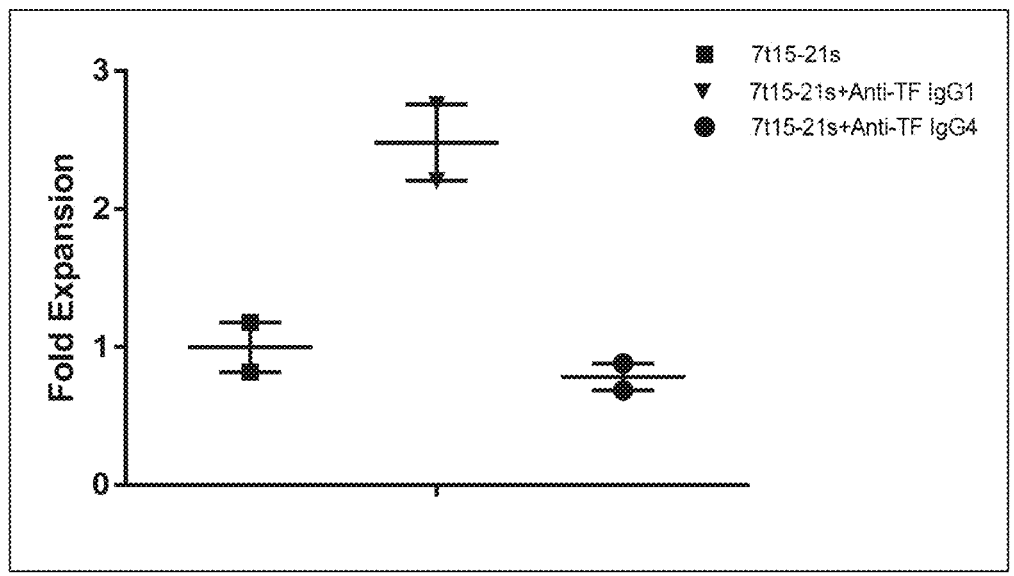

FIG. 181 shows proliferation of NK cells upon stimulation with 7t15-21s, 7t15-21s+anti-TF antibody (IgG1), or 7t15-21s+anti-TF antibody (IgG4).

Figure 182:
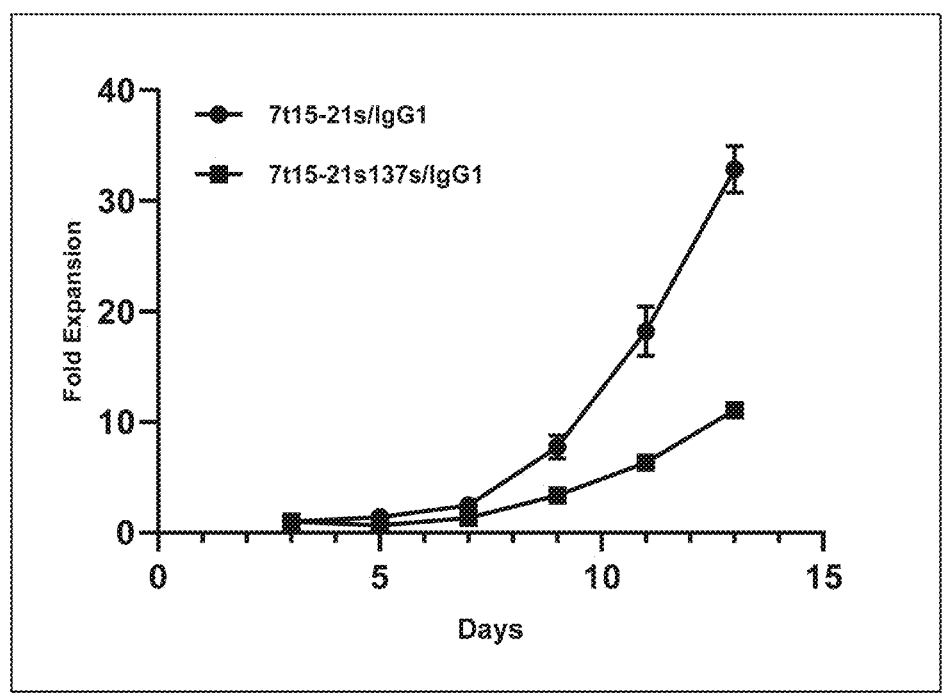

FIG. 182 shows NK cell expansion induced by the 7t15-21s+anti-TF antibody (IgG1) and by the 7t15-21s137L (short version)+anti-TF antibody (IgG1).

Figure 183:
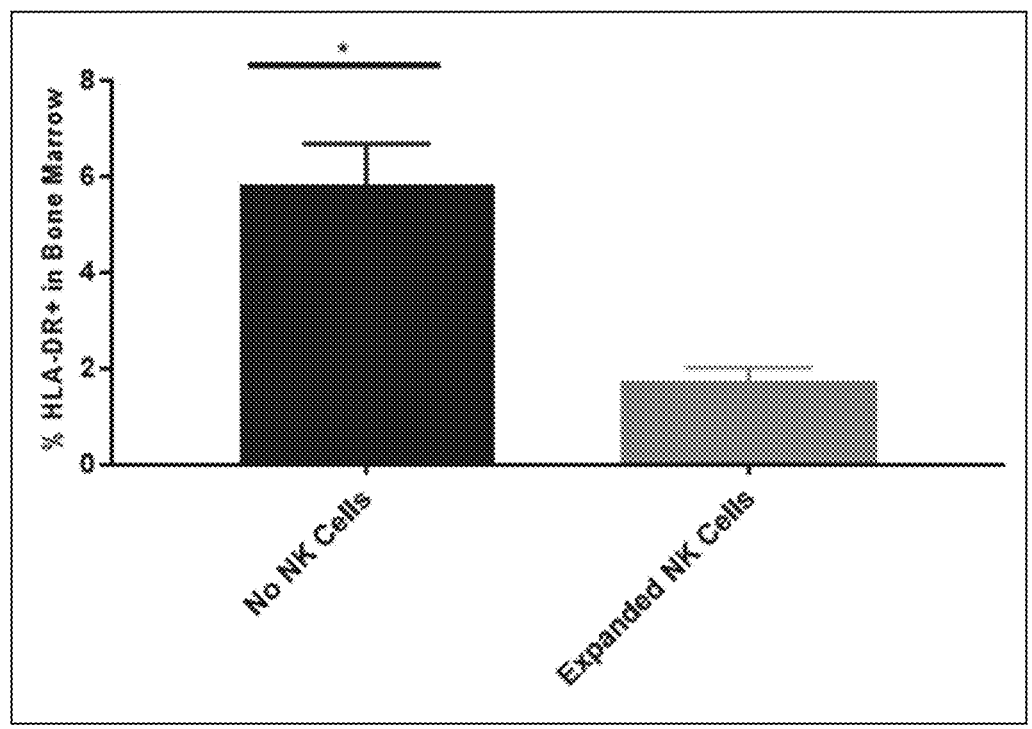

FIG. 183 shows clearance of Daudi tumor cells in NSG mice upon treatment with NK cells activated by the 7t15-21s and anti-TF antibody (IgG1) complex.

Figures 184A, 184B, 184C, 184D, 184E:
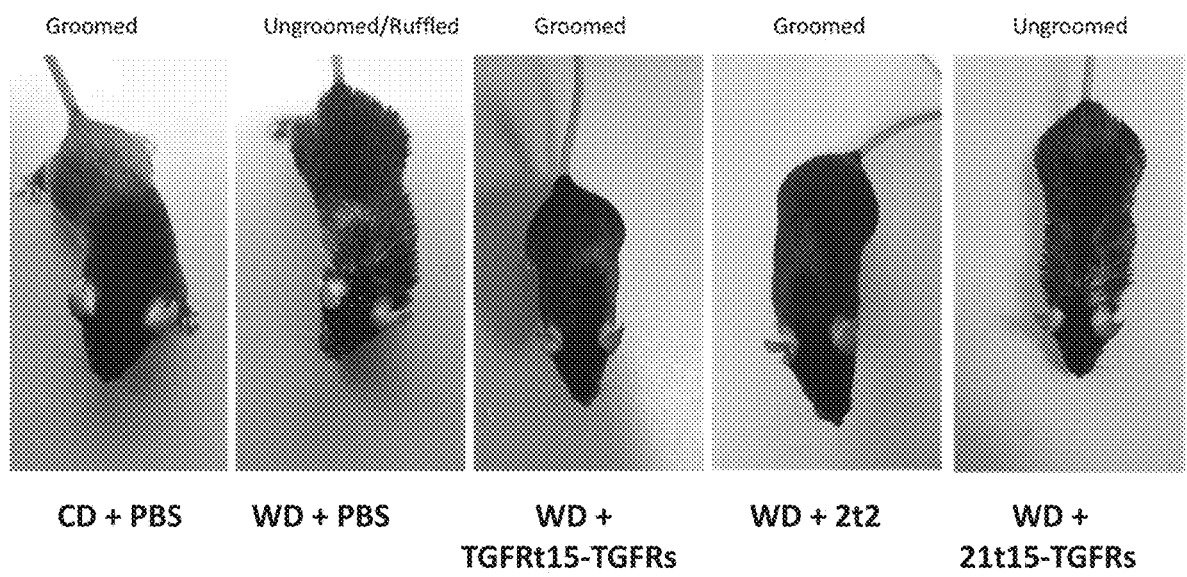

FIGS. 184A-184E show improvement of skin texture in ApoE$^{-/-}$ mice fed with a Western diet and treated with 2t2 or TGFRt15-TGFRs. FIG. 184A is a representative picture of a chow diet-fed ApoE$^{-/-}$ mouse taken one week after PBS treatment. FIG. 184B is a representative picture of a Western diet-fed ApoE$^{-/-}$ mouse taken one week after PBS treatment. FIG. 184C shows a representative picture of a Western diet-fed ApoE$^{-/-}$ mouse taken one week after TGFRt15-TGFRs treatment. FIG. 184D shows a representative picture of a Western diet-fed ApoE$^{-/-}$ mouse taken one week after 2t2 treatment. FIG. 184E shows a representative picture of a Western diet-fed ApoE$^{-/-}$ mouse taken one week after treatment with 21t15-TGFRs.

Figure 185:
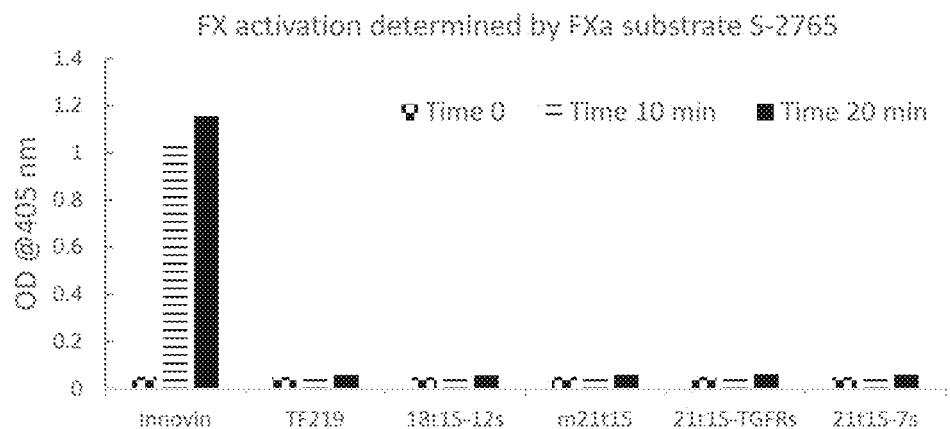

FIG. 185 shows a graph of Factor X (FX) activation following treatment with single-chain or multi-chain chimeric polypeptides.

Figure 186:
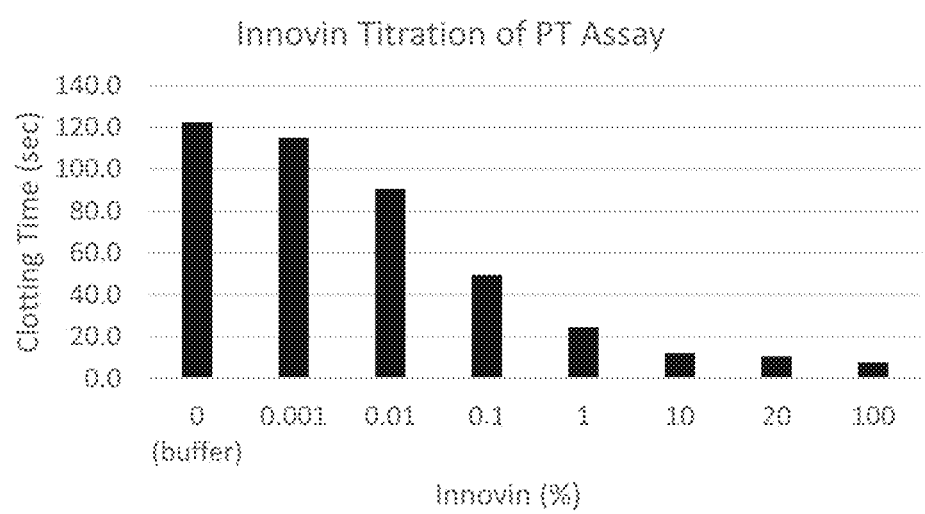

FIG. 186 shows clotting time for a buffer with varying concentrations of Innovin in a prothrombin time (PT) test.

Figure 187:
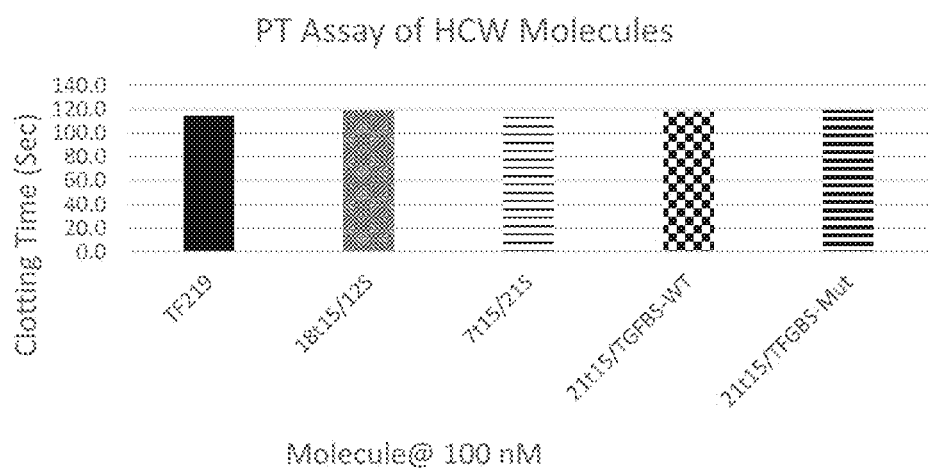

FIG. 187 shows clotting time for multi-chain chimeric polypeptides in a PT Assay.

Figure 188:
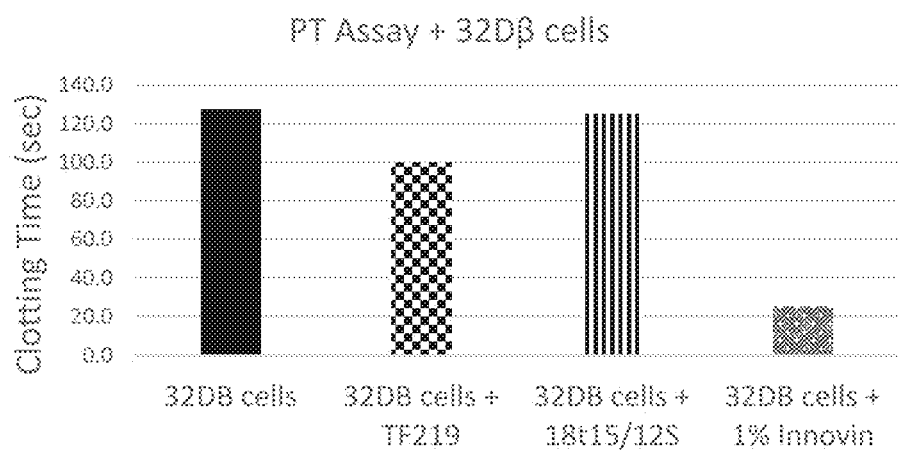

FIG. 188 shows clotting time of the multi-chain chimeric polypeptides in a PT assay when mixed with 32DB cells.

Figure 189:
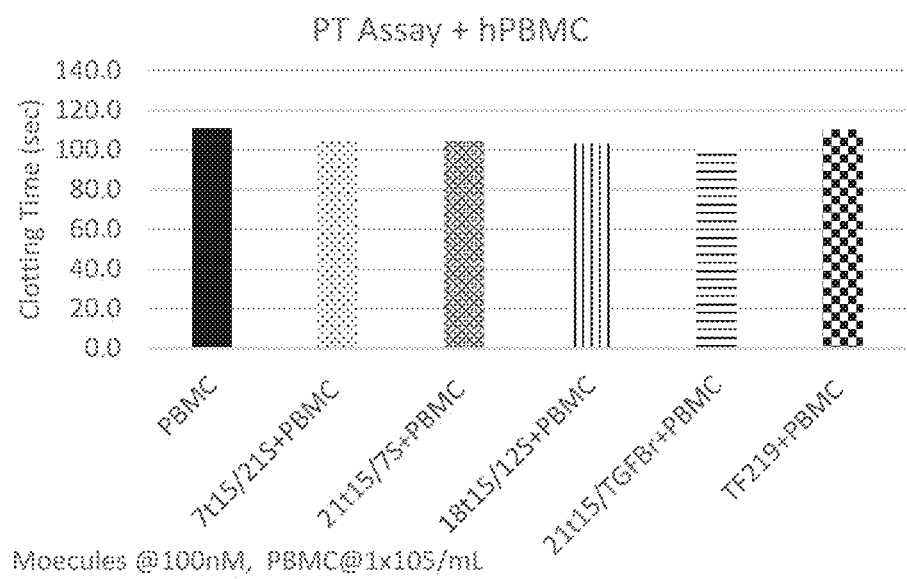

FIG. 189 shows clotting time of multi-chain chimeric polypeptides in a PT assay when mixed with human PBMC.

Figure 190:
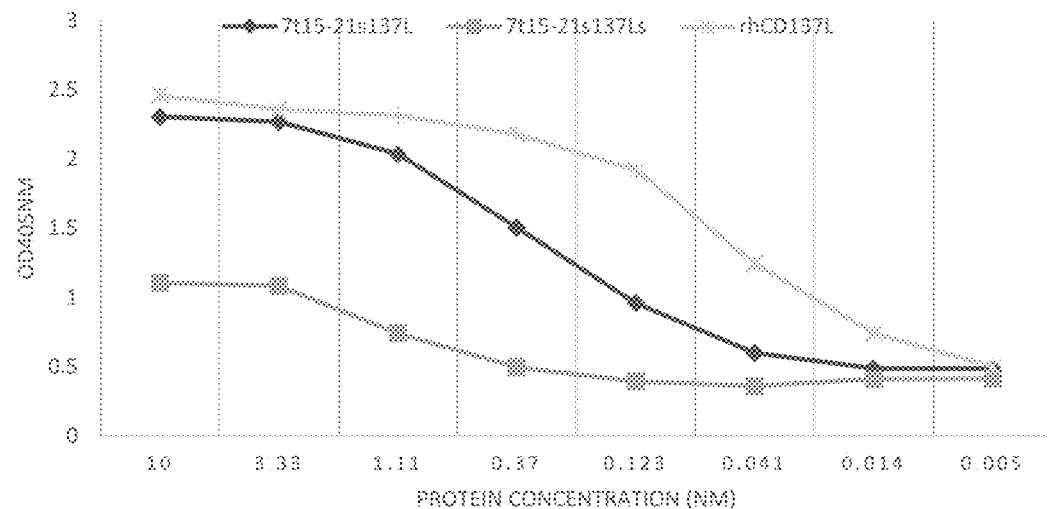
Figure 191A:
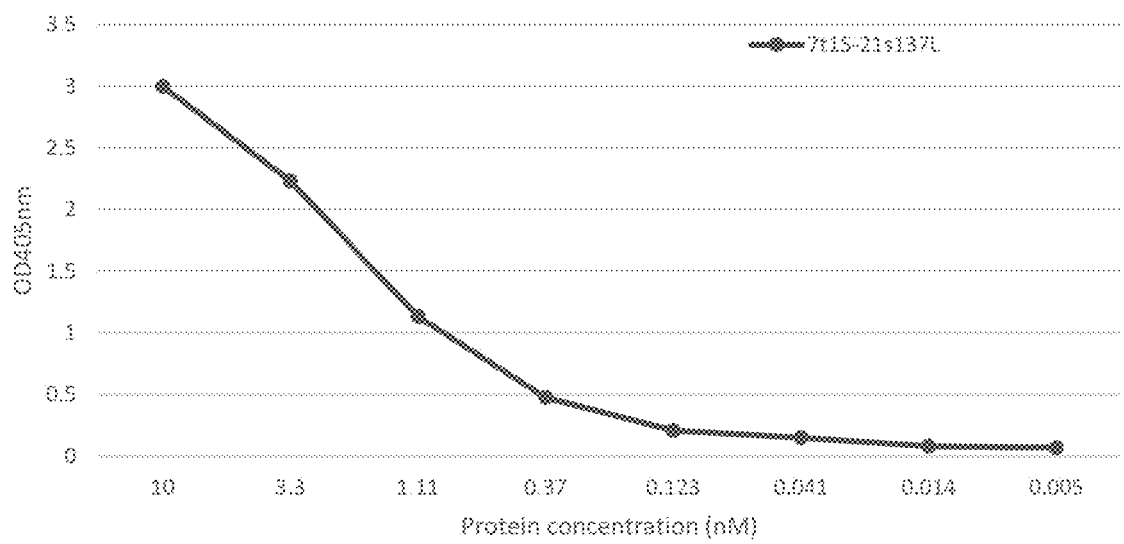
Figure 191B:
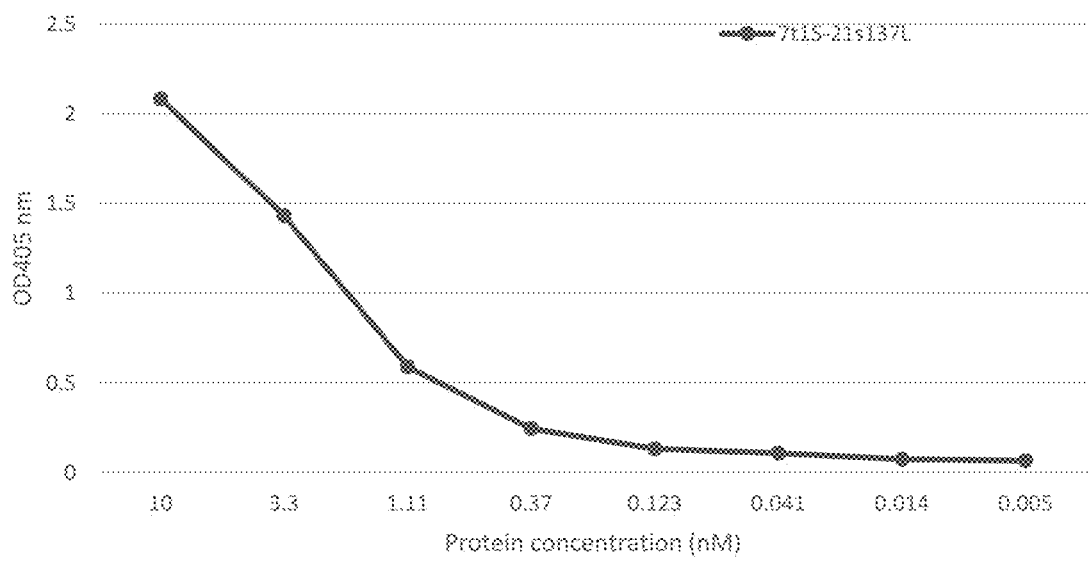
Figure 191C:
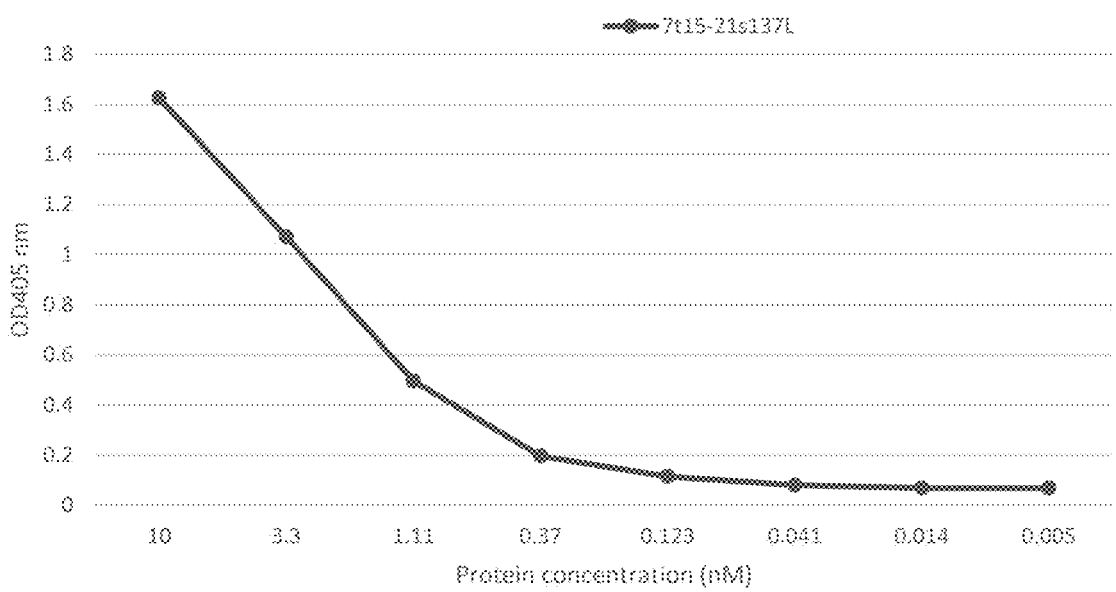
Figure 191D:
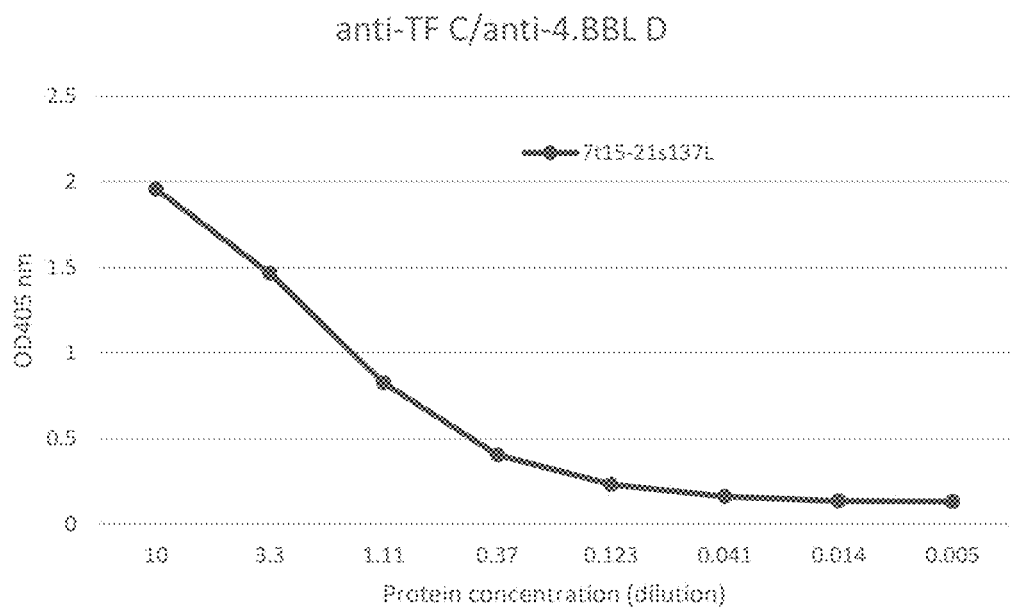

FIG. 190 shows binding of 7t15-21s137L (long version) and 7t15-21s137L (short version) to CD137 (4.1BB).

FIG. 191A-191D show detection of IL7, IL21, IL15, and 4.1BBL in 7t15-21s137L (long version) by the respective antibodies using ELISA.

Figure 192:
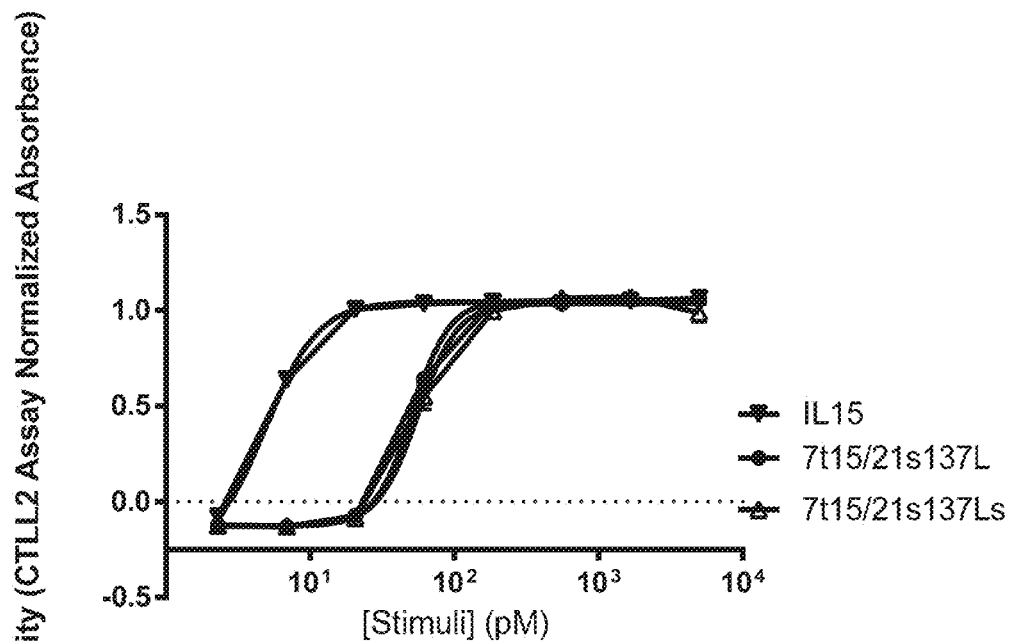

FIG. 192 shows IL-15 activity of 7t15-21s137L (long version) and 7t15-21s137L (short version) as evaluated by a IL2Rαβγ-containing CTLL2 cell proliferation assay.

Figure 193:
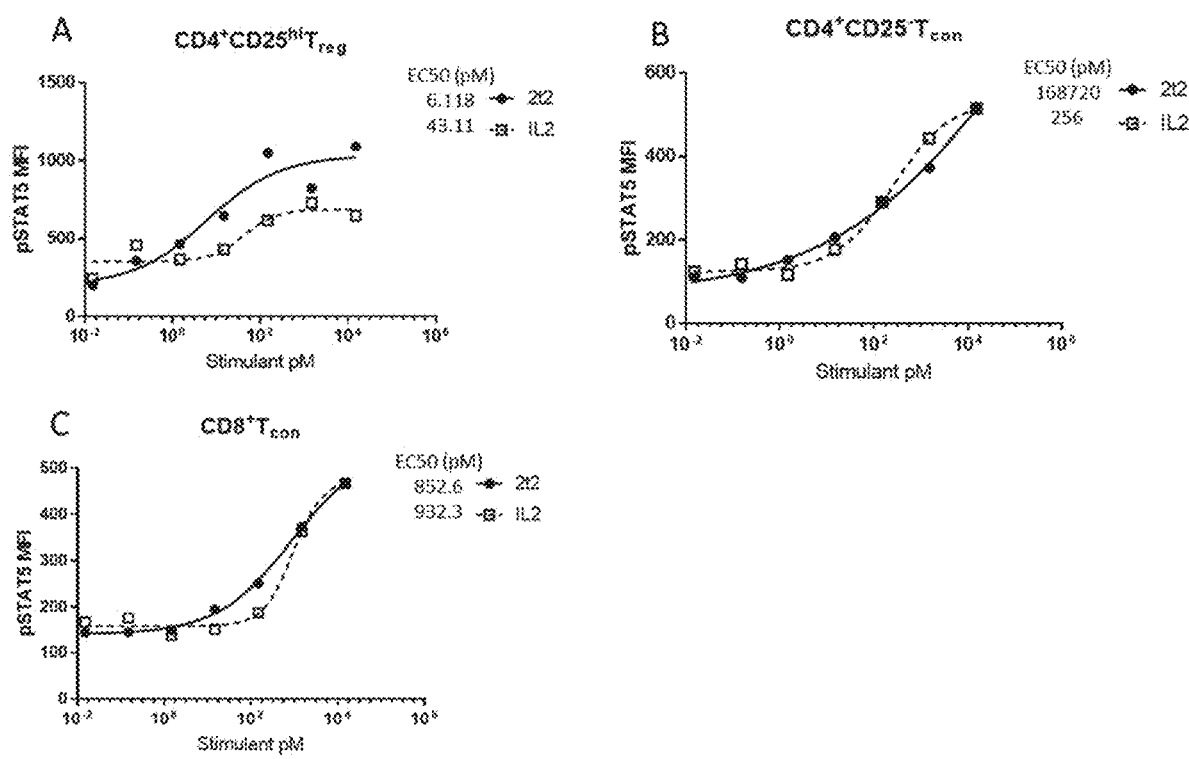

FIG. 193A-193C show human blood lymphocyte pStat5a responses in CD4$^+$CD25$^{hi}$T$_{reg}$ cells, CD4$^+$CD25$^-$T$_{con}$ cells, or in CD8$^+$ T$_{con}$ cells in response to 2t2 or IL2 treatment. FIG. 193A shows pSTAT5 responses in CD4$^+$CD25$^{hi}$T$_{reg}$ cells. FIG. 193B shows pSTAT5 responses in CD4$^+$CD25$^-$T$_{con}$ cells. FIG. 193C shows pSTAT5 responses in CD8$^+$ T$_{con}$ cells.

Figure 194:
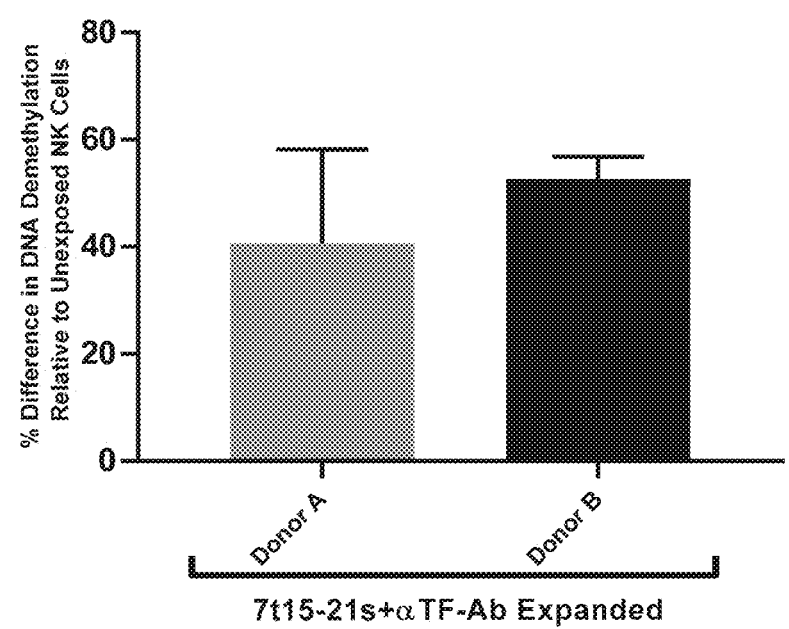

FIG. 194 is a graph showing the percentage different in DNA demethylation in NK cells (relative to unexposed NK cells) from two different donors following expansion with 7t15-21s+anti-tissue factor (TF)-antibody (IgG1) (50 nM).

DETAILED DESCRIPTION

Provided herein are a variety of single-chain and multi-chain chimeric polypeptides, methods of using them, and kits including them. In some embodiments, the single-chain and multi-chain chimeric polypeptides include a linker domain positioned between two target-binding domains. In some embodiments, the linker domain is or includes a soluble tissue factor domain. In some embodiments, the linker domain can be recognized by a cognate IgG1 antibody (e.g., a monoclonal antibody). In some embodiments, a single-chain or multi-chain chimeric polypeptide provided herein can be used to stimulate an immune cell, induce or increase proliferation of an immune cell, induce differentiation of an immune cell, or treat a subject in need thereof (e.g., a subject having cancer or an aging-related disease or condition).

Single Chain Chimeric Polypeptides

Some embodiments of any of the methods described herein include the use of any of the single chain chimeric polypeptides described herein. Some embodiments of any of the kits described herein include any of the single-chain chimeric polypeptides described herein. The single-chain chimeric polypeptides provided herein include a first target-binding domain, a linker domain, and a second target-binding domain, where the first target-binding domain and the second target-binding domain are each independently selected from the group consisting of a soluble interleukin or cytokine protein, an antigen-binding domain, and a soluble interleukin or cytokine receptor, and ligands of co-stimulatory molecules.

In some examples of any of the single-chain chimeric polypeptides described herein, the single-chain chimeric polypeptide can have a total length of about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids, about 360 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 950 amino acids to about 1000 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids.

In some embodiments of any of the single-chain chimeric polypeptides described herein, the first target-binding domain (e.g., any of the exemplary target-binding domains described herein or known in the art) and the linker domain (e.g., any of the exemplary linker described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the linker domain (e.g., any of the exemplary linker domains described herein). In some embodiments of any of the single-chain chimeric polypeptides described herein, the linker domain (e.g., any of the exemplary linker domains described herein) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the linker domain (e.g., any of the exemplary linker domains described herein) and the second target-binding domain (e.g., any of the exemplary target-binding domains described herein or known in the art).

In some embodiments of any of the single-chain chimeric polypeptides described herein, the first target-binding domain (e.g., any of the exemplary target-binding domains described herein or known in the art) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the second target-binding domain (e.g., any of the exemplary target-binding domains described herein or known in the art). In some embodiments of any of the single-chain chimeric polypeptides described herein, the second target-binding domain (e.g., any of the exemplary target-binding domains described herein or known in the art) and the linker domain (e.g., any of the exemplary linker domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the second target-binding domain (e.g., any of the exemplary target-binding domains described herein or known in the art) and the linker domain (e.g., any of the exemplary linker domains described herein or known in the art).

Non-limiting aspects of these chimeric polypeptides, nucleic acids, vectors, cells, and methods are described below, and can be used in any combination without limitation. Additional aspects of these chimeric polypeptides, nucleic acids, vectors, cells, and methods are known in the art.

Multi-Chain Chimeric Polypeptides

Some embodiments of any of the methods described herein include the use of any of the multi-chain chimeric polypeptides described herein. Some embodiments of any of the kits described herein include any of the multi-chain chimeric polypeptides described herein.

The multi-chain chimeric polypeptides provided herein include: (a) a first chimeric polypeptide including: (i) a first target-binding domain; (ii) a linker domain; and (iii) a first domain of a pair of affinity domains; and (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains.

Figure 1:
FIG. 1 shows a schematic diagram of an exemplary IL-7/IL-15RαSu DNA construct.
Figure 2:
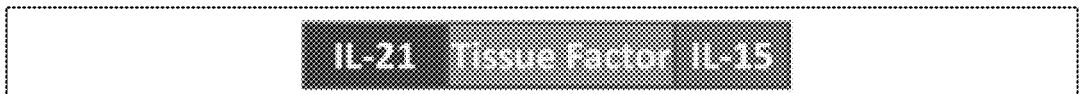
FIG. 2 shows a schematic diagram of an exemplary IL-21/TF/IL-15 DNA construct.

In some examples of any of the multi-chain chimeric polypeptides described herein the total length of first chimeric polypeptide and/or the second chimeric polypeptide can each independently be about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids, about 360 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 950 amino acids to about 1000 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids. Diagrams of exemplary multi-chain chimeric polypeptides provided herein are depicted in FIGS. 1 and 2.

In some embodiments of any of the multi-chain chimeric polypeptides described herein, the first target-binding domain (e.g., any of the first target-binding domains described herein) and the linker domain (e.g., any of the exemplary linker domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the first target-binding domain (e.g., any of the exemplary first target-binding domains described herein) and the linker domain (e.g., any of the exemplary linker domains described herein) in the first chimeric polypeptide.

In some embodiments of any of the multi-chain chimeric polypeptides described herein, the linker domain (e.g., any of the exemplary linker domains described herein) and the first domain of the pair of affinity domains (e.g., any of the exemplary first domains of any of the exemplary pairs of affinity domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the linker domain (e.g., any of the exemplary linker domains described herein) and the first domain of the pair of affinity domains (e.g., any of the exemplary first domains of any of the exemplary pairs of affinity domains described herein) in the first chimeric polypeptide.

In some embodiments of any of the multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the second chimeric polypeptide. In some embodiments of any of the multi-chain chimeric polypeptides described herein, the second chimeric polypeptide further comprises a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the second chimeric polypeptide.

Tissue Factor

Human tissue factor is a 263 amino-acid transmembrane protein containing three domains: (1) a 219-amino acid N-terminal extracellular domain (residues 1-219); (2) a 22-amino acid transmembrane domain (residues 220-242); and (3) a 21-amino acid cytoplasmic C-terminal tail (residues 242-263) ((UniProtKB Identifier Number: P13726). The cytoplasmic tail contains two phosphorylation sites at $Ser^{253}$ and $Ser^{258}$, and one S-palmitoylation site at $Cys^{245}$. Deletion or mutation of the cytoplasmic domain was not found to affect tissue factor coagulation activity. Tissue factor has one S-palmitoylation site in the intracellular domain of the protein at $Cys^{245}$. The $Cys^{245}$ is located at the amino acid terminus of the intracellular domain and close to the membrane surface. The tissue factor transmembrane domain is composed of a single-spanning α-helix.

The extracellular domain of tissue factor, composed of two fibronectin type III domains, is connected to the transmembrane domain through a six-amino acid linker. This linker provides conformational flexibility to decouple the tissue factor extracellular domain from its transmembrane and cytoplasmic domains. Each tissue factor fibronectin type III module is composed of two overlapping β sheets with the top sheet domain containing three antiparallel β-strands and the bottom sheet containing four β-strands. The β-strands are connected by β-loops between strand βA and βB, βC and βD, and βE and βF, all of which are conserved in conformation in the two modules. There are three short α-helix segments connecting the β-strands. A unique feature of tissue factor is a 17-amino acid β-hairpin between strand β10 and strand β11, which is not a common element of the fibronectin superfamily. The N-terminal domain also contains a 12 amino acid loop between β6F and β7G that is not present in the C-terminal domain and is unique to tissue factor. Such a fibronectin type III domain structure is a feature of the immunoglobulin-like family of protein folds and is conserved among a wide variety of extracellular proteins.

The zymogen FVII is rapidly converted to FVIIa by limited proteolysis once it binds to tissue to form the active tissue factor-FVIIa complex. The FVIIa, which circulates as an enzyme at a concentration of approximately 0.1 nM (1% of plasma FVII), can also bind directly to tissue factor. The allosteric interaction between tissue factor and FVIIa on the tissue factor-FVIIa complex greatly increases the enzymatic activity of FVIIa: an approximate 20- to 100-fold increase in the rate of hydrolysis of small, chromogenic peptidyl substrates, and nearly a million-fold increase in the rate of activation of the natural macromolecular substrates FIX and FX. In concert with allosteric activation of the active site of FVIIa upon binding to tissue factor, the formation of tissue factor-FVIIa complex on phospholipid bilayer (i.e., upon exposure of phosphatidyl-L-serine on membrane surfaces) increases the rate of FIX or FX activation, in a $Ca^{2+}$-dependent manner, an additional 1,000-fold. The roughly million-fold overall increase in FX activation by tissue factor-FVIIa-phospholipid complex relative to free FVIIa is a critical regulatory point for the coagulation cascade.

FVII is a ~50 kDa, single-chain polypeptide consisting of 406 amino acid residues, with an N-terminal γ-carboxyglutamate-rich (GLA) domain, two epidermal growth factor-like domains (EGF1 and EFG2), and a C-terminal serine protease domain. FVII is activated to FVIIa by a specific proteolytic cleavage of the Ile-$^{154}$-Arg$^{152}$ bond in the short linker region between the EGF2 and the protease domain. This cleavage results in the light and heavy chains being held together by a single disulfide bond of Cys$^{135}$ and Cys$^{262}$. FVIIa binds phospholipid membrane in a $Ca^{2+}$-dependent manner through its N-terminal GLA-domain. Immediately C-terminal to the GLA domain is an aromatic stack and two EGF domains. The aromatic stack connects the GLA to EGF1 domain which binds a single $Ca^{2+}$ ion. Occupancy of this $Ca^{2+}$-binding site increases FVIIa amidolytic activity and tissue factor association. The catalytic triad consist of His$^{193}$, Asp$^{242}$, and Ser$^{344}$, and binding of a single $Ca^{2+}$ ion within the FVIIa protease domain is critical for its catalytic activity. Proteolytic activation of FVII to FVIIa frees the newly formed amino terminus at Ile$^{153}$ to fold back and be inserted into the activation pocket forming a salt bridge with the carboxylate of Asp$^{343}$ to generate the oxyanion hole. Formation of this salt bridge is critical for FVIIa activity. However, oxyanion hole formation does not occur in free FVIIa upon proteolytic activation. As a result, FVIIa circulates in a zymogen-like state that is poorly recognized by plasma protease inhibitors, allowing it to circulate with a half-life of approximately 90 minutes.

Tissue factor-mediated positioning of the FVIIa active site above the membrane surface is important for FVIIa towards cognate substrates. Free FVIIa adopts a stable, extended structure when bound to the membrane with its active site positioned ~80 Å above the membrane surface. Upon FVIIa binding to tissue factor, the FVa active site is repositioned ~6 Å closer to the membrane. This modulation may aid in a proper alignment of the FVIIa catalytic triad with the target substrate cleavage site. Using GLA-domainless FVIIa, it has been shown that the active site was still positioned a similar distance above the membrane, demonstrating that tissue factor is able to fully support FVIIa active site positioning even in the absence of FVIIa-membrane interaction. Additional data showed that tissue factor supported full FVIIa proteolytic activity as long as the tissue factor extracellular domain was tethered in some way to the membrane surface. However, raising the active site of FVIIa greater than 80 Å above the membrane surface greatly reduced the ability of the tissue factor-FVIIa complex to activate FX but did not diminish tissue factor-FVIIa amidolytic activity.

Alanine scanning mutagenesis has been used to assess the role of specific amino acid side chains in the tissue factor extracellular domain for interaction with FVIIa (Gibbs et al., *Biochemistry* 33(47): 14003-14010, 1994; Schullek et al., *J Biol Chem* 269(30): 19399-19403, 1994). Alanine substitution identified a limited number of residue positions at which alanine replacements cause 5- to 10-fold lower affinity for FVIIa binding. Most of these residue side chains were found to be well-exposed to solvent in the crystal structure, concordant with macromolecular ligand interaction. The FVIIa ligand-binding site is located over an extensive region at the boundary between the two modules. In the C-module, residues Arg$^{135}$ and Phe$^{140}$ located on the protruding B-C loop provide an independent contact with FVIIa. Leu$^{133}$ is located at the base of the fingerlike structure and packed into the cleft between the two modules. This provides continuity to a major cluster of important binding residues consisting of Lys$^{20}$, Thr$^{60}$, Asp$^{58}$, and Ile$^{22}$. Thr$^{60}$ is only partially solvent-exposed and may play a local structural role rather than making a significant contact with ligand. The binding site extends onto the concave side of the intermodule angle involving Glu$^{24}$ and Gln$^{110}$, and potentially the more distant residue Val$^{207}$. The binding region extends from Asp58 onto a convex surface area formed by Lys$^{48}$, Lys$^{46}$, Gln$^{37}$, Asp$^{44}$, and Trp$^{45}$. Trp$^{45}$ and Asp$^{44}$ do not interact independently with FVIIa, indicating that the mutational effect at the Trp$^{45}$ position may reflect a structural importance of this side chain for the local packing of the adjacent Asp$^{44}$ and Gln$^{37}$ side chain. The interactive area further includes two surface-exposed aromatic residues, Phe$^{76}$ and Tyr$^{78}$, which form part of the hydrophobic cluster in the N-module.

The known physiologic substrates of tissue factor-FVIIa are FVII, FIX, and FX and certain proteinase-activated receptors. Mutational analysis has identified a number of residues that, when mutated, support full FVIIa amidolytic activity towards small peptidyl substrates but are deficient in their ability to support macromolecular substrate (i.e., FVII, FIX, and FX) activation (Ruf et al., *J Biol Chem* 267(31): 22206-22210, 1992; Ruf et al., *J Biol Chem* 267(9): 6375-6381, 1992; Huang et al., *J Biol Chem* 271(36): 21752-21757, 1996; Kirchhofer et al., *Biochemistry* 39(25): 7380-7387, 2000). The tissue factor loop region at residues 159-165, and residues in or adjacent to this flexible loop have been shown to be critical for the proteolytic activity of the tissue factor-FVIIa complex. This defines the proposed substrate-binding exosite region of tissue factor that is quite distant from the FVIIa active site. A substitution of the glycine residue by a marginally bulkier residue alanine, significantly impairs tissue factor-FVIIa proteolytic activity. This suggests that the flexibility afforded by glycine is critical for the loop of residues 159-165 for tissue factor macromolecular substrate recognition.

The residues Lys$^{165}$ and Lys$^{166}$ have also been demonstrated to be important for substrate recognition and binding. Mutation of either of these residues to alanine results in a significant decrease in the tissue factor co-factor function. Lys$^{165}$ and Lys$^{166}$ face away from each other, with Lys$^{165}$ pointing towards FVIIa in most tissue factor-FVIIa structures, and Lys$^{166}$ pointing into the substrate binding exosite region in the crystal structure. Putative salt bridge formation between Lys$^{165}$ of and Gla$^{35}$ of FVIIa would support the notion that tissue factor interaction with the GLA domain of FVIIa modulates substrate recognition. These results suggest that the C-terminal portion of the tissue factor ectodomain directly interacts with the GLA-domain, the possible adjacent EGF1 domains, of FIX and FX, and that the presence of the FVIIa GLA-domain may modulate these interactions either directly or indirectly.

Exemplary Linker Domains and IgG1 Antibody Constructs

In some examples of any of the methods, compositions, or kits described herein, the linker domain can be or include any antigen that is recognized by a cognate IgG1 antibody (e.g., a monoclonal antibody). IgG1 antibodies are distinguished from other IgG classes of antibodies by their constant region, particularly in hinge regions and upper CH2 domains (see, e.g., Vadarsson et al., IgG Subclasses and Allotypes: From Structure to Effector Functions, Front Immunol., 5, Article 520, 2014). Human IgG1 is the only known IgG subclass which binds to human CD16a and activates the signaling of human CD16a.

Any of a variety of linker domains can be used in the single-chain chimeric polypeptides and multi-chain chimeric polypeptides provided herein. In certain embodiments, a linker domain is recognized by an antibody (e.g., an IgG1 antibody) or antibody fragment. In some embodiments, the linker domain is a kappa light chain of an antibody that is recognized by a cognate anti-kappa light chain IgG1 antibody. In some embodiments, the linker domain is a lambda light chain of an antibody that is recognized by a cognate anti-lambda light chain human IgG1 antibody. A variety of kappa light chains and lambda light chains are known in the art (see, e.g., Smith et al., Antigen Nature and Complexity Influence Human Antibody Light Chain Usage and Specificity, Vaccine, 34(25): 2813-2820, 2016). In some embodiments, the linker domain is or comprises a human polypeptide (e.g., a human kappa light chain of an antibody or a human lambda light chain of an antibody) that is recognized by a cognate human IgG1 antibody (e.g., a monoclonal antibody). In some embodiments, the cognate human IgG1 antibody includes at least two antigen-binding domains, and each antigen-binding domain binds specifically to the linker domain. In some embodiments, the cognate human IgG1 antibody includes at least two antigen-binding domains, and only a subset (e.g., one) of the antigen-binding domains bind specifically to the linker domain. In some embodiments, a linker domain can be any of the soluble tissue factor domains described herein.

In some embodiments of any of the methods, compositions, and kits described herein, an IgG1 antibody construct can be an IgG1 antibody (e.g., a monoclonal or a polyclonal IgG1 antibody that binds specifically to the linker domain). In some embodiments of any of the methods, compositions, and kits described herein, an IgG1 antibody construct can be an antibody or an antibody fragment that includes an IgG1 Fc region (e.g., a human IgG1 Fc region) and that binds specifically to the linker domain. As is known in the art, the IgG1 Fc region binds to CD16a (FcRgammaIII) (e.g., human CD16a) and induces its intracellular signaling. In some embodiments, an IgG1 antibody construct can be a single chain or a multi-chain polypeptide that includes an Fc region that is capable of binding specifically to CD16a (FcRgammaIII) (e.g., human CD16a) and is capable of inducing its intracellular signaling in a natural killer cell (e.g., a human natural killer cell), and specifically binds to the linker domain. In some embodiments, an IgG1 antibody construct can be a single chain or a multi-chain polypeptide that includes an Fc region that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, or at least 99% identical) to a wildtype IgG1 Fc domain (e.g., a wildtype human IgG1 Fc domain, e.g., SEQ ID NO: 96) and is capable of binding specifically to CD16a (FcRgammaIII) (e.g., human CD16a), and is capable of inducing its intracellular signaling in a natural killer cell (e.g., a human natural killer cell), and specifically binds to the linker domain. In some embodiments of any of the methods, compositions, or kits described herein, the IgG1 antibody construct can be an antibody or antibody fragment that specifically binds to the linker domain and includes a non-IgG1 Fc region (e.g., an IgG2, IgG3, or IgG4 Fc region) that has been altered (e.g., by substituting 1, 2, 3, 4, 5, 6, 7, 8, 9, 10, 11, 12, 13, 14, 15, 16, 17, 18, 19, or 20 amino acids in the wildtype non-IgG1 Fc region) such that the non-IgG1 Fc region is capable of binding to CD16a (FcRgammaIII) (e.g., human CD16a) and inducing its intracellular signaling in a natural killer cell (e.g., a human natural killer cell). In some embodiments of any of the methods, compositions, or kits described herein, the IgG1 antibody construct binds specifically to the linker domain and includes a non-human Fc region (e.g., a Fc region from a non-human antibody) that has been altered (e.g., by substituting 1, 2, 3, 4, 5, 6, 7, 8, 9, 10, 11, 12, 13, 14, 15, 16, 17, 18, 19, or 20 amino acids in the wildtype non-human Fc region) such that the non-human Fc region is capable of binding to human CD16a (human FcRgammaIII) and inducing its intracellular signaling in a natural killer cell (e.g., a human natural killer cell).

```
Wildtype Human IgG1 Fc Region (SEQ ID NO: 96)
PCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVF

SCSVMHEALHNHYTQKSLSLSPGK.

Wildtype Human IgG2 Fc Region (SEQ ID NO: 97)
APPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLP

APIEKTISKTKGQPREPQVYTLPPSREEMTKNQVSLTCLVKGFYPSDIS

VEWESNGQPENNYKTTPPMLDSDGSFFLYSKLTVDKSRWQQGNVFSCSV

MHEALHNHYTQKSLSLSPGK.

Wildtype Human IgG3 Fc Region (SEQ ID NO: 98)
APELLGGPSVFLFPPKPKDTLMISRTPEVTCVVVDVSHEDPEVQFKWYV

DGVEVHNAKTKPREEQYNSTFRVVSVLTVLHQDWLNGKEYKCKVSNKAL

PAPIEKTISKTKGQPREPQVYTLPPSREEMTKNQVSLTCLVKGFYPSDI

AVEWESSGQPENNYNTTPPMLDSDGSFFLYSKLTVDKSRWQQGNIFSCS

VMHEALHNRFTQKSLSLSPGK.

Wildtype Human IgG4 Fc Region (SEQ ID NO: 99)
APEFLGGPSVFLFPPKPKDTLMISRTPEVTCVVVDVSQEDPEVQFNWYV

DGVEVHNAKTKPREEQFNSTYRVVSVLTVLHQDWLNGKEYKCKVSNKGL

PSSIEKTISKAKGQPREPQVYTLPPSQEEMTKNQVSLTCLVKGFYPSDI

AVEWESNGQPENNYKTTPPVLDSDGSFFLYSRLTVDKSRWQEGNVFSCS

VMHEALHNHYTQKSLSLSLGK.
```

In some embodiments, the linker domain can have a total length of about 20 amino acids to about 220 amino acids, about 20 amino acids to about 215 amino acids, about 20 amino acids to about 210 amino acids, about 20 amino acids to about 205 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids, about 30 amino acids to about 220 amino acids, about 30 amino acids to about 215 amino acids, about 30 amino acids to about 210 amino acids, about 30 amino acids to about 205 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 60 amino acids, about 30 amino acids to about 50 amino acids, about 30 amino acids to about 40 amino acids, about 40 amino acids to about 220 amino acids, about 40 amino acids to about 215 amino acids, about 40 amino acids to about 210 amino acids, about 40 amino acids to about 205 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 60 amino acids, about 40 amino acids to about 50 amino acids, about 50 amino acids to about 220 amino acids, about 50 amino acids to about 215 amino acids, about 50 amino acids to about 210 amino acids, about 50 amino acids to about 205 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 60 amino acids, about 60 amino acids to about 220 amino acids, about 60 amino acids to about 215 amino acids, about 60 amino acids to about 210 amino acids, about 60 amino acids to about 205 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 70 amino acids to about 220 amino acids, about 70 amino acids to about 215 amino acids, about 70 amino acids to about 210 amino acids, about 70 amino acids to about 205 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 80 amino acids to about 220 amino acids, about 80 amino acids to about 215 amino acids, about 80 amino acids to about 210 amino acids, about 80 amino acids to about 205 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 90 amino acids to about 220 amino acids, about 90 amino acids to about 215 amino acids, about 90 amino acids to about 210 amino acids, about 90 amino acids to about 205 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 100 amino acids to about 220 amino acids, about 100 amino acids to about 215 amino acids, about 100 amino acids to about 210 amino acids, about 100 amino acids to about 205 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 110 amino acids to about 220 amino acids, about 110 amino acids to about 215 amino acids, about 110 amino acids to about 210 amino acids, about 110 amino acids to about 205 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 220 amino acids, about 115 amino acids to about 215 amino acids, about 115 amino acids to about 210 amino acids, about 115 amino acids to about 205 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 220 amino acids, about 120 amino acids to about 215 amino acids, about 120 amino acids to about 210 amino acids, about 120 amino acids to about 205 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 220 amino acids, about 125 amino acids to about 215 amino acids, about 125 amino acids to about 210 amino acids, about 125 amino acids to about 205 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 220 amino acids, about 130 amino acids to about 215 amino acids, about 130 amino acids to about 210 amino acids, about 130 amino acids to about 205 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 220 amino acids, about 135 amino acids to about 215 amino acids, about 135 amino acids to about 210 amino acids, about 135 amino acids to about 205 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 220 amino acids, about 140 amino acids to about 215 amino acids, about 140 amino acids to about 210 amino acids, about 140 amino acids to about 205 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 220 amino acids, about 145 amino acids to about 215 amino acids, about 145 amino acids to about 210 amino acids, about 145 amino acids to about 205 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 220 amino acids, about 150 amino acids to about 215 amino acids, about 150 amino acids to about 210 amino acids, about 150 amino acids to about 205 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 220 amino acids, about 155 amino acids to about 215 amino acids, about 155 amino acids to about 210 amino acids, about 155 amino acids to about 205 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 220 amino acids, about 160 amino acids to about 215 amino acids, about 160 amino acids to about 210 amino acids, about 160 amino acids to about 205 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 220 amino acids, about 165 amino acids to about 215 amino acids, about 165 amino acids to about 210 amino acids, about 165 amino acids to about 205 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 220 amino acids, about 170 amino acids to about 215 amino acids, about 170 amino acids to about 210 amino acids, about 170 amino acids to about 205 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 220 amino acids, about 175 amino acids to about 215 amino acids, about 175 amino acids to about 210 amino acids, about 175 amino acids to about 205 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 220 amino acids, about 180 amino acids to about 215 amino acids, about 180 amino acids to about 210 amino acids, about 180 amino acids to about 205 amino acids, about 180 amino acids to about 200 amino acids, about 180 amino acids to about 195 amino acids, about 180 amino acids to about 190 amino acids, about 180 amino acids to about 185 amino acids, about 185 amino acids to about 220 amino acids, about 185 amino acids to about 215 amino acids, about 185 amino acids to about 210 amino acids, about 185 amino acids to about 205 amino acids, about 185 amino acids to about 200 amino acids, about 185 amino acids to about 195 amino acids, about 185 amino acids to about 190 amino acids, about 190 amino acids to about 220 amino acids, about 190 amino acids to about 215 amino acids, about 190 amino acids to about 210 amino acids, about 190 amino acids to about 205 amino acids, about 190 amino acids to about 200 amino acids, about 190 amino acids to about 195 amino acids, about 195 amino acids to about 220 amino acids, about 195 amino acids to about 215 amino acids, about 195 amino acids to about 210 amino acids, about 195 amino acids to about 205 amino acids, about 195 amino acids to about 200 amino acids, about 200 amino acids to about 220 amino acids, about 200 amino acids to about 215 amino acids, about 200 amino acids to about 210 amino acids, about 200 amino acids to about 205 amino acids, about 205 amino acids to about 220 amino acids, about 205 amino acids to about 215 amino acids, about 205 amino acids to about 210 amino acids, about 210 amino acids to about 220 amino acids, about 210 amino acids to about 215 amino acids, or about 215 amino acids to about 220 amino acids.

Soluble Tissue Factor Domain

In some examples of any of the methods, compositions, or kits described herein, the linker domain can be a soluble tissue factor domain. In some embodiments, the soluble tissue factor domain can be a wildtype tissue factor polypeptide lacking the signal sequence, the transmembrane domain, and the intracellular domain. In some examples, the soluble tissue factor domain can be a tissue factor mutant, wherein a wildtype tissue factor polypeptide lacking the signal sequence, the transmembrane domain, and the intracellular domain, and has been further modified at selected amino acids. In some examples, the soluble tissue factor domain can be a soluble human tissue factor domain. In some examples, the soluble tissue factor domain can be a soluble mouse tissue factor domain. In some examples, the soluble tissue factor domain can be a soluble rat tissue factor domain. Non-limiting examples of soluble human tissue factor domains, a mouse soluble tissue factor domain, a rat soluble tissue factor domain, and mutant soluble tissue factor domains are shown below.

Exemplary Soluble Human Tissue Factor Domain
(SEQ ID NO: 1)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE.

Exemplary Nucleic Acid Encoding Soluble Human Tissue Factor Domain
(SEQ ID NO: 2)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG.

Exemplary Soluble Mouse Tissue Factor Domain
(SEQ ID NO: 3)
AGIPEKAFNLTWISTDFKTILEWQPKPTNYTYTVQISDRSRNWKNKCFS

TTDTECDLTDEIVKDVTWAYEAKVLSVPRRNSVHGDGDQLVIHGEEPPF

TNAPKFLPYRDTNLGQPVIQQFEQDGRKLNVVVKDSLTLVRKNGTFLTL

RQVFGKDLGYIITYRKGSSTGKKTNITNTNEFSIDVEEGVSYCFFVQAM

IFSRKTNQNSPGSSTVCTEQWKSFLGE.

Exemplary Soluble Rat Tissue Factor Domain
(SEQ ID NO: 4)
AGTPPGKAFNLTWISTDFKTILEWQPKPTNYTYTVQISDRSRNWKYKCT

GTTDTECDLTDEIVKDVNWTYEARVLSVPWRNSTHGKETLFGTHGEEPP

FTNARKFLPYRDTKIGQPVIQKYEQGGTKLKVTVKDSFTLVRKNGTFLT

LRQVFGNDLGYILTYRKDSSTGRKTNTTHTNEFLIDVEKGVSYCFFAQA

VIFSRKTNHKSPESITKCTEQWKSVLGE.

Exemplary Mutant Soluble Human Tissue Factor Domain
(SEQ ID NO: 5)
SGTTNTVAAYNLTWKSTNFATALEWEPKPVNQVYTVQISTKSGDWKSKC

FYTTDTECALTDEIVKDVKQTYLARVFSYPAGNVESTGSAGEPLYENSP

EFTPYLETNLGQPTIQSFEQVGTKVNVTVEDERTLVARNNTALSLRDVF

GKDLIYTLYYWKSSSSGKKTAKTNTNEFLIDVDKGENYCFSVQAVIPSR

TVNRKSTDSPVECMGQEKGEFRE.

Exemplary Mutant Soluble Human Tissue Factor Domain
(SEQ ID NO: 6)
SGTTNTVAAYNLTWKSTNFATALEWEPKPVNQVYTVQISTKSGDAKSKC

FYTTDTECALTDEIVKDVKQTYLARVFSYPAGNVESTGSAGEPLAENSP

EFTPYLETNLGQPTIQSFEQVGTKVNVTVEDERTLVARNNTALSLRDVF

GKDLIYTLYYWKSSSSGKKTAKTNTNEFLIDVDKGENYCFSVQAVIPSR

TVNRKSTDSPVECMGQEKGEFRE.

In some embodiments, a soluble tissue factor domain can include a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 1, 3, 4, 5, or 6. In some embodiments, a soluble tissue factor domain can include a sequence of SEQ ID NO: 1, 3, 4, 5, or 6 with one to twenty amino acids (e.g., 2, 3, 4, 5, 6, 7, 8, 9, 10, 11, 12, 13, 14, 15, 16, 17, 18, 19, or 20) amino acids removed from its N-terminus and/or one to twenty amino acids (e.g., 2, 3, 4, 5, 6, 7, 8, 9, 10, 11, 12, 13, 14, 15, 16, 17, 18, 19, or 20) amino acids removed from its C-terminus.

As will be appreciated by those of skill in the art, mutation of amino acids that are conserved between different mammalian species is more likely to decrease the activity and/or structural stability of the protein, while mutation of amino acids that are not conserved between different mammalian species is less likely to decrease the activity and/or structural stability of the protein.

In some examples, the soluble tissue factor domain is not capable of binding to Factor VIIa. In some examples, the soluble tissue factor domain does not convert inactive Factor X into Factor Xa. In some embodiments, the single-chain chimeric polypeptide does not stimulate blood coagulation in a mammal.

In some examples, the soluble tissue factor domain can be a soluble human tissue factor domain. In some embodiments, the soluble tissue factor domain can be a soluble mouse tissue factor domain. In some embodiments, the soluble tissue factor domain can be a soluble rat tissue factor domain.

In some examples, the soluble tissue factor domain does not include one or more (e.g., two, three, four, five, six or seven) of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the mutant soluble tissue factor possesses the amino acid sequence of SEQ ID NO: 5 or SEQ ID NO: 6.

In some examples, the soluble tissue factor domain can be encoded by a nucleic acid including a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 2.

In some embodiments, the soluble tissue factor domain can have a total length of about 20 amino acids to about 220 amino acids, about 20 amino acids to about 215 amino acids, about 20 amino acids to about 210 amino acids, about 20 amino acids to about 205 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids, about 30 amino acids to about 220 amino acids, about 30 amino acids to about 215 amino acids, about 30 amino acids to about 210 amino acids, about 30 amino acids to about 205 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 60 amino acids, about 30 amino acids to about 50 amino acids, about 30 amino acids to about 40 amino acids, about 40 amino acids to about 220 amino acids, about 40 amino acids to about 215 amino acids, about 40 amino acids to about 210 amino acids, about 40 amino acids to about 205 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 60 amino acids, about 40 amino acids to about 50 amino acids, about 50 amino acids to about 220 amino acids, about 50 amino acids to about 215 amino acids, about 50 amino acids to about 210 amino acids, about 50 amino acids to about 205 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 60 amino acids, about 60 amino acids to about 220 amino acids, about 60 amino acids to about 215 amino acids, about 60 amino acids to about 210 amino acids, about 60 amino acids to about 205 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 70 amino acids to about 220 amino acids, about 70 amino acids to about 215 amino acids, about 70 amino acids to about 210 amino acids, about 70 amino acids to about 205 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 80 amino acids to about 220 amino acids, about 80 amino acids to about 215 amino acids, about 80 amino acids to about 210 amino acids, about 80 amino acids to about 205 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 90 amino acids to about 220 amino acids, about 90 amino acids to about 215 amino acids, about 90 amino acids to about 210 amino acids, about 90 amino acids to about 205 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 100 amino acids to about 220 amino acids, about 100 amino acids to about 215 amino acids, about 100 amino acids to about 210 amino acids, about 100 amino acids to about 205 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 110 amino acids to about 220 amino acids, about 110 amino acids to about 215 amino acids, about 110 amino acids to about 210 amino acids, about 110 amino acids to about 205 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 220 amino acids, about 115 amino acids to about 215 amino acids, about 115 amino acids to about 210 amino acids, about 115 amino acids to about 205 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 220 amino acids, about 120 amino acids to about 215 amino acids, about 120 amino acids to about 210 amino acids, about 120 amino acids to about 205 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 220 amino acids, about 125 amino acids to about 215 amino acids, about 125 amino acids to about 210 amino acids, about 125 amino acids to about 205 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 220 amino acids, about 130 amino acids to about 215 amino acids, about 130 amino acids to about 210 amino acids, about 130 amino acids to about 205 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 220 amino acids, about 135 amino acids to about 215 amino acids, about 135 amino acids to about 210 amino acids, about 135 amino acids to about 205 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 220 amino acids, about 140 amino acids to about 215 amino acids, about 140 amino acids to about 210 amino acids, about 140 amino acids to about 205 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 220 amino acids, about 145 amino acids to about 215 amino acids, about 145 amino acids to about 210 amino acids, about 145 amino acids to about 205 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 220 amino acids, about 150 amino acids to about 215 amino acids, about 150 amino acids to about 210 amino acids, about 150 amino acids to about 205 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 220 amino acids, about 155 amino acids to about 215 amino acids, about 155 amino acids to about 210 amino acids, about 155 amino acids to about 205 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 220 amino acids, about 160 amino acids to about 215 amino acids, about 160 amino acids to about 210 amino acids, about 160 amino acids to about 205 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 220 amino acids, about 165 amino acids to about 215 amino acids, about 165 amino acids to about 210 amino acids, about 165 amino acids to about 205 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 220 amino acids, about 170 amino acids to about 215 amino acids, about 170 amino acids to about 210 amino acids, about 170 amino acids to about 205 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 220 amino acids, about 175 amino acids to about 215 amino acids, about 175 amino acids to about 210 amino acids, about 175 amino acids to about 205 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 220 amino acids, about 180 amino acids to about 215 amino acids, about 180 amino acids to about 210 amino acids, about 180 amino acids to about 205 amino acids, about 180 amino acids to about 200 amino acids, about 180 amino acids to about 195 amino acids, about 180 amino acids to about 190 amino acids, about 180 amino acids to about 185 amino acids, about 185 amino acids to about 220 amino acids, about 185 amino acids to about 215 amino acids, about 185 amino acids to about 210 amino acids, about 185 amino acids to about 205 amino acids, about 185 amino acids to about 200 amino acids, about 185 amino acids to about 195 amino acids, about 185 amino acids to about 190 amino acids, about 190 amino acids to about 220 amino acids, about 190 amino acids to about 215 amino acids, about 190 amino acids to about 210 amino acids, about 190 amino acids to about 205 amino acids, about 190 amino acids to about 200 amino acids, about 190 amino acids to about 195 amino acids, about 195 amino acids to about 220 amino acids, about 195 amino acids to about 215 amino acids, about 195 amino acids to about 210 amino acids, about 195 amino acids to about 205 amino acids, about 195 amino acids to about 200 amino acids, about 200 amino acids to about 220 amino acids, about 200 amino acids to about 215 amino acids, about 200 amino acids to about 210 amino acids, about 200 amino acids to about 205 amino acids, about 205 amino acids to about 220 amino acids, about 205 amino acids to about 215 amino acids, about 205 amino acids to about 210 amino acids, about 210 amino acids to about 220 amino acids, about 210 amino acids to about 215 amino acids, or about 215 amino acids to about 220 amino acids.

Linker Sequences

In some embodiments, the linker sequence can be a flexible linker sequence. Non-limiting examples of linker sequences that can be used are described in Klein et al., Protein Engineering, Design & Selection Vol. 27, No. 10, pp. 325-330, 2014; Priyanka et al., Protein Sci., 2013 February; 22(2):153-167. In some examples, the linker sequence is a synthetic linker sequence.

In some embodiments of any of the single-chain chimeric polypeptides or any of the multi-chain chimeric polypeptides described herein, the polypeptide can include one, two, three, four, five, six, seven, eight, nine, or ten linker sequence(s) (e.g., the same or different linker sequences, e.g., any of the exemplary linker sequences described herein or known in the art). In some embodiments of any of the single-chain chimeric polypeptides or any of the multi-chain chimeric polypeptides described herein, the polypeptide can include one, two, three, four, five, six, seven, eight, nine, or ten linker sequence(s) (e.g., the same or different linker sequences, e.g., any of the exemplary linker sequences described herein or known in the art).

In some embodiments, a linker sequence can have a total length of 1 amino acid to about 100 amino acids, 1 amino acid to about 90 amino acids, 1 amino acid to about 80 amino acids, 1 amino acid to about 70 amino acids, 1 amino acid to about 60 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, about 2 amino acids to about 100 amino acids, about 2 amino acids to about 90 amino acids, about 2 amino acids to about 80 amino acids, about 2 amino acids to about 70 amino acids, about 2 amino acids to about 60 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about 90 amino acids, about 4 amino acids to about 80 amino acids, about 4 amino acids to about 70 amino acids, about 4 amino acids to about 60 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 100 amino acids, about 6 amino acids to about 90 amino acids, about 6 amino acids to about 80 amino acids, about 6 amino acids to about 70 amino acids, about 6 amino acids to about 60 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 90 amino acids, about 8 amino acids to about 80 amino acids, about 8 amino acids to about 70 amino acids, about 8 amino acids to about 60 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 100 amino acids, about 10 amino acids to about 90 amino acids, about 10 amino acids to about 80 amino acids, about 10 amino acids to about 70 amino acids, about 10 amino acids to about 60 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 100 amino acids, about 12 amino acids to about 90 amino acids, about 12 amino acids to about 80 amino acids, about 12 amino acids to about 70 amino acids, about 12 amino acids to about 60 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 100 amino acids, about 14 amino acids to about 90 amino acids, about 14 amino acids to about 80 amino acids, about 14 amino acids to about 70 amino acids, about 14 amino acids to about 60 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 100 amino acids, about 16 amino acids to about 90 amino acids, about 16 amino acids to about 80 amino acids, about 16 amino acids to about 70 amino acids, about 16 amino acids to about 60 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 24 amino acids, about 16 amino acids to about 22 amino acids, about 16 amino acids to about 20 amino acids, about 16 amino acids to about 18 amino acids, about 18 amino acids to about 100 amino acids, about 18 amino acids to about 90 amino acids, about 18 amino acids to about 80 amino acids, about 18 amino acids to about 70 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 24 amino acids, about 18 amino acids to about 22 amino acids, about 18 amino acids to about 20 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 24 amino acids, about 20 amino acids to about 22 amino acids, about 22 amino acids to about 100 amino acids, about 22 amino acids to about 90 amino acids, about 22 amino acids to about 80 amino acids, about 22 amino acids to about 70 amino acids, about 22 amino acids to about 60 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 22 amino acids to about 24 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 100 amino acids, about 60 amino acids to about 90 amino acids, about 60 amino acids to about 80 amino acids, about 60 amino acids to about 70 amino acids, about 70 amino acids to about 100 amino acids, about 70 amino acids to about 90 amino acids, about 70 amino acids to about 80 amino acids, about 80 amino acids to about 100 amino acids, about 80 amino acids to about 90 amino acids, or about 90 amino acids to about 100 amino acids.

In some embodiments, the linker sequence is rich in glycine (Gly or G) residues. In some embodiments, the linker sequence is rich in serine (Ser or S) residues. In some embodiments, the linker sequence is rich in glycine and serine residues. In some embodiments, the linker sequence has one or more glycine-serine residue pairs (GS), e.g., 1, 2, 3, 4, 5, 6, 7, 8, 9, or 10 or more GS pairs. In some embodiments, the linker sequence has one or more Gly-Gly-Gly-Ser (GGGS) sequences, e.g., 1, 2, 3, 4, 5, 6, 7, 8, 9, or 10 or more GGGS sequences. In some embodiments, the linker sequence has one or more Gly-Gly-Gly-Gly-Ser (GGGGS) sequences, e.g., 1, 2, 3, 4, 5, 6, 7, 8, 9, or 10 or more GGGGS sequences. In some embodiments, the linker sequence has one or more Gly-Gly-Ser-Gly (GGSG) sequences, e.g., 1, 2, 3, 4, 5, 6, 7, 8, 9, or 10 or more GGSG sequences.

In some embodiments, the linker sequence can comprise or consist of GGGGSGGGGSGGGGS (SEQ ID NO: 7). In some embodiments, the linker sequence can be encoded by a nucleic acid comprising or consisting of:

```
(SEQ ID NO: 8)
GGCGGTGGAGGATCCGGAGGAGGTGGCTCCGGCGGCGGAGGATCT.
```

In some embodiments, the linker sequence can comprise or consist of: GGGSGGGS (SEQ ID NO: 9).

Target-Binding Domains

In some embodiments of any of the single-chain chimeric polypeptides or any of the multi-chain chimeric polypeptides described herein, the first target-binding domain, the second target-binding domain, and/or the additional one or more target-binding domains can be an antigen-binding domain (e.g., any of the exemplary antigen-binding domains described herein or known in the art), a soluble interleukin or cytokine protein (e.g., any of the exemplary soluble interleukin proteins or soluble cytokine proteins described herein or known in the art), a soluble interleukin or cytokine receptor (e.g., any of the exemplary soluble interleukin receptors or soluble cytokine receptors described herein or known in the art), and ligands of co-stimulatory molecules (e.g., any of the exemplary ligands of co-stimulatory molecules described herein or known in the art).

In some embodiments of any of the single-chain chimeric polypeptides or any of the multi-chain chimeric polypeptides described herein, one or more of the first target-binding domain (e.g., any of the exemplary first target binding domains described herein or known in the art), the second target-binding domain (e.g., any of the exemplary second target binding domains described herein or known in the art), and the one or more additional target binding domains can each, independently, bind specifically to a target selected from the group of: CD16a, CD28, CD3 (e.g., one or more of CD3α, CD3β, CD3δ, CD3ε, and CD3γ), CD33, CD20, CD19, CD22, CD40, CD47, CD52, CD70, CD80, CD86, CD123, CD137, CD272, IL-1R, IL-1, VEGF, IL-6R, IL-4, IL-10, PDL-1, PDL-2, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, B7-H4, HVEM, EPCAM, BCMA, P-cadherin, CEACAM5, VISTA, a UL16-binding protein, HLA-DR, DLL4, TYRO3, AXL, MER, CD122, CD155, PDGF-DD, ILT3, ILT4, TIGIT, MHCII, LAG3, OX40, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the single-chain chimeric polypeptides or any of the multi-chain chimeric polypeptides described herein, the first target-binding domain, the second target-binding domain, and/or the one or more additional target-binding domains, can be a soluble interleukin, soluble cytokine protein, or soluble cell surface protein. In some examples, the soluble interleukin, soluble cytokine protein, or soluble cell surface protein is selected from the group of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

In some embodiments of any of the single-chain chimeric polypeptides or any of the multi-chain chimeric polypeptides described herein, the first target-binding domain, the second target-binding domain, and/or the one or more additional target-binding domains, can be a soluble interleukin receptor, a soluble cytokine receptor, or a soluble cell surface receptor. In some examples, the soluble interleukin receptor, the soluble cytokine receptor, or the soluble cell surface receptor is soluble TGF-β receptor II (TGF-βRII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

In some embodiments of any of the single-chain chimeric polypeptides or any of the multi-chain chimeric polypeptides described herein, the first target-binding domain, the second target-binding domain, and/or the one or more additional target-binding domains, can be a ligand of a co-stimulatory molecule. Non-limiting examples of ligands of a co-stimulatory molecule include soluble CD80, soluble CD86, soluble CD40, soluble ICOSL, soluble CD70, soluble OX40L, soluble 4-1BBL, soluble GITRL, soluble LIGHT, soluble TIM3, soluble TIM4, soluble ICAM1, soluble LFA3, soluble CD1d, or soluble LLT-1.

In some embodiments of any of the single-chain chimeric polypeptides or any of the multi-chain chimeric polypeptides described herein, the first target-binding domain, the second target-binding domain, and/or the one or more additional target-binding domains can each independent have a total number of amino acids of about 5 amino acids to about 1000 amino acids, about 5 amino acids to about 950 amino acids, about 5 amino acids to about 900 amino acids, about 5 amino acids to about 850 amino acids, about 5 amino acids to about 800 amino acids, about 5 amino acids to about 750 amino acids, about 5 amino acids to about 700 amino acids, about 5 amino acids to about 650 amino acids, about 5 amino acids to about 600 amino acids, about 5 amino acids to about 550 amino acids, about 5 amino acids to about 500 amino acids, about 5 amino acids to about 450 amino acids, about 5 amino acids to about 400 amino acids, about 5 amino acids to about 350 amino acids, about 5 amino acids to about 300 amino acids, about 5 amino acids to about 280 amino acids, about 5 amino acids to about 260 amino acids, about 5 amino acids to about 240 amino acids, about 5 amino acids to about 220 amino acids, about 5 amino acids to about 200 amino acids, about 5 amino acids to about 195 amino acids, about 5 amino acids to about 190 amino acids, about 5 amino acids to about 185 amino acids, about 5 amino acids to about 180 amino acids, about 5 amino acids to about 175 amino acids, about 5 amino acids to about 170 amino acids, about 5 amino acids to about 165 amino acids, about 5 amino acids to about 160 amino acids, about 5 amino acids to about 155 amino acids, about 5 amino acids to about 150 amino acids, about 5 amino acids to about 145 amino acids, about 5 amino acids to about 140 amino acids, about 5 amino acids to about 135 amino acids, about 5 amino acids to about 130 amino acids, about 5 amino acids to about 125 amino acids, about 5 amino acids to about 120 amino acids, about 5 amino acids to about 115 amino acids, about 5 amino acids to about 110 amino acids, about 5 amino acids to about 105 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 10 amino acids to about 1000 amino acids, about 10 amino acids to about 950 amino acids, about 10 amino acids to about 900 amino acids, about 10 amino acids to about 850 amino acids, about 10 amino acids to about 800 amino acids, about 10 amino acids to about 750 amino acids, about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 280 amino acids, about 10 amino acids to about 260 amino acids, about 10 amino acids to about 240 amino acids, about 10 amino acids to about 220 amino acids, about 10 amino acids to about 200 amino acids, about 10 amino acids to about 195 amino acids, about 10 amino acids to about 190 amino acids, about 10 amino acids to about 185 amino acids, about 10 amino acids to about 180 amino acids, about 10 amino acids to about 175 amino acids, about 10 amino acids to about 170 amino acids, about 10 amino acids to about 165 amino acids, about 10 amino acids to about 160 amino acids, about 10 amino acids to about 155 amino acids, about 10 amino acids to about 150 amino acids, about 10 amino acids to about 145 amino acids, about 10 amino acids to about 140 amino acids, about 10 amino acids to about 135 amino acids, about 10 amino acids to about 130 amino acids, about 10 amino acids to about 125 amino acids, about 10 amino acids to about 120 amino acids, about 10 amino acids to about 115 amino acids, about 10 amino acids to about 110 amino acids, about 10 amino acids to about 105 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 1000 amino acids, about 15 amino acids to about 950 amino acids, about 15 amino acids to about 900 amino acids, about 15 amino acids to about 850 amino acids, about 15 amino acids to about 800 amino acids, about 15 amino acids to about 750 amino acids, about 15 amino acids to about 700 amino acids, about 15 amino acids to about 650 amino acids, about 15 amino acids to about 600 amino acids, about 15 amino acids to about 550 amino acids, about 15 amino acids to about 500 amino acids, about 15 amino acids to about 450 amino acids, about 15 amino acids to about 400 amino acids, about 15 amino acids to about 350 amino acids, about 15 amino acids to about 300 amino acids, about 15 amino acids to about 280 amino acids, about 15 amino acids to about 260 amino acids, about 15 amino acids to about 240 amino acids, about 15 amino acids to about 220 amino acids, about 15 amino acids to about 200 amino acids, about 15 amino acids to about 195 amino acids, about 15 amino acids to about 190 amino acids, about 15 amino acids to about 185 amino acids, about 15 amino acids to about 180 amino acids, about 15 amino acids to about 175 amino acids, about 15 amino acids to about 170 amino acids, about 15 amino acids to about 165 amino acids, about 15 amino acids to about 160 amino acids, about 15 amino acids to about 155 amino acids, about 15 amino acids to about 150 amino acids, about 15 amino acids to about 145 amino acids, about 15 amino acids to about 140 amino acids, about 15 amino acids to about 135 amino acids, about 15 amino acids to about 130 amino acids, about 15 amino acids to about 125 amino acids, about 15 amino acids to about 120 amino acids, about 15 amino acids to about 115 amino acids, about 15 amino acids to about 110 amino acids, about 15 amino acids to about 105 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 280 amino acids, about 20 amino acids to about 260 amino acids, about 20 amino acids to about 240 amino acids, about 20 amino acids to about 220 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 280 amino acids, about 25 amino acids to about 260 amino acids, about 25 amino acids to about 240 amino acids, about 25 amino acids to about 220 amino acids, about 25 amino acids to about 200 amino acids, about 25 amino acids to about 195 amino acids, about 25 amino acids to about 190 amino acids, about 25 amino acids to about 185 amino acids, about 25 amino acids to about 180 amino acids, about 25 amino acids to about 175 amino acids, about 25 amino acids to about 170 amino acids, about 25 amino acids to about 165 amino acids, about 25 amino acids to about 160 amino acids, about 25 amino acids to about 155 amino acids, about 25 amino acids to about 150 amino acids, about 25 amino acids to about 145 amino acids, about 25 amino acids to about 140 amino acids, about 25 amino acids to about 135 amino acids, about 25 amino acids to about 130 amino acids, about 25 amino acids to about 125 amino acids, about 25 amino acids to about 120 amino acids, about 25 amino acids to about 115 amino acids, about 25 amino acids to about 110 amino acids, about 25 amino acids to about 105 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 280 amino acids, about 30 amino acids to about 260 amino acids, about 30 amino acids to about 240 amino acids, about 30 amino acids to about 220 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 280 amino acids, about 35 amino acids to about 260 amino acids, about 35 amino acids to about 240 amino acids, about 35 amino acids to about 220 amino acids, about 35 amino acids to about 200 amino acids, about 35 amino acids to about 195 amino acids, about 35 amino acids to about 190 amino acids, about 35 amino acids to about 185 amino acids, about 35 amino acids to about 180 amino acids, about 35 amino acids to about 175 amino acids, about 35 amino acids to about 170 amino acids, about 35 amino acids to about 165 amino acids, about 35 amino acids to about 160 amino acids, about 35 amino acids to about 155 amino acids, about 35 amino acids to about 150 amino acids, about 35 amino acids to about 145 amino acids, about 35 amino acids to about 140 amino acids, about 35 amino acids to about 135 amino acids, about 35 amino acids to about 130 amino acids, about 35 amino acids to about 125 amino acids, about 35 amino acids to about 120 amino acids, about 35 amino acids to about 115 amino acids, about 35 amino acids to about 110 amino acids, about 35 amino acids to about 105 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 280 amino acids, about 40 amino acids to about 260 amino acids, about 40 amino acids to about 240 amino acids, about 40 amino acids to about 220 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 280 amino acids, about 45 amino acids to about 260 amino acids, about 45 amino acids to about 240 amino acids, about 45 amino acids to about 220 amino acids, about 45 amino acids to about 200 amino acids, about 45 amino acids to about 195 amino acids, about 45 amino acids to about 190 amino acids, about 45 amino acids to about 185 amino acids, about 45 amino acids to about 180 amino acids, about 45 amino acids to about 175 amino acids, about 45 amino acids to about 170 amino acids, about 45 amino acids to about 165 amino acids, about 45 amino acids to about 160 amino acids, about 45 amino acids to about 155 amino acids, about 45 amino acids to about 150 amino acids, about 45 amino acids to about 145 amino acids, about 45 amino acids to about 140 amino acids, about 45 amino acids to about 135 amino acids, about 45 amino acids to about 130 amino acids, about 45 amino acids to about 125 amino acids, about 45 amino acids to about 120 amino acids, about 45 amino acids to about 115 amino acids, about 45 amino acids to about 110 amino acids, about 45 amino acids to about 105 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 1000 amino acids, about 55 amino acids to about 950 amino acids, about 55 amino acids to about 900 amino acids, about 55 amino acids to about 850 amino acids, about 55 amino acids to about 800 amino acids, about 55 amino acids to about 750 amino acids, about 55 amino acids to about 700 amino acids, about 55 amino acids to about 650 amino acids, about 55 amino acids to about 600 amino acids, about 55 amino acids to about 550 amino acids, about 55 amino acids to about 500 amino acids, about 55 amino acids to about 450 amino acids, about 55 amino acids to about 400 amino acids, about 55 amino acids to about 350 amino acids, about 55 amino acids to about 300 amino acids, about 55 amino acids to about 280 amino acids, about 55 amino acids to about 260 amino acids, about 55 amino acids to about 240 amino acids, about 55 amino acids to about 220 amino acids, about 55 amino acids to about 200 amino acids, about 55 amino acids to about 195 amino acids, about 55 amino acids to about 190 amino acids, about 55 amino acids to about 185 amino acids, about 55 amino acids to about 180 amino acids, about 55 amino acids to about 175 amino acids, about 55 amino acids to about 170 amino acids, about 55 amino acids to about 165 amino acids, about 55 amino acids to about 160 amino acids, about 55 amino acids to about 155 amino acids, about 55 amino acids to about 150 amino acids, about 55 amino acids to about 145 amino acids, about 55 amino acids to about 140 amino acids, about 55 amino acids to about 135 amino acids, about 55 amino acids to about 130 amino acids, about 55 amino acids to about 125 amino acids, about 55 amino acids to about 120 amino acids, about 55 amino acids to about 115 amino acids, about 55 amino acids to about 110 amino acids, about 55 amino acids to about 105 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 280 amino acids, about 60 amino acids to about 260 amino acids, about 60 amino acids to about 240 amino acids, about 60 amino acids to about 220 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 1000 amino acids, about 65 amino acids to about 950 amino acids, about 65 amino acids to about 900 amino acids, about 65 amino acids to about 850 amino acids, about 65 amino acids to about 800 amino acids, about 65 amino acids to about 750 amino acids, about 65 amino acids to about 700 amino acids, about 65 amino acids to about 650 amino acids, about 65 amino acids to about 600 amino acids, about 65 amino acids to about 550 amino acids, about 65 amino acids to about 500 amino acids, about 65 amino acids to about 450 amino acids, about 65 amino acids to about 400 amino acids, about 65 amino acids to about 350 amino acids, about 65 amino acids to about 300 amino acids, about 65 amino acids to about 280 amino acids, about 65 amino acids to about 260 amino acids, about 65 amino acids to about 240 amino acids, about 65 amino acids to about 220 amino acids, about 65 amino acids to about 200 amino acids, about 65 amino acids to about 195 amino acids, about 65 amino acids to about 190 amino acids, about 65 amino acids to about 185 amino acids, about 65 amino acids to about 180 amino acids, about 65 amino acids to about 175 amino acids, about 65 amino acids to about 170 amino acids, about 65 amino acids to about 165 amino acids, about 65 amino acids to about 160 amino acids, about 65 amino acids to about 155 amino acids, about 65 amino acids to about 150 amino acids, about 65 amino acids to about 145 amino acids, about 65 amino acids to about 140 amino acids, about 65 amino acids to about 135 amino acids, about 65 amino acids to about 130 amino acids, about 65 amino acids to about 125 amino acids, about 65 amino acids to about 120 amino acids, about 65 amino acids to about 115 amino acids, about 65 amino acids to about 110 amino acids, about 65 amino acids to about 105 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 280 amino acids, about 70 amino acids to about 260 amino acids, about 70 amino acids to about 240 amino acids, about 70 amino acids to about 220 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 1000 amino acids, about 75 amino acids to about 950 amino acids, about 75 amino acids to about 900 amino acids, about 75 amino acids to about 850 amino acids, about 75 amino acids to about 800 amino acids, about 75 amino acids to about 750 amino acids, about 75 amino acids to about 700 amino acids, about 75 amino acids to about 650 amino acids, about 75 amino acids to about 600 amino acids, about 75 amino acids to about 550 amino acids, about 75 amino acids to about 500 amino acids, about 75 amino acids to about 450 amino acids, about 75 amino acids to about 400 amino acids, about 75 amino acids to about 350 amino acids, about 75 amino acids to about 300 amino acids, about 75 amino acids to about 280 amino acids, about 75 amino acids to about 260 amino acids, about 75 amino acids to about 240 amino acids, about 75 amino acids to about 220 amino acids, about 75 amino acids to about 200 amino acids, about 75 amino acids to about 195 amino acids, about 75 amino acids to about 190 amino acids, about 75 amino acids to about 185 amino acids, about 75 amino acids to about 180 amino acids, about 75 amino acids to about 175 amino acids, about 75 amino acids to about 170 amino acids, about 75 amino acids to about 165 amino acids, about 75 amino acids to about 160 amino acids, about 75 amino acids to about 155 amino acids, about 75 amino acids to about 150 amino acids, about 75 amino acids to about 145 amino acids, about 75 amino acids to about 140 amino acids, about 75 amino acids to about 135 amino acids, about 75 amino acids to about 130 amino acids, about 75 amino acids to about 125 amino acids, about 75 amino acids to about 120 amino acids, about 75 amino acids to about 115 amino acids, about 75 amino acids to about 110 amino acids, about 75 amino acids to about 105 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 280 amino acids, about 80 amino acids to about 260 amino acids, about 80 amino acids to about 240 amino acids, about 80 amino acids to about 220 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 80 amino acids to about 85 amino acids, about 85 amino acids to about 1000 amino acids, about 85 amino acids to about 950 amino acids, about 85 amino acids to about 900 amino acids, about 85 amino acids to about 850 amino acids, about 85 amino acids to about 800 amino acids, about 85 amino acids to about 750 amino acids, about 85 amino acids to about 700 amino acids, about 85 amino acids to about 650 amino acids, about 85 amino acids to about 600 amino acids, about 85 amino acids to about 550 amino acids, about 85 amino acids to about 500 amino acids, about 85 amino acids to about 450 amino acids, about 85 amino acids to about 400 amino acids, about 85 amino acids to about 350 amino acids, about 85 amino acids to about 300 amino acids, about 85 amino acids to about 280 amino acids, about 85 amino acids to about 260 amino acids, about 85 amino acids to about 240 amino acids, about 85 amino acids to about 220 amino acids, about 85 amino acids to about 200 amino acids, about 85 amino acids to about 195 amino acids, about 85 amino acids to about 190 amino acids, about 85 amino acids to about 185 amino acids, about 85 amino acids to about 180 amino acids, about 85 amino acids to about 175 amino acids, about 85 amino acids to about 170 amino acids, about 85 amino acids to about 165 amino acids, about 85 amino acids to about 160 amino acids, about 85 amino acids to about 155 amino acids, about 85 amino acids to about 150 amino acids, about 85 amino acids to about 145 amino acids, about 85 amino acids to about 140 amino acids, about 85 amino acids to about 135 amino acids, about 85 amino acids to about 130 amino acids, about 85 amino acids to about 125 amino acids, about 85 amino acids to about 120 amino acids, about 85 amino acids to about 115 amino acids, about 85 amino acids to about 110 amino acids, about 85 amino acids to about 105 amino acids, about 85 amino acids to about 100 amino acids, about 85 amino acids to about 95 amino acids, about 85 amino acids to about 90 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 280 amino acids, about 90 amino acids to about 260 amino acids, about 90 amino acids to about 240 amino acids, about 90 amino acids to about 220 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 90 amino acids to about 95 amino acids, about 95 amino acids to about 1000 amino acids, about 95 amino acids to about 950 amino acids, about 95 amino acids to about 900 amino acids, about 95 amino acids to about 850 amino acids, about 95 amino acids to about 800 amino acids, about 95 amino acids to about 750 amino acids, about 95 amino acids to about 700 amino acids, about 95 amino acids to about 650 amino acids, about 95 amino acids to about 600 amino acids, about 95 amino acids to about 550 amino acids, about 95 amino acids to about 500 amino acids, about 95 amino acids to about 450 amino acids, about 95 amino acids to about 400 amino acids, about 95 amino acids to about 350 amino acids, about 95 amino acids to about 300 amino acids, about 95 amino acids to about 280 amino acids, about 95 amino acids to about 260 amino acids, about 95 amino acids to about 240 amino acids, about 95 amino acids to about 220 amino acids, about 95 amino acids to about 200 amino acids, about 95 amino acids to about 195 amino acids, about 95 amino acids to about 190 amino acids, about 95 amino acids to about 185 amino acids, about 95 amino acids to about 180 amino acids, about 95 amino acids to about 175 amino acids, about 95 amino acids to about 170 amino acids, about 95 amino acids to about 165 amino acids, about 95 amino acids to about 160 amino acids, about 95 amino acids to about 155 amino acids, about 95 amino acids to about 150 amino acids, about 95 amino acids to about 145 amino acids, about 95 amino acids to about 140 amino acids, about 95 amino acids to about 135 amino acids, about 95 amino acids to about 130 amino acids, about 95 amino acids to about 125 amino acids, about 95 amino acids to about 120 amino acids, about 95 amino acids to about 115 amino acids, about 95 amino acids to about 110 amino acids, about 95 amino acids to about 105 amino acids, about 95 amino acids to about 100 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 100 amino acids to about 105 amino acids, about 105 amino acids to about 1000 amino acids, about 105 amino acids to about 950 amino acids, about 105 amino acids to about 900 amino acids, about 105 amino acids to about 850 amino acids, about 105 amino acids to about 800 amino acids, about 105 amino acids to about 750 amino acids, about 105 amino acids to about 700 amino acids, about 105 amino acids to about 650 amino acids, about 105 amino acids to about 600 amino acids, about 105 amino acids to about 550 amino acids, about 105 amino acids to about 500 amino acids, about 105 amino acids to about 450 amino acids, about 105 amino acids to about 400 amino acids, about 105 amino acids to about 350 amino acids, about 105 amino acids to about 300 amino acids, about 105 amino acids to about 280 amino acids, about 105 amino acids to about 260 amino acids, about 105 amino acids to about 240 amino acids, about 105 amino acids to about 220 amino acids, about 105 amino acids to about 200 amino acids, about 105 amino acids to about 195 amino acids, about 105 amino acids to about 190 amino acids, about 105 amino acids to about 185 amino acids, about 105 amino acids to about 180 amino acids, about 105 amino acids to about 175 amino acids, about 105 amino acids to about 170 amino acids, about 105 amino acids to about 165 amino acids, about 105 amino acids to about 160 amino acids, about 105 amino acids to about 155 amino acids, about 105 amino acids to about 150 amino acids, about 105 amino acids to about 145 amino acids, about 105 amino acids to about 140 amino acids, about 105 amino acids to about 135 amino acids, about 105 amino acids to about 130 amino acids, about 105 amino acids to about 125 amino acids, about 105 amino acids to about 120 amino acids, about 105 amino acids to about 115 amino acids, about 105 amino acids to about 110 amino acids, about 110 amino acids to about 1000 amino acids, about 110 amino acids to about 950 amino acids, about 110 amino acids to about 900 amino acids, about 110 amino acids to about 850 amino acids, about 110 amino acids to about 800 amino acids, about 110 amino acids to about 750 amino acids, about 110 amino acids to about 700 amino acids, about 110 amino acids to about 650 amino acids, about 110 amino acids to about 600 amino acids, about 110 amino acids to about 550 amino acids, about 110 amino acids to about 500 amino acids, about 110 amino acids to about 450 amino acids, about 110 amino acids to about 400 amino acids, about 110 amino acids to about 350 amino acids, about 110 amino acids to about 300 amino acids, about 110 amino acids to about 280 amino acids, about 110 amino acids to about 260 amino acids, about 110 amino acids to about 240 amino acids, about 110 amino acids to about 220 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 1000 amino acids, about 115 amino acids to about 950 amino acids, about 115 amino acids to about 900 amino acids, about 115 amino acids to about 850 amino acids, about 115 amino acids to about 800 amino acids, about 115 amino acids to about 750 amino acids, about 115 amino acids to about 700 amino acids, about 115 amino acids to about 650 amino acids, about 115 amino acids to about 600 amino acids, about 115 amino acids to about 550 amino acids, about 115 amino acids to about 500 amino acids, about 115 amino acids to about 450 amino acids, about 115 amino acids to about 400 amino acids, about 115 amino acids to about 350 amino acids, about 115 amino acids to about 300 amino acids, about 115 amino acids to about 280 amino acids, about 115 amino acids to about 260 amino acids, about 115 amino acids to about 240 amino acids, about 115 amino acids to about 220 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 1000 amino acids, about 120 amino acids to about 950 amino acids, about 120 amino acids to about 900 amino acids, about 120 amino acids to about 850 amino acids, about 120 amino acids to about 800 amino acids, about 120 amino acids to about 750 amino acids, about 120 amino acids to about 700 amino acids, about 120 amino acids to about 650 amino acids, about 120 amino acids to about 600 amino acids, about 120 amino acids to about 550 amino acids, about 120 amino acids to about 500 amino acids, about 120 amino acids to about 450 amino acids, about 120 amino acids to about 400 amino acids, about 120 amino acids to about 350 amino acids, about 120 amino acids to about 300 amino acids, about 120 amino acids to about 280 amino acids, about 120 amino acids to about 260 amino acids, about 120 amino acids to about 240 amino acids, about 120 amino acids to about 220 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 1000 amino acids, about 125 amino acids to about 950 amino acids, about 125 amino acids to about 900 amino acids, about 125 amino acids to about 850 amino acids, about 125 amino acids to about 800 amino acids, about 125 amino acids to about 750 amino acids, about 125 amino acids to about 700 amino acids, about 125 amino acids to about 650 amino acids, about 125 amino acids to about 600 amino acids, about 125 amino acids to about 550 amino acids, about 125 amino acids to about 500 amino acids, about 125 amino acids to about 450 amino acids, about 125 amino acids to about 400 amino acids, about 125 amino acids to about 350 amino acids, about 125 amino acids to about 300 amino acids, about 125 amino acids to about 280 amino acids, about 125 amino acids to about 260 amino acids, about 125 amino acids to about 240 amino acids, about 125 amino acids to about 220 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 1000 amino acids, about 130 amino acids to about 950 amino acids, about 130 amino acids to about 900 amino acids, about 130 amino acids to about 850 amino acids, about 130 amino acids to about 800 amino acids, about 130 amino acids to about 750 amino acids, about 130 amino acids to about 700 amino acids, about 130 amino acids to about 650 amino acids, about 130 amino acids to about 600 amino acids, about 130 amino acids to about 550 amino acids, about 130 amino acids to about 500 amino acids, about 130 amino acids to about 450 amino acids, about 130 amino acids to about 400 amino acids, about 130 amino acids to about 350 amino acids, about 130 amino acids to about 300 amino acids, about 130 amino acids to about 280 amino acids, about 130 amino acids to about 260 amino acids, about 130 amino acids to about 240 amino acids, about 130 amino acids to about 220 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 1000 amino acids, about 135 amino acids to about 950 amino acids, about 135 amino acids to about 900 amino acids, about 135 amino acids to about 850 amino acids, about 135 amino acids to about 800 amino acids, about 135 amino acids to about 750 amino acids, about 135 amino acids to about 700 amino acids, about 135 amino acids to about 650 amino acids, about 135 amino acids to about 600 amino acids, about 135 amino acids to about 550 amino acids, about 135 amino acids to about 500 amino acids, about 135 amino acids to about 450 amino acids, about 135 amino acids to about 400 amino acids, about 135 amino acids to about 350 amino acids, about 135 amino acids to about 300 amino acids, about 135 amino acids to about 280 amino acids, about 135 amino acids to about 260 amino acids, about 135 amino acids to about 240 amino acids, about 135 amino acids to about 220 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 1000 amino acids, about 140 amino acids to about 950 amino acids, about 140 amino acids to about 900 amino acids, about 140 amino acids to about 850 amino acids, about 140 amino acids to about 800 amino acids, about 140 amino acids to about 750 amino acids, about 140 amino acids to about 700 amino acids, about 140 amino acids to about 650 amino acids, about 140 amino acids to about 600 amino acids, about 140 amino acids to about 550 amino acids, about 140 amino acids to about 500 amino acids, about 140 amino acids to about 450 amino acids, about 140 amino acids to about 400 amino acids, about 140 amino acids to about 350 amino acids, about 140 amino acids to about 300 amino acids, about 140 amino acids to about 280 amino acids, about 140 amino acids to about 260 amino acids, about 140 amino acids to about 240 amino acids, about 140 amino acids to about 220 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 1000 amino acids, about 145 amino acids to about 950 amino acids, about 145 amino acids to about 900 amino acids, about 145 amino acids to about 850 amino acids, about 145 amino acids to about 800 amino acids, about 145 amino acids to about 750 amino acids, about 145 amino acids to about 700 amino acids, about 145 amino acids to about 650 amino acids, about 145 amino acids to about 600 amino acids, about 145 amino acids to about 550 amino acids, about 145 amino acids to about 500 amino acids, about 145 amino acids to about 450 amino acids, about 145 amino acids to about 400 amino acids, about 145 amino acids to about 350 amino acids, about 145 amino acids to about 300 amino acids, about 145 amino acids to about 280 amino acids, about 145 amino acids to about 260 amino acids, about 145 amino acids to about 240 amino acids, about 145 amino acids to about 220 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 1000 amino acids, about 155 amino acids to about 950 amino acids, about 155 amino acids to about 900 amino acids, about 155 amino acids to about 850 amino acids, about 155 amino acids to about 800 amino acids, about 155 amino acids to about 750 amino acids, about 155 amino acids to about 700 amino acids, about 155 amino acids to about 650 amino acids, about 155 amino acids to about 600 amino acids, about 155 amino acids to about 550 amino acids, about 155 amino acids to about 500 amino acids, about 155 amino acids to about 450 amino acids, about 155 amino acids to about 400 amino acids, about 155 amino acids to about 350 amino acids, about 155 amino acids to about 300 amino acids, about 155 amino acids to about 280 amino acids, about 155 amino acids to about 260 amino acids, about 155 amino acids to about 240 amino acids, about 155 amino acids to about 220 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 1000 amino acids, about 160 amino acids to about 950 amino acids, about 160 amino acids to about 900 amino acids, about 160 amino acids to about 850 amino acids, about 160 amino acids to about 800 amino acids, about 160 amino acids to about 750 amino acids, about 160 amino acids to about 700 amino acids, about 160 amino acids to about 650 amino acids, about 160 amino acids to about 600 amino acids, about 160 amino acids to about 550 amino acids, about 160 amino acids to about 500 amino acids, about 160 amino acids to about 450 amino acids, about 160 amino acids to about 400 amino acids, about 160 amino acids to about 350 amino acids, about 160 amino acids to about 300 amino acids, about 160 amino acids to about 280 amino acids, about 160 amino acids to about 260 amino acids, about 160 amino acids to about 240 amino acids, about 160 amino acids to about 220 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 1000 amino acids, about 165 amino acids to about 950 amino acids, about 165 amino acids to about 900 amino acids, about 165 amino acids to about 850 amino acids, about 165 amino acids to about 800 amino acids, about 165 amino acids to about 750 amino acids, about 165 amino acids to about 700 amino acids, about 165 amino acids to about 650 amino acids, about 165 amino acids to about 600 amino acids, about 165 amino acids to about 550 amino acids, about 165 amino acids to about 500 amino acids, about 165 amino acids to about 450 amino acids, about 165 amino acids to about 400 amino acids, about 165 amino acids to about 350 amino acids, about 165 amino acids to about 300 amino acids, about 165 amino acids to about 280 amino acids, about 165 amino acids to about 260 amino acids, about 165 amino acids to about 240 amino acids, about 165 amino acids to about 220 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 1000 amino acids, about 170 amino acids to about 950 amino acids, about 170 amino acids to about 900 amino acids, about 170 amino acids to about 850 amino acids, about 170 amino acids to about 800 amino acids, about 170 amino acids to about 750 amino acids, about 170 amino acids to about 700 amino acids, about 170 amino acids to about 650 amino acids, about 170 amino acids to about 600 amino acids, about 170 amino acids to about 550 amino acids, about 170 amino acids to about 500 amino acids, about 170 amino acids to about 450 amino acids, about 170 amino acids to about 400 amino acids, about 170 amino acids to about 350 amino acids, about 170 amino acids to about 300 amino acids, about 170 amino acids to about 280 amino acids, about 170 amino acids to about 260 amino acids, about 170 amino acids to about 240 amino acids, about 170 amino acids to about 220 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 1000 amino acids, about 175 amino acids to about 950 amino acids, about 175 amino acids to about 900 amino acids, about 175 amino acids to about 850 amino acids, about 175 amino acids to about 800 amino acids, about 175 amino acids to about 750 amino acids, about 175 amino acids to about 700 amino acids, about 175 amino acids to about 650 amino acids, about 175 amino acids to about 600 amino acids, about 175 amino acids to about 550 amino acids, about 175 amino acids to about 500 amino acids, about 175 amino acids to about 450 amino acids, about 175 amino acids to about 400 amino acids, about 175 amino acids to about 350 amino acids, about 175 amino acids to about 300 amino acids, about 175 amino acids to about 280 amino acids, about 175 amino acids to about 260 amino acids, about 175 amino acids to about 240 amino acids, about 175 amino acids to about 220 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 1000 amino acids, about 180 amino acids to about 950 amino acids, about 180 amino acids to about 900 amino acids, about 180 amino acids to about 850 amino acids, about 180 amino acids to about 800 amino acids, about 180 amino acids to about 750 amino acids, about 180 amino acids to about 700 amino acids, about 180 amino acids to about 650 amino acids, about 180 amino acids to about 600 amino acids, about 180 amino acids to about 550 amino acids, about 180 amino acids to about 500 amino acids, about 180 amino acids to about 450 amino acids, about 180 amino acids to about 400 amino acids, about 180 amino acids to about 350 amino acids, about 180 amino acids to about 300 amino acids, about 180 amino acids to about 280 amino acids, about 180 amino acids to about 260 amino acids, about 180 amino acids to about 240 amino acids, about 180 amino acids to about 220 amino acids, about 180 amino acids to about 200 amino acids, about 180 amino acids to about 195 amino acids, about 180 amino acids to about 190 amino acids, about 180 amino acids to about 185 amino acids, about 185 amino acids to about 1000 amino acids, about 185 amino acids to about 950 amino acids, about 185 amino acids to about 900 amino acids, about 185 amino acids to about 850 amino acids, about 185 amino acids to about 800 amino acids, about 185 amino acids to about 750 amino acids, about 185 amino acids to about 700 amino acids, about 185 amino acids to about 650 amino acids, about 185 amino acids to about 600 amino acids, about 185 amino acids to about 550 amino acids, about 185 amino acids to about 500 amino acids, about 185 amino acids to about 450 amino acids, about 185 amino acids to about 400 amino acids, about 185 amino acids to about 350 amino acids, about 185 amino acids to about 300 amino acids, about 185 amino acids to about 280 amino acids, about 185 amino acids to about 260 amino acids, about 185 amino acids to about 240 amino acids, about 185 amino acids to about 220 amino acids, about 185 amino acids to about 200 amino acids, about 185 amino acids to about 195 amino acids, about 185 amino acids to about 190 amino acids, about 190 amino acids to about 1000 amino acids, about 190 amino acids to about 950 amino acids, about 190 amino acids to about 900 amino acids, about 190 amino acids to about 850 amino acids, about 190 amino acids to about 800 amino acids, about 190 amino acids to about 750 amino acids, about 190 amino acids to about 700 amino acids, about 190 amino acids to about 650 amino acids, about 190 amino acids to about 600 amino acids, about 190 amino acids to about 550 amino acids, about 190 amino acids to about 500 amino acids, about 190 amino acids to about 450 amino acids, about 190 amino acids to about 400 amino acids, about 190 amino acids to about 350 amino acids, about 190 amino acids to about 300 amino acids, about 190 amino acids to about 280 amino acids, about 190 amino acids to about 260 amino acids, about 190 amino acids to about 240 amino acids, about 190 amino acids to about 220 amino acids, about 190 amino acids to about 200 amino acids, about 190 amino acids to about 195 amino acids, about 195 amino acids to about 1000 amino acids, about 195 amino acids to about 950 amino acids, about 195 amino acids to about 900 amino acids, about 195 amino acids to about 850 amino acids, about 195 amino acids to about 800 amino acids, about 195 amino acids to about 750 amino acids, about 195 amino acids to about 700 amino acids, about 195 amino acids to about 650 amino acids, about 195 amino acids to about 600 amino acids, about 195 amino acids to about 550 amino acids, about 195 amino acids to about 500 amino acids, about 195 amino acids to about 450 amino acids, about 195 amino acids to about 400 amino acids, about 195 amino acids to about 350 amino acids, about 195 amino acids to about 300 amino acids, about 195 amino acids to about 280 amino acids, about 195 amino acids to about 260 amino acids, about 195 amino acids to about 240 amino acids, about 195 amino acids to about 220 amino acids, about 195 amino acids to about 200 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 450 amino acids, about 220 amino acids to about 400 amino acids, about 220 amino acids to about 350 amino acids, about 220 amino acids to about 300 amino acids, about 220 amino acids to about 280 amino acids, about 220 amino acids to about 260 amino acids, about 220 amino acids to about 240 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 450 amino acids, about 240 amino acids to about 400 amino acids, about 240 amino acids to about 350 amino acids, about 240 amino acids to about 300 amino acids, about 240 amino acids to about 280 amino acids, about 240 amino acids to about 260 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 450 amino acids, about 260 amino acids to about 400 amino acids, about 260 amino acids to about 350 amino acids, about 260 amino acids to about 300 amino acids, about 260 amino acids to about 280 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 450 amino acids, about 280 amino acids to about 400 amino acids, about 280 amino acids to about 350 amino acids, about 280 amino acids to about 300 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1000 amino acids, about 850 amino acids to about 950 amino acids, about 850 amino acids to about 900 amino acids, about 900 amino acids to about 1000 amino acids, about 900 amino acids to about 950 amino acids, or about 950 amino acids to about 1000 amino acids.

Any of the target-binding domains described herein can bind to its target with a dissociation equilibrium constant ($K_D$) of less than $1\times10^{-7}$M, less than $1\times10^{-8}$M, less than $1\times10^{-9}$M, less than $1\times10^{-10}$ M, less than $1\times10^{-11}$M, less than $1\times10^{-12}$M, or less than $1\times10^{-13}$ M. In some embodiments, the antigen-binding protein constructs provided herein can bind to an identifying antigen with a $K_D$ of about $1\times10^{-3}$M to about $1\times10^{-5}$M, about $1\times10^{-4}$M to about $1\times10^{-6}$M, about $1\times10^{-5}$M to about $1\times10^{-7}$ M, about $1\times10^{-6}$M to about $1\times10^{-8}$M, about $1\times10^{-7}$ M to about $1\times10^{-9}$M, about $1\times10^{-8}$M to about $1\times10^{-10}$ M, or about $1\times10^{-9}$M to about $1\times10^{-11}$M (inclusive).

Any of the target-binding domains described herein can bind to its target with a $K_D$ of between about 1 pM to about 30 nM (e.g., about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 90 pM, about 2 pM to about 80 pM, about 2 pM to about 70 pM, about 2 pM to about 60 pM, about 2 pM to about 50 pM, about 2 pM to about 40 pM, about 2 pM to about 30 pM, about 2 pM to about 20 pM, about 2 pM to about 10 pM, about 2 pM to about 5 pM, about 2 pM to about 4 pM, about 2 pM to about 3 pM, about 5 pM to about 30 nM, about 5 pM to about 25 nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 90 pM, about 5 pM to about 80 pM, about 5 pM to about 70 pM, about 5 pM to about 60 pM, about 5 pM to about 50 pM, about 5 pM to about 40 pM, about 5 pM to about 30 pM, about 5 pM to about 20 pM, about 5 pM to about 10 pM, about 10 pM to about 30 nM, about 10 pM to about 25 nM, about 10 pM to about 20 nM, about 10 pM to about 15 nM, about 10 pM to about 10 nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about 10 pM to about 200 pM, about 10 pM to about 150 pM, about 10 pM to about 100 pM, about 10 pM to about 90 pM, about 10 pM to about 80 pM, about 10 pM to about 70 pM, about 10 pM to about 60 pM, about 10 pM to about 50 pM, about 10 pM to about 40 pM, about 10 pM to about 30 pM, about 10 pM to about 20 pM, about 15 pM to about 30 nM, about 15 pM to about 25 nM, about 15 pM to about 20 nM, about 15 pM to about 15 nM, about 15 pM to about 10 nM, about 15 pM to about 5 nM, about 15 pM to about 2 nM, about 15 pM to about 1 nM, about 15 pM to about 950 pM, about 15 pM to about 900 pM, about 15 pM to about 850 pM, about 15 pM to about 800 pM, about 15 pM to about 750 pM, about 15 pM to about 700 pM, about 15 pM to about 650 pM, about 15 pM to about 600 pM, about 15 pM to about 550 pM, about 15 pM to about 500 pM, about 15 pM to about 450 pM, about 15 pM to about 400 pM, about 15 pM to about 350 pM, about 15 pM to about 300 pM, about 15 pM to about 250 pM, about 15 pM to about 200 pM, about 15 pM to about 150 pM, about 15 pM to about 100 pM, about 15 pM to about 90 pM, about 15 pM to about 80 pM, about 15 pM to about 70 pM, about 15 pM to about 60 pM, about 15 pM to about 50 pM, about 15 pM to about 40 pM, about 15 pM to about 30 pM, about 15 pM to about 20 pM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about 20 pM to about 400 pM, about 20 pM to about 350 pM, about 20 pM to about 300 pM, about 20 pM to about 250 pM, about 20 pM to about 20 pM, about 200 pM to about 150 pM, about 20 pM to about 100 pM, about 20 pM to about 90 pM, about 20 pM to about 80 pM, about 20 pM to about 70 pM, about 20 pM to about 60 pM, about 20 pM to about 50 pM, about 20 pM to about 40 pM, about 20 pM to about 30 pM, about 30 pM to about 30 nM, about 30 pM to about 25 nM, about 30 pM to about 30 nM, about 30 pM to about 15 nM, about 30 pM to about 10 nM, about 30 pM to about 5 nM, about 30 pM to about 2 nM, about 30 pM to about 1 nM, about 30 pM to about 950 pM, about 30 pM to about 900 pM, about 30 pM to about 850 pM, about 30 pM to about 800 pM, about 30 pM to about 750 pM, about 30 pM to about 700 pM, about 30 pM to about 650 pM, about 30 pM to about 600 pM, about 30 pM to about 550 pM, about 30 pM to about 500 pM, about 30 pM to about 450 pM, about 30 pM to about 400 pM, about 30 pM to about 350 pM, about 30 pM to about 300 pM, about 30 pM to about 250 pM, about 30 pM to about 200 pM, about 30 pM to about 150 pM, about 30 pM to about 100 pM, about 30 pM to about 90 pM, about 30 pM to about 80 pM, about 30 pM to about 70 pM, about 30 pM to about 60 pM, about 30 pM to about 50 pM, about 30 pM to about 40 pM, about 40 pM to about 30 nM, about 40 pM to about 25 nM, about 40 pM to about 30 nM, about 40 pM to about 15 nM, about 40 pM to about 10 nM, about 40 pM to about 5 nM, about 40 pM to about 2 nM, about 40 pM to about 1 nM, about 40 pM to about 950 pM, about 40 pM to about 900 pM, about 40 pM to about 850 pM, about 40 pM to about 800 pM, about 40 pM to about 750 pM, about 40 pM to about 700 pM, about 40 pM to about 650 pM, about 40 pM to about 600 pM, about 40 pM to about 550 pM, about 40 pM to about 500 pM, about 40 pM to about 450 pM, about 40 pM to about 400 pM, about 40 pM to about 350 pM, about 40 pM to about 300 pM, about 40 pM to about 250 pM, about 40 pM to about 200 pM, about 40 pM to about 150 pM, about 40 pM to about 100 pM, about 40 pM to about 90 pM, about 40 pM to about 80 pM, about 40 pM to about 70 pM, about 40 pM to about 60 pM, about 40 pM to about 50 pM, about 50 pM to about 30 nM, about 50 pM to about 25 nM, about 50 pM to about 30 nM, about 50 pM to about 15 nM, about 50 pM to about 10 nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 90 pM, about 50 pM to about 80 pM, about 50 pM to about 70 pM, about 50 pM to about 60 pM, about 60 pM to about 30 nM, about 60 pM to about 25 nM, about 60 pM to about 30 nM, about 60 pM to about 15 nM, about 60 pM to about 10 nM, about 60 pM to about 5 nM, about 60 pM to about 2 nM, about 60 pM to about 1 nM, about 60 pM to about 950 pM, about 60 pM to about 900 pM, about 60 pM to about 850 pM, about 60 pM to about 800 pM, about 60 pM to about 750 pM, about 60 pM to about 700 pM, about 60 pM to about 650 pM, about 60 pM to about 600 pM, about 60 pM to about 550 pM, about 60 pM to about 500 pM, about 60 pM to about 450 pM, about 60 pM to about 400 pM, about 60 pM to about 350 pM, about 60 pM to about 300 pM, about 60 pM to about 250 pM, about 60 pM to about 200 pM, about 60 pM to about 150 pM, about 60 pM to about 100 pM, about 60 pM to about 90 pM, about 60 pM to about 80 pM, about 60 pM to about 70 pM, about 70 pM to about 30 nM, about 70 pM to about 25 nM, about 70 pM to about 30 nM, about 70 pM to about 15 nM, about 70 pM to about 10 nM, about 70 pM to about 5 nM, about 70 pM to about 2 nM, about 70 pM to about 1 nM, about 70 pM to about 950 pM, about 70 pM to about 900 pM, about 70 pM to about 850 pM, about 70 pM to about 800 pM, about 70 pM to about 750 pM, about 70 pM to about 700 pM, about 70 pM to about 650 pM, about 70 pM to about 600 pM, about 70 pM to about 550 pM, about 70 pM to about 500 pM, about 70 pM to about 450 pM, about 70 pM to about 400 pM, about 70 pM to about 350 pM, about 70 pM to about 300 pM, about 70 pM to about 250 pM, about 70 pM to about 200 pM, about 70 pM to about 150 pM, about 70 pM to about 100 pM, about 70 pM to about 90 pM, about 70 pM to about 80 pM, about 80 pM to about 30 nM, about 80 pM to about 25 nM, about 80 pM to about 30 nM, about 80 pM to about 15 nM, about 80 pM to about 10 nM, about 80 pM to about 5 nM, about 80 pM to about 2 nM, about 80 pM to about 1 nM, about 80 pM to about 950 pM, about 80 pM to about 900 pM, about 80 pM to about 850 pM, about 80 pM to about 800 pM, about 80 pM to about 750 pM, about 80 pM to about 700 pM, about 80 pM to about 650 pM, about 80 pM to about 600 pM, about 80 pM to about 550 pM, about 80 pM to about 500 pM, about 80 pM to about 450 pM, about 80 pM to about 400 pM, about 80 pM to about 350 pM, about 80 pM to about 300 pM, about 80 pM to about 250 pM, about 80 pM to about 200 pM, about 80 pM to about 150 pM, about 80 pM to about 100 pM, about 80 pM to about 90 pM, about 90 pM to about 30 nM, about 90 pM to about 25 nM, about 90 pM to about 30 nM, about 90 pM to about 15 nM, about 90 pM to about 10 nM, about 90 pM to about 5 nM, about 90 pM to about 2 nM, about 90 pM to about 1 nM, about 90 pM to about 950 pM, about 90 pM to about 900 pM, about 90 pM to about 850 pM, about 90 pM to about 800 pM, about 90 pM to about 750 pM, about 90 pM to about 700 pM, about 90 pM to about 650 pM, about 90 pM to about 600 pM, about 90 pM to about 550 pM, about 90 pM to about 500 pM, about 90 pM to about 450 pM, about 90 pM to about 400 pM, about 90 pM to about 350 pM, about 90 pM to about 300 pM, about 90 pM to about 250 pM, about 90 pM to about 200 pM, about 90 pM to about 150 pM, about 90 pM to about 100 pM, about 100 pM to about 30 nM, about 100 pM to about 25 nM, about 100 pM to about 30 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 150 pM to about 30 nM, about 150 pM to about 25 nM, about 150 pM to about 30 nM, about 150 pM to about 15 nM, about 150 pM to about 10 nM, about 150 pM to about 5 nM, about 150 pM to about 2 nM, about 150 pM to about 1 nM, about 150 pM to about 950 pM, about 150 pM to about 900 pM, about 150 pM to about 850 pM, about 150 pM to about 800 pM, about 150 pM to about 750 pM, about 150 pM to about 700 pM, about 150 pM to about 650 pM, about 150 pM to about 600 pM, about 150 pM to about 550 pM, about 150 pM to about 500 pM, about 150 pM to about 450 pM, about 150 pM to about 400 pM, about 150 pM to about 350 pM, about 150 pM to about 300 pM, about 150 pM to about 250 pM, about 150 pM to about 200 pM, about 200 pM to about 30 nM, about 200 pM to about 25 nM, about 200 pM to about 30 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 30 nM, about 300 pM to about 25 nM, about 300 pM to about 30 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 30 nM, about 400 pM to about 25 nM, about 400 pM to about 30 nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 500 pM to about 30 nM, about 500 pM to about 25 nM, about 500 pM to about 30 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 30 nM, about 600 pM to about 25 nM, about 600 pM to about 30 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 30 nM, about 700 pM to about 25 nM, about 700 pM to about 30 nM, about 700 pM to about 15 nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 30 nM, about 800 pM to about 25 nM, about 800 pM to about 30 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 30 nM, about 900 pM to about 25 nM, about 900 pM to about 30 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 30 nM, about 1 nM to about 25 nM, about 1 nM to about 20 nM, about 1 nM to about 15 nM, about 1 nM to about 10 nM, about 1 nM to about 5 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 4 nM to about 30 nM, about 4 nM to about 25 nM, about 4 nM to about 20 nM, about 4 nM to about 15 nM, about 4 nM to about 10 nM, about 4 nM to about 5 nM, about 5 nM to about 30 nM, about 5 nM to about 25 nM, about 5 nM to about 20 nM, about 5 nM to about 15 nM, about 5 nM to about 10 nM, about 10 nM to about 30 nM, about 10 nM to about 25 nM, about 10 nM to about 20 nM, about 10 nM to about 15 nM, about 15 nM to about 30 nM, about 15 nM to about 25 nM, about 15 nM to about 20 nM, about 20 nM to about 30 nM, and about 20 nM to about 25 nM).

Any of the target-binding domains described herein can bind to its target with a $K_D$ of between about 1 nM to about 10 nM (e.g., about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 10 nM, about 5 nM to about 9 nM, about 5 nM to about 8 nM, about 5 nM to about 7 nM, about 5 nM to about 6 nM, about 6 nM to about 10 nM, about 6 nM to about 9 nM, about 6 nM to about 8 nM, about 6 nM to about 7 nM, about 7 nM to about 10 nM, about 7 nM to about 9 nM, about 7 nM to about 8 nM, about 8 nM to about 10 nM, about 8 nM to about 9 nM, and about 9 nM to about 10 nM).

A variety of different methods known in the art can be used to determine the $K_D$ values of any of the antigen-binding protein constructs described herein (e.g., an electrophoretic mobility shift assay, a filter binding assay, surface plasmon resonance, and a biomolecular binding kinetics assay, etc.).

Antigen-Binding Domains

In some embodiments of any of the single-chain chimeric polypeptides or any of the multi-chain chimeric polypeptides described herein, the first target-binding domain and the second target-binding domain bind specifically to the same antigen. In some embodiments of any of the single-chain chimeric polypeptides or any of the multi-chain chimeric polypeptides described herein, the first target-binding domain and the second target-binding domain bind specifically to the same epitope. In some embodiments of any of the single-chain chimeric polypeptides or any of the multi-chain chimeric polypeptides, the first target-binding domain and the second target-binding domain include the same amino acid sequence.

In some embodiments of any of the single-chain chimeric polypeptides or any of the multi-chain chimeric polypeptides described herein, the first target-binding domain and the second target-binding domain bind specifically to different antigens.

In some embodiments of any of the single-chain chimeric polypeptides or any of the multi-chain chimeric polypeptides described herein, one or both of the first target-binding domain and the second target-binding domain is an antigen-binding domain. In some embodiments of any of the single-chain chimeric polypeptides or any of the multi-chain chimeric polypeptides described herein, the first target-binding domain and the second target-binding domain are each an antigen-binding domain.

In some embodiments of any of the single-chain chimeric polypeptides or any of the multi-chain chimeric polypeptides described herein, the antigen-binding domain includes or is a scFv or a single domain antibody (e.g., a $V_HH$ or a $V_{NAR}$ domain).

In some examples, an antigen-binding domain (e.g., any of the antigen-binding domains described herein) can bind specifically to any one of CD16a (see, e.g., those described in U.S. Pat. No. 9,035,026), CD28 (see, e.g., those described in U.S. Pat. No. 7,723,482), CD3 (see, e.g., those described in U.S. Pat. No. 9,226,962), CD33 (see, e.g., those described in U.S. Pat. No. 8,759,494), CD20 (see, e.g., those described in WO 2014/026054), CD19 (see, e.g., those described in U.S. Pat. No. 9,701,758), CD22 (see, e.g., those described in WO 2003/104425), CD123 (see, e.g., those described in WO 2014/130635), IL-1R (see, e.g., those described in U.S. Pat. No. 8,741,604), IL-1 (see, e.g., those described in WO 2014/095808), VEGF (see, e.g., those described in U.S. Pat. No. 9,090,684), IL-6R (see, e.g., those described in U.S. Pat. No. 7,482,436), IL-4 (see, e.g., those described in U.S. Patent Application Publication No. 2012/0171197), IL-10 (see, e.g., those described in U.S. Patent Application Publication No. 2016/0340413), PDL-1 (see, e.g., those described in Drees et al., *Protein Express. Purif.* 94:60-66, 2014), TIGIT (see, e.g., those described in U.S. Patent Application Publication No. 2017/0198042), PD-1 (see, e.g., those described in U.S. Pat. No. 7,488,802), TIM3 (see, e.g., those described in U.S. Pat. No. 8,552,156), CTLA4 (see, e.g., those described in WO 2012/120125), MICA (see, e.g., those described in WO 2016/154585), MICB (see, e.g., those described in U.S. Pat. No. 8,753,640), IL-6 (see, e.g., those described in Gejima et al., *Human Antibodies* 11(4):121-129, 2002), IL-8 (see, e.g., those described in U.S. Pat. No. 6,117,980), TNFα (see, e.g., those described in Geng et al., *Immunol. Res.* 62(3):377-385, 2015), CD26a (see, e.g., those described in WO 2017/189526), CD36 (see, e.g., those described in U.S. Patent Application Publication No. 2015/0259429), ULBP2 (see, e.g., those described in U.S. Pat. No. 9,273,136), CD30 (see, e.g., those described in Homach et al., *Scand. J. Immunol.* 48(5):497-501, 1998), CD200 (see, e.g., those described in U.S. Pat. No. 9,085,623), IGF-1R (see, e.g., those described in U.S. Patent Application Publication No. 2017/0051063), MUC4AC (see, e.g., those described in WO 2012/170470), MUC5AC (see, e.g., those described in U.S. Pat. No. 9,238,084), Trop-2 (see, e.g., those described in WO 2013/068946), CMET (see, e.g., those described in Edwardraja et al., *Biotechnol. Bioeng.* 106(3):367-375, 2010), EGFR (see, e.g., those described in Akbari et al., *Protein Expr. Purif.* 127:8-15, 2016), HER1 (see, e.g., those described in U.S. Patent Application Publication No. 2013/0274446), HER2 (see, e.g., those described in Cao et al., *Biotechnol. Lett.* 37(7):1347-1354, 2015), HER3 (see, e.g., those described in U.S. Pat. No. 9,505,843), PSMA (see, e.g., those described in Parker et al., *Protein Expr. Purif.* 89(2):136-145, 2013), CEA (see, e.g., those described in WO 1995/015341), B7H3 (see, e.g., those described in U.S. Pat. No. 9,371,395), EPCAM (see, e.g., those described in WO 2014/159531), BCMA (see, e.g., those described in Smith et al., *Mol. Ther.* 26(6):1447-1456, 2018), P-cadherin (see, e.g., those described in U.S. Pat. No. 7,452,537), CEACAM5 (see, e.g., those described in U.S. Pat. No. 9,617,345), a UL16-binding protein (see, e.g., those described in WO 2017/083612), HLA-DR (see, e.g., Pistillo et al., *Exp. Clin. Immunogenet.* 14(2):123-130, 1997), DLL4 (see, e.g., those described in WO 2014/007513), TYRO3 (see, e.g., those described in WO 2016/166348), AXL (see, e.g., those described in WO 2012/175692), MER (see, e.g., those described in WO 2016/106221), CD122 (see, e.g., those described in U.S. Patent Application Publication No. 2016/0367664), CD155 (see, e.g., those described in WO 2017/149538), and PDGF-DD (see, e.g., those described in U.S. Pat. No. 9,441,034). The antigen-binding domains present in any of the single-chain chimeric polypeptides or any of the multi-chain polypeptides described herein are each independently selected from the group consisting of: a VHH domain, a VNAR domain, and a scFv.

In some embodiments, the first target binding domain, the second target-binding domain, and/or one or more of the one or more additional antigen-binding domains can be an anti-CD3 scFv. In some embodiments, the anti-CD3 scFv can include a heavy chain variable domain including a sequence that is at least 70% identical (e.g., at least 75% identical, at least 80% identical, at least 85% identical, at least 90% identical, at least 95% identical, at least 99% identical, or 100% identical) to QVQLQQSGAELARP-GASVKMSCKASGYTFTRYTMHWVKQRPGQGLEWI-GYINPSRGY TNYNQKFKDKATLTTDKSSSTAYMQ LSSLTSEDSAVYYCARYYDDHYCLDYWGQGTT LTVSS (SEQ ID NO: 16) and/or a light chain variable domain including a sequence that is at least 70% identical (e.g., at least 75% identical, at least 80% identical, at least 85% identical, at least 90% identical, at least 95% identical, at least 99% identical, or 100% identical) to (SEQ ID NO: 17)
QIVLTQSPAIMSASPGEKVTMTCSASSSVSYMNWYQQKSGTSPKRWIYD

TSKLASGVPAHFRGSGSGTSYSLTISGMEAEDAATYYCQQWSSNPFTFG

SGTKLEINR.

In some embodiments, a scFv (e.g., any of the scFvs described herein) can include a linker sequence (e.g., any of the exemplary linker sequences described herein or known in the art) between the heavy chain variable domain and the light chain variable domain. In some embodiments, the anti-CD3 scFv can include a heavy chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to CAAGTTCAGCTCCAGCAAAGCGGCGCCGAA CTCGCTCGGCCCGGCGCTTCCGTGAA GATGTCTTGTAAGGCCTCCGGCTATACCTT-CACCCGGTACACAATGCACTGGGTCAA GCAACGGCCCGGTCAAGGTTTAGAGTGGATTGGC-TATATCAACCCCTCCCGGGGCTA TACCAACTA-CAACCAGAAGTTCAAGGACAAAGCCACCCTCAC-CACCGACAAGTCCA GCAGCACCGCTTACATGCAGCTGAGCTCTTTAA-CATCCGAGGATTCCGCCGTGTACT ACTGCGCTCGGTACTACGACGATCATTACTGCCTC-GATTACTGGGGCCAAGGTACCA CCT-TAACAGTCTCCTCC (SEQ ID NO: 18), and/or a light chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to (SEQ ID NO: 19)
CAGATCGTGCTGACCCAGTCCCCCGCTATTATGAGCGCTAGCCCCGGTG

AAAAGGTGACTATGACATGCAGCGCCAGCTCTTCCGTGAGCTACATGAA

CTGGTATCAGCAGAAGTCCGGCACCAGCCCTAAAAGGTGGATCTACGAC

ACCAGCAAGCTGGCCAGCGGCGTCCCCGCTCACTTTCGGGGCTCCGGCT

CCGGAACAAGCTACTCTCTGACCATCAGCGGCATGGAAGCCGAGGATGC

CGCTACCTATTACTGTCAGCAGTGGAGCTCCAACCCCTTCACCTTTGGA

TCCGGCACCAAGCTCGAGATTAATCGT.

In some embodiments, an anti-CD3 scFv can include a sequence that is at least 70% identical (e.g., at least 75% identical, at least 80% identical, at least 85% identical, at least 90% identical, at least 95% identical, at least 99% identical, or 100% identical) to QIVLTQSPAIM-SASPGEKVTMTCSAS S SVSYMNWYQQKSGTSPKR-WIYDTSKLASGVPA HFRGSGSGTSYSLTISGMEAE-DAATYYCQQWSSNPFTFGSGTKLEINRGGGGSGGGG SG GGGSQVQLQQSGAELARPGASVKMSCK-ASGYTFTRYTMHWVKQRPGQGLEWIGYINP SRGYTNYNQKFKDKATLTTDKSSSTAYMQLSSLT-SEDSAVYYCARYYDDHYCLDYWG QGTTLTVSS (SEQ ID NO: 20). In some embodiments, an anti-CD3 scFv can include the six CDRs present in SEQ ID NO: 20.

In some embodiments, an anti-CD3 scFv can include a sequence encoded by a nucleic acid sequence that is at least 70% identical (e.g., at least 75% identical, at least 80% identical, at least 85% identical, at least 90% identical, at least 95% identical, at least 99% identical, or 100% identical) to (SEQ ID NO: 21)
CAGATCGTGCTGACCCAGTCCCCCGCTATTATGAGCGCTAGCCCCGGTG

AAAAGGTGACTATGACATGCAGCGCCAGCTCTTCCGTGAGCTACATGAA

CTGGTATCAGCAGAAGTCCGGCACCAGCCCTAAAAGGTGGATCTACGAC

ACCAGCAAGCTGGCCAGCGGCGTCCCCGCTCACTTTCGGGGCTCCGGCT

CCGGAACAAGCTACTCTCTGACCATCAGCGGCATGGAAGCCGAGGATGC

-continued
CGCTACCTATTACTGTCAGCAGTGGAGCTCCAACCCCTTCACCTTTGGA

TCCGGCACCAAGCTCGAGATTAATCGTGGAGGCGGAGGTAGCGGAGGAG

GCGGATCCGGCGGTGGAGGTAGCCAAGTTCAGCTCCAGCAAAGCGGCGC

CGAACTCGCTCGGCCCGGCGCTTCCGTGAAGATGTCTTGTAAGGCCTCC

GGCTATACCTTCACCCGGTACACAATGCACTGGGTCAAGCAACGGCCCG

GTCAAGGTTTAGAGTGGATTGGCTATATCAACCCCTCCCGGGGCTATAC

CAACTACAACCAGAAGTTCAAGGACAAAGCCACCCTCACCACCGACAAG

TCCAGCAGCACCGCTTACATGCAGCTGAGCTCTTTAACATCCGAGGATT

CCGCCGTGTACTACTGCGCTCGGTACTACGACGATCATTACTGCCTCGA

TTACTGGGGCCAAGGTACCACCTTAACAGTCTCCTCC.

In some embodiments, the first target binding domain, the second target-binding domain, and/or one or more of the one or more additional antigen-binding domains can be an anti-CD28 scFv. In some embodiments, the anti-CD28 scFv can include a heavy chain variable domain including a sequence that is at least 70% identical (e.g., at least 75% identical, at least 80% identical, at least 85% identical, at least 90% identical, at least 95% identical, at least 99% identical, or 100% identical) to (SEQ ID NO: 22)
DIEMTQSPAIMSASLGERVTMTCTASSSVSSSYFHWYQQKPGSSPKLCI

YSTSNLASGVPPRFSGSGSTSYSLTISSMEAEDAATYFCHQYHRSPTFG

GGTKLETKR.

and/or a light chain variable domain including a sequence that is at least 70% identical (e.g., at least 75% identical, at least 80% identical, at least 85% identical, at least 90% identical, at least 95% identical, at least 99% identical, or 100% identical) to VQLQQSGPELVKPGASVKMSCK-ASGYTFTSYVIQWVKQKPGQGLEWIGSINPYNDYTK YNEKFKGKATLTSDKSSITAYMEFSSLTSEDSALYY-CARWGDGNYWGRGTTLTVSS (SEQ ID NO: 23). In some embodiments, the anti-CD28 scFv can include a heavy chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to GACATCGAGATGACACAGTCCCCCGCTATCAT-GAGCGCCTCTTTAGGAGAACGTGTG ACCATGACTTGTACAGCTTCCTCCAGCGT-GAGCAGCTCCTATTTCCACTGGTACCAG CAGAAACCCGGCTCCTCCCCTAAACTGTGTATC-TACTCCACAAGCAATTTAGCTAGC GGCGTGCCTCCTCGTTT-TAGCGGCTCCGGCAGCACCTCTTACTCTTTAAC-CATTAGCT CTATGGAGGCCGAAGATGCCGCCACAT-ACTTTTGCCATCAGTACCACCGGTCCCCTA CCTTTGGCGGAGGCACAAAGCTGGAGAC-CAAGCGG (SEQ ID NO: 24), and/or a light chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to (SEQ ID NO: 25)
GTGCAGCTGCAGCAGTCCGGACCCGAACTGGTCAAGCCCGGTGCCTCCG

TGAAAATGTCTTGTAAGGCTTCTGGCTACACCTTTACCTCCTACGTCAT

CCAATGGGTGAAGCAGAAGCCCGGTCAAGGTCTCGAGTGGATCGGCAGC

ATCAATCCCTACAACGATTACACCAAGTATAACGAAAAGTTTAAGGGCA

AGGCCACTCTGACAAGCGACAAGAGCTCCATTACCGCCTACATGGAGTT

TTCCTCTTTAACTTCTGAGGACTCCGCTTTATACTATTGCGCTCGTTGG

GGCGATGGCAATTATTGGGGCCGGGGAACTACTTTAACAGTGAGCTCC.

In some embodiments, an anti-CD28 scFv can include a sequence that is at least 70% identical (e.g., at least 75% identical, at least 80% identical, at least 85% identical, at least 90% identical, at least 95% identical, at least 99% identical, or 100% identical) to VQLQQSGPELVKP-GASVKMSCKASGYTFTSYVIQWVKQKPGQ-GLEWIGSINPYNDYTK YNEKFKGKATLTSDKSSI-TAYMEFSSLTSEDSALYYCARWGDGNYWGRGTTLTV SSGG GGSGGGGSGGGGSDIEMTQSPAIM-SASLGERVTMTCTASSSVSSSYFHWYQQKPGSSPK LCIYSTSNLASGVPPRFSGSGSTSYSLTISSMEAE-DAATYFCHQYHRSPTFGGGTKLETKR (SEQ ID NO: 26). In some embodiments, an anti-CD28 scFv can include the six CDRs present in SEQ ID NO: 26.

In some embodiments, an anti-CD28 scFv can include a sequence encoded by a nucleic acid sequence that is at least 70% identical (e.g., at least 75% identical, at least 80% identical, at least 85% identical, at least 90% identical, at least 95% identical, at least 99% identical, or 100% identical) to (SEQ ID NO: 27)
GTGCAGCTGCAGCAGTCCGGACCCGAACTGGTCAAGCCCGGTGCCTCCG

TGAAAATGTCTTGTAAGGCTTCTGGCTACACCTTTACCTCCTACGTCAT

CCAATGGGTGAAGCAGAAGCCCGGTCAAGGTCTCGAGTGGATCGGCAGC

ATCAATCCCTACAACGATTACACCAAGTATAACGAAAAGTTTAAGGGCA

AGGCCACTCTGACAAGCGACAAGAGCTCCATTACCGCCTACATGGAGTT

TTCCTCTTTAACTTCTGAGGACTCCGCTTTATACTATTGCGCTCGTTGG

GGCGATGGCAATTATTGGGGCCGGGGAACTACTTTAACAGTGAGCTCCG

GCGGCGGCGGAAGCGGAGGTGGAGGATCTGGCGGTGGAGGCAGCGACAT

CGAGATGACACAGTCCCCCGCTATCATGAGCGCCTCTTTAGGAGAACGT

GTGACCATGACTTGTACAGCTTCCTCCAGCGTGAGCAGCTCCTATTTCC

ACTGGTACCAGCAGAAACCCGGCTCCTCCCCTAAACTGTGTATCTACTC

CACAAGCAATTTAGCTAGCGGCGTGCCTCCTCGTTTTAGCGGCTCCGGC

AGCACCTCTTACTCTTTAACCATTAGCTCTATGGAGGCCGAAGATGCCG

CCACATACTTTTGCCATCAGTACCACCGGTCCCCTACCTTTGGCGGAGG

CACAAAGCTGGAGACCAAGCGG.

In some embodiments, any of the antigen-binding domains described herein is a BiTe, a (scFv)₂, a nanobody, a nanobody-HSA, a DART, a TandAb, a scDiabody, a scDiabody-CH3, scFv-CH-CL-scFv, a HSAbody, scDiabody-HAS, or a tandem-scFv. Additional examples of antigen-binding domains that can be used in any of the single-chain chimeric polypeptides or multi-chain chimeric polypeptides described herein are known in the art.

A VHH domain is a single monomeric variable antibody domain that can be found in camelids. A VNAR domain is a single monomeric variable antibody domain that can be found in cartilaginous fish. Non-limiting aspects of VHH domains and VNAR domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014; Muyldermans, *J. Biotechnol.* 74:277-302, 2001; Muyldermans et al., *Trends Biochem. Sci.* 26:230-235, 2001; Muyldermans, *Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

In some embodiments, each of the antigen-binding domains in the single-chain chimeric polypeptides or multi-chain chimeric polypeptides described herein are both VHH domains, or at least one antigen-binding domain is a VHH domain. In some embodiments, each of the antigen-binding domains in the single-chain chimeric polypeptides or multi-chain chimeric polypeptides described herein are both VNAR domains, or at least one antigen-binding domain is a VNAR domain. In some embodiments, each of the antigen-binding domains in the single-chain chimeric polypeptides or multi-chain chimeric polypeptides described herein are both scFv domains, or at least one antigen-binding domain is a scFv domain. DARTs are described in, e.g., Garber, *Nature Reviews Drug Discovery* 13:799-801, 2014.

In some embodiments of any of the antigen-binding domains described herein, the antigen-binding domain can bind to an antigen selected from the group consisting of: a protein, a carbohydrate, a lipid, and a combination thereof.

Additional examples and aspects of antigen-binding domains are known in the art.

Soluble Interleukin or Cytokine Protein

In some embodiments of any of the single-chain chimeric polypeptides or multi-chain chimeric polypeptides described herein, one or both of the first target-binding domain and the second target-binding domain can be a soluble interleukin protein, soluble cytokine protein, or soluble cell surface protein. In some embodiments, the soluble interleukin, soluble cytokine protein, or soluble cell surface protein is selected from the group of: IL-2, IL-3, IL-7, IL-8, IL-10, IL-12, IL-15, IL-17, IL-18, IL-21, PDGF-DD, SCF, FLT3L, MICA, MICB, and a ULP16-binding protein (e.g., ULBP1, ULBP2, ULBP3, ULBP4, ULBP5, or ULBP6. Non-limiting examples of soluble IL-2, IL-3, IL-7, IL-8, IL-10, IL-15, IL-17, IL-18, IL-21, PDGF-DD, SCF and FLT3L.

Human Soluble IL-2
(SEQ ID NO: 28)
APTSSSTKKT QLQLEHLLLD LQMILNGINN YKNPKLTRML TFKFY

MPKKA TELKHLQCLE EELKPLEEVL NLAQSKNFHL RPRDLISNIN

VIVLELKGSE TTFMCEYADE TATIVEFLNR WITFCQSIIS TLT.

Human Soluble IL-3
(SEQ ID NO: 29)
APMTQTTPLKT SWVNCSNMID EIITHLKQPPLPLLDFNNLN GED

QDILMEN NLRRPNLEAF NRAVKSLQNA SAIESILKNL LPCLPLAT

AA PTRHPIHIKD GDWNEFRRKL TFYLKTLENA QAQQTTLSLA IF.

Human Soluble IL-8
(SEQ ID NO: 31)
EGAVLPRSAK ELRCQCIKTYSKPFHPKFIK ELRVIESGPH CANT EIIVKL SDGRELCLDP KENWVQRVVE KFLKRAENS.
Human Soluble IL-10 (SEQ ID NO: 32)
SPGQGTQSENSC THFPGNLPNM LRDLRDAFSR VKTFFQMKDQ LDN

LLLKESL LEDFKGYLGC QALSEMIQFY LEEVMPQAEN QDPDIKAH

VN SLGENLKTLR LRLRRCHRFL PCENKSKAVE QVKNAFNKLQ EK

GIYKAMSE FDIFINYIEA YMTMKIRN.

Human Soluble IL-12β (p40)
(SEQ ID NO: 33)
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS.

Nucleic Acid Encoding Human Soluble IL-12β (p40)
(SEQ ID NO: 34)

ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

AAGGAGCCCAAGAATAAGACCTTTTTAAGGTGTGAGGCCAAAAACTACA

GCGGTCGTTTCACTTGTTGGTGGCTGACCACCATTTCCACCGATTTAAC

CTTCTCCGTGAAAAGCAGCCGGGGAAGCTCCGACCCTCAAGGTGTGACA

TGTGGAGCCGCTACCCTCAGCGCTGAGAGGGTTCGTGGCGATAACAAGG

AATACGAGTACAGCGTGGAGTGCCAAGAAGATAGCGCTTGTCCCGCTGC

CGAAGAATCTTTACCCATTGAGGTGATGGTGGACGCCGTGCACAAACTC

AAGTACGAGAACTACACCTCCTCCTTCTTTATCCGGGACATCATTAAGC

CCGATCCTCCTAAGAATTTACAGCTGAAGCCTCTCAAAAATAGCCGGCA

AGTTGAGGTCTCTTGGGAATATCCCGACACTTGGAGCACACCCCACAGC

TACTTCTCTTTAACCTTTTGTGTGCAAGTTCAAGGTAAAAGCAAGCGGG

AGAAGAAAGACCGGGTGTTTACCGACAAAACCAGCGCCACCGTCATCTG

TCGGAAGAACGCCTCCATCAGCGTGAGGGCTCAAGATCGTTATTACTCC

AGCAGCTGGTCCGAGTGGGCCAGCGTGCCTTGTTCC.

Human Soluble IL-12α (p35)
(SEQ ID NO: 35)
RNLPVATPDPGMFPCLHESQNLLRAVSNMLQKARQTLEFYPCTSEEIDH
EDITKDKTSTVEACLPLELTKNESCLNSRETSFITNGSCLASRKTSFMM
ALCLSSIYEDLKMYQVEFKTMNAKLLMDPKRQIFLDQNMLAVIDELMQA
LNFNSETVPQKSSLEEPDFYKTKIKLCILLHAFRIRAVTIDRVMSYLNA
S.

Nucleic Acid Encoding Human Soluble IL-12α (p35)
(SEQ ID NO: 36)
CGTAACCTCCCCGTGGCTACCCCCGATCCCGGAATGTTCCCTTGTTTAC
ACCACAGCCAGAATTTACTGAGGGCCGTGAGCAACATGCTGCAGAAAGC
TAGGCAGACTTTAGAATTTTACCCTTGCACCAGCGAGGAGATCGACCAT
GAAGATATCACCAAGGACAAGACATCCACCGTGGAGGCTTGTTTACCTC
TGGAGCTGACAAAGAACGAGTCTTGTCTCAACTCTCGTGAAACCAGCTT
CATCACAAATGGCTCTTGTTTAGCTTCCCGGAAGACCTCCTTTATGATG
GCTTTATGCCTCAGCTCCATCTACGAGGATTTAAAGATGTACCAAGTGG
AGTTCAAGACCATGAACGCCAAGCTGCTCATGGACCCTAAACGGCAGAT
CTTTTTAGACCAGAACATGCTGGCTGTGATTGATGAGCTGATGCAAGCT
TTAAACTTCAACTCCGAGACCGTCCCTCAGAAGTCCTCCCTCGAGGAGC
CCGATTTTTACAAGACAAAGATCAAACTGTGCATTTTACTCCACGCCTT
TAGGATCCGGGCCGTGACCATTGACCGGGTCATGAGCTATTTAAACGCC
AGC.

Exemplary Human Soluble IL-12
(SEQ ID NO: 37)
IWELKKDVYVVELDWYPDAPGEMVVLTCDTPEEDGITWTLDQSSEVLGS
GKTLTIQVKEFGDAGQYTCHKGGEVLSHSLLLLHKKEDGIWSTDILKDQ
KEPKNKTFLRCEAKNYSGRFTCWWLTTISTDLTFSVKSSRGSSDPQGVT
CGAATLSAERVRGDNKEYEYSVECQEDSACPAAEESLPIEVMVDAVHKL
KYENYTSSFFIRDIIKPDPPKNLQLKPLKNSRQVEVSWEYPDTWSTPHS
YFSLTFCVQVQGKSKREKKDRVFTDKTSATVICRKNASISVRAQDRYYS
SSWSEWASVPCSGGGGSGGGGSGGGGSRNLPVATPDPGMFPCLHEISQN
LLRAVSNMLQKARQTLEFYPCTSEEIDHEDITKDKTSTVEACLPLELTK
NESCLNSRETSFITNGSCLASRKTSFMMALCLSSIYEDLKMYQVEFKTM
NAKLLMDPKRQIFLDQNMLAVIDELMQALNFNSETVPQKSSLEEPDFYK
TKIKLCILLHAFRIRAVTIDRVMSYLNAS.

Nucleic Acid Encoding Exemplary Human Soluble IL-12
(SEQ ID NO: 38)
ATTTGGGAACTGAAGAAGGACGTCTACGTGGTCGAACTGGACTGGTATC
CCGATGCTCCCGGCGAAATGGTGGTGCTCACTTGTGACACCCCCGAAGA
AGACGGCATCACTTGGACCCTCGATCAGAGCAGCGAGGTGCTGGGCTCC
GGAAAGACCCTCACAATCCAAGTTAAGGAGTTCGGAGACGCTGGCCAAT
ACACATGCCACAAGGGAGGCGAGGTGCTCAGCCATTCCTTATTATTATT
ACACAAGAAGGAAGACGGAATCTGGTCCACCGACATTTTAAAAGATCAG
AAGGAGCCCAAGAATAAGACCTTTTTAAGGTGTGAGGCCAAAAACTACA
GCGGTCGTTTCACTTGTTGGTGGCTGACCACCATTTCCACCGATTTAAC
CTTCTCCGTGAAAAGCAGCCGGGGAAGCTCCGACCCTCAAGGTGTGACA
TGTGGAGCCGCTACCCTCAGCGCTGAGAGGGTTCGTGGCGATAACAAGG
AATACGAGTACAGCGTGGAGTGCCAAGAAGATAGCGCTTGTCCCGCTGC
CGAAGAATCTTTACCCATTGAGGTGATGGTGGACGCCGTGCACAAACTC
AAGTACGAGAACTACACCTCCTCCTTCTTTATCCGGGACATCATTAAGC
CCGATCCTCCTAAGAATTTACAGCTGAAGCCTCTCAAAAATAGCCGGCA
AGTTGAGGTCTCTTGGGAATATCCCGACACTTGGAGCACACCCCACAGC
TACTTCTCTTTAACCTTTTGTGTGCAAGTTCAAGGTAAAAGCAAGCGGG
AGAAGAAAGACCGGGTGTTTACCGACAAAACCAGCGCCACCGTCATCTG
TCGGAAGAACGCCTCCATCAGCGTGAGGGCTCAAGATCGTTATTACTCC
AGCAGCTGGTCCGAGTGGGCCAGCGTGCCTTGTTCCGGCGGTGGAGGAT
CCGGAGGAGGTGGCTCCGGCGGCGGAGGATCTCGTAACCTCCCCGTGGC
TACCCCCGATCCCGGAATGTTCCCTTGTTTACACCACAGCCAGAATTTA
CTGAGGGCCGTGAGCAACATGCTGCAGAAAGCTAGGCAGACTTTAGAAT
TTTACCCTTGCACCAGCGAGGAGATCGACCATGAAGATATCACCAAGGA
CAAGACATCCACCGTGGAGGCTTGTTTACCTCTGGAGCTGACAAAGAAC
GAGTCTTGTCTCAACTCTCGTGAAACCAGCTTCATCACAAATGGCTCTT
GTTTAGCTTCCCGGAAGACCTCCTTTATGATGGCTTTATGCCTCAGCTC
CATCTACGAGGATTTAAAGATGTACCAAGTGGAGTTCAAGACCATGAAC
GCCAAGCTGCTCATGGACCCTAAACGGCAGATCTTTTTAGACCAGAACA
TGCTGGCTGTGATTGATGAGCTGATGCAAGCTTTAAACTTCAACTCCGA
GACCGTCCCTCAGAAGTCCTCCCTCGAGGAGCCCGATTTTTACAAGACA
AAGATCAAACTGTGCATTTTACTCCACGCCTTTAGGATCCGGGCCGTGA
CCATTGACCGGGTCATGAGCTATTTAAACGCCAGC.

Human Soluble IL-15
(SEQ ID NO: 39)
NWVNVISDLKKI EDLIQSMHID ATLYTESDVH PSCKVTAMKC FLL
ELQVISL ESGDASIHDT VENLIILANN SLSSNGNVTE SGCKECEE
LE EKNIKEFLQS FVHIVQMFIN IS.

Soluble IL-17
(SEQ ID NO: 40)
GITIPRN PGCPNSEDKN FPRTVMVNLN IHNRNTNTNP KRSSDYYN
RS TSPWNLHRNE DPERYPSVIW EAKCRHLGCI NADGNVDYHM NS
VPIQQEIL VLRREPPHCP NSFRLEKILV SVGCTCVTPI VHHVA.

Soluble IL-18 (SEQ ID NO: 41)
YFGKLESKLSVIRNLNDQVLFIDQGNRPLFEDMTDSDCRDNAPRTIFII
SMYKDSQPRGMAVTISVKCEKISTLSCENKIISFKEMNPPDNIKDTKSD
IIFFQRSVPGHDNKMQFESSSYEGYFLACEKERDLFKLILKKEDELGDR
SIMFTVQNED.

Nucleic Acid Encoding Human Soluble IL-18
(SEQ ID NO: 42)
TACTTCGGCAAACTGGAATCCAAGCTGAGCGTGATCCGGAATTTAAACG
ACCAAGTTCTGTTTATCGATCAAGGTAACCGGCCTCTGTTCGAGGACAT

```
GACCGACTCCGATTGCCGGGACAATGCCCCCCGGACCATCTTCATTATC
TCCATGTACAAGGACAGCCAGCCCCGGGGCATGGCTGTGACAATTAGCG
TGAAGTGTGAGAAAATCAGCACTTTATCTTGTGAGAACAAGATCATCTC
CTTTAAGGAAATGAACCCCCCCGATAACATCAAGGACACCAAGTCCGAT
ATCATCTTCTTCCAGCGGTCCGTGCCCGGTCACGATAACAAGATGCAGT
TCGAATCCTCCTCCTACGAGGGCTACTTTTTAGCTTGTGAAAAGGAGAG
GGATTTATTCAAGCTGATCCTCAAGAAGGAGGACGAGCTGGGCGATCGT
TCCATCATGTTCACCGTCCAAAACGAGGAT.
```

Human Soluble PDGF-DD
(SEQ ID NO: 45)
RDTSATPQSASI KALRNANLRR DESNHLTDLY RRDETIQVKG NGY VQSPRFP NSYPRNLLLT WRLHSQENTR IQLVFDNQFG LEEAENDI CR YDFVEVEDIS ETSTIIRGRW CGHKEVPPRI KSRTNQIKIT FK SDDYFVAK PGFKIYYSLL EDFQPAAASE TNWESVTSSI SGVSYNS PSV TDPTLIADAL DKKIAEFDTV EDLLKYFNPE SWQEDLENMY L DTPRYRGRS YHDRKSKVDL DRLNDDAKRYSCTPRNYSVN IREELKL ANV VFFPRCLLVQ RCGGNCGCGT VNWRSCTCNS GKTVKKYHEV L QFEPGHIKR RGRAKTMALV DIQLDHHERC DCICSSRPPR.

Human Soluble SCF
(SEQ ID NO: 46)
EGICRNRVTNNVKDV TKLVANLPKD YMITLKYVPG MDVLPSHCWI SEMVVQLSDS LTDLLDKFSN ISEGLSNYSI IDKLVNIVDD LVECV KENSS KDLKKSFKSP EPRLFTPEEF FRIFNRSIDA FKDFVVASET SDCVVSSTLS PEKDSRVSVT KPFMLPPVAA SSLRNDSSSS NRKAK NPPGD SSLHWAAMAL PALFSLIIGF AFGALYWKKR QPSLTRAVEN IQINEEDNEI SMLQEKEREF QEV.

Human Soluble FLT3L
(SEQ ID NO: 47)
tqdcsfqhspissd favkirelsd yllqdypvtv asnlqdeelc g glwrlvlaq rwmerlktva gskmqgller vnteihfvtk cafqpp pscl rfvqtnisrl lqetseqlva lkpwitrqnf srclelqcqp dsstlpppws prpleatapt apqppllllll llpvgllla aawcl hwqrt rrrtprpgeq vppvpspqdl llveh.

Exemplary soluble cell surface proteins include soluble MICA, MICB, and a ULP16 binding protein (e.g., ULBP1, ULBP2, ULBP3, ULBP4, ULBP5, or ULBP6). Exemplary sequences for soluble MICA, MICB, ULBP1, ULBP2, ULBP3, ULBP4, ULBP5, and ULBP6 are listed below.

Human Soluble MICA
(SEQ ID NO: 48)
ephslry nitvlswdgs vqsgfltevh ldgqpflrcd rqkcrakp qg qwaedvlgnk twdretrdlt gngkdlrmtl ahikdqkegl hs lqeirvce ihednstrss qhfyydgelf lsqnletkew tmpqssr aqt lamnvrnflk edamktkthy hamhadclqe lrrylksgvv l rrtvppmvn vtrseasegn itvtcrasgf ypwnitlswr qdgvsl shdt qqwgdvlpdg ngtyqtwvat ricqgeeqrf tcymehsgnh sthpvpsgkv lvlqshwqtf hvsavaaaai fviiifyvrc ckkkt saaeg pelvslqvld qhpvgtsdhr datqlgfqpl msdlgstgst ega.

Human Soluble MICH
(SEQ ID NO: 49)
aephslry nlmvlsqdes vqsgflaegh ldgqpflryd rqkrrak pqg qwaedvlgak twdtetedlt engqdlrrtl thikdqkggl h slqeirvce ihedsstrgs rhfyydgelf lsqnletqes tvpqss raqt lamnvtnfwk edamktkthy ramqadclqk lqrylksgva irrtvppmvn vtcsevsegn itvtcrassf yprnitltwr qdgvs lshnt qqwgdvlpdg ngtyqtwvat rirqgeeqrf tcymehsgnh gthpvpsgkv lvlqsqrtdf pyvsaampcf viiiilcvpc ckkkt saaeg pelvslqvld qhpvgtgdhrdaaqlgfqpl msatgstgst ega.

Human Soluble ULBP1
(SEQ ID NO: 50)
wvdthcicydfiit pksrpepqwc evqglvderp flhydcvnhk a kafaslgkk vnvtktweeq tetlrdvvdf lkgqlldiqv enlipi eplt lqarmscehe ahghgrgswq flfngqkfll fdsnnrkwta lhpgakkmte kweknrdvtm ffqkislgdc kmwleeflmy weqml dptkp pslapg.

Human SolubleULBP2
(SEQ ID NO: 51)
gradphslcyditvi pkfrpgprwc avqgqvdekt flhydcgnkt vtpvsplgkk lnvttawkaq npvlrevvdi lteqlrdiql enyt pkeplt lqarmsceqk aeghssgswq fsfdgqifll fdsekrmwt t vhpgarkmke kwendkvvam sfhyfsmgdc igwledflmg md stlepsag aplams.

Human Soluble ULBP3
(SEQ ID NO: 52)
dahslwynfti ihlprhgqqw cevqsqvdqk nflsydcgsd kvls mghlee qlyatdawgk qlemlrevgq rlrleladte ledftpsgp l tlqvrmscec eadgyirgsw qfsfdgrkfl lfdsnnrkwt vvh agarrmk ekwekdsglt tffkmvsmrd ckswlrdflm hrkkrlep ta pptmapg.

Human Soluble ULBP4
(SEQ ID NO: 53)
hslcfnftik slsrpgqpwc eaqvflnknl flqynsdnnm vkplg llgkk vyatstwgel tqtlgevgrd lrmllcdikp qiktsdpstl qvemfcgrea erctgaswqf atngeksllf dammnmtwtvi nheas kiket wkkdrgleky frklskgdcd hwlreflghw eampeptvsp vnasdihwss sslpdrwiil gafillvlmg ivlicvwwqn gewqa glwpl rts.

Human Soluble ULBP5
(SEQ ID NO: 54)
gladp hslcyditvi pkfrpgprwc avqgqvdekt flhydcgskt -continued vtpvsplgkk lnvttawkaq npvlrevvdi lteqlldiql enyip keplt lqarmsceqk aeghsgswq lsfdgqifll fdsenrmwtt vhpgarkmke kwendkdmtm sfhyismgdc tgwledflmg mdstl epsag apptmssg.

Human Soluble ULBP6

(SEQ ID NO: 55)
rrddp hslcyditvi pkfrpgprwc avqgqvdekt flhydcgnkt vtpvsplgkk lnvtmawkaq npvlrevvdi lteqlldiql enytp keplt lqarmsceqk aeghssgswq fsidgqtfll fdsekrmwtt vhpgarkmke kwendkdvam sfhyismgdc igwledflmg mdstl epsag aplamssg.

In some embodiments, a soluble IL-12 protein can include a first sequence that is at least 70% identical (e.g., at least 75% identical, at least 80% identical, at least 85% identical, at least 90% identical, at least 95% identical, at least 99% identical, or 100% identical) to SEQ ID NO: 33, and a second sequence that is at least 70% identical (e.g., at least 75% identical, at least 80% identical, at least 85% identical, at least 90% identical, at least 95% identical, at least 99% identical, or 100% identical) to SEQ ID NO: 35. In some embodiments, the soluble IL-12 can further include a linker sequence (e.g., any of the exemplary linker sequences described herein or known in the art) between the first sequence and the second sequence.

In some embodiments, a soluble IL-12 protein is encoded by a first nucleic acid encoding a first sequence at least 70% identical (e.g., at least 75% identical, at least 80% identical, at least 85% identical, at least 90% identical, at least 95% identical, at least 99% identical, or 100% identical) to SEQ ID NO: 34, and a second nucleic acid sequence encoding a second sequence that is at least 70% identical (e.g., at least 75% identical, at least 80% identical, at least 85% identical, at least 90% identical, at least 95% identical, at least 99% identical, or 100% identical) to SEQ ID NO: 36. In some embodiments, the nucleic acid encoding a soluble IL-12 protein further includes a nucleic acid sequence encoding a linker sequence (e.g., any of the exemplary linker sequences described herein or known in the art) between the first nucleic acid and the second nucleic acid.

In some embodiments, a soluble IL-12 protein includes a sequence that is at least 70% identical (e.g., at least 75% identical, at least 80% identical, at least 85% identical, at least 90% identical, at least 95% identical, at least 99% identical, or 100% identical) to SEQ ID NO: 37. In some embodiments, a soluble IL-12 protein is encoded by a nucleic acid including a sequence at least 70% identical (e.g., at least 75% identical, at least 80% identical, at least 85% identical, at least 90% identical, at least 95% identical, at least 99% identical, or 100% identical) to SEQ ID NO: 38.

In some embodiments, a soluble IL-18 protein can include a sequence that is at least 70% identical (e.g., at least 75% identical, at least 80% identical, at least 85% identical, at least 90% identical, at least 95% identical, at least 99% identical, or 100% identical) to SEQ ID NO: 41. In some embodiments, a soluble IL-18 protein is encoded by a nucleic acid including a sequence at least 70% identical (e.g., at least 75% identical, at least 80% identical, at least 85% identical, at least 90% identical, at least 95% identical, at least 99% identical, or 100% identical) to SEQ ID NO: 42.

Additional examples of soluble interleukin proteins and soluble cytokine proteins are known in the art.

Soluble Interleukin or Cytokine Receptor

In some embodiments of any of the single-chain chimeric polypeptides or multi-chain chimeric polypeptides described herein, one or both of the first target-binding domain and the second target-binding domain is a soluble interleukin receptor or a soluble cytokine receptor. In some embodiments, the soluble receptor is a soluble TGF-β receptor II (TGF-βRII) (see, e.g., those described in Yung et al., *Am. J. Resp. Crit. Care Med.* 194(9):1140-1151, 2016), a soluble TGF-β RIII (see, e.g., those described in Heng et al., *Placenta* 57:320, 2017), a soluble NKG2D (see, e.g., Cosman et al., *Immunity* 14(2):123-133, 2001; Costa et al., *Front. Immunol., Vol.* 9, Article 1150, May 29, 2018; doi: 10.3389/fimmu.2018.01150), a soluble NKp30 (see, e.g., Costa et al., *Front. Immunol.*, Vol. 9, Article 1150, May 29, 2018; doi: 10.3389/fimmu.2018.01150), a soluble NKp44 (see, e.g., those described in Costa et al., *Front. Immunol.*, Vol. 9, Article 1150, May 29, 2018; doi: 10.3389/fimmu.2018.01150), a soluble NKp46 (see, e.g., Mandelboim et al., *Nature* 409:1055-1060, 2001; Costa et al., *Front. Immunol.*, Vol. 9, Article 1150, May 29, 2018; doi: 10.3389/fimmu.2018.01150), a soluble DNAM-1 (see, e.g., those described in Costa et al., *Front. Immunol.*, Vol. 9, Article 1150, May 29, 2018; doi: 10.3389/fimmu.2018.01150), a scMHCI (see, e.g., those described in Washburn et al., *PLoS One* 6(3):e18439, 2011), a scMHCII (see, e.g., those described in Bishwajit et al., *Cellular Immunol.* 170(1):25-33, 1996), a scTCR (see, e.g., those described in Weber et al., *Nature* 356(6372):793-796, 1992), a soluble CD155 (see, e.g., those described in Tahara-Hanaoka et al., *Int. Immunol.* 16(4):533-538, 2004), or a soluble CD28 (see, e.g., Hebbar et al., *Clin. Exp. Immunol.* 136:388-392, 2004).

In some embodiments, a soluble TGFβ RII receptor can include a first sequence that is at least 70% identical (e.g., at least 75% identical, at least 80% identical, at least 85% identical, at least 90% identical, at least 95% identical, at least 99% identical, or 100% identical) to IPPHVQKSVNNDMIVTDNNGAVKFPQLCKFCDVRF-STCDNQKSCMSNCSITSICEKPQEV CVAVWRKNDEN-ITLETVCHDPKLPYHDFILEDAASPKCI-MKEKKKPGETFFMCSCSSDE CNDNIIFSEEYNTSNPD (SEQ ID NO: 56), and a second sequence that is at least 70% identical (e.g., at least 75% identical, at least 80% identical, at least 85% identical, at least 90% identical, at least 95% identical, at least 99% identical, or 100% identical) to IPPHVQKSVNNDMIVTDNNGAVKFPQLCKFCDVRF-STCDNQKSCMSNCSITSICEKPQEV CVAVWRKNDEN-ITLETVCHDPKLPYHDFILEDAASPKCI-MKEKKKPGETFFMCSCSSDE CNDNIIFSEEYNTSNPD (SEQ ID NO: 56). In some embodiments, the soluble TGF-β RII receptor can further include a linker sequence (e.g., any of the exemplary linker sequences described herein or known in the art) between the first sequence and the second sequence.

In some embodiments, a soluble TGF-β RII receptor is encoded by a first nucleic acid encoding a first sequence at least 70% identical (e.g., at least 75% identical, at least 80% identical, at least 85% identical, at least 90% identical, at least 95% identical, at least 99% identical, or 100% identical) to ATCCCCCCCCATGTGCAAAAGAGCGT-GAACAACGATATGATCGTGACCGACAACAA CGGCGCCGTGAAGTTTCCCCAGCTCTGCAAG TTCTGCGATGTCAGGTTCAGCACCTG CGA-TAATCAGAAGTCCTGCATGTCCAACTGCACGAT-CACCTCCATCTGCGAGAAGC CCAAGAAGTGTGCGTGGCCGTGTGGCGGAAAAATGACGAGAACATCACCCTGGAGACCGTGTGTCACGACCCCAAGCTCCCTTATCACGACTTCATTCTGGAGGACGCTGCCT CCCCCAAATGCATCATGAAGGAGAAGAAGAAGCCCGGAGAGACCTTCTTTATGTGT TCCTGTAGCAGCGACGAGTGTAACGACAACATCATCTTCAGCGAAGAGTACAACAC CAGCAACCCTGAT (SEQ ID NO: 57), and a second nucleic acid sequence encoding a second sequence that is at least 70% identical (e.g., at least 75% identical, at least 80% identical, at least 85% identical, at least 90% identical, at least 95% identical, at least 99% identical, or 100% identical) to ATCCCCCCCCATGTGCAAAAGAGCGTGAACAACGATATGATCGTGACCGACAACAA CGGCGCCGTGAAGTTTCCCCAGCTCTGCAAGTTCTGCGATGTCA GGTTCAGCACCTG CGATAATCAGAAGTCCTGCATGTCCAACTGCACGATCACCTCCATCTGCGAGAAGCC CCAAGAAGTGTGCGTGGCCGTGTGGCGGAAAAATGACGAGAACATCACCCTGGAGA CCGTGTGTCACGACCCCAAGCTCCCTTATCACGACTTCATTCTGGAGGACGCTGCCT CCCCCAAATGCATCATGAAGGAGAAGAAGAAGCCCGGAGAGACCTTCTTTATGTGT TCCTGTAGCAGCGACGAGTGTAACGACAACATCATCTTCAGCGAAGAGTACAACAC CAGCAACCCTGAT (SEQ ID NO: 57). In some embodiments, the nucleic acid encoding a soluble TGF-β RII receptor further includes a nucleic acid sequence encoding a linker sequence (e.g., any of the exemplary linker sequences described herein or known in the art) between the first nucleic acid and the second nucleic acid.

In some embodiments, a soluble TGF-β RII receptor includes a sequence that is at least 70% identical (e.g., at least 75% identical, at least 80% identical, at least 85% identical, at least 90% identical, at least 95% identical, at least 99% identical, or 100% identical) to (SEQ ID NO: 60)
IPPHVQKSVNNDMIVTDNNGAVKFPQLCKFCDVRFSTCDNQKSCMSN

CSITSICEKPQEVCVAVWRKNDENITLETVCHDPKLPYHDFILEDAA

SPKCIMKEKKKPGETFFMCSCSSDECNDNIIFSEEYNTSNPDGGGGS

GGGGSGGGGSIPPHVQKSVNNDMIVTDNNGAVKFPQLCKFCDVRFST

CDNQKSCMSNCSITSICEKPQEVCVAVWRKNDENITLETVCHDPKLP

YHDFILEDAASPKCIMKEKKKPGETFFMCSCSSDECNDNIIFSEEYN

TSNPD

In some embodiments, a soluble TGF-β RII receptor is encoded by a nucleic acid including a sequence at least 70% identical (e.g., at least 75% identical, at least 80% identical, at least 85% identical, at least 90% identical, at least 95% identical, at least 99% identical, or 100% identical) to (SEQ ID NO: 61)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCACG

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCACAATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC.

Additional examples of soluble interleukin receptors and soluble cytokine receptors are known in the art.

Ligands of Co-Stimulatory Molecules

In some embodiments of any of the single-chain chimeric polypeptides or multi-chain chimeric polypeptides described herein, one or both of the first target-binding domain and the second target-binding domain is a ligand of a co-stimulatory molecule. In some embodiments, the ligand of a co-stimulatory molecule is a soluble CD80 (see, e.g., those described in Haile et al., *J Immunol*. 2013 Sep. 1; 191(5):2829-36, and those described WO2004/076488 A1), a soluble CD86 (see, e.g., those described in Jeannin et al., *Immunity*. 2000 September; 13(3):303-12, and those described in WO 2004/076488 A1), a soluble CD40 (see, e.g., those described in Elgueta et al., *Immunological Reviews*, 229(1), doi.org/10.1111/j.1600-065X.2009.00782.x, and those described in WO 2001/083755 A2), a soluble ICOSL (see, e.g., those described in Chattopadyhay et al., *J. Immunol.*, Sep. 15, 2006, 177 (6) 3920-3929), a soluble CD70 (see, e.g., those described in Miller et al., *J. Neurosurg.*, 2010 August; 113(2):280-5, and those described in US 2009/0148942 A1), a soluble OX40L (see, e.g., those described in Kondo et al., *Hum. Immunol.*, 2007 July; 68(7):563-71. Epub 2007 Apr. 13), a soluble 4-1BBL (see, e.g., those described in Wang et al., *Cancer Immunol Immunother.*, 2012 April; 61(4):489-95), a soluble GITRL (see, e.g., those described in Stone et al., *J. Virol.*, 2006 February; 80(4):1762-72), a soluble LIGHT (see, e.g., those described in Maeda et al., *J. Immunol.*, 2018 Jul. 1; 201(1):202-214), a soluble TIM3 (see, e.g., those described in Clayton et al., *J. Virol.*, 2015 April; 89(7):3723-36), a soluble TIM4 (see, e.g., those described in Rhein et al., *J. Virol.*, 2016 Jun. 10; 90(13):6097-6111), soluble a ICAM1 (see, e.g., those described in Witkowsa and Borawska, Eur Cytokine Netw. 2004 April-June; 15(2):91-8), a soluble LFA3 (see, e.g., those described in Menshawy et al., *Comparative Clinical Pathology*, 27(3), 721-727, doi.org/10.1007/s00580-018-2657-x), a soluble CD1d (see, e.g., those described in Brennan et al., PNAS, Aug. 1, 2017 114 (31) 8348-8353), or a soluble LLT-1 (see, e.g., those described in Chalan et al., PLoS ONE, 10(7), e0132436, doi.org/10.1371/journal.pone.0132436).

In some embodiments, a soluble CD80, a soluble CD86, a soluble CD40, a soluble ICOSL, a soluble CD70, a soluble OX40L, a soluble 4-1BBL, a soluble GITRL, a soluble LIGHT, a soluble TIM3, a soluble TIM4, a soluble ICAM1, a soluble LFA3, a soluble CD1d, or a soluble LLT-1 can include a sequence that is at least 70% identical (e.g., at least 75% identical, at least 80% identical, at least 85% identical, at least 90% identical, at least 95% identical, at least 99% identical, or 100% identical) to the wild type sequence.

Additional examples of ligands of a co-stimulatory molecules are known in the art.

Additional Antigen-Binding Domains

Some embodiments of any of the single-chain chimeric polypeptides or multi-chain chimeric polypeptides described herein can further include one or more (e.g., two, three, four, five, six, seven, eight, nine, or ten) additional target-binding domains (e.g., any of the exemplary target-binding domains described herein or known in the art) at its N- and/or C-terminus.

In some embodiments, the single-chain chimeric polypeptide or multi-chain chimeric polypeptide can include one or more (e.g., two, three, four, five, six, seven, eight, nine, or ten) additional target-binding domains (e.g., any of the exemplary target-binding domains described herein or known in the art) at its N-terminus. In some embodiments, one of the one or more additional target-binding domains (e.g., any of the exemplary target-binding domains described herein or known in the art) at the N-terminus of the single-chain chimeric polypeptide or multi-chain chimeric polypeptide can directly abut the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains described herein). In some embodiments, the single-chain chimeric polypeptide or multi-chain chimeric polypeptide further includes a linker sequence (e.g., any of the exemplary linker sequences described herein or known in the art) between one of the at least one additional target-binding domains (e.g., any of the exemplary target-binding domains described herein or known in the art) at the N-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains described herein).

In some embodiments of any of the single-chain chimeric polypeptides or multi-chain chimeric polypeptide described herein, the polypeptide includes one or more (e.g., two, three, four, five, six, seven, eight, nine, or ten) additional target-binding domains (e.g., any of the exemplary target-binding domains described herein or known in the art) at its C-terminus. In some embodiments, one of the one or more additional target-binding domains (e.g., any of the exemplary target-binding domains described herein or known in the art) at the C-terminus of the single-chain chimeric polypeptide or the multi-chain chimeric polypeptide directly abuts the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains described herein or known in the art). In some embodiments, the single-chain chimeric polypeptide or multi-chain chimeric polypeptide further comprises a linker sequence (e.g., any of the exemplary linker sequences described herein or known in the art) between one of the at least one additional target-binding domains (e.g., any of the exemplary target-binding domains described herein or known in the art) at the C-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains described herein).

In some embodiments of any of the single-chain chimeric polypeptides or multi-chain chimeric polypeptides described herein, the polypeptide comprises one or more (e.g., two, three, four, five, six, seven, eight, nine, or ten) additional target binding domains (e.g., any of the exemplary target-binding domains described herein or known in the art) at its N-terminus and its C-terminus. In some embodiments, one of the one or more additional antigen binding domains (e.g., any of the exemplary target-binding domains described herein or known in the art) at the N-terminus of the single-chain chimeric polypeptide or the multi-chain chimeric polypeptide directly abuts the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains described herein). In some embodiments, the single-chain chimeric polypeptide or multi-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the N-terminus and the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains). In some embodiments, one of the one or more additional antigen binding domains (e.g., any of the exemplary target-binding domains described herein or known in the art) at the C-terminus directly abuts the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains). In some embodiments, the single-chain chimeric polypeptide or multi-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the C-terminus and the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains described herein).

In some embodiments of any of the single-chain chimeric polypeptides or multi-chain chimeric polypeptides described herein, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same antigen. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same epitope. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) include the same amino acid sequence.

In some embodiments of any of the single-chain chimeric polypeptides or multi-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same antigen. In some embodiments, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same epitope. In some embodiments, the first target-binding domain, the second target-binding domain, and the one or more (e.g., two, three, four, five, six, seven, eight, nine, or ten) additional target-binding domains each comprise the same amino acid sequence.

In some embodiments of any of the single-chain chimeric polypeptides or multi-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) bind specifically to different antigens.

In some embodiments of any of the single-chain chimeric polypeptides or multi-chain chimeric polypeptides described herein, one or more of the first target-binding domain, the second target-binding domain, and the one or more target-binding domains is an antigen-binding domain (e.g., any of the exemplary antigen-binding domains described herein or known in the art). In some embodiments of any of the single-chain chimeric polypeptides or multi-chain chimeric polypeptides described herein, the first target-binding domain, the second target-binding domain, and the one or more additional target-binding domains are each an antigen-binding domain (e.g., any of the exemplary antigen-binding domains described herein or known in the art). In some embodiments, the antigen-binding domain can include a scFv or a single domain antibody.

In some embodiments of any of the single-chain chimeric polypeptides or multi-chain chimeric polypeptides described herein, one or more (e.g., two, three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more target-binding domains (e.g., any of the exemplary target-binding domains described herein or known in the art) bind specifically to a target selected from the group consisting of: CD16a, CD28, CD3, CD33, CD20, CD19, CD22, CD40, CD47, CD52, CD70, CD80, CD86, CD123, CD137, CD272, IL-1R, IL-1, VEGF, IL-6R, IL-4, IL-10, PDL-1, PDL-2, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, B7-H4, HVEM, EPCAM, BCMA, P-cadherin, CEACAM5, VISTA, a UL16-binding protein, HLA-DR, DLL4, TYRO3, AXL, MER, CD122, CD155, PDGF-DD, ILT3, ILT4, TIGIT, MHCII, LAG3, OX40, a ligand of TGF-β receptor II (TGF-β RII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the single-chain chimeric polypeptides or multi-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin, soluble cytokine protein, or soluble cell surface protein. Non-limiting examples of soluble interleukin proteins, soluble cytokine proteins, or soluble cell surface proteins include: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

In some embodiments of any of the single-chain chimeric polypeptides or multi-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine receptor. Non-limiting examples of soluble interleukin receptors and soluble cytokine receptors include: a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

In some embodiments of any of the multi-chain chimeric polypeptides described herein, the first chimeric polypeptide further includes one or more (e.g., two, three, four, five, six, seven, eight, nine, or ten) additional target-binding domain(s) (e.g., any of the exemplary target-binding domains described herein or known in the art), where at least one of the one or more additional antigen-binding domain(s) is positioned between the linker domain (e.g., any of the exemplary linker domains described herein or known in the art) and the first domain of the pair of affinity domains (e.g., any of the exemplary first domains of any of the exemplary pairs of affinity domains described herein). In some embodiments, the first chimeric polypeptide of a multi-chain chimeric polypeptide can further include a linker sequence (e.g., any of the exemplary linker sequences described herein or known in the art) between the linker domain (e.g., any of the exemplary linker domains described herein) and the at least one of the one or more additional target-binding domain(s) (e.g., any of the exemplary target-binding domains described herein or known in the art), and/or a linker sequence (e.g., any of the exemplary linker sequences described herein or known in the art) between the at least one of the one or more additional target-binding domain(s) (e.g., any of the exemplary target-binding domains described herein or known in the art) and the first domain of the pair of affinity domains (e.g., any of the exemplary first domains described herein of any of the exemplary pairs of affinity domains described herein).

In some embodiments of any of the multi-chain chimeric polypeptides described herein, the first chimeric polypeptide further includes one or more (e.g., two, three, four, five, six, seven, eight, nine, or ten) additional target-binding domains at the N-terminal and/or C-terminal end of the first chimeric polypeptide. In some embodiments, at least one of the one or more additional target-binding domains (e.g., any of the exemplary target-binding domains described herein or known in the art) directly abuts the first domain of the pair of affinity domains (e.g., any of the exemplary first domains described herein of any of the exemplary pairs of affinity domains described herein) in the first chimeric polypeptide of a multi-chain chimeric polypeptide. In some embodiments, the first chimeric polypeptide of a multi-chain chimeric polypeptide further includes a linker sequence (e.g., any of the exemplary linker sequences described herein or known in the art) between the at least one of the one or more additional target-binding domains (e.g., any of the exemplary target-binding domains described herein or known in the art) and the first domain of the pair of affinity domains (e.g., any of the exemplary first domains described herein of any of the exemplary pairs of affinity domains described herein). In some embodiments, the at least one of the one or more additional target-binding domains (e.g., any of the exemplary target-binding domains described herein or known in the art) directly abuts the first target-binding domain (e.g., any of the exemplary target-binding domains described herein or known in the art) in the first chimeric polypeptide of a multi-chain chimeric polypeptide. In some embodiments, the first chimeric polypeptide of a multi-chain chimeric polypeptide further comprises a linker sequence (e.g., any of the exemplary linker sequences described herein or known in the art) between the at least one of the one or more additional target-binding domains (e.g., any of the exemplary target-binding domains described herein or known in the art) and the first target-binding domain (e.g., any of the exemplary target-binding domains described herein or known in the art).

In some embodiments of any of the multi-chain chimeric polypeptides described herein, at least one of the one or more additional target-binding domains (e.g., any of the exemplary target-binding domains described herein or known in the art) is disposed at the N- and/or C-terminus of the first chimeric polypeptide, and at least one of the one or more additional target-binding domains (e.g., any of the exemplary target-binding domains described herein or known in the art) is positioned between the linker domain (e.g., any of the exemplary linker domains described herein or known in the art) and the first domain of the pair of affinity domains (e.g., any of the exemplary first domains of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the N-terminus directly abuts the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide of a multi-chain chimeric polypeptide. In some embodiments, the first chimeric polypeptide of a multi-chain chimeric polypeptide further comprises a linker sequence (e.g., any of the linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the C-terminus directly abuts the first target-binding domain (e.g., any of the exemplary target-binding domains described herein or known in the art) or the first domain of the pair of affinity domains (e.g., any of the exemplary first domains of any of the exemplary pairs of affinity domains described herein) in the first chimeric polypeptide of a multi-chain chimeric polypeptide. In some embodiments, the first chimeric polypeptide of a multi-chain chimeric polypeptide further includes a linker sequence (e.g., any of the exemplary linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one of the one or more additional target-binding domains (e.g., any of the exemplary target-binding domains described herein or known in the art) positioned between the linker domain (e.g., any of the exemplary linker domains described herein) and the first domain of the pair of affinity domains (e.g., any of the first domains described herein or any of the exemplary pairs of affinity domains described herein), directly abuts the linker domain and/or the first domain of the pair of affinity domains. In some embodiments, the first chimeric polypeptide of a multi-chain chimeric polypeptide further comprises a linker sequence (e.g., any of the exemplary linker sequences described herein or known in the art) disposed (i) between the linker domain (e.g., any of the exemplary linker domains described herein) and the at least one of the one or more additional target-binding domains (e.g., any of the exemplary target-binding domains described herein or known in the art) positioned between the linker domain (e.g., any of the exemplary linker domains described herein) and the first domain of the pair of affinity domains (e.g., any of the exemplary first domains of any of the exemplary pairs of affinity domains described herein), and/or (ii) between the first domain of the pair of affinity domains and the at least one of the one or more additional target-binding domains positioned between the linker domain and the first domain of the pair of affinity domains.

In some embodiments of any of the multi-chain chimeric polypeptides described herein, the second chimeric polypeptide further includes one or more (e.g., two, three, four, five, six, seven, eight, nine, or ten) additional target-binding domains (e.g., any of the exemplary target-binding domains described herein or known in the art) at the N-terminal end and/or the C-terminal end of the second chimeric polypeptide. In some embodiments, at least one of the one or more additional target-binding domains (e.g., any of the exemplary target-binding domains described herein or known in the art) directly abuts the second domain of the pair of affinity domains (e.g., any of the exemplary second domains of any of the exemplary pairs of affinity domains described herein) in the second chimeric polypeptide of a multi-chain chimeric polypeptide. In some embodiments, the second chimeric polypeptide of a multi-chain chimeric polypeptide further includes a linker sequence (e.g., any of the exemplary linker sequences described herein or known in the art) between at least one of the one or more additional target-binding domains (e.g., any of the exemplary target-binding domains described herein or known in the art) and the second domain of the pair of affinity domains (e.g., any of the second domains described herein of any of the exemplary pairs of affinity domains described herein) in the second chimeric polypeptide. In some embodiments, at least one of the one or more additional target-binding domains (e.g., any of the exemplary target-binding domains described herein or known in the art) directly abuts the second target-binding domain (e.g., any of the target-binding domains described herein or known in the art) in the second chimeric polypeptide of a multi-chain chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target binding domains described herein or known in the art) and the second target-binding domain (e.g., any of the exemplary target binding domains described herein or known in the art) in the second chimeric polypeptide.

In some embodiments of any of the multi-chain chimeric polypeptides described herein, two or more (e.g., three or more, four or more, five or more, six or more, seven or more, eight or more, nine or more, or ten or more) of the first target-binding domain, the second target-binding domain, and the one or more additional target-binding domains bind specifically to the same antigen. In some embodiments, two or more (e.g., three or more, four or more, five or more, six or more, seven or more, eight or more, nine or more, or ten or more) of the first target-binding domain, the second target-binding domain, and the one or more additional target-binding domains bind specifically to the same epitope. In some embodiments, two or more (e.g., three or more, four or more, five or more, six or more, seven or more, eight or more, nine or more, or ten or more) of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence.

In some embodiments of any of the multi-chain chimeric polypeptides described herein, the first target-binding domain, the second target-binding domain, and the one or more additional target-binding domains bind specifically to different antigens. In some embodiments of any of the multi-chain chimeric polypeptides described herein, one or more (e.g., two or more, three or more, four or more, five or more, six or more, seven or more, eight or more, nine or more, or ten or more) of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain (e.g., a scFv or a single-domain antibody).

Pairs of Affinity Domains

In some embodiments, a multi-chain chimeric polypeptide includes: 1) a first chimeric polypeptide that includes a first domain of a pair of affinity domains, and 2) a second chimeric polypeptide that includes a second domain of a pair of affinity domains such that the first chimeric polypeptide and the second chimeric polypeptide associate through the binding of the first domain and the second domain of the pair of affinity domains. In some embodiments, the pair of affinity domains is a sushi domain from an alpha chain of an IL-15 receptor (IL15Rα) (e.g., a human IL-15 receptor (IL-15Rα)) and a soluble IL-15 (e.g., a human soluble IL-15). A sushi domain, also known as a short consensus repeat or type 1 glycoprotein motif, is a common motif in protein-protein interaction. Sushi domains have been identified on a number of protein-binding molecules, including complement components C1r, C1s, factor H, and C2m, as well as the nonimmunologic molecules factor XIII and β2-glycoprotein. A typical Sushi domain has approximately 60 amino acid residues and contains four cysteines (Ranganathan, Pac. Symp Biocomput. 2000:155-67). The first cysteine can form a disulfide bond with the third cysteine, and the second cysteine can form a disulfide bridge with the fourth cysteine. In some embodiments in which one member of the pair of affinity domains is a soluble IL-15, the soluble IL-15 has a D8N or D8A amino acid substitution. In some embodiments in which one member of the pair of affinity domains is an alpha chain of human IL-15 receptor (IL15Rα), the human IL15Rα is a mature full-length IL15Rα. In some embodiments, the pair of affinity domains is barnase and barnstar. In some embodiments, the pair of affinity domains is a PKA and an AKAP. In some embodiments, the pair of affinity domains is an adapter/docking tag module based on mutated RNase I fragments (Rossi, *Proc Natl Acad Sci USA*. 103:6841-6846, 2006; Sharkey et al., *Cancer Res*. 68:5282-5290, 2008; Rossi et al., *Trends Pharmacol Sci*. 33:474-481, 2012) or SNARE modules based on interactions of the proteins syntaxin, synaptotagmin, synaptobrevin, and SNAP25 (Deyev et al., *Nat Biotechnol*. 1486-1492, 2003).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains and the second domain of the pair of affinity domains bind to each other with a dissociation equilibrium constant ($K_D$) of less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the first domain of the pair of affinity domains and the second domain of the pair of affinity domains bind to each other with a $K_D$ of about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, about $1\times10^{-9}$ M to about $1\times10^{-11}$ M, about $1\times10^{-10}$ M to about $1\times10^{-12}$ M, about $1\times10^{-11}$ M to about $1\times10^{-13}$ M, about $1\times10^{-14}$ M to about $1\times10^{-5}$ M, about $1\times10^{-5}$ M to about $1\times10^{-6}$ M, about $1\times10^{-6}$ M to about $1\times10^{-7}$ M, about $1\times10^{-7}$ M to about $1\times10^{-8}$ M, about $1\times10^{-8}$ M to about $1\times10^{-9}$ M, about $1\times10^{-9}$ M to about $1\times10^{-10}$ M, about $1\times10^{-10}$ M to about $1\times10^{-11}$ M, about $1\times10^{-11}$ M to about $1\times10^{-12}$ M, or about $1\times10^{-12}$ M to about $1\times10^{-13}$ M (inclusive). Any of a variety of different methods known in the art can be used to determine the $K_D$ value of the binding of the first domain of the pair of affinity domains and the second domain of the pair of affinity domains (e.g., an electrophoretic mobility shift assay, a filter binding assay, surface plasmon resonance, and a biomolecular binding kinetics assay, etc.).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains, the second domain of the pair of affinity domains, or both is about 10 to 100 amino acids in length. For example, a first domain of a pair of affinity domains, a second domain of a pair of affinity domains, or both can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a first domain of a pair of affinity domains, a second domain of a pair of affinity domains, or both is about 10, 15, 20, 25, 30, 35, 40, 45, 50, 55, 60, 65, 70, 75, 80, 85, 90, 95, or 100 amino acids in length.

In some embodiments, any of the first and/or second domains of a pair of affinity domains disclosed herein can include one or more additional amino acids (e.g., 1, 2, 3, 5, 6, 7, 8, 9, 10, or more amino acids) at its N-terminus and/or C-terminus, so long as the function of the first and/or second domains of a pair of affinity domains remains intact. For example, a sushi domain from an alpha chain of human IL-15 receptor (IL15Rα) can include one or more additional amino acids at the N-terminus and/or the C-terminus, while still retaining the ability to bind to a soluble IL-15. Additionally or alternatively, a soluble IL-15 can include one or more additional amino acids at the N-terminus and/or the C-terminus, while still retaining the ability to bind to a sushi domain from an alpha chain of human IL-15 receptor (IL15Rα).

A non-limiting example of a sushi domain from an alpha chain of IL-15 receptor alpha (IL15Rα) can include a sequence that is at least 70% identical, at least 75% identical, at least 80% identical, at least 85% identical, at least 90% identical, at least 95% identical, at least 99% identical, or 100% identical to ITCPPPMSVEHADIWVKSYSLYSRERYICNSGFKRKAGTSSLTECVLNKATNVAHWTTPSLKCIR (SEQ ID NO: 10). In some embodiments, a sushi domain from an alpha chain of IL15Rα can be encoded by a nucleic acid including (SEQ ID NO: 11)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG.

In some embodiments, a soluble IL-15 can include a sequence that is at least 70% identical, at least 75% identical, at least 80% identical, at least 85% identical, at least 90% identical, at least 95% identical, at least 99% identical, or 100% identical to NWVNVISDLKKIEDLIQSMHIDATLYTESDVHPSCKVTAMKCFLLELQVISLESGDASIHDTVENLIILANNSLSSNGNVTESGCKECEELEEKNIKEFLQSFVHIVQMFINTS (SEQ ID NO: 39). In some embodiments, a soluble IL-15 can be encoded by a nucleic acid including the sequence of

```
                                      (SEQ ID NO: 110)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC.
```

Signal Sequence

In some embodiments, a single-chain chimeric polypeptide includes a signal sequence at its N-terminal end. As will be understood by those of ordinary skill in the art, a signal sequence is an amino acid sequence that is present at the N-terminus of a number of endogenously produced proteins that directs the protein to the secretory pathway (e.g., the protein is directed to reside in certain intracellular organelles, to reside in the cell membrane, or to be secreted from the cell). Signal sequences are heterogeneous and differ greatly in their primary amino acid sequences. However, signal sequences are typically 16 to 30 amino acids in length and include a hydrophilic, usually positively charged N-terminal region, a central hydrophobic domain, and a C-terminal region that contains the cleavage site for signal peptidase.

In some embodiments, a single-chain chimeric polypeptide includes a signal sequence having an amino acid sequence MKWVTFISLLFLFSSAYS (SEQ ID NO: 62). In some embodiments, a single chain chimeric polypeptide includes a signal sequence encoded by the nucleic acid sequence

```
                                       (SEQ ID NO: 63)
ATGAAATGGGTGACCTTTATTTCTTTACTGTTCCTCTTTAGCAGCGCCT

ACTCC.
                                       (SEQ ID NO: 64)
ATGAAGTGGGTCACATTTATCTCTTTACTGTTCCTCTTCTCCAGCGCCT

ACAGC.

or
                                       (SEQ ID NO: 65)
ATGAAATGGGTGACCTTTATTTCTTTACTGTTCCTCTTTAGCAGCGCCT

ACTCC.
```

In some embodiments, a single-chain chimeric polypeptide includes a signal sequence having an amino acid sequence MKCLLYLAFLFLGVNC (SEQ ID NO: 66). In some embodiments, a single-chain chimeric polypeptide includes a signal sequence having an amino acid sequence MGQIVTMFEALPHIIDEVINIVIIVLIIITSIKAVYN-FATCGILALVSFLFLAGRSCG (SEQ ID NO: 67). In some embodiments, a single-chain chimeric polypeptide includes a signal sequence having an amino acid sequence MPNHQSGSPTGS SDLLL SGKKQRPHLALRRKRRRE-MRKINRKVRRMNLAPIKEKTAWQ HLQALISE-AEEVLKTSQTPQNSLTLFLALLSVLGPPVTG (SEQ ID NO: 68). In some embodiments, a single-chain chimeric polypeptide includes a signal sequence having an amino acid sequence MDSKGSSQKGSRLLLLLVVSNLLLCQGVVS (SEQ ID NO: 69). Those of ordinary skill in the art will be aware of other appropriate signal sequences for use in a single-chain chimeric polypeptide.

In some embodiments, a single-chain chimeric polypeptide includes a signal sequence that is about 10 to 100 amino acids in length. For example, a signal sequence can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a signal sequence is about 10, 15, 20, 25, 30, 35, 40, 45, 50, 55, 60, 65, 70, 75, 80, 85, 90, 95, or 100 amino acids in length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKWVTFISLL-FLFSSAYS (SEQ ID NO: 62) can include one or more additional amino acids at the N-terminus or C-terminus, while still retaining the ability to direct the single-chain chimeric polypeptide to the secretory pathway.

In some embodiments, a single-chain chimeric polypeptide includes a signal sequence that directs the single-chain chimeric polypeptide into the extracellular space. Such embodiments are useful in producing single-chain chimeric polypeptides that are relatively easy to be isolated and/or purified.

In some embodiments, a multi-chain chimeric polypeptide includes a first chimeric polypeptide that includes a signal sequence at its N-terminal end. In some embodiments, a multi-chain chimeric polypeptide includes a second chimeric polypeptide that includes a signal sequence at its N-terminal end. In some embodiments, both the first chimeric polypeptide of a multi-chain chimeric polypeptide and a second chimeric polypeptide of the multi-chain chimeric polypeptide include a signal sequence. As will be understood by those of ordinary skill in the art, a signal sequence is an amino acid sequence that is present at the N-terminus of a number of endogenously produced proteins that directs the protein to the secretory pathway (e.g., the protein is directed to reside in certain intracellular organelles, to reside in the cell membrane, or to be secreted from the cell). Signal sequences are heterogeneous and differ greatly in their primary amino acid sequences. However, signal sequences are typically 16 to 30 amino acids in length and include a hydrophilic, usually positively charged N-terminal region, a central hydrophobic domain, and a C-terminal region that contains the cleavage site for signal peptidase.

In some embodiments, a first chimeric polypeptide of a multi-chain chimeric polypeptide, a second chimeric polypeptide of the multi-chain chimeric polypeptide, or both includes a signal sequence having an amino acid sequence MKWVTFISLLFLFSSAYS (SEQ ID NO: 62). In some embodiments, a first chimeric polypeptide of a multi-chain chimeric polypeptide, a second chimeric polypeptide of the multi-chain chimeric polypeptide, or both includes a signal sequence encoded by the nucleic acid sequence

```
                                           (SEQ ID NO: 63)
ATGAAATGGGTGACCTTTATTTCTTTACTGTTCCTCTTTAGCAGCGCCT

ACTCC.
                                           (SEQ ID NO: 64)
ATGAAGTGGGTCACATTTATCTCTTTACTGTTCCTCTTCTCCAGCGCCT

ACAGC.
or
                                           (SEQ ID NO: 65)
ATGAAATGGGTGACCTTTATTTCTTTACTGTTCCTCTTTAGCAGCGCCT

ACTCC.
```

In some embodiments, a first chimeric polypeptide of a multi-chain chimeric polypeptide, a second chimeric polypeptide of the multi-chain chimeric polypeptide, or both includes a signal sequence having an amino acid sequence MKCLLYLAFLFLGVNC (SEQ ID NO: 66). In some embodiments, a first chimeric polypeptide of a multi-chain chimeric polypeptide, a second chimeric polypeptide of the multi-chain chimeric polypeptide, or both includes a signal sequence having an amino acid sequence MGQIVTMFEALPHIIDEVINIVIIVLIIITSIKAVYNFATCGILALVSFLFLAGRSCG (SEQ ID NO: 67). In some embodiments, a first chimeric polypeptide of a multi-chain chimeric polypeptide, a second chimeric polypeptide of the multi-chain chimeric polypeptide, or both includes a signal sequence having an amino acid sequence MPNHQSGSPTGSSDLLLSGKKQRPHLALRRKRRREMRKINRKVRRMNLAPIKEKTAWQ HLQALISEAEEVLKTSQTPQNSLTLFLALLSVLGPPVTG (SEQ ID NO: 68). In some embodiments, a first chimeric polypeptide of a multi-chain chimeric polypeptide, a second chimeric polypeptide of the multi-chain chimeric polypeptide, or both includes a signal sequence having an amino acid sequence MDSKGSSQKGSRLLLLLVVSNLLLCQGVVS (SEQ ID NO: 69). Those of ordinary skill in the art will be aware of other appropriate signal sequences for use in a first chimeric polypeptide and/or a second chimeric polypeptide of multi-chain chimeric polypeptides described herein.

In some embodiments, a first chimeric polypeptide of a multi-chain chimeric polypeptide, a second chimeric polypeptide of the multi-chain chimeric polypeptide, or both includes a signal sequence that is about 10 to 100 amino acids in length. For example, a signal sequence can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a signal sequence is about 10, 15, 20, 25, 30, 35, 40, 45, 50, 55, 60, 65, 70, 75, 80, 85, 90, 95, or 100 amino acids in length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKCLLYLAFLFLGVNC (SEQ ID NO: 66) can include one or more additional amino acids at the N-terminus or C-terminus, while still retaining the ability to direct a first chimeric polypeptide of a multi-chain chimeric polypeptide, a second chimeric polypeptide of the multi-chain chimeric polypeptide, or both to the secretory pathway.

In some embodiments, a first chimeric polypeptide of a multi-chain chimeric polypeptide, a second chimeric polypeptide of the multi-chain chimeric polypeptide, or both includes a signal sequence that directs the multi-chain chimeric polypeptide into the extracellular space. Such embodiments are useful in producing multi-chain chimeric polypeptides that are relatively easy to be isolated and/or purified.

Peptide Tags

In some embodiments, a single-chain chimeric polypeptide includes a peptide tag (e.g., at the N-terminal end or the C-terminal end of the single-chain chimeric polypeptide). In some embodiments, a single-chain chimeric polypeptide includes two or more peptide tags.

Exemplary peptide tags that can be included in a single-chain chimeric polypeptide include, without limitation, Avi-Tag (GLNDIFEAQKIEWHE; SEQ ID NO: 70), a calmodulin-tag (KRRWKKNFIAVSAANRFKKISSSGAL; SEQ ID NO: 71), a polyglutamate tag (EEEEEE; SEQ ID NO: 72), an E-tag (GAPVPYPDPLEPR; SEQ ID NO: 73), a FLAG-tag (DYKDDDDK; SEQ ID NO: 74), an HA-tag, a peptide from hemagglutinin (YPYDVPDYA; SEQ ID NO: 75), a his-tag (HHHHH (SEQ ID NO: 76); HHHHHH (SEQ ID NO: 77); HHHHHHH (SEQ ID NO: 78); HHHHHHHH (SEQ ID NO: 79); HHHHHHHH (SEQ ID NO: 80); or HHHHHHHHH (SEQ ID NO: 81)), a myc-tag (EQKLISEEDL; SEQ ID NO: 82), NE-tag (TKENPRSNQEESYDDNES; SEQ ID NO: 83), S-tag (KETAAAKFERQHMDS; SEQ ID NO: 84), SBP-tag (MDEKTTGWRGGHVVEGLAGELEQLRARLEHHPQGQREP; SEQ ID NO: 85), Softag 1 (SLAELLNAGLGGS; SEQ ID NO: 86), Softag 3 (TQDPSRVG; SEQ ID NO: 87), Spot-tag (PDRVRAVSHWSS; SEQ ID NO: 88), Strep-tag (WSHPQFEK; SEQ ID NO: 89), TC tag (CCPGCC; SEQ ID NO: 90), Ty tag (EVHTNQDPLD; SEQ ID NO: 91), V5 tag (GKPIPNPLLGLDST; SEQ ID NO: 92), VSV-tag (YTDIEMNRLGK; SEQ ID NO: 93), and Xpress tag (DLYDDDDK; SEQ ID NO: 94). In some embodiments, tissue factor protein is a peptide tag.

Peptide tags that can be included in a single-chain chimeric polypeptide can be used in any of a variety of applications related to the single-chain chimeric polypeptide. For example, a peptide tag can be used in the purification of a single-chain chimeric polypeptide. As one non-limiting example, a single-chain chimeric polypeptide can include a myc tag; and can be purified using an antibody that recognizes the myc tag(s). One non-limiting example of an antibody that recognizes a myc tag is 9E10, available from the non-commercial Developmental Studies Hybridoma Bank. As another non-limiting example, a single-chain chimeric polypeptide can include a histidine tag, and can be purified using a nickel or cobalt chelate. Those of ordinary skill in the art will be aware of other suitable tags and agent that bind those tags for use in purifying a single-chain chimeric polypeptide. In some embodiments, a peptide tag is removed from the single-chain chimeric polypeptide after purification. In some embodiments, a peptide tag is not removed from the single-chain chimeric polypeptide after purification.

Peptide tags that can be included in a single-chain chimeric polypeptide can be used, for example, in immunoprecipitation of the single-chain chimeric polypeptide, imaging of the single-chain chimeric polypeptide (e.g., via Western blotting, ELISA, flow cytometry, and/or immunocytochemistry), and/or solubilization of the single-chain chimeric polypeptide.

In some embodiments, a single-chain chimeric polypeptide includes a peptide tag that is about 10 to 100 amino acids in length. For example, a peptide tag can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a peptide tag is about 10, 15, 20, 25, 30, 35, 40, 45, 50, 55, 60, 65, 70, 75, 80, 85, 90, 95, or 100 amino acids in length.

Peptide tags included in a single-chain chimeric polypeptide can be of any suitable length. For example, peptide tags can be 5, 6, 7, 8, 9, 10, 11, 12, 13, 14, 15, 16, 17, 18, 19, 20, or more amino acids in length. In embodiments in which a single-chain chimeric polypeptide includes two or more peptide tags, the two or more peptide tags can be of the same or different lengths. In some embodiments, any of the peptide tags disclosed herein may include one or more additional amino acids (e.g., 1, 2, 3, 5, 6, 7, 8, 9, 10, or more amino acids) at the N-terminus and/or C-terminus, so long as the function of the peptide tag remains intact. For example, a myc tag having the amino acid sequence EQKLISEEDL (SEQ ID NO: 82) can include one or more additional amino acids (e.g., at the N-terminus and/or the C-terminus of the peptide tag), while still retaining the ability to be bound by an antibody (e.g., 9E10).

In some embodiments, a multi-chain chimeric polypeptide includes a first chimeric polypeptide that includes a peptide tag (e.g., at the N-terminal end or the C-terminal end of the first chimeric polypeptide). In some embodiments, a multi-chain chimeric polypeptide includes a second chimeric polypeptide that includes a peptide tag (e.g., at the N-terminal end or the C-terminal end of the second chimeric polypeptide). In some embodiments, both the first chimeric polypeptide of a multi-chain chimeric polypeptide and a second chimeric polypeptide of the multi-chain chimeric polypeptide include a peptide tag. In some embodiments, a first chimeric polypeptide of a multi-chain chimeric polypeptide, a second chimeric polypeptide of the multi-chain chimeric polypeptide, or both include two or more peptide tags.

Exemplary peptide tags that can be included in a first chimeric polypeptide of a multi-chain chimeric polypeptide, a second chimeric polypeptide of the multi-chain chimeric polypeptide, or both include, without limitation, AviTag (GLNDIFEAQKIEWHE; SEQ ID NO: 70), a calmodulin-tag (KRRWKKNFIAVSAANRFKKISSSGAL; SEQ ID NO: 71), a polyglutamate tag (EEEEEE; SEQ ID NO: 72), an E-tag (GAPVPYPDPLEPR; SEQ ID NO: 73), a FLAG-tag (DYKDDDDK; SEQ ID NO: 74), an HA-tag, a peptide from hemagglutinin (YPYDVPDYA; SEQ ID NO: 75), a his-tag (HHHHH (SEQ ID NO: 76); HHHHHH (SEQ ID NO: 77); HHHHHHH (SEQ ID NO: 78); HHHHHHHH (SEQ ID NO: 79); HHHHHHHHH (SEQ ID NO: 80); or HHHHHHHHHH (SEQ ID NO: 81), a myc-tag (EQKLISEEDL; SEQ ID NO: 82), NE-tag (TKENPRSNQEESYDDNES; SEQ ID NO: 83), S-tag, (KETAAAKFERQHMDS; SEQ ID NO: 84), SBP-tag (MDEKTTGWRGGHVVEGLAGELEQLRARLEHHPQGQREP; SEQ ID NO: 85), Softag 1 (SLAELLNAGLGGS; SEQ ID NO: 86), Softag 3 (TQDPSRVG; SEQ ID NO: 87), Spot-tag (PDRVRAVSHWSS; SEQ ID NO: 88), Strep-tag (WSHPQFEK; SEQ ID NO: 89), TC tag (CCPGCC; SEQ ID NO: 90), Ty tag (EVHTNQDPLD; SEQ ID NO: 91), V5 tag (GKPIPNPLLGLDST; SEQ ID NO: 92), VSV-tag (YTDIEMNRLGK; SEQ ID NO: 93), and Xpress tag (DLYDDDDK; SEQ ID NO: 94). In some embodiments, tissue factor protein is a peptide tag.

Peptide tags that can be included in a first chimeric polypeptide of a multi-chain chimeric polypeptide, a second chimeric polypeptide of the multi-chain chimeric polypeptide, or both can be used in any of a variety of applications related to the multi-chain chimeric polypeptide. For example, a peptide tag can be used in the purification of a multi-chain chimeric polypeptide. As one non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both can include a myc tag; the multi-chain chimeric polypeptide that includes the myc-tagged first chimeric polypeptide, the myc-tagged second chimeric polypeptide, or both can be purified using an antibody that recognizes the myc tag(s). One non-limiting example of an antibody that recognizes a myc tag is 9E10, available from the non-commercial Developmental Studies Hybridoma Bank. As another non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both can include a histidine tag; the multi-chain chimeric polypeptide that includes the histidine-tagged first chimeric polypeptide, the histidine-tagged second chimeric polypeptide, or both can be purified using a nickel or cobalt chelate. Those of ordinary skill in the art will be aware of other suitable tags and agent that bind those tags for use in purifying multi-chain chimeric polypeptide. In some embodiments, a peptide tag is removed from the first chimeric polypeptide and/or the second chimeric polypeptide of the multi-chain chimeric polypeptide after purification. In some embodiments, a peptide tag is not removed from the first chimeric polypeptide and/or the second chimeric polypeptide of the multi-chain chimeric polypeptide after purification.

Peptide tags that can be included in a first chimeric polypeptide of a multi-chain chimeric polypeptide, a second chimeric polypeptide of the multi-chain chimeric polypeptide, or both can be used, for example, in immunoprecipitation of the multi-chain chimeric polypeptide, imaging of the multi-chain chimeric polypeptide (e.g., via Western blotting, ELISA, flow cytometry, and/or immunocytochemistry), and/or solubilization of the multi-chain chimeric polypeptide.

In some embodiments, a first chimeric polypeptide of a multi-chain chimeric polypeptide, a second chimeric polypeptide of the multi-chain chimeric polypeptide, or both includes a peptide tag that is about 10 to 100 amino acids in length. For example, a peptide tag can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a peptide tag is about 10, 15, 20, 25, 30, 35, 40, 45, 50, 55, 60, 65, 70, 75, 80, 85, 90, 95, or 100 amino acids in length.

Peptide tags included in a first chimeric polypeptide of a multi-chain chimeric polypeptide, a second chimeric polypeptide of the multi-chain chimeric polypeptide, or both can be of any suitable length. For example, peptide tags can be 5, 6, 7, 8, 9, 10, 11, 12, 13, 14, 15, 16, 17, 18, 19, 20, or more amino acids in length. In embodiments in which a multi-chain chimeric polypeptide includes two or more peptide tags, the two or more peptide tags can be of the same or different lengths. In some embodiments, any of the peptide tags disclosed herein may include one or more additional amino acids (e.g., 1, 2, 3, 5, 6, 7, 8, 9, 10, or more amino acids) at the N-terminus and/or C-terminus, so long as the function of the peptide tag remains intact. For example, a myc tag having the amino acid sequence EQKLISEEDL (SEQ ID NO: 82) can include one or more additional amino acids (e.g., at the N-terminus and/or the C-terminus of the peptide tag), while still retaining the ability to be bound by an antibody (e.g., 9E10).

Exemplary Embodiments of Single-Chain Chimeric Polypeptides—Type A

In some embodiments of any of the single-chain chimeric polypeptides described herein, the first target-binding domain and/or the second target-binding domain can independently bind specifically to CD3 (e.g., human CD3) or CD28 (e.g., human CD28). In some embodiments, the first target-binding domain binds specifically to CD3 (e.g., human CD3) and the second target-binding domain binds specifically to CD28 (e.g., human CD28). In some embodiments, the first target-binding domain binds specifically to CD28 (e.g., human CD28) and the second target-binding domain binds specifically to CD3 (e.g., human CD3).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, one or both of the first target-binding domain and the second target-binding domain is an antigen-binding domain. In some embodiments of these single-chain chimeric polypeptides, the first target-binding domain and the second target-binding domain are each an antigen-binding domain (e.g., any of the exemplary antigen-binding domains described herein). In some embodiments of these single-chain chimeric polypeptides, the antigen-binding domain includes a scFv or a single domain antibody.

A non-limiting example of an scFv that binds specifically to CD3 can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 20)
QIVLTQSPAMSASPGEKVTMTCSASSSVSYMNWYQQKSGTSPKRWIYDT

SKLASGVPAHFRGSGSGTSYSLTISGMEAEDAATYYCQQWSSNPFTFGS

GTKLEINRGGGSGGGGSGGGGSQVQLQQSGAELARPGASVKMSCKASG

YTFTRYTMEIWVKQRPGQGLEWIGYINPSRGYTNYNQKFKDKATLTTDK

SSSTAYMQLSSLTSEDSAVYYCARYYDDHYCLDYWGQGTTLTVSS.

In some embodiments, an scFv that binds specifically to CD3 can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 12)
CAGATCGTGCTGACCCAAAGCCCCGCCATCATGAGCGCTAGCCCCGGTG

AGAAGGTGACCATGACATGCTCCGCTTCCAGCTCCGTGTCCTACATGAA

CTGGTATCAGCAGAAAAGCGGAACCAGCCCCAAAAGGTGGATCTACGAC

ACCAGCAAGCTGGCCTCCGGAGTGCCCGCTCATTTCCGGGGCTCTGGAT

CCGGCACCAGCTACTCTTTAACCATTTCCGGCATGGAAGCTGAAGACGC

TGCCACCTACTATTGCCAGCAATGGAGCAGCAACCCCTTCACATTCGGA

TCTGGCACCAAGCTCGAAATCAATCGTGGAGGAGGTGGCAGCGGCGGCG

GTGGATCCGGCGGAGGAGGAAGCCAAGTTCAACTCCAGCAGAGCGGCGC

TGAACTGGCCCGGCCCGGCGCCTCCGTCAAGATGAGCTGCAAGGCTTCC

GGCTATACATTTACTCGTTACACAATGCATTGGGTCAAGCAGAGGCCCG

GTCAAGGTTTAGAGTGGATCGGATATATCAACCCTTCCGGGGCTACAC

CAACTATAACCAAAAGTTCAAGGATAAAGCCACTTTAACCACTGACAAG

AGCTCCTCCACCGCCTACATGCAGCTGTCCTCTTTAACCAGCGAGGACT

CCGCTGTTTACTACTGCGCTAGGTATTACGACGACCACTACTGTTTAGA

CTATTGGGGACAAGGTACCACTTTAACCGTCAGCAGC.

A non-limiting example of an scFv that binds specifically to CD28 can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 26)
VQLQQSGPELVKPGASVKMSCKASGYTFTSYVIQWVKQKPGQGLEWIGS

INPYNDYTKYNEKFKGKATLTSDKSSITAYMEFSSLTSEDSALYYCARW

GDGNYWGRGTTLTVSSGGGGSGGGGSGGGGSDIEMTQSPAIMSASLGER

VTMTCTASSSVSSSYFHWYQQKPGSSPKLCIYSTSNLASGVPPRFSGSG

STSYSLTISSMEAEDAATYFCHQYHRSPTFGGGTKLETKR.

In some embodiments, an scFv that binds specifically to CD28 can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 13)
GTCCAGCTGCAGCAGAGCGGACCCGAACTCGTGAAACCCGGTGCTTCCG

TGAAAATGTCTTGTAAGGCCAGCGGATACACCTTCACCTCCTATGTGAT

CCAGTGGGTCAAACAGAAGCCCGGACAAGGTCTCGAGTGGATCGGCAGC

ATCAACCCTTACAACGACTATACCAAATACAACGAGAAGTTTAAGGGAA

AGGCTACTTTAACCTCCGACAAAAGCTCCATCACAGCCTACATGGAGTT

CAGCTCTTTAACATCCGAGGACAGCGCTCTGTACTATTGCGCCCGGTGG

GGCGACGGCAATTACTGGGGACGGGGCACAACACTGACCGTGAGCAGCG

GAGGCGGAGGCTCCGGCGGAGGCGGATCTGGCGGTGGCGGCTCCGACAT

CGAGATGACCCAGTCCCCCGCTATCATGTCCGCCTCTTTAGGCGAGCGG

GTCACAATGACTTGTACAGCCTCCTCCAGCGTCTCCTCCTCCTACTTCC

ATTGGTACCAACAGAAACCCGGAAGCTCCCCTAAACTGTGCATCTACAG

CACCAGCAATCTCGCCAGCGGCGTGCCCCCTAGGTTTTCCGGAAGCGGA

AGCACCAGCTACTCTTTAACCATCTCCTCCATGGAGGCTGAGGATGCCG

CCACCTACTTTTGTCACCAGTACCACCGGTCCCCCACCTTCGGAGGCGG

CACCAAACTGGAGACAAAGAGG.

In some embodiments of these single-chain chimeric polypeptides, the first target-binding domain and/or the second target-binding domain is a soluble receptor (e.g., a soluble CD28 receptor or a soluble CD3 receptor). In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 100)
QIVLTQSPAIMSASPGEKVTMTCSASSSVSYMNWYQQKSGTSPKRWIYD

TSKLASGVPAHFRGSGSGTSYSLTISGMEAEDAATYYCQQWSSNPFTFG

SGTKLEINRGGGGSGGGGSGGGGSQVQLQQSGAELARPGASVKMSCKAS

GYTFTRYTMEIWVKQRPGQGLEWIGYINPSRGYTNYNQKFKDKATLTTD

KSSSTAYMQLSSLTSEDSAVYYCARYYDDHYCLDYWGQGTTLTVSSSGT

TNTVAAYNLTWKSTNFKTILEWEPKPVNQVYTVQISTKSGDWKSKCFYT

TDTECDLTDEIVKDVKQTYLARVFSYPAGNVESTGSAGEPLYENSPEFT

PYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVN

RKSTDSPVECMGQEKGEFREVQLQQSGPELVKPGASVKMSCKASGYTFT

SYVIQWVKQKPGQGLEWIGSINPYNDYTKYNEKFKGKATLTSDKSSITA

YMEFSSLTSEDSALYYCARWGDGNYWGRGTTLTVSSGGGGSGGGGSGGG

GSDIEMTQSPAIMSASLGERVTMTCTASSSVSSSYFHWYQQKPGSSPKL

CIYSTSNLASGVPPRFSGSGSTSYSLTISSMEAEDAATYFCHQYHRSPT

FGGGTKLETKR.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 101)
CAGATCGTGCTGACCCAAAGCCCCGCCATCATGAGCGCTAGCCCCGGTG

AGAAGGTGACCATGACATGCTCCGCTTCCAGCTCCGTGTCCTACATGAA

CTGGTATCAGCAGAAAAGCGGAACCAGCCCCAAAAGGTGGATCTACGAC

ACCAGCAAGCTGGCCTCCGGAGTGCCCGCTCATTTCCGGGGCTCTGGAT

CCGGCACCAGCTACTCTTTAACCATTTCCGGCATGGAAGCTGAAGACGC

TGCCACCTACTATTGCCAGCAATGGAGCAGCAACCCCTTCACATTCGGA

TCTGGCACCAAGCTCGAAATCAATCGTGGAGGAGGTGGCAGCGGCGGCG

GTGGATCCGGCGGAGGAGGAAGCCAAGTTCAACTCCAGCAGAGCGGCGC

TGAACTGGCCCGGCCCGGCGCCTCCGTCAAGATGAGCTGCAAGGCTTCC

GGCTATACATTTACTCGTTACACAATGCATTGGGTCAAGCAGAGGCCCG

GTCAAGGTTTAGAGTGGATCGGATATATCAACCCTTCCCGGGGCTACAC

CAACTATAACCAAAAGTTCAAGGATAAAGCCACTTTAACCACTGACAAG

AGCTCCTCCACCGCCTACATGCAGCTGTCCTCTTTAACCAGCGAGGACT

CCGCTGTTTACTACTGCGCTAGGTATTACGACGACCACTACTGTTTAGA

CTATTGGGGACAAGGTACCACTTTAACCGTCAGCAGCTCCGGCACCACC

AATACCGTGGCCGCTTATAACCTCACATGGAAGAGCACCAACTTCAAGA

CAATTCTGGAATGGGAACCCAAGCCCGTCAATCAAGTTTACACCGTGCA

GATCTCCACCAAATCCGGAGACTGGAAGAGCAAGTGCTTCTACACAACA

GACACCGAGTGTGATTTAACCGACGAAATCGTCAAGGACGTCAAGCAAA

CCTATCTGGCTCGGGTCTTTTCCTACCCCGCTGGCAATGTCGAGTCCAC

CGGCTCCGCTGGCGAGCCTCTCTACGAGAATTCCCCCGAATTCACCCCT

TATTTAGAGACCAATTTAGGCCAGCCTACCATCCAGAGCTTCGAGCAAG

TTGGCACCAAGGTGAACGTCACCGTCGAGGATGAAAGGACTTTAGTGCG

GCGGAATAACACATTTTTATCCCTCCGGGATGTGTTCGGCAAAGACCTC

ATCTACACACTGTACTATTGGAAGTCCAGCTCCTCCGGCAAAAAGACCG

CTAAGACCAACACCAACGAGTTTTTAATTGACGTGGACAAAGGCGAGAA

CTACTGCTTCAGCGTGCAAGCCGTGATCCCTTCTCGTACCGTCAACCGG

AAGAGCACAGATTCCCCCGTTGAGTGCATGGGCCAAGAAAAGGGCGAGT

TCCGGGAGGTCCAGCTGCAGCAGAGCGGACCCGAACTCGTGAAACCCGG

TGCTTCCGTGAAAATGTCTTGTAAGGCCAGCGGATACACCTTCACCTCC

TATGTGATCCAGTGGGTCAAACAGAAGCCCGGACAAGGTCTCGAGTGGA

TCGGCAGCATCAACCCTTACAACGACTATACCAAATACAACGAGAAGTT

TAAGGGAAAGGCTACTTTAACCTCCGACAAAAGCTCCATCACAGCCTAC

ATGGAGTTCAGCTCTTTAACATCCGAGGACAGCGCTCTGTACTATTGCG

CCCGGTGGGGCGACGGCAATTACTGGGGACGGGGCACAACACTGACCGT

GAGCAGCGGAGGCGGAGGCTCCGGCGGAGGCGGATCTGGCGGTGGCGGC

TCCGACATCGAGATGACCCAGTCCCCCGCTATCATGTCCGCCTCTTTAG

GCGAGCGGGTCACAATGACTTGTACAGCCTCCTCCAGCGTCTCCTCCTC

CTACTTCCATTGGTACCAACAGAAACCCGGAAGCTCCCCTAAACTGTGC

ATCTACAGCACCAGCAATCTCGCCAGCGGCGTGCCCCCTAGGTTTTCCG

GAAGCGGAAGCACCAGCTACTCTTTAACCATCTCCTCCATGGAGGCTGA

GGATGCCGCCACCTACTTTTGTCACCAGTACCACCGGTCCCCCACCTTC

GGAGGCGGCACCAAACTGGAGACAAAGAGG.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 102)
MKWVTFISLLFLFSSAYSQIVLTQSPAIMSASPGEKVTMTCSASSSVSY

MNWYQQKSGTSPKRWIYDTSKLASGVPAHFRGSGSGTSYSLTISGMEAE

DAATYYCQQWSSNPFTFGSGTKLEINRGGGGSGGGGSGGGGSQVQLQQS

GAELARPGASVKMSCKASGYTFTRYTMHWVKQRPGQGLEWIGYINPSRG

YTNYNQKFKDKATLTTDKSSSTAYMQLSSLTSEDSAVYYCARYYDDHYC

LDYWGQGTTLTVSSSGTTNTVAAYNLTWKSTNFKTILEWEPKPVNQVYT

VQISTKSGDWKSKCFYTTDTECDLTDEIVKDVKQTYLARVFSYPAGNVE

STGSAGEPLYENSPEFTPYLETNLGQPTIQSFEQVGTKVNVTVEDERTL

VRRNNTFLSLRDVFGKDLIYTLYYWKSSSSGKKTAKTNTNEFLIDVDKG

ENYCFSVQAVIPSRTVNRKSTDSPVECMGQEKGEFREVQLQQSGPELVK

PGASVKMSCKASGYTFTSYVIQWVKQKPGQGLEWIGSINPYNDYTKYNE

-continued

KFKGKATLTSDKSSITAYMEFSSLTSEDSALYYCARWGDGNYWGRGTTL

TVSSGGGGSGGGGSGGGGSDIEMTQSPAIMSASLGERVTMTCTASSSVS

SSYFHWYQQKPGSSPKLCIYSTSNLASGVPPRFSGSGSTSYSLTISSME

AEDAATYFCHQYHRSPTFGGGTKLETKR.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 103)
ATGAAGTGGGTGACCTTCATCAGCTTATTATTTTTATTCAGCTCCGCCT

ATTCCCAGATCGTGCTGACCCAAAGCCCCGCCATCATGAGCGCTAGCCC

CGGTGAGAAGGTGACCATGACATGCTCCGCTTCCAGCTCCGTGTCCTAC

ATGAACTGGTATCAGCAGAAAGCGGAACCAGCCCCAAAAGGTGGATCT

ACGACACCAGCAAGCTGGCCTCCGGAGTGCCCGCTCATTTCCGGGCTC

TGGATCCGGCACCAGCTACTCTTTAACCATTTCCGGCATGGAAGCTGAA

GACGCTGCCACCTACTATTGCCAGCAATGGAGCAGCAACCCCTTCACAT

TCGGATCTGGCACCAAGCTCGAAATCAATCGTGGAGGAGGTGGCAGCGG

CGGCGGTGGATCCGGCGGAGGAGGAAGCCAAGTTCAACTCCAGCAGAGC

GGCGCTGAACTGGCCCGGCCCGGCGCCTCCGTCAAGATGAGCTGCAAGG

CTTCCGGCTATACATTTACTCGTTACACAATGCATTGGGTCAAGCAGAG

GCCCGGTCAAGGTTTAGAGTGGATCGGATATATCAACCCTTCCGGGGC

TACACCAACTATAACCAAAAGTTCAAGGATAAAGCCACTTTAACCACTG

ACAAGAGCTCCTCCACCGCCTACATGCAGCTGTCCTCTTTAACCAGCGA

GGACTCCGCTGTTTACTACTGCGCTAGGTATTACGACGACCACTACTGT

TTAGACTATTGGGGACAAGGTACCACTTTAACCGTCAGCAGCTCCGGCA

CCACCAATACCGTGGCCGCTTATAACCTCACATGGAAGAGCACCAACTT

CAAGACAATTCTGGAATGGGAACCCAAGCCCGTCAATCAAGTTTACACC

GTGCAGATCTCCACCAAATCCGGAGACTGGAAGAGCAAGTGCTTCTACA

CAACAGACACCGAGTGTGATTTAACCGACGAAATCGTCAAGGACGTCAA

GCAAACCTATCTGGCTCGGGTCTTTTCCTACCCCGCTGGCAATGTCGAG

TCCACCGGCTCCGCTGGCGAGCCTCTCTACGAGAATTCCCCCGAATTCA

CCCCTTATTTAGAGACCAATTTAGGCCAGCCTACCATCCAGAGCTTCGA

GCAAGTTGGCACCAAGGTGAACGTCACCGTCGAGGATGAAAGGACTTTA

GTGCGGCGGAATAACACATTTTTATCCCTCCGGGATGTGTTCGGCAAAG

ACCTCATCTACACACTGTACTATTGGAAGTCCAGCTCCTCCGGCAAAAA

GACCGCTAAGACCAACACCAACGAGTTTTTAATTGACGTGGACAAAGGC

GAGAACTACTGCTTCAGCGTGCAAGCCGTGATCCCTTCTCGTACCGTCA

ACCGGAAGAGCACAGATTCCCCCGTTGAGTGCATGGGCCAAGAAAAGGG

CGAGTTCCGGGAGGTCCAGCTGCAGCAGAGCGGACCCGAACTCGTGAAA

CCCGGTGCTTCCGTGAAAATGTCTTGTAAGGCCAGCGGATACACCTTCA

CCTCCTATGTGATCCAGTGGGTCAAACAGAAGCCCGGACAAGGTCTCGA

GTGGATCGGCAGCATCAACCCTTACAACGACTATACCAAATACAACGAG

AAGTTTAAGGGAAAGGCTACTTTAACCTCCGACAAAAGCTCCATCACAG

CCTACATGGAGTTCAGCTCTTTAACATCCGAGGACAGCGCTCTGTACTA

TTGCGCCCGGTGGGGCGACGGCAATTACTGGGGACGGGGCACAACACTG

ACCGTGAGCAGCGGAGGCGGAGGCTCCGGCGGAGGCGGATCTGGCGGTG

GCGGCTCCGACATCGAGATGACCCAGTCCCCCGCTATCATGTCCGCCTC

TTTAGGCGAGCGGGTCACAATGACTTGTACAGCCTCCTCCAGCGTCTCC

TCCTCCTACTTCCATTGGTACCAACAGAAACCCGGAAGCTCCCCTAAAC

TGTGCATCTACAGCACCAGCAATCTCGCCAGCGGCGTGCCCCCTAGGTT

TTCCGGAAGCGGAAGCACCAGCTACTCTTTAACCATCTCCTCCATGGAG

GCTGAGGATGCCGCCACCTACTTTTGTCACCAGTACCACCGGTCCCCCA

CCTTCGGAGGCGGCACCAAACTGGAGACAAAGAGG.

Exemplary Embodiments of Single-Chain Chimeric Polypeptides—Type B

In some embodiments of any of the single-chain chimeric polypeptides described herein, the first target-binding domain and/or the second target-binding domain can independently bind specifically to an IL-2 receptor (e.g., human IL-2 receptor).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, the first target-binding domain and the second target-binding domain is a soluble human IL-2 protein. A non-limiting example of an IL-2 protein that binds specifically to an IL-2 receptor can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 28)
APTSSSTKKTQLQLEHLLLDLQMILNGINNYKNPKLTRMLTFKFYMPKK

ATELKHLQCLEEELKPLEEVLNLAQSKNFHLRPRDLISNINVIVLELKG

SETTFMCEYADETATIVEFLNRWITFCQSIISTLT.

In some embodiments, an IL-2 protein that binds specifically to an IL-2 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 104)
GCACCTACTTCAAGTTCTACAAAGAAAACACAGCTACAACTGGAGCATT

TACTGCTGGATTTACAGATGATTTTGAATGGAATTAATAATTACAAGAA

TCCCAAACTCACCAGGATGCTCACATTTAAGTTTTACATGCCCAAGAAG

GCCACAGAACTGAAACATCTTCAGTGTCTAGAAGAAGAACTCAAACCTC

TGGAGGAAGTGCTAAATTTAGCTCAAAGCAAAAACTTTCACTTAAGACC

CAGGGACTTAATCAGCAATATCAACGTAATAGTTCTGGAACTAAAGGGA

TCTGAAACAACATTCATGTGTGAATATGCTGATGAGACAGCAACCATTG

TAGAATTTCTGAACAGATGGATTACCTTTTGTCAAAGCATCATCTCAAC

ACTAACT.

In some embodiments, an IL-2 protein that binds specifically to an IL-2 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 105)
GCCCCCACCTCCTCCTCCACCAAGAAGACCCAGCTGCAGCTGGAGCATT

TACTGCTGGATTTACAGATGATTTTAAACGGCATCAACAACTACAAGAA

CCCCAAGCTGACTCGTATGCTGACCTTCAAGTTCTACATGCCCAAGAAG

GCCACCGAGCTGAAGCATTTACAGTGTTTAGAGGAGGAGCTGAAGCCCC

TCGAGGAGGTGCTGAATTTAGCCCAGTCCAAGAATTTCCATTTAAGGCC

CCGGGATTTAATCAGCAACATCAACGTGATCGTTTTAGAGCTGAAGGGC

TCCGAGACCACCTTCATGTGCGAGTACGCCGACGAGACCGCCACCATCG

TGGAGTTTTTAAATCGTTGGATCACCTTCTGCCAGTCCATCATCTCCAC

TTTAACC.

In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 106)
APTSSSTKKTQLQLEHLLLDLQMILNGINNYKNPKLTRMLTFKFYMPKK

ATELKHLQCLEEELKPLEEVLNLAQSKNFHLRPRDLISNINVIVLELKG

SETTFMCEYADETATIVEFLNRWITFCQSIISTLTSGTTNTVAAYNLTW

KSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPT

IQSFEQVGTKVNVTVEDERTLVRRNNTFLSLRDVFGKDLIYTLYYWKSS

SSGKKTAKTNTNEFLIDVDKGENYCFSVQAVIPSRTVNRKSTDSPVECM

GQEKGEFREAPTSSSTKKTQLQLEHLLLDLQMILNGINNYKNPKLTRML

TFKFYMPKKATELKHLQCLEEELKPLEEVLNLAQSKNFHLRPRDLISNI

NVIVLELKGSETTFMCEYADETATIVEFLNRWITFCQSIISTLT.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 107)
GCCCCCACCTCCTCCTCCACCAAGAAGACCCAGCTGCAGCTGGAGCATT

TACTGCTGGATTTACAGATGATTTTAAACGGCATCAACAACTACAAGAA

CCCCAAGCTGACTCGTATGCTGACCTTCAAGTTCTACATGCCCAAGAAG

GCCACCGAGCTGAAGCATTTACAGTGTTTAGAGGAGGAGCTGAAGCCCC

TCGAGGAGGTGCTGAATTTAGCCCAGTCCAAGAATTTCCATTTAAGGCC

CCGGGATTTAATCAGCAACATCAACGTGATCGTTTTAGAGCTGAAGGGC

TCCGAGACCACCTTCATGTGCGAGTACGCCGACGAGACCGCCACCATCG

TGGAGTTTTTAAATCGTTGGATCACCTTCTGCCAGTCCATCATCTCCAC

TTTAACCAGCGGCACAACCAACACAGTCGCTGCCTATAACCTCACTTGG

AAGAGCACCAACTTCAAAACCATCCTCGAATGGGAACCCAAACCCGTTA

ACCAAGTTTACACCGTGCAGATCAGCACCAAGTCCGGCGACTGGAAGTC

CAAATGTTTCTATACCACCGACACCGAGTGCGATCTCACCGATGAGATC

GTGAAAGATGTGAAACAGACCTACCTCGCCCGGGTGTTTAGCTACCCCG

CCGGCAATGTGGAGAGCACTGGTTCCGCTGGCGAGCCTTTATACGAGAA

CAGCCCCGAATTTACCCCTTACCTCGAGACCAATTTAGGACAGCCCACC

ATCCAAAGCTTTGAGCAAGTTGGCACAAAGGTGAATGTGACAGTGGAGG

ACGAGCGGACTTTAGTGCGGCGGAACAACACCTTTCTCAGCCTCCGGGA

TGTGTTCGGCAAAGATTTAATCTACACACTGTATTACTGGAAGTCCTCT

TCCTCCGGCAAGAAGACAGCTAAAACCAACACAAACGAGTTTTTAATCG

ACGTGGATAAAGGCGAAAACTACTGTTTCAGCGTGCAAGCTGTGATCCC

CTCCCGGACCGTGAATAGGAAAAGCACCGATAGCCCCGTTGAGTGCATG

GGCCAAGAAAAGGGCGAGTTCCGGGAGGCACCTACTTCAAGTTCTACAA

AGAAAACACAGCTACAACTGGAGCATTTACTGCTGGATTTACAGATGAT

TTTGAATGGAATTAATAATTACAAGAATCCCAAACTCACCAGGATGCTC

ACATTTAAGTTTTACATGCCCAAGAAGGCCACAGAACTGAAACATCTTC

AGTGTCTAGAAGAAGAACTCAAACCTCTGGAGGAAGTGCTAAATTTAGC

TCAAAGCAAAAACTTTCACTTAAGACCCAGGGACTTAATCAGCAATATC

-continued
AACGTAATAGTTCTGGAACTAAAGGGATCTGAAACAACATTCATGTGTG

AATATGCTGATGAGACAGCAACCATTGTAGAATTTCTGAACAGATGGAT

TACCTTTTGTCAAAGCATCATCTCAACACTAACT.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 108)
MKWVTFISLLFLFSSAYSAPTSSSTKKTQLQLEHLLLDLQMILNGINNY

KNPKLTRMLTFKFYMPKKATELKHLQCLEEELKPLEEVLNLAQSKNFHL

RPRDLISNINVIVLELKGSETTFMCEYADETATIVEFLNRWITFCQSII

STLTSGTTNTVAAYNLTWKSTNFKTILEWEPKPVNQVYTVQISTKSGDW

KSKCFYTTDTECDLTDEIVKDVKQTYLARVFSYPAGNVESTGSAGEPLY

ENSPEFTPYLETNLGQPTIQSFEQVGTKVNVTVEDERTLVRRNNTFLSL

RDVFGKDLIYTLYYWKSSSSGKKTAKTNTNEFLIDVDKGENYCFSVQAV

IPSRTVNRKSTDSPVECMGQEKGEFREAPTSSSTKKTQLQLEHLLLDLQ

MILNGINNYKNPKLTRMLTFKFYMPKKATELKHLQCLEEELKPLEEVLN

LAQSKNFHLRPRDLISNINVIVLELKGSETTFMCEYADETATIVEFLNR

WITFCQSIISTLT.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 109)
ATGAAGTGGGTGACCTTCATCAGCCTGCTGTTCCTGTTCTCCAGCGCCT

ACTCCGCCCCCACCTCCTCCTCCACCAAGAAGACCCAGCTGCAGCTGGA

GCATTTACTGCTGGATTTACAGATGATTTTAAACGGCATCAACAACTAC

AAGAACCCCAAGCTGACTCGTATGCTGACCTTCAAGTTCTACATGCCCA

AGAAGGCCACCGAGCTGAAGCATTTACAGTGTTTAGAGGAGGAGCTGAA

GCCCCTCGAGGAGGTGCTGAATTTAGCCCAGTCCAAGAATTTCCATTTA

AGGCCCCGGGATTTAATCAGCAACATCAACGTGATCGTTTTAGAGCTGA

AGGGCTCCGAGACCACCTTCATGTGCGAGTACGCCGACGAGACCGCCAC

CATCGTGGAGTTTTTAAATCGTTGGATCACCTTCTGCCAGTCCATCATC

TCCACTTTAACCAGCGGCACAACCAACACAGTCGCTGCCTATAACCTCA

CTTGGAAGAGCACCAACTTCAAAACCATCCTCGAATGGGAACCCAAACC

CGTTAACCAAGTTTACACCGTGCAGATCAGCACCAAGTCCGGCGACTGG

AAGTCCAAATGTTTCTATACCACCGACACCGAGTGCGATCTCACCGATG

AGATCGTGAAGATGTGAAACAGACCTACCTCGCCCGGGTGTTTAGCTA

CCCCGCCGGCAATGTGGAGAGCACTGGTTCCGCTGGCGAGCCTTTATAC

-continued
GAGAACAGCCCCGAATTTACCCCTTACCTCGAGACCAATTTAGGACAGC

CCACCATCCAAAGCTTTGAGCAAGTTGGCACAAAGGTGAATGTGACAGT

GGAGGACGAGCGGACTTTAGTGCGGCGGAACAACACCTTTCTCAGCCTC

CGGGATGTGTTCGGCAAAGATTTAATCTACACACTGTATTACTGGAAGT

CCTCTTCCTCCGGCAAGAAGACAGCTAAAACCAACACAAACGAGTTTTT

AATCGACGTGGATAAAGGCGAAAACTACTGTTTCAGCGTGCAAGCTGTG

ATCCCCTCCCGGACCGTGAATAGGAAAAGCACCGATAGCCCCGTTGAGT

GCATGGGCCAAGAAAAGGGCGAGTTCCGGGAGGCACCTACTTCAAGTTC

TACAAAGAAAACACAGCTACAACTGGAGCATTTACTGCTGGATTTACAG

ATGATTTTGAATGGAATTAATAATTACAAGAATCCCAAACTCACCAGGA

TGCTCACATTTAAGTTTTACATGCCCAAGAAGGCCACAGAACTGAAACA

TCTTCAGTGTCTAGAAGAAGAACTCAAACCTCTGGAGGAAGTGCTAAAT

TTAGCTCAAAGCAAAAACTTTCACTTAAGACCCAGGGACTTAATCAGCA

ATATCAACGTAATAGTTCTGGAACTAAAGGGATCTGAAACAACATTCAT

GTGTGAATATGCTGATGAGACAGCAACCATTGTAGAATTTCTGAACAGA

TGGATTACCTTTTGTCAAAGCATCATCTCAACACTAACT.

Exemplary Embodiments of Single-Chain Chimeric Polypeptides—Type C

In some embodiments of any of the single-chain chimeric polypeptides described herein, the first target-binding domain and/or the second target-binding domain can independently bind specifically to an IL-15 receptor (e.g., a human IL-15 receptor).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, the first target-binding domain and the second target-binding domain is a soluble human IL-15 protein. A non-limiting example of an IL-15 protein that binds specifically to an IL-15 receptor can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 109)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS.

In some embodiments, an IL-15 protein that binds specifically to an IL-15 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 111)
AACTGGGTGAACGTGATCAGCGATTTAAAGAAGATCGAGGATTTAATCC

AGAGCATGCACATCGACGCCACTCTGTACACTGAGAGCGACGTGCACCC

TAGCTGCAAGGTGACTGCCATGAAGTGCTTTTTACTGGAGCTGCAAGTT

ATCTCTTTAGAGAGCGGCGATGCCAGCATCCACGACACTGTGGAGAATT

TAATCATTTTAGCCAACAACTCTTTAAGCAGCAACGGCAACGTGACAGA

GAGCGGCTGCAAGGAGTGCGAGGAGCTGGAGGAGAAGAACATCAAGGAG

TTTTTACAGAGCTTCGTGCACATCGTGCAGATGTTCATCAACACTAGC.

In some embodiments, an IL-15 protein that binds specifically to an IL-15 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 110)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC.

In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 112)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTSSGTTNTVAAYNLTWKSTNFKTILEWEPKPVNQV

YTVQISTKSGDWKSKCFYTTDTECDLTDEIVKDVKQTYLARVFSYPAGN

VESTGSAGEPLYENSPEFTPYLETNLGQPTIQSFEQVGTKVNVTVEDER

TLVRRNNTFLSLRDVFGKDLIYTLYYWKSSSSGKKTAKTNTNEFLIDVD

KGENYCFSVQAVIPSRTVNRKSTDSPVECMGQEKGEFRENWVNVISDLK

KIEDLIQSMHIDATLYTESDVHPSCKVTAMKCFLLELQVISLESGDASI

HDTVENLIILANNSLSSNGNVTESGCKECEELEEKNIKEFLQSFVHIVQ

MFINTS.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 113)
AACTGGGTGAACGTGATCAGCGATTTAAAGAAGATCGAGGATTTAATCC

AGAGCATGCACATCGACGCCACTCTGTACACTGAGAGCGACGTGCACCC

TAGCTGCAAGGTGACTGCCATGAAGTGCTTTTTACTGGAGCTGCAAGTT

ATCTCTTTAGAGAGCGGCGATGCCAGCATCCACGACACTGTGGAGAATT

TAATCATTTTAGCCAACAACTCTTTAAGCAGCAACGGCAACGTGACAGA

GAGCGGCTGCAAGGAGTGCGAGGAGCTGGAGGAGAAGAACATCAAGGAG

TTTTTACAGAGCTTCGTGCACATCGTGCAGATGTTCATCAACACTAGCA

GCGGCACAACCAACACAGTCGCTGCCTATAACCTCACTTGGAAGAGCAC

CAACTTCAAAACCATCCTCGAATGGGAACCCAAACCCGTTAACCAAGTT

TACACCGTGCAGATCAGCACCAAGTCCGGCGACTGGAAGTCCAAATGTT

TCTATACCACCGACACCGAGTGCGATCTCACCGATGAGATCGTGAAAGA

TGTGAAACAGACCTACCTCGCCCGGGTGTTTAGCTACCCCGCCGGCAAT

GTGGAGAGCACTGGTTCCGCTGGCGAGCCTTTATACGAGAACAGCCCCG

AATTTACCCCTTACCTCGAGACCAATTTAGGACAGCCCACCATCCAAAG

CTTTGAGCAAGTTGGCACAAAGGTGAATGTGACAGTGGAGGACGAGCGG

ACTTTAGTGCGGCGGAACAACACCTTTCTCAGCCTCCGGGATGTGTTCG

GCAAAGATTTAATCTACACACTGTATTACTGGAAGTCCTCTTCCTCCGG

CAAGAAGACAGCTAAAACCAACACAAACGAGTTTTTAATCGACGTGGAT

AAAGGCGAAAACTACTGTTTCAGCGTGCAAGCTGTGATCCCCTCCCGGA

CCGTGAATAGGAAAAGCACCGATAGCCCCGTTGAGTGCATGGGCCAAGA

AAAGGGCGAGTTCCGGGAGAACTGGGTGAACGTCATCAGCGATTTAAAG

AAGATCGAAGATTTAATTCAGTCCATGCATATCGACGCCACTTTATACA

CAGAATCCGACGTGCACCCCTCTTGTAAGGTGACCGCCATGAAATGTTT

TTTACTGGAGCTGCAAGTTATCTCTTTAGAGAGCGGAGACGCTAGCATC

CACGACACCGTGGAGAATTTAATCATTTTAGCCAATAACTCTTTATCCA

-continued

GCAACGGCAACGTGACAGAGTCCGGCTGCAAGGAGTGCGAAGAGCTGGA

GGAGAAGAACATCAAGGAGTTTCTGCAATCCTTTGTGCACATTGTCCAG

ATGTTCATCAATACCTCC.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 114)
MKWVTFISLLFLFSSAYSNWVNVISDLKKIEDLIQSMHIDATLYTESDV

HPSCKVTAMKCFLLELQVISLESGDASIHDTVENLIILANNSLSSNGNV

TESGCKECEELEEKNIKEFLQSFVHIVQMFINTSSGTTNTVAAYNLTWK

STNFKTILEWEPKPVNQVYTVQISTKSGDWKSKCFYTTDTECDLTDEIV

KDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSS

SGKKTAKTNTNEFLIDVDKGENYCFSVQAVIPSRTVNRKSTDSPVECMG

QEKGEFRENWVNVISDLKKIEDLIQSMHIDATLYTESDVHPSCKVTAMK

CFLLELQVISLESGDASIHDTVENLIILANNSLSSNGNVTESGCKECEE

LEEKNIKEFLQSFVHIVQMFINTS.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 115)
ATGAAGTGGGTGACCTTCATCAGCCTGCTGTTCCTGTTCTCCAGCGCCT

ACTCCAACTGGGTGAACGTGATCAGCGATTTAAAGAAGATCGAGGATTT

AATCCAGAGCATGCACATCGACGCCACTCTGTACACTGAGAGCGACGTG

CACCCTAGCTGCAAGGTGACTGCCATGAAGTGCTTTTTACTGGAGCTGC

AAGTTATCTCTTTAGAGAGCGGCGATGCCAGCATCCACGACACTGTGGA

GAATTTAATCATTTTAGCCAACAACTCTTTAAGCAGCAACGGCAACGTG

ACAGAGAGCGGCTGCAAGGAGTGCGAGGAGCTGGAGGAGAAGAACATCA

AGGAGTTTTTACAGAGCTTCGTGCACATCGTGCAGATGTTCATCAACAC

TAGCAGCGGCACAACCAACACAGTCGCTGCCTATAACCTCACTTGGAAG

AGCACCAACTTCAAAACCATCCTCGAATGGGAACCCAAACCCGTTAACC

AAGTTTACACCGTGCAGATCAGCACCAAGTCCGGCGACTGGAAGTCCAA

ATGTTTCTATACCACCGACACCGAGTGCGATCTCACCGATGAGATCGTG

AAAGATGTGAAACAGACCTACCTCGCCCGGGTGTTTAGCTACCCCGCCG

GCAATGTGGAGAGCACTGGTTCCGCTGGCGAGCCTTTATACGAGAACAG

CCCCGAATTTACCCCTTACCTCGAGACCAATTTAGGACAGCCCACCATC

CAAAGCTTTGAGCAAGTTGGCACAAAGGTGAATGTGACAGTGGAGGACG

AGCGGACTTTAGTGCGGCGGAACAACACCTTTCTCAGCCTCCGGGATGT

GTTCGGCAAAGATTTAATCTACACACTGTATTACTGGAAGTCCTCTTCC

TCCGGCAAGAAGACAGCTAAAACCAACACAAACGAGTTTTTAATCGACG

TGGATAAAGGCGAAAACTACTGTTTCAGCGTGCAAGCTGTGATCCCCTC

CCGGACCGTGAATAGGAAAAGCACCGATAGCCCCGTTGAGTGCATGGGC

CAAGAAAAGGGCGAGTTCCGGGAGAACTGGGTGAACGTCATCAGCGATT

TAAAGAAGATCGAAGATTTAATTCAGTCCATGCATATCGACGCCACTTT

ATACACAGAATCCGACGTGCACCCCTCTTGTAAGGTGACCGCCATGAAA

TGTTTTTTACTGGAGCTGCAAGTTATCTCTTTAGAGAGCGGAGACGCTA

GCATCCACGACACCGTGGAGAATTTAATCATTTTAGCCAATAACTCTTT

ATCCAGCAACGGCAACGTGACAGAGTCCGGCTGCAAGGAGTGCGAAGAG

CTGGAGGAGAAGAACATCAAGGAGTTTCTGCAATCCTTTGTGCACATTG

TCCAGATGTTCATCAATACCTCC.

Exemplary Multi-Chain Chimeric Polypeptides—Type A

In some embodiments of any of the multi-chain chimeric polypeptides described herein, the first target-binding domain and the second targeting-binding domain each independently bind specifically to a receptor of IL-18 or a receptor of IL-12. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is an agonistic antigen-binding domain. In some embodiments of these multi-chain chimeric polypeptides, the first target-binding domain and the second target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12.

In some embodiments of these multi-chain chimeric polypeptides, the first target-binding domain includes a soluble IL-18 (e.g., a soluble human IL-18).

In some embodiments of these multi-chain chimeric polypeptides, the soluble human IL-18 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 41)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNED.

In some embodiments of these multi-chain chimeric polypeptides, the soluble human IL-18 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 42)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT.

In some embodiments of these multi-chain chimeric polypeptides, the second target-binding domain includes a soluble IL-12 (e.g., a soluble human IL-12). In some embodiments of these multi-chain chimeric polypeptides, the soluble human IL-12 includes a sequence of soluble human IL-12β (p40) and a sequence of soluble human IL-12α (p35). In some embodiments of these multi-chain chimeric polypeptides, the soluble human IL-12 further includes a linker sequence (e.g., any of the exemplary linker sequences described herein) between the sequence of soluble IL-12β (p40) and the sequence of soluble human IL-12α (p35). In some examples of these multi-chain chimeric polypeptides, the linker sequence comprises GGGGSGGGGSGGGGS (SEQ ID NO: 7).

In some embodiments of these multi-chain chimeric polypeptides, the sequence of soluble human IL-12β (p40) comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 33)
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS.

In some embodiments of these multi-chain chimeric polypeptides, the soluble human IL-12β (p40) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 34)
ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

AAGGAGCCCAAGAATAAGACCTTTTTAAGGTGTGAGGCCAAAAACTACA

GCGGTCGTTTCACTTGTTGGTGGCTGACCACCATTTCCACCGATTTAAC

CTTCTCCGTGAAAAGCAGCCGGGGAAGCTCCGACCCTCAAGGTGTGACA

TGTGGAGCCGCTACCCTCAGCGCTGAGAGGGTTCGTGGCGATAACAAGG

AATACGAGTACAGCGTGGAGTGCCAAGAAGATAGCGCTTGTCCCGCTGC

CGAAGAATCTTTACCCATTGAGGTGATGGTGGACGCCGTGCACAAACTC

In some embodiments of these multi-chain chimeric polypeptides, the soluble human IL-12α (p35) includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 35)
RNLPVATPDPGMFPCLEMSQNLLRAVSNMLQKARQTLEFYPCTSEEIDH

EDITKDKTSTVEACLPLELTKNESCLNSRETSFITNGSCLASRKTSFMM

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

S.

In some embodiments of these multi-chain chimeric polypeptides, the soluble human IL-12α (p35) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 36)
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 116)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNEDSGTTNTVAAYNLTWKSTNFKTILEWEPKPVNQVYTVQIS

TKSGDWKSKCFYTTDTECDLTDEIVKDVKQTYLARVFSYPAGNVESTGS

AGEPLYENSPEFTPYLETNLGQPTIQSFEQVGTKVNVTVEDERTLVRRN

NTFLSLRDVFGKDLIYTLYYWKSSSSGKKTAKTNTNEFLIDVDKGENYC

FSVQAVIPSRTVNRKSTDSPVECMGQEKGEFRENWVNVISDLKKIEDLI

QSMHIDATLYTESDVHPSCKVTAMKCFLLELQVISLESGDASIHDTVEN

LIILANNSLSSNGNVTESGCKECEELEEKNIKEFLQSFVHIVQMFINT

S.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 117)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACAGAGCTGGGCGATCGT

TCCATCATGTTCACCGTCCAAAACGAGGATAGCGGCACAACCAACACAG

TCGCTGCCTATAACCTCACTTGGAAGAGCACCAACTTCAAAACCATCCT

CGAATGGGAACCCAAACCCGTTAACCAAGTTTACACCGTGCAGATCAGC

ACCAAGTCCGGCGACTGGAAGTCCAAATGTTTCTATACCACCGACACCG

AGTGCGATCTCACCGATGAGATCGTGAAAGATGTGAAACAGACCTACCT

CGCCCGGGTGTTTAGCTACCCCGCCGGCAATGTGGAGAGCACTGGTTCC

GCTGGCGAGCCTTTATACGAGAACAGCCCCGAATTTACCCCTTACCTCG

AGACCAATTTAGGACAGCCCACCATCCAAAGCTTTGAGCAAGTTGGCAC

AAAGGTGAATGTGACAGTGGAGGACGAGCGGACTTTAGTGCGGCGGAAC

AACACCTTTCTCAGCCTCCGGGATGTGTTCGGCAAAGATTTAATCTACA

CACTGTATTACTGGAAGTCCTCTTCCTCCGGCAAGAAGACAGCTAAAAC

CAACACAAACGAGTTTTTAATCGACGTGGATAAAGGCGAAAACTACTGT

TTCAGCGTGCAAGCTGTGATCCCCTCCCGGACCGTGAATAGGAAAAGCA

CCGATAGCCCCGTTGAGTGCATGGGCCAAGAAAAGGGCGAGTTCCGGGA

GAACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTTACTGGAGCTGCAAGT

TATCTCTTTAGAGAGCGGAGACGCTAGCATCCACGACACCGTGGAGAAT

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTC

C.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 118)
MKWVTFISLLFLFSSAYSYFGKLESKLSVIRNLNDQVLFIDQGNRPLFE

DMTDSDCRDNAPRTIFIISMYKDSQPRGMAVTISVKCEKISTLSCENKI

ISFKEMNPPDNIKDTKSDIIFFQRSVPGHDNKMQFESSSYEGYFLACEK

ERDLFKLILKKEDELGDRSIMFTVQNEDSGTTNTVAAYNLTWKSTNFKT

ILEWEPKPVNQVYTVQISTKSGDWKSKCFYTTDTECDLTDEIVKDVKQT

YLARVFSYPAGNVESTGSAGEPLYENSPEFTPYLETNLGQPTIQSFEQV

GTKVNVTVEDERTLVRRNNTFLSLRDVFGKDLIYTLYYWKSSSSGKKTA

KTNTNEFLIDVDKGENYCFSVQAVIPSRTVNRKSTDSPVECMGQEKGEF

RENWVNVISDLKKIEDLIQSMHIDATLYTESDVHPSCKVTAMKCFLLEL

QVISLESGDASIHDTVENLIILANNSLSSNGNVTESGCKECEELEEKNI

KEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 119)
ATGAAGTGGGTCACATTTATCTCTTTACTGTTCCTCTTCTCCAGCGCCT

ACAGCTACTTCGGCAAACTGGAATCCAAGCTGAGCGTGATCCGGAATTT

AAACGACCAAGTTCTGTTTATCGATCAAGGTAACCGGCCTCTGTTCGAG

GACATGACCGACTCCGATTGCCGGGACAATGCCCCCCGGACCATCTTCA

TTATCTCCATGTACAAGGACAGCCAGCCCCGGGGCATGGCTGTGACAAT

TAGCGTGAAGTGTGAGAAAATCAGCACTTTATCTTGTGAGAACAAGATC

ATCTCCTTTAAGGAAATGAACCCCCCCGATAACATCAAGGACACCAAGT

CCGATATCATCTTCTTCCAGCGGTCCGTGCCCGGTCACGATAACAAGAT

GCAGTTCGAATCCTCCTCCTACGAGGGCTACTTTTTAGCTTGTGAAAAG

GAGAGGGATTTATTCAAGCTGATCCTCAAGAAGGAGGACGAGCTGGGCG

ATCGTTCCATCATGTTCACCGTCCAAAACGAGGATAGCGGCACAACCAA

CACAGTCGCTGCCTATAACCTCACTTGGAAGAGCACCAACTTCAAAACC

ATCCTCGAATGGGAACCCAAACCCGTTAACCAAGTTTACACCGTGCAGA

TCAGCACCAAGTCCGGCGACTGGAAGTCCAAATGTTTCTATACCACCGA

CACCGAGTGCGATCTCACCGATGAGATCGTGAAAGATGTGAAACAGACC

TACCTCGCCCGGGTGTTTAGCTACCCCGCCGGCAATGTGGAGAGCACTG

GTTCCGCTGGCGAGCCTTTATACGAGAACAGCCCCGAATTTACCCCTTA

CCTCGAGACCAATTTAGGACAGCCCACCATCCAAAGCTTTGAGCAAGTT

GGCACAAAGGTGAATGTGACAGTGGAGGACGAGCGGACTTTAGTGCGGC

GGAACAACACCTTTCTCAGCCTCCGGGATGTGTTCGGCAAAGATTTAAT

CTACACACTGTATTACTGGAAGTCCTCTTCCTCCGGCAAGAAGACAGCT

AAAACCAACACAAACGAGTTTTTAATCGACGTGGATAAAGGCGAAAACT

ACTGTTTCAGCGTGCAAGCTGTGATCCCCTCCCGGACCGTGAATAGGAA

AAGCACCGATAGCCCCGTTGAGTGCATGGGCCAAGAAAAGGGCGAGTTC

CGGGAGAACTGGGTGAACGTCATCAGCGATTTAAAGAAGATCGAAGATT

TAATTCAGTCCATGCATATCGACGCCACTTTATACACAGAATCCGACGT

GCACCCCTCTTGTAAGGTGACCGCCATGAAATGTTTTTTACTGGAGCTG

CAAGTTATCTCTTTAGAGAGCGGAGACGCTAGCATCCACGACACCGTGG

AGAATTTAATCATTTTAGCCAATAACTCTTTATCCAGCAACGGCAACGT

GACAGAGTCCGGCTGCAAGGAGTGCGAAGAGCTGGAGGAGAAGAACATC

AAGGAGTTTCTGCAATCCTTTGTGCACATTGTCCAGATGTTCATCAATA

CCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 120)
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCSGGGGSGGGGSGGGGSRNLPVATPDPGMFPCLHHSQNL

LRAVSNMLQKARQTLEFYPCTSEEIDHEDITKDKTSTVEACLPLELTKN

ESCLNSRETSFITNGSCLASRKTSFMMALCLSSIYEDLKMYQVEFKTMN

AKLLMDPKRQIFLDQNMLAVIDELMQALNFNSETVPQKSSLEEPDFYKT

KIKLCILLHAFRIRAVTIDRVMSYLNASITCPPPMSVEHADIWVKSYSL

YSRERYICNSGFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 121)
ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

AAGGAGCCCAAGAATAAGACCTTTTTAAGGTGTGAGGCCAAAAACTACA

GCGGTCGTTTCACTTGTTGGTGGCTGACCACCATTTCCACCGATTTAAC

CTTCTCCGTGAAAAGCAGCCGGGGAAGCTCCGACCCTCAAGGTGTGACA

TGTGGAGCCGCTACCCTCAGCGCTGAGAGGGTTCGTGGCGATAACAAGG

AATACGAGTACAGCGTGGAGTGCCAAGAAGATAGCGCTTGTCCCGCTGC

CGAAGAATCTTTACCCATTGAGGTGATGGTGGACGCCGTGCACAAACTC

AAGTACGAGAACTACACCTCCTCCTTCTTTATCCGGGACATCATTAAGC

CCGATCCTCCTAAGAATTTACAGCTGAAGCCTCTCAAAAATAGCCGGCA

AGTTGAGGTCTCTTGGGAATATCCCGACACTTGGAGCACACCCCACAGC

TACTTCTCTTTAACCTTTTGTGTGCAAGTTCAAGGTAAAAGCAAGCGGG

AGAAGAAAGACCGGGTGTTTACCGACAAAACCAGCGCCACCGTCATCTG

TCGGAAGAACGCCTCCATCAGCGTGAGGGCTCAAGATCGTTATTACTCC

AGCAGCTGGTCCGAGTGGGCCAGCGTGCCTTGTTCCGGCGGTGGAGGAT

CCGGAGGAGGTGGCTCCGGCGGCGGAGGATCTCGTAACCTCCCCGTGGC

TACCCCCGATCCCGGAATGTTCCCTTGTTTACACCACAGCCAGAATTTA

CTGAGGGCCGTGAGCAACATGCTGCAGAAAGCTAGGCAGACTTTAGAAT

TTTACCCTTGCACCAGCGAGGAGATCGACCATGAAGATATCACCAAGGA

CAAGACATCCACCGTGGAGGCTTGTTTACCTCTGGAGCTGACAAAGAAC

GAGTCTTGTCTCAACTCTCGTGAAACCAGCTTCATCACAAATGGCTCTT

GTTTAGCTTCCCGGAAGACCTCCTTTATGATGGCTTTATGCCTCAGCTC

CATCTACGAGGATTTAAAGATGTACCAAGTGGAGTTCAAGACCATGAAC

GCCAAGCTGCTCATGGACCCTAAACGGCAGATCTTTTTAGACCAGAACA

TGCTGGCTGTGATTGATGAGCTGATGCAAGCTTTAAACTTCAACTCCGA

GACCGTCCCTCAGAAGTCCTCCCTCGAGGAGCCCGATTTTTACAAGACA

AAGATCAAACTGTGCATTTTACTCCACGCCTTTAGGATCCGGGCCGTGA

CCATTGACCGGGTCATGAGCTATTTAAACGCCAGCATTACATGCCCCCC

TCCCATGAGCGTGGAGCACGCCGACATCTGGGTGAAGAGCTATAGCCTC

TACAGCCGGGAGAGGTATATCTGTAACAGCGGCTTCAAGAGGAAGGCCG

GCACCAGCAGCCTCACCGAGTGCGTGCTGAATAAGGCTACCAACGTGGC

TCACTGGACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 122)
MKWVTFISLLFLFSSAYSIWELKKDVYVVELDWYPDAPGEMVVLTCDTP

EEDGITWTLDQSSEVLGSGKTLTIQVKEFGDAGQYTCHKGGEVLSHSLL

LLHKKEDGIWSTDILKDQKEPKNKTFLRCEAKNYSGRFTCWWLTTISTD

LTFSVKSSRGSSDPQGVTCGAATLSAERVRGDNKEYEYSVECQEDSACP

AAEESLPIEVMVDAVHKLKYENYTSSFFIRDIIKPDPPKNLQLKPLKNS

RQVEVSWEYPDTWSTPHSYFSLTFCVQVQGKSKREKKDRVFTDKTSATV

ICRKNASISVRAQDRYYSSSWSEWASVPCSGGGGSGGGGSGGGGSRNLP

VATPDPGMFPCLUESQNLLRAVSNMLQKARQTLEFYPCTSEEIDHEDIT

KDKTSTVEACLPLELTKNESCLNSRETSFITNGSCLASRKTSFMMALCL

SSIYEDLKMYQVEFKTMNAKLLMDPKRQIFLDQNMLAVIDELMQALNFN

SETVPQKSSLEEPDFYKTKIKLCILLHAFRIRAVTIDRVMSYLNASITC

PPPMSVEHADIWVKSYSLYSRERYICNSGFKRKAGTSSLTECVLNKATN

VAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 123)
ATGAAATGGGTGACCTTTATTTCTTTACTGTTCCTCTTTAGCAGCGCCT

ACTCCATTTGGGAACTGAAGAAGGACGTCTACGTGGTCGAACTGGACTG

GTATCCCGATGCTCCCGGCGAAATGGTGGTGCTCACTTGTGACACCCCC

GAAGAAGACGGCATCACTTGGACCCTCGATCAGAGCAGCGAGGTGCTGG

GCTCCGGAAAGACCCTCACAATCCAAGTTAAGGAGTTCGGAGACGCTGG

CCAATACACATGCCACAAGGGAGGCGAGGTGCTCAGCCATTCCTTATTA

TTATTACACAAGAAGGAAGACGGAATCTGGTCCACCGACATTTTAAAAG

ATCAGAAGGAGCCCAAGAATAAGACCTTTTTAAGGTGTGAGGCCAAAAA

CTACAGCGGTCGTTTCACTTGTTGGTGGCTGACCACCATTTCCACCGAT

TTAACCTTCTCCGTGAAAAGCAGCCGGGGAAGCTCCGACCCTCAAGGTG

TGACATGTGGAGCCGCTACCCTCAGCGCTGAGAGGGTTCGTGGCGATAA

CAAGGAATACGAGTACAGCGTGGAGTGCCAAGAAGATAGCGCTTGTCCC

```
GCTGCCGAAGAATCTTTACCCATTGAGGTGATGGTGGACGCCGTGCACA

AACTCAAGTACGAGAACTACACCTCCTCCTTCTTTATCCGGGACATCAT

TAAGCCCGATCCTCCTAAGAATTTACAGCTGAAGCCTCTCAAAAATAGC

CGGCAAGTTGAGGTCTCTTGGGAATATCCCGACACTTGGAGCACACCCC

ACAGCTACTTCTCTTTAACCTTTTGTGTGCAAGTTCAAGGTAAAAGCAA

GCGGGAGAAGAAAGACCGGGTGTTTACCGACAAAACCAGCGCCACCGTC

ATCTGTCGGAAGAACGCCTCCATCAGCGTGAGGGCTCAAGATCGTTATT

ACTCCAGCAGCTGGTCCGAGTGGGCCAGCGTGCCTTGTTCCGGCGGTGG

AGGATCCGGAGGAGGTGGCTCCGGCGGCGGAGGATCTCGTAACCTCCCC

GTGGCTACCCCCGATCCCGGAATGTTCCCTTGTTTACACCACAGCCAGA

ATTTACTGAGGGCCGTGAGCAACATGCTGCAGAAAGCTAGGCAGACTTT

AGAATTTTACCCTTGCACCAGCGAGGAGATCGACCATGAAGATATCACC

AAGGACAAGACATCCACCGTGGAGGCTTGTTTACCTCTGGAGCTGACAA

AGAACGAGTCTTGTCTCAACTCTCGTGAAACCAGCTTCATCACAAATGG

CTCTTGTTTAGCTTCCCGGAAGACCTCCTTTATGATGGCTTTATGCCTC

AGCTCCATCTACGAGGATTTAAAGATGTACCAAGTGGAGTTCAAGACCA

TGAACGCCAAGCTGCTCATGGACCCTAAACGGCAGATCTTTTTAGACCA

GAACATGCTGGCTGTGATTGATGAGCTGATGCAAGCTTTAAACTTCAAC

TCCGAGACCGTCCCTCAGAAGTCCTCCCTCGAGGAGCCCGATTTTTACA

AGACAAAGATCAAACTGTGCATTTTACTCCACGCCTTTAGGATCCGGGC

CGTGACCATTGACCGGGTCATGAGCTATTTAAACGCCAGCATTACATGC

CCCCCTCCCATGAGCGTGGAGCACGCCGACATCTGGGTGAAGAGCTATA

GCCTCTACAGCCGGGAGAGGTATATCTGTAACAGCGGCTTCAAGAGGAA

GGCCGGCACCAGCAGCCTCACCGAGTGCGTGCTGAATAAGGCTACCAAC

GTGGCTCACTGGACAACACCCTCTTTAAAGTGCATCCGG.
```

Exemplary Multi-Chain Chimeric Polypeptides—Type B

In some embodiments of any of the multi-chain chimeric polypeptides described herein, the first target-binding domain and the second targeting-binding domain each independently bind specifically to a receptor of IL-21 or to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble TGF-β receptor (e.g., a soluble TGF-β RII receptor). In some embodiments of these multi-chain chimeric polypeptides, the first target-binding domain and the second target-binding domain are each independently a soluble IL-21 or a soluble TGF-β receptor (e.g., a soluble TGF-β RII receptor). In some embodiments of these multi-chain chimeric polypeptides, the first target-binding domain and the second target-binding domain both bind specifically to a receptor of IL-21 or to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to TGF-β. In some embodiments of these multi-chain chimeric polypeptides, the first target-binding domain binds specifically to TGF-β, and the second target-binding domain bind specifically to a receptor for IL-21.

In some embodiments of these multi-chain chimeric polypeptides, the first target-binding domain includes a soluble IL-21 (e.g., a soluble human IL-21). In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 125)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC.

In some embodiments of these multi-chain chimeric polypeptides, the second target-binding domain includes a soluble TGF-β receptor (e.g., a soluble TGF-β RII receptor (e.g., a soluble human TGF-β RII receptor)). In some embodiments of these multi-chain chimeric polypeptides, the soluble human TGF-β RII includes a first sequence of soluble human TGF-β RII and a second sequence of soluble human TGF-β RII. In some embodiments of these multi-chain chimeric polypeptides, the soluble human TGF-β RII includes a linker disposed between the first sequence of soluble human TGF-β RII and the second sequence of soluble human TGF-β RII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCACG

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT.

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCACA

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC.

In some embodiments of these multi-chain chimeric polypeptides, the soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 61)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCACG

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

```
                                           -continued
GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCACAATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGCTGCAGCAGCGACGAATGCAACGACAATATCATCTTTAGCGAGG

AATACAATACCAGCAACCCCGAC.
```

In some embodiments of these multi-chain polypeptides, the human TGFβRII receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 60)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD.
```

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 126)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDSSGTTNTVAAYNLTW

KSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPT

IQSFEQVGTKVNVTVEDERTLVRRNNTFLSLRDVFGKDLIYTLYYWKSS

SSGKKTAKTNTNEFLIDVDKGENYCFSVQAVIPSRTVNRKSTDSPVECM

GQEKGEFRENWVNVISDLKKIEDLIQSMHIDATLYTESDVHPSCKVTAM

KCFLLELQVISLESGDASIHDTVENLIILANNSLSSNGNVTESGCKECE

ELEEKNIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 127)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCCTCCGGCACCACCAATACCGTGGCCGCTTATAACCTCACATGG

AAGAGCACCAACTTCAAGACAATTCTGGAATGGGAACCCAAGCCCGTCA

ATCAAGTTTACACCGTGCAGATCTCCACCAAATCCGGAGACTGGAAGAG

CAAGTGCTTCTACACAACAGACACCGAGTGTGATTTAACCGACGAAATC

GTCAAGGACGTCAAGCAAACCTATCTGGCTCGGGTCTTTTCCTACCCCG

CTGGCAATGTCGAGTCCACCGGCTCCGCTGGCGAGCCTCTCTACGAGAA

TTCCCCCGAATTCACCCCTTATTTAGAGACCAATTTAGGCCAGCCTACC

ATCCAGAGCTTCGAGCAAGTTGGCACCAAGGTGAACGTCACCGTCGAGG

ATGAAAGGACTTTAGTGCGGCGGAATAACACATTTTTATCCCTCCGGGA

TGTGTTCGGCAAAGACCTCATCTACACACTGTACTATTGGAAGTCCAGC

TCCTCCGGCAAAAAGACCGCTAAGACCAACACCAACGAGTTTTTAATTG

ACGTGGACAAAGGCGAGAACTACTGCTTCAGCGTGCAAGCCGTGATCCC

TTCTCGTACCGTCAACCGGAAGAGCACAGATTCCCCCGTTGAGTGCATG

GGCCAAGAAAAGGGCGAGTTCCGGGAGAACTGGGTGAACGTCATCAGCG

ATTTAAAGAAGATCGAAGATTTAATTCAGTCCATGCATATCGACGCCAC

TTTATACACAGAATCCGACGTGCACCCCTCTTGTAAGGTGACCGCCATG

AAATGTTTTTTACTGGAGCTGCAAGTTATCTCTTTAGAGAGCGGAGACG

CTAGCATCCACGACACCGTGGAGAATTTAATCATTTTAGCCAATAACTC

TTTATCCAGCAACGGCAACGTGACAGAGTCCGGCTGCAAGGAGTGCGAA

GAGCTGGAGGAGAAGAACATCAAGGAGTTTCTGCAATCCTTTGTGCACA

TTGTCCAGATGTTCATCAATACCTCC.
```

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 128)
MKWVTFISLLFLFSSAYSQGQDRHMIRMRQLIDIVDQLKNYVNDLVPEF

LPAPEDVETNCEWSAFSCFQKAQLKSANTGNNERIINVSIKKLKRKPPS
```

TNAGRRQKHRLTCPSCDSYEKKPPKEFLERFKSLLQKMIHQHLSSRTHG

SEDSSGTTNTVAAYNLTWKSTNFKTILEWEPKPVNQVYTVQISTKSGDW

KSKCFYTTDTECDLTDEIVKDVKQTYLARVFSYPAGNVESTGSAGEPLY

ENSPEFTPYLETNLGQPTIQSFEQVGTKVNVTVEDERTLVRRNNTFLSL

RDVFGKDLIYTLYYWKSSSSGKKTAKTNTNEFLIDVDKGENYCFSVQAV

IPSRTVNRKSTDSPVECMGQEKGEFRENWVNVISDLKKIEDLIQSMHID

ATLYTESDVHPSCKVTAMKCFLLELQVISLESGDASIHDTVENLIILAN

NSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 129)
ATGAAGTGGGTGACCTTCATCAGCCTGCTGTTCCTGTTCTCCAGCGCCT

ACTCCCAGGGCCAGGACAGGCACATGATCCGGATGAGGCAGCTCATCGA

CATCGTCGACCAGCTGAAGAACTACGTGAACGACCTGGTGCCCGAGTTT

CTGCCTGCCCCCGAGGACGTGGAGACCAACTGCGAGTGGTCCGCCTTCT

CCTGCTTTCAGAAGGCCCAGCTGAAGTCCGCCAACACCGGCAACAACGA

GCGGATCATCAACGTGAGCATCAAGAAGCTGAAGCGGAAGCCTCCCTCC

ACAAACGCCGGCAGGAGGCAGAAGCACAGGCTGACCTGCCCCAGCTGTG

ACTCCTACGAGAAGAAGCCCCCCAAGGAGTTCCTGGAGAGGTTCAAGTC

CCTGCTGCAGAAGATGATCCATCAGCACCTGTCCTCCAGGACCCACGGC

TCCGAGGACTCCTCCGGCACCACCAATACCGTGGCCGCTTATAACCTCA

CATGGAAGAGCACCAACTTCAAGACAATTCTGGAATGGGAACCCAAGCC

CGTCAATCAAGTTTACACCGTGCAGATCTCCACCAAATCCGGAGACTGG

AAGAGCAAGTGCTTCTACACAACAGACACCGAGTGTGATTTAACCGACG

AAATCGTCAAGGACGTCAAGCAAACCTATCTGGCTCGGGTCTTTTCCTA

CCCCGCTGGCAATGTCGAGTCCACCGGCTCCGCTGGCGAGCCTCTCTAC

GAGAATTCCCCCGAATTCACCCCTTATTTAGAGACCAATTTAGGCCAGC

CTACCATCCAGAGCTTCGAGCAAGTTGGCACCAAGGTGAACGTCACCGT

CGAGGATGAAAGGACTTTAGTGCGGCGGAATAACACATTTTTATCCCTC

CGGGATGTGTTCGGCAAAGACCTCATCTACACACTGTACTATTGGAAGT

CCAGCTCCTCCGGCAAAAAGACCGCTAAGACCAACACCAACGAGTTTTT

AATTGACGTGGACAAAGGCGAGAACTACTGCTTCAGCGTGCAAGCCGTG

ATCCCTTCTCGTACCGTCAACCGGAAGAGCACAGATTCCCCCGTTGAGT

GCATGGGCCAAGAAAGGGCGAGTTCCGGGAGAACTGGGTGAACGTCAT

CAGCGATTTAAAGAAGATCGAAGATTTAATTCAGTCCATGCATATCGAC

GCCACTTTATACACAGAATCCGACGTGCACCCCTCTTGTAAGGTGACCG

CCATGAAATGTTTTTTACTGGAGCTGCAAGTTATCTCTTTAGAGAGCGG

AGACGCTAGCATCCACGACACCGTGGAGAATTTAATCATTTTAGCCAAT

AACTCTTTATCCAGCAACGGCAACGTGACAGAGTCCGGCTGCAAGGAGT

GCGAAGAGCTGGAGGAGAAGAACATCAAGGAGTTTCTGCAATCCTTTGT

GCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 129)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDITCPPPM

SVEHADIWVKSYSLYSRERYICNSGFKRKAGTSSLTECVLNKATNVAHW

TTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 131)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCACG

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCACAATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAGAGAAAAAGAAGCCTGGCGAGACCTTTT

TCATGTGCTCCTGCAGCAGCGACGAATGCAACGACAATATCATCTTTAG

-continued
CGAGGAATACAATACCAGCAACCCCGACATCACGTGTCCTCCTCCTATG

TCCGTGGAACACGCAGACATCTGGGTCAAGAGCTACAGCTTGTACTCCA

GGGAGCGGTACATTTGTAACTCTGGTTTCAAGCGTAAAGCCGGCACGTC

CAGCCTGACGGAGTGCGTGTTGAACAAGGCCACGAATGTCGCCCACTGG

ACAACCCCCAGTCTCAAATGTATTAGA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 132)
MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDITCPPPMSVEHADIWVKSYSLYSRERYICNSGFKRKAG

TSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 133)
ACTCCATCCCCCCCCATGTGCAAAAGAGCGTGAACAACGATATGATCG

TGACCGACAACAACGGCGCCGTGAAGTTTCCCCAGCTCTGCAAGTTCTG

CGATGTCAGGTTCAGCACCTGCGATAATCAGAAGTCCTGCATGTCCAAC

TGCACGATCACCTCCATCTGCGAGAAGCCCCAAGAAGTGTGCGTGGCCG

TGTGGCGGAAAAATGACGAGAACATCACCCTGGAGACCGTGTGTCACGA

CCCCAAGCTCCCTTATCACGACTTCATTCTGGAGGACGCTGCCTCCCCC

AAATGCATCATGAAGGAGAAGAAGAAGCCCGGAGAGACCTTCTTTATGT

GTTCCTGTAGCAGCGACGAGTGTAACGACAACATCATCTTCAGCGAAGA

GTACAACACCAGCAACCCTGATGGAGGTGGCGGATCCGGAGGTGGAGGT

TCTGGTGGAGGTGGGAGTATTCCTCCCCACGTGCAGAAGAGCGTGAATA

ATGACATGATCGTGACCGATAACAATGGCGCCGTGAAATTTCCCCAGCT

GTGCAAATTCTGCGATGTGAGGTTTTCCACCTGCGACAACCAGAAGTCC

TGTATGAGCAACTGCACAATCACCTCCATCTGTGAGAAGCCTCAGGAGG

TGTGCGTGGCTGTCTGGCGGAAGAATGACGAGAATATCACCCTGGAAAC

CGTCTGCCACGATCCCAAGCTGCCCTACCACGATTTCATCCTGGAAGAC

GCCGCCAGCCCTAAGTGCATCATGAAAGAGAAAAAGAAGCCTGGCGAGA

-continued
CCTTTTTCATGTGCTCCTGCAGCAGCGACGAATGCAACGACAATATCAT

CTTTAGCGAGGAATACAATACCAGCAACCCCGACATCACGTGTCCTCCT

CCTATGTCCGTGGAACACGCAGACATCTGGGTCAAGAGCTACAGCTTGT

ACTCCAGGGAGCGGTACATTTGTAACTCTGGTTTCAAGCGTAAAGCCGG

CACGTCCAGCCTGACGGAGTGCGTGTTGAACAAGGCCACGAATGTCGCC

CACTGGACAACCCCCAGTCTCAAATGTATTAGA.

Exemplary Multi-Chain Chimeric Polypeptides—Type C

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the first target-binding domain includes a soluble IL-21 (e.g., a soluble human IL-21).

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 134)
CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 125)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC.

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 135)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 136)
GATTGTGATATTGAAGGTAAAGATGGCAAACAATATGAGAGTGTTCTAA

TGGTCAGCATCGATCAATTATTGGACAGCATGAAAGAAATTGGTAGCAA

TTGCCTGAATAATGAATTTAACTTTTTTAAAAGACATATCTGTGATGCT

AATAAGGAAGGTATGTTTTTATTCCGTGCTGCTCGCAAGTTGAGGCAAT

TTCTTAAAATGAATAGCACTGGTGATTTTGATCTCCACTTATTAAAAGT

TTCAGAAGGCACAACAATACTGTTGAACTGCACTGGCCAGGTTAAAGGA

AGAAAACCAGCTGCCCTGGGTGAAGCCCAACCAACAAAGAGTTTGGAAG

AAAATAAATCTTTAAAGGAACAGAAAAAACTGAATGACTTGTGTTTCCT

AAAGAGACTATTACAAGAGATAAAAACTTGTTGGAATAAAATTTTGATG

GGCACTAAAGAACAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 126)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDSSGTTNTVAAYNLTW

KSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPT

IQSFEQVGTKVNVTVEDERTLVRRNNTFLSLRDVFGKDLIYTLYYWKSS

SSGKKTAKTNTNEFLIDVDKGENYCFSVQAVIPSRTVNRKSTDSPVECM

GQEKGEFRENWVNVISDLKKIEDLIQSMHIDATLYTESDVHPSCKVTAM

KCFLLELQVISLESGDASIHDTVENLIILANNSLSSNGNVTESGCKECE

ELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 127)
CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCCTCAGGCACTACAAATACTGTGGCAGCATATAATTTAACTTGG

AAATCAACTAATTTCAAGACAATTTTGGAGTGGGAACCCAAACCCGTCA

ATCAAGTCTACACTGTTCAAATAAGCACTAAGTCAGGAGATTGGAAAAG

CAAATGCTTTTACACAACAGACACAGAGTGTGACCTCACCGACGAGATT

GTGAAGGATGTGAAGCAGACGTACTTGGCACGGGTCTTCTCCTACCCGG

CAGGGAATGTGGAGAGCACCGGTTCTGCTGGGGAGCCTCTGTATGAGAA

CTCCCCAGAGTTCACACCTTACCTGGAGACAAACCTCGGACAGCCAACA

ATTCAGAGTTTTGAACAGGTGGGAACAAAAGTGAATGTGACCGTAGAAG

ATGAACGGACTTTAGTCAGAAGGAACAACACTTTCCTAAGCCTCCGGGA

TGTTTTTGGCAAGGACTTAATTTATACACTTTATTATTGGAAATCTTCA

AGTTCAGGAAAGAAAACAGCCAAAACAAACACTAATGAGTTTTTGATTG

ATGTGGATAAAGGAGAAAACTACTGTTTCAGTGTTCAAGCAGTGATTCC

CTCCCGAACAGTTAACCGGAAGAGTACAGACAGCCCGGTAGAGTGTATG

GGCCAGGAGAAGGGGAATTCAGAGAAACTGGGTGAACGTCATCAGCG

ATTTAAAGAAGATCGAAGATTTAATTCAGTCCATGCATATCGACGCCAC

TTTATACACAGAATCCGACGTGCACCCCTCTTGTAAGGTGACCGCCATG

AAATGTTTTTTACTGGAGCTGCAAGTTATCTCTTTAGAGAGCGGAGACG

CTAGCATCCACGACACCGTGGAGAATTTAATCATTTTAGCCAATAACTC

TTTATCCAGCAACGGCAACGTGACAGAGTCCGGCTGCAAGGAGTGCGAA

GAGCTGGAGGAGAAGAACATCAAGGAGTTTCTGCAATCCTTTGTGCACA

TTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 128)
MGVKVLFALICIAVAEAQGQDRHMIRMRQLIDIVDQLKNYVNDLVPEFL

PAPEDVETNCEWSAFSCFQKAQLKSANTGNNERIINVSIKKLKRKPPST

NAGRRQKHRLTCPSCDSYEKKPPKEFLERFKSLLQKMIHQHLSSRTHGS

EDSSGTTNTVAAYNLTWKSTNFKTILEWEPKPVNQVYTVQISTKSGDWK

SKCFYTTDTECDLTDEIVKDVKQTYLARVFSYPAGNVESTGSAGEPLYE

NSPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAVI

PSRTVNRKSTDSPVECMGQEKGEFRENWVNVISDLKKIEDLIQSMHIDA

TLYTESDVHPSCKVTAMKCFLLELQVISLESGDASIHDTVENLIILANN

SLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 129)
ATGGGAGTGAAAGTTCTTTTTGCCCTTATTTGTATTGCTGTGGCCGAGG

CCCAAGGTCAAGATCGCCACATGATTAGAATGCGTCAACTTATAGATAT

TGTTGATCAGCTGAAAAATTATGTGAATGACTTGGTCCCTGAATTTCTG

CCAGCTCCAGAAGATGTAGAGACAAACTGTGAGTGGTCAGCTTTTTCCT

GTTTTCAGAAGGCCCAACTAAAGTCAGCAAATACAGGAAACAATGAAAG

GATAATCAATGTATCAATTAAAAAGCTGAAGAGGAAACCACCTTCCACA

AATGCAGGGAGAAGACAGAAACACAGACTAACATGCCCTTCATGTGATT

CTTATGAGAAAAAACCACCCAAAGAATTCCTAGAAAGATTCAAATCACT

TCTCCAAAAGATGATTCATCAGCATCTGTCCTCTAGAACACACGGAAGT

GAAGATTCCTCAGGCACTACAAATACTGTGGCAGCATATAATTTAACTT

GGAAATCAACTAATTTCAAGACAATTTTGGAGTGGGAACCCAAACCCGT

CAATCAAGTCTACACTGTTCAAATAAGCACTAAGTCAGGAGATTGGAAA

AGCAAATGCTTTTACACAACAGACACAGAGTGTGACCTCACCGACGAGA

TTGTGAAGGATGTGAAGCAGACGTACTTGGCACGGGTCTTCTCCTACCC

```
GGCAGGGAATGTGGAGAGCACCGGTTCTGCTGGGGAGCCTCTGTATGAG

AACTCCCCAGAGTTCACACCTTACCTGGAGACAAACCTCGGACAGCCAA

CAATTCAGAGTTTTGAACAGGTGGGAACAAAAGTGAATGTGACCGTAGA

AGATGAACGGACTTTAGTCAGAAGGAACAACACTTTCCTAAGCCTCCGG

GATGTTTTTGGCAAGGACTTAATTTATACACTTTATTATTGGAAATCTT

CAAGTTCAGGAAAGAAAACAGCCAAAACAAACACTAATGAGTTTTTGAT

TGATGTGGATAAAGGAGAAAACTACTGTTTCAGTGTTCAAGCAGTGATT

CCCTCCCGAACAGTTAACCGGAAGAGTACAGACAGCCCGGTAGAGTGTA

TGGGCCAGGAGAAAGGGGAATTCAGAGAAAACTGGGTGAACGTCATCAG

CGATTTAAAGAAGATCGAAGATTTAATTCAGTCCATGCATATCGACGCC

ACTTTATACACAGAATCCGACGTGCACCCCTCTTGTAAGGTGACCGCCA

TGAAATGTTTTTTACTGGAGCTGCAAGTTATCTCTTTAGAGAGCGGAGA

CGCTAGCATCCACGACACCGTGGAGAATTTAATCATTTTAGCCAATAAC

TCTTTATCCAGCAACGGCAACGTGACAGAGTCCGGCTGCAAGGAGTGCG

AAGAGCTGGAGGAGAAGAACATCAAGGAGTTTCTGCAATCCTTTGTGCA

CATTGTCCAGATGTTCATCAATACCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 137)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEHITCPPPMSVEHADIWVKSYSLYSRERYICNSGFKRKAGTSSLTE

CVLNKATNVAHWTTPSLKCIR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 138)
GATTGTGATATTGAAGGTAAAGATGGCAAACAATATGAGAGTGTTCTAA

TGGTCAGCATCGATCAATTATTGGACAGCATGAAAGAAATTGGTAGCAA

TTGCCTGAATAATGAATTTAACTTTTTTAAAAGACATATCTGTGATGCT

AATAAGGAAGGTATGTTTTTATTCCGTGCTGCTCGCAAGTTGAGGCAAT

TTCTTAAAATGAATAGCACTGGTGATTTTGATCTCCACTTATTAAAAGT

TTCAGAAGGCACAACAATACTGTTGAACTGCACTGGCCAGGTTAAAGGA

AGAAAACCAGCTGCCCTGGGTGAAGCCCAACCAACAAAGAGTTTGGAAG

AAAATAAATCTTTAAAGGAACAGAAAAAACTGAATGACTTGTGTTTCCT

AAAGAGACTATTACAAGAGATAAAAACTTGTTGGAATAAAATTTTGATG

GGCACTAAAGAACACATCACGTGCCCTCCCCCCATGTCCGTGGAACACG

CAGACATCTGGGTCAAGAGCTACAGCTTGTACTCCAGGGAGCGGTACAT

TTGTAACTCTGGTTTCAAGCGTAAAGCCGGCACGTCCAGCCTGACGGAG

TGCGTGTTGAACAAGGCCACGAATGTCGCCCACTGGACAACCCCCAGTC

TCAAATGCATTAGA.
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 139)
MGVKVLFALICIAVAEADCDIEGKDGKQYESVLMVSIDQLLDSMKEIGS

NCLNNEFNFFKRHICDANKEGMFLFRAARKLRQFLKMNSTGDFDLHLLK

VSEGTTILLNCTGQVKGRKPAALGEAQPTKSLEENKSLKEQKKLNDLCF

LKRLLQEIKTCWNKILMGTKEHITCPPPMSVEHADIWVKSYSLYSRERY

ICNSGFKRKAGTSSLTECVLNKATNVAHWTTPSLKCIR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 140)
ATGGGAGTGAAAGTTCTTTTTGCCCTTATTTGTATTGCTGTGGCCGAGG

CCGATTGTGATATTGAAGGTAAAGATGGCAAACAATATGAGAGTGTTCT

AATGGTCAGCATCGATCAATTATTGGACAGCATGAAAGAAATTGGTAGC

AATTGCCTGAATAATGAATTTAACTTTTTTAAAAGACATATCTGTGATG

CTAATAAGGAAGGTATGTTTTTATTCCGTGCTGCTCGCAAGTTGAGGCA

ATTTCTTAAAATGAATAGCACTGGTGATTTTGATCTCCACTTATTAAAA

GTTTCAGAAGGCACAACAATACTGTTGAACTGCACTGGCCAGGTTAAAG

GAAGAAAACCAGCTGCCCTGGGTGAAGCCCAACCAACAAAGAGTTTGGA

AGAAAATAAATCTTTAAAGGAACAGAAAAAACTGAATGACTTGTGTTTC

CTAAAGAGACTATTACAAGAGATAAAAACTTGTTGGAATAAAATTTTGA

TGGGCACTAAAGAACACATCACGTGCCCTCCCCCCATGTCCGTGGAACA

CGCAGACATCTGGGTCAAGAGCTACAGCTTGTACTCCAGGGAGCGGTAC

ATTTGTAACTCTGGTTTCAAGCGTAAAGCCGGCACGTCCAGCCTGACGG

AGTGCGTGTTGAACAAGGCCACGAATGTCGCCCACTGGACAACCCCCAG

TCTCAAATGCATTAGA.
```

Exemplary Multi-Chain Chimeric Polypeptides—Type D
In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 124)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 134)
CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCC.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 125)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC.
```

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 135)
DCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM
GTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 136)
GATTGTGATATTGAAGGTAAAGATGGCAAACAATATGAGAGTGTTCTAA
TGGTCAGCATCGATCAATTATTGGACAGCATGAAAGAAATTGGTAGCAA
TTGCCTGAATAATGAATTTAACTTTTTTAAAAGACATATCTGTGATGCT
AATAAGGAAGGTATGTTTTTATTCCGTGCTGCTCGCAAGTTGAGGCAAT
TTCTTAAAATGAATAGCACTGGTGATTTTGATCTCCACTTATTAAAAGT
TTCAGAAGGCACAACAATACTGTTGAACTGCACTGGCCAGGTTAAAGGA
AGAAAACCAGCTGCCCTGGGTGAAGCCCAACCAACAAAGAGTTTGGAAG
AAAATAAATCTTTAAAGGAACAGAAAAAACTGAATGACTTGTGTTTCCT
AAAGAGACTATTACAAGAGATAAAAACTTGTTGGAATAAAATTTTGATG
GGCACTAAAGAACAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 141)
DCDIEGKDGKQYESVLMVSIDQLLDSMKEIGSNCLNNEFNEFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM
GTKEHSGTTNTVAAYNLTWKSTNFKTILEWEPKPVNQVYTVQISTKSGD
WKSKCFYTTDTECDLTDEIVKDVKQTYLARVFSYPAGNVESTGSAGEPL
YENSPEFTPYLETNLGQPTIQSFEQVGTKVNVTVEDERTLVRRNNTFLS
LRDVEGKDLIYTLYYWKSSSSGKKTAKTNTNEFLIDVDKGENYCFSVQA
VIPSRTVNRKSTD SPVECMGQEKGEFRENWVNVISDLKKIEDLIQSMH
IDATLYTESDVHPSCKVTAMKCFLLELQVISLESGDASIHDTVENLIIL
ANNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 142)
GATTGCGACATCGAGGGCAAGGACGGCAAGCAGTACGAGAGCGTGCTGA
TGGTGTCCATCGACCAGCTGCTGGACAGCATGAAGGAGATCGGCTCCAA
CTGCCTCAACAACGAGTTCAACTTCTTCAAGCGGCACATCTGCGACGCC
AACAAGGAGGGCATGTTCCTGTTCAGGGCCGCCAGGAAACTGCGGCAGT
TCCTGAAGATGAACTCCACCGGCGACTTCGACCTGCACCTGCTGAAGGT
GTCCGAGGGCACCACCATCCTGCTGAACTGCACCGGACAGGTGAAGGGC
CGGAAACCTGCTGCTCTGGGAGAGGCCCAACCCACCAAGAGCCTGGAGG
AGAACAAGTCCCTGAAGGAGCAGAAGAAGCTGAACGACCTGTGCTTCCT
GAAGAGGCTGCTGCAGGAGATCAAGACCTGCTGGAACAAGATCCTGATG
GGCACCAAGGAGCATAGCGGCACAACCAACACAGTCGCTGCCTATAACC
TCACTTGGAAGAGCACCAACTTCAAAACCATCCTCGAATGGGAACCCAA
ACCCGTTAACCAAGTTTACACCGTGCAGATCAGCACCAAGTCCGGCGAC
TGGAAGTCCAAATGTTTCTATACCACCGACACCGAGTGCGATCTCACCG
ATGAGATCGTGAAAGATGTGAAACAGACCTACCTCGCCCGGGTGTTTAG
CTACCCCGCCGGCAATGTGGAGAGCACTGGTTCCGCTGGCGAGCCTTTA
TACGAGAACAGCCCCGAATTTACCCCTTACCTCGAGACCAATTTAGGAC
AGCCCACCATCCAAAGCTTTGAGCAAGTTGGCACAAAGGTGAATGTGAC
AGTGGAGGACGAGCGGACTTTAGTGCGGCGGAACAACACCTTTCTCAGC
CTCCGGGATGTGTTCGGCAAAGATTTAATCTACACACTGTATTACTGGA
AGTCCTCTTCCTCCGGCAAGAAGACAGCTAAAACCAACACAAACGAGTT
TTTAATCGACGTGGATAAAGGCGAAAACTACTGTTTCAGCGTGCAAGCT
GTGATCCCCTCCCGGACCGTGAATAGGAAAAGCACCGATAGCCCCGTTG
AGTGCATGGGCCAAGAAAAGGGCGAGTTCCGGGAGAACTGGGTGAACGT
CATCAGCGATTTAAAGAAGATCGAAGATTTAATTCAGTCCATGCATATC
GACGCCACTTTATACACAGAATCCGACGTGCACCCCTCTTGTAAGGTGA
CCGCCATGAAATGTTTTTTACTGGAGCTGCAAGTTATCTCTTTAGAGAG
CGGAGACGCTAGCATCCACGACACCGTGGAGAATTTAATCATTTTAGCC
AATAACTCTTTATCCAGCAACGGCAACGTGACAGAGTCCGGCTGCAAGG
AGTGCGAAGAGCTGGAGGAGAAGAACATCAAGGAGTTTCTGCAATCCTT
TGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 143)
MKWVTFISLLFLFSSAYSDCDIEGKDGKQYESVLMVSIDQLLDSMKEIG
SNCLNNEFNFFKRHICDANKEGMFLFRAARKLRQFLKMNSTGDFDLHLL
KVSEGTTILLNCTGQVKGRKPAALGEAQPTKSLEENKSLKEQKKLNDLC
FLKRLLQEIKTCWNKILMGTKEHSGTTNTVAAYNLTWKSTNFKTILEWE

PKPVNQVYTVQISTKSGDWKSKCFYTTDTECDLTDEIVKDVKQTYLARV

FSYPAGNVESTGSAGEPLYENSPEFTPYLETNLGQPTIQSFEQVGTKVN

VTVEDERTLVRRNNTFLSLRDVFGKDLIYTLYYWKSSSSGKKTAKTNTN

EFLIDVDKGENYCFSVQAVIPSRTVNRKSTDSPVECMGQEKGEFRENWV

NVISDLKKIEDLIQSMHIDATLYTESDVHPSCKVTAMKCFLLELQVISL

ESGDASIHDTVENLIILANNSLSSNGNVTESGCKECEELEEKNIKEFLQ

SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 144)
ATGAAGTGGGTGACCTTCATCAGCCTGCTGTTCCTGTTCTCCAGCGCCT

ACTCCGATTGCGACATCGAGGGCAAGGACGGCAAGCAGTACGAGAGCGT

GCTGATGGTGTCCATCGACCAGCTGCTGGACAGCATGAAGGAGATCGGC

TCCAACTGCCTCAACAACGAGTTCAACTTCTTCAAGCGGCACATCTGCG

ACGCCAACAAGGAGGGCATGTTCCTGTTCAGGGCCGCCAGGAAACTGCG

GCAGTTCCTGAAGATGAACTCCACCGGCGACTTCGACCTGCACCTGCTG

AAGGTGTCCGAGGGCACCACCATCCTGCTGAACTGCACCGGACAGGTGA

AGGGCCGGAAACCTGCTGCTCTGGGAGAGGCCCAACCCACCAAGAGCCT

GGAGGAGAACAAGTCCCTGAAGGAGCAGAAGAAGCTGAACGACCTGTGC

TTCCTGAAGAGGCTGCTGCAGGAGATCAAGACCTGCTGGAACAAGATCC

TGATGGGCACCAAGGAGCATAGCGGCACAACCAACACAGTCGCTGCCTA

TAACCTCACTTGGAAGAGCACCAACTTCAAAACCATCCTCGAATGGGAA

CCCAAACCCGTTAACCAAGTTTACACCGTGCAGATCAGCACCAAGTCCG

GCGACTGGAAGTCCAAATGTTTCTATACCACCGACACCGAGTGCGATCT

CACCGATGAGATCGTGAAAGATGTGAAACAGACCTACCTCGCCCGGGTG

TTTAGCTACCCCGCCGGCAATGTGGAGAGCACTGGTTCCGCTGGCGAGC

CTTTATACGAGAACAGCCCCGAATTTACCCCTTACCTCGAGACCAATTT

AGGACAGCCCACCATCCAAAGCTTTGAGCAAGTTGGCACAAAGGTGAAT

GTGACAGTGGAGGACGAGCGGACTTTAGTGCGGCGGAACAACACCTTTC

TCAGCCTCCGGGATGTGTTCGGCAAAGATTTAATCTACACACTGTATTA

CTGGAAGTCCTCTTCCTCCGGCAAGAAGACAGCTAAAACCAACACAAAC

GAGTTTTTAATCGACGTGGATAAAGGCGAAAACTACTGTTTCAGCGTGC

AAGCTGTGATCCCCTCCCGGACCGTGAATAGGAAAAGCACCGATAGCCC

CGTTGAGTGCATGGGCCAAGAAAAGGGCGAGTTCCGGGAGAACTGGGTG

AACGTCATCAGCGATTTAAAGAAGATCGAAGATTTAATTCAGTCCATGC

ATATCGACGCCACTTTATACACAGAATCCGACGTGCACCCCTCTTGTAA

GGTGACCGCCATGAAATGTTTTTTACTGGAGCTGCAAGTTATCTCTTTA

GAGAGCGGAGACGCTAGCATCCACGACACCGTGGAGAATTTAATCATTT

TAGCCAATAACTCTTTATCCAGCAACGGCAACGTGACAGAGTCCGGCTG

CAAGGAGTGCGAAGAGCTGGAGGAGAAGAACATCAAGGAGTTTCTGCAA

TCCTTTGTGCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 145)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDSITCPPPMSVEHADI

WVKSYSLYSRERYICNSGFKRKAGTSSLTECVLNKATNVAHWTTPSLKC

IR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 146)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCCATTACATGCCCCCCTCCCATGAGCGTGGAGCACGCCGACATC

TGGGTGAAGAGCTATAGCCTCTACAGCCGGGAGAGGTATATCTGTAACA

GCGGCTTCAAGAGGAAGGCCGGCACCAGCAGCCTCACCGAGTGCGTGCT

GAATAAGGCTACCAACGTGGCTCACTGGACAACACCCTCTTTAAAGTGC

ATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 147)
MKWVTFISLLFLFSSAYSQGQDRHMIRMRQLIDIVDQLKNYVNDLVPEF

LPAPEDVETNCEWSAFSCFQKAQLKSANTGNNERIINVSIKKLKRKPPS

TNAGRRQKHRLTCPSCDSYEKKPPKEFLERFKSLLQKMIHQHLSSRTHG

SEDSITCPPPMSVEHADIWVKSYSLYSRERYICNSGFKRKAGTSSLTEC

VLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 148)
ATGAAGTGGGTGACCTTCATCAGCCTGCTGTTCCTGTTCTCCAGCGCCT

ACTCCCAGGGCCAGGACAGGCACATGATCCGGATGAGGCAGCTCATCGA

CATCGTCGACCAGCTGAAGAACTACGTGAACGACCTGGTGCCCGAGTTT

CTGCCTGCCCCCGAGGACGTGGAGACCAACTGCGAGTGGTCCGCCTTCT

CCTGCTTTCAGAAGGCCCAGCTGAAGTCCGCCAACACCGGCAACAACGA

GCGGATCATCAACGTGAGCATCAAGAAGCTGAAGCGGAAGCCTCCCTCC

ACAAACGCCGGCAGGAGGCAGAAGCACAGGCTGACCTGCCCCAGCTGTG

ACTCCTACGAGAAGAAGCCCCCCAAGGAGTTCCTGGAGAGGTTCAAGTC

CCTGCTGCAGAAGATGATCCATCAGCACCTGTCCTCCAGGACCCACGGC

TCCGAGGACTCCATTACATGCCCCCCTCCCATGAGCGTGGAGCACGCCG

ACATCTGGGTGAAGAGCTATAGCCTCTACAGCCGGGAGAGGTATATCTG

TAACAGCGGCTTCAAGAGGAAGGCCGGCACCAGCAGCCTCACCGAGTGC

GTGCTGAATAAGGCTACCAACGTGGCTCACTGGACAACACCCTCTTTAA

AGTGCATCCGG.

Exemplary Multi-Chain Chimeric Polypeptides—Type E

In some embodiments of any of the multi-chain chimeric polypeptides described herein, the first target-binding domain and the second targeting-binding domain each independently bind specifically to a receptor for IL-18 (e.g., a soluble human IL-18), a receptor for IL-12 (e.g., a soluble human IL-12), or CD16 (e.g., an anti-CD16 scFv). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-12.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12. In some embodiments of these multi-chain chimeric polypeptides, the first target-binding domain binds specifically to CD16, and the second target-binding domain binds specifically to a receptor for IL-18. In some embodiments of these multi-chain chimeric polypeptides, the first target-binding domain binds specifically to a receptor for IL-18, and the second target-binding domain bind specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-18 (e.g., a soluble human IL-18).

In some embodiments of these multi-chain chimeric polypeptides, the soluble human IL-18 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 41)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNED.

In some embodiments of these multi-chain chimeric polypeptides, the soluble human IL-18 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 42)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT.

In some embodiments of these multi-chain chimeric polypeptides, the second target-binding domain includes a soluble IL-12 (e.g., a soluble human IL-12). In some embodiments of these multi-chain chimeric polypeptides, the soluble human IL-15 includes a sequence of soluble human IL-12β (p40) and a sequence of soluble human IL-12α (p35). In some embodiments of these multi-chain chimeric polypeptides, the soluble IL-15 (e.g., soluble human IL-15) further includes a linker sequence (e.g., any of the exemplary linker sequences described herein) between the sequence of soluble IL-12β (p40) and the sequence of soluble human IL-12α (p35). In some examples of these multi-chain chimeric polypeptides, the linker sequence comprises GGGGSGGGGSGGGGS (SEQ ID NO: 7).

In some embodiments of these multi-chain chimeric polypeptides, the sequence of soluble human IL-12β (p40) comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 33)
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS.

In some embodiments of these multi-chain chimeric polypeptides, the soluble human IL-120 (p40) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 34)
ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

AAGGAGCCCAAGAATAAGACCTTTTTAAGGTGTGAGGCCAAAAACTACA

GCGGTCGTTTCACTTGTTGGTGGCTGACCACCATTTCCACCGATTTAAC

CTTCTCCGTGAAAAGCAGCCGGGGAAGCTCCGACCCTCAAGGTGTGACA

TGTGGAGCCGCTACCCTCAGCGCTGAGAGGGTTCGTGGCGATAACAAGG

AATACGAGTACAGCGTGGAGTGCCAAGAAGATAGCGCTTGTCCCGCTGC

CGAAGAATCTTTACCCATTGAGGTGATGGTGGACGCCGTGCACAAACTC

AAGTACGAGAACTACACCTCCTCCTTCTTTATCCGGGACATCATTAAGC

CCGATCCTCCTAAGAATTTACAGCTGAAGCCTCTCAAAAATAGCCGGCA

AGTTGAGGTCTCTTGGGAATATCCCGACACTTGGAGCACACCCCACAGC

TACTTCTCTTTAACCTTTTGTGTGCAAGTTCAAGGTAAAAGCAAGCGGG

AGAAGAAAGACCGGGTGTTTACCGACAAAACCAGCGCCACCGTCATCTG

TCGGAAGAACGCCTCCATCAGCGTGAGGGCTCAAGATCGTTATTACTCC

AGCAGCTGGTCCGAGTGGGCCAGCGTGCCTTGTTCC.

In some embodiments of these multi-chain chimeric polypeptides, the soluble human IL-12α (p35) includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 35)
RNLPVATPDPGMFPCLEMSQNLLRAVSNMLQKARQTLEFYPCTSEEIDH

EDITKDKTSTVEACLPLELTKNESCLNSRETSFITNGSCLASRKTSFMM

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

S.

In some embodiments of these multi-chain chimeric polypeptides, the soluble human IL-12α (p35) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 36)
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC.

In some embodiments of these multi-chain chimeric polypeptides, the additional target-binding domain includes an scFv that specifically binds to CD16 (e.g., an anti-CD16 scFv).

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 149)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 150)
TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

AACAACAGGCCCTCCGGCATCCCTGACAGGTTCTCCGGATCCTCCTCCG

GCAACACCGCCTCCCTGACCATCACAGGCGCTCAGGCCGAGGACGAGGC

TGACTACTACTGCAACTCCAGGGACTCCTCCGGCAACCATGTGGTGTTC

GGCGGCGGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 151)
EVQLVESGGGVVRPGGSLRLSCAASGFTFDDYGMSWVRQAPGKGLEWVS

GMWNGGSTGYADSVKGRFTISRDNAKNSLYLQMNSLRAEDTAVYYCARG

RSLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 152)
GAGGTGCAGCTGGTGGAGTCCGGAGGAGGAGTGGTGAGGCCTGGAGGCT

CCCTGAGGCTGAGCTGTGCTGCCTCCGGCTTCACCTTCGACGACTACGG

CATGTCCTGGGTGAGGCAGGCTCCTGGAAAGGGCCTGGAGTGGGTGTCC

GGCATCAACTGGAACGGCGGATCCACCGGCTACGCCGATTCCGTGAAGG

GCAGGTTCACCATCAGCAGGGACAACGCCAAGAACTCCCTGTACCTGCA

GATGAACTCCCTGAGGGCCGAGGACACCGCCGTGTACTACTGCGCCAGG

GGCAGGTCCCTGCTGTTCGACTACGGGGACAGGGCACCCTGGTGACCG

TGTCCAGG.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 116)
YFGKLESKLSVIRNLNQVLFIDQGNRPLFEDMTDSDCRDNAPRTIFIIS

MYKDSQPRGMAVTISVKCEKISTLSCENKIISFKEMNPPDNIKDTKSDI

IFFQRSVPGHDNKMQFESSSYEGYFLACEKERDLFKLILKKEDELGDRS

IMFTVQNEDSGTTNTVAAYNLTWKSTNFKTILEWEPKPVNQVYTVQIST

KSGDWKSKCFYTTDTECDLTDEIVKDVKQTYLARVFSYPAGNVESTGSA

GEPLYENSPEFTPYLETNLGQPTIQSFEQVGTKVNVTVEDERTLVRRNN

TFLSLRDVFGKDLIYTLYYWKSSSSGKKTAKTNTNEFLIDVDKGENYCF

SVQAVIPSRTVNRKSTDSPVECMGQEKGEFRENWVNVISDLKKIEDLIQ

SMHIDATLYTESDVHPSCKVTAMKCFLLELQVISLESGDASIHDTVENL

IILANNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 117)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGATAGCGGCACAACCAACACAG

TCGCTGCCTATAACCTCACTTGGAAGAGCACCAACTTCAAAACCATCCT

CGAATGGGAACCCAAACCCGTTAACCAAGTTTACACCGTGCAGATCAGC

ACCAAGTCCGGCGACTGGAAGTCCAAATGTTTCTATACCACCGACACCG

AGTGCGATCTCACCGATGAGATCGTGAAAGATGTGAAACAGACCTACCT

CGCCCGGGTGTTTAGCTACCCCGCCGGCAATGTGGAGAGCACTGGTTCC

GCTGGCGAGCCTTTATACGAGAACAGCCCCGAATTTACCCCTTACCTCG

AGACCAATTTAGGACAGCCCACCATCCAAAGCTTTGAGCAAGTTGGCAC

AAAGGTGAATGTGACAGTGGAGGACGAGCGGACTTTAGTGCGGCGGAAC

AACACCTTTCTCAGCCTCCGGGATGTGTTCGGCAAAGATTTAATCTACA

CACTGTATTACTGGAAGTCCTCTTCCTCCGGCAAGAAGACAGCTAAAAC

CAACACAAACGAGTTTTTAATCGACGTGGATAAAGGCGAAAACTACTGT

TTCAGCGTGCAAGCTGTGATCCCCTCCCGGACCGTGAATAGGAAAAGCA

CCGATAGCCCCGTTGAGTGCATGGGCCAAGAAAAGGGCGAGTTCCGGGA

GAACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTTACTGGAGCTGCAAGT

TATCTCTTTAGAGAGCGGAGACGCTAGCATCCACGACACCGTGGAGAAT

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTCC
.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 118)
MKWVTFISLLFLFSSAYSYFGKLESKLSVIRNLNDQVLFIDQGNRPLFE

DMTDSDCRDNAPRTIFIISMYKDSQPRGMAVTISVKCEKISTLSCENKI

ISFKEMNPPDNIKDTKSDIIFFQRSVPGHDNKMQFESSSYEGYFLACEK

-continued
ERDLFKLILKKEDELGDRSIMFTVQNEDSGTTNTVAAYNLTWKSTNFKT

ILEWEPKPVNQVYTVQISTKSGDWKSKCFYTTDTECDLTDEIVKDVKQT

YLARVFSYPAGNVESTGSAGEPLYENSPEFTPYLETNLGQPTIQSFEQV

GTKVNVTVEDERTLVRRNNTFLSLRDVFGKDLIYTLYYWKSSSSGKKTA

KTNTNEFLIDVDKGENYCFSVQAVIPSRTVNRKSTDSPVECMGQEKGEF

RENWVNVISDLKKIEDLIQSMHIDATLYTESDVHPSCKVTAMKCFLLEL

QVISLESGDASIHDTVENLIILANNSLSSNGNVTESGCKECEELEEKNI

KEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 119)
ATGAAGTGGGTCACATTTATCTCTTTACTGTTCCTCTTCTCCAGCGCCT

ACAGCTACTTCGGCAAACTGGAATCCAAGCTGAGCGTGATCCGGAATTT

AAACGACCAAGTTCTGTTTATCGATCAAGGTAACCGGCCTCTGTTCAG

GACATGACCGACTCCGATTGCCGGGACAATGCCCCCCGGACCATCTTCA

TTATCTCCATGTACAAGGACAGCCAGCCCCGGGGCATGGCTGTGACAAT

TAGCGTGAAGTGTGAGAAAATCAGCACTTTATCTTGTGAGAACAAGATC

ATCTCCTTTAAGGAAATGAACCCCCCCGATAACATCAAGGACACCAAGT

CCGATATCATCTTCTTCCAGCGGTCCGTGCCCGGTCACGATAACAAGAT

GCAGTTCGAATCCTCCTCCTACGAGGGCTACTTTTTAGCTTGTGAAAAG

GAGAGGGATTTATTCAAGCTGATCCTCAAGAAGGAGGACGAGCTGGGCG

ATCGTTCCATCATGTTCACCGTCCAAAACGAGGATAGCGGCACAACCAA

CACAGTCGCTGCCTATAACCTCACTTGGAAGAGCACCAACTTCAAAACC

ATCCTCGAATGGGAACCCAAACCCGTTAACCAAGTTTACACCGTGCAGA

TCAGCACCAAGTCCGGCGACTGGAAGTCCAAATGTTTCTATACCACCGA

CACCGAGTGCGATCTCACCGATGAGATCGTGAAAGATGTGAAACAGACC

TACCTCGCCCGGGTGTTTAGCTACCCCGCCGGCAATGTGGAGAGCACTG

GTTCCGCTGGCGAGCCTTTATACGAGAACAGCCCCGAATTTACCCCTTA

CCTCGAGACCAATTTAGGACAGCCCACCATCCAAAGCTTTGAGCAAGTT

GGCACAAAGGTGAATGTGACAGTGGAGGACGAGCGGACTTTAGTGCGGC

GGAACAACACCTTTCTCAGCCTCCGGGATGTGTTCGGCAAAGATTTAAT

CTACACACTGTATTACTGGAAGTCCTCTTCCTCCGGCAAGAAGACAGCT

AAAACCAACACAAACGAGTTTTTAATCGACGTGGATAAAGGCGAAAACT

ACTGTTTCAGCGTGCAAGCTGTGATCCCCTCCCGGACCGTGAATAGGAA

AAGCACCGATAGCCCCGTTGAGTGCATGGGCCAAGAAAAGGGCGAGTTC

CGGGAGAACTGGGTGAACGTCATCAGCGATTTAAAGAAGATCGAAGATT

TAATTCAGTCCATGCATATCGACGCCACTTTATACACAGAATCCGACGT

GCACCCCTCTTGTAAGGTGACCGCCATGAAATGTTTTTTACTGGAGCTG

-continued
CAAGTTATCTCTTTAGAGAGCGGAGACGCTAGCATCCACGACACCGTGG

AGAATTTAATCATTTTAGCCAATAACTCTTTATCCAGCAACGGCAACGT

GACAGAGTCCGGCTGCAAGGAGTGCGAAGAGCTGGAGGAGAAGAACATC

AAGGAGTTTCTGCAATCCTTTGTGCACATTGTCCAGATGTTCATCAATA

CCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 153)
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCSGGGGSGGGGSGGGGSRNLPVATPDPGMFPCLHHSQNL

LRAVSNMLQKARQTLEFYPCTSEEIDHEDITKDKTSTVEACLPLELTKN

ESCLNSRETSFITNGSCLASRKTSFMMALCLSSIYEDLKMYQVEFKTMN

AKLLMDPKRQIFLDQNMLAVIDELMQALNFNSETVPQKSSLEEPDFYKT

KIKLCILLHAFRIRAVTIDRVMSYLNASITCPPPMSVEHADIWVKSYSL

YSRERYICNSGFKRKAGTSSLTECVLNKATNVAHWTTPSLKCIRSELTQ

DPAVSVALGQTVRITCQGDSLRSYYASWYQQKPGQAPVLVIYGKNNRPS

GIPDRFSGSSSGNTASLTITGAQAEDEADYYCNSRDSSGNHVVFGGGTK

LTVGHGGGGSGGGGSGGGGSEVQLVESGGGVVRPGGSLRLSCAASGFTF

DDYGMSWVRQAPGKGLEWVSGINWNGGSTGYADSVKGRFTISRDNAKNS

LYLQMNSLRAEDTAVYYCARGRSLLFDYWGQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 154)
ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

```
AAGGAGCCCAAGAATAAGACCTTTTTAAGGTGTGAGGCCAAAAACTACA
GCGGTCGTTTCACTTGTTGGTGGCTGACCACCATTTCCACCGATTTAAC
CTTCTCCGTGAAAAGCAGCCGGGGAAGCTCCGACCCTCAAGGTGTGACA
TGTGGAGCCGCTACCCTCAGCGCTGAGAGGGTTCGTGGCGATAACAAGG
AATACGAGTACAGCGTGGAGTGCCAAGAAGATAGCGCTTGTCCCGCTGC
CGAAGAATCTTTACCCATTGAGGTGATGGTGGACGCCGTGCACAAACTC
AAGTACGAGAACTACACCTCCTCCTTCTTTATCCGGGACATCATTAAGC
CCGATCCTCCTAAGAATTTACAGCTGAAGCCTCTCAAAAATAGCCGGCA
AGTTGAGGTCTCTTGGGAATATCCCGACACTTGGAGCACACCCCACAGC
TACTTCTCTTTAACCTTTTGTGTGCAAGTTCAAGGTAAAAGCAAGCGGG
AGAAGAAAGACCGGGTGTTTACCGACAAAACCAGCGCCACCGTCATCTG
TCGGAAGAACGCCTCCATCAGCGTGAGGGCTCAAGATCGTTATTACTCC
AGCAGCTGGTCCGAGTGGGCCAGCGTGCCTTGTTCCGGCGGTGGAGGAT
CCGGAGGAGGTGGCTCCGGCGGCGGAGGATCTCGTAACCTCCCCGTGGC
TACCCCCGATCCCGGAATGTTCCCTTGTTTACACCACAGCCAGAATTTA
CTGAGGGCCGTGAGCAACATGCTGCAGAAAGCTAGGCAGACTTTAGAAT
TTTACCCTTGCACCAGCGAGGAGATCGACCATGAAGATATCACCAAGGA
CAAGACATCCACCGTGGAGGCTTGTTTACCTCTGGAGCTGACAAAGAAC
GAGTCTTGTCTCAACTCTCGTGAAACCAGCTTCATCACAAATGGCTCTT
GTTTAGCTTCCCGGAAGACCTCCTTTATGATGGCTTTATGCCTCAGCTC
CATCTACGAGGATTTAAAGATGTACCAAGTGGAGTTCAAGACCATGAAC
GCCAAGCTGCTCATGGACCCTAAACGGCAGATCTTTTTAGACCAGAACA
TGCTGGCTGTGATTGATGAGCTGATGCAAGCTTTAAACTTCAACTCCGA
GACCGTCCCTCAGAAGTCCTCCCTCGAGGAGCCCGATTTTTACAAGACA
AAGATCAAACTGTGCATTTTACTCCACGCCTTTAGGATCCGGGCCGTGA
CCATTGACCGGGTCATGAGCTATTTAAACGCCAGCATTACATGCCCCCC
TCCCATGAGCGTGGAGCACGCCGACATCTGGGTGAAGAGCTATAGCCTC
TACAGCCGGGAGAGGTATATCTGTAACAGCGGCTTCAAGAGGAAGGCCG
GCACCAGCAGCCTCACCGAGTGCGTGCTGAATAAGGCTACCAACGTGGC
TCACTGGACAACACCCTCTTTAAAGTGCATCCGGTCCGAGCTGACCCAG
GACCCTGCTGTGTCCGTGGCTCTGGGCCAGACCGTGAGGATCACCTGCC
AGGGCGACTCCCTGAGGTCCTACTACGCCTCCTGGTACCAGCAGAAGCC
CGGCCAGGCTCCTGTGCTGGTGATCTACGGCAAGAACAACAGGCCCTCC
GGCATCCCTGACAGGTTCTCCGGATCCTCCTCCGGCAACACCGCCTCCC
TGACCATCACAGGCGCTCAGGCCGAGGACGAGGCTGACTACTACTGCAA
CTCCAGGGACTCCTCCGGCAACCATGTGGTGTTCGGCGGCGGCACCAAG
CTGACCGTGGGCCATGGCGGCGGCGGCTCCGGAGGCGGCGGCAGCGGCG
GAGGAGGATCCGAGGTGCAGCTGGTGGAGTCCGGAGGAGGAGTGGTGAG
GCCTGGAGGCTCCCTGAGGCTGAGCTGTGCTGCCTCCGGCTTCACCTTC
GACGACTACGGCATGTCCTGGGTGAGGCAGGCTCCTGGAAAGGGCCTGG
AGTGGGTGTCCGGCATCAACTGGAACGGCGGATCCACCGGCTACGCCGA
TTCCGTGAAGGGCAGGTTCACCATCAGCAGGGACAACGCCAAGAACTCC
CTGTACCTGCAGATGAACTCCCTGAGGGCCGAGGACACCGCCGTGTACT
ACTGCGCCAGGGGCAGGTCCCTGCTGTTCGACTACTGGGGACAGGGCAC
CCTGGTGACCGTGTCCAGG.
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 155)
MKWVTFISLLFLFSSAYSIWELKKDVYVVELDWYPDAPGEMVVLTCDTP
EEDGITWTLDQSSEVLGSGKTLTIQVKEFGDAGQYTCHKGGEVLSHSLL
LLHKKEDGIWSTDILKDQKEPKNKTFLRCEAKNYSGRFTCWWLTTISTD
LTFSVKSSRGSSDPQGVTCGAATLSAERVRGDNKEYEYSVECQEDSACP
AAEESLPIEVMVDAVUKLKYENYTSSFFIRDIIKPDPPKNLQLKPLKNS
RQVEVSWEYPDTWSTPHSYFSLTFCVQVQGKSKREKKDRVFTDKTSATV
ICRKNASISVRAQDRYYSSSWSEWASVPCSGGGGSGGGGSGGGGSRNLP
VATPDPGMFPCLHEISQNLLRAVSNMLQKARQTLEFYPCTSEEIDUEDI
TKDKTSTVEACLPLELTKNESCLNSRETSFITNGSCLASRKTSFMMALC
LSSIYEDLKMYQVEFKTMNAKLLMDPKRQIFLDQNMLAVIDELMQALNF
NSETVPQKSSLEEPDFYKTKIKLCILLHAFRIRAVTIDRVMSYLNASIT
CPPPMSVEHADIWVKSYSLYSRERYICNSGFKRKAGTSSLTECVLNKAT
NVAHWTTPSLKCIRSELTQDPAVSVALGQTVRITCQGDSLRSYYASWYQ
QKPGQAPVLVIYGKNNRPSGIPDRFSGSSSGNTASLTITGAQAEDEADY
YCNSRDSSGNHVVFGGGTKLTVGHGGGSGGGGSGGGGSEVQLVESGGG
VVRPGGSLRLSCAASGFTFDDYGMSWVRQAPGKGLEWVSGINWNGGSTG
YADSVKGRFTISRDNAKNSLYLQMNSLRAEDTAVYYCARGRSLLFDYWG
QGTLVTVSR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 156)
ATGAAATGGGTGACCTTTATTTCTTTACTGTTCCTCTTTAGCAGCGCCT
ACTCCATTTGGGAACTGAAGAAGGACGTCTACGTGGTCGAACTGGACTG
GTATCCCGATGCTCCCGGCGAAATGGTGGTGCTCACTTGTGACACCCCC
GAAGAAGACGGCATCACTTGGACCCTCGATCAGAGCAGCGAGGTGCTGG
GCTCCGGAAAGACCCTCACAATCCAAGTTAAGGAGTTCGGAGACGCTGG
CCAATACACATGCCACAAGGGAGGCGAGGTGCTCAGCCATTCCTTATTA
```

```
TTATTACACAAGAAGGAAGACGGAATCTGGTCCACCGACATTTTAAAAG
ATCAGAAGGAGCCCAAGAATAAGACCTTTTTAAGGTGTGAGGCCAAAAA
CTACAGCGGTCGTTTCACTTGTTGGTGGCTGACCACCATTTCCACCGAT
TTAACCTTCTCCGTGAAAAGCAGCCGGGGAAGCTCCGACCCTCAAGGTG
TGACATGTGGAGCCGCTACCCTCAGCGCTGAGAGGGTTCGTGGCGATAA
CAAGGAATACGAGTACAGCGTGGAGTGCCAAGAAGATAGCGCTTGTCCC
GCTGCCGAAGAATCTTTACCCATTGAGGTGATGGTGGACGCCGTGCACA
AACTCAAGTACGAGAACTACACCTCCTCCTTCTTTATCCGGGACATCAT
TAAGCCCGATCCTCCTAAGAATTTACAGCTGAAGCCTCTCAAAAATAGC
CGGCAAGTTGAGGTCTCTTGGGAATATCCCGACACTTGGAGCACACCCC
ACAGCTACTTCTCTTTAACCTTTTGTGTGCAAGTTCAAGGTAAAAGCAA
GCGGGAGAAGAAAGACCGGGTGTTTACCGACAAAACCAGCGCCACCGTC
ATCTGTCGGAAGAACGCCTCCATCAGCGTGAGGGCTCAAGATCGTTATT
ACTCCAGCAGCTGGTCCGAGTGGGCCAGCGTGCCTTGTTCCGGCGGTGG
AGGATCCGGAGGAGGTGGCTCCGGCGGCGGAGGATCTCGTAACCTCCCC
GTGGCTACCCCCGATCCCGGAATGTTCCCTTGTTTACACCACAGCCAGA
ATTTACTGAGGGCCGTGAGCAACATGCTGCAGAAAGCTAGGCAGACTTT
AGAATTTTACCCTTGCACCAGCGAGGAGATCGACCATGAAGATATCACC
AAGGACAAGACATCCACCGTGGAGGCTTGTTTACCTCTGGAGCTGACAA
AGAACGAGTCTTGTCTCAACTCTCGTGAAACCAGCTTCATCACAAATGG
CTCTTGTTTAGCTTCCCGGAAGACCTCCTTTATGATGGCTTTATGCCTC
AGCTCCATCTACGAGGATTTAAAGATGTACCAAGTGGAGTTCAAGACCA
TGAACGCCAAGCTGCTCATGGACCCTAAACGGCAGATCTTTTTAGACCA
GAACATGCTGGCTGTGATTGATGAGCTGATGCAAGCTTTAAACTTCAAC
TCCGAGACCGTCCCTCAGAAGTCCTCCCTCGAGGAGCCCGATTTTTACA
AGACAAAGATCAAACTGTGCATTTTACTCCACGCCTTTAGGATCCGGGC
CGTGACCATTGACCGGGTCATGAGCTATTTAAACGCCAGCATTACATGC
CCCCCTCCCATGAGCGTGGAGCACGCCGACATCTGGGTGAAGAGCTATA
GCCTCTACAGCCGGGAGAGGTATATCTGTAACAGCGGCTTCAAGAGGAA
GGCCGGCACCAGCAGCCTCACCGAGTGCGTGCTGAATAAGGCTACCAAC
GTGGCTCACTGGACAACACCCTCTTTAAAGTGCATCCGGTCCGAGCTGA
CCCAGGACCCTGCTGTGTCCGTGGCTCTGGGCCAGACCGTGAGGATCAC
CTGCCAGGGCGACTCCCTGAGGTCCTACTACGCCTCCTGGTACCAGCAG
AAGCCCGGCCAGGCTCCTGTGCTGGTGATCTACGGCAAGAACAACAGGC
CCTCCGGCATCCCTGACAGGTTCTCCGGATCCTCCTCCGGCAACACCGC
CTCCCTGACCATCACAGGCGCTCAGGCCGAGGACGAGGCTGACTACTAC
TGCAACTCCAGGGACTCCTCCGGCAACCATGTGGTGTTCGGCGGCGGCA
CCAAGCTGACCGTGGGCCATGCGGCGGCGGCTCCGGAGGCGGCGGCAG
CGGCGGAGGAGGATCCGAGGTGCAGCTGGTGGAGTCCGGAGGAGGAGTG
GTGAGGCCTGGAGGCTCCCTGAGGCTGAGCTGTGCTGCCTCCGGCTTCA
CCTTCGACGACTACGGCATGTCCTGGGTGAGGCAGGCTCCTGGAAAGGG
```
```
CCTGGAGTGGGTGTCCGGCATCAACTGGAACGGCGGATCCACCGGCTAC
GCCGATTCCGTGAAGGGCAGGTTCACCATCAGCAGGGACAACGCCAAGA
ACTCCCTGTACCTGCAGATGAACTCCCTGAGGGCCGAGGACACCGCCGT
GTACTACTGCGCCAGGGGCAGGTCCCTGCTGTTCGACTACTGGGGACAG
GGCACCCTGGTGACCGTGTCCAGG.
```

Exemplary Multi-Chain Chimeric Polypeptides—Type F

In some embodiments of any of the multi-chain chimeric polypeptides described herein, the first target-binding domain and the second targeting-binding domain each independently bind specifically to a receptor for IL-7 (e.g., a soluble human IL-7), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein)

between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of any of the multi-chain chimeric polypeptides described herein, the first target-binding domain binds specifically to a receptor IL-7 and the second target-binding domain binds specifically to CD16 or a receptor for IL-21. In some embodiments of any of the multi-chain chimeric polypeptides described herein, the first target-binding domain includes a soluble IL-7 protein. In some embodiments of any of the multi-chain chimeric polypeptides described herein, the soluble IL-7 protein is a soluble human IL-7. In some embodiments of any of the multi-chain chimeric polypeptides described herein, the second antigen-binding domain includes a target-binding domain that binds specifically to CD16. In some embodiments of any of the multi-chain chimeric polypeptides described herein, the second target-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-7 (e.g., a soluble human IL-7).

In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 135)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM
GTKEH.
```

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 136)
GATTGTGATATTGAAGGTAAAGATGGCAAACAATATGAGAGTGTTCTAA

TGGTCAGCATCGATCAATTATTGGACAGCATGAAAGAAATTGGTAGCAA

TTGCCTGAATAATGAATTTAACTTTTTTAAAAGACATATCTGTGATGCT

AATAAGGAAGGTATGTTTTTATTCCGTGCTGCTCGCAAGTTGAGGCAAT

TTCTTAAAATGAATAGCACTGGTGATTTTGATCTCCACTTATTAAAAGT

TTCAGAAGGCACAACAATACTGTTGAACTGCACTGGCCAGGTTAAAGGA

AGAAAACCAGCTGCCCTGGGTGAAGCCCAACCAACAAAGAGTTTGGAAG

AAAATAAATCTTTAAAGGAACAGAAAAAACTGAATGACTTGTGTTTCCT

AAAGAGACTATTACAAGAGATAAAAACTTGTTGGAATAAAATTTTGATG

GGCACTAAAGAACAC.
```

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 197)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA
```

```
CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT.
```

In some embodiments of these multi-chain chimeric polypeptides, the sequence of soluble human IL-21 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 124)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 134)
CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCC.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 125)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC.
```

In some embodiments of these multi-chain chimeric polypeptides, the additional target-binding domain includes an scFv that specifically binds to CD16 (e.g., an anti-CD16 scFv).

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 149)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGH.
```

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 150)
TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

AACAACAGGCCCTCCGGCATCCCTGACAGGTTCTCCGGATCCTCCTCCG

GCAACACCGCCTCCCTGACCATCACAGGCGCTCAGGCCGAGGACGAGGC

TGACTACTACTGCAACTCCAGGGACTCCTCCGGCAACCATGTGGTGTTC

GGCGGCGGCACCAAGCTGACCGTGGGCCAT.
```

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 151)
EVQLVESGGGVVRPGGSLRLSCAASGFTFDDYGMSWVRQAPGKGLEWVS

GMWNGGSTGYADSVKGRFTISRDNAKNSLYLQMNSLRAEDTAVYYCARG

RSLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 152)
GAGGTGCAGCTGGTGGAGTCCGGAGGAGGAGTGGTGAGGCCTGGAGGCT

CCCTGAGGCTGAGCTGTGCTGCCTCCGGCTTCACCTTCGACGACTACGG

CATGTCCTGGGTGAGGCAGGCTCCTGGAAAGGGCCTGGAGTGGGTGTCC

GGCATCAACTGGAACGGCGGATCCACCGGCTACGCCGATTCCGTGAAGG

GCAGGTTCACCATCAGCAGGGACAACGCCAAGAACTCCCTGTACCTGCA

GATGAACTCCCTGAGGGCCGAGGACACCGCCGTGTACTACTGCGCCAGG

GGCAGGTCCCTGCTGTTCGACTACGGGGACAGGGCACCCTGGTGACCG

TGTCCAGG.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 141)
DCDIEGKDGKQYESVLMVSIDQLLDSMKEIGSNCLNNEFNEFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEHSGTTNTVAAYNLTWKSTNFKTILEWEPKPVNQVYTVQISTKSGD

WKSKCFYTTDTECDLTDEIVKDVKQTYLARVFSYPAGNVESTGSAGEPL

YENSPEFTPYLETNLGQPTIQSFEQVGTKVNVTVEDERTLVRRNNTFLS

LRDVFGKDLIYTLYYWKSSSSGKKTAKTNTNEFLIDVDKGENYCFSVQA

VIPSRTVNRKSTDSPVECMGQEKGEFRENWVNVISDLKKIEDLIQSMHI

DATLYTESDVHPSCKVTAMKCFLLELQVISLESGDASIHDTVENLIILA

NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 142)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCATAGCGGCACAACCAACACAGTCGCTGCCTATAACC

TCACTTGGAAGAGCACCAACTTCAAAACCATCCTCGAATGGGAACCCAA

ACCCGTTAACCAAGTTTACACCGTGCAGATCAGCACCAAGTCCGGCGAC

TGGAAGTCCAAATGTTTCTATACCACCGACACCGAGTGCGATCTCACCG

ATGAGATCGTGAAAGATGTGAAACAGACCTACCTCGCCCGGGTGTTTAG

CTACCCCGCCGGCAATGTGGAGAGCACTGGTTCCGCTGGCGAGCCTTTA

TACGAGAACAGCCCCGAATTTACCCCTTACCTCGAGACCAATTTAGGAC

AGCCCACCATCCAAAGCTTTGAGCAAGTTGGCACAAAGGTGAATGTGAC

AGTGGAGGACGAGCGGACTTTAGTGCGGCGGAACAACACCTTTCTCAGC

CTCCGGGATGTGTTCGGCAAAGATTTAATCTACACACTGTATTACTGGA

AGTCCTCTTCCTCCGGCAAGAAGACAGCTAAAACCAACACAAACGAGTT

TTTAATCGACGTGGATAAAGGCGAAAACTACTGTTTCAGCGTGCAAGCT

GTGATCCCCTCCCGGACCGTGAATAGGAAAAGCACCGATAGCCCCGTTG

AGTGCATGGGCCAAGAAAAGGGCGAGTTCCGGGAGAACTGGGTGAACGT

CATCAGCGATTTAAAGAAGATCGAAGATTTAATTCAGTCCATGCATATC

GACGCCACTTTATACACAGAATCCGACGTGCACCCCTCTTGTAAGGTGA

CCGCCATGAAATGTTTTTTACTGGAGCTGCAAGTTATCTCTTTAGAGAG

CGGAGACGCTAGCATCCACGACACCGTGGAGAATTTAATCATTTTAGCC

AATAACTCTTTATCCAGCAACGGCAACGTGACAGAGTCCGGCTGCAAGG

AGTGCGAAGAGCTGGAGGAGAAGAACATCAAGGAGTTTCTGCAATCCTT

TGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 143)
MKWVTFISLLFLFSSAYSDCDIEGKDGKQYESVLMVSIDQLLDSMKEIG

SNCLNNEFNEFKRHICDANKEGMELFRAARKLRQFLKMNSTGDFDLHLL

KVSEGTTILLNCTGQVKGRKPAALGEAQPTKSLEENKSLKEQKKLNDLC

FLKRLLQEIKTCWNKILMGTKEHSGTTNTVAAYNLTWKSTNEKTILEWE

-continued

PKPVNQVYTVQISTKSGDWKSKCEYTTDTECDLTDEIVKDVKQTYLARV

FSYPAGNVESTGSAGEPLYENSPEFTPYLETNLGQPTIQSFEQVGTKVN

VTVEDERTLVRRNNTELSLRDVEGKDLIYTLYYWKSSSSGKKTAKTNTN

EFLIDVDKGENYCFSVQAVIPSRTVNRKSTDSPVECMGQEKGEFRENWV

NVISDLKKIEDLIQSMHIDATLYTESDVHPSCKVTAMKCELLELQVISL

ESGDASIHDTVENLIILANNSLSSNGNVTESGCKECEELEEKNIKEFLQ

SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 144)
ATGAAGTGGGTGACCTTCATCAGCCTGCTGTTCCTGTTCTCCAGCGCCT

ACTCCGATTGCGACATCGAGGGCAAGGACGGCAAGCAGTACGAGAGCGT

GCTGATGGTGTCCATCGACCAGCTGCTGGACAGCATGAAGGAGATCGGC

TCCAACTGCCTCAACAACGAGTTCAACTTCTTCAAGCGGCACATCTGCG

ACGCCAACAAGGAGGGCATGTTCCTGTTCAGGGCCGCCAGGAAACTGCG

GCAGTTCCTGAAGATGAACTCCACCGGCGACTTCGACCTGCACCTGCTG

AAGGTGTCCGAGGGCACCACCATCCTGCTGAACTGCACCGGACAGGTGA

AGGGCCGGAAACCTGCTGCTCTGGGAGAGGCCCAACCCACCAAGAGCCT

GGAGGAGAACAAGTCCCTGAAGGAGCAGAAGAAGCTGAACGACCTGTGC

TTCCTGAAGAGGCTGCTGCAGGAGATCAAGACCTGCTGGAACAAGATCC

TGATGGGCACCAAGGAGCATAGCGGCACAACCAACACAGTCGCTGCCTA

TAACCTCACTTGGAAGAGCACCAACTTCAAAACCATCCTCGAATGGGAA

CCCAAACCCGTTAACCAAGTTTACACCGTGCAGATCAGCACCAAGTCCG

GCGACTGGAAGTCCAAATGTTTCTATACCACCGACACCGAGTGCGATCT

CACCGATGAGATCGTGAAAGATGTGAAACAGACCTACCTCGCCCGGGTG

TTTAGCTACCCCGCCGGCAATGTGGAGAGCACTGGTTCCGCTGGCGAGC

CTTTATACGAGAACAGCCCCGAATTTACCCCTTACCTCGAGACCAATTT

AGGACAGCCCACCATCCAAAGCTTTGAGCAAGTTGGCACAAAGGTGAAT

GTGACAGTGGAGGACGAGCGGACTTTAGTGCGGCGGAACAACACCTTTC

TCAGCCTCCGGGATGTGTTCGGCAAAGATTTAATCTACACACTGTATTA

CTGGAAGTCCTCTTCCTCCGGCAAGAAGACAGCTAAAACCAACACAAAC

GAGTTTTTAATCGACGTGGATAAAGGCGAAAACTACTGTTTCAGCGTGC

AAGCTGTGATCCCCTCCCGGACCGTGAATAGGAAAAGCACCGATAGCCC

CGTTGAGTGCATGGGCCAAGAAAAGGGCGAGTTCCGGGAGAACTGGGTG

AACGTCATCAGCGATTTAAAGAAGATCGAAGATTTAATTCAGTCCATGC

ATATCGACGCCACTTTATACACAGAATCCGACGTGCACCCCTCTTGTAA

GGTGACCGCCATGAAATGTTTTTTACTGGAGCTGCAAGTTATCTCTTTA

GAGAGCGGAGACGCTAGCATCCACGACACCGTGGAGAATTTAATCATTT

TAGCCAATAACTCTTTATCCAGCAACGGCAACGTGACAGAGTCCGGCTG

CAAGGAGTGCGAAGAGCTGGAGGAGAAGAACATCAAGGAGTTTCTGCAA

TCCTTTGTGCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 157)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGHGGGGSGGGGSGGGGSEVQLVESGGGVVRPGGSLRLSCAA

SGFFDDYGMSWVRQAPGKGLEWVSGINWNGGSTGYADSVKGRFTISRDN

AKNSLYLQMNSLRAEDTAVYYCARGRSLLFDYWGQGTLVTVSRITCPPP

MSVEHADIWVKSYSLYSRERYICNSGFKRKAGTSSLTECVLNKATNVAH

WTTPSLKCIRQGQDRHMIRMRQLIDIVDQLKNYVNDLVPEFLPAPEDVE

TNCEWSAFSCFQKAQLKSANTGNNERIINVSIKKLKRKPPSTNAGRRQK

HRLTCPSCDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 158)
TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

AACAACAGGCCCTCCGGCATCCCTGACAGGTTCTCCGGATCCTCCTCCG

GCAACACCGCCTCCCTGACCATCACAGGCGCTCAGGCCGAGGACGAGGC

TGACTACTACTGCAACTCCAGGGACTCCTCCGGCAACCATGTGGTGTTC

GGCGGCGGCACCAAGCTGACCGTGGGCCATGGCGGCGGCGGCTCCGGAG

GCGGCGGCAGCGGCGGAGGAGGATCCGAGGTGCAGCTGGTGGAGTCCGG

AGGAGGAGTGGTGAGGCCTGGAGGCTCCCTGAGGCTGAGCTGTGCTGCC

TCCGGCTTCACCTTCGACGACTACGGCATGTCCTGGGTGAGGCAGGCTC

CTGGAAAGGGCCTGGAGTGGGTGTCCGGCATCAACTGGAACGGCGGATC

CACCGGCTACGCCGATTCCGTGAAGGGCAGGTTCACCATCAGCAGGGAC

AACGCCAAGAACTCCCTGTACCTGCAGATGAACTCCCTGAGGGCCGAGG

ACACCGCCGTGTACTACTGCGCCAGGGGCAGGTCCCTGCTGTTCGACTA

CTGGGGACAGGGCACCCTGGTGACCGTGTCCAGGATTACATGCCCCCCT

CCCATGAGCGTGGAGCACGCCGACATCTGGGTGAAGAGCTATAGCCTCT

```
ACAGCCGGGAGAGGTATATCTGTAACAGCGGCTTCAAGAGGAAGGCCGG
CACCAGCAGCCTCACCGAGTGCGTGCTGAATAAGGCTACCAACGTGGCT
CACTGGACAACACCCTCTTTAAAGTGCATCCGGCAGGGCCAGGACAGGC
ACATGATCCGGATGAGGCAGCTCATCGACATCGTCGACCAGCTGAAGAA
CTACGTGAACGACCTGGTGCCCGAGTTTCTGCCTGCCCCCGAGGACGTG
GAGACCAACTGCGAGTGGTCCGCCTTCTCCTGCTTTCAGAAGGCCCAGC
TGAAGTCCGCCAACACCGGCAACAACGAGCGGATCATCAACGTGAGCAT
CAAGAAGCTGAAGCGGAAGCCTCCCTCCACAAACGCCGGCAGGAGGCAG
AAGCACAGGCTGACCTGCCCCAGCTGTGACTCCTACGAGAAGAAGCCCC
CCAAGGAGTTCCTGGAGAGGTTCAAGTCCCTGCTGCAGAAGATGATCCA
TCAGCACCTGTCCTCCAGGACCCACGGCTCCGAGGACTCC.
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 159)
MKWVTFISLLFLFSSAYSSELTQDPAVSVALGQTVRITCQGDSLRSYYA

SWYQQKPGQAPVLVIYGKNNRPSGIPDRFSGSSSGNTASLTITGAQAED

EADYYCNSRDSSGNHVVFGGGTKLTVGHGGGGSGGGGSGGGGSEVQLVE

SGGGVVRPGGSLRLSCAASGFTFDDYGMSWVRQAPGKGLEWVSGINWNG

GSTGYADSVKGRFTISRDNAKNSLYLQMNSLRAEDTAVYYCARGRSLLF

DYWGQGTLVTVSRITCPPPMSVEHADIWVKSYSLYSRERYICNSGFKRK

AGTSSLTECVLNKATNVAHWTTPSLKCIRQGQDRHMIRMIRQLIDIVDQ

LKNYVNDLVPEFLPAPEDVETNCEWSAFSCFQKAQLKSANTGNNERIIN

VSIKKLKRKPPSTNAGRRQKHRLTCPSCDSYEKKPPKEFLERFKSLLQK

MIHQHLSSRTHGSEDS.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 160)
ATGAAGTGGGTGACCTTCATCAGCCTGCTGTTCCTGTTCTCCAGCGCCT

ACTCCTCCGAGCTGACCCAGGACCCTGCTGTGTCCGTGGCTCTGGGCCA

GACCGTGAGGATCACCTGCCAGGGCGACTCCCTGAGGTCCTACTACGCC

TCCTGGTACCAGCAGAAGCCCGGCCAGGCTCCTGTGCTGGTGATCTACG

GCAAGAACAACAGGCCCTCCGGCATCCCTGACAGGTTCTCCGGATCCTC

CTCCGGCAACACCGCCTCCCTGACCATCACAGGCGCTCAGGCCGAGGAC

GAGGCTGACTACTACTGCAACTCCAGGGACTCCTCCGGCAACCATGTGG

TGTTCGGCGGCGGCACCAAGCTGACCGTGGGCCATGGCGGCGGCGGCTC

CGGAGGCGGCGGCAGCGGCGGAGGAGGATCCGAGGTGCAGCTGGTGGAG

TCCGGAGGAGGAGTGGTGAGGCCTGGAGGCTCCCTGAGGCTGAGCTGTG

CTGCCTCCGGCTTCACCTTCGACGACTACGGCATGTCCTGGGTGAGGCA

GGCTCCTGGAAAGGGCCTGGAGTGGGTGTCCGGCATCAACTGGAACGGC

GGATCCACCGGCTACGCCGATTCCGTGAAGGGCAGGTTCACCATCAGCA

GGGACAACGCCAAGAACTCCCTGTACCTGCAGATGAACTCCCTGAGGGC

CGAGGACACCGCCGTGTACTACTGCGCCAGGGGCAGGTCCCTGCTGTTC

GACTACTGGGGACAGGGCACCCTGGTGACCGTGTCCAGGATTACATGCC

CCCCTCCCATGAGCGTGGAGCACGCCGACATCTGGGTGAAGAGCTATAG

CCTCTACAGCCGGGAGAGGTATATCTGTAACAGCGGCTTCAAGAGGAAG

GCCGGCACCAGCAGCCTCACCGAGTGCGTGCTGAATAAGGCTACCAACG

TGGCTCACTGGACAACACCCTCTTTAAAGTGCATCCGGCAGGGCCAGGA

CAGGCACATGATCCGGATGAGGCAGCTCATCGACATCGTCGACCAGCTG

AAGAACTACGTGAACGACCTGGTGCCCGAGTTTCTGCCTGCCCCGAGGA

CGTGGAGACCAACTGCGAGTGGTCCGCCTTCTCCTGCTTTCAGAAGGCC

CAGCTGAAGTCCGCCAACACCGGCAACAACGAGCGGATCATCAACGTGA

GCATCAAGAAGCTGAAGCGGAAGCCTCCCTCCACAAACGCCGGCAGGAG

GCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGA

TCCATCAGCACCTGTCCTCCAGGACCCACGGCTCCGAGGACTCC.
```

Exemplary Multi-Chain Chimeric Polypeptides—Type G

In some embodiments of any of the multi-chain chimeric polypeptides described herein, the first target-binding domain and the second targeting-binding domain each independently bind specifically to TGF-β (e.g., a human TGFβRII receptor), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein)

between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of any of the multi-chain chimeric polypeptides described herein, the first target-binding domain and the second targeting-binding domain each independently bind specifically to TGF-β, CD16, or a receptor for IL-21. In some embodiments of any of the multi-chain chimeric polypeptides described herein, the first target-binding domain binds specifically to a TGF-β and the second target-binding domain binds specifically to CD16 or a receptor of IL-21. In some embodiments of any of the multi-chain chimeric polypeptides described herein, the first target-binding domain is a soluble TGF-β receptor. In some embodiments of any of the multi-chain chimeric polypeptides described herein, soluble TGF-β receptor is a soluble TGFβRII receptor. In some embodiments of any of the multi-chain chimeric polypeptides described herein, the second target-binding domain binds specifically to CD16. In some embodiments of any of the multi-chain chimeric polypeptides described herein, the second antigen-binding domain includes an antigen-binding domain that binds specifically to CD16. In some embodiments of any of the multi-chain chimeric polypeptides described herein, the second antigen-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the second target-binding domain includes a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a TGF βRII receptor (e.g., a soluble human TGF βRII receptor). In some embodiments of these multi-chain chimeric polypeptides, the soluble human TGF-βRII includes a first sequence of soluble human TGF-β RII and a second sequence of soluble human TGF-β RII. In some embodiments of these multi-chain chimeric polypeptides, the soluble human TGF-β RII includes a linker disposed between the first sequence of soluble human TGF-β RII and the second sequence of soluble human TGF-β RII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT.

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 60)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD.

In some embodiments of these multi-chain chimeric polypeptides, the soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC.

In some embodiments of these multi-chain chimeric polypeptides, the sequence of soluble human IL-21 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 134)
CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 125)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC.

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 149)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 150)
TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

AACAACAGGCCCTCCGGCATCCCTGACAGGTTCTCCGGATCCTCCTCCG

GCAACACCGCCTCCCTGACCATCACAGGCGCTCAGGCCGAGGACGAGGC

TGACTACTACTGCAACTCCAGGGACTCCTCCGGCAACCATGTGGTGTTC

GGCGGCGGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 151)
EVQLVESGGGVVRPGGSLRLSCAASGFTFDDYGMSWVRQAPGKGLEWVS

GMWNGGSTGYADSVKGRFTISRDNAKNSLYLQMNSLRAEDTAVYYCARG

RSLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 152)
GAGGTGCAGCTGGTGGAGTCCGGAGGAGGAGTGGTGAGGCCTGGAGGCT

CCCTGAGGCTGAGCTGTGCTGCCTCCGGCTTCACCTTCGACGACTACGG

CATGTCCTGGGTGAGGCAGGCTCCTGGAAAGGGCCTGGAGTGGGTGTCC

GGCATCAACTGGAACGGCGGATCCACCGGCTACGCCGATTCCGTGAAGG

GCAGGTTCACCATCAGCAGGGACAACGCCAAGAACTCCCTGTACCTGCA

GATGAACTCCCTGAGGGCCGAGGACACCGCCGTGTACTACTGCGCCAGG

GGCAGGTCCCTGCTGTTCGACTACTGGGGACAGGGCACCCTGGTGACCG

TGTCCAGG.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDSGTTNTV

AAYNLTWKSTNFKTILEWEPKPVNQVYTVQISTKSGDWKSKCFYTTDTE

CDLTDEIVKDVKQTYLARVFSYPAGNVESTGSAGEPLYENSPEFTPYLE

TNLGQPTIQSFEQVGTKVNVTVEDERTLVRRNNTFLSLRDVFGKDLIYT

LYYWKSSSSGKKTAKTNTNEFLIDVDKGENYCFSVQAVIPSRTVNRKST

DSPVECMGQEKGEFRENWVNVISDLKKIEDLIQSMHIDATLYTESDVHP

SCKVTAMKCFLLELQVISLESGDASIHDTVENLIILANNSLSSNGNVTE

SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACAGCGGCACAACCAACACAGTC

GCTGCCTATAACCTCACTTGGAAGAGCACCAACTTCAAAACCATCCTCG

AATGGGAACCCAAACCCGTTAACCAAGTTTACACCGTGCAGATCAGCAC

CAAGTCCGGCGACTGGAAGTCCAAATGTTTCTATACCACCGACACCGAG

TGCGATCTCACCGATGAGATCGTGAAAGATGTGAAACAGACCTACCTCG

CCCGGGTGTTTAGCTACCCCGCCGGCAATGTGGAGAGCACTGGTTCCGC

TGGCGAGCCTTTATACGAGAACAGCCCCGAATTTACCCCTTACCTCGAG

ACCAATTTAGGACAGCCCACCATCCAAAGCTTTGAGCAAGTTGGCACAA

AGGTGAATGTGACAGTGGAGGACGAGCGGACTTTAGTGCGGCGGAACAA

CACCTTTCTCAGCCTCCGGGATGTGTTCGGCAAAGATTTAATCTACACA

CTGTATTACTGGAAGTCCTCTTCCTCCGGCAAGAAGACAGCTAAAACCA

ACACAAACGAGTTTTTAATCGACGTGGATAAAGGCGAAAACTACTGTTT

CAGCGTGCAAGCTGTGATCCCCTCCCGGACCGTGAATAGGAAAAGCACC

GATAGCCCCGTTGAGTGCATGGGCCAAGAAAAGGGCGAGTTCCGGGAGA

ACTGGGTGAACGTCATCAGCGATTTAAAGAAGATCGAAGATTTAATTCA

GTCCATGCATATCGACGCCACTTTATACACAGAATCCGACGTGCACCCC

TCTTGTAAGGTGACCGCCATGAAATGTTTTTTACTGGAGCTGCAAGTTA

TCTCTTTAGAGAGCGGAGACGCTAGCATCCACGACACCGTGGAGAATTT

AATCATTTTAGCCAATAACTCTTTATCCAGCAACGGCAACGTGACAGAG

TCCGGCTGCAAGGAGTGCGAAGAGCTGGAGGAGAAGAACATCAAGGAGT

TTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)
MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDSGTTNTVAAYNLTWKSTNFKTILEWEPKPVNQVYTVQI

STKSGDWKSKCFYTTDTECDLTDEIVKDVKQTYLARVFSYPAGNVESTG

SAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENY

CFSVQAVIPSRTVNRKSTDSPVECMGQEKGEFRENWVNVISDLKKIEDL

IQSMHIDATLYTESDVHPSCKVTAMKCFLLELQVISLESGDASIHDTVE

NLIILANNSLSSNGNVTESGCKECEELEEKNIKEFLQSFVHIVQMFINT

S.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)
ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGCG

ATGTCAGGTTCAGCACCTGCGATAATCAGAAGTCCTGCATGTCCAACTGC

AGCATCACCTCCATCTGCGAGAAGCCCCAAGAAGTGTGCGTGGCCGTGTG

GCGGAAAAATGACGAGAACATCACCCTGGAGACCGTGTGTCACGACCCCA

AGCTCCCTTATCACGACTTCATTCTGGAGGACGCTGCCTCCCCCAAATGC

ATCATGAAGGAGAAGAAGAAGCCCGGAGAGACCTTCTTTATGTGTTCCTG

TAGCAGCGACGAGTGTAACGACAACATCATCTTCAGCGAAGAGTACAACA

CCAGCAACCCTGATGGAGGTGGCGGATCCGGAGGTGGAGGTTCTGGTGGA

GGTGGGAGTATTCCTCCCCACGTGCAGAAGAGCGTGAATAATGACATGAT

CGTGACCGATAACAATGGCGCCGTGAAATTTCCCCAGCTGTGCAAATTCT

GCGATGTGAGGTTTTCCACCTGCGACAACCAGAAGTCCTGTATGAGCAAC

TGCTCCATCACCTCCATCTGTGAGAAGCCTCAGGAGGTGTGCGTGGCTGT

CTGGCGGAAGAATGACGAGAATATCACCCTGGAAACCGTCTGCCACGATC

CCAAGCTGCCCTACCACGATTTCATCCTGGAAGACGCCGCCAGCCCTAAG

TGCATCATGAAAGAGAAAAAGAAGCCTGGCGAGACCTTTTTCATGTGCTC

CTGCAGCAGCGACGAATGCAACGACAATATCATCTTTAGCGAGGAATACA

ATACCAGCAACCCCGACAGCGGCACAACCAACACAGTCGCTGCCTATAAC

CTCACTTGGAAGAGCACCAACTTCAAAACCATCCTCGAATGGGAACCCAA

ACCCGTTAACCAAGTTTACACCGTGCAGATCAGCACCAAGTCCGGCGACT

GGAAGTCCAAATGTTTCTATACCACCGACACCGAGTGCGATCTCACCGAT

GAGATCGTGAAAGATGTGAAACAGACCTACCTCGCCCGGGTGTTTAGCTA

CCCCGCCGGCAATGTGGAGAGCACTGGTTCCGCTGGCGAGCCTTTATACG

AGAACAGCCCCGAATTTACCCCTTACCTCGAGACCAATTTAGGACAGCCC

ACCATCCAAAGCTTTGAGCAAGTTGGCACAAAGGTGAATGTGACAGTGGA

GGACGAGCGGACTTTAGTGCGGCGGAACAACACCTTTCTCAGCCTCCGGG

ATGTGTTCGGCAAAGATTTAATCTACACACTGTATTACTGGAAGTCCTCT

TCCTCCGGCAAGAAGACAGCTAAAACCAACACAAACGAGTTTTTAATCGA

CGTGGATAAAGGCGAAAACTACTGTTTCAGCGTGCAAGCTGTGATCCCCT

CCCGGACCGTGAATAGGAAAAGCACCGATAGCCCCGTTGAGTGCATGGGC

CAAGAAAAGGGCGAGTTCCGGGAGAACTGGGTGAACGTCATCAGCGATTT

AAAGAAGATCGAAGATTTAATTCAGTCCATGCATATCGACGCCACTTTAT

ACACAGAATCCGACGTGCACCCCTCTTGTAAGGTGACCGCCATGAAATGT

TTTTTACTGGAGCTGCAAGTTATCTCTTTAGAGAGCGGAGACGCTAGCAT

CCACGACACCGTGGAGAATTTAATCATTTTAGCCAATAACTCTTTATCCA

GCAACGGCAACGTGACAGAGTCCGGCTGCAAGGAGTGCGAAGAGCTGGAG

GAGAAGAACATCAAGGAGTTTCTGCAATCCTTTGTGCACATTGTCCAGAT

GTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 157)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGHGGGGSGGGGSGGGGSEVQLVESGGGVVRPGGSLRLSCAA

SGFTFDDYGMSWVRQAPGKGLEWVSGINWNGGSTGYADSVKGRFTISRD

NAKNSLYLQMNSLRAEDTAVYYCARGRSLLFDYWGQGTLVTVSRITCPP

PMSVEHADIWVKSYSLYSRERYICNSGFKRKAGTSSLTECVLNKATNVA

HWTTPSLKCIRQGQDRHMIRMRQLIDIVDQLKNYVNDLVPEFLPAPEDV

ETNCEWSAFSCFQKAQLKSANTGNNERIINVSIKKLRKPPSTNAGRRQ

KHRLTCPSCDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

AACAACAGGCCCTCCGGCATCCCTGACAGGTTCTCCGGATCCTCCTCCG

GCAACACCGCCTCCCTGACCATCACAGGCGCTCAGGCCGAGGACGAGGC

TGACTACTACTGCAACTCCAGGGACTCCTCCGGCAACCATGTGGTGTTC

GGCGGCGGCACCAAGCTGACCGTGGGCCATGGCGGCGGCGGCTCCGGAG

GCGGCGGCAGCGGCGGAGGAGGATCCGAGGTGCAGCTGGTGGAGTCCGG

AGGAGGAGTGGTGAGGCCTGGAGGCTCCCTGAGGCTGAGCTGTGCTGCC

```
TCCGGCTTCACCTTCGACGACTACGGCATGTCCTGGGTGAGGCAGGCTC

CTGGAAAGGGCCTGGAGTGGGTGTCCGGCATCAACTGGAACGGCGGATC

CACCGGCTACGCCGATTCCGTGAAGGGCAGGTTCACCATCAGCAGGGAC

AACGCCAAGAACTCCCTGTACCTGCAGATGAACTCCCTGAGGGCCGAGG

ACACCGCCGTGTACTACTGCGCCAGGGGCAGGTCCCTGCTGTTCGACTA

CTGGGGACAGGGCACCCTGGTGACCGTGTCCAGGATTACATGCCCCCT

CCCATGAGCGTGGAGCACGCCGACATCTGGGTGAAGAGCTATAGCCTCT

ACAGCCGGGAGAGGTATATCTGTAACAGCGGCTTCAAGAGGAAGGCCGG

CACCAGCAGCCTCACCGAGTGCGTGCTGAATAAGGCTACCAACGTGGCT

CACTGGACAACACCCTCTTTAAAGTGCATCCGGCAGGGCCAGGACAGGC

ACATGATCCGGATGAGGCAGCTCATCGACATCGTCGACCAGCTGAAGAA

CTACGTGAACGACCTGGTGCCCGAGTTTCTGCCTGCCCCCGAGGACGTG

GAGACCAACTGCGAGTGGTCCGCCTTCTCCTGCTTTCAGAAGGCCCAGC

TGAAGTCCGCCAACACCGGCAACAACGAGCGGATCATCAACGTGAGCAT

CAAGAAGCTGAAGCGGAAGCCTCCCTCCACAAACGCCGGCAGGAGGCAG

AAGCACAGGCTGACCTGCCCCAGCTGTGACTCCTACGAGAAGAAGCCCC

CCAAGGAGTTCCTGGAGAGGTTCAAGTCCCTGCTGCAGAAGATGATCCA

TCAGCACCTGTCCTCCAGGACCCACGGCTCCGAGGACTCC.
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 159)
MKWVTFISLLFLFSSAYSSELTQDPAVSVALGQTVRITCQGDSLRSYYA

SWYQQKPGQAPVLVIYGKNNRPSGIPDRFSGSSSGNTASLTITGAQAED

EADYYCNSRDSSGNHVVFGGGTKLTVGHGGGSGGGGSGGGGSEVQLVE

SGGGVVRPGGSLRLSCAASGFTFDDYGMSWVRQAPGKGLEWVSGINWNG

GSTGYADSVKGRFTISRDNAKNSLYLQMNSLRAEDTAVYYCARGRSLLF

DYWGQGTLVTVSRITCPPPMSVEHADIWVKSYSLYSRERYICNSGFKRK

AGTSSLTECVLNKATNVAHWTTPSLKCIRQGQDRHMIRMIRQLIDIVDQ

LKNYVNDLVPEFLPAPEDVETNCEWSAFSCFQKAQLKSANTGNNERIIN

VSIKKLKRKPPSTNAGRRQKHRLTCPSCDSYEKKPPKEFLERFKSLLQK

MIHQHLSSRTHGSEDS.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 160)
ATGAAGTGGGTGACCTTCATCAGCCTGCTGTTCCTGTTCTCCAGCGCCT

ACTCCTCCGAGCTGACCCAGGACCCTGCTGTGTCCGTGGCTCTGGGCCA

GACCGTGAGGATCACCTGCCAGGGCGACTCCCTGAGGTCCTACTACGCC

TCCTGGTACCAGCAGAAGCCCGGCCAGGCTCCTGTGCTGGTGATCTACG

GCAAGAACAACAGGCCCTCCGGCATCCCTGACAGGTTCTCCGGATCCTC

CTCCGGCAACACCGCCTCCCTGACCATCACAGGCGCTCAGGCCGAGGAC

GAGGCTGACTACTACTGCAACTCCAGGGACTCCTCCGGCAACCATGTGG

TGTTCGGCGGCGGCACCAAGCTGACCGTGGGCCATGGCGGCGGCGGCTC

CGGAGGCGGCGGCAGCGGCGGAGGAGGATCCGAGGTGCAGCTGGTGGAG

TCCGGAGGAGGAGTGGTGAGGCCTGGAGGCTCCCTGAGGCTGAGCTGTG

CTGCCTCCGGCTTCACCTTCGACGACTACGGCATGTCCTGGGTGAGGCA

GGCTCCTGGAAAGGGCCTGGAGTGGGTGTCCGGCATCAACTGGAACGGC

GGATCCACCGGCTACGCCGATTCCGTGAAGGGCAGGTTCACCATCAGCA

GGGACAACGCCAAGAACTCCCTGTACCTGCAGATGAACTCCCTGAGGGC

CGAGGACACCGCCGTGTACTACTGCGCCAGGGGCAGGTCCCTGCTGTTC

GACTACTGGGGACAGGGCACCCTGGTGACCGTGTCCAGGATTACATGCC

CCCTCCCATGAGCGTGGAGCACGCCGACATCTGGGTGAAGAGCTATAG

CCTCTACAGCCGGGAGAGGTATATCTGTAACAGCGGCTTCAAGAGGAAG

GCCGGCACCAGCAGCCTCACCGAGTGCGTGCTGAATAAGGCTACCAACG

TGGCTCACTGGACAACACCCTCTTTAAAGTGCATCCGGCAGGGCCAGGA

CAGGCACATGATCCGGATGAGGCAGCTCATCGACATCGTCGACCAGCTG

AAGAACTACGTGAACGACCTGGTGCCCGAGTTTCTGCCTGCCCCCGAGG

ACGTGGAGACCAACTGCGAGTGGTCCGCCTTCTCCTGCTTTCAGAAGGC

CCAGCTGAAGTCCGCCAACACCGGCAACAACGAGCGGATCATCAACGTG

AGCATCAAGAAGCTGAAGCGGAAGCCTCCCTCCACAAACGCCGGCAGGA

GGCAGAAGCACAGGCTGACCTGCCCCAGCTGTGACTCCTACGAGAAGAA

GCCCCCCAAGGAGTTCCTGGAGAGGTTCAAGTCCCTGCTGCAGAAGATG

ATCCATCAGCACCTGTCCTCCAGGACCCACGGCTCCGAGGACTCC.
```

Exemplary Multi-Chain Chimeric Polypeptides—Type H

In some embodiments of any of the multi-chain chimeric polypeptides described herein, the first target-binding domain and the second targeting-binding domain each independently bind specifically to a receptor of IL-7. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to a receptor for IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain include a soluble IL-7 (e.g., a soluble human IL-7). In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 135)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 141)
DCDIEGKDGKQYESVLMVSIDQLLDSMKEIGSNCLNNEFNEFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEHSGTTNTVAAYNLTWKSTNFKTILEWEPKPVNQVYTVQISTKSGD

WKSKCFYTTDTECDLTDEIVKDVKQTYLARVFSYPAGNVESTGSAGEPL

YENSPEFTPYLETNLGQPTIQSFEQVGTKVNVTVEDERTLVRRNNTFLS

LRDVEGKDLIYTLYYWKSSSSGKKTAKTNTNEFLIDVDKGENYCFSVQA

VIPSRTVNRKSTDSPVECMGQEKGEFRENWVNVISDLKKIEDLIQSMHI

DATLYTESDVHPSCKVTAMKCFLLELQVISLESGDASIHDTVENLIILA

NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 142)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCATAGCGGCACAACCAACACAGTCGCTGCCTATAACC

TCACTTGGAAGAGCACCAACTTCAAAACCATCCTCGAATGGGAACCCAA

ACCCGTTAACCAAGTTTACACCGTGCAGATCAGCACCAAGTCCGGCGAC

-continued

TGGAAGTCCAAATGTTTCTATACCACCGACACCGAGTGCGATCTCACCG

ATGAGATCGTGAAAGATGTGAAACAGACCTACCTCGCCCGGGTGTTTAG

CTACCCCGCCGGCAATGTGGAGAGCACTGGTTCCGCTGGCGAGCCTTTA

TACGAGAACAGCCCCGAATTTACCCCTTACCTCGAGACCAATTTAGGAC

AGCCCACCATCCAAAGCTTTGAGCAAGTTGGCACAAAGGTGAATGTGAC

AGTGGAGGACGAGCGGACTTTAGTGCGGCGGAACAACACCTTTCTCAGC

CTCCGGGATGTGTTCGGCAAAGATTTAATCTACACACTGTATTACTGGA

AGTCCTCTTCCTCCGGCAAGAAGACAGCTAAAACCAACACAAACGAGTT

TTTAATCGACGTGGATAAAGGCGAAAACTACTGTTTCAGCGTGCAAGCT

GTGATCCCCTCCCGGACCGTGAATAGGAAAAGCACCGATAGCCCCGTTG

AGTGCATGGGCCAAGAAAAGGGCGAGTTCCGGGAGAACTGGGTGAACGT

CATCAGCGATTTAAAGAAGATCGAAGATTTAATTCAGTCCATGCATATC

GACGCCACTTTATACACAGAATCCGACGTGCACCCCTCTTGTAAGGTGA

CCGCCATGAAATGTTTTTTACTGGAGCTGCAAGTTATCTCTTTAGAGAG

CGGAGACGCTAGCATCCACGACACCGTGGAGAATTTAATCATTTTAGCC

AATAACTCTTTATCCAGCAACGGCAACGTGACAGAGTCCGGCTGCAAGG

AGTGCGAAGAGCTGGAGGAGAAGAACATCAAGGAGTTTCTGCAATCCTT

TGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 143)
MKWVTFISLLFLFSSAYSDCDIEGKDGKQYESVLMVSIDQLLDSMKEIG

SNCLNNEFNEFKRHICDANKEGMELFRAARKLRQFLKMNSTGDFDLHLL

KVSEGTTILLNCTGQVKGRKPAALGEAQPTKSLEENKSLKEQKKLNDLC

FLKRLLQEIKTCWNKILMGTKEHSGTTNTVAAYNLTWKSTNEKTILEWE

PKPVNQVYTVQISTKSGDWKSKCEYTTDTECDLTDEIVKDVKQTYLARV

FSYPAGNVESTGSAGEPLYENSPEFTPYLETNLGQPTIQSFEQVGTKVN

VTVEDERTLVRRNNTELSLRDVEGKDLIYTLYYWKSSSSGKKTAKTNTN

EFLIDVDKGENYCFSVQAVIPSRTVNRKSTDSPVECMGQEKGEFRENWV

NVISDLKKIEDLIQSMHIDATLYTESDVHPSCKVTAMKCELLELQVISL

ESGDASIHDTVENLIILANNSLSSNGNVTESGCKECEELEEKNIKEFLQ

SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 144)
ATGAAGTGGGTGACCTTCATCAGCCTGCTGTTCCTGTTCTCCAGCGCCT

ACTCCGATTGCGACATCGAGGGCAAGGACGGCAAGCAGTACGAGAGCGT

GCTGATGGTGTCCATCGACCAGCTGCTGGACAGCATGAAGGAGATCGGC

TCCAACTGCCTCAACAACGAGTTCAACTTCTTCAAGCGGCACATCTGCG

ACGCCAACAAGGAGGGCATGTTCCTGTTCAGGGCCGCCAGGAAACTGCG

GCAGTTCCTGAAGATGAACTCCACCGGCGACTTCGACCTGCACCTGCTG

AAGGTGTCCGAGGGCACCACCATCCTGCTGAACTGCACCGGACAGGTGA

AGGGCCGGAAACCTGCTGCTCTGGGAGAGGCCCAACCCACCAAGAGCCT

GGAGGAGAACAAGTCCCTGAAGGAGCAGAAGAAGCTGAACGACCTGTGC

TTCCTGAAGAGGCTGCTGCAGGAGATCAAGACCTGCTGGAACAAGATCC

TGATGGGCACCAAGGAGCATAGCGGCACAACCAACACAGTCGCTGCCTA

TAACCTCACTTGGAAGAGCACCAACTTCAAAACCATCCTCGAATGGGAA

CCCAAACCCGTTAACCAAGTTTACACCGTGCAGATCAGCACCAAGTCCG

GCGACTGGAAGTCCAAATGTTTCTATACCACCGACACCGAGTGCGATCT

CACCGATGAGATCGTGAAAGATGTGAAACAGACCTACCTCGCCCGGGTG

TTTAGCTACCCCGCCGGCAATGTGGAGAGCACTGGTTCCGCTGGCGAGC

CTTTATACGAGAACAGCCCCGAATTTACCCCTTACCTCGAGACCAATTT

AGGACAGCCCACCATCCAAAGCTTTGAGCAAGTTGGCACAAAGGTGAAT

GTGACAGTGGAGGACGAGCGGACTTTAGTGCGGCGGAACAACACCTTTC

TCAGCCTCCGGGATGTGTTCGGCAAAGATTTAATCTACACACTGTATTA

CTGGAAGTCCTCTTCCTCCGGCAAGAAGACAGCTAAAACCAACACAAAC

GAGTTTTTAATCGACGTGGATAAAGGCGAAAACTACTGTTTCAGCGTGC

AAGCTGTGATCCCCTCCCGGACCGTGAATAGGAAAAGCACCGATAGCCC

CGTTGAGTGCATGGGCCAAGAAAAGGGCGAGTTCCGGGAGAACTGGGTG

AACGTCATCAGCGATTTAAAGAAGATCGAAGATTTAATTCAGTCCATGC

ATATCGACGCCACTTTATACACAGAATCCGACGTGCACCCCTCTTGTAA

GGTGACCGCCATGAAATGTTTTTTACTGGAGCTGCAAGTTATCTCTTTA

GAGAGCGGAGACGCTAGCATCCACGACACCGTGGAGAATTTAATCATTT

TAGCCAATAACTCTTTATCCAGCAACGGCAACGTGACAGAGTCCGGCTG

CAAGGAGTGCGAAGAGCTGGAGGAGAAGAACATCAAGGAGTTTCTGCAA

TCCTTTGTGCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 137)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

-continued
GTKEHITCPPPMSVEHADIWVKSYSLYSRERYICNSGFKRKAGTSSLTE

CVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 138)
GATTGTGATATTGAAGGTAAAGATGGCAAACAATATGAGAGTGTTCTAA

TGGTCAGCATCGATCAATTATTGGACAGCATGAAAGAAATTGGTAGCAA

TTGCCTGAATAATGAATTTAACTTTTTTAAAAGACATATCTGTGATGCT

AATAAGGAAGGTATGTTTTTATTCCGTGCTGCTCGCAAGTTGAGGCAAT

TTCTTAAAATGAATAGCACTGGTGATTTTGATCTCCACTTATTAAAAGT

TTCAGAAGGCACAACAATACTGTTGAACTGCACTGGCCAGGTTAAAGGA

AGAAAACCAGCTGCCCTGGGTGAAGCCCAACCAACAAAGAGTTTGGAAG

AAAATAAATCTTTAAAGGAACAGAAAAAACTGAATGACTTGTGTTTCCT

AAAGAGACTATTACAAGAGATAAAAACTTGTTGGAATAAAATTTTGATG

GGCACTAAAGAACACATCACGTGCCCTCCCCCCATGTCCGTGGAACACG

CAGACATCTGGGTCAAGAGCTACAGCTTGTACTCCAGGGAGCGGTACAT

TTGTAACTCTGGTTTCAAGCGTAAAGCCGGCACGTCCAGCCTGACGGAG

TGCGTGTTGAACAAGGCCACGAATGTCGCCCACTGGACAACCCCCAGTC

TCAAATGCATTAGA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 139)
MKWVTFISLLFLFSSAYSDCDIEGKDGKQYESVLMVSIDQLLDSMKEIG

SNCLNNEFNFFKRHICDANKEGMFLFRAARKLRQFLKMNSTGDFDLHLL

KVSEGTTILLNCTGQVKGRKPAALGEAQPTKSLEENKSLKEQKKLNDLC

FLKRLLQEIKTCWNKILMGTKEHITCPPPMSVEHADIWVKSYSLYSRER

YICNSGFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 140)
ATGAAGTGGGTGACCTTCATCAGCCTGCTGTTCCTGTTCTCCAGCGCCT

ACTCCGATTGCGACATCGAGGGCAAGGACGGCAAGCAGTACGAGAGCGT

GCTGATGGTGTCCATCGACCAGCTGCTGGACAGCATGAAGGAGATCGGC

TCCAACTGCCTCAACAACGAGTTCAACTTCTTCAAGCGGCACATCTGCG

ACGCCAACAAGGAGGGCATGTTCCTGTTCAGGGCCGCCAGGAAACTGCG

GCAGTTCCTGAAGATGAACTCCACCGGCGACTTCGACCTGCACCTGCTG

AAGGTGTCCGAGGGCACCACCATCCTGCTGAACTGCACCGGACAGGTGA

AGGGCCGGAAACCTGCTGCTCTGGGAGAGGCCCAACCCACCAAGAGCCT

GGAGGAGAACAAGTCCCTGAAGGAGCAGAAGAAGCTGAACGACCTGTGC

TTCCTGAAGAGGCTGCTGCAGGAGATCAAGACCTGCTGGAACAAGATCC

TGATGGGCACCAAGGAGCATATTACATGCCCCCCTCCCATGAGCGTGGA

GCACGCCGACATCTGGGTGAAGAGCTATAGCCTCTACAGCCGGGAGAGG

TATATCTGTAACAGCGGCTTCAAGAGGAAGGCCGGCACCAGCAGCCTCA

CCGAGTGCGTGCTGAATAAGGCTACCAACGTGGCTCACTGGACAACACC

CTCTTTAAAGTGCATCCGG.

Exemplary Multi-Chain Chimeric Polypeptides—Type I

In some embodiments of any of the multi-chain chimeric polypeptides described herein, the first target-binding domain and the second targeting-binding domain each independently bind specifically to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain is a soluble TGF-β receptor (e.g., a soluble TGF-β RII receptor, e.g., a soluble human TGF-β RII). In some embodiments of these multi-chain chimeric polypeptides, the soluble human TGF-β RII includes a first sequence of soluble human TGF-βRII and a second sequence of soluble human TGF-β RII. In some embodiments of these multi-chain chimeric polypeptides, the soluble human TGF-βRII includes a linker disposed between the first sequence of soluble human TGF-β RII and the second sequence of soluble human TGF-β RII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNC

SITSICEKPQEVCVAVWRKNDENITLETVCHDPKLPYHDFILEDAASPK

CIMKEKKKPGETFFMCSCSSDECNDNIIFSEEYNTSNPD.

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT.

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 60)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDSGTTNTV

AAYNLTWKSTNFKTILEWEPKPVNQVYTVQISTKSGDWKSKCFYTTDTE

CDLTDEIVKDVKQTYLARVFSYPAGNVESTGS AGEPLYENSPEFTPYL

ETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKS

TDSPVECMGQEKGEFRENWVNVISDLKKIEDLIQSMHIDATLYTESDVH

PSCKVTAMKCFLLELQVISLESGDASIHDTVENLIILANNSLSSNGNVT

ESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACAGCGGCACAACCAACACAGTC

GCTGCCTATAACCTCACTTGGAAGAGCACCAACTTCAAAACCATCCTCG

AATGGGAACCCAAACCCGTTAACCAAGTTTACACCGTGCAGATCAGCAC

CAAGTCCGGCGACTGGAAGTCCAAATGTTTCTATACCACCGACACCGAG

TGCGATCTCACCGATGAGATCGTGAAAGATGTGAAACAGACCTACCTCG

CCCGGGTGTTTAGCTACCCCGCCGGCAATGTGGAGAGCACTGGTTCCGC

TGGCGAGCCTTTATACGAGAACAGCCCCGAATTTACCCCTTACCTCGAG

ACCAATTTAGGACAGCCCACCATCCAAAGCTTTGAGCAAGTTGGCACAA

AGGTGAATGTGACAGTGGAGGACGAGCGGACTTTAGTGCGGCGGAACAA

CACCTTTCTCAGCCTCCGGGATGTGTTCGGCAAAGATTTAATCTACACA

CTGTATTACTGGAAGTCCTCTTCCTCCGGCAAGAAGACAGCTAAAACCA

ACACAAACGAGTTTTTAATCGACGTGGATAAAGGCGAAAACTACTGTTT

CAGCGTGCAAGCTGTGATCCCCTCCCGGACCGTGAATAGGAAAAGCACC

GATAGCCCCGTTGAGTGCATGGGCCAAGAAAAGGGCGAGTTCCGGGAGA

ACTGGGTGAACGTCATCAGCGATTTAAAGAAGATCGAAGATTTAATTCA

GTCCATGCATATCGACGCCACTTTATACACAGAATCCGACGTGCACCCC

TCTTGTAAGGTGACCGCCATGAAATGTTTTTTACTGGAGCTGCAAGTTA

TCTCTTTAGAGAGCGGAGACGCTAGCATCCACGACACCGTGGAGAATTT

AATCATTTTAGCCAATAACTCTTTATCCAGCAACGGCAACGTGACAGAG

TCCGGCTGCAAGGAGTGCGAAGAGCTGGAGGAGAAGAACATCAAGGAGT

TTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 163)
MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDSGTTNTVAAYNLTWKSTNFKTILEWEPKPVNQVYTVQI

STKSGDWKSKCFYTTDTECDLTDEIVKDVKQTYLARVFSYPAGNVESTG

SAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENY

CFSVQAVIPSRTVNRKSTDSPVECMGQEKGEFRENWVNVISDLKKIEDL

IQSMHIDATLYTESDVHPSCKVTAMKCFLLELQVISLESGDASIHDTVE

NLIILANNSLSSNGNVTESGCKECEELEEKNIKEFLQSFVHIVQMFINT

S.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 164)
ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCTCCATCACCTCCATCTGTGAAGAGCCTCAGGAGGT

GTGCGTGGCTGTCTGGCGGAAGAATGACGAGAATATCACCCTGGAAACC
```

-continued
```
GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACAGCGGCACAACCAACA

CAGTCGCTGCCTATAACCTCACTTGGAAGAGCACCAACTTCAAAACCAT

CCTCGAATGGGAACCCAAACCCGTTAACCAAGTTTACACCGTGCAGATC

AGCACCAAGTCCGGCGACTGGAAGTCCAAATGTTTCTATACCACCGACA

CCGAGTGCGATCTCACCGATGAGATCGTGAAAGATGTGAAACAGACCTA

CCTCGCCCGGGTGTTTAGCTACCCCGCCGGCAATGTGGAGAGCACTGGT

TCCGCTGGCGAGCCTTTATACGAGAACAGCCCCGAATTTACCCCTTACC

TCGAGACCAATTTAGGACAGCCCACCATCCAAAGCTTTGAGCAAGTTGG

CACAAAGGTGAATGTGACAGTGGAGGACGAGCGGACTTTAGTGCGGCGG

AACAACACCTTTCTCAGCCTCCGGGATGTGTTCGGCAAAGATTTAATCT

ACACACTGTATTACTGGAAGTCCTCTTCCTCCGGCAAGAAGACAGCTAA

AACCAACACAAACGAGTTTTTAATCGACGTGGATAAAGGCGAAAACTAC

TGTTTCAGCGTGCAAGCTGTGATCCCCTCCCGGACCGTGAATAGGAAAA

GCACCGATAGCCCCGTTGAGTGCATGGGCCAAGAAAAGGGCGAGTTCCG

GGAGAACTGGGTGAACGTCATCAGCGATTTAAAGAAGATCGAAGATTTA

ATTCAGTCCATGCATATCGACGCCACTTTATACACAGAATCCGACGTGC

ACCCCTCTTGTAAGGTGACCGCCATGAAATGTTTTTTACTGGAGCTGCA

AGTTATCTCTTTAGAGAGCGGAGACGCTAGCATCCACGACACCGTGGAG

AATTTAATCATTTTAGCCAATAACTCTTTATCCAGCAACGGCAACGTGA

CAGAGTCCGGCTGCAAGGAGTGCGAAGAGCTGGAGGAGAAGAACATCAA

GGAGTTTCTGCAATCCTTTGTGCACATTGTCCAGATGTTCATCAATACC

TCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 130)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDITCPPPM

SVEHADIWVKSYSLYSRERYICNSGFKRKAGTSSLTECVLNKATNVAHW

TTPSLKCIR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 131)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACATTACATGCCCCCCTCCCATG

AGCGTGGAGCACGCCGACATCTGGGTGAAGAGCTATAGCCTCTACAGCC

GGGAGAGGTATATCTGTAACAGCGGCTTCAAGAGGAAGGCCGGCACCAG

CAGCCTCACCGAGTGCGTGCTGAATAAGGCTACCAACGTGGCTCACTGG

ACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 132)
MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDITCPPPMSVEHADIWVKSYSLYSRERYICNSGFKRKAG

TSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 133)
ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCTCCATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACATTACATGCCCCCCTC

CCATGAGCGTGGAGCACGCCGACATCTGGGTGAAGAGCTATAGCCTCTA

CAGCCGGGAGAGGTATATCTGTAACAGCGGCTTCAAGAGGAAGGCCGGC

ACCAGCAGCCTCACCGAGTGCGTGCTGAATAAGGCTACCAACGTGGCTC

ACTGGACAACACCCTCTTTAAAGTGCATCCGG.

Exemplary Multi-Chain Chimeric Polypeptides—Type J

In some embodiments of any of the multi-chain chimeric polypeptides described herein, the first target-binding domain and the second targeting-binding domain each independently bind specifically to a receptor of IL-7, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments, the second chimeric polypeptide can include an additional target-binding domain. In some embodiments, the additional target-binding domain and the In some embodiments of these multi-chain chimeric polypeptides, one or more of the first target-binding domain, the second target-binding domain and the additional target-binding domain is an agonistic antigen-binding domain. In some embodiments of these multi-chain chimeric polypeptides, the first target-binding domain, the second target-binding domain, and the additional target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, the first target-binding domain binds specifically to a receptor for IL-7, and the second target-binding domain binds specifically to a receptor for IL-21 or a receptor for CD137L. In some embodiments, the additional target-binding domain binds specifically to a receptor for IL-21 or a receptor for CD137L.

In some embodiments of these multi-chain chimeric polypeptides, the first target-binding domain is a soluble IL-7 (e.g., a soluble human IL-7). In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 135)
DCDIEGKDGKQYESVLMVSIDQLLDSMKEIGSNCLNNEFNFFKRHICD

ANKEGMFLFRAARKLRQFLKMNSTGDFDLHLLKVSEGTTILLNCTGQV

KGRKPAALGEAQPTKSLEENKSLKEQKKLNDLCFLKRLLQEIKTCWNK

ILMGTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT.

In some embodiments of these multi-chain chimeric polypeptides, the second target-binding domain or the additional target-binding domain binds specifically to a receptor for IL-21. In some embodiments of these multi-chain chimeric polypeptides, the second target-binding domain or the additional target-binding domain is a soluble IL-21 (e.g., a soluble human IL-21).

In some embodiments of these multi-chain chimeric polypeptides, a soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.

In some embodiments of these multi-chain chimeric polypeptides, a soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 125)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC.

In some embodiments of these multi-chain chimeric polypeptides, the second target-binding domain binds specifically to a receptor for CD137L. In some embodiments of these multi-chain chimeric polypeptides, the second chimeric polypeptide further comprises an additional target-binding domain that binds specifically to a receptor for CD137L. In some embodiments of these multi-chain chimeric polypeptides, the second target-binding domain and/or the additional target-binding domain is a soluble CD137L (e.g., a soluble human CD137L).

In some embodiments of these multi-chain chimeric polypeptides, a soluble human CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 165)
REGPELSPDDPAGLLDLRQGMFAQLVAQNVLLIDGPLSWYSDPGLAGVS

LTGGLYKEDTKELVVAKAGVYYVFFQLELRRVVAGEGSGSVSLALHLQP

LRSAAGAAALALTVDLPPASSEARNSAFGFQGRLLHLSAGQRLGVHLHT

EARARHAWQLTQGATVLGLFRVTPEIPAGLPSPRSE.

In some embodiments of these multi-chain chimeric polypeptides, a soluble human CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 166)
CGCGAGGGTCCCGAGCTTTCGCCCGACGATCCCGCCGGCCTCTTGGACC

TGCGGCAGGGCATGTTTGCGCAGCTGGTGGCCCAAAATGTTCTGCTGAT

CGATGGGCCCCTGAGCTGGTACAGTGACCCAGGCCTGGCAGGCGTGTCC

CTGACGGGGGGCCTGAGCTACAAAGAGGACACGAAGGAGCTGGTGGTGG

CCAAGGCTGGAGTCTACTATGTCTTCTTTCAACTAGAGCTGCGGCGCGT

GGTGGCCGGCGAGGGCTCAGGCTCCGTTTCACTTGCGCTGCACCTGCAG

CCACTGCGCTCTGCTGCTGGGGCCGCCGCCCTGGCTTTGACCGTGGACC

TGCCACCCGCCTCCTCCGAGGCTCGGAACTCGGCCTTCGGTTTCCAGGG

CCGCTTGCTGCACCTGAGTGCCGGCCAGCGCCTGGGCGTCCATCTTCAC

ACTGAGGCCAGGGCACGCCATGCCTGGCAGCTTACCCAGGGCGCCACAG

TCTTGGGACTCTTCCGGGTGACCCCCGAAATCCCAGCCGGACTCCCTTC

ACCGAGGTCGGAA.

In some embodiments of these multi-chain chimeric polypeptides, a soluble human CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 167)
DPAGLLDLRQGMFAQLVAQNVLLIDGPLSWYSDPGLAGVSLTGGLSYKE

DTKELVVAKAGVYYVFFQLELRRVVAGEGSGSVSLALHLQPLRSAAGAA

ALALTVDLPPASSEARNSAFGFQGRLLHLSAGQRLGVHLHTEARARHAW

QLTQGATVLGLFRVTPEI.

In some embodiments of these multi-chain chimeric polypeptides, a soluble human CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 168)
GATCCCGCCGGCCTCTTGGACCTGCGGCAGGGCATGTTTGCGCAGCTGG

TGGCCCAAAATGTTCTGCTGATCGATGGGCCCCTGAGCTGGTACAGTGA

CCCAGGCCTGGCAGGCGTGTCCCTGACGGGGGGCCTGAGCTACAAAGAG

GACACGAAGGAGCTGGTGGTGGCCAAGGCTGGAGTCTACTATGTCTTCT

TTCAACTAGAGCTGCGGCGCGTGGTGGCCGGCGAGGGCTCAGGCTCCGT

TTCACTTGCGCTGCACCTGCAGCCACTGCGCTCTGCTGCTGGGGCCGCC

GCCCTGGCTTTGACCGTGGACCTGCCACCCGCCTCCTCCGAGGCTCGGA

ACTCGGCCTTCGGTTTCCAGGGCCGCTTGCTGCACCTGAGTGCCGGCCA

GCGCCTGGGCGTCCATCTTCACACTGAGGCCAGGGCACGCCATGCCTGG

CAGCTTACCCAGGGCGCCACAGTCTTGGGACTCTTCCGGGTGACCCCCG

AAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 141)
DCDIEGKDGKQYESVLMVSIDQLLDSMKEIGSNCLNNEFNEFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEHSGTTNTVAAYNLTWKSTNFKTILEWEPKPVNQVYTVQISTKSGD

WKSKCFYTTDTECDLTDEIVKDVKQTYLARVFSYPAGNVESTGSAGEPL

YENSPEFTPYLETNLGQPTIQSFEQVGTKVNVTVEDERTLVRRNNTFLS

LRDVEGKDLIYTLYYWKSSSSGKKTAKTNTNEFLIDVDKGENYCFSVQA

VIPSRTVNRKSTDSPVECMGQEKGEFRENWVNVISDLKKIEDLIQSMHI

DATLYTESDVHPSCKVTAMKCFLLELQVISLESGDASIHDTVENLIILA

NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 142)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCATAGCGGCACAACCAACACAGTCGCTGCCTATAACC

TCACTTGGAAGAGCACCAACTTCAAAACCATCCTCGAATGGGAACCCAA

ACCCGTTAACCAAGTTTACACCGTGCAGATCAGCACCAAGTCCGGCGAC

TGGAAGTCCAAATGTTTCTATACCACCGACACCGAGTGCGATCTCACCG

ATGAGATCGTGAAAGATGTGAAACAGACCTACCTCGCCCGGGTGTTTA

GCTACCCCGCCGGCAATGTGGAGAGCACTGGTTCCGCTGGCGAGCCTTT

ATACGAGAACAGCCCCGAATTTACCCCTTACCTCGAGACCAATTTAGGA

CAGCCCACCATCCAAAGCTTTGAGCAAGTTGGCACAAAGGTGAATGTGA

CAGTGGAGGACGAGCGGACTTTAGTGCGGCGGAACAACACCTTTCTCAG

CCTCCGGGATGTGTTCGGCAAAGATTTAATCTACACACTGTATTACTGG

AAGTCCTCTTCCTCCGGCAAGAAGACAGCTAAAACCAACACAAACGAGT

TTTTAATCGACGTGGATAAAGGCGAAAACTACTGTTTCAGCGTGCAAGC

TGTGATCCCCTCCCGGACCGTGAATAGGAAAAGCACCGATAGCCCCGTT

GAGTGCATGGGCCAAGAAAAGGGCGAGTTCCGGGAGAACTGGGTGAACG

TCATCAGCGATTTAAAGAAGATCGAAGATTTAATTCAGTCCATGCATAT

CGACGCCACTTTATACACAGAATCCGACGTGCACCCCTCTTGTAAGGTG

ACCGCCATGAAATGTTTTTTACTGGAGCTGCAAGTTATCTCTTTAGAGA

GCGGAGACGCTAGCATCCACGACACCGTGGAGAATTTAATCATTTTAGC

CAATAACTCTTTATCCAGCAACGGCAACGTGACAGAGTCCGGCTGCAAG

GAGTGCGAAGAGCTGGAGGAGAAGAACATCAAGGAGTTTCTGCAATCCT

TTGTGCACATTGTCCAGATGTTCATCAATACCTCC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 143)
MKWVTFISLLFLFSSAYSDCDIEGKDGKQYESVLMVSIDQLLDSMKEIG

SNCLNNEFNFFKRHICDANKEGMFLFRAARKLRQFLKMNSTGDFDLHLL

KVSEGTTILLNCTGQVKGRKPAALGEAQPTKSLEENKSLKEQKKLNDLC

FLKRLLQEIKTCWNKILMGTKEHSGTTNTVAAYNLTWKSTNFKTILEWE

PKPVNQVYTVQISTKSGDWKSKCFYTTDTECDLTDEIVKDVKQTYLARV

FSYPAGNVESTGSAGEPLYENSPEFTPYLETNLGQPTIQSFEQVGTKVN

VTVEDERTLVRRNNTFLSLRDVFGKDLIYTLYYWKSSSSGKKTAKTNTN

EFLIDVDKGENYCFSVQAVIPSRTVNRKSTDSPVECMGQEKGEFRENWV

NVISDLKKIEDLIQSMHIDATLYTESDVHPSCKVTAMKCFLLELQVISL

ESGDASIHDTVENLIILANNSLSSNGNVTESGCKECEELEEKNIKEFLQ

SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 144)
ATGAAGTGGGTGACCTTCATCAGCCTGCTGTTCCTGTTCTCCAGCGCCT

ACTCCGATTGCGACATCGAGGGCAAGGACGGCAAGCAGTACGAGAGCGT

GCTGATGGTGTCCATCGACCAGCTGCTGGACAGCATGAAGGAGATCGGC

TCCAACTGCCTCAACAACGAGTTCAACTTCTTCAAGCGGCACATCTGCG

ACGCCAACAAGGAGGGCATGTTCCTGTTCAGGGCCGCCAGGAAACTGCG

GCAGTTCCTGAAGATGAACTCCACCGGCGACTTCGACCTGCACCTGCTG

AAGGTGTCCGAGGGCACCACCATCCTGCTGAACTGCACCGGACAGGTGA

AGGGCCGGAAACCTGCTGCTCTGGGAGAGGCCCAACCCACCAAGAGCCT

GGAGGAGAACAAGTCCCTGAAGGAGCAGAAGAAGCTGAACGACCTGTGC

```
TTCCTGAAGAGGCTGCTGCAGGAGATCAAGACCTGCTGGAACAAGATCC

TGATGGGCACCAAGGAGCATAGCGGCACAACCAACACAGTCGCTGCCTA

TAACCTCACTTGGAAGAGCACCAACTTCAAAACCATCCTCGAATGGGAA

CCCAAACCCGTTAACCAAGTTTACACCGTGCAGATCAGCACCAAGTCCG

GCGACTGGAAGTCCAAATGTTTCTATACCACCGACACCGAGTGCGATCT

CACCGATGAGATCGTGAAAGATGTGAAACAGACCTACCTCGCCCGGGTG

TTTAGCTACCCCGCCGGCAATGTGGAGAGCACTGGTTCCGCTGGCGAGC

CTTTATACGAGAACAGCCCCGAATTTACCCCTTACCTCGAGACCAATTT

AGGACAGCCCACCATCCAAAGCTTTGAGCAAGTTGGCACAAAGGTGAAT

GTGACAGTGGAGGACGAGCGGACTTTAGTGCGGCGGAACAACACCTTTC

TCAGCCTCCGGGATGTGTTCGGCAAAGATTTAATCTACACACTGTATTA

CTGGAAGTCCTCTTCCTCCGGCAAGAAGACAGCTAAAACCAACACAAAC

GAGTTTTTAATCGACGTGGATAAAGGCGAAAACTACTGTTTCAGCGTGC

AAGCTGTGATCCCCTCCCGGACCGTGAATAGGAAAAGCACCGATAGCCC

CGTTGAGTGCATGGGCCAAGAAAAGGGCGAGTTCCGGGAGAACTGGGTG

AACGTCATCAGCGATTTAAAGAAGATCGAAGATTTAATTCAGTCCATGC

ATATCGACGCCACTTTATACACAGAATCCGACGTGCACCCCTCTTGTAA

GGTGACCGCCATGAAATGTTTTTTACTGGAGCTGCAAGTTATCTCTTTA

GAGAGCGGAGACGCTAGCATCCACGACACCGTGGAGAATTTAATCATTT

TAGCCAATAACTCTTTATCCAGCAACGGCAACGTGACAGAGTCCGGCTG

CAAGGAGTGCGAAGAGCTGGAGGAGAAGAACATCAAGGAGTTTCTGCAA

TCCTTTGTGCACATTGTCCAGATGTTCATCAATACCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 169)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDSITCPPPMSVEHADI

WVKSYSLYSRERYICNSGFKRKAGTSSLTECVLNKATNVAHWTTPSLKC

IRGGGGSGGGGSGGGGSREGPELSPDDPAGLLDLRQGMFAQLVAQNVLL

IDGPLSWYSDPGLAGVSLTGGLSYKEDTKELVVAKAGVYYVFFQLELRR

VVAGEGSGSVSLALHLQPLRSAAGAAALALTVDLPPASSEARNSAFGFQ

GRLLHLSAGQRLGVHLHTEARARHAWQLTQGATVLGLFRVTPEIPAGLP

SPRSE.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 170)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCCATTACATGCCCCCCTCCCATGAGCGTGGAGCACGCCGACATC

TGGGTGAAGAGCTATAGCCTCTACAGCCGGGAGAGGTATATCTGTAACA

GCGGCTTCAAGAGGAAGGCCGGCACCAGCAGCCTCACCGAGTGCGTGCT

GAATAAGGCTACCAACGTGGCTCACTGGACAACACCCTCTTTAAAGTGC

ATCCGGGGCGGTGGAGGATCCGGAGGAGGTGGCTCCGGCGGCGGAGGAT

CTCGCGAGGGTCCCGAGCTTTCGCCCGACGATCCCGCCGGCCTCTTGGA

CCTGCGGCAGGGCATGTTTGCGCAGCTGGTGGCCCAAAATGTTCTGCTG

ATCGATGGGCCCCTGAGCTGGTACAGTGACCCAGGCCTGGCAGGCGTGT

CCCTGACGGGGGGCCTGAGCTACAAAGAGGACACGAAGGAGCTGGTGGT

GGCCAAGGCTGGAGTCTACTATGTCTTCTTTCAACTAGAGCTGCGGCGC

GTGGTGGCCGGCGAGGGCTCAGGCTCCGTTTCACTTGCGCTGCACCTGC

AGCCACTGCGCTCTGCTGCTGGGGCCGCCGCCCTGGCTTTGACCGTGGA

CCTGCCACCCGCCTCCTCCGAGGCTCGGAACTCGGCCTTCGGTTTCCAG

GGCCGCTTGCTGCACCTGAGTGCCGGCCAGCGCCTGGGCGTCCATCTTC

ACACTGAGGCCAGGGCACGCCATGCCTGGCAGCTTACCCAGGGCGCCAC

AGTCTTGGGACTCTTCCGGGTGACCCCCGAAATCCCAGCCGGACTCCCT

TCACCGAGGTCGGAA.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 171)
MKWVTFISLLFLFSSAYSQGQDRHMIRMRQLIDIVDQLKNYVNDLVPEF

LPAPEDVETNCEWSAFSCFQKAQLKSANTGNNERIINVSIKKLKRKPPS

TNAGRRQKHRLTCPSCDSYEKKPPKEFLERFKSLLQKMIHQHLSSRTHG

SEDSITCPPPMSVEHADIWVKSYSLYSRERYICNSGFKRKAGTSSLTEC

VLNKATNVAHWTTPSLKCIRGGGGSGGGGSGGGGSREGPELSPDDPAGL

LDLRQGMFAQLVAQNVLLIDGPLSWYSDPGLAGVSLTGGLSYKEDTKEL

VVAKAGVYYVFFQLELRRVVAGEGSGSVSLALHLQPLRSAAGAAALALT
```

VDLPPASSEARNSAFGFQGRLLHLSAGQRLGVHLHTEARARHAWQLTQG

ATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 172)
ATGAAGTGGGTGACCTTCATCAGCCTGCTGTTCCTGTTCTCCAGCGCCT

ACTCCCAGGGCCAGGACAGGCACATGATCCGGATGAGGCAGCTCATCGA

CATCGTCGACCAGCTGAAGAACTACGTGAACGACCTGGTGCCCGAGTTT

CTGCCTGCCCCCGAGGACGTGGAGACCAACTGCGAGTGGTCCGCCTTCT

CCTGCTTTCAGAAGGCCCAGCTGAAGTCCGCCAACACCGGCAACAACGA

GCGGATCATCAACGTGAGCATCAAGAAGCTGAAGCGGAAGCCTCCCTCC

ACAAACGCCGGCAGGAGGCAGAAGCACAGGCTGACCTGCCCCAGCTGTG

ACTCCTACGAGAAGAAGCCCCCCAAGGAGTTCCTGGAGAGGTTCAAGTC

CCTGCTGCAGAAGATGATCCATCAGCACCTGTCCTCCAGGACCCACGGC

TCCGAGGACTCCATTACATGCCCCCCTCCCATGAGCGTGGAGCACGCCG

ACATCTGGGTGAAGAGCTATAGCCTCTACAGCCGGGAGAGGTATATCTG

TAACAGCGGCTTCAAGAGGAAGGCCGGCACCAGCAGCCTCACCGAGTGC

GTGCTGAATAAGGCTACCAACGTGGCTCACTGGACAACACCCTCTTTAA

AGTGCATCCGGGGCGGTGGAGGATCCGGAGGAGGTGGCTCCGGCGGCGG

AGGATCTCGCGAGGGTCCCGAGCTTTCGCCCGACGATCCCGCCGGCCTC

TTGGACCTGCGGCAGGGCATGTTTGCGCAGCTGGTGGCCCAAAATGTTC

TGCTGATCGATGGGCCCCTGAGCTGGTACAGTGACCCAGGCCTGGCAGG

CGTGTCCCTGACGGGGGGCCTGAGCTACAAAGAGGACACGAAGGAGCTG

GTGGTGGCCAAGGCTGGAGTCTACTATGTCTTCTTTCAACTAGAGCTGC

GGCGCGTGGTGGCCGGCGAGGGCTCAGGCTCCGTTTCACTTGCGCTGCA

CCTGCAGCCACTGCGCTCTGCTGCTGGGGCCGCCGCCCTGGCTTTGACC

GTGGACCTGCCACCCGCCTCCTCCGAGGCTCGGAACTCGGCCTTCGGTT

TCCAGGGCCGCTTGCTGCACCTGAGTGCCGGCCAGCGCCTGGGCGTCCA

TCTTCACACTGAGGCCAGGGCACGCCATGCCTGGCAGCTTACCCAGGGC

GCCACAGTCTTGGGACTCTTCCGGGTGACCCCCGAAATCCCAGCCGGAC

TCCCTTCACCGAGGTCGGAA.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 173)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDSITCPPPMSVEHADI

WVKSYSLYSRERYICNSGFKRKAGTSSLTECVLNKATNVAHWTTPSLKC

IRGGGGSGGGGSGGGGSDPAGLLDLRQGMFAQLVAQNVLLIDGPLSWYS

DPGLAGVSLTGGLSYKEDTKELVVAKAGVYYVFFQLELRRVVAGEGSGS

VSLALHLQPLRSAAGAAALALTVDLPPASSEARNSAFGFQGRLLHLSAG

QRLGVHLHTEARARHAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 174)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCCATTACATGCCCCCCTCCCATGAGCGTGGAGCACGCCGACATC

TGGGTGAAGAGCTATAGCCTCTACAGCCGGGAGAGGTATATCTGTAACA

GCGGCTTCAAGAGGAAGGCCGGCACCAGCAGCCTCACCGAGTGCGTGCT

GAATAAGGCTACCAACGTGGCTCACTGGACAACACCCTCTTTAAAGTGC

ATCCGGGGCGGTGGAGGATCCGGAGGAGGTGGCTCCGGCGGCGGAGGAT

CTGATCCCGCCGGCCTCTTGGACCTGCGGCAGGGCATGTTTGCGCAGCT

GGTGGCCCAAAATGTTCTGCTGATCGATGGGCCCCTGAGCTGGTACAGT

GACCCAGGCCTGGCAGGCGTGTCCCTGACGGGGGGCCTGAGCTACAAAG

AGGACACGAAGGAGCTGGTGGTGGCCAAGGCTGGAGTCTACTATGTCTT

CTTTCAACTAGAGCTGCGGCGCGTGGTGGCCGGCGAGGGCTCAGGCTCC

GTTTCACTTGCGCTGCACCTGCAGCCACTGCGCTCTGCTGCTGGGGCCG

CCGCCCTGGCTTTGACCGTGGACCTGCCACCCGCCTCCTCCGAGGCTCG

GAACTCGGCCTTCGGTTTCCAGGGCCGCTTGCTGCACCTGAGTGCCGGC

CAGCGCCTGGGCGTCCATCTTCACACTGAGGCCAGGGCACGCCATGCCT

GGCAGCTTACCCAGGGCGCCACAGTCTTGGGACTCTTCCGGGTGACCCC

CGAAATC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 175)
MKWVTFISLLFLFSSAYSQGQDRHMIRMIRQLIDIVDQLKNYVNDLVPE

FLPAPEDVETNCEWSAFSCFQKAQLKSANTGNNERIINVSIKKLKRKPP

STNAGRRQKHRLTCPSCDSYEKKPPKEFLERFKSLLQKMIHQHLSSRTH

GSEDSITCPPPMSVEHADIWVKSYSLYSRERYICNSGFKRKAGTSSLTE

CVLNKATNVAHWTTPSLKCIRGGGGSGGGGSGGGGSDPAGLLDLRQGMF

AQLVAQNVLLIDGPLSWYSDPGLAGVSLTGGLSYKEDTKELVVAKAGVY

YVFFQLELRRVVAGEGSGSVSLALHLQPLRSAAGAAALALTVDLPPASS

EARNSAFGFQGRLLHLSAGQRLGVHLHTEARARHAWQLTQGATVLGLFR

VTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 176)
ATGAAGTGGGTGACCTTCATCAGCCTGCTGTTCCTGTTCTCCAGCGCCT

ACTCCCAGGGCCAGGACAGGCACATGATCCGGATGAGGCAGCTCATCGA

CATCGTCGACCAGCTGAAGAACTACGTGAACGACCTGGTGCCCGAGTTT

CTGCCTGCCCCCGAGGACGTGGAGACCAACTGCGAGTGGTCCGCCTTCT

CCTGCTTTCAGAAGGCCCAGCTGAAGTCCGCCAACACCGGCAACAACGA

GCGGATCATCAACGTGAGCATCAAGAAGCTGAAGCGGAAGCCTCCCTCC

ACAAACGCCGGCAGGAGGCAGAAGCACAGGCTGACCTGCCCCAGCTGTG

ACTCCTACGAGAAGAAGCCCCCCAAGGAGTTCCTGGAGAGGTTCAAGTC

CCTGCTGCAGAAGATGATCCATCAGCACCTGTCCTCCAGGACCCACGGC

TCCGAGGACTCCATTACATGCCCCCCTCCCATGAGCGTGGAGCACGCCG

ACATCTGGGTGAAGAGCTATAGCCTCTACAGCCGGGAGAGGTATATCTG

TAACAGCGGCTTCAAGAGGAAGGCCGGCACCAGCAGCCTCACCGAGTGC

GTGCTGAATAAGGCTACCAACGTGGCTCACTGGACAACACCCTCTTTAA

AGTGCATCCGGGGCGGTGGAGGATCCGGAGGAGGTGGCTCCGGCGGCGG

AGGATCTGATCCCGCCGGCCTCTTGGACCTGCGGCAGGGCATGTTTGCG

CAGCTGGTGGCCCAAAATGTTCTGCTGATCGATGGGCCCCTGAGCTGGT

ACAGTGACCCAGGCCTGGCAGGCGTGTCCCTGACGGGGGCCTGAGCTA

CAAAGAGGACACGAAGGAGCTGGTGGTGGCCAAGGCTGGAGTCTACTAT

GTCTTCTTTCAACTAGAGCTGCGGCGCGTGGTGGCCGGCGAGGGCTCAG

GCTCCGTTTCACTTGCGCTGCACCTGCAGCCACTGCGCTCTGCTGCTGG

GGCCGCCGCCCTGGCTTTGACCGTGGACCTGCCACCCGCCTCCTCCGAG

GCTCGGAACTCGGCCTTCGGTTTCCAGGGCCGCTTGCTGCACCTGAGTG

-continued

CCGGCCAGCGCCTGGGCGTCCATCTTCACACTGAGGCCAGGGCACGCCA

TGCCTGGCAGCTTACCCAGGGCGCCACAGTCTTGGGACTCTTCCGGGTG

ACCCCCGAAATC.

Exemplary Multi-Chain Chimeric Polypeptides—Type K

In some embodiments of any of the multi-chain chimeric polypeptides described herein, the first target-binding domain and the second targeting-binding domain each independently bind specifically to a receptor of IL-7 or TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to a receptor for IL-7, and the second target-binding domain binds specifically to TGF-β. In some embodiments of these multi-chain chimeric polypeptides, the first target-binding domain binds specifically to TGF-β, and the second target-binding domain binds specifically to a receptor for IL-7.

In some embodiments of these multi-chain chimeric polypeptides, the first target-binding domain includes a soluble IL-7 protein (e.g., a soluble human IL-7 protein). In some embodiments of these multi-chain chimeric polypeptides, the soluble human IL-7 protein includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 135)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCGATGG

GCACCAAGGAGCAT.

In some embodiments of these multi-chain chimeric polypeptides, the second target-binding domain comprises a target-binding domain that binds specifically to TGF-β. In some embodiments of these multi-chain chimeric polypeptides, the second target-binding domain is a soluble TGF-β receptor (e.g., a soluble TGF-β RII receptor, e.g., a soluble human TGF-β RII receptor). In some embodiments of these multi-chain chimeric polypeptides, the soluble human TGF-β RII includes a first sequence of soluble human TGF-β RII and a second sequence of soluble human TGF-β RII. In some embodiments of these multi-chain chimeric polypeptides, the soluble human TGF-β RII includes a linker disposed between the first sequence of soluble human TGF-β RII and the second sequence of soluble human TGF-β RII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTTATGTGTTCCT

GTAGCAGCGACGAGTGTAACGACAACATCATCTTCAGCGAAGAGTACAA

CACCAGCAACCCTGAT.

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 60)
IPPHVQKSVNNDMIVTDNNGAVKFPQLCKFCDVRFSTCDNQKSMSNCSI

TSICEKPQEVCVAVWRKNDENITLETVCHDPKLPYHDFILEDAASPKCI

MKEKKKPGETFFMCSCSSDECNDNIIFSEEYNTSNPDGGGGSGGGGSGG

GGSIPPHVQKSVNNDMIVTDNNGAVKFPQLCKFCDVRFSTCDNQKSCMS

NCSITSICEKPQEVCVAVWRKNDENITLETVCHDPKLPYHDFILEDAAS

PKCIMKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 141)
DCDIEGKDGKQYESVLMVSIDQLLDSMKEIGSNCLNNEFNEFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEHSGTTNTVAAYNLTWKSTNEKTILEWEPKPVNQVYTVQISTKSGD

WKSKCEYTTDTECDLTDEIVKDVKQTYLARVESYPAGNVESTGSAGEPL

YENSPEFTPYLETNLGQPTIQSFEQVGTKVNVTVEDERTLVRRNNTFLS

LRDVEGKDLIYTLYYWKSSSSGKKTAKTNTNEFLIDVDKGENYCFSVQA

VIPSRTVNRKSTDSPVECMGQEKGEFRENWVNVISDLKKIEDLIQSMHI

DATLYTESDVHPSCKVTAMKCELLELQVISLESGDASIHDTVENLIILA

NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 142)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCATAGCGGCACAACCAACACAGTCGCTGCCTATAACC

TCACTTGGAAGAGCACCAACTTCAAAACCATCCTCGAATGGGAACCCAA

ACCCGTTAACCAAGTTTACACCGTGCAGATCAGCACCAAGTCCGGCGAC

TGGAAGTCCAAATGTTTCTATACCACCGACACCGAGTGCGATCTCACCG

ATGAGATCGTGAAAGATGTGAAACAGACCTACCTCGCCCGGGTGTTTAG

CTACCCCGCCGGCAATGTGGAGAGCACTGGTTCCGCTGGCGAGCCTTTA

TACGAGAACAGCCCCGAATTTACCCCTTACCTCGAGACCAATTTAGGAC

AGCCCACCATCCAAAGCTTTGAGCAAGTTGGCACAAAGGTGAATGTGAC

AGTGGAGGACGAGCGGACTTTAGTGCGGCGGAACAACACCTTTCTCAGC

CTCCGGGATGTGTTCGGCAAAGATTTAATCTACACACTGTATTACTGGA

AGTCCTCTTCCTCCGGCAAGAAGACAGCTAAAACCAACACAAACGAGTT

TTTAATCGACGTGGATAAAGGCGAAAACTACTGTTTCAGCGTGCAAGCT

GTGATCCCCTCCCGGACCGTGAATAGGAAAAGCACCGATAGCCCCGTTG

AGTGCATGGGCCAAGAAAAGGGCGAGTTCCGGGAGAACTGGGTGAACGT

CATCAGCGATTTAAAGAAGATCGAAGATTTAATTCAGTCCATGCATATC

```
GACGCCACTTTATACACAGAATCCGACGTGCACCCCTCTTGTAAGGTGA

CCGCCATGAAATGTTTTTTACTGGAGCTGCAAGTTATCTCTTTAGAGAG

CGGAGACGCTAGCATCCACGACACCGTGGAGAATTTAATCATTTTAGCC

AATAACTCTTTATCCAGCAACGGCAACGTGACAGAGTCCGGCTGCAAGG

AGTGCGAAGAGCTGGAGGAGAAGAACATCAAGGAGTTTCTGCAATCCTT

TGTGCACATTGTCCAGATGTTCATCAATACCTCC.
```

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 143)
MKWVTFISLLFLFSSAYSDCDIEGKDGKQYESVLMVSDQLLDSMKEIGS

NCLNNEFNFFKRHICDANKEGMFLFRAARKLRQFLKMNSTGDFDLHLLK

VSEGTTILLNCTGQVKGRKPAALGEAQPTKSLEENKSLKEQKKLNDLCF

LKRLLQEIKTCWNKILMGTKEHSGTTNTVAAYNLTWKSTNFKTILEWEP

KPVNQVYTVQISTKSGDWKSKCFYTTDTECDLTDEIVKDVKQTYLARVF

SYPAGNVESTGSAGEPLYENSPEFTPYLETNLGQPTIQSFEQVGTKVNV

TVEDERTLVRRNNTFLSLRDVFGKDLIYTLYYWKSSSSGKKTAKTNTNE

FLIDVDKGENYCFSVQAVIPSRTVNRKSTDSPVECMGQEKGEFRENWVN

VISDLKKIEDLIQSMHIDATLYTESDVHPSCKVTAMKCFLLELQVISLE

SGDASIHDTVENLIILANNSLSSNGNVTESGCKECEELEEKNIKEFLQS

FVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 144)
ATGAAGTGGGTGACCTTCATCAGCCTGCTGTTCCTGTTCTCCAGCGCCT

ACTCCGATTGCGACATCGAGGGCAAGGACGGCAAGCAGTACGAGAGCGT

GCTGATGGTGTCCATCGACCAGCTGCTGGACAGCATGAAGGAGATCGGC

TCCAACTGCCTCAACAACGAGTTCAACTTCTTCAAGCGGCACATCTGCG

ACGCCAACAAGGAGGGCATGTTCCTGTTCAGGGCCGCCAGGAAACTGCG

GCAGTTCCTGAAGATGAACTCCACCGGCGACTTCGACCTGCACCTGCTG

AAGGTGTCCGAGGGCACCACCATCCTGCTGAACTGCACCGGACAGGTGA

AGGGCCGGAAACCTGCTGCTCTGGGAGAGGCCCAACCCACCAAGAGCCT

GGAGGAGAACAAGTCCCTGAAGGAGCAGAAGAAGCTGAACGACCTGTGC

TTCCTGAAGAGGCTGCTGCAGGAGATCAAGACCTGCTGGAACAAGATCC

TGATGGGCACCAAGGAGCATAGCGGCACAACCAACACAGTCGCTGCCTA

TAACCTCACTTGGAAGAGCACCAACTTCAAAACCATCCTCGAATGGGAA

CCCAAACCCGTTAACCAAGTTTACACCGTGCAGATCAGCACCAAGTCCG

GCGACTGGAAGTCCAAATGTTTCTATACCACCGACACCGAGTGCGATCT

CACCGATGAGATCGTGAAAGATGTGAAACAGACCTACCTCGCCCGGGTG

TTTAGCTACCCCGCCGGCAATGTGGAGAGCACTGGTTCCGCTGGCGAGC

CTTTATACGAGAACAGCCCCGAATTTACCCCTTACCTCGAGACCAATTT

AGGACAGCCCACCATCCAAAGCTTTGAGCAAGTTGGCACAAAGGTGAAT

GTGACAGTGGAGGACGAGCGGACTTTAGTGCGGCGGAACAACACCTTTC

TCAGCCTCCGGGATGTGTTCGGCAAAGATTTAATCTACACACTGTATTA

CTGGAAGTCCTCTTCCTCCGGCAAGAAGACAGCTAAAACCAACACAAAC

GAGTTTTTAATCGACGTGGATAAAGGCGAAAACTACTGTTTCAGCGTGC

AAGCTGTGATCCCCTCCCGGACCGTGAATAGGAAAAGCACCGATAGCCC

CGTTGAGTGCATGGGCCAAGAAAAGGGCGAGTTCCGGGAGAACTGGGTG

AACGTCATCAGCGATTTAAAGAAGATCGAAGATTTAATTCAGTCCATGC

ATATCGACGCCACTTTATACACAGAATCCGACGTGCACCCCTCTTGTAA

GGTGACCGCCATGAAATGTTTTTTACTGGAGCTGCAAGTTATCTCTTTA

GAGAGCGGAGACGCTAGCATCCACGACACCGTGGAGAATTTAATCATTT

TAGCCAATAACTCTTTATCCAGCAACGGCAACGTGACAGAGTCCGGCTG

CAAGGAGTGCGAAGAGCTGGAGGAGAAGAACATCAAGGAGTTTCTGCAA

TCCTTTGTGCACATTGTCCAGATGTTCATCAATACCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 130)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDITCPPPM

SVEHADIWVKSYSLYSRERYICNSGFKRKAGTSSLTECVLNKATNVAHW

TTPSLKCIR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 131)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACATTACATGCCCCCCTCCCATG

AGCGTGGAGCACGCCGACATCTGGGTGAAGAGCTATAGCCTCTACAGCC

GGGAGAGGTATATCTGTAACAGCGGCTTCAAGAGGAAGGCCGGCACCAG

CAGCCTCACCGAGTGCGTGCTGAATAAGGCTACCAACGTGGCTCACTGG

ACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 132)
MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDITCPPPMSVEHADIWVKSYSLYSRERYICNSGFKRKAG

TSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 133)
ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCTCCATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACATTACATGCCCCCCTC

CCATGAGCGTGGAGCACGCCGACATCTGGGTGAAGAGCTATAGCCTCTA

CAGCCGGGAGAGGTATATCTGTAACAGCGGCTTCAAGAGGAAGGCCGGC

ACCAGCAGCCTCACCGAGTGCGTGCTGAATAAGGCTACCAACGTGGCTC

ACTGGACAACACCCTCTTTAAAGTGCATCCGG.

Exemplary Multi-Chain Chimeric Polypeptides—Type L

In some embodiments of any of the multi-chain chimeric polypeptides described herein, the first target-binding domain and the second targeting-binding domain each independently bind specifically to TGF-β, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional target-binding domain is an agonistic antigen-binding domain. In some embodiments of these multi-chain chimeric polypeptides, the first target-binding domain, the second target-binding domain, and the additional target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, the first target-binding domain binds specifically to TGF-β and the second target-binding domain binds specifically to a receptor for IL-21 or a receptor for CD137L.

In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGF-β RII includes a first sequence of soluble human TGF-β RII and a second sequence of soluble human TGF-β RII. In some embodiments of these multi-chain chimeric polypeptides, the soluble human TGF-β RII includes a linker disposed between the first sequence of soluble human TGF-β RII and the second sequence of soluble human TGF-β RII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNC

SITSICEKPQEVCVAVWRKNDENITLETVCHDPKLPYHDFILEDAASP

KCIMKEKKKPGETFFMCSCSSDECNDNIIFSEEYNTSNPD.

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSN

CSITSICEKPQEVCVAVWRKNDENITLETVCHDPKLPYHDFILEDAA

SPKCIMKEKKKPGETFFMCSCSSDECNDNIIFSEEYNTSNPD.

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATCCCCCCCCATGTGCAAAAGAGCGTGAACAACGATATGATCGTGA

CCGACAACAACGGCGCCGTGAAGTTTCCCCAGCTCTGCAAGTTCTG

CGATGTCAGGTTCAGCACCTGCGATAATCAGAAGTCCTGCATGTCC

AACTGCAGCATCACCTCCATCTGCGAGAAGCCCCAAGAAGTGTGCG

TGGCCGTGTGGCGGAAAAATGACGAGAACATCACCCTGGAGACCGT

GTGTCACGACCCCAAGCTCCCTTATCACGACTTCATTCTGGAGGAC

GCTGCCTCCCCCAAATGCATCATGAAGGAGAAGAAGAAGCCCGGAG

AGACCTTCTTTATGTGTTCCTGTAGCAGCGACGAGTGTAACGACAA

CATCATCTTCAGCGAAGAGTACAACACCAGCAACCCTGAT.

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTG

ACCGATAACAATGGCGCCGTGAAATTTCCCCAGCTGTGCAAATTC

TGCGATGTGAGGTTTTCCACCTGCGACAACCAGAAGTCCTGTATG

AGCAACTGCTCCATCACCTCCATCTGTGAGAAGCCTCAGGAGGTG

TGCGTGGCTGTCTGGCGGAAGAATGACGAGAATATCACCCTGGAA

ACCGTCTGCCACGATCCCAAGCTGCCCTACCACGATTTCATCCTG

GAAGACGCCGCCAGCCCTAAGTGCATCATGAAAGAGAAAAAGAAG

CCTGGCGAGACCTTTTTCATGTGCTCCTGCAGCAGCGACGAATGC

AACGACAATATCATCTTTAGCGAGGAATACAATACCAGCAACCCC

GAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 60)
IPPHVQKSVNNDMIVTDNNGAVKFPQLCKFCDVRFSTCDNQKSCM

SNCSITSICEKPQEVCVAVWRKNDENITLETVCHDPKLPYHDFIL

EDAASPKCIMKEKKKPGETFFMCSCSSDECNDNIIFSEEYNTSNP

DGGGGSGGGGSGGGGSIPPHVQKSVNNDMIVTDNNGAVKFPQLCK

FCDVRFSTCDNQKSCMSNCSITSICEKPQEVCVAVWRKNDENITL

ETVCHDPKLPYHDFILEDAASPKCIMKEKKKPGETFFMCSCSSDE

CNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
ATCCCCCCCCATGTGCAAAAGAGCGTGAACAACGATATGATCGT

GACCGACAACAACGGCGCCGTGAAGTTTCCCCAGCTCTGCAAGT

TCTGCGATGTCAGGTTCAGCACCTGCGATAATCAGAAGTCCTGC

ATGTCCAACTGCAGCATCACCTCCATCTGCGAGAAGCCCCAAGA

AGTGTGCGTGGCCGTGTGGCGGAAAAATGACGAGAACATCACCC

TGGAGACCGTGTGTCACGACCCCAAGCTCCCTTATCACGACTTC

ATTCTGGAGGACGCTGCCTCCCCAAATGCATCATGAAGGAGAA

GAAGAAGCCCGGAGAGACCTTCTTTATGTGTTCCTGTAGCAGCG

ACGAGTGTAACGACAACATCATCTTCAGCGAAGAGTACAACACC

AGCAACCCTGATGGAGGTGGCGGATCCGGAGGTGGAGGTTCTGG

TGGAGGTGGGAGTATTCCTCCCCACGTGCAGAAGAGCGTGAATA

ATGACATGATCGTGACCGATAACAATGGCGCCGTGAAATTTCCC

CAGCTGTGCAAATTCTGCGATGTGAGGTTTTCCACCTGCGACAA

CCAGAAGTCCTGTATGAGCAACTGCTCCATCACCTCCATCTGTG

AGAAGCCTCAGGAGGTGTGCGTGGCTGTCTGGCGGAAGAATGAC

GAGAATATCACCCTGGAAACCGTCTGCCACGATCCCAAGCTGCC

CTACCACGATTTCATCCTGGAAGACGCCGCCAGCCCTAAGTGCA

TCATGAAAGAGAAAAAGAAGCCTGGCGAGACCTTTTTCATGTGC

TCCTGCAGCAGCGACGAATGCAACGACAATATCATCTTTAGCGA

GGAATACAATACCAGCAACCCCGAC.

In some embodiments of these multi-chain chimeric polypeptides, the second target-binding domain or the additional target-binding domain binds specifically to a receptor for IL-21. In some embodiments of these multi-chain chimeric polypeptides, the second target-binding domain or the additional target-binding domain includes a soluble IL-21 (e.g., a soluble human IL-21).

In some embodiments of these multi-chain chimeric polypeptides, a soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
QGQDRHMIRMRQLIDIVDQLKNYVNDLVPEFLPAPEDVETNCEW

SAFSCFQKAQLKSANTGNNERIINVSIKKLKRKPPSTNAGRRQK

HRLTCPSCDSYEKKPPKEFLERFKSLLQKMIHQHLSSRTHGSED

S.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 125)
CAGGGCCAGGACAGGCACATGATCCGGATGAGGCAGCTCATCGA

CATCGTCGACCAGCTGAAGAACTACGTGAACGACCTGGTGCCCG

AGTTTCTGCCTGCCCCCGAGGACGTGGAGACCAACTGCGAGTGG

TCCGCCTTCTCCTGCTTTCAGAAGGCCCAGCTGAAGTCCGCCAA

CACCGGCAACAACGAGCGGATCATCAACGTGAGCATCAAGAAGC

TGAAGCGGAAGCCTCCCTCCACAAACGCCGGCAGGAGGCAGAAG

CACAGGCTGACCTGCCCCAGCTGTGACTCCTACGAGAAGAAGCC

CCCCAAGGAGTTCCTGGAGAGGTTCAAGTCCCTGCTGCAGAAGA

-continued
```
TGATCCATCAGCACCTGTCCTCCAGGACCCACGGCTCCGAGGAC

TCC.
```

In some embodiments of these multi-chain chimeric polypeptides, the second target-binding domain or the additional target-binding domain binds specifically to a receptor for CD137L. In some embodiments of these multi-chain chimeric polypeptides, the second target-binding domain and/or the additional target-binding domain includes a soluble CD137L (e.g., a soluble human CD137L).

In some embodiments of these multi-chain chimeric polypeptides, a soluble CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                   (SEQ ID NO: 165)
REGPELSPDDPAGLLDLRQGMFAQLVAQNVLLIDGPLSWYSDP

GLAGVSLTGGLSYKEDTKELVVAKAGVYYVFFQLELRRVVAGE

GSGSVSLALHLQPLRSAAGAAALALTVDLPPASSEARNSAFGF

QGRLLHLSAGQRLGVHLHTEARARHAWQLTQGATVLGLFRVTP

EIPAGLPSPRSE.
```

In some embodiments of these multi-chain chimeric polypeptides, a soluble CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                   (SEQ ID NO: 166)
CGCGAGGGTCCCGAGCTTTCGCCCGACGATCCCGCCGGCCTC

TTGGACCTGCGGCAGGGCATGTTTGCGCAGCTGGTGGCCCAA

AATGTTCTGCTGATCGATGGGCCCCTGAGCTGGTACAGTGAC

CCAGGCCTGGCAGGCGTGTCCCTGACGGGGGGCCTGAGCTAC

AAAGAGGACACGAAGGAGCTGGTGGTGGCCAAGGCTGGAGTC

TACTATGTCTTCTTTCAACTAGAGCTGCGGCGCGTGGTGGCC

GGCGAGGGCTCAGGCTCCGTTTCACTTGCGCTGCACCTGCAG

CCACTGCGCTCTGCTGCTGGGGCCGCCGCCCTGGCTTTGACC

GTGGACCTGCCACCCGCCTCCTCCGAGGCTCGGAACTCGGCC

TTCGGTTTCCAGGGCCGCTTGCTGCACCTGAGTGCCGGCCAG

CGCCTGGGCGTCCATCTTCACACTGAGGCCAGGGCACGCCAT

GCCTGGCAGCTTACCCAGGGCGCCACAGTCTTGGGACTCTTC

CGGGTGACCCCCGAAATCCCAGCCGGACTCCCTTCACCGAGG

TCGGAA.
```

In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

```
                                   (SEQ ID NO: 167)
DPAGLLDLRQGMFAQLVAQNVLLIDGPLSWYSDPGLAGVSLT

GGLSYKEDTKELVVAKAGVYYVFFQLELRRVVAGEGSGSVSL

ALHLQPLRSAAGAAALALTVDLPPASSEARNSAFGFQGRLLH

LSAGQRLGVHLHTEARARHAWQLTQGATVLGLFRVTPEI.
```

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

```
                                   (SEQ ID NO: 168)
GATCCCGCCGGCCTCTTGGACCTGCGGCAGGGCATGTTTGCG

CAGCTGGTGGCCCAAAATGTTCTGCTGATCGATGGGCCCCTG

AGCTGGTACAGTGACCCAGGCCTGGCAGGCGTGTCCCTGACG

GGGGGCCTGAGCTACAAAGAGGACACGAAGGAGCTGGTGGTG

GCCAAGGCTGGAGTCTACTATGTCTTCTTTCAACTAGAGCTG

CGGCGCGTGGTGGCCGGCGAGGGCTCAGGCTCCGTTTCACTT

GCGCTGCACCTGCAGCCACTGCGCTCTGCTGCTGGGGCCGCC

GCCCTGGCTTTGACCGTGGACCTGCCACCCGCCTCCTCCGAG

GCTCGGAACTCGGCCTTCGGTTTCCAGGGCCGCTTGCTGCAC

CTGAGTGCCGGCCAGCGCCTGGGCGTCCATCTTCACACTGAG

GCCAGGGCACGCCATGCCTGGCAGCTTACCCAGGGCGCCACA

GTCTTGGGACTCTTCCGGGTGACCCCCGAAATC.
```

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                   (SEQ ID NO: 161)
IPPHVQKSVNNDMIVTDNNGAVKFPQLCKFCDVRFSTCDNQK

SCMSNCSITSICEKPQEVCVAVWRKNDENITLETVCHDPKLP

YHDFILEDAASPKCIMKEKKKPGETFFMCSCSSDECNDNIIF

SEEYNTSNPDGGGGSGGGGSGGGGSIPPHVQKSVNNDMIVTD

NNGAVKFPQLCKFCDVRFSTCDNQKSCMSNCSITSICEKPQE

VCVAVWRKNDENITLETVCHDPKLPYHDFILEDAASPKCIMK

EKKKPGETFFMCSCSSDECNDNIIFSEEYNTSNPDSGTTNTV

AAYNLTWKSTNFKTILEWEPKPVNQVYTVQISTKSGDWKSKC

FYTTDTECDLTDEIVKDVKQTYLARVFSYPAGNVESTGSAGE

PLYENSPEFTPYLETNLGQPTIQSFEQVGTKVNVTVEDERTL

VRRNNTFLSLRDVFGKDLIYTLYYWKSSSSGKKTAKTNTNEF

LIDVDKGENYCFSVQAVIPSRTVNRKSTDSPVECMGQEKGEF

RENWVNVISDLKKIEDLIQSMHIDATLYTESDVHPSCKVTAM
```

KCELLELQVISLESGDASIHDTVENLIILANNSLSSNGNVTE

SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)
ATCCCCCCCCATGTGCAAAAGAGCGTGAACAACGATATGATC

GTGACCGACAACAACGGCGCCGTGAAGTTTCCCCAGCTCTGC

AAGTTCTGCGATGTCAGGTTCAGCACCTGCGATAATCAGAAG

TCCTGCATGTCCAACTGCAGCATCACCTCCATCTGCGAGAAG

CCCCAAGAAGTGTGCGTGGCCGTGTGGCGAAAAATGACGAG

AACATCACCCTGGAGACCGTGTGTCACGACCCCAAGCTCCCT

TATCACGACTTCATTCTGGAGGACGCTGCCTCCCCCAAATGC

ATCATGAAGGAGAAGAAGAAGCCCGGAGAGACCTTCTTTATG

TGTTCCTGTAGCAGCGACGAGTGTAACGACAACATCATCTTC

AGCGAAGAGTACAACACCAGCAACCCTGATGGAGGTGGCGGA

TCCGGAGGTGGAGGTTCTGGTGGAGGTGGGAGTATTCCTCCC

CACGTGCAGAAGAGCGTGAATAATGACATGATCGTGACCGAT

AACAATGGCGCCGTGAAATTTCCCCAGCTGTGCAAATTCTGC

GATGTGAGGTTTTCCACCTGCGACAACCAGAAGTCCTGTATG

AGCAACTGCTCCATCACCTCCATCTGTGAGAAGCCTCAGGAG

GTGTGCGTGGCTGTCTGGCGGAAGAATGACGAGAATATCACC

CTGGAAACCGTCTGCCACGATCCCAAGCTGCCCTACCACGAT

TTCATCCTGGAAGACGCCGCCAGCCCTAAGTGCATCATGAAA

GAGAAAAAGAAGCCTGGCGAGACCTTTTTCATGTGCTCCTGC

AGCAGCGACGAATGCAACGACAATATCATCTTTAGCGAGGAA

TACAATACCAGCAACCCCGACAGCGGCACAACCAACACAGTC

GCTGCCTATAACCTCACTTGGAAGAGCACCAACTTCAAAACC

ATCCTCGAATGGGAACCCAAACCCGTTAACCAAGTTTACACC

GTGCAGATCAGCACCAAGTCCGGCGACTGGAAGTCCAAATGT

TTCTATACCACCGACACCGAGTGCGATCTCACCGATGAGATC

GTGAAAGATGTGAAACAGACCTACCTCGCCCGGGTGTTTAGC

TACCCCGCCGGCAATGTGGAGAGCACTGGTTCCGCTGGCGAG

CCTTTATACGAGAACAGCCCCGAATTTACCCCTTACCTCGAG

ACCAATTTAGGACAGCCCACCATCCAAAGCTTTGAGCAAGTT

GGCACAAAGGTGAATGTGACAGTGGAGGACGAGCGGACTTTA

GTGCGGCGGAACAACACCTTTCTCAGCCTCCGGGATGTGTTC

GGCAAAGATTTAATCTACACACTGTATTACTGGAAGTCCTCT

TCCTCCGGCAAGAAGACAGCTAAAACCAACACAAACGAGTTT

TTAATCGACGTGGATAAAGGCGAAAACTACTGTTTCAGCGTG

CAAGCTGTGATCCCCTCCCGGACCGTGAATAGGAAAAGCACC

GATAGCCCCGTTGAGTGCATGGGCCAAGAAAAGGGCGAGTTC

CGGGAGAACTGGGTGAACGTCATCAGCGATTTAAAGAAGATC

GAAGATTTAATTCAGTCCATGCATATCGACGCCACTTTATAC

ACAGAATCCGACGTGCACCCCTCTTGTAAGGTGACCGCCATG

CAAGTTATCTCTTTAGAGAGCGGAGACGCTAGCATCCACGAC

AAATGTTTTTTACTGGAGCTGACCGTGGAGAATTTAATCATT

TTAGCCAATAACTCTTTATCCAGCAACGGCAACGTGACAGAG

TCCGGCTGCAAGGAGTGCGAAGAGCTGGAGGAGAAGAACATC

AAGGAGTTTCTGCAATCCTTTGTGCACATTGTCCAGATGTTC

ATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)
MKWVTFISLLFLFSSAYSIPPHVQKSVNNDMIVTDNNGAVKF

PQLCKFCDVRFSTCDNQKSCMSNCSITSICEKPQEVCVAVWR

KNDENITLETVCHDPKLPYHDFILEDAASPKCIMKEKKKPGE

TFFMCSCSSDECNDNIIFSEEYNTSNPDGGGSGGGSGGGG

SIPPHVQKSVNNDMIVTDNNGAVKFPQLCKFCDVRFSTCDNQ

KSCMSNCSITSICEKPQEVCVAVWRKNDENITLETVCHDPKL

PYHDFILEDAASPKCIMKEKKKPGETFFMCSCSSDECNDNII

FSEEYNTSNPDSGTTNTVAAYNLTWKSTNFKTILEWEPKPVN

QVYTVQISTKSGDWKSKCFYTTDTECDLTDEIVKDVKQTYLA

RVFSYPAGNVESTGSAGEPLYENSPEFTPYLETNLGQPTIQS

FEQVGTKVNVTVEDERTLVRRNNTFLSLRDVFGKDLIYTLYY

WKSSSSGKKTAKTNTNEFLIDVDKGENYCFSVQAVIPSRTVN

RKSTDSPVECMGQEKGEFRENWVNVISDLKKIEDLIQSMHID

ATLYTESDVHPSCKVTAMKCFLLELQVISLESGDASIHDTVE

NLIILANNSLSSNGNVTESGCKECEELEEKNIKEFLQSFVHI

VQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)
```
ATGAAGTGGGTGACCTTCATCAGCCTGCTGTTCCTGTTCTCCAGCGCCT
ACTCCATCCCCCCCCATGTGCAAAAGAGCGTGAACAACGATATGATCGT
GACCGACAACAACGGCGCCGTGAAGTTTCCCCAGCTCTGCAAGTTCTGC
GATGTCAGGTTCAGCACCTGCGATAATCAGAAGTCCTGCATGTCCAACT
GCAGCATCACCTCCATCTGCGAGAAGCCCCAAGAAGTGTGCGTGGCCGT
GTGGCGGAAAAATGACGAGAACATCACCCTGGAGACCGTGTGTCACGAC
CCCAAGCTCCCTTATCACGACTTCATTCTGGAGGACGCTGCCTCCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC
CTTTTTCATGTGCTCCTGCAGCAGCGACGAATGCAACGACAATATCATC
TTTAGCGAGGAATACAATACCAGCAACCCCGACAGCGGCACAACCAACA
CAGTCGCTGCCTATAACCTCACTTGGAAGAGCACCAACTTCAAAACCAT
CCTCGAATGGGAACCCAAACCCGTTAACCAAGTTTACACCGTGCAGATC
AGCACCAAGTCCGGCGACTGGAAGTCCAAATGTTTCTATACCACCGACA
CCGAGTGCGATCTCACCGATGAGATCGTGAAAGATGTGAAACAGACCTA
CCTCGCCCGGGTGTTTAGCTACCCCGCCGGCAATGTGGAGAGCACTGGT
TCCGCTGGCGAGCCTTTATACGAGAACAGCCCCGAATTTACCCCTTACC
TCGAGACCAATTTAGGACAGCCCACCATCCAAAGCTTTGAGCAAGTTGG
CACAAAGGTGAATGTGACAGTGGAGGACGAGCGGACTTTAGTGCGGCGG
AACAACACCTTTCTCAGCCTCCGGGATGTGTTCGGCAAAGATTTAATCT
ACACACTGTATTACTGGAAGTCCTCTTCCTCCGGCAAGAAGACAGCTAA
AACCAACACAAACGAGTTTTTAATCGACGTGGATAAAGGCGAAAACTAC
TGTTTCAGCGTGCAAGCTGTGATCCCCTCCCGGACCGTGAATAGGAAAA
GCACCGATAGCCCCGTTGAGTGCATGGGCAAGAAAAGGGCGAGTTCCG
GGAGAACTGGGTGAACGTCATCAGCGATTTAAAGAAGATCGAAGATTTA
ATTCAGTCCATGCATATCGACGCCACTTTATACACAGAATCCGACGTGC
ACCCCTCTTGTAAGGTGACCGCCATGAAATGTTTTTTACTGGAGCTGCA
AGTTATCTCTTTAGAGAGCGGAGACGCTAGCATCCACGACACCGTGGAG
AATTTAATCATTTTAGCCAATAACTCTTTATCCAGCAACGGCAACGTGA
CAGAGTCCGGCTGCAAGGAGTGCGAAGAGCTGGAGGAGAAGAACATCAA
GGAGTTTCTGCAATCCTTTGTGCACATTGTCCAGATGTTCATCAATACC
TCC
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 169)
```
QGQDRHMIRMRQLIDIVDQLKNYVNDLVPEFLPAPEDVETNCEWSAFSC
FQKAQLKSANTGNNERIINVSIKKLRKPPSTNAGRRQKHRLTCPSCDS
YEKKPPKEFLERFKSLLQKMIHQHLSSRTHGSEDSITCPPPMSVEHADI
WVKSYSLYSRERYICNSGFKRKAGTSSLTECVLNKATNVAHWTTPSLKC
IRGGGGSGGGGSGGGGSREGPELSPDDPAGLLDLRQGMFAQLVAQNVLL
IDGPLSWYSDPGLAGVSLTGGLSYKEDTKELVVAKAGVYYVFFQLELRR
VVAGEGSGSVSLALHLQPLRSAAGAAALALTVDLPPASSEARNSAFGFQ
GRLLHLSAGQRLGVHLHTEARARHAWQLTQGATVLGLFRVTPEIPAGLP
SPRSE
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 170)
```
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCCATTACATGCCCCCCTCCCATGAGCGTGGAGCACGCCGACATC
TGGGTGAAGAGCTATAGCCTCTACAGCCGGGAGAGGTATATCTGTAACA
GCGGCTTCAAGAGGAAGGCCGGCACCAGCAGCCTCACCGAGTGCGTGCT
GAATAAGGCTACCAACGTGGCTCACTGGACAACACCCTCTTTAAAGTGC
ATCCGGGGCGGTGGAGGATCCGGAGGAGGTGGCTCCGGCGGCGGAGGAT
CTCGCGAGGGTCCCGAGCTTTCGCCCGACGATCCCGCCGGCCTCTTGGA
CCTGCGGCAGGGCATGTTTGCGCAGCTGGTGGCCCAAAATGTTCTGCTG
ATCGATGGGCCCCTGAGCTGGTACAGTGACCCAGGCCTGGCAGGCGTGT
CCCTGACGGGGGGCCTGAGCTACAAAGAGGACACGAAGGAGCTGGTGGT
GGCCAAGGCTGGAGTCTACTATGTCTTCTTTCAACTAGAGCTGCGGCGC
GTGGTGGCCGGCGAGGGCTCAGGCTCCGTTTCACTTGCGCTGCACCTGC
AGCCACTGCGCTCTGCTGCTGGGGCCGCCGCCCTGGCTTTGACCGTGGA
CCTGCCACCCGCCTCCTCCGAGGCTCGGAACTCGGCCTTCGGTTTCCAG
GGCCGCTTGCTGCACCTGAGTGCCGGCCAGCGCCTGGGCGTCCATCTTC
```

ACACTGAGGCCAGGGCACGCCATGCCTGGCAGCTTACCCAGGGCGCCAC

AGTCTTGGGACTCTTCCGGGTGACCCCCGAAATCCCAGCCGGACTCCCT

TCACCGAGGTCGGAA

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 171)
MKWVTFISLLFLFSSAYSQGQDRHMIRMRQLIDIVDQLKNYVNDLVPEF

LPAPEDVETNCEWSAFSCFQKAQLKSANTGNNERIINVSIKKLKRKPPS

TNAGRRQKHRLTCPSCDSYEKKPPKEFLERFKSLLQKMIHQHLSSRTHG

SEDSITCPPPMSVEHADIWVKSYSLYSRERYICNSGFKRKAGTSSLTEC

VLNKATNVAHWTTPSLKCIRGGGGSGGGGSGGGGSREGPELSPDDPAGL

LDLRQGMFAQLVAQNVLLIDGPLSWYSDPGLAGVSLTGGLSYKEDTKEL

VVAKAGVYYVFFQLELRRVVAGEGSGSVSLALHLQPLRSAAGAAALALT

VDLPPASSEARNSAFGFQGRLLHLSAGQRLGVHLHTEARARHAWQLTQG

ATVLGLFRVTPEIPAGLPSPRSE

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 172)
ATGAAGTGGGTGACCTTCATCAGCCTGCTGTTCCTGTTCTCCAGCGCCT

ACTCCCAGGGCCAGGACAGGCACATGATCCGGATGAGGCAGCTCATCGA

CATCGTCGACCAGCTGAAGAACTACGTGAACGACCTGGTGCCCGAGTTT

CTGCCTGCCCCCGAGGACGTGGAGACCAACTGCGAGTGGTCCGCCTTCT

CCTGCTTTCAGAAGGCCCAGCTGAAGTCCGCCAACACCGGCAACAACGA

GCGGATCATCAACGTGAGCATCAAGAAGCTGAAGCGGAAGCCTCCCTCC

ACAAACGCCGGCAGGAGGCAGAAGCACAGGCTGACCTGCCCCAGCTGTG

ACTCCTACGAGAAGAAGCCCCCCAAGGAGTTCCTGGAGAGGTTCAAGTC

CCTGCTGCAGAAGATGATCCATCAGCACCTGTCCTCCAGGACCCACGGC

TCCGAGGACTCCATTACATGCCCCCCTCCCATGAGCGTGGAGCACGCCG

ACATCTGGGTGAAGAGCTATAGCCTCTACAGCCGGGAGAGGTATATCTG

TAACAGCGGCTTCAAGAGGAAGGCCGGCACCAGCAGCCTCACCGAGTGC

GTGCTGAATAAGGCTACCAACGTGGCTCACTGGACAACACCCTCTTTAA

AGTGCATCCGGGGCGGTGGAGGATCCGGAGGAGGTGGCTCCGGCGGCGG

AGGATCTCGCGAGGGTCCCGAGCTTTCGCCCGACGATCCCGCCGGCCTC

TTGGACCTGCGGCAGGGCATGTTTGCGCAGCTGGTGGCCCAAAATGTTC

TGCTGATCGATGGGCCCCTGAGCTGGTACAGTGACCCAGGCCTGGCAGG

CGTGTCCCTGACGGGGGGCCTGAGCTACAAAGAGGACACGAAGGAGCTG

GTGGTGGCCAAGGCTGGAGTCTACTATGTCTTCTTTCAACTAGAGCTGC

GGCGCGTGGTGGCCGGCGAGGGCTCAGGCTCCGTTTCACTTGCGCTGCA

CCTGCAGCCACTGCGCTCTGCTGCTGGGGCCGCCGCCCTGGCTTTGACC

GTGGACCTGCCACCCGCCTCCTCCGAGGCTCGGAACTCGGCCTTCGGTT

TCCAGGGCCGCTTGCTGCACCTGAGTGCCGGCCAGCGCCTGGGCGTCCA

TCTTCACACTGAGGCCAGGGCACGCCATGCCTGGCAGCTTACCCAGGGC

GCCACAGTCTTGGGACTCTTCCGGGTGACCCCCGAAATCCCAGCCGGAC

TCCCTTCACCGAGGTCGGAA

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 173)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDSITCPPPMSVEHADI

WVKSYSLYSRERYICNSGFKRKAGTSSLTECVLNKATNVAHWTTPSLKC

IRGGGGSGGGGSGGGGSDPAGLLDLRQGMFAQLVAQNVLLIDGPLSWYS

DPGLAGVSLTGGLSYKEDTKELVVAKAGVYYVFFQLELRRVVAGEGSGS

VSLALHLQPLRSAAGAAALALTVDLPPASSEARNSAFGFQGRLLHLSAG

QRLGVHLHTEARARHAWQLTQGATVLGLFRVTPEI

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 174)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCCATTACATGCCCCCCTCCCATGAGCGTGGAGCACGCCGACATC

TGGGTGAAGAGCTATAGCCTCTACAGCCGGGAGAGGTATATCTGTAACA

GCGGCTTCAAGAGGAAGGCCGGCACCAGCAGCCTCACCGAGTGCGTGCT

-continued

```
GAATAAGGCTACCAACGTGGCTCACTGGACAACACCCTCTTTAAAGTGC
ATCCGGGGCGGTGGAGGATCCGGAGGAGGTGGCTCCGGCGGCGGAGGAT
CTGATCCCGCCGGCCTCTTGGACCTGCGGCAGGGCATGTTTGCGCAGCT
GGTGGCCCAAAATGTTCTGCTGATCGATGGGCCCCTGAGCTGGTACAGT
GACCCAGGCCTGGCAGGCGTGTCCCTGACGGGGGCCTGAGCTACAAAG
AGGACACGAAGGAGCTGGTGGTGGCCAAGGCTGGAGTCTACTATGTCTT
CTTTCAACTAGAGCTGCGGCGCGTGGTGGCCGGCGAGGGCTCAGGCTCC
GTTTCACTTGCGCTGCACCTGCAGCCACTGCGCTCTGCTGCTGGGGCCA
CCGCCCTGGCTTTGACCGTGGACCTGCCACCCGCCTCCTCCGAGGCTCG
GAACTCGGCCTTCGGTTTCCAGGGCCGCTTGCTGCACCTGAGTGCCGGC
CAGCGCCTGGGCGTCCATCTTCACACTGAGGCCAGGGCACGCCATGCCT
GGCAGCTTACCCAGGGCGCCACAGTCTTGGGACTCTTCCGGGTGACCCC
CGAAATC
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 175)
```
MKWVTFISLLFLFSSAYSQGQDRHMIRMRQLIDIVDQLKNYVNDLVPEF
LPAPEDVETNCEWSAFSCFQKAQLKSANTGNNERIINVSIKKLKRKPPS
TNAGRRQKHRLTCPSCDSYEKKPPKEFLERFKSLLQKMIHQHLSSRTHG
SEDSITCPPPMSVEHADIWVKSYSLYSRERYICNSGFKRKAGTSSLTEC
VLNKATNVAHWTTPSLKCIRGGGGSGGGGSGGGGSDPAGLLDLRQGMFA
QLVAQNVLLIDGPLSWYSDPGLAGVSLTGGLSYKEDTKELVVAKAGVYY
VFFQLELRRVVAGEGSGSVSLALHLQPLRSAAGAAALALTVDLPPASSE
ARNSAFGFQGRLLHLSAGQRLGVHLHTEARARHAWQLTQGATVLGLFRV
TPEI
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 176)
```
ATGAAGTGGGTGACCTTCATCAGCCTGCTGTTCCTGTTCTCCAGCGCCT
ACTCCCAGGGCCAGGACAGGCACATGATCCGGATGAGGCAGCTCATCGA
CATCGTCGACCAGCTGAAGAACTACGTGAACGACCTGGTGCCCGAGTTT
CTGCCTGCCCCCGAGGACGTGGAGACCAACTGCGAGTGGTCCGCCTTCT
CCTGCTTTCAGAAGGCCCAGCTGAAGTCCGCCAACACCGGCAACAACGA
GCGGATCATCAACGTGAGCATCAAGAAGCTGAAGCGGAAGCCTCCCTCC
ACAAACGCCGGCAGGAGGCAGAAGCACAGGCTGACCTGCCCCAGCTGTG
ACTCCTACGAGAAGAAGCCCCCCAAGGAGTTCCTGGAGAGGTTCAAGTC
CCTGCTGCAGAAGATGATCCATCAGCACCTGTCCTCCAGGACCCACGGC
TCCGAGGACTCCATTACATGCCCCCCTCCCATGAGCGTGGAGCACGCCG
ACATCTGGGTGAAGAGCTATAGCCTCTACAGCCGGGAGAGGTATATCTG
TAACAGCGGCTTCAAGAGGAAGGCCGGCACCAGCAGCCTCACCGAGTGC
GTGCTGAATAAGGCTACCAACGTGGCTCACTGGACAACACCCTCTTTAA
AGTGCATCCGGGGCGGTGGAGGATCCGGAGGAGGTGGCTCCGGCGGCGG
AGGATCTGATCCCGCCGGCCTCTTGGACCTGCGGCAGGGCATGTTTGCG
CAGCTGGTGGCCCAAAATGTTCTGCTGATCGATGGGCCCCTGAGCTGGT
ACAGTGACCCAGGCCTGGCAGGCGTGTCCCTGACGGGGGCCTGAGCTA
CAAAGAGGACACGAAGGAGCTGGTGGTGGCCAAGGCTGGAGTCTACTAT
GTCTTCTTTCAACTAGAGCTGCGGCGCGTGGTGGCCGGCGAGGGCTCAG
GCTCCGTTTCACTTGCGCTGCACCTGCAGCCACTGCGCTCTGCTGCTGG
GGCCGCCGCCCTGGCTTTGACCGTGGACCTGCCACCCGCCTCCTCCGAG
GCTCGGAACTCGGCCTTCGGTTTCCAGGGCCGCTTGCTGCACCTGAGTG
CCGGCCAGCGCCTGGGCGTCCATCTTCACACTGAGGCCAGGGCACGCCA
TGCCTGGCAGCTTACCCAGGGCGCCACAGTCTTGGGACTCTTCCGGGTG
ACCCCCGAAATC
```

Exemplary Multi-Chain Chimeric Polypeptides—Type M

In some embodiments of any of the multi-chain chimeric polypeptides described herein, the first target-binding domain and the second targeting-binding domain each independently bind specifically to TGF-β or a receptor of IL-21. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a TGF-β (e.g., a soluble TGF-β receptor, e.g., a soluble TGFβRII receptor).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to TGF-β or a receptor for IL-21. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGF-β RII includes a first sequence of soluble human TGF-β RII and a second sequence of soluble human TGF-β RII. In some embodiments of these multi-chain chimeric polypeptides, the soluble human TGF-β RII includes a linker disposed between the first sequence of soluble human TGF-β RII and the second sequence of soluble human TGF-β RII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD
```

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 58)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD
```

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 57)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTTATGTGTTCCT

GTAGCAGCGACGAGTGTAACGACAACATCATCTTCAGCGAAGAGTACAA

CACCAGCAACCCTGAT
```

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 59)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA
```

-continued
```
GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC
```

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 60)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD
```

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 198)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC
```

In some embodiments of these multi-chain chimeric polypeptides, the second target-binding domain binds specifically to a receptor for IL-21. In some embodiments of these multi-chain chimeric polypeptides, the second target-binding domain includes a soluble IL-21 (e.g., a human soluble IL-21). In some embodiments of these multi-chain chimeric polypeptides, the soluble IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 124)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.
```

In some embodiments of these multi-chain chimeric polypeptides, the soluble IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 125)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC.
```

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 161)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDSGTTNTV

AAYNLTWKSTNFKTILEWEPKPVNQVYTVQISTKSGDWKSKCFYTTDTE

CDLTDEIVKDVKQTYLARVFSYPAGNVESTGSAGEPLYENSPEFTPYLE
```

TNLGQPTIQSFEQVGTKVNVTVEDERTLVRRNNTFLSLRDVFGKDLIYT

LYYWKSSSSGKKTAKTNTNEFLIDVDKGENYCFSVQAVIPSRTVNRKST

DSPVECMGQEKGEFRENWVNVISDLKKIEDLIQSMHIDATLYTESDVHP

SCKVTAMKCFLLELQVISLESGDASIHDTVENLIILANNSLSSNGNVTE

SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACAGCGGCACAACCAACACAGTC

GCTGCCTATAACCTCACTTGGAAGAGCACCAACTTCAAAACCATCCTCG

AATGGGAACCCAAACCCGTTAACCAAGTTTACACCGTGCAGATCAGCAC

CAAGTCCGGCGACTGGAAGTCCAAATGTTTCTATACCACCGACACCGAG

TGCGATCTCACCGATGAGATCGTGAAAGATGTGAAACAGACCTACCTCG

CCCGGGTGTTTAGCTACCCCGCCGGCAATGTGGAGAGCACTGGTTCCGC

TGGCGAGCCTTTATACGAGAACAGCCCCGAATTTACCCCTTACCTCGAG

ACCAATTTAGGACAGCCCACCATCCAAAGCTTTGAGCAAGTTGGCACAA

AGGTGAATGTGACAGTGGAGGACGAGCGGACTTTAGTGCGGCGGAACAA

CACCTTTCTCAGCCTCCGGGATGTGTTCGGCAAAGATTTAATCTACACA

CTGTATTACTGGAAGTCCTCTTCCTCCGGCAAGAAGACAGCTAAAACCA

ACACAAACGAGTTTTTAATCGACGTGGATAAAGGCGAAAACTACTGTTT

CAGCGTGCAAGCTGTGATCCCCTCCCGGACCGTGAATAGGAAAAGCACC

GATAGCCCCGTTGAGTGCATGGGCCAAGAAAAGGGCGAGTTCCGGGAGA

ACTGGGTGAACGTCATCAGCGATTTAAAGAAGATCGAAGATTTAATTCA

GTCCATGCATATCGACGCCACTTTATACACAGAATCCGACGTGCACCCC

TCTTGTAAGGTGACCGCCATGAAATGTTTTTTACTGGAGCTGCAAGTTA

TCTCTTTAGAGAGCGGAGACGCTAGCATCCACGACACCGTGGAGAATTT

AATCATTTTAGCCAATAACTCTTTATCCAGCAACGGCAACGTGACAGAG

TCCGGCTGCAAGGAGTGCGAAGAGCTGGAGGAGAAGAACATCAAGGAGT

TTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)
MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDSGTTNTVAAYNLTWKSTNFKTILEWEPKPVNQVYTVQI

STKSGDWKSKCFYTTDTECDLTDEIVKDVKQTYLARVFSYPAGNVESTG

SAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENY

CFSVQAVIPSRTVNRKSTDSPVECMGQEKGEFRENWVNVISDLKKIEDL

IQSMHIDATLYTESDVHPSCKVTAMKCFLLELQVISLESGDASIHDTVE

NLIILANNSLSSNGNVTESGCKECEELEEKNIKEFLQSFVHIVQMFINT

S.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)
ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

```
CCCAAGCTCCCTTATCACGACTTCATTCTGGAGGACGCTGCCTCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC
CTTTTTCATGTGCTCCTGCAGCAGCGACGAATGCAACGACAATATCATC
TTTAGCGAGGAATACAATACCAGCAACCCCGACAGCGGCACAACCAACA
CAGTCGCTGCCTATAACCTCACTTGGAAGAGCACCAACTTCAAAACCAT
CCTCGAATGGGAACCCAAACCCGTTAACCAAGTTTACACCGTGCAGATC
AGCACCAAGTCCGGCGACTGGAAGTCCAAATGTTTCTATACCACCGACA
CCGAGTGCGATCTCACCGATGAGATCGTGAAAGATGTGAAACAGACCTA
CCTCGCCCGGGTGTTTAGCTACCCCGCCGGCAATGTGGAGAGCACTGGT
TCCGCTGGCGAGCCTTTATACGAGAACAGCCCCGAATTTACCCCTTACC
TCGAGACCAATTTAGGACAGCCCACCATCCAAAGCTTTGAGCAAGTTGG
CACAAAGGTGAATGTGACAGTGGAGGACGAGCGGACTTTAGTGCGGCGG
AACAACACCTTTCTCAGCCTCCGGGATGTGTTCGGCAAAGATTTAATCT
ACACACTGTATTACTGGAAGTCCTCTTCCTCCGGCAAGAAGACAGCTAA
AACCAACACAAACGAGTTTTTAATCGACGTGGATAAAGGCGAAAACTAC
TGTTTCAGCGTGCAAGCTGTGATCCCCTCCCGGACCGTGAATAGGAAAA
GCACCGATAGCCCCGTTGAGTGCATGGGCCAAGAAAAGGGCGAGTTCCG
GGAGAACTGGGTGAACGTCATCAGCGATTTAAAGAAGATCGAAGATTTA
ATTCAGTCCATGCATATCGACGCCACTTTATACACAGAATCCGACGTGC
ACCCCTCTTGTAAGGTGACCGCCATGAATGTTTTTTACTGGAGCTGCA
AGTTATCTCTTTAGAGAGCGGAGACGCTAGCATCCACGACACCGTGGAG
AATTTAATCATTTTAGCCAATAACTCTTTATCCAGCAACGGCAACGTGA
CAGAGTCCGGCTGCAAGGAGTGCGAAGAGCTGGAGGAGAAGAACATCAA
GGAGTTTCTGCAATCCTTTGTGCACATTGTCCAGATGTTCATCAATACC
TCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 177)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDITCPPPM

SVEHADIWVKSYSLYSRERYICNSGFKRKAGTSSLTECVLNKATNVAHW

TTPSLKCIRQGQDRHMIRMRQLIDIVDQLKNYVNDLVPEFLPAPEDVET

NCEWSAFSCFQKAQLKSANTGNNERIINVSIKKLKRKPPSTNAGRRQKH

RLTCPSCDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
(SEQ ID NO: 178)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGACATTACATGCCCCCCTCCCATG
AGCGTGGAGCACGCCGACATCTGGGTGAAGAGCTATAGCCTCTACAGCC
GGGAGAGGTATATCTGTAACAGCGGCTTCAAGAGGAAGGCCGGCACCAG
CAGCCTCACCGAGTGCGTGCTGAATAAGGCTACCAACGTGGCTCACTGG
ACAACACCCTCTTTAAAGTGCATCCGGCAGGGCCAGGACAGGCACATGA
TCCGGATGAGGCAGCTCATCGACATCGTCGACCAGCTGAAGAACTACGT
GAACGACCTGGTGCCCGAGTTTCTGCCTGCCCCCGAGGACGTGGAGACC
```

```
AACTGCGAGTGGTCCGCCTTCTCCTGCTTTCAGAAGGCCCAGCTGAAGT

CCGCCAACACCGGCAACAACGAGCGGATCATCAACGTGAGCATCAAGAA

GCTGAAGCGGAAGCCTCCCTCCACAAACGCCGGCAGGAGGCAGAAGCAC

AGGCTGACCTGCCCCAGCTGTGACTCCTACGAGAAGAAGCCCCCAAGG

AGTTCCTGGAGAGGTTCAAGTCCCTGCTGCAGAAGATGATCCATCAGCA

CCTGTCCTCCAGGACCCACGGCTCCGAGGACTCC.
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 179)
```
MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDITCPPPMSVEHADIWVKSYSLYSRERYICNSGFKRKAG

TSSLTECVLNKATNVAHWTTPSLKCIRQGQDRHMIRMRQLIDIVDQLKN

YVNDLVPEFLPAPEDVETNCEWSAFSCFQKAQLKSANTGNNERIINVSI

KKLKRKPPSTNAGRRQKHRLTCPSCDSYEKKPPKEFLERFKSLLQKMIH

QHLSSRTHGSEDS.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 180)
```
ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCTCCATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACATTACATGCCCCCCTC

CCATGAGCGTGGAGCACGCCGACATCTGGGTGAAGAGCTATAGCCTCTA

CAGCCGGGAGAGGTATATCTGTAACAGCGGCTTCAAGAGGAAGGCCGGC

ACCAGCAGCCTCACCGAGTGCGTGCTGAATAAGGCTACCAACGTGGCTC

ACTGGACAACACCCTCTTTAAAGTGCATCCGGCAGGGCCAGGACAGGCA

CATGATCCGGATGAGGCAGCTCATCGACATCGTCGACCAGCTGAAGAAC

TACGTGAACGACCTGGTGCCCGAGTTTCTGCCTGCCCCCGAGGACGTGG

AGACCAACTGCGAGTGGTCCGCCTTCTCCTGCTTTCAGAAGGCCCAGCT

GAAGTCCGCCAACACCGGCAACAACGAGCGGATCATCAACGTGAGCATC

AAGAAGCTGAAGCGGAAGCCTCCCTCCACAAACGCCGGCAGGAGGCAGA

AGCACAGGCTGACCTGCCCCAGCTGTGACTCCTACGAGAAGAAGCCCCC

CAAGGAGTTCCTGGAGAGGTTCAAGTCCCTGCTGCAGAAGATGATCCAT

CAGCACCTGTCCTCCAGGACCCACGGCTCCGAGGACTCC.
```

Exemplary Multi-Chain Chimeric Polypeptides—Type N

In some embodiments of any of the multi-chain chimeric polypeptides described herein, the first target-binding domain and the second targeting-binding domain each independently bind specifically to TGF-β or CD16. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 (e.g., an anti-CD16 scFv) or a TGF-β (e.g., a soluble TGF-β receptor, e.g., a soluble TGFβRII receptor).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to TGF-β or CD16. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGF-β RII includes a first sequence of soluble human TGF-β RII and a second sequence of soluble human TGF-β RII. In some embodiments of these multi-chain chimeric polypeptides, the soluble human TGF-β RII includes a linker disposed between the first sequence of soluble human TGF-β RII and the second sequence of soluble human TGF-β RII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT.

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

-continued
```
GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC.
```

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 60)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD
```

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                   (SEQ ID NO: 198)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC.
```

In some embodiments of these multi-chain chimeric polypeptides, the second target-binding domain binds specifically to CD16. In some embodiments of these multi-chain chimeric polypeptides, the second target-binding domain includes an anti-CD16 scFv. In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                   (SEQ ID NO: 149)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGH
```

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                   (SEQ ID NO: 150)
TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

AACAACAGGCCCTCCGGCATCCCTGACAGGTTCTCCGGATCCTCCTCCG

GCAACACCGCCTCCCTGACCATCACAGGCGCTCAGGCCGAGGACGAGGC

TGACTACTACTGCAACTCCAGGGACTCCTCCGGCAACCATGTGGTGTTC

GGCGGCGGCACCAAGCTGACCGTGGGCCAT
```

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                   (SEQ ID NO: 151)
EVQLVESGGGVVRPGGSLRLSCAASGFTFDDYGMSWVRQAPGKGLEWVS

GINWNGGSTGYADSVKGRFTISRDNAKNSLYLQMNSLRAEDTAVYYCAR

GRSLLFDYWGQGTLVTVSR
```

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 152)
GAGGTGCAGCTGGTGGAGTCCGGAGGAGGAGTGGTGAGGCCTGGAGGCT

CCCTGAGGCTGAGCTGTGCTGCCTCCGGCTTCACCTTCGACGACTACGG

CATGTCCTGGGTGAGGCAGGCTCCTGGAAAGGGCCTGGAGTGGGTGTCC

GGCATCAACTGGAACGGCGGATCCACCGGCTACGCCGATTCCGTGAAGG

GCAGGTTCACCATCAGCAGGGACAACGCCAAGAACTCCCTGTACCTGCA

GATGAACTCCCTGAGGGCCGAGGACACCGCCGTGTACTACTGCGCCAGG

GGCAGGTCCCTGCTGTTCGACTACTGGGGACAGGGCACCCTGGTGACCG

TGTCCAGG

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDSGTTNTV

AAYNLTWKSTNFKTILEWEPKPVNQVYTVQISTKSGDWKSKCFYTTDTE

CDLTDEIVKDVKQTYLARVFSYPAGNVESTGSAGEPLYENSPEFTPYLE

TNLGQPTIQSFEQVGTKVNVTVEDERTLVRRNNTFLSLRDVFGKDLIYT

LYYWKSSSSGKKTAKTNTNEFLIDVDKGENYCFSVQAVIPSRTVNRKST

DSPVECMGQEKGEFRENWVNVISDLKKIEDLIQSMHIDATLYTESDVHP

SCKVTAMKCFLLELQVISLESGDASIHDTVENLIILANNSLSSNGNVTE

SGCKECEELEEKNIKEFLQSFVHIVQMFINTS

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACAGCGGCACAACCAACACAGTC

GCTGCCTATAACCTCACTTGGAAGAGCACCAACTTCAAAACCATCCTCG

AATGGGAACCCAAACCCGTTAACCAAGTTTACACCGTGCAGATCAGCAC

CAAGTCCGGCGACTGGAAGTCCAAATGTTTCTATACCACCGACACCGAG

TGCGATCTCACCGATGAGATCGTGAAAGATGTGAAACAGACCTACCTCG

CCCGGGTGTTTAGCTACCCCGCCGGCAATGTGGAGAGCACTGGTTCCGC

TGGCGAGCCTTTATACGAGAACAGCCCCGAATTTACCCCTTACCTCGAG

ACCAATTTAGGACAGCCCACCATCCAAAGCTTTGAGCAAGTTGGCACAA

AGGTGAATGTGACAGTGGAGGACGAGCGGACTTTAGTGCGGCGGAACAA

CACCTTTCTCAGCCTCCGGGATGTGTTCGGCAAAGATTTAATCTACACA

CTGTATTACTGGAAGTCCTCTTCCTCCGGCAAGAAGACAGCTAAAACCA

ACACAAACGAGTTTTTAATCGACGTGGATAAAGGCGAAAACTACTGTTT

CAGCGTGCAAGCTGTGATCCCCTCCCGGACCGTGAATAGGAAAAGCACC

GATAGCCCCGTTGAGTGCATGGGCCAAGAAAAGGGCGAGTTCCGGGAGA

ACTGGGTGAACGTCATCAGCGATTTAAAGAAGATCGAAGATTTAATTCA

GTCCATGCATATCGACGCCACTTTATACACAGAATCCGACGTGCACCCC

TCTTGTAAGGTGACCGCCATGAAATGTTTTTTACTGGAGCTGCAAGTTA

TCTCTTTAGAGAGCGGAGACGCTAGCATCCACGACACCGTGGAGAATTT

AATCATTTTAGCCAATAACTCTTTATCCAGCAACGGCAACGTGACAGAG

TCCGGCTGCAAGGAGTGCGAAGAGCTGGAGGAGAAGAACATCAAGGAGT

TTCTGCAATCCTTTGTGCACATTGTCCAGATGTTCATCAATACCTCC

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)
MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

-continued

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDSGTTNTVAAYNLTWKSTNFKTILEWEPKPVNQVYTVQI

STKSGDWKSKCFYTTDTECDLTDEIVKDVKQTYLARVFSYPAGNVESTG

SAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENY

CFSVQAVIPSRTVNRKSTDSPVECMGQEKGEFRENWVNVISDLKKIEDL

IQSMHIDATLYTESDVHPSCKVTAMKCFLLELQVISLESGDASIHDTVE

NLIILANNSLSSNGNVTESGCKECEELEEKNIKEFLQSFVHIVQMFINT

S

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)
ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCTCCATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACAGCGGCACAACCAACA

CAGTCGCTGCCTATAACCTCACTTGGAAGAGCACCAACTTCAAAACCAT

CCTCGAATGGGAACCCAAACCCGTTAACCAAGTTTACACCGTGCAGATC

AGCACCAAGTCCGGCGACTGGAAGTCCAAATGTTTCTATACCACCGACA

CCGAGTGCGATCTCACCGATGAGATCGTGAAAGATGTGAAACAGACCTA

CCTCGCCCGGGTGTTTAGCTACCCCGCCGGCAATGTGGAGAGCACTGGT

TCCGCTGGCGAGCCTTTATACGAGAACAGCCCCGAATTTACCCCTTACC

TCGAGACCAATTTAGGACAGCCCACCATCCAAAGCTTTGAGCAAGTTGG

CACAAAGGTGAATGTGACAGTGGAGGACGAGCGGACTTTAGTGCGGCGG

AACAACACCTTTCTCAGCCTCCGGGATGTGTTCGGCAAAGATTTAATCT

ACACACTGTATTACTGGAAGTCCTCTTCCTCCGGCAAGAAGACAGCTAA

AACCAACACAAACGAGTTTTTAATCGACGTGGATAAAGGCGAAAACTAC

TGTTTCAGCGTGCAAGCTGTGATCCCCTCCCGGACCGTGAATAGGAAAA

GCACCGATAGCCCCGTTGAGTGCATGGGCCAAGAAAAGGGCGAGTTCCG

GGAGAACTGGGTGAACGTCATCAGCGATTTAAAGAAGATCGAAGATTTA

ATTCAGTCCATGCATATCGACGCCACTTTATACACAGAATCCGACGTGC

ACCCCTCTTGTAAGGTGACCGCCATGAAATGTTTTTTACTGGAGCTGCA

AGTTATCTCTTTAGAGAGCGGAGACGCTAGCATCCACGACACCGTGGAG

AATTTAATCATTTTAGCCAATAACTCTTTATCCAGCAACGGCAACGTGA

CAGAGTCCGGCTGCAAGGAGTGCGAAGAGCTGGAGGAGAAGAACATCAA

GGAGTTTCTGCAATCCTTTGTGCACATTGTCCAGATGTTCATCAATACC

TCC

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 181)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDITCPPPM

SVEHADIWVKSYSLYSRERYICNSGFKRKAGTSSLTECVLNKATNVAHW

TTPSLKCIRSELTQDPAVSVALGQTVRITCQGDSLRSYYASWYQQKPGQ

APVLVIYGKNNRPSGIPDRFSGSSSGNTASLTITGAQAEDEADYYCNSR

DSSGNHVVFGGGTKLTVGHGGGGSGGGGSGGGGSEVQLVESGGGVVRPG

GSLRLSCAASGFTFDDYGMSWVRQAPGKGLEWVSGINWNGGSTGYADSV

KGRFTISRDNAKNSLYLQMNSLRAEDTAVYYCARGRSLLFDYWGQGTLV

TVSR

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGACATTACATGCCCCCCTCCCATG
AGCGTGGAGCACGCCGACATCTGGGTGAAGAGCTATAGCCTCTACAGCC
GGGAGAGGTATATCTGTAACAGCGGCTTCAAGAGGAAGGCCGGCACCAG
CAGCCTCACCGAGTGCGTGCTGAATAAGGCTACCAACGTGGCTCACTGG
ACAACACCCTCTTTAAAGTGCATCCGGTCCGAGCTGACCCAGGACCCTG
CTGTGTCCGTGGCTCTGGGCCAGACCGTGAGGATCACCTGCAGGGCGA
CTCCCTGAGGTCCTACTACGCCTCCTGGTACCAGCAGAAGCCCGGCCAG
GCTCCTGTGCTGGTGATCTACGGCAAGAACAACAGGCCCTCCGGCATCC
CTGACAGGTTCTCCGGATCCTCCTCCGGCAACACCGCCTCCCTGACCAT
CACAGGCGCTCAGGCCGAGGACGAGGCTGACTACTACTGCAACTCCAGG
GACTCCTCCGGCAACCATGTGGTGTTCGGCGGCGGCACCAAGCTGACCG
TGGGCCATGGCGGCGGCGGCTCCGGAGGCGGCGGCAGCGGCGGAGGAGG
ATCCGAGGTGCAGCTGGTGGAGTCCGGAGGAGGAGTGGTGAGGCCTGGA
GGCTCCCTGAGGCTGAGCTGTGCTGCCTCCGGCTTCACCTTCGACGACT
ACGGCATGTCCTGGGTGAGGCAGGCTCCTGGAAAGGGCCTGGAGTGGGT
GTCCGGCATCAACTGGAACGGCGGATCCACCGGCTACGCCGATTCCGTG
AAGGGCAGGTTCACCATCAGCAGGGACAACGCCAAGAACTCCCTGTACC
TGCAGATGAACTCCCTGAGGGCCGAGGACACCGCCGTGTACTACTGCGC
CAGGGGCAGGTCCCTGCTGTTCGACTACTGGGGACAGGGCACCCTGGTG
ACCGTGTCCAGG

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 183)
MKWVTFISLLFLFSSAYSIPPHVQKSVNNDMIVTDNNGAVKFPQLCKFC
DVRFSTCDNQKSCMSNCSITSICEKPQEVCVAVWRKNDENITLETVCHD
PKLPYHDFILEDAASPKCIMKEKKKPGETFFMCSCSSDECNDNIIFSEE
YNTSNPDGGGGSGGGGSGGGGSIPPHVQKSVNNDMIVTDNNGAVKFPQL
CKFCDVRFSTCDNQKSCMSNCSITSICEKPQEVCVAVWRKNDENITLET
VCHDPKLPYHDFILEDAASPKCIMKEKKKPGETFFMCSCSSDECNDNII
FSEEYNTSNPDITCPPPMSVEHADIWVKSYSLYSRERYICNSGFKRKAG
TSSLTECVLNKATNVAHWTTPSLKCIRSELTQDPAVSVALGQTVRITCQ
GDSLRSYYASWYQQKPGQAPVLVIYGKNNRPSGIPDRFSGSSSGNTASL
TITGAQAEDEADYYCNSRDSSGNHVVFGGGTKLTVGHGGGGSGGGGSGG
GGSEVQLVESGGGVVRPGGSLRLSCAASGFTFDDYGMSWVRQAPGKGLE
WVSGINWNGGSTGYADSVKGRFTISRDNAKNSLYLQMNSLRAEDTAVYY
CARGRSLLFDYWGQGTLVTVSR

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
ATGAAGTGGGTGACCTTCATCAGCCTGCTGTTCCTGTTCTCCAGCGCCT
ACTCCATCCCCCCCCATGTGCAAAAGAGCGTGAACAACGATATGATCGT
GACCGACAACAACGGCGCCGTGAAGTTTCCCCAGCTCTGCAAGTTCTGC
GATGTCAGGTTCAGCACCTGCGATAATCAGAAGTCCTGCATGTCCAACT
GCAGCATCACCTCCATCTGCGAGAAGCCCCAAGAAGTGTGCGTGGCCGT
GTGGCGGAAAAATGACGAGAACATCACCCTGGAGACCGTGTGTCACGAC
CCCAAGCTCCCTTATCACGACTTCATTCTGGAGGACGCTGCCTCCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC
CTTTTTCATGTGCTCCTGCAGCAGCGACGAATGCAACGACAATATCATC
TTTAGCGAGGAATACAATACCAGCAACCCCGACATTACATGCCCCCCTC

-continued

```
CCATGAGCGTGGAGCACGCCGACATCTGGGTGAAGAGCTATAGCCTCTA

CAGCCGGGAGAGGTATATCTGTAACAGCGGCTTCAAGAGGAAGGCCGGC

ACCAGCAGCCTCACCGAGTGCGTGCTGAATAAGGCTACCAACGTGGCTC

ACTGGACAACACCCTCTTTAAAGTGCATCCGGTCCGAGCTGACCCAGGA

CCCTGCTGTGTCCGTGGCTCTGGGCCAGACCGTGAGGATCACCTGCCAG

GGCGACTCCCTGAGGTCCTACTACGCCTCCTGGTACCAGCAGAAGCCCG

GCCAGGCTCCTGTGCTGGTGATCTACGGCAAGAACAACAGGCCCTCCGG

CATCCCTGACAGGTTCTCCGGATCCTCCTCCGGCAACACCGCCTCCCTG

ACCATCACAGGCGCTCAGGCCGAGGACGAGGCTGACTACTACTGCAACT

CCAGGGACTCCTCCGGCAACCATGTGGTGTTCGGCGGCGGCACCAAGCT

GACCGTGGGCCATGGCGGCGGCGGCTCCGGAGGCGGCGGCAGCGGCGGA

GGAGGATCCGAGGTGCAGCTGGTGGAGTCCGGAGGAGGAGTGGTGAGGC

CTGGAGGCTCCCTGAGGCTGAGCTGTGCTGCCTCCGGCTTCACCTTCGA

CGACTACGGCATGTCCTGGGTGAGGCAGGCTCCTGGAAAGGGCCTGGAG

TGGGTGTCCGGCATCAACTGGAACGGCGGATCCACCGGCTACGCCGATT

CCGTGAAGGGCAGGTTCACCATCAGCAGGGACAACGCCAAGAACTCCCT

GTACCTGCAGATGAACTCCCTGAGGGCCGAGGACACCGCCGTGTACTAC

TGCGCCAGGGGCAGGTCCCTGCTGTTCGACTACGGGGACAGGGCACCC

TGGTGACCGTGTCCAGG
```

Exemplary Multi-Chain Chimeric Polypeptides—Type O

In some embodiments of any of the multi-chain chimeric polypeptides described herein, the first target-binding domain and the second targeting-binding domain each independently bind specifically to TGF-β or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor to TGF-β (e.g., a soluble TGF-β receptor, e.g., a soluble TGFβRII receptor) or CD137L.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to CD137L. In some embodiments of these multi-chain chimeric polypeptides, the first target-binding domain or the additional target-binding domain is a soluble TGF-β receptor (e.g., a soluble TGFβRII receptor, e.g., a soluble human TGFβRII receptor).

In some embodiments of these multi-chain chimeric polypeptides, the soluble human TGF-β RII includes a first sequence of soluble human TGF-β RII and a second sequence of soluble human TGF-β RII. In some embodiments of these multi-chain chimeric polypeptides, the soluble human TGF-β RII includes a linker disposed between the first sequence of soluble human TGF-β RII and the second sequence of soluble human TGF-β RII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNC

SITSICEKPQEVCVAVWRKNDENITLETVCHDPKLPYHDFILEDAASPK

CCIMKEKKKPGETFFMCSCSSDENDNIIFSEEYNTSNPD

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 60)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

CTCCCTTATCACGACTTCATTCTGGAGGACGCTGCCTCCCCCAAATGCA

TCATGAAGGAGAAGAAGAAGCCCGGAGAGACCTTCTTTATGTGTTCCTG

TAGCAGCGACGAGTGTAACGACAACATCATCTTCAGCGAAGAGTACAAC

ACCAGCAACCCTGATGGAGGTGGCGGATCCGGAGGTGGAGGTTCTGGTG

GAGGTGGGAGTATTCCTCCCCACGTGCAGAAGAGCGTGAATAATGACAT

GATCGTGACCGATAACAATGGCGCCGTGAAATTTCCCCAGCTGTGCAAA

TTCTGCGATGTGAGGTTTTCCACCTGCGACAACCAGAAGTCCTGTATGA

GCAACTGCTCCATCACCTCCATCTGTGAGAAGCCTCAGGAGGTGTGCGT

GGCTGTCTGGCGGAAGAATGACGAGAATATCACCCTGGAAACCGTCTGC

CACGATCCCAAGCTGCCCTACCACGATTTCATCCTGGAAGACGCCGCCA

GCCCTAAGTGCATCATGAAAGAGAAAAAGAAGCCTGGCGAGACCTTTTT

CATGTGCTCCTGCAGCAGCGACGAATGCAACGACAATATCATCTTTAGC

GAGGAATACAATACCAGCAACCCCGAC

In some embodiments of these multi-chain chimeric polypeptides, the second target-binding domain includes a soluble CD137L protein (e.g., a soluble human CD137L protein). In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 165)
REGPELSPDDPAGLLDLRQGMFAQLVAQNVLLIDGPLSWYSDPGLAGVS

LTGGLSYKEDTKELVVAKAGVYYVFFQLELRRVVAGEGSGSVSLALHLQ

PLRSAAGAAALALTVDLPPASSEARNSAFGFQGRLLHLSAGQRLGVHLH

TEARARHAWQLTQGATVLGLFRVTPEIPAGLPSPRSE

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 166)
CGCGAGGGTCCCGAGCTTTCGCCCGACGATCCCGCCGGCCTCTTGGACC

TGCGGCAGGGCATGTTTGCGCAGCTGGTGGCCCAAAATGTTCTGCTGAT

CGATGGGCCCCTGAGCTGGTACAGTGACCCAGGCCTGGCAGGCGTGTCC

CTGACGGGGGCCTGAGCTACAAAGAGGACACGAAGGAGCTGGTGGTGG

CCAAGGCTGGAGTCTACTATGTCTTCTTTCAACTAGAGCTGCGGCGCGT

GGTGGCCGGCGAGGGCTCAGGCTCCGTTTCACTTGCGCTGCACCTGCAG

CCACTGCGCTCTGCTGCTGGGGCCGCCGCCCTGGCTTTGACCGTGGACC

TGCCACCCGCCTCCTCCGAGGCTCGGAACTCGGCCTTCGGTTTCCAGGG

CCGCTTGCTGCACCTGAGTGCCGGCCAGCGCCTGGGCGTCCATCTTCAC

ACTGAGGCCAGGGCACGCCATGCCTGGCAGCTTACCCAGGGCGCCACAG

TCTTGGGACTCTTCCGGGTGACCCCCGAAATCCCAGCCGGACTCCCTTC

ACCGAGGTCGGAA

In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 167)
DPAGLLDLRQGMFAQLVAQNVLLIDGPLSWYSDPGLAGVSLTGGL-
SYKE

DTKELVVAKAGVYYVFFQLELRRVVAGEGSGSVSLALHLQPLR-
SAAGAA

ALALTVDLPPASSEARNSAFGFQGRLLHLSAGQRLGVHLHTEARAR-
HAW

QLTQGATVLGLFRVTPEI

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 168)
GATCCCGCCGGCCTCTTGGACCTGCGGCAGGGCATGTTTGCGCAGCTGG

TGGCCCAAAATGTTCTGCTGATCGATGGGCCCCTGAGCTGGTACAGTGA

CCCAGGCCTGGCAGGCGTGTCCCTGACGGGGGCCTGAGCTACAAAGAG

GACACGAAGGAGCTGGTGGTGGCCAAGGCTGGAGTCTACTATGTCTTCT

TTCAACTAGAGCTGCGGCGCGTGGTGGCCGGCGAGGGCTCAGGCTCCGT

TTCACTTGCGCTGCACCTGCAGCCACTGCGCTCTGCTGCTGGGGCCGCC

GCCCTGGCTTTGACCGTGGACCTGCCACCCGCCTCCTCCGAGGCTCGGA

ACTCGGCCTTCGGTTTCCAGGGCCGCTTGCTGCACCTGAGTGCCGGCCA

GCGCCTGGGCGTCCATCTTCACACTGAGGCCAGGGCACGCCATGCCTGG

CAGCTTACCCAGGGCGCCACAGTCTTGGGACTCTTCCGGGTGACCCCCG

AAATC

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDSGTTNTV

AAYNLTWKSTNFKTILEWEPKPVNQVYTVQISTKSGDWKSKCFYTTDTE

CDLTDEIVKDVKQTYLARVFSYPAGNVESTGSAGEPLYENSPEFTPYLE

TNLGQPTIQSFEQVGTKVNVTVEDERTLVRRNNTFLSLRDVFGKDLIYT

LYYWKSSSSGKKTAKTNTNEFLIDVDKGENYCFSVQAVIPSRTVNRKST

DSPVECMGQEKGEFRENWNVISDLKKIEDLIQSMHIDATLYTESDVHP

SCKVTAMKCFLLELQVISLESGDASIHDTVENLIILAMNSLSSNGNVTE

SGCKECEELEEKNIKEFLQSFVHIVQMFINTS

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

-continued
GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACAGCGGCACAACCAACACAGTC

GCTGCCTATAACCTCACTTGGAAGAGCACCAACTTCAAAACCATCCTCG

AATGGGAACCCAAACCCGTTAACCAAGTTTACACCGTGCAGATCAGCAC

CAAGTCCGGCGACTGGAAGTCCAAATGTTTCTATACCACCGACACCGAG

TGCGATCTCACCGATGAGATCGTGAAAGATGTGAAACAGACCTACCTCG

CCCGGGTGTTTAGCTACCCCGCCGGCAATGTGGAGAGCACTGGTTCCGC

TGGCGAGCCTTTATACGAGAACAGCCCCGAATTTACCCCTTACCTCGAG

ACCAATTTAGGACAGCCCACCATCCAAAGCTTTGAGCAAGTTGGCACAA

AGGTGAATGTGACAGTGGAGGACGAGCGGACTTTAGTGCGGCGGAACAA

CACCTTTCTCAGCCTCCGGGATGTGTTCGGCAAAGATTTAATCTACACA

CTGTATTACTGGAAGTCCTCTTCCTCCGGCAAGAAGACAGCTAAAACCA

ACACAAACGAGTTTTTAATCGACGTGGATAAAGGCGAAAACTACTGTTT

CAGCGTGCAAGCTGTGATCCCCTCCCGGACCGTGAATAGGAAAAGCACC

GATAGCCCCGTTGAGTGCATGGGCCAAGAAAAGGGCGAGTTCCGGGAGA

ACTGGGTGAACGTCATCAGCGATTTAAAGAAGATCGAAGATTTAATTCA

GTCCATGCATATCGACGCCACTTTATACACAGAATCCGACGTGCACCCC

TCTTGTAAGGTGACCGCCATGAAATGTTTTTTACTGGAGCTGCAAGTTA

TCTCTTTAGAGAGCGGAGACGCTAGCATCCACGACACCGTGGAGAATTT

AATCATTTTAGCCAATAACTCTTTATCCAGCAACGGCAACGTGACAGAG

TCCGGCTGCAAGGAGTGCGAAGAGCTGGAGGAGAAGAACATCAAGGAGT

TTCTGCAATCCTTTGTGCACATTGTCCAGATGTTCATCAATACCTCC

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)
MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDSGTTNTVAAYNLTWKSTNFKTILEWEPKPVNQVYTVQI

STKSGDWKSKCFYTTDTECDLTDEIVKDVKQTYLARVFSYPAGNVESTG

SAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENY

CFSVQAVIPSRTVNRKSTDSPVECMGQEKGEFRENWVNVISDLKKIEDL

IQSMHIDATLYTESDVHPSCKVTAMKCFLLELQVISLESGDASIHDTVE

NLIILANNSLSSNGNVTESGCKECEELEEKNIKEFLQSFVHIVQMFINT

S

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)
ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCTCCATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACAGCGGCACAACCAACA

CAGTCGCTGCCTATAACCTCACTTGGAAGAGCACCAACTTCAAAACCAT

```
CCTCGAATGGGAACCCAAACCCGTTAACCAAGTTTACACCGTGCAGATC
AGCACCAAGTCCGGCGACTGGAAGTCCAAATGTTTCTATACCACCGACA
CCGAGTGCGATCTCACCGATGAGATCGTGAAAGATGTGAAACAGACCTA
CCTCGCCCGGGTGTTTAGCTACCCCGCCGGCAATGTGGAGAGCACTGGT
TCCGCTGGCGAGCCTTTATACGAGAACAGCCCCGAATTTACCCCTTACC
TCGAGACCAATTTAGGACAGCCCACCATCCAAAGCTTTGAGCAAGTTGG
CACAAAGGTGAATGTGACAGTGGAGGACGAGCGGACTTTAGTGCGGCGG
AACAACACCTTTCTCAGCCTCCGGGATGTGTTCGGCAAAGATTTAATCT
ACACACTGTATTACTGGAAGTCCTCTTCCTCCGGCAAGAAGACAGCTAA
AACCAACACAAACGAGTTTTTAATCGACGTGGATAAAGGCGAAAACTAC
TGTTTCAGCGTGCAAGCTGTGATCCCCTCCCGGACCGTGAATAGGAAAA
GCACCGATAGCCCCGTTGAGTGCATGGGCCAAGAAAAGGGCGAGTTCCG
GGAGAACTGGGTGAACGTCATCAGCGATTTAAAGAAGATCGAAGATTTA
ATTCAGTCCATGCATATCGACGCCACTTTATACACAGAATCCGACGTGC
ACCCCTCTTGTAAGGTGACCGCCATGAATGTTTTTTACTGGAGCTGCA
AGTTATCTCTTTAGAGAGCGGAGACGCTAGCATCCACGACACCGTGGAG
AATTTAATCATTTTAGCCAATAACTCTTTATCCAGCAACGGCAACGTGA
CAGAGTCCGGCTGCAAGGAGTGCGAAGAGCTGGAGGAGAAGAACATCAA
GGAGTTTCTGCAATCCTTTGTGCACATTGTCCAGATGTTCATCAATACC
TCC
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
```
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPDITCPPPM
SVEHADIWVKSYSLYSRERYICNSGFKRKAGTSSLTECVLNKATNVAHW
TTPSLKCIRGGGGSGGGGSGGGGSREGPELSPDDPAGLLDLRQGMFAQL
VAQNVLLIDGPLSWYSDPGLAGVSLTGGLSYKEDTKELVVAKAGVYYVF
FQLELRRVVAGEGSGSVSLALHLQPLRSAAGAAALALTVDLPPASSEAR
NSAFGFQGRLLHLSAGQRLGVHLHTEARARHAWQLTQGATVLGLFRVTP
EIPAGLPSPRSE
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)
```
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGACATTACATGCCCCCCTCCCATG
AGCGTGGAGCACGCCGACATCTGGGTGAAGAGCTATAGCCTCTACAGCC
GGGAGAGGTATATCTGTAACAGCGGCTTCAAGAGGAAGGCCGGCACCAG
CAGCCTCACCGAGTGCGTGCTGAATAAGGCTACCAACGTGGCTCACTGG
ACAACACCCTCTTTAAAGTGCATCCGGGGCGGTGGAGGATCCGGAGGAG
GTGGCTCCGGCGGCGGAGGATCTCGCGAGGGTCCCGAGCTTTCGCCCGA
CGATCCCGCCGGCCTCTTGGACCTGCGGCAGGGCATGTTTGCGCAGCTG
GTGGCCCAAAATGTTCTGCTGATCGATGGGCCCCTGAGCTGGTACAGTG
ACCCAGGCCTGGCAGGCGTGTCCCTGACGGGGGGCCTGAGCTACAAAGA
GGACACGAAGGAGCTGGTGGTGGCCAAGGCTGGAGTCTACTATGTCTTC
TTTCAACTAGAGCTGCGGCGCGTGGTGGCCGGCGAGGGCTCAGGCTCCG
TTTCACTTGCGCTGCACCTGCAGCCACTGCGCTCTGCTGCTGGGGCCGC
CGCCCTGGCTTTGACCGTGGACCTGCCACCCGCCTCCTCCGAGGCTCGG
AACTCGGCCTTCGGTTTCCAGGGCCGCTTGCTGCACCTGAGTGCCGGCC
AGCGCCTGGGCGTCCATCTTCACACTGAGGCCAGGGCACGCCATGCCTG
GCAGCTTACCCAGGGCGCCACAGTCTTGGGACTCTTCCGGGTGACCCCC
GAAATCCCAGCCGGACTCCCTTCACCGAGGTCGGAA
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
MKWVTFISLLFLFSSAYSIPPHVQKSVNNDMIVTDNNGAVKFPQLCKFC
DVRFSTCDNQKSCMSNCSITSICEKPQEVCVAVWRKNDENITLETVCHD
PKLPYHDFILEDAASPKCIMKEKKKPGETFFMCSCSSDECNDNIIFSEE
YNTSNPDGGGGSGGGGSGGGGSIPPHVQKSVNNDMIVTDNNGAVKFPQL
CKFCDVRFSTCDNQKSCMSNCSITSICEKPQEVCVAVWRKNDENITLET
VCHDPKLPYHDFILEDAASPKCIMKEKKKPGETFFMCSCSSDECNDNII
FSEEYNTSNPDITCPPPMSVEHADIWVKSYSLYSRERYICNSGFKRKAG
TSSLTECVLNKATNVAHWTTPSLKCIRGGGGSGGGGSGGGGSREGPELS
PDDPAGLLDLRQGMFAQLVAQNVLLIDGPLSWYSDPGLAGVSLTGGLSY
KEDTKELVVAKAGVYYVFFQLELRRVVAGEGSGSVSLALHLQPLRSAAG
AAALALTVDLPPASSEARNSAFGFQGRLLHLSAGQRLGVHLHTEARARH
AWQLTQGATVLGLFRVTPEIPAGLPSPRSE

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
ATGAAGTGGGTGACCTTCATCAGCCTGCTGTTCCTGTTCTCCAGCGCCT
ACTCCATCCCCCCCCATGTGCAAAAGAGCGTGAACAACGATATGATCGT
GACCGACAACAACGGCGCCGTGAAGTTTCCCCAGCTCTGCAAGTTCTGC
GATGTCAGGTTCAGCACCTGCGATAATCAGAAGTCCTGCATGTCCAACT
GCAGCATCACCTCCATCTGCGAGAAGCCCCAAGAAGTGTGCGTGGCCGT
GTGGCGGAAAAATGACGAGAACATCACCCTGGAGACCGTGTGTCACGAC
CCCAAGCTCCCTTATCACGACTTCATTCTGGAGGACGCTGCCTCCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC
CTTTTTCATGTGCTCCTGCAGCAGCGACGAATGCAACGACAATATCATC
TTTAGCGAGGAATACAATACCAGCAACCCCGACATTACATGCCCCCCTC
CCATGAGCGTGGAGCACGCCGACATCTGGGTGAAGAGCTATAGCCTCTA
CAGCCGGGAGAGGTATATCTGTAACAGCGGCTTCAAGAGGAAGGCCGGC
ACCAGCAGCCTCACCGAGTGCGTGCTGAATAAGGCTACCAACGTGGCTC
ACTGGACAACACCCTCTTTAAAGTGCATCCGGGGCGGTGGAGGATCCGG
AGGAGGTGGCTCCGGCGGCGGAGGATCTCGCGAGGGTCCCGAGCTTTCG
CCCGACGATCCCGCCGGCCTCTTGGACCTGCGGCAGGGCATGTTTGCGC
AGCTGGTGGCCCAAAATGTTCTGCTGATCGATGGGCCCCTGAGCTGGTA
CAGTGACCCAGGCCTGGCAGGCGTGTCCCTGACGGGGGGCCTGAGCTAC
AAAGAGGACACGAAGGAGCTGGTGGTGGCCAAGGCTGGAGTCTACTATG
TCTTCTTTCAACTAGAGCTGCGGCGCGTGGTGGCCGGCGAGGGCTCAGG
CTCCGTTTCACTTGCGCTGCACCTGCAGCCACTGCGCTCTGCTGCTGGG
GCCGCCGCCCTGGCTTTGACCGTGGACCTGCCACCCGCCTCCTCCGAGG
CTCGGAACTCGGCCTTCGGTTTCCAGGGCCGCTTGCTGCACCTGAGTGC
CGGCCAGCGCCTGGGCGTCCATCTTCACACTGAGGCCAGGGCACGCCAT
GCCTGGCAGCTTACCCAGGGCGCCACAGTCTTGGGACTCTTCCGGGTGA
CCCCCGAAATCCCAGCCGGACTCCCTTCACCGAGGTCGGAA.

Compositions/Kits

Also provided herein are compositions (e.g., pharmaceutical compositions) that include at least one of any of the single-chain chimeric polypeptides, multi-chain chimeric polypeptides, any of the cells, or any of the nucleic acids described herein. In some embodiments, the compositions include at least one of any of the single-chain chimeric polypeptides described herein. In some embodiments, the compositions include at least one of any of the multi-chain chimeric polypeptides described herein. In some embodiments, the compositions include any of the immune cells (e.g., any of the immune cells described herein, e.g., any of the immune cells produced using any of the methods described herein).

In some embodiments, the pharmaceutical compositions are formulated for different routes of administration (e.g., intravenous, subcutaneous). In some embodiments, the pharmaceutical compositions can include a pharmaceutically acceptable carrier (e.g., phosphate buffered saline).

Single or multiple administrations of pharmaceutical compositions can be given to a subject in need thereof depending on for example: the dosage and frequency as required and tolerated by the subject. The formulation should provide a sufficient quantity of active agent to effectively treat, prevent or ameliorate conditions, diseases or symptoms.

Also provided herein are kits that include any of the single-chain chimeric polypeptides, multi-chain chimeric polypeptides, compositions, nucleic acids, or cells (e.g., immune cells) described herein. In some embodiments, the kits can include instructions for performing any of the methods described herein. In some embodiments, the kits can include at least one dose of any of the pharmaceutical compositions described herein.

Also provided herein is an immune cell (e.g., an activated NK cell or T cell) produced by any of the methods described herein. Also provided herein are pharmaceutical compositions that include any of the activated immune cells (e.g., an activated NK cell or T cell) produced by any of the methods described herein. Also provided herein are kits that include any of the pharmaceutical compositions described herein that include any of the activated immune cells (e.g., an activated NK cell or T cell) produced by any of the methods described herein.

Also provided herein are kits that include (i) any of the single-chain chimeric polypeptides described herein, and (ii) any of the IgG1 antibody constructs described herein. Also provided herein are kits that include (ii) any of the multi-chain chimeric polypeptides described herein, and (ii) any of the IgG1 antibody constructs described herein. In some embodiments of any of the kits described herein, the kits further include instructions for performing any of the methods described herein.

Nucleic Acids/Vectors

Also provided herein are nucleic acids that encode any of the single-chain chimeric polypeptides described herein. Also provided herein are vectors that include any of the nucleic acids encoding any of the single-chain chimeric polypeptides described herein.

Also provided herein are nucleic acids that encode any of the multi-chain chimeric polypeptides described herein. In some embodiments, a first nucleic acid can encode the first chimeric polypeptide and a second nucleic acid can encode the second chimeric polypeptide. In some embodiments, a single nucleic acid can encode both the first chimeric polypeptide and the second chimeric polypeptide.

Also provided herein are vectors that include any of the nucleic acids encoding any of the multi-chain chimeric polypeptides described herein. In some embodiments, a first vector can include a nucleic acid encoding the first chimeric polypeptide and a second vector can include a nucleic acid encoding the second chimeric polypeptide. In some embodiments, a single vector can include a first nucleic acid encoding the first chimeric polypeptide and a second nucleic acid encoding the second chimeric polypeptide.

Also provided herein are nucleic acids that encode any of the IgG1 antibody constructs described herein.

Any of the vectors described herein can be an expression vector. For example, an expression vector can include a promoter sequence operably linked to the sequence encoding the single-chain chimeric polypeptide, or the first chimeric polypeptide and the second chimeric polypeptide of a multi-chain chimeric polypeptide.

Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, e.g., include sufficient cis-acting elements for expression; other elements for expression can be supplied by the host mammalian cell or in an in vitro expression system. Skilled practitioners will be capable of selecting suitable vectors and mammalian cells for making any of the single-chain chimeric polypeptides or multi-chain chimeric polypeptides described herein.

Cells

Also provided herein are cells (e.g., any of the exemplary cells described herein or known in the art) comprising any of the nucleic acids described herein that encode any of the single-chain chimeric polypeptides described herein.

Also provided herein are cells (e.g., any of the exemplary cells described herein or known in the art) that include any of the vectors described herein that encode any of the single-chain chimeric polypeptides described herein.

Also provided herein are cells (e.g., any of the exemplary cells described herein or known in the art) comprising any of the nucleic acids described herein that encode any of the multi-chain chimeric polypeptides described herein (e.g., encoding both the first and second chimeric polypeptides). Also provided herein are cells (e.g., any of the exemplary cells described herein or known in the art) comprising any of the nucleic acids described herein that encode any of the first chimeric polypeptides described herein. Also provided are cells (e.g., any of the exemplary cells described herein or known in the art) comprising any of the nucleic acids described herein that encode any of the second chimeric polypeptides described herein.

Also provided herein are cells (e.g., any of the exemplary cells described herein or known in the art) that include any of the vectors described herein that encode any of the multi-chain chimeric polypeptides described herein (e.g., encoding both the first and second chimeric polypeptides). Also provided herein are cells (e.g., any of the exemplary cells described herein or known in the art) that include any of the vectors described herein that encode any of the first chimeric polypeptides described herein. Also provided herein are cells (e.g., any of the exemplary cells described herein or known in the art) that include any of the vectors described herein that encode any of the second chimeric polypeptides described herein).

In some embodiments of any of the methods described herein, the cell can be a eukaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. Non-limiting examples of mammalian cells include Chinese hamster ovary cells and human embryonic kidney cells (e.g., HEK293 cells).

Methods of introducing nucleic acids and expression vectors into a cell (e.g., a eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalefection, hydrodynamic delivery, magnetofection, viral transduction (e.g., adenoviral and lentiviral transduction), and nanoparticle transfection.

Methods of Producing Single-Chain and Multi-Chain Chimeric Polypeptides

Also provided herein are methods of producing any of the single-chain chimeric polypeptides described herein that include culturing any of the cells described herein in a culture medium under conditions sufficient to result in the production of the single-chain chimeric polypeptide; and recovering the single-chain chimeric polypeptide from the cell and/or the culture medium.

The recovery of the single-chain chimeric polypeptide from a culture medium or a cell (e.g., a eukaryotic cell) can be performed using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Also provided herein are single-chain chimeric polypeptides (e.g., any of the single-chain chimeric polypeptides described herein) produced by any of the methods described herein.

Also provided herein are methods of producing any of the multi-chain chimeric polypeptides described herein that include culturing any of the cells described herein in a culture medium under conditions sufficient to result in the production of the multi-chain chimeric polypeptide; and recovering the multi-chain chimeric polypeptide from the cell and/or the culture medium.

Also provided herein are method of producing any of the multi-chain chimeric polypeptides described herein that include: culturing any of cells described herein in a first culture medium under conditions sufficient to result in the production of the first chimeric polypeptide; recovering the first chimeric polypeptide from the cell and/or the first culture medium; culturing any of the cells described herein in a second culture medium under conditions sufficient to result in the production of the second chimeric polypeptide; recovering the second chimeric polypeptide from the cell and/or the second culture medium; and combining (e.g., mixing) the recovered first chimeric polypeptide and the recovered second chimeric polypeptide to form the multi-chain chimeric polypeptide (e.g., any of the multi-chain chimeric polypeptides described herein).

The recovery of the multi-chain chimeric polypeptide, the first chimeric polypeptide, or the second chimeric polypeptide from a cell (e.g., a eukaryotic cell) can be performed using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Also provided herein are multi-chain chimeric polypeptides (e.g., any of the multi-chain chimeric polypeptides described herein), first chimeric polypeptides (e.g., any of the first chimeric polypeptides), or second chimeric polypeptides (e.g., any of the second chimeric polypeptides described herein) produced by any of the methods described herein.

Methods of culturing cells are well known in the art. Cells can be maintained in vitro under conditions that favor proliferation, differentiation and growth. Briefly, cells can be cultured by contacting a cell (e.g., any cell) with a cell culture medium that includes the necessary growth factors and supplements to support cell viability and growth.

Methods of Promoting the Activation and Proliferation of an Immune Cell

Also provided herein are methods of promoting the activation and proliferation of an immune cell (e.g., an any of the exemplary immune cells described herein or known in the art) that include contacting an immune cell in a liquid culture medium including an effective amount of (i) any of the single-chain or multi-chain chimeric polypeptides described herein, and (ii) an IgG1 antibody construct that comprises at least one antigen-binding domain that binds specifically to the linker domain (e.g., a monoclonal or polyclonal human, mouse, rabbit, or goat IgG1 antibody that binds specifically to a linker domain or any of the other exemplary IgG1 antibody constructs described herein), under conditions that allow for the activation and proliferation of the immune cell.

In some embodiments of these methods, the IgG1 antibody construct includes at least one antigen-binding domain that binds specifically to the linker domain. In some embodiments of these methods, the IgG1 antibody construct is a monoclonal IgG1 antibody, where both of the antigen-binding domains in the monoclonal IgG1 antibody bind specifically to the linker domain. In some embodiments of these methods, the IgG1 antibody construct is a bispecific IgG1 antibody, where one of the two antigen-binding domains in the bispecific IgG1 antibody binds specifically to the linker domain.

In some embodiments of these methods, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days.

In some embodiments of any of the methods described herein, the liquid culture medium is a serum-free liquid culture medium. In some embodiments of any of the methods described herein, the liquid culture medium is a chemically-defined liquid culture medium.

In some embodiments of any of the methods described herein, the liquid culture medium includes the single-chain or multi-chain chimeric polypeptide and the IgG1 antibody construct at a molar ratio of about 0.5:1 to about 2:1 (e.g., about 0.8:1 to about 1.2:1).

In some embodiments of any of the methods described herein, the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments of any of the methods described herein, the immune cell is a T-cell or a natural killer cell.

In some embodiments of any of the methods described herein, the immune cell was previously obtained from a subject. Some embodiments of any of the methods described herein further include obtaining the immune cell from the subject prior to the contacting step.

In some embodiments of any of the methods described herein, the immune cell has previously been genetically modified to express a chimeric antigen receptor or a recombinant T-cell receptor.

Some embodiments of any of the methods described herein further includes, after the contacting step, introducing into the immune cell a nucleic acid encoding a chimeric antigen-receptor or a recombinant T-cell receptor.

Some embodiments of any of the methods described herein further include, before the contacting step, introducing into the immune cell a nucleic acid encoding a chimeric antigen-receptor or a recombinant T-cell receptor.

Some embodiments of any of the methods described herein further include, after the contacting step, isolating the immune cell.

In some embodiments of any of the methods described herein, after the contacting step, the immune cell has an increased level of expression or secretion of one or more proteins selected from the group consisting of: 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step.

Some embodiments of any of the methods described herein further include, after the contacting step, administering the immune cell to a subject in need thereof. In some embodiments of any of the methods described herein, the subject has been identified or diagnosed as having an age-related disease or condition. In some embodiments of any of the methods described herein, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been diagnosed or identified as having an infectious disease. In some embodiments of any of the methods described herein, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is an activated immune cell produced by any of the methods described herein. Also provided herein are pharmaceutical compositions that include any of the immune cells produced by any of the methods described herein. Also provided herein are kits that include any of the pharmaceutical compositions including any of the activated immune cells produced by any of the methods described herein.

Methods of Stimulating an Immune Cell

Also provided herein are methods of stimulating an immune cell (e.g., any of the exemplary immune cells described herein or known in the art) that include contacting an immune cell with an effective amount of any of the single-chain chimeric polypeptides or any of the multi-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell). In some examples, the contacting further includes contacting the immune cell with an effective amount of any of the IgG1 antibody constructs described herein.

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the single-chain chimeric polypeptide or multi-chain chimeric polypeptide is administered to a subject (e.g., a mammal, e.g., a human) in an amount sufficient to result in stimulation of an immune cell in the subject. In some embodiments of any of the methods, compositions, and kits described herein, the IgG1 antibody construct (e.g., any of the exemplary IgG1 antibody constructs described herein is administered to the subject in combination (e.g., simultaneously or sequentially) with administration of the single-chain chimeric polypeptide or multi-chain chimeric polypeptide (e.g., any of the single-chain chimeric polypeptides or multi-chain chimeric polypeptides described herein).

In some examples of any of the methods described herein, the immune cell can be an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

Some embodiments of these methods can further include, after the contacting step, introducing into the immune cell (e.g., any of the immune cells described herein) a nucleic acid encoding a chimeric antigen-receptor or a recombinant T-cell receptor. Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Activation of an immune cell can be determined using methods known in the art. For example, activation of an immune cell can be determined by detecting the levels of cytokines, chemokines that are secreted or cytotoxicity granules, activating receptors, and regulatory molecules that are upregulated upon activation of an immune cell. Non-limiting examples of cytokines and chemokines that are secreted or cytotoxicity granules, activating receptors, and regulatory molecules that are upregulated upon activation of an immune cell include: IL-2, interferon-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, perforin, TGFβ, STAT3, STAT4, STAT5, RORγT, FOXP3, GATA3, granzyme A, granzyme B, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ. The detection of these cytokines and chemokines can be performed using an immunoassay (e.g., an enzyme-linked immunosorbent assay). For example, activation of an immune cell can result in an increase of about 1% to about 800% (e.g., about 1% to about 750%, about 1% to about 700%, about 1% to about 650%, about 1% to about 600%, about 1% to about 550%, about 1% to about 500%, about 1% to about 450%, about 1% to about 400%, about 1% to about 350%, about 1% to about 300%, about 1% to about 280%, about 1% to about 260%, about 1% to about 240%, about 1% to about 220%, about 1% to about 200%, about 1% to about 180%, about 1% to about 160%, about 1% to about 140%, about 1% to about 120%, about 1% to about 100%, about 1% to about 90%, about 1% to about 80%, about 1% to about 70%, about 1% to about 60%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 800%, about 5% to about 750%, about 5% to about 700%, about 5% to about 650%, about 5% to about 600%, about 5% to about 550%, about 5% to about 500%, about 5% to about 450%, about 5% to about 400%, about 5% to about 350%, about 5% to about 300%, about 5% to about 280%, about 5% to about 260%, about 5% to about 240%, about 5% to about 220%, about 5% to about 200%, about 5% to about 180%, about 5% to about 160%, about 5% to about 140%, about 5% to about 120%, about 5% to about 100%, about 5% to about 90%, about 5% to about 80%, about 5% to about 70%, about 5% to about 60%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 800%, about 10% to about 750%, about 10% to about 700%, about 10% to about 650%, about 10% to about 600%, about 10% to about 550%, about 10% to about 500%, about 10% to about 450%, about 10% to about 400%, about 10% to about 350%, about 10% to about 300%, about 10% to about 280%, about 10% to about 260%, about 10% to about 240%, about 10% to about 220%, about 10% to about 200%, about 10% to about 180%, about 10% to about 160%, about 10% to about 140%, about 10% to about 120%, about 10% to about 100%, about 10% to about 90%, about 10% to about 80%, about 10% to about 70%, about 10% to about 60%, about 10% to about 50%, about 10% to about 45%, about 10% to about 40%, about 10% to about 35%, about 10% to about 30%, about 10% to about 25%, about 10% to about 20%, about 10% to about 15%, about 15% to about 800%, about 15% to about 750%, about 15% to about 700%, about 15% to about 650%, about 15% to about 600%, about 15% to about 550%, about 15% to about 500%, about 15% to about 450%, about 15% to about 400%, about 15% to about 350%, about 15% to about 300%, about 15% to about 280%, about 15% to about 260%, about 15% to about 240%, about 15% to about 220%, about 15% to about 200%, about 15% to about 180%, about 15% to about 160%, about 15% to about 140%, about 15% to about 120%, about 15% to about 100%, about 15% to about 90%, about 15% to about 80%, about 15% to about 70%, about 15% to about 60%, about 15% to about 50%, about 15% to about 45%, about 15% to about 40%, about 15% to about 35%, about 15% to about 30%, about 15% to about 25%, about 15% to about 20%, about 20% to about 800%, about 20% to about 750%, about 20% to about 700%, about 20% to about 650%, about 20% to about 600%, about 20% to about 550%, about 20% to about 500%, about 20% to about 450%, about 20% to about 400%, about 20% to about 350%, about 20% to about 300%, about 20% to about 280%, about 20% to about 260%, about 20% to about 240%, about 20% to about 220%, about 20% to about 200%, about 20% to about 180%, about 20% to about 160%, about 20% to about 140%, about 20% to about 120%, about 20% to about 100%, about 20% to about 90%, about 20% to about 80%, about 20% to about 70%, about 20% to about 60%, about 20% to about 50%, about 20% to about 45%, about 20% to about 40%, about 20% to about 35%, about 20% to about 30%, about 20% to about 25%, about 25% to about 800%, about 25% to about 750%, about 25% to about 700%, about 25% to about 650%, about 25% to about 600%, about 25% to about 550%, about 25% to about 500%, about 25% to about 450%, about 25% to about 400%, about 25% to about 350%, about 25% to about 300%, about 25% to about 280%, about 25% to about 260%, about 25% to about 240%, about 25% to about 220%, about 25% to about 200%, about 25% to about 180%, about 25% to about 160%, about 25% to about 140%, about 25% to about 120%, about 25% to about 100%, about 25% to about 90%, about 25% to about 80%, about 25% to about 70%, about 25% to about 60%, about 25% to about 50%, about 25% to about 45%, about 25% to about 40%, about 25% to about 35%, about 35% to about 800%, about 35% to about 750%, about 35% to about 700%, about 35% to about 650%, about 35% to about 600%, about 35% to about 550%, about 35% to about 500%, about 35% to about 450%, about 35% to about 400%, about 35% to about 350%, about 35% to about 300%, about 35% to about 280%, about 35% to about 260%, about 35% to about 240%, about 35% to about 220%, about 35% to about 200%, about 35% to about 180%, about 35% to about 160%, about 35% to about 140%, about 35% to about 120%, about 35% to about 100%, about 35% to about 90%, about 35% to about 80%, about 35% to about 70%, about 35% to about 60%, about 35% to about 50%, about 35% to about 45%, about 35% to about 40%, about 40% to about 800%, about 40% to about 750%, about 40% to about 700%, about 40% to about 650%, about 40% to about 600%, about 40% to about 550%, about 40% to about 500%, about 40% to about 450%, about 40% to about 400%, about 40% to about 350%, about 40% to about 300%, about 40% to about 280%, about 40% to about 260%, about 40% to about 240%, about 40% to about 220%, about 40% to about 200%, about 40% to about 180%, about 40% to about 160%, about 40% to about 140%, about 40% to about 120%, about 40% to about 100%, about 40% to about 90%, about 40% to about 80%, about 40% to about 70%, about 40% to about 60%, about 40% to about 50%, about 40% to about 45%, about 45% to about 800%, about 45% to about 750%, about 45% to about 700%, about 45% to about 650%, about 45% to about 600%, about 45% to about 550%, about 45% to about 500%, about 45% to about 450%, about 45% to about 400%, about 45% to about 350%, about 45% to about 300%, about 45% to about 280%, about 45% to about 260%, about 45% to about 240%, about 45% to about 220%, about 45% to about 200%, about 45% to about 180%, about 45% to about 160%, about 45% to about 140%, about 45% to about 120%, about 45% to about 100%, about 45% to about 90%, about 45% to about 80%, about 45% to about 70%, about 45% to about 60%, about 45% to about 50%, about 50% to about 800%, about 50% to about 750%, about 50% to about 700%, about 50% to about 650%, about 50% to about 600%, about 50% to about 550%, about 50% to about 500%, about 50% to about 450%, about 50% to about 400%, about 50% to about 350%, about 50% to about 300%, about 50% to about 280%, about 50% to about 260%, about 50% to about 240%, about 50% to about 220%, about 50% to about 200%, about 50% to about 180%, about 50% to about 160%, about 50% to about 140%, about 50% to about 120%, about 50% to about 100%, about 50% to about 90%, about 50% to about 80%, about 50% to about 70%, about 50% to about 60%, about 60% to about 800%, about 60% to about 750%, about 60% to about 700%, about 60% to about 650%, about 60% to about 600%, about 60% to about 550%, about 60% to about 500%, about 60% to about 450%, about 60% to about 400%, about 60% to about 350%, about 60% to about 300%, about 60% to about 280%, about 60% to about 260%, about 60% to about 240%, about 60% to about 220%, about 60% to about 200%, about 60% to about 180%, about 60% to about 160%, about 60% to about 140%, about 60% to about 120%, about 60% to about 100%, about 60% to about 90%, about 60% to about 80%, about 60% to about 70%, about 70% to about 800%, about 70% to about 750%, about 70% to about 700%, about 70% to about 650%, about 70% to about 600%, about 70% to about 550%, about 70% to about 500%, about 70% to about 450%, about 70% to about 400%, about 70% to about 350%, about 70% to about 300%, about 70% to about 280%, about 70% to about 260%, about 70% to about 240%, about 70% to about 220%, about 70% to about 200%, about 70% to about 180%, about 70% to about 160%, about 70% to about 140%, about 70% to about 120%, about 70% to about 100%, about 70% to about 90%, about 70% to about 80%, about 80% to about 800%, about 80% to about 750%, about 80% to about 700%, about 80% to about 650%, about 80% to about 600%, about 80% to about 550%, about 80% to about 500%, about 80% to about 450%, about 80% to about 400%, about 80% to about 350%, about 80% to about 300%, about 80% to about 280%, about 80% to about 260%, about 80% to about 240%, about 80% to about 220%, about 80% to about 200%, about 80% to about 180%, about 80% to about 160%, about 80% to about 140%, about 80% to about 120%, about 80% to about 100%, about 80% to about 90%, about 90% to about 800%, about 90% to about 750%, about 90% to about 700%, about 90% to about 650%, about 90% to about 600%, about 90% to about 550%, about 90% to about 500%, about 90% to about 450%, about 90% to about 400%, about 90% to about 350%, about 90% to about 300%, about 90% to about 280%, about 90% to about 260%, about 90% to about 240%, about 90% to about 220%, about 90% to about 200%, about 90% to about 180%, about 90% to about 160%, about 90% to about 140%, about 90% to about 120%, about 90% to about 100%, about 100% to about 800%, about 100% to about 750%, about 100% to about 700%, about 100% to about 650%, about 100% to about 600%, about 100% to about 550%, about 100% to about 500%, about 100% to about 450%, about 100% to about 400%, about 100% to about 350%, about 100% to about 300%, about 100% to about 280%, about 100% to about 260%, about 100% to about 240%, about 100% to about 220%, about 100% to about 200%, about 100% to about 180%, about 100% to about 160%, about 100% to about 140%, about 100% to about 120%, about 120% to about 800%, about 120% to about 750%, about 120% to about 700%, about 120% to about 650%, about 120% to about 600%, about 120% to about 550%, about 120% to about 500%, about 120% to about 450%, about 120% to about 400%, about 120% to about 350%, about 120% to about 300%, about 120% to about 280%, about 120% to about 260%, about 120% to about 240%, about 120% to about 220%, about 120% to about 200%, about 120% to about 180%, about 120% to about 160%, about 120% to about 140%, about 140% to about 800%, about 140% to about 750%, about 140% to about 700%, about 140% to about 650%, about 140% to about 600%, about 140% to about 550%, about 140% to about 500%, about 140% to about 450%, about 140% to about 400%, about 140% to about 350%, about 140% to about 300%, about 140% to about 280%, about 140% to about 260%, about 140% to about 240%, about 140% to about 220%, about 140% to about 200%, about 140% to about 180%, about 160% to about 800%, about 160% to about 750%, about 160% to about 700%, about 160% to about 650%, about 160% to about 600%, about 160% to about 550%, about 160% to about 500%, about 160% to about 450%, about 160% to about 400%, about 160% to about 350%, about 160% to about 300%, about 160% to about 280%, about 160% to about 260%, about 160% to about 240%, about 160% to about 220%, about 160% to about 200%, about 160% to about 180%, about 180% to about 800%, about 180% to about 750%, about 180% to about 700%, about 180% to about 650%, about 180% to about 600%, about 180% to about 550%, about 180% to about 500%, about 180% to about 450%, about 180% to about 400%, about 180% to about 350%, about 180% to about 300%, about 180% to about 280%, about 180% to about 260%, about 180% to about 240%, about 180% to about 220%, about 180% to about 200%, about 200% to about 800%, about 200% to about 750%, about 200% to about 700%, about 200% to about 650%, about 200% to about 600%, about 200% to about 550%, about 200% to about 500%, about 200% to about 450%, about 200% to about 400%, about 200% to about 350%, about 200% to about 300%, about 200% to about 280%, about 200% to about 260%, about 200% to about 240%, about 200% to about 220%, about 220% to about 800%, about 220% to about 750%, about 220% to about 700%, about 220% to about 650%, about 220% to about 600%, about 220% to about 550%, about 220% to about 500%, about 220% to about 450%, about 220% to about 400%, about 220% to about 350%, about 220% to about 300%, about 220% to about 280%, about 220% to about 260%, about 220% to about 240%, about 240% to about 800%, about 240% to about 750%, about 240% to about 700%, about 240% to about 650%, about 240% to about 600%, about 240% to about 550%, about 240% to about 500%, about 240% to about 450%, about 240% to about 400%, about 240% to about 350%, about 240% to about 300%, about 240% to about 280%, about 240% to about 260%, about 260% to about 800%, about 260% to about 750%, about 260% to about 700%, about 260% to about 650%, about 260% to about 600%, about 260% to about 550%, about 260% to about 500%, about 260% to about 450%, about 260% to about 400%, about 260% to about 350%, about 260% to about 300%, about 260% to about 280%, about 280% to about 800%, about 280% to about 750%, about 280% to about 700%, about 280% to about 650%, about 280% to about 600%, about 280% to about 550%, about 280% to about 500%, about 280% to about 450%, about 280% to about 400%, about 280% to about 350%, about 280% to about 300%, about 300% to about 800%, about 300% to about 750%, about 300% to about 700%, about 300% to about 650%, about 300% to about 600%, about 300% to about 550%, about 300% to about 500%, about 300% to about 450%, about 300% to about 400%, about 300% to about 350%, about 350% to about 800%, about 350% to about 750%, about 350% to about 700%, about 350% to about 650%, about 350% to about 600%, about 350% to about 550%, about 350% to about 500%, about 350% to about 450%, about 350% to about 400%, about 400% to about 800%, about 400% to about 750%, about 400% to about 700%, about 400% to about 650%, about 400% to about 600%, about 400% to about 550%, about 400% to about 500%, about 400% to about 450%, about 450% to about 800%, about 450% to about 750%, about 450% to about 700%, about 450% to about 650%, about 450% to about 600%, about 450% to about 550%, about 450% to about 500%, about 500% to about 800%, about 500% to about 750%, about 500% to about 700%, about 500% to about 650%, about 500% to about 600%, about 500% to about 550%, about 550% to about 800%, about 550% to about 750%, about 550% to about 700%, about 550% to about 650%, about 550% to about 600%, about 600% to about 800%, about 600% to about 750%, about 600% to about 700%, about 600% to about 650%, about 650% to about 800%, about 650% to about 750%, about 650% to about 700%, about 700% to about 800%, about 700% to about 750%, or about 750% to about 800%) of one or more of any of the cytokines, chemokines, cytotoxicity granules, activating receptors or regulatory molecules described herein (e.g., one or more of any of IL-2, interferon-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, granzymes, perforin, TGFβ, STAT3, STAT4, STAT5, RORγT, FOXP3, and GATA3) (e.g., as compared to the level of the one or more cytokines and chemokines in a control not contacted with any of the single-chain chimeric polypeptides or any of the multi-chain chimeric polypeptides described herein).

Methods of Inducing or Increasing Proliferation of an Immune Cell

Also provided herein are methods of inducing or increasing proliferation of an immune cell (e.g., any of the exemplary immune cells described herein or known in the art) that include contacting an immune cell with an effective amount of any of the single-chain chimeric polypeptides or any of the multi-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell)). In some examples, the immune cell is further contacted in vitro with any of the IgG1 antibody constructs described herein in combination (e.g., simultaneously or sequentially) with contacting the immune cell in vitro with the single-chain chimeric polypeptide or multi-chain chimeric polypeptide (e.g., any of the single-chain chimeric polypeptides or multi-chain chimeric polypeptides described herein).

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the single-chain chimeric polypeptide or multi-chain chimeric polypeptide is administered to a subject (e.g., a mammal, e.g., a human) in an amount sufficient to result in stimulation of an immune cell in the subject. In such embodiments, the subject can further be administered any of the IgG1 antibody constructs described herein.

In some examples of any of the methods described herein, the immune cell can be an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8$^+$ T cell, a CD4$^+$ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

Some embodiments of these methods can further include, after the contacting step, introducing into the immune cell (e.g., any of the immune cells described herein) a nucleic acid encoding a chimeric antigen-receptor or a recombinant T-cell receptor. Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Detection of the proliferation of an immune cell can be performed using methods known in the art, e.g., cytometry (e.g., fluorescence-assisted flow cytometry), microscopy, and immunofluorescence microscopy, e.g., by comparing the rate of increase in the concentration of the immune cell in a sample not contacted with a single-chain chimeric polypeptide or a multi-chain chimeric polypeptide to the rate of increase in the concentration of the immune cell in a similar sample contacted with any of the single-chain chimeric polypeptides described herein or any of the multi-chain chimeric polypeptides described herein).

In other examples, the proliferation of an immune cell can be indirectly detected by detecting an increase in the level of one or more cytokines or chemokines secreted or cytotoxicity granules, activating receptors, regulatory molecules upregulated by proliferating immune cells (e.g., one or more of IL-2, IFN-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, perforin, TGFβ, STAT3, RORγT, FOXP3, STATE, GATA3, granzyme A, granzyme B, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ) (e.g., as compared to the level of the one or more cytokines and chemokines in a control not contacted with any of the single-chain chimeric polypeptides described herein).

In some embodiments, the methods provided herein can result in an increase (e.g., about 1% to about 800% increase, or any of the subranges of this range described herein) in the rate of increase in the concentration of the immune cell in a sample contacted with any of the single-chain chimeric polypeptides any of the multi-chain chimeric polypeptides described herein as compared to the rate of increase in a similar control sample not contacted with any of the single-chain chimeric polypeptides any of the multi-chain chimeric polypeptides described herein.

Methods of Inducing Differentiation of an Immune Cell

Also provided herein are method of inducing differentiation of an immune cell (e.g., any of the exemplary immune cells described herein or known in the art) into a memory or memory-like immune cell that include contacting an immune cell with an effective amount of any of the single-chain chimeric polypeptides or any of the multi-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell). In some examples, the immune cell is further contacted in vitro with an effective amount of any of the IgG1 antibody constructs described herein.

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the single-chain chimeric polypeptide or multi-chain chimeric polypeptide is administered to a subject (e.g., a mammal, e.g., a human) in an amount sufficient to result in stimulation of an immune cell in the subject. In some examples, the immune cell is contacted in vivo with any of the IgG1 antibody constructs described herein in combination (e.g., simultaneously or sequentially) with contacting the immune cell in vivo with the single-chain chimeric polypeptide or multi-chain chimeric polypeptide (e.g., any of the single-chain chimeric polypeptides or any of the multi-chain chimeric polypeptides described herein).

In some examples of any of the methods described herein, the immune cell can be an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

Some embodiments of these methods can further include, after the contacting step, introducing into the immune cell (e.g., any of the immune cells described herein) a nucleic acid encoding a chimeric antigen-receptor or a recombinant T-cell receptor. Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

In some examples, the immune cell is a NK cell, and the detection of a memory NK cell can include, e.g., the detection of the level of one or more of IL-12, IL-18, IL-33, STAT4, Zbtb32, DNAM-1, BIM, Noxa, SOCS1, BNIP3, BNIP3L, IFN-γ, TNFα, CXCL16, CXCR6, NKG2D, TRAIL, CD49, CD25, CD69, CD62L, Ly49D, CD49b, and Ly79H. A description of NK memory cells and methods of detecting the same is described in O'Sullivan et al., *Immunity* 43:634-645, 2015.

In some examples, the immune cell is a T cell, and the detection of memory T cells can include, e.g., the detection of the level of expression of one or more of CD45RO, CCR7, L-selectin (CD62L), CD44, CD45RA, integrin αeβ7, CD43, CD27, CD28, IL-7Rα, CD95, IL-2Rα, CXCR3, and LFA-1. In some examples, the immune cell is a B cell and the detection of memory B cells can include, e.g., the detection of the level of expression of CD27. Other types and markers of memory or memory-like immune cells are known in the art.

Methods of Treatment

Also provided herein are methods of treating a subject in need thereof (e.g., any of the exemplary subjects described herein or known in the art) that include administering to the subject a therapeutically effective amount of any of the single-chain chimeric polypeptides or any of the multi-chain chimeric polypeptides described herein or any of the compositions (e.g., pharmaceutical compositions) described herein. In some embodiments, a subject can further be administered a therapeutically effective amount of any of the IgG1 antibody constructs described herein.

In some embodiments of these methods, the subject has been identified or diagnosed as having a cancer. Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, these methods can result in a reduction in the number, severity, or frequency of one or more symptoms of the cancer in the subject (e.g., as compared to the number, severity, or frequency of the one or more symptoms of the cancer in the subject prior to treatment). In some embodiments, these methods can result in a reduction (e.g., about 1% reduction to about 99% reduction, about 1% reduction to about 95% reduction, about 1% reduction to about 90% reduction, about 1% reduction to about 85% reduction, about 1% reduction to about 80% reduction, about 1% reduction to about 75% reduction, about 1% reduction to about 70% reduction, about 1% reduction to about 65% reduction, about 1% reduction to about 60% reduction, about 1% reduction to about 55% reduction, about 1% reduction to about 50% reduction, about 1% reduction to about 45% reduction, about 1% reduction to about 40% reduction, about 1% reduction to about 35% reduction, about 1% reduction to about 30% reduction, about 1% reduction to about 25% reduction, about 1% reduction to about 20% reduction, about 1% reduction to about 15% reduction, about 1% reduction to about 10% reduction, about 1% reduction to about 5% reduction, about 5% reduction to about 99% reduction, about 5% reduction to about 95% reduction, about 5% reduction to about 90% reduction, about 5% reduction to about 85% reduction, about 5% reduction to about 80% reduction, about 5% reduction to about 75% reduction, about 5% reduction to about 70% reduction, about 5% reduction to about 65% reduction, about 5% reduction to about 60% reduction, about 5% reduction to about 55% reduction, about 5% reduction to about 50% reduction, about 5% reduction to about 45% reduction, about 5% reduction to about 40% reduction, about 5% reduction to about 35% reduction, about 5% reduction to about 30% reduction, about 5% reduction to about 25% reduction, about 5% reduction to about 20% reduction, about 5% reduction to about 15% reduction, about 5% reduction to about 10% reduction, about 10% reduction to about 99% reduction, about 10% reduction to about 95% reduction, about 10% reduction to about 90% reduction, about 10% reduction to about 85% reduction, about 10% reduction to about 80% reduction, about 10% reduction to about 75% reduction, about 10% reduction to about 70% reduction, about 10% reduction to about 65% reduction, about 10% reduction to about 60% reduction, about 10% reduction to about 55% reduction, about 10% reduction to about 50% reduction, about 10% reduction to about 45% reduction, about 10% reduction to about 40% reduction, about 10% reduction to about 35% reduction, about 10% reduction to about 30% reduction, about 10% reduction to about 25% reduction, about 10% reduction to about 20% reduction, about 10% reduction to about 15% reduction, about 15% reduction to about 99% reduction, about 15% reduction to about 95% reduction, about 15% reduction to about 90% reduction, about 15% reduction to about 85% reduction, about 15% reduction to about 80% reduction, about 15% reduction to about 75% reduction, about 15% reduction to about 70% reduction, about 15% reduction to about 65% reduction, about 15% reduction to about 60% reduction, about 15% reduction to about 55% reduction, about 15% reduction to about 50% reduction, about 15% reduction to about 45% reduction, about 15% reduction to about 40% reduction, about 15% reduction to about 35% reduction, about 15% reduction to about 30% reduction, about 15% reduction to about 25% reduction, about 15% reduction to about 20% reduction, about 20% reduction to about 99% reduction, about 20% reduction to about 95% reduction, about 20% reduction to about 90% reduction, about 20% reduction to about 85% reduction, about 20% reduction to about 80% reduction, about 20% reduction to about 75% reduction, about 20% reduction to about 70% reduction, about 20% reduction to about 65% reduction, about 20% reduction to about 60% reduction, about 20% reduction to about 55% reduction, about 20% reduction to about 50% reduction, about 20% reduction to about 45% reduction, about 20% reduction to about 40% reduction, about 20% reduction to about 35% reduction, about 20% reduction to about 30% reduction, about 20% reduction to about 25% reduction, about 25% reduction to about 99% reduction, about 25% reduction to about 95% reduction, about 25% reduction to about 90% reduction, about 25% reduction to about 85% reduction, about 25% reduction to about 80% reduction, about 25% reduction to about 75% reduction, about 25% reduction to about 70% reduction, about 25% reduction to about 65% reduction, about 25% reduction to about 60% reduction, about 25% reduction to about 55% reduction, about 25% reduction to about 50% reduction, about 25% reduction to about 45% reduction, about 25% reduction to about 40% reduction, about 25% reduction to about 35% reduction, about 25% reduction to about 30% reduction, about 30% reduction to about 99% reduction, about 30% reduction to about 95% reduction, about 30% reduction to about 90% reduction, about 30% reduction to about 85% reduction, about 30% reduction to about 80% reduction, about 30% reduction to about 75% reduction, about 30% reduction to about 70% reduction, about 30% reduction to about 65% reduction, about 30% reduction to about 60% reduction, about 30% reduction to about 55% reduction, about 30% reduction to about 50% reduction, about 30% reduction to about 45% reduction, about 30% reduction to about 40% reduction, about 30% reduction to about 35% reduction, about 35% reduction to about 99% reduction, about 35% reduction to about 95% reduction, about 35% reduction to about 90% reduction, about 35% reduction to about 85% reduction, about 35% reduction to about 80% reduction, about 35% reduction to about 75% reduction, about 35% reduction to about 70% reduction, about 35% reduction to about 65% reduction, about 35% reduction to about 60% reduction, about 35% reduction to about 55% reduction, about 35% reduction to about 50% reduction, about 35% reduction to about 45% reduction, about 35% reduction to about 40% reduction, about 40% reduction to about 99% reduction, about 40% reduction to about 95% reduction, about 40% reduction to about 90% reduction, about 40% reduction to about 85% reduction, about 40% reduction to about 80% reduction, about 40% reduction to about 75% reduction, about 40% reduction to about 70% reduction, about 40% reduction to about 65% reduction, about 40% reduction to about 60% reduction, about 40% reduction to about 55% reduction, about 40% reduction to about 50% reduction, about 40% reduction to about 45% reduction, about 45% reduction to about 99% reduction, about 45% reduction to about 95% reduction, about 45% reduction to about 90% reduction, about 45% reduction to about 85% reduction, about 45% reduction to about 80% reduction, about 45% reduction to about 75% reduction, about 45% reduction to about 70% reduction, about 45% reduction to about 65% reduction, about 45% reduction to about 60% reduction, about 45% reduction to about 55% reduction, about 45% reduction to about 50% reduction, about 50% reduction to about 99% reduction, about 50% reduction to about 95% reduction, about 50% reduction to about 90% reduction, about 50% reduction to about 85% reduction, about 50% reduction to about 80% reduction, about 50% reduction to about 75% reduction, about 50% reduction to about 70% reduction, about 50% reduction to about 65% reduction, about 50% reduction to about 60% reduction, about 50% reduction to about 55% reduction, about 55% reduction to about 99% reduction, about 55% reduction to about 95% reduction, about 55% reduction to about 90% reduction, about 55% reduction to about 85% reduction, about 55% reduction to about 80% reduction, about 55% reduction to about 75% reduction, about 55% reduction to about 70% reduction, about 55% reduction to about 65% reduction, about 55% reduction to about 60% reduction, about 60% reduction to about 99% reduction, about 60% reduction to about 95% reduction, about 60% reduction to about 90% reduction, about 60% reduction to about 85% reduction, about 60% reduction to about 80% reduction, about 60% reduction to about 75% reduction, about 60% reduction to about 70% reduction, about 60% reduction to about 65% reduction, about 65% reduction to about 99% reduction, about 65% reduction to about 95% reduction, about 65% reduction to about 90% reduction, about 65% reduction to about 85% reduction, about 65% reduction to about 80% reduction, about 65% reduction to about 75% reduction, about 65% reduction to about 70% reduction, about 70% reduction to about 99% reduction, about 70% reduction to about 95% reduction, about 70% reduction to about 90% reduction, about 70% reduction to about 85% reduction, about 70% reduction to about 80% reduction, about 70% reduction to about 75% reduction, about 75% reduction to about 99% reduction, about 75% reduction to about 95% reduction, about 75% reduction to about 90% reduction, about 75% reduction to about 85% reduction, about 75% reduction to about 80% reduction, about 80% reduction to about 99% reduction, about 80% reduction to about 95% reduction, about 80% reduction to about 90% reduction, about 80% reduction to about 85% reduction, about 85% reduction to about 99% reduction, about 85% reduction to about 95% reduction, about 85% reduction to about 90% reduction, about 90% reduction to about 99% reduction, about 90% reduction to about 95% reduction, or about 95% reduction to about 99% reduction) in the volume of one or more solid tumors in the subject (e.g., as compared to the volume of the one or more solid tumors prior to treatment or at the start of treatment). In some embodiments, the these methods can reduce (e.g., about 1% reduction to about 99% reduction, or any of the subranges of this range described herein) the risk of developing a metastasis or developing one or more additional metastasis in a subject (e.g., as compared to the risk of developing a metastasis or developing one or more additional metastasis in a subject prior to treatment or in a similar subject or a population of subjects administered a different treatment).

In some examples of these methods, the subject has been identified or diagnosed as having an aging-related disease or condition. Non-limiting examples of aging-related diseases and conditions include Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples, these methods can result in a reduction in the number, severity, or frequency of one or more symptoms of the aging-related disease or condition in the subject (e.g., as compared to the number, severity, or frequency of the one or more symptoms of the aging-related disease or condition in the subject prior to treatment). In some examples, the methods can result in a decrease (e.g., about 1% decrease to about 99% decrease, an about 1% decrease to about 95% decrease, about 1% decrease to about 90% decrease, about 1% decrease to about 85% decrease, about 1% decrease to about 80% decrease, about 1% decrease to about 75% decrease, about 1% to about 70% decrease, about 1% decrease to about 65% decrease, about 1% decrease to about 60% decrease, about 1% decrease to about 55% decrease, about 1% decrease to about 50% decrease, about 1% decrease to about 45% decrease, about 1% decrease to about 40% decrease, about 1% decrease to about 35% decrease, about 1% decrease to about 30% decrease, about 1% decrease to about 25% decrease, about 1% decrease to about 20% decrease, about 1% decrease to about 15% decrease, about 1% decrease to about 10% decrease, about 1% decrease to about 5% decrease, about 5% decrease to about 99% decrease, an about 5% decrease to about 95% decrease, about 5% decrease to about 90% decrease, about 5% decrease to about 85% decrease, about 5% decrease to about 80% decrease, about 5% decrease to about 75% decrease, about 5% to about 70% decrease, about 5% decrease to about 65% decrease, about 5% decrease to about 60% decrease, about 5% decrease to about 55% decrease, about 5% decrease to about 50% decrease, about 5% decrease to about 45% decrease, about 5% decrease to about 40% decrease, about 5% decrease to about 35% decrease, about 5% decrease to about 30% decrease, about 5% decrease to about 25% decrease, about 5% decrease to about 20% decrease, about 5% decrease to about 15% decrease, about 5% decrease to about 10% decrease, about 10% decrease to about 99% decrease, an about 10% decrease to about 95% decrease, about 10% decrease to about 90% decrease, about 10% decrease to about 85% decrease, about 10% decrease to about 80% decrease, about 10% decrease to about 75% decrease, about 10% to about 70% decrease, about 10% decrease to about 65% decrease, about 10% decrease to about 60% decrease, about 10% decrease to about 55% decrease, about 10% decrease to about 50% decrease, about 10% decrease to about 45% decrease, about 10% decrease to about 40% decrease, about 10% decrease to about 35% decrease, about 10% decrease to about 30% decrease, about 10% decrease to about 25% decrease, about 10% decrease to about 20% decrease, about 10% decrease to about 15% decrease, about 15% decrease to about 99% decrease, an about 15% decrease to about 95% decrease, about 15% decrease to about 90% decrease, about 15% decrease to about 85% decrease, about 15% decrease to about 80% decrease, about 15% decrease to about 75% decrease, about 15% to about 70% decrease, about 15% decrease to about 65% decrease, about 15% decrease to about 60% decrease, about 15% decrease to about 55% decrease, about 15% decrease to about 50% decrease, about 15% decrease to about 45% decrease, about 15% decrease to about 40% decrease, about 15% decrease to about 35% decrease, about 15% decrease to about 30% decrease, about 15% decrease to about 25% decrease, about 15% decrease to about 20% decrease, about 20% decrease to about 99% decrease, an about 20% decrease to about 95% decrease, about 20% decrease to about 90% decrease, about 20% decrease to about 85% decrease, about 20% decrease to about 80% decrease, about 20% decrease to about 75% decrease, about 20% to about 70% decrease, about 20% decrease to about 65% decrease, about 20% decrease to about 60% decrease, about 20% decrease to about 55% decrease, about 20% decrease to about 50% decrease, about 20% decrease to about 45% decrease, about 20% decrease to about 40% decrease, about 20% decrease to about 35% decrease, about 20% decrease to about 30% decrease, about 20% decrease to about 25% decrease, about 25% decrease to about 99% decrease, an about 25% decrease to about 95% decrease, about 25% decrease to about 90% decrease, about 25% decrease to about 85% decrease, about 25% decrease to about 80% decrease, about 25% decrease to about 75% decrease, about 25% to about 70% decrease, about 25% decrease to about 65% decrease, about 25% decrease to about 60% decrease, about 25% decrease to about 55% decrease, about 25% decrease to about 50% decrease, about 25% decrease to about 45% decrease, about 25% decrease to about 40% decrease, about 25% decrease to about 35% decrease, about 25% decrease to about 30% decrease, about 30% decrease to about 99% decrease, an about 30% decrease to about 95% decrease, about 30% decrease to about 90% decrease, about 30% decrease to about 85% decrease, about 30% decrease to about 80% decrease, about 30% decrease to about 75% decrease, about 30% to about 70% decrease, about 30% decrease to about 65% decrease, about 30% decrease to about 60% decrease, about 30% decrease to about 55% decrease, about 30% decrease to about 50% decrease, about 30% decrease to about 45% decrease, about 30% decrease to about 40% decrease, about 30% decrease to about 35% decrease, about 35% decrease to about 99% decrease, an about 35% decrease to about 95% decrease, about 35% decrease to about 90% decrease, about 35% decrease to about 85% decrease, about 35% decrease to about 80% decrease, about 35% decrease to about 75% decrease, about 35% to about 70% decrease, about 35% decrease to about 65% decrease, about 35% decrease to about 60% decrease, about 35% decrease to about 55% decrease, about 35% decrease to about 50% decrease, about 35% decrease to about 45% decrease, about 35% decrease to about 40% decrease, about 40% decrease to about 99% decrease, an about 40% decrease to about 95% decrease, about 40% decrease to about 90% decrease, about 40% decrease to about 85% decrease, about 40% decrease to about 80% decrease, about 40% decrease to about 75% decrease, about 40% to about 70% decrease, about 40% decrease to about 65% decrease, about 40% decrease to about 60% decrease, about 40% decrease to about 55% decrease, about 40% decrease to about 50% decrease, about 40% decrease to about 45% decrease, about 45% decrease to about 99% decrease, an about 45% decrease to about 95% decrease, about 45% decrease to about 90% decrease, about 45% decrease to about 85% decrease, about 45% decrease to about 80% decrease, about 45% decrease to about 75% decrease, about 45% to about 70% decrease, about 45% decrease to about 65% decrease, about 45% decrease to about 60% decrease, about 45% decrease to about 55% decrease, about 45% decrease to about 50% decrease, about 50% decrease to about 99% decrease, an about 50% decrease to about 95% decrease, about 50% decrease to about 90% decrease, about 50% decrease to about 85% decrease, about 50% decrease to about 80% decrease, about 50% decrease to about 75% decrease, about 50% to about 70% decrease, about 50% decrease to about 65% decrease, about 50% decrease to about 60% decrease, about 50% decrease to about 55% decrease, about 55% decrease to about 99% decrease, an about 55% decrease to about 95% decrease, about 55% decrease to about 90% decrease, about 55% decrease to about 85% decrease, about 55% decrease to about 80% decrease, about 55% decrease to about 75% decrease, about 55% to about 70% decrease, about 55% decrease to about 65% decrease, about 55% decrease to about 60% decrease, about 60% decrease to about 99% decrease, an about 60% decrease to about 95% decrease, about 60% decrease to about 90% decrease, about 60% decrease to about 85% decrease, about 60% decrease to about 80% decrease, about 60% decrease to about 75% decrease, about 60% to about 70% decrease, about 60% decrease to about 65% decrease, about 65% decrease to about 99% decrease, an about 65% decrease to about 95% decrease, about 65% decrease to about 90% decrease, about 65% decrease to about 85% decrease, about 65% decrease to about 80% decrease, about 65% decrease to about 75% decrease, about 65% to about 70% decrease, about 70% decrease to about 99% decrease, an about 70% decrease to about 95% decrease, about 70% decrease to about 90% decrease, about 70% decrease to about 85% decrease, about 70% decrease to about 80% decrease, about 70% decrease to about 75% decrease, about 75% decrease to about 99% decrease, an about 75% decrease to about 95% decrease, about 75% decrease to about 90% decrease, about 75% decrease to about 85% decrease, about 75% decrease to about 80% decrease, about 80% decrease to about 99% decrease, an about 80% decrease to about 95% decrease, about 80% decrease to about 90% decrease, about 80% decrease to about 85% decrease, about 85% decrease to about 99% decrease, an about 85% decrease to about 95% decrease, about 85% decrease to about 90% decrease, about 90% decrease to about 99% decrease, an about 90% decrease to about 95% decrease, or about 95% decrease to about 99% decrease) in the number of senescent cells in the subject (e.g., a decrease in the number of senescent cells in one or more specific tissues involved and/or implicated in the aging-related disease or disorder in the subject), e.g., as compared to the number of senescent cells in the subject prior to treatment.

In some examples of these methods, the subject has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus. In some embodiments, these method can result in a decrease in the infectious titer (e.g., viral titer) in a subject (e.g., as compared to the infectious titer in the subject prior to treatment). In some embodiments, these methods can result in a reduction in the number, severity, or frequency of one or more symptoms of the infectious disease (e.g., viral infection) in the subject (e.g., as compared to the number, severity, or frequency of the one or more symptoms of the infectious disease in the subject prior to treatment).

The term "subject" refers to any mammal. In some embodiments, the subject or "subject in need of treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon) or a human; or rodent (e.g., a mouse, a guinea pig, a hamster, or a rat). In some embodiments, the subject or "subject in need of treatment" may be a non-human mammal, especially mammals that are conventionally used as models for demonstrating therapeutic efficacy in humans (e.g., murine, lapine, porcine, canine or primate animals) may be employed.

Methods of Killing a Cancer Cell, an Infected Cell, or a Senescent Cell

Also provided herein are methods of killing a cancer cell (e.g., any of the exemplary types of cancer described herein or known in the art), an infected cell (e.g., a cell infected with any of the exemplary viruses described herein or known in the art), or a senescent cell (e.g., a senescent cancer cell, a senescent fibroblast, or a senescent endothelial cell) in a subject in need thereof (e.g., any of the exemplary subjects described herein or known in the art) that include administering to the subject a therapeutically effective amount of any of the single-chain chimeric polypeptides or any of the multi-chain chimeric polypeptides described herein or any of the compositions (e.g., pharmaceutical compositions) described herein. In some embodiments, the subject can further be administered a therapeutically effective amount of any of the of IgG1 antibody constructs described herein.

In some embodiments of these methods, the subject has been identified or diagnosed as having a cancer. Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. Non-limiting examples of aging-related diseases and conditions include Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. Non-limiting examples of an infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Senescent Cells

Senescence is a form of irreversible growth arrest accompanied by phenotypic changes, resistance to apoptosis and activation of damage-sensing signaling pathways. Cellular senescence was first described in cultured human fibroblast cells that lost their ability to proliferate, reaching permanent arrest after about 50 population doublings (referred to as the Hayflick limit). Senescence is considered a stress response that can be induced by a wide range of intrinsic and extrinsic insults, including oxidative and genotoxic stress, DNA damage, telomere attrition, oncogenic activation, mitochondrial dysfunction, or chemotherapeutic agents.

Senescent cells remain metabolically active and can influence the tissue hemostasis, disease and aging through their secretory phenotype. Senescence is considered as a physiologic process and is important in promoting wound healing, tissue homeostasis, regeneration, and fibrosis regulation. For instance, transient induction of senescent cells is observed during would healing and contributes to wound resolution. Perhaps one of the most important roles of senescence is its role in tumor suppression. However, the accumulation of senescent cells also drives aging and aging-related diseases and conditions. The senescent phenotype also can trigger chronic inflammatory responses and consequently augment chronic inflammatory conditions to promote tumor growth. The connection between senescence and aging was initially based on observations that senescent cells accumulate in aged tissue. The use of transgenic models has enabled the detection of senescent cells systematically in many age-related pathologies. Strategies to selectively eliminate senescent cells have demonstrated that senescent cells can indeed play a causal role in aging and related pathologies.

Senescent cells display important and unique properties which include changes in morphology, chromatin organization, gene expression, and metabolism. There are several biochemical and functional properties associated with cellular senescence, such as (i) increased expression of p16 and p21, inhibitors of cyclin-dependent kinases, (ii) presence of senescence-associated β-galactosidase, a marker of lysosomal activity, (iii) appearance of senescence-associated heterochromatin foci and downregulation of lamin B1 levels, (iv) resistance to apoptosis caused by an increased expression of anti-apoptotic BCL-family protein, and (v) upregulation of CD26 (DPP4), CD36 (Scavenger receptor), forkhead box 4 (FOXO4), and secretory carrier membrane protein 4 (SCAMP4). Senescent cells also express an inflammatory signature, the so-called senescence-associated secretory phenotype (SASP). Through SASP, the senescent cells produce a wide range of inflammatory cytokines (IL-6, IL-8), growth factors (TGF-β), chemokines (CCL-2), and matrix metalloproteinases (MMP-3, MMP-9) that operate in a cell-autonomous manner to reinforce senescence (autocrine effects) and communicate with and modify the microenvironment (paracrine effects). SASP factors can contribute to tumor suppression by triggering senescence surveillance, an immune-mediated clearance of senescent cells. However, chronic inflammation is also a known driver of tumorigenesis, and accumulating evidence indicates that chronic SASP can also boost cancer and aging-related diseases.

The secretion profile of senescent cells is context dependent. For instance, the mitochondrial dysfunction-associated senescence (MiDAS), induced by different mitochondrial dysfunction in human fibroblasts, led to the appearance of a SASP that was deficient in IL-1-dependent inflammatory factors. A decrease in the NAD+/NADH ratio activated AMPK signaling which induced MiDAS through the activation of p53. As a result, p53 inhibited NF-κB signaling which is a crucial inducer of pro-inflammatory SASP. In contrast, the cellular senescence caused by persistent DNA damage in human cells induced an inflammatory SASP, which was dependent on the activation of ataxia-telangiectasia mutated (ATM) kinase but not on that of p53. In particular, the expression and secretion levels of IL-6 and IL-8 were increased. It was also demonstrated that cellular senescence caused by the ectopic expression p16INK4a and p21CIP1 induced the senescent phenotype in human fibroblasts without an inflammatory SASP indicating that the growth arrest itself did not stimulate SASP.

One of the most defining characteristics of senescence is stable growth arrest. This is achieved by two important pathways, the p16/Rb and the p53/p21, both of which are central in tumor suppression. DNA damage results in: (1) high deposition of γH2Ax (histone coding gene) and 53BP1 (involved in DNA damage response) in chromatin: this leads to activation of a kinase cascade eventually resulting in p53 activation, and (2) activation of p16INK4a and ARF (both encoded by CDKN2A) and P15INK4b (encoded by CDKN2B): p53 induces transcription of cyclin-dependent kinase inhibitor (p21) and along with both p16INK4a and p15INK4b block genes for cell cycle progression (CDK4 and CDK6). This eventually leads to hypophosphorylation of Retinoblastoma protein (Rb) and cell cycle arrest at the G1 phase.

Selectively killing senescent cells has been shown to significantly improve the health span of mice in the context of normal aging and ameliorates the consequences of age-related disease or cancer therapy (Ovadya, *J Clin Invest.* 128(4):1247-1254, 2018). In nature, the senescent cells are normally removed by the innate immune cells. Induction of senescence not only prevents the potential proliferation and transformation of damaged/altered cells, but also favors tissue repair through the production of SASP factors that function as chemoattractants mainly for Natural Killer (NK) cells (such as IL-15 and CCL2) and macrophages (such as CFS-1 and CCL2). These innate immune cells mediate the immunosurveillance mechanism for eliminating stressed cells. Senescent cells usually up-regulate the NK-cell activating receptor NKG2D and DNAM-1 ligands, which belong to a family of stress-inducible ligands: an important component of the frontline immune defense against infectious diseases and malignancies. Upon receptor activation, NK cells can then specifically induce the death of senescent cells through their cytolytic machinery. A role for NK cells in the immune surveillance of senescent cells has been pointed out in liver fibrosis (Sagiv, *Oncogene* 32(15): 1971-1977, 2013), hepatocellular carcinoma (Iannello, *J Exp Med* 210(10): 2057-2069, 2013), multiple myeloma (Soriani, *Blood* 113(15): 3503-3511, 2009), and glioma cells stressed by dysfunction of the mevalonate pathway (Ciaglia, *Int J Cancer* 142(1): 176-190, 2018). Endometrial cells undergo acute cellular senescence and do not differentiate into decidual cells. The differentiated decidual cells secrete IL-15 and thereby recruit uterine NK cells to target and eliminate the undifferentiated senescent cells thus helping to re-model and rejuvenate the endometrium (Brighton, *Elife* 6: e31274, 2017). With a similar mechanism, during liver fibrosis, p53-expressing senescent liver satellite cells skewed the polarization of resident Kupfer macrophages and freshly infiltrated macrophages toward the pro-inflammatory M1 phenotype, which display senolytic activity. F4/80+ macrophages have been shown to play a key role in the clearance of mouse uterine senescent cells to maintain postpartum uterine function.

Senescent cells recruit NK cells by mainly upregulating ligands to NKG2D (expressed on NK cells), chemokines, and other SASP factors. In vivo models of liver fibrosis have shown effective clearance of senescent cells by activated NK cells (Krizhanovsky, *Cell* 134(4): 657-667, 2008). Studies have described various models to study senescence including liver fibrosis (Krizhanovsky, *Cell* 134(4): 657-667, 2008), osteoarthritis (Xu, *J Gerontol A Biol Sci Med Sci* 72(6): 780-785, 2017), and Parkinson's disease (Chinta, *Cell Rep* 22(4): 930-940, 2018). Animal models for studying senescent cells are described in: Krizhanovsky, *Cell* 134(4): 657-667, 2008; Baker, *Nature* 479(7372): 232-236, 2011; Farr, *Nat Med* 23(9): 1072-1079, 2017; Bourgeois, *FEBS Lett* 592(12): 2083-2097, 2018; Xu, *Nat Med* 24(8): 1246-1256, 2018).

Methods of Increasing Glucose Consumption of an Immune Cell

Also provided herein are methods of increasing the glucose consumption of an immune cell that include: contacting an immune cell (e.g., any of the immune cells described herein) in a liquid culture medium (e.g., any of the liquid culture media described herein) including an effective amount of (i) a single-chain chimeric polypeptide comprising a first target-binding domain, a linker domain, and a second target-binding domain (e.g., any of the single-chain chimeric polypeptides described herein), and optionally (ii) an IgG1 antibody construct that includes at least one antigen-binding domain that binds specifically to the linker domain (e.g., any of the exemplary IgG1 antibody constructs described herein), under conditions that allow for glucose consumption in the immune cell, where the first target-binding domain and the second target-binding domain are each independently selected from the group of: a soluble interleukin or cytokine protein, an antigen-binding domain, a soluble interleukin or cytokine receptor, and ligands of co-stimulatory molecules.

Also provided herein are methods of increasing the glucose consumption of an immune cell that include: contacting an immune cell in a liquid culture medium comprising (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains (e.g., any of the multi-chain chimeric polypeptides described herein); and (2) an effective amount of an IgG1 antibody construct including at least one antigen-binding domain that binds specifically to the linker domain, under conditions that allow for glucose consumption in the immune cell.

In some embodiments of any of the methods described herein, the increase in glucose consumption is compared to the level of glucose consumption in a similar immune cell not contacted with the single-chain chimeric polypeptide or the multi-chain chimeric polypeptide, and optionally the IgG1 antibody construct that includes at least one antigen-binding domain that binds specifically to the soluble tissue factor domain.

Non-limiting assays that can be used to detect glucose consumption include, e.g., assays that include the use of radiolabeled 3-O-methylglucose or radiolabeled 2-deoxyglucose, or an enzymatic, fluorometric assay for detecting 2-deoxyglucose. Additional examples of assays that can be used to detect glucose consumption are described in, e.g., Yamamoto et al., *Curr. Protoc. Pharmacol.*, Chapter 12, Unit 12.14.1-22, December 2011; Zou et al., *J. Biochem. Biophys. Methods* 64(3):207-215, September 2005; and MacKrell et al., *Diabetes p.* 1-9, published online on Mar. 13, 2012.

In some embodiments of these methods, the liquid culture medium includes the single-chain chimeric polypeptide or the multi-chain chimeric polypeptide, and the IgG1 antibody construct. In some examples of these methods, the IgG1 antibody construct is a monoclonal IgG1 antibody, where both of the antigen-binding domains in the monoclonal IgG1 antibody bind specifically to the soluble tissue factor domain. In some examples of these methods, the IgG1 antibody construct is a bispecific IgG1 antibody, where one of the two antigen-binding domains in the bispecific IgG1 antibody binds specifically to the soluble tissue factor domain.

In some embodiments of any of the methods described herein, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days).

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the single-chain chimeric polypeptide or the multi-chain chimeric polypeptide, and the IgG1 antibody construct at a molar ratio of about 0.5:1 to about 2:1 (e.g., about 0.8:1 to about 1.2:1).

In some embodiments of these methods, the immune cell is selected from the group of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments of any of the methods described herein, the immune cell is a T-cell or a natural killer cell.

In some examples of these methods, the immune cell was previously obtained from a subject. Some embodiments of these methods further include obtaining the immune cell from the subject prior to the contacting step. In some embodiments of these methods, the immune cell has previously been genetically modified to express a chimeric antigen receptor or a recombinant T-cell receptor. Some embodiments of these methods further include, after the contacting step, introducing into the immune cell a nucleic acid encoding a chimeric antigen-receptor or a recombinant T-cell receptor. Some embodiments of these methods further include, before the contacting step, introducing into the immune cell a nucleic acid encoding a chimeric antigen-receptor or a recombinant T-cell receptor. Some embodiments of these methods further include, after the contacting step, isolating the immune cell. Some embodiments of these methods further include, after the contacting step, administering the immune cell to a subject in need thereof.

In some examples of these methods, the subject has been identified or diagnosed as having an age-related disease or condition. In some examples of these methods, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Oxidative Phosphorylation of an Immune Cell

Also provided herein are methods of increasing the oxidative phosphorylation of an immune cell that include: contacting an immune cell (e.g., any of the immune cells described herein) in a liquid culture medium (e.g., any of the liquid culture media described herein) including an effective amount of (i) a single-chain chimeric polypeptide comprising a first target-binding domain, a linker domain, and a second target-binding domain (e.g., any of the exemplary single-chain chimeric polypeptides described herein), and optionally (ii) an IgG1 antibody construct that comprises at least one antigen-binding domain that binds specifically to the linker domain (e.g., any of the exemplary IgG1 antibody constructs described herein), under conditions that allow for oxidative phosphorylation in the immune cell, where the first target-binding domain and the second target-binding domain are each independently selected from the group of: a soluble interleukin or cytokine protein, an antigen-binding domain, a soluble interleukin or cytokine receptor, and ligands of co-stimulatory molecules.

Also provided herein are methods of increasing the oxidative phosphorylation of an immune cell that include: contacting an immune cell (e.g., any of the immune cells described herein) in a liquid culture medium (e.g., any of the liquid culture media described herein) comprising (1) an effective amount of a multi-chain chimeric polypeptide including: (a) a first chimeric polypeptide comprising: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains (e.g., any of the multi-chain chimeric polypeptides described herein); and (2) an effective amount of an IgG1 antibody construct including at least one antigen-binding domain that binds specifically to the linker domain (e.g., any of the exemplary IgG1 antibody constructs described herein), under conditions that allow for oxidative phosphorylation in the immune cell.

In some embodiments of any of the methods described herein, the increase in oxidative phosphorylation is compared to the level of oxidative phosphorylation in a similar immune cell not contacted with the single-chain chimeric polypeptide of the multi-chain chimeric polypeptide, and optionally the IgG1 antibody construct that includes at least one antigen-binding domain that binds specifically to the soluble tissue factor domain.

Non-limiting assays that can be used to detect oxidative phosphorylation include, e.g., immunofluorescent assays and colorimetric assays. A non-limiting commercial assay that can be used to determine the level of oxidative phosphorylation is MitoTox™ Complete OXPHOS Activity Assay (Abcam). Additional examples of assays that can be used to detect oxidative phosphorylation are described in, e.g., Chance et al., *Nature* 175:1120-1121, 1955; Pullman et al., *Science* 123(3208):1105-1107, 1956; Van Bergen et al., *Mitochondrion* 15:24-33, 2014; and Rocha et al., *Sci. Rep.* 5:15037, 2015.

In some embodiments of these methods, the liquid culture medium includes the single-chain chimeric polypeptide or the multi-chain chimeric polypeptide, and the IgG1 antibody construct. In some examples of these methods, the IgG1 antibody construct is a monoclonal IgG1 antibody, where both of the antigen-binding domains in the monoclonal IgG1 antibody bind specifically to the soluble tissue factor domain. In some examples of these methods, the IgG1 antibody construct is a bispecific IgG1 antibody, where one of the two antigen-binding domains in the bispecific IgG1 antibody binds specifically to the soluble tissue factor domain.

In some embodiments of any of the methods described herein, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days).

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the single-chain chimeric polypeptide or the multi-chain chimeric polypeptide, and the IgG1 antibody construct at a molar ratio of about 0.5:1 to about 2:1 (e.g., about 0.8:1 to about 1.2:1).

In some embodiments of these methods, the immune cell is selected from the group of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments of any of the methods described herein, the immune cell is a T-cell or a natural killer cell.

In some examples of these methods, the immune cell was previously obtained from a subject. Some embodiments of these methods further include obtaining the immune cell from the subject prior to the contacting step. In some embodiments of these methods, the immune cell has previously been genetically modified to express a chimeric antigen receptor or a recombinant T-cell receptor. Some embodiments of these methods further include, after the contacting step, introducing into the immune cell a nucleic acid encoding a chimeric antigen-receptor or a recombinant T-cell receptor. Some embodiments of these methods further include, before the contacting step, introducing into the immune cell a nucleic acid encoding a chimeric antigen-receptor or a recombinant T-cell receptor. Some embodiments of these methods further include, after the contacting step, isolating the immune cell. Some embodiments of these methods further include, after the contacting step, administering the immune cell to a subject in need thereof.

In some examples of these methods, the subject has been identified or diagnosed as having an age-related disease or condition. In some examples of these methods, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus. Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Aerobic Glycolysis of an Immune Cell

Also provided herein are methods of increasing the aerobic glycolysis of an immune cell that include: contacting an immune cell (e.g., any of the immune cells described herein) in a liquid culture medium (e.g., any of the liquid culture media described herein) including an effective amount of (i) a single-chain chimeric polypeptide including a first target-binding domain, a linker domain, and a second target-binding domain (e.g., any of the single-chain chimeric polypeptides described herein), and optionally (ii) an IgG1 antibody construct that includes at least one antigen-binding domain that binds specifically to the linker domain (e.g., any of the exemplary IgG1 antibody constructs described herein), under conditions that allow for aerobic glycolysis in the immune cell, where the first target-binding domain and the second target-binding domain are each independently selected from the group of: a soluble interleukin or cytokine protein, an antigen-binding domain, a soluble interleukin or cytokine receptor, and ligands of co-stimulatory molecules.

Also provided herein are methods of increasing the aerobic glycolysis of an immune cell that include: contacting an immune cell (e.g., any of the immune cells described herein) in a liquid culture medium (e.g., any of the liquid culture media described herein) including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains (e.g., any of the multi-chain chimeric polypeptides described herein); and (2) an effective amount of an IgG1 antibody construct including at least one antigen-binding domain that binds specifically to the linker domain (e.g., any of the exemplary IgG1 antibody constructs described herein), under conditions that allow for aerobic glycolysis in the immune cell.

In some embodiments of any of the methods described herein, the increase in aerobic glycolysis is compared to the level of aerobic glycolysis in a similar immune cell not contacted with the single-chain chimeric polypeptide or the multi-chain chimeric polypeptide, and optionally the IgG1 antibody construct that includes at least one antigen-binding domain that binds specifically to the soluble tissue factor domain.

Non-limiting assays that can be used to detect aerobic glycolysis include, e.g., detection of ATP and/or $CO_2$ production, e.g., using gas chromatography/mass spectrometry, or extracellular acidification rate. Additional examples of assays that can be used to detect aerobic glycolysis are described in, e.g., Zhang et al., *Bone* 114:150-160, 2018; Zhao et al., *J. Breast Cancer* 21(2):112-123, 2018; Li et al., *Cell Comm. Signal.* 16(1):26, 2018; Cai et al., *J. Exp. Clin. Cancer Res.* 37(1):104, 2018; and Zhang et al., *Oncol. Rep.* 40(2):1156-1164, 2018.

In some embodiments of these methods, the liquid culture medium includes the single-chain chimeric polypeptide or the multi-chain chimeric polypeptide, and the IgG1 antibody construct. In some examples of these methods, the IgG1 antibody construct is a monoclonal IgG1 antibody, where both of the antigen-binding domains in the monoclonal IgG1 antibody bind specifically to the soluble tissue factor domain. In some examples of these methods, the IgG1 antibody construct is a bispecific IgG1 antibody, where one of the two antigen-binding domains in the bispecific IgG1 antibody binds specifically to the soluble tissue factor domain.

In some embodiments of any of the methods described herein, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days).

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the single-chain chimeric polypeptide or the multi-chain chimeric polypeptide, and the IgG1 antibody construct at a molar ratio of about 0.5:1 to about 2:1 (e.g., about 0.8:1 to about 1.2:1).

In some embodiments of these methods, the immune cell is selected from the group of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments of any of the methods described herein, the immune cell is a T-cell or a natural killer cell.

In some examples of these methods, the immune cell was previously obtained from a subject. Some embodiments of these methods further include obtaining the immune cell from the subject prior to the contacting step. In some embodiments of these methods, the immune cell has previously been genetically modified to express a chimeric antigen receptor or a recombinant T-cell receptor. Some embodiments of these methods further include, after the contacting step, introducing into the immune cell a nucleic acid encoding a chimeric antigen-receptor or a recombinant T-cell receptor. Some embodiments of these methods further include, before the contacting step, introducing into the immune cell a nucleic acid encoding a chimeric antigen-receptor or a recombinant T-cell receptor. Some embodiments of these methods further include, after the contacting step, isolating the immune cell. Some embodiments of these methods further include, after the contacting step, administering the immune cell to a subject in need thereof.

In some examples of these methods, the subject has been identified or diagnosed as having an age-related disease or condition. In some examples of these methods, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Extracellular Acidification Rate (ECAR) of an Immune Cell

Also provided herein are method of increasing the extracellular acidification rate (ECAR) of an immune cell that include: contacting an immune cell (e.g., any of the immune cells described herein) in a liquid culture medium (e.g., any of the liquid culture media described herein) including an effective amount of (i) a single-chain chimeric polypeptide including a first target-binding domain, a linker domain, and a second target-binding domain (e.g., any of the single-chain chimeric polypeptides described herein), and optionally (ii) an IgG1 antibody construct that includes at least one antigen-binding domain that binds specifically to the linker domain (e.g., any of the exemplary IgG1 antibody constructs described herein), under conditions that allow for extracellular acidification by the immune cell, where the first target-binding domain and the second target-binding domain are each independently selected from the group of: a soluble interleukin or cytokine protein, an antigen-binding domain, a soluble interleukin or cytokine receptor, and ligands of co-stimulatory molecules.

Also provided herein are methods of increasing the extracellular acidification rate (ECAR) of an immune cell that include: contacting an immune cell (e.g., any of the immune cells described herein) in a liquid culture medium (e.g., any of the liquid culture media described herein) including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains (e.g., any of the multi-chain chimeric polypeptides described herein); and (2) an effective amount of an IgG1 antibody construct including at least one antigen-binding domain that binds specifically to the linker domain (e.g., any of the exemplary IgG1 antibody constructs described herein), under conditions that allow for extracellular acidification by the immune cell.

In some embodiments of any of the methods described herein, the increase in extracellular acidification rate (ECAR) is compared to the level of extracellular acidification rate (ECAR) in a similar immune cell not contacted with the single-chain chimeric polypeptide or the multi-chain chimeric polypeptide, and optionally the IgG1 antibody construct that includes at least one antigen-binding domain that binds specifically to the soluble tissue factor domain.

Non-limiting commercial assays that can be used to detect extracellular acidification rate (ECAR) include, e.g., Glycolysis Assay (Extracellular Acidification Kit) (ab197244 or ab197245) (Abcam), MITO-ID® Extracellular pH Sensor Kit (ENZ-51048) (Enzo Life Sciences), and pH-Xtra™—Glycolysis Assay (Extracellular Acidification). Additional examples of assays that can be used to detect extracellular acidification rate (ECAR) are described in, e.g., Owicki et al., *Biosens. Bioelectron.* 7(4):255-272, 1992; Hynes et al., *Analytical Biochem.* 390(1):21-28, 2009; Trevani et al., *J. Immunol.* 162(8):4849-4857, 1999; and Mookerjee et al., *J. Vis. Exp.* 106:53464, 2015.

In some embodiments of these methods, the liquid culture medium includes the single-chain chimeric polypeptide or the multi-chain chimeric polypeptide, and the IgG1 antibody construct. In some examples of these methods, the IgG1 antibody construct is a monoclonal IgG1 antibody, where both of the antigen-binding domains in the monoclonal IgG1 antibody bind specifically to the soluble tissue factor domain. In some examples of these methods, the IgG1 antibody construct is a bispecific IgG1 antibody, where one of the two antigen-binding domains in the bispecific IgG1 antibody binds specifically to the soluble tissue factor domain.

In some embodiments of any of the methods described herein, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days).

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the single-chain chimeric polypeptide or the multi-chain chimeric polypeptide, and the IgG1 antibody construct at a molar ratio of about 0.5:1 to about 2:1 (e.g., about 0.8:1 to about 1.2:1).

In some embodiments of these methods, the immune cell is selected from the group of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments of any of the methods described herein, the immune cell is a T-cell or a natural killer cell.

In some examples of these methods, the immune cell was previously obtained from a subject. Some embodiments of these methods further include obtaining the immune cell from the subject prior to the contacting step. In some embodiments of these methods, the immune cell has previously been genetically modified to express a chimeric antigen receptor or a recombinant T-cell receptor. Some embodiments of these methods further include, after the contacting step, introducing into the immune cell a nucleic acid encoding a chimeric antigen-receptor or a recombinant T-cell receptor. Some embodiments of these methods further include, before the contacting step, introducing into the immune cell a nucleic acid encoding a chimeric antigen-receptor or a recombinant T-cell receptor. Some embodiments of these methods further include, after the contacting step, isolating the immune cell. Some embodiments of these methods further include, after the contacting step, administering the immune cell to a subject in need thereof.

In some examples of these methods, the subject has been identified or diagnosed as having an age-related disease or condition. In some examples of these methods, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus. Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Mitochondrial Oxygen Consumption Rate of an Immune Cell

Also provided herein are methods of increasing the mitochondrial oxygen consumption rate of an immune cell that include: contacting an immune cell (e.g., any of the immune cells described herein) in a liquid culture medium (e.g., any of the liquid culture media described herein) including an effective amount of (i) a single-chain chimeric polypeptide comprising a first target-binding domain, a linker domain, and a second target-binding domain (e.g., any of the single-chain chimeric polypeptides described herein), and optionally (ii) an IgG1 antibody construct that includes at least one antigen-binding domain that binds specifically to the linker domain (e.g., any of the exemplary IgG1 antibody constructs described herein), under conditions that allow for mitochondrial oxygen consumption rate by the immune cell, where the first target-binding domain and the second target-binding domain are each independently selected from the group of: a soluble interleukin or cytokine protein, an antigen-binding domain, a soluble interleukin or cytokine receptor, and ligands of co-stimulatory molecules.

Also provided herein are methods of increasing the mitochondrial oxygen consumption rate of an immune cell that include: contacting an immune cell (e.g., any of the immune cells described herein) in a liquid culture medium (e.g., any of the liquid culture media described herein) including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains (e.g., any of the multi-chain chimeric polypeptides described herein); and (2) an effective amount of an IgG1 antibody construct including at least one antigen-binding domain that binds specifically to the linker domain (e.g., any of the exemplary IgG1 antibody constructs described herein), under conditions that allow for mitochondrial oxygen consumption rate by the immune cell.

In some embodiments of any of the methods described herein, the increase in mitochondrial oxygen consumption rate is compared to the level of mitochondrial oxygen consumption rate in a similar immune cell not contacted with the single-chain chimeric polypeptide or the multi-chain chimeric polypeptide, and optionally the IgG1 antibody construct that includes at least one antigen-binding domain that binds specifically to the soluble tissue factor domain.

Non-limiting commercial assays that can be used to detect mitochondrial oxygen consumption rate include, e.g., assays that include the use of an electrode or a commercially available kit, e.g., Oxygen Consumption Rate Assay Kit (Cayman Chemical), the Seahorse assay (as described in Sakamuri et al., *Geroscience* 40(3):347-356, 2018). Additional examples of assays that can be used to detect mitochondrial oxygen consumption rate are described in, e.g., Li et al., *Mitochondrial Disorders*, pp. 63-72, December 2011; Kumagi et al., *Synapse* e22067, August 2018; Takahashi et al., *J. Physiol. Sci.* 67(6):731-737, 2017; and Iihoshi et al., *Toxicol. Lett.* 277:109-114, 2017.

In some embodiments of these methods, the liquid culture medium includes the single-chain chimeric polypeptide or the multi-chain chimeric polypeptide, and the IgG1 antibody construct. In some examples of these methods, the IgG1 antibody construct is a monoclonal IgG1 antibody, where both of the antigen-binding domains in the monoclonal IgG1 antibody bind specifically to the soluble tissue factor domain. In some examples of these methods, the IgG1 antibody construct is a bispecific IgG1 antibody, where one of the two antigen-binding domains in the bispecific IgG1 antibody binds specifically to the soluble tissue factor domain.

In some embodiments of any of the methods described herein, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days).

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the single-chain chimeric polypeptide or the multi-chain chimeric polypeptide, and the IgG1 antibody construct at a molar ratio of about 0.5:1 to about 2:1 (e.g., about 0.8:1 to about 1.2:1).

In some embodiments of these methods, the immune cell is selected from the group of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments of any of the methods described herein, the immune cell is a T-cell or a natural killer cell.

In some examples of these methods, the immune cell was previously obtained from a subject. Some embodiments of these methods further include obtaining the immune cell from the subject prior to the contacting step. In some embodiments of these methods, the immune cell has previously been genetically modified to express a chimeric antigen receptor or a recombinant T-cell receptor. Some embodiments of these methods further include, after the contacting step, introducing into the immune cell a nucleic acid encoding a chimeric antigen-receptor or a recombinant T-cell receptor. Some embodiments of these methods further include, before the contacting step, introducing into the immune cell a nucleic acid encoding a chimeric antigen-receptor or a recombinant T-cell receptor. Some embodiments of these methods further include, after the contacting step, isolating the immune cell. Some embodiments of these methods further include, after the contacting step, administering the immune cell to a subject in need thereof.

In some examples of these methods, the subject has been identified or diagnosed as having an age-related disease or condition. In some examples of these methods, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus. Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Additional Therapeutic Agents

Some embodiments of any of the methods described herein can further include administering to a subject (e.g., any of the subjects described herein) a therapeutically effective amount of one or more additional therapeutic agents. The one or more additional therapeutic agents can be administered to the subject at substantially the same time as a single-chain chimeric polypeptide (e.g., any of the single-chain chimeric polypeptides described herein), multi-chain chimeric polypeptides (e.g., any of the multi-chain chimeric polypeptides described herein), or an activated immune cell (e.g., an activated NK cell or an activated T cell) (e.g., administered as a single formulation or two or more formulations to the subject). In some embodiments, one or more additional therapeutic agents can be administered to the subject prior to administration of a single-chain chimeric polypeptide (e.g., any of the single-chain chimeric polypeptides described herein), multi-chain chimeric polypeptides (e.g., any of the multi-chain chimeric polypeptides described herein), or an activated immune cell (e.g., an activated NK cell or an activated T cell). In some embodiments, one or more additional therapeutic agents can be administered to the subject after administration of a single-chain chimeric polypeptide (e.g., any of the single-chain chimeric polypeptides described herein), multi-chain chimeric polypeptides (e.g., any of the multi-chain chimeric polypeptides described herein), or an activated immune cell (e.g., an activated NK cell or an activated T cell) to the subject.

Non-limiting examples of additional therapeutic agents include: anti-cancer drugs, activating receptor agonists, immune checkpoint inhibitors, agents for blocking HLA-specific inhibitory receptors, Glucogen Synthase Kinase (GSK) 3 inhibitors, and antibodies.

Non-limiting examples of anticancer drugs include antimetabolic drugs (e.g., 5-fluorouracil (5-FU), 6-mercaptopurine (6-MP), capecitabine, cytarabine, floxuridine, fludarabine, gemcitabine, hydroxycarbamide, methotrexate, 6-thioguanine, cladribine, nelarabine, pentostatin, or pemetrexed), plant alkaloids (e.g., vinblastine, vincristine, vindesine, camptothecin, 9-methoxycamptothecin, coronaridine, taxol, naucleaorals, diprenylated indole alkaloid, montamine, schischkiniin, protoberberine, berberine, sanguinarine, chelerythrine, chelidonine, liriodenine, clivorine, β-carboline, antofine, tylophorine, cryptolepine, neocryptolepine, corynoline, sampangine, carbazole, crinamine, montanine, ellipticine, paclitaxel, docetaxel, etoposide, tenisopide, irinotecan, topotecan, or acridone alkaloids), proteasome inhibitors (e.g., lactacystin, disulfiram, epigallocatechin-3-gallate, marizomib (salinosporamide A), oprozomib (ONX-0912), delanzomib (CEP-18770), epoxomicin, MG132, beta-hydroxy beta-methylbutyrate, bortezomib, carfilzomib, or ixazomib), antitumor antibiotics (e.g., doxorubicin, daunorubicin, epirubicin, mitoxantrone, idarubicin, actinomycin, plicamycin, mitomycin, or bleomycin), histone deacetylase inhibitors (e.g., vorinostat, panobinostat, belinostat, givinostat, abexinostat, depsipeptide, entinostat, phenyl butyrate, valproic acid, trichostatin A, dacinostat, mocetinostat, pracinostat, nicotinamide, cambinol, tenovin 1, tenovin 6, sirtinol, ricolinostat, tefinostat, kevetrin, quisinostat, resminostat, tacedinaline, chidamide, or selisistat), tyrosine kinase inhibitors (e.g., axitinib, dasatinib, encorafinib, erlotinib, imatinib, nilotinib, pazopanib, and sunitinib), and chemotherapeutic agents (e.g., all-trans retinoic acid, azacitidine, azathioprine, doxifluridine, epothilone, hydroxyurea, imatinib, teniposide, tioguanine, valrubicin, vemurafenib, and lenalidomide). Additional examples of chemotherapeutic agents include alkylating agents, e.g., mechlorethamine, cyclophosphamide, chlorambucil, melphalan, ifosfamide, thiotepa, hexamethylmelamine, busulfan, altretamine, procarbazine, dacarbazine, temozolomide, carmustine, lumustine, streptozocin, carboplatin, cisplatin, and oxaliplatin.

Non-limiting examples of activating receptor agonists include any agonists for activating receptors which activate and enhance the cytotoxicity of NK cells, including anti-CD16 antibodies (e.g., anti-CD16/CD30 bispecific monoclonal antibody (BiMAb)) and Fc-based fusion proteins. Non-limiting examples of checkpoint inhibitors include anti-PD-1 antibodies (e.g., MEDI0680), anti-PD-L1 antibodies (e.g., BCD-135, BGB-A333, CBT-502, CK-301, CS1001, FAZ053, KN035, MDX-1105, MSB2311, SHR-1316, anti-PD-L1/CTLA-4 bispecific antibody KN046, anti-PD-L1/TGFβRII fusion protein M7824, anti-PD-L1/TIM-3 bispecific antibody LY3415244, atezolizumab, or avelumab), anti-TIM3 antibodies (e.g., TSR-022, Sym023, or MBG453) and anti-CTLA-4 antibodies (e.g., AGEN1884, MK-1308, or an anti-CTLA-4/OX40 bispecific antibody ATOR-1015). Non-limiting examples of agents for blocking HLA-specific inhibitory receptors include monalizumab (e.g., an anti-HLA-E NKG2A inhibitory receptor monoclonal antibody). Non-limiting examples of GSK3 inhibitor include tideglusib or CHIR99021. Non-limiting examples of antibodies that can be used as additional therapeutic agents include anti-CD26 antibodies (e.g., YS110), anti-CD36 antibodies, and any other antibody or antibody construct that can bind to and activate an Fc receptor (e.g., CD16) on a NK cell. In some embodiments, an additional therapeutic agent can be insulin or metformin.

EXAMPLES

The invention is further described in the following examples, which do not limit the scope of the invention described in the claims.

Example 1. Construction of Exemplary Multi-Chain Chimeric Polypeptides and Evaluation of Properties Thereof Two multi-chain chimeric polypeptides were generated and their properties were evaluated. Each of the two multi-chain chimeric polypeptides included a first chimeric polypeptide that included a soluble tissue factor domain covalently linked a first target-binding domain and a first domain of an affinity pair of domains. The second chimeric polypeptide in each of the two multi-chain chimeric polypeptides included a second domain of the affinity pair of domains, and a second target-binding domain.

Description of Logic Underlying Construction of Multi-Chain Chimeric Polypeptides Tissue Factor (TF) is a stable, transmembrane protein containing 236 amino acid residues. The truncated, recombinant 219-amino-acid extracellular domain of tissue factor is soluble and is known to be expressed at high levels in bacteria or mammalian cells. Without wishing to be bound to a particular theory, the applicants speculated that the 219-aa tissue factor could be used as a connector linker for creation of unique multi-chain chimeric polypeptides.

First chimeric polypeptides including soluble tissue factor domain were produced at high levels by CHO-K1 cells grown in fermentation broth. These first chimeric polypeptides were purified by an anti-tissue factor monoclonal antibody (mAb) coupled on a solid matrix. Notably, tissue factor contains binding sites for FVIIa and FX. The catalytic activity of the tissue factor-FVIIa complex for FX is approximately 1 million-fold lower when tissue factor is not anchored to a phospholipid bilayer. Thus, without wishing to be bound to a particular theory, applicants speculated that using the 219-aa extracellular domain of tissue factor without the transmembrane in construction of the first chimeric polypeptides may eliminate the pro-coagulation activity of tissue factor in the first chimeric polypeptides. In an effort to further reduce or eliminate the pro-coagulation activity of the 219-aa tissue factor, select mutations in tissue factor can be made, specifically at seven amino acid residues that are known to contribute to binding energy of the FVIIa binding site.

Characterization of Binding Interactions for Described Chimeric Polypeptides

To determine if the first and second chimeric polypeptides bind to each other to form multi-chain chimeric polypeptides, in vitro binding assays were performed. To determine if the first chimeric polypeptide comprising soluble tissue factor domain are recognized and bound by anti-TF mAb, in vitro binding assays were performed. Notably, the data indicated that the mutated tissue factor proteins are still recognized and selectively bound by the anti-TF mAb which is known to bind to the FX binding site on tissue factor. To determine if the first chimeric polypeptides comprising soluble tissue factor domain covalently linked to scFvs or cytokines (see FIG. 1 and FIG. 2) possess functional scFvs or cytokines, in vitro binding assays were performed. The data from the aforementioned assays were consistent with the purified first chimeric polypeptides having the expected biological activities (e.g., scFvs selectively bind expected target antigens or cytokines selectively bind expected receptors or binding proteins).

In addition, experiments performed using the two multi-chain chimeric polypeptides including a first and second chimeric polypeptide bound to each other demonstrate the expected target binding activity (e.g., the multi-chain chimeric polypeptide binds specifically to the target specifically recognized by the first target-binding domain and the target specifically recognized by the second target-binding domain).

Based on the aforementioned results, applicants concluded that the soluble tissue factor connector linker provided or enabled appropriate display of the polypeptides encoding either scFvs, interleukins, cytokines, interleukin receptors, or cytokine receptors in three-dimensional space relative to soluble tissue factor domain and relative to one another such that each retained expected biological properties (and activities).

When both the first and second chimeric polypeptides were co-expressed, the heterodimeric complexes were secreted into the fermentation broths at high levels. The complexes were captured and readily purified by anti-TF mAb conjugated to a solid matrix using affinity chromatography. The first and second target-binding domains of these multi-chain chimeric polypeptides retained their expected biological activities as assayed by in vitro binding assays. Thus, the assembly of the multi-chain chimeric polypeptides provides the appropriate spatial display and folding of the domains for biological activities. Importantly, the spatial arrangement of the multi-chain chimeric polypeptides does not interfere with the FX binding site on tissue factor which enables the use of anti-TF mAb for affinity purification.

Characterization of Stability for Described Chimeric Polypeptides

Both purified multi-chain chimeric polypeptides are expected to be stable. These multi-chain chimeric polypeptides are structurally intact and expected to be fully biologically active when they are incubated in human serum at 37° C. for 72 hours.

Characterization of Propensity of Described Chimeric Polypeptides to Aggregate

Both purified multi-chain chimeric polypeptides are expected not to form aggregates when stored at 4° C. in PBS.

Characterization of Viscosity of Described Chimeric Polypeptides

Compositions including the multi-chain chimeric polypeptides are not expected to have any viscosity issues when formulated at a concentration as high as 50 mg/mL in PBS.

Discussion of Multi-Chain Chimeric Polypeptide Platform for Use in Selectively Binding Clinically Relevant Targets The data from our studies show that our platform technologies can be utilized to create molecules that could be fused to target-binding domains derived from antibodies, in any formats as discussed above, adhesion molecules, receptors, cytokines, chemokines etc. With the appropriate target-binding domain, the resulting multi-chain chimeric polypeptides could promote conjugation of various immune effector cells and mediate destruction of target cells, including cancer cells, virally-infected cells, or senescent cells. Other domains in the multi-chain chimeric polypeptides stimulate, activate, and attract the immune system for enhancing cytotoxicity of effector cells for the targeted cells.

Example 2: Creation of an IL-7/IL-15RαSu DNA Construct

In a non-limiting example, an IL-7/IL-15RαSu DNA construct was created (see FIG. 1). The human IL-7 sequence, human IL-15RαSu sequence, human IL-15 sequence, and human tissue factor 219 sequence were obtained from the UniProt website and DNA for these sequences was synthesized by Genewiz. A DNA construct was made linking the IL-7 sequence to the IL-15RαSu sequence. The final IL-7/IL-15RαSu DNA construct sequence was synthesized by Genewiz.

Example 3: Creation of an IL-21/TF/IL-15 DNA Construct

In a non-limiting example, an IL-21/TF/IL-15 construct was made (see FIG. 2) by linking the IL-21 sequence to the N-terminus coding region of tissue factor 219, and further linking the IL-21/TF construct with the N-terminus coding region of IL-15.

Example 4: Secretion of IL-7/IL-15RαSu and IL-21/TF/IL-15 Fusion Proteins

Figure 3:
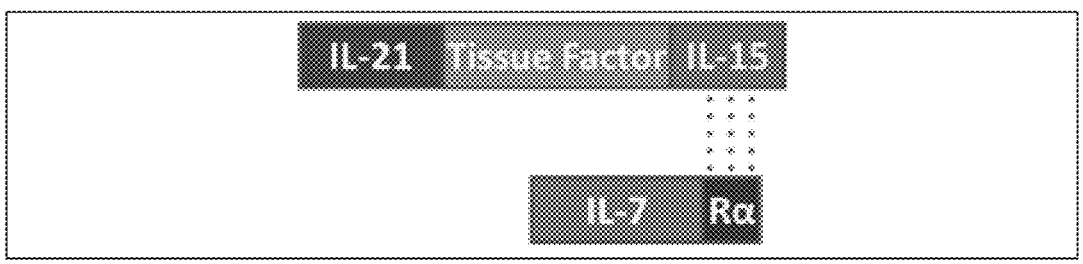
FIG. 3 shows a schematic diagram of the interaction between the exemplary IL-7/IL-15RαSu and IL-21/TF/IL-15 DNA constructs.
Figure 4:
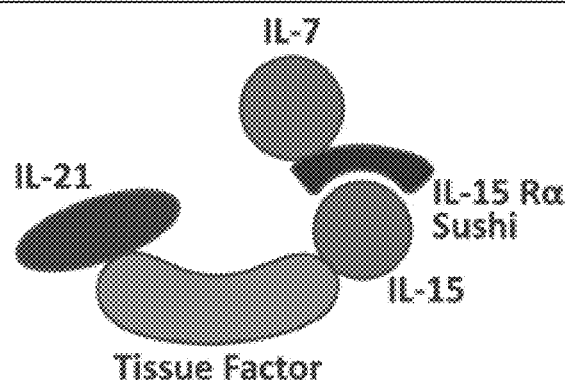
FIG. 4 shows a schematic diagram of the interaction between the exemplary IL-7/IL-15RαSu and IL-21/TF/IL-15 fusion proteins resulting in an IL-21/TF/IL-15:IL-7/IL-15RαSu complex (21t15-7s).

The IL-7/IL-15RαSu and IL-21/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-21/TF/IL-15:IL-7/IL-15RαSu protein complex (referred to as 21t15-7s, see FIGS. 3 and 4). The 21t15-7s protein was purified from CHO-K1 cell culture supernatant using anti-TF antibody affinity chromatography and size exclusion chromatography resulting in soluble (non-aggregated) protein complexes consisting of IL-7/IL-15RαSu and IL-21/TF/IL-15 fusion proteins.

In some cases, the leader (signal sequence) peptide is cleaved from the intact polypeptide to generate the mature form that may be soluble or secreted.

Example 5: Purification of 21t15-7s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Cell culture harvest of 21t15-7s was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was neutralized to pH 7.5-8.0 by adding 1M Tris base. The neutralized sample was then buffer exchanged into PBS using Amicon® centrifugal filters with a 30 KDa molecular weight cutoff. The buffer-exchanged protein sample was stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide and stored at 2-8° C.

Example 6: Creation of a TGF-βRII/IL-15RαSu DNA Construct

Figure 8:
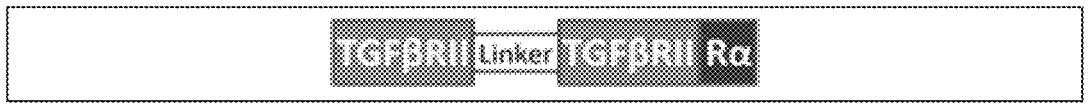
FIG. 8 shows a schematic diagram of an exemplary TGF-βRII/IL-15RαSu DNA construct.

In a non-limiting example, a TGF-βRII/IL-15RαSu DNA construct was created (see FIG. 8). The human TGF-βRII sequence, human IL-15RαSu sequence, human IL-15 sequence, and human tissue factor 219 sequence were obtained from the UniProt website and DNA for these sequences was synthesized by Genewiz. A DNA construct was made linking the TGF-βRII sequences (separated by a linker) to the IL-15RαSu sequence. The final TGF-βRII/IL-15RαSu DNA construct sequence was synthesized by Genewiz.

Example 7: Creation of an IL-21/TF/IL-15 DNA Construct

Figure 9:
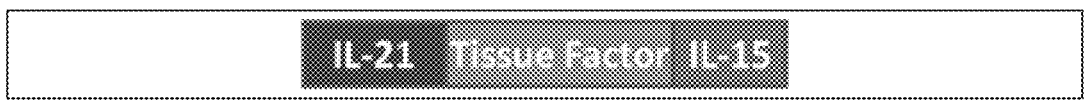
FIG. 9 shows a schematic diagram of an exemplary IL-21/TF/IL-15 DNA construct.

In a non-limiting example, an IL-21/TF/IL-15 construct was made (see FIG. 9) by linking the IL-21 sequence to the N-terminus coding region of tissue factor 219, and further linking the IL-21/TF construct with the N-terminus coding region of IL-15.

Example 8: Secretion of TGF-βRII/IL-15RαSu and IL-21/TF/IL-15 Fusion Proteins

The TGF-βRII/IL-15RαSu and IL-21/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-21/TF/IL-15:TGF-β RII/IL-15RαSu protein complex (referred to as 21t15-TGFRs, see FIGS. 10 and 11). The 21t15-TGFRs protein was purified from CHO-K1 cell culture supernatant using anti-TF antibody affinity chromatography and size exclusion chromatography resulting in soluble (non-aggregated) protein complexes consisting of TGF-β RII/IL-15RαSu and IL-21/TF/IL-15 fusion proteins.

Example 9: Size Exclusion Chromatography

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.7 mL/min. A capillary loop was used to inject 200λ of 1 mg/mL of 7t15-21s complex onto the column. The injection was chased with 1.25 column volumes of PBS.

Example 10: SDS-PAGE of 21t15-7s and 21t15-TGFRs

To determine the purity and protein molecular weight, the purified 21t15-7s or 21t15-TGFRs protein sample were analyzed using 4-12% NuPage Bis-Tris protein gel SDS-PAGE. The gel will be stained with InstantBlue™ for about 30 min, followed by destaining overnight in purified water.

Example 11: Glycosylation of 21t15-7s and 21t15-TGFRs in CHO-K1 Cells

Glycosylation of 21t15-7s in CHO-K1 cells or 21t15-TGFRs in CHO-K1 cells were confirmed using the Protein Deglycosylation Mix II kit (New England Biolabs), according to the manufacturer's instructions.

Example 12: Recombinant Protein Quantitation of 21t15-7s and 21t15-TGFRs Complexes The 21t15-7s complex or the 21t15-TGFRs complex were detected and quantified using standard sandwich ELISA methods. Anti-human tissue factor antibody (IgG1) served as the capture antibody and biotinylated anti-human IL-21, IL-15, or IL-7 antibody (21t15-7s) or biotinylated anti-human IL-21, IL-15, or TGF-βRII antibody (21t15-TGFRs) served as the detection antibody. Tissue factor in purified 21t15-7s or 21t15-TGFRs protein complexes was detected using an anti-human tissue factor capture antibody, and anti-human tissue factor antibody (IgG1) detection antibody. The anti-TF ELISA will be compared to purified tissue factor at similar concentrations.

Figure 5:
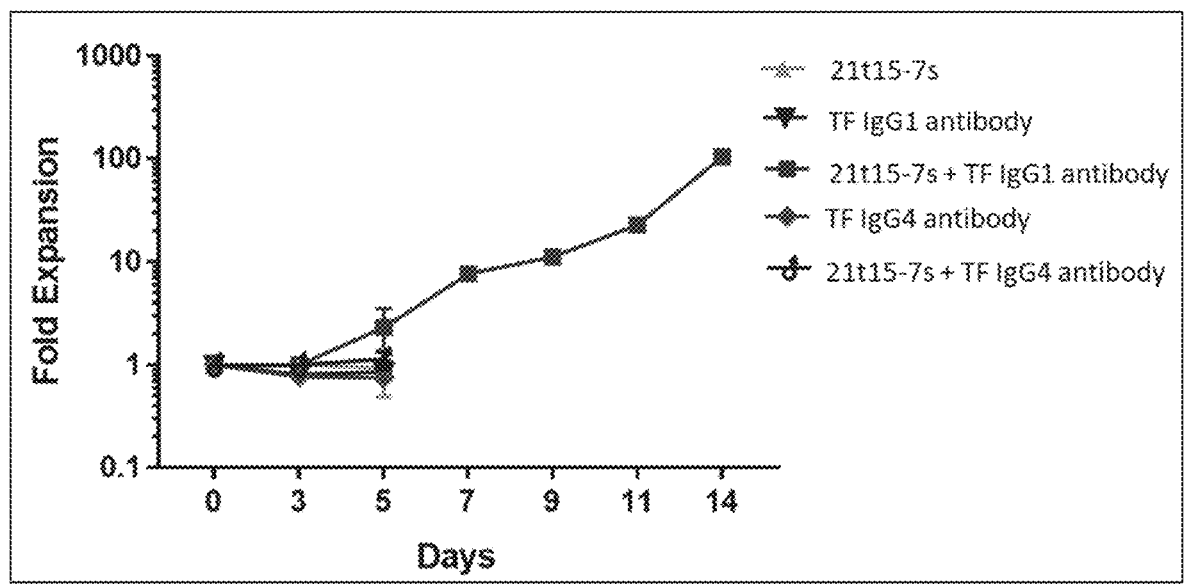
FIG. 5 shows the expansion of primary natural killer (NK) cells by stimulation with 21t15-7s+anti-TF IgG1 antibody.

Example 13: Expansion Capacity of Primary Natural Killer (NK) Cells by 21t15-7s Complex+Anti-TF IgG1 Antibody or 21t15-TGFRs Complex+Anti-TF IgG1 Antibody To assess the 21t15-7s complex's ability to expand primary natural killer (NK) cells, 21t15-7s complex and 21t15-7s complex+anti-TF IgG1 antibody was added to NK cells obtained from samples of fresh human leukocytes. Cells were stimulated with 50 nM of 21t15-7s complex with or without 25 nM of anti-TF IgG1 or anti-TF IgG4 antibody at 37° and 5% CO$_2$. Cells were maintained at concentration at 0.5×10$^6$/mL not exceeding 2.0×10$^6$/mL by counting every 48-72 hours and media was replenished with fresh stimulator. Cells stimulated with 21t15-7s complex or anti-TF IgG1 antibody or anti-TF IgG4 antibody or anti-TF IgG4+21t15-7s complex were maintained up to day 5. FIG. 5 shows expansion of primary NK cells upon incubation with 21t15-7s complex+anti-TF IgG1 antibody.

Figure 12:
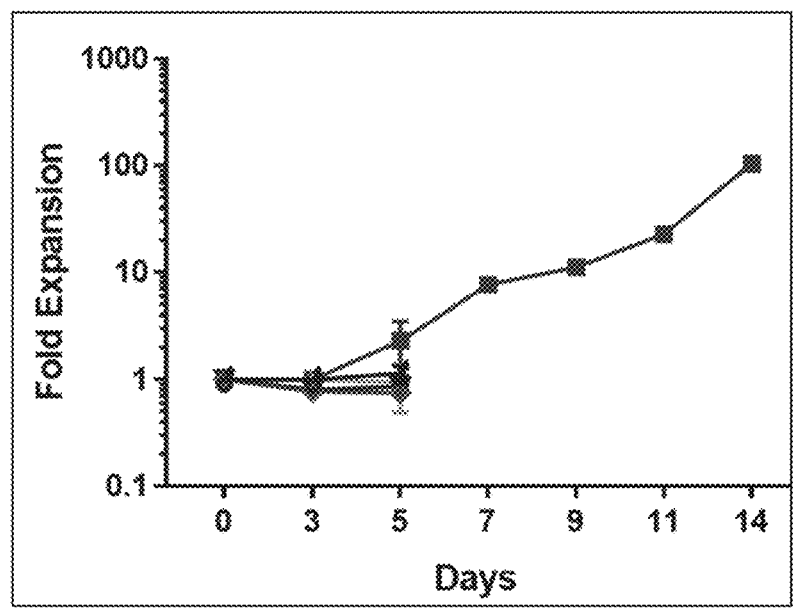
FIG. 12 shows the expansion of primary natural killer (NK) cells by stimulation with 21t15-TGFRs+anti-TF IgG1 antibody (dark line with squares) or primary NK cells contacted with 21t15-TGFRs alone, anti-TF IgG1 antibody, anti-TF IgG4 antibody, or with a combination of 21t15-TGFRs+anti-TF IgG4 antibody (all other data shown).
Figure 18:
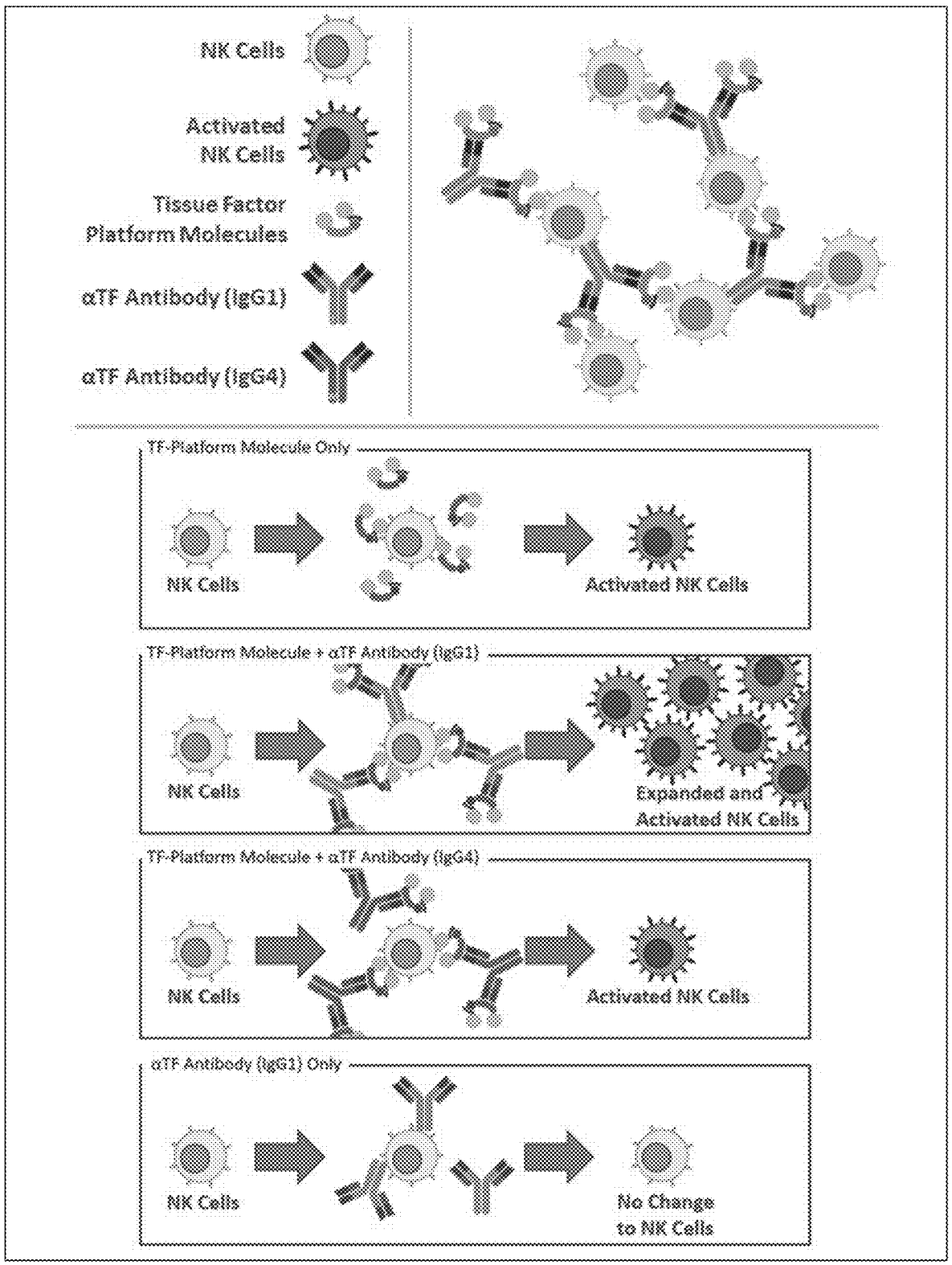
FIG. 18 shows in diagrammatic form the activation and expansion of primary natural killer (NK) cells by stimulation with 21t15-TGFRs+anti-TF IgG1 antibody.

To assess the 21t15-TGFRs complex's ability to expand primary natural killer (NK) cells, 21t15-TGFRs complex and 21t15-TGFRs complex+anti-TF IgG1 antibody was added to NK cells obtained from samples of fresh human leukocytes. Cells were stimulated with 50 nM of 21t15-TGFRs complex with or without 25 nM of anti-TF IgG1 or anti-TF IgG4 antibody at 37° C. and 5% CO$_2$. Cells were maintained at concentration at 0.5×10$^6$/mL not exceeding 2.0×10$^6$/mL by counting every 48-72 hours and media was replenished with fresh stimulator. Cells stimulated with 21t15-TGFRs complex or anti-TF IgG1 antibody or anti-TF IgG4 antibody or anti-TF IgG4+21t15-TGFRs complex were maintained up to day 5. FIG. 12 shows expansion of primary NK cells upon incubation with 21t15-TGFRs complex+anti-TF IgG1 antibody. FIG. 18 is a schematic summarizing these results.

Figure 6:
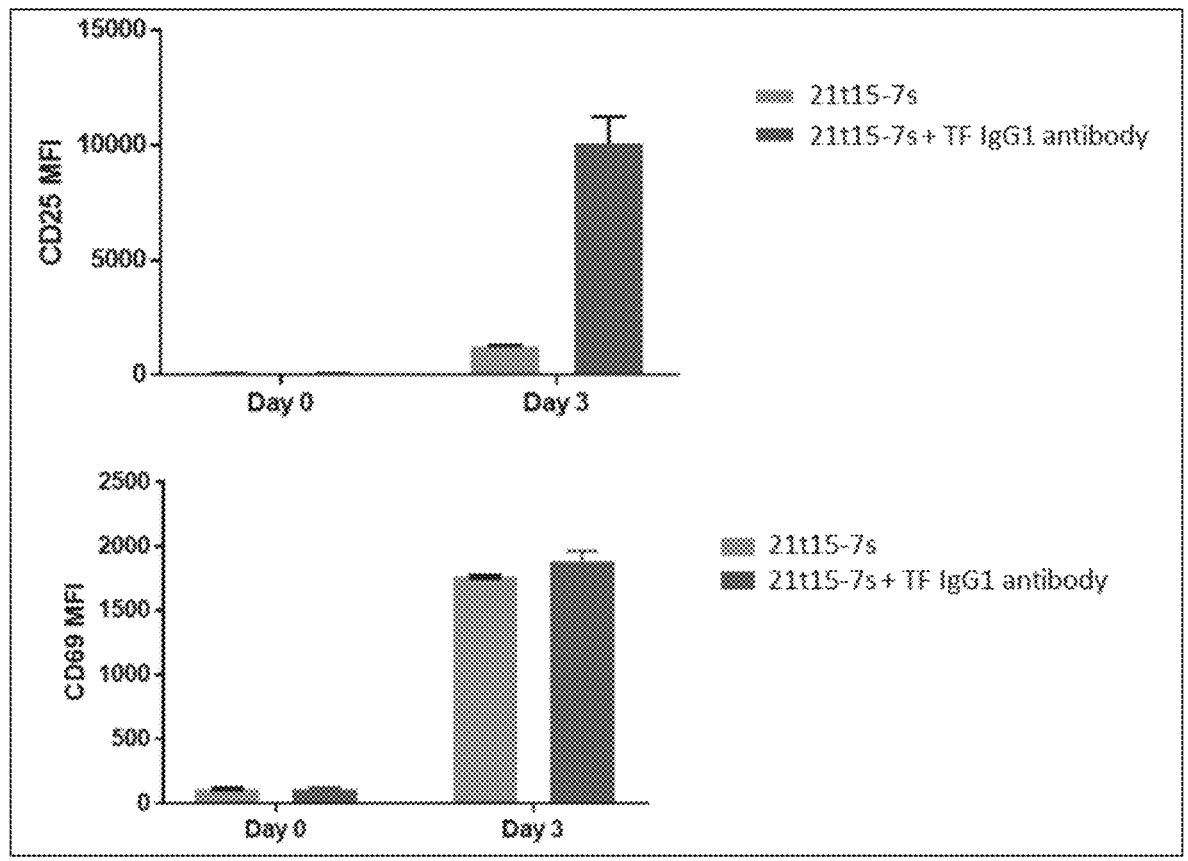
FIG. 6 shows activation of expanded primary NK cells, using CD25 MFI and CD69 MFI as markers of NK cell activation.

Example 14: Activation of Expanded NK Cells by the 21t15-7s Complex+Anti-TF IgG1 Antibody or the 21t15-TGFRs Complex+Anti-TF IgG1 Antibody Primary NK cells can be induced ex vivo following overnight stimulation of purified NK cells with 21t15-7s complex+anti-TF IgG1 antibody. Fresh human leukocytes were obtained from a blood bank and CD56+ NK cells were isolated with the RosetteSep/human NK cell reagent (StemCell Technologies). The purity of NK cells was >80% and confirmed by staining with CD56-BV421 and CD16-BV510 specific antibodies (BioLegend). Cells were counted and resuspended in 1×10$^6$/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells were stimulated with 50 nM of 21t15-7s with or without 25 nM of TF antibody at 37° C. and 5% CO$_2$. Cells were counted every 48-72 hours and maintained at a concentration of 0.5×10$^6$/mL to 2.0×10$^6$/mL until day 14. Media was periodically replenished with fresh stimulator. Cells were harvested and surface stained at day 3 with CD56-BV421, CD16-BV510, CD25-PE, CD69-APCFire750 specific antibodies (Biolegend and analyzed by Flow Cytometry-Celeste-BD Bioscience). FIG. 6 shows the activation markers CD25 MFI and CD69 MFI. The activation marker CD25 MFI increased with 21t15-7s complex+anti-TF IgG1 antibody stimulation, but not 21t15-7s complex stimulation. The activation marker CD69 MFI increased with both 21t15-7s complex+anti-TF IgG1 antibody and with 21t15-7s complex, alone.

Figure 13:
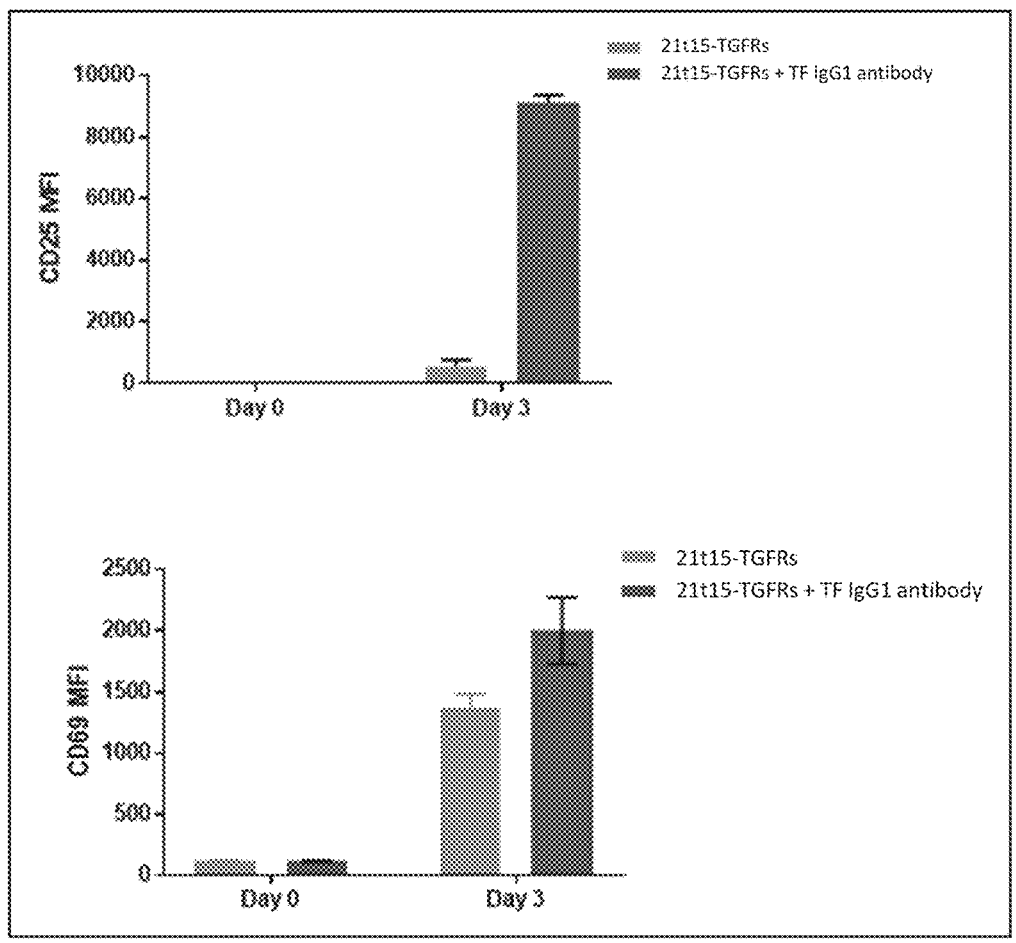
FIG. 13 shows activation of expanded primary NK cells, using CD25 MFI (top) and CD69 MFI (bottom) as markers of NK cell activation.

Primary NK cells can be induced ex vivo following overnight stimulation of purified NK cells with 21t15-TGFRs complex+anti-TF IgG1 antibody. Fresh human leukocytes were obtained from a blood bank and CD56+ NK cells were isolated with the RosetteSep/human NK cell reagent (StemCell Technologies). The purity of NK cells was >80% and confirmed by staining with CD56-BV421 and CD16-BV510 specific antibodies (BioLegend). Cells were counted and resuspended in 1×10$^6$/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells were stimulated with 50 nM of 21t15-TGFRs with or without 25 nM of anti-TF IgG1 antibody at 37° C. and 5% CO$_2$. Cells were counted every 48-72 hours and maintained at a concentration of 0.5×10⁶/mL to 2.0×10⁶/mL until day 14. Media was periodically replenished with fresh stimulator. Cells were harvested and surface stained at day 3 with CD56-BV421, CD16-BV510, CD25-PE, CD69-APC-Fire750 specific antibodies (Biolegend and analyzed by Flow Cytometry-Celeste-BD Bioscience). FIG. 13 shows the activation markers CD25 MFI and CD69 MFI. The activation marker CD25 MFI increased with 21t15-TGFRs complex+anti-TF IgG1 antibody stimulation, but not 21t15-TGFRs complex stimulation. The activation marker CD69 MFI increased with both 21t15-TGFRs complex+anti-TF IgG1 antibody and with 21t15-TGFRs complex, alone.

Example 15: Cytotoxicity of NK Cells Against Human Tumor Cells

Figure 7:
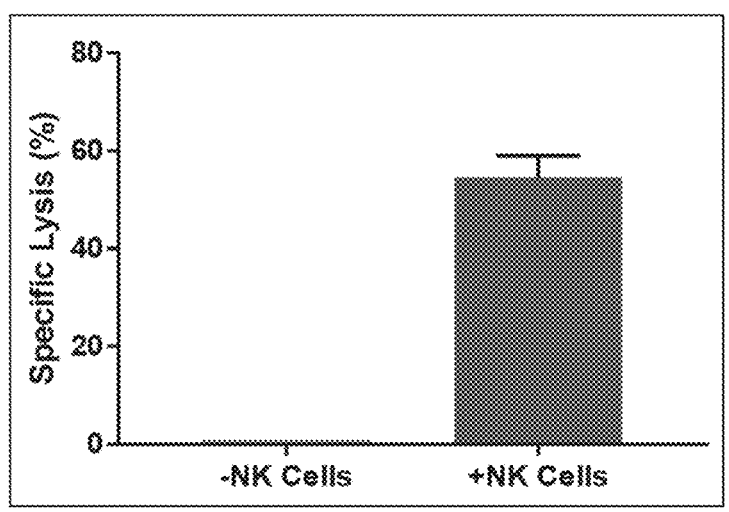
FIG. 7 shows cytotoxic activity of expanded NK cells against K562 human tumor cells, wherein NK cells stimulated with 21t15-7s+anti-TF IgG1 antibody demonstrate greater specific lysis of K562 cells than NK cells not stimulated with 21t15-7s+anti-TF IgG1 antibody.

Fresh human leukocytes were obtained from a blood bank. NK cells were isolated via negative selection using the RosetteSep/human NK cell reagent (StemCell Technologies). The purity of NK cells was >80% and confirmed by staining with CD56-BV421 and CD16-BV510 specific antibodies (BioLegend). Cells were counted and resuspended in 1×10⁶/mL in a 24 well, flat bottom plate in 1 mL of complete media (RPMI 1640 (Gibco)), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies) and 10% FBS (Hyclone). Cells were stimulated with 21t15-7s 50 nM and 25 nM of anti-TF IgG1 antibody for up to 14 days at 37° C. and 5% $CO_2$. Cells were counted every 48-72 hours and maintained at a concentration of 0.5×10⁶/mL to 2.0×10⁶/mL until day 14. Media was periodically replenished with fresh stimulator. On day 14, cells were harvested and washed 2 times. K562 human tumor cells were harvested and labeled with Celltrace violet. Celltrace violet-labeled K562 cells were mixed with the in vitro expanded NK cells and incubated at 37° C. for 20 hours. The mixture was harvested and the percentage of dead K562 cells were determined by propidium iodide staining and flow cytometry. FIG. 7 shows increased specific lysis of K562 cells when incubated with expanded NK cells.

Example 16: Creation of an IL-21/IL-15RαSu DNA Construct

In a non-limiting example, an IL-21/IL-15RαSu DNA construct was created. The human IL-21 sequence and human IL-15RαSu sequence were obtained from the UniProt website and DNA for these sequences was synthesized by Genewiz. A DNA construct was made linking the IL-21 sequence to the IL-15RαSu sequence. The final IL-21/IL-15RαSu DNA construct sequence was synthesized by Genewiz. See FIG. 14.

Example 17: Creation of an IL-7/TF/IL-15 DNA Construct

Figure 15:
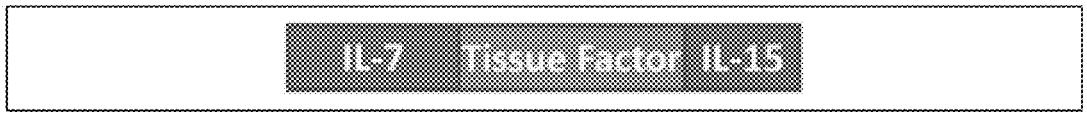
FIG. 15 shows a schematic diagram of an exemplary IL-7/TF/IL-15 DNA construct.

In a non-limiting example, an IL-7/TF/IL-15 construct was made by linking the IL-7 sequence to the N-terminus coding region of tissue factor 219, and further linking the IL-7/TF construct with the N-terminus coding region of IL-15. See FIG. 15.

Example 18: Creation of an IL-21/IL-15Rα Sushi DNA Construct

In a non-limiting example, a second chimeric polypeptide of IL-21/IL-15RαSu was generated. The human IL-21 and human IL-15Rα sushi sequences were obtained from the UniProt website and DNA for these sequences was synthesized by Genewiz. A DNA construct was made linking the IL-21 sequence to the IL-15Rα sushi sequence. The final IL-21/IL-15RαSu DNA construct sequence was synthesized by Genewiz.

Example 19: Creation of an IL-7/TF/IL-15 DNA Construct

In a non-limiting example, an exemplary first chimeric polypeptide of IL-7/TF/IL-15 was made by linking the IL-7 sequence to the N-terminus coding region of tissue factor 219, and further linking the IL-7/TF construct with the N-terminus coding region of IL-15. The nucleic acid sequence encoding the first chimeric polypeptide of IL-7/TF/IL-15 (including leader sequence), synthesized by Genewiz.

Example 20: Secretion of IL-21/IL-15RαSu and IL-7/TF/IL-15 Fusion Proteins

Figure 16:
FIG. 16 shows a schematic diagram of the interaction between the exemplary IL-21/IL-15RαSu and IL-7/TF/IL-15 DNA constructs.
Figure 17:
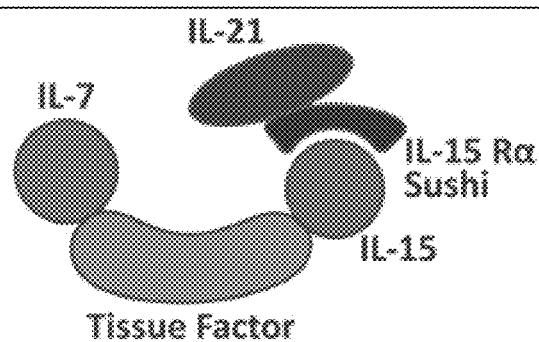
FIG. 17 shows a schematic diagram of the interaction between the exemplary IL-21/IL-15RαSu and IL-7/TF/IL-15 fusion proteins resulting in an IL-7/TF/IL-15:IL-21/IL-15RαSu complex (7t15-21s).

The IL-21/IL-15RαSu and IL-7/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-7/TF/IL-15:IL-21/IL-15RαSu protein complex (referred to as 7t15-21s). The 7t15-21s protein was purified from CHO-K1 cell culture supernatant using anti-TF antibody (IgG1) affinity chromatography and size exclusion chromatography resulting in soluble (non-aggregated) protein complexes consisting of IL-21/IL-15RαSu and IL-7/TF/IL-15 fusion proteins. See, FIGS. 16 and 17.

Figure 19:
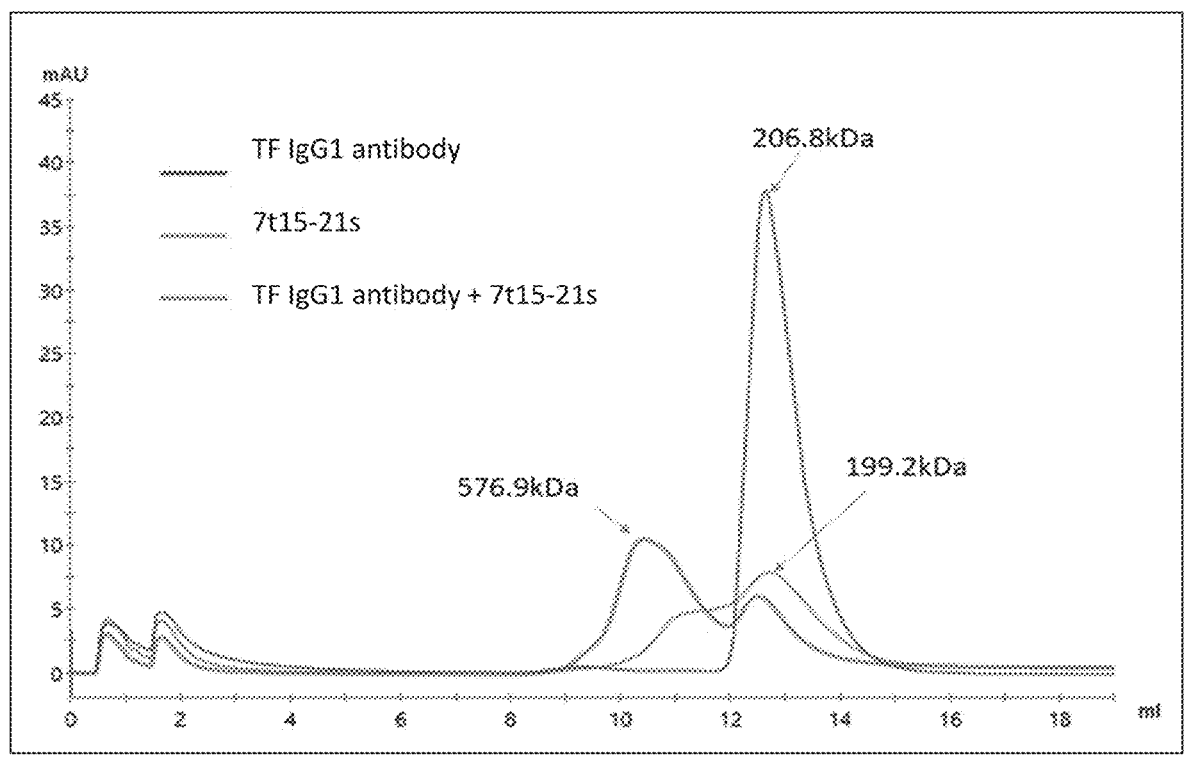
FIG. 19 shows size exclusion chromatography (SEC) profiles of anti-TF IgG1 antibody, 7t15-21s and the complex containing equal amounts of anti-TF IgG1 antibody and 7t15-21s.

Example 21: Analytical Size Exclusion Chromatography (SEC) Analysis of IL-21/IL-15RαSu and IL-7/TF/IL-15 Fusion Proteins To determine if anti-tissue factor monoclonal antibody and 7t15-21s can form an antibody-fusion-molecule complex, analytical size exclusion chromatography (SEC) was performed. A Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. Samples of the anti-TF mAb (1 mg/mL), 7t15-21s (1 mg/mL), and a mixture of combined at a 1:1 ratio, so the final concentration of each protein is 0.5 mg/mL) were in PBS. Each sample was injected into the Superdex 200 column using a capillary loop, and analyzed by SEC. The SEC chromatograph of each sample was shown in FIG. 19. The SEC results indicated that there are two protein peaks for 7t15-21s, likely representing a dimer (with an apparent molecular weight of 199.2 kDa) and a higher oligomer of 7t15-21s, and there is one peak (with an apparent molecular weight of 206.8 kDa) for the anti-TF mAb. However, as expected, a new protein peak with a higher molecular weight (with an apparent molecular weight of 576.9 kDa) was formed in the mixture sample containing the anti-TF mAb and 7t15-21s, indicating that the anti-TF mAb and 7t15-21s form an antibody-antigen complex through the binding of anti-TF mAb to TF in the fusion protein complex.

Example 22: Expansion Capacity of Primary Natural Killer (NK) Cells by 7t15-21s Complex+Anti-TF IgG1 Antibody To assess the 7t15-21s complex's ability to expand primary natural killer (NK) cells, 7t15-21s complex and 7t15-21s complex+anti-TF IgG1 antibody are added to NK cells obtained from samples of fresh human leukocytes. Cells are stimulated with 50 nM of 7t15-21s complex with or without 25 nM of anti-TF IgG1 or anti-TF IgG4 antibody at 37° C. and 5% $CO_2$. Cells are maintained at concentration at $0.5 \times 10^6$/mL not exceeding $2.0 \times 10^6$/mL by counting every 48-72 hours and media is replenished with fresh stimulator. Cells stimulated with 7t15-21s complex or anti-TF IgG1 antibody or anti-TF IgG4 antibody or anti-TF IgG4+7t15-21s complex are maintained up to day 5. Expansion of primary NK cells upon incubation with 21t15-7s complex+anti-TF IgG1 antibody is observed.

Example 23: Activation of Expanded NK Cells by the 7t15-21s Complex+Anti-TF IgG1 Antibody Primary NK cells are induced ex vivo following overnight stimulation of purified NK cells with 7t15-21s complex+TF IgG1 antibody. Fresh human leukocytes are obtained from a blood bank and CD56+ NK cells are isolated with the RosetteSep/human NK cell reagent (StemCell Technologies). The purity of NK cells is >80% and is confirmed by staining with CD56-BV421 and CD16-BV510 specific antibodies (BioLegend). Cells are counted and resuspended in $1 \times 10^6$/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells are stimulated with 50 nM of 7t15-21s with or without 25 nM of anti-TF IgG1 antibody at 37° C. and 5% $CO_2$. Cells are counted every 48-72 hours and maintained at a concentration of $0.5 \times 10^6$/mL to $2.0 \times 10^6$/mL until day 14. Media is periodically replenished with fresh stimulator. Cells are harvested and surface stained at day 3 with CD56-BV421, CD16-BV510, CD25-PE, CD69-APCFire750 specific antibodies (Biolegend and analyzed by Flow Cytometry-Celeste-BD Bioscience). The activation marker CD25 MFI are observed to increase with 7t15-21s complex+anti-TF IgG1 antibody stimulation, but not 7t15-21s complex stimulation. The activation marker CD69 MFI is observed to increase with both 7t15-21s complex+anti-TF IgG1 antibody and with 7t15-21s complex, alone.

Example 24: Increase in Glucose Metabolism in NK Cells Using 7t15-21s and 21t15-7s in Combination with an Anti-TF IgG1 Antibody A set of experiments was performed to determine the effect of (1) 7t15-21s in combination with an anti-TF IgG1 antibody or (2) 21t15-7s in combination with an anti-TF IgG1 antibody on oxygen consumption rate (OCR) and extracellular acidification rate (ECAR) on NK cells purified from human blood. In these experiments, fresh human leukocytes were obtained from the blood bank and NK cells were isolated via negative selection using the RosetteSep/human NK cell reagent (StemCell Technologies). The purity of NK cells was >80% and confirmed by staining with CD56-BV421 and CD16-BV510 specific antibodies (BioLegend). The cells were counted and resuspended at a concentration of $1 \times 10^6$/mL in a 24-well flat-bottom plate in 1 mL of complete media (RPMI 1640 (Gibco) supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). The cells were stimulated with (1) 100 nM anti-TF IgG1 antibody, (2) 50 nM 7t15-21s and 100 nM anti-TF IgG1 antibody, or (3) 50 nM 21t15-7s and 100 nM anti-TF IgG1, for up to day 5 at 37° C., 5% $CO_2$. The cells were maintained at concentration at $0.5 \times 10^6$/mL not exceeding $2.0 \times 10^6$/mL until day 5 by counting every 48 hours and media was replenished with fresh stimulator. Extracellular flux assays on expanded NK cells were performed using a XFp Analyzer (Seahorse Bioscience). The harvested cells were washed and plated at $2.0 \times 10^5$ cells/well in at least duplicate for extracellular flux analysis of OCR (Oxygen Consumption Rate) and ECAR (Extracellular Acidification Rate). Glycolysis stress tests were performed in Seahorse Media containing 2 mM of glutamine. The following were used during the assay: 10 mM glucose; 100 nM oligomycin; and 100 mM 2-deoxy-D-glycose (2DG).

Figure 20:
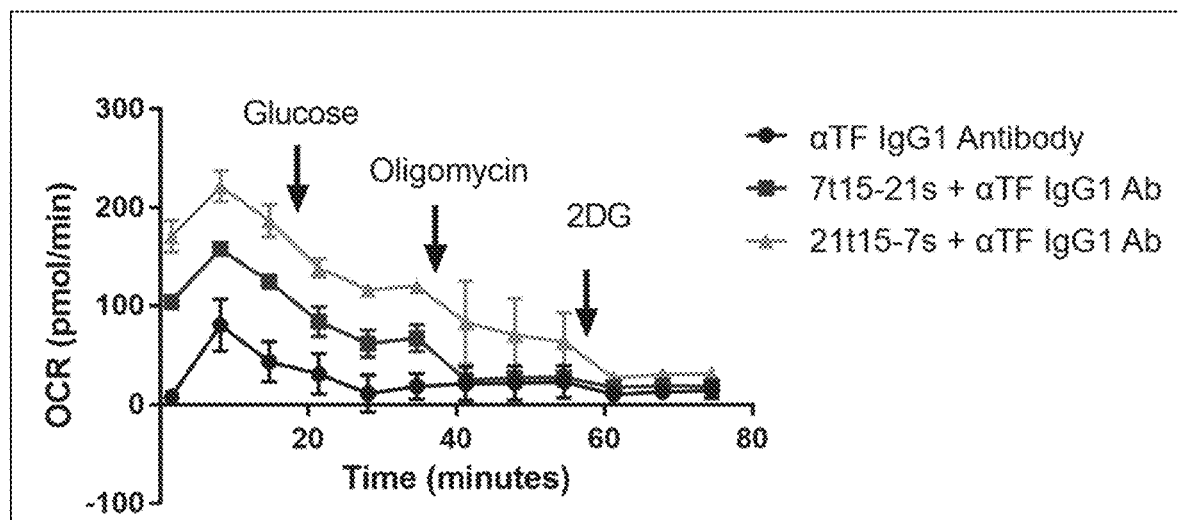
FIG. 20 is a graph showing the oxygen consumption rate (OCR) in pmoles/min for human NK cells isolated from blood ($1 \times 10^6$ cells/mL) and stimulated with (1) 50 nM anti-TF IgG1 (IgG1), (2) 100 nM 7t15-21s and 50 nM anti-TF IgG1, or (3) 100 nM 21t15-7s and 50 nM anti-TF IgG1 for up to 5 days at 37° C., 5% $CO_2$ in RPMI 1640 supplemented with 4 mM L-glutamine, penicillin, streptomycin, non-essential amino acids, sodium pyruvate, and 10% fetal bovine serum. Cells were maintained at a concentration of $0.5 \times 10^6$ cells/mL to $2.0 \times 10^6$ cells/mL until day 5. Glycolysis stress tests were performed in Seahorse media containing 2 mM glutamine. The drug concentrations used during the assay were as follows: 10 mM glucose, 100 nm oligomycin, and 100 mM 2-deoxy-D-glucose.
Figure 21:
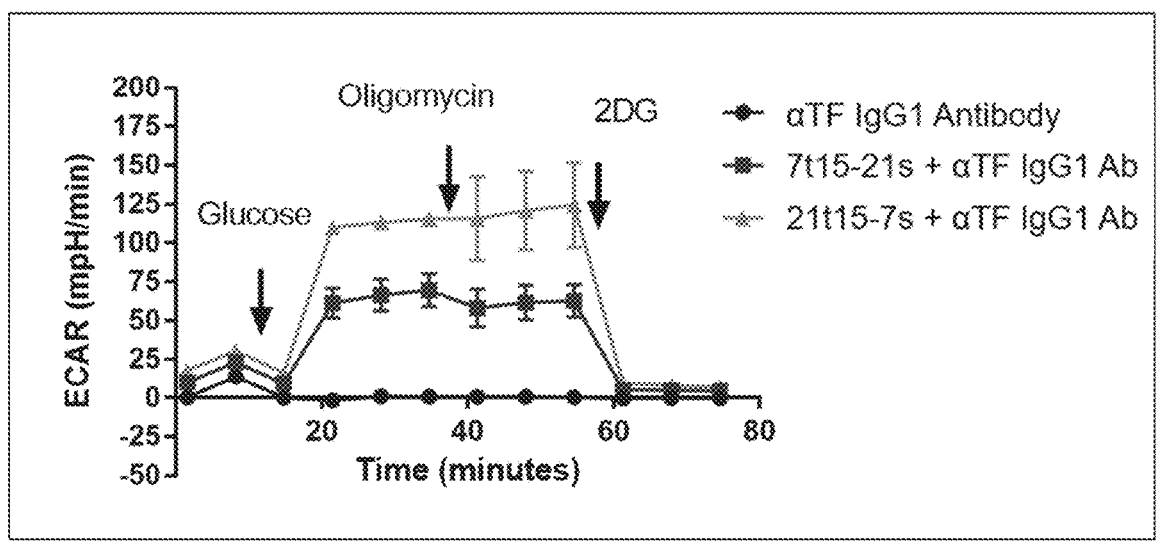
FIG. 21 is a graph showing the extracellular acidification rate (ECAR) in mpH/minute for human NK cells isolated from blood ($1 \times 10^6$ cells/mL) and stimulated with (1) 50 nM anti-TF IgG1 (IgG1), (2) 100 nM 7t15-21s and 50 nM anti-TF IgG1, or (3) 100 nM 21t15-7s and 50 nM anti-TF IgG1 for up to 5 days at 37° C., 5% $CO_2$ in RPMI 1640 supplemented with 4 mM L-glutamine, penicillin, streptomycin, non-essential amino acids, sodium pyruvate, and 10% fetal bovine serum. Cells were maintained at a concentration of $0.5 \times 10^6$ cells/mL to $2.0 \times 10^6$ cells/mL until day 5. Glycolysis stress tests were performed in Seahorse media containing 2 mM glutamine. The drug concentrations used during the assay were as follows: 10 mM glucose, 100 nm oligomycin, and 100 mM 2-deoxy-D-glucose.

The data show that the combinations of (1) 100 nM 7t15-21s and 50 nM anti-TF IgG1 antibody, and (2) 100 nM 21t15-7s and 50 nM anti-TF IgG1 result in a significant increase in oxygen consumption rate (FIG. 20) and extracellular acidification rate (ECAR) (FIG. 21).

Example 25: Increase in Glucose Metabolism in NK Cells Using 18t15-12s

Figure 22:
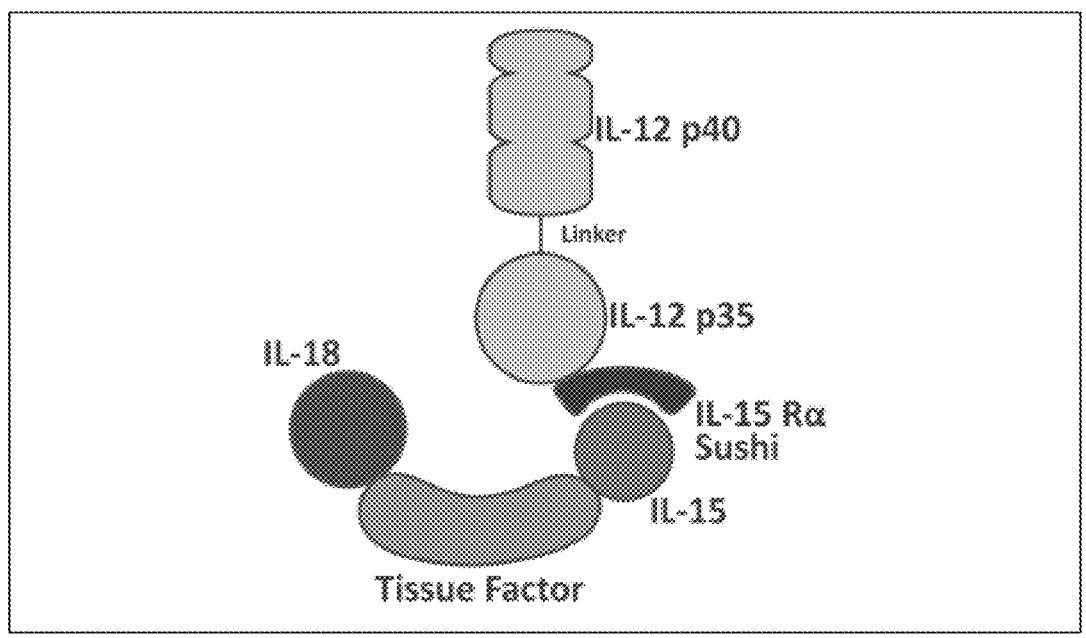
FIG. 22 is a schematic showing the structure of the 18t15-12s construct.

A set of experiments was performed to determine the effect of the construct of 18t15-12s (FIG. 22) on oxygen consumption rate and extracellular acidification rate (ECAR) on NK cells purified from human blood.

In these experiments, fresh human leukocytes were obtained from the blood bank from two different human donors and NK cells were isolated via negative selection using the RosetteSep/human NK cell reagent (StemCell Technologies). The purity of NK cells was >80% and confirmed by staining with CD56-BV421 and CD16-BV510 specific antibodies (BioLegend). The cells were counted and resuspended in $2 \times 10^6$/mL in 24-well, flat-bottom plates in 1 mL of complete media (RPMI 1640 (Gibco) supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies) and 10% FBS (Hyclone)). The cells were stimulated with either (1) media alone, (2) 100 nM 18t15-12s, or (3) mixture of single cytokines recombinant human IL-12 (0.25 µg), recombinant human IL-15 (1.25 µg), and recombinant human IL-18 (1.25 µg) overnight at 37° C., 5% $CO_2$. On the next day, the cells were harvested and extracellular flux assays on expanded NK cells were performed using a XFp Analyzer (Seahorse Bioscience). The harvested cells washed and plated $2.0 \times 10^5$ cells/well in at least duplicate for extracellular flux analysis of OCR (Oxygen Consumption Rate) and ECAR (Extracellular Acidification Rate). The glycolysis stress tests were performed in Seahorse Media contain 2 mM of glutamine. The following were used during the assay: 10 mM glucose; 100 nM oligomycin; and 100 mM 2-deoxy-D-glycose (2DG).

Figure 23:
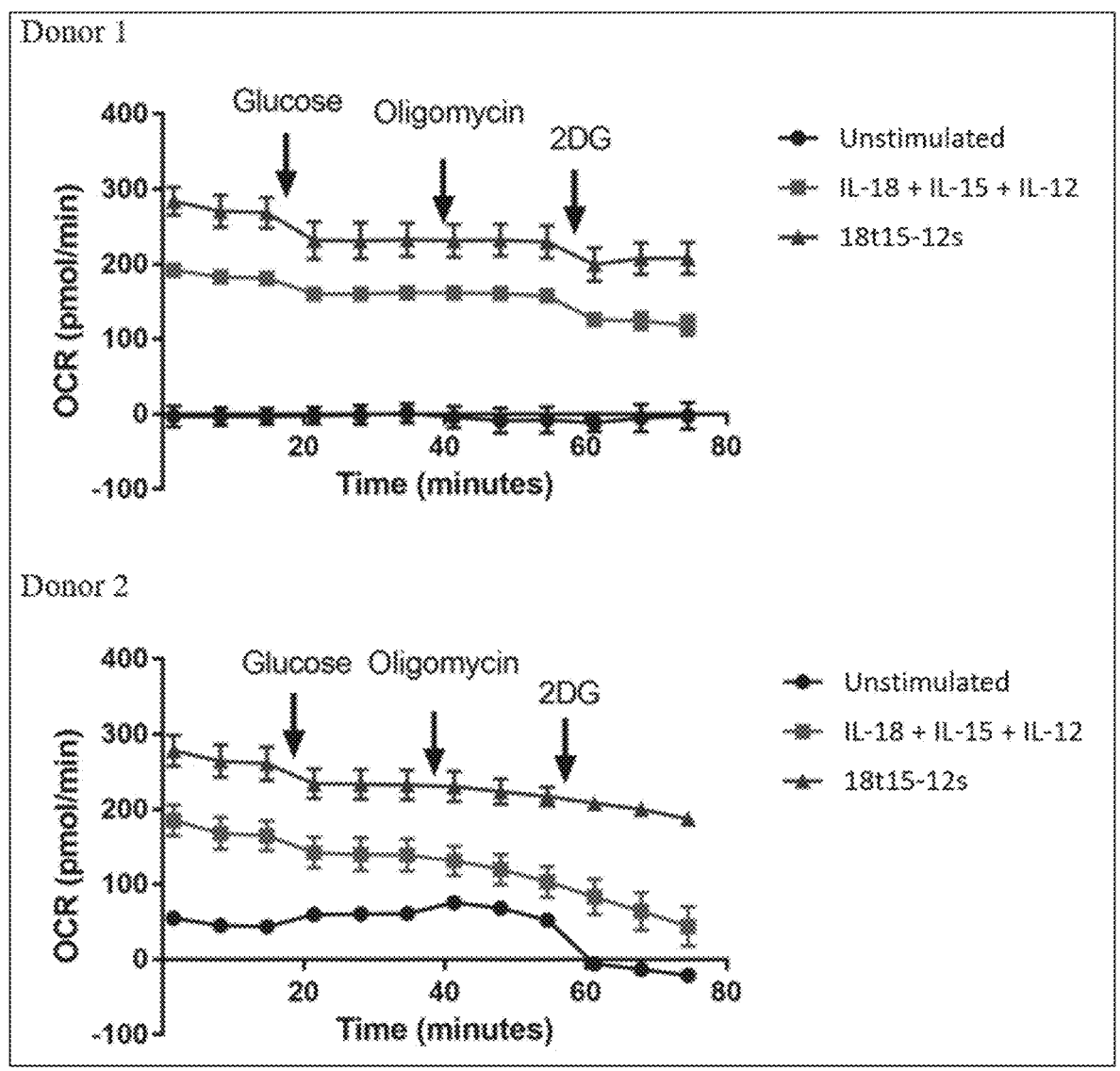
FIG. 23 are two graphs showing the oxygen consumption rate (OCR) in pmoles/min for human NK cells isolated from blood ($2 \times 10^6$ cells/mL) of two different donors. The isolated NK cells were left unstimulated or were stimulated with (1) 100 nM 18t15-12s ("1812") or a mixture of (2) recombinant human IL-12 (0.25 µg), recombinant human IL-15 (1.25 µg), and recombinant human IL-18 (1.25 µg) ("single cytokines"), overnight at 37° C., 5% $CO_2$ in RPMI 1640 supplemented with 4 mM L-glutamine, penicillin, streptomycin, non-essential amino acids, sodium pyruvate, and 10% fetal bovine serum. On the next day, the cells were harvested and extracellular flux assays on expanded NK cells were performed using a XFp Analyzer (Seahorse Bioscience). The harvested cells were washed and plated at $2.0 \times 10^5$ cells/well in at least duplicate for extracellular flux analysis of oxygen consumption rate. Glycolysis stress tests were performed in Seahorse Media contain 2 mM glutamine. Drug concentrations during the assay were: 10 mM glucose, 100 nM oligomycin, and 100 mM 2-deoxy-D-glucose.
Figure 24:
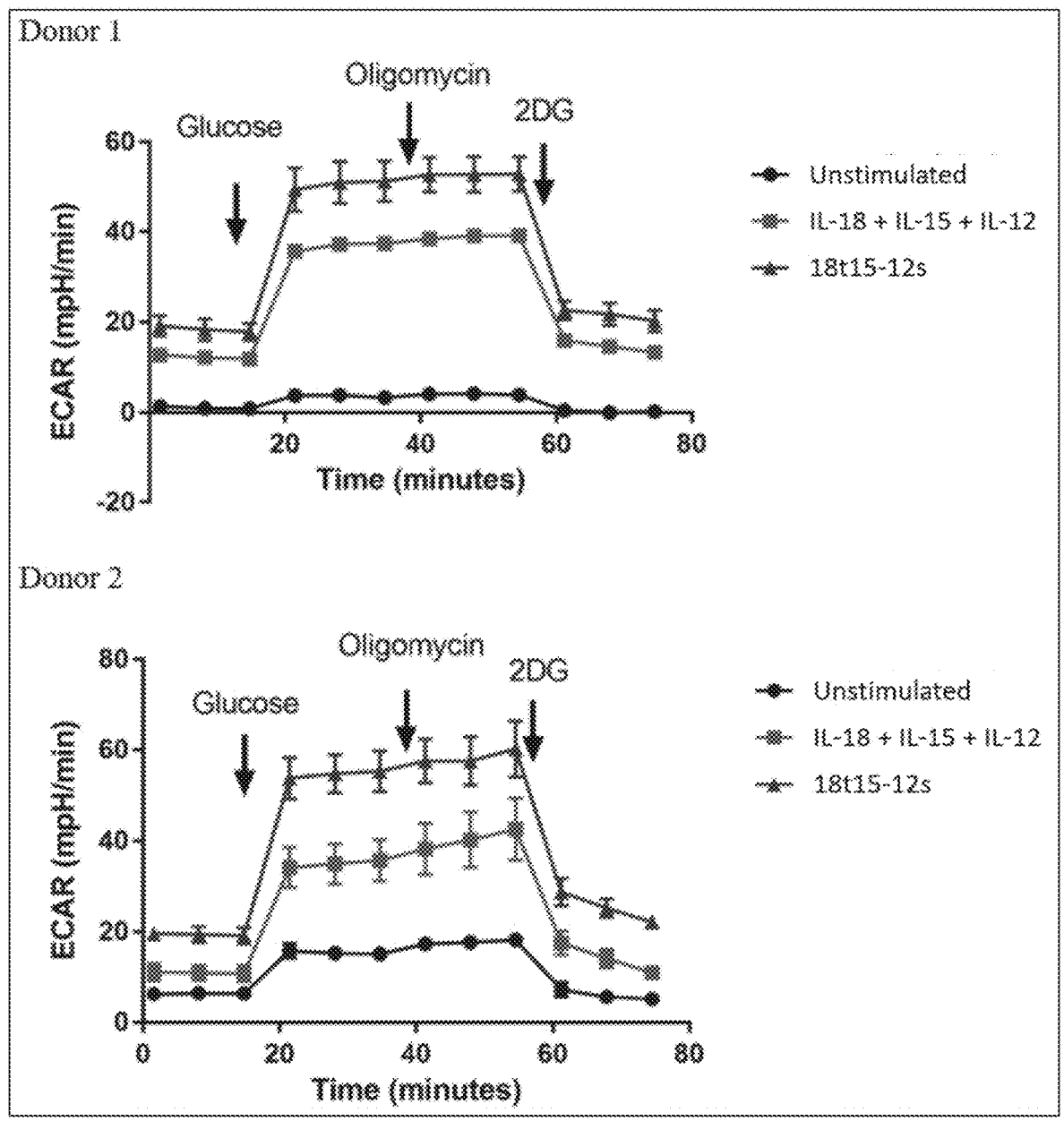
FIG. 24 are two graphs showing the extracellular acidification rate (ECAR) in mpH/minute for human NK cells isolated from blood ($2 \times 10^6$ cells/mL) of two different donors. The isolated NK cells were left unstimulated or were stimulated with (1) 100 nM 18t15-12s ("1812") or a mixture of (2) recombinant human IL-12 (0.25 µg), recombinant human IL-15 (1.25 µg), and recombinant human IL-18 (1.25 µg) ("single cytokines"), overnight at 37° C., 5% $CO_2$ in RPMI 1640 supplemented with 4 mM L-glutamine, penicillin, streptomycin, non-essential amino acids, sodium pyruvate, and 10% fetal bovine serum. On the next day, the cells were harvested and extracellular flux assays on expanded NK cells were performed using a XFp Analyzer (Seahorse Bioscience). The harvested cells were washed and plated at $2.0 \times 10^6$ cells/well in at least duplicate for extracellular flux analysis of extracellular flux analysis (ECAR). Glycolysis stress tests were performed in Seahorse Media contain 2 mM glutamine. Drug concentrations during the assay were: 10 mM glucose, 100 nM oligomycin, and 100 mM 2-deoxy-D-glucose.

The data show that the 18t15-12s results in significantly increased oxygen consumption rate (FIG. 23) and extracellular acidification rate (ECAR) as compared to the same cells activated with a combination of recombinant human IL-12, recombinant human IL-15, and recombinant human IL-18 (FIG. 24).

Example 26: Creation of an IL-12/IL-15RαSu DNA Construct

Figure 25:
FIG. 25 shows a schematic diagram of an exemplary IL-12/IL-15RαSu DNA construct.

In a non-limiting example, an IL-12/IL-15RαSu DNA construct was created. (see FIG. 25) The human IL-12 subunit sequences, human IL-15RαSu sequence, human IL-15 sequence, human tissue factor 219 sequence, and human IL-18 sequence were obtained from the UniProt website and DNA for these sequences was synthesized by Genewiz. A DNA construct was made linking the IL-12 subunit beta (p40) to IL-12 subunit alpha (p35) with a GS (3) linker to generate a single chain version of IL-12 and then directly linking the IL-12 sequence to the IL-15RαSu sequence. The final IL-12/IL-15RαSu DNA construct sequence was synthesized by Genewiz.

The nucleic acid sequence of the IL12/IL-15RαSu construct (including signal peptide sequence) is as follows (SEQ ID NO: 123):

```
(Signal peptide)
ATGAAATGGGTGACCTTTATTTCTTTACTGTTCCTCTTTAGCAGCGCCT

ACTCC (Human IL-12subunitbeta(p40))
ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

CACATGCCACAAGGGAGGCGAGGTGCTCAGCCATTCCTTATTATTATTA

CACAAGAAGGAAGACGGAATCTGGTCCACCGACATTTTAAAAGATCAGA

AGGAGCCCAAGAATAAGACCTTTTTAAGGTGTGAGGCCAAAAACTACAG

CGGTCGTTTCACTTGTTGGTGGCTGACCACCATTTCCACCGATTTAACC

TTCTCCGTGAAAAGCAGCCGGGGAAGCTCCGACCCTCAAGGTGTGACAT

GTGGAGCCGCTACCCTCAGCGCTGAGAGGGTTCGTGGCGATAACAAGGA

ATACGAGTACAGCGTGGAGTGCCAAGAAGATAGCGCTTGTCCCGCTGCC

GAAGAATCTTTACCCATTGAGGTGATGGTGGACGCCGTGCACAAACTCA

AGTACGAGAACTACACCTCCTCCTTCTTTATCCGGGACATCATTAAGCC

CGATCCTCCTAAGAATTTACAGCTGAAGCCTCTCAAAAATAGCCGGCAA

GTTGAGGTCTCTTGGGAATATCCCGACACTTGGAGCACACCCCACAGCT

ACTTCTCTTTAACCTTTTGTGTGCAAGTTCAAGGTAAAAGCAAGCGGGA

GAAGAAAGACCGGGTGTTTACCGACAAAACCAGCGCCACCGTCATCTGT

CGGAAGAACGCCTCCATCAGCGTGAGGGCTCAAGATCGTTATTACTCCA

GCAGCTGGTCCGAGTGGGCCAGCGTGCCTTGTTCC (Linker)
GGCGGTGGAGGATCCGGAGGAGGTGGCTCCGGCGGCGGAGGATCT (Human IL-12subunit alpha (p35))
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC (Human IL-115R a sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG
```

Example 27: Creation of an IL-18/TF/IL-15 DNA Construct

Figure 26:
FIG. 26 shows a schematic diagram of an exemplary IL-18/TF/IL-15 DNA construct.

In a non-limiting example, an IL-18/TF/IL-15 construct was made (see FIG. 26) linking the IL-18 sequence to the N-terminus coding region of tissue factor 219, and further linking the IL-18/TF construct with the N-terminus coding region of IL-15. The nucleic acid sequence of the IL-18/TF/IL-15 construct (including leader sequence), synthesized by Genewiz, is as follows (SEQ ID NO: 119):

```
(Signal peptide)
ATGAAGTGGGTCACATTTATCTCTTTACTGTTCCTCTTCTCCAGCGCCT

ACAGC (Human IL-18)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT (HumanTissueFactor219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG
```

-continued

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

Example 28: Secretion of IL-12/IL-15RαSu and IL-18/TF/IL-15 Fusion Proteins

Figure 27:
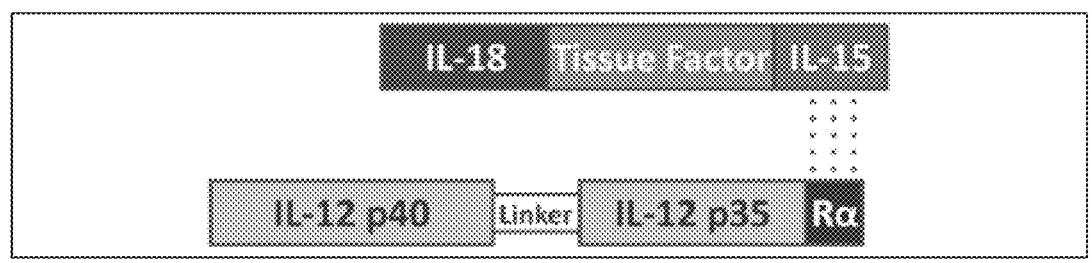
FIG. 27 shows a schematic diagram of the interaction between the exemplary IL-12/IL-15RαSu and IL-18/TF/IL-15 DNA constructs.
Figure 28:
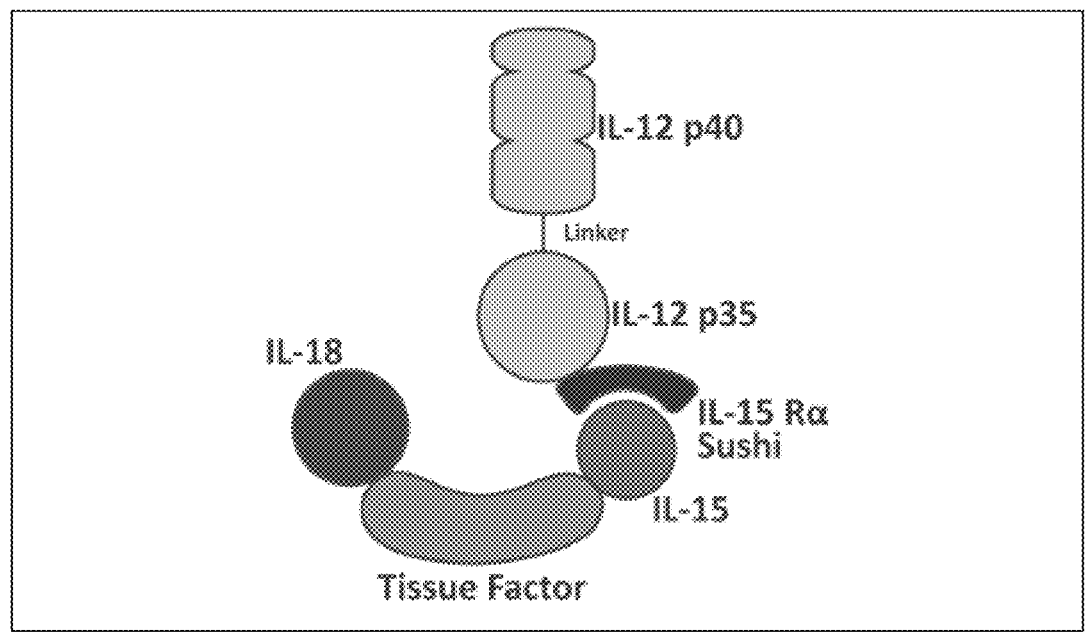
FIG. 28 shows a schematic diagram of the interaction between the exemplary IL-12/IL-15RαSu and IL-18/TF/IL-15 fusion proteins resulting in IL-18/TF/IL-15:IL-12/IL-15RαSu complex (18t15-12s).

The IL-12/IL-15RαSu and IL-18/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-18/TF/IL-15:IL-12/IL-15RαSu protein complex (referred to as 18t15-12s, see FIGS. 27 and 28). The 18t15-12s protein was purified from CHO-K1 cell culture supernatant using anti-TF antibody affinity chromatography and size exclusion chromatography resulting in soluble (non-aggregated) protein complexes consisting of IL-12/IL-15RαSu and IL-18/TF/IL-15 fusion proteins.

The amino acid sequence of the IL12/IL-15RαSu fusion protein (including signal peptide sequence) is as follows (SEQ ID NO: 122):

(Signal peptide)
MKWVTFISLLFLFSSAYS (Human IL-12 subunit beta(p40))
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDH

EDITKDKTSTVEACLPLELTKNESCLNSRETSFITNGSCLASRKTSFMM

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

S (Human IL-15R a sushi domain)
ITCPPPMSVEHADIWVKSYSLYSRERYICNSGFKRKAGTSSLTECVLNK

ATNVAHWTTPSLKCIR

The amino acid sequence of the IL-18/TF/IL-15 fusion protein (including signal peptide sequence) is as follows (SEQ ID NO: 118):

(Signal peptide)
MKWVTFISLLFLFSSAYS (Human IL-18)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

TIFFQRSVPGHDNKMQFESSSYEGYFLACEKERDLFKLILKKEDELGDR

SIMFTVQNED (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

In some cases, the leader (signal sequence) peptide is cleaved from the intact polypeptide to generate the mature form that may be soluble or secreted.

Example 29: Purification of 18t15-12s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Figure 29:
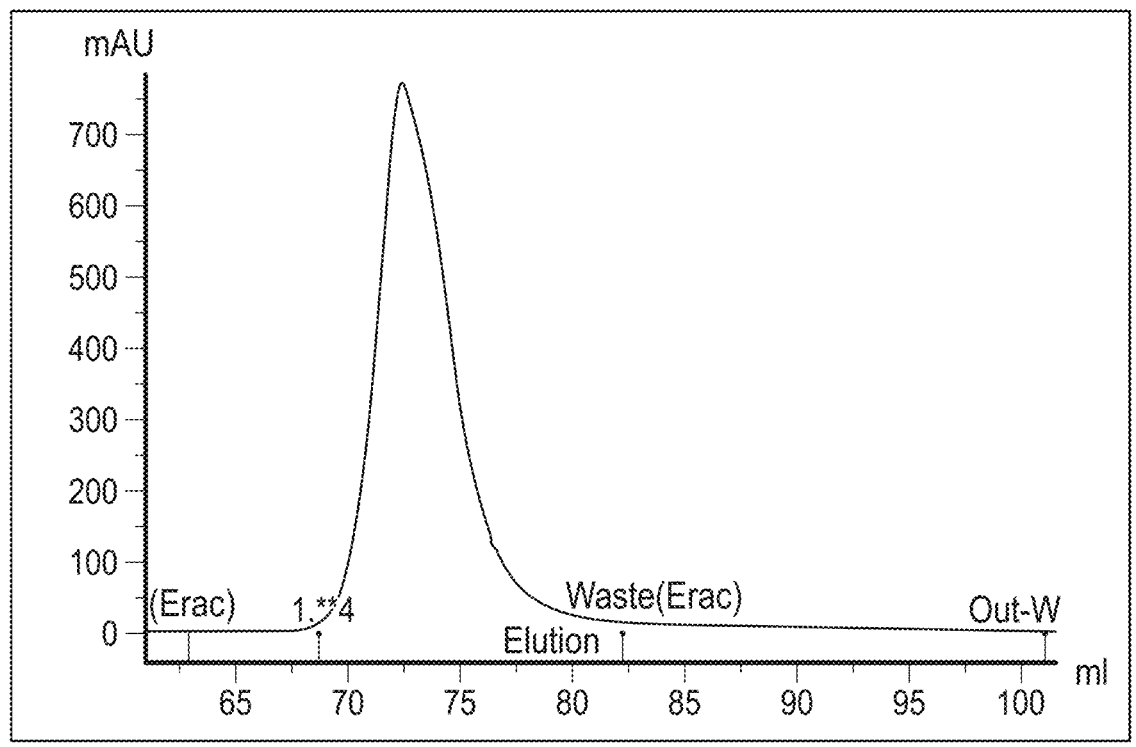
FIG. 29 shows a chromatograph of 18t15-12s purification elution from an anti-TF affinity column.

Cell culture harvest of 18t15-12s was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was neutralized to pH 7.5-8.0 by adding 1M Tris base. The neutralized sample was then buffer exchanged into PBS using Amicon® centrifugal filters with a 30 KDa molecular weight cutoff. FIG. 29 shows that the 18t15-12s complex binds the anti-TF antibody affinity column, wherein TF is an 18t15-12s binding partner. The buffer-exchanged protein sample is stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide and stored at 2-8° C.

Example 30: Size Exclusion Chromatography of 18t15-12s

Figure 30:
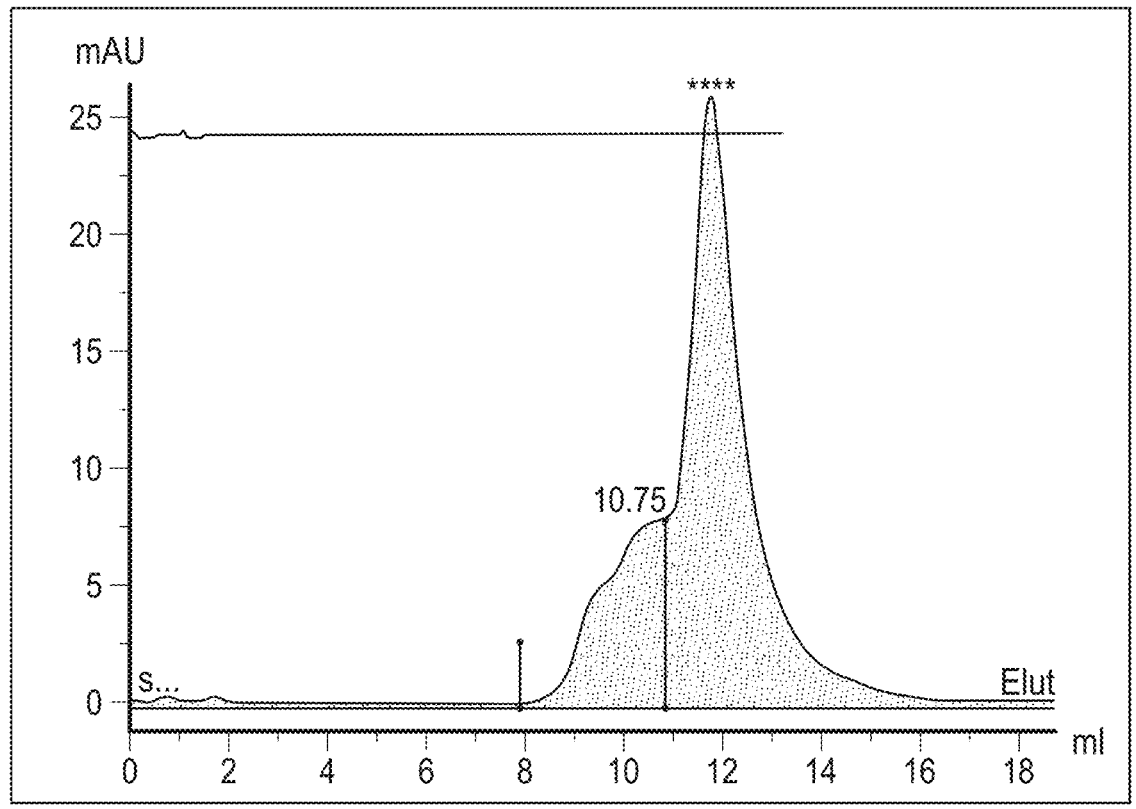
FIG. 30 shows an exemplary chromatographic profile of anti-TF antibody/SEC-purified 18t15-12s protein following elution on an analytical size exclusion column, demonstrating separation of monomeric multiprotein 18t15-12s complexes from protein aggregates.

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.8 mL/min. A capillary loop was used to inject 200 µL of 1 mg/mL of 18t15-12s complex onto the column. The injection was chased with 1.25 column volumes of PBS. The SEC chromatograph is shown in FIG. 30. There is a main 18t15-12s protein peak with a minor high molecular weight peak, likely due to differing degrees of glycosylation of 18t15-12s dimers or aggregates.

Example 31: SDS-PAGE of 18t15-12s

Figure 31:
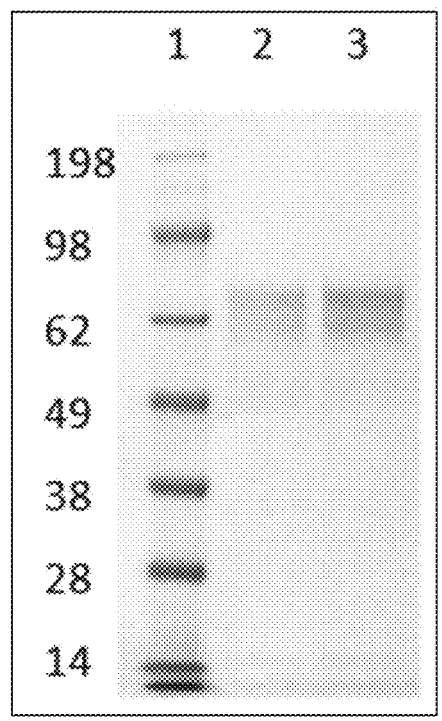
FIG. 31 shows an example of a 4-12% SDS-PAGE of the 18t15-12s complex following disulfide bond reduction. Lane 1: SeeBlue Plus2 marker; Lane 2: anti-TF antibody-purified 18t15-12s (0.5 µg); Lane 3: anti-TF antibody-purified 18t15-12s (1 µg).

To determine the purity and protein molecular weight, the purified 18t15-12s protein sample was analyzed using 4-12% NuPage Bis-Tris protein gel SDS-PAGE. The gel was stained with InstantBlue™ for about 30 min, followed by destaining overnight in purified water. FIG. 31 shows an example SDS gel of anti-TF antibody affinity purified 18t15-12s, with bands at the expected molecular weights (66 kDa and 56 kDa).

Example 32: Glycosylation of 18t15-12s in CHO-K1 Cells

Figure 32:
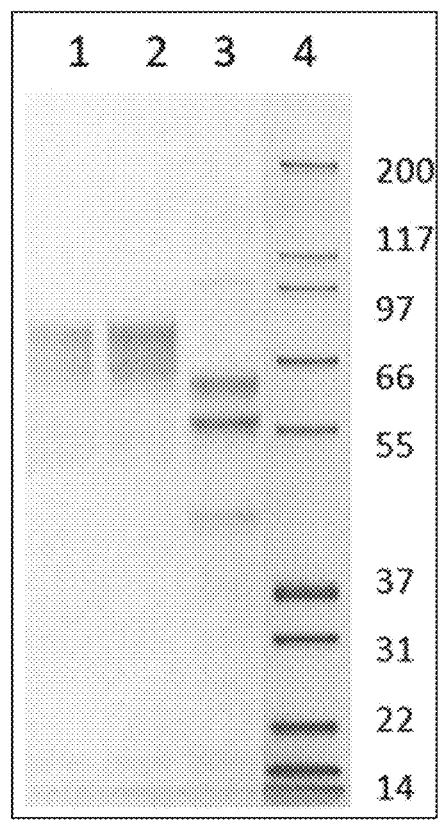
FIG. 32 shows SDS PAGE analysis of deglycosylated and non-deglycosylated 18t15-12s. Lane 1: anti-TF antibody-purified 18t15-12s (0.5 µg), non-deglycosylated; Lane 2: anti-TF antibody-purified 18t15-12s (1 µg), non-deglycosylated; Lane 3: 18t15-12s (1 µg), deglycosylated, Lane 4: Mark12 unstained maker.
Figure 33:
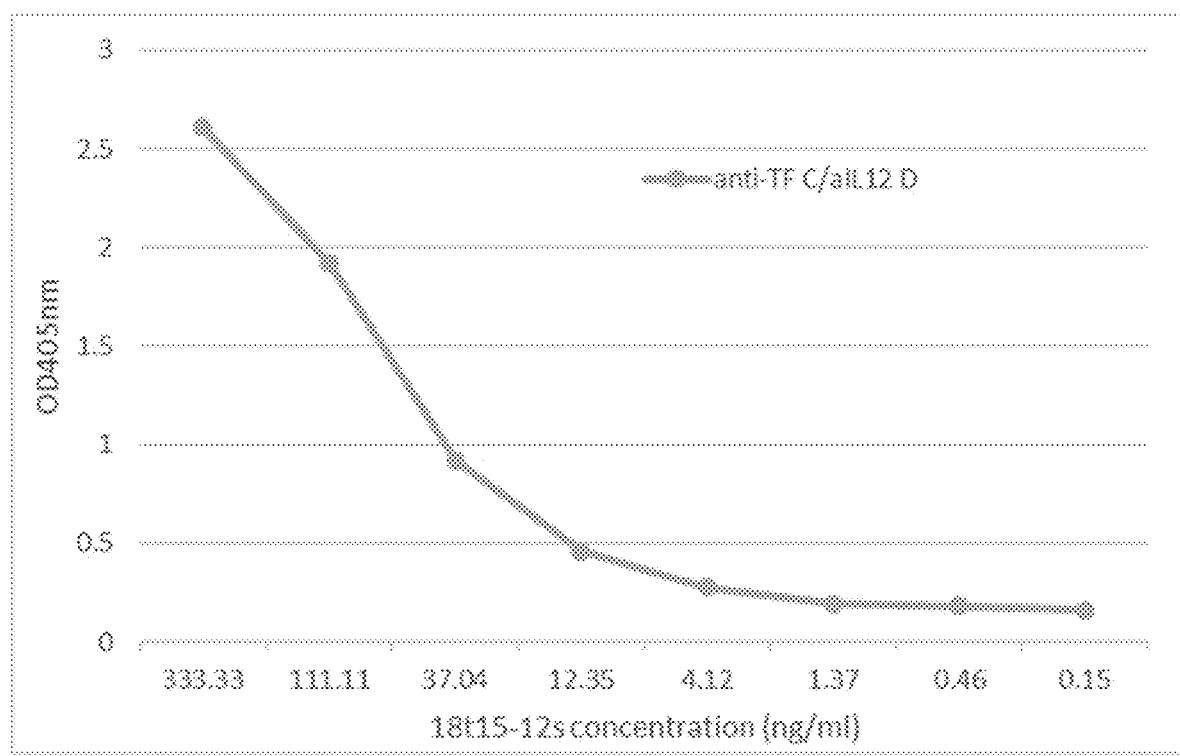
FIG. 33 shows a sandwich ELISA for the 18t15-12s complex, comprising an anti-human tissue factor capture antibody and a biotinylated anti-human IL-12 detection antibody (BAF 219).
Figure 34:
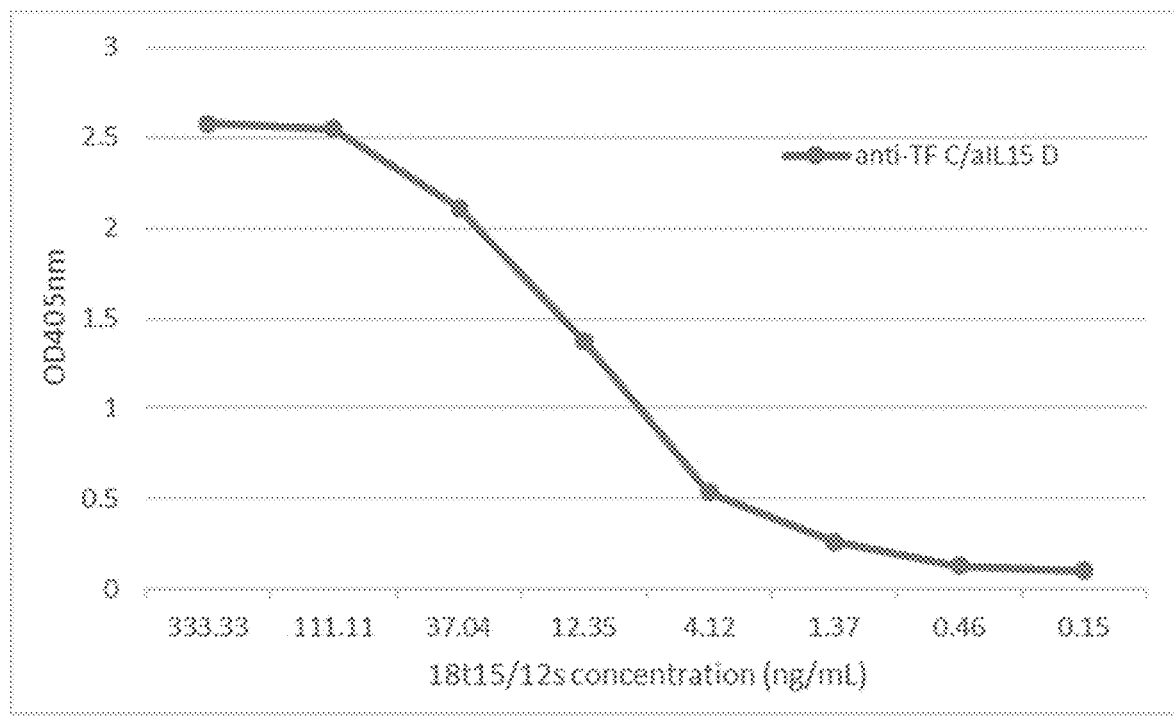
FIG. 34 shows a sandwich ELISA for the 18t15-12s complex, comprising an anti-human tissue factor capture antibody and a biotinylated anti-human IL-15 detection antibody (BAM 247).
Figure 35:
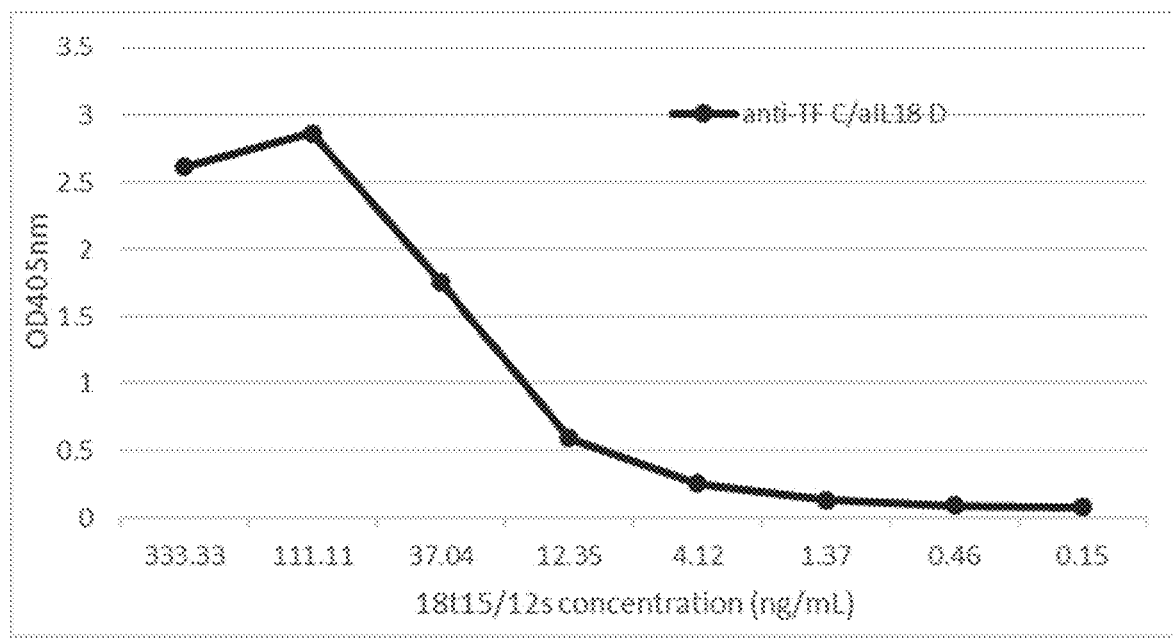
FIG. 35 shows a sandwich ELISA for the 18t15-12s complex, comprising an anti-human tissue factor capture antibody and a biotinylated anti-human IL-18 detection antibody (D045-6).
Figure 36:
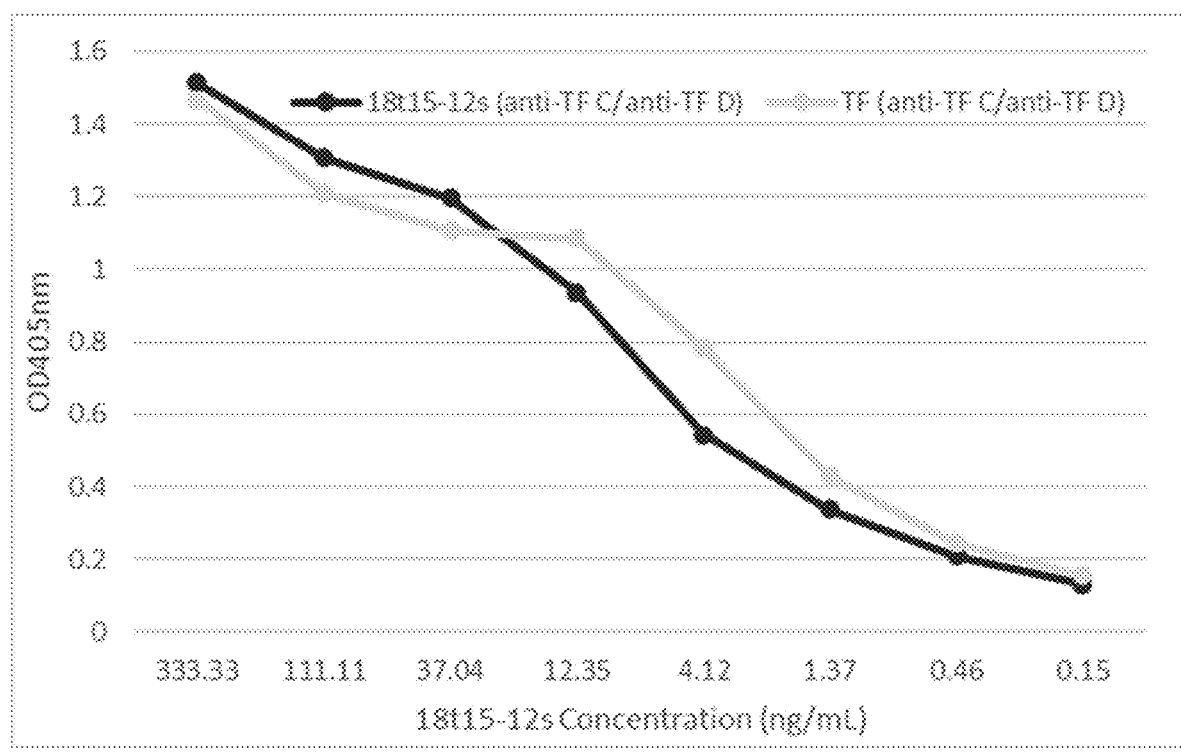
FIG. 36 shows a sandwich ELISA for the 18t15-12s complex, comprising an anti-human tissue factor (I43) capture antibody and an anti-human tissue factor detection antibody.
Figure 37:
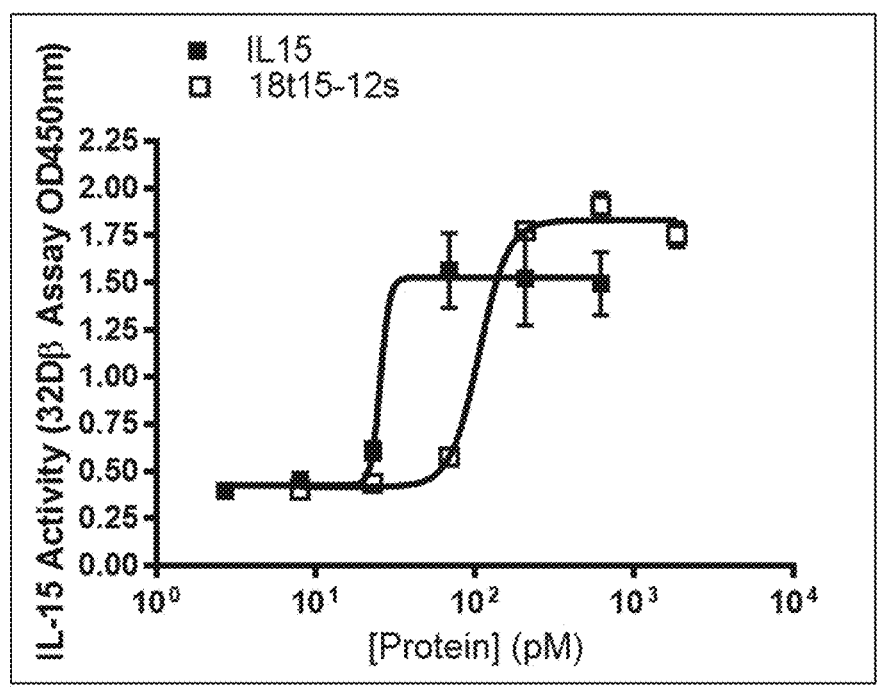
FIG. 37 shows proliferation of IL-15-dependent 32Dβ cells mediated by the 18t15-12s complex (open squares) and recombinant IL-15 (black squares).

Glycosylation of 18t15-12s in CHO-K1 cells was confirmed using the Protein Deglycosylation Mix II kit (New England Biolabs), according to the manufacturer's instructions. FIG. 32 shows an example SDS PAGE of deglycosylated and non-deglycosylated 18t15-12s. Deglycosylation reduces the molecular weight of 18t15-12s as seen in FIG. 32, lane 4.

Example 33: Recombinant Protein Quantitation of 18t15-12s Complexes

The 18t15-12s complex was detected and quantified using standard sandwich ELISA methods (see FIGS. 33-36). Anti-human tissue factor antibody served as the capture antibody and biotinylated anti-human IL-12, IL-15, or IL-18 antibody (BAF 219, BAM 247, D045-6, all R&D Systems) served as the detection antibody. Tissue factor in purified 18t15-12s protein complexes was also detected using an anti-human tissue factor capture antibody (143), and anti-human tissue factor antibody detection antibody. The I43/anti-TF Ab ELISA was compared to purified tissue factor at similar concentrations.

Example 34: Immunostimulatory Capacity of the 18t15-12s Complex

To assess the IL-15 immunostimulatory activity of the 18t15-12s complex, increasing concentrations of 18t15-12s was added to 32Dβ cells (104 cell/well) in 200 µL IMDM: 10% FBS media. The 32Dβ cells were incubated for 3 days at 37° C. On the fourth day, WST-1 proliferation reagent (10 µL/well) was added and after 4 hours, absorbance was measured at 450 nm to determine cell proliferation based on cleavage of WST-1 to a soluble formazan dye. Bioactivity of human recombinant IL-15 was assessed as a positive control. As shown in FIG. 37, 18t15-12s demonstrated IL-15-dependent cell proliferation of 32Dβ cells. The 18t15-12s complex demonstrated reduced activity compared to human recombinant IL-15, possibly due to the linkage of IL-18 and tissue factor to the IL-15 domain.

Figure 38:
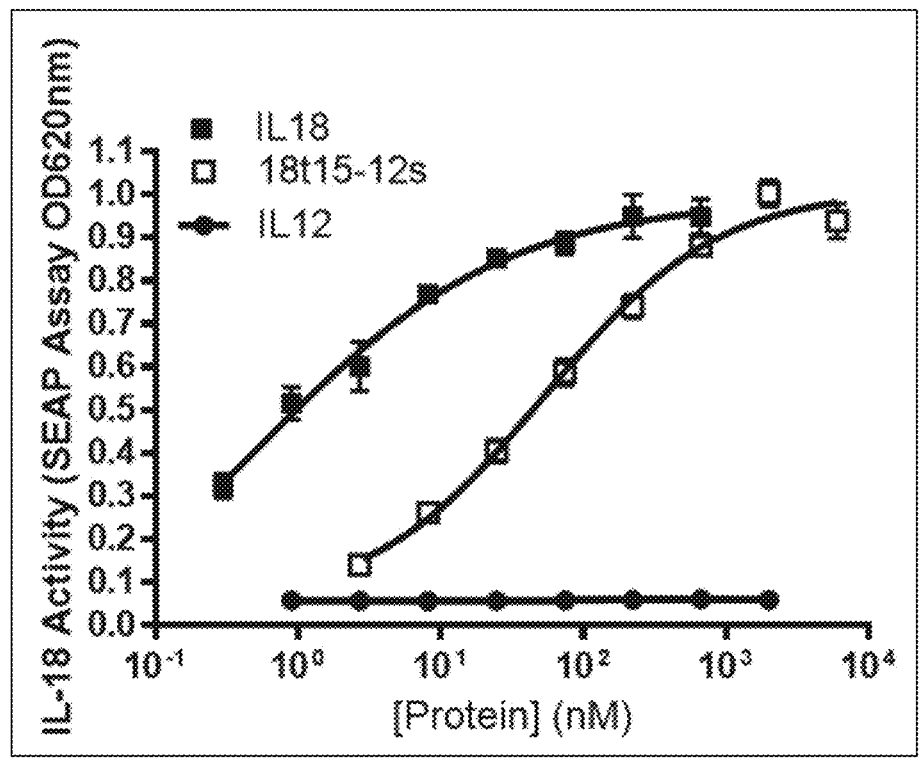
FIG. 38 shows biological activity of IL-18 within the 18t15-12s complex (open squares), where recombinant IL-18 (black squares) and recombinant IL-12 (black circles) serve as positive and negative controls, respectively.
Figure 39:
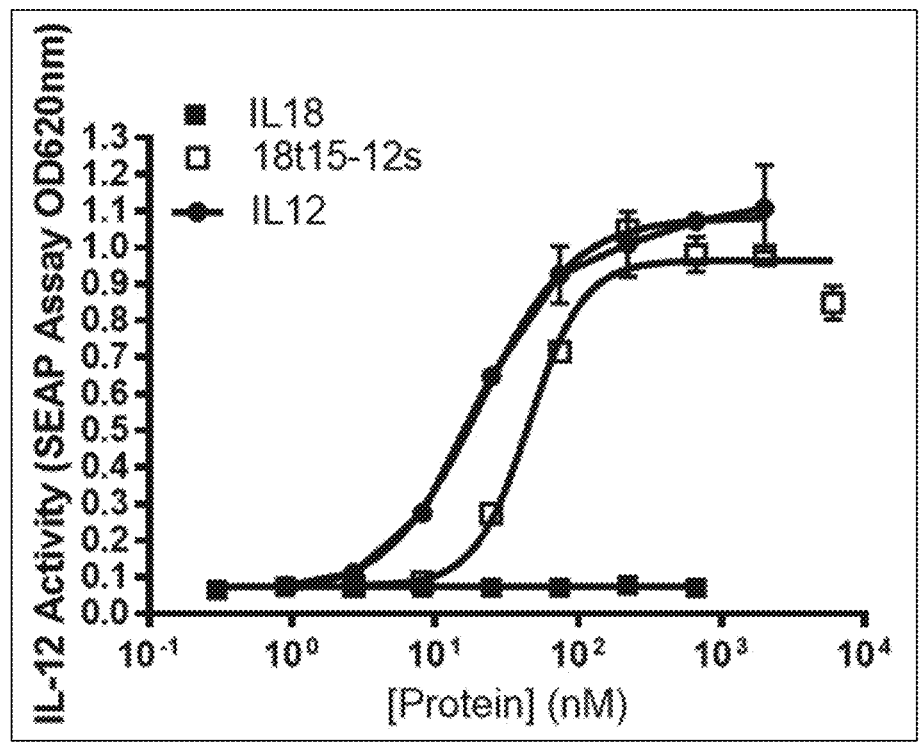
FIG. 39 shows biological activity of IL-12 within the 18t15-12s complex (open squares), where recombinant IL-12 (black circles) and recombinant IL-18 (open squares) serve as positive and negative controls, respectively.

In order to assess the individual activities of IL-12 and IL-18 in the 18t15-12s complex, 18t15-12s was added to HEK-Blue IL-12 and HEK-Blue IL-18 reporter cells ($5 \times 10^4$ cell/well; hkb-il12 and hkb-hmil18, InvivoGen) in 200 µL IMDM:10% heat-inactivated FBS media. Cells were incubated for overnight at 37° C. 20 µl of induced HEK-Blue IL-12 and HEK-Blue IL-18 reporter cell supernatant was added to 180 µl of QUANTI-Blue (InvivoGen), and incubated for 1-3 hours at 37° C. IL-12 or IL-18 activity was assessed by measuring absorbance at 620 nm. Human recombinant IL-12 or IL-18 was assessed as a positive or negative control. As shown in FIGS. 38 and 39, the each of the cytokine domains of the 18t15-12s complex retain specific biological activity. The activity of 18t15-12s was reduced compared to that of human recombinant IL-18 or IL-12, possibly due to linkage of IL-15 and tissue factor to the IL-18 domain and linkage of IL-12 to the IL-15Rα sushi domain.

Example 35: Induction of Cytokine-Induced Memory-Like NK Cells by the 18t15-12s Complex Cytokine-induced memory-like NK cells can be induced ex vivo following overnight stimulation of purified NK cells with saturating amounts of IL-12 (10 ng/mL), IL-15 (50 ng/mL), and IL-18 (50 ng/mL). These memory-like properties have been measured through expression of IL-2 receptor α (IL-2Rα, CD25), CD69 (and other activation markers), and increased IFN-γ production. To evaluate the ability of 18t15-12s complexes to promote generation of cytokine-induced memory-like NK cells, purified human NK cells (>95% CD56+) were stimulated for 14-18 hours with 0.01 nM to 10000 nM of the 18t15-12s complex or a combination of individual cytokines (recombinant IL-12 (10 ng/mL), IL-18 (50 ng/mL), and IL-15 (50 ng/mL)). Cell-surface CD25 and CD 69 expression and intracellular IFN-γ levels were assessed by antibody-staining and flow cytometry.

Fresh human leukocytes were obtained from a blood bank and CD56+ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2 \times 10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either a mixture of cytokines hIL-12 (10 ng/mL) (Biolegend), hIL-18 (50 ng/mL) (R&D Systems) and hIL-15 (50 ng/mL) (NCI) or with 0.01 nM to 10000 nM of the 18t15-12s at 37° C., 5% $CO_2$ for 14-18 hrs. The cells were then harvested and surface stained with CD56-BV421, CD16-BV510, CD25-PE, CD69-APC-Fire750 specific antibodies (BioLegend) for 30 minutes.

Figure 40A:
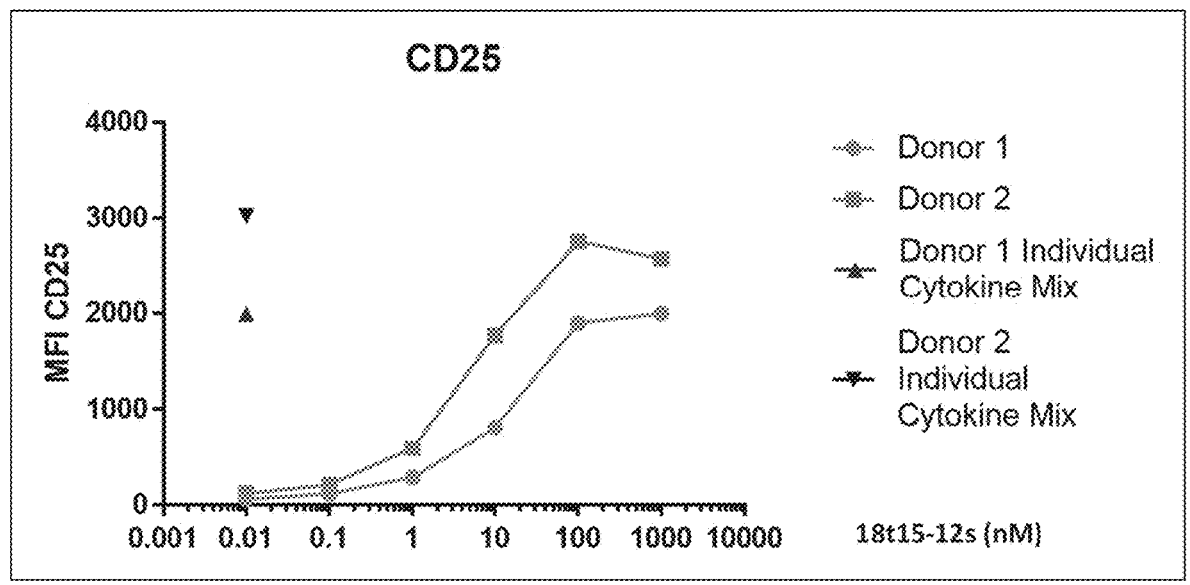
FIG. 40A shows a flow cytometry graph of cell-surface CD25 expression of NK cells induced by the 18t15-12s complex.
Figure 40B:
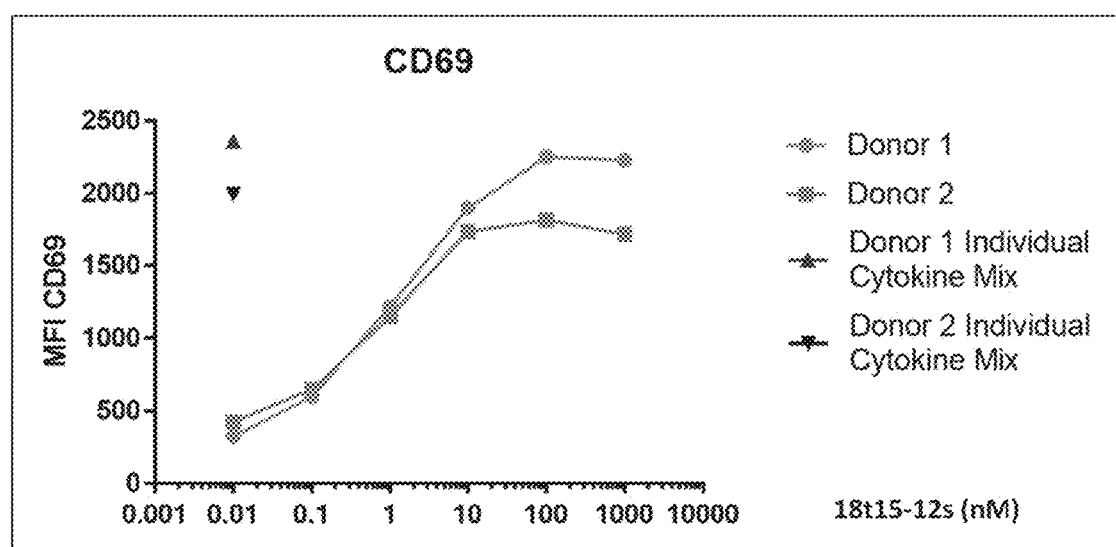
FIG. 40B shows a flow cytometry graph of cell-surface CD69 expression of NK cells induced by the 18t15-12s complex.

After staining, cells were washed (1500 RPM for 5 minutes at room temperature) in FACS buffer (1×PBS (Hyclone), with 0.5% BSA (EMD Millipore) and 0.001% sodium azide (Sigma)). After two washes, cells were analyzed using a BD FACSCelesta™ flow cytometer (Plotted Data-Mean Fluorescence Intensity, see FIGS. 40A and 40B).

Figure 41:
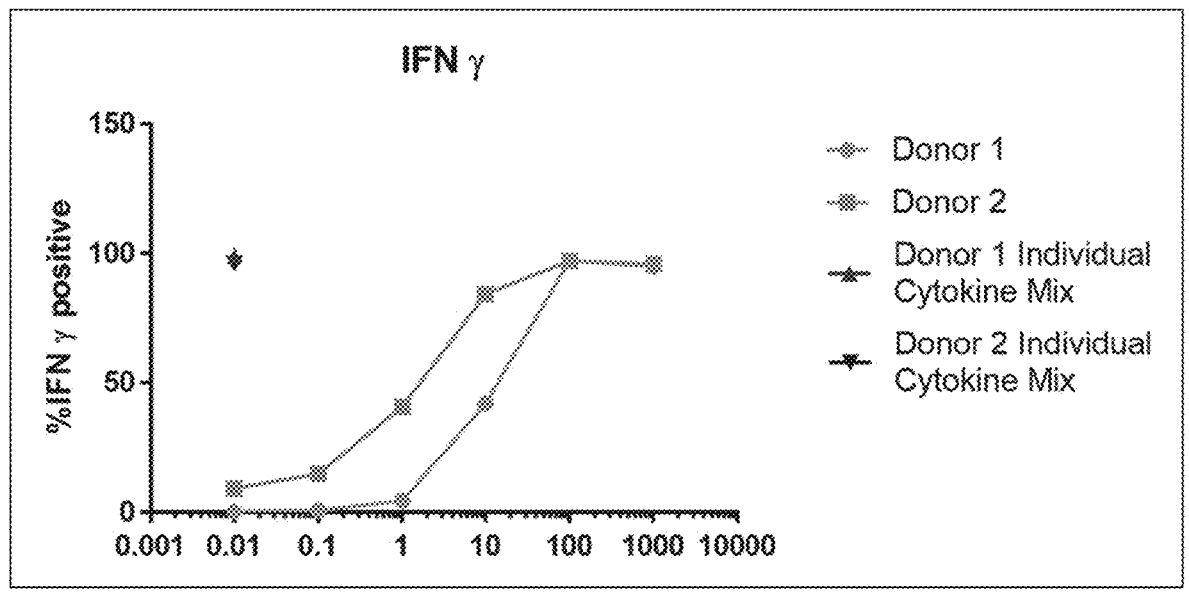
FIG. 41 shows a flow cytometry graph of intracellular interferon gamma expression of NK cells induced by the 18t15-12s complex.

Fresh human leukocytes were obtained from a blood bank and CD56+ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2×10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either a cytokine mix of hIL-12 (10 ng/mL) (Biolegend), hIL-18 (50 ng/mL) (R&D), and hIL-15 (50 ng/mL) (NCI), or 0.01 nM to 10000 nM of the 18t15-12s complex at 37° C., 5% CO2 for 14-18 hrs. The cells were then treated with 10 μg/mL of Brefeldin A (Sigma) and 1× of Monensin (eBioscience) for 4 hrs before harvesting and staining for CD56-BV421, CD16-BV510, CD25-PE, CD69-APCFire750 for 30 minutes. After staining, cells were washed (1500 RPM for 5 minutes in room temperature) in FACS buffer (1×PBS (Hyclone), with 0.5% BSA (EMD Millipore) and 0.001% sodium azide (Sigma)) and fixed for 10 minutes at room temperature. After fixation, cells were washed (1500 RPM for 5 minutes in room temperature) in 1× permeabilized buffer (eBioscience) and stained with IFN-γ-PE Ab (Biolegend) for 30 minutes at room temperature. Cells were washed once again with 1× permeabilized buffer and then washed with FACS buffer. Cell pellets were resuspended in 300 μls of FACS buffer and analyzed using a BD FACSCelesta™ flow cytometer (Plotted % of IFN-γ Positive Cells, see FIG. 41).

Example 36: In Vitro Cytotoxicity of NK Cells Against Human Tumor Cells

Figure 42:
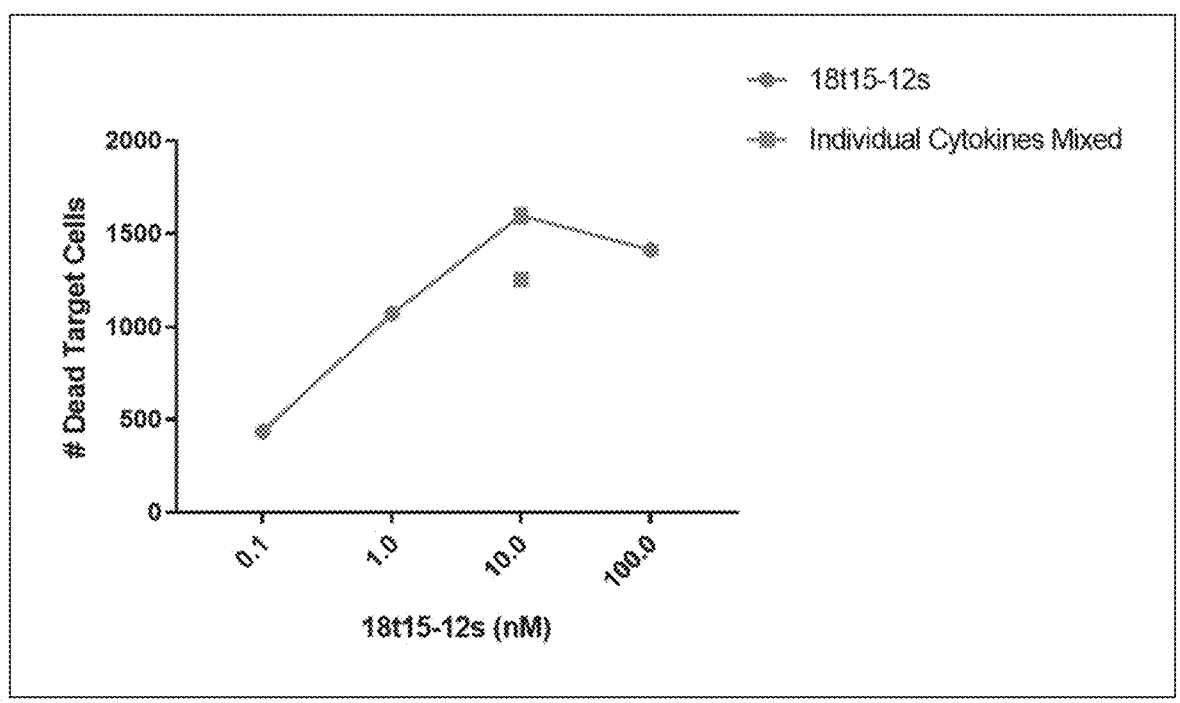
FIG. 42 shows a bar graph showing cytotoxicity of 18t15-12s induced human NK cells against K562. K562 cells (labeled with Celltrace violet) at $1 \times 10^{\wedge}5$/well and human NK cells (NK cells were isolated from human blood buffy coat with StemCell human NK cell purification kit) at $2 \times 10^{\wedge}5$/well were incubated with 18t15-12s in RPMI-10 for 20 hours. Cell mixtures were harvested, stained with propidium iodide (PI), and analyzed using a BD FACSCelesta™ flow cytometer. The graph represents duplicated samples.

Human myelogenous leukemia cells, K562 (CellTrace violet labelled), were incubated with purified human NK cells in the presence of increasing concentrations of the 18t15-12s complex or a mixture of cytokines as a control. After 20 hours, the cultures were harvested, stained with propidium iodide (PI), and assessed by flow cytometry. As shown in FIG. 42, the 18t15-12s complex induced human NK cytotoxicity against K562, at levels similar or greater than the cytokine mixture, wherein both the 18t15-12s complex and the cytokine mixture induced greater cytotoxicity than the medium control.

Figure 43:
FIG. 43 shows a schematic diagram of an exemplary IL-12/IL-15RαSu/αCD16 DNA construct.

Example 37: Creation of IL-12/IL-15RαSu/αCD16scFv and IL-18/TF/IL-15 DNA Constructs In a non-limiting example, IL-12/IL-15RαSu/αCD16scFv and IL-18/TF/IL-15 DNA constructs were created (see FIG. 43). The human IL-12 subunit sequences, human IL-15RαSu sequence, human IL-15 sequence, human tissue factor 219 sequence, and human IL-18 sequence were synthesized by Genewiz. A DNA construct was made linking the IL-12 subunit beta (p40) to IL-12 subunit alpha (p35) with a GS (3) linker to generate a single chain version of IL-12, directly linking the IL-12 sequence to the IL-15RαSu sequence, and directly linking the IL-12/IL-15RαSu construct to the N-terminus coding region of αCD16scFv (referred as 18t15-12s16).

The nucleic acid sequence of the IL-12/IL-15RαSu/αCD16scFv construct is as follows (SEQ ID NO: 156):

```
(Signal peptide)
ATGAAATGGGTGACCTTTATTTCTTTACTGTTCCTCTTTAGCAGCGCCT
ACTCC (Human IL-12 subunit beta (p40))
ATTTGGGAACTGAAGAAGGACGTCTACGTGGTCGAACTGGACTGGTATC
CCGATGCTCCCGGCGAAATGGTGGTGCTCACTTGTGACACCCCCGAAGA
AGACGGCATCACTTGGACCCTCGATCAGAGCAGCGAGGTGCTGGGCTCC
GGAAAGACCCTCACAATCCAAGTTAAGGAGTTCGGAGACGCTGGCCAAT
ACACATGCCACAAGGGAGGCGAGGTGCTCAGCCATTCCTTATTATTATT
ACACAAGAAGGAAGACGGAATCTGGTCCACCGACATTTTAAAAGATCAG
AAGGAGCCCAAGAATAAGACCTTTTTAAGGTGTGAGGCCAAAAACTACA
GCGGTCGTTTCACTTGTTGGTGGCTGACCACCATTTCCACCGATTTAAC
CTTCTCCGTGAAAAGCAGCCGGGGAAGCTCCGACCCTCAAGGTGTGACA
TGTGGAGCCGCTACCCTCAGCGCTGAGAGGGTTCGTGGCGATAACAAGG
AATACGAGTACAGCGTGGAGTGCCAAGAAGATAGCGCTTGTCCCGCTGC
CGAAGAATCTTTACCCATTGAGGTGATGGTGGACGCCGTGCACAAACTC
AAGTACGAGAACTACACCTCCTCCTTCTTTATCCGGGACATCATTAAGC
CCGATCCTCCTAAGAATTTACAGCTGAAGCCTCTCAAAAATAGCCGGCA
AGTTGAGGTCTCTTGGGAATATCCCGACACTTGGAGCACACCCCACAGC
TACTTCTCTTTAACCTTTTGTGTGCAAGTTCAAGGTAAAAGCAAGCGGG
AGAAGAAAGACCGGGTGTTTACCGACAAAACCAGCGCCACCGTCATCTG
TCGGAAGAACGCCTCCATCAGCGTGAGGGCTCAAGATCGTTATTACTCC
AGCAGCTGGTCCGAGTGGGCCAGCGTGCCTTGTTCC (Linker)
GGCGGTGGAGGATCCGGAGGAGGTGGCTCCGGCGGCGGAGGATCT (Human IL-12 subunit alpha (p35))
CGTAACCTCCCCGTGGCTACCCCCGATCCCGGAATGTTCCCTTGTTTAC
ACCACAGCCAGAATTTACTGAGGGCCGTGAGCAACATGCTGCAGAAAGC
TAGGCAGACTTTAGAATTTTACCCTTGCACCAGCGAGGAGATCGACCAT
GAAGATATCACCAAGGACAAGACATCCACCGTGGAGGCTTGTTTACCTC
TGGAGCTGACAAAGAACGAGTCTTGTCTCAACTCTCGTGAAACCAGCTT
CATCACAAATGGCTCTTGTTTAGCTTCCCGGAAGACCTCCTTTATGATG
GCTTTATGCCTCAGCTCCATCTACGAGGATTTAAAGATGTACCAAGTGG
AGTTCAAGACCATGAACGCCAAGCTGCTCATGGACCCTAAACGGCAGAT
CTTTTTAGACCAGAACATGCTGGCTGTGATTGATGAGCTGATGCAAGCT
TTAAACTTCAACTCCGAGACCGTCCCTCAGAAGTCCTCCCTCGAGGAGC
CCGATTTTTACAAGACAAAGATCAAACTGTGCATTTTACTCCACGCCTT
TAGGATCCGGGCCGTGACCATTGACCGGGTCATGAGCTATTTAAACGCC
AGC
```

```
(Human IL-15R a sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG (anti-Human CD16 light chain variable domain)
TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

AACAACAGGCCCTCCGGCATCCCTGACAGGTTCTCCGGATCCTCCTCCG

GCAACACCGCCTCCCTGACCATCACAGGCGCTCAGGCCGAGGACGAGGC

TGACTACTACTGCAACTCCAGGGACTCCTCCGGCAACCATGTGGTGTTC

GGCGGCGGCACCAAGCTGACCGTGGGCCAT (Linker)
GGCGGCGGCGGCTCCGGAGGCGGCGGCAGCGGCGGAGGAGGATCC (anti-Human CD16 heavy chain variable domain)
GAGGTGCAGCTGGTGGAGTCCGGAGGAGGAGTGGTGAGGCCTGGAGGCT

CCCTGAGGCTGAGCTGTGCTGCCTCCGGCTTCACCTTCGACGACTACGG

CATGTCCTGGGTGAGGCAGGCTCCTGGAAAGGGCCTGGAGTGGGTGTCC

GGCATCAACTGGAACGGCGGATCCACCGGCTACGCCGATTCCGTGAAGG

GCAGGTTCACCATCAGCAGGGACAACGCCAAGAACTCCCTGTACCTGCA

GATGAACTCCCTGAGGGCCGAGGACACCGCCGTGTACTACTGCGCCAGG

GGCAGGTCCCTGCTGTTCGACTACTGGGGACAGGGCACCCTGGTGACCG

TGTCCAGG
```

Figure 44:
FIG. 44 shows a schematic diagram of an exemplary IL-18/TF/IL-15 DNA construct.

Constructs were also made linking the IL-18 sequence to the N-terminus coding region of tissue factor 219, and linking the IL-18/TF construct with the N-terminus coding region of IL-15 (see FIG. 44). The nucleic acid sequence of the IL-18/TF/IL-15 construct (including leader sequence) is as follows (SEQ ID NO: 119):

```
(Signal peptide)
ATGAAGTGGGTCACATTTATCTCTTTACTGTTCCTCTTCTCCAGCGCCT

ACAGC (Human IL-18)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT (Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC
```

Figure 45:
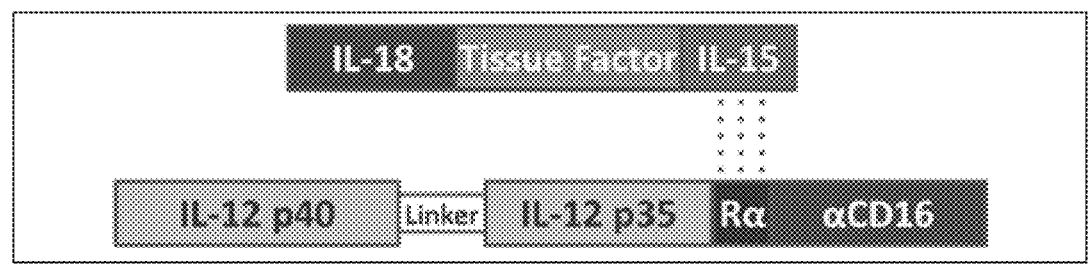
FIG. 45 shows a schematic diagram of the interaction between the exemplary IL-12/IL-15RαSu/αCD16scFv and IL-18/TF/IL-15 DNA constructs.
Figure 46:
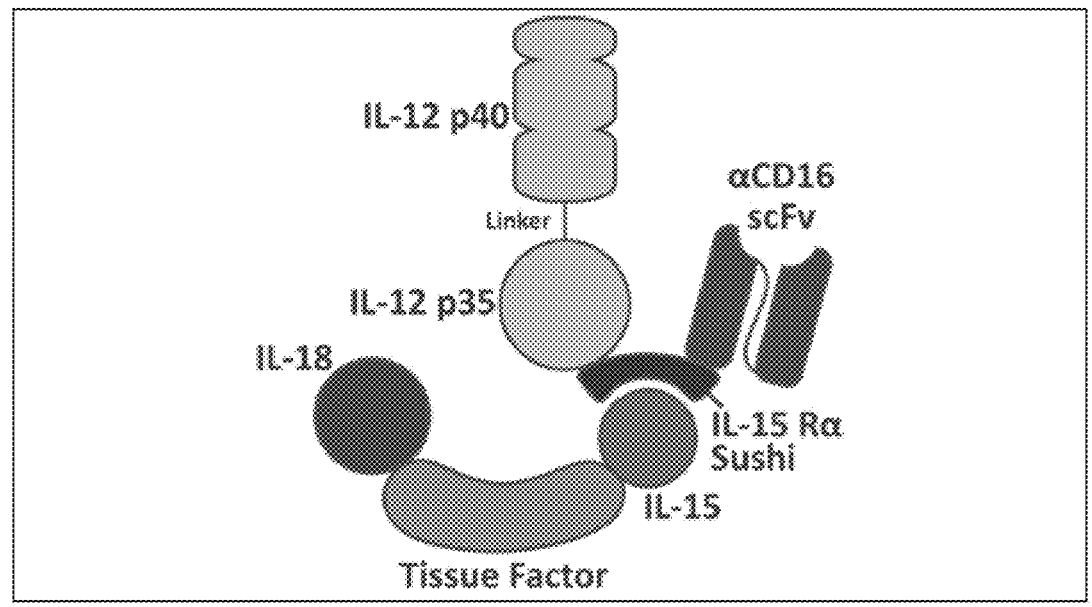
FIG. 46 shows a schematic diagram of an exemplary 18t15-12s/αCD16 protein complex.

Example 38: Secretion of IL-12/IL-15RαSu/αCD16scFv and IL-18/TF/IL-15 Fusion Proteins The IL-12/IL-15RαSu/αCD16scFv and IL-18/TF/IL-15 constructs were cloned into a pMSGV-1 modified retrovirus expression vector (Hughes, *Hum Gene Ther* 16:457-72, 2005, herein incorporated by reference), and the expression vector was transfected into CHO-K1 cells. Co-expression of the two constructs in CHO-K1 cells resulted in secretion of a soluble IL-18/TF/IL-15:IL-12/IL-15RαSu/αCD16scFv protein complex (referred to as 18t15-12s/αCD16). Co-expression of the two constructs in CHO-K1 cells resulted in secretion of the soluble IL-18/TF/IL-15:IL-12/IL-15RαSu/αCD16scFv protein complex (referred to as 18t15-12s/αCD16, see FIGS. 45 and 46), which can be purified by anti-TF antibody affinity and other chromatography methods. In some cases, the signal peptide is cleaved from the intact polypeptide to generate the mature form.

The amino acid sequence of the IL-12/IL-15RαSu/αCD16scFv fusion protein (including signal peptide sequence) is as follows (SEQ ID NO: 155):

(Signal peptide)
MKWVTFISLLFLFSSAYS (Human IL-12 subunit beta (p40))
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDH

EDITKDKTSTVEACLPLELTKNESCLNSRETSFITNGSCLASRKTSFMM

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

S (Human IL-115R a sushi domain)
ITCPPPMSVEHADIWVKSYSLYSRERYICNSGFKRKAGTSSLTECVLNK

ATNVAHWTTPSLKCIR (anti-Human CD16 light chain variable domain)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGH (Linker)
GGGGSGGGGSGGGGS (anti-Human CD16 heavy chain variable domain)
EVQLVESGGGVVRPGGSLRLSCAASGFTFDDYGMSWVRQAPGKGLEWVS

GINWNGGSTGYADSVKGRFTISRDNAKNSLYLQMNSLRAEDTAVYYCAR

GRSLLFDYWGQGTLVTVSR

The amino acid sequence of the IL-18/TF/IL-15
fusion protein (including leader
sequence) is as follows (SEQ ID NO: 118):
(Signal peptide)
MKWVTFISLLFLFSSAYS (Human IL-18)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNED (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQNIFINTS

Example 39: Creation of IL-18/IL-15RαSu and IL-12/TF/IL-15 DNA Constructs

In a non-limiting example, IL-18/IL-15RαSu and IL-12/TF/IL-15 DNA constructs were created. The human IL-18 subunit sequences, human IL-15RαSu sequence, human IL-12 sequence, human tissue factor 219 sequence, and human IL-15 sequence were synthesized by Genewiz. A DNA construct was made linking IL-18 directly to IL-15RαSu. An additional construct was also made linking IL-12 sequence to the N-terminus coding region of human tissue factor 219 form, and further linking the IL-12/TF construct to the N-terminus coding region of IL-15. As described above, a single-chain version of IL-12 (p40-linker-p35) was used.

The nucleic acid sequence of the IL-18/IL-15RαSu construct (including signal peptide sequence) is as follows (SEQ ID NO: 189):

(Signal peptide)
ATGAAGTGGGTCACATTTATCTCTTTACTGTTCCTCTTCTCCAGCGCCT

ACAGC (Human IL-18)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT (Human IL-115R a sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG

The nucleic acid sequence of the IL-12/TF/IL-15 construct (including leader sequence) is as follows (SEQ ID NO: 190):

(Signal peptide)
ATGAAATGGGTGACCTTTATTTCTTTACTGTTCCTCTTTAGCAGCGCCT

ACTCC (Human IL-12 subunit beta (p40))
ATTTGGGAACTGAAGAAGGACGTCTACGTGGTCGAACTGGACTGGTATC

CCGATGCTCCCGGCGAAATGGTGGTGCTCACTTGTGACACCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

AAGGAGCCCAAGAATAAGACCTTTTTAAGGTGTGAGGCCAAAAACTACA

GCGGTCGTTTCACTTGTTGGTGGCTGACCACCATTTCCACCGATTTAAC

CTTCTCCGTGAAAAGCAGCCGGGGAAGCTCCGACCCTCAAGGTGTGACA

TGTGGAGCCGCTACCCTCAGCGCTGAGAGGGTTCGTGGCGATAACAAGG

AATACGAGTACAGCGTGGAGTGCCAAGAAGATAGCGCTTGTCCCGCTGC

CGAAGAATCTTTACCCATTGAGGTGATGGTGGACGCCGTGCACAAACTC

AAGTACGAGAACTACACCTCCTCCTTCTTTATCCGGGACATCATTAAGC

CCGATCCTCCTAAGAATTTACAGCTGAAGCCTCTCAAAAATAGCCGGCA

AGTTGAGGTCTCTTGGGAATATCCCGACACTTGGAGCACACCCCACAGC

TACTTCTCTTTAACCTTTTGTGTGCAAGTTCAAGGTAAAAGCAAGCGGG

AGAAGAAAGACCGGGTGTTTACCGACAAAACCAGCGCCACCGTCATCTG

TCGGAAGAACGCCTCCATCAGCGTGAGGGCTCAAGATCGTTATTACTCC

AGCAGCTGGTCCGAGTGGGCCAGCGTGCCTTGTTCC (Linker)
GGCGGTGGAGGATCCGGAGGAGGTGGCTCCGGCGGCGGAGGATCT (Human IL-12 subunit alpha (p35))
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC (Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

Example 40: Secretion of IL-18/IL-15RαSu and IL-12/TF/IL-15 Fusion Proteins

The IL-18/IL-15RαSu and IL-12/TF/IL-15 constructs were cloned into a pMSGV-1 modified retrovirus expression vector (Hughes, *Hum Gene Ther* 16:457-72, 2005 herein incorporated by reference), and the expression vector was transfected into CHO-K1 cells. Co-expression of the two constructs in CHO-K1 cells resulted in secretion of a soluble IL-12/TF/IL-15:IL-18/IL-15RαSu protein complex (referred to as 12t15/s18), which can be purified by anti-TF antibody affinity and other chromatography methods.

The amino acid sequence of the IL-18/IL-15RαSu fusion protein (including signal peptide sequence) is as follows (SEQ ID NO: 191):

(Signal peptide)
MKWVTFISLLFLFSSAYS (Human IL-18)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

TIFFQRSVPGHDNKMQFESSSYEGYFLACEKERDLFKLILKKEDELGDR

SIMFTVQNED

-continued (Human IL-115R a sushi domain)
ITCPPPMSVEHADIWVKSYSLYSRERYICNSGFKRKAGTSSLTECVLNK

ATNVAHWTTPSLKCIR

The amino acid sequence of the IL-12/TF/IL-
15fusionprotein(including leader sequence)is as
follows(SEQ ID NO: 192):(Signal peptide)
MKWVTFISLLFLFSSAYS (Human IL-12 subunit beta (p40))
IWELKKDVYVVELDWYPDAPGEMVVLTCDTPEEDGITWTLDQSSEVLG

SGKTLTIQVKEFGDAGQYTCHKGGEVLSHSLLLLHKKEDGIWSTDILK

DQKEPKNKTFLRCEAKNYSGRFTCWWLTTISTDLTFSVKSSRGSSDPQ

GVTCGAATLSAERVRGDNKEYEYSVECQEDSACPAAEESLPIEVMVDA

VHKLKYENYTSSFFIRDIIKPDPPKNLQLKPLKNSRQVEVSWEYPDTW

STPHSYFSLTFCVQVQGKSKREKKDRVFTDKTSATVICRKNASISVRA

QDRYYSSSWSEWASVPCS (Linker)
GGGGSGGGGSGGGGS (Human IL-12 subunit alpha (p35))
RNLPVATPDPGMFPCLUESQNLLRAVSNMLQKARQTLEFYPCTSEEID

HEDITKDKTSTVEACLPLELTKNESCLNSRETSFITNGSCLASRKTSF

MMALCLSSIYEDLKMYQVEFKTMNAKLLMDPKRQIFLDQNMLAVIDEL

MQALNFNSETVPQKSSLEEPDFYKTKIKLCILLHAFRIRAVTIDRVMS

YLNAS (Human Tissue Factor 219)
SGTTNTVAAYNLTWKSTNFKTILEWEPKPVNQVYTVQISTKSGDWKSK

CFYTTDTECDLTDEIVKDVKQTYLARVFSYPAGNVESTGSAGEPLYEN

SPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAV

IPSRTVNRKSTDSPVECMGQEKGEFRE (Human IL-15)
NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS

In some cases, the leader peptide is cleaved from the intact polypeptide to generate the mature form that may be soluble or secreted.

Example 41: Recombinant Protein Quantitation of the 18t15-12s16 Complex

Figure 47:
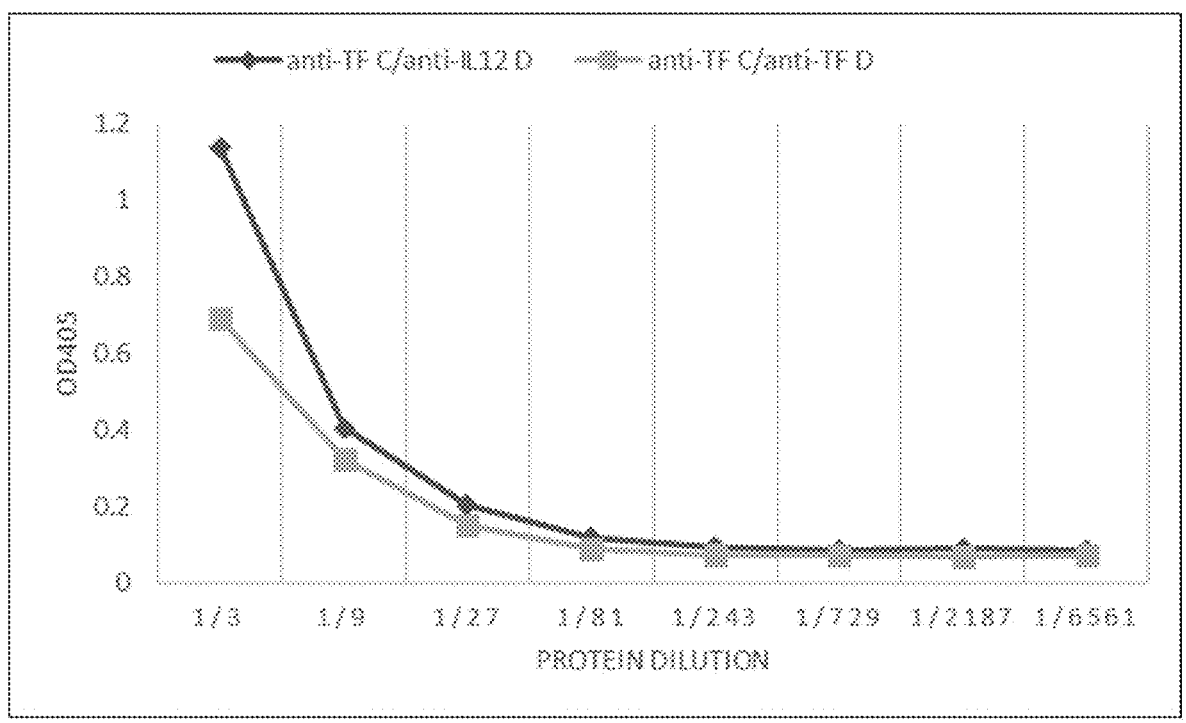
FIG. 47 shows a sandwich ELISA for the 18t15-12s16 complex, comprising an anti-human tissue factor capture antibody and a biotinylated anti-human IL-12 (dark line) or an anti-human tissue factor detection antibody (light line).

The 18t15-12s16 complex (comprising IL-12/IL-15RαSu/αCD16scFv; IL-18/TF/IL-15) was detected and quantified using standard sandwich ELISA methods (see FIG. 47). Anti-human tissue factor antibody/IL-2 or anti-TF antibody/IL-18 served as the capture antibody and biotinylated anti-human IL-12 or IL-18 antibody (BAF 219, D045-6, both R&D Systems) served as the detection antibody. Tissue factor was also detected using an anti-human tissue factor antibody (143), and anti-human tissue factor antibody detection antibody.

Example 42: Creation of TGFβRII/IL-15RαSu and IL-21/TF/IL-15 DNA Constructs

Figure 48:
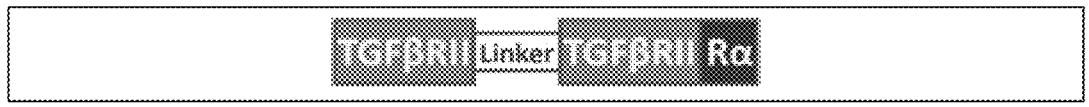
FIG. 48 shows a schematic diagram of an exemplary TGFβRII/IL-15RαSu DNA construct.

In a non-limiting example, a TGFβRII/IL-15RαSu DNA construct was created (see FIG. 48). The human TGFβRII dimer and human IL-21 sequences were obtained from the UniProt website and DNA for these sequences was synthesized by Genewiz. A DNA construct was made linking the TGFβRII to another TGFβRII with a linker to generate a single chain version of TGFβRII and then directly linking the TGFβRII single chain dimer sequence to the N-terminal coding region of IL-15RαSu.

The nucleic acid sequences of the TGFβRII/IL-15RαSu construct (including signal sequence) is as follows (SEQ ID NO: 133):

(Signal peptide)
ATGAAGTGGGTGACCTTCATCAGCCTGCTGTTCCTGTTCTCCAGCGCCT

ACTCC (Human TGF βRII—1$^{st}$ fragment)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCACG

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT (Linker)
GGAGGTGGCGGATCCGGAGGTGGAGGTTCTGGTGGAGGTGGGAGT (Human TGF βRII—2$^{nd}$ fragment)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCACA

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC (Human IL-15R a sushi domain)
ATCACGTGTCCTCCTCCTATGTCCGTGGAACACGCAGACATCTGGGTCA

AGAGCTACAGCTTGTACTCCAGGGAGCGGTACATTTGTAACTCTGGTTT

CAAGCGTAAAGCCGGCACGTCCAGCCTGACGGAGTGCGTGTTGAACAAG

GCCACGAATGTCGCCCACTGGACAACCCCCAGTCTCAAATGTATTAGA

Figure 49:
FIG. 49 shows a schematic diagram of an exemplary IL-21/TF/IL-15 construct.

Additionally, an IL-21/TF/IL-15 construct was made linking the IL-21 sequence to the N-terminus coding region of tissue factor 219, and further linking the IL-21/TF construct to the N-terminus coding region of IL-15 (see FIG. 49). The nucleic acid sequence of the IL-21/TF/IL-15 construct (including leader sequence) is as follows (SEQ ID NO: 129):

(Signal peptide)
ATGAAGTGGGTGACCTTCATCAGCCTGCTGTTCCTGTTCTCCAGCGCCT

ACTCC (Human IL-21)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC (Human Tissue Factor 219)
TCCGGCACCACCAATACCGTGGCCGCTTATAACCTCACATGGAAGAGCA

CCAACTTCAAGACAATTCTGGAATGGGAACCCAAGCCCGTCAATCAAGT

TTACACCGTGCAGATCTCCACCAAATCCGGAGACTGGAAGAGCAAGTGC

TTCTACACAACAGACACCGAGTGTGATTTAACCGACGAAATCGTCAAGG

ACGTCAAGCAAACCTATCTGGCTCGGGTCTTTTCCTACCCCGCTGGCAA

TGTCGAGTCCACCGGCTCCGCTGGCGAGCCTCTCTACGAGAATTCCCCC

GAATTCACCCCTTATTTAGAGACCAATTTAGGCCAGCCTACCATCCAGA

GCTTCGAGCAAGTTGGCACCAAGGTGAACGTCACCGTCGAGGATGAAAG

GACTTTAGTGCGGCGGAATAACACATTTTTATCCCTCCGGGATGTGTTC

GGCAAAGACCTCATCTACACACTGTACTATTGGAAGTCCAGCTCCTCCG

GCAAAAAGACCGCTAAGACCAACACCAACGAGTTTTTAATTGACGTGGA

CAAAGGCGAGAACTACTGCTTCAGCGTGCAAGCCGTGATCCCTTCTCGT

ACCGTCAACCGGAAGAGCACAGATTCCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCCTTGTAAGGTGACCGCCATGAAATGTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

Example 43: Secretion of TGFβRII/IL-15RαSu and IL-21/TF/IL-15 Fusion Proteins

Figure 50:
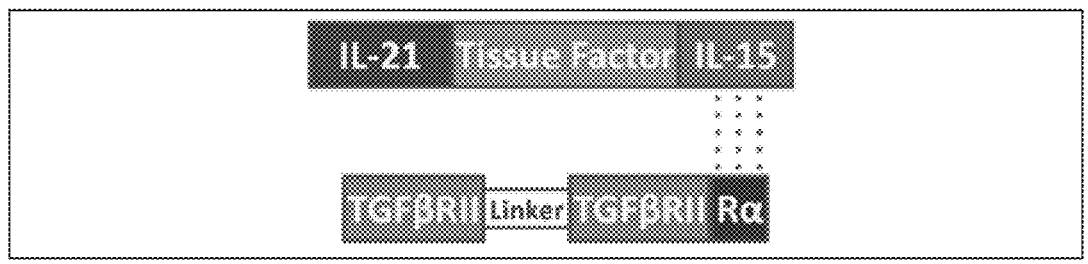
FIG. 50 shows a schematic diagram of the interaction between the exemplary IL-IL-21/TF/IL-15 and TGFβRII/IL-15RαSu constructs.
Figure 51:
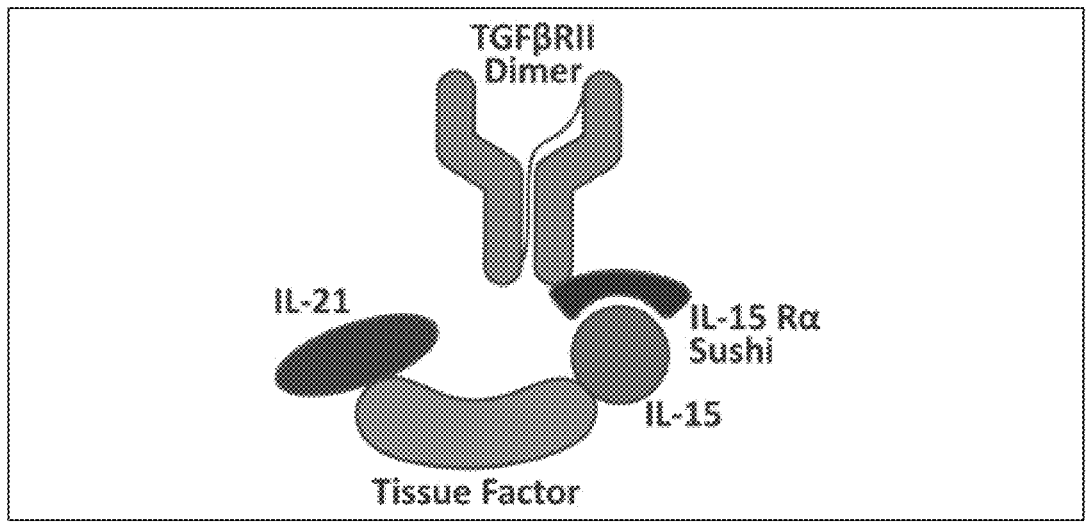
FIG. 51 shows a schematic diagram of the interaction between the exemplary TGFβRII/IL-15RαSu and IL-21/TF/IL-15 fusion proteins, resulting in an IL-21/TF/IL-15/TGFβRII/IL-15RαSu complex (21t15-TGFRs).

The TGFβRII/IL-15RαSu and IL-21/TF/IL-15 DNA constructs were cloned into a pMSGV-1 modified retrovirus expression vector (as described in Hughes et al., *Hum Gene Ther* 16:457-72, 2005, herein incorporated by reference), and the expression vector was transfected into CHO-K1 cells. Co-expression of the two constructs in CHO-K1 cells resulted in secretion of the soluble IL-21/TF/IL-15: TGFβRII/IL-15RαSu protein complex (referred to as 21t15-TGFRs, see FIGS. 50 and 51). The 21t15-TGFRs complex was purified from CHO-K1 cell culture supernatant using anti-TF antibody affinity chromatography and other chromatography methods.

The amino acid sequence of the TGFβRII/IL-15RαSu construct (including signal peptide sequence) is as follows (SEQ ID NO: 132):

(Signal peptide)
MKWVTFISLLFLFSSAYS (Human TGF βRII-1$^{st}$ fragment)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD (Linker)
GGGGSGGGGSGGGGS (Human TGF βRII-2$^{nd}$ fragment)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNK

ATNVAHWTTPSLKCIR

The amino acid sequence of the mature IL-21/TF/IL-15fusion protein (including signal peptide sequence)is as follows (SEQ ID NO: 128):

(Signal peptide)
MKWVTFISLLFLFSSAYS (Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

In some cases, the leader peptide is cleaved from the intact polypeptide to generate a mature form that may be soluble or secreted.

Example 44: Purification of 21t15-TGFRs by Immunoaffinity Chromatography

An anti-TF antibody affinity column was connected to a GE Healthcare AKTA™ Avant protein purification system. The flow rate was 4 mL/min for all steps except the elution step, which was 2 mL/min.

Figure 52:
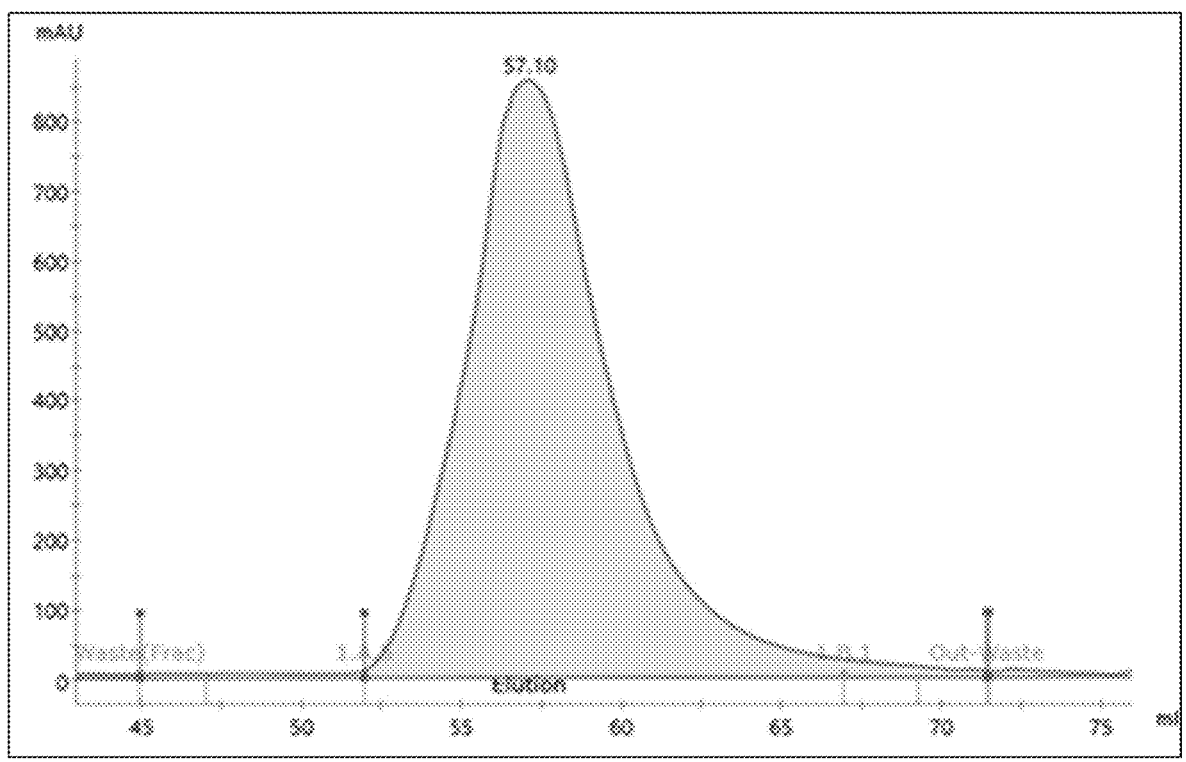
FIG. 52 shows a chromatograph of 21t15-TGFRs purification elution from an anti-TF antibody affinity column.

Cell culture harvest of 21t15-TGFRs was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was then neutralized to pH 7.5-8.0 by adding 1M Tris base. The neutralized sample was then buffer exchanged into PBS using Amicon® centrifugal filters with a 30 KDa molecular weight cutoff. FIG. 52 shows that the 21t15-TGFRs complex binds anti-TF antibody affinity column, wherein TF is a 21t15-TGFRs binding partner. The buffer-exchanged protein sample is stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide, and stored at 2-8° C.

Example 45: Size Exclusion Chromatography of 21t15-TGFRs

Figure 53:
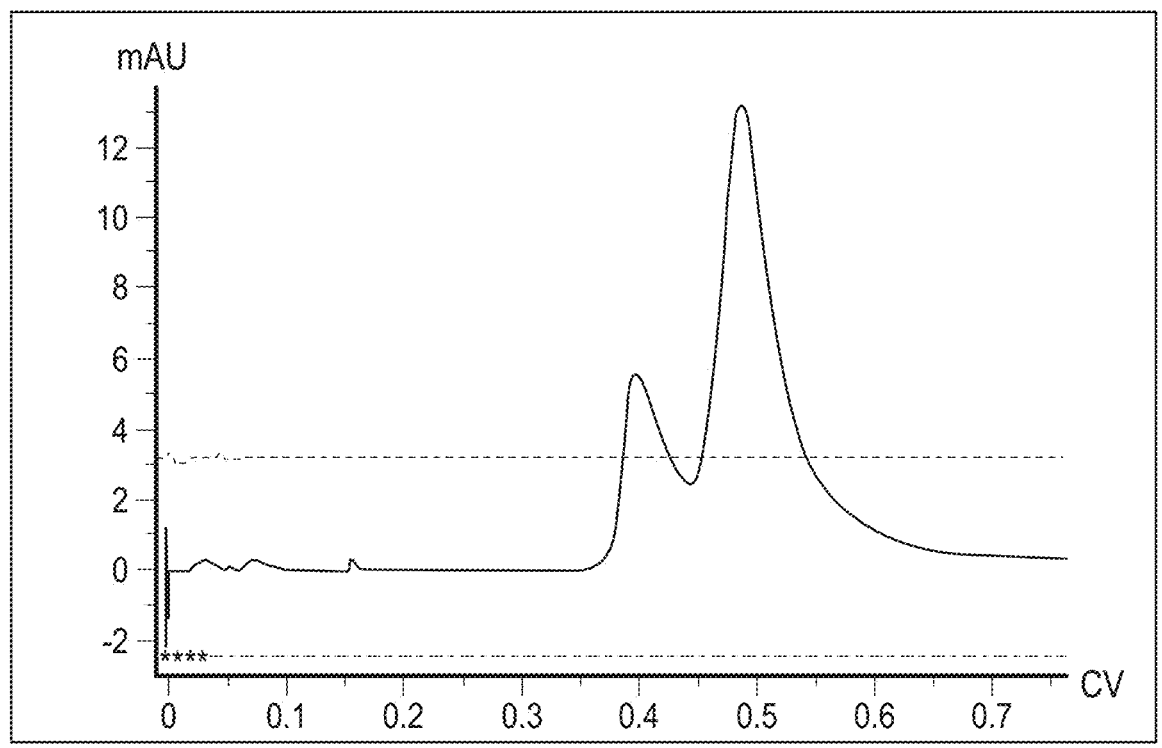
FIG. 53 shows an exemplary 21t15-TGFRs size exclusion chromatograph showing a main protein peak and a high molecular weight peak

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.8 mL/min. A capillary loop was used to inject 2004, of 1 mg/mL of 21t15-TGFRs complex onto the column. The injection was then chased with 1.25 column volumes of PBS. The SEC chromatograph was shown in FIG. 53. There were two protein peaks, likely representing a monomer and dimer forms of 21t15-TGFRs.

Example 46: SDS-PAGE of 21t15-TGFRs

Figure 10:
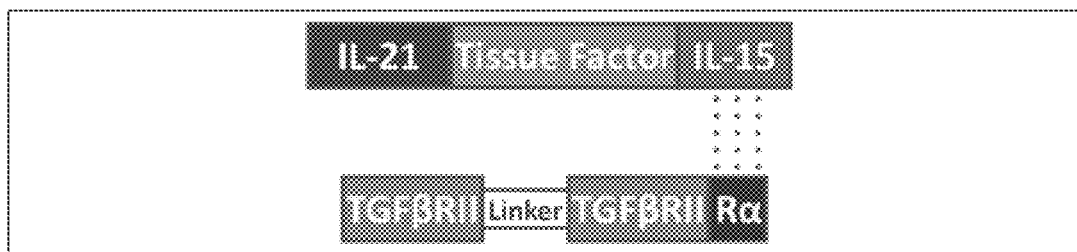
FIG. 10 shows a schematic diagram of the interaction between the exemplary TGF-βRII/IL-15RαSu and IL-21/TF/IL-15 DNA constructs.
Figure 11:
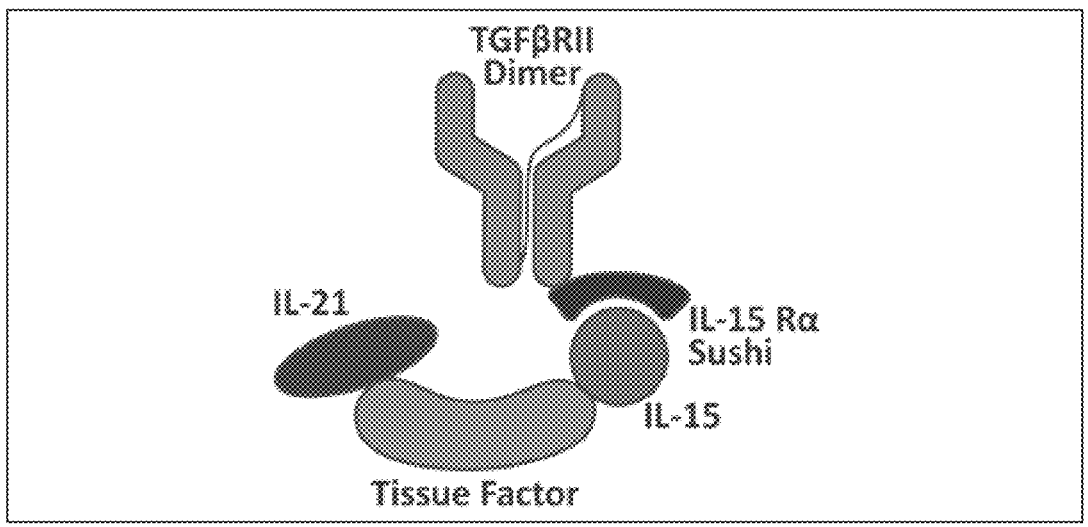
FIG. 11 shows a schematic diagram of the interaction between the exemplary TGF-βRII/IL-15RαSu and IL-21/TF/IL-15 fusion proteins resulting in an IL-21/TF/IL-15: TGF-βRII/IL-15RαSU complex (21t15-TGFRs).
Figure 54:
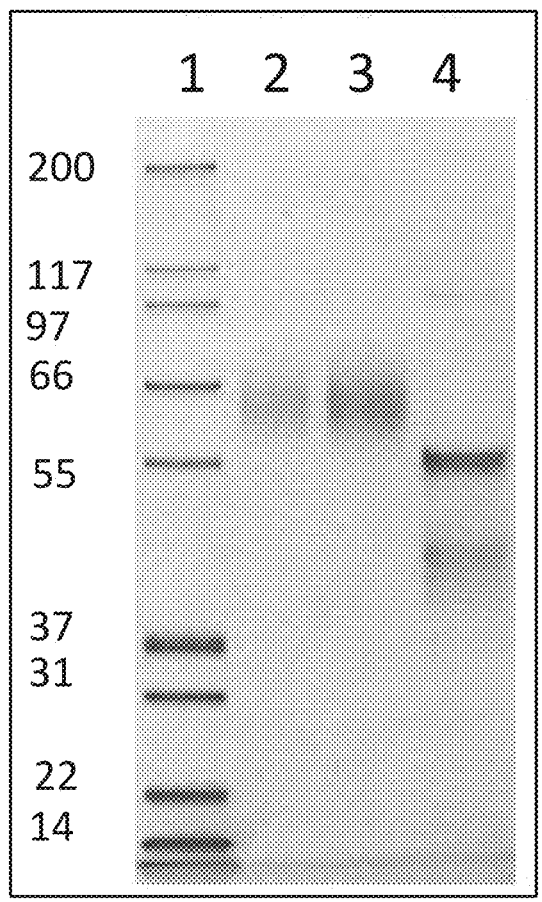
FIG. 54 shows an example of a 4-12% SDS-PAGE of the 21t15-TGFRs complex following disulfide bond reduction. Lane 1: Mark12 unstained marker (numbers on the left side indicate molecular weights in kDa); Lane 2: 21t15-TGFRs (0.5 μg); Lane 3: 21t15-TGFRs (1 μg); Lane 4: 21t15-TGFRs, deglycosylated (1 μg), wherein the MW was the expected size of 53 kDa and 39.08 kDa.
Figure 55:
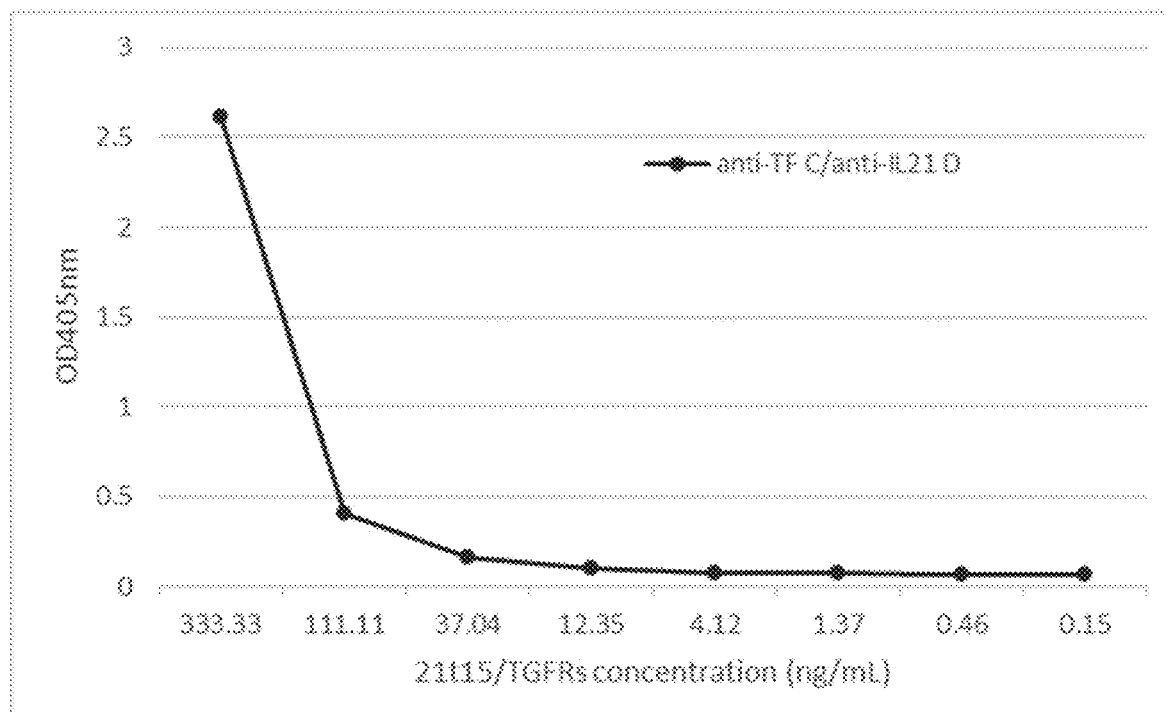
FIG. 55 shows a sandwich ELISA for the 21t15-TGFRs complex, comprising an anti-human tissue factor capture antibody and a biotinylated anti-human IL-21 detection antibody (13-7218-81, BioLegend).
Figure 56:
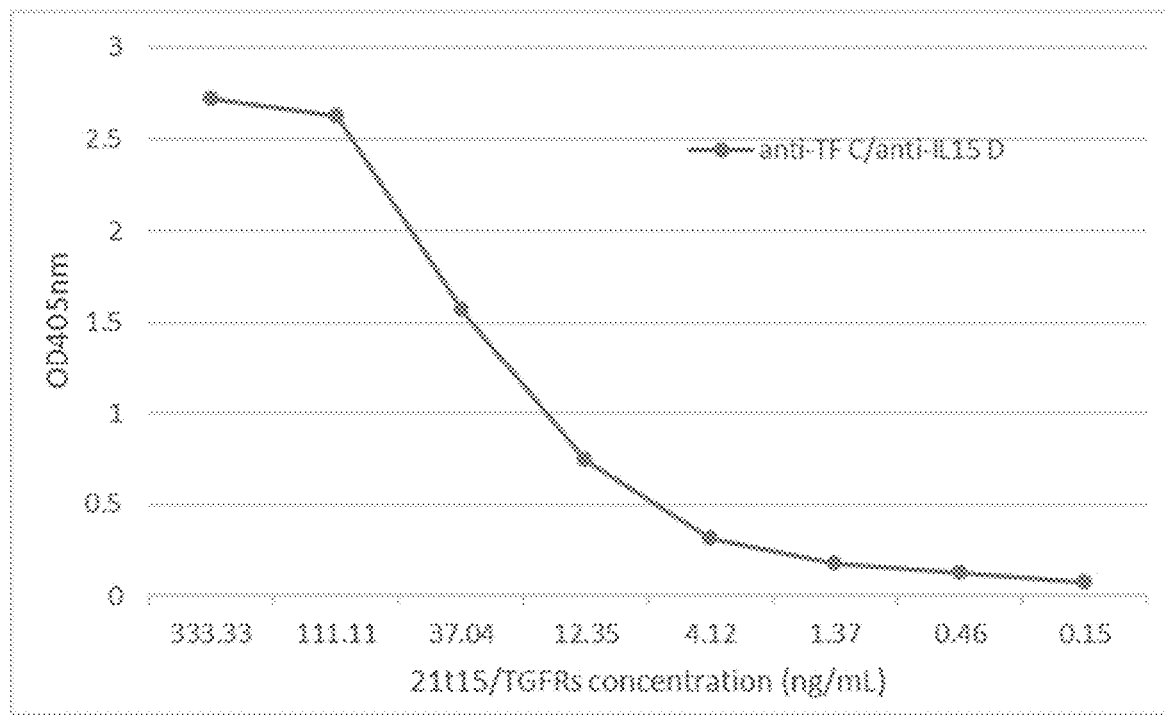
FIG. 56 shows a sandwich ELISA for the 21t15-TGFRs complex, comprising an anti-human tissue factor capture antibody and a biotinylated anti-human IL-15 detection antibody (BAM 247, R&D Systems).
Figure 57:
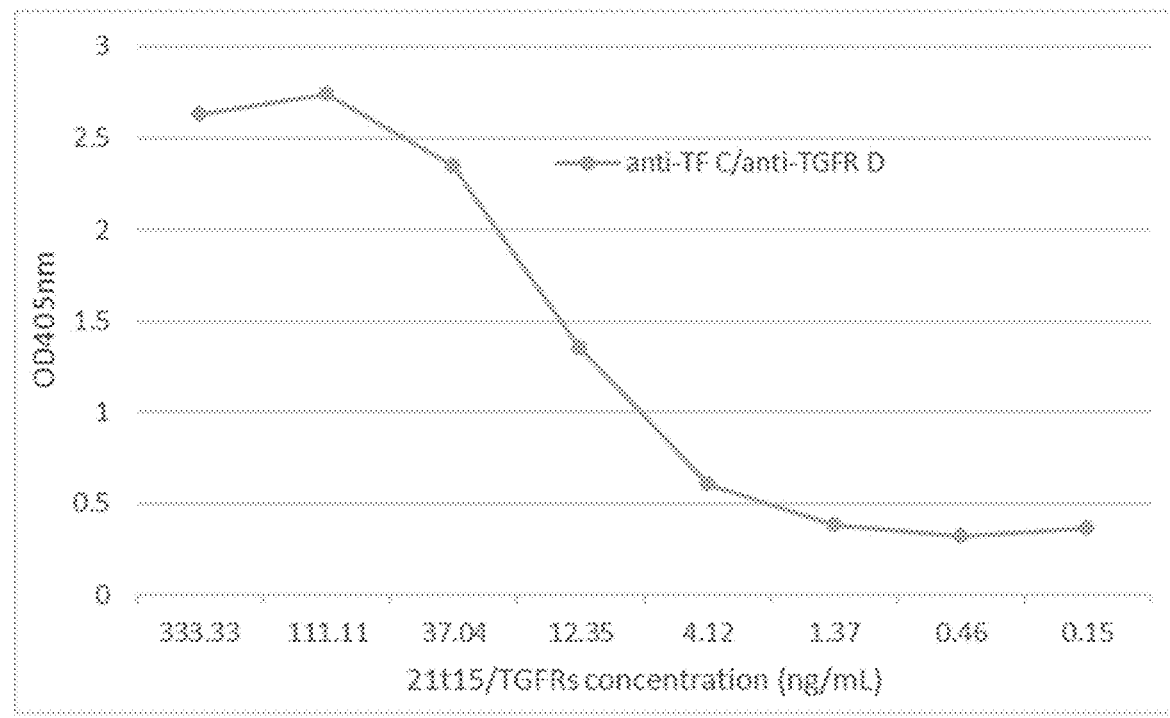
FIG. 57 shows a sandwich ELISA for the 21t15-TGFRs complex, comprising an anti-human tissue factor capture antibody and a biotinylated anti-human TGFβRII detection antibody (BAF241, R&D Systems).
Figure 58:
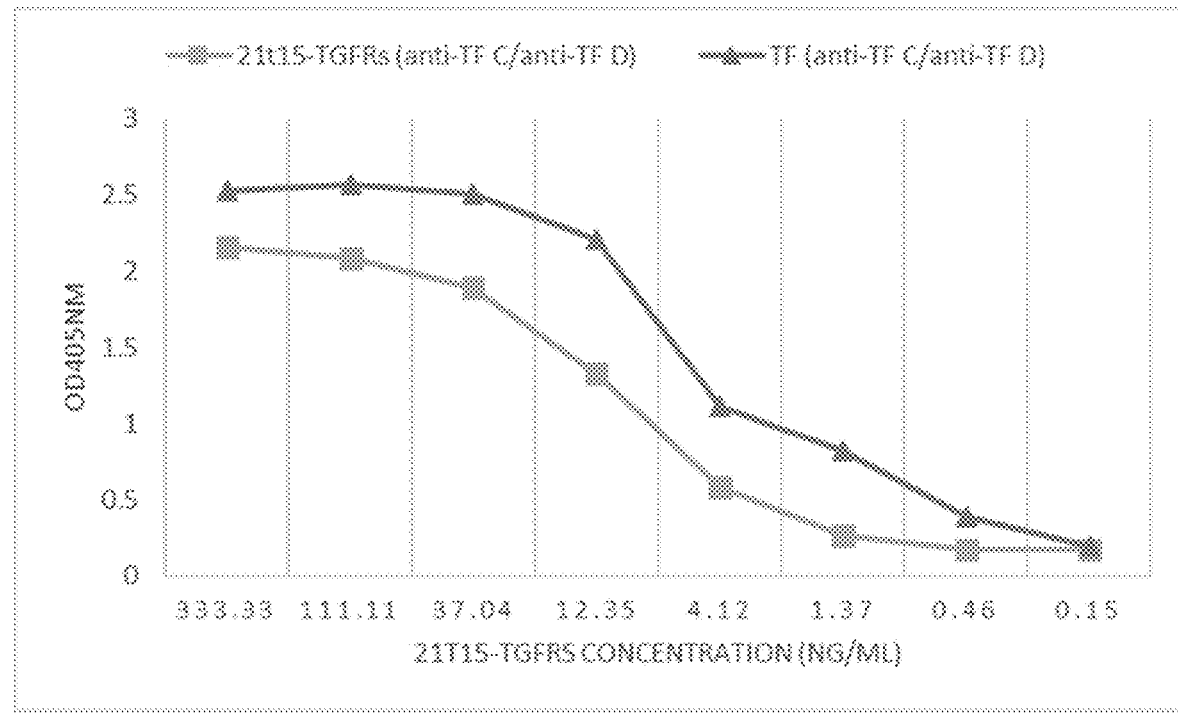
FIG. 58 shows a sandwich ELISA for the 21t15-TGFRs complex, comprising an anti-human tissue factor (I43) capture antibody and an anti-human tissue factor detection antibody.

To determine the purity and protein molecular weight, the purified 21t15-TGFRs complex protein sample was analyzed using 4-12% NuPage Bis-Tris protein gel SDS-PAGE under reduced conditions. The gel was stained with InstantBlue™ for about 30 min, followed by destaining overnight in purified water. FIG. 54 shows an example SDS gel of anti-TF antibody affinity purified 21t15-TGFRs, with bands at 39.08 kDa and 53 kDa. Glycosylation of 21t15-TGFRs in CHO cells was confirmed using the Protein Deglycosylation Mix II kit (New England Biolabs) and the manufacturer's instructions. FIG. 10 shows an example SDS PAGE of deglycosylated and non-deglycosylated 21t15-TGFRs. Deglycosylation reduces the molecular weight of 21t15-TGFRs, as seen in lane 4 of FIG. 54.

Example 47: Recombinant Protein Quantitation of 21t15-TGFRs Complexes

The 21t15-TGFRs complex was detected and quantified using standard sandwich ELISA methods (see FIGS. 55-59). Anti-human tissue factor antibody served as the capture antibody and biotinylated anti-human IL-21, IL-15, or TGFβRII served as the detection antibody. Tissue factor was also detected using an anti-human tissue factor capture antibody (143), and anti-human tissue factor antibody detection antibody. The I43/anti-TF Ab ELISA was compared to purified tissue factor at similar concentrations.

Example 48: Immunostimulatory Capacity of the 21t15-TGFRs Complex

Figure 59:
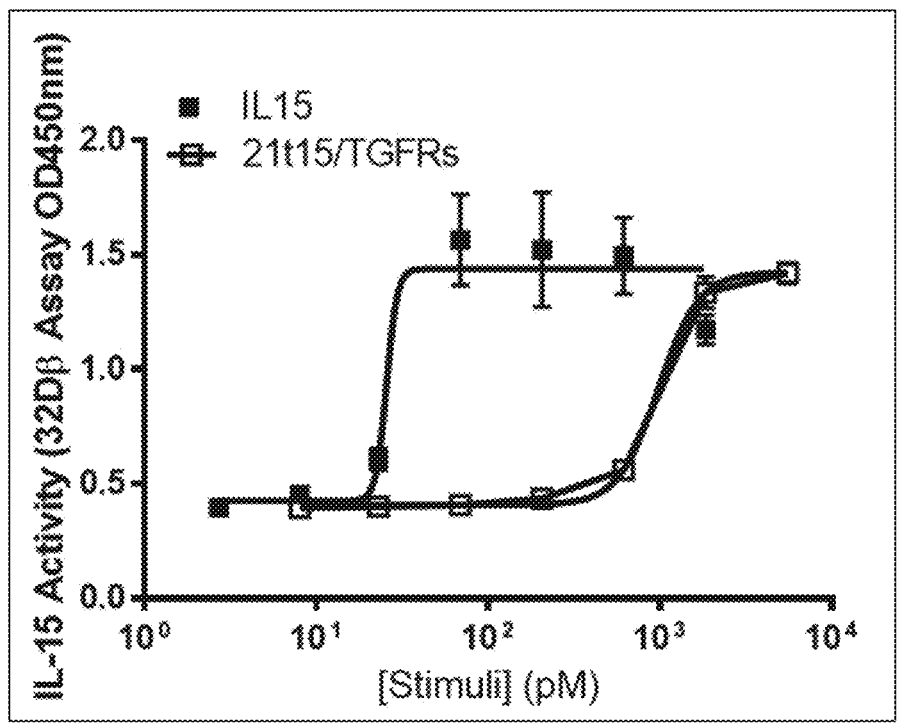
FIG. 59 shows IL-15-dependent proliferation of 32Dβ cells mediated by the 21t15-TGFRs complex (open squares) compared to IL-15 (black squares).

To assess the IL-15 immunostimulatory activity of the 21t15-TGFRs complexes, increasing concentrations of 21t15-TGFRs was added to 32Dβ cells ($10^4$ cell/well) in 200 µL IMDM:10% FBS media and cells were incubated for 3 days at 37° C. On the fourth day, WST-1 proliferation reagent (10 µL/well) then was added and after 4 hours, absorbance was measured at 450 nm to determine cell proliferation based on cleavage of WST-1 to a soluble formazan dye. Bioactivity of the human recombinant IL-15 was assessed as a positive control. As shown in FIG. 59, 21t15-TGFRs demonstrated IL-15-dependent 32Dβ cell proliferation. The 21t15-TGFRs complex was reduced compared to that of human recombinant IL-15, possibly due to the linkage of IL-21 and tissue factor to the IL-15 domain.

Figure 60:
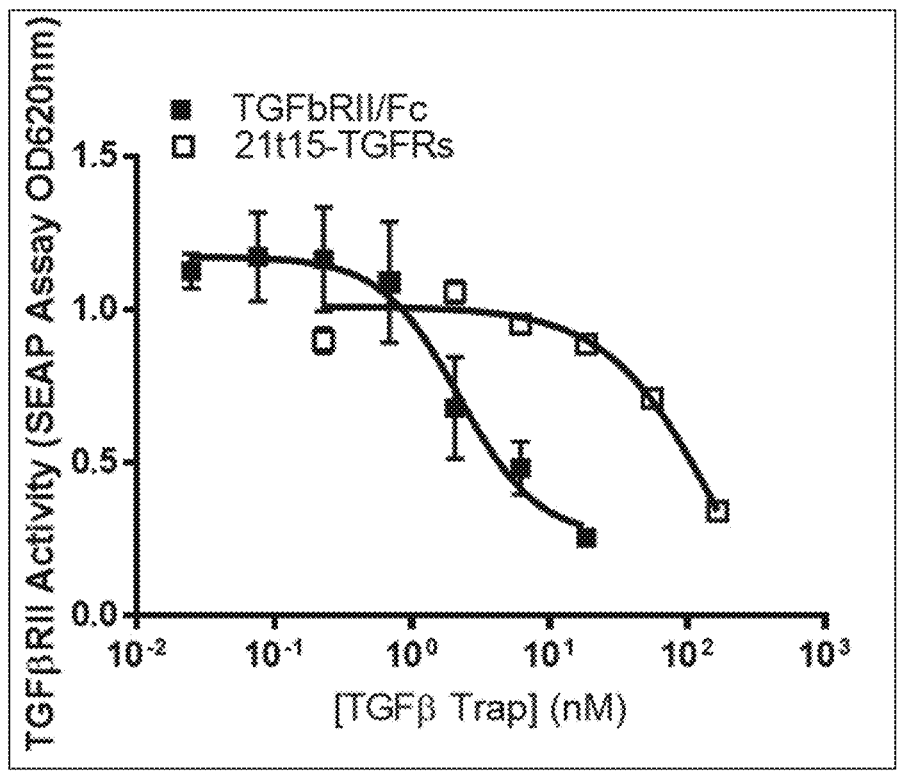
FIG. 60 shows biological activity of the TGFβRII domain within the 21t15-TGFRs complex (open squares). TGFβRII/Fc (black squares) served as a positive control.

Additionally, HEK-Blue TGFβ reporter cells (hkb-tgfb, InvivoGen) were used to measure the ability of 21t15-TGFRs to block TGFβ1 activity (FIG. 60). Increasing concentrations of 21t15-TGFRs were mixed with 0.1 nM of TGFβ1 and added to HEK-Blue TGFβ reporter cells (2.5× $10^4$ cell/well) in 200 µL IMDM:10% heat-inactivated FBS media. Cells were incubated overnight at 37° C. The next day, 20 µl of induced HEK-Blue TGFβ reporter cell supernatant was added to 180 µl of QUANTI-Blue (InvivoGen) and incubated for 1-3 hours at 37° C. 21t15-TGFRs activity was assessed by measuring absorbance at 620 nm. Human recombinant TGFβRII/Fc activity was assessed as a positive control.

These results demonstrate that TGFβRII domain of the 21t15-TGFRs complex retains its ability to trap TGFβ1. The ability of 21t15-TGFRs to block TGFβ1 activity was reduced compared to that of human recombinant TGFβRII/Fc, possibly due to the linkage of TGFβRII to the IL-15Rα sushi domain.

Example 49: Induction of Cytokine-Induced Memory-Like NK Cells by the 21t15-TGFRs Complex Cytokine-induced memory-like NK cells can be induced ex vivo following overnight stimulation of purified NK cells with saturating amounts of cytokines. These memory-like properties can be measured through expression of IL-2 receptor α (IL-2Rα, CD25), CD69 (and other activation markers), and increased IFN-γ production. To evaluate the ability of 21t15-TGFRs complexes to promote generation of cytokine-induced memory-like NK cells, purified human NK cells (>95% CD56+) were stimulated for 14-18 hours with 1 nM to 100 nM of the 21t15-TGFRs complex. Cell-surface CD25 and CD 69 expression and intracellular IFN-γ levels were assessed by antibody-staining and flow cytometry.

Figure 61A:
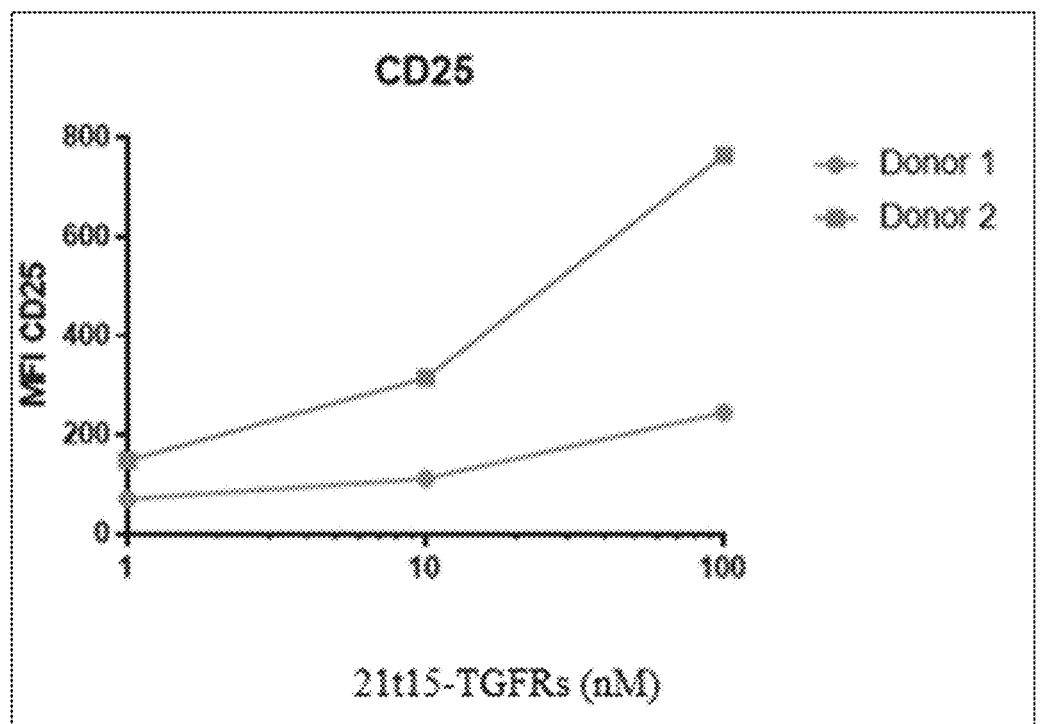
FIG. 61A shows a flow cytometry graph of cell-surface CD25 expression of NK cells induced by the 21t15-TGFRs complex.
Figure 61B:
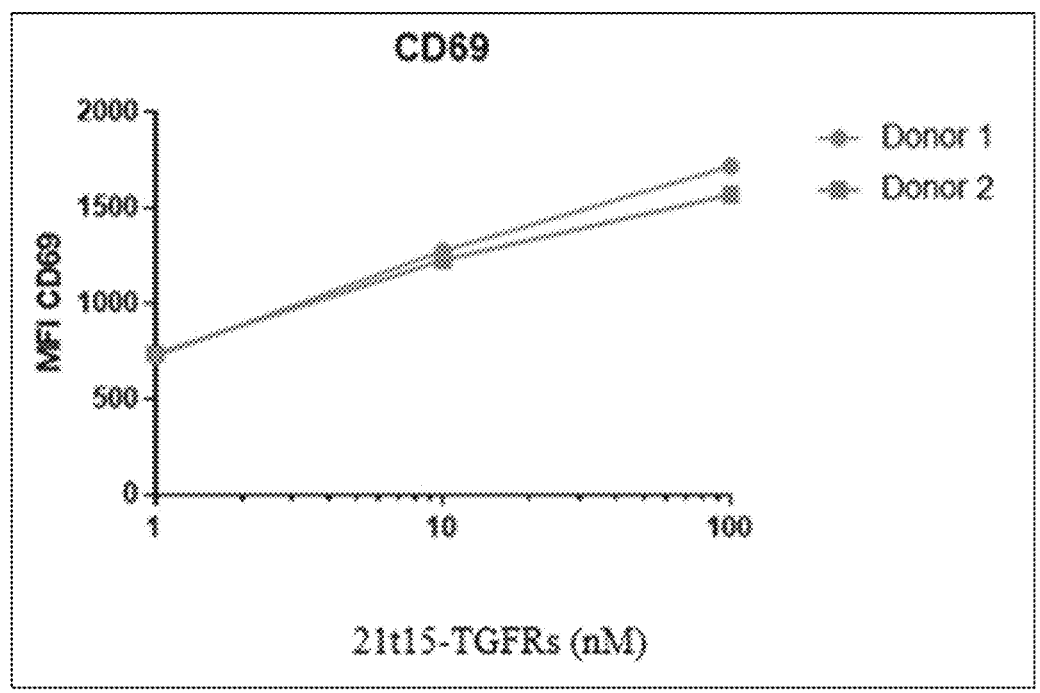
FIG. 61B shows a flow cytometry graph of cell-surface CD69 expression of NK cells induced by the 21t15-TGFRs complex.

Fresh human leukocytes were obtained from a blood bank and CD56+ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 (BioLegend). Cells were counted and resuspended in 0.2×$10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-21 (50 ng/mL) (Biolegend) and hIL-15 (50 ng/mL) (NCI) or with 1 nM, 10 nM, or 100 nM 21t15-TGFRs complex overnight at 37° C., 5% $CO_2$ for 14-18 hrs. The cells were then harvested and surface stained for CD56-BV421, CD16-BV510, CD25-PE, CD69-APCFire750 for 30 minutes. After staining, cells were washed (1500 RPM for 5 minutes at room temperature) in FACS buffer (1×PBS (Hyclone) with 0.5% BSA (EMD Millipore) and 0.001% sodium azide (Sigma)). After two washes, cells were analyzed using a BD FACSCelesta™ flow cytometer (Plotted Data-Mean Fluorescence Intensity, see FIGS. 61A and 61B).

Figure 62:
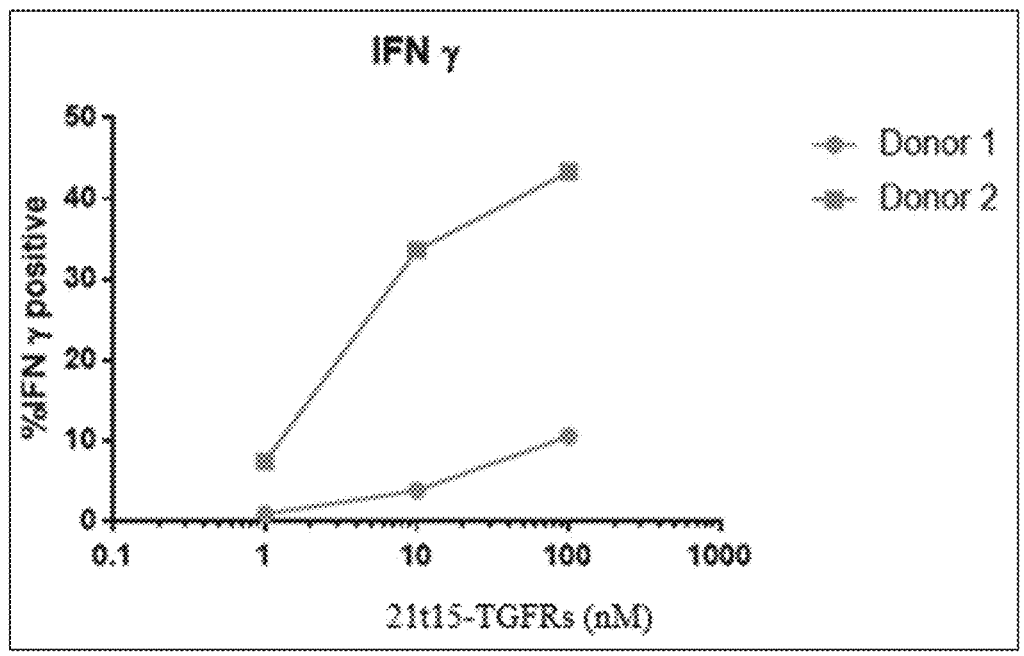
FIG. 62 shows a flow cytometry graph of intracellular interferon gamma expression of NK cells induced by the 21t15-TGFRs complex.

Fresh human leukocytes were obtained from a blood bank and CD56+ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in 0.2×10⁶/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-21 (50 ng/mL) (Biolegend) and hIL-15 (50 ng/mL) (NCI) or with 1 nM, 10 nM, or 100 nM 21t15-TGFRs complex overnight at 37° C., 5% CO₂ for 14-18 hrs. The cells were then treated with 10 μg/mL of Brefeldin A (Sigma) and 1× of Monensin (eBioscience) for 4 hrs. Cells were harvested and surface stained with CD56-BV421, CD16-BV510, CD25-PE, CD69-APCFire750 specific antibodies for 30 minutes. After staining, cells were washed (1500 RPM for 5 minutes at room temperature) in FACS buffer (1×PBS (Hyclone) with 0.5% BSA (EMD Millipore) and 0.001% sodium azide (Sigma)) and fixed for 10 minutes at room temperature. After fixation, cells were washed (1500 RPM for 5 minutes at room temperature) with 1× permeabilized buffer (eBioscience) and stained for intracellular IFN-γ-PE Ab (Biolegend) for 30 minutes at room temperature. Cells were washed once again with 1× permeabilized buffer and then washed with FACS buffer. Cell pellets were resuspended in 300 μls of FACS Buffer and analyzed using a BD FACSCelesta™ flow cytometer. (Plotted % of IFN-γ Positive Cells, see FIG. 62).

Example 50: In Vitro Cytotoxicity of NK Cells Against Human Tumor Cells

Figure 63:
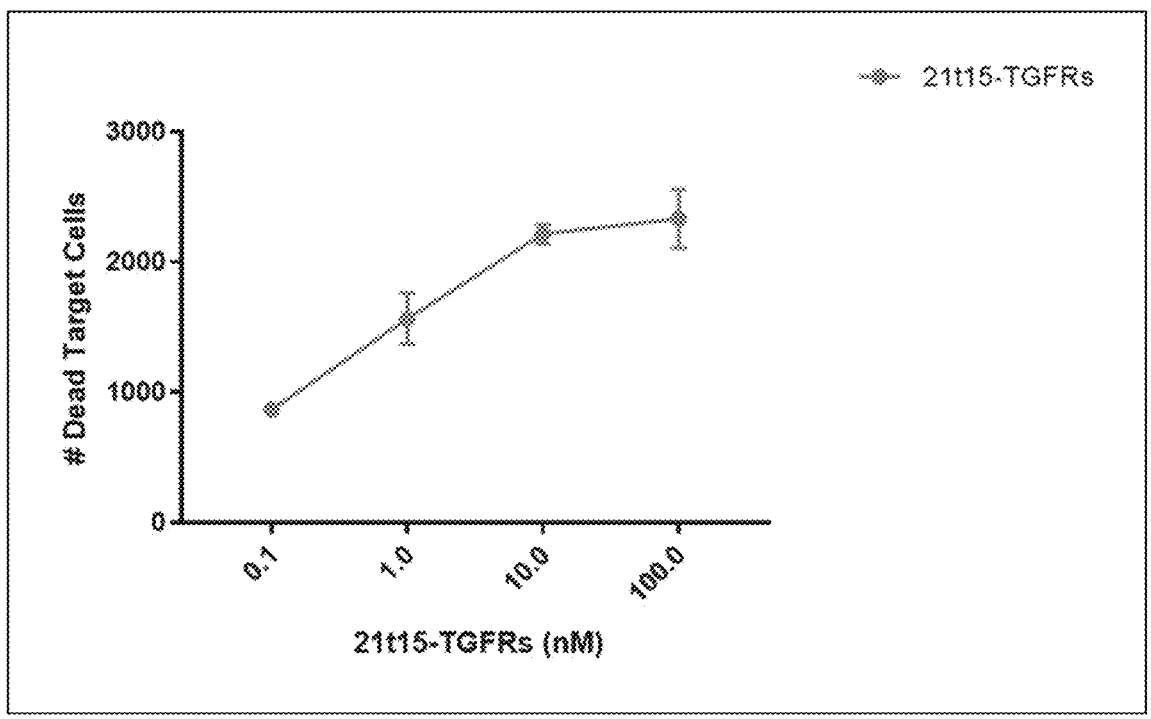
FIG. 63 shows a bar graph showing cytotoxicity of 21t15-TGFRs-induced human NK cells against K562. K562 cells (labeled with Celltrace violet) at 1×10^5/well and human NK cells (NK cells were isolated from human blood buffy coat with StemCell human NK cell purification kit) at 2×10^5/well were incubated with 18t15-12s in RPMI-10 for 20 hours. Cell mixtures were harvested, stained with propidium iodide (PI), and analyzed using a BD FACSCelesta™ flow cytometer. The graph represents duplicated samples.
Figure 64:
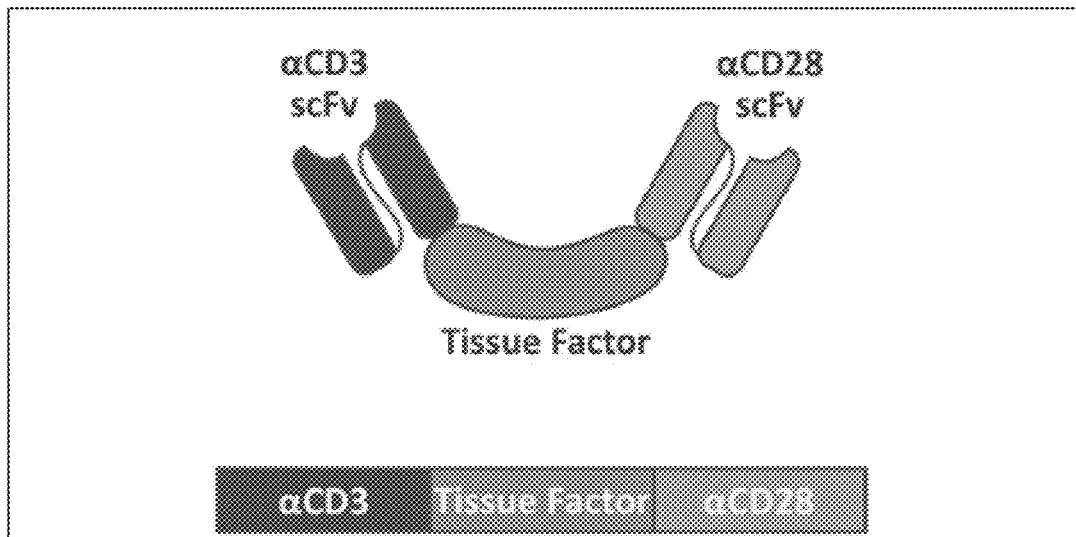
FIG. 64 are schematic diagrams of an exemplary αCD3scFv/TF/αCD28scFv single-chain chimeric polypeptide.

K562 (CellTrace violet labelled), human myelogenous leukemia cells, were incubated with purified human NK cells (using StemCell human NK cell purification kit (E:T ratio; 2:1)) in the presence of increasing concentrations of the 21t15-TGFRs complex. After 20 hours, the cultures were harvested, stained with propidium iodide (PI), and assessed by flow cytometry. As shown in FIG. 63, the 21t15-TGFRs complex induced human NK cytotoxicity against K562, as compared to control.

Example 51: Creation of an IL-21/TF Mutant/IL-15 DNA Construct and Resulting Fusion Protein Complex with TGFβRII/IL-15RαSu In a non-limiting example, an IL-21/TF mutant/IL-15 DNA construct was made by linking IL-21 directly to the N-terminus coding region of a tissue factor 219 mutant, and further linking the IL-21/TF mutant to the N-terminus coding region of IL-15.

The nucleic acid sequence of the IL-21/TF mutant/IL-15 construct (including signal peptide sequence) is as follows (SEQ ID NO: 193, shaded nucleotides are mutant and the mutant codons are underlined):

```
(Signal sequence)
ATGAAGTGGGTGACCTTCATCAGCCTGCTGTTCCTGTTCTCCAGCGCCT

ACTCC (Human IL-21)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC (Human Tissue Factor 219 mutants)
TCCGGCACCACCAATACCGTGGCCGCTTATAACCTCACATGGAAGAGCA

CCAACTTCGCGACAGCTCTGGAATGGGAACCCAAGCCCGTCAATCAAGT

TTACACCGTGCAGATCTCCACCAAATCCGGAGACTGGAAGAGCAAGTGC

TTCTACACAACAGACACCGAGTGTGCTTTAACCGACGAAATCGTCAAGG

ACGTCAAGCAAACCTATCTGGCTCGGGTCTTTTCCTACCCCGCTGGCAA

TGTCGAGTCCACCGGCTCCGCTGGCGAGCCTCTCTACGAGAATTCCCCC

GAATTCACCCCTTATTTAGAGACCAATTTAGGCCAGCCTACCATCCAGA

GCTTCGAGCAAGTTGGCACCAAGGTGAACGTCACCGTCGAGGATGAAAG

GACTTTAGTGGCGCGGAATAACACAGCTTTATCCCTCCGGGATGTGTTC

GGCAAAGACCTCATCTACACACTGTACTATTGGAAGTCCAGCTCCTCCG

GCAAAAAGACCGCTAAGACCAACACCAACGAGTTTTTAATTGACGTGGA

CAAAGGCGAGAACTACTGCTTCAGCGTGCAAGCCGTGATCCCTTCTCGT

ACCGTCAACCGGAAGAGCACAGATTCCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC
```

The amino acid sequence of the IL-21/TF mutant/IL-15 construct (including signal peptide sequence) is as follows (SEQ ID NO: 194, substituted residues are shaded):

(Signal peptide)
MKWVTFISLLFLFSSAYS (Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS (Human Tissue Factor 219)
SGTTNTVAAYNLTWKSTNFATALEWEPKPVNQVYTVQISTKSGDWKSKC

FYTTDTECALTDEIVKDVKQTYLARVFSYPAGNVESTGSAGEPLYENSP

EFTPYLETNLGQPTIQSFEQVGTKVNVTVEDERTLVARNNTALSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

In some cases, the leader peptide is cleaved from the intact polypeptide to generate a mature form that may be soluble or secreted.

In some embodiments, the IL-21/TF mutant/IL-15 DNA construct may be combined with an TGFβRII/IL-15RαSu DNA construct, transfected into cells using a retroviral vector as described above, and expressed as IL-21/TF mutant/IL-15 and TGFβRII/IL-15RαSu fusion proteins. The IL-15RαSu domain of the TGFβRII/IL-15RαSu fusion protein binds to the IL-15 domain of the IL-21/TF mutant/IL-15 fusion protein to create an IL-21/TF mutant/IL-15:TGFβRII/IL-15RαSu complex.

Example 52: Creation of IL-21/IL-15RαSu and TGFβRII/TF/IL-15 DNA Constructs and the Resulting Fusion Protein Complex In a non-limiting example, an IL-21/IL-15RαSu DNA construct was made by linking IL-21 directly to the IL-15RαSu subunit sequence. The nucleic acid sequence of the IL-21/IL-15RαSu construct (including signal sequence) is as follows (SEQ ID NO: 148):

(Signal sequence)
ATGAAGTGGGTGACCTTCATCAGCCTGCTGTTCCTGTTCTCCAGCGCCT

ACTCC (Human IL-21)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG

The amino acid sequence of the IL-21/IL-15RαSu construct (including signal peptide sequence) is as follows (SEQ ID NO: 147):

(Signal peptide)
MKWVTFISLLFLFSSAYS (Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLNK

ATNVAHWTTPSLKCIR

In some cases, the leader peptide is cleaved from the intact polypeptide to generate a mature form that may be soluble or secreted.

In some embodiments, the IL-21/IL-15RαSu DNA construct may be combined with a TGFβRII/TF/IL-15 DNA construct, transfected into a retroviral vector as described above, and expressed as IL-21/IL-15RαSu and TGFβRII/TF/IL-15 fusion proteins. The IL-15RαSu domain of the IL-21/IL-15RαSu fusion protein binds to the IL-15 domain of the TGFβRII/TF/IL-15 fusion protein to create a TGFβRII/TF/IL-15:IL-21/IL-15RαSu complex.

The TGFβRII/TF/IL-15RαSu DNA construct was created by linking the TGFβRII sequence to the N-terminus coding region of human tissue factor 219 form, and then linking the TGFβRII/TF construct to the N-terminus coding region of IL-15. As described above, a single-chain version of TGFβRII (TGFβRII-linker-TGFβRII) was used. The nucleic acid sequence of the TGFβRII/TF/IL-15 construct (including leader sequence) is as follows (SEQ ID NO: 164):

(Signal peptide)
ATGAAGTGGGTGACCTTCATCAGCCTGCTGTTCCTGTTCTCCAGCGCCT

ACTCC (Human TGF βRII-1$^{st}$ fragment)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCACG

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

-continued

```
GTAGCAGCGACGAGTGTAACGACAACATCATCTTCAGCGAAGAGTACAA

CACCAGCAACCCTGAT (Linker)
GGAGGTGGCGGATCCGGAGGTGGAGGTTCTGGTGGAGGTGGGAGT (Human TGF βRII-2nd fragment)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCACA

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC (Human Tissue Factor 219)
TCCGGCACCACCAATACCGTGGCCGCTTATAACCTCACATGGAAGAGCA

CCAACTTCAAGACAATTCTGGAATGGGAACCCAAGCCCGTCAATCAAGT

TTACACCGTGCAGATCTCCACCAAATCCGGAGACTGGAAGAGCAAGTGC

TTCTACACAACAGACACCGAGTGTGATTTAACCGACGAAATCGTCAAGG

ACGTCAAGCAAACCTATCTGGCTCGGGTCTTTTCCTACCCCGCTGGCAA

TGTCGAGTCCACCGGCTCCGCTGGCGAGCCTCTCTACGAGAATTCCCCC

GAATTCACCCCTTATTTAGAGACCAATTTAGGCCAGCCTACCATCCAGA

GCTTCGAGCAAGTTGGCACCAAGGTGAACGTCACCGTCGAGGATGAAAG

GACTTTAGTGCGGCGGAATAACACATTTTTATCCCTCCGGGATGTGTTC

GGCAAAGACCTCATCTACACACTGTACTATTGGAAGTCCAGCTCCTCCG

GCAAAAAGACCGCTAAGACCAACACCAACGAGTTTTTAATTGACGTGGA

CAAAGGCGAGAACTACTGCTTCAGCGTGCAAGCCGTGATCCCTTCTCGT

ACCGTCAACCGGAAGAGCACAGATTCCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC
```

The amino acid sequence of the TGFβRII/TF/IL-15 fusion protein (including signal peptide) is as follows (SEQ ID NO: 163):

```
(Signal peptide)
MKWVTFISLLFLFSSAYS (Human TGF βRII-1st fragment)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD (Linker)
GGGGSGGGGSGGGGS (Human TGF βRII-2nd fragment)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

Example 53: Production of an Exemplary Single-Chain Chimeric Polypeptides

An exemplary single-chain chimeric polypeptide including a first target-binding domain that is an anti-CD3 scFv, a soluble human tissue factor domain, and a second target-binding domain that is an anti-CD28 scFv was generated (αCD3scFv/TF/αCD28scFv) (FIG. 64). The nucleic acid and amino acid sequences of this single-chain chimeric polypeptide are shown below.

Nucleic Acid Encoding Exemplary Single-Chain Chimeric Polypeptide (αCD3scFv/TF/αCD28scFv) (SEQ ID NO: 103)

```
(Signal peptide)
ATGAAGTGGGTGACCTTCATCAGCTTATTATTTTTATTCAGCTCCGCCT

ATTCC (αCD3 light chain variable region)
CAGATCGTGCTGACCCAAAGCCCCGCCATCATGAGCGCTAGCCCCGGTG

AGAAGGTGACCATGACATGCTCCGCTTCCAGCTCCGTGTCCTACATGAA

CTGGTATCAGCAGAAAAGCGGAACCAGCCCCAAAAGGTGGATCTACGAC

ACCAGCAAGCTGGCCTCCGGAGTGCCCGCTCATTTCCGGGGCTCTGGAT

CCGGCACCAGCTACTCTTTAACCATTCTATTGCGCCCGGTGGGGCGACG

GCAATTACTGGGGACGGGGCACAACACTGACCGTGAGCAGC
```

-continued (Linker)
GGAGGCGGAGGCTCCGGCGGAGGCGGATCTGGCGGTGGCGGCTCC (αCD28 light chain variable region)
GACATCGAGATGACCCAGTCCCCCGCTATCATGTCCGCCTCTTTAGGCG

AGCGGGTCACAATGACTTGTACAGCCTCCTCCAGCGTCTCCTCCTCCTA

CTTCCATTGGTACCAACAGAAACCCGGAAGCTCCCCTAAACTGTGCATC

TACAGCACCAGCAATCTCGCCAGCGGCGTGCCCCCTAGGTTTTCCGGAA

GCGGAAGCACCAGCTACTCTTTAACCATCTCCTCCATGGAGGCTGAGGA

TGCCGCCACCTACTTTTGTCACCAGTACCACCGGTCCCCCACCTTCGGA

GGCGGCACCAAACTGGAGACAAAGAGG

Exemplary Single-Chain Chimeric Polypeptide (αCD3scFv/TF/αCD28scFv) (SEQ ID NO: 102)

(Signal peptide)
MKWVTFISLLFLFSSAYS (αCD3 light chain variable region)
QIVLTQSPAIMSASPGEKVTMTCSASSSVSYMNWYQQKSGTSPKRWIYD

TSKLASGVPAHFRGSGSGTSYSLTISGMEAEDAATYYCQQWSSNPFTFG

SGTKLEINR (Linker)
GGGGSGGGGSGGGGS (αCD3 heavy chain variable region)
QVQLQQSGAELARPGASVKMSCKASGYTFTRYTMHWVKQRPGQGLEWIG

YINPSRGYTNYNQKFKDKATLTTDKSSSTAYMQLSSLTSEDSAVYYCAR

YYDDHYCLDYWGQGTTLTVSS (Human tissue factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (αCD28 light chain variable region)
VQLQQSGPELVKPGASVKMSCKASGYTFTSYVIQWVKQPGQGLEWIGS

INPYNDYTKYNEKFKGKATLTSDKSSITAYMEFSSLTSEDSALYYCARW

GDGNYWGRGTTLTVSS (Linker)
GGGGSGGGGSGGGGS (αCD28 heavy chain variable region)
DIEMTQSPAIMSASLGERVTMTCTASSSVSSSYFHWYQQKPGSSPKLCI

YSTSNLASGVPPRFSGSGSTSYSLTISSMEAEDAATYFCHQYHRSPTFG

GGTKLETKR

Figure 65:
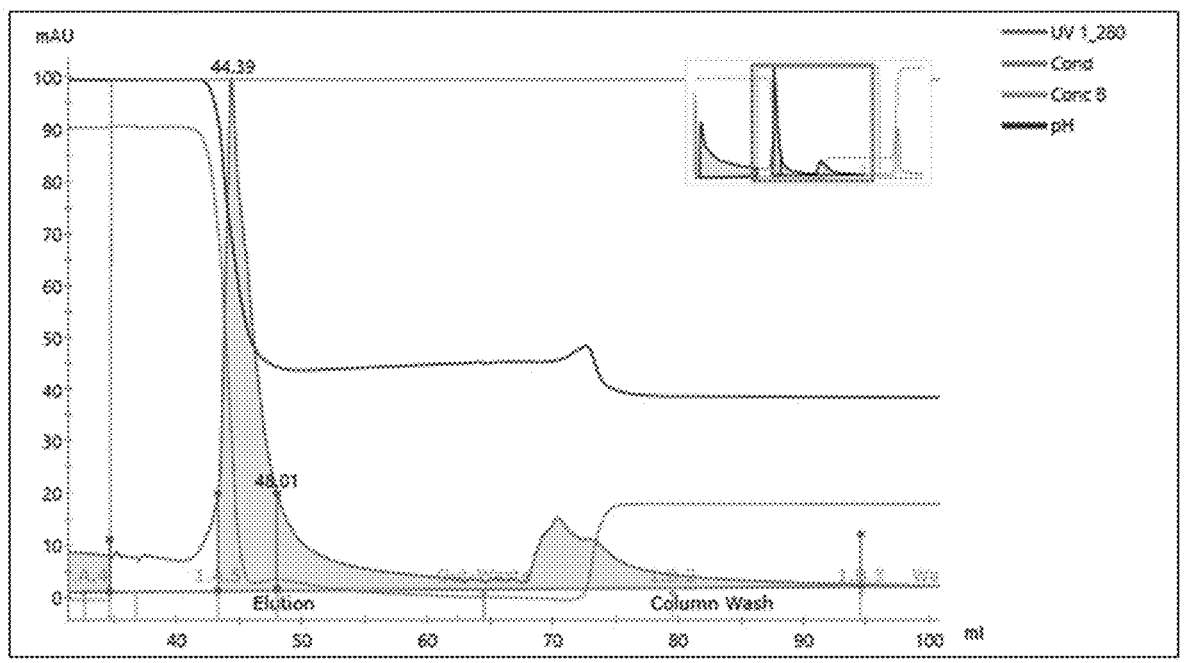
FIG. 65 is a chromatograph showing the elution of an exemplary αCD3scFv/TF/αCD28scFv single-chain chimeric polypeptide from an anti-tissue factor affinity column.

A second exemplary single-chain chimeric polypeptide including a first target-binding domain that is an anti-CD28 scFv, a soluble human tissue factor domain, and a second target-binding domain that is an anti-CD3 scFv was generated (αCD28scFv/TF/αCD3scFv) (FIG. 65). The nucleic acid and amino acid sequences of this single-chain chimeric polypeptide are shown below.

Nucleic Acid Encoding Exemplary Single-Chain Chimeric Polypeptide (αCD28scFv/TF/αCD3scFv) (SEQ ID NO: 195)

(Signal peptide)
ATGAAATGGGTCACCTTCATCTCTTTACTGTTTTTATTTAGCAGCGCCT

ACAGC (αCD28 light chain variable region)
GTGCAGCTGCAGCAGTCCGGACCCGAACTGGTCAAGCCCGGTGCCTCCG

TGAAAATGTCTTGTAAGGCTTCTGGCTACACCTTTACCTCCTACGTCAT

CCAATGGGTGAAGCAGAAGCCCGGTCAAGGTCTCGAGTGGATCGGCAGC

ATCAATCCCTACAACGATTACACCAAGTATAACGAAAAGTTTAAGGGCA

AGGCCACTCTGACAAGCGACAAGAGCTCCATTACCGCCTACATGGAGTT

TTCCTCTTTAACTTCTGAGGACTCCGCTTTATACTATTGCGCTCGTTGG

GGCGATGGCAATTATTGGGGCCGGGGAACTACTTTAACAGTGAGCTCC (Linker)
GGCGGCGGCGGAAGCGGAGGTGGAGGATCTGGCGGTGGAGGCAGC (αCD28 heavy chain variable region)
GACATCGAGATGACACAGTCCCCCGCTATCATGAGCGCCTCTTTAGGAG

AACGTGTGACCATGACTTGTACAGCTTCCTCCAGCGTGAGCAGCTCCTA

TTTCCACTGGTACCAGCAGAAACCCGGCTCCTCCCCTAAACTGTGTATC

TACTCCACAAGCAATTTAGCTAGCGGCGTGCCTCCTCGTTTTAGCGGCT

CCGGCAGCACCTCTTACTCTTTAACCATTAGCTCTATGGAGGCCGAAGA

TGCCGCCACATACTTTTGCCATCAGTACCACCGGTCCCCTACCTTTGGC

GGAGGCACAAAGCTGGAGACCAAGCGG (Human tissue factor 219 form)
AGCGGCACCACCAACACAGTGGCCGCCTACAATCTGACTTGGAAATCCA

CCAACTTCAAGACCATCCTCGAGTGGGAGCCCAAGCCCGTTAATCAAGT

TTATACCGTGCAGATTTCCACCAAGAGCGGCGACTGGAAATCCAAGTGC

TTCTATACCACAGACACCGAGTGCGATCTCACCGACGAGATCGTCAAAG

ACGTGAAGCAGACATATTTAGCTAGGGTGTTCTCCTACCCCGCTGGAAA

CGTGGAGAGCACCGGATCCGCTGGAGAGCCTTTATACGAGAACTCCCCC

GAATTCACCCCCTATCTGGAAACCAATTTAGGCCAGCCCACCATCCAGA

GCTTCGAACAAGTTGGCACAAAGGTGAACGTCACCGTCGAAGATGAGAG

GACTTTAGTGCGGAGGAACAATACATTTTTATCCTTACGTGACGTCTTC

GGCAAGGATTTAATCTACACACTGTATTACTGGAAGTCTAGCTCCTCCG

GCAAGAAGACCGCCAAGACCAATACCAACGAATTTTTAATTGACGTGGA

CAAGGGCGAGAACTACTGCTTCTCCGTGCAAGCTGTGATCCCCTCCCGG

ACAGTGAACCGGAAGTCCACCGACTCCCCCGTGGAGTGCATGGGCCAAG

AGAAGGGAGAGTTTCGTGAG (αCD3 light chain variable region)
CAGATCGTGCTGACCCAGTCCCCCGCTATTATGAGCGCTAGCCCCGGTG

AAAAGGTGACTATGACATGCAGCGCCAGCTCTTCCGTGAGCTACATGAA

CTGGTATCAGCAGAAGTCCGGCACCAGCCCTAAAAGGTGGATCTACGAC

ACCAGCAAGCTGGCCAGCGGCGTCCCCGCTCACTTTCGGGGCTCCGGCT

```
-continued
CCGGAACAAGCTACTCTCTGACCATCAGCGGCATGGAAGCCGAGGATGC

CGCTACCTATTACTGTCAGCAGTGGAGCTCCAACCCCTTCACCTTTGGA

TCCGGCACCAAGCTCGAGATTAATCGT (Linker)
GGAGGCGGAGGTAGCGGAGGAGGCGGATCCGGCGGTGGAGGTAGC (αCD3 heavy chain variable region)
CAAGTTCAGCTCCAGCAAAGCGGCGCCGAACTCGCTCGGCCCGGCGCTT

CCGTGAAGATGTCTTGTAAGGCCTCCGGCTATACCTTCACCCGGTACAC

AATGCACTGGGTCAAGCAACGGCCCGGTCAAGGTTTAGAGTGGATTGGC

TATATCAACCCCTCCCGGGGCTATACCAACTACAACCAGAAGTTCAAGG

ACAAAGCCACCCTCACCACCGACAAGTCCAGCAGCACCGCTTACATGCA

GCTGAGCTCTTTAACATCCGAGGATTCCGCCGTGTACTACTGCGCTCGG

TACTACGACGATCATTACTGCCTCGATTACTGGGGCCAAGGTACCACCT

TAACAGTCTCCTCC
```

Exemplary Single-Chain Chimeric Polypeptide (αCD28scFv/TF/αCD3scFv) (SEQ ID NO: 196)

```
(Signal peptide)
MKWVTFISLLFLFSSAYS (αCD28 light chain variable region)
VQLQQSGPELVKPGASVKMSCKASGYTFTSYVIQWVKQKPGQGLEWIGS

INPYNDYTKYNEKFKGKATLTSDKSSITAYMEFSSLTSEDSALYYCARW

GDGNYWGRGTTLTVSS (Linker)
GGGGSGGGGSGGGGS (αCD28 heavy chain variable region)
DIEMTQSPAIMSASLGERVTMTCTASSSVSSSYFHWYQQKPGSSPKLCI

YSTSNLASGVPPRFSGSGSTSYSLTISSMEAEDAATYFCHQYHRSPTFG

GGTKLETKR (Human tissue factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (αCD3 light chain variable region)
QIVLTQSPAIMSASPGEKVTMTCSASSSVSYMNWYQQKSGTSPKRWIYD

TSKLASGVPAHFRGSGSGTSYSLTISGMEAEDAATYYCQQWSSNPFTFG

SGTKLEINR (Linker)
GGGGSGGGGSGGGGS (αCD3 heavy chain variable region)
QVQLQQSGAELARPGASVKMSCKASGYTFTRYTMHWVKQRPGQGLEWIG

YINPSRGYTNYNQKFKDKATLTTDKSSSTAYMQLSSLTSEDSAVYYCAR

YYDDHYCLDYWGQGTTLTVSS
```

The nucleic acid encoding αCD3scFv/TF/αCD28scFv was cloned into a modified retrovirus expression vectors as described previously (Hughes et al., *Hum Gene Ther* 16:457-72, 2005). The expression vector encoding αCD3scFv/TF/αCD28scFv was transfected into CHO-K1 cells. Expression of the expression vector in CHO-K1 cells allowed for secretion of the soluble αCD3scFv/TF/αCD28scFv single-chain chimeric polypeptide (referred to as 3t28), which can be purified by anti-TF antibody affinity and other chromatography methods.

An anti-tissue factor affinity column was used to purify the αCD3scFv/TF/αCD28scFv single-chain chimeric polypeptide. The anti-tissue factor affinity column was connected to a GE Healthcare AKTA Avant system. A flow rate of 4 mL/min was used for all steps except the elution step, which was 2 mL/min.

Cell culture harvest including αCD3scFv/TF/αCD28scFv single-chain chimeric polypeptide was adjusted to pH 7.4 with 1M Tris base and loaded onto the anti-TF antibody affinity column (described above) which was equilibrated with 5 column volumes of PBS. After sample loading, the column was washed with 5 column volumes PBS, followed by elution with 6 column volumes 0.1 M acetic acid, pH 2.9. An A280 elution peak was collected and then neutralized to pH 7.5-8.0 by adding 1 M Tris base. The neutralized sample was then buffer exchanged into PBS using Amicon centrifugal filters with a 30 kDa molecular weight cutoff. The data in FIG. 65 show that the anti-tissue factor affinity column can bind the αCD3scFv/TF/αCD28scFv single-chain chimeric polypeptide, which contains a human soluble tissue factor domain. The buffer-exchanged protein sample was stored at 2-8° C. for further biochemical analysis and biological activity testing.

After each elution, the anti-tissue factor affinity column was stripped using 6 column volumes of 0.1 M glycine, pH 2.5. The column was then neutralized using 10 column volumes of PBS, 0.05% NaN$_3$, and stored at 2-8° C.

Figure 66:
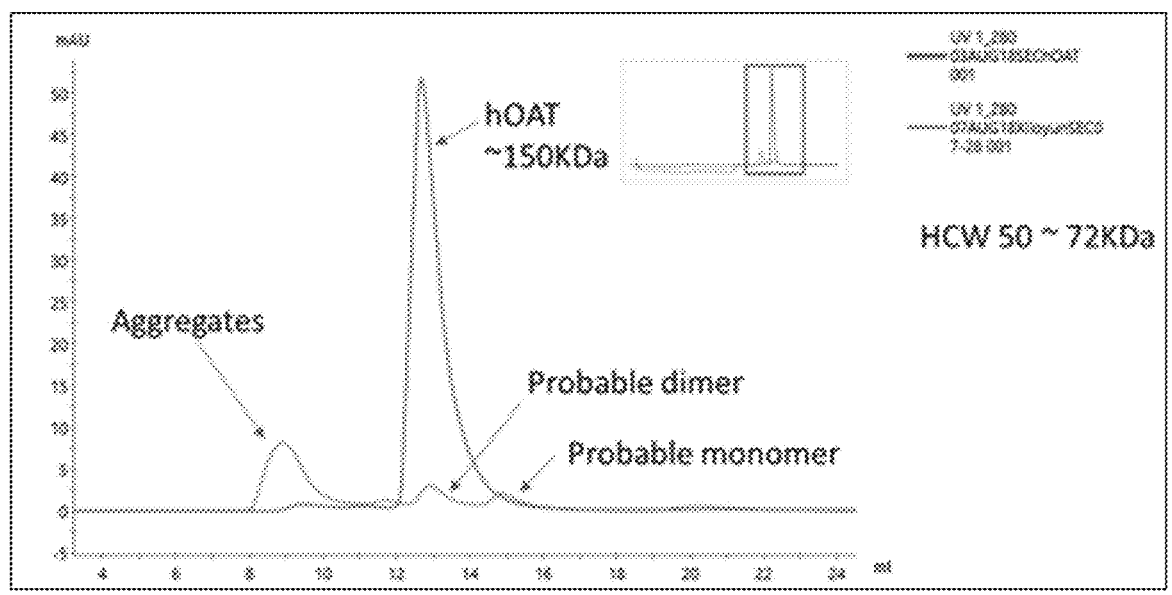
FIG. 66 is a chromatograph showing the elution of a Superdex 200 Increase 10/300 GL gel filtration column loaded with an exemplary αCD3scFv/TF/αCD28scFv single-chain chimeric polypeptide.

Analytical size exclusion chromatography (SEC) was performed on the αCD3scFv/TF/αCD28scFv single-chain chimeric polypeptide using a Superdex 200 Increase 10/300 GL gel filtration column (from GE Healthcare) connected to an AKTA Avant system (from GE Healthcare). The column was equilibrated with 2 column volumes of PBS. A flow rate of 0.8 mL/min was used. Two hundred μL of αCD3scFv/TF/αCD28scFv single-chain chimeric polypeptide (1 mg/mL) was injected onto the column using a capillary loop. After injection of the single-chain chimeric polypeptide, 1.25 column volumes of PBS were flowed into the column. The SEC chromatograph is shown in FIG. 66. The data show that there are 3 protein peaks, likely representing a monomer and dimer or other different forms of the αCD3scFv/TF/αCD28scFv single-chain chimeric polypeptide.

Figure 67:
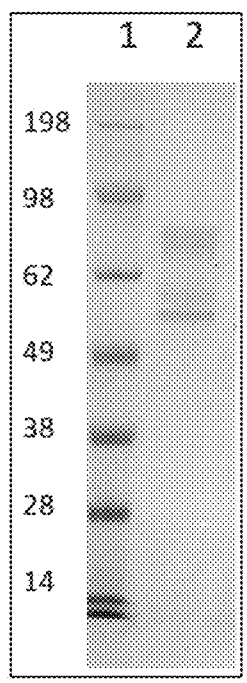
FIG. 67 is a sodium dodecyl sulfate polyacrylamide gel (4-12% NuPage Bis-Tris gel) of an exemplary αCD3scFv/TF/αCD28scFv single-chain chimeric polypeptide purified using an anti-tissue factor affinity column.

To determine the purity and protein molecular weight of the αCD3scFv/TF/αCD28scFv single-chain chimeric polypeptide, the purified αCD3scFv/TF/αCD28scFv protein sample from anti-tissue factor affinity column was analyzed by standard sodium dodecyl sulfate polyacrylamide gel (4-12% NuPage Bis-Tris gel) electrophoresis (SDS-PAGE) method under reduced conditions. The gel was stained with InstantBlue for about 30 minutes and destained overnight with purified water. FIG. 67 shows the SDS gel of the αCD3scFv/TF/αCD28scFv single-chain chimeric polypeptide purified using an anti-tissue factor affinity column. The results show that the purified αCD3scFv/TF/αCD28scFv single-chain chimeric polypeptide has the expected molecular weight (72 kDa) in reduced SDS gel.

Figure 68:
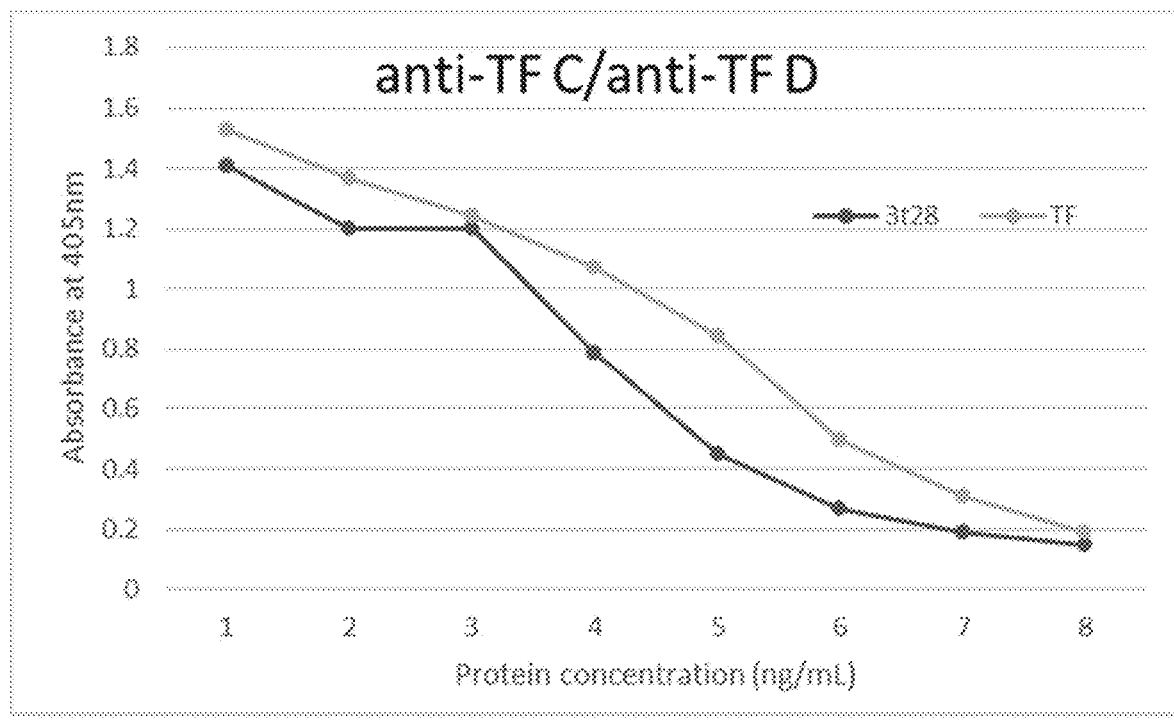
FIG. 68 is a graph showing the ELISA quantitation of an exemplary αCD3scFv/TF/αCD28scFv single-chain chimeric polypeptide performed using the methods described in Example 53. Purified tissue factor was used as the control.

Example 54: Functional Characterization of αCD3scFv/TF/αCD28scFv Single-Chain Chimeric Polypeptide ELISA-based methods confirmed the formation of the αCD3scFv/TF/αCD28scFv single-chain chimeric polypeptide. The αCD3scFv/TF/αCD28scFv single-chain chimeric polypeptide was detected using an anti-TF antibody (I43)/anti-TF antibody-specific ELISA with a capture antibody, anti-human tissue factor antibody (143), and a detection antibody, anti-TF antibody (FIG. 68). A purified tissue factor protein with a similar concentration was used as a control.

Figure 69:
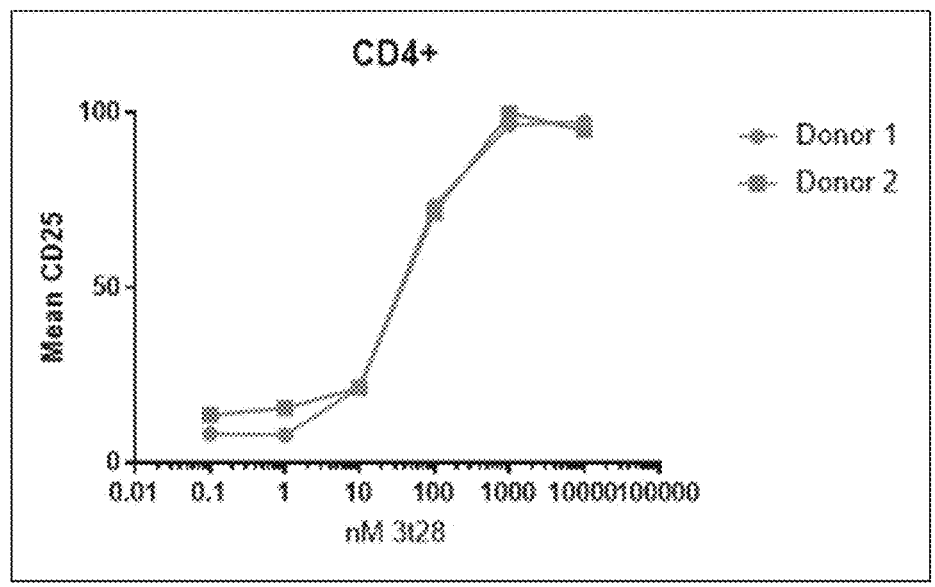
FIG. 69 is a graph showing the ability of an exemplary αCD3scFv/TF/αCD28scFv single-chain chimeric polypeptide to stimulate CD25 expression in CD4⁺ T-cells isolated from blood from two donors. The experiments were performed as described in Example 54.
Figure 70:
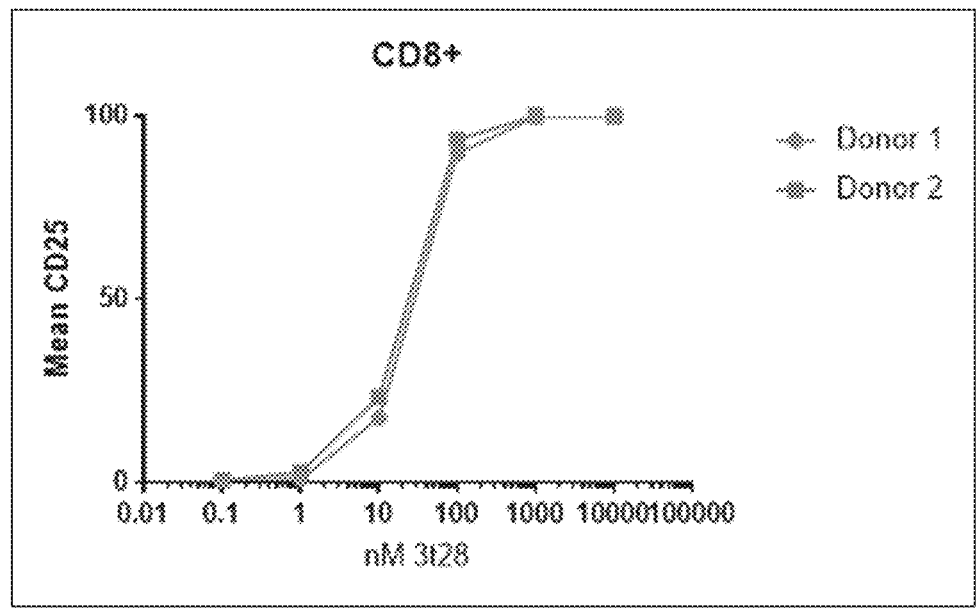
FIG. 70 is a graph showing the ability of an exemplary αCD3scFv/TF/αCD28scFv single-chain chimeric polypeptide to stimulate CD25 expression in CD8⁺ T-cells isolated from blood from two donors. The experiments were performed as described in Example 54.

A further in vitro experiment was performed to determine whether the αCD3scFv/TF/αCD28scFv single-chain chimeric polypeptide is capable of activating human peripheral blood mononuclear cells (PBMCs). Fresh human leukocytes were obtained from the blood bank and peripheral blood mononuclear cells (PBMC) were isolated using density gradient Histopaque (Sigma). The cells were counted and resuspended in $0.2 \times 10^6$/mL in a 96-well flat bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with αCD3scFv/TF/αCD28scFv single-chain chimeric polypeptide from 0.01 nM to 1000 nM for 3 days at 37° C., 5% $CO_2$. After 72 hours, the cells were harvested and surface stained for CD4-488, CD8-PerCP Cy5.5, CD25-BV421, CD69-APCFire750, CD62L-PE Cy7, and CD44-PE specific antibodies (Biolegend) for 30 minutes. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were resuspended in 300 μL of FACS buffer and analyzed by Flow Cytometry (Celesta-BD Bioscience). The data in FIGS. 69 and 70 show that the αCD3scFv/TF/αCD28scFv single-chain chimeric polypeptide is able to stimulate both CD8$^+$ and CD4$^+$ T-cells.

Figure 71:
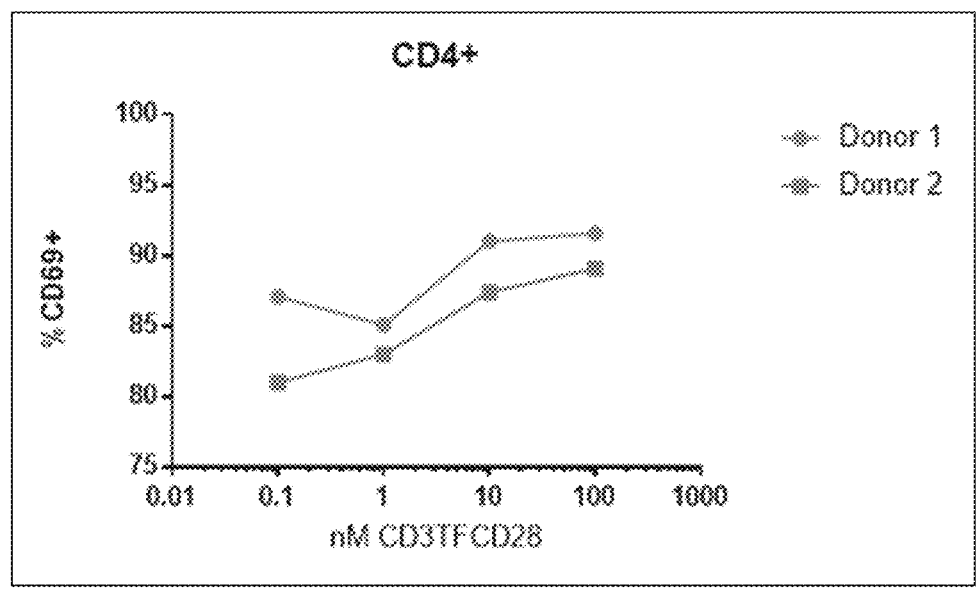
FIG. 71 is a graph showing the ability of an exemplary αCD3scFv/TF/αCD28scFv single-chain chimeric polypeptide to stimulate CD69 expression in CD4⁺ T-cells isolated from blood from two donors. The experiments were performed as described in Example 54.

A further experiment was performed, in which PBMCs isolated from blood using Histopaque (Sigma) were counted and resuspended in $0.2 \times 10^6$/mL in a 96-well flat bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were then stimulated with the αCD3scFv/TF/αCD28scFv single-chain chimeric polypeptide from 0.01 nM to 1000 nM for 3 days at 37° C., 5% $CO_2$. After 72 hours, the cells were harvested and surface stained for CD4-488, CD8-PerCP Cy5.5, CD25-BV421, CD69-APC-Fire750, CD62L-PE Cy7, and CD44-PE (Biolegend) for 30 minutes. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were resuspended in 300 μL of FACS buffer and analyzed by Flow Cytometry (Celesta-BD Bioscience). The data again show that the αCD3scFv/TF/αCD28scFv single-chain chimeric polypeptide was able to stimulate activation of CD4$^+$ T cells (FIG. 71).

Example 55: Construction of Exemplary Multi-Chain Chimeric Polypeptides and Evaluation of Properties Thereof Two multi-chain chimeric polypeptides were generated and their properties were evaluated. Each of the two multi-chain chimeric polypeptides included a first chimeric polypeptide that included a soluble tissue factor domain covalently linked a first target-binding domain and a first domain of an affinity pair of domains. The second chimeric polypeptide in each of the two multi-chain chimeric polypeptides included a second domain of the affinity pair of domains, and a second target-binding domain.

Description of Logic Underlying Construction of Multi-Chain Chimeric Polypeptides Tissue Factor (TF) is a stable, transmembrane protein containing 236 amino acid residues. The truncated, recombinant 219-amino-acid extracellular domain of tissue factor is soluble and is known to be expressed at high levels in bacteria or mammalian cells. Without wishing to be bound to a particular theory, the applicants speculated that the 219-aa tissue factor could be used as a connector linker for creation of unique multi-chain chimeric polypeptides.

First chimeric polypeptides including soluble tissue factor domain were produced at high levels by CHO-K1 cells grown in fermentation broth. These first chimeric polypeptides were purified by an anti-tissue factor monoclonal antibody (mAb) coupled on a solid matrix. Notably, tissue factor contains binding sites for FVIIa and FX. The catalytic activity of the tissue factor-FVIIa complex for FX is approximately 1 million-fold lower when tissue factor is not anchored to a phospholipid bilayer. Thus, without wishing to be bound to a particular theory, applicants speculated that using the 219-aa extracellular domain of tissue factor without the transmembrane in construction of the first chimeric polypeptides may eliminate the pro-coagulation activity of tissue factor in the first chimeric polypeptides. In an effort to further reduce or eliminate the pro-coagulation activity of the 219-aa tissue factor, select mutations in tissue factor can be made, specifically at seven amino acid residues that are known to contribute to binding energy of the FVIIa binding site.

Characterization of Binding Interactions for Described Chimeric Polypeptides

Figure 72:
FIG. 72 shows a schematic diagram of an exemplary IL-7/IL-15RαSu DNA construct.
Figure 73:
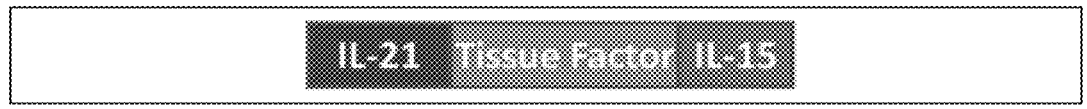
FIG. 73 shows a schematic diagram of an exemplary IL-21/TF/IL-15 DNA construct.

To determine if the first and second chimeric polypeptides bind to each other to form multi-chain chimeric polypeptides, in vitro binding assays were performed. To determine if the first chimeric polypeptide comprising soluble tissue factor domain are recognized and bound by anti-TF mAb, in vitro binding assays were performed. Notably, the data indicated that the mutated tissue factor proteins are still recognized and selectively bound by the anti-TF mAb which is known to bind to the FX binding site on tissue factor. To determine if the first chimeric polypeptides comprising soluble tissue factor domain covalently linked to scFvs or cytokines (see FIG. 72 and FIG. 73) possess functional scFvs or cytokines, in vitro binding assays were performed. The data from the aforementioned assays were consistent with the purified first chimeric polypeptides having the expected biological activities (e.g., scFvs selectively bind expected target antigens or cytokines selectively bind expected receptors or binding proteins).

In addition, experiments performed using the two multi-chain chimeric polypeptides including a first and second chimeric polypeptide bound to each other demonstrate the expected target binding activity (e.g., the multi-chain chimeric polypeptide binds specifically to the target specifically recognized by the first target-binding domain and the target specifically recognized by the second target-binding domain).

Based on the aforementioned results, applicants concluded that the soluble tissue factor connector linker provided or enabled appropriate display of the polypeptides encoding either scFvs, interleukins, cytokines, interleukin receptors, or cytokine receptors in three-dimensional space relative to soluble tissue factor domain and relative to one another such that each retained expected biological properties (and activities).

When both the first and second chimeric polypeptides were co-expressed, the heterodimeric complexes were secreted into the fermentation broths at high levels. The complexes were captured and readily purified by anti-TF mAb conjugated to a solid matrix using affinity chromatography. The first and second target-binding domains of these multi-chain chimeric polypeptides retained their expected biological activities as assayed by in vitro binding assays. Thus, the assembly of the multi-chain chimeric polypeptides provides the appropriate spatial display and folding of the domains for biological activities. Importantly, the spatial arrangement of the multi-chain chimeric polypeptides does not interfere with the FX binding site on tissue factor which enables the use of anti-TF mAb for affinity purification.

Characterization of Stability for Described Chimeric Polypeptides

Both purified multi-chain chimeric polypeptides are expected to be stable. These multi-chain chimeric polypeptides are structurally intact and expected to be fully biologically active when they are incubated in human serum at 37° C. for 72 hours.

Characterization of Propensity of Described Chimeric Polypeptides to Aggregate

Both purified multi-chain chimeric polypeptides are expected not to form aggregates when stored at 4° C. in PBS.

Characterization of Viscosity of Described Chimeric Polypeptides

Compositions including the multi-chain chimeric polypeptides are not expected to have any viscosity issues when formulated at a concentration as high as 50 mg/mL in PBS.

Discussion of Multi-Chain Chimeric Polypeptide Platform for Use in Selectively Binding Clinically Relevant Targets The data from our studies show that our platform technologies can be utilized to create molecules that could be fused to target-binding domains derived from antibodies, in any formats as discussed above, adhesion molecules, receptors, cytokines, chemokines etc. With the appropriate target-binding domain, the resulting multi-chain chimeric polypeptides could promote conjugation of various immune effector cells and mediate destruction of target cells, including cancer cells, virally-infected cells, or senescent cells. Other domains in the multi-chain chimeric polypeptides stimulate, activate, and attract the immune system for enhancing cytotoxicity of effector cells for the targeted cells.

Example 56: Creation of an IL-7/IL-15RαSu DNA Construct

In a non-limiting example, an IL-7/IL-15RαSu DNA construct was created (see FIG. 72). The human IL-7 sequence, human IL-15RαSu sequence, human IL-15 sequence, and human tissue factor 219 sequence were obtained from the UniProt website and DNA for these sequences was synthesized by Genewiz. A DNA construct was made linking the IL-7 sequence to the IL-15RαSu sequence. The final IL-7/IL-15RαSu DNA construct sequence was synthesized by Genewiz.

The nucleic acid sequence encoding the second chimeric polypeptide of IL-7/IL-15RαSu construct (including signal peptide sequence) is as follows (SEQ ID NO: 140):

```
GATTGTGATATTGAAGGTAAAGATGGCAAACAATATGAGAGTGTTCTAA

TGGTCAGCATCGATCAATTATTGGACAGCATGAAAGAAATTGGTAGCAA
```

-continued

```
TTGCCTGAATAATGAATTTAACTTTTTTAAAAGACATATCTGTGATGCT

AATAAGGAAGGTATGTTTTTATTCCGTGCTGCTCGCAAGTTGAGGCAAT

TTCTTAAAATGAATAGCACTGGTGATTTTGATCTCCACTTATTAAAAGT

TTCAGAAGGCACAACAATACTGTTGAACTGCACTGGCCAGGTTAAAGGA

AGAAAACCAGCTGCCCTGGGTGAAGCCCAACCAACAAAGAGTTTGGAAG

AAAATAAATCTTTAAAGGAACAGAAAAAACTGAATGACTTGTGTTTCCT

AAAGAGACTATTACAAGAGATAAAAACTTGTTGGAATAAAATTTTGATG

GGCACTAAAGAACAC (Human IL-15R α sushi domain)
ATCACGTGCCCTCCCCCCATGTCCGTGGAACACGCAGACATCTGGGTCA

AGAGCTACAGCTTGTACTCCAGGGAGCGGTACATTTGTAACTCTGGTTT

CAAGCGTAAAGCCGGCACGTCCAGCCTGACGGAGTGCGTGTTGAACAAG

GCCACGAATGTCGCCCACTGGACAACCCCCAGTCTCAAATGCATTAGA
```

The second chimeric polypeptide of IL-7/IL-15RαSu construct (including signal peptide sequence) is as follows (SEQ ID NO: 139):

```
(Signal peptide)
MKWVTFISLLFLFSSAYS (Human IL-7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

Example 57: Creation of an IL-21/TF/IL-15 DNA Construct

In a non-limiting example, an IL-21/TF/IL-15 construct was made (see FIG. 73) by linking the IL-21 sequence to the N-terminus coding region of tissue factor 219, and further linking the IL-21/TF construct with the N-terminus coding region of IL-15.

The nucleic acid sequence encoding the first chimeric polypeptide of IL-21/TF/IL-15 construct (including leader sequence), synthesized by Genewiz, is as follows (SEQ ID NO: 129):

(Signal peptide)
ATGGGAGTGAAAGTTCTTTTTGCCCTTATTTGTATTGCTGTGGCCGAGG

CC (Human IL-21 fragment)
CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCC (Human Tissue Factor 219)
TCAGGCACTACAAATACTGTGGCAGCATATAATTTAACTTGGAAATCAA

CTAATTTCAAGACAATTTTGGAGTGGGAACCCAAACCCGTCAATCAAGT

CTACACTGTTCAAATAAGCACTAAGTCAGGAGATTGGAAAAGCAAATGC

TTTTACACAACAGACACAGAGTGTGACCTCACCGACGAGATTGTGAAGG

ATGTGAAGCAGACGTACTTGGCACGGGTCTTCTCCTACCCGGCAGGGAA

TGTGGAGAGCACCGGTTCTGCTGGGGAGCCTCTGTATGAGAACTCCCA

GAGTTCACACCTTACCTGGAGACAAACCTCGGACAGCCAACAATTCAGA

GTTTTGAACAGGTGGGAACAAAAGTGAATGTGACCGTAGAAGATGAACG

GACTTTAGTCAGAAGGAACAACACTTTCCTAAGCCTCCGGGATGTTTTT

GGCAAGGACTTAATTTATACACTTTATTATTGGAAATCTTCAAGTTCAG

GAAAGAAAACAGCCAAAACAAACACTAATGAGTTTTTGATTGATGTGGA

TAAAGGAGAAAACTACTGTTTCAGTGTTCAAGCAGTGATTCCCTCCCGA

ACAGTTAACCGGAAGAGTACAGACAGCCCGGTAGAGTGTATGGGCCAGG

AGAAAGGGGAATTCAGAGAA (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

The first chimeric polypeptide of IL-21/TF/IL-15
construct including leader sequence is
SEQ ID NO: 128:

(Signal peptide)
MGVKVLFALICIAVAEA (Human IL-21)
QGQDRHMIRMRQLIDIVDQLKNYVNDLVPEFLPAPEDVETNCEWSAFS

CFQKAQLKSANTGNNERIINVSIKKLKRKPPSTNAGRRQKHRLTCPSC

DSYEKKPPKEFLERFKSLLQKMIHQLSSRTHGSEDS (Human Tissue Factor 219)
SGTTNTVAAYNLTWKSTNFKTILEWEPKPVNQVYTVQISTKSGDWKSK

CFYTTDTECDLTDEIVKDVKQTYLARVFSYPAGNVESTGSAGEPLYEN

SPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAV

IPSRTVNRKSTDSPVECMGQEKGEFRE (Human IL-15)
NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS

Example 58: Secretion of IL-7/IL-15RαSu and IL-21/TF/IL-15 Fusion Proteins

Figure 74:
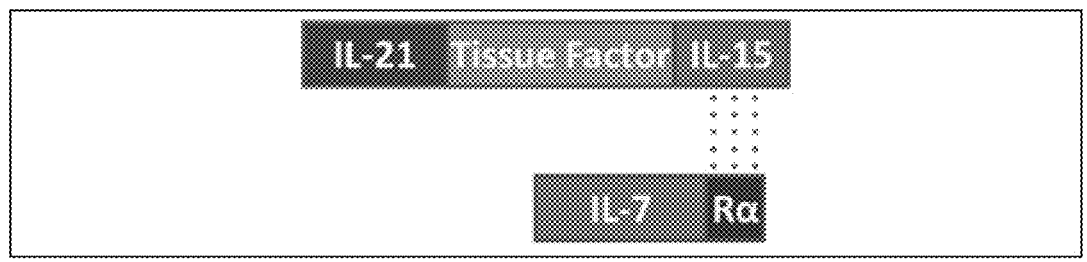
FIG. 74 shows a schematic diagram of the interaction between the exemplary IL-7/IL-15RαSu and IL-21/TF/IL-15 DNA constructs.
Figure 75:
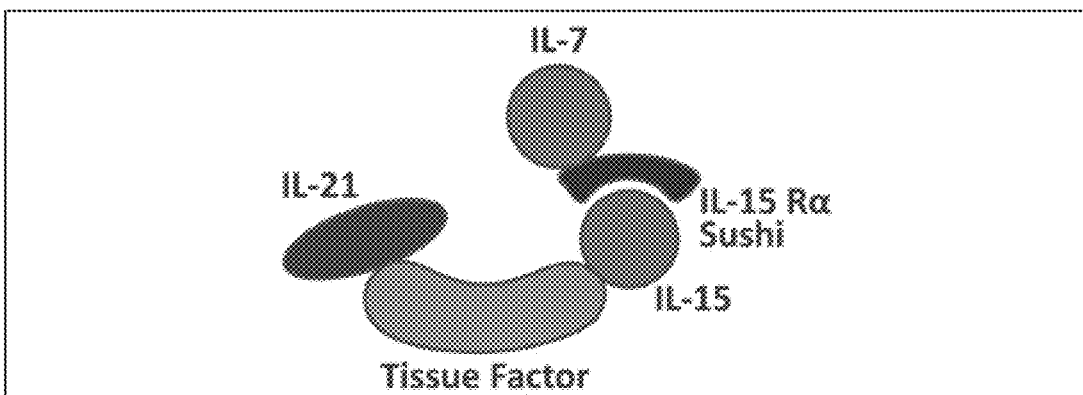
FIG. 75 shows a schematic diagram of the interaction between the exemplary IL-7/IL-15RαSu and IL-21/TF/IL-15 fusion proteins resulting in an IL-21/TF/IL-15:IL-7/IL-15RαSu complex (21t15-7s).

The IL-7/IL-15RαSu and IL-21/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-21/TF/IL-15:IL-7/IL-15RαSu protein complex (referred to as 21t15-7s, see FIGS. 74 and 75). The 21t15-7s protein was purified from CHO-K1 cell culture supernatant using anti-TF antibody affinity chromatography and size exclusion chromatography resulting in soluble (non-aggregated) protein complexes consisting of IL-7/IL-15RαSu and IL-21/TF/IL-15 fusion proteins.

In some cases, the leader (signal sequence) peptide is cleaved from the intact polypeptide to generate the mature form that may be soluble or secreted.

Example 59: Purification of 21t15-7s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Cell culture harvest of 21t15-7s was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was neutralized to pH 7.5-8.0 by adding 1M Tris base. The neutralized sample was then buffer exchanged into PBS using Amicon® centrifugal filters with a 30 KDa molecular weight cutoff. The buffer-exchanged protein sample was stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide and stored at 2-8° C.

Example 60: Creation of a TGF-βRII/IL-15RαSu DNA Construct

Figure 76:
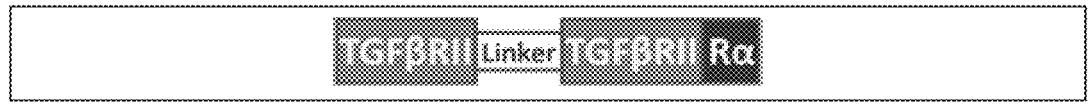
FIG. 76 shows a schematic diagram of an exemplary TGF-βRII/IL-15RαSu DNA construct.

In a non-limiting example, a TGF-βRII/IL-15RαSu DNA construct was created (see FIG. 76). The human TGF-βRII sequence, human IL-15RαSu sequence, human IL-15 sequence, and human tissue factor 219 sequence were obtained from the UniProt website and DNA for these sequences was synthesized by Genewiz. A DNA construct was made linking the TGF-βRII sequences (separated by a linker) to the IL-15RαSu sequence. The final TGF-βRII/IL-15RαSu DNA construct sequence was synthesized by Genewiz.

Example 61: Creation of an IL-21/TF/IL-15 DNA Construct

Figure 77:
FIG. 77 shows a schematic diagram of an exemplary IL-21/TF/IL-15 DNA construct.

In a non-limiting example, an IL-21/TF/IL-15 construct was made (see FIG. 77) by linking the IL-21 sequence to the N-terminus coding region of tissue factor 219, and further linking the IL-21/TF construct with the N-terminus coding region of IL-15.

Example 62: Secretion of TGF-βRII/IL-15RαSu and IL-21/TF/IL-15 Fusion Proteins

Figure 78:
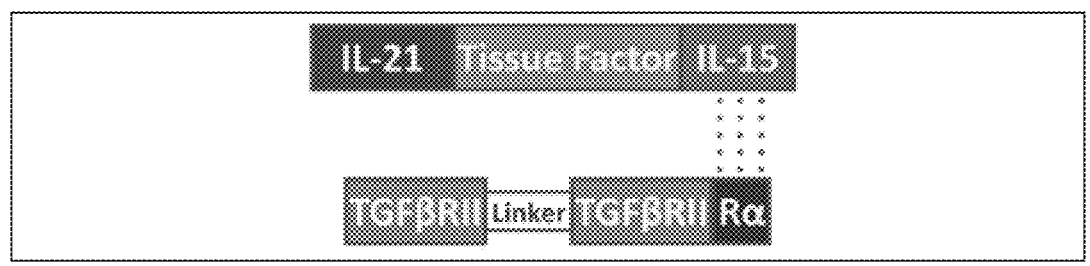
FIG. 78 shows a schematic diagram of the interaction between the exemplary TGF-β RII/IL-15RαSu and IL-21/TF/IL-15 DNA constructs.
Figure 79:
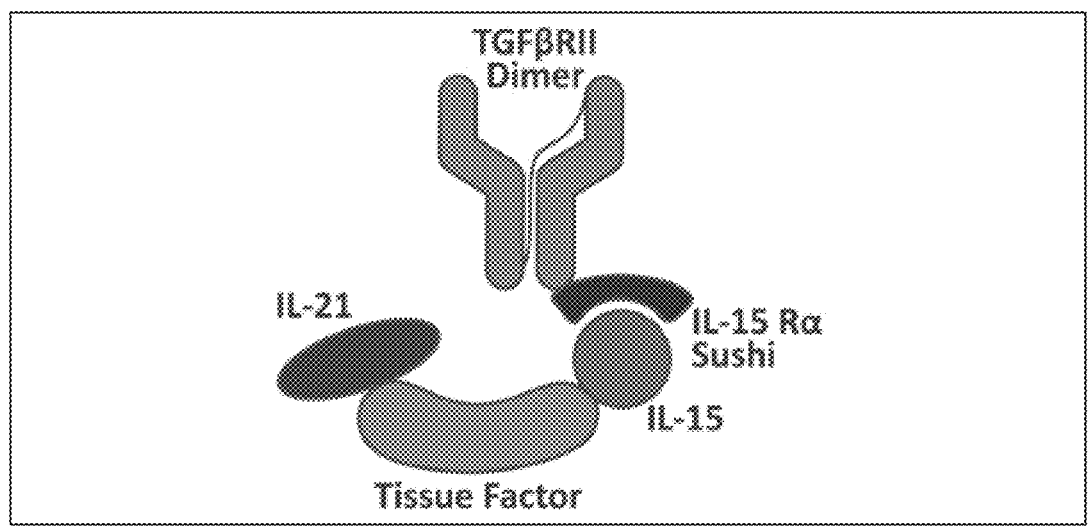
FIG. 79 shows a schematic diagram of the interaction between the exemplary TGF-βRII/IL-15RαSu and IL-21/TF/IL-15 fusion proteins resulting in an IL-21/TF/IL-15:15RαSU complex (21t15-TGFRs).

The TGF-βRII/IL-15RαSu and IL-21/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-21/TF/IL-15:TGF-βRII/IL-15RαSu protein complex (referred to as 21t15-TGFRs, see FIGS. 78 and 79). The 21t15-TGFRs protein was purified from CHO-K1 cell culture supernatant using anti-TF antibody affinity chromatography and size exclusion chromatography resulting in soluble (non-aggregated) protein complexes consisting of TGF-βRII/IL-15RαSu and IL-21/TF/IL-15 fusion proteins.

Example 63: Size Exclusion Chromatography

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.7 mL/min. A capillary loop was used to inject 200μ, of 1 mg/mL of 7t15-21s complex onto the column. The injection was chased with 1.25 column volumes of PBS.

Example 64: SDS-PAGE of 21t15-7s and 21t15-TGFRs

To determine the purity and protein molecular weight, the purified 21t15-7s or 21t15-TGFRs protein sample were analyzed using 4-12% NuPage Bis-Tris protein gel SDS-PAGE. The gel will be stained with InstantBlue™ for about 30 min, followed by destaining overnight in purified water.

Example 65: Glycosylation of 21t15-7s and 21t15-TGFRs in CHO-K1 Cells

Glycosylation of 21t15-7s in CHO-K1 cells or 21t15-TGFRs in CHO-K1 cells were confirmed using the Protein Deglycosylation Mix II kit (New England Biolabs), according to the manufacturer's instructions.

Example 66: Recombinant Protein Quantitation of 21t15-7s and 21t15-TGFRs Complexes The 21t15-7s complex or the 21t15-TGFRs complex were detected and quantified using standard sandwich ELISA methods. Anti-human tissue factor antibody (IgG1) served as the capture antibody and biotinylated anti-human IL-21, IL-15, or IL-7 antibody (21t15-7s) or biotinylated anti-human IL-21, IL-15, or TGF-βRII antibody (21t15-TGFRs) served as the detection antibody. Tissue factor in purified 21t15-7s or 21t15-TGFRs protein complexes was detected using an anti-human tissue factor capture antibody, and anti-human tissue factor antibody (IgG1) detection antibody. The anti-TF ELISA will be compared to purified tissue factor at similar concentrations.

Example 67: Creation of an IL-21/IL-15RαSu DNA Construct

In a non-limiting example, an IL-21/IL-15RαSu DNA construct was created. The human IL-21 sequence and human IL-15RαSu sequence were obtained from the UniProt website and DNA for these sequences was synthesized by Genewiz. A DNA construct was made linking the IL-21 sequence to the IL-15RαSu sequence. The final IL-21/IL-15RαSu DNA construct sequence was synthesized by Genewiz. See FIG. 80.

Example 68: Creation of an IL-7/TF/IL-15 DNA Construct

In a non-limiting example, an IL-7/TF/IL-15 construct was made by linking the IL-7 sequence to the N-terminus coding region of tissue factor 219, and further linking the IL-7/TF construct with the N-terminus coding region of IL-15. See FIG. 81.

Example 69: Creation of an IL-21/IL-15Rα Sushi DNA Construct

In a non-limiting example, a second chimeric polypeptide of IL-21/IL-15RαSu was generated. The human IL-21 and human IL-15Rα sushi sequences were obtained from the UniProt website and DNA for these sequences was synthesized by Genewiz. A DNA construct was made linking the IL-21 sequence to the IL-15Rα sushi sequence. The final IL-21/IL-15RαSu DNA construct sequence was synthesized by Genewiz.

The nucleic acid sequence encoding the second chimeric polypeptide of IL-21/IL-15RαSu domain (including leader sequence), synthesized by Genewiz, is as follows (SEQ ID NO: 148):

```
(Signal peptide)
ATGAAGTGGGTGACCTTCATCAGCCTGCTGTTCCTGTTCTCCAGCGCC

TACTCC (Human IL-21)
CAGGGCCAGGACAGGCACATGATCCGGATGAGGCAGCTCATCGACATC

GTCGACCAGCTGAAGAACTACGTGAACGACCTGGTGCCCGAGTTTCTG

CCTGCCCCCGAGGACGTGGAGACCAACTGCGAGTGGTCCGCCTTCTCC

TGCTTTCAGAAGGCCCAGCTGAAGTCCGCCAACACCGGCAACAACGAG

CGGATCATCAACGTGAGCATCAAGAAGCTGAAGCGGAAGCCTCCCTCC

ACAAACGCCGGCAGGAGGCAGAAGCACAGGCTGACCTGCCCCAGCTGT

GACTCCTACGAGAAGAAGCCCCCCAAGGAGTTCCTGGAGAGGTTCAAG
```

```
TCCCTGCTGCAGAAGATGATCCATCAGCACCTGTCCTCCAGGACCCAC

GGCTCCGAGGACTCC (Human IL-15R α sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGC

TTCAAGAGGAAGGCCGGCACCAGCAGCCTCACCGAGTGCGTGCTGAAT

AAGGCTACCAACGTGGCTCACTGGACAACACCCTCTTTAAAGTGCATC

CGG
```

The second chimeric polypeptide of IL-21/IL-15Rα sushi domain (including leader sequence) is as follows (SEQ ID NO: 147):

```
(Signal Sequence)
MKWVTFISLLFLFSSAYS (Human IL-21)
QGQDRHMIRMRQLIDIVDQLKNYVNDLVPEFLPAPEDVETNCEWSAFS

CFQKAQLKSANTGNNERIINVSIKKLKRKPPSTNAGRRQKHRLTCPSC

DSYEKKPPKEFLERFKSLLQKMIHQHLSSRTHGSEDS (Human IL-15Rα sushi domain)
ITCPPPMSVEHADIWVKSYSLYSRERYICNSGFKRKAGTSSLTECVLN

KATNVAHWTTPSLKCIR
```

Example 70: Creation of an IL-7/TF/IL-15 DNA Construct

In a non-limiting example, an exemplary first chimeric polypeptide of IL-7/TF/IL-15 was made by linking the IL-7 sequence to the N-terminus coding region of tissue factor 219, and further linking the IL-7/TF construct with the N-terminus coding region of IL-15. The nucleic acid sequence encoding the first chimeric polypeptide of IL-7/TF/IL-15 (including leader sequence), synthesized by Genewiz, is as follows (SEQ ID NO: 144):

```
(Signal peptide)
ATGAAGTGGGTGACCTTCATCAGCCTGCTGTTCCTGTTCTCCAGCGCC

TACTCC (Human IL-7 fragment)
GATTGCGACATCGAGGGCAAGGACGGCAAGCAGTACGAGAGCGTGCTG

ATGGTGTCCATCGACCAGCTGCTGGACAGCATGAAGGAGATCGGCTCC

AACTGCCTCAACAACGAGTTCAACTTCTTCAAGCGGCACATCTGCGAC

GCCAACAAGGAGGGCATGTTCCTGTTCAGGGCCGCCAGGAAACTGCGG

CAGTTCCTGAAGATGAACTCCACCGGCGACTTCGACCTGCACCTGCTG

AAGGTGTCCGAGGGCACCACCATCCTGCTGAACTGCACCGGACAGGTG

AAGGGCCGGAAACCTGCTGCTCTGGGAGAGGCCCAACCCACCAAGAGC

CTGGAGGAGAACAAGTCCCTGAAGGAGCAGAAGAAGCTGAACGACCTG

TGCTTCCTGAAGAGGCTGCTGCAGGAGATCAAGACCTGCTGGAACAAG

ATCCTGATGGGCACCAAGGAGCAT (Human Tissue Factor 219)
AGCGGCACAACCAACACAGTCGCTGCCTATAACCTCACTTGGAAGAGC

ACCAACTTCAAAACCATCCTCGAATGGGAACCCAAACCCGTTAACCAA

GTTTACACCGTGCAGATCAGCACCAAGTCCGGCGACTGGAAGTCCAAA

TGTTTCTATACCACCGACACCGAGTGCGATCTCACCGATGAGATCGTG

AAAGATGTGAAACAGACCTACCTCGCCCGGGTGTTTAGCTACCCCGCC

GGCAATGTGGAGAGCACTGGTTCCGCTGGCGAGCCTTTATACGAGAAC

AGCCCCGAATTTACCCCTTACCTCGAGACCAATTTAGGACAGCCCACC

ATCCAAAGCTTTGAGCAAGTTGGCACAAAGGTGAATGTGACAGTGGAG

GACGAGCGGACTTTAGTGCGGCGGAACAACACCTTTCTCAGCCTCCGG

GATGTGTTCGGCAAAGATTTAATCTACACACTGTATTACTGGAAGTCC

TCTTCCTCCGGCAAGAAGACAGCTAAAACCAACACAAACGAGTTTTTA

ATCGACGTGGATAAAGGCGAAAACTACTGTTTCAGCGTGCAAGCTGTG

ATCCCCTCCCGGACCGTGAATAGGAAAAGCACCGATAGCCCCGTTGAG

TGCATGGGCCAAGAAAAGGGCGAGTTCCGGGAG (Human IL-15)
AACTGGGTGAACGTCATCAGCGATTTAAAGAAGATCGAAGATTTAATT

CAGTCCATGCATATCGACGCCACTTTATACACAGAATCCGACGTGCAC

CCCTCTTGTAAGGTGACCGCCATGAAATGTTTTTTACTGGAGCTGCAA

GTTATCTCTTTAGAGAGCGGAGACGCTAGCATCCACGACACCGTGGAG

AATTTAATCATTTTAGCCAATAACTCTTTATCCAGCAACGGCAACGTG

ACAGAGTCCGGCTGCAAGGAGTGCGAAGAGCTGGAGGAGAAGAACATC

AAGGAGTTTCTGCAATCCTTTGTGCACATTGTCCAGATGTTCATCAAT

ACCTCC
```

The first chimeric polypeptide of IL-7/TF/IL-15 (including leader sequence), is as follows (SEQ ID NO: 143):

```
(Signal peptide)
MKWVTFISLLFLFSSAYS (Human IL-7)
DCDIEGKDGKQYESVLMVSIDQLLDSMKEIGSNCLNNEFNFFKRHICD

ANKEGMFLFRAARKLRQFLKMNSTGDFDLHLLKVSEGTTILLNCTGQV

KGRKPAALGEAQPTKSLEENKSLKEQKKLNDLCFLKRLLQEIKTCWNK

ILMGTKEH (Human Tissue Factor 219)
SGTTNTVAAYNLTWKSTNFKTILEWEPKPVNQVYTVQISTKSGDWKSK

CFYTTDTECDLTDEIVKDVKQTYLARVFSYPAGNVESTGSAGEPLYEN

SPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAV

IPSRTVNRKSTDSPVECMGQEKGEFRE (Human IL-15)
NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS
```

Example 71: Secretion of IL-21/IL-15RαSu and IL-7/TF/IL-15 Fusion Proteins

The IL-21/IL-15RαSu and IL-7/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-7/TF/IL-15:IL-21/IL-15RαSu protein complex (referred to as 7t15-21s). The 7t15-21s protein was purified from CHO-K1 cell culture supernatant using anti-TF antibody (IgG1) affinity chromatography and size exclusion chromatography resulting in soluble (non-aggregated) protein complexes consisting of IL-21/IL-15RαSu and IL-7/TF/IL-15 fusion proteins. See, FIGS. 82 and 83.

Figure 84:
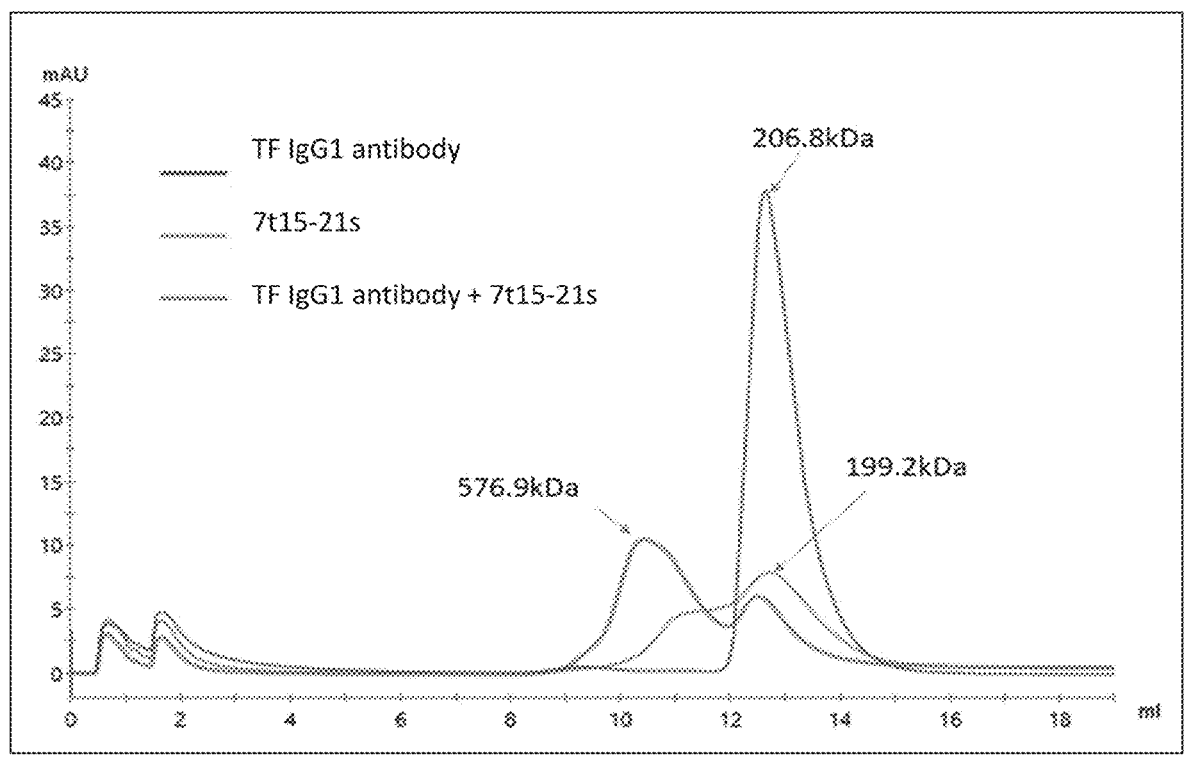
FIG. 84 shows size exclusion chromatography (SEC) profiles of anti-TF IgG1 antibody, 7t15-21s and the complex containing equal amounts of anti-TF IgG1 antibody and 7t15-21s.

Example 72: Analytical Size Exclusion Chromatography (SEC) Analysis of IL-21/IL-15RαSu and IL-7/TF/IL-15 Fusion Proteins To determine if anti-tissue factor monoclonal antibody and 7t15-21s can form an antibody-fusion-molecule complex, analytical size exclusion chromatography (SEC) was performed. A Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. Samples of the anti-TF mAb (1 mg/mL), 7t15-21s (1 mg/mL), and a mixture of combined at a 1:1 ratio, so the final concentration of each protein is 0.5 mg/mL) were in PBS. Each sample was injected into the Superdex 200 column using a capillary loop, and analyzed by SEC. The SEC chromatograph of each sample was shown in FIG. 84. The SEC results indicated that there are two protein peaks for 7t15-21s, likely representing a dimer (with an apparent molecular weight of 199.2 kDa) and a higher oligomer of 7t15-21s, and there is one peak (with an apparent molecular weight of 206.8 kDa) for the anti-TF mAb. However, as expected, a new protein peak with a higher molecular weight (with an apparent molecular weight of 576.9 kDa) was formed in the mixture sample containing the anti-TF mAb and 7t15-21s, indicating that the anti-TF mAb and 7t15-21s form an antibody-antigen complex through the binding of anti-TF mAb to TF in the fusion protein complex.

Example 73: Expansion Capacity of Primary Natural Killer (NK) Cells by 7t15-21s Complex+Anti-TF IgG1 Antibody To assess the 7t15-21s complex's ability to expand primary natural killer (NK) cells, 7t15-21s complex and 7t15-21s complex+anti-TF IgG1 antibody are added to NK cells obtained from samples of fresh human leukocytes. Cells are stimulated with 50 nM of 7t15-21s complex with or without 25 nM of anti-TF IgG1 or anti-TF IgG4 antibody at 37° C. and 5% $CO_2$. Cells are maintained at concentration at $0.5 \times 10^6$/mL not exceeding $2.0 \times 10^6$/mL by counting every 48-72 hours and media is replenished with fresh stimulator. Cells stimulated with 7t15-21s complex or anti-TF IgG1 antibody or anti-TF IgG4 antibody or anti-TF IgG4+7t15-21s complex are maintained up to day 5. Expansion of primary NK cells upon incubation with 21t15-7s complex+anti-TF IgG1 antibody is observed.

Example 74: Activation of Expanded NK Cells by the 7t15-21s Complex+Anti-TF IgG1 Antibody Primary NK cells are induced ex vivo following overnight stimulation of purified NK cells with 7t15-21s complex+anti-TF IgG1 antibody. Fresh human leukocytes are obtained from a blood bank and CD56+ NK cells are isolated with the RosetteSep/human NK cell reagent (StemCell Technologies). The purity of NK cells is >80% and is confirmed by staining with CD56-BV421 and CD16-BV510 specific antibodies (BioLegend). Cells are counted and resuspended in $1 \times 10^6$/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells are stimulated with 50 nM of 7t15-21s with or without 25 nM of anti-TF IgG1 antibody at 37° C. and 5% $CO_2$. Cells are counted every 48-72 hours and maintained at a concentration of $0.5 \times 10^6$/mL to $2.0 \times 10^6$/mL until day 14. Media is periodically replenished with fresh stimulator. Cells are harvested and surface stained at day 3 with CD56-BV421, CD16-BV510, CD25-PE, CD69-APCFire750 specific antibodies (Biolegend and analyzed by Flow Cytometry-Celeste-BD Bioscience). The activation marker CD25 MFI are observed to increase with 7t15-21s complex+anti-TF IgG1 antibody stimulation, but not 7t15-21s complex stimulation. The activation marker CD69 MFI is observed to increase with both 7t15-21s complex+anti-TF IgG1 antibody and with 7t15-21s complex, alone.

Example 75: 7t15-16s21 Fusion Protein Generation and Characterization

Figure 85:
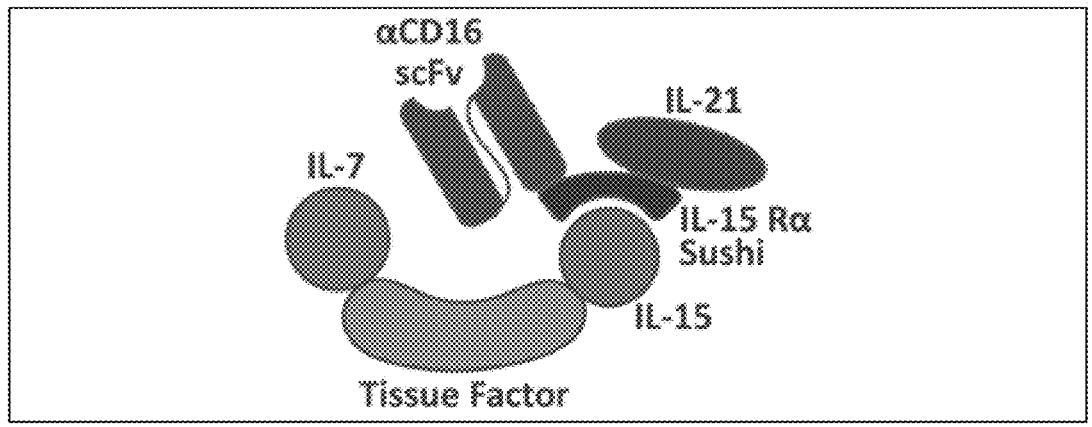
FIG. 85 shows a schematic of the 7t15-16s21 construct.
Figure 86:
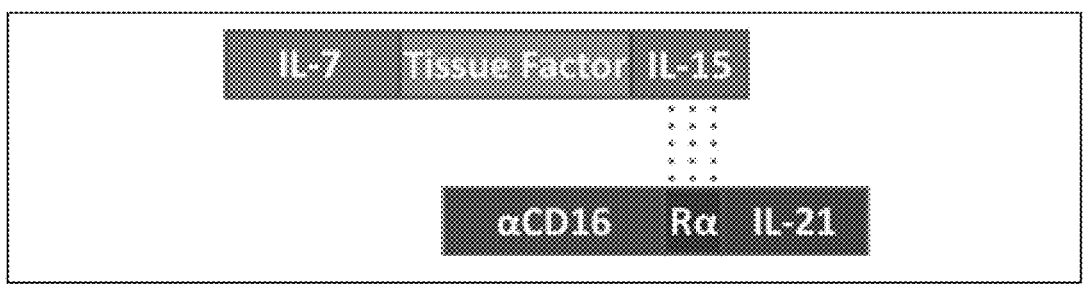
FIG. 86 shows an additional schematic of the 7t15-16s21 construct.

A fusion protein complex was generated comprising of anti-CD16scFv/IL-15RαSu/IL-21 and IL-7/TF/IL-15 fusion proteins. The human IL-7 and IL-21 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15. See, FIGS. 85 and 86.

The nucleic acid and protein sequences of a construct comprising IL-7 linked to the N-terminus of tissue factor 219 following with the N-terminus of IL-15 are shown below.

The nucleic acid sequence of the IL-7/TF/IL-15 construct (including signal peptide sequence) is as follows:

```
(Signal peptide)
ATGAAGTGGGTGACCTTCATCAGCCTGCTGTTCCTGTTCTCCAGCGCC

TACTCC (Human IL-7)
GATTGCGACATCGAGGGCAAGGACGGCAAGCAGTACGAGAGCGTGCTG

ATGGTGTCCATCGACCAGCTGCTGGACAGCATGAAGGAGATCGGCTCC

AACTGCCTCAACAACGAGTTCAACTTCTTCAAGCGGCACATCTGCGAC

GCCAACAAGGAGGGCATGTTCCTGTTCAGGGCCGCCAGGAAACTGCGG

CAGTTCCTGAAGATGAACTCCACCGGCGACTTCGACCTGCACCTGCTG

AAGGTGTCCGAGGGCACCACCATCCTGCTGAACTGCACCGGACAGGTG
```

```
AAGGGCCGGAAACCTGCTGCTCTGGGAGAGGCCCAACCCACCAAGAGC

CTGGAGGAGAACAAGTCCCTGAAGGAGCAGAAGAAGCTGAACGACCTG

TGCTTCCTGAAGAGGCTGCTGCAGGAGATCAAGACCTGCTGGAACAAG

ATCCTGATGGGCACCAAGGAGCAT (Human Tissue Factor 219)
AGCGGCACAACCAACACAGTCGCTGCCTATAACCTCACTTGGAAGAGC

ACCAACTTCAAAACCATCCTCGAATGGGAACCCAAACCCGTTAACCAA

GTTTACACCGTGCAGATCAGCACCAAGTCCGGCGACTGGAAGTCCAAA

TGTTTCTATACCACCGACACCGAGTGCGATCTCACCGATGAGATCGTG

AAAGATGTGAAACAGACCTACCTCGCCCGGGTGTTTAGCTACCCCGCC

GGCAATGTGGAGAGCACTGGTTCCGCTGGCGAGCCTTTATACGAGAAC

AGCCCCGAATTTACCCCTTACCTCGAGACCAATTTAGGACAGCCCACC

ATCCAAAGCTTTGAGCAAGTTGGCACAAAGGTGAATGTGACAGTGGAG

GACGAGCGGACTTTAGTGCGGCGGAACAACACCTTTCTCAGCCTCCGG

GATGTGTTCGGCAAAGATTTAATCTACACACTGTATTACTGGAAGTCC

TCTTCCTCCGGCAAGAAGACAGCTAAAACCAACACAAACGAGTTTTTA

ATCGACGTGGATAAAGGCGAAAACTACTGTTTCAGCGTGCAAGCTGTG

ATCCCCTCCCGGACCGTGAATAGGAAAAGCACCGATAGCCCCGTTGAG

TGCATGGGCCAAGAAAAGGGCGAGTTCCGGGAG (Human IL-15)
AACTGGGTGAACGTCATCAGCGATTTAAAGAAGATCGAAGATTTAATT

CAGTCCATGCATATCGACGCCACTTTATACACAGAATCCGACGTGCAC

CCCTCTTGTAAGGTGACCGCCATGAAATGTTTTTTACTGGAGCTGCAA

GTTATCTCTTTAGAGAGCGGAGACGCTAGCATCCACGACACCGTGGAG

AATTTAATCATTTTAGCCAATAACTCTTTATCCAGCAACGGCAACGTG

ACAGAGTCCGGCTGCAAGGAGTGCGAAGAGCTGGAGGAGAAGAACATC

AAGGAGTTTCTGCAATCCTTTGTGCACATTGTCCAGATGTTCATCAAT

ACCTCC
```

The amino acid sequence of IL-7/TF/IL-15 fusion protein (including the leader sequence) is as follows:

```
(Signal peptide)
MKWVTFISLLFLFSSAYS (Human IL-7)
DCDIEGKDGKQYESVLMVSIDQLLDSMKEIGSNCLNNEFNFFKRHICD

ANKEGMFLFRAARKLRQFLKMNSTGDFDLHLLKVSEGTTILLNCTGQV

KGRKPAALGEAQPTKSLEENKSLKEQKKLNDLCFLKRLLQEIKTCWNK

ILMGTKEH (Human Tissue Factor 219)
SGTTNTVAAYNLTWKSTNFKTILEWEPKPVNQVYTVQISTKSGDWKSK

CFYTTDTECDLTDEIVKDVKQTYLARVFSYPAGNVESTGSAGEPLYEN

SPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAV

IPSRTVNRKSTDSPVECMGQEKGEFRE (Human IL-15)
NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS
```

Constructs were also made by linking the anti-CD16scFv sequence to the N-terminus coding region of IL-15RαSu chain followed by the N-terminus coding region of IL-21 which was synthesized by Genewiz. The nucleic acid and protein sequences of a construct comprising the anti-CD16scFv linked to the N-terminus of IL-15RαSu chain followed by the N-terminus coding region of IL-21 are shown below.

The nucleic acid sequence of the anti-CD16SscFv/IL-15 RαSu/IL-21 construct (including signal peptide sequence) is as follows:

```
(Signal peptide)
ATGAAGTGGGTGACCTTCATCAGCCTGCTGTTCCTGTTCTCCAGCGCC

TACTCC ((Anti-human CD16scFv)
TCCGAGCTGACCCAGGACCCTGCTGTGTCCGTGGCTCTGGGCCAGACC

GTGAGGATCACCTGCCAGGGCGACTCCCTGAGGTCCTACTACGCCTCC

TGGTACCAGCAGAAGCCCGGCCAGGCTCCTGTGCTGGTGATCTACGGC

AAGAACAACAGGCCCTCCGGCATCCCTGACAGGTTCTCCGGATCCTCC

TCCGGCAACACCGCCTCCCTGACCATCACAGGCGCTCAGGCCGAGGAC

GAGGCTGACTACTACTGCAACTCCAGGGACTCCTCCGGCAACCATGTG

GTGTTCGGCGGCGGCACCAAGCTGACCGTGGGCCATGGCGGCGGCGGC

TCCGGAGGCGGCGGCAGCGGCGGAGGAGGATCCGAGGTGCAGCTGGTG

GAGTCCGGAGGAGGAGTGGTGAGGCCTGGAGGCTCCCTGAGGCTGAGC

TGTGCTGCCTCCGGCTTCACCTTCGACGACTACGGCATGTCCTGGGTG

AGGCAGGCTCCTGGAAAGGGCCTGGAGTGGGTGTCCGGCATCAACTGG

AACGGCGGATCCACCGGCTACGCCGATTCCGTGAAGGGCAGGTTCACC

ATCAGCAGGGACAACGCCAAGAACTCCCTGTACCTGCAGATGAACTCC

CTGAGGGCCGAGGACACCGCCGTGTACTACTGCGCCAGGGGCAGGTCC

CTGCTGTTCGACTACTGGGGACAGGGCACCCTGGTGACCGTGTCCAGG (Human IL-15R α sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGC

TTCAAGAGGAAGGCCGGCACCAGCAGCCTCACCGAGTGCGTGCTGAAT

AAGGCTACCAACGTGGCTCACTGGACAACACCCTCTTTAAAGTGCATC

CGG (Human IL-21)
CAGGGCCAGGACAGGCACATGATCCGGATGAGGCAGCTCATCGACATC

GTCGACCAGCTGAAGAACTACGTGAACGACCTGGTGCCCGAGTTTCTG

CCTGCCCCCGAGGACGTGGAGACCAACTGCGAGTGGTCCGCCTTCTCC
```

-continued

```
TGCTTTCAGAAGGCCCAGCTGAAGTCCGCCAACACCGGCAACAACGAG

CGGATCATCAACGTGAGCATCAAGAAGCTGAAGCGGAAGCCTCCCTCC

ACAAACGCCGGCAGGAGGCAGAAGCACAGGCTGACCTGCCCCAGCTGT

GACTCCTACGAGAAGAAGCCCCCAAGGAGTTCCTGGAGAGGTTCAAG

TCCCTGCTGCAGAAGATGATCCATCAGCACCTGTCCTCCAGGACCCAC

GGCTCCGAGGACTCC
```

The amino acid sequence of the anti-CD16scFv/IL-15RαSu/IL-21 construct (including signal peptide sequence) is as follows:

```
(Signal peptide)
MKWVTFISLLFLFSSAYS (Anti-human CD16scFv)
SELTQDPAVSVALGQTVRITCQGDSLRSYYASWYQQKPGQAPVLVIYG

KNNRPSGIPDRFSGSSSGNTASLTITGAQAEDEADYYCNSRDSSGNHV

VFGGGTKLTVGHGGGGSGGGGSGGGGSEVQLVESGGGVVRPGGSLRLS

CAASGFTFDDYGMSWVRQAPGKGLEWVSGINWNGGSTGYADSVKGRFT

ISRDNAKNSLYLQMNSLRAEDTAVYYCARGRSLLFDYWGQGTLVTVSR (Human IL-15R α sushi domain)
ITCPPPMSVEHADIWVKSYSLYSRERYICNSGFKRKAGTSSLTECVLN

KATNVAHWTTPSLKCIR (Human IL-21)
QGQDRHMIRMRQLIDIVDQLKNYVNDLVPEFLPAPEDVETNCEWSAFS

CFQKAQLKSANTGNNERIINVSIKKLKRKPPSTNAGRRQKHRLTCPSC

DSYEKKPPKEFLERFKSLLQKMIHQHLSSRTHGSEDS
```

In some cases, the leader peptide is cleaved from the intact polypeptide to generate the mature form that may be soluble or secreted.

The anti-CD16scFv/IL-15RαSu/IL-21 and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. Hum Gene Ther 2005; 16:457-72), and the expression vectors were transfected into CHO-K1 cells. Co-expression of the two constructs in CHO-K1 cells allowed for formation and secretion of the soluble IL-7/TF/IL-15:anti-CD16scFv/IL-15RαSu/IL-21 protein complex (referred to as 7t15-16s21), which can be purified by anti-TF antibody-based affinity and other chromatography methods.

Binding of 7t15-16s21 to CHO Cells Expressing Human CD16b

Figure 87A:
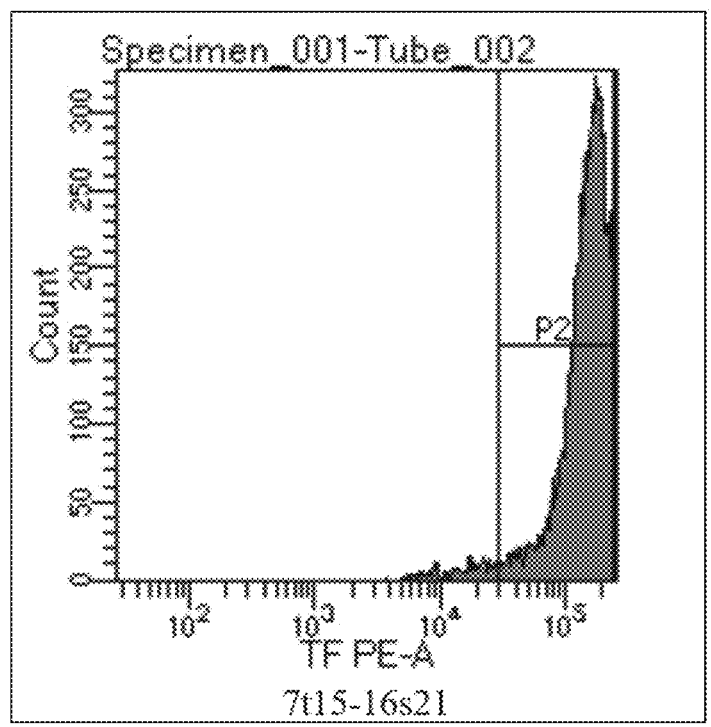
FIGS. 87A and 87B are graphs showing binding of 7t15-16s21 to CHO cells expressing human CD16b as compared to a control protein.
Figure 87B:
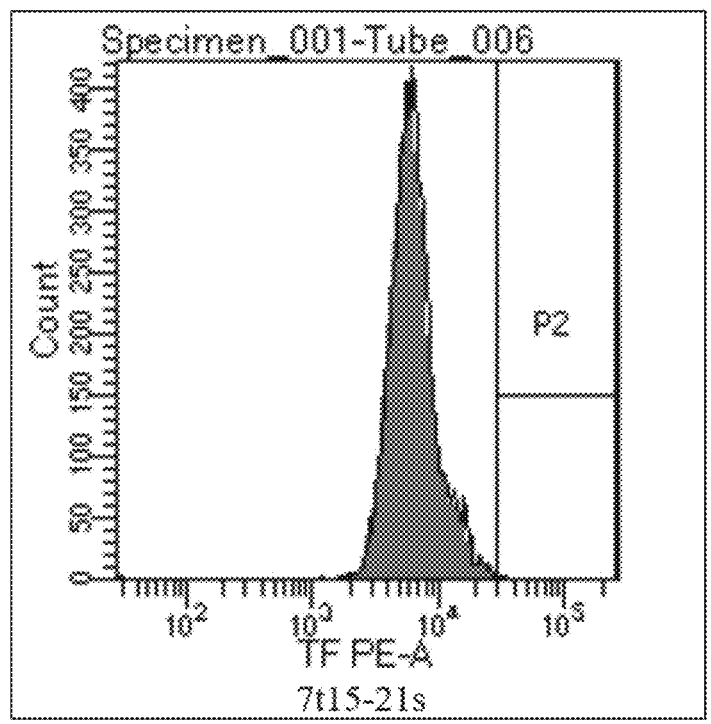

CHO cells were transfected with human CD16b in a pMC plasmid and selected with 10 μg/mL of blasticidin for 10 days. The CHO cells stably expressing CD16b were stained with 1.2 μg/mL of 7t15-16s21 (containing anti-human CD16 scFv) or 18t15-12s (does not contain anti-human CD16 scFv) as a negative control, and then stained with biotinylated anti-human tissue factor and PE conjugated streptavidin. Only anti-human CD16scFv containing 7t15-16s21 stained the cells as shown in FIG. 87A. 18t15-12s did not stain the CHO cells expressing human CD16b as showed in FIG. 87B.

Detection of IL-15, IL-21, and IL-7 in 7t15-16s21 Using ELISA

Figure 88A:
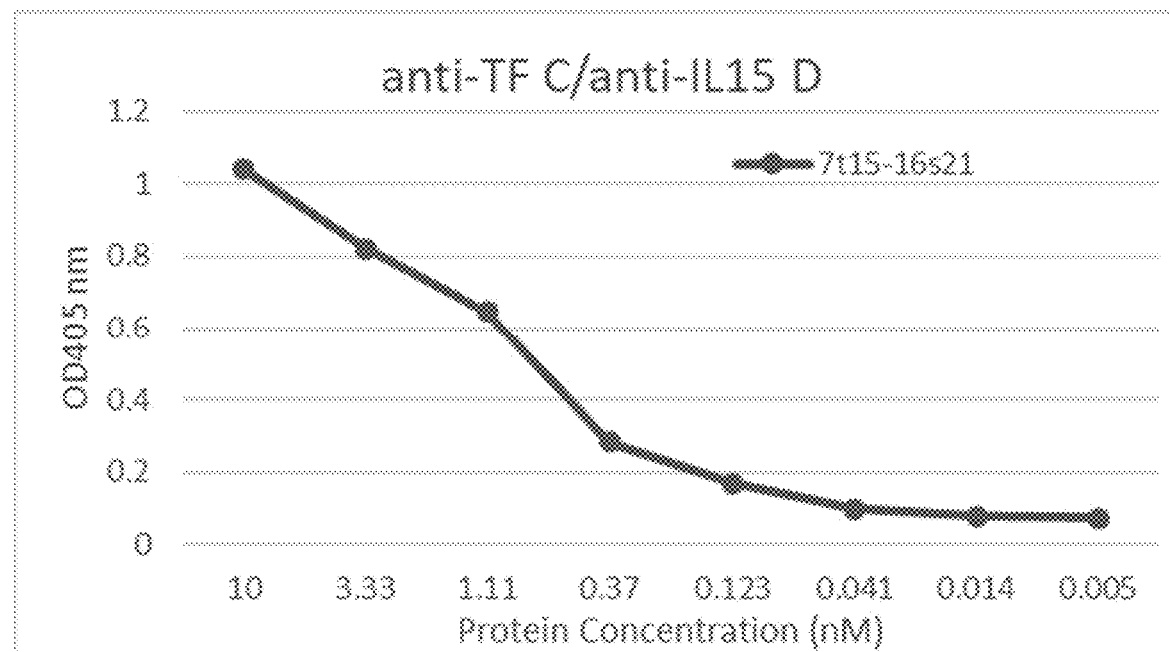
FIGS. 88A-88C are results from ELISA experiments using antibodies against IL-15, IL-21, and IL-7 in detecting 7t15-16s21.
Figure 88B:
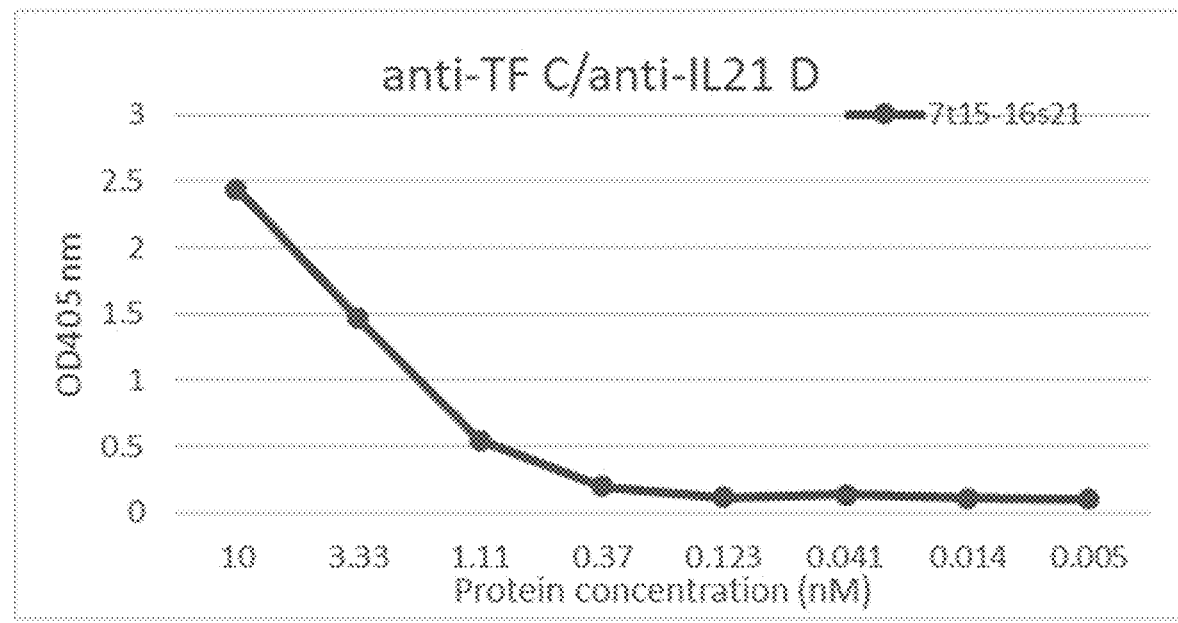
Figure 88C:
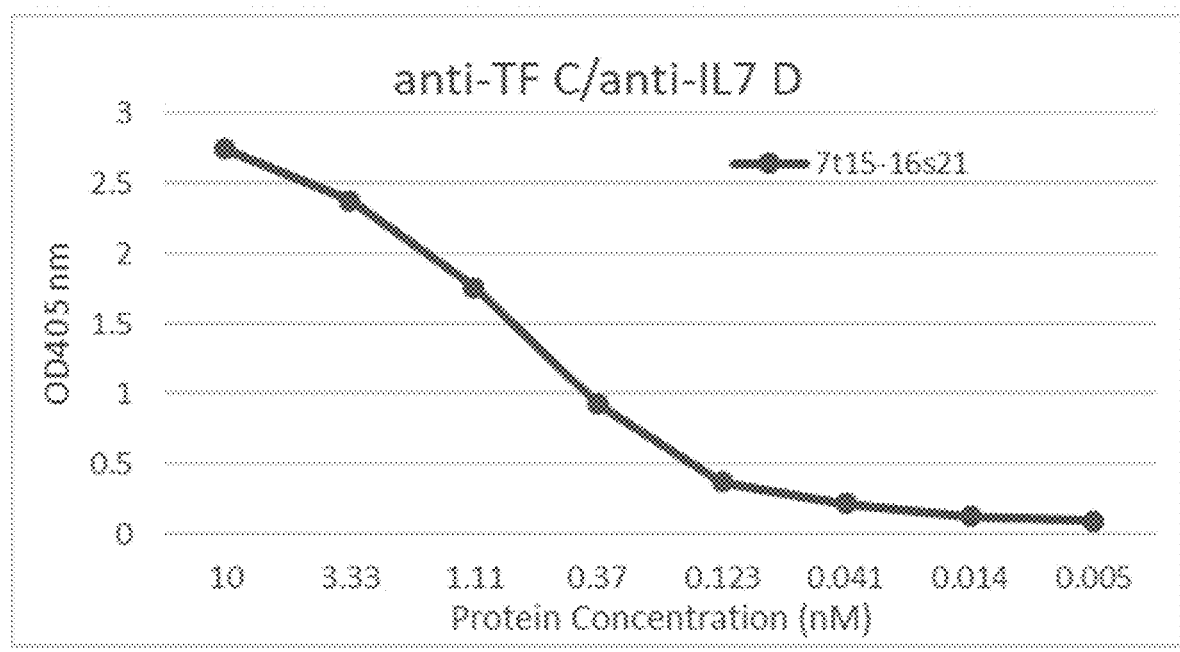

A 96-well plate was coated with 100 μL (8 μg/mL) of anti-TF antibody in R5 (coating buffer) and incubated at room temperature (RT) for 2 hrs. The plates were washed 3 times and blocked with 100 μL of 1% BSA in PBS. Serial dilution of 7t15-16s21 (at a 1:3 ratio) were added to the wells, and incubated at RT for 60 min. Following 3 washes, 50 ng/mL of biotinylated-anti-IL15 antibody (BAM247, R&D Systems), 500 ng/mL of biotinylated-anti-IL-21 antibody (13-7218-81, R&D Systems), or 500 ng/mL of biotinylated-anti-IL-7 antibody (506602, R&D Systems) was added to the wells and incubated at RT for 60 min. The plate was washed 3 times, and incubated with 0.25 μg/mL of HRP-SA (Jackson ImmunoResearch) at 100 μL per well for 30 min at RT, followed by 4 washes and incubation with 100 μl of ABTS for 2 mins at RT. Absorbance was read at 405 nm. As shown in FIGS. 88A-88C, the IL-15, IL-21, and IL-7 domains in 7t15-16s21 were detected by the individual antibodies.

Figure 89:
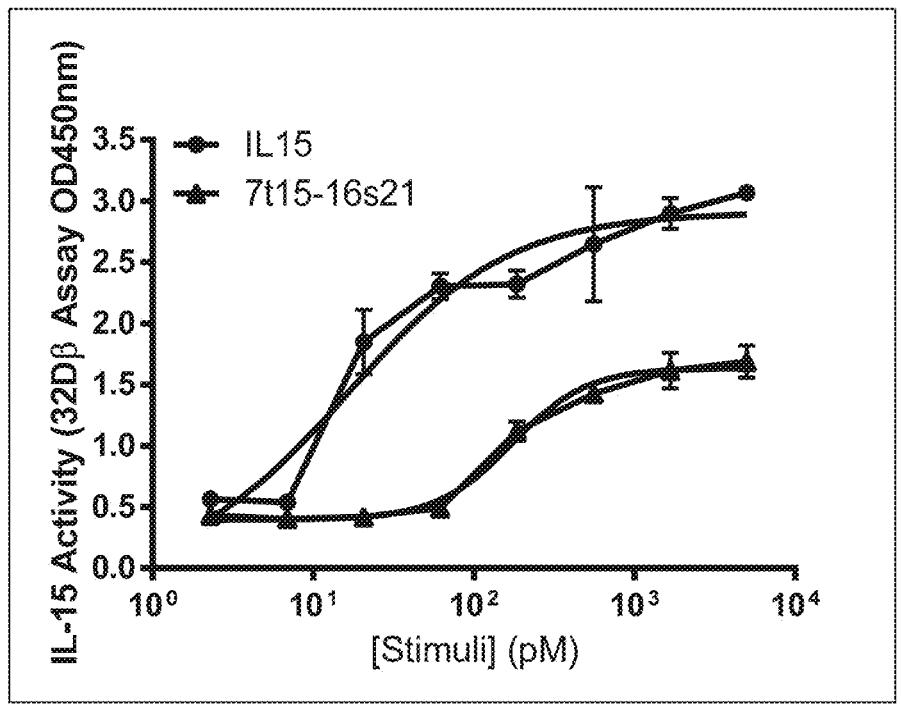
FIG. 89 shows results of the 32Dβ cell proliferation assay with 7t15-16s21 or recombinant IL-15.

The IL-15 in 7t15-16s21 Promotes IL-2Rβ and Common γ Chain Containing 32Dβ Cell Proliferation To analyze the activity of IL-15 in 7t15-16s21, the IL-15 activity of 7t15-16s21 was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted 7t15-16s21 or IL-15 were added to the cells (FIG. 89). Cells were incubated in a $CO_2$ incubator at 37° C. for 3 days. Cell proliferation was detected by adding 10 μl of WST1 to each well on day 3 and incubating for an additional 3 hours in a $CO_2$ incubator at 37° C. The absorbance at 450 nm was measured by analyzing the amount of formazan dye produced. As shown in FIG. 5, 7t15-16s21 and IL-15 promoted 32Dβ cell proliferation, with the $EC_{50}$ of 7t15-16s21 and IL-15 being 172.2 pM and 16.63 pM, respectively.

Purification Elution Chromatograph of 7t15-16s21 from Anti-TF Affinity Column

Figure 90:
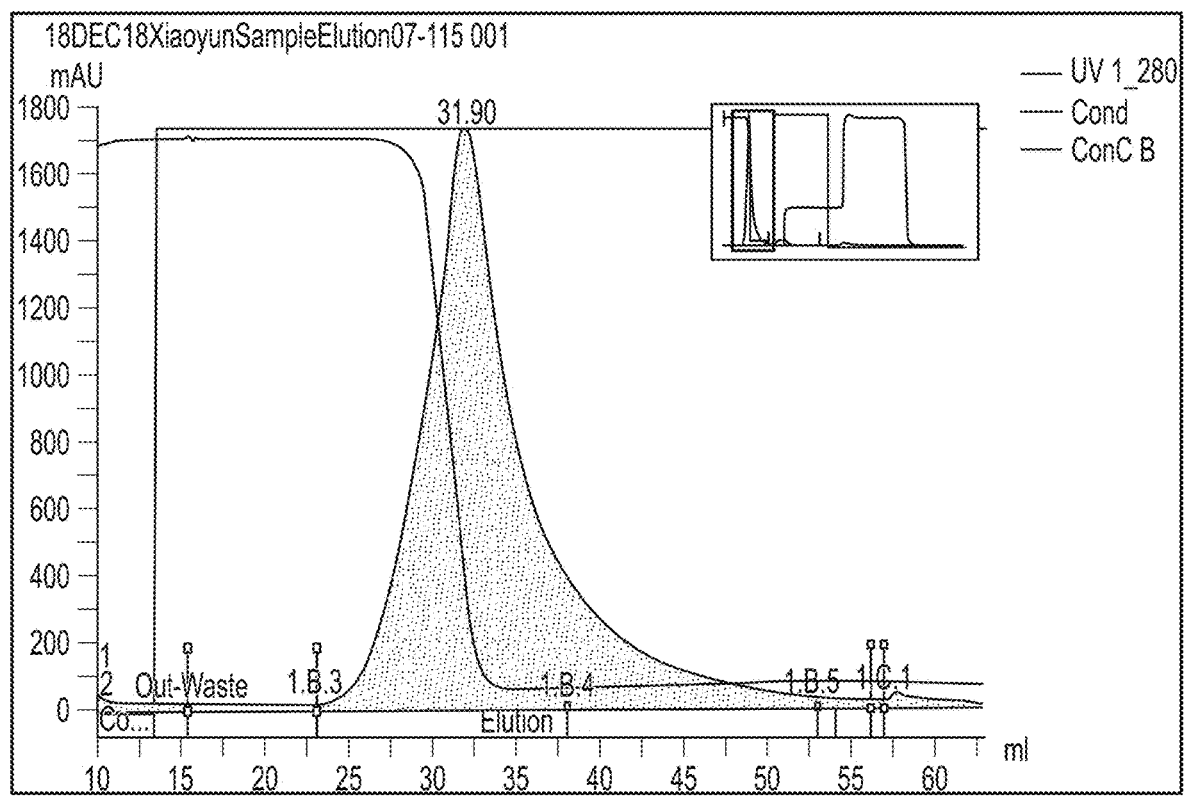
FIG. 90 is a line graph showing the chromatographic profile of 7t15-16s21 protein containing cell culture supernatant following binding and elution on anti-TF antibody resin.

7t15-16s21 harvested from cell culture was loaded onto the anti-TF affinity column equilibrated with 5 column volumes of PBS. The column was then washed with 5 column volumes of PBS, followed by elution with 6 column volumes of 0.1M acetic acid (pH 2.9). A280 elution peak was collected and neutralized to pH 7.5-8.0 with 1M Tris base. The neutralized sample was buffer exchanged into PBS using Amicon centrifugal filters with a 30 KDa molecular weight cutoff. FIG. 90 is a line graph showing the chromatographic profile of 7t15-16s21 protein containing cell culture supernatant following binding and elution on anti-TF antibody resin. As shown in FIG. 90, the anti-TF antibody affinity column bound 7t15-16s21 which contains TF. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of 7t15-16s21

Figure 91:
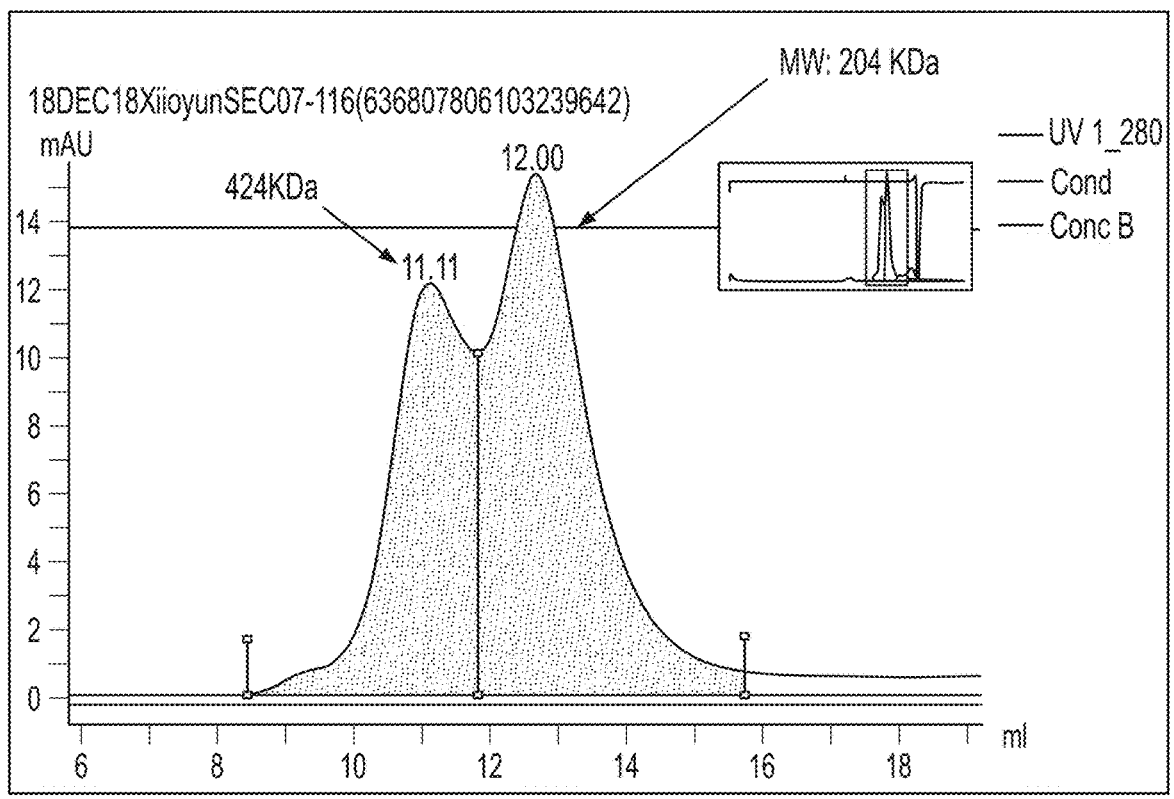
FIG. 91 shows the analytical SEC Profile of 7t15-16s21.

To perform size exclusion chromatography (SEC) analysis for 7t15-16s21, a Superdex 200 Increase 10/300 GL gel filtration column (GE Healthcare) connected to an AKTA Avant system (GE Healthcare) was used. The column was equilibrated with 2 column volumes of PBS. The flow rate was 0.7 mL/min. A sample containing 7t15-16s21 in PBS was injected into the Superdex 200 column using a capillary loop, and analyzed by SEC. As shown in FIG. 91, the SEC results showed two protein peaks for 7t15-16s21.

Example 76: TGFRt15-16s21 Fusion Protein Generation and Characterization

Figure 92:
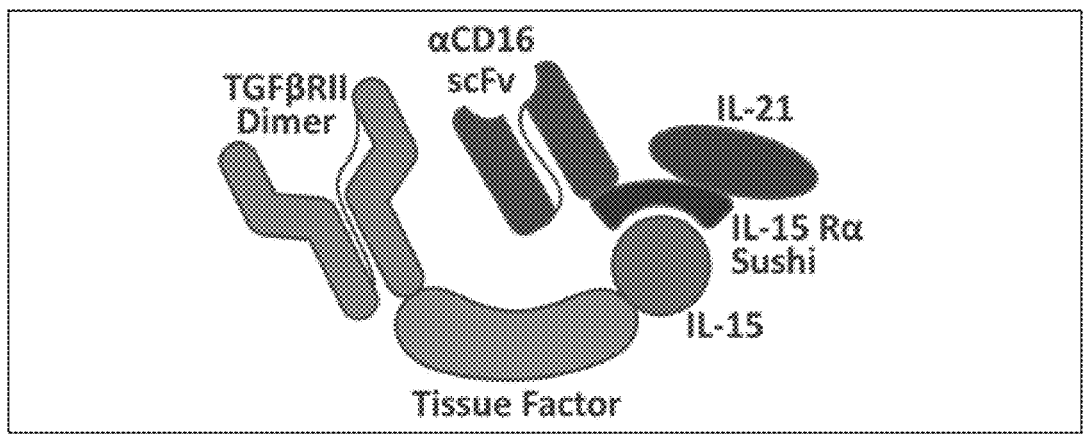
FIG. 92 shows a schematic of the TGFRt15-16s21 construct.
Figure 93:
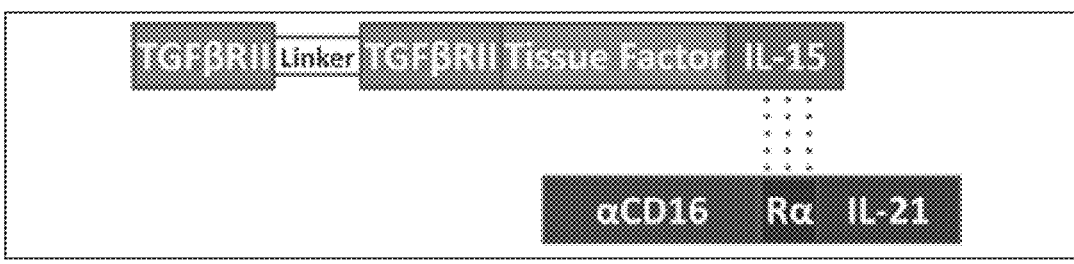
FIG. 93 shows an additional schematic of the TGFRt15-16s21 construct.

A fusion protein complex was generated comprising anti-human CD16scFv/IL-15RαSu/IL21 and TGFβ Receptor II/TF/IL-15 fusion proteins (FIGS. 92 and 93). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G45(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the two TGFβ Receptor II/TF/IL-15 construct (including signal peptide sequence) is as follows:

(Signal peptide)
ATGAAGTGGGTGACCTTCATCAGCCTGCTGTTCCTGTTCTCCAGCGCC

TACTCC (Two Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

AGCATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCTCCATCACCTCCATCTGTGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGAC (Human Tissue Factor 219)
AGCGGCACAACCAACACAGTCGCTGCCTATAACCTCACTTGGAAGAGC

ACCAACTTCAAAACCATCCTCGAATGGGAACCCAAACCCGTTAACCAA

GTTTACACCGTGCAGATCAGCACCAAGTCCGGCGACTGGAAGTCCAAA

TGTTTCTATACCACCGACACCGAGTGCGATCTCACCGATGAGATCGTG

AAAGATGTGAAACAGACCTACCTCGCCCGGGTGTTTAGCTACCCCGCC

GGCAATGTGGAGAGCACTGGTTCCGCTGGCGAGCCTTTATACGAGAAC

AGCCCCGAATTTACCCCTTACCTCGAGACCAATTTAGGACAGCCCACC

ATCCAAAGCTTTGAGCAAGTTGGCACAAAGGTGAATGTGACAGTGGAG

GACGAGCGGACTTTAGTGCGGCGGAACAACACCTTTCTCAGCCTCCGG

GATGTGTTCGGCAAAGATTTAATCTACACACTGTATTACTGGAAGTCC

TCTTCCTCCGGCAAGAAGACAGCTAAAACCAACACAAACGAGTTTTTA

ATCGACGTGGATAAAGGCGAAAACTACTGTTTCAGCGTGCAAGCTGTG

ATCCCCTCCCGGACCGTGAATAGGAAAAGCACCGATAGCCCCGTTGAG

TGCATGGGCCAAGAAAAGGGCGAGTTCCGGGAG (Human IL-15)
AACTGGGTGAACGTCATCAGCGATTTAAAGAAGATCGAAGATTTAATT

CAGTCCATGCATATCGACGCCACTTTATACACAGAATCCGACGTGCAC

CCCTCTTGTAAGGTGACCGCCATGAAATGTTTTTTACTGGAGCTGCAA

GTTATCTCTTTAGAGAGCGGAGACGCTAGCATCCACGACACCGTGGAG

AATTTAATCATTTTAGCCAATAACTCTTTATCCAGCAACGGCAACGTG

ACAGAGTCCGGCTGCAAGGAGTGCGAAGAGCTGGAGGAGAAGAACATC

AAGGAGTTTCTGCAATCCTTTGTGCACATTGTCCAGATGTTCATCAAT

ACCTCC

The amino acid sequence of TGFβ Receptor II/TF/IL-15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNC

SITSICEKPQEVCVAVWRKNDENITLETVCHDPKLPYHDFILEDAASP

KCIMKEKKKPGETFFMCSCSSDECNDNIIFSEEYNTSNPDGGGGSGGG

GSGGGGSIPPHVQKSVNNDMIVTDNNGAVKFPQLCKFCDVRFSTCDNQ

KSCMSNCSITSICEKPQEVCVAVWRKNDENITLETVCHDPKLPYHDFI

LEDAASPKCIMKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKS

KCFYTTDTECDLTDEIVKDVKQTYLARVFSYPAGNVESTGSAGEPLY

ENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFS

VQAVIPSRTVNRKSTDSPVECMGQEKGEFRE (Human IL-15)
NWVNVISDLKKIEDLIQSMHIDATLYTESDVHPSCKVTAMKCFLLEL

QVISLESGDASIHDTVENLIILANNSLSSNGNVTESGCKECEELEEK

NIKEFLQSFVHIVQMFINTS

Constructs were also made by attaching anti-human CD16scFv directly linking to the N-terminus coding region of IL-15RαSu chain followed by the N-terminus coding region of IL-21 which was synthesized by Genewiz. The nucleic acid and protein sequences of a construct comprising the anti-human CD16scFv linked to the N-terminus of IL-15RαSu followed by the N-terminus coding region of IL-21 are shown below.

The nucleic acid sequence of the anti-CD16scFv/IL-15 RαSu/IL-21 construct (including signal peptide sequence) is as follows:

(Signal peptide)
ATGAAGTGGGTGACCTTCATCAGCCTGCTGTTCCTGTTCTCCAGCGC

CTACTCC (Anti-human CD16scFv)
TCCGAGCTGACCCAGGACCCTGCTGTGTCCGTGGCTCTGGGCCAGAC

CGTGAGGATCACCTGCCAGGGCGACTCCCTGAGGTCCTACTACGCCT

CCTGGTACCAGCAGAAGCCCGGCCAGGCTCCTGTGCTGGTGATCTAC

GGCAAGAACAACAGGCCCTCCGGCATCCCTGACAGGTTCTCCGGATC

CTCCTCCGGCAACACCGCCTCCCTGACCATCACAGGCGCTCAGGCCG

AGGACGAGGCTGACTACTACTGCAACTCCAGGGACTCCTCCGGCAAC

CATGTGGTGTTCGGCGGCGGCACCAAGCTGACCGTGGGCCATGGCGG

CGGCGGCTCCGGAGGCGGCGGCAGCGGCGGAGGAGGATCCGAGGTGC

AGCTGGTGGAGTCCGGAGGAGGAGTGGTGAGGCCTGGAGGCTCCCTG

AGGCTGAGCTGTGCTGCCTCCGGCTTCACCTTCGACGACTACGGCAT

GTCCTGGGTGAGGCAGGCTCCTGGAAAGGGCCTGGAGTGGGTGTCCG

GCATCAACTGGAACGGCGGATCCACCGGCTACGCCGATTCCGTGAAG

GGCAGGTTCACCATCAGCAGGGACAACGCCAAGAACTCCCTGTACCT

GCAGATGAACTCCCTGAGGGCCGAGGACACCGCCGTGTACTACTGCG

CCAGGGGCAGGTCCCTGCTGTTCGACTACTGGGGACAGGGCACCCTG

GTGACCGTGTCCAGG (Human IL-15R α sushi domain)
ATTACATGCCCCCCTCCCATGAGCGTGGAGCACGCCGACATCTGGGT

GAAGAGCTATAGCCTCTACAGCCGGGAGAGGTATATCTGTAACAGCG

GCTTCAAGAGGAAGGCCGGCACCAGCAGCCTCACCGAGTGCGTGCTG

AATAAGGCTACCAACGTGGCTCACTGGACAACACCCTCTTTAAAGTG

CATCCGG (Human IL-21)
CAGGGCCAGGACAGGCACATGATCCGGATGAGGCAGCTCATCGACAT

CGTCGACCAGCTGAAGAACTACGTGAACGACCTGGTGCCCGAGTTTC

TGCCTGCCCCCGAGGACGTGGAGACCAACTGCGAGTGGTCCGCCTTC

TCCTGCTTTCAGAAGGCCCAGCTGAAGTCCGCCAACACCGGCAACAA

CGAGCGGATCATCAACGTGAGCATCAAGAAGCTGAAGCGGAAGCCTC

CCTCCACAAACGCCGGCAGGAGGCAGAAGCACAGGCTGACCTGCCCC

AGCTGTGACTCCTACGAGAAGAAGCCCCCCAAGGAGTTCCTGGAGAG

GTTCAAGTCCCTGCTGCAGAAGATGATCCATCAGCACCTGTCCTCCA

GGACCCACGGCTCCGAGGACTCC

The amino acid sequence of the anti-CD16scFv/IL-15RαSu/IL-21 construct (including signal peptide sequence) is as follows:

(Signal peptide)
MKWVTFISLLFLFSSAYS (Anti-human CD16scFv)
SELTQDPAVSVALGQTVRITCQGDSLRSYYASWYQQKPGQAPVLVIY

GKNNRPSGIPDRFSGSSSGNTASLTITGAQAEDEADYYCNSRDSSGN

HVVFGGGTKLTVGHGGGGSGGGGSGGGGSEVQLVESGGGVVRPGGSL

RLSCAASGFTFDDYGMSWVRQAPGKGLEWVSGINWNGGSTGYADSVK

GRFTISRDNAKNSLYLQMNSLRAEDTAVYYCARGRSLLFDYWGQGTL

VTVSR (Human IL-15R α sushi domain)
ITCPPPMSVEHADIWVKSYSLYSRERYICNSGFKRKAGTSSLTECVL

NKATNVAHWTTPSLKCIR (Human IL-21)
QGQDRHMIRMRQLIDIVDQLKNYVNDLVPEFLPAPEDVETNCEWSAF

SCFQKAQLKSANTGNNERIINVSIKKLKRKPPSTNAGRRQKHRLTCP

SCDSYEKKPPKEFLERFKSLLQKMIHQHL      SSRTHGSEDS

In some cases, the leader peptide is cleaved from the intact polypeptide to generate the mature form that may be soluble or secreted.

The anti-CD16scFv/IL-15RαSu/IL-21 and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:CD16scFv/IL-15RαSu/IL-21 protein complex (referred to as TGFRt15-16s21), which can be purified by anti-TF antibody-based affinity and other chromatography methods.

Interaction Between TGFRt15-16s21 and CHO Cells Expressing Human CD16b

Figure 94A:
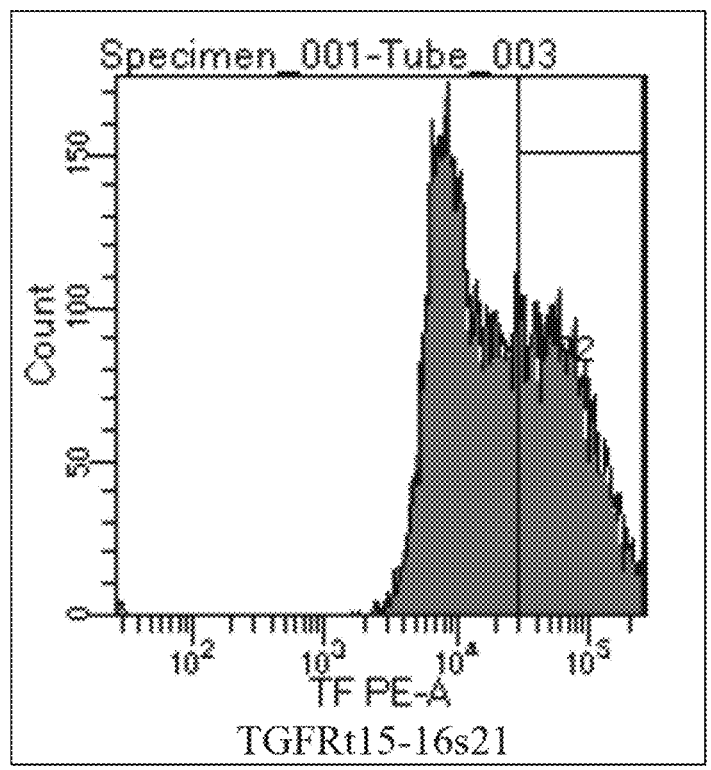
FIGS. 94A and 94B show binding affinity of TGFRt15-16s21 and 7t15-21s with CHO cells expressing human CD16b.
Figure 94B:
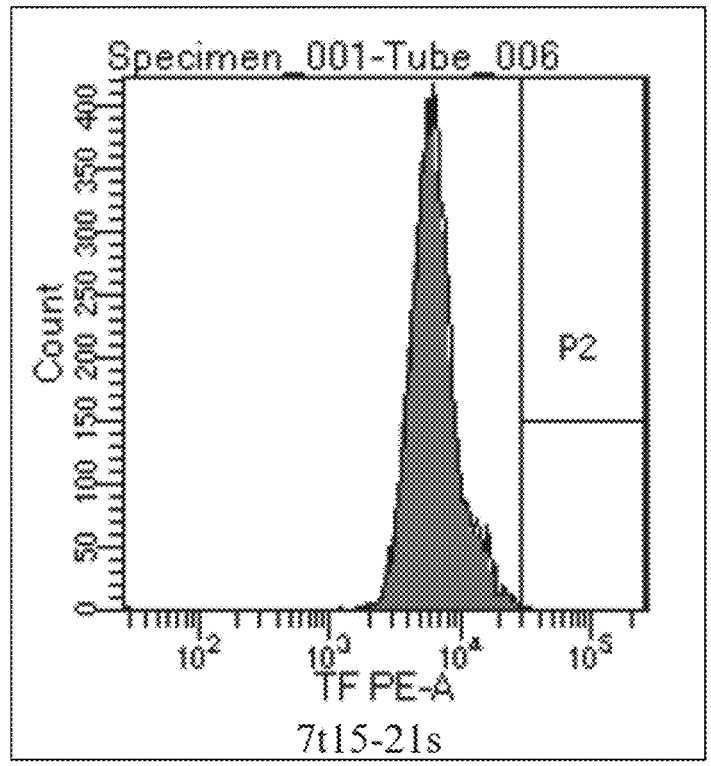

CHO cells were transfected with human CD16b in a pMC plasmid and selected with 10 μg/mL of blasticidin for 10 days. Cells stably expressing CD16b were stained with 1.2 μg/mL of TGFRt15-16s21 (containing anti-human CD16 scFv) or 7t15-21s (no anti-human CD16 scFv) as a negative control, and with biotinylated anti-human tissue factor antibody and PE conjugated streptavidin. As shown in FIGS. 94A and 94B, TGFRt15-16s21, which contains anti-human CD16scFv, showed positive binding, while 7t15-21s did not show binding.

Effect of TGFRt15-16s21 on TGF/31 Activity in HEK-Blue TGFβ Cells

Figure 95:
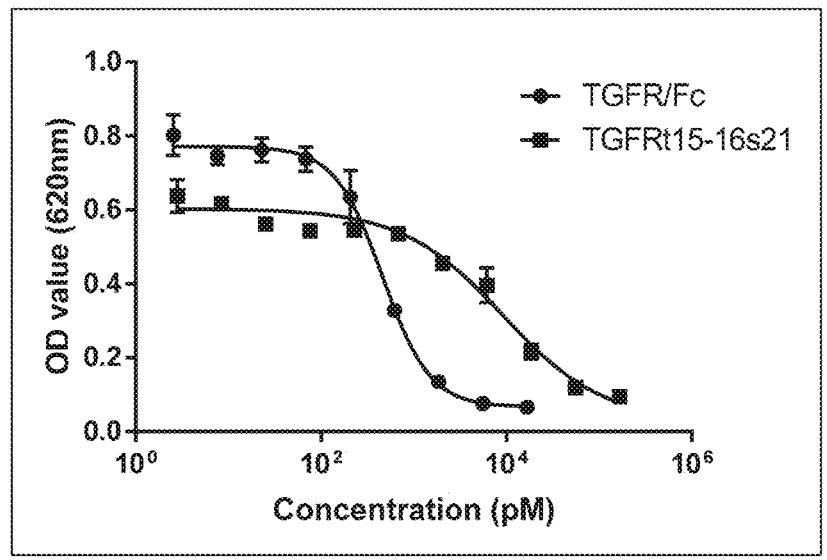
FIG. 95 shows results of TGFβ1 inhibition by TGFRt15-16s21 and TGFR-Fc.

To evaluate the activity of TGFβRII in TGFRt15-16s21, the effect of TGFRt15-16s21 on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μl cells were added to each well ($2.5\times10^4$ cells/well) and followed with 50 μL 0.1 nM TGFβ1 (R&D systems). TGFRt15-16s21 or TGFR-Fc (R&D Systems) prepared at a 1:3 serial dilution was then added to the plate to reach a total volume of 200 μL. After 24 hrs of incubation at 37° C., 40 μL of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. The $IC_{50}$ of each protein sample was calculated with GraphPad Prism 7.04. The $IC_{50}$ of TGFRt15-16s21 and TGFR-Fc were 9127 pM and 460.6 pM respectively. These results showed that the TGFβRII domain in TGFRt15-16s21 was able to block the activity of TGFβ-1 in HEK-Blue TGFβ cells. See, FIG. 95.

Figure 96:
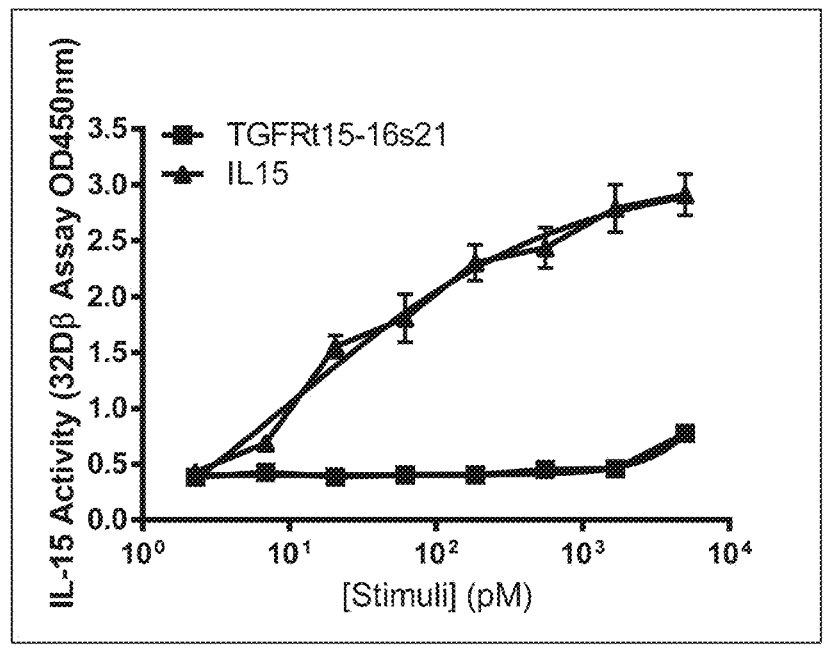
FIG. 96 shows results of 32Dβ cell proliferation assay with TGFRt15-16s21 or recombinant IL-15.

The IL-15 in TGFRt15-16s21 Promotes IL-2Rβ and Common γ Chain Containing 32Dβ Cell Proliferation To analyze the activity of IL-15 in TGFRt15-16s21, the IL-15 activity of TGFRt15-16s21 was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted TGFRt15-16s21 or IL-15 were added to the cells (FIG. 96). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The absorbance at 450 nm was measured by analyzing the amount of formazan dye produced. As shown in FIG. 96, TGFRt15-16s21 and IL-15 promoted 32Dβ cell proliferation, with the $EC_{50}$ of TGFRt15-16s21 and IL-15 being 51298 pM and 10.63 pM, respectively.

Detection of IL-15, IL-21, and TGFβRII in TGFRt15-16s21 Using ELISA

Figure 97A:
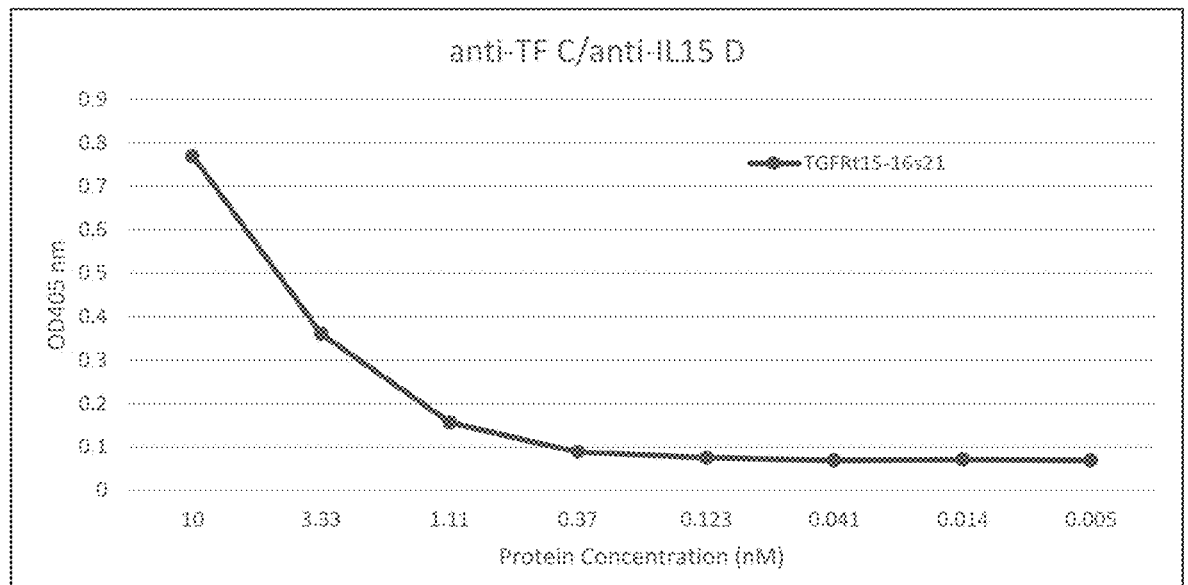
FIGS. 97A-97C show results of detecting IL-15, IL-21, and TGFβRII in TGFRt15-16s21 with corresponding antibodies using ELISA.
Figure 97B:
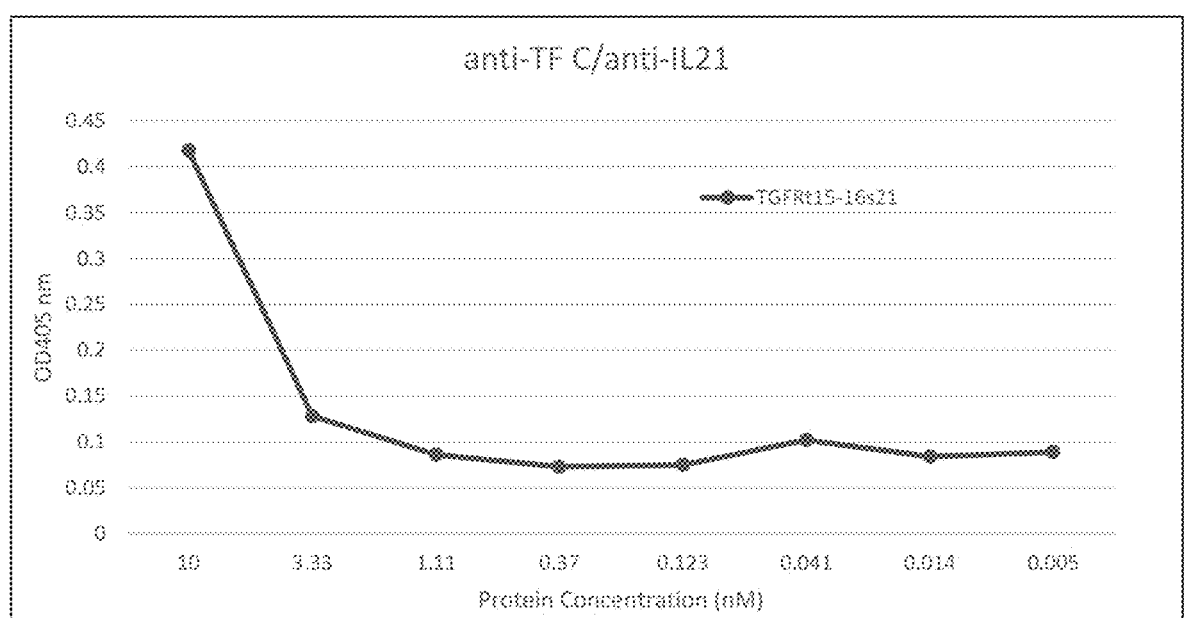
Figure 97C:
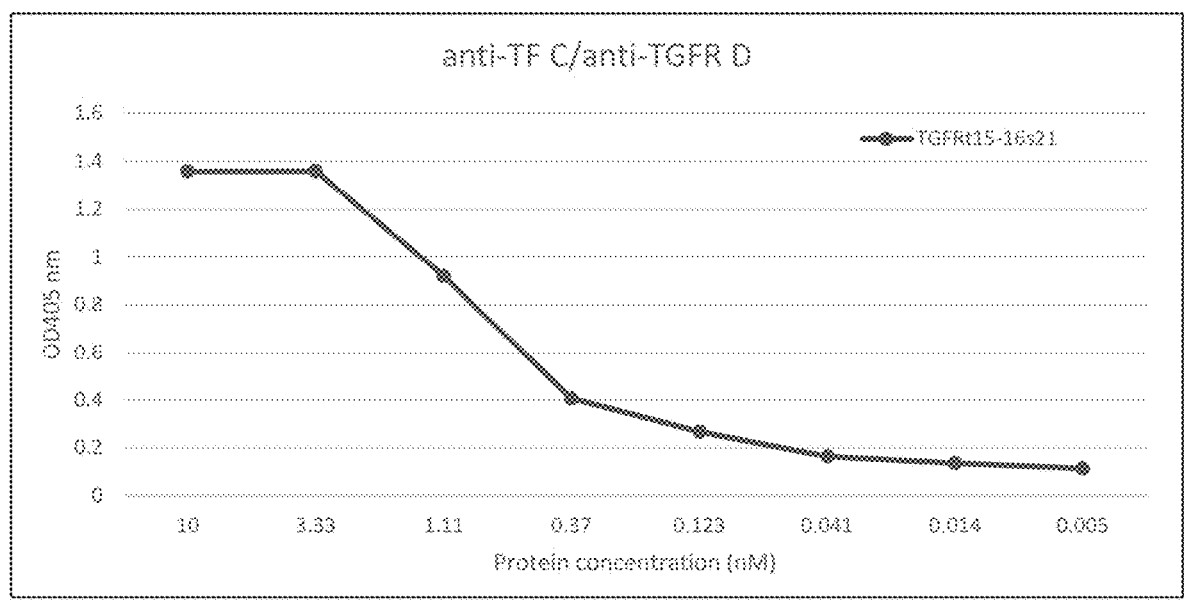

A 96-well plate was coated with 100 μL (8 μg/mL) of anti-TF antibody in R5 (coating buffer) and incubated at room temperature (RT) for 2 hrs. The plates were washed 3 times and blocked with 100 μL of 1% BSA in PBS. TGFRt15-16s21 serially diluted at a 1:3 ratio was added and incubated at RT for 60 min. Following three washes, 50 ng/mL of biotinylated-anti-IL-15 antibody (BAM247, R&D Systems), 500 ng/mL of biotinylated-anti-IL-21 antibody (13-7218-81, R&D Systems), or 200 ng/mL of biotinylated-anti-TGFβRII antibody (BAF241, R&D Systems) was applied per well, and incubated at RT for 60 min. Following three washes, incubation with 0.25 μg/mL of HRP-SA (Jackson ImmunoResearch at 100 μL per well for 30 min at RT was carried out, followed by 4 washes and incubation with 100 μL of ABTS for 2 mins at RT. Absorbance was read at 405 nm. As shown in FIGS. 97A-97C, the IL-15, IL-21, and TGFβRII domains in TGFRt15-16s21 were detected by the respective antibodies.

Figure 14:
FIG. 14 shows a schematic diagram of an exemplary IL-21/IL-15RαSu DNA construct.

Purification Elution Chromatograph of TGFRt15-16s21 Using Anti-TF Antibody Affinity Column TGFRt15-16s21 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 14, the anti-TF antibody affinity column bound to TGFRt15-16s21 which contains tissue factor as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE of TGFRt15-16s21

Figure 98:
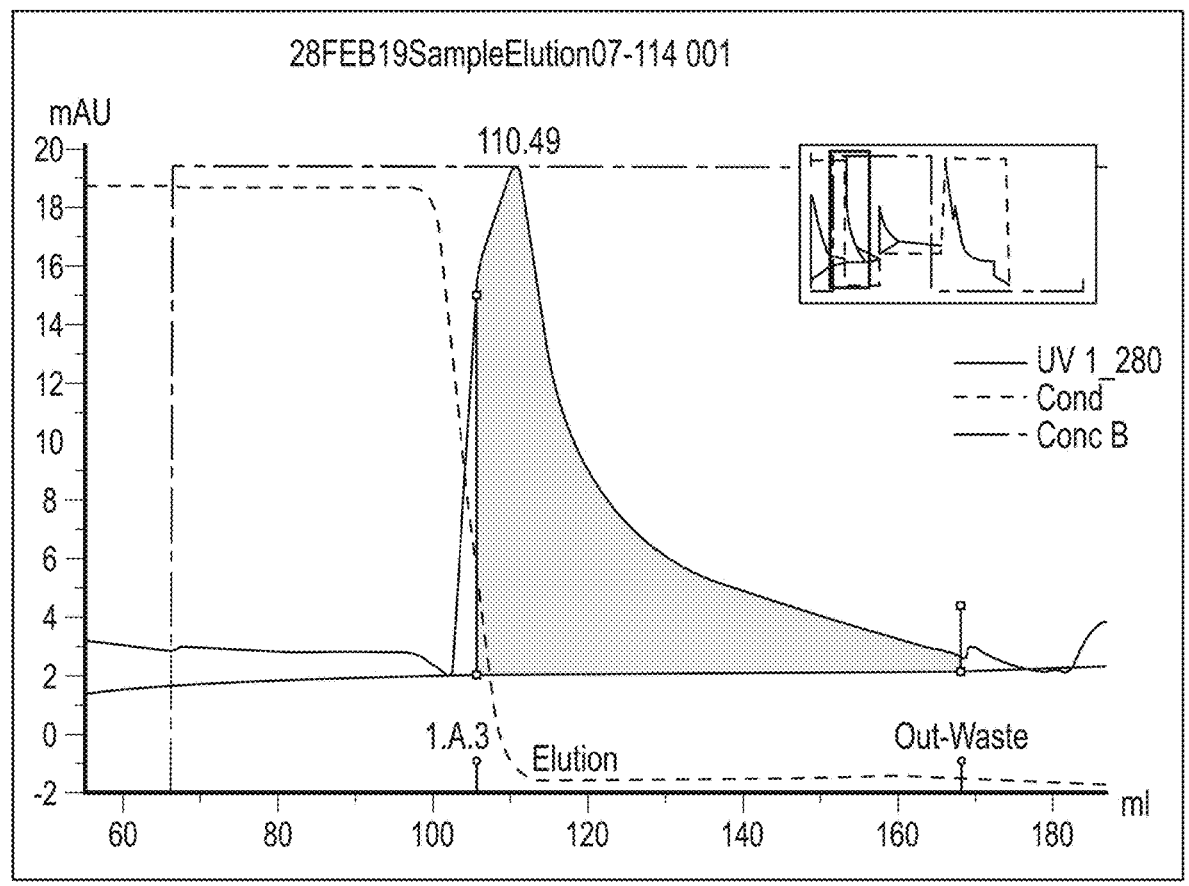
FIG. 98 is a line graph showing the chromatographic profile of TGFRt15-16s21 protein containing cell culture supernatant following binding and elution on anti-TF antibody resin.

To determine the purity and molecular weight of the TGFRt15-16s21 protein, protein sample purified with anti-TF antibody affinity column (FIG. 98) was analyzed by sodium dodecyl sulfate polyacrylamide gel (4-12% NuPage Bis-Tris gel) electrophoresis (SDS-PAGE) under reduced condition. After electrophoresis, the gel was stained with InstantBlue for about 30 min, followed by destaining overnight in purified water.

Figure 99:
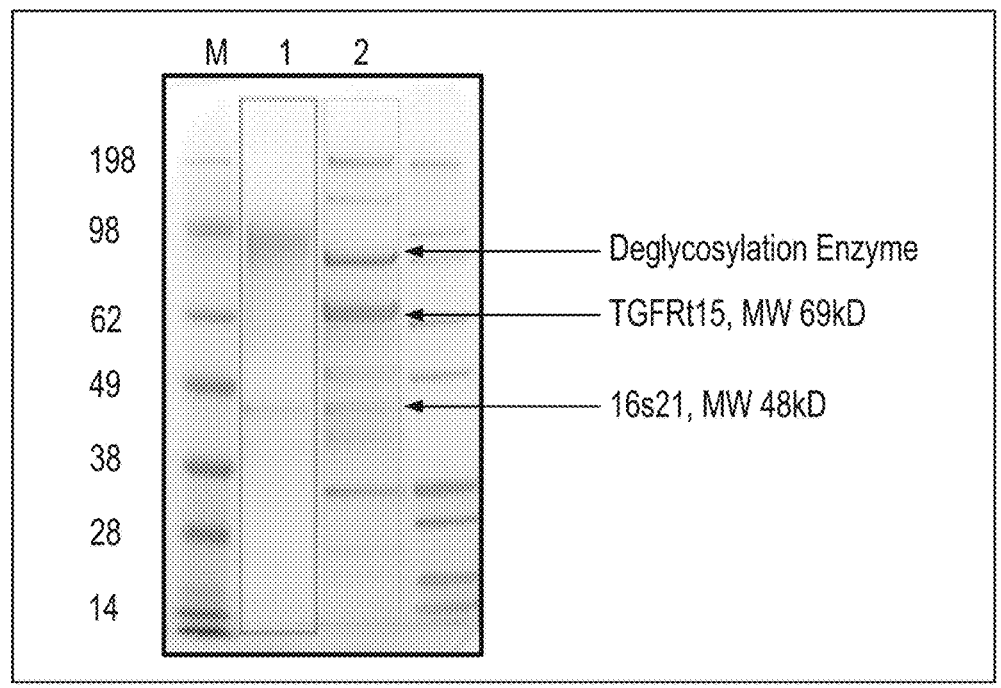
FIG. 99 shows results of a reduced SDS-PAGE analysis of TGFRt15-16s21.

To verify that the TGFRt15-16s21 protein undergoes glycosylation after translation in CHO cells, a deglycosylation experiment was conducted using the Protein Deglycosylation Mix II kit from New England Biolabs according to the manufacturer's instructions. FIG. 99 shows results from the reduced SDS-PAGE analysis of the sample in non-deglycosylated (lane 1 in red outline) and deglycosylated (lane 2 in yellow outline) state. The results showed that the TGFRt15-16s21 protein is glycosylated when expressed in CHO cells. After deglycosylation, the purified sample showed expected molecular weights (69 kDa and 48 kDa) in the reduced SDS gel. Lane M was loaded with 104, of SeeBlue Plus2 Prestained Standard.

Example 77: 7t15-7s Fusion Protein Generation and Characterization

A fusion protein complex was generated comprising IL-7/TF/IL-15 and IL-7/IL-15RαSu fusion proteins. The human IL-7, tissue factor 219, and IL-15 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15.

The nucleic acid and protein sequences of a construct comprising IL-7 linked to the N-terminus of tissue factor 219 following with the N-terminus of IL-15 are shown below.

The nucleic acid sequence of 7t15 construct (including signal peptide sequence) is as follows:

```
(Signal peptide)
ATGAAGTGGGTGACCTTCATCAGCCTGCTGTTCCTGTTCTCCAGCGC
CTACTCC
```

(Human IL7)
GATTGCGACATCGAGGGCAAGGACGGCAAGCAGTACGAGAGCGTGCT

GATGGTGTCCATCGACCAGCTGCTGGACAGCATGAAGGAGATCGGCT

CCAACTGCCTCAACAACGAGTTCAACTTCTTCAAGCGGCACATCTGC

GACGCCAACAAGGAGGGCATGTTCCTGTTCAGGGCCGCCAGGAAACT

GCGGCAGTTCCTGAAGATGAACTCCACCGGCGACTTCGACCTGCACC

TGCTGAAGGTGTCCGAGGGCACCACCATCCTGCTGAACTGCACCGGA

CAGGTGAAGGGCCGGAAACCTGCTGCTCTGGGAGAGGCCCAACCCAC

CAAGAGCCTGGAGGAGAACAAGTCCCTGAAGGAGCAGAAGAAGCTGA

ACGACCTGTGCTTCCTGAAGAGGCTGCTGCAGGAGATCAAGACCTGC

TGGAACAAGATCCTGATGGGCACCAAGGAGCAT (Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACC

AAGTTTACACCGTGCAGATCAGCACCAAGTCCGGCGACTGGAAGTCC

AAATGTTTCTATACCACCGACACCGAGTGCGATCTCACCGATGAGAT

CGTGAAAGATGTGAAACAGACCTACCTCGCCCGGGTGTTTAGCTACC

CCGCCGGCAATGTGGAGAGCACTGGTTCCGCTGGCGAGCCTTTATAC

GAGAACAGCCCCGAATTTACCCCTTACCTCGAGACCAATTTAGGACA

GCCCACCATCCAAAGCTTTGAGCAAGTTGGCACAAAGGTGAATGTGA

CAGTGGAGGACGAGCGGACTTTAGTGCGGCGGAACAACACCTTTCTC

AGCCTCCGGGATGTGTTCGGCAAAGATTTAATCTACACACTGTATTA

CTGGAAGTCCTCTTCCTCCGGCAAGAAGACAGCTAAAACCAACACAA

ACGAGTTTTTAATCGACGTGGATAAAGGCGAAAACTACTGTTTCAGC

GTGCAAGCTGTGATCCCCTCCCGGACCGTGAATAGGAAAAGCACCGA

TAGCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAAT

TCAGTCCATGCATATCGACGCCACTTTATACACAGAATCCGACGTGC

ACCCCTCTTGTAAGGTGACCGCCATGAAATGTTTTTTACTGGAGCTG

CAAGTTATCTCTTTAGAGAGCGGAGACGCTAGCATCCACGACACCGT

GGAGAATTTAATCATTTTAGCCAATAACTCTTTATCCAGCAACGGCA

ACGTGACAGAGTCCGGCTGCAAGGAGTGCGAAGAGCTGGAGGAGAAG

AACATCAAGGAGTTTCTGCAATCCTTTGTGCACATTGTCCAGATGTT

CATCAATACCTCC

The amino acid sequence of 7t15 fusion protein (including the leader sequence) is as follows:

(Signal peptide)
MKWVTFISLLFLFSSAYS (Human IL7)
DCDIEGKDGKQYESVLMVSIDQLLDSMKEIGSNCLNNEFNFFKRHICD

ANKEGMFLFRAARKLRQFLKMNSTGDFDLHLLKVSEGTTILLNCTGQV

KGRKPAALGEAQPTKSLEENKSLKEQKKLNDLCFLKRLLQEIKTCWNK

ILMGTKEH (Human Tissue Factor 219)
SGTTNTVAAYNLTWKSTNFKTILEWEPKPVNQVYTVQISTKSGDWKSK

CFYTTDTECDLTDEIVKDVKQTYLARVFSYPAGNVESTGSAGEPLYEN

SPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAV

IPSRTVNRKSTDSPVECMGQEKGEFRE (Human IL-15)
NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS

Constructs were also made by linking the IL-7 sequence to the N-terminus coding region of IL-15RαSu chain which was synthesized by Genewiz. The nucleic acid and protein sequences of a construct comprising the IL-7 linked to the N-terminus of IL-15RαSu chain are shown below.

The nucleic acid sequence of 7s construct (including signal peptide sequence) is as follows:

(Signal peptide)
ATGAAGTGGGTGACCTTCATCAGCCTGCTGTTCCTGTTCTCCAGCGCC

TACTCC (Human IL7)
GATTGCGACATCGAGGGCAAGGACGGCAAGCAGTACGAGAGCGTGCTG

ATGGTGTCCATCGACCAGCTGCTGGACAGCATGAAGGAGATCGGCTCC

AACTGCCTCAACAACGAGTTCAACTTCTTCAAGCGGCACATCTGCGAC

GCCAACAAGGAGGGCATGTTCCTGTTCAGGGCCGCCAGGAAACTGCGG

CAGTTCCTGAAGATGAACTCCACCGGCGACTTCGACCTGCACCTGCTG

AAGGTGTCCGAGGGCACCACCATCCTGCTGAACTGCACCGGACAGGTG

AAGGGCCGGAAACCTGCTGCTCTGGGAGAGGCCCAACCCACCAAGAGC

CTGGAGGAGAACAAGTCCCTGAAGGAGCAGAAGAAGCTGAACGACCTG

TGCTTCCTGAAGAGGCTGCTGCAGGAGATCAAGACCTGCTGGAACAAG

ATCCTGATGGGCACCAAGGAGCAT (Human IL-15R α sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGC

TTCAAGAGGAAGGCCGGCACCAGCAGCCTCACCGAGTGCGTGCTGAAT

AAGGCTACCAACGTGGCTCACTGGACAACACCCTCTTTAAAGTGCATC

CGG

The amino acid sequence of 7s fusion protein
(including the leader sequence) is asfollows:

(Signal peptide)
MKWVTFISLLFLFSSAYS (Human IL7)
DCDIEGKDGKQYESVLMVSIDQLLDSMKEIGSNCLNNEFNFFKRHICD

ANKEGMFLFRAARKLRQFLKMNSTGDFDLHLLKVSEGTTILLNCTGQV

-continued
KGRKPAALGEAQPTKSLEENKSLKEQKKLNDLCFLKRLLQEIKTCWNK

ILMGTKEH (Human IL-15R α sushi domain)
ITCPPPMSVEHADIWVKSYSLYSRERYICNSGFKRKAGTSSLTECVLN

KATNVAHWTTPSLKCIR

Figure 100:
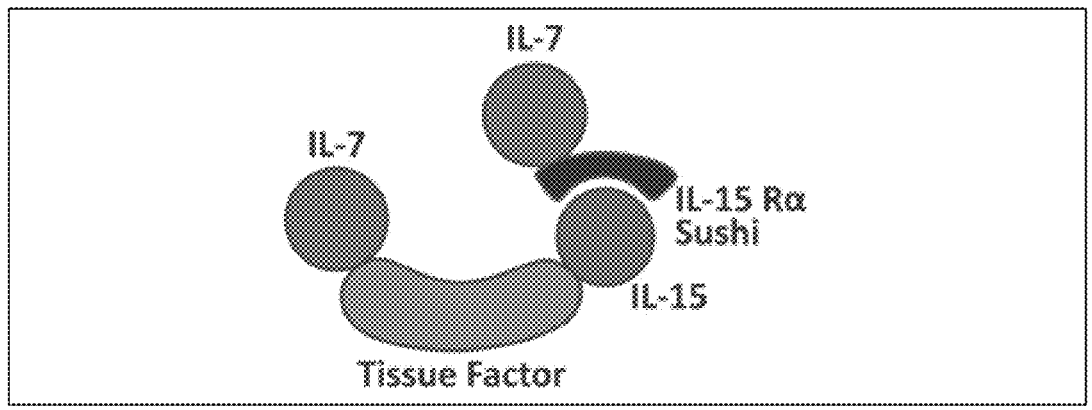
FIG. 100 shows a schematic of the 7t15-7s construct.
Figure 101:
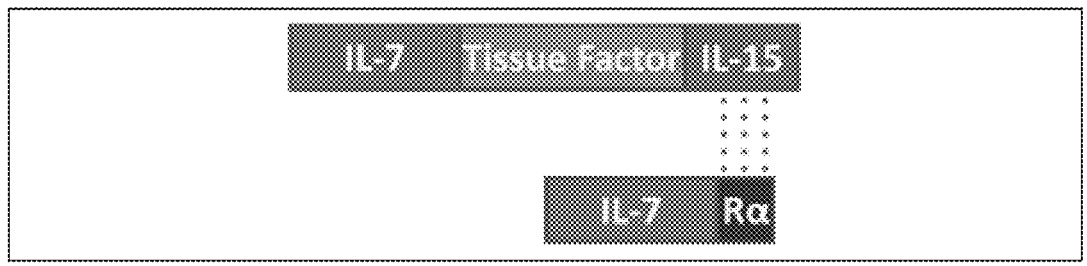
FIG. 101 shows an additional schematic of the 7t15-7s construct.

The IL-7/TF/IL-15 and IL-7/IL-15RαSu constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15:1L-7/IL-15RαSu protein complex (referred to as 7t15-7s), which can be purified by anti-TF antibody affinity and other chromatography methods. See, FIGS. 100 and 101.

Figure 102:
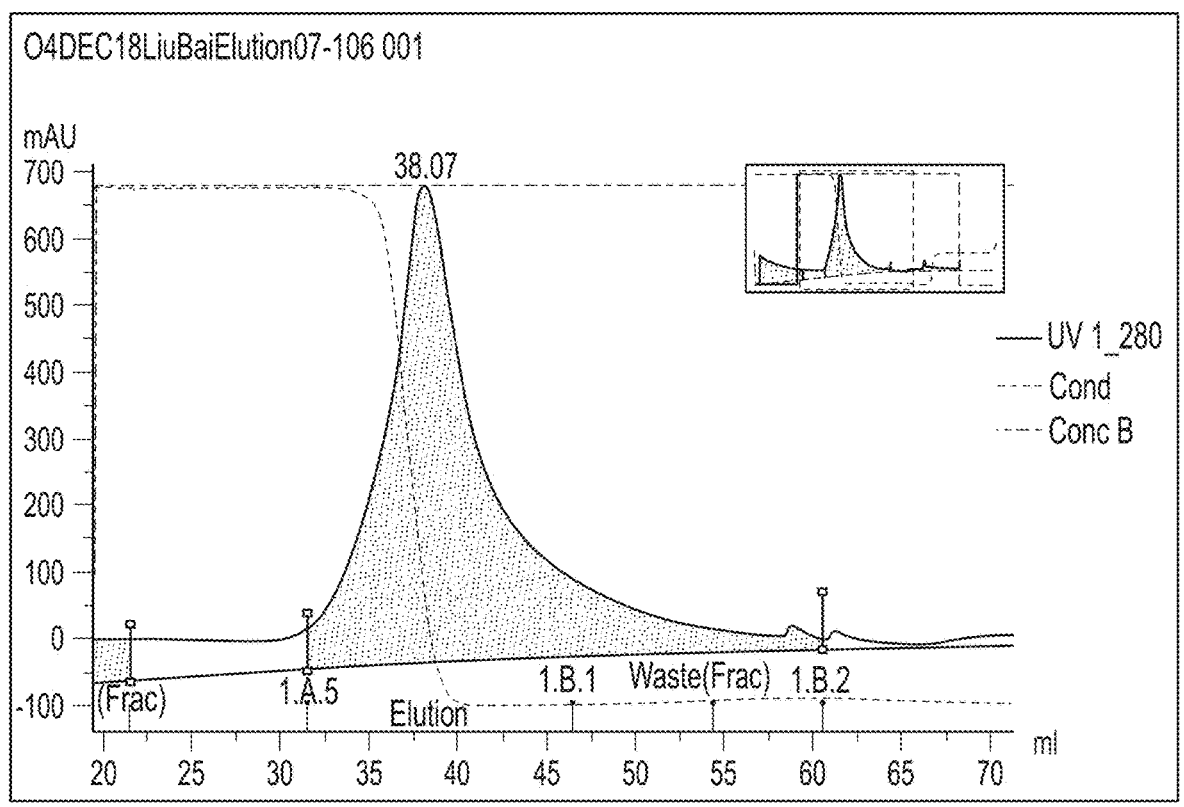
FIG. 102 is a line graph showing the chromatographic profile of 7t15-7s protein containing cell culture supernatant following binding and elution on anti-TF antibody resin.

Purification Elution Chromatograph of 7t15-7s Using Anti-TF Antibody Affinity Column 7t15-7s harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 102, the anti-TF antibody affinity column bound to 7t15-7s which contains tissue factor (TF) as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except the elution step, which was 2 mL/min.

Immunostimulation of 7t15-7s in C57BL/6 Mice

7t15-7s is a multi-chain polypeptide (a type A multi-chain polypeptide described herein) that includes the first polypeptide that is a soluble fusion of human IL-7, human tissue factor 219 fragment and human IL-15 (7t15), and the second polypeptide that is a soluble fusion of human IL-7 and sushi domain of human IL-15 receptor alpha chain (7s).

Figure 103:
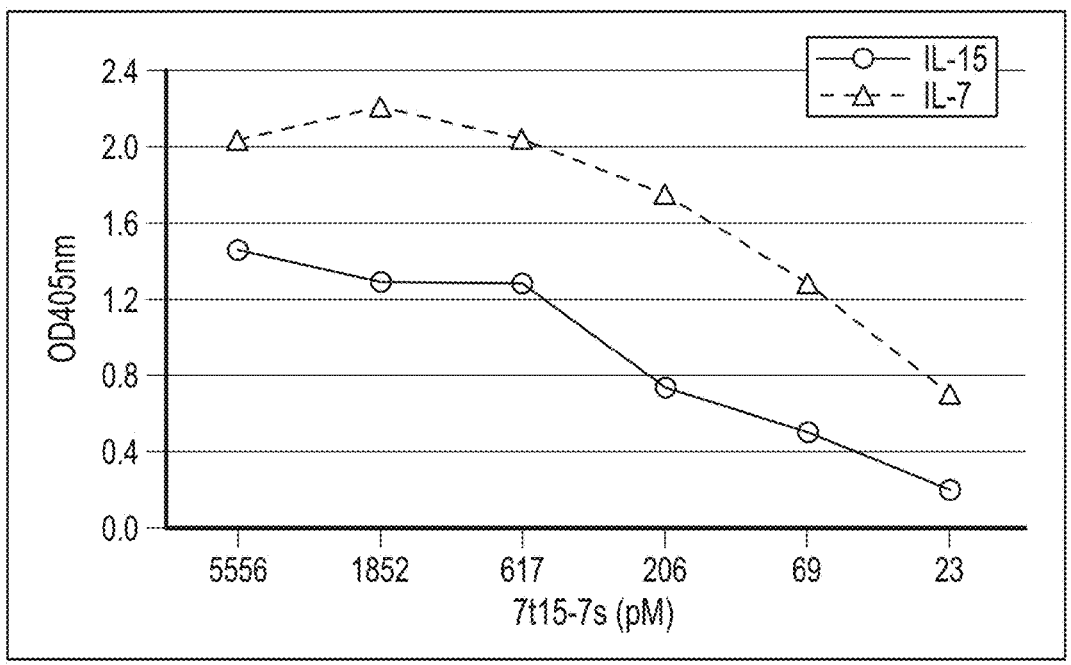
FIG. 103 shows detection of TF, IL-15 and IL-7 in 7t15-7s using ELISA.
Figure 104A:
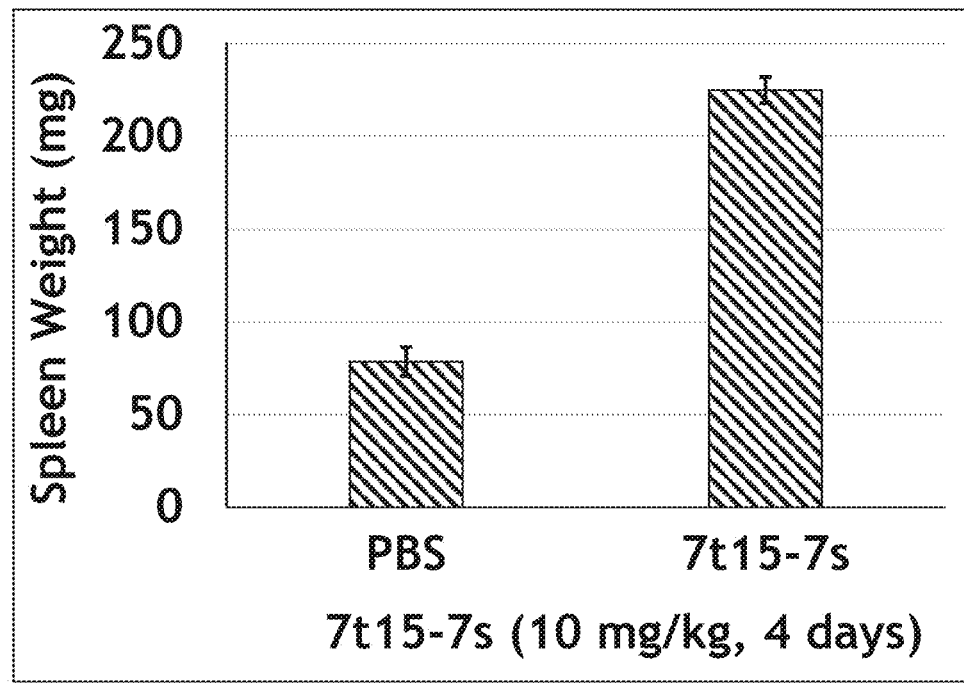
FIGS. 104A and 104B show spleen weight and the percentages of immune cell types in 7t15-7s-treated and control-treated mice.
Figure 104B:
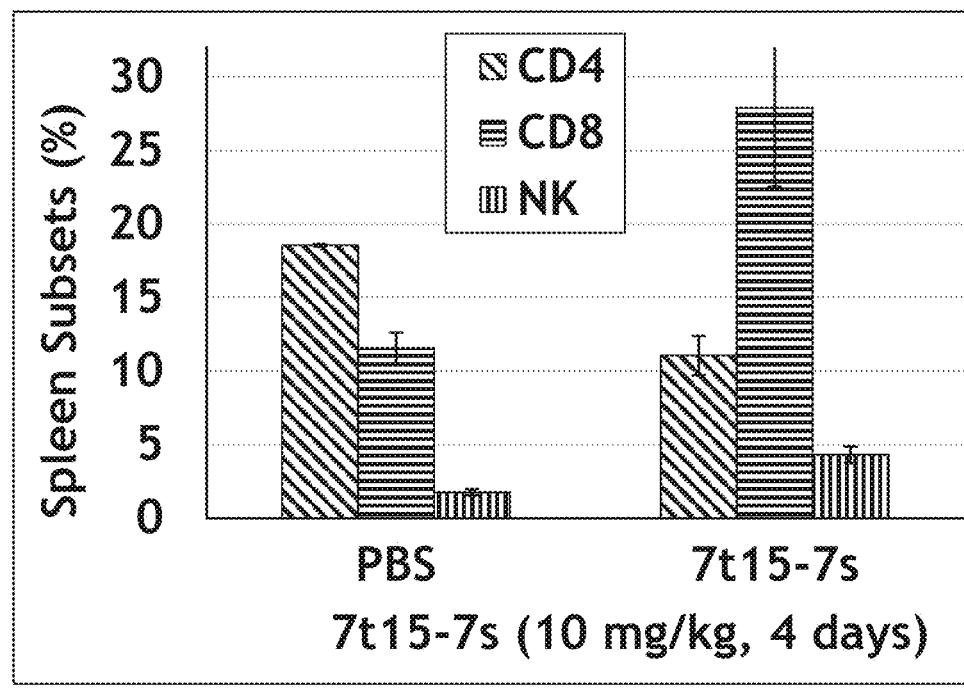

CHO cells were co-transfected with the IL7-TF-IL15 (7t15) and IL7-IL15Rα sushi domain (7s) vectors. The 7t15-7s complex was purified from the transfected CHO cell culture supernatant. The IL-7, IL-15 and tissue factor (TF) components were demonstrated in the complex by ELISA as shown in FIG. 103. A humanized anti-TF monoclonal antibody was used as the capture antibody to determine TF in 7t15-7s, and biotinylated anti-human IL-15 antibody (R&D systems) and biotinylated anti-human IL-7 antibody (R&D Systems) were used as the detection antibodies to respectively detect IL-15 and IL-7 in 7t15-7s, followed by peroxidase conjugated streptavidin (Jackson ImmunoResearch Lab) and ABTS substrate (Surmodics IVD, Inc.). 7t15-7s was subcutaneously injected into C57BL/6 mice at 10 mg/kg to determine the immunostimulatory activity of 7t15-7s in vivo. C57BL/6 mice subcutaneously treated with PBS were used as control. The mouse spleens were collected and weighed day 4 post treatment. Single splenocytes suspensions were prepared, and with fluorochrome-conjugated anti-CD4, anti-CD8, and anti-NK1.1 antibodies and the percentage of CD4$^+$ T cells, CD8$^+$ T cells, and NK cells was analyzed by flow cytometry. The results showed that 7t15-7s was effective at expanding splenocytes based on spleen weight (FIG. 104A) and specifically, the percentages of CD8$^+$ T cells and NK cells were higher compared to control-treated mice (FIG. 104B).

Example 78: TGFRt15-TGFRs Fusion Protein Generation and Characterization

A fusion protein complex was generated comprising of TGFβ Receptor II/IL-15RαSu and TGFβ Receptor II/TF/IL-15 fusion proteins. The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G45(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the two TGFβ Receptor II/TF/IL-15 construct (including signal peptide sequence) is as follows:

(Signal peptide)
ATGAAGTGGGTGACCTTCATCAGCCTGCTGTTCCTGTTCTCCAGCGCC

TACTCC (Two Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

AGCATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCTCCATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

```
CCTGGCGAGACCTTTTTCATGTGCTCCTGCAGCAGCGACGAATGCAAC

GACAATATCATCTTTAGCGAGGAATACAATACCAGCAACCCCGAC
```

(Human Tissue Factor 219)
```
AGCGGCACAACCAACACAGTCGCTGCCTATAACCTCACTTGGAAGAGC

ACCAACTTCAAAACCATCCTCGAATGGGAACCCAAACCCGTTAACCAA

GTTTACACCGTGCAGATCAGCACCAAGTCCGGCGACTGGAAGTCCAAA

TGTTTCTATACCACCGACACCGAGTGCGATCTCACCGATGAGATCGTG

AAAGATGTGAAACAGACCTACCTCGCCCGGGTGTTTAGCTACCCCGCC

GGCAATGTGGAGAGCACTGGTTCCGCTGGCGAGCCTTTATACGAGAAC

AGCCCCGAATTTACCCCTTACCTCGAGACCAATTTAGGACAGCCCACC

ATCCAAAGCTTTGAGCAAGTTGGCACAAAGGTGAATGTGACAGTGGAG

GACGAGCGGACTTTAGTGCGGCGGAACAACACCTTTCTCAGCCTCCGG

GATGTGTTCGGCAAAGATTTAATCTACACACTGTATTACTGGAAGTCC

TCTTCCTCCGGCAAGAAGACAGCTAAAACCAACACAAACGAGTTTTTA

ATCGACGTGGATAAAGGCGAAAACTACTGTTTCAGCGTGCAAGCTGTG

ATCCCCTCCCGGACCGTGAATAGGAAAAGCACCGATAGCCCCGTTGAG

TGCATGGGCCAAGAAAAGGGCGAGTTCCGGGAG
```

(Human IL-15)
```
AACTGGGTGAACGTCATCAGCGATTTAAAGAAGATCGAAGATTTAATT

CAGTCCATGCATATCGACGCCACTTTATACACAGAATCCGACGTGCAC

CCCTCTTGTAAGGTGACCGCCATGAAATGTTTTTTACTGGAGCTGCAA

GTTATCTCTTTAGAGAGCGGAGACGCTAGCATCCACGACACCGTGGAG

AATTTAATCATTTTAGCCAATAACTCTTTATCCAGCAACGGCAACGTG

ACAGAGTCCGGCTGCAAGGAGTGCGAAGAGCTGGAGGAGAAGAACATC

AAGGAGTTTCTGCAATCCTTTGTGCACATTGTCCAGATGTTCATCAAT

ACCTCC
```

The amino acid sequence of TGFβ Receptor II/TF/IL-15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNC

SITSICEKPQEVCVAVWRKNDENITLETVCHDPKLPYHDFILEDAASP

KCIMKEKKKPGETFFMCSCSSDECNDNIIFSEEYNTSNPDGGGGSGGG

GSGGGGSIPPHVQKSVNNDMIVTDNNGAVKFPQLCKFCDVRFSTCDNQ

KSCMSNCSITSICEKPQEVCVAVWRKNDENITLETVCHDPKLPYHDFI

LEDAASPKCIMKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSK

CFYTTDTECDLTDEIVKDVKQTYLARVFSYPAGNVESTGSAGEPLYEN

SPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAV

IPSRTVNRKSTDSPVECMGQEKGEFRE

-continued (Human IL-15)
NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS

Constructs were also made by attaching two TGFβ Receptor II directly to the IL-15RαSu chain which was synthesized by Genewiz. The nucleic acid and protein sequences of a construct comprising the TGFβ Receptor II linked to the N-terminus of IL-15RαSu are shown below.

The nucleic acid sequence of the TGFβ Receptor II/IL-15 RαSu construct (including signal peptide sequence) is as follows:

(Signal peptide)
ATGAAGTGGGTGACCTTCATCAGCCTGCTGTTCCTGTTCTCCAGCGCC

TACTCC (Two human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

AGCATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCTCCATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGAC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG

The amino acid sequence of the two TGFβ Receptor II/IL-15RαSu construct (including signal peptide sequence) is as follows:

```
(Signal peptide)
MKWVTFISLLFLFSSAYS (Two human TGFβ Receptor II extra-cellular domains)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD (Human IL-15R a sushi domain)
ITCPPPMSVEHADIWVKSYSLYSRERYICNSGFKRKAGTSSLTECVLNK

ATNVAHWTTPSLKCIR
```

In some cases, the leader peptide is cleaved from the intact polypeptide to generate the mature form that may be soluble or secreted.

Figure 105:
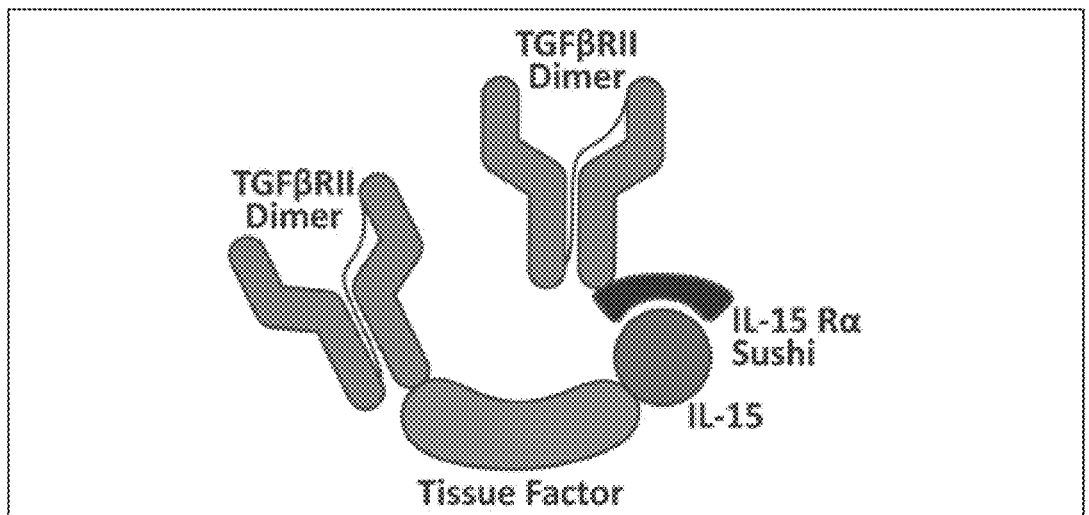
FIG. 105 shows a schematic of the TGFRt15-TGFRs construct.
Figure 106:
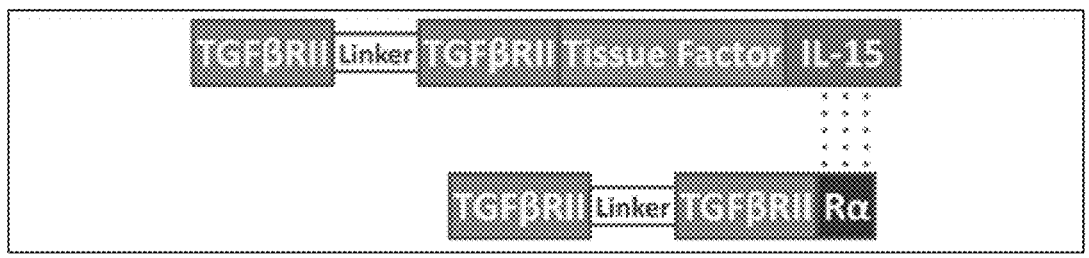
FIG. 106 shows an additional schematic of the TGFRt15-TGFRs construct.

The TGFβR/IL-15RαSu and TGFβR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFβR/TF/IL-15:TGFβR/IL-15RαSu protein complex (referred to as TGFRt15-TGFRs), which can be purified by anti-TF antibody affinity and other chromatography methods. See, FIGS. 105 and 106.

Effect of TGFRt15-TGFRs on TGFβ1 Activity in HEK-Blue TGFβ Cells

Figure 107:
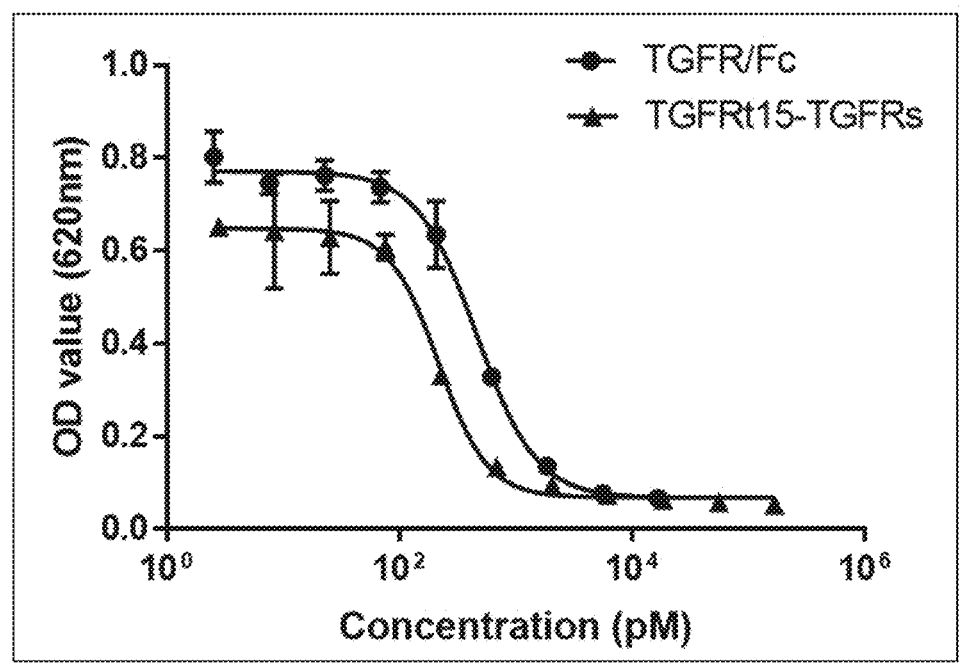
FIG. 107 shows results of TGFβ1 inhibition by TGFRt15-TGFRs and TGFR-Fc.

To evaluate the activity of TGFβRII in TGFRt15-TGFRs, the effect of TGFRt15-16s21 on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μL cells were added to each well ($2.5\times10^4$ cells/well) and followed with 50 μL 0.1 nM TGFβ1 (R&D systems). TGFRt15-16s21 or TGFR-Fc (R&D Systems) prepared at a 1:3 serial dilution was then added to the plate to reach a total volume of 200 μL. After 24 hrs of incubation at 37° C., 40 μL of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. See, FIG. 107. The $IC_{50}$ of each protein sample was calculated with GraphPad Prism 7.04. The $IC_{50}$ of TGFRt15-TGFRs and TGFR-Fc were 216.9 pM and 460.6 pM respectively. These results showed that the TGFβRII domain in TGFRt15-TGFRs was able to block the activity of TGFβ1 in HEK-Blue TGFβ cells.

Figure 108:
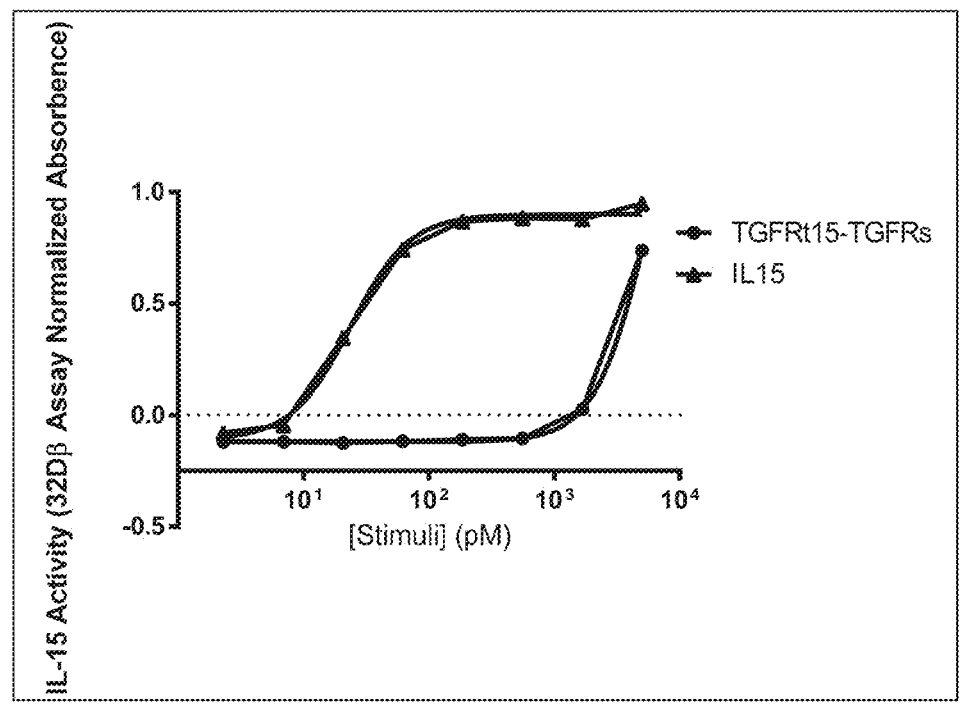
FIG. 108 shows results of 32Dβ cell proliferation assay with TGFRt15-TGFRs or recombinant IL-15

The IL-15 in TGFRt15-TGFRs Promotes IL-2Rβ and Common γ Chain Containing 32Dβ Cell Proliferation To evaluate the activity of IL-15 in TGFRt15-TGFRs, the IL-15 activity of TGFRt15-TGFRs was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted TGFRt15-TGFRs or IL-15 were added to the cells (FIG. 108). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The absorbance at 450 nm was measured by analyzing the amount of formazan dye produced. As shown in FIG. 108, TGFRt15-TGFRs and IL-15 promoted 32Dβ cell proliferation, with the $EC_{50}$ of TGFRt15-16s21 and IL-15 being 1901 pM and 10.63 pM, respectively.

Figure 109A:
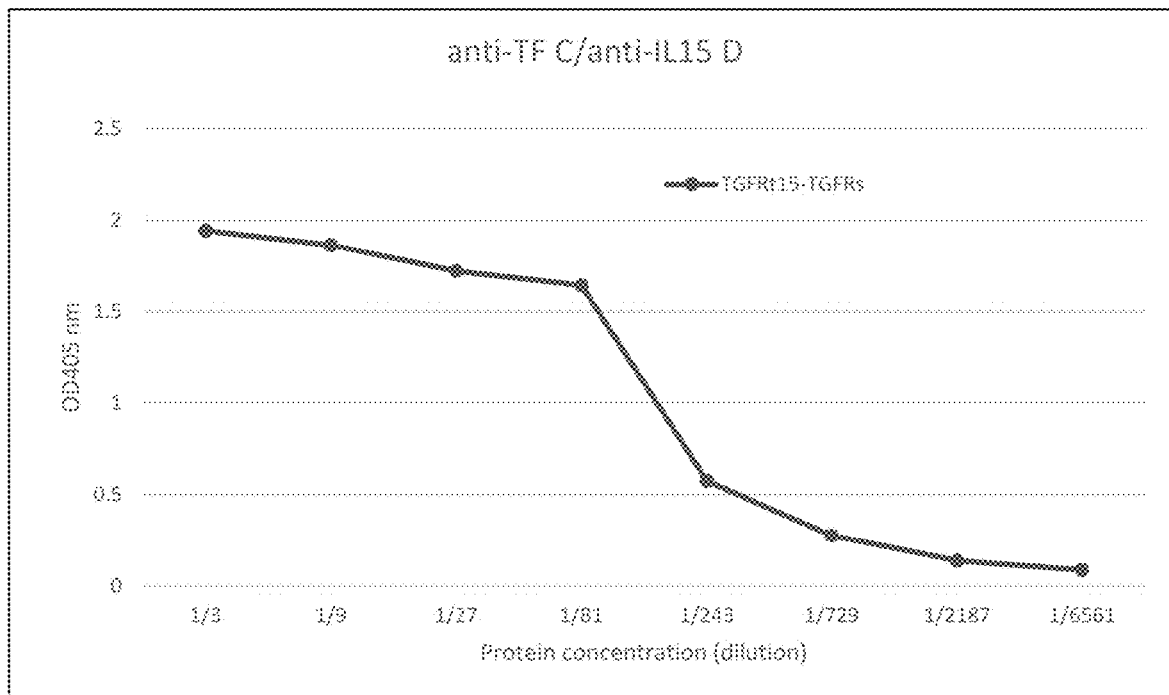
FIGS. 109A and 109B show results of detecting IL-15 and TGFβRII in TGFRt15-TGFRs with corresponding antibodies using ELISA.
Figure 109B:
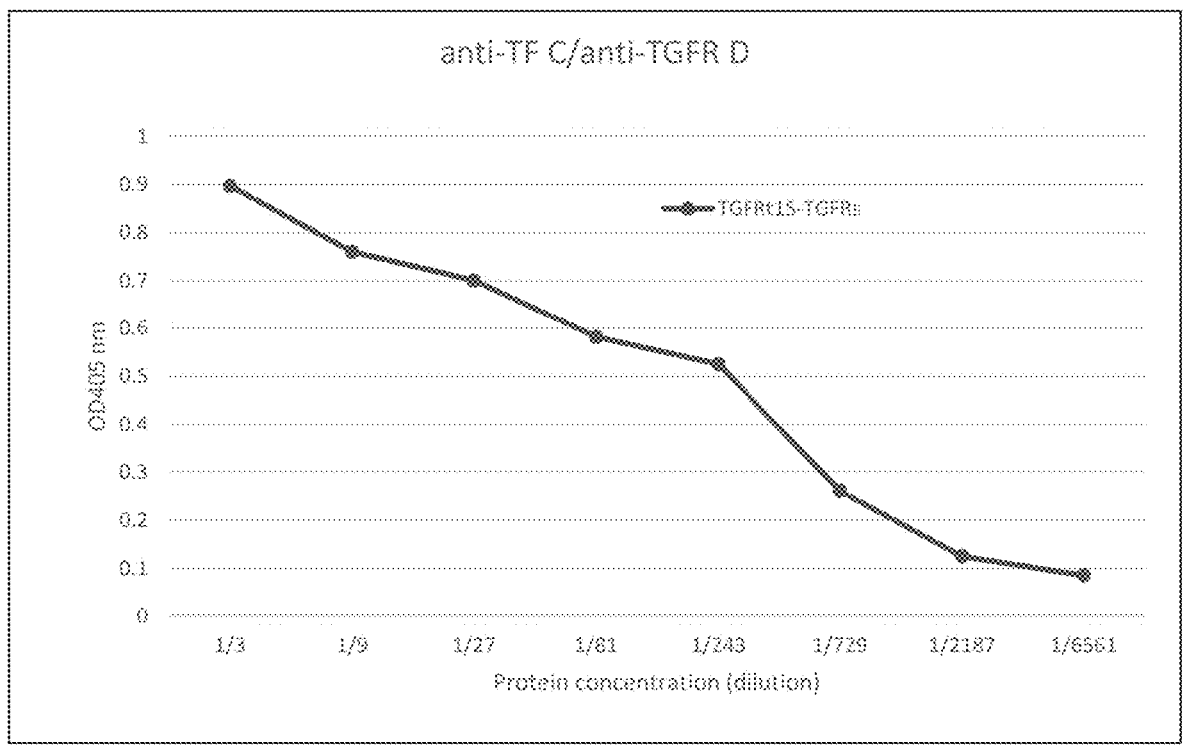

Detection of IL-15 and TGFβRII Domains in TGFRt15-TGFRs with Corresponding Antibodies Using ELISA A 96-well plate was coated with 100 μL (8 μg/mL) of anti-TF antibody in R5 (coating buffer) and incubated at room temperature (RT) for 2 hrs. The plates were washed 3 times and blocked with 100 μL of 1% BSA in PBS. TGFRt15-TGFRs was added at a 1:3 serial dilution, and incubated at RT for 60 min. After 3 washes, 50 ng/mL of biotinylated-anti-IL-15 antibody (BAM247, R&D Systems), or 200 ng/mL of biotinylated-anti-TGFβRII antibody (BAF241, R&D Systems) was added to the wells and incubated at RT for 60 min. Next the plates were washed 3 times, and 0.25 μg/mL of HRP-SA (Jackson ImmunoResearch) at 100 μL per well was added and incubated for 30 min at RT, followed by 4 washes and incubation with 100 μL of ABTS for 2 mins at RT. Absorbance at 405 nm was read. As shown in FIGS. 109A and 109B, the IL-15 and TGFβRII domains in TGFRt15-TGFRs were detected by the individual antibodies.

Figure 110:
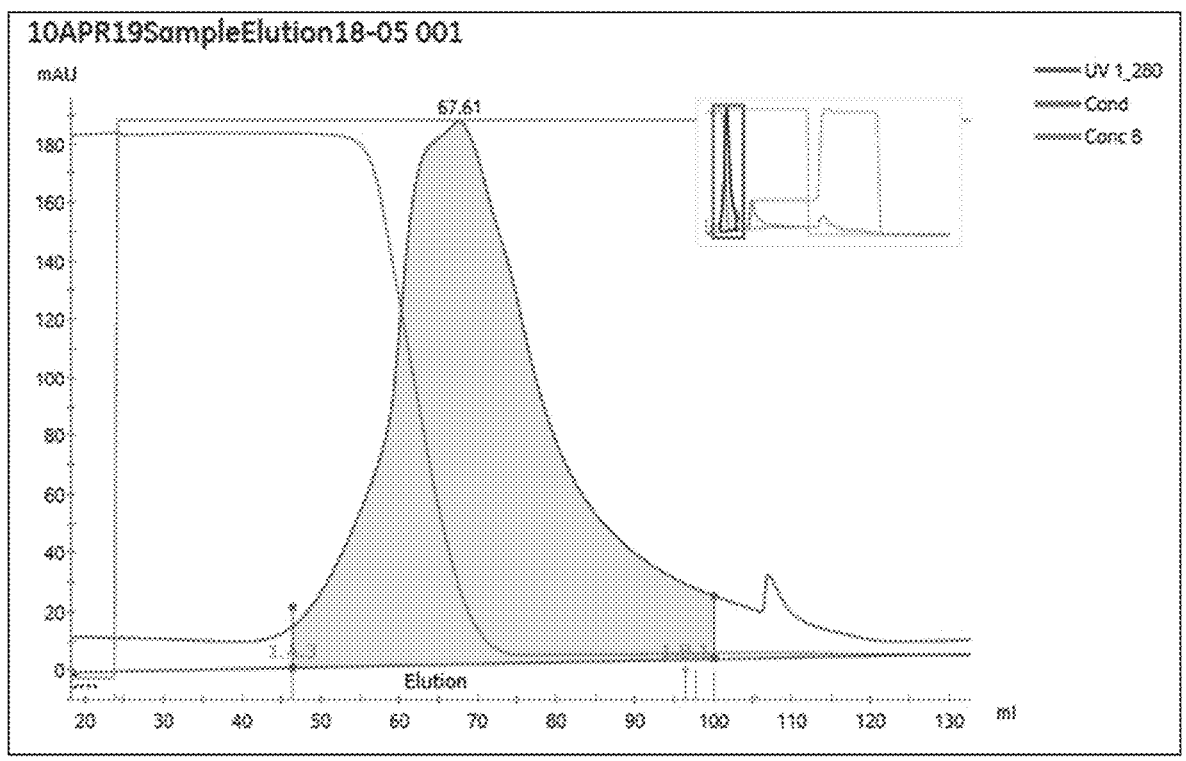
FIG. 110 is a line graph showing the chromatographic profile of TGFRt15-TGFRs protein containing cell culture supernatant following binding and elution on anti-TF antibody resin.

Purification Elution Chromatograph of TGFRt15-TGFRs from Anti-TF Antibody Affinity Column TGFRt15-TGFRs harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 110, the anti-TF antibody affinity column bound to TGFRt15-TGFRs which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of TGFRt15-TGFRs

Figure 111:
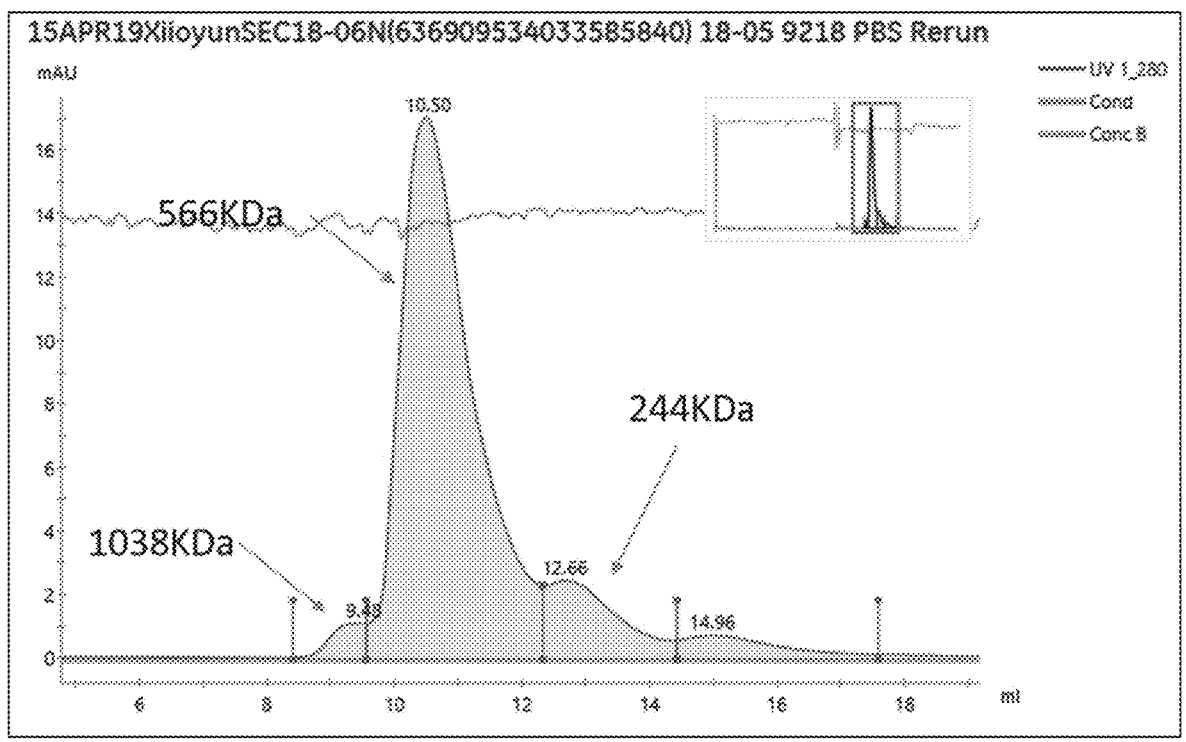
FIG. 111 shows the analytical SEC profile of TGFRt15-TGFRs.

A Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. A sample containing TGFRt15-TGFRs in PBS was injected into the Superdex 200 column using a capillary loop, and analyzed by SEC. The SEC chromatograph of the sample is shown in FIG. 111. The SEC results showed four protein peaks for TGFRt15-TGFRs Reduced SDS-PAGE Analysis of TGFRt15-TGFRs To determine the purity and molecular weight of the TGFRt15-TGFRs protein, protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

Figure 112:
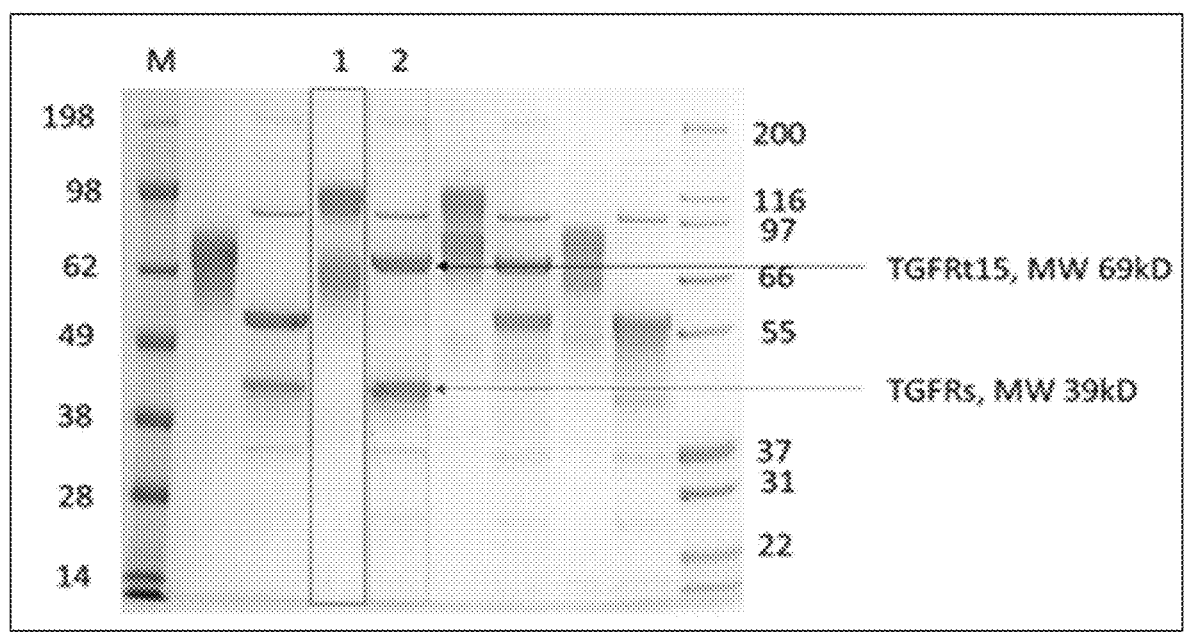
FIG. 112 shows TGFRt15-TGFRs before and after deglycosylation as analyzed by reduced SDS-PAGE.

To verify that the TGFRt15-TGFRs protein undergoes glycosylation after translation in CHO cells, a deglycosylation experiment was conducted using the Protein Deglycosylation Mix II kit from New England Biolabs and the manufacturer's instructions. FIG. 112 shows the reduced SDS-PAGE analysis of the sample in non-deglycosylated (lane 1 in red outline) and deglycosylated (lane 2 in yellow outline) state. The results showed that the TGFRt15-TGFRs protein is glycosylated when expressed in CHO cells. After deglycosylation, the purified sample showed expected molecular weights (69 kDa and 39 kDa) in the reduced SDS gel. Lane M was loaded with 10 ul of SeeBlue Plus2 Prestained Standard.

Immunostimulatory Activity of TGFRt15-TGFRs in C57BL/6 Mice

TGFRt15-TGFRs is a multi-chain polypeptide (a type A multi-chain polypeptide described herein) that includes a first polypeptide that is a soluble fusion of two TGFβRII domains, human tissue factor 219 fragment and human IL-15, and the second polypeptide that is a soluble fusion of two TGFβRII domains and sushi domain of human IL-15 receptor alpha chain.

Figure 113A:
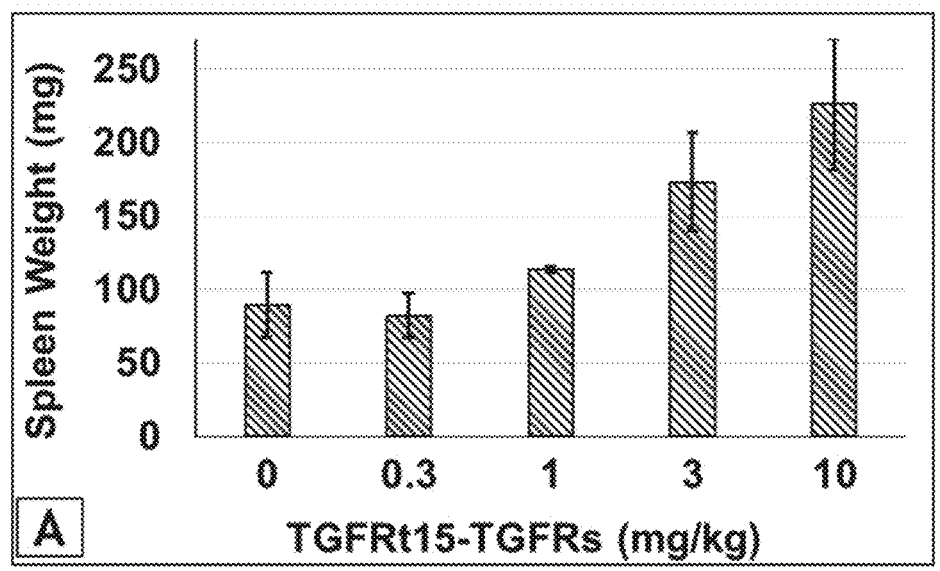
FIGS. 113A and 113B show spleen weight and the percentages of immune cell types in TGFRt15-TGFRs-treated and control-treated mice.
Figure 113B:
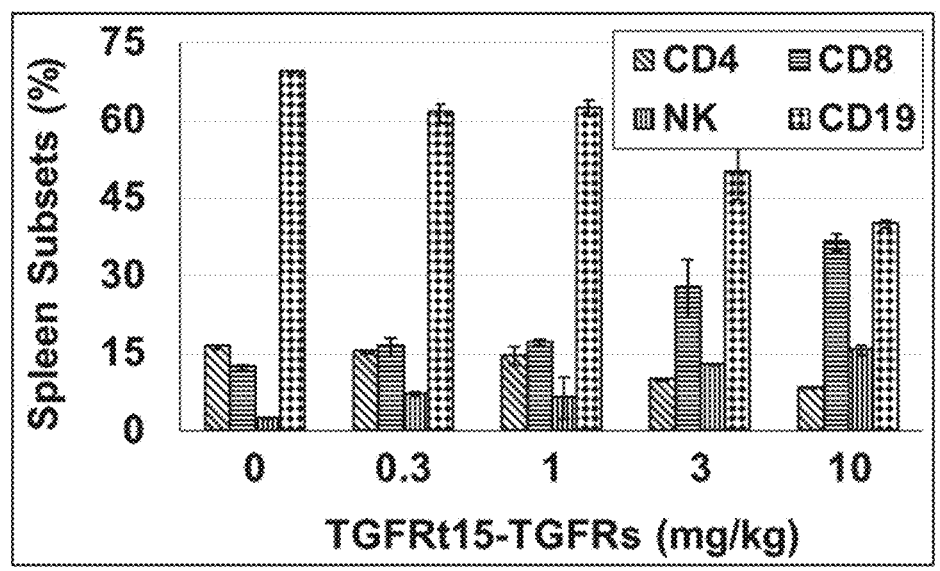

Wild type C57BL/6 mice were treated subcutaneously with either control solution or with TGFRt15-TGFRs at a dosage of 0.3 mg/kg, 1 mg/kg, 3 mg/kg, or 10 mg/kg. Four days after treatment, spleen weight and the percentages of various immune cell types present in the spleen were evaluated. As shown in FIG. 113A, the spleen weight in mice treated with TGFRt15-TGFRs increased with increasing dosage of TGFRt15-TGFRs. Moreover, the spleen weight in mice treated with 1 mg/kg, 3 mg/kg, and 10 mg/kg of TGFRt15-TGFRs were higher as compared to mice treated with the control solution, respectively. In addition, the percentages of $CD4^+$ T cells, $CD8^+$ T cells, NK cells, and $CD19^+$ B cells present in the spleen of control-treated and TGFRt15-TGFRs-treated mice were evaluated. As shown in FIG. 113B, in the spleens of mice treated with TGFRt15-TGFRs, the percentages of $CD8^+$ T cells and NK cells both increased with increasing dosage of TGFRt15-TGFRs. Specifically, the percentages of $CD8^+$ T cells were higher in mice treated with 0.3 mg/kg, 3 mg/kg, and 10 mg/kg of TGFRt15-TGFRs compared to control-treated mice, and the percentages of NK cells were higher in mice treated with 0.3 mg/kg, 1 mg/kg, 3 mg/kg, and 10 mg/kg of TGFRt15-TGFRs compared to control-treated mice. These results demonstrate that TGFRt15-TGFRs is able to stimulate immune cells in the spleen, in particular $CD8^+$ T cells and NK cells.

The pharmacokinetics of TGFRt15-TGFRs molecules were evaluated in wild type C57BL/6 mice. The mice were treated subcutaneously with TGFRt15-TGFRs at a dosage of 3 mg/kg. The mouse blood was drained from tail vein at various time points and the serum was prepared. The TGFRt15-TGFRs concentrations in mouse serum was determined with ELISA (capture: anti-human tissue factor antibody; detection: biotinylated anti-human TGFβ receptor antibody and followed by peroxidase conjugated streptavidin and ABTS substrate). The results showed that the half-life of TGFRt15-TGFRs was 12.66 hours in C57BL/6 mice.

Figure 114A:
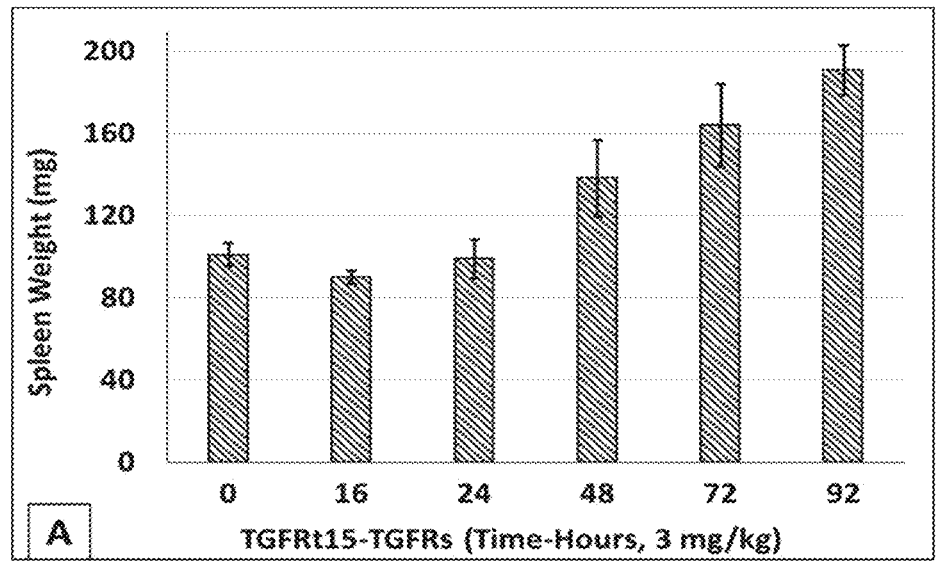
FIGS. 114A and 114B show the spleen weight and immunostimulation over 92 hours in mice treated with TGFRt15-TGFRs.
Figure 114B:
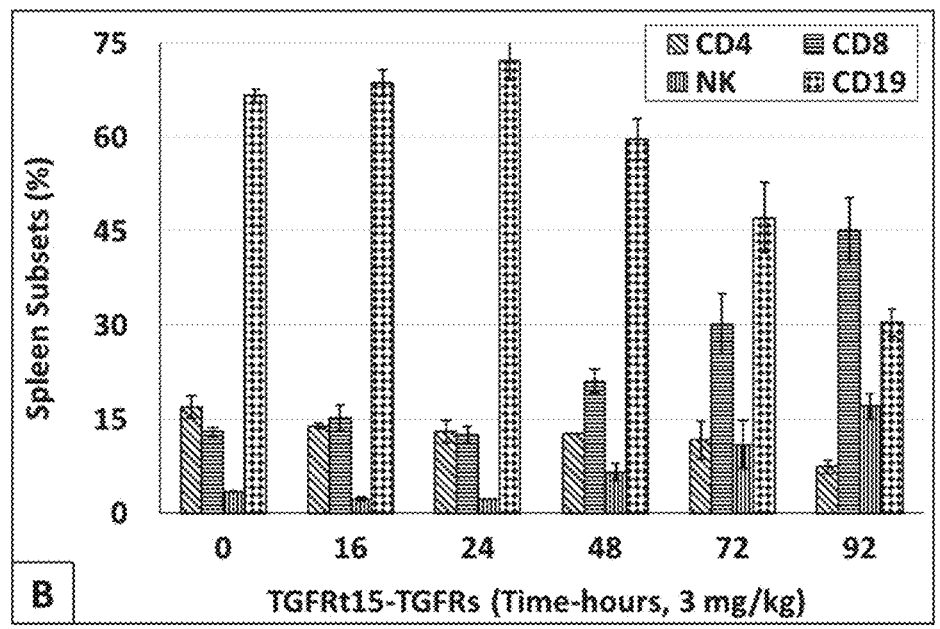

The mouse splenocytes were prepared in order to evaluate the immunostimulatory activity of TGFRt15-TGFRs over time in mice. As shown in FIG. 114A, the spleen weight in mice treated with TGFRt15-TGFRs increased 48 hours posttreatment and continued to increase over time. In addition, the percentages of $CD4^+$ T cells, $CD8^+$ T cells, NK cells, and $CD19^+$ B cells present in the spleen of control-treated and TGFRt15-TGFRs-treated mice were evaluated. As shown in FIG. 114B, in the spleens of mice treated with TGFRt15-TGFRs, the percentages of $CD8^+$ T cells and NK cells both increased at 48 hours after treatment and were higher and higher overtime after the single dose treatment. These results further demonstrate that TGFRt15-TGFRs is able to stimulate immune cells in the spleen, in particular $CD8^+$ T cells and NK cells.

Figure 115A:
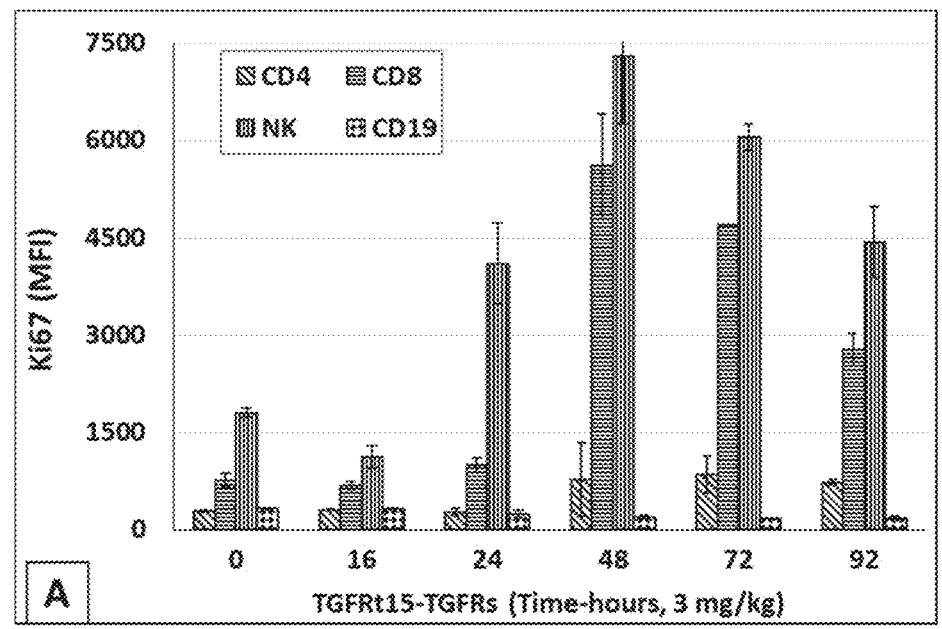
FIG. 115A shows spleen weight in mice treated with 7t15-7s as compared to PBS control.
Figure 115B:
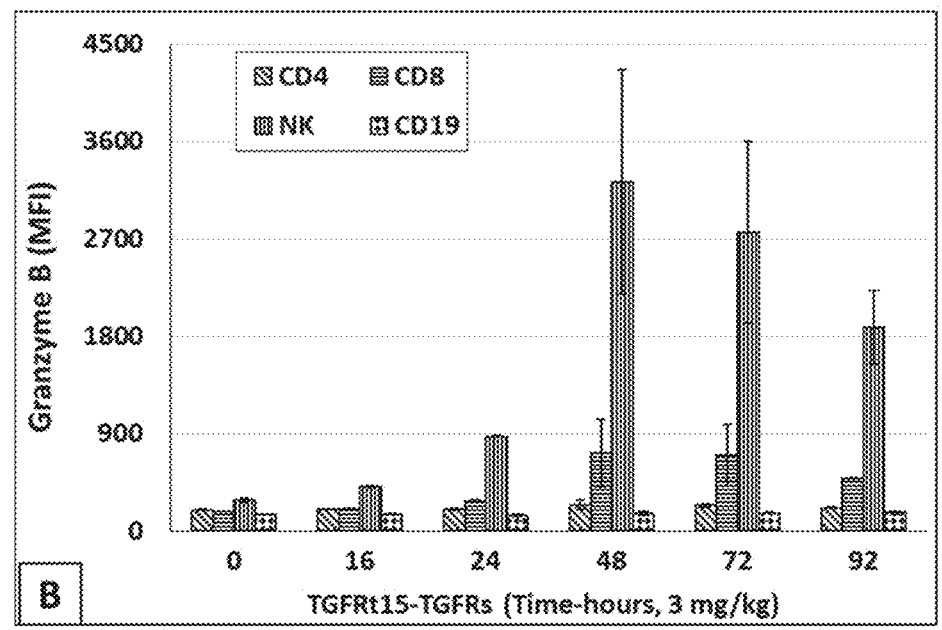
FIG. 115B shows the percentage of CD4$^+$ T cells, CD8$^+$ T cells, and NK cells in mice treated with 7t15-7s as compared to PBS control.

Furthermore, the dynamic proliferation of immune cells based on Ki67 expression of splenocytes and cytotoxicity potential based on granzyme B expression were evaluated in splenocytes isolated from mice following a single dose (3 mg/kg) of TGFRt15-TGFRs. As shown in FIGS. 115A and 115B, in the spleens of mice treated with TGFRt15-TGFRs, the expression of Ki67 and granzyme B by NK cells increased at 24 hours after treatment and its expression of $CD8^+$ T cells and NK cells both increased at 48 hours and later time points after the single dose treatment. These results demonstrate that TGFRt15-TGFRs not only increases the numbers of $CD8^+$ T cells and NK cells but also enhance the cytotoxicity of these cells. The single dose treatment of TGFRt15-TGFRs led $CD8^+$ T cells and NK cells to proliferate for at least 4 days.

Figure 116:
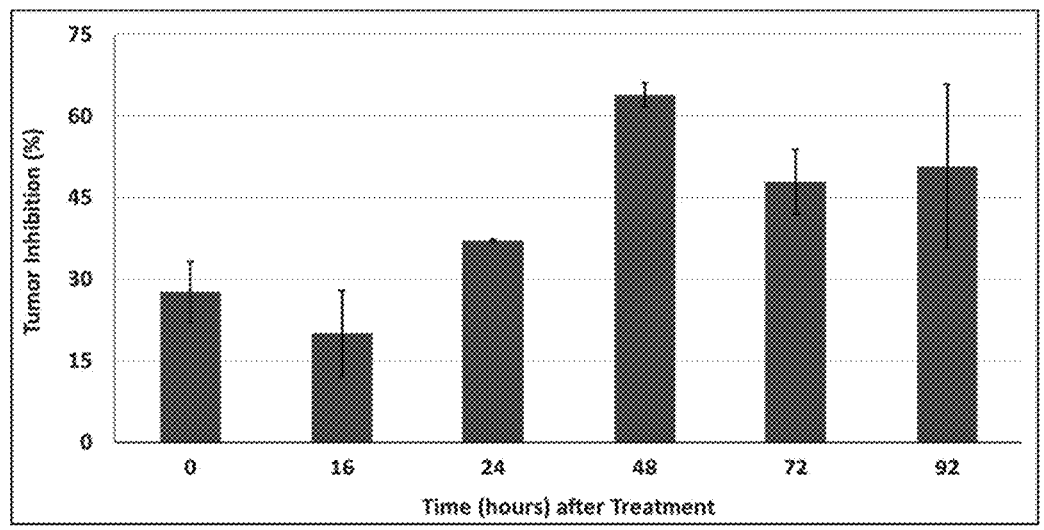
FIG. 116 shows enhancement of cytotoxicity of splenocytes by TGFRt15-TGFRs in C57BL/6 Mice.

The cytotoxicity of the splenocytes from TGFRt15-TGFRs-treated mice against tumor cells was also evaluated. Mouse Moloney leukemia cells (Yac-1) were labeled with CellTrace Violet and were used as tumor target cells. Splenocytes were prepared from TGFRt15-TGFRs (3 mg/kg)-treated mouse spleens at various time points post treatment and were used as effector cells. The target cells were mixed with effector cells at an E:T ratio=10:1 and incubated at 37° C. for 20 hours. Target cell viability was assessed by analysis of propidium iodide positive, violet-labeled Yac-1 cells using flow cytometry. Percentage of Yac-1 tumor inhibition was calculated using the formula, (1-[viable Yac-1 cell number in experimental sample]/[viable Yac-1 cell number in the sample without splenocytes])×100. As shown in FIG. 116, splenocytes from TGFRt15-TGFRs-treated mice had stronger cytotoxicity against Yac-1 cells than the control mouse splenocytes.

Tumor Size Analysis in Response to Chemotherapy and/or TGFRt15-TGFRs

Figure 117:
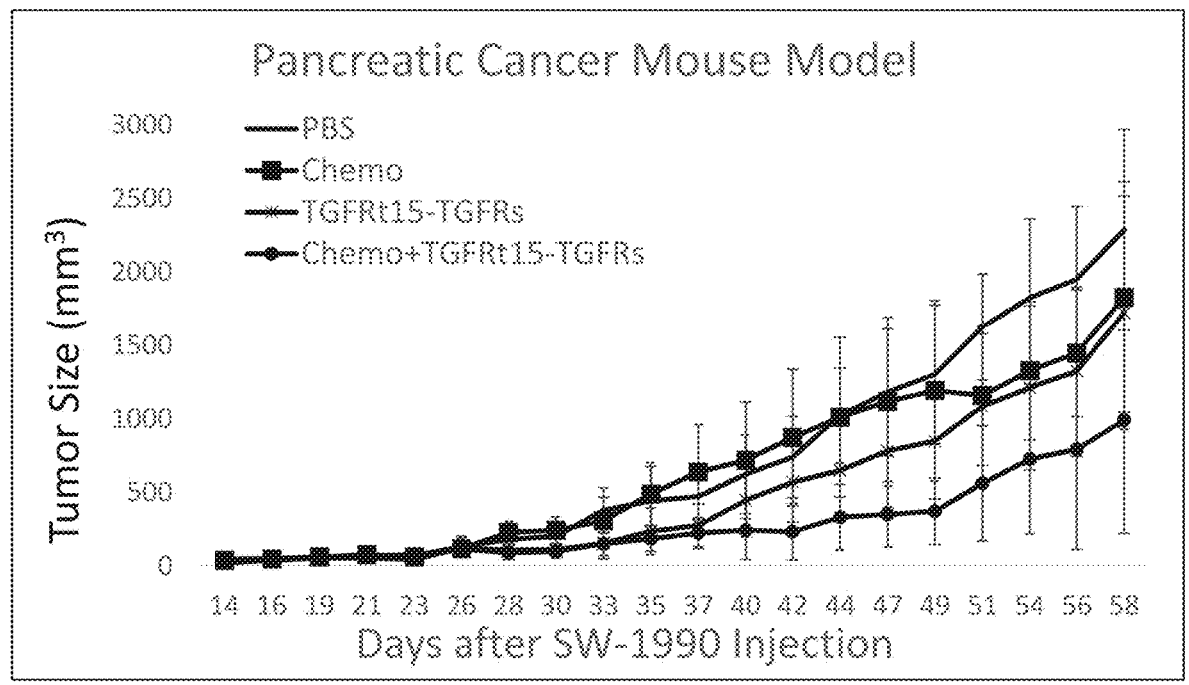
FIG. 117 shows changes in tumor size in response to PBS treatment, chemotherapy alone, TGFRt15-TGFRs alone, or chemotherapy and TGFRt15-TGFRs combination, in a pancreatic cancer mouse model.

Pancreatic cancer cells (SW1990, ATCC® CRL-2172) were subcutaneously (s.c.) injected into C57BL/6 scid mice (The Jackson Laboratory, 001913, $2 \times 10^6$ cells/mouse, in 1004, HBSS) to establish the pancreatic cancer mouse model. Two weeks after tumor cell injection, chemotherapy was initiated in these mice intraperitoneally with a combination of Abraxane (Celgene, 68817-134, 5 mg/kg, i.p.) and Gemcitabine (Sigma Aldrich, G6423, 40 mg/kg, i.p.), followed by immunotherapy with TGFRt15-TGFRs (3 mg/kg, s.c.) in 2 days. The procedure above was considered one treatment cycle and was repeated for another 3 cycles (1 cycle/week). Control groups were set up as the SW1990-injected mice that received PBS, chemotherapy (Gemcitabine and Abraxane), or TGFRt15-TGFRs alone. Along with the treatment cycles, tumor size of each animal was measured and recorded every other day, until the termination of the experiment 2 months after the SW1990 cells were injected. Measurement of the tumor volumes were analyzed by group and the results indicated that the animals receiving a combination of chemotherapy and TGFRt15-TGFRs had significantly smaller tumors comparing to the PBS group, whereas neither chemotherapy nor TGFRt15-TGFRs therapy alone work as sufficiently as the combination (FIG. 117).

In Vitro Senescent B16F10 Melanoma Model

Figure 118:
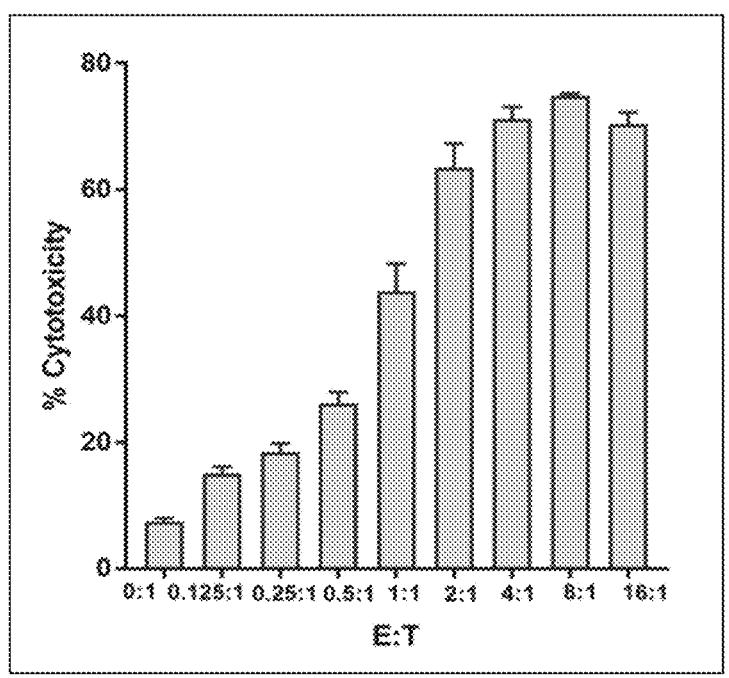
FIG. 118 shows the cytotoxicity of NK cells isolated from mice treated with TGFRt15-TGFRs.

Next, in vitro killing of senescent B16F10 melanoma cells by activated mouse NK cells was evaluated. B16F10 senescence cells (B16F10-SNC) cells were labelled with Cell-Trace violet and incubated for 16 hrs with different E:T ratio of in vitro 2t2-activated mouse NK cells (isolated from spleen of C57BL/6 mice injected with TGFRt15-TGFRs 10 mg/kg for 4 days). The cells were trypsinized, washed and resuspended in complete media containing propidium iodide (PI) solution. The cytotoxicity was assessed by flow cytometry (FIG. 118).

In Vivo Efficacy of TGFRt15-TGFRs in a Melanoma Mouse Model

Figure 119A:
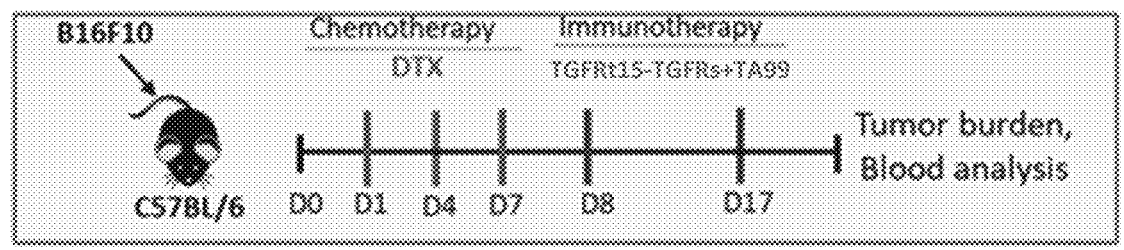
FIGS. 119A-119E show results of the in vivo efficacy of TGFRt15-TGFRs in a melanoma mouse model.
Figure 119B:
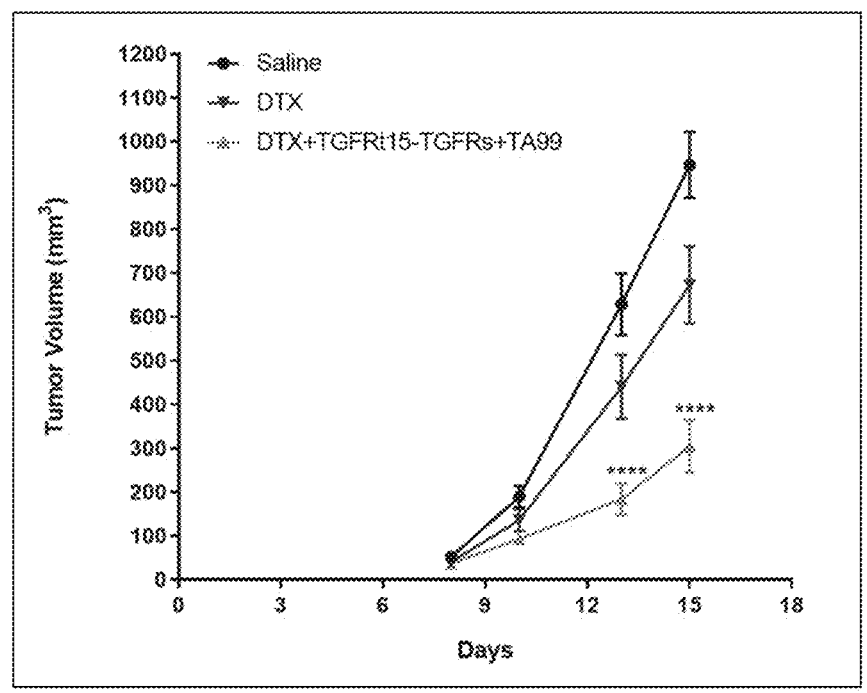
Figure 119C:
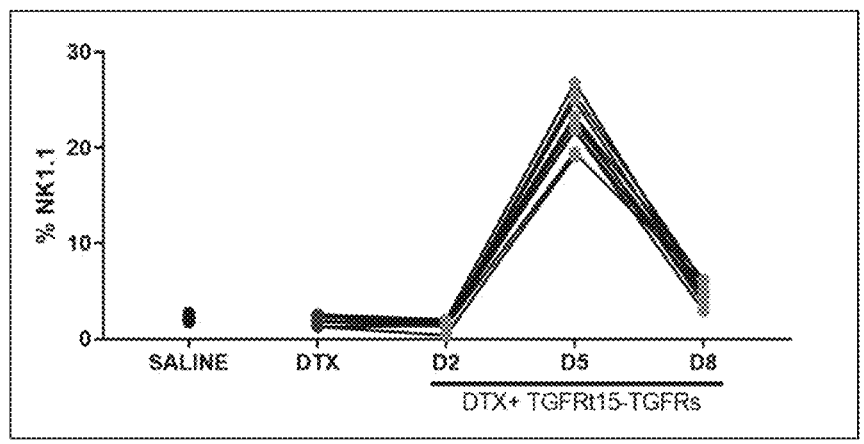
Figure 119D:
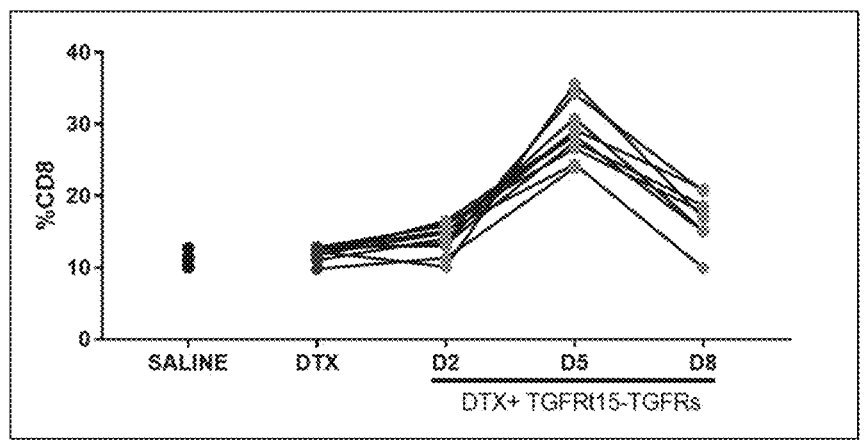
Figure 119E:
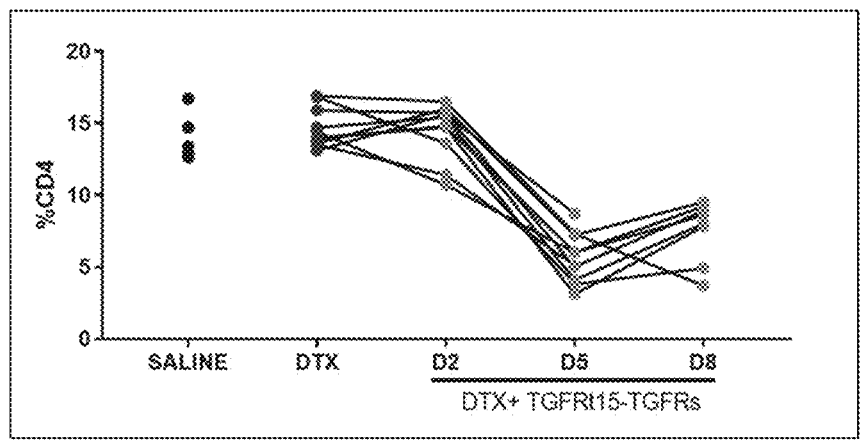

Next, the in vivo efficacy of TGFRt15-TGFRs in a melanoma mouse model was evaluated using a combination treatment containing TGFRt15-TGFRs. FIG. 119A shows a schematic of the treatment regimen. C57BL/6 mice were subcutaneously injected with $0.5 \times 10^6$ B16F10 melanoma cells, and treated with three doses of chemotherapy docetaxel (10 mg/kg) at day 1, day 4 and day 7 followed by treatment with a single dose of a combination immunotherapy of TGFRt15-TGFRs (3 mg/kg)+TA99 (200 µg) (anti-Trp1 antibody). As shown in FIG. 119B, tumor growth was monitored by caliper measurement, and tumor volume was calculated using the formula $V=(L \times W^2)/2$, where L is the largest tumor diameter and W is the perpendicular tumor diameter (N=10, ****p<0.001, Multiple t test analyses). Next, peripheral blood analysis of immune cell subsets in B16F10 tumor model was carried out. Blood was drawn from submandibular vein pre-immunotherapy and post-immunotherapy treatment at days 2, 5 and 8. The RBCs were lysed in ACK lysis buffer and the lymphocytes were washed and stained with fluorescently labelled anti-NK1.1, anti-CD8 and anti-CD4 antibodies. The cells were analyzed by Flow Cytometry (Celesta-BD Bioscience).

Example 79: 7t15-21s137L (Long Version) Fusion Protein Creation and Characterization A fusion protein complex was generated comprising of IL-21/IL-15RαSu/CD137L and IL-7/TF/IL-15 fusion proteins. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of the 7t15 construct (including signal peptide sequence) is as follows:

(Signal peptide)
ATGAAGTGGGTGACCTTCATCAGCCTGCTGTTCCTGTTCTCCAGCGCCT
ACTCC (Human IL7)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT (Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

The amino acid sequence of 7t15 fusion protein (including the leader sequence) is as follows:

(Signal peptide)
MKWVTFISLLFLFSSAYS (Human IL7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

-continued

RKPAALGEAQPTKSLEENKSLKEQKKLNDLCFLKRLLQEIKTCWNKILM
GTKEH (Human Tissue Factor 219)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS The nucleic acid and protein sequences of the 21s137L are shown below. The nucleic acid sequence of the 21s137L construct (including signal peptide sequence) is as follows:

(Signal peptide)
ATGAAGTGGGTGACCTTCATCAGCCTGCTGTTCCTGTTCTCCAGCGCCT
ACTCC (Human IL-21)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCC (Human IL-15R α sushi domain)
ATTACATGCCCCCCTCCCATGAGCGTGGAGCACGCCGACATCTGGGTGA
AGAGCTATAGCCTCTACAGCCGGGAGAGGTATATCTGTAACAGCGGCTT
CAAGAGGAAGGCCGGCACCAGCAGCCTCACCGAGTGCGTGCTGAATAAG
GCTACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGAC
CTGCGGCAGGGCATGTTTGCGCAGCTGGTGGCCCAAAATGTTCTGCTG
ATCGATGGGCCCCTGAGCTGGTACAGTGACCCAGGCCTGGCAGGCGTG
TCCCTGACGGGGGCCTGAGCTACAAAGAGGACACGAAGGAGCTGGTG
GTGGCCAAGGCTGGAGTCTACTATGTCTTCTTTCAACTAGAGCTGCGG
CGCGTGGTGGCCGGCGAGGGCTCAGGCTCCGTTTCACTTGCGCTGCAC
CTGCAGCCACTGCGCTCTGCTGCTGGGGCCGCCGCCCTGGCTTTGACC
GTGGACCTGCCACCCGCCTCCTCCGAGGCTCGGAACTCGGCCTTCGGT TTCCAGGGCCGCTTGCTGCACCTGAGTGCCGGCCAGCGCCTGGGCGTC
CATCTTCACACTGAGGCCAGGGCACGCCATGCCTGGCAGCTTACCCAG
GGCGCCACAGTCTTGGGACTCTTCCGGGTGACCCCCGAAATCCCAGCC
GGACTCCCTTCACCGAGGTCGGAA The amino acid sequence of 21s137L fusion protein (including the leader sequence) is as follows:

(Signal peptide)
MKWVTFISLLFLFSSAYS (Human IL-21)
QGQDRHMIRMRQLIDIVDQLKNYVNDLVPEFLPAPEDVETNCEWSAFS
CFQKAQLKSANTGNNERIINVSIKKLKRKPPSTNAGRRQKHRLTCPSC
DSYEKKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLN
KATNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGV
SLTGGLSYKEDTKELVVAKAGVYYVFFQLELRRVVAGEGSGSVSLALH
LQPLRSAAGAAALALTVDLPPASSEARNSAFGFQGRLLHLSAGQRLGV
HLHTEARARHAWQLTQGATVLGLFRVTPEIPAGLPSPRSE In some cases, the leader peptide is cleaved from the intact polypeptide to generate the mature form that may be soluble or secreted.

The IL-21/IL-15RαSu/CD137L and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15: IL-21/IL-15RαSu/CD137L protein complex (referred to as 7t15-21s137L), which can be purified by anti-TF antibody affinity and other chromatography methods.

Figure 120:
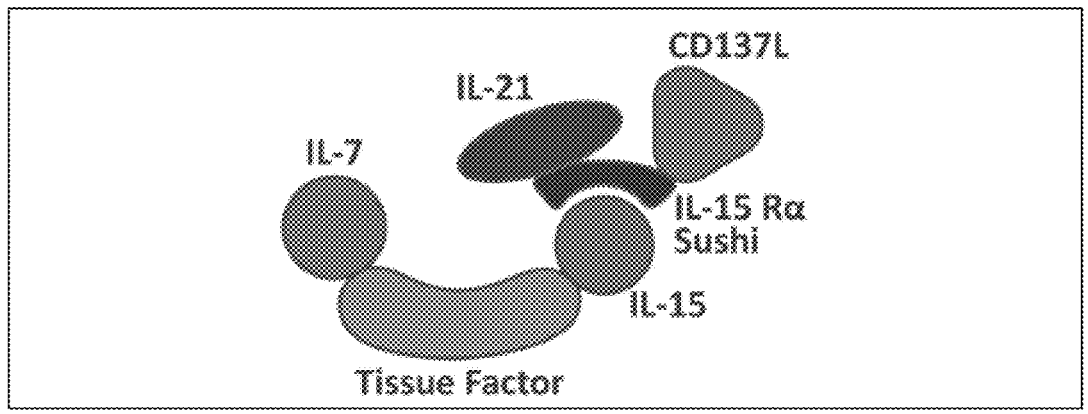
FIG. 120 shows a schematic of the 7t15-21s137L (long version) construct.
Figure 121:
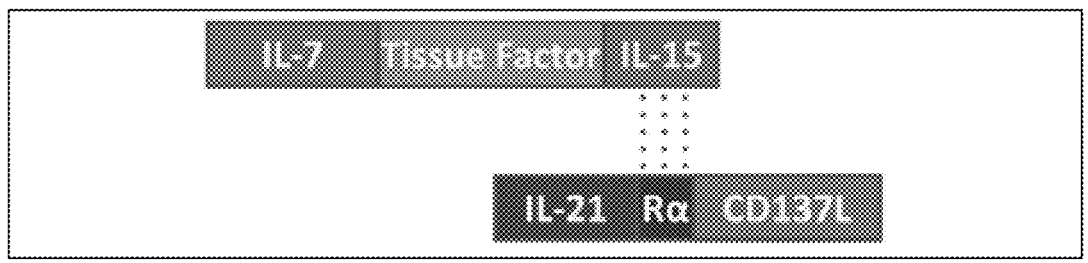
Figure 122:
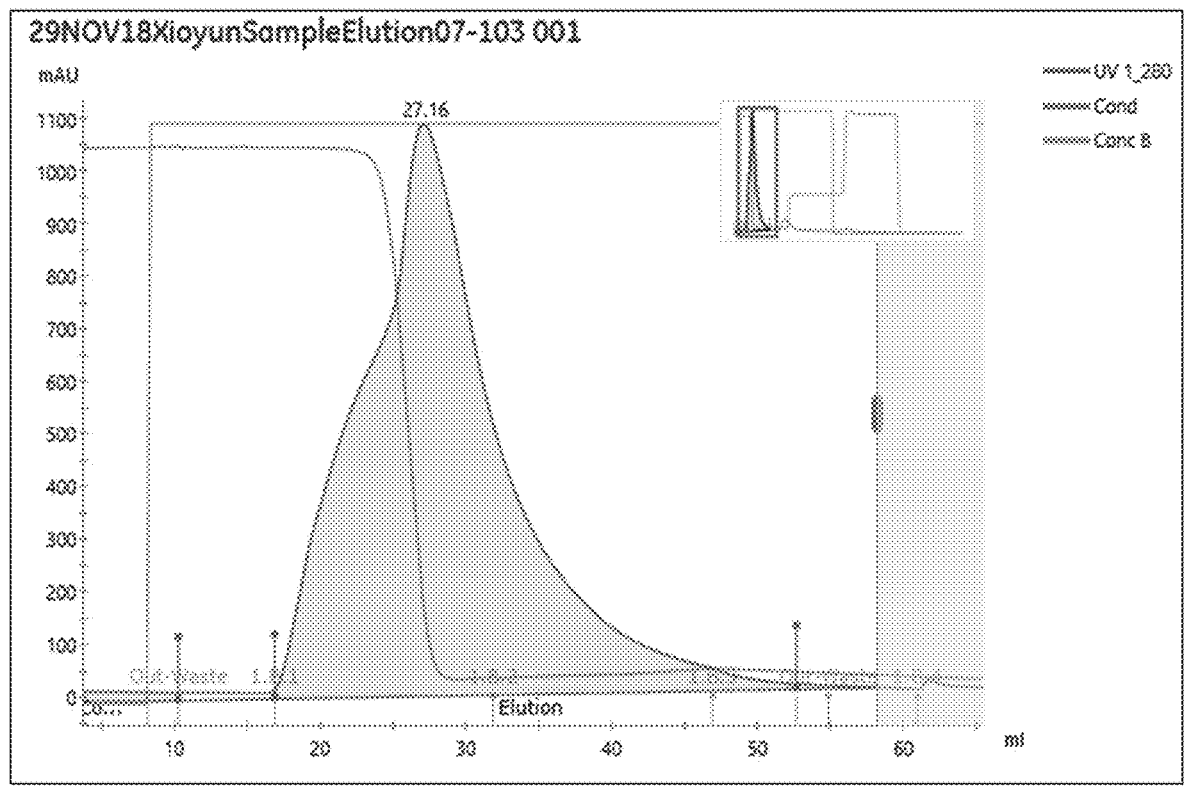
Figure 123:
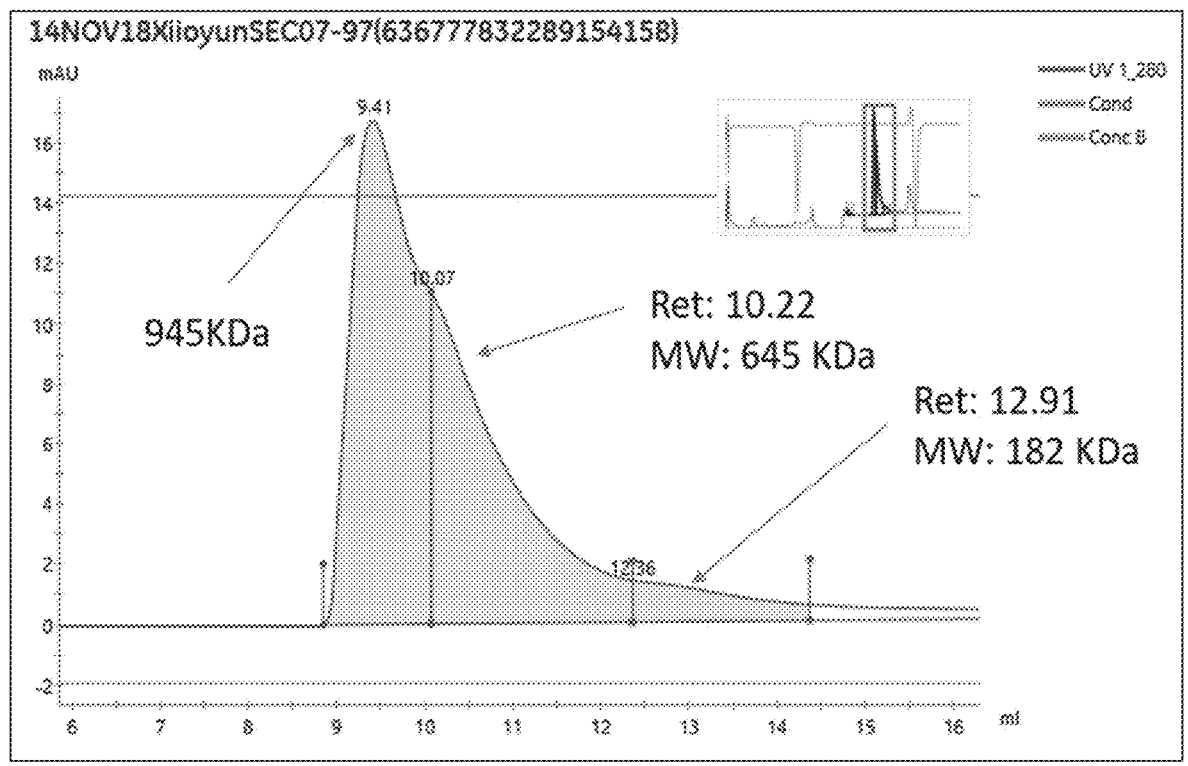
Figure 124:
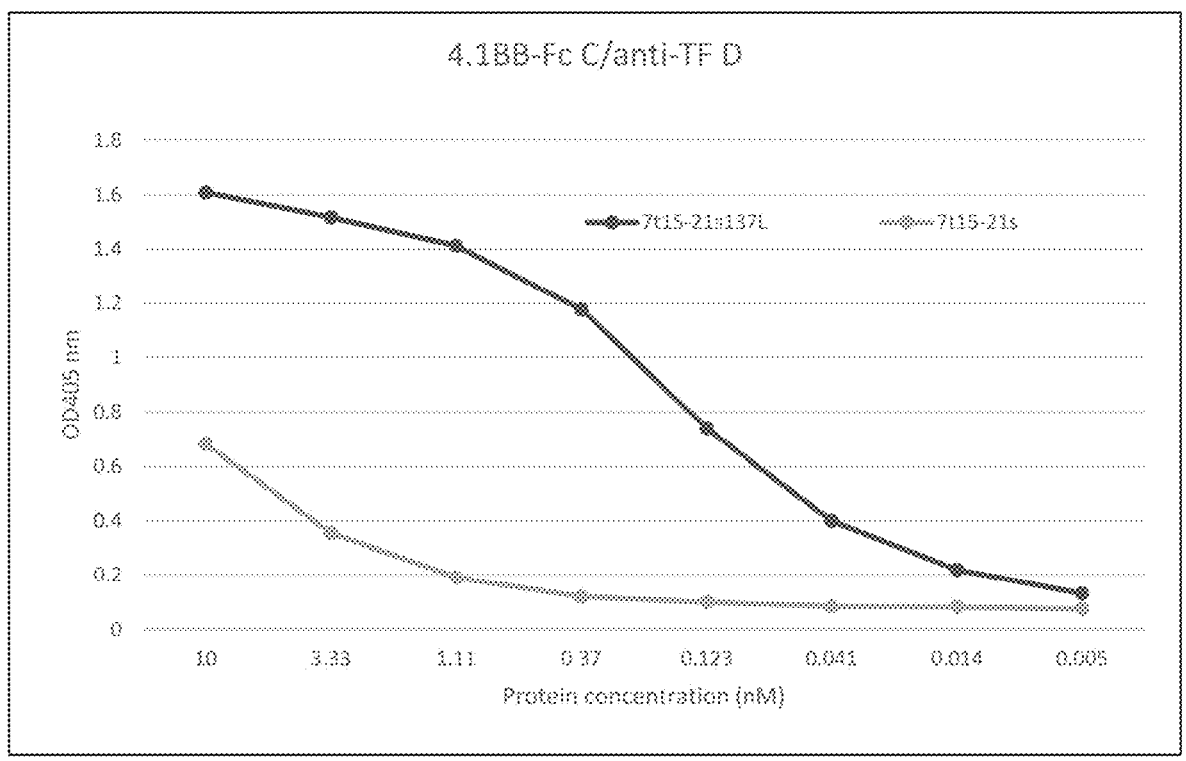

Purification Elution Chromatograph of 7t15-21s137L Using Anti-TF Antibody Affinity Column 7t15-21s137L (FIGS. 120 and 121) harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 122, the anti-TF antibody affinity column bound to 7t15-21s137L which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min. FIG. 123 shows the analytical SEC profile of 7t15-21s137L.

Example 80: 7t15-21s137L (Short Version) Fusion Protein Generation and Characterization A fusion protein complex was generated comprising of IL-21/IL-15RαSu/CD137L and IL-7/TF/IL-15 fusion proteins. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of 7t15 construct (including signal peptide sequence) is as follows:

```
(Signal peptide)
ATGAAGTGGGTGACCTTCATCAGCCTGCTGTTCCTGTTCTCCAGCGCC

TACTCC (Human IL7)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT (Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC
```

The amino acid sequence of 7t15 fusion protein (including the leader sequence) is as follows:

```
(Signal peptide)
MKWVTFISLLFLFSSAYS (Human IL7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

The nucleic acid and protein sequences of the 21s137L (short version) are shown below. The nucleic acid sequence of 21s137L (short version) construct (including signal peptide sequence) is as follows:

```
(Signal peptide)
ATGAAGTGGGTGACCTTCATCAGCCTGCTGTTCCTGTTCTCCAGCGCCT

ACTCC (Human IL-21)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC
```

-continued

TGCAGAAGATGATCCATCAGCACCTGTCCTCCAGGACCCACGGCTCCGA

GGACTCC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137 Ligand short version)
GATCCCGCCGGCCTCTTGGACCTGCGGCAGGGCATGTTTGCGCAGCTGG

TGGCCCAAAATGTTCTGCTGATCGATGGGCCCCTGAGCTGGTACAGTGA

CCCAGGCCTGGCAGGCGTGTCCCTGACGGGGGCCTGAGCTACAAAGAG

GACACGAAGGAGCTGGTGGTGGCCAAGGCTGGAGTCTACTATGTCTTCT

TTCAACTAGAGCTGCGGCGCGTGGTGGCCGGCGAGGGCTCAGGCTCCGT

TTCACTTGCGCTGCACCTGCAGCCACTGCGCTCTGCTGCTGGGGCCGCC

GCCCTGGCTTTGACCGTGGACCTGCCACCCGCCTCCTCCGAGGCTCGGA

ACTCGGCCTTCGGTTTCCAGGGCCGCTTGCTGCACCTGAGTGCCGGCCA

GCGCCTGGGCGTCCATCTTCACACTGAGGCCAGGGCACGCCATGCCTGG

CAGCTTACCCAGGGCGCCACAGTCTTGGGACTCTTCCGGGTGACCCCCG

AAATC

The amino acid sequence of the 21s137L (short version) construct (including signal peptide sequence) is as follows:

(Signal peptide)
MKWVTFISLLFLFSSAYS (Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLNK

ATNVAHWTTPSLKCIR ((G4S)3 linker)
GGGGSGGGGSGGGGS (Human CD137 Ligand short version)
DPAGLLDLRQGMFAQLVAQNVLLIDGPLSWYSDPGLAGVSLTGGLSYKE

DTKELVVAKAGVYYVFFQLELRRVVAGEGSGSVSLALHLQPLRSAAGAA

ALALTVDLPPASSEARNSAFGFQGRLLHLSAGQRLGVHLHTEARARHAW

QLTQGATVLGLFRVTPEI

The IL-21/IL-15RαSu/CD137L (short version) and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15: IL-21/IL-15RαSu/CD137L protein complex (referred to as 7t15-21s137L (short version)), which can be purified by anti-TF antibody affinity and other chromatography methods.

Binding of 7t15-21s137L (Short Version) to CD137 (4.1BB)

On day 1, a 96-well plate was coated with 100 μL (2.5 μg/mL) of GAH IgG Fc (G-102-C, R&D Systems) in R5 (coating buffer) or R5 only and incubated at 4° C., overnight. On day 2, the plates were washed three times and blocked with 300 μL of 1% BSA in PBS at 37° C. for 2 hrs. 10 ng/mL of 4.1BB/Fc (838-4B, R&D Systems) was added at 100 μL/well and incubated for 2 hrs at RT. After three washes, the 7t15-21s137L or 7t15-21s serially diluted at a 1/3 ratio (starting at 10 nM), and incubated at 4° C. overnight. On day 3, following 3 washes, 300 ng/mL of biotinylated-anti-hTF antibody (BAF2339, R&D Systems) was added at 100 μL per well and incubated at RT for 2 hrs. The plate was then washed three times and incubated with 0.25 μg/mL of HRP-SA (Jackson ImmuneResearch) at 100 μL per well for 30 min, followed by 3 washes and incubation with 100 μL of ABTS for 2 mins at RT. Absorbance was read at 405 nm. As shown in FIG. 124, 7t15-21s137L (short version) showed significant interaction with 4.1BB/Fc (blue line) as compared to 7t15-21s.

Detection of IL-15, IL-21, and IL-7 in 7t15-21s137L (Short Version) with ELISA

A 96-well plate was coated with 100 μL (8 μg/mL) of anti-TF antibody in R5 (coating buffer) and incubated at RT for 2 hrs. The plates were washed 3 times and blocked with 100 of 1% BSA in PBS. 7t15-21s137L (short version), serially diluted at a 1:3 ratio was added, and incubated at RT for 60 min. After three washes, 50 ng/mL of biotinylated-anti-IL15 antibody (BAM247, R&D Systems), 500 ng/mL of biotinylated-anti-IL21 antibody (13-7218-81, R&D Systems), or 500 ng/mL of biotinylated-anti-IL7 antibody (506602, R&D Systems) was added to the wells and incubated at RT for 60 min. After three washes and incubation with 0.25 μg/mL of HRP-SA (Jackson ImmunoResearch) at 100 μL per well was carried out for 30 min at RT, followed by four washes and incubation with 100 μL of ABTS for 2 mins at RT. Absorbance was read at 405 nm. As shown in FIGS. 125A-125C, the IL-15, IL-21, and IL-7 domains in 7t15-21s137L (short version) were detected by the respective antibodies.

The IL-15 in 7t15-1s137L (Short Version) Promotes IL2Rαβγ Containing CTLL2 Cell Proliferation To evaluate the IL-15 activity of 7t15-21s137L (short version), 7t15-21s137L (short version) was compared with recombinant IL15 in promoting proliferation of IL2Rαβγ expressing CTLL2 cells. IL-15-dependent CTLL2 cells were washed 5 times with IMDM-10% FBS and seeded to the wells at 2×10⁴ cells/well. Serially diluted 7t15-21s137L (short version) or IL-15 were added to the cells (FIG. 126). Cells were incubated in a CO$_2$ incubator at 37° C. for 3 days. Cell proliferation was detected by adding 10 μL of WST1 to each well on day 3 and incubated for an additional 3 hours in a CO$_2$ incubator at 37° C. The amount of formazan dye produced was analyzed by measuring the absorbance at 450 nm. As shown in FIG. 126, 7t15-21s137L (short version) and IL-15 promoted CTLL2 cell proliferation. The EC$_{50}$ of 7t15-21s137L (short version) and IL-15 was 55.91 pM and 6.22 pM. respectively.

The IL-21 in 7t15-1s137L (Short Version) Promotes IL21R Containing B9 Cell Proliferation To evaluate the IL-21 activity of 7t15-21s137L (short version), 7t15-21s137L (short version) was compared with recombinant IL-21 in promoting proliferation of IL-21R expressing B9 cells. IL-21R containing B9 cells were washed 5 times with RPMI-10% FBS and seeded to the wells at $1 \times 10^4$ cells/well. Serially diluted 7t15-21s137L (short version) or IL-21 were added to the cells (FIG. 127). Cells were incubated in a $CO_2$ incubator at 37° C. for 5 days. Cell proliferation was detected by adding 10 µL of WST1 to each well on day 5 and incubated for an additional 4 hours in a $CO_2$ incubator at 37° C. The amount of formazan dye produced was analyzed by measuring the absorbance at 450 nm. As shown in FIG. 127, 7t15-21s137L (short version) and IL-21 promoted B9 cell proliferation. The $EC_{50}$ of 7t15-21s137L (short version) and IL-21 was 104.1 nM and 72.55 nM. respectively.

Example 86: 7t15-TGFRs Fusion Protein Generation and Characterization

A fusion protein complex was generated comprising of TGFβ Receptor II/IL-15RαSu and IL-7/TF/IL-15 fusion proteins (FIGS. 128 and 129). The human TGFβ Receptor II (Ile24-Asp159), tissue factor 219, IL-15, and IL-7 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of the 7t15 construct (including signal peptide sequence) is as follows:

```
(Signal peptide)
ATGAAGTGGGTGACCTTCATCAGCCTGCTGTTCCTGTTCTCCAGCGCCT

ACTCC (Human IL7)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT (Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG
```

-continued
```
ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC
```

The amino acid sequence of 7t15 fusion protein (including the leader sequence) is as follows:

```
(Signal peptide)
MKWVTFISLLFLFSSAYS (Human IL7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

Constructs were also made by attaching two TGFβ Receptor II directly to the IL-15RαSu chain which was synthesized by Genewiz. The nucleic acid and protein sequences of a construct comprising the TGFβ Receptor II linked to the N-terminus of IL-15RαSu are shown below.

The nucleic acid sequence of the TGFRs construct (including signal peptide sequence) is as follows:

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG

The amino acid sequence of TGFRs fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNK

ATNVAHWTTPSLKCIR

Effect of 7t15-TGFRs on TGFβ1 Activity in HEK-Blue TGFβ Cells

To evaluate the activity of TGFβR in 7t15-TGFRs, the effect of 7t15-TGFRs on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5 \times 10^5$ cells/mL. In a flat-bottom 96-well plate, 50 µL cells were added to each well ($2.5 \times 10^4$ cells/well) and followed with 50 µL 0.1 nM TGFβ1 (R&D systems). 7t15-TGFRs or TGFR-Fc (R&D Systems) prepared at a 1:3 serial dilution was then added to the plate to reach a total volume of 200 µL. After 24 hrs of incubation at 37° C., 40 µL of induced HEK-Blue TGFβ cell supernatant was added to 160 µL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. See, FIG. 130. The $IC_{50}$ of each protein sample was calculated with GraphPad Prism 7.04. The $IC_{50}$ of 7t15-TGFRs and TGFR-Fc were 1142 pM and 558.6 pM respectively. These results showed that the TGFβR in 7t15-TGFRs was able to block the activity of TGFβ1 in HEK-Blue TGFβ cells.

Detection of IL-15, TGFβRII, and IL-7 in 7t15-TGFRs with ELISA

A 96-well plate was coated with 100 µL (8 µg/mL) of anti-TF antibody in R5 (coating buffer) and incubated at room temperature (RT) for 2 hrs. The plates were washed three times and blocked with 100 µL of 1% BSA in PBS. Serial dilution of 7t15-TGFRs (1:3 ratio) was added, and incubated at RT for 60 mins. After 3 washes, 50 ng/mL of biotinylated-anti-IL-15 antibody (BAM247, R&D Systems), 200 ng/mL of biotinylated-anti-TGFbRII antibody (BAF241, R&D Systems), or 500 ng/mL of biotinylated-anti-IL-7 antibody (506602, R&D Systems) was added and incubated at RT for 60 min. Following three washes, incubation with 0.25 µg/mL of HRP-SA (Jackson ImmunoResearch) at 100 µL per well was carried out for 30 min at RT, followed by 4 washes and incubation with 100 µL of ABTS for 2 mins at RT. Absorbance was read at 405 nm. As shown in FIGS. 131A-131C, the IL-15, TGFR, and IL-7 in 7t15-TGFRs were detected by the respective antibodies.

The IL-15 in 7t15-TGFRs Promotes IL-2Rβ and Common γ Chain Containing 32Dβ Cell Proliferation To evaluate the activity of IL-15 in 7t15-TGFRs, 7t15-TGFRs was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2 \times 10^4$ cells/well. Serially-diluted 7t15-TGFRs or IL-15 were added to the cells (FIG. 132). Cells were incubated in a $CO_2$ incubator at 37° C. for 3 days. Cell proliferation was detected by adding 10 µL of WST1 to each well on day 3 and incubating for an additional 3 hours in a $CO_2$ incubator at 37° C. The amount of formazan dye produced was analyzed by measuring the absorbance at 450 nm. As shown in FIG. 132, 7t15-TGFRs and IL-15 promoted 32Dβ cell proliferation, with the $EC_{50}$ of 7t15-TGFRs and IL-15 being 126 nM and 16.63 pM, respectively.

Purification Elution Chromatograph of 7t15-TGFRs Using Anti-TF Antibody Affinity Column 7t15-TGFRs harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 133, the anti-TF antibody affinity column can bind 7t15-TGFRs which contains TF as a fusion partner of 7t15-TGFRs. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE Analysis of 7t15-TGFRs

To determine the purity and molecular weight of the protein, 7t15-TGFRs protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water. To verify that the 7t15-TGFRs protein undergoes glycosylation after translation in CHO cells, a deglycosylation experiment was conducted using the Protein Deglycosylation Mix II kit from New England Biolabs and the manufacturer's instructions. FIG. 134 shows reduced SDS-PAGE analysis of the sample in non-deglycosylated (lane 1 in red outline) and deglycosylated (lane 2 in yellow outline) state. These results showed that the protein is glycosylated when it is expressed in CHO cells. After deglycosylation, the purified sample showed expected molecular weights (55 kDa and 39 kDa) in reduced SDS gel. Lane M was loaded with 10 ul of SeeBlue Plus2 Prestained Standard.

Characterization of 7t15-TGFRs

7t15-TGFRs is a multi-chain polypeptide (a type A multi-chain polypeptide described herein) that includes the first polypeptide that is a soluble fusion of human IL-7, human tissue factor 219 fragment and human IL-15 (7t15), and the second polypeptide that is a soluble fusion of single chain two TGFβRII domains and sushi domain of human IL-15 receptor alpha chain (TGFRs).

CHO cells were co-transfected with 7t15 and TGFRs vectors. The 7t15-TGFRs complex was purified from the transfected CHO cell culture supernatant. The IL-7, IL-15, TGFβ receptor and tissue factor (TF) components were demonstrated in the complex by ELISA as shown in FIG. 135. A humanized anti-TF monoclonal antibody was used as the capture antibody to determine TF in 7t15-TGFRs, and biotinylated antibodies against human IL-15 antibody (R&D systems), human IL-7 (Biolegend), anti-TGFβ receptor (R&D Systems) were used as the detection antibodies to respectively determine IL-7, IL-15 and TGFβ receptor in 7t15-TGFRs. Peroxidase conjugated streptavidin (Jackson ImmunoResearch Lab) and ABTS substrate (Surmodics IVD, Inc.) were then used to detect the bound biotinylated antibodies. The results were analyzed by ELISA (FIG. 135).

In Vivo Characterization of 7t15-TGFRs in C57BL/6 Mice

To determine the immunostimulatory activity of 7t15-TGFRs in vivo, C57BL/6 mice were subcutaneously treated with control solution (PBS) or 7t15-TGFRs at 0.3, 1, 3 and 10 mg/kg. The treated mice were euthanized. The mouse spleens were collected and weighed day 4 post treatment. Single splenocyte suspensions were prepared and stained with fluorochrome-conjugated anti-CD4, anti-CD8, and anti-NK1.1 antibodies and the percentage of $CD4^+$ T cells, $CD8^+$ T cells, and NK cells was analyzed by flow cytometry. The results showed that 7t15-TGFRs was effective at expanding splenocytes based on spleen weight (FIG. 136A), especially at 1-10 mg/kg. The percentages of $CD8^+$ T cells and NK cells were higher compared to control-treated mice (FIG. 136B) at all doses tested.

CD44 Expression of $CD4^+$ and $CD8^+$ T Cells

It has been known that IL-15 induces CD44 expression on T cells and development of memory T cells. CD44 expression of $CD4^+$ and $CD8^+$ T cells in the 7t15-TGFRs treated mice were assessed. C57BL/6 mice were subcutaneously treated with 7t15-TGFRs. The splenocytes were stained with fluorochrome-conjugated anti-CD4, anti-CD8 and anti-CD44 monoclonal antibodies for immunocyte subsets. The percentages of $CD4^+CD44^{high}$ T cells of total CD4+ T cells and $CD8^+CD44^{high}$ T cells of total $CD8^+$ T cells were analyzed by flow cytometry. As shown in FIGS. 137A and 137B, 7t15-TGFRs significantly activated $CD4^+$ and $CD8^+$ T cells to differentiate into memory T cells.

Furthermore, the dynamic proliferation of immune cells based on Ki67 expression of splenocytes and cytotoxicity potential based on granzyme B expression of the splenocytes induced by 7t15-TGFRs after the single dose treatment of mouse were also evaluated. C57BL/6 mice were subcutaneously treated with 7t15-TGFRs at 3 mg/kg. The treated mice were euthanized and the splenocytes were prepared. The prepared splenocytes were stained with fluorochrome-conjugated anti-CD4, anti-CD8, and anti-NK1.1 (NK) antibodies for immunocyte subsets and then intracellularly stained with anti-Ki67 antibody for cell proliferation and anti-granzyme B antibody for cytotoxic marker. The mean fluorescent intensity (MFI) of Ki67 and granzyme B of corresponding immunocyte subsets was analyzed by flow cytometry. As shown in FIGS. 138A and 138B, in the spleens of mice treated with 7t15-TGFRs, the expression of Ki67 and granzyme B by $CD8^+$ T cells and NK cells increased compared with PBS control treatment. These results demonstrate that 7t15-TGFRs is not only to increase numbers of $CD8^+$ T cells and NK cells but also enhance potential cytotoxicity of these cells.

Additionally, cytotoxicity of the mouse splenocytes against tumor cells was also evaluated. Mouse Yac-1 cells were labeled with CellTrace Violet and used as tumor target cells. The splenocytes were prepared from 7t15-TGFRs-treated mice and used as effector cells. The target cells were mixed with effector cells at E:T ratio=10:1 in RPMI-10 medium with or without 7t15-TGFRs at 100 nM and incubated at 37° C. for 20 hours. Target Yac-1 cell inhibition was assessed by analysis of viable violet-labeled Yac-1 cells using flow cytometry. Percentage of Yac-1 inhibition was calculated using a formula, (1-viable Yac-1 cell number in experimental sample/viable Yac-1 cell number in the sample without splenocytes)×100. As shown in FIG. 139, 7t15-TGFRs-treated mouse splenocytes had stronger cytotoxicity against Yac-1 cells than the control mouse splenocytes and addition of 7t15-TGFRs during cytotoxic assay further enhanced cytotoxicity of splenocytes against Yac-1 target cells.

Example 81: TGFRt15-21s137L Fusion Protein Generation and Characterization

A fusion protein complex was generated comprising IL-21/IL-15RαSu/CD137L and TGFβ Receptor II/TF/IL-15 fusion proteins. The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G45(3) linker to generate a single chain version of TGFβ Receptor II and then directly linking to the N-terminus coding region of tissue factor 219 followed by the N-terminus coding region of IL-15.

The nucleic acid sequence of the TGFRt15 construct (including signal peptide sequence) is as follows:

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC (Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

The amino acid sequence of TGFRt15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

The nucleic acid and protein sequences of the 21s137L are shown below. The nucleic acid sequence of the 21s137L construct (including signal peptide sequence) is as follows:

(Signal peptide)
ATGAAGTGGGTGACCTTCATCAGCCTGCTGTTCCTGTTCTCCAGCGCCT

ACTCC (Human IL-21)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

```
-continued
CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGAC

CTGCGGCAGGGCATGTTTGCGCAGCTGGTGGCCCAAAATGTTCTGCTG

ATCGATGGGCCCCTGAGCTGGTACAGTGACCCAGGCCTGGCAGGCGTG

TCCCTGACGGGGGGCCTGAGCTACAAAGAGGACACGAAGGAGCTGGTG

GTGGCCAAGGCTGGAGTCTACTATGTCTTCTTTCAACTAGAGCTGCGG

CGCGTGGTGGCCGGCGAGGGCTCAGGCTCCGTTTCACTTGCGCTGCAC

CTGCAGCCACTGCGCTCTGCTGCTGGGGCCGCCGCCCTGGCTTTGACC

GTGGACCTGCCACCCGCCTCCTCCGAGGCTCGGAACTCGGCCTTCGGT

TTCCAGGGCCGCTTGCTGCACCTGAGTGCCGGCCAGCGCCTGGGCGTC

CATCTTCACACTGAGGCCAGGGCACGCCATGCCTGGCAGCTTACCCAG

GGCGCCACAGTCTTGGGACTCTTCCGGGTGACCCCCGAAATCCCAGCC

GGACTCCCTTCACCGAGGTCGGAA
```

The amino acid sequence of 21s137L fusion protein (including the leader sequence) is as follows:

```
(Signal peptide)
MKWVTFISLLFLFSSAYS (Human IL-21)
QGQDRHMIRMRQLIDIVDQLKNYVNDLVPEFLPAPEDVETNCEWSAFS

CFQKAQLKSANTGNNERIINVSIKKLKRKPPSTNAGRRQKHRLTCPSC

DSYEKKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLN

KATNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGV

SLTGGLSYKEDTKELVVAKAGVYYVFFQLELRRVVAGEGSGSVSLALH

LQPLRSAAGAAALALTVDLPPASSEARNSAFGFQGRLLHLSAGQRLGV

HLHTEARARHAWQLTQGATVLGLFRVTPEIPAGLPSPRSE
```

In some cases, the leader peptide is cleaved from the intact polypeptide to generate the mature form that may be soluble or secreted.

The IL-21/IL-15RαSu/CD137L and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15: IL-21/IL-15RαSu/CD137L protein complex (referred to as TGFRt15-21s137L), which can be purified by anti-TF antibody affinity and other chromatography methods. See, FIGS. 140 and 141.

Purification Elution Chromatograph of TGFRt15-21s137L Using Anti-TF Antibody Affinity Column TGFRt15-21s137L harvest from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 142, the anti-TF antibody affinity column bound to TGFRt15-21s137L which contains TF as a fusion partner of TGFRt15-21s137L. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Example 82: TGFRt15-TGFRs21 Fusion Protein Generation and Characterization

A fusion protein complex was generated comprising of TGFβ Receptor II/IL-15RαSu/IL-21 and TGFβ Receptor II/TF/IL-15 fusion proteins. The human TGFβ Receptor II (Ile24-Asp159), tissue factor 219, IL-21, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

(Signal peptide)
ATGAAGTGGGTGACCTTCATCAGCCTGCTGTTCCTGTTCTCCAGCGCC

TACTCC (Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

AGCATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCTCCATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGAC (Human Tissue Factor 219)
AGCGGCACAACCAACACAGTCGCTGCCTATAACCTCACTTGGAAGAGC

ACCAACTTCAAAACCATCCTCGAATGGGAACCCAAACCCGTTAACCAA

GTTTACACCGTGCAGATCAGCACCAAGTCCGGCGACTGGAAGTCCAAA

TGTTTCTATACCACCGACACCGAGTGCGATCTCACCGATGAGATCGTG

AAAGATGTGAAACAGACCTACCTCGCCCGGGTGTTTAGCTACCCCGCC

GGCAATGTGGAGAGCACTGGTTCCGCTGGCGAGCCTTTATACGAGAAC

AGCCCCGAATTTACCCCTTACCTCGAGACCAATTTAGGACAGCCCACC

ATCCAAAGCTTTGAGCAAGTTGGCACAAAGGTGAATGTGACAGTGGAG

GACGAGCGGACTTTAGTGCGGCGGAACAACACCTTTCTCAGCCTCCGG

GATGTGTTCGGCAAAGATTTAATCTACACACTGTATTACTGGAAGTCC

TCTTCCTCCGGCAAGAAGACAGCTAAAACCAACACAAACGAGTTTTTA

ATCGACGTGGATAAAGGCGAAAACTACTGTTTCAGCGTGCAAGCTGTG

ATCCCCTCCCGGACCGTGAATAGGAAAAGCACCGATAGCCCCGTTGAG

TGCATGGGCCAAGAAAAGGGCGAGTTCCGGGAG (Human IL-15)
AACTGGGTGAACGTCATCAGCGATTTAAAGAAGATCGAAGATTTAATT

CAGTCCATGCATATCGACGCCACTTTATACACAGAATCCGACGTGCAC

CCCTCTTGTAAGGTGACCGCCATGAAATGTTTTTTACTGGAGCTGCAA

GTTATCTCTTTAGAGAGCGGAGACGCTAGCATCCACGACACCGTGGAG

AATTTAATCATTTTAGCCAATAACTCTTTATCCAGCAACGGCAACGTG

ACAGAGTCCGGCTGCAAGGAGTGCGAAGAGCTGGAGGAGAAGAACATC

AAGGAGTTTCTGCAATCCTTTGTGCACATTGTCCAGATGTTCATCAAT

ACCTCC

The amino acid sequence of TGFRt15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNC

SITSICEKPQEVCVAVWRKNDENITLETVCHDPKLPYHDFILEDAASP

KCIMKEKKKPGETFFMCSCSSDECNDNIIFSEEYNTSNPDGGGGSGGG

GSGGGGSIPPHVQKSVNNDMIVTDNNGAVKFPQLCKFCDVRFSTCDNQ

KSCMSNCSITSICEKPQEVCVAVWRKNDENITLETVCHDPKLPYHDFI

LEDAASPKCIMKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKS

KCFYTTDTECDLTDEIVKDVKQTYLARVFSYPAGNVESTGSAGEPLY

ENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFS

VQAVIPSRTVNRKSTDSPVECMGQEKGEFRE (Human IL-15)
NWVNVISDLKKIEDLIQSMHIDATLYTESDVHPSCKVTAMKCFLLEL

QVISLESGDASIHDTVENLIILANNSLSSNGNVTESGCKECEELEEK

NIKEFLQSFVHIVQMFINTS

Constructs were also made by attaching two TGFβ Receptor II directly to the IL-15RαSu chain, followed by the N-terminus coding region of IL-21, which was synthesized by Genewiz. The nucleic acid and protein sequences of a construct comprising the TGFβ Receptor II linked to the N-terminus of IL-15RαSu following with the N-terminus of IL-21 are shown below.

The nucleic acid sequence of the TGFRs21 construct (including signal peptide sequence) is as follows:

(Signal peptide)
ATGAAGTGGGTGACCTTCATCAGCCTGCTGTTCCTGTTCTCCAGCGC

CTACTCC (Human TGFβ Receptor II fragments)
ATCCCCCCCCATGTGCAAAAGAGCGTGAACAACGATATGATCGTGAC

CGACAACAACGGCGCCGTGAAGTTTCCCCAGCTCTGCAAGTTCTGCG

ATGTCAGGTTCAGCACCTGCGATAATCAGAAGTCCTGCATGTCCAAC

TGCAGCATCACCTCCATCTGCGAGAAGCCCCAAGAAGTGTGCGTGGC

CGTGTGGCGGAAAAATGACGAGAACATCACCCTGGAGACCGTGTGTC

ACGACCCCAAGCTCCCTTATCACGACTTCATTCTGGAGGACGCTGCC

```
-continued
TCCCCCAAATGCATCATGAAGGAGAAGAAGAAGCCCGGAGAGACCTT

CTTTATGTGTTCCTGTAGCAGCGACGAGTGTAACGACAACATCATCT

TCAGCGAAGAGTACAACACCAGCAACCCTGATGGAGGTGGCGGATCC

GGAGGTGGAGGTTCTGGTGGAGGTGGGAGTATTCCTCCCCACGTGCA

GAAGAGCGTGAATAATGACATGATCGTGACCGATAACAATGGCGCCG

TGAAATTTCCCCAGCTGTGCAAATTCTGCGATGTGAGGTTTTCCACC

TGCGACAACCAGAAGTCCTGTATGAGCAACTGCTCCATCACCTCCAT

CTGTGAGAAGCCTCAGGAGGTGTGCGTGGCTGTCTGGCGGAAGAATG

ACGAGAATATCACCCTGGAAACCGTCTGCCACGATCCCAAGCTGCCC

TACCACGATTTCATCCTGGAAGACGCCGCCAGCCCTAAGTGCATCAT

GAAAGAGAAAAAGAAGCCTGGCGAGACCTTTTTCATGTGCTCCTGCA

GCAGCGACGAATGCAACGACAATATCATCTTTAGCGAGGAATACAAT

ACCAGCAACCCCGAC (Human IL-15R α sushi domain)
ATTACATGCCCCCCTCCCATGAGCGTGGAGCACGCCGACATCTGGGT

GAAGAGCTATAGCCTCTACAGCCGGGAGAGGTATATCTGTAACAGCG

GCTTCAAGAGGAAGGCCGGCACCAGCAGCCTCACCGAGTGCGTGCTG

AATAAGGCTACCAACGTGGCTCACTGGACAACACCCTCTTTAAAGTG

CATCCGG (Human IL-21)
CAGGGCCAGGACAGGCACATGATCCGGATGAGGCAGCTCATCGACAT

CGTCGACCAGCTGAAGAACTACGTGAACGACCTGGTGCCCGAGTTTC

TGCCTGCCCCCGAGGACGTGGAGACCAACTGCGAGTGGTCCGCCTTC

TCCTGCTTTCAGAAGGCCCAGCTGAAGTCCGCCAACACCGGCAACAA

CGAGCGGATCATCAACGTGAGCATCAAGAAGCTGAAGCGGAAGCCTC

CCTCCACAAACGCCGGCAGGAGGCAGAAGCACAGGCTGACCTGCCCC

AGCTGTGACTCCTACGAGAAGAAGCCCCCCAAGGAGTTCCTGGAGAG

GTTCAAGTCCCTGCTGCAGAAGATGATCCATCAGCACCTGTCCTCCA

GGACCCACGGCTCCGAGGACTCC
```

The amino acid sequence of TGFRs21 fusion protein (including the leader sequence) is as follows:

```
(Signal peptide)
MKWVTFISLLFLFSSAYS (Human TGFβ Receptor II)
IPPHVQKSVNNDMIVTDNNGAVKFPQLCKFCDVRFSTCDNQKSCMSN

CSITSICEKPQEVCVAVWRKNDENITLETVCHDPKLPYHDFILEDAA

SPKCIMKEKKKPGETFFMCSCSSDECNDNIIFSEEYNTSNPDGGGGS

GGGGSGGGGSIPPHVQKSVNNDMIVTDNNGAVKFPQLCKFCDVRFST

CDNQKSCMSNCSITSICEKPQEVCVAVWRKNDENITLETVCHDPKLP

YHDFILEDAASPKCIMKEKKKPGETFFMCSCSSDECNDNIIFSEEYN

TSNPD (Human IL-15R α sushi domain)
ITCPPPMSVEHADIWVKSYSLYSRERYICNSGFKRKAGTSSLTECVL

NKATNVAHWTTPSLKCIR (Human IL-21)
QGQDRHMIRMRQLIDIVDQLKNYVNDLVPEFLPAPEDVETNCEWSAF

SCFQKAQLKSANTGNNERIINVSIKKLKRKPPSTNAGRRQKHRLTCP

SCDSYEKKPPKEFLERFKSLLQKMIHQHLSSRTHGSEDS
```

In some cases, the leader peptide is cleaved from the intact polypeptide to generate the mature form that may be soluble or secreted.

The TGFR/IL-15RαSu/IL-21 and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. Hum Gene Ther 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/IL-21 protein complex (referred to as TGFRt15-TGFRs21), which can be purified by anti-TF antibody affinity and other chromatography methods. See, FIGS. 143 and 144.

Purification Elution Chromatograph of TGFRt15-TGFRs21 Using Anti-TF Antibody Affinity Column TGFRt15-TGFRs21 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 145, the anti-TF antibody affinity column bound to TGFRt15-TGFRs21 which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE Analysis of TGFRt15-TGFRs21

To determine the purity and molecular weight of the protein, TGFRt15-TGFRs21 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the TGFRt15-TGFRs21 protein undergoes glycosylation after translation in CHO cells, a deglycosylation experiment was conducted using the Protein Deglycosylation Mix II kit from New England Biolabs and the manufacturer's instructions. FIG. 146 shows the reduced SDS-PAGE analysis of the sample in non-deglycosylated (lane 1 in red outline) and deglycosylated (lane 2 in yellow outline) state. It is clear that the protein is glycosylated when it is expressed in CHO cells. After deglycosylation, the purified sample showed expected molecular weights (69 kDa and 55 kDa) in reduced SDS gel. Lane M was loaded with 10 ul of SeeBlue Plus2 Prestained Standard.

Immunostimulation of TGFRt15-TGFRs21 in C57BL/6 Mice

TGFRt15-TGFRs21 is a multi-chain polypeptide (a type A multi-chain polypeptide described herein) that includes the first polypeptide that is a soluble fusion of single chain two TGFβRII domains, human tissue factor 219 fragment and human IL-15 (TGFRt15), and the second polypeptide that is a soluble fusion of single chain two TGFβRII domains, sushi domain of human IL-15 receptor alpha chain and human IL-21 (TGFRs21).

CHO cells were co-transfected with TGFRt15 and TGFRs21 vectors. The TGFRt15-TGFRs21 complex was purified from the transfected CHO cell culture supernatant. The TGFβ receptor, IL-15, IL-21 and tissue factor (TF) components were demonstrated in the complex by ELISA as shown in FIGS. 147A and 147B. A humanized anti-TF monoclonal antibody was used as the capture antibody to determine TF in TGFRt15-TGFRs21, biotinylated anti-human IL-15 antibody (R&D systems), biotinylated anti-human TGFβ receptor antibody (R&D systems), and biotinylated anti-human IL-21 antibody (R&D Systems) were used as the detection antibodies to respectively determine IL-15, TGFβ receptor, and IL-21 in TGFRt15-TGFRs21. For detection, peroxidase conjugated streptavidin (Jackson ImmunoResearch Lab) and ABTS were used.

Wild type C57BL/6 mice were treated subcutaneously with either control solution (PBS) or with TGFRt15-TGFRs21 at 3 mg/kg. Four days after treatment, spleen weight and the percentages of various immune cell types present in the spleen were evaluated. As shown in FIG. 148A, the percentages of CD4$^+$ T cells, CD8$^+$ T cells, and NK cells present in the spleen of control-treated and TGFRt15-TGFRs21-treated mice were evaluated. The dynamic proliferation of immune cells based on Ki67 expression after TGFRt15-TGFRs21 treatment was also evaluated. The splenocytes were stained with fluorochrome-conjugated anti-CD4, anti-CD8, and anti-NK1.1 (NK) antibodies and then intracellularly stained with anti-Ki67 antibody. The percentage of CD4$^+$ T cells, CD8$^+$ T cells, and NK cells and the mean fluorescent intensity (MFI) of Ki67 of corresponding immunocyte subsets were analyzed by flow cytometry (FIGS. 148A and 148B). Furthermore, cytotoxicity potential based on granzyme B expression of the splenocytes induced by TGFRt15-TGFRs21 after the single dose treatment of mouse was also evaluated. As shown in FIG. 149, in the spleens of mice treated with TGFRt15-TGFRs21, the expression of granzyme B by NK cells increased after treatment. The splenocytes from TGFRt15-TGFRs21-treated mice were stained with fluorochrome-conjugated anti-CD4, anti-CD8, and anti-NK1.1 (NK) antibodies and then intracellularly stained with anti-granzyme B antibody. The mean fluorescent intensity (MFI) of granzyme B of corresponding immunocyte subsets was analyzed by flow cytometry (FIG. 149).

As shown in FIG. 148A, in the spleens of mice treated with TGFRt15-TGFRs21, the percentages of CD8$^+$ T cells and NK cells both increased on day 4 after a single TGFRt15-TGFRs21 treatment. These results demonstrate that TGFRt15-TGFRs21 is able to induce immune cells to proliferate in mouse spleen, in particular CD8$^+$ T cells and NK cells.

Additionally, cytotoxicity of the mouse splenocytes against tumor cells was also evaluated. Mouse Yac-1 cells were labeled with CellTrace Violet and used as tumor target cells. The splenocytes were prepared from TGFRt15-TGFRs21-treated mice and used as effector cells. The target cells were mixed with effector cells at E:T ratio=10:1 in RPMI-10 medium with or without TGFRt15-TGFRs21 at 100 nM and incubated at 37° C. for 24 hours. Target Yac-1 cell inhibition was assessed by analysis of viable violet-labeled Yac-1 cells using flow cytometry. Percentage of Yac-1 inhibition was calculated using a formula, (1−[viable Yac-1 cell number in experimental sample]/[viable Yac-1 cell number in the sample without splenocytes])×100. As shown in FIG. 150, TGFRt15-TGFRs21-treated mouse splenocytes had stronger cytotoxicity against Yac-1 cells than the control mouse cells in the presence of TGFRt15-TGFRs21 during cytotoxic assay (shown in legend of FIG. 150).

Example 83: TGFRt15-TGFRs16 Fusion Protein Generation

A fusion protein complex was generated comprising of TGFβ Receptor II/IL-15RαSu/anti-CD16scFv and TGFβ Receptor II/TF/IL-15 fusion proteins (See, FIGS. 151 and 152). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G45(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGC

CTACTCC (Human TGFβ Receptor II fragments)
ATCCCCCCCCATGTGCAAAAGAGCGTGAACAACGATATGATCGTGAC

CGACAACAACGGCGCCGTGAAGTTTCCCCAGCTCTGCAAGTTCTGCG

ATGTCAGGTTCAGCACCTGCGATAATCAGAAGTCCTGCATGTCCAAC

TGCAGCATCACCTCCATCTGCGAGAAGCCCCAAGAAGTGTGCGTGGC

CGTGTGGCGGAAAAATGACGAGAACATCACCCTGGAGACCGTGTGTC

ACGACCCCAAGCTCCCTTATCACGACTTCATTCTGGAGGACGCTGCC

TCCCCCAAATGCATCATGAAGGAGAAGAAGAAGCCCGGAGAGACCTT

CTTTATGTGTTCCTGTAGCAGCGACGAGTGTAACGACAACATCATCT

TCAGCGAAGAGTACAACACCAGCAACCCTGATGGAGGTGGCGGATCC

GGAGGTGGAGGTTCTGGTGGAGGTGGGAGTATTCCTCCCCACGTGCA

GAAGAGCGTGAATAATGACATGATCGTGACCGATAACAATGGCGCCG

TGAAATTTCCCCAGCTGTGCAAATTCTGCGATGTGAGGTTTTCCACC
```

```
TGCGACAACCAGAAGTCCTGTATGAGCAACTGCTCCATCACCTCCAT

CTGTGAGAAGCCTCAGGAGGTGTGCGTGGCTGTCTGGCGGAAGAATG

ACGAGAATATCACCCTGGAAACCGTCTGCCACGATCCCAAGCTGCCC

TACCACGATTTCATCCTGGAAGACGCCGCCAGCCCTAAGTGCATCAT

GAAAGAGAAAAAGAAGCCTGGCGAGACCTTTTTCATGTGCTCCTGCA

GCAGCGACGAATGCAACGACAATATCATCTTTAGCGAGGAATACAAT

ACCAGCAACCCCGAC (Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACC

AAGTTTACACCGTGCAGATCAGCACCAAGTCCGGCGACTGGAAGTCC

AAATGTTTCTATACCACCGACACCGAGTGCGATCTCACCGATGAGAT

CGTGAAAGATGTGAAACAGACCTACCTCGCCCGGGTGTTTAGCTACC

CCGCCGGCAATGTGGAGAGCACTGGTTCCGCTGGCGAGCCTTTATAC

GAGAACAGCCCCGAATTTACCCCTTACCTCGAGACCAATTTAGGACA

GCCCACCATCCAAAGCTTTGAGCAAGTTGGCACAAAGGTGAATGTGA

CAGTGGAGGACGAGCGGACTTTAGTGCGGCGGAACAACACCTTTCTC

AGCCTCCGGGATGTGTTCGGCAAACATTTAATCTACACACTGTATTA

CTGGAAGTCCTCTTCCTCCGGCAAGAAGACAGCTAAAACCAACACAA

ACGAGTTTTTAATCGACGTGGATAAAGGCGAAAACTACTGTTTCAGC

GTGCAAGCTGTGATCCCCTCCCGGACCGTGAATAGGAAAAGCACCGA

TAGCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAAT

TCAGTCCATGCATATCGACGCCACTTTATACACAGAATCCGACGTGC

ACCCCTCTTGTAAGGTGACCGCCATGAAATGTTTTTTACTGGAGCTG

CAAGTTATCTCTTTAGAGAGCGGAGACGCTAGCATCCACGACACCGT

GGAGAATTTAATCATTTTAGCCAATAACTCTTTATCCAGCAACGGCA

ACGTGACAGAGTCCGGCTGCAAGGAGTGCGAAGAGCTGGAGGAGAAG

AACATCAAGGAGTTTCTGCAATCCTTTGTGCACATTGTCCAGATGTT

CATCAATACCTCC
```

The amino acid sequence of TGFRt15 fusion protein (including the leader sequence) is as follows:

```
(Signal peptide)
MKWVTFISLLFLFSSAYS (Human TGFβ Receptor II)
IPPHVQKSVNNDMIVTDNNGAVKFPQLCKFCDVRFSTCDNQKSCMSN

CSITSICEKPQEVCVAVWRKNDENITLETVCHDPKLPYHDFILEDAA

SPKCIMKEKKKPGETFFMCSCSSDECNDNIIFSEEYNTSNPDGGGGS

GGGGSGGGGSIPPHVQKSVNNDMIVTDNNGAVKFPQLCKFCDVRFST

CDNQKSCMSNCSITSICEKPQEVCVAVWRKNDENITLETVCHDPKLP

YHDFILEDAASPKCIMKEKKKPGETFFMCSCSSDECNDNIIFSEEYN

TSNPD (Human Tissue Factor 219)
SGTTNTVAAYNLTWKSTNFKTILEWEPKPVNQVYTVQISTKSGDWKS

KCFYTTDTECDLTDEIVKDVKQTYLARVFSYPAGNVESTGSAGEPLY

ENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFS

VQAVIPSRTVNRKSTDSPVECMGQEKGEFRE (Human IL-15)
NWVNVISDLKKIEDLIQSMHIDATLYTESDVHPSCKVTAMKCFLLEL

QVISLESGDASIHDTVENLIILANNSLSSNGNVTESGCKECEELEEK

NIKEFLQSFVHIVQMFINTS
```

Constructs were also made by attaching two TGFβ Receptor II directly to the IL-15RαSu chain, followed by the anti-CD16scFv sequence, which was synthesized by Genewiz. The nucleic acid and protein sequences of a construct comprising the TGFβ Receptor II linked to the N-terminus of IL-15RαSu following with the anti-CD16scFv sequence are shown below.

The nucleic acid sequence of the TGFRs16 construct (including signal peptide sequence) is as follows:

(Signal peptide)
ATGAAGTGGGTGACCTTCATCAGCCTGCTGTTCCTGTTCTCCAGCGC

CTACTCC (Human TGFβ Receptor II fragments)
ATCCCCCCCCATGTGCAAAAGAGCGTGAACAACGATATGATCGTGAC

CGACAACAACGGCGCCGTGAAGTTTCCCCAGCTCTGCAAGTTCTGCG

ATGTCAGGTTCAGCACCTGCGATAATCAGAAGTCCTGCATGTCCAAC

TGCAGCATCACCTCCATCTGCGAGAAGCCCCAAGAAGTGTGCGTGGC

CGTGTGGCGGAAAAAATGACGAGAACATCACCCTGGAGACCGTGTGTC

ACGACCCCAAGCTCCCTTATCACGACTTCATTCTGGAGGACGCTGCC

TCCCCCAAATGCATCATGAAGGAGAAGAAGAAGCCCGGAGAGACCTT

CTTTATGTGTTCCTGTAGCAGCGACGAGTGTAACGACAACATCATCT

TCAGCGAAGAGTACAACACCAGCAACCCTGATGGAGGTGGCGGATCC

GGAGGTGGAGGTTCTGGTGGAGGTGGGAGTATTCCTCCCCACGTGCA

GAAGAGCGTGAATAATGACATGATCGTGACCGATAACAATGGCGCCG

TGAAATTTCCCCAGCTGTGCAAATTCTGCGATGTGAGGTTTTCCACC

TGCGACAACCAGAAGTCCTGTATGAGCAACTGCTCCATCACCTCCAT

CTGTGAGAAGCCTCAGGAGGTGTGCGTGGCTGTCTGGCGGAAGAATG

ACGAGAATATCACCCTGGAAACCGTCTGCCACGATCCCAAGCTGCCC

TACCACGATTTCATCCTGGAAGACGCCGCCAGCCCTAAGTGCATCAT

GAAAGAGAAAAAGAAGCCTGGCGAGACCTTTTTCATGTGCTCCTGCA

GCAGCGACGAATGCAACGACAATATCATCTTTAGCGAGGAATACAAT

ACCAGCAACCCCGAC (Human IL-15R α sushi domain)
ATTACATGCCCCCTCCCATGAGCGTGGAGCACGCCGACATCTGGGT

GAAGAGCTATAGCCTCTACAGCCGGGAGAGGTATATCTGTAACAGCG

GCTTCAAGAGGAAGGCCGGCACCAGCAGCCTCACCGAGTGCGTGCTG

AATAAGGCTACCAACGTGGCTCACTGGACAACACCCTCTTTAAAGTG

CATCCGG (Anti-human CD16scFv)
TCCGAGCTGACCCAGGACCCTGCTGTGTCCGTGGCTCTGGGCCAGAC

CGTGAGGATCACCTGCCAGGGCGACTCCCTGAGGTCCTACTACGCCT

CCTGGTACCAGCAGAAGCCCGGCCAGGCTCCTGTGCTGGTGATCTAC

GGCAAGAACAACAGGCCCTCCGGCATCCCTGACAGGTTCTCCGGATC

CTCCTCCGGCAACACCGCCTCCCTGACCATCACAGGCGCTCAGGCCG

AGGACGAGGCTGACTACTACTGCAACTCCAGGGACTCCTCCGGCAAC

CATGTGGTGTTCGGCGGCGGCACCAAGCTGACCGTGGGCCATGGCGG

CGGCGGCTCCGGAGGCGGCGGCAGCGGCGGAGGAGGATCCGAGGTGC

AGCTGGTGGAGTCCGGAGGAGGAGTGGTGAGGCCTGGAGGCTCCCTG

AGGCTGAGCTGTGCTGCCTCCGGCTTCACCTTCGACGACTACGGCAT

GTCCTGGGTGAGGCAGGCTCCTGGAAAGGGCCTGGAGTGGGTGTCCG

GCATCAACTGGAACGGCGGATCCACCGGCTACGCCGATTCCGTGAAG

GGCAGGTTCACCATCAGCAGGGACAACGCCAAGAACTCCCTGTACCT

GCAGATGAACTCCCTGAGGGCCGAGGACACCGCCGTGTACTACTGCG

CCAGGGGCAGGTCCCTGCTGTTCGACTACTGGGGACAGGGCACCCTG

GTGACCGTGTCCAGG

The amino acid sequence of TGFRs16 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSN

CSITSICEKPQEVCVAVWRKNDENITLETVCHDPKLPYHDFILEDAA

SPKCIMKEKKKPGETFFMCSCSSDECNDNIIFSEEYNTSNPDGGGGS

GGGGSGGGGSIPPHVQKSVNNDMIVTDNNGAVKFPQLCKFCDVRFST

CDNQKSCMSNCSITSICEKPQEVCVAVWRKNDENITLETVCHDPKLP

YHDFILEDAASPKCIMKEKKKPGETFFMCSCSSDECNDNIIFSEEYN

TSNPD (Human IL-15R α sushi domain)
ITCPPPMSVEHADIWVKSYSLYSRERYICNSGFKRKAGTSSLTECVL

NKATNVAHWTTPSLKCIR (Anti-human CD16scFv)
SELTQDPAVSVALGQTVRITCQGDSLRSYYASWYQQKPGQAPVLVIY

GKNNRPSGIPDRFSGSSSGNTASLTITGAQAEDEADYYCNSRDSSGN

HVVFGGGTKLTVGHGGGGSGGGGSGGGGSEVQLVESGGGVVRPGGSL

RLSCAASGFTFDDYGMSWVRQAPGKGLEWVSGINWNGGSTGYADSVK

GRFTISRDNAKNSLYLQMNSLRAEDTAVYYCARGRSLLFDYWGQGTL

VTVSR

In some cases, the leader peptide is cleaved from the intact polypeptide to generate the mature form that may be soluble or secreted.

The TGFR/IL-15RαSu/anti-CD16scFv and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/anti-CD16scFv protein complex (referred to as TGFRt15-TGFRs16), which can be purified by anti-TF antibody affinity and other chromatography methods.

Example 84: The TGFRt15-TGFRs137L Fusion Protein Generation

A fusion protein complex was generated comprising of TGFβ Receptor II/IL-15RαSu/CD137L and TGFβ Receptor II/TF/IL-15 fusion proteins (see, FIGS. 153 and 154). The human TGFβ Receptor II (Ile24-Asp159), tissue factor 219, CD137L, and IL-15 sequences were obtained from the UniProt website and DNA for these sequences was synthesized by Genewiz. Specifically, a construct was made linking two TGFβ Receptor II sequences with a G45(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

-continued
```
TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC (Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC
```

The amino acid sequence of TGFRt15 fusion protein (including the leader sequence) is as follows:

```
(Signal peptide)
MKWVTFISLLFLFSSAYS (Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD
```

```
(Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

Constructs were also made by attaching two TGFβ Receptor II directly to the IL-15RαSu chain, followed by a (G4S)3 linker and the CD137L sequence, which was synthesized by Genewiz. The nucleic acid and protein sequences of a construct comprising the TGFβ Receptor II linked to the N-terminus of IL-15RαSu following with a (G4S)3 linker and the CD137L sequence are shown below.

The nucleic acid sequence of the TGFRs137L construct (including signal peptide sequence) is as follows:

```
(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG
```

-continued ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGAC

CTGCGGCAGGGCATGTTTGCGCAGCTGGTGGCCCAAAATGTTCTGCTG

ATCGATGGGCCCCTGAGCTGGTACAGTGACCCAGGCCTGGCAGGCGTG

TCCCTGACGGGGGGCCTGAGCTACAAAGAGGACACGAAGGAGCTGGTG

GTGGCCAAGGCTGGAGTCTACTATGTCTTCTTTCAACTAGAGCTGCGG

CGCGTGGTGGCCGGCGAGGGCTCAGGCTCCGTTTCACTTGCGCTGCAC

CTGCAGCCACTGCGCTCTGCTGCTGGGGCCGCCGCCCTGGCTTTGACC

GTGGACCTGCCACCCGCCTCCTCCGAGGCTCGGAACTCGGCCTTCGGT

TTCCAGGGCCGCTTGCTGCACCTGAGTGCCGGCCAGCGCCTGGGCGTC

CATCTTCACACTGAGGCCAGGGCACGCCATGCCTGGCAGCTTACCCAG

GGCGCCACAGTCTTGGGACTCTTCCGGGTGACCCCCGAAATCCCAGCC

GGACTCCCTTCACCGAGGTCGGAA

The amino acid sequence of TGFRs137L fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNC

SITSICEKPQEVCVAVWRKNDENITLETVCHDPKLPYHDFILEDAASP

KCIMKEKKKPGETFFMCSCSSDECNDNIIFSEEYNTSNPDGGGGSGGG

GSGGGGSIPPHVQKSVNNDMIVTDNNGAVKFPQLCKFCDVRFSTCDNQ

KSCMSNCSITSICEKPQEVCVAVWRKNDENITLETVCHDPKLPYHDFI

LEDAASPKCIMKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVL

NKATNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAG

VSLTGGLSYKEDTKELVVAKAGVYYVFFQLELRRVVAGEGSGSVSLA

LHLQPLRSAAGAAALALTVDLPPASSEARNSAFGFQGRLLHLSAGQR

LGVHLHTEARARHAWQLTQGATVLGLFRVTPEIPAGLPSPRSE

In some cases, the leader peptide is cleaved from the intact polypeptide to generate the mature form that may be soluble or secreted.

The TGFR/IL-15RαSu/CD137L and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. Hum Gene Ther 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/CD137L protein complex (referred to as TGFRt15-TGFRs137L), which can be purified by anti-TF antibody affinity and other chromatography methods.

Example 85: Production and Characterization of the Exemplary Single-Chain Chimeric Polypeptide 2t2

An exemplary single-chain chimeric polypeptide including a first target-binding domain that binds to an IL-2 receptor, a soluble human tissue factor domain, and a second target-binding domain that binds to an IL-2 receptor was generated (IL-2/TF/IL-2, or 2t2) (FIG. 155). The nucleic acid and amino acid sequences of this single-chain chimeric polypeptide are shown below.

Nucleic Acid Encoding Exemplary Single-Chain Chimeric Polypeptide (IL-2/TF/IL-2) (SEQ ID NO: 109)

(Signal peptide)
ATGAAGTGGGTGACCTTCATCAGCCTGCTGTTCCTGTTCTCCAGCGC

CTACTCC (First IL-2 fragment)
GCCCCCACCTCCTCCTCCACCAAGAAGACCCAGCTGCAGCTGGAGCA

TTTACTGCTGGATTTACAGATGATTTTAAACGGCATCAACAACTACA

AGAACCCCAAGCTGACTCGTATGCTGACCTTCAAGTTCTACATGCCC

AAGAAGGCCACCGAGCTGAAGCATTTACAGTGTTTAGAGGAGGAGCT

GAAGCCCCTCGAGGAGGTGCTGAATTTAGCCCAGTCCAAGAATTTCC

ATTTAAGGCCCCGGGATTTAATCAGCAACATCAACGTGATCGTTTTA

GAGCTGAAGGGCTCCGAGACCACCTTCATGTGCGAGTACGCCGACGA

GACCGCCACCATCGTGGAGTTTTTAAATCGTTGGATCACCTTCTGCC

AGTCCATCATCTCCACTTTAACC (Human tissue factor 219 form)
AGCGGCACAACCAACACAGTCGCTGCCTATAACCTCACTTGGAAGAG

CACCAACTTCAAAACCATCCTCGAATGGGAACCCAAACCCGTTAACC

AAGTTTACACCGTGCAGATCAGCACCAAGTCCGGCGACTGGAAGTCC

AAATGTTTCTATACCACCGACACCGAGTGCGATCTCACCGATGAGAT

CGTGAAAGATGTGAAACAGACCTACCTCGCCCGGGTGTTTAGCTACC

CCGCCGGCAATGTGGAGAGCACTGGTTCCGCTGGCGAGCCTTTATAC

GAGAACAGCCCCGAATTTACCCCTTACCTCGAGACCAATTTAGGACA

GCCCACCATCCAAAGCTTTGAGCAAGTTGGCACAAAGGTGAATGTGA

CAGTGGAGGACGAGCGGACTTTAGTGCGGCGGAACAACACCTTTCTC

AGCCTCCGGGATGTGTTCGGCAAAGATTTAATCTACACACTGTATTA

CTGGAAGTCCTCTTCCTCCGGCAAGAAGACAGCTAAAACCAACACAA

ACGAGTTTTTAATCGACGTGGATAAAGGCGAAAACTACTGTTTCAGC

GTGCAAGCTGTGATCCCCTCCCGGACCGTGAATAGGAAAAGCACCGA

TAGCCCCGTTGAGTGCATGGGCCAAGAAAAGGGCGAGTTCCGGGAG (Second IL-2 fragment)
GCACCTACTTCAAGTTCTACAAAGAAAACACAGCTACAACTGGAGCA

TTTACTGCTGGATTTACAGATGATTTTGAATGGAATTAATAATTACA

-continued

```
AGAATCCCAAACTCACCAGGATGCTCACATTTAAGTTTTACATGCCC

AAGAAGGCCACAGAACTGAAACATCTTCAGTGTCTAGAAGAAGAACT

CAAACCTCTGGAGGAAGTGCTAAATTTAGCTCAAAGCAAAAACTTTC

ACTTAAGACCCAGGGACTTAATCAGCAATATCAACGTAATAGTTCTG

GAACTAAAGGGATCTGAAACAACATTCATGTGTGAATATGCTGATGA

GACAGCAACCATTGTAGAATTTCTGAACAGATGGATTACCTTTTGTC

AAAGCATCATCTCAACACTAACT
```

Exemplary Single-Chain Chimeric Polypeptide (IL-2/TF/IL-2) (SEQ ID NO: 108)

```
(Signal peptide)
MKWVTFISLLFLFSSAYS (Human IL-2)
APTSSSTKKTQLQLEHLLLDLQMILNGINNYKNPKLTRMLTFKFYMP

KKATELKHLQCLEEELKPLEEVLNLAQSKNFHLRPRDLISNINVIVL

ELKGSETTFMCEYADETATIVEFLNRWITFCQSIISTLT (Human Tissue Factor 219)
SGTTNTVAAYNLTWKSTNFKTILEWEPKPVNQVYTVQISTKSGDWKS

KCFYTTDTECDLTDEIVKDVKQTYLARVFSYPAGNVESTGSAGEPLY

ENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFS

VQAVISRTVNRKSTDSPVECMGQEKGEFRE (Human IL-2)
APTSSSTKKTQLQLEHLLLDLQMILNGINNYKNPKLTRMLTFKFYMP

KKATELKHLQCLEEELKPLEEVLNLAQSKNFHLRPRDLISNINVIVL

ELKGSETTFMCEYADETATIVEFLNRWITFCQSIISTLT
```

The nucleic acid encoding IL-2/TF/IL-2 was cloned into a modified retrovirus expression vector as described previously (Hughes et al., Hum Gene Ther 16:457-72, 2005). The expression vector encoding IL-2/TF/IL-2 was transfected into CHO-K1 cells. Expression of the expression vector in CHO-K1 cells allowed for secretion of the soluble IL-2/TF/IL-2 single-chain chimeric polypeptide (referred to as 2t2), which can be purified by anti-TF antibody affinity and other chromatography methods.

IL-2 and 2t2 Promoted IL-2R/3 and Common γ Chain Containing 32Dβ Cell Proliferation in a Similar Manner To evaluate the IL-2 activity of 2t2, 2t2 was compared with recombinant IL-2 for promoting proliferation of 32Dβ cells that express IL-2R13 and common γ chain. IL-2 dependent 32Dβ cells were washed 5 times with IMDM-10% FBS and seeded to the wells at $2\times10^4$ cells/well. Serial dilutions of 2t2 or IL-2 were added to the cells (FIG. 156). Cells were incubated in a $CO_2$ incubator at 37° C. for 3 days. Cell proliferation was detected by adding 10 µl of WST1 to each well on day 3 and incubating for an additional 3 hours in a $CO_2$ incubator at 37° C. The amount of formazan dye produced was analyzed by measuring the absorbance at 450 nm. As shown in FIG. 156, 2t2 and IL-2 activated 32Dβ cells in a similar manner. The $EC_{50}$ of 2t2 and IL-2 was 158.1 pM and 140 pM. respectively.

2t2 Showed Improved Ability to Promote IL-2Rαβγ Containing CTLL-2 Cell Proliferation as Compared to IL-2

To evaluate the IL-2 activity of 2t2, 2t2 was compared with recombinant IL-2 for promoting proliferation of CTLL-2 cells that express IL-2Rα, IL-2R13 and common γ chain. IL-2 dependent CTLL-2 cells were washed 5 times with IMDM-10% FBS and seeded to the wells at $2\times10^4$ cells/well. Serial dilutions of 2t2 or IL-2 were added to the cells (FIG. 157). Cells were incubated in a $CO_2$ incubator at 37° C. for 3 days. Cell proliferation was detected by adding 10 µl of WST1 to each well in the day 3 and incubating for an additional 3 hours in a $CO_2$ incubator at 37° C. The amount of formazan dye produced was analyzed by measuring the absorbance at 450 nm. As shown in FIG. 157, 2t2 promoted CTLL-2 cell proliferation 4-5-fold stronger than IL-2. The $EC_{50}$ of 2t2 was 123.2 pM and IL-2 was 548.2 pM.

2t2 Suppressed the Increase of the High Fat-Induced Hyperglycemia in $ApoE^{-/-}$ Mice Six-week-old female $ApoE^{-/-}$ mice (Jackson Lab) were fed with standard chow diet or high diet fat containing 21% fat, 0.15% cholesterol, 34.1% sucrose, 19.5% casein, and 15% starch (TD88137, Harlan Laboratories) and maintained in the standard conditions. At week 7, mice fed with high fat diet were randomly assigned into the control group and treatment group. Mice then received either 2t2 (treatment group) or PBS (chow diet group and control group) per subcutaneous injection at a dosage of 3 mg/kg. Three days post dosing, the mice were fasted overnight, and blood samples were collected through retro-orbital venous plexus puncture. Overnight fasting glucose levels were measured using a OneTouch Glucometer. As shown in FIG. 158, the results showed that 2t2 injection effectively suppresses the increase of glucose levels in $ApoE^{-/-}$ mice.

2t2 Significantly Upregulate the Ratio of $CD4^+CD25^+$ $FoxP3^+$ T Regulatory (Treg) Cells in Blood Lymphocytes Six-week-old female $ApoE^{-/-}$ mice (Jackson Lab) were fed with standard chow diet or high diet fat containing 21% fat, 0.15% cholesterol, 34.1% sucrose, 19.5% casein, and 15% starch (TD88137, Harlan Laboratories) and maintained in the standard conditions. At week 7, mice fed with the high fat diet were randomly assigned into control group and treatment group. Mice then received either 2t2 (treatment group) or PBS (chow diet group and control group) per subcutaneous injection at a dosage of 3 mg/kg. Three days after the dosing, overnight fasting blood samples were collected through retro-orbital venous plexus puncture and incubated with ACK lysing buffer (Thermo Fisher Scientific) at 37° C. for 5 minutes. Samples were then resuspended in FACS buffer (1×PBS (Hyclone) with 0.5% BSA (EMD Millipore) and 0.001% sodium azide (Sigma)) and surface stained with FITC-anti-CD4 and APC-anti-CD25 antibodies (BioLegend) for 30 minutes. Surface-stained samples were further fixed and premetallized with Fix/Perm buffer (BioLegend) and intracellular stained with PE-anti-Foxp3 antibody (BioLegend). After staining, cells were washed twice with FACs buffer followed by centrifugation at 1500 RPM for 5 minutes at room temperature. The cells were analyzed by flow cytometry (Celesta-BD Bioscience). As shown in FIG. 159, 2t2 treatment significantly increased Treg populations in blood lymphocytes (3.5%±0.32) compared to the untreated groups (0.4%±0.16 for chow diet group and 0.46%±0.09 for high fat diet group).

Purification Elution Chromatograph of 2t2 from Anti-TF Antibody Affinity Column

2t2 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid, pH 2.9. A280 elution peak was collected and then neutralized to pH 7.5-8.0 with 1M Tris base. The neutralized sample was then buffer exchanged into PBS using Amicon centrifugal filters with a 30 kDa molecular weight cutoff. As shown in FIG. 160, the anti-TF antibody affinity column bound to 2t2 which contains TF as a fusion domain. The buffer-exchanged protein sample was stored at 2-8° C. for further biochemical analyses and biological activity tests. After each elution, the anti-TF antibody affinity column was stripped using 6 column volumes of 0.1M glycine, pH 2.5. The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of 2t2

To analyze 2t2 using analytical size exclusion chromatography (SEC), a Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. A sample containing 2t2 in PBS was injected into the Superdex 200 column using a capillary loop, and analyzed by SEC. The SEC chromatograph of the sample is shown in FIG. 161. The SEC results indicated two protein peaks for 2t2.

Reduced SDS-PAGE of 2t2

To determine the purity and molecular weight of the protein, 2t2 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the 2t2 protein undergoes glycosylation after translation in CHO cells, a deglycosylation experiment was conducted using the Protein Deglycosylation Mix II kit from New England Biolabs according to the manufacturer's instructions. FIGS. 162A and 162B show the reduced SDS-PAGE analysis of the sample in non-deglycosylated (lane 1 in red outline) and deglycosylated (lane 2 in yellow outline) state. The results show that the 2t2 protein is glycosylated when expressed in CHO cells. After deglycosylation, the purified sample ran with expected molecular weights (56 kDa) in reduced SDS gel. Lane M was loaded with 10 of SeeBlue Plus2 Prestained Standard.

In Vivo Characterization of 2t2

2t2 was subcutaneously injected into C57BL/6 mice at various doses to determine the immunostimulatory activity of 2t2 in vivo. Mice were subcutaneously treated with control solution (PBS) or 2t2 at 0.1, 0.4, 2 and 10 mg/kg. The treated mice were euthanized day 3 post treatment. The mouse spleens were collected and weighed day 3 post treatment. Single splenocyte suspensions were prepared, and the prepared splenocytes were stained for $CD4^+$ T cells, $CD8^+$ T cells and NK cells (with fluorochrome-conjugated anti-CD4, -CD8, and -NK1.1 antibodies), and analyzed by flow cytometry. The results showed that 2t2 was effective at expanding splenocytes based on spleen weight (FIG. 163A) especially at 0.1-10 mg/kg. The percentage of $CD8^+$ T cells were higher compared to control-treated mice (FIG. 163B) at 2 and 10 mg/kg. The percentage of NK cells were higher compared to control-treated mice (FIG. 163B) at all doses tested.

It has been known that IL-2 upregulates CD25 expression by immunocytes. We therefore accessed CD25 expression of $CD4^+$ T cells, $CD8^+$ T cells and NK cells in the 2t2 treated mice. C57BL/6 mice were subcutaneously treated with 2t2 as described in the paragraph above. The splenocytes were stained with fluorochrome-conjugated anti-CD4, -CD8, -CD25 and -NK1.1 monoclonal antibodies. The CD25 expression (MFI) of splenocyte subsets was analyzed by flow cytometry. As shown in FIG. 164, at the doses and time points tested, 2t2 significantly upregulated CD25 expression by $CD4^+$ T cells but not CD8+ T cells or NK cells.

The pharmacokinetics of 2t2 in C57BL/6 mice were also investigated. 2t2 was subcutaneously injected into C57BL/6 mice at 1 mg/kg. The mouse blood was drawn from tail vein at various time points as shown in FIG. 165 and the serum was prepared. 2t2 concentrations were determined with ELISA (Capture: anti-tissue factor antibody; Detection: biotinylated anti-human IL-2 antibody followed by SA-HRP and ABTS substrate). The half-life of 2t2 was 1.83 hours calculated with PK Solutions 2.0 (Summit Research Services).

2t2 Attenuated the Formation of High Fat-Induced Atherosclerotic Plaques in $ApoE^{-/-}$ Mice Six-week-old female $ApoE^{-/-}$ mice (The Jackson Laboratory) were fed with standard chow diet or high diet fat (21% fat, 0.15% cholesterol, 34.1% sucrose, 19.5% casein, and 15% starch) (TD88137, Harlan Laboratories) and maintained in the standard conditions. At week 7, mice fed with high fat diet (HFD) were randomly assigned into control group and treatment group. Mice were then administrated either 2t2 (treatment group) or PBS (chow diet group and control group) subcutaneously at a dosage of 3 mg/kg weekly for 4 weeks. At week 12, all mice were euthanized by isoflurane. Aortas were collected, opened longitudinally and stained with Sudan IV solution (0.5%) using en face method. The percentage of plaque area (red color as shown in FIG. 166A) relative to total aorta area was then quantified with Image J software. FIG. 166A shows a representative view of atherosclerotic plaques from each group. FIG. 166B shows the results of quantitative analysis of atherosclerotic plaques of each group. The percentage of plaque areas in control group (HF Diet) was much higher than the treatment group (HFD+2t2), being 10.28% vs 4.68%.

2t2 Suppresses the Progression of Type 2 Diabetes.

Male BKS.Cg-Dock7$^m$ +/+ Lepr$^{db}$/J (db/db (Jackson Lab)) mice were fed with standard chow diet and received drinking water ad libitum. At the age of six weeks, mice were randomly assigned into control group and treatment group. The treatment group received 2t2 by subcutaneous injection at 3 mg/kg bi-weekly, while control group received vehicle (PBS) only. Overnight fasting glucose levels were measure weekly using a OneTouch Glucometer. The results showed that 2t2 effectively suppressed the increase of glucose levels in BKS.Cg-Dock7$^m$+/+Lepr$^{db}$/J mice (FIG. 167).

2t2 Significantly Upregulates the Ratio of $CD4^+CD25^+$ $FoxP3^+$ T Regulatory Cells in Blood Lymphocytes after the First Injection Male BKS.Cg-Dock7$^m$ +/+ Lepr$^{db}$/J (db/db) (The Jackson Laboratory) mice were fed with standard chow diet and received drinking water ad libitum. At the age of six weeks, mice were randomly assigned into control group and treatment group. The treatment group received 2t2 by subcutaneous injection at 3 mg/kg bi-weekly, while the control group received vehicle (PBS) only. Four days after the first drug injection, overnight fasting blood samples were collected and incubated with ACK lysing buffer (Thermo Fisher Scientific) at 37° C. for 5 minutes. Samples were then resuspended in FACS buffer (1×PBS (Hyclone) with 0.5% BSA (EMD Millipore) and 0.001% sodium azide (Sigma))

and surface stained with FITC-anti-CD4 and APC-anti-CD25 antibodies (BioLegend) for 30 minutes. Surface-stained samples were further fixed and premetallized with Fix/Perm buffer (BioLegend) and intracellular stained with PE-anti-Foxp3 antibody (BioLegend). After staining, cells were washed twice with FACs buffer and were analyzed by flow cytometry (Celesta-BD Bioscience). The percentage of CD4+CD25+FoxP3+ Tregs in blood lymphocytes were measured. As shown in FIG. 168, the results showed that 2t2 significantly upregulated the ratio of Tregs in blood lymphocytes. * p<0.05.

Example 86: Production and Characterization of the Exemplary Single-Chain Chimeric Polypeptide 15t15

A second exemplary single-chain chimeric polypeptide including a first target-binding domain that binds to an IL-15 receptor, a soluble human tissue factor domain, and a second target-binding domain that binds to an IL-15 receptor was generated (IL-15/TF/IL-15 or 15t15) (FIG. 169). The nucleic acid and amino acid sequences of this single-chain chimeric polypeptide are shown below.

Nucleic Acid Encoding Exemplary Single-Chain Chimeric Polypeptide (IL-15/TF/IL-15) (SEQ ID NO: 115)

```
(Signal peptide)
ATGAAGTGGGTGACCTTCATCAGCCTGCTGTTCCTGTTCTCCAGCGC

CTACTCC (First IL-15 fragment)
AACTGGGTGAACGTGATCAGCGATTTAAAGAAGATCGAGGATTTAAT

CCAGAGCATGCACATCGACGCCACTCTGTACACTGAGAGCGACGTGC

ACCCTAGCTGCAAGGTGACTGCCATGAAGTGCTTTTTACTGGAGCTG

CAAGTTATCTCTTTAGAGAGCGGCGATGCCAGCATCCACGACACTGT

GGAGAATTTAATCATTTTAGCCAACAACTCTTTAAGCAGCAACGGCA

ACGTGACAGAGAGCGGCTGCAAGGAGTGCGAGGAGCTGGAGGAGAAG

AACATCAAGGAGTTTTTACAGAGCTTCGTGCACATCGTGCAGATGTT

CATCAACACTAGC (Human tissue factor 219 form)
AGCGGCACAACCAACACAGTCGCTGCCTATAACCTCACTTGGAAGAG

CACCAACTTCAAAACCATCCTCGAATGGGAACCCAAACCCGTTAACC

AAGTTTACACCGTGCAGATCAGCACCAAGTCCGGCGACTGGAAGTCC

AAATGTTTCTATACCACCGACACCGAGTGCGATCTCACCGATGAGAT

CGTGAAAGATGTGAAACAGACCTACCTCGCCCGGGTGTTTAGCTACC

CCGCCGGCAATGTGGAGAGCACTGGTTCCGCTGGCGAGCCTTTATAC

GAGAACAGCCCCGAATTTACCCCTTACCTCGAGACCAATTTAGGACA

GCCCACCATCCAAAGCTTTGAGCAAGTTGGCACAAAGGTGAATGTGA

CAGTGGAGGACGAGCGGACTTTAGTGCGGCGGAACAACACCTTTCTC

AGCCTCCGGGATGTGTTCGGCAAAGATTTAATCTACACACTGTATTA

CTGGAAGTCCTCTTCCTCCGGCAAGAAGACAGCTAAAACCAACACAA

ACGAGTTTTTAATCGACGTGGATAAAGGCGAAAACTACTGTTTCAGC
```

```
GTGCAAGCTGTGATCCCCTCCCGGACCGTGAATAGGAAAAGCACCGA

TAGCCCCGTTGAGTGCATGGGCCAAGAAAAGGGCGAGTTCCGGGAG (Second IL-15 fragment)
AACTGGGTGAACGTCATCAGCGATTTAAAGAAGATCGAAGATTTAAT

TCAGTCCATGCATATCGACGCCACTTTATACACAGAATCCGACGTGC

ACCCCTCTTGTAAGGTGACCGCCATGAAATGTTTTTTACTGGAGCTG

CAAGTTATCTCTTTAGAGAGCGGAGACGCTAGCATCCACGACACCGT

GGAGAATTTAATCATTTTAGCCAATAACTCTTTATCCAGCAACGGCA

ACGTGACAGAGTCCGGCTGCAAGGAGTGCGAAGAGCTGGAGGAGAAG

AACATCAAGGAGTTTCTGCAATCCTTTGTGCACATTGTCCAGATGTT

CATCAATACCTCC
```

Exemplary Single-Chain Chimeric Polypeptide (IL-15/TF/IL-15) (SEQ ID NO: 114)

```
(Signal peptide)
MKWVTFISLLFLFSSAYS (Human IL-15)
NWVNVISDLKKIEDLIQSMHIDATLYTESDVHPSCKVTAMKCFLLEL

QVISLESGDASIHDTVENLIILANNSLSSNGNVTESGCKECEELEEK

NIKEFLQSFVHIVQMFINTS (Human Tissue Factor 219)
SGTTNTVAAYNLTWKSTNFKTILEWEPKPVNQVYTVQISTKSGDWKS

KCFYTTDTECDLTDEIVKDVKQTYLARVFSYPAGNVESTGSAGEPLY

ENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFS

VQAVIPSRTVNRKSTDSPVECMGQEKGEFRE (Human IL-15)
NWVNVISDLKKIEDLIQSMHIDATLYTESDVHPSCKVTAMKCFLLEL

QVISLESGDASIHDTVENLIILANNSLSSNGNVTESGCKECEELEEK

NIKEFLQSFVHIVQMFINTS
```

The nucleic acid encoding IL-15/TF/IL-15 was cloned into a modified retrovirus expression vector as described previously (Hughes et al., *Hum Gene Ther* 16:457-72, 2005). The expression vector encoding IL-15/TF/IL-15 was transfected into CHO-K1 cells. Expression of the expression vector in CHO-K1 cells allowed for secretion of the soluble IL-15/TF/IL-15 single-chain chimeric polypeptide (referred to as 15t15), which can be purified by anti-TF antibody affinity and other chromatography methods.

15t15 Promotes IL-2R/3 and Common γ Chain Containing 32Dβ Cell Proliferation

IL-15 activity of 15t15 was compared with recombinant IL-15 in IL2Rβ and common γ chain expressed 32Dβ cells. IL-15 dependent 32Dβ cells were washed five times with IMDM-10% FBS and seeded to the wells at $2 \times 10^4$ cells/well. Serial dilutions of 15t15 or IL-15 were added to the cells (FIG. 170). Cells were incubated in a $CO_2$ incubator at 37° C. for 3 days. Cell proliferation was detected by adding 10 μl of WST1 to each well in the day 3 and incubating for an additional 3 hours in a $CO_2$ incubator at 37° C. The amount of formazan dye produced was analyzed by measuring the absorbance at 450 nm. As shown in FIG. 170, 15t15 promoted 32Dβ cell proliferation less efficiently as compared to IL-15. The $EC_{50}$ of 15t15 and IL-15 was 161.4 pM and 1.6 pM, respectively.

Purification Elution Chromatograph of 15t15 from Anti-TF Antibody Affinity Column 15t15 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid, pH 2.9. A280 elution peak was collected and then neutralized to pH 7.5-8.0 with 1M Tris base. The neutralized sample was then buffer exchanged into PBS using Amicon centrifugal filters with a 30 kDa molecular weight cutoff. As shown in FIG. 171, the anti-TF antibody affinity column bound to 15t15 which contains TF as a fusion domain. The buffer-exchanged protein sample was stored at 2-8° C. for further biochemical analyses and biological activity tests. After each elution, the anti-TF antibody affinity column was stripped using 6 column volumes of 0.1M glycine, pH 2.5. The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE of 15t15

To determine the purity and molecular weight of the protein, 15t15 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the 15t15 protein undergoes glycosylation after translation in CHO cells, a deglycosylation experiment was conducted using the Protein Deglycosylation Mix II kit from New England Biolabs and the manufacturer's instructions. FIGS. 172A and 172B show the reduced SDS-PAGE analysis of the sample in non-deglycosylated (lane 1 in red outline) and deglycosylated (lane 2 in yellow outline) state. The results showed that the 15t15 protein is glycosylated when expressed in CHO cells. After deglycosylation, the purified sample ran with expected molecular weights (50 kDa) in reduced SDS gel. Lane M was loaded with 10 μL of SeeBlue Plus2 Prestained Standard.

Example 87: Stimulation of NK Cells In Vitro by Multi-Chain Chimeric Polypeptide Constructs Alone or in Combination with an Anti-TF Antibody A set of experiments was performed to assess the changes in surface phenotype of NK cells after stimulation with 18t15-12s, 18t15-12s16, and 7t15-21s+anti-TF antibody. In these experiments, fresh human leukocytes were obtained from the blood bank and CD56+ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended at $0.2\times10^6$/mL in a 96-well flat-bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 18t15-12s (100 nM); 18t15-12s16 (100 nM); a mixture of single cytokines rhIL15 (50 ng/mL) (Miltenyi), rhIL18 (50 ng/mL) (Invivogen), and rhIL-12 (10 ng/mL) (Peprotech); 7t15-21s+anti-TF antibody (100 nM-50 nM); 7t15-21s (100 nM); or anti-TF antibody (50 nM) at 37° C. and 5% $CO_2$ for 16 hours. The next day, the cells were harvested and surface stained for 30 minutes for CD56, CD16, CD25, CD69, CD27, CD62L, NKp30, and NKp44. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIG. 173 shows that overnight incubation of purified NK cells with 18t15-12s, 18t15-12s16, and 7t15-21s+anti-TF antibody resulted in an increase in the percentage of cells expressing CD25, CD69, NKp44, and NKp30 activation markers and a decrease in the percentage of cells expressing CD62L. All activation marker data is from CD56+ gated lymphocytes.

A set of experiments was performed to assess changes in the surface phenotype of lymphocyte populations after stimulation with 18t15-12s, 18t15-12s16, and 7t15-21s. In these experiments, fresh human leukocytes were obtained from the blood bank. Peripheral blood lymphocytes were isolated with the Ficoll-PAQUE Plus (GE Healthcare) density gradient media. The cells were counted and resuspended at $0.2\times10^6$/mL in a 96-well flat-bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 18t15-12s (100 nM); 18t15-12s16 (100 nM), a mixture of single cytokines rhIL15 (50 ng/mL) (Miltenyi), rhIL18 (50 ng/mL) (Invivogen), and rhIL-12 (10 ng/mL) (Peprotech); 7t15-21s (100 nM)+anti-TF antibody (50 nM); 7t15-21s (100 nM); or anti-TF antibody (50 nM) at 37° C. and 5% $CO_2$ for 16 hours. The next day, the cells were harvested and surface stained for 30 minutes for CD4 or CD8, CD62L, and CD69. After surface staining, cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIG. 174 shows that overnight incubation of purified lymphocyte populations (CD4 and CD8 T cells) with 18t15-12s, 18t15-12s16, or 7t15-21s+anti-TF antibody resulted in an increase in the percentage of CD8 and CD4 T cells expressing CD69. Additionally, incubation with 7t15-21s+anti-TF antibody resulted in an increase in the percentage of CD8 and CD4 T cells expressing CD62L (FIG. 174).

Example 88: Induction of Proliferation of NK Cells In Vitro by 7t15-21s and Anti-TF Antibody A set of experiments was performed to determine the effect of 7t15-21s or the combination of 7t15-21s+anti-TF antibody on immune cell proliferation. In these experiments, fresh human leukocytes were obtained from the blood bank and CD56+ NK cells were isolated with the RosetteSep/human NK cell reagent (StemCell Technologies). The purity of NK cells was >90% and confirmed by staining with CD56-BV421, CD16-BV510, CD25-PE, and CD69-APC-Fire750 antibodies (BioLegend). The cells were counted and resuspended in $2\times10^6$/mL in a 24 well flat bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 7t15-21s (100 nM), 7t15-21s+anti-TF antibody (IgG1 Ab, 50 nM) or 7t15-21s (100 nM)+anti-TF antibody IgG4 (50 nM) for 5 days. After every 2 days, the cells were resuspended at $2\times10^6$/mL with fresh media with the multi-chain chimeric polypeptides and in some instances, the anti-TF antibodies described mentioned above. After 5 days, cells were counted using trypan blue to access the fold-expansion (Data shown for 3 healthy donors). FIG. 175 shows 7t15-21s+anti-TF antibody treatment provided a greater fold-increase in NK cell expansion than treatment with 7t15-21s alone or 7t15-21s+anti-TF antibody IgG4.

A set of experiments was performed to determine NK proliferation following treatment with the combination of 7t15-21s+anti-TF antibody. In these experiments, fresh human leukocytes were obtained from the blood bank and CD56$^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended in $2\times10^6$/mL in a 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 7t15-21s (100 nM) and anti-TF antibody (50 nM) for up to 15 days. After every 2 days, cells were resuspended at $2\times10^6$/mL with fresh media containing 100 nM 7t15-21s and 50 nM of anti-TF antibody. As the volume of the cultures increased, the cells were transferred to higher volume flasks. At the indicated time points, the cells were counted using trypan blue to access the fold-expansion (data shown for 1 healthy donor). FIG. 176 shows that 7t15-21s+anti-TF antibody treatment provided a >200-fold increase in NK cell expansion over 2 weeks in culture.

A set of experiments was performed to determine changes in the cell surface phenotype of NK cells expanded following treatment with 7t15-21s+anti-TF antibody. In these experiments, fresh human leukocytes were obtained from the blood bank and CD56$^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended in $2\times10^6$/mL in a 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 7t15-21s (100 nM) and anti-TF antibody (50 nM) for 15 days. After every 2 days, the cells were resuspended at $2\times10^6$/mL with fresh media containing 100 nM 7t15-21s and 50 nM of anti-TF antibody. As the volume of the cultures increased, the cells were transferred to higher volume flasks. To assess the change in the phenotype of NK cells, expanded cells were stained with antibodies for cell-surface CD56, CD16, CD25, CD69, CD62L, and CD57 (BioLegend). After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). The cell surface phenotype of NK cells on Day 0 and Day 15 were compared. FIG. 177 shows that incubation of NK cells with 7t15-21s+anti-TF antibody resulted in an increase in the percentage of CD16$^+$CD56$^+$ NK cells expressing CD25 and CD69, and a decrease in the percentage of CD16$^+$CD56$^+$ NK cells expressing CD62L and CD57.

Example 89: Induction of Proliferation of Immune Cells In Vivo

A set of experiments was performed to determine the effect 7t15-21s+anti-TF antibody-expanded NK cells in NSG mice following treatment with 7t15-21s, TGFRt15-TGFRs, and 2t2. In these experiments, fresh human leukocytes were obtained from the blood bank and CD56$^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended in $2\times10^6$/mL in a 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 7t15-21s (100 nM) and anti-TF antibody (50 nM) for 15 days. After every 2 days, the cells were resuspended at $2\times10^6$/mL with fresh media containing 100 nM 7t15-21s and 50 nM of anti-TF antibody. As the volume of the cultures increased, the cells were transferred to higher volume flasks. The cells were counted using trypan blue to access the fold-expansion. 7t15-21s+anti-TF antibody-expanded NK cells were washed three times in warm HBSS Buffer (Hyclone) at 1000 RPM for 10 minutes at room temperature. The 7t15-21s+anti-TF antibody-expanded-NK cells were resuspended in $10\times10^6$/0.2 mL HBSS buffer and injected intravenously into the tail vein of NSG mice (NOD scid gamma mouse) (Jackson Laboratories). The transferred NK cells were supported every 48 hours with either 7t15-21s (10 ng/dose, i.p.), TGFRt15-TGFRs (10 ng/dose, i.p.) or 2t2 (10 ng/dose, i.p.) for up to 21 days. Engraftment and persistence of the human 7t15-21s+anti-TF antibody-expanded NK cells were measured every week in blood staining for hCD45, mCD45, hCD56, hCD3, and hCD16 antibodies by flow cytometry (Celesta-BD Bioscience) (Data represent 3 mice per group). FIG. 178 indicates that treatment of mice bearing adoptively-transferred 7t15-21s+anti-TF antibody-expanded NK cells with 7t15-21s-, TGFRt15-TGFRs-, or 2t2-induced expansion and persistence of the adoptively transferred NK cells compared to control treated mice.

Example 90: NK-Mediated Cytotoxicity Following Treatment with Multi-Chain Construct+Anti-TF Antibody A set of experiments was performed to determine the effective killing of chemical-induced senescent human fibroblasts by 7t15-21s+anti-TF antibody-expanded NK cells. In these experiments, human lung fibroblasts (IMR-90 and WI-38) were treated with doxorubicin (0.8 µM) for 48 hours. The cells were rested for 48 hours and then treated with doxorubicin (0.8 µM) again for 48 hours. Doxorubicin-containing culture medium was changed and the cells were rested in culture medium for 7 days. FIG. 179A shows beta galactosidase staining confirming senescence induction. NK cells isolated from healthy donors were expanded as follows: NK cells were treated with 7t15-21s (100 nM) and anti-TF antibody (50 nM) for 15 days. After every 2 days, cells were resuspended at $2\times10^6$/mL with fresh media containing 100 nM of 7t15-21s and 50 nM of anti-TF antibody. As the volume of the cultures increased, the cells were transferred to higher volume flasks. The cells were counted using trypan blue to access the fold-expansion. On the day of experiment, the target cells were trypsinized, labeled with Cell Trace Violet (CTV), and added to expanded NK cells at an Effector (NK):Target ratio (ET) of 4:1. The cell mixture was incubated for 20 hours. Non-senescent target fibroblast cells and untreated senescent human fibroblasts were included as controls. After incubation, the cells were trypsinized, washed, and resuspended in Propidium Iodide (PI) solution. The cytotoxicity of the 7t15-21s+anti-TF antibody-expanded NK cells against the chemical-induced senescent human fibroblasts was accessed by flow cytometry based on PI staining of the CTV-labeled cells. FIG. 179B shows percent of dead (PI$^+$) target cells for non-senescent cells (left two bars) and for senescent cells (right two bars). The results demonstrate that 7t15-21s expanded human NK cells effectively kill non-senescent and senescent cells (FIG. 179B).

A set of experiments was performed to assess the effective killing of UV-induced senescent human fibroblasts by 7t15-21s+anti-TF antibody-expanded NK cells. In these experiments, human foreskin fibroblasts (HFF) were grown in 48-well plates ($0.1\times10^6$ cells/well) overnight and treated with ultraviolet (UV) B light (3250J/m$^2$) twice a day for 5 days. The culture medium was changed every 3 days. After UV exposure, the cells were kept for 2 days, trypsinized, and transferred to T175 flask. After 4 days, the cells were trypsinized and beta galactosidase staining and gene expression (senescence markers and NK ligand) analysis was performed to confirm induction of senescence. FIG. 180A shows beta galactosidase staining confirming the induction of senescence. FIG. 180B shows gene expression for senescence markers and an NK ligand, which further confirm the induction of senescence.

To assess killing of UV-induced senescent human fibroblasts, NK cells isolated from healthy donors were expanded as follows: NK cells were treated with 7t15-21s (100 nM) and anti-TF antibody (50 nM) for 15 days. After every 2 days, the cells were resuspended at $2\times10^6$/mL with fresh media containing 100 nM of 7t15-21s and 50 nM of anti-TF antibody. As the volume of the cultures increased, the cells were transferred to higher volume flasks. The cells were counted using trypan blue to access the fold-expansion. On the day of experiment, target cells (UV-induced senescent human fibroblasts) were trypsinized, labeled with Cell Trace Violet (CTV), and added to expanded NK cells at an Effector (NK):Target (HFF) ratio of 4:1. The cell mixture was incubated for 10 hours. Untreated target cells were included as a control. After incubation, the cells were trypsinized, washed, and resuspended in propidium iodide (PI) solution and analyzed by flow cytometry. FIG. 180C shows the percentage of dead (PI$^+$) target cells for non-senescent cells (two left bars) and for senescent cells (two right bars). The results demonstrate that 7t15-21s-expanded human NK cells effectively kill non-senescent and senescent cells.

Example 91: Activation and Proliferation of NK Cells In Vitro

Fresh human leukocytes were obtained from the blood bank and CD56$^+$ NK cells were isolated with the RosetteSep/human NK cell reagent (StemCell Technologies). The purity of NK cells was >90% and confirmed by staining with CD56-BV421, CD16-BV510, CD25-PE, and CD69-APC-Fire750 antibodies (BioLegend). The cells were counted and resuspended at $2\times10^6$/mL in 24-well flat-bottom plates in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone).

The cells were stimulated with the following molecules: 7t15-21s (100 nM), 7t15-21s (100 nM)+anti-TF antibody (IgG1 Ab, 50 nM), or 7t15-21s (100 nM)+anti-TF antibody (IgG4 Ab, 50 nM) for 5 days. After every 2 days, the cells were resuspended at $2\times10^6$/mL with fresh media with the supplemented molecules. After 5 days, the cells were counted using trypan blue to access the fold-expansion (data shown for 3 healthy donors). The results showed that the 7t15-21s+anti-TF antibody (IgG1) treatment provided a greater fold increase in NK cell expansion than treatment with 7t15-21s alone or with 7t15-21s+anti-TF antibody (IgG4) (FIG. 181).

Fresh human leukocytes were obtained from the blood bank and CD56$^+$ NK cells were isolated with the RosetteSep/human NK cell reagent (StemCell Technologies). The purity of NK cells was >90% and confirmed by staining with CD56-BV421, CD16-BV510, CD25-PE, and CD69-APC-Fire750 antibodies (BioLegend). The cells were counted and resuspended at $2\times10^6$/mL in 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone). The cells were stimulated with either 7t15-21s (100 nM) and anti-TF antibody (IgG1) (50 nM), or with 7t15-21s137L short version (41BBs) (100 nM) and anti-TF antibody (IgG1) (50 nM) for up to 13 days. After every 2 days, the cells were resuspended at $2\times10^6$/mL with fresh media with supplemented molecules. As the volume of the cultures increased, the cells were transferred to higher volume flasks. At the indicated time points as shown in FIG. 182, the cells were counted using trypan blue to assess the fold-expansion (data shown for 3 healthy donors). The results showed that the 7t15-21s+anti-TF antibody (IgG1) treatment provided a >30-fold increase in NK cell expansion over 13 days in culture (FIG. 182).

Example 92: Treatment of a Subject Having a Cancer

Daudi tumor cells (Human Burkitt's lymphoma) (ATCC) were cultured in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). Daudi cells were washed three times in warm HBSS Buffer (Hyclone) at 1000 RPM for 10 minutes at room temperature. The cells were resuspended in $10\times10^6$/0.2 mL HBSS buffer and injected intravenously into the tail vein of NSG mice (NOD scid gamma mouse) (The Jackson Laboratory). After day 10, bone marrow was harvested from untreated NSG mice to evaluate tumor cell engraftment. Engraftment of Daudi cells in bone marrow was verified by flow cytometry (Celesta-BD Bioscience) using PE-conjugated anti-human HLA-DR antibody (BioLegend).

Fresh human leukocytes were obtained from the blood bank and CD56$^+$ NK cells were isolated with the RosetteSep/human NK cell reagent (StemCell Technologies). The purity of NK cells was >90% and confirmed by staining with CD56-BV421, CD16-BV510, CD25-PE, and CD69-APC-Fire750 antibodies (BioLegend). The cells were counted and resuspended at $2\times10^6$/mL in 24-well flat-bottom plates in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with 7t15-21s (100 nM) and anti-TF antibody (IgG1) (50 nM) for 15 days. After every 2 days, the cells were resuspended at $2\times10^6$/mL with fresh media with supplemented molecules. As the volume of the cultures increased, the cells were transferred to higher volume flasks. The cells were counted using trypan blue to assess the fold-expansion.

The 7t15-21s+anti-TF antibody (IgG1)-expanded NK cells were washed three times in warm HBSS Buffer (Hyclone) at 1000 RPM for 10 minutes at room temperature. The NK cells were resuspended in $10\times10^6$/0.2 mL HBSS buffer and injected intravenously into the tail vein of NSG mice bearing Daudi tumors on day 10. The transferred NK cells were supported every 48 hours with 2t2 (10 ng/dose, i.p.) for up to 7 days. After day 7 post-NK cell transfer, the percentage of HLA-DR+ Daudi cells in the bone marrow was determined by flow cytometry. The data show that adoptive transfer of the 7t15-21s+anti-TF antibody (IgG1)-expanded NK cells resulted in a decrease in Daudi tumor cells in the bone marrow of NSG mice (FIG. 183).

Example 93: Improvement of the Texture and/or Appearance and/or Hair

The ApoE$^{-/-}$ mice were fed with chow diet (shown as "CD" in FIG. 184A) or Western diet (shown as "WD" in FIGS. 184B-E) from Day 0. On Day 44 (Week 7), the mice were administrated subcutaneously with PBS (FIGS. 184A and 184B), 3 mg/kg of TGFRt15-TGFRs (FIG. 184C), 2t2 (FIG. 195D), or anti-TF antibody (IgG4) (FIG. 184E). The pictures were taken one week after treatment on Day 51 (Week 8). Compared to the PBS control group (FIG. 184B), the skin texture was significantly improved in mice fed with a Western diet and treated with 2t2 or TGFRt15-TGFRs (FIGS. 184C and 184D).

Example 94: Tissue Factor Coagulation Assays Following Treatment with Single-Chain or Multi-Chain Chimeric Polypeptides A set of experiments was performed to assess blood coagulation following treatment with single-chain or multi-chain chimeric polypeptides. To initiate the blood coagulation cascade pathway, tissue factor (TF) binds to Factor VIIa (FVIIa) to form a TF/FVIIa complex. The TF/FVIIa complex then binds Factor X (FX) and converts FX to FXa.

Factor VIIa (FVIIa) Activity Assay

One assay to measure blood coagulation involves measuring Factor VIIa (FVIIa) activity. This type of assay requires the presence of tissue factor and calcium. The TF/FVIIa complex activity can be measured by a small substrate or by a natural protein substrate, for example, Factor X (FX). When FX is used as a substrate, phospholipids are also required for TF/FVIIa activity. In this assay, FVIIa activity is determined with FVIIa-specific chromogenic substrate S-2288 (Diapharma, West Chester, Ohio). The color change of the S-2288 substrate can be measured spectrophotometrically and is proportional to the proteolytic activity of FVIIa (e.g., the TF/FVIIa complex).

In these experiments, the FVIIa activity of the following groups were compared: the 219-amino acid extracellular domain of tissue factor domain (TF$_{219}$), a multi-chain chimeric polypeptide with a wild-type tissue factor domain, and a multi-chain chimeric polypeptide with a mutant tissue factor domain. The chimeric polypeptides containing mutant tissue factor molecules were constructed with mutations to the TF domain at amino acid sites: Lys20, Ile22, Asp58, Arg135, and Phe140.

In order to assess activity of FVIIa, FVIIa, and TF$_{219}$ or a TF$_{219}$-containing multi-chain chimeric polypeptide were mixed at an equal molar concentration (10 nM) in all wells of a 96-well ELISA plate in a total volume of 70 µL. After incubation for 10 minutes at 37° C., 10 µL of 8 mM S-2288 substrate was added to start the reaction. The incubation was then kept at 37° C. for 20 minutes. Finally, color change was monitored by reading absorbance at 405 nm. The OD values of different TF/VIIa complexes are shown in Table 1 and Table 2. Table 1 shows a comparison of TF$_{219}$, 21t15-21s wild-type (WT) and 21t15-21s mutant (Mut). Table 2 shows a comparison of TF$_{219}$, 21t15-TGFRs wild-type (WT), and 21t15-TGFRs mutant (Mut). These data show that TF$_{219}$-containing multi-chain chimeric polypeptides (e.g., 21t15-21s-WT, 21t15-21s-Mut, 21t15-TGFRS-WT, and 21t15-TGFRS-Mut) have lower FVIIa activity than TF$_{219}$ when the chromogenic S-2288 was used as a substrate. Notably, the multi-chain chimeric polypeptides containing TF$_{219}$ mutations showed much lower FVIIa activity when compared to multi-chain chimeric polypeptides containing wild type TF$_{219}$.

TABLE 1

| | FVIIa activity |
|---|---|
| Molecule | OD value at 405 nm |
| TF$_{219}$ | 0.307 |
| 21t15/21S-WT | 0.136 |
| 21t15/21S-Mut | 0.095 |

WT: wild type of TF$_{219}$,
Mut: TF$_{219}$ containing mutations.

TABLE 2

| | FVIIa activity |
|---|---|
| Molecule | OD value at 405 nm |
| TF$_{219}$ | 0.345 |
| 21t15/TGFRS-WT | 0.227 |
| 21t15/TGFRS-Mut | 0.100 |

WT: wild type of TF$_{219}$,
Mut: TF$_{219}$ containing mutations.

Factor X (FX) Activation Assay

An additional assay to measure blood coagulation involves measuring activation of Factor X (FX). Briefly, TF/VIIa activates blood coagulation Factor X (FX) to Factor Xa (FXa) in the presence of calcium and phospholipids. TF$_{243}$, which contains the transmembrane domain of TF, has much higher activity in activating FX to FXa than TF$_{219}$, which does not contain the transmembrane domain. TF/VIIa dependent activation of FX is determined by measuring FXa activity using an FXa-specific chromogenic substrate S-2765 (Diapharma, West Chester, Ohio). The color change of S-2765 can be monitored spectrophotometrically and is proportional to the proteolytic activity of FXa.

In these experiments, FX activation with a multi-chain chimeric polypeptide (18t15-12s, mouse (m)21t15, 21t15-TGFRs, and 21t15-7s) was compared with a positive control (Innovin) or TF$_{219}$. TF$_{219}$ (or TF$_{219}$-containing multi-chain chimeric polypeptides)/FVIIa complexes were mixed at an equal molar concentration (0.1 nM each) in a volume of 50 µL in round bottom wells of a 96-well ELISA plate, after which 10 µL of 180 nM FX was added. After 15 minutes of incubation at 37° C., during which time FX was converted to FXa, 8 µL of 0.5 M EDTA (which chelates calcium and thus terminates FX activation by TF/VIIa) was added to each well to stop FX activation. Next, 10 µL of 3.2 mM S-2765 substrate was added to the reaction mixture. Immediately, the plate absorbance was measured at 405 nm and was recorded as the absorbance at time 0. The plate was then incubated for 10-20 minutes at 37° C. The color change was monitored by reading absorbance at 405 nm following the incubation. Results of FX activation as measured by FXa activity using chromogenic substrate S-2765 are shown in FIG. 185. In this experiment, Innovin, which is a commercial prothrombin reagent containing lipidated recombinant human $TF_{243}$, was used as a positive control for FX activation. Innovin was reconstituted with purified water to about 10 nM of $TF_{243}$. Next, 0.1 nM TF/VIIa complex was made by mixing an equal volume of 0.2 nM of FVIIa with 0.2 nM of Innovin. Innovin demonstrated very potent FX activation activity, while $TF_{219}$ and $TF_{219}$-containing multi-chain chimeric polypeptides had very low FX activation activity, confirming that $TF_{219}$ is not active in a TF/FVIIa complex for activating natural substrate FX in vivo.

Prothrombin Time Test

A third assay to measure blood coagulation is the prothrombin time (PT) test, which measures blood clotting activity. Here, the PT test was performed using commercially available normal human plasma (Ci-Trol Coagulation Control, Level I). For a standard PT test, clot reactions were initiated by addition of Innovin, a lipidated recombinant human $TF_{243}$, in the presence of calcium. Clotting time was monitored and reported by STart PT analyzer (Diagnostica Stago, Parsippany, N.J.). PT assays were started by injecting 0.2 mL of various dilutions of Innovin diluted in PT assay buffer (50 mM Tris-HCl, pH 7.5, 14.6 mM $CaCl_2$), 0.1% BSA) into cuvettes containing 0.1 mL of normal human plasma prewarmed at 37° C. In the PT assay, shorter PT time (clotting time) indicates a higher TF-dependent clotting activity while longer PT (clotting time) means lower TF-dependent clotting activity.

As seen in FIG. 186, addition of different amounts of Innovin (e.g., Innovin reconstituted with purified water equivalent to 10 nM of lipidated recombinant human $TF_{243}$ was considered to be 100% Innovin) to the PT assay demonstrated a dose-response relationship, where lower concentrations of $TF_{243}$ resulted in a longer PT time (lower clotting activity). For example, 0.001% Innovin had a PT time greater than 110 seconds, which was almost the same as buffer alone.

In another experiment, the PT test was conducted on $TF_{219}$ and multi-chain chimeric polypeptides including: 18t15-12s, 7t15-21s, 21t15-TGFRs-WT, and 21t15-TGFRs-Mut. FIG. 187 show that $TF_{219}$ and $TF_{219}$-containing multi-chain chimeric polypeptides (at a concentration of 100 nM) had prolonged PT times indicating extremely low or no clotting activity.

Studies were also conducted to evaluate whether incubating the multi-chain chimeric polypeptides in the presence of other cells carrying receptors for the cytokine components of the multi-chain chimeric polypeptide (32Dβ or human PBMCs) would affect the clotting time in the PT assay. To examine whether cells that express IL-15 receptor (32Dβ cells) or IL-15 and IL-21 receptors (PBMCs) would bind IL-15-containing multi-chain chimeric polypeptides to mimic natural TF as a cellular FVIIa receptor, $TF_{219}$-containing multi-chain chimeric polypeptides (at a concentration of 100 nM for each molecule) were diluted in the PT assay buffer and preincubated with 32Dβ cells (at $2\times10^5$ cells/mL) or PBMC (at $1\times10^5$ cells/mL) for 20-30 minutes at room temperature. The PT assay was then conducted as described above. FIGS. 188 and 189 shows that $TF_{219}$ and $TF_{219}$-containing multi-chain chimeric polypeptides mixed with 32Dβ cells (FIG. 188) or PBMC (FIG. 189) at a final concentration of 100 nM had prolonged PT times similar to 0.001-0.01% Innovin (equivalent to 0.1 pM to 1.0 pM of $TF_{243}$). Expressed in percentage of relative $TF_{243}$ activity, $TF_{219}$-containing multi-chain chimeric polypeptides had 100,000 to 1,000,000 times lower TF dependent clotting activity when compared to Innovin. This demonstrated that $TF_{219}$-containing multi-chain chimeric polypeptides had extremely low or no TF-dependent clotting activity, even while the molecules were bound to an intact cell membrane surface, such as 32Dβ or PBMCs.

Example 95: Characterization of 7t15-21s137L (Long Version)

The nucleic acid sequence of the 7t15 construct (including signal peptide sequence) is as follows (SEQ ID NO: 144):

```
(Signal peptide)
ATGAAGTGGGTGACCTTCATCAGCCTGCTGTTCCTGTTCTCCAGCGC

CTACTCC (Human IL7)
GATTGCGACATCGAGGGCAAGGACGGCAAGCAGTACGAGAGCGTGCT

GATGGTGTCCATCGACCAGCTGCTGGACAGCATGAAGGAGATCGGCT

CCAACTGCCTCAACAACGAGTTCAACTTCTTCAAGCGGCACATCTGC

GACGCCAACAAGGAGGGCATGTTCCTGTTCAGGGCCGCCAGGAAACT

GCGGCAGTTCCTGAAGATGAACTCCACCGGCGACTTCGACCTGCACC

TGCTGAAGGTGTCCGAGGGCACCACCATCCTGCTGAACTGCACCGGA

CAGGTGAAGGGCCGGAAACCTGCTGCTCTGGGAGAGGCCCAACCCAC

CAAGAGCCTGGAGGAGAACAAGTCCCTGAAGGAGCAGAAGAAGCTGA

ACGACCTGTGCTTCCTGAAGAGGCTGCTGCAGGAGATCAAGACCTGC

TGGAACAAGATCCTGATGGGCACCAAGGAGCAT (Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACC

AAGTTTACACCGTGCAGATCAGCACCAAGTCCGGCGACTGGAAGTCC

AAATGTTTCTATACCACCGACACCGAGTGCGATCTCACCGATGAGAT

CGTGAAAGATGTGAAACAGACCTACCTCGCCCGGGTGTTTAGCTACC

CCGCCGGCAATGTGGAGAGCACTGGTTCCGCTGGCGAGCCTTTATAC

GAGAACAGCCCCGAATTTACCCCTTACCTCGAGACCAATTTAGGACA

GCCCACCATCCAAAGCTTTGAGCAAGTTGGCACAAAGGTGAATGTGA

CAGTGGAGGACGAGCGGACTTTAGTGCGGCGGAACAACACCTTTCTC

AGCCTCCGGGATGTGTTCGGCAAAGATTTAATCTACACACTGTATTA

CTGGAAGTCCTCTTCCTCCGGCAAGAAGACAGCTAAAACCAACACAA
```

```
ACGAGTTTTTAATCGACGTGGATAAAGGCGAAAACTACTGTTTCAGC

GTGCAAGCTGTGATCCCCTCCCGGACCGTGAATAGGAAAAGCACCGA

TAGCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAAT

TCAGTCCATGCATATCGACGCCACTTTATACACAGAATCCGACGTGC

ACCCCTCTTGTAAGGTGACCGCCATGAAATGTTTTTACTGGAGCTG

CAAGTTATCTCTTTAGAGAGCGGAGACGCTAGCATCCACGACACCGT

GGAGAATTTAATCATTTTAGCCAATAACTCTTTATCCAGCAACGGCA

ACGTGACAGAGTCCGGCTGCAAGGAGTGCGAAGAGCTGGAGGAGAAG

AACATCAAGGAGTTTCTGCAATCCTTTGTGCACATTGTCCAGATGTT

CATCAATACCTCC
```

The amino acid sequence of 7t15 fusion protein (including the leader sequence) is as follows (SEQ ID NO: 143):

```
(Signal peptide)
MKWVTFISLLFLFSSAYS (Human IL7)
DCDIEGKDGKQYESVLMVSIDQLLDSMKEIGSNCLNNEFNFFKRHIC

DANKEGMFLFRAARKLRQFLKMNSTGDFDLHLLKVSEGTTILLNCTG

QVKGRKPAALGEAQPTKSLEENKSLKEQKKLNDLCFLKRLLQEIKTC

WNKILMGTKEH (Human Tissue Factor 219)
SGTTNTVAAYNLTWKSTNFKTILEWEPKPVNQVYTVQISTKSGDWKS

KCFYTTDTECDLTDEIVKDVKQTYLARVFSYPAGNVESTGSAGEPLY

ENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFS

VQAVIPSRTVNRKSTDSPVECMGQEKGEFRE (Human IL-15)
NWVNVISDLKKIEDLIQSMHIDATLYTESDVHPSCKVTAMKCFLLEL

QVISLESGDASIHDTVENLIILANNSLSSNGNVTESGCKECEELEEK

NIKEFLQSFVHIVQMFINTS
```

The nucleic acid sequence of the 21s137L construct (including signal peptide sequence) is as follows (SEQ ID NO: 172):

```
(Signal peptide)
ATGAAGTGGGTGACCTTCATCAGCCTGCTGTTCCTGTTCTCCAGCGC

CTACTCC (Human IL-21)
CAGGGCCAGGACAGGCACATGATCCGGATGAGGCAGCTCATCGACAT

CGTCGACCAGCTGAAGAACTACGTGAACGACCTGGTGCCCGAGTTTC

TGCCTGCCCCCGAGGACGTGGAGACCAACTGCGAGTGGTCCGCCTTC

TCCTGCTTTCAGAAGGCCCAGCTGAAGTCCGCCAACACCGGCAACAA

CGAGCGGATCATCAACGTGAGCATCAAGAAGCTGAAGCGGAAGCCTC

CTCCACAAACGCCGGCAGGAGGCAGAAGCACAGGCTGACCTGCCCC

AGCTGTGACTCCTACGAGAAGAAGCCCCCCAAGGAGTTCCTGGAGAG

GTTCAAGTCCCTGCTGCAGAAGATGATCCATCAGCACCTGTCCTCCA

GGACCCACGGCTCCGAGGACTCC (Human IL-15R α sushi domain)
ATTACATGCCCCCCTCCCATGAGCGTGGAGCACGCCGACATCTGGGT

GAAGAGCTATAGCCTCTACAGCCGGGAGAGGTATATCTGTAACAGCG

GCTTCAAGAGGAAGGCCGGCACCAGCAGCCTCACCGAGTGCGTGCTG

AATAAGGCTACCAACGTGGCTCACTGGACAACACCCTCTTTAAAGTG

CATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGA

CCTGCGGCAGGGCATGTTTGCGCAGCTGGTGGCCCAAAATGTTCTGC

TGATCGATGGGCCCCTGAGCTGGTACAGTGACCCAGGCCTGGCAGGC

GTGTCCCTGACGGGGGGCCTGAGCTACAAGAGGACACGAAGGAGCT

GGTGGTGGCCAAGGCTGGAGTCTACTATGTCTTCTTTCAACTAGAGC

TGCGGCGCGTGGTGGCCGGCGAGGGCTCAGGCTCCGTTTCACTTGCG

CTGCACCTGCAGCCACTGCGCTCTGCTGCTGGGGCCGCCGCCCTGGC

TTTGACCGTGGACCTGCCACCCGCCTCCTCCGAGGCTCGGAACTCGG

CCTTCGGTTTCCAGGGCCGCTTGCTGCACCTGAGTGCCGGCCAGCGC

CTGGGCGTCCATCTTCACACTGAGGCCAGGGCACGCCATGCCTGGCA

GCTTACCCAGGGCGCCACAGTCTTGGGACTCTTCCGGGTGACCCCCG

AAATCCCAGCCGGACTCCCTTCACCGAGGTCGGAA
```

The amino acid sequence of 21s137L fusion protein (including the leader sequence) is as follows (SEQ ID NO: 171):

```
(Signal peptide)
MKWVTFISLLFLFSSAYS (Human IL-21)
QGQDRHMIRMRQLIDIVDQLKNYVNDLVPEFLPAPEDVETNCEWSAF

SCFQKAQLKSANTGNNERIINVSIKKLKRKPPSTNAGRRQKHRLTCP

SCDSYEKKPPKEFLERFKSLLQKMIHQHLSSRTHGSEDS (Human IL-15R α sushi domain)
ITCPPPMSVEHADIWVKSYSLYSRERYICNSGFKRKAGTSSLTECVL

NKATNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAG

VSLTGGLSYKEDTKELVVAKAGVYYVFFQLELRRVVAGEGSGSVSLA

LHLQPLRSAAGAAALALTVDLPPASSEARNSAFGFQGRLLHLSAGQR

LGVHLHTEARARHAWQLTQGATVLGLFRVTPEIPAGLPSPRSE
```

The following experiment was conducted to evaluate whether the CD137L portion in 7t15-21s137L was intact to bind to CD137 (4.1BB). On day 1, a 96-well plate was coated with 100 μL (2.5 μg/mL) of GAH IgG Fc (G-102-C, R&D Systems) in R5 (coating buffer), overnight. On day 2, the plates were washed three times and blocked with 300 μL of 1% BSA in PBS at 37° C. for 2 hrs. 10 ng/ml of 4.1BB/Fc (838-4B, R&D Systems) was added at 100 μl/well for 2 hrs at room temperature. Following three washes, 7t15-21s137L (long version) or 7t15-21s137Ls (short version) was added starting at 10 nM, or recombinant human 4.1BBL starting at 180 ng/mL, with 1/3 dilution, followed by incubation at 4° C. overnight. On day 3, the plates were washed three times, and 500 ng/mL of biotinylate-goat anti-human 4.1BBL (BAF2295, R&D Systems) was applied at 100 μL per well, followed by incubation at RT for 2 hrs. The plates were washed three times, and incubated with 0.25 μg/mL of HRP-SA (Jackson ImmuneResearch) at 100 μL per well for 30 min. The plates were then washed three times, and incubated with 100 μL of ABTS for 2 mins at RT. The results were read at 405 nm. As shown in FIG. 190, both 7t15-21s137L (long version) and 7t15-21s137L (short version) could interact with 4.1BB/Fc (dark diamond and gray square) compared to the recombinant human 4.1BB ligand (rhCD137L, light gray star). 7t15-21s137L (long version) (dark diamond) interacted better with 4.1BB/Fc as compared to 7t15-21s137L (short version) (gray square).

The following experiments were conducted to evaluate whether the components IL7, IL21, IL15, and 4.1BBL in 7t15-21s137L (long version) were intact to be detected by the individual antibody using ELISA. A 96-well plate was coated with 100 μL (4 μg/mL) of anti-TF (human IgG1) in R5 (coating buffer) and incubated at RT for 2 hrs. The plates were washed three times, and blocked with 100 μL of 1% BSA in PBS. Purified 7t15-21s137L (long version) was added starting at 10 nM, and at 1/3 dilution, followed by incubation at RT for 60 min. The plates were washed three times, and 500 ng/mL of biotinylate-anti-IL7 (506602, R&D Systems), 500 ng/mL of biotinylate-anti-IL21 (13-7218-81, R&D Systems), 50 ng/mL of biotinylate-anti-IL15 (BAM247, R&D Systems), or 500 ng/ml of biotinylate-goat anti-human 4.1BBL (BAF2295, R&D Systems) was added per well and incubated at room temperature for 60 min. The plates were washed three times and incubated with 0.25 μg/mL of HRP-SA (Jackson ImmunoResearch) at 100 μL per well for 30 min at RT. The plates were washed four times, and incubated with 100 μL of ABTS for 2 mins at room temperature. The absorbance results were read at 405 nm. As shown in FIG. 191A-191D, the components including IL7, IL21, IL15, and 4.1BBL in 7t15-21s137L (long version) were detected by the individual antibodies.

The following experiment was conducted to evaluate the activity of IL15 in 7t15-21s137L (long version) and 7t15-21s137L (short version). The ability of 7t15-21s137L (long version) and 7t15-21s137L (short version) to promote proliferation of IL2Rαβγ-expressing CTLL2 cells was compared with that of recombinant IL15. IL15 dependent CTLL2 cells were washed five times with IMDM-10% FBS and seeded to the wells at $2 \times 10^4$ cells/well. Serially diluted 7t15-21s137L (long version), 7t15-21s137L (short version), or IL15 were added to the cells. Cells were incubated in a $CO_2$ incubator at 37° C. for 3 days. Cell proliferation was detected by adding 20 μL of PrestoBlue (A13261, ThermoFisher) to each well on day 3 and incubated for an additional 4 hours in a $CO_2$ incubator at 37° C. Raw absorbance at 570-610 nm was read in a micro-titer plate reader. As shown in FIG. 192, 7t15-21s137L (long version), 7t15-21s137L (short version), and IL15 all promoted CTLL2 cell proliferation. The $EC_{50}$ of 7t15-21s137L (long version), 7t15-21s137L (short version), and IL15 is 51.19 pM, 55.75 pM, and 4.947 pM, respectively.

Example 96: Induction of Treg Cells by 2t2

The peripheral blood mononuclear cells (PBMC) of a healthy donor (Donor 163) were isolated from 5 mL of whole blood buffy coats by Ficoll Paque Plus (GE17144003). The PBMC were then lysed with ACK to remove red blood cells. Cells were washed with IMDM-10% FBS and counted. $1.8 \times 10^6$ cells (100 μL/tube) were seeded to the flow tubes and incubated with 50 μL of descending 2t2 or IL2 (15000, 1500, 150, 15, 1.5, 0.15, or 0 pM) and 50 μL of pre-staining antibodies (anti-CD8-BV605 and anti-CD127-AF647). Cells were incubated for 30 min at 37° C. in water bath. 200 μL of pre-warmed BD Phosflow Fix Buffer I (Cat #557870, Becton Dickinson Biosciences) was added for 10 min at 37° C. in water bath to stop the stimulation. Cells ($4.5 \times 10^5$ cells/100 μL) were transferred to a V-shape 96-well plate and were spun down followed by permeabilization with 100 μL of −20° C. pre-cooled BD Phosflow Perm Buffer III (Cat # BD Biosciences) for 30 min on ice. The cells were then extensively washed ×2 with 200 μL of FACS buffer and stained with a panel of fluorescent antibodies (anti-CD25-PE, CD4-PerCP-Cy5.5, CD56-BV421, CD45RA-PE-Cy7 and pSTAT5a-AF488) to distinguish between different lymphocyte subpopulations and evaluate the pSTAT5a status. Cells were spun down and resuspended in 200 μL of FACS buffer for FACSCelesta analysis. As shown in Figure C1A, 6 pM of 2t2 was sufficient to induce the phosphorylation of Stat5a in $CD4^+CD25^{hi}$ $T_{reg}$ cells while 43.11 pM of IL-2 was required to induce phosphorylation of Stat5a in the same population of lymphocytes. In contrast, 2t2 was less active (FIG. 193B) or equally active (FIG. 193C) as compared to IL2 in inducing phosphorylation of Stat5a in $CD4^+CD25^-T_{con}$ and $CD8^+$ $T_{con}$ cells. These results suggest that 2t2 is superior as compared to IL2 in activating $T_{reg}$ in human PBMC, and that 2t2 demonstrates increased $T_{reg}$ selectivity compared to IL-2 in human blood lymphocyte pStat5a responses.

Example 97: Differentiation of the Immune Cell into a Memory-Like Immune Cell

Fresh human leukocytes were obtained from the blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 (BioLegend). The cells were counted and resuspended at a density of $2 \times 10^6$ cells/mL in RPMI 1640 medium (Gibco) supplemented with 2 mM L-glutamine (Thermo Life Technologies), antibiotics (penicillin, 10,000 units/mL; streptomycin, 10,000 μg/mL; Thermo Life Technologies), and 10% FBS (Hyclone). The cells (1 mL) were transferred into a 24-well flat bottom plate, and subjected to either: no treatment, or expanded with 7t15-21s+anti-tissue factor (TF)-antibody (IgG1) (50 nM) for 14 days with medium. The cells were replenished with fresh 7t15-21s+anti-TF-antibody (IgG1) (50 nM) to keep the cell density at approximately $1 \times 10^6$ cells/mL.

Unexpanded NK cells to treatment groups were used as positive controls for full DNA methylation levels (Data not shown). NK cells were pelleted ($1 \times 10^6$), and genomic DNA (nDNA) isolated using the QIAamp UCP DNA Micro Kit (Qiagen). 500 ng of purified nDNA was subjected to sodium bisulfite treatment using the EZ DNA Methylation-Direct kit (Zymo Research) according to the manufacturer's protocol. Bisulfite treatment introduces methylation-dependent changes in the DNA with demethylated cytosines being converted into uracil, whereas methylated cytosines remain unchanged. The bisulfite-treated nDNA (10-50 ng) was used as template to PCR amplify a 228 bp region of the IFNγ promoter containing two CpG sites (CpG-186 and CpG-54, position relative to the transcription start site, TSS), known to be heavily regulated by DNA methylation in T cells, using the Pyromark PCR kit (Qiagen) with the forward primer IFNG127F (5'-ATGGTATAGGTGGGTATAATGG-3') (SEQ ID NO: 30) and the biotinylated reverse primer IFNG355R-bio (biotin-5'-CAATATACTA-CACCTCCTCTAACTAC-3') (SEQ ID NO: 43) (GE-NEWIZ). The PCR conditions were 15 min at 95° C., 48 cycles of 30 sec at 95° C., 30 sec at 56° C., 60 sec at 72° C. followed by 10 min at 72° C. The integrity and quality of the PCR amplified products were visualized on a 1.2% TAE agarose gel. The DNA methylation status of these two CpG sites was determined by pyrosequencing, which is the gold standard technique to quantitatively measure DNA methylation at single CpG-site. Pyrosequencing reactions were performed at Johns Hopkins University Genetic Resources Core Facility using the DNA sequencing primers C186-IFNG135F (5'-GGTGGGTATAATGGG-3') (SEQ ID NO: 14) and C54-IFNG261F (5'-ATTATTTTATTTTAAAAAAT-TTGTG-3') (SEQ ID NO: 15), specific to the CpG sites-186 and -54, respectively. Commercially available non-methylated and methylated DNA (Zymo Research) were used as controls for DNA methylation. The methylation percentages of the two CpG sites (−186 and −54) were pooled for each treatment. The percent difference in DNA methylation was calculated relative to the levels of DNA methylation at the two CpG sites observed in unexposed NK cells.

Analysis of the DNA methylation status of these two IFNγ CpG sites revealed higher levels of DNA demethylation in NK cells supported by 7t15-21s+anti-TF-antibody compared to unexposed NK cells (FIG. 194). These 7t15-21s+ anti-TF-antibody supported NK cells exhibited 47.70%±11.76 difference in DNA methylation (i.e., demethylation) compared to unexposed NK cells. The DNA methylation levels of these two IFNγ CpG sites correlated with increased expression of IFNγ following treatment with 7t15-21s+anti-TF-antibody. These data suggest that long-term exposure of NK cells (14 days expansion in culture) with a combination regimen of 7t15-21s+anti-TF-antibody is able to induce DNA demethylation of the two hypomethylated IFNγ CpG sites (−186 and −54) and that 7t15-21s+anti-TF-antibody (IgG1) can epigenetically reprogram gene expression of IFNγ via DNA demethylation of CpG sites leading to interconversion of NK cells into innate immune memory NK cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Exemplary Embodiments

Embodiment A1. A single-chain chimeric polypeptide comprising:
(i) a first target-binding domain;
(ii) a soluble tissue factor domain; and
(iii) a second target-binding domain.

Embodiment A2. The single-chain chimeric polypeptide of embodiment A1, wherein the first target-binding domain and the soluble tissue factor domain directly abut each other.

Embodiment A3. The single-chain chimeric polypeptide of embodiment A1, wherein the single-chain chimeric polypeptide further comprises a linker sequence between the first target-binding domain and the soluble tissue factor domain.

Embodiment A4. The single-chain chimeric polypeptide of any one of embodiments A1-A3, wherein the soluble tissue factor domain and the second target-binding domain directly abut each other.

Embodiment A5. The single-chain chimeric polypeptide of any one of embodiments A1-A3, wherein the single-chain chimeric polypeptide further comprises a linker sequence between the soluble tissue factor domain and the second target-binding domain.

Embodiment A6. The single-chain chimeric polypeptide of embodiment A1, wherein the first target-binding domain and the second target-binding domain directly abut each other.

Embodiment A7. The single-chain chimeric polypeptide of embodiment A1, wherein the single-chain chimeric polypeptide further comprises a linker sequence between the first target-binding domain and the second target-binding domain.

Embodiment A8. The single-chain chimeric polypeptide of embodiment A6 or A7, wherein the second target-binding domain and the soluble tissue factor domain directly abut each other.

Embodiment A9. The single-chain chimeric polypeptide of embodiment A6 or A7, wherein the single-chain chimeric polypeptide further comprises a linker sequence between the second target-binding domain and the soluble tissue factor domain.

Embodiment A10. The single-chain chimeric polypeptide of any one of embodiments A1-A9, wherein the first target-binding domain and the second target-binding domain bind specifically to the same antigen.

Embodiment A11. The single-chain chimeric polypeptide of embodiment A10, wherein the first target-binding domain and the second target-binding domain bind specifically to the same epitope.

Embodiment A12. The single-chain chimeric polypeptide of embodiment A11, wherein the first target-binding domain and the second target-binding domain comprise the same amino acid sequence.

Embodiment A13. The single-chain chimeric polypeptide of any one of embodiments A1-A9, wherein the first target-binding domain and the second target-binding domain bind specifically to different antigens.

Embodiment A14. The single-chain chimeric polypeptide of any one of embodiments A1-A13, wherein one or both of the first target-binding domain and the second target-binding domain is an antigen-binding domain.

Embodiment A15. The single-chain chimeric polypeptide of embodiment A14, wherein the first target-binding domain and the second target-binding domain are each an antigen-binding domain.

Embodiment A16. The single-chain chimeric polypeptide of embodiment A13, wherein antigen-binding domain comprises a scFv or a single domain antibody.

Embodiment A17. The single-chain chimeric polypeptide of any one of embodiments A1-A16, wherein one or both of the first target-binding domain and the second target-binding domain bind to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-D, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment A18. The single-chain chimeric polypeptide of any one of embodiments A1-A16, wherein one or both of the first target-binding domain and the second target-binding domain is a soluble interleukin, soluble cytokine protein, or soluble cell surface protein.

Embodiment A19. The single-chain chimeric polypeptide of embodiment A18, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-D, SCF, FLT3L, MICA, MICB, and a ULP16-binding protein.

Embodiment A20. The single-chain chimeric polypeptide of any one of embodiments A1-A16, wherein one or both of the first target-binding domain and the second target-binding domain is a soluble interleukin, soluble cytokine receptor, or soluble cell surface receptor.

Embodiment A21. The single-chain chimeric polypeptide of embodiment A20, wherein the soluble interleukin receptor, soluble cytokine receptor, or soluble cell surface receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment A22. The single-chain chimeric polypeptide of any one of embodiments A1-A21, wherein the soluble tissue factor domain is a soluble human tissue factor domain.

Embodiment A23. The single-chain chimeric polypeptide of embodiment A22, wherein the soluble human tissue factor domain comprises a sequence that is at least 80% identical to SEQ ID NO: 1.

Embodiment A24. The single-chain chimeric polypeptide of embodiment A23, wherein the soluble human tissue factor domain comprises a sequence that is at least 90% identical to SEQ ID NO: 1.

Embodiment A25. The single-chain chimeric polypeptide of embodiment A24, wherein the soluble human tissue factor domain comprises a sequence that is at least 95% identical to SEQ ID NO: 1.

Embodiment A26. The single-chain chimeric polypeptide of any one of embodiments A22-A25, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment A27. The single-chain chimeric polypeptide of embodiment A26, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment A28. The single-chain chimeric polypeptide of any one of embodiments A1-A27, wherein the soluble tissue factor domain is not capable of binding Factor VIIa.

Embodiment A29. The single-chain chimeric polypeptide of any one of embodiments A1-A28, wherein the soluble tissue factor domain does not convert inactive Factor X into Factor Xa.

Embodiment A30. The single-chain chimeric polypeptide of any one of embodiments A1-A29, wherein the single-chain chimeric polypeptide does not stimulate blood coagulation in a mammal.

Embodiment A31. The single-chain chimeric polypeptide of any one of embodiments A1-A30, wherein the single-chain chimeric polypeptide further comprises one or more additional target-binding domains at its N- and/or C-terminus.

Embodiment A32. The single-chain chimeric polypeptide of embodiment A31, wherein the single-chain chimeric polypeptide comprises one or more additional target-binding domains at its N-terminus.

Embodiment A33. The single-chain chimeric polypeptide of embodiment A32, wherein one or more additional target-binding domains directly abuts the first target-binding domain, the second target-binding domain, or the soluble tissue factor domain.

Embodiment A34. The single-chain chimeric polypeptide of embodiment A33, wherein the single-chain chimeric polypeptide further comprises a linker sequence between one of the at least one additional target-binding domains and the first target-binding domain, the second target-binding domain, or the soluble tissue factor domain.

Embodiment A35. The single-chain chimeric polypeptide of embodiment A31, wherein the single-chain chimeric polypeptide comprises one or more additional target-binding domains at its C-terminus.

Embodiment A36. The single-chain chimeric polypeptide of embodiment A35, wherein one of the one or more additional target-binding domains directly abuts the first target-binding domain, the second target-binding domain, or the soluble tissue factor domain.

Embodiment A37. The single-chain chimeric polypeptide of embodiment A35, wherein the single-chain chimeric polypeptide further comprises a linker sequence between one of the at least one additional target-binding domains and the first target-binding domain, the second target-binding domain, or the soluble tissue factor domain.

Embodiment A38. The single-chain chimeric polypeptide of embodiment A31, wherein the single-chain chimeric polypeptide comprises one or more additional target binding domains at its N-terminus and the C-terminus.

Embodiment A39. The single-chain chimeric polypeptide of embodiment A38, wherein one of the one or more additional antigen binding domains at the N-terminus directly abuts the first target-binding domain, the second target-binding domain, or the soluble tissue factor domain.

Embodiment A40. The single-chain chimeric polypeptide of embodiment A38, wherein the single-chain chimeric polypeptide further comprises a linker sequence between one of the one or more additional antigen-binding domains at the N-terminus and the first target-binding domain, the second target-binding domain, or the soluble tissue factor domain.

Embodiment A41. The single-chain chimeric polypeptide of embodiment A38, wherein one of the one or more additional antigen binding domains at the C-terminus directly abuts the first target-binding domain, the second target-binding domain, or the soluble tissue factor domain.

Embodiment A42. The single-chain chimeric polypeptide of embodiment A38, wherein the single-chain chimeric polypeptide further comprises a linker sequence between one of the one or more additional antigen-binding domains at the C-terminus and the first target-binding domain, the second target-binding domain, or the soluble tissue factor domain.

Embodiment A43. The single-chain chimeric polypeptide of any one of embodiments A31-A42, wherein two or more of the first target-binding domain, the second target-binding domain, and the one or more additional target-binding domains bind specifically to the same antigen.

Embodiment A44. The single-chain chimeric polypeptide of embodiment A43, wherein two or more of the first target-binding domain, the second target-binding domain, and the one or more additional target-binding domains bind specifically to the same epitope.

Embodiment A45. The single-chain chimeric polypeptide of embodiment A44, wherein two or more of the first target-binding domain, the second target-binding domain, and the one or more additional target-binding domains comprise the same amino acid sequence.

Embodiment A46. The single-chain chimeric polypeptide of embodiment A43, wherein the first target-binding domain, the second target-binding domain, and the one or more additional target-binding domains each bind specifically to the same antigen.

Embodiment A47. The single-chain chimeric polypeptide of embodiment A46, wherein the first target-binding domain, the second target-binding domain, and the one or more additional target-binding domains each bind specifically to the same epitope.

Embodiment A48. The single-chain chimeric polypeptide of embodiment A47, wherein the first target-binding domain, the second target-binding domain, and the one or more additional target-binding domains each comprise the same amino acid sequence.

Embodiment A49. The single-chain chimeric polypeptide of any one of embodiments A31-A42, wherein the first target-binding domain, the second target-binding domain, and the one or more additional target-binding domains bind specifically to different antigens.

Embodiment A50. The single-chain chimeric polypeptide of any one of embodiments A31-A49, wherein one or more of the first target-binding domain, the second target-binding domain, and the one or more target-binding domains is an antigen-binding domain.

Embodiment A51. The single-chain chimeric polypeptide of embodiment A50, wherein the first target-binding domain, the second target-binding domain, and the one or more additional target-binding domains are each an antigen-binding domain.

Embodiment A52. The single-chain chimeric polypeptide of embodiment A51, wherein antigen-binding domain comprises a scFv or a single domain antibody.

Embodiment A53. The single-chain chimeric polypeptide of any one of embodiments A31-A52, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-D, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment A54. The single-chain chimeric polypeptide of any one of embodiments A31-A52, wherein one or more of the first target-binding domain, the second target-binding domain, and the one or more additional target-binding domains is a soluble interleukin, soluble cytokine protein, or soluble cell surface protein.

Embodiment A55. The single-chain chimeric polypeptide of embodiment A54, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-D, SCF, FLT3L, MICA, MICB, and a ULP16-binding protein.

Embodiment A56. The single-chain chimeric polypeptide of any one of embodiments A31-A52, wherein one or more of the first target-binding domain, the second target-binding domain, and the one or more additional target-binding domains is a soluble interleukin receptor, soluble cytokine receptor, or soluble cell surface receptor.

Embodiment A57. The single-chain chimeric polypeptide of embodiment A56, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment A58. The single-chain chimeric polypeptide of any one of embodiments A1-A57, wherein the single-chain chimeric polypeptide further comprises a signal sequence at its N-terminal end.

Embodiment A59. The single-chain chimeric polypeptide of any one of embodiments A1-A58, wherein the single-chain chimeric polypeptide further comprises a peptide tag positioned at the N-terminal end or the C-terminal end of the single-chain chimeric polypeptide.

Embodiment A60. A composition comprising any of the single-chain chimeric polypeptides of embodiments A1-A59.

Embodiment A61. The composition of embodiment A60, wherein the composition is a pharmaceutical composition.

Embodiment A62. A kit comprising at least one dose of the composition of embodiment A60 or A61.

Embodiment A63. Nucleic acid encoding any of the single-chain chimeric polypeptides of any one of embodiments A1-A59.

Embodiment A64. A vector comprising the nucleic acid of embodiment A63.

Embodiment A65. The vector of embodiment A64, wherein the vector is an expression vector.

Embodiment A66. A cell comprising the nucleic acid of embodiment A63 or the vector of embodiment A64 or A65.

Embodiment A67. A method of producing a single-chain chimeric polypeptide, the method comprising:
culturing the cell of embodiment A66 in a culture medium under conditions sufficient to result in the production of the single-chain chimeric polypeptide; and
recovering the single-chain chimeric polypeptide from the cell and/or the culture medium.

Embodiment A68. A single-chain chimeric polypeptide produced by the method of embodiment A67.

Embodiment A69. The single-chain chimeric polypeptide of embodiment A26, wherein the soluble human tissue factor domain comprises a sequence that is at least 80% identical to SEQ ID NO: 5.

Embodiment A70. The single-chain chimeric polypeptide of embodiment A69, wherein the soluble human tissue factor domain comprises a sequence that is at least 90% identical to SEQ ID NO: 5.

Embodiment A71. The single-chain chimeric polypeptide of embodiment A70, wherein the soluble human tissue factor domain comprises a sequence that is at least 95% identical to SEQ ID NO: 5.

Embodiment A72. The single-chain chimeric polypeptide of embodiment A71, wherein the soluble human tissue factor domain comprises a sequence that is 100% identical to SEQ ID NO: 5.

Embodiment A73. The single-chain chimeric polypeptide of embodiment A26, wherein the soluble human tissue factor domain comprises a sequence that is at least 80% identical to SEQ ID NO: 6.

Embodiment A74. The single-chain chimeric polypeptide of embodiment A73, wherein the soluble human tissue factor domain comprises a sequence that is at least 90% identical to SEQ ID NO: 6.

Embodiment A75. The single-chain chimeric polypeptide of embodiment A74, wherein the soluble human tissue factor domain comprises a sequence that is at least 95% identical to SEQ ID NO: 6.

Embodiment A76. The single-chain chimeric polypeptide of embodiment A75, wherein the soluble human tissue factor domain comprises a sequence that is 100% identical to SEQ ID NO: 6.

Embodiment B1. A single-chain chimeric polypeptide comprising:
(i) a first target-binding domain;
(ii) a soluble tissue factor domain; and
(iii) a second target-binding domain,
wherein:
the first target-binding domain and the second target-binding domain each specifically bind to an IL-2 receptor; or
the first target-binding domain and the second target-binding domain each specifically bind to an IL-15 receptor.

Embodiment B2. The single-chain chimeric polypeptide of embodiment B1, wherein the first target-binding domain and the soluble tissue factor domain directly abut each other.

Embodiment B3. The single-chain chimeric polypeptide of embodiment B1, wherein the single-chain chimeric polypeptide further comprises a linker sequence between the first target-binding domain and the soluble tissue factor domain.

Embodiment B4. The single-chain chimeric polypeptide of any one of embodiments B1-B3, wherein the soluble tissue factor domain and the second target-binding domain directly abut each other.

Embodiment B5. The single-chain chimeric polypeptide of any one of embodiments B1-B3, wherein the single-chain chimeric polypeptide further comprises a linker sequence between the soluble tissue factor domain and the second target-binding domain.

Embodiment B6. The single-chain chimeric polypeptide of embodiment B1, wherein the first target-binding domain and the second target-binding domain directly abut each other.

Embodiment B7. The single-chain chimeric polypeptide of embodiment B1, wherein the single-chain chimeric polypeptide further comprises a linker sequence between the first target-binding domain and the second target-binding domain.

Embodiment B8. The single-chain chimeric polypeptide of embodiment B6 or B7, wherein the second target-binding domain and the soluble tissue factor domain directly abut each other.

Embodiment B9. The single-chain chimeric polypeptide of embodiment B6 or B7, wherein the single-chain chimeric polypeptide further comprises a linker sequence between the second target-binding domain and the soluble tissue factor domain.

Embodiment B10. The single-chain chimeric polypeptide of any one of embodiments B1-B9, wherein both the first target-binding domain and the second target-binding domain is a soluble interleukin protein.

Embodiment B11. The single-chain chimeric polypeptide of embodiment B10, wherein the first target-binding domain and the second target-binding domain is a soluble IL-2 protein.

Embodiment B12. The single-chain chimeric polypeptide of embodiment B11, wherein the soluble IL-2 protein is a soluble human IL-2 protein.

Embodiment B13. The single-chain chimeric polypeptide of embodiment B12, wherein the soluble human IL-2 protein comprises SEQ ID NO: 28.

Embodiment B14. The single-chain chimeric polypeptide of embodiment B10, wherein the first target-binding domain and the second target-binding domain is a soluble IL-15 protein.

Embodiment B15. The single-chain chimeric polypeptide of embodiment B14, wherein the soluble IL-15 protein is a soluble human IL-15 protein.

Embodiment B16. The single-chain chimeric polypeptide of embodiment B15, wherein the soluble human IL-15 protein comprises SEQ ID NO: 39.

Embodiment B17. The single-chain chimeric polypeptide of any one of embodiments B1-B16, wherein the soluble tissue factor domain is a soluble human tissue factor domain.

Embodiment B18. The single-chain chimeric polypeptide of embodiment B17, wherein the soluble human tissue factor domain comprises a sequence that is at least 80% identical to SEQ ID NO: 1.

Embodiment B19. The single-chain chimeric polypeptide of embodiment B18, wherein the soluble human tissue factor domain comprises a sequence that is at least 90% identical to SEQ ID NO: 1.

Embodiment B20. The single-chain chimeric polypeptide of embodiment B19, wherein the soluble human tissue factor domain comprises a sequence that is at least 95% identical to SEQ ID NO: 1.

Embodiment B21. The single-chain chimeric polypeptide of any one of embodiments B17-B20, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment B22. The single-chain chimeric polypeptide of embodiment B21, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment B23. The single-chain chimeric polypeptide of any one of embodiments B1-B22, wherein the soluble tissue factor domain is not capable of binding Factor VIIa.

Embodiment B24. The single-chain chimeric polypeptide of any one of embodiments B1-B23, wherein the soluble tissue factor domain does not convert inactive Factor X into Factor Xa.

Embodiment B25. The single-chain chimeric polypeptide of any one of embodiments B1-B24, wherein the single-chain chimeric polypeptide does not stimulate blood coagulation in a mammal.

Embodiment B26. The single-chain chimeric polypeptide of any one of embodiments B1-B25, wherein the single-chain chimeric polypeptide further comprises one or more additional target-binding domains at its N- and/or C-terminus.

Embodiment B27. The single-chain chimeric polypeptide of embodiment B26, wherein the single-chain chimeric polypeptide comprises one or more additional target-binding domains at its N-terminus.

Embodiment B28. The single-chain chimeric polypeptide of embodiment B27, wherein one or more additional target-binding domains directly abuts the first target-binding domain, the second target-binding domain, or the soluble tissue factor domain.

Embodiment B29. The single-chain chimeric polypeptide of embodiment B28, wherein the single-chain chimeric polypeptide further comprises a linker sequence between one of the at least one additional target-binding domains and the first target-binding domain, the second target-binding domain, or the soluble tissue factor domain.

Embodiment B30. The single-chain chimeric polypeptide of embodiment B26, wherein the single-chain chimeric polypeptide comprises one or more additional target-binding domains at its C-terminus.

Embodiment B31. The single-chain chimeric polypeptide of embodiment B30, wherein one of the one or more additional target-binding domains directly abuts the first target-binding domain, the second target-binding domain, or the soluble tissue factor domain.

Embodiment B32. The single-chain chimeric polypeptide of embodiment B30, wherein the single-chain chimeric polypeptide further comprises a linker sequence between one of the at least one additional target-binding domains and the first target-binding domain, the second target-binding domain, or the soluble tissue factor domain.

Embodiment B33. The single-chain chimeric polypeptide of embodiment B26, wherein the single-chain chimeric polypeptide comprises one or more additional target binding domains at its N-terminus and the C-terminus.

Embodiment B34. The single-chain chimeric polypeptide of embodiment B33, wherein one of the one or more additional antigen binding domains at the N-terminus directly abuts the first target-binding domain, the second target-binding domain, or the soluble tissue factor domain.

Embodiment B35. The single-chain chimeric polypeptide of embodiment B33, wherein the single-chain chimeric polypeptide further comprises a linker sequence between one of the one or more additional antigen-binding domains at the N-terminus and the first target-binding domain, the second target-binding domain, or the soluble tissue factor domain.

Embodiment B36. The single-chain chimeric polypeptide of embodiment B33, wherein one of the one or more additional antigen binding domains at the C-terminus directly abuts the first target-binding domain, the second target-binding domain, or the soluble tissue factor domain.

Embodiment B37. The single-chain chimeric polypeptide of embodiment B33, wherein the single-chain chimeric polypeptide further comprises a linker sequence between one of the one or more additional antigen-binding domains at the C-terminus and the first target-binding domain, the second target-binding domain, or the soluble tissue factor domain.

Embodiment B38. The single-chain chimeric polypeptide of any one of embodiments B26-B37, wherein each of the first target-binding domain, the second target-binding domain, and the one or more additional target-binding domains bind specifically to an IL-2 receptor or an IL-15 receptor.

Embodiment B39. The single-chain chimeric polypeptide of embodiment B38, wherein each of the first target-binding domain, the second target-binding domain, and the one or more additional target-binding domains comprise the same amino acid sequence.

Embodiment B40. The single-chain chimeric polypeptide of any one of embodiments B26-B37, wherein the one or more additional target-binding domains is an antigen-binding domain.

Embodiment B41. The single-chain chimeric polypeptide of embodiment B40, wherein the antigen-binding domain comprises a scFv or a single domain antibody.

Embodiment B42. The single-chain chimeric polypeptide of any one of embodiments B26-B37, B40, and B41, wherein the one or more additional target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment B43. The single-chain chimeric polypeptide of any one of embodiments B6-B37, B40, and B41, wherein the one or more additional target-binding domains is a soluble interleukin or cytokine protein.

Embodiment B44. The single-chain chimeric polypeptide of embodiment B43, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment B45. The single-chain chimeric polypeptide of any one of embodiments B6-B37, B40, and B41, wherein the one or more additional target-binding domains is a soluble interleukin or cytokine receptor.

Embodiment B46. The single-chain chimeric polypeptide of embodiment B45, wherein the soluble receptor is a soluble TGF-β receptor II (TGF-βRII) and a soluble TGF-βRIII.

Embodiment B47. The single-chain chimeric polypeptide of any one of embodiments B1-B46, wherein the single-chain chimeric polypeptide further comprises a signal sequence at its N-terminal end.

Embodiment B48. The single-chain chimeric polypeptide of any one of embodiments B1-B47, wherein the single-chain chimeric polypeptide further comprises a peptide tag positioned at the N-terminal end or the C-terminal end of the single-chain chimeric polypeptide.

Embodiment B49. A composition comprising any of the single-chain chimeric polypeptides of embodiments B1-B48.

Embodiment B50. The composition of embodiment B49, wherein the composition is a pharmaceutical composition.

Embodiment B51. A kit comprising at least one dose of the composition of embodiment B49 or B50.

Embodiment B52. A nucleic acid encoding any of the single-chain chimeric polypeptides of any one of embodiments B1-B48.

Embodiment B53. A vector comprising the nucleic acid of embodiment B52.

Embodiment B54. The vector of embodiment B53, wherein the vector is an expression vector.

Embodiment B55. A cell comprising the nucleic acid of embodiment B52 or the vector of embodiment B53 or B54.

Embodiment B56. A method of producing a single-chain chimeric polypeptide, the method comprising:
culturing the cell of embodiment B55 in a culture medium under conditions sufficient to result in the production of the single-chain chimeric polypeptide; and
recovering the single-chain chimeric polypeptide from the cell and/or the culture medium.

Embodiment B57. A single-chain chimeric polypeptide produced by the method of embodiment B56.

Embodiment B58. The single-chain chimeric polypeptide of embodiment B21, wherein the soluble human tissue factor domain comprises a sequence that is at least 80% identical to SEQ ID NO: 5.

Embodiment B59. The single-chain chimeric polypeptide of embodiment B58, wherein the soluble human tissue factor domain comprises a sequence that is at least 90% identical to SEQ ID NO: 5.

Embodiment B60. The single-chain chimeric polypeptide of embodiment B59, wherein the soluble human tissue factor domain comprises a sequence that is at least 95% identical to SEQ ID NO: 5.

Embodiment B61. The single-chain chimeric polypeptide of embodiment B60, wherein the soluble human tissue factor domain comprises a sequence that is 100% identical to SEQ ID NO: 5.

Embodiment B62. The single-chain chimeric polypeptide of embodiment B21, wherein the soluble human tissue factor domain comprises a sequence that is at least 80% identical to SEQ ID NO: 6.

Embodiment B63. The single-chain chimeric polypeptide of embodiment B62, wherein the soluble human tissue factor domain comprises a sequence that is at least 90% identical to SEQ ID NO: 6.

Embodiment B64. The single-chain chimeric polypeptide of embodiment B63, wherein the soluble human tissue factor domain comprises a sequence that is at least 95% identical to SEQ ID NO: 6.

Embodiment B65. The single-chain chimeric polypeptide of embodiment B64, wherein the soluble human tissue factor domain comprises a sequence that is 100% identical to SEQ ID NO: 6.

Embodiment C1. A multi-chain chimeric polypeptide comprising:
(a) a first chimeric polypeptide comprising:
(i) a first target-binding domain;
(ii) a soluble tissue factor domain; and
(iii) a first domain of a pair of affinity domains;
(b) a second chimeric polypeptide comprising:
(i) a second domain of a pair of affinity domains; and
(ii) a second target-binding domain,
wherein the first chimeric polypeptide and the second chimeric polypeptide associate through the binding of the first domain and the second domain of the pair of affinity domains.

Embodiment C2. The multi-chain chimeric polypeptide of embodiment C1, wherein the first target-binding domain and the soluble tissue factor domain directly abut each other in the first chimeric polypeptide.

Embodiment C3. The multi-chain chimeric polypeptide of embodiment C1, wherein the first chimeric polypeptide further comprises a linker sequence between the first target-binding domain and the soluble tissue factor domain in the first chimeric polypeptide.

Embodiment C4. The multi-chain chimeric polypeptide of any one of embodiments C1-C3, wherein the soluble tissue factor domain and the first domain of the pair of affinity domains directly abut each other in the first chimeric polypeptide.

Embodiment C5. The multi-chain chimeric polypeptide of any one of embodiments C1-C3, wherein the first chimeric polypeptide further comprises a linker sequence between the soluble tissue factor domain and the first domain of the pair of affinity domains in the first chimeric polypeptide.

Embodiment C6. The multi-chain chimeric polypeptide of any one of embodiments C1-C5, wherein the second domain of the pair of affinity domains and the second target-binding domain directly abut each other in the second chimeric polypeptide.

Embodiment C7. The multi-chain chimeric polypeptide of any one of embodiments C1-C5, wherein second chimeric polypeptide further comprises a linker sequence between the second domain of the pair of affinity domains and the second target-binding domain in the second chimeric polypeptide.

Embodiment C8. The multi-chain chimeric polypeptide of any one of embodiments C1-C7, wherein the first target-binding domain and the second target-binding domain bind specifically to the same antigen.

Embodiment C9. The multi-chain chimeric polypeptide of embodiment C8, wherein the first target-binding domain and the second target-binding domain bind specifically to the same epitope.

Embodiment C10. The multi-chain chimeric polypeptide of embodiment C9, wherein the first target-binding domain and the second target-binding domain comprise the same amino acid sequence.

Embodiment C11. The multi-chain chimeric polypeptide of any one of embodiments C1-C7, wherein the first target-binding domain and the second target-binding domain bind specifically to different antigens.

Embodiment C12. The multi-chain chimeric polypeptide of any one of embodiments C1-C11, wherein one or both of the first target-binding domain and the second target-binding domain is an antigen-binding domain.

Embodiment C13. The multi-chain chimeric polypeptide of embodiment C12, wherein the first target-binding domain and the second target-binding domain are each antigen-binding domains.

Embodiment C14. The multi-chain chimeric polypeptide of embodiment C12 or C13, wherein antigen-binding domain comprises a scFv or a single domain antibody.

Embodiment C15. The multi-chain chimeric polypeptide of any one of embodiments C1-C14, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment C16. The multi-chain chimeric polypeptide of any one of embodiments C1-C14, wherein one or both of the first target-binding domain and the second target-binding domain is a soluble interleukin or cytokine protein.

Embodiment C17. The multi-chain chimeric polypeptide of embodiment C16, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment C18. The multi-chain chimeric polypeptide of any one of embodiments C1-C14, wherein one or both of the first target-binding domain and the second target-binding domain is a soluble interleukin receptor, a soluble cytokine receptor, or a soluble cell surface receptor.

Embodiment C19. The multi-chain chimeric polypeptide of embodiment C18, wherein the soluble receptor is a soluble TGF-β receptor II (TGF-βRII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment C20. The multi-chain chimeric polypeptide of any one of embodiments C1-C19, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment C21. The multi-chain chimeric polypeptide of embodiment C20, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment C22. The multi-chain chimeric polypeptide of any one of embodiments C1-C19, wherein the first chimeric polypeptide further comprises one or more additional target-binding domains at the N-terminal and/or C-terminal end of the first chimeric polypeptide.

Embodiment C23. The multi-chain chimeric polypeptide of embodiment C22, wherein at least one of the one or more additional target-binding domains directly abuts the first domain of the pair of affinity domains in the first chimeric polypeptide.

Embodiment C24. The multi-chain chimeric polypeptide of embodiment C22, wherein the first chimeric polypeptide further comprises a linker sequence between the at least one of the one or more additional target-binding domains and the first domain of the pair of affinity domains.

Embodiment C25. The multi-chain chimeric polypeptide of embodiment C22, wherein the at least one of the one or more additional target-binding domains directly abuts the first target-binding domain in the first chimeric polypeptide.

Embodiment C26. The multi-chain chimeric polypeptide of embodiment C22, wherein the first chimeric polypeptide further comprises a linker sequence between the at least one of the one or more additional target-binding domains and the first target-binding domain.

Embodiment C27. The multi-chain chimeric polypeptide of embodiment C22, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment C28. The multi-chain chimeric polypeptide of embodiment C27, wherein the at least one additional target-binding domain of the one or more additional target-binding domains disposed at the N-terminus directly abuts the first target-binding domain or the first domain of the pair of affinity domains in the first chimeric polypeptide.

Embodiment C29. The multi-chain chimeric polypeptide of embodiment C27, wherein the first chimeric polypeptide further comprises a linker sequence disposed between the at least one additional target-binding domain and the first target-binding domain or the first domain of the pair of affinity domains in the first chimeric polypeptide.

Embodiment C30. The multi-chain chimeric polypeptide of embodiment C27, wherein the at least one additional target-binding domain of the one or more additional target-binding domains disposed at the C-terminus directly abuts the first target-binding domain or the first domain of the pair of affinity domains in the first chimeric polypeptide.

Embodiment C31. The multi-chain chimeric polypeptide of embodiment C27, wherein the first chimeric polypeptide further comprises a linker sequence disposed between the at least one additional target-binding domain and the first target-binding domain or the first domain of the pair of affinity domains in the first chimeric polypeptide.

Embodiment C32. The multi-chain chimeric polypeptide of embodiment C27, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment C33. The multi-chain chimeric polypeptide of embodiment C27, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment C34. The multi-chain chimeric polypeptide of any one of embodiments C1-C33, wherein the second chimeric polypeptide further comprises one or more additional target-binding domains at the N-terminal end or the C-terminal end of the second chimeric polypeptide.

Embodiment C35. The multi-chain chimeric polypeptide of embodiment C34, wherein at least one of the one or more additional target-binding domains directly abuts the second domain of the pair of affinity domains in the second chimeric polypeptide.

Embodiment C36. The multi-chain chimeric polypeptide of embodiment C34, wherein the second chimeric polypeptide further comprises a linker sequence between at least one of the one or more additional target-binding domains and the second domain of the pair of affinity domains in the second chimeric polypeptide.

Embodiment C37. The multi-chain chimeric polypeptide of embodiment C34, wherein at least one of the one or more additional target-binding domains directly abuts the second target-binding domain in the second chimeric polypeptide.

Embodiment C38. The multi-chain chimeric polypeptide of embodiment C34, wherein the second chimeric polypeptide further comprises a linker sequence between at least one of the one or more additional target-binding domains and the second target-binding domain in the second chimeric polypeptide.

Embodiment C39. The multi-chain chimeric polypeptide of any one of embodiments C20-C38, wherein two or more of the first target-binding domain, the second target-binding domain, and the one or more additional target-binding domains bind specifically to the same antigen.

Embodiment C40. The multi-chain chimeric polypeptide of embodiment C39, wherein two or more of the first target-binding domain, the second target-binding domain, and the one or more additional target-binding domains bind specifically to the same epitope.

Embodiment C41. The multi-chain chimeric polypeptide of embodiment C40, wherein two or more of the first target-binding domain, the second target-binding domain, and the one or more additional target-binding domains comprise the same amino acid sequence.

Embodiment C42. The multi-chain chimeric polypeptide of embodiment C39, wherein the first target-binding domain, the second target-binding domain, and the one or more additional target-binding domains each bind specifically to the same antigen.

Embodiment C43. The multi-chain chimeric polypeptide of embodiment C42, wherein the first target-binding domain, the second target-binding domain, and the one or more additional target-binding domains each bind specifically to the same epitope.

Embodiment C44. The multi-chain chimeric polypeptide of embodiment C43, wherein the first target-binding domain, the second target-binding domain, and the one or more additional target-binding domains each comprise the same amino acid sequence.

Embodiment C45. The multi-chain chimeric polypeptide of any one of embodiments C20-C38, wherein the first target-binding domain, the second target-binding domain, and the one or more additional target-binding domains bind specifically to different antigens.

Embodiment C46. The multi-chain chimeric polypeptide of any one of embodiments C20-C45, wherein one or more of the first target-binding domain, the second target-binding domain, and the one or more target-binding domains is an antigen-binding domain.

Embodiment C47. The multi-chain chimeric polypeptide of embodiment C46, wherein the first target-binding domain, the second target-binding domain, and the one or more additional target-binding domains are each an antigen-binding domain.

Embodiment C48. The multi-chain chimeric polypeptide of embodiment C47, wherein antigen-binding domain comprises a scFv.

Embodiment C49. The multi-chain chimeric polypeptide of any one of embodiments C20-C48, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment C50. The multi-chain chimeric polypeptide of any one of embodiments C20-C48, wherein one or more of the first target-binding domain, the second target-binding domain, and the one or more additional target-binding domains is a soluble interleukin, a soluble cytokine protein, or a soluble cell surface protein.

Embodiment C51. The multi-chain chimeric polypeptide of embodiment C50, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment C52. The multi-chain chimeric polypeptide of any one of embodiments C20-C48, wherein one or more of the first target-binding domain, the second target-binding domain, and the one or more additional target-binding domains is a soluble interleukin receptor, a soluble cytokine receptor, or a soluble cell surface receptor.

Embodiment C53. The multi-chain chimeric polypeptide of embodiment C52, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment C54. The multi-chain chimeric polypeptide of any one of embodiments C1-C53, wherein the first chimeric polypeptide further comprises a peptide tag at the N-terminal end or the C-terminal end of the first chimeric polypeptide.

Embodiment C55. The multi-chain chimeric polypeptide of any one of embodiments C1-C53, wherein the second chimeric polypeptide further comprises a peptide tag at the N-terminal end or the C-terminal end of the second chimeric polypeptide.

Embodiment C56. The multi-chain chimeric polypeptide of any one of embodiments C1-C55, wherein the soluble tissue factor domain is a soluble human tissue factor domain.

Embodiment C57. The multi-chain chimeric polypeptide of embodiment C56, wherein the soluble human tissue factor domain comprises a sequence that is at least 80% identical to SEQ ID NO: 1.

Embodiment C58. The multi-chain chimeric polypeptide of embodiment C57, wherein the soluble human tissue factor domain comprises a sequence that is at least 90% identical to SEQ ID NO: 1.

Embodiment C59. The multi-chain chimeric polypeptide of embodiment C58, wherein the soluble human tissue factor domain comprises a sequence that is at least 95% identical to SEQ ID NO: 1.

Embodiment C60. The multi-chain chimeric polypeptide of any one of embodiments C56-059, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment C61. The multi-chain chimeric polypeptide of embodiment C60, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment C62. The multi-chain chimeric polypeptide of any one of embodiments C1-C61, wherein the soluble tissue factor domain is not capable of binding to Factor VIIa.

Embodiment C63. The multi-chain chimeric polypeptide of any one of embodiments C1-C62, wherein the soluble tissue factor domain does not convert inactive Factor X into Factor Xa.

Embodiment C64. The multi-chain chimeric polypeptide of any one of embodiments C1-C63, wherein the multi-chain chimeric polypeptide does not stimulate blood coagulation in a mammal.

Embodiment C65. The multi-chain chimeric polypeptide of any one of embodiments C1-C64, wherein the pair of affinity domains is a sushi domain from an alpha chain of human IL-15 receptor (IL15Rα) and a soluble IL-15.

Embodiment C66. The multi-chain chimeric polypeptide of embodiment C65, wherein the soluble IL15 has a D8N or D8A amino acid substitution.

Embodiment C67. The multi-chain chimeric polypeptide of embodiment C65 or C66, wherein the human IL15Rα is a mature full-length IL15Rα.

Embodiment C68. The multi-chain chimeric polypeptide of any one of embodiments C1-C64, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment C69. The multi-chain chimeric polypeptide of any one of embodiments C1-C68, wherein the first chimeric polypeptide and/or the second chimeric polypeptide further comprises a signal sequence at its N-terminal end.

Embodiment C70. A composition comprising any of the multi-chain chimeric polypeptides of embodiments C1-C69.

Embodiment C71. The composition of embodiment C70, wherein the composition is a pharmaceutical composition.

Embodiment C72. A kit comprising at least one dose of the composition of embodiment C70 or C71.

Embodiment C73. Nucleic acid encoding any of the multi-chain chimeric polypeptides of any one of embodiments C1-C69.

Embodiment C74. A vector comprising the nucleic acid of embodiment C73.

Embodiment C75. The vector of embodiment C74, wherein the vector is an expression vector.

Embodiment C76. A cell comprising the nucleic acid of embodiment C73 or the vector of embodiment C74 or C75.

Embodiment C77. A method of producing a multi-chain chimeric polypeptide, the method comprising:

culturing the cell of embodiment C76 in a culture medium under conditions sufficient to result in the production of the multi-chain chimeric polypeptide; and recovering the multi-chain chimeric polypeptide from the cell and/or the culture medium.

Embodiment C78. A multi-chain chimeric polypeptide produced by the method of embodiment C77.

Embodiment C79. The multi-chain chimeric polypeptide of embodiment A56, wherein the soluble human tissue factor domain comprises a sequence that is at least 80% identical to SEQ ID NO: 5.

Embodiment C80. The multi-chain chimeric polypeptide of embodiment C79, wherein the soluble human tissue factor domain comprises a sequence that is at least 90% identical to SEQ ID NO: 5.

Embodiment C81. The multi-chain chimeric polypeptide of embodiment C80, wherein the soluble human tissue factor domain comprises a sequence that is at least 95% identical to SEQ ID NO: 5.

Embodiment C82. The multi-chain chimeric polypeptide of embodiment C81, wherein the soluble human tissue factor domain comprises a sequence that is 100% identical to SEQ ID NO: 5.

Embodiment C83. The multi-chain chimeric polypeptide of embodiment C56, wherein the soluble human tissue factor domain comprises a sequence that is at least 80% identical to SEQ ID NO: 6.

Embodiment C84. The multi-chain chimeric polypeptide of embodiment C83, wherein the soluble human tissue factor domain comprises a sequence that is at least 90% identical to SEQ ID NO: 6.

Embodiment C85. The multi-chain chimeric polypeptide of embodiment C84, wherein the soluble human tissue factor domain comprises a sequence that is at least 95% identical to SEQ ID NO: 6.

Embodiment C86. The multi-chain chimeric polypeptide of embodiment C85, wherein the soluble human tissue factor domain comprises a sequence that is 100% identical to SEQ ID NO: 6.

Embodiment D1. A multi-chain chimeric polypeptide comprising:

(a) a first chimeric polypeptide comprising:
(i) a first target-binding domain;
(ii) a soluble tissue factor domain; and
(iii) a first domain of a pair of affinity domains;
(b) a second chimeric polypeptide comprising:
(i) a second domain of a pair of affinity domains; and
(ii) a second target-binding domain,
wherein:
the first chimeric polypeptide and the second chimeric polypeptide associate through the binding of the first domain and the second domain of the pair of affinity domains;
the first target-binding domain and the second targeting-binding domain each independently bind specifically to a receptor of IL-18 or a receptor of IL-12.

Embodiment D2. The multi-chain chimeric polypeptide of embodiment D1, wherein the first target-binding domain and the soluble tissue factor domain directly abut each other in the first chimeric polypeptide.

Embodiment D3. The multi-chain chimeric polypeptide of embodiment D1, wherein the first chimeric polypeptide further comprises a linker sequence between the first target-binding domain and the soluble tissue factor domain in the first chimeric polypeptide.

Embodiment D4. The multi-chain chimeric polypeptide of any one of embodiments D1-D3, wherein the soluble tissue factor domain and the first domain of the pair of affinity domains directly abut each other in the first chimeric polypeptide.

Embodiment D5. The multi-chain chimeric polypeptide of any one of embodiments D1-D3, wherein the first chimeric polypeptide further comprises a linker sequence between the soluble tissue factor domain and the first domain of the pair of affinity domains in the first chimeric polypeptide.

Embodiment D6. The multi-chain chimeric polypeptide of any one of embodiments D1-D5, wherein the second domain of the pair of affinity domains and the second target-binding domain directly abut each other in the second chimeric polypeptide.

Embodiment D7. The multi-chain chimeric polypeptide of any one of embodiments D1-D5, wherein second chimeric polypeptide further comprises a linker sequence between the second domain of the pair of affinity domains and the second target-binding domain in the second chimeric polypeptide.

Embodiment D8. The multi-chain chimeric polypeptide of any one of embodiments D1-D7, wherein the soluble tissue factor domain is a soluble human tissue factor domain.

Embodiment D9. The multi-chain chimeric polypeptide of embodiment D8, wherein the soluble human tissue factor domain comprises a sequence that is at least 80% identical to SEQ ID NO: 1.

Embodiment D10. The multi-chain chimeric polypeptide of embodiment D9, wherein the soluble human tissue factor domain comprises a sequence that is at least 90% identical to SEQ ID NO: 1.

Embodiment D11. The multi-chain chimeric polypeptide of embodiment D10, wherein the soluble human tissue factor domain comprises a sequence that is at least 95% identical to SEQ ID NO: 1.

Embodiment D12. The multi-chain chimeric polypeptide of any one of embodiments D8-D11, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment D13. The multi-chain chimeric polypeptide of embodiment D12, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment D14. The multi-chain chimeric polypeptide of any one of embodiments D1-D13, wherein the soluble tissue factor domain is not capable of binding to Factor VIIa.

Embodiment D15. The multi-chain chimeric polypeptide of any one of embodiments D1-D14, wherein the soluble tissue factor domain does not convert inactive Factor X into Factor Xa.

Embodiment D16. The multi-chain chimeric polypeptide of any one of embodiments D1-D15, wherein the multi-chain chimeric polypeptide does not stimulate blood coagulation in a mammal.

Embodiment D17. The multi-chain chimeric polypeptide of any one of embodiments D1-D16, wherein the first chimeric polypeptide further comprises a peptide tag at the N-terminal end or the C-terminal end of the first chimeric polypeptide.

Embodiment D18. The multi-chain chimeric polypeptide of any one of embodiments D1-D17, wherein the second chimeric polypeptide further comprises a peptide tag at the N-terminal end or the C-terminal end of the second chimeric polypeptide.

Embodiment D19. The multi-chain chimeric polypeptide of any one of embodiments D1-D18, wherein the first chimeric polypeptide and/or the second chimeric polypeptide further comprises a signal sequence at its N-terminal end.

Embodiment D20. The multi-chain chimeric polypeptide of embodiment D19, wherein the signal sequence comprises SEQ ID NO: 62.

Embodiment D21. The multi-chain chimeric polypeptide of embodiment D20, wherein the signal sequence is SEQ ID NO: 62.

Embodiment D22. The multi-chain chimeric polypeptide of any one of embodiments D1-D21, wherein the pair of affinity domains is a sushi domain from an alpha chain of human IL-15 receptor (IL15Rα) and a soluble IL-15.

Embodiment D23. The multi-chain chimeric polypeptide of embodiment D22, wherein the soluble IL-15 has a D8N or D8A amino acid substitution.

Embodiment D24. The multi-chain chimeric polypeptide of embodiment D22, wherein the soluble IL-15 comprises a sequence that is 80% identical to SEQ ID NO: 39.

Embodiment D25. The multi-chain chimeric polypeptide of embodiment D24, wherein the soluble IL-15 comprises a sequence that is 90% identical to SEQ ID NO: 39.

Embodiment D26. The multi-chain chimeric polypeptide of embodiment D25, wherein the soluble IL-15 comprises a sequence that is 95% identical to SEQ ID NO: 39.

Embodiment D27. The multi-chain chimeric polypeptide of embodiment D26, wherein the soluble IL-15 comprises SEQ ID NO: 39.

Embodiment D28. The multi-chain chimeric polypeptide of any one of embodiments D22-D27, wherein the sushi domain of IL15Rα comprises a sushi domain from human IL15Rα.

Embodiment D29. The multi-chain chimeric polypeptide of embodiment D28, wherein the sushi domain from human IL15Rα comprises a sequence that is 80% identical to SEQ ID NO: 10.

Embodiment D30. The multi-chain chimeric polypeptide of embodiment D29, wherein the sushi domain from human IL15Rα comprises a sequence that is 90% identical to SEQ ID NO: 10.

Embodiment D31. The multi-chain chimeric polypeptide of embodiment D30, wherein the sushi domain from human IL15Rα comprises a sequence that is 95% identical to SEQ ID NO: 10.

Embodiment D32. The multi-chain chimeric polypeptide of embodiment D31, wherein the sushi domain from human IL15Rα comprises SEQ ID NO: 10.

Embodiment D33. The multi-chain chimeric polypeptide of embodiment D28, wherein the sushi domain from human IL15Rα is a mature full-length IL15Rα.

Embodiment D34. The multi-chain chimeric polypeptide of any one of embodiments D1-D21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment D35. The multi-chain chimeric polypeptide of any one of embodiments D1-D34, wherein one or both of the first target-binding domain and the second target-binding domain is an agonistic antigen-binding domain.

Embodiment D36. The multi-chain chimeric polypeptide of embodiment D35, wherein the first target-binding domain and the second target-binding domain are each agonistic antigen-binding domains.

Embodiment D37. The multi-chain chimeric polypeptide of embodiment D35 or D36, wherein antigen-binding domain comprises a scFv or single-domain antibody.

Embodiment D38. The multi-chain chimeric polypeptide of any one of embodiments D1-D34, wherein one or both of the first target-binding domain and the second target-binding domain is a soluble IL-15 or a soluble IL-18.

Embodiment D39. The multi-chain chimeric polypeptide of embodiment D38, wherein the first target-binding domain and the second target-binding domain are each independently a soluble IL-15 or a soluble IL-18.

Embodiment D40. The multi-chain chimeric polypeptide of any one of embodiments D1-D39, wherein the first target-binding domain and the second target-binding domain both bind specifically to a receptor of IL-18 or a receptor of IL-12.

Embodiment D41. The multi-chain chimeric polypeptide of embodiment B40, wherein the first target-binding domain and the second target-binding domain bind specifically to the same epitope.

Embodiment D42. The multi-chain chimeric polypeptide of embodiment D41, wherein the first target-binding domain and the second target-binding domain comprise the same amino acid sequence.

Embodiment D43. The multi-chain chimeric polypeptide of any one of embodiments D1-D39, wherein the first target-binding domain binds specifically to a receptor for IL-12, and the second target-binding domain binds specifically to a receptor for IL-18.

Embodiment D44. The multi-chain chimeric polypeptide of any one of embodiments D1-D39, wherein the first target-binding domain binds specifically to a receptor for IL-18, and the second target-binding domain bind specifically to a receptor for IL-12.

Embodiment D45. The multi-chain chimeric polypeptide of embodiment D44, wherein the first target-binding domain comprises a soluble IL-18.

Embodiment D46. The multi-chain chimeric polypeptide of embodiment D45, wherein the soluble IL-18 is a soluble human IL-18.

Embodiment D47. The multi-chain chimeric polypeptide of embodiment D46, wherein the soluble human IL-18 comprises a sequence at least 80% identical to SEQ ID NO: 41.

Embodiment D48. The multi-chain chimeric polypeptide of embodiment D47, wherein the soluble human IL-18 comprises a sequence at least 90% identical to SEQ ID NO: 41.

Embodiment D49. The multi-chain chimeric polypeptide of embodiment D48, wherein the soluble human IL-18 comprises a sequence at least 95% identical to SEQ ID NO: 41.

Embodiment D50. The multi-chain chimeric polypeptide of embodiment D49, wherein the soluble human IL-18 comprises a sequence of SEQ ID NO: 41.

Embodiment D51. The multi-chain chimeric polypeptide of any one of embodiments D44-D50, wherein the second target-binding domain comprises a soluble IL-12.

Embodiment D52. The multi-chain chimeric polypeptide of embodiment D51, wherein the soluble IL-18 is a soluble human IL-12.

Embodiment D53. The multi-chain chimeric polypeptide of embodiment D52, wherein the soluble human IL-15 comprises a sequence of soluble human IL-12β (p40) and a sequence of soluble human IL-12α (p35).

Embodiment D54. The multi-chain chimeric polypeptide of embodiment D53, wherein the soluble human IL-15 further comprises a linker sequence between the sequence of soluble IL-12 (p40) and the sequence of soluble human IL-12α (p35).

Embodiment D55. The multi-chain chimeric polypeptide of embodiment D54, wherein the linker sequence comprises SEQ ID NO: 7.

Embodiment D56. The multi-chain chimeric polypeptide of any one of embodiments D53-D55, wherein the sequence of soluble human IL-12β (p40) comprises a sequence that is at least 80% identical to SEQ ID NO: 33.

Embodiment D57. The multi-chain chimeric polypeptide of embodiment D56, wherein the sequence of soluble human IL-12β (p40) comprises a sequence that is at least 90% identical to SEQ ID NO: 33.

Embodiment D58. The multi-chain chimeric polypeptide of embodiment D57, wherein the sequence of soluble human IL-12β (p40) comprises a sequence that is at least 95% identical to SEQ ID NO: 33.

Embodiment D59. The multi-chain chimeric polypeptide of embodiment D58, wherein the sequence of soluble human IL-12β (p40) comprises SEQ ID NO: 33.

Embodiment D60. The multi-chain chimeric polypeptide of any one of embodiments D53-D59, wherein the sequence of soluble human IL-12α (p35) comprises a sequence that is at least 80% identical to SEQ ID NO: 35.

Embodiment D61. The multi-chain chimeric polypeptide of embodiment D60, wherein the sequence of soluble human IL-12α (p35) comprises a sequence that is at least 90% identical to SEQ ID NO: 35.

Embodiment D62. The mule-chain chimeric polypeptide of embodiment D61, wherein the sequence of soluble human IL-12α (p35) comprises a sequence that is at least 95% identical to SEQ ID NO: 35.

Embodiment D63. The multi-chain chimeric polypeptide of embodiment D62, wherein the sequence of soluble human IL-12α (p35) comprises SEQ ID NO: 35.

Embodiment D64. The multi-chain chimeric polypeptide of embodiment D1, wherein the first chimeric polypeptide comprises a sequence that is at least 80% identical to SEQ ID NO: 116.

Embodiment D65. The multi-chain chimeric polypeptide of embodiment D64, wherein the first chimeric polypeptide comprises a sequence that is at least 90% identical to SEQ ID NO: 116.

Embodiment D66. The multi-chain chimeric polypeptide of embodiment D65, wherein the first chimeric polypeptide comprises a sequence that is at least 95% identical to SEQ ID NO: 116.

Embodiment D67. The multi-chain chimeric polypeptide of embodiment D66, wherein the first chimeric polypeptide comprises SEQ ID NO: 116.

Embodiment D68. The multi-chain chimeric polypeptide of embodiment D67, wherein the first chimeric polypeptide comprises SEQ ID NO: 118.

Embodiment D69. The multi-chain chimeric polypeptide of any one of embodiments D1 and D64-D68, wherein the second chimeric polypeptide comprises a sequence that is at least 80% identical to SEQ ID NO: 120.

Embodiment D70. The multi-chain chimeric polypeptide of embodiment D69, wherein the second chimeric polypeptide comprises a sequence that is at least 90% identical to SEQ ID NO: 120.

Embodiment D71. The multi-chain chimeric polypeptide of embodiment D70, wherein the second chimeric polypeptide comprises a sequence that is at least 95% identical to SEQ ID NO: 120.

Embodiment D72. The multi-chain chimeric polypeptide of embodiment D71, wherein the second chimeric polypeptide comprises SEQ ID NO: 120.

Embodiment D73. The multi-chain chimeric polypeptide of embodiment D72, wherein the second chimeric polypeptide comprises SEQ ID NO: 122.

Embodiment D74. The multi-chain chimeric polypeptide of any one of embodiments D1-D63, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment D75. The multi-chain chimeric polypeptide of embodiment D74, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment D76. The multi-chain chimeric polypeptide of any one of embodiments D1-D63, wherein the first chimeric polypeptide further comprises one or more additional target-binding domains at the N-terminal and/or C-terminal end of the first chimeric polypeptide.

Embodiment D77. The multi-chain chimeric polypeptide of embodiment D76, wherein at least one of the one or more additional target-binding domains directly abuts the first domain of the pair of affinity domains in the first chimeric polypeptide.

Embodiment D78. The multi-chain chimeric polypeptide of embodiment D76, wherein the first chimeric polypeptide further comprises a linker sequence between the at least one of the one or more additional target-binding domains and the first domain of the pair of affinity domains.

Embodiment D79. The multi-chain chimeric polypeptide of embodiment D76, wherein the at least one of the one or more additional target-binding domains directly abuts the first target-binding domain in the first chimeric polypeptide.

Embodiment D80. The multi-chain chimeric polypeptide of embodiment D76, wherein the first chimeric polypeptide further comprises a linker sequence between the at least one of the one or more additional target-binding domains and the first target-binding domain.

Embodiment D81. The multi-chain chimeric polypeptide of embodiment D76, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment D82. The multi-chain chimeric polypeptide of embodiment D81, wherein the at least one additional target-binding domain of the one or more additional target-binding domains disposed at the N-terminus directly abuts the first target-binding domain or the first domain of the pair of affinity domains in the first chimeric polypeptide.

Embodiment D83. The multi-chain chimeric polypeptide of embodiment D81, wherein the first chimeric polypeptide further comprises a linker sequence disposed between the at least one additional target-binding domain and the first target-binding domain or the first domain of the pair of affinity domains in the first chimeric polypeptide.

Embodiment D84. The multi-chain chimeric polypeptide of embodiment D81, wherein the at least one additional target-binding domain of the one or more additional target-binding domains disposed at the C-terminus directly abuts the first target-binding domain or the first domain of the pair of affinity domains in the first chimeric polypeptide.

Embodiment D85. The multi-chain chimeric polypeptide of embodiment D81, wherein the first chimeric polypeptide further comprises a linker sequence disposed between the at least one additional target-binding domain and the first target-binding domain or the first domain of the pair of affinity domains in the first chimeric polypeptide.

Embodiment D86. The multi-chain chimeric polypeptide of embodiment D81, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment D87. The multi-chain chimeric polypeptide of embodiment D81, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment D88. The multi-chain chimeric polypeptide of any one of embodiments D1-D63 and D74-D87, wherein the second chimeric polypeptide further comprises one or more additional target-binding domains at the N-terminal end or the C-terminal end of the second chimeric polypeptide.

Embodiment D89. The multi-chain chimeric polypeptide of embodiment D88, wherein at least one of the one or more additional target-binding domains directly abuts the second domain of the pair of affinity domains in the second chimeric polypeptide.

Embodiment D90. The multi-chain chimeric polypeptide of embodiment D88, wherein the second chimeric polypeptide further comprises a linker sequence between at least one of the one or more additional target-binding domains and the second domain of the pair of affinity domains in the second chimeric polypeptide.

Embodiment D91. The multi-chain chimeric polypeptide of embodiment D88, wherein at least one of the one or more additional target-binding domains directly abuts the second target-binding domain in the second chimeric polypeptide.

Embodiment D92. The multi-chain chimeric polypeptide of embodiment D88, wherein the second chimeric polypeptide further comprises a linker sequence between at least one of the one or more additional target-binding domains and the second target-binding domain in the second chimeric polypeptide.

Embodiment D93. The multi-chain chimeric polypeptide of any one of embodiments D74-D92, wherein two or more of the first target-binding domain, the second target-binding domain, and the one or more additional target-binding domains bind specifically to the same antigen.

Embodiment D94. The multi-chain chimeric polypeptide of embodiment D93, wherein two or more of the first target-binding domain, the second target-binding domain, and the one or more additional target-binding domains bind specifically to the same epitope.

Embodiment D95. The multi-chain chimeric polypeptide of embodiment D94, wherein two or more of the first target-binding domain, the second target-binding domain, and the one or more additional target-binding domains comprise the same amino acid sequence.

Embodiment D96. The multi-chain chimeric polypeptide of any one of embodiments D74-D92, wherein the first target-binding domain, the second target-binding domain, and the one or more additional target-binding domains bind specifically to different antigens.

Embodiment D97. The multi-chain chimeric polypeptide of any one of embodiments D74-D96, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment D98. The multi-chain chimeric polypeptide of any one of embodiments D74-D96, wherein the one or more additional target-binding domains is a soluble interleukin, soluble cytokine protein, or soluble cell surface protein.

Embodiment D99. The multi-chain chimeric polypeptide of embodiment D98, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment D100. The multi-chain chimeric polypeptide of any one of embodiments D74-D96, wherein the one or more additional target-binding domains is a soluble interleukin receptor, soluble cytokine receptor, or soluble cell surface receptor.

Embodiment D101. The multi-chain chimeric polypeptide of embodiment D100, wherein the soluble receptor is a soluble TGF-β receptor II (TGF-β RII), a soluble TGF-βRIII, a soluble NKG2D, a soluble NKP30, a soluble NKp44, a soluble NKp46, a soluble DNAM-1, a scMHCI, a scMHCII, a scTCR, a soluble CD155, a soluble CD122, or a soluble CD28.

Embodiment D102. A composition comprising any of the multi-chain chimeric polypeptides of embodiments D1-D101.

Embodiment D103. The composition of embodiment D102, wherein the composition is a pharmaceutical composition.

Embodiment D104. A kit comprising at least one dose of the composition of embodiment D102 or D103.

Embodiment D105. Nucleic acid encoding any of the multi-chain chimeric polypeptides of any one of embodiments D1-D101.

Embodiment D106. A vector comprising the nucleic acid of embodiment D105.

Embodiment D107. The vector of embodiment D106, wherein the vector is an expression vector.

Embodiment D108. A cell comprising the nucleic acid of embodiment D105 or the vector of embodiment D106 or D107.

Embodiment D109. A method of producing a multi-chain chimeric polypeptide, the method comprising:
culturing the cell of embodiment D108 in a culture medium under conditions sufficient to result in the production of the multi-chain chimeric polypeptide; and
recovering the multi-chain chimeric polypeptide from the cell and/or the culture medium.

Embodiment D110. A multi-chain chimeric polypeptide produced by the method of embodiment D109.

Embodiment D111. The multi-chain chimeric polypeptide of embodiment D8, wherein the soluble human tissue factor domain comprises a sequence that is at least 80% identical to SEQ ID NO: 5.

Embodiment D112. The multi-chain chimeric polypeptide of embodiment D111, wherein the soluble human tissue factor domain comprises a sequence that is at least 90% identical to SEQ ID NO: 5.

Embodiment D113. The multi-chain chimeric polypeptide of embodiment D112, wherein the soluble human tissue factor domain comprises a sequence that is at least 95% identical to SEQ ID NO: 5.

Embodiment D114. The multi-chain chimeric polypeptide of embodiment D113, wherein the soluble human tissue factor domain comprises a sequence that is 100% identical to SEQ ID NO: 5.

Embodiment D115. The multi-chain chimeric polypeptide of embodiment D8, wherein the soluble human tissue factor domain comprises a sequence that is at least 80% identical to SEQ ID NO: 6.

Embodiment D116. The multi-chain chimeric polypeptide of embodiment D115, wherein the soluble human tissue factor domain comprises a sequence that is at least 90% identical to SEQ ID NO: 6.

Embodiment D117. The multi-chain chimeric polypeptide of embodiment D116, wherein the soluble human tissue factor domain comprises a sequence that is at least 95% identical to SEQ ID NO: 6.

Embodiment D118. The multi-chain chimeric polypeptide of embodiment D117, wherein the soluble human tissue factor domain comprises a sequence that is 100% identical to SEQ ID NO: 6.

Embodiment E1. A multi-chain chimeric polypeptide comprising:
(a) a first chimeric polypeptide comprising:
(i) a first target-binding domain;
(ii) a soluble tissue factor domain; and
(iii) a first domain of a pair of affinity domains;
(b) a second chimeric polypeptide comprising:
(i) a second domain of a pair of affinity domains; and
(ii) a second target-binding domain,
wherein:
the first chimeric polypeptide and the second chimeric polypeptide associate through the binding of the first domain and the second domain of the pair of affinity domains; and
the first target-binding domain and the second targeting-binding domain each independently bind specifically to a receptor of IL-21 or a ligand of tumor growth factor receptor β II (TGFβRII).

Embodiment E2. The multi-chain chimeric polypeptide of embodiment E1, wherein the first target-binding domain and the soluble tissue factor domain directly abut each other in the first chimeric polypeptide.

Embodiment E3. The multi-chain chimeric polypeptide of embodiments E1, wherein the first chimeric polypeptide further comprises a linker sequence between the first target-binding domain and the soluble tissue factor domain in the first chimeric polypeptide.

Embodiment E4. The multi-chain chimeric polypeptide of any one of embodiments E1-E3, wherein the soluble tissue factor domain and the first domain of the pair of affinity domains directly abut each other in the first chimeric polypeptide.

Embodiment E5. The multi-chain chimeric polypeptide of any one of embodiments E1-E3, wherein the first chimeric polypeptide further comprises a linker sequence between the soluble tissue factor domain and the first domain of the pair of affinity domains in the first chimeric polypeptide.

Embodiment E6. The multi-chain chimeric polypeptide of any one of embodiments E1-E5, wherein the second domain of the pair of affinity domains and the second target-binding domain directly abut each other in the second chimeric polypeptide.

Embodiment E7. The multi-chain chimeric polypeptide of any one of embodiments E1-E5, wherein second chimeric polypeptide further comprises a linker sequence between the second domain of the pair of affinity domains and the second target-binding domain in the second chimeric polypeptide.

Embodiment E8. The multi-chain chimeric polypeptide of any one of embodiments E1-E7, wherein the soluble tissue factor domain is a soluble human tissue factor domain.

Embodiment E9. The multi-chain chimeric polypeptide of embodiment E8, wherein the soluble human tissue factor domain comprises a sequence that is at least 80% identical to SEQ ID NO: 1.

Embodiment E10. The multi-chain chimeric polypeptide of embodiment E9, wherein the soluble human tissue factor domain comprises a sequence that is at least 90% identical to SEQ ID NO: 1.

Embodiment E11. The multi-chain chimeric polypeptide of embodiment E10, wherein the soluble human tissue factor domain comprises a sequence that is at least 95% identical to SEQ ID NO: 1.

Embodiment E12. The multi-chain chimeric polypeptide of any one of embodiments E8-E11, wherein the soluble human tissue factor domain does not comprise one or more of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment E13. The multi-chain chimeric polypeptide of embodiment E12, wherein the soluble human tissue factor domain does not comprise any of:
a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment E14. The multi-chain chimeric polypeptide of any one of embodiments E1-E13, wherein the soluble tissue factor domain is not capable of binding to Factor VIIa.

Embodiment E15. The multi-chain chimeric polypeptide of any one of embodiments E1-E14, wherein the soluble tissue factor domain does not convert inactive Factor X into Factor Xa.

Embodiment E16. The multi-chain chimeric polypeptide of any one of embodiments E1-E15, wherein the multi-chain chimeric polypeptide does not stimulate blood coagulation in a mammal.

Embodiment E17. The multi-chain chimeric polypeptide of any one of embodiments E1-E16, wherein the first chimeric polypeptide further comprises a peptide tag at the N-terminal end or the C-terminal end of the first chimeric polypeptide.

Embodiment E18. The multi-chain chimeric polypeptide of any one of embodiments E1-E17, wherein the second chimeric polypeptide further comprises a peptide tag at the N-terminal end or the C-terminal end of the second chimeric polypeptide.

Embodiment E19. The multi-chain chimeric polypeptide of any one of embodiments E1-E18, wherein the first chimeric polypeptide and/or the second chimeric polypeptide further comprises a signal sequence at its N-terminal end.

Embodiment E20. The multi-chain chimeric polypeptide of embodiment E19, wherein the signal sequence comprises SEQ ID NO: 62.

Embodiment E21. The multi-chain chimeric polypeptide of embodiment E20, wherein the signal sequence is SEQ ID NO: 62.

Embodiment E22. The multi-chain chimeric polypeptide of any one of embodiments E1-E21, wherein the pair of affinity domains is a sushi domain from an alpha chain of human IL-15 receptor (IL15Rα and a soluble IL-15.

Embodiment E23. The multi-chain chimeric polypeptide of embodiment E22, wherein the soluble IL-15 has a D8N or D8A amino acid substitution.

Embodiment E24. The multi-chain chimeric polypeptide of embodiment E22, wherein the soluble IL-15 comprises a sequence that is 80% identical to SEQ ID NO: 39.

Embodiment E25. The multi-chain chimeric polypeptide of embodiment E24, wherein the soluble IL-15 comprises a sequence that is 90% identical to SEQ ID NO: 39.

Embodiment E26. The multi-chain chimeric polypeptide of embodiment E25, wherein the soluble IL-15 comprises a sequence that is 95% identical to SEQ ID NO: 39.

Embodiment E27. The multi-chain chimeric polypeptide of embodiment E26, wherein the soluble IL-15 comprises SEQ ID NO: 39.

Embodiment E28. The multi-chain chimeric polypeptide of any one of embodiments E22-E27, wherein the sushi domain of IL15Rα comprises a sushi domain from human IL15Rα.

Embodiment E29. The multi-chain chimeric polypeptide of embodiment E28, wherein the sushi domain from human IL15Rα comprises a sequence that is 80% identical to SEQ ID NO: 10.

Embodiment E30. The multi-chain chimeric polypeptide of embodiment E29, wherein the sushi domain from human IL15Rα comprises a sequence that is 90% identical to SEQ ID NO: 10.

Embodiment E31. The multi-chain chimeric polypeptide of embodiment E30, wherein the sushi domain from human IL15Rα comprises a sequence that is 95% identical to SEQ ID NO: 10.

Embodiment E32. The multi-chain chimeric polypeptide of embodiment E31, wherein the sushi domain from human IL15Rα comprises SEQ ID NO: 10.

Embodiment E33. The multi-chain chimeric polypeptide of embodiment E28, wherein the sushi domain from human IL15Rα is a mature full-length IL15Rα.

Embodiment E34. The multi-chain chimeric polypeptide of any one of embodiments E1-E21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment E35. The multi-chain chimeric polypeptide of any one of embodiments E1-E34, wherein one or both of the first target-binding domain and the second target-binding domain is an antigen-binding domain.

Embodiment E36. The multi-chain chimeric polypeptide of embodiment E35, wherein the first target-binding domain and the second target-binding domain are antigen-binding domains.

Embodiment E37. The multi-chain chimeric polypeptide of embodiment E35 or E36, wherein antigen-binding domain comprises a scFv or single-domain antibody.

Embodiment E38. The multi-chain chimeric polypeptide of any one of embodiments E1-E34, wherein one or both of the first target-binding domain and the second target-binding domain is a soluble IL-21 or a soluble TGFβRII.

Embodiment E39. The multi-chain chimeric polypeptide of any one of embodiments E1-E38, wherein the first target-binding domain and the second target-binding domain both bind specifically to a receptor of IL-21 or a ligand of TGFβRII.

Embodiment E40. The multi-chain chimeric polypeptide of embodiment E39, wherein the first target-binding domain and the second target-binding domain bind specifically to the same epitope.

Embodiment E41. The multi-chain chimeric polypeptide of embodiment E40, wherein the first target-binding domain and the second target-binding domain comprise the same amino acid sequence.

Embodiment E42. The multi-chain chimeric polypeptide of any one of embodiments E1-E38, wherein the first target-binding domain binds specifically to a ligand of TGFβRII, and the second target-binding domain binds specifically to a receptor for IL-21.

Embodiment E43. The multi-chain chimeric polypeptide of any one of embodiments E1-E38, wherein the first target-binding domain binds specifically to a receptor for IL-21, and the second target-binding domain bind specifically to a ligand of TGFβRII.

Embodiment E44. The multi-chain chimeric polypeptide of embodiment E43, wherein the first target-binding domain comprises a soluble IL-21.

Embodiment E45. The multi-chain chimeric polypeptide of embodiment E44, wherein the soluble IL-21 is a soluble human IL-21.

Embodiment E46. The multi-chain chimeric polypeptide of embodiment E45, wherein the soluble human IL-21 comprises a sequence at least 80% identical to SEQ ID NO: 124.

Embodiment E47. The multi-chain chimeric polypeptide of embodiment E46, wherein the soluble human IL-21 comprises a sequence at least 90% identical to SEQ ID NO: 124.

Embodiment E48. The multi-chain chimeric polypeptide of embodiment E47, wherein the soluble human IL-21 comprises a sequence at least 95% identical to SEQ ID NO: 124.

Embodiment E49. The multi-chain chimeric polypeptide of embodiment E48, wherein the soluble human IL-21 comprises a sequence of SEQ ID NO: 124.

Embodiment E50. The multi-chain chimeric polypeptide of any one of embodiments E43-E49, wherein the second target-binding domain comprises a soluble TGFβRII.

Embodiment E51. The multi-chain chimeric polypeptide of embodiment E50, wherein the soluble TGFβRII is a soluble human TGFβRII.

Embodiment E52. The multi-chain chimeric polypeptide of embodiment E51, wherein the soluble human TGFβRII comprises a first sequence of soluble human TGFβRII and a second sequence of soluble human TGFβRII.

Embodiment E53. The multi-chain chimeric polypeptide of embodiment E52, wherein the soluble human TGFβRII further comprises a linker sequence between the first sequence of soluble human TGFβRII and the second sequence of soluble human TGFβRII.

Embodiment E54. The multi-chain chimeric polypeptide of embodiment E53, wherein the linker sequence comprises SEQ ID NO: 7.

Embodiment E55. The multi-chain chimeric polypeptide of any one of embodiments E52-E54, wherein the first sequence of soluble human TGFβRII comprises a sequence that is at least 80% identical to SEQ ID NO: 56.

Embodiment E56. The multi-chain chimeric polypeptide of embodiment E55, wherein the first sequence of soluble human TGFβRII comprises a sequence that is at least 90% identical to SEQ ID NO: 56.

Embodiment E57. The multi-chain chimeric polypeptide of embodiment E56, wherein the first sequence of soluble human TGFβRII comprises a sequence that is at least 95% identical to SEQ ID NO: 56.

Embodiment E58. The multi-chain chimeric polypeptide of embodiment E57, wherein the first sequence of soluble human TGFβRII comprises SEQ ID NO: 56.

Embodiment E59. The multi-chain chimeric polypeptide of any one of embodiments E52-E58, wherein the second sequence of soluble human TGFβRII comprises a sequence that is at least 80% identical to SEQ ID NO: 56.

Embodiment E60. The multi-chain chimeric polypeptide of embodiment E59, wherein the second sequence of soluble human TGFβRII comprises a sequence that is at least 90% identical to SEQ ID NO: 56.

Embodiment E61. The mule-chain chimeric polypeptide of embodiment E60, wherein the second sequence of soluble human TGFβRII comprises a sequence that is at least 95% identical to SEQ ID NO: 56.

Embodiment E62. The multi-chain chimeric polypeptide of embodiment E61, wherein the second sequence of soluble human TGFβRII comprises SEQ ID NO: 56.

Embodiment E63. The multi-chain chimeric polypeptide of embodiment E1, wherein the first chimeric polypeptide comprises a sequence that is at least 80% identical to SEQ ID NO: 126.

Embodiment E64. The multi-chain chimeric polypeptide of embodiment E63, wherein the first chimeric polypeptide comprises a sequence that is at least 90% identical to SEQ ID NO: 126.

Embodiment E65. The multi-chain chimeric polypeptide of embodiment E64, wherein the first chimeric polypeptide comprises a sequence that is at least 95% identical to SEQ ID NO: 126.

Embodiment E66. The multi-chain chimeric polypeptide of embodiment E65, wherein the first chimeric polypeptide comprises SEQ ID NO: 126.

Embodiment E67. The multi-chain chimeric polypeptide of embodiment E66, wherein the first chimeric polypeptide comprises SEQ ID NO: 128.

Embodiment E68. The multi-chain chimeric polypeptide of any one of embodiments E1 and E63-E67, wherein the second chimeric polypeptide comprises a sequence that is at least 80% identical to SEQ ID NO: 130.

Embodiment E69. The multi-chain chimeric polypeptide of embodiment E68, wherein the second chimeric polypeptide comprises a sequence that is at least 90% identical to SEQ ID NO: 130.

Embodiment E70. The multi-chain chimeric polypeptide of embodiment E69, wherein the second chimeric polypeptide comprises a sequence that is at least 95% identical to SEQ ID NO: 130.

Embodiment E71. The multi-chain chimeric polypeptide of embodiment E70, wherein the second chimeric polypeptide comprises SEQ ID NO: 130.

Embodiment E72. The multi-chain chimeric polypeptide of embodiment E71, wherein the second chimeric polypeptide comprises SEQ ID NO: 132.

Embodiment E73. The multi-chain chimeric polypeptide of any one of embodiments E1-E62, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment E74. The multi-chain chimeric polypeptide of embodiment E73, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment E75. The multi-chain chimeric polypeptide of any one of embodiments E1-E62, wherein the first chimeric polypeptide further comprises one or more additional target-binding domains at the N-terminal and/or C-terminal end of the first chimeric polypeptide.

Embodiment E76. The multi-chain chimeric polypeptide of embodiment E75, wherein at least one of the one or more additional target-binding domains directly abuts the first domain of the pair of affinity domains in the first chimeric polypeptide.

Embodiment E77. The multi-chain chimeric polypeptide of embodiment E75, wherein the first chimeric polypeptide further comprises a linker sequence between the at least one of the one or more additional target-binding domains and the first domain of the pair of affinity domains.

Embodiment E78. The multi-chain chimeric polypeptide of embodiment E75, wherein the at least one of the one or more additional target-binding domains directly abuts the first target-binding domain in the first chimeric polypeptide.

Embodiment E79. The multi-chain chimeric polypeptide of embodiment E75, wherein the first chimeric polypeptide further comprises a linker sequence between the at least one of the one or more additional target-binding domains and the first target-binding domain.

Embodiment E80. The multi-chain chimeric polypeptide of embodiment E75, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment E81. The multi-chain chimeric polypeptide of embodiment E80, wherein the at least one additional target-binding domain of the one or more additional target-binding domains disposed at the N-terminus directly abuts the first target-binding domain or the first domain of the pair of affinity domains in the first chimeric polypeptide.

Embodiment E82. The multi-chain chimeric polypeptide of embodiment E80, wherein the first chimeric polypeptide further comprises a linker sequence disposed between the at least one additional target-binding domain and the first target-binding domain or the first domain of the pair of affinity domains in the first chimeric polypeptide.

Embodiment E83. The multi-chain chimeric polypeptide of embodiment E80, wherein the at least one additional target-binding domain of the one or more additional target-binding domains disposed at the C-terminus directly abuts the first target-binding domain or the first domain of the pair of affinity domains in the first chimeric polypeptide.

Embodiment E84. The multi-chain chimeric polypeptide of embodiment E80, wherein the first chimeric polypeptide further comprises a linker sequence disposed between the at least one additional target-binding domain and the first target-binding domain or the first domain of the pair of affinity domains in the first chimeric polypeptide.

Embodiment E85. The multi-chain chimeric polypeptide of embodiment E80, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment E86. The multi-chain chimeric polypeptide of embodiment E80, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment E87. The multi-chain chimeric polypeptide of any one of embodiments E1-E62 and E73-E86, wherein the second chimeric polypeptide further comprises one or more additional target-binding domains at the N-terminal end or the C-terminal end of the second chimeric polypeptide.

Embodiment E88. The multi-chain chimeric polypeptide of embodiment E87, wherein at least one of the one or more additional target-binding domains directly abuts the second domain of the pair of affinity domains in the second chimeric polypeptide.

Embodiment E89. The multi-chain chimeric polypeptide of embodiment E87, wherein the second chimeric polypeptide further comprises a linker sequence between at least one of the one or more additional target-binding domains and the second domain of the pair of affinity domains in the second chimeric polypeptide.

Embodiment E90. The multi-chain chimeric polypeptide of embodiment E87, wherein at least one of the one or more additional target-binding domains directly abuts the second target-binding domain in the second chimeric polypeptide.

Embodiment E91. The multi-chain chimeric polypeptide of embodiment E87, wherein the second chimeric polypeptide further comprises a linker sequence between at least one of the one or more additional target-binding domains and the second target-binding domain in the second chimeric polypeptide.

Embodiment E92. The multi-chain chimeric polypeptide of any one of embodiments E73-E91, wherein two or more of the first target-binding domain, the second target-binding domain, and the one or more additional target-binding domains bind specifically to the same antigen.

Embodiment E93. The multi-chain chimeric polypeptide of embodiment E92, wherein two or more of the first target-binding domain, the second target-binding domain, and the one or more additional target-binding domains bind specifically to the same epitope.

Embodiment E94. The multi-chain chimeric polypeptide of embodiment E93, wherein two or more of the first target-binding domain, the second target-binding domain, and the one or more additional target-binding domains comprise the same amino acid sequence.

Embodiment E95. The multi-chain chimeric polypeptide of any one of embodiments E73-E91, wherein the first target-binding domain, the second target-binding domain, and the one or more additional target-binding domains bind specifically to different antigens.

Embodiment E96. The multi-chain chimeric polypeptide of any one of embodiments E73-E95, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-D, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment E97. The multi-chain chimeric polypeptide of any one of embodiments E73-E95, wherein the one or more additional target-binding domains is a soluble interleukin, soluble cytokine protein, or soluble cell surface protein.

Embodiment E98. The multi-chain chimeric polypeptide of embodiment E97, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment E99. The multi-chain chimeric polypeptide of any one of embodiments E73-E95, wherein the one or more additional target-binding domains is a soluble interleukin or cytokine receptor.

Embodiment E100. The multi-chain chimeric polypeptide of embodiment E99, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment E101. A composition comprising any of the multi-chain chimeric polypeptides of embodiments E1-E100.

Embodiment E102. The composition of embodiment E101, wherein the composition is a pharmaceutical composition.

Embodiment E103. A kit comprising at least one dose of the composition of embodiment E101 or E102.

Embodiment E104. Nucleic acid encoding any of the multi-chain chimeric polypeptides of any one of embodiments E1-E100.

Embodiment E105. A vector comprising the nucleic acid of embodiment E104.

Embodiment E106. The vector of embodiment E105, wherein the vector is an expression vector.

Embodiment E107. A cell comprising the nucleic acid of embodiment C161 or the vector of embodiment E105 or E106.

Embodiment E108. A method of producing a multi-chain chimeric polypeptide, the method comprising:
culturing the cell of embodiment E107 in a culture medium under conditions sufficient to result in the production of the multi-chain chimeric polypeptide; and
recovering the multi-chain chimeric polypeptide from the cell and/or the culture medium.

Embodiment E109. A multi-chain chimeric polypeptide produced by the method of embodiment E108.

Embodiment E110. The multi-chain chimeric polypeptide of embodiment E12, wherein the soluble human tissue factor domain comprises a sequence that is at least 80% identical to SEQ ID NO: 5.

Embodiment E111. The multi-chain chimeric polypeptide of embodiment E110, wherein the soluble human tissue factor domain comprises a sequence that is at least 90% identical to SEQ ID NO: 5.

Embodiment E112. The multi-chain chimeric polypeptide of embodiment E111, wherein the soluble human tissue factor domain comprises a sequence that is at least 95% identical to SEQ ID NO: 5.

Embodiment E113. The multi-chain chimeric polypeptide of embodiment E112, wherein the soluble human tissue factor domain comprises a sequence that is 100% identical to SEQ ID NO: 5.

Embodiment E114. The multi-chain chimeric polypeptide of embodiment E12, wherein the soluble human tissue factor domain comprises a sequence that is at least 80% identical to SEQ ID NO: 6.

Embodiment E115. The multi-chain chimeric polypeptide of embodiment E114, wherein the soluble human tissue factor domain comprises a sequence that is at least 90% identical to SEQ ID NO: 6.

Embodiment E116. The multi-chain chimeric polypeptide of embodiment E115, wherein the soluble human tissue factor domain comprises a sequence that is at least 95% identical to SEQ ID NO: 6.

Embodiment E117. The multi-chain chimeric polypeptide of embodiment E116, wherein the soluble human tissue factor domain comprises a sequence that is 100% identical to SEQ ID NO: 6.

Embodiment F1. A multi-chain chimeric polypeptide comprising:
(c) a first chimeric polypeptide comprising:
(i) a first target-binding domain;
(ii) a soluble tissue factor domain; and
(iii) a first domain of a pair of affinity domains;
(d) a second chimeric polypeptide comprising:
(i) a second domain of a pair of affinity domains; and
(ii) a second target-binding domain,
wherein:
the first chimeric polypeptide and the second chimeric polypeptide associate through the binding of the first domain and the second domain of the pair of affinity domains;
the first target-binding domain and the second targeting-binding domain each independently bind specifically to a receptor of IL-21 or a receptor of IL-7.

Embodiment F2. The multi-chain chimeric polypeptide of embodiment F1, wherein the first target-binding domain and the soluble tissue factor domain directly abut each other in the first chimeric polypeptide.

Embodiment F3. The multi-chain chimeric polypeptide of embodiment F1, wherein the first chimeric polypeptide further comprises a linker sequence between the first target-binding domain and the soluble tissue factor domain in the first chimeric polypeptide.

Embodiment F4. The multi-chain chimeric polypeptide of any one of embodiments F1-F3, wherein the soluble tissue factor domain and the first domain of the pair of affinity domains directly abut each other in the first chimeric polypeptide.

Embodiment F5. The multi-chain chimeric polypeptide of any one of embodiments F1-F3, wherein the first chimeric polypeptide further comprises a linker sequence between the soluble tissue factor domain and the first domain of the pair of affinity domains in the first chimeric polypeptide.

Embodiment F6. The multi-chain chimeric polypeptide of any one of embodiments F1-F5, wherein the second domain of the pair of affinity domains and the second target-binding domain directly abut each other in the second chimeric polypeptide.

Embodiment F7. The multi-chain chimeric polypeptide of any one of embodiments F1-F5, wherein second chimeric polypeptide further comprises a linker sequence between the second domain of the pair of affinity domains and the second target-binding domain in the second chimeric polypeptide.

Embodiment F8. The multi-chain chimeric polypeptide of any one of embodiments F1-F7, wherein the soluble tissue factor domain is a soluble human tissue factor domain.

Embodiment F9. The multi-chain chimeric polypeptide of embodiment F8, wherein the soluble human tissue factor domain comprises a sequence that is at least 80% identical to SEQ ID NO: 1.

Embodiment F10. The multi-chain chimeric polypeptide of embodiment F9, wherein the soluble human tissue factor domain comprises a sequence that is at least 90% identical to SEQ ID NO: 1.

Embodiment F11. The multi-chain chimeric polypeptide of embodiment F10, wherein the soluble human tissue factor domain comprises a sequence that is at least 95% identical to SEQ ID NO: 1.

Embodiment F12. The multi-chain chimeric polypeptide of embodiment F11, wherein the soluble human tissue factor domain comprises SEQ ID NO: 1.

Embodiment F13. The multi-chain chimeric polypeptide of embodiment F8, wherein the soluble human tissue factor domain comprises a sequence that is at least 80% identical to SEQ ID NO: 5.

Embodiment F14. The multi-chain chimeric polypeptide of embodiment F13, wherein the soluble human tissue factor domain comprises a sequence that is at least 90% identical to SEQ ID NO: 5.

Embodiment F15. The multi-chain chimeric polypeptide of embodiment F14, wherein the soluble human tissue factor domain comprises a sequence that is at least 95% identical to SEQ ID NO: 5.

Embodiment F16. The multi-chain chimeric polypeptide of embodiment F15, wherein the soluble human tissue factor domain comprises SEQ ID NO: 5.

Embodiment F17. The multi-chain chimeric polypeptide of embodiment F8, wherein the soluble human tissue factor domain comprises a sequence that is at least 80% identical to SEQ ID NO: 6.

Embodiment F18. The multi-chain chimeric polypeptide of embodiment F17, wherein the soluble human tissue factor domain comprises a sequence that is at least 90% identical to SEQ ID NO: 6.

Embodiment F19. The multi-chain chimeric polypeptide of embodiment F18, wherein the soluble human tissue factor domain comprises a sequence that is at least 95% identical to SEQ ID NO: 6.

Embodiment F20. The multi-chain chimeric polypeptide of embodiment F19, wherein the soluble human tissue factor domain comprises SEQ ID NO: 6.

Embodiment F21. The multi-chain chimeric polypeptide of any one of embodiments F8-F11, F13-F15, and F17-F19, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment F22. The multi-chain chimeric polypeptide of embodiment F21, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment F23. The multi-chain chimeric polypeptide of any one of embodiments F1-F22, wherein the soluble tissue factor domain is not capable of binding to Factor VIIa.

Embodiment F24. The multi-chain chimeric polypeptide of any one of embodiments F1-F23, wherein the soluble tissue factor domain does not convert inactive Factor X into Factor Xa.

Embodiment F25. The multi-chain chimeric polypeptide of any one of embodiments F1-F24, wherein the multi-chain chimeric polypeptide does not stimulate blood coagulation in a mammal.

Embodiment F26. The multi-chain chimeric polypeptide of any one of embodiments F1-F25, wherein the first chimeric polypeptide further comprises a peptide tag at the N-terminal end or the C-terminal end of the first chimeric polypeptide.

Embodiment F27. The multi-chain chimeric polypeptide of any one of embodiments F1-F26, wherein the second chimeric polypeptide further comprises a peptide tag at the N-terminal end or the C-terminal end of the second chimeric polypeptide.

Embodiment F28. The multi-chain chimeric polypeptide of any one of embodiments F1-F27, wherein the first chimeric polypeptide and/or the second chimeric polypeptide further comprises a signal sequence at its N-terminal end.

Embodiment F29. The multi-chain chimeric polypeptide of embodiment F28, wherein the signal sequence comprises SEQ ID NO: 62.

Embodiment F30. The multi-chain chimeric polypeptide of embodiment F28, wherein the signal sequence is SEQ ID NO: 44.

Embodiment F31. The multi-chain chimeric polypeptide of any one of embodiments F1-F30, wherein the pair of affinity domains is a sushi domain from an alpha chain of human IL-15 receptor (IL15Rα) and a soluble IL-15.

Embodiment F32. The multi-chain chimeric polypeptide of embodiment F31, wherein the soluble IL-15 has a D8N or D8A amino acid substitution.

Embodiment F33. The multi-chain chimeric polypeptide of embodiment F31, wherein the soluble IL-15 comprises a sequence that is at least 80% identical to SEQ ID NO: 39.

Embodiment F34. The multi-chain chimeric polypeptide of embodiment F33, wherein the soluble IL-15 comprises a sequence that is at least 90% identical to SEQ ID NO: 39.

Embodiment F35. The multi-chain chimeric polypeptide of embodiment F34, wherein the soluble IL-15 comprises a sequence that is at least 95% identical to SEQ ID NO: 39.

Embodiment F36. The multi-chain chimeric polypeptide of embodiment F35, wherein the soluble IL-15 comprises SEQ ID NO: 39.

Embodiment F37. The multi-chain chimeric polypeptide of any one of embodiments F31-F36, wherein the sushi domain of IL15Rα comprises a sushi domain from human IL15Rα.

Embodiment F38. The multi-chain chimeric polypeptide of embodiment F37, wherein the sushi domain from human IL15Rα comprises a sequence that is at least 80% identical to SEQ ID NO: 10.

Embodiment F39. The multi-chain chimeric polypeptide of embodiment F38, wherein the sushi domain from human IL15Rα comprises a sequence that is at least 90% identical to SEQ ID NO: 10.

Embodiment F40. The multi-chain chimeric polypeptide of embodiment F39, wherein the sushi domain from human IL15Rα comprises a sequence that is at least 95% identical to SEQ ID NO: 10.

Embodiment F41. The multi-chain chimeric polypeptide of embodiment F40, wherein the sushi domain from human IL15Rα comprises SEQ ID NO: 10.

Embodiment F42. The multi-chain chimeric polypeptide of embodiment F37, wherein the sushi domain from human IL15Rα is a mature full-length IL15Rα.

Embodiment F43. The multi-chain chimeric polypeptide of any one of embodiments F1-F30, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment F44. The multi-chain chimeric polypeptide of any one of embodiments F1-F43, wherein one or both of the first target-binding domain and the second target-binding domain is an agonistic antigen-binding domain.

Embodiment F45. The multi-chain chimeric polypeptide of embodiment F44, wherein the first target-binding domain and the second target-binding domain are each agonistic antigen-binding domains.

Embodiment F46. The multi-chain chimeric polypeptide of embodiment F44 or F45, wherein antigen-binding domain comprises a scFv or single-domain antibody.

Embodiment F47. The multi-chain chimeric polypeptide of any one of embodiments F1-F43, wherein one or both of the first target-binding domain and the second target-binding domain is a soluble IL-21 or a soluble IL-7.

Embodiment F48. The multi-chain chimeric polypeptide of embodiment F47, wherein the first target-binding domain and the second target-binding domain are each independently a soluble IL-21 or a soluble IL-7.

Embodiment F49. The multi-chain chimeric polypeptide of any one of embodiments F1-F48, wherein the first target-binding domain and the second target-binding domain both bind specifically to a receptor of IL-21 or a receptor of IL-7.

Embodiment F50. The multi-chain chimeric polypeptide of embodiment F49, wherein the first target-binding domain and the second target-binding domain bind specifically to the same epitope.

Embodiment F51. The multi-chain chimeric polypeptide of embodiment F50, wherein the first target-binding domain and the second target-binding domain comprise the same amino acid sequence.

Embodiment F52. The multi-chain chimeric polypeptide of any one of embodiments F1-F48, wherein the first target-binding domain binds specifically to a receptor for IL-21, and the second target-binding domain binds specifically to a receptor for IL-7.

Embodiment F53. The multi-chain chimeric polypeptide of any one of embodiments F1-F48, wherein the first target-binding domain binds specifically to a receptor for IL-7, and the second target-binding domain bind specifically to a receptor for IL-21.

Embodiment F54. The multi-chain chimeric polypeptide of embodiment F53, wherein the first target-binding domain comprises a soluble IL-21.

Embodiment F55. The multi-chain chimeric polypeptide of embodiment F54, wherein the soluble IL-21 is a soluble human IL-21.

Embodiment F56. The multi-chain chimeric polypeptide of embodiment F55, wherein the soluble human IL-21 comprises a sequence at least 80% identical to SEQ ID NO: 124.

Embodiment F57. The multi-chain chimeric polypeptide of embodiment F56, wherein the soluble human IL-21 comprises a sequence at least 90% identical to SEQ ID NO: 124.

Embodiment F58. The multi-chain chimeric polypeptide of embodiment F57, wherein the soluble human IL-21 comprises a sequence at least 95% identical to SEQ ID NO: 124.

Embodiment F59. The multi-chain chimeric polypeptide of embodiment F58, wherein the soluble human IL-21 comprises a sequence of SEQ ID NO: 124.

Embodiment F60. The multi-chain chimeric polypeptide of any one of embodiments F53-F59, wherein the second target-binding domain comprises a soluble IL-7.

Embodiment F61. The multi-chain chimeric polypeptide of embodiment F60, wherein the soluble IL-7 is a soluble human IL-7.

Embodiment F62. The multi-chain chimeric polypeptide of embodiment F61, wherein the soluble human IL-7 comprises a sequence at least 80% identical to SEQ ID NO: 135.

Embodiment F63. The multi-chain chimeric polypeptide of embodiment F62, wherein the soluble human IL-7 comprises a sequence at least 90% identical to SEQ ID NO: 135.

Embodiment F64. The multi-chain chimeric polypeptide of embodiment F63, wherein the soluble human IL-7 comprises a sequence at least 95% identical to SEQ ID NO: 135.

Embodiment F65. The multi-chain chimeric polypeptide of embodiment F64, wherein the soluble human IL-7 comprises a sequence of SEQ ID NO: 135.

Embodiment F66. The multi-chain chimeric polypeptide of embodiment F1, wherein the first chimeric polypeptide comprises a sequence that is at least 80% identical to SEQ ID NO: 141.

Embodiment F67. The multi-chain chimeric polypeptide of embodiment F66, wherein the first chimeric polypeptide comprises a sequence that is at least 90% identical to SEQ ID NO: 141.

Embodiment F68. The multi-chain chimeric polypeptide of embodiment F67, wherein the first chimeric polypeptide comprises a sequence that is at least 95% identical to SEQ ID NO: 141.

Embodiment F69. The multi-chain chimeric polypeptide of embodiment F68, wherein the first chimeric polypeptide comprises SEQ ID NO: 141.

Embodiment F70. The multi-chain chimeric polypeptide of embodiment F69, wherein the first chimeric polypeptide comprises SEQ ID NO: 143.

Embodiment F71. The multi-chain chimeric polypeptide of any one of embodiments F1 and F66-F70, wherein the second chimeric polypeptide comprises a sequence that is at least 80% identical to SEQ ID NO: 145.

Embodiment F72. The multi-chain chimeric polypeptide of embodiment F71, wherein the second chimeric polypeptide comprises a sequence that is at least 90% identical to SEQ ID NO: 145.

Embodiment F73. The multi-chain chimeric polypeptide of embodiment F72, wherein the second chimeric polypeptide comprises a sequence that is at least 95% identical to SEQ ID NO: 145.

Embodiment F74. The multi-chain chimeric polypeptide of embodiment F73, wherein the second chimeric polypeptide comprises SEQ ID NO: 145.

Embodiment F75. The multi-chain chimeric polypeptide of embodiment F74, wherein the second chimeric polypeptide comprises SEQ ID NO: 147.

Embodiment F76. The multi-chain chimeric polypeptide of embodiment F1, wherein the first chimeric polypeptide comprises a sequence that is at least 80% identical to SEQ ID NO: 126.

Embodiment F77. The multi-chain chimeric polypeptide of embodiment F76, wherein the first chimeric polypeptide comprises a sequence that is at least 90% identical to SEQ ID NO: 126.

Embodiment F78. The multi-chain chimeric polypeptide of embodiment F77, wherein the first chimeric polypeptide comprises a sequence that is at least 95% identical to SEQ ID NO: 126.

Embodiment F79. The multi-chain chimeric polypeptide of embodiment F68, wherein the first chimeric polypeptide comprises SEQ ID NO: 126.

Embodiment F80. The multi-chain chimeric polypeptide of embodiment F69, wherein the first chimeric polypeptide comprises SEQ ID NO: 128.

Embodiment F81. The multi-chain chimeric polypeptide of any one of embodiments F1 and F76-F80, wherein the second chimeric polypeptide comprises a sequence that is at least 80% identical to SEQ ID NO: 137.

Embodiment F82. The multi-chain chimeric polypeptide of embodiment F81, wherein the second chimeric polypeptide comprises a sequence that is at least 90% identical to SEQ ID NO: 137.

Embodiment F83. The multi-chain chimeric polypeptide of embodiment F82, wherein the second chimeric polypeptide comprises a sequence that is at least 95% identical to SEQ ID NO: 137.

Embodiment F84. The multi-chain chimeric polypeptide of embodiment F83, wherein the second chimeric polypeptide comprises SEQ ID NO: 137.

Embodiment F85. The multi-chain chimeric polypeptide of embodiment F84, wherein the second chimeric polypeptide comprises SEQ ID NO: 139.

Embodiment F86. The multi-chain chimeric polypeptide of any one of embodiments F1-F65, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment F87. The multi-chain chimeric polypeptide of embodiment F86, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment F88. The multi-chain chimeric polypeptide of any one of embodiments F1-F65, wherein the first chimeric polypeptide further comprises one or more additional target-binding domains at the N-terminal and/or C-terminal end of the first chimeric polypeptide.

Embodiment F89. The multi-chain chimeric polypeptide of embodiment F88, wherein at least one of the one or more additional target-binding domains directly abuts the first domain of the pair of affinity domains in the first chimeric polypeptide.

Embodiment F90. The multi-chain chimeric polypeptide of embodiment F88, wherein the first chimeric polypeptide further comprises a linker sequence between the at least one of the one or more additional target-binding domains and the first domain of the pair of affinity domains.

Embodiment F91. The multi-chain chimeric polypeptide of embodiment F88, wherein the at least one of the one or more additional target-binding domains directly abuts the first target-binding domain in the first chimeric polypeptide.

Embodiment F92. The multi-chain chimeric polypeptide of embodiment F88, wherein the first chimeric polypeptide further comprises a linker sequence between the at least one of the one or more additional target-binding domains and the first target-binding domain.

Embodiment F93. The multi-chain chimeric polypeptide of embodiment F88, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment F94. The multi-chain chimeric polypeptide of embodiment F93, wherein the at least one additional target-binding domain of the one or more additional target-binding domains disposed at the N-terminus directly abuts the first target-binding domain or the first domain of the pair of affinity domains in the first chimeric polypeptide.

Embodiment F95. The multi-chain chimeric polypeptide of embodiment F93, wherein the first chimeric polypeptide further comprises a linker sequence disposed between the at least one additional target-binding domain and the first target-binding domain or the first domain of the pair of affinity domains in the first chimeric polypeptide.

Embodiment F96. The multi-chain chimeric polypeptide of embodiment F93, wherein the at least one additional target-binding domain of the one or more additional target-binding domains disposed at the C-terminus directly abuts the first target-binding domain or the first domain of the pair of affinity domains in the first chimeric polypeptide.

Embodiment F97. The multi-chain chimeric polypeptide of embodiment F93, wherein the first chimeric polypeptide further comprises a linker sequence disposed between the at least one additional target-binding domain and the first target-binding domain or the first domain of the pair of affinity domains in the first chimeric polypeptide.

Embodiment F98. The multi-chain chimeric polypeptide of embodiment F93, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment F99. The multi-chain chimeric polypeptide of embodiment F93, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment F100. The multi-chain chimeric polypeptide of any one of embodiments F1-F65 and F86-F99, wherein the second chimeric polypeptide further comprises one or more additional target-binding domains at the N-terminal end or the C-terminal end of the second chimeric polypeptide.

Embodiment F101. The multi-chain chimeric polypeptide of embodiment F100, wherein at least one of the one or more additional target-binding domains directly abuts the second domain of the pair of affinity domains in the second chimeric polypeptide.

Embodiment F102. The multi-chain chimeric polypeptide of embodiment F100, wherein the second chimeric polypeptide further comprises a linker sequence between at least one of the one or more additional target-binding domains and the second domain of the pair of affinity domains in the second chimeric polypeptide.

Embodiment F103. The multi-chain chimeric polypeptide of embodiment F100, wherein at least one of the one or more additional target-binding domains directly abuts the second target-binding domain in the second chimeric polypeptide.

Embodiment F104. The multi-chain chimeric polypeptide of embodiment F100, wherein the second chimeric polypeptide further comprises a linker sequence between at least one of the one or more additional target-binding domains and the second target-binding domain in the second chimeric polypeptide.

Embodiment F105. The multi-chain chimeric polypeptide of any one of embodiments F86-F104, wherein two or more of the first target-binding domain, the second target-binding domain, and the one or more additional target-binding domains bind specifically to the same antigen.

Embodiment F106. The multi-chain chimeric polypeptide of embodiment F105, wherein two or more of the first target-binding domain, the second target-binding domain, and the one or more additional target-binding domains bind specifically to the same epitope.

Embodiment F107. The multi-chain chimeric polypeptide of embodiment F106, wherein two or more of the first target-binding domain, the second target-binding domain, and the one or more additional target-binding domains comprise the same amino acid sequence.

Embodiment F108. The multi-chain chimeric polypeptide of any one of embodiments F86-F104, wherein the first target-binding domain, the second target-binding domain, and the one or more additional target-binding domains bind specifically to different antigens.

Embodiment F109. The multi-chain chimeric polypeptide of any one of embodiments F86-F108, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment F110. The multi-chain chimeric polypeptide of any one of embodiments F86-F108, wherein the one or more additional target-binding domains is a soluble interleukin, soluble cytokine protein, or soluble cell surface protein.

Embodiment F111. The multi-chain chimeric polypeptide of embodiment F110, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment F112. The multi-chain chimeric polypeptide of any one of embodiments F86-F108, wherein the one or more additional target-binding domains is a soluble interleukin receptor, soluble cytokine receptor, or soluble cell surface receptor.

Embodiment F113. The multi-chain chimeric polypeptide of embodiment F112, wherein the soluble receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, or a soluble CD28.

Embodiment F114. A composition comprising any of the multi-chain chimeric polypeptides of embodiments F1-F113.

Embodiment F115. The composition of embodiment F114, wherein the composition is a pharmaceutical composition.

Embodiment F116. A kit comprising at least one dose of the composition of embodiment F114 or F115.

Embodiment F117. Nucleic acid encoding any of the multi-chain chimeric polypeptides of any one of embodiments F1-F113.

Embodiment F118. A vector comprising the nucleic acid of embodiment F117.

Embodiment F119. The vector of embodiment F118, wherein the vector is an expression vector.

Embodiment F120. A cell comprising the nucleic acid of embodiment F117 or the vector of embodiment F118 or F119.

Embodiment F121. A method of producing a multi-chain chimeric polypeptide, the method comprising:

culturing the cell of embodiment F120 in a culture medium under conditions sufficient to result in the production of the multi-chain chimeric polypeptide; and recovering the multi-chain chimeric polypeptide from the cell and/or the culture medium.

Embodiment F122. A multi-chain chimeric polypeptide produced by the method of embodiment F121.

Embodiment G1. A multi-chain chimeric polypeptide comprising:

(e) a first chimeric polypeptide comprising:
(i) a first target-binding domain;
(ii) a soluble tissue factor domain; and
(iii) a first domain of a pair of affinity domains;
(f) a second chimeric polypeptide comprising:
(i) a second domain of a pair of affinity domains; and
(ii) a second target-binding domain,
wherein:
the first chimeric polypeptide and the second chimeric polypeptide associate through the binding of the first domain and the second domain of the pair of affinity domains; and the first target-binding domain and the second targeting-binding domain each independently bind specifically to: a receptor for IL-7, CD16, a receptor for IL-21, TGF-β, or a receptor for CD137L.

Embodiment G2. The multi-chain chimeric polypeptide of embodiment G1, wherein the first target-binding domain and the soluble tissue factor domain directly abut each other in the first chimeric polypeptide.

Embodiment G3. The multi-chain chimeric polypeptide of embodiment G1, wherein the first chimeric polypeptide further comprises a linker sequence between the first target-binding domain and the soluble tissue factor domain in the first chimeric polypeptide.

Embodiment G4. The multi-chain chimeric polypeptide of any one of embodiments G1-G3, wherein the soluble tissue factor domain and the first domain of the pair of affinity domains directly abut each other in the first chimeric polypeptide.

Embodiment G5. The multi-chain chimeric polypeptide of any one of embodiments G1-G3, wherein the first chimeric polypeptide further comprises a linker sequence between the soluble tissue factor domain and the first domain of the pair of affinity domains in the first chimeric polypeptide.

Embodiment G6. The multi-chain chimeric polypeptide of any one of embodiments G1-G5, wherein the second domain of the pair of affinity domains and the second target-binding domain directly abut each other in the second chimeric polypeptide.

Embodiment G7. The multi-chain chimeric polypeptide of any one of embodiments G1-G5, wherein second chimeric polypeptide further comprises a linker sequence between the second domain of the pair of affinity domains and the second target-binding domain in the second chimeric polypeptide.

Embodiment G8. The multi-chain chimeric polypeptide of any one of embodiments G1-G7, wherein the soluble tissue factor domain is a soluble human tissue factor domain.

Embodiment G9. The multi-chain chimeric polypeptide of embodiment G8, wherein the soluble human tissue factor domain comprises a sequence that is at least 80% identical to SEQ ID NO: 1.

Embodiment G10. The multi-chain chimeric polypeptide of embodiment G9, wherein the soluble human tissue factor domain comprises a sequence that is at least 90% identical to SEQ ID NO: 1.

Embodiment G11. The multi-chain chimeric polypeptide of embodiment G10, wherein the soluble human tissue factor domain comprises a sequence that is at least 95% identical to SEQ ID NO: 1.

Embodiment G12. The multi-chain chimeric polypeptide of any one of embodiments G8-G11, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment G13. The multi-chain chimeric polypeptide of embodiment G12, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment G14. The multi-chain chimeric polypeptide of any one of embodiments G1-G13, wherein the soluble tissue factor domain is not capable of binding to Factor VIIa.

Embodiment G15. The multi-chain chimeric polypeptide of any one of embodiments G1-G14, wherein the soluble tissue factor domain does not convert inactive Factor X into Factor Xa.

Embodiment G16. The multi-chain chimeric polypeptide of any one of embodiments G1-G15, wherein the multi-chain chimeric polypeptide does not stimulate blood coagulation in a mammal.

Embodiment G17. The multi-chain chimeric polypeptide of any one of embodiments G1-G16, wherein the first chimeric polypeptide further comprises a peptide tag at the N-terminal end or the C-terminal end of the first chimeric polypeptide.

Embodiment G18. The multi-chain chimeric polypeptide of any one of embodiments G1-G17, wherein the second chimeric polypeptide further comprises a peptide tag at the N-terminal end or the C-terminal end of the second chimeric polypeptide.

Embodiment G19. The multi-chain chimeric polypeptide of any one of embodiments G1-G18, wherein the first chimeric polypeptide and/or the second chimeric polypeptide further comprises a signal sequence at its N-terminal end.

Embodiment G20. The multi-chain chimeric polypeptide of embodiment G19, wherein the signal sequence comprises SEQ ID NO: 62.

Embodiment G21. The multi-chain chimeric polypeptide of embodiment G20, wherein the signal sequence is SEQ ID NO: 62.

Embodiment G22. The multi-chain chimeric polypeptide of any one of embodiments G1-G21, wherein the pair of affinity domains is a sushi domain from an alpha chain of human IL-15 receptor (IL15Rα) and a soluble IL-15.

Embodiment G23. The multi-chain chimeric polypeptide of embodiment G22, wherein the soluble IL-15 has a D8N or D8A amino acid substitution.

Embodiment G24. The multi-chain chimeric polypeptide of embodiment G22, wherein the soluble IL-15 comprises a sequence that is 80% identical to SEQ ID NO: 39.

Embodiment G25. The multi-chain chimeric polypeptide of embodiment G24, wherein the soluble IL-15 comprises a sequence that is 90% identical to SEQ ID NO: 39.

Embodiment G26. The multi-chain chimeric polypeptide of embodiment G25, wherein the soluble IL-15 comprises a sequence that is 95% identical to SEQ ID NO: 39.

Embodiment G27. The multi-chain chimeric polypeptide of embodiment G26, wherein the soluble IL-15 comprises SEQ ID NO: 39.

Embodiment G28. The multi-chain chimeric polypeptide of any one of embodiments G22-G27, wherein the sushi domain of IL15Rα comprises a sushi domain from human IL15Rα.

Embodiment G29. The multi-chain chimeric polypeptide of embodiment G28, wherein the sushi domain from human IL15Rα comprises a sequence that is 80% identical to SEQ ID NO: 10.

Embodiment G30. The multi-chain chimeric polypeptide of embodiment G29, wherein the sushi domain from human IL15Rα comprises a sequence that is 90% identical to SEQ ID NO: 10.

Embodiment G31. The multi-chain chimeric polypeptide of embodiment G30, wherein the sushi domain from human IL15Rα comprises a sequence that is 95% identical to SEQ ID NO: 10.

Embodiment G32. The multi-chain chimeric polypeptide of embodiment G31, wherein the sushi domain from human IL15Rα comprises SEQ ID NO: 10.

Embodiment G33. The multi-chain chimeric polypeptide of embodiment G28, wherein the sushi domain from human IL15Rα is a mature full-length IL15Rα.

Embodiment G34. The multi-chain chimeric polypeptide of any one of embodiments G1-G21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment G35. The multi-chain chimeric polypeptide of any one of embodiments G1-G34, wherein the first target-binding domain and the second targeting-binding domain each independently bind specifically to a receptor for IL-7, CD16, or a receptor for IL-21.

Embodiment G36. The multi-chain chimeric polypeptide of embodiment G35, wherein the first target-binding domain binds specifically to a receptor IL-7 and the second target-binding domain binds specifically to CD16 or a receptor for IL-21.

Embodiment G37. The multi-chain chimeric polypeptide of embodiment G36, wherein the first target-binding domain comprises a soluble IL-7 protein.

Embodiment G38. The multi-chain chimeric polypeptide of embodiment G37, wherein the soluble IL-7 protein is a soluble human IL-7.

Embodiment G39. The multi-chain chimeric polypeptide of any one of embodiments G36-G38, wherein the second antigen-binding domain comprises an antigen-binding domain that binds specifically to CD16.

Embodiment G40. The multi-chain chimeric polypeptide of embodiment G39, wherein the second antigen-binding domain comprises an scFv that binds specifically to CD16.

Embodiment G41. The multi-chain chimeric polypeptide of any one of embodiments G36-G38, wherein the second antigen-binding domain bind specifically to a receptor for IL-21.

Embodiment G42. The multi-chain chimeric polypeptide of embodiment G41, wherein the second antigen-binding domain comprises a soluble IL-21.

Embodiment G43. The multi-chain chimeric polypeptide of embodiment G42, wherein the soluble IL-21 is a soluble human IL-21.

Embodiment G44. The multi-chain chimeric polypeptide of any one of embodiments G36-G40, wherein the second chimeric polypeptide further comprises an additional target-binding domain that binds specifically to a receptor for IL-21.

Embodiment G45. The multi-chain chimeric polypeptide of embodiment G44, wherein the additional target-binding domain comprises a soluble IL-21.

Embodiment G46. The multi-chain chimeric polypeptide of embodiment G45, wherein the soluble IL-21 is a soluble human IL-12.

Embodiment G47. The multi-chain chimeric polypeptide of any one of embodiments G1-G34, wherein the first target-binding domain and the second targeting-binding domain each independently bind specifically to TGF-β, CD16, or a receptor for IL-21.

Embodiment G48. The multi-chain chimeric polypeptide of embodiment G47, wherein the first target-binding domain binds specifically to a TGF-β and the second target-binding domain binds specifically to CD16 or a receptor of IL-21.

Embodiment G49. The multi-specific chimeric polypeptide of embodiment G48, wherein the first target-binding domain is a soluble TGF-β receptor.

Embodiment G50. The multi-specific chimeric polypeptide of embodiment G49, wherein soluble TGF-β receptor is a soluble TGFβRII receptor.

Embodiment G51. The multi-specific chimeric polypeptide of any one of embodiments G48-G50, wherein the second target-binding domain binds specifically to CD16.

Embodiment G52. The multi-specific chimeric polypeptide of embodiment G51, wherein the second antigen-binding domain comprises an antigen-binding domain that binds specifically to CD16.

Embodiment G53. The multi-chain chimeric polypeptide of embodiment G52, wherein the second antigen-binding domain comprises an scFv that binds specifically to CD16.

Embodiment G54. The multi-chain chimeric polypeptide of any one of embodiments G48-G50, wherein the second target-binding domain binds specifically to a receptor for IL-21.

Embodiment G55. The multi-chain chimeric polypeptide of embodiment G54, wherein the second target-binding domain comprises a soluble IL-21.

Embodiment G56. The multi-chain chimeric polypeptide of embodiment G55, wherein the second target-binding domain comprises a soluble human IL-21.

Embodiment G57. The multi-chain chimeric polypeptide of any one of embodiments G48-G53, wherein the second chimeric polypeptide further comprises an additional target-binding domain that binds specifically to a receptor for IL-21.

Embodiment G58. The multi-chain chimeric polypeptide of embodiment G57, wherein the additional target-binding domain comprises a soluble IL-21.

Embodiment G59. The multi-chain chimeric polypeptide of embodiment G58, wherein the soluble IL-21 is a soluble human IL-21.

Embodiment G60. The multi-chain chimeric polypeptide of any one of embodiments G1-G34, wherein the first target-binding domain and the second target-binding domain each independently bind specifically to a receptor for IL-7.

Embodiment G61. The multi-chain chimeric polypeptide of embodiment G60, wherein the first target-binding domain and the second target-binding domain include a soluble IL-7.

Embodiment G62. The multi-chain chimeric polypeptide of embodiment G61, wherein the soluble IL-7 is a soluble human IL-7.

Embodiment G63. The multi-chain chimeric polypeptide of any one of embodiments G1-G34, wherein the first target-binding domain and the second target-binding domain each independently bind specifically to TGF-β.

Embodiment G64. The multi-specific chimeric polypeptide of embodiment G63, wherein the first target-binding domain and the second target-binding domain is a soluble TGF-β receptor.

Embodiment G65. The multi-specific chimeric polypeptide of embodiment G64, wherein the soluble TGF-β receptor is a soluble TGFβRII receptor.

Embodiment G66. The multi-specific chimeric polypeptide of any one of embodiments G1-G34, wherein the first target-binding domain and the second targeting-binding domain each independently bind specifically to a receptor for IL-7, a receptor for IL-21, or a receptor for CD137L.

Embodiment G67. The multi-chain chimeric polypeptide of embodiment G66, wherein the first target-binding domain binds specifically to a receptor for IL-7 and the second target-binding domain binds specifically to a receptor for IL-21 or a receptor for CD137L.

Embodiment G68. The multi-specific chimeric polypeptide of embodiment G67, wherein the first target-binding domain is a soluble IL-7.

Embodiment G69. The multi-specific chimeric polypeptide of embodiment G68, wherein the soluble IL-7 is a soluble human IL-7.

Embodiment G70. The multi-chain chimeric polypeptide of any one of embodiments G67-G69, wherein the second target-binding domain binds specifically to a receptor for IL-21.

Embodiment G71. The multi-chain chimeric polypeptide of embodiment G70, wherein the second target-binding domain is a soluble IL-21.

Embodiment G72. The multi-chain chimeric polypeptide of embodiment G71, wherein the soluble IL-21 is a soluble human IL-21.

Embodiment G73. The multi-chain chimeric polypeptide of any one of embodiments G67-G69, wherein the second antigen-binding domain binds specifically to a receptor for CD137L.

Embodiment G74. The multi-chain chimeric polypeptide of embodiment G73, wherein the second antigen-binding domain is a soluble CD137L.

Embodiment G75. The multi-chain chimeric polypeptide of embodiment G74, wherein the soluble CD137L is a soluble human CD137L.

Embodiment G76. The multi-chain chimeric polypeptide of any one of embodiments G67-G72, wherein the second chimeric polypeptide further comprises an additional target-binding domain that binds specifically to a receptor for CD137L.

Embodiment G77. The multi-chain chimeric polypeptide of embodiment G76, wherein the additional target-binding domain comprises a soluble CD137L.

Embodiment G78. The multi-chain chimeric polypeptide of embodiment G77, wherein the soluble CD137L is a soluble human CD137L.

Embodiment G79. The multi-chain chimeric polypeptide of any one of embodiments G1-G34, wherein the first target-binding domain and the second targeting-binding domain each independently bind specifically to a receptor for IL-7 or TGF-β.

Embodiment G80. The multi-chain chimeric polypeptide of embodiment G79, wherein the first target-binding domain binds specifically to a receptor IL-7 and the second target-binding domain binds specifically to TGF-β.

Embodiment G81. The multi-chain chimeric polypeptide of embodiment G80, wherein the first target-binding domain comprises a soluble IL-7 protein.

Embodiment G82. The multi-chain chimeric polypeptide of embodiment G81, wherein the soluble IL-7 protein is a soluble human IL-7.

Embodiment G83. The multi-chain chimeric polypeptide of any one of embodiments G80-G82, wherein the second antigen-binding domain comprises an antigen-binding domain that binds specifically to TGF-β.

Embodiment G84. The multi-specific chimeric polypeptide of embodiment G83, wherein the second target-binding domain is a soluble TGF-β receptor.

Embodiment G85. The multi-specific chimeric polypeptide of embodiment G84, wherein the soluble TGF-β receptor is a soluble TGFβRII receptor.

Embodiment G86. The multi-chain chimeric polypeptide of any one of embodiments G1-G34, wherein the first target-binding domain and the second targeting-binding domain each independently bind specifically to TGF-β, a receptor for IL-21, or a receptor for CD137L.

Embodiment G87. The multi-chain chimeric polypeptide of embodiment G86, wherein the first target-binding domain binds specifically to a TGF-β and the second target-binding domain binds specifically to a receptor for IL-21 or a receptor for CD137L.

Embodiment G88. The multi-specific chimeric polypeptide of embodiment G87, wherein the first target-binding domain is a soluble TGF-β receptor.

Embodiment G89. The multi-specific chimeric polypeptide of embodiment G88, wherein the soluble TGF-β receptor is a soluble TGFβRII receptor.

Embodiment G90. The multi-specific chimeric polypeptide of any one of embodiments G87-G89, wherein the second target-binding domain binds specifically to a receptor for IL-21.

Embodiment G91. The multi-chain chimeric polypeptide of embodiment G90, wherein the second target-binding domain comprises a soluble IL-21.

Embodiment G92. The multi-chain chimeric polypeptide of embodiment G91, wherein the second target-binding domain comprises a soluble human IL-21.

Embodiment G93. The multi-specific chimeric polypeptide of any one of embodiments G87-G89, wherein the second target-binding domain binds specifically to a receptor for CD137L.

Embodiment G94. The multi-chain chimeric polypeptide of embodiment G93, wherein the second target-binding domain comprises a soluble CD137L.

Embodiment G95. The multi-chain chimeric polypeptide of embodiment G94, wherein the second target-binding domain comprises a soluble human CD137L.

Embodiment G96. The multi-chain chimeric polypeptide of any one of embodiments G87-G92, wherein the second chimeric polypeptide further comprises an additional target-binding domain that binds specifically to a receptor for CD137L.

Embodiment G97. The multi-chain chimeric polypeptide of embodiment G96, wherein the additional target-binding domain comprises a soluble CD137L.

Embodiment G98. The multi-chain chimeric polypeptide of embodiment G97, wherein the soluble CD137L is a soluble human CD137L.

Embodiment G99. The multi-chain chimeric polypeptide of any one of embodiments G1-G34, wherein the first target-binding domain and the second targeting-binding domain each independently bind specifically to TGF-β or a receptor for IL-21.

Embodiment G100. The multi-chain chimeric polypeptide of embodiment G99, wherein the first target-binding domain binds specifically to a TGF-β and the second target-binding domain binds specifically to TGF-β or a receptor for IL-21.

Embodiment G101. The multi-specific chimeric polypeptide of embodiment G100, wherein the first target-binding domain is a soluble TGF-β receptor.

Embodiment G102. The multi-specific chimeric polypeptide of embodiment G101, wherein the soluble TGF-β receptor is a soluble TGFβRII receptor.

Embodiment G103. The multi-specific chimeric polypeptide of any one of embodiments G100-G102, wherein the second target-binding domain binds specifically to a receptor for IL-21.

Embodiment G104. The multi-chain chimeric polypeptide of embodiment G103, wherein the second target-binding domain comprises a soluble IL-21.

Embodiment G105. The multi-chain chimeric polypeptide of embodiment G104, wherein the second target-binding domain comprises a soluble human IL-21.

Embodiment G106. The multi-specific chimeric polypeptide of any one of embodiments G100-G102, wherein the second target-binding domain binds specifically to TGF-β.

Embodiment G107. The multi-specific chimeric polypeptide of embodiment G106, wherein the first target-binding domain is a soluble TGF-β receptor.

Embodiment G108. The multi-specific chimeric polypeptide of embodiment G107, wherein the soluble TGF-β receptor is a soluble TGFβRII receptor.

Embodiment G109. The multi-specific chimeric polypeptide of any one of embodiments G100-G105, wherein the second polypeptide further comprises an additional target-binding domain that binds specifically to TGF-β.

Embodiment G110. The multi-specific chimeric polypeptide of embodiment G109, wherein the first target-binding domain is a soluble TGF-β receptor.

Embodiment G111. The multi-specific chimeric polypeptide of embodiment G110, wherein the soluble TGF-β receptor is a soluble TGFβRII receptor.

Embodiment G112. The multi-chain chimeric polypeptide of any one of embodiments G1-G34, wherein the first target-binding domain and the second targeting-binding domain each independently bind specifically to TGF-β or IL-16.

Embodiment G113. The multi-chain chimeric polypeptide of embodiment G112, wherein the first target-binding domain binds specifically to a TGF-β and the second target-binding domain binds specifically to TGF-β or IL-16.

Embodiment G114. The multi-specific chimeric polypeptide of embodiment G113, wherein the first target-binding domain is a soluble TGF-β receptor.

Embodiment G115. The multi-specific chimeric polypeptide of embodiment G114, wherein the soluble TGF-β receptor is a soluble TGFβRII receptor.

Embodiment G116. The multi-specific chimeric polypeptide of any one of embodiments G113-G115, wherein the second target-binding domain binds specifically to IL-16.

Embodiment G117. The multi-specific chimeric polypeptide of embodiment G116, wherein the second antigen-binding domain comprises an antigen-binding domain that binds specifically to CD16.

Embodiment G118. The multi-chain chimeric polypeptide of embodiment G117, wherein the second antigen-binding domain comprises an scFv that binds specifically to CD16.

Embodiment G119. The multi-specific chimeric polypeptide of any one of embodiments G113-G115, wherein the second target-binding domain binds specifically to TGF-β.

Embodiment G120. The multi-specific chimeric polypeptide of embodiment G119, wherein the first target-binding domain is a soluble TGF-β receptor.

Embodiment G121. The multi-specific chimeric polypeptide of embodiment G120, wherein the soluble TGF-β receptor is a soluble TGFβRII receptor.

Embodiment G122. The multi-specific chimeric polypeptide of any one of embodiments G113-G118, wherein the second chimeric polypeptide further comprises an additional target-binding domain that binds specifically to TGF-β.

Embodiment G123. The multi-specific chimeric polypeptide of embodiment G122, wherein the first target-binding domain is a soluble TGF-β receptor.

Embodiment G124. The multi-specific chimeric polypeptide of embodiment G123, wherein the soluble TGF-β receptor is a soluble TGFβRII receptor.

Embodiment G125. The multi-chain chimeric polypeptide of any one of embodiments G1-G34, wherein the first target-binding domain and the second targeting-binding domain each independently bind specifically to a TGF-β or a receptor for CD137L.

Embodiment G126. The multi-chain chimeric polypeptide of embodiment G125, wherein the first target-binding domain binds specifically to TGF-β and the second target-binding domain binds specifically to a receptor for CD137L.

Embodiment G127. The multi-specific chimeric polypeptide of embodiment G126, wherein the first target-binding domain is a soluble TGF-β receptor.

Embodiment G128. The multi-specific chimeric polypeptide of embodiment G127, wherein the soluble TGF-β receptor is a soluble TGFβRII receptor.

Embodiment G129. The multi-chain chimeric polypeptide of embodiment G128, wherein the second target-binding domain comprises a soluble CD137L protein.

Embodiment G130. The multi-chain chimeric polypeptide of embodiment G129, wherein the soluble CD137L protein is a soluble human CD137L.

Embodiment G131. The multi-chain chimeric polypeptide of any one of embodiments G126-G130, wherein the second chimeric polypeptide further comprises an additional target-binding domain that binds specifically to TGF-β.

Embodiment G132. The multi-specific chimeric polypeptide of embodiment G131, wherein the additional target-binding domain is a soluble TGF-β receptor.

Embodiment G133. The multi-specific chimeric polypeptide of embodiment G132, wherein the soluble TGF-β receptor is a soluble TGFβRII receptor.

Embodiment G134. The multi-chain chimeric polypeptide of embodiment G1, wherein the first chimeric polypeptide comprises a sequence that is at least 80% identical to SEQ ID NO: 141.

Embodiment G135. The multi-chain chimeric polypeptide of embodiment G134, wherein the first chimeric polypeptide comprises a sequence that is at least 90% identical to SEQ ID NO: 141.

Embodiment G136. The multi-chain chimeric polypeptide of embodiment G135, wherein the first chimeric polypeptide comprises a sequence that is at least 95% identical to SEQ ID NO: 141.

Embodiment G137. The multi-chain chimeric polypeptide of embodiment G136, wherein the first chimeric polypeptide comprises SEQ ID NO: 141.

Embodiment G138. The multi-chain chimeric polypeptide of embodiment G137, wherein the first chimeric polypeptide comprises SEQ ID NO: 143.

Embodiment G139. The multi-chain chimeric polypeptide of any one of embodiments G1 and G134-G138, wherein the second chimeric polypeptide comprises a sequence that is at least 80% identical to SEQ ID NO: 157.

Embodiment G140. The multi-chain chimeric polypeptide of embodiment G139, wherein the second chimeric polypeptide comprises a sequence that is at least 90% identical to SEQ ID NO: 157.

Embodiment G141. The multi-chain chimeric polypeptide of embodiment G140, wherein the second chimeric polypeptide comprises a sequence that is at least 95% identical to SEQ ID NO: 157.

Embodiment G142. The multi-chain chimeric polypeptide of embodiment G141, wherein the second chimeric polypeptide comprises SEQ ID NO: 157.

Embodiment G143. The multi-chain chimeric polypeptide of embodiment G142, wherein the second chimeric polypeptide comprises SEQ ID NO: 159.

Embodiment G144. The multi-chain chimeric polypeptide of embodiment G1, wherein the first chimeric polypeptide comprises a sequence that is at least 80% identical to SEQ ID NO: 161.

Embodiment G145. The multi-chain chimeric polypeptide of embodiment G144, wherein the first chimeric polypeptide comprises a sequence that is at least 90% identical to SEQ ID NO: 161.

Embodiment G146. The multi-chain chimeric polypeptide of embodiment G145, wherein the first chimeric polypeptide comprises a sequence that is at least 95% identical to SEQ ID NO: 161.

Embodiment G147. The multi-chain chimeric polypeptide of embodiment G146, wherein the first chimeric polypeptide comprises SEQ ID NO: 161.

Embodiment G148. The multi-chain chimeric polypeptide of embodiment G147, wherein the first chimeric polypeptide comprises SEQ ID NO: 163.

Embodiment G149. The multi-chain chimeric polypeptide of any one of embodiments G1 and G144-G148, wherein the second chimeric polypeptide comprises a sequence that is at least 80% identical to SEQ ID NO: 157.

Embodiment G150. The multi-chain chimeric polypeptide of embodiment G149, wherein the second chimeric polypeptide comprises a sequence that is at least 90% identical to SEQ ID NO: 157.

Embodiment G151. The multi-chain chimeric polypeptide of embodiment G150, wherein the second chimeric polypeptide comprises a sequence that is at least 95% identical to SEQ ID NO: 157.

Embodiment G152. The multi-chain chimeric polypeptide of embodiment G151, wherein the second chimeric polypeptide comprises SEQ ID NO: 157.

Embodiment G153. The multi-chain chimeric polypeptide of embodiment G152, wherein the second chimeric polypeptide comprises SEQ ID NO: 159.

Embodiment G154. The multi-chain chimeric polypeptide of embodiment G1, wherein the first chimeric polypeptide comprises a sequence that is at least 80% identical to SEQ ID NO: 141.

Embodiment G155. The multi-chain chimeric polypeptide of embodiment G154, wherein the first chimeric polypeptide comprises a sequence that is at least 90% identical to SEQ ID NO: 141.

Embodiment G156. The multi-chain chimeric polypeptide of embodiment G155, wherein the first chimeric polypeptide comprises a sequence that is at least 95% identical to SEQ ID NO: 141.

Embodiment G157. The multi-chain chimeric polypeptide of embodiment G156, wherein the first chimeric polypeptide comprises SEQ ID NO: 141.

Embodiment G158. The multi-chain chimeric polypeptide of embodiment G157, wherein the first chimeric polypeptide comprises SEQ ID NO: 143.

Embodiment G159. The multi-chain chimeric polypeptide of any one of embodiments G1 and G154-G158, wherein the second chimeric polypeptide comprises a sequence that is at least 80% identical to SEQ ID NO: 137.

Embodiment G160. The multi-chain chimeric polypeptide of embodiment G159, wherein the second chimeric polypeptide comprises a sequence that is at least 90% identical to SEQ ID NO: 137.

Embodiment G161. The multi-chain chimeric polypeptide of embodiment G160, wherein the second chimeric polypeptide comprises a sequence that is at least 95% identical to SEQ ID NO: 137.

Embodiment G162. The multi-chain chimeric polypeptide of embodiment G161, wherein the second chimeric polypeptide comprises SEQ ID NO: 137.

Embodiment G163. The multi-chain chimeric polypeptide of embodiment G162, wherein the second chimeric polypeptide comprises SEQ ID NO: 139.

Embodiment G164. The multi-chain chimeric polypeptide of embodiment G1, wherein the first chimeric polypeptide comprises a sequence that is at least 80% identical to SEQ ID NO: 161.

Embodiment G165. The multi-chain chimeric polypeptide of embodiment G164, wherein the first chimeric polypeptide comprises a sequence that is at least 90% identical to SEQ ID NO: 161.

Embodiment G166. The multi-chain chimeric polypeptide of embodiment G165, wherein the first chimeric polypeptide comprises a sequence that is at least 95% identical to SEQ ID NO: 161.

Embodiment G167. The multi-chain chimeric polypeptide of embodiment G166, wherein the first chimeric polypeptide comprises SEQ ID NO: 161.

Embodiment G168. The multi-chain chimeric polypeptide of embodiment G167, wherein the first chimeric polypeptide comprises SEQ ID NO: 163.

Embodiment G169. The multi-chain chimeric polypeptide of any one of embodiments G1 and G164-G168, wherein the second chimeric polypeptide comprises a sequence that is at least 80% identical to SEQ ID NO: 130.

Embodiment G170. The multi-chain chimeric polypeptide of embodiment G169, wherein the second chimeric polypeptide comprises a sequence that is at least 90% identical to SEQ ID NO: 130.

Embodiment G171. The multi-chain chimeric polypeptide of embodiment G170, wherein the second chimeric polypeptide comprises a sequence that is at least 95% identical to SEQ ID NO: 130.

Embodiment G172. The multi-chain chimeric polypeptide of embodiment G171, wherein the second chimeric polypeptide comprises SEQ ID NO: 130.

Embodiment G173. The multi-chain chimeric polypeptide of embodiment G172, wherein the second chimeric polypeptide comprises SEQ ID NO: 132.

Embodiment G174. The multi-chain chimeric polypeptide of embodiment G1, wherein the first chimeric polypeptide comprises a sequence that is at least 80% identical to SEQ ID NO: 141.

Embodiment G175. The multi-chain chimeric polypeptide of embodiment G174, wherein the first chimeric polypeptide comprises a sequence that is at least 90% identical to SEQ ID NO: 141.

Embodiment G176. The multi-chain chimeric polypeptide of embodiment G175, wherein the first chimeric polypeptide comprises a sequence that is at least 95% identical to SEQ ID NO: 141.

Embodiment G177. The multi-chain chimeric polypeptide of embodiment G176, wherein the first chimeric polypeptide comprises SEQ ID NO: 141.

Embodiment G178. The multi-chain chimeric polypeptide of embodiment G177, wherein the first chimeric polypeptide comprises SEQ ID NO: 143.

Embodiment G179. The multi-chain chimeric polypeptide of any one of embodiments G1 and G174-G178, wherein the second chimeric polypeptide comprises a sequence that is at least 80% identical to SEQ ID NO: 169.

Embodiment G180. The multi-chain chimeric polypeptide of embodiment G179, wherein the second chimeric polypeptide comprises a sequence that is at least 90% identical to SEQ ID NO: 169.

Embodiment G181. The multi-chain chimeric polypeptide of embodiment G180, wherein the second chimeric polypeptide comprises a sequence that is at least 95% identical to SEQ ID NO: 169.

Embodiment G182. The multi-chain chimeric polypeptide of embodiment G181, wherein the second chimeric polypeptide comprises SEQ ID NO: 169.

Embodiment G183. The multi-chain chimeric polypeptide of embodiment G182, wherein the second chimeric polypeptide comprises SEQ ID NO: 171.

Embodiment G184. The multi-chain chimeric polypeptide of embodiment G1, wherein the first chimeric polypeptide comprises a sequence that is at least 80% identical to SEQ ID NO: 141

Embodiment G185. The multi-chain chimeric polypeptide of embodiment G184, wherein the first chimeric polypeptide comprises a sequence that is at least 90% identical to SEQ ID NO: 141.

Embodiment G186. The multi-chain chimeric polypeptide of embodiment G185, wherein the first chimeric polypeptide comprises a sequence that is at least 95% identical to SEQ ID NO: 141.

Embodiment G187. The multi-chain chimeric polypeptide of embodiment G186, wherein the first chimeric polypeptide comprises SEQ ID NO: 141.

Embodiment G188. The multi-chain chimeric polypeptide of embodiment G187, wherein the first chimeric polypeptide comprises SEQ ID NO: 143.

Embodiment G189. The multi-chain chimeric polypeptide of any one of embodiments G1 and G184-G188, wherein the second chimeric polypeptide comprises a sequence that is at least 80% identical to SEQ ID NO: 173.

Embodiment G190. The multi-chain chimeric polypeptide of embodiment G189, wherein the second chimeric polypeptide comprises a sequence that is at least 90% identical to SEQ ID NO: 173.

Embodiment G191. The multi-chain chimeric polypeptide of embodiment G190, wherein the second chimeric polypeptide comprises a sequence that is at least 95% identical to SEQ ID NO: 173.

Embodiment G192. The multi-chain chimeric polypeptide of embodiment G191, wherein the second chimeric polypeptide comprises SEQ ID NO: 173.

Embodiment G193. The multi-chain chimeric polypeptide of embodiment G192, wherein the second chimeric polypeptide comprises SEQ ID NO: 175.

Embodiment G194. The multi-chain chimeric polypeptide of embodiment G1, wherein the first chimeric polypeptide comprises a sequence that is at least 80% identical to SEQ ID NO: 141.

Embodiment G195. The multi-chain chimeric polypeptide of embodiment G194, wherein the first chimeric polypeptide comprises a sequence that is at least 90% identical to SEQ ID NO: 141.

Embodiment G196. The multi-chain chimeric polypeptide of embodiment G195, wherein the first chimeric polypeptide comprises a sequence that is at least 95% identical to SEQ ID NO: 141.

Embodiment G197. The multi-chain chimeric polypeptide of embodiment G196, wherein the first chimeric polypeptide comprises SEQ ID NO: 141.

Embodiment G198. The multi-chain chimeric polypeptide of embodiment G197, wherein the first chimeric polypeptide comprises SEQ ID NO: 143.

Embodiment G199. The multi-chain chimeric polypeptide of any one of embodiments G1 and G194-G198, wherein the second chimeric polypeptide comprises a sequence that is at least 80% identical to SEQ ID NO: 129.

Embodiment G200. The multi-chain chimeric polypeptide of embodiment G199, wherein the second chimeric polypeptide comprises a sequence that is at least 90% identical to SEQ ID NO: 130.

Embodiment G201. The multi-chain chimeric polypeptide of embodiment G200, wherein the second chimeric polypeptide comprises a sequence that is at least 95% identical to SEQ ID NO: 130.

Embodiment G202. The multi-chain chimeric polypeptide of embodiment G201, wherein the second chimeric polypeptide comprises SEQ ID NO: 130.

Embodiment G203. The multi-chain chimeric polypeptide of embodiment G202, wherein the second chimeric polypeptide comprises SEQ ID NO: 132.

Embodiment G204. The multi-chain chimeric polypeptide of embodiment G1, wherein the first chimeric polypeptide comprises a sequence that is at least 80% identical to SEQ ID NO: 161.

Embodiment G205. The multi-chain chimeric polypeptide of embodiment G204, wherein the first chimeric polypeptide comprises a sequence that is at least 90% identical to SEQ ID NO: 161.

Embodiment G206. The multi-chain chimeric polypeptide of embodiment G205, wherein the first chimeric polypeptide comprises a sequence that is at least 95% identical to SEQ ID NO: 161.

Embodiment G207. The multi-chain chimeric polypeptide of embodiment G206, wherein the first chimeric polypeptide comprises SEQ ID NO: 161.

Embodiment G208. The multi-chain chimeric polypeptide of embodiment G207, wherein the first chimeric polypeptide comprises SEQ ID NO: 163.

Embodiment G209. The multi-chain chimeric polypeptide of any one of embodiments G1 and G204-G208, wherein the second chimeric polypeptide comprises a sequence that is at least 80% identical to SEQ ID NO: 169.

Embodiment G210. The multi-chain chimeric polypeptide of embodiment G209, wherein the second chimeric polypeptide comprises a sequence that is at least 90% identical to SEQ ID NO: 169.

Embodiment G211. The multi-chain chimeric polypeptide of embodiment G210, wherein the second chimeric polypeptide comprises a sequence that is at least 95% identical to SEQ ID NO: 169.

Embodiment G212. The multi-chain chimeric polypeptide of embodiment G211, wherein the second chimeric polypeptide comprises SEQ ID NO: 169.

Embodiment G213. The multi-chain chimeric polypeptide of embodiment G212, wherein the second chimeric polypeptide comprises SEQ ID NO: 171.

Embodiment G214. The multi-chain chimeric polypeptide of embodiment G1, wherein the first chimeric polypeptide comprises a sequence that is at least 80% identical to SEQ ID NO: 161.

Embodiment G215. The multi-chain chimeric polypeptide of embodiment G214, wherein the first chimeric polypeptide comprises a sequence that is at least 90% identical to SEQ ID NO: 161.

Embodiment G216. The multi-chain chimeric polypeptide of embodiment G215, wherein the first chimeric polypeptide comprises a sequence that is at least 95% identical to SEQ ID NO: 161.

Embodiment G217. The multi-chain chimeric polypeptide of embodiment GE216, wherein the first chimeric polypeptide comprises SEQ ID NO: 161.

Embodiment G218. The multi-chain chimeric polypeptide of embodiment G217, wherein the first chimeric polypeptide comprises SEQ ID NO: 163.

Embodiment G219. The multi-chain chimeric polypeptide of any one of embodiments G1 and G214-G218, wherein the second chimeric polypeptide comprises a sequence that is at least 80% identical to SEQ ID NO: 177.

Embodiment G220. The multi-chain chimeric polypeptide of embodiment G219, wherein the second chimeric polypeptide comprises a sequence that is at least 90% identical to SEQ ID NO: 177.

Embodiment G221. The multi-chain chimeric polypeptide of embodiment G220, wherein the second chimeric polypeptide comprises a sequence that is at least 95% identical to SEQ ID NO: 177.

Embodiment G222. The multi-chain chimeric polypeptide of embodiment G221, wherein the second chimeric polypeptide comprises SEQ ID NO: 177.

Embodiment G223. The multi-chain chimeric polypeptide of embodiment G222, wherein the second chimeric polypeptide comprises SEQ ID NO: 179.

Embodiment G224. The multi-chain chimeric polypeptide of embodiment G1, wherein the first chimeric polypeptide comprises a sequence that is at least 80% identical to SEQ ID NO: 161.

Embodiment G225. The multi-chain chimeric polypeptide of embodiment G224, wherein the first chimeric polypeptide comprises a sequence that is at least 90% identical to SEQ ID NO: 161.

Embodiment G226. The multi-chain chimeric polypeptide of embodiment G225, wherein the first chimeric polypeptide comprises a sequence that is at least 95% identical to SEQ ID NO: 161.

Embodiment G227. The multi-chain chimeric polypeptide of embodiment G226, wherein the first chimeric polypeptide comprises SEQ ID NO: 161.

Embodiment G228. The multi-chain chimeric polypeptide of embodiment G227, wherein the first chimeric polypeptide comprises SEQ ID NO: 163.

Embodiment G229. The multi-chain chimeric polypeptide of any one of embodiments G1 and G224-G228, wherein the second chimeric polypeptide comprises a sequence that is at least 80% identical to SEQ ID NO: 181.

Embodiment G230. The multi-chain chimeric polypeptide of embodiment G229, wherein the second chimeric polypeptide comprises a sequence that is at least 90% identical to SEQ ID NO: 181.

Embodiment G231. The multi-chain chimeric polypeptide of embodiment G230, wherein the second chimeric polypeptide comprises a sequence that is at least 95% identical to SEQ ID NO: 181.

Embodiment G232. The multi-chain chimeric polypeptide of embodiment G231, wherein the second chimeric polypeptide comprises SEQ ID NO: 181.

Embodiment G233. The multi-chain chimeric polypeptide of embodiment G232, wherein the second chimeric polypeptide comprises SEQ ID NO: 183.

Embodiment G234. The multi-chain chimeric polypeptide of embodiment G1, wherein the first chimeric polypeptide comprises a sequence that is at least 80% identical to SEQ ID NO: 161.

Embodiment G235. The multi-chain chimeric polypeptide of embodiment G234, wherein the first chimeric polypeptide comprises a sequence that is at least 90% identical to SEQ ID NO: 161.

Embodiment G236. The multi-chain chimeric polypeptide of embodiment G235, wherein the first chimeric polypeptide comprises a sequence that is at least 95% identical to SEQ ID NO: 161.

Embodiment G237. The multi-chain chimeric polypeptide of embodiment G236, wherein the first chimeric polypeptide comprises SEQ ID NO: 161.

Embodiment G238. The multi-chain chimeric polypeptide of embodiment G237, wherein the first chimeric polypeptide comprises SEQ ID NO: 163.

Embodiment G239. The multi-chain chimeric polypeptide of any one of embodiments G1 and G234-G238, wherein the second chimeric polypeptide comprises a sequence that is at least 80% identical to SEQ ID NO: 185

Embodiment G240. The multi-chain chimeric polypeptide of embodiment G239, wherein the second chimeric polypeptide comprises a sequence that is at least 90% identical to SEQ ID NO: 185.

Embodiment G241. The multi-chain chimeric polypeptide of embodiment G240, wherein the second chimeric polypeptide comprises a sequence that is at least 95% identical to SEQ ID NO: 185.

Embodiment G242. The multi-chain chimeric polypeptide of embodiment G241, wherein the second chimeric polypeptide comprises SEQ ID NO: 185.

Embodiment G243. The multi-chain chimeric polypeptide of embodiment G242, wherein the second chimeric polypeptide comprises SEQ ID NO: 187.

Embodiment G244. The multi-chain chimeric polypeptide of any one of embodiments G1-G133, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment G245. The multi-chain chimeric polypeptide of embodiment G244, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment G246. The multi-chain chimeric polypeptide of any one of embodiments G1-G133, wherein the first chimeric polypeptide further comprises one or more additional target-binding domains at the N-terminal and/or C-terminal end of the first chimeric polypeptide.

Embodiment G247. The multi-chain chimeric polypeptide of embodiment G246, wherein at least one of the one or more additional target-binding domains directly abuts the first domain of the pair of affinity domains in the first chimeric polypeptide.

Embodiment G248. The multi-chain chimeric polypeptide of embodiment G246, wherein the first chimeric polypeptide further comprises a linker sequence between the at least one of the one or more additional target-binding domains and the first domain of the pair of affinity domains.

Embodiment G249. The multi-chain chimeric polypeptide of embodiment G246, wherein the at least one of the one or more additional target-binding domains directly abuts the first target-binding domain in the first chimeric polypeptide.

Embodiment G250. The multi-chain chimeric polypeptide of embodiment G246, wherein the first chimeric polypeptide further comprises a linker sequence between the at least one of the one or more additional target-binding domains and the first target-binding domain.

Embodiment G251. The multi-chain chimeric polypeptide of embodiment G246, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment G252. The multi-chain chimeric polypeptide of embodiment G251, wherein the at least one additional target-binding domain of the one or more additional target-binding domains disposed at the N-terminus directly abuts the first target-binding domain or the first domain of the pair of affinity domains in the first chimeric polypeptide.

Embodiment G253. The multi-chain chimeric polypeptide of embodiment G251, wherein the first chimeric polypeptide further comprises a linker sequence disposed between the at least one additional target-binding domain and the first target-binding domain or the first domain of the pair of affinity domains in the first chimeric polypeptide.

Embodiment G254. The multi-chain chimeric polypeptide of embodiment G251, wherein the at least one additional target-binding domain of the one or more additional target-binding domains disposed at the C-terminus directly abuts the first target-binding domain or the first domain of the pair of affinity domains in the first chimeric polypeptide.

Embodiment G255. The multi-chain chimeric polypeptide of embodiment G251, wherein the first chimeric polypeptide further comprises a linker sequence disposed between the at least one additional target-binding domain and the first target-binding domain or the first domain of the pair of affinity domains in the first chimeric polypeptide.

Embodiment G256. The multi-chain chimeric polypeptide of embodiment G251, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment G257. The multi-chain chimeric polypeptide of embodiment G251, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment G258. The multi-chain chimeric polypeptide of any one of embodiments G44-G46, G57-G59, G76-G78, G96-G98, G109-G111, G122-G124, and G131-G133, wherein the second chimeric polypeptide further comprises the additional target-binding domain at the N-terminal end or the C-terminal end of the second chimeric polypeptide.

Embodiment G259. The multi-chain chimeric polypeptide of embodiment G258, wherein the additional target-binding domain directly abuts the second domain of the pair of affinity domains in the second chimeric polypeptide.

Embodiment G260. The multi-chain chimeric polypeptide of embodiment G258, wherein the second chimeric polypeptide further comprises a linker sequence between the additional target-binding domain and the second domain of the pair of affinity domains in the second chimeric polypeptide.

Embodiment G261. The multi-chain chimeric polypeptide of embodiment G258, wherein the additional target-binding domain directly abuts the second target-binding domain in the second chimeric polypeptide.

Embodiment G262. The multi-chain chimeric polypeptide of embodiment G258, wherein the second chimeric polypeptide further comprises a linker sequence between the additional target-binding domain and the second target-binding domain in the second chimeric polypeptide.

Embodiment G263. A composition comprising any of the multi-chain chimeric polypeptides of embodiments G1-G262.

Embodiment G264. The composition of embodiment G263, wherein the composition is a pharmaceutical composition.

Embodiment G265. A kit comprising at least one dose of the composition of embodiment G263 or G264.

Embodiment G266. Nucleic acid encoding any of the multi-chain chimeric polypeptides of any one of embodiments G1-G262.

Embodiment G267. A vector comprising the nucleic acid of embodiment G266.

Embodiment G268. The vector of embodiment G267, wherein the vector is an expression vector.

Embodiment G269. A cell comprising the nucleic acid of embodiment G266 or the vector of embodiment G267 or G268.

Embodiment G270. A method of producing a multi-chain chimeric polypeptide, the method comprising:

culturing the cell of embodiment G269 in a culture medium under conditions sufficient to result in the production of the multi-chain chimeric polypeptide; and recovering the multi-chain chimeric polypeptide from the cell and/or the culture medium.

Embodiment G271. A multi-chain chimeric polypeptide produced by the method of embodiment G327.

Embodiment G272. The multi-chain chimeric polypeptide of embodiment G8, wherein the soluble human tissue factor domain comprises a sequence that is at least 80% identical to SEQ ID NO: 5.

Embodiment G273. The multi-chain chimeric polypeptide of embodiment G272, wherein the soluble human tissue factor domain comprises a sequence that is at least 90% identical to SEQ ID NO: 5.

Embodiment G274. The multi-chain chimeric polypeptide of embodiment G273, wherein the soluble human tissue factor domain comprises a sequence that is at least 95% identical to SEQ ID NO: 5.

Embodiment G275. The multi-chain chimeric polypeptide of embodiment G274, wherein the soluble human tissue factor domain comprises a sequence that is 100% identical to SEQ ID NO: 5.

Embodiment G276. The multi-chain chimeric polypeptide of embodiment G8, wherein the soluble human tissue factor domain comprises a sequence that is at least 80% identical to SEQ ID NO: 6.

Embodiment G277. The multi-chain chimeric polypeptide of embodiment G276, wherein the soluble human tissue factor domain comprises a sequence that is at least 90% identical to SEQ ID NO: 6.

Embodiment G278. The multi-chain chimeric polypeptide of embodiment G277, wherein the soluble human tissue factor domain comprises a sequence that is at least 95% identical to SEQ ID NO: 6.

Embodiment G279. The multi-chain chimeric polypeptide of embodiment G279, wherein the soluble human tissue factor domain comprises a sequence that is 100% identical to SEQ ID NO: 6.

Embodiment H1. A method of promoting the activation and proliferation of a natural killer cell or a T cell, the method comprising:

contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, under conditions that allow for the activation and proliferation of the natural killer cell or the T cell, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules.

Embodiment H2. The method of embodiment H1, wherein the first target-binding domain and the linker domain directly abut each other.

Embodiment H3. The method of embodiment H1, wherein the single-chain chimeric polypeptide further comprises a linker sequence between the first target-binding domain and the linker domain.

Embodiment H4. The method of any one of embodiments H1-H3, wherein the linker domain and the second target-binding domain directly abut each other.

Embodiment H5. The method of any one of embodiments H1-H3, wherein the single-chain chimeric polypeptide further comprises a linker sequence between the linker domain and the second target-binding domain.

Embodiment H6. The method of embodiment H1, wherein the first target-binding domain and the second target-binding domain directly abut each other.

Embodiment H7. The method of embodiment H1, wherein the single-chain chimeric polypeptide further comprises a linker sequence between the first target-binding domain and the second target-binding domain.

Embodiment H8. The method of embodiment H6 or H7, wherein the second target-binding domain and the linker domain directly abut each other.

Embodiment H9. The method of embodiment H6 or H7, wherein the single-chain chimeric polypeptide further comprises a linker sequence between the second target-binding domain and the linker domain.

Embodiment H10. The method of any one of embodiments H1-H9, wherein the first target-binding domain and the second target-binding domain bind specifically to the same antigen.

Embodiment H11. The method of embodiment H10, wherein the first target-binding domain and the second target-binding domain bind specifically to the same epitope.

Embodiment H12. The method of embodiment H11, wherein the first target-binding domain and the second target-binding domain comprise the same amino acid sequence.

Embodiment H13. The method of any one of embodiments H1-H9, wherein the first target-binding domain and the second target-binding domain bind specifically to different antigens.

Embodiment H14. The method of any one of embodiments H1-H13, wherein one or both of the first target-binding domain and the second target-binding domain is an antigen-binding domain.

Embodiment H15. The method of embodiment H14, wherein the first target-binding domain and the second target-binding domain are each an antigen-binding domain.

Embodiment H16. The method of embodiment H14 or H15, wherein antigen-binding domain comprises a scFv or a single domain antibody.

Embodiment H17. The method of any one of embodiments H1-H16, wherein one or both of the first target-binding domain and the second target-binding domain bind to a target selected from the group consisting of: CD16a, CD28, CD3, CD33, CD20, CD19, CD22, CD52, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H18. The method of any one of embodiments H1-H16, wherein one or both of the first target-binding domain and the second target-binding domain is a soluble interleukin, soluble cytokine protein, or soluble cell surface protein.

Embodiment H19. The method of embodiment H18, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H20. The method of any one of embodiments H1-H16, wherein one or both of the first target-binding domain and the second target-binding domain is a soluble interleukin receptor, soluble cytokine receptor, or soluble cell surface receptor.

Embodiment H21. The method of embodiment H20, wherein the soluble interleukin receptor, soluble cytokine receptor, or soluble cell surface receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment H22. The method of any one of embodiments H1-H21, wherein the linker domain is a soluble tissue factor domain.

Embodiment H23. The method of embodiment H22, wherein the soluble tissue factor domain is a soluble human tissue factor domain.

Embodiment H24. The method of embodiment H23, wherein the soluble human tissue factor domain comprises a sequence that is at least 80% identical to SEQ ID NO: 1.

Embodiment H25. The method of embodiment H24, wherein the soluble human tissue factor domain comprises a sequence that is at least 90% identical to SEQ ID NO: 1.

Embodiment H26. The method of embodiment H25, wherein the soluble human tissue factor domain comprises a sequence that is at least 95% identical to SEQ ID NO: 1.

Embodiment H27. The method of any one of embodiments H23-H26, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H28. The method of embodiment H27, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H29. The method of any one of embodiments H22-H28, wherein the soluble tissue factor domain is not capable of binding Factor VIIa.

Embodiment H30. The method of any one of embodiments H22-H29, wherein the soluble tissue factor domain does not convert inactive Factor X into Factor Xa.

Embodiment H31. The method of any one of embodiments H22-H30, wherein the single-chain chimeric polypeptide does not stimulate blood coagulation in a mammal.

Embodiment H32. The method of any one of embodiments H22-H31, wherein the IgG1 antibody construct comprises at least one antigen-binding domain that binds specifically to the soluble tissue factor domain.

Embodiment H33. The method of any one of embodiments H1-H21, wherein the linker domain is selected from the group consisting of: a kappa chain and a lambda chain.

Embodiment H34. The method of any one of embodiments H1-H33, wherein the IgG1 antibody construct is a monoclonal IgG1 antibody, where both of the antigen-binding domains in the monoclonal IgG1 antibody bind specifically to the linker domain.

Embodiment H35. The method of any one of embodiments H1-H33, wherein the IgG1 antibody construct is a bispecific IgG1 antibody, where one of the two antigen-binding domains in the bispecific IgG1 antibody binds specifically to the linker domain.

Embodiment H36. The method of any one of embodiments H1-H35, wherein the single-chain chimeric polypeptide further comprises one or more additional target-binding domains at its N- and/or C-terminus.

Embodiment H37. The method of embodiment H36, wherein the single-chain chimeric polypeptide comprises one or more additional target-binding domains at its N-terminus.

Embodiment H38. The method of embodiment H37, wherein one or more additional target-binding domains directly abuts the first target-binding domain, the second target-binding domain, or the linker domain.

Embodiment H39. The method of embodiment H38, wherein the single-chain chimeric polypeptide further comprises a linker sequence between one of the at least one additional target-binding domains and the first target-binding domain, the second target-binding domain, or the linker domain.

Embodiment H40. The method of embodiment H36, wherein the single-chain chimeric polypeptide comprises one or more additional target-binding domains at its C-terminus.

Embodiment H41. The method of embodiment H40, wherein one of the one or more additional target-binding domains directly abuts the first target-binding domain, the second target-binding domain, or the linker domain.

Embodiment H42. The method of embodiment H40, wherein the single-chain chimeric polypeptide further comprises a linker sequence between one of the at least one additional target-binding domains and the first target-binding domain, the second target-binding domain, or the linker domain.

Embodiment H43. The method of embodiment H36, wherein the single-chain chimeric polypeptide comprises one or more additional target binding domains at its N-terminus and the C-terminus.

Embodiment H44. The method of embodiment H43, wherein one of the one or more additional target-binding domains at the N-terminus directly abuts the first target-binding domain, the second target-binding domain, or the linker domain.

Embodiment H45. The method of embodiment H43, wherein the single-chain chimeric polypeptide further comprises a linker sequence between one of the one or more additional target-binding domains at the N-terminus and the first target-binding domain, the second target-binding domain, or the linker domain.

Embodiment H46. The method of embodiment H43, wherein one of the one or more additional target-binding domains at the C-terminus directly abuts the first target-binding domain, the second target-binding domain, or the linker domain.

Embodiment H47. The method of embodiment H43, wherein the single-chain chimeric polypeptide further comprises a linker sequence between one of the one or more additional target-binding domains at the C-terminus and the first target-binding domain, the second target-binding domain, or the linker domain.

Embodiment H48. The method of any one of embodiments H36-H47, wherein two or more of the first target-binding domain, the second target-binding domain, and the one or more additional target-binding domains bind specifically to the same antigen.

Embodiment H49. The method of embodiment H48, wherein two or more of the first target-binding domain, the second target-binding domain, and the one or more additional target-binding domains bind specifically to the same epitope.

Embodiment H50. The method of embodiment H49, wherein two or more of the first target-binding domain, the second target-binding domain, and the one or more additional target-binding domains comprise the same amino acid sequence.

Embodiment H51. The method of embodiment H48, wherein the first target-binding domain, the second target-binding domain, and the one or more additional target-binding domains each bind specifically to the same antigen.

Embodiment H52. The method of embodiment H51, wherein the first target-binding domain, the second target-binding domain, and the one or more additional target-binding domains each bind specifically to the same epitope.

Embodiment H53. The method of embodiment H52, wherein the first target-binding domain, the second target-binding domain, and the one or more additional target-binding domains each comprise the same amino acid sequence.

Embodiment H54. The method of any one of embodiments H36-H47, wherein the first target-binding domain, the second target-binding domain, and the one or more additional target-binding domains bind specifically to different antigens.

Embodiment H55. The method of any one of embodiments H36-H54, wherein one or more of the first target-binding domain, the second target-binding domain, and the one or more target-binding domains is an antigen-binding domain.

Embodiment H56. The method of embodiment H55, wherein the first target-binding domain, the second target-binding domain, and the one or more additional target-binding domains are each an antigen-binding domain.

Embodiment H57. The method of embodiment H55 or H56, wherein the antigen-binding domain comprises a scFv or a single domain antibody.

Embodiment H58. The method of any one of embodiments H36-H57, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H59. The method of any one of embodiments H36-H57, wherein one or more of the first target-binding domain, the second target-binding domain, and the one or more additional target-binding domains is a soluble interleukin, soluble cytokine protein, or soluble cell surface protein.

Embodiment H60. The method of embodiment H59, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H61. The method of any one of embodiments H36-H57, wherein one or more of the first target-binding domain, the second target-binding domain, and the one or more additional target-binding domains is a soluble interleukin receptor, soluble cytokine receptor, or soluble cell surface receptor.

Embodiment H62. The method of embodiment H61, wherein the soluble interleukin receptor, soluble cytokine receptor, or soluble cell surface receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment H63. The method of any one of embodiments H36-H57, wherein one or more of the first target-binding domain, the second target-binding domain, and the one or more additional target-binding domains is a ligand of a co-stimulatory molecule.

Embodiment H64. The method of embodiment H63, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H65. The method of any one of embodiments H1-H64, wherein the single-chain chimeric polypeptide further comprises a peptide tag positioned at the N-terminal end or the C-terminal end of the single-chain chimeric polypeptide.

Embodiment H66. The method of any one of embodiments H1-H65, wherein the contacting step is performed for a period of about 2 hours to about 20 days.

Embodiment H67. The method of embodiment H66, wherein the contacting step is performed for a period of about 1 day to about 15 days.

Embodiment H68. The method of any one of embodiments H1-H67, wherein the liquid culture medium is a serum-free liquid culture medium.

Embodiment H69. The method of any one of embodiments H1-H67, wherein the liquid culture medium is a chemically-defined liquid culture medium.

Embodiment H70. The method of any one of embodiments H1-H69, wherein the liquid culture medium comprises the single-chain chimeric polypeptide and the IgG1 antibody construct at a molar ratio of about 0.5:1 to about 2:1.

Embodiment H71. The method of embodiment H70, wherein the liquid culture medium comprises the single-chain chimeric polypeptide and the IgG1 antibody construct at a molar ratio of about 0.8:1 to about 1.2:1.

Embodiment H72. The method of any one of embodiments H1-H71, wherein the NK cell or T cell was previously obtained from a subject.

Embodiment H73. The method of embodiment H72, wherein the method further comprises obtaining the NK cell or T cell from the subject prior to the contacting step.

Embodiment H74. The method of any one of embodiments H1-H73, wherein the NK cell or T cell has previously been genetically modified to express a chimeric antigen receptor or a recombinant T-cell receptor.

Embodiment H75. The method of any one of embodiments H1-H73, wherein the method further comprises, after the contacting step, introducing into the NK cell or the T cell a nucleic acid encoding a chimeric antigen-receptor or a recombinant T-cell receptor.

Embodiment H76. The method of any one of embodiments H1-H73, wherein the method further comprises, before the contacting step, introducing into the NK cell or the T cell a nucleic acid encoding a chimeric antigen-receptor or a recombinant T-cell receptor.

Embodiment H77. The method of any one of embodiments H1-H76, wherein the method further comprises, after the contacting step, isolating the NK cell or the T cell.

Embodiment H78. The method of any one of embodiments H1-H77, wherein after the contacting step, the NK cell or the T cell has an increased level of expression or secretion of one or more proteins selected from the group consisting of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step.

Embodiment H79. The method of any one of embodiments H1-H78, wherein the method further comprises, after the contacting step, administering the NK cell or the T cell to a subject in need thereof.

Embodiment H80. The method of embodiment H79, wherein the subject has been identified or diagnosed as having an age-related disease or condition.

Embodiment H81. The method of embodiment H80, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H82. The method of embodiment H79, wherein the subject has been identified or diagnosed as having a cancer.

Embodiment H83. The method of embodiment H82, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H84. The method of embodiment H79, wherein the subject has been diagnosed or identified as having an infectious disease.

Embodiment H85. The method of embodiment H84, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment H86. An activated NK cell or T cell produced by the method of any one of embodiments H1-H78.

Embodiment H87. A pharmaceutical composition comprising the activated NK cell or the activated T cell of embodiment H86.

Embodiment H88. A kit comprising a pharmaceutical composition comprising the activated NK cell or the activated T cell of embodiment H86.

Embodiment H89. A method of killing a cancer cell, an infected cell, or a senescent cell in a subject in need thereof, the method comprising administering to the subject a therapeutically effective amount of the activated NK cell or the activated T cell of embodiment H86 or the pharmaceutical composition of embodiment H87.

Embodiment H90. The method of embodiment H89, wherein the subject has been identified or diagnosed as having a cancer.

Embodiment H91. The method of embodiment H90, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H92. The method of embodiment H89, wherein the subject has been identified or diagnosed as having an aging-related disease or condition.

Embodiment H93. The method of embodiment H92, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H94. A method of treating a subject in need thereof, the method comprising administering to the subject a therapeutically effective amount of the activated NK cell or the activated T cell of embodiment H86 or the pharmaceutical composition of embodiment H87.

Embodiment H95. The method of embodiment H94, wherein the subject has been identified or diagnosed as having a cancer.

Embodiment H96. The method of embodiment H95, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H97. The method of embodiment H94, wherein the subject has been identified or diagnosed as having an aging-related disease or condition.

Embodiment H98. The method of embodiment H97, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H99. The method of embodiment H94, wherein the subject has been diagnosed or identified as having an infectious disease.

Embodiment H100. The method of embodiment H99, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment H101. A kit comprising:
(i) a single-chain chimeric polypeptide comprising a first target-binding domain, a linker domain, and a second target-binding domain, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules; and
(ii) an IgG1 antibody construct comprising at least one antigen-binding domain that binds specifically to the linker domain.

Embodiment H102. The kit of embodiment H101, wherein the first target-binding domain and the linker domain directly abut each other.

Embodiment H103. The kit of embodiment H101, wherein the single-chain chimeric polypeptide further comprises a linker sequence between the first target-binding domain and the linker domain.

Embodiment H104. The kit of any one of embodiments H101-H103, wherein the linker domain and the second target-binding domain directly abut each other.

Embodiment H105. The kit of any one of embodiments H101-H103, wherein the single-chain chimeric polypeptide further comprises a linker sequence between the linker domain and the second target-binding domain.

Embodiment H106. The kit of embodiment H101, wherein the first target-binding domain and the second target-binding domain directly abut each other.

Embodiment H107. The kit of embodiment H101, wherein the single-chain chimeric polypeptide further comprises a linker sequence between the first target-binding domain and the second target-binding domain.

Embodiment H108. The kit of embodiment H106 or H107, wherein the second target-binding domain and the linker domain directly abut each other.

Embodiment H109. The kit of embodiment H106 or H107, wherein the single-chain chimeric polypeptide further comprises a linker sequence between the second target-binding domain and the linker domain.

Embodiment H110. The kit of any one of embodiments H101-H109, wherein the first target-binding domain and the second target-binding domain bind specifically to the same antigen.

Embodiment H111. The kit of embodiment H110, wherein the first target-binding domain and the second target-binding domain bind specifically to the same epitope.

Embodiment H112. The kit of embodiment H111, wherein the first target-binding domain and the second target-binding domain comprise the same amino acid sequence.

Embodiment H113. The kit of any one of embodiments H101-H109, wherein the first target-binding domain and the second target-binding domain bind specifically to different antigens.

Embodiment H114. The kit of any one of embodiments H101-H113, wherein one or both of the first target-binding domain and the second target-binding domain is an antigen-binding domain.

Embodiment H115. The kit of embodiment H114, wherein the first target-binding domain and the second target-binding domain are each an antigen-binding domain.

Embodiment H116. The kit of embodiment H114 or H115, wherein the antigen-binding domain comprises a scFv or a single domain antibody.

Embodiment H117. The kit of any one of embodiments H101-H116, wherein one or both of the first target-binding domain and the second target-binding domain bind to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H118. The kit of any one of embodiments H101-H116, wherein one or both of the first target-binding domain and the second target-binding domain is a soluble interleukin, soluble cytokine protein, or soluble cell surface protein.

Embodiment H119. The kit of embodiment H118, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H120. The kit of any one of embodiments H101-H116, wherein one or both of the first target-binding domain and the second target-binding domain is a soluble interleukin or cytokine receptor.

Embodiment H121. The kit of embodiment H120, wherein the soluble interleukin or cytokine receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment H122. The kit of any one of embodiments H101-H121, wherein the linker domain is a soluble tissue factor domain.

Embodiment H123. The kit of embodiment H122, wherein the soluble tissue factor domain is a soluble human tissue factor domain.

Embodiment H124. The kit of embodiment H123, wherein the soluble human tissue factor domain comprises a sequence that is at least 80% identical to SEQ ID NO: 1.

Embodiment H125. The kit of embodiment H124, wherein the soluble human tissue factor domain comprises a sequence that is at least 90% identical to SEQ ID NO: 1.

Embodiment H126. The kit of embodiment H125, wherein the soluble human tissue factor domain comprises a sequence that is at least 95% identical to SEQ ID NO: 1.

Embodiment H127. The kit of any one of embodiments H123-H126, wherein the soluble human tissue factor domain does not comprise one or more of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment H128. The kit of embodiment H127, wherein the soluble human tissue factor domain does not comprise any of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment H129. The kit of any one of embodiments H122-H128, wherein the soluble tissue factor domain is not capable of binding Factor VIIa.

Embodiment H130. The kit of any one of embodiments H122-H129, wherein the soluble tissue factor domain does not convert inactive Factor X into Factor Xa.

Embodiment H131. The kit of any one of embodiments H122-H130, wherein the single-chain chimeric polypeptide does not stimulate blood coagulation in a mammal.

Embodiment H132. The kit of any one of embodiments H122-H131, wherein the IgG1 antibody construct comprises at least one antigen-binding domain that binds specifically to the soluble tissue factor domain.

Embodiment H133. The kit of any one of embodiments H101-H121, wherein the linker domain is selected from the group consisting of: a kappa chain and a lambda chain.

Embodiment H134. The kit of any one of embodiments H101-H133, wherein the IgG1 antibody construct is a monoclonal IgG1 antibody, where both antigen-binding domains in the monoclonal IgG1 antibody bind specifically to the linker domain.

Embodiment H135. The kit of any one of embodiments H101-H133, wherein the IgG1 antibody construct is a bispecific IgG1 antibody, where one of the two antigen-binding domains in the bispecific IgG1 antibody binds specifically to the linker domain.

Embodiment H136. The kit of any one of embodiments H101-H135, wherein the single-chain chimeric polypeptide further comprises one or more additional target-binding domains at its N- and/or C-terminus.

Embodiment H137. The kit of embodiment H136, wherein the single-chain chimeric polypeptide comprises one or more additional target-binding domains at its N-terminus.

Embodiment H138. The kit of embodiment H137, wherein one or more additional target-binding domains directly abuts the first target-binding domain, the second target-binding domain, or the linker domain.

Embodiment H139. The kit of embodiment H138, wherein the single-chain chimeric polypeptide further comprises a linker sequence between one of the at least one additional target-binding domains and the first target-binding domain, the second target-binding domain, or the linker domain.

Embodiment H140. The kit of embodiment H136, wherein the single-chain chimeric polypeptide comprises one or more additional target-binding domains at its C-terminus.

Embodiment H141. The kit of embodiment H140, wherein one of the one or more additional target-binding domains directly abuts the first target-binding domain, the second target-binding domain, or the linker domain.

Embodiment H142. The kit of embodiment H140, wherein the single-chain chimeric polypeptide further comprises a linker sequence between one of the at least one additional target-binding domains and the first target-binding domain, the second target-binding domain, or the linker domain.

Embodiment H143. The kit of embodiment H136, wherein the single-chain chimeric polypeptide comprises one or more additional target binding domains at its N-terminus and the C-terminus.

Embodiment H144. The kit of embodiment H143, wherein one of the one or more additional target-binding domains at the N-terminus directly abuts the first target-binding domain, the second target-binding domain, or the linker domain.

Embodiment H145. The kit of embodiment H143, wherein the single-chain chimeric polypeptide further comprises a linker sequence between one of the one or more additional target-binding domains at the N-terminus and the first target-binding domain, the second target-binding domain, or the linker domain.

Embodiment H146. The kit of embodiment H143, wherein one of the one or more additional target-binding domains at the C-terminus directly abuts the first target-binding domain, the second target-binding domain, or the linker domain.

Embodiment H147. The kit of embodiment H143, wherein the single-chain chimeric polypeptide further comprises a linker sequence between one of the one or more additional target-binding domains at the C-terminus and the first target-binding domain, the second target-binding domain, or the linker domain.

Embodiment H148. The kit of any one of embodiments H136-H147, wherein two or more of the first target-binding domain, the second target-binding domain, and the one or more additional target-binding domains bind specifically to the same antigen.

Embodiment H149. The kit of embodiment H148, wherein two or more of the first target-binding domain, the second target-binding domain, and the one or more additional target-binding domains bind specifically to the same epitope.

Embodiment H150. The kit of embodiment H149, wherein two or more of the first target-binding domain, the second target-binding domain, and the one or more additional target-binding domains comprise the same amino acid sequence.

Embodiment H151. The kit of embodiment H148, wherein the first target-binding domain, the second target-binding domain, and the one or more additional target-binding domains each bind specifically to the same antigen.

Embodiment H152. The kit of embodiment H151, wherein the first target-binding domain, the second target-binding domain, and the one or more additional target-binding domains each bind specifically to the same epitope.

Embodiment H153. The kit of embodiment H152, wherein the first target-binding domain, the second target-binding domain, and the one or more additional target-binding domains each comprise the same amino acid sequence.

Embodiment H154. The kit of any one of embodiments H136-H147, wherein the first target-binding domain, the second target-binding domain, and the one or more additional target-binding domains bind specifically to different antigens.

Embodiment H155. The kit of any one of embodiments H136-H154, wherein one or more of the first target-binding domain, the second target-binding domain, and the one or more target-binding domains is an antigen-binding domain.

Embodiment H156. The kit of embodiment H155, wherein the first target-binding domain, the second target-binding domain, and the one or more additional target-binding domains are each an antigen-binding domain.

Embodiment H157. The kit of embodiment H155 or H156, wherein the antigen-binding domain comprises a scFv or a single domain antibody.

Embodiment H158. The kit of any one of embodiments H136-H157, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H159. The kit of any one of embodiments H136-H157, wherein one or more of the first target-binding domain, the second target-binding domain, and the one or more additional target-binding domains is a soluble interleukin, soluble cytokine protein, or soluble cell surface protein.

Embodiment H160. The kit of embodiment H159, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H161. The kit of any one of embodiments H136-H157, wherein one or more of the first target-binding domain, the second target-binding domain, and the one or more additional target-binding domains is a soluble interleukin or cytokine receptor.

Embodiment H162. The kit of embodiment H161, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment H163. The method of any one of embodiments H136-H162, wherein one or both of the first target-binding domain and the second target-binding domain is a ligand of a co-stimulatory molecule.

Embodiment H164. The kit of embodiment H163, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H165. The kit of any one of embodiments H101-H164, wherein the single-chain chimeric polypeptide further comprises a peptide tag positioned at the N-terminal end or the C-terminal end of the single-chain chimeric polypeptide.

Embodiment H166. A method of promoting the activation and proliferation of a natural killer cell or a T cell, the method comprising:
  contacting a natural killer cell or a T cell in a liquid culture medium comprising:
  (1) an effective amount of a multi-chain chimeric polypeptide comprising:
    (c) a first chimeric polypeptide comprising:
      (i) a first target-binding domain;
      (ii) a linker domain; and
      (iii) a first domain of a pair of affinity domains;
    (d) a second chimeric polypeptide comprising:
      (i) a second domain of a pair of affinity domains; and
      (ii) a second target-binding domain,
      wherein the first chimeric polypeptide and the second chimeric polypeptide associate through the binding of the first domain and the second domain of the pair of affinity domains; and (2) an effective amount of an IgG1 antibody construct comprising at least one antigen-binding domain that binds specifically to the linker domain,
under conditions that allow for the activation and proliferation of the natural killer cell or the T cell.

Embodiment H167. The method of embodiment H166, wherein the first target-binding domain and the linker domain directly abut each other in the first chimeric polypeptide.

Embodiment H168. The method of embodiment H166, wherein the first chimeric polypeptide further comprises a linker sequence between the first target-binding domain and the linker domain in the first chimeric polypeptide.

Embodiment H169. The method of any one of embodiments H166-H168, wherein the linker domain and the first domain of the pair of affinity domains directly abut each other in the first chimeric polypeptide.

Embodiment H170. The method of any one of embodiments H166-H168, wherein the first chimeric polypeptide further comprises a linker sequence between the linker domain and the first domain of the pair of affinity domains in the first chimeric polypeptide.

Embodiment H171. The method of any one of embodiments H166-H170, wherein the second domain of the pair of affinity domains and the second target-binding domain directly abut each other in the second chimeric polypeptide.

Embodiment H172. The method of any one of embodiments H166-H170, wherein the second chimeric polypeptide further comprises a linker sequence between the second domain of the pair of affinity domains and the second target-binding domain in the second chimeric polypeptide.

Embodiment H173. The method of any one of embodiments H166-H172, wherein the first target-binding domain and the second target-binding domain bind specifically to the same antigen.

Embodiment H174. The method of embodiment H173, wherein the first target-binding domain and the second target-binding domain bind specifically to the same epitope.

Embodiment H175. The method of embodiment H174, wherein the first target-binding domain and the second target-binding domain comprise the same amino acid sequence.

Embodiment H176. The method of any one of embodiments H166-H172, wherein the first target-binding domain and the second target-binding domain bind specifically to different antigens.

Embodiment H177. The method of any one of embodiments H166-H176, wherein one or both of the first target-binding domain and the second target-binding domain is an antigen-binding domain.

Embodiment H178. The method of embodiment H177, wherein the first target-binding domain and the second target-binding domain are each antigen-binding domains.

Embodiment H179. The method of embodiment H177 or H178, wherein the antigen-binding domain comprises a scFv or a single domain antibody.

Embodiment H180. The method of any one of embodiments H166-H179, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H181. The method of any one of embodiments H166-H179, wherein one or both of the first target-binding domain and the second target-binding domain is a soluble interleukin, soluble cytokine protein, or soluble cell surface protein.

Embodiment H182. The method of embodiment H181, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H183. The method of any one of embodiments H166-H179, wherein one or both of the first target-binding domain and the second target-binding domain is a soluble interleukin or cytokine receptor.

Embodiment H184. The method of embodiment H183, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment H185. The method of any one of embodiments H166-H184, wherein the first chimeric polypeptide further comprises one or more additional target-binding domain(s), where at least one of the one or more target-binding domain(s) is positioned between the linker domain and the first domain of the pair of affinity domains.

Embodiment H186. The method of embodiment H185, wherein the first chimeric polypeptide further comprises a linker sequence between the linker domain and the at least one of the one or more target antigen-binding domain(s), and/or a linker sequence between the at least one of the one or more target antigen-binding domain(s) and the first domain of the pair of affinity domains.

Embodiment H187. The method of any one of embodiments H166-H184, wherein the first chimeric polypeptide further comprises one or more additional target-binding domains at the N-terminal and/or C-terminal end of the first chimeric polypeptide.

Embodiment H188. The method of embodiment H187, wherein at least one of the one or more additional target-binding domains directly abuts the first domain of the pair of affinity domains in the first chimeric polypeptide.

Embodiment H189. The method of embodiment H187, wherein the first chimeric polypeptide further comprises a linker sequence between the at least one of the one or more additional target-binding domains and the first domain of the pair of affinity domains.

Embodiment H190. The method of embodiment H187, wherein the at least one of the one or more additional target-binding domains directly abuts the first target-binding domain in the first chimeric polypeptide.

Embodiment H191. The method of embodiment H187, wherein the first chimeric polypeptide further comprises a linker sequence between the at least one of the one or more additional target-binding domains and the first target-binding domain.

Embodiment H192. The method of embodiment H187, wherein at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide.

Embodiment H193. The method of embodiment H192, wherein the at least one additional target-binding domain of the one or more additional target-binding domains disposed at the N-terminus directly abuts the first target-binding domain or the first domain of the pair of affinity domains in the first chimeric polypeptide.

Embodiment H194. The method of embodiment H192, wherein the first chimeric polypeptide further comprises a linker sequence disposed between the at least one additional target-binding domain and the first target-binding domain or the first domain of the pair of affinity domains in the first chimeric polypeptide.

Embodiment H195. The method of embodiment H192, wherein the at least one additional target-binding domain of the one or more additional target-binding domains disposed at the C-terminus directly abuts the first target-binding domain or the first domain of the pair of affinity domains in the first chimeric polypeptide.

Embodiment H196. The method of embodiment H192, wherein the first chimeric polypeptide further comprises a linker sequence disposed between the at least one additional target-binding domain and the first target-binding domain or the first domain of the pair of affinity domains in the first chimeric polypeptide.

Embodiment H197. The method of embodiment H192, wherein the at least one of the one or more additional target-binding domains positioned between the linker domain and the first domain of the pair of affinity domains, directly abuts the linker domain and/or the first domain of the pair of affinity domains.

Embodiment H198. The method of embodiment H192, wherein the first chimeric polypeptide further comprises a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

Embodiment H199. The method of any one of embodiments H166-H198, wherein the second chimeric polypeptide further comprises one or more additional target-binding domains at the N-terminal end and/or the C-terminal end of the second chimeric polypeptide.

Embodiment H200. The method of embodiment H199, wherein at least one of the one or more additional target-binding domains directly abuts the second domain of the pair of affinity domains in the second chimeric polypeptide.

Embodiment H201. The method of embodiment H199, wherein the second chimeric polypeptide further comprises a linker sequence between at least one of the one or more additional target-binding domains and the second domain of the pair of affinity domains in the second chimeric polypeptide.

Embodiment H202. The method of embodiment H199, wherein at least one of the one or more additional target-binding domains directly abuts the second target-binding domain in the second chimeric polypeptide.

Embodiment H203. The method of embodiment H199, wherein the second chimeric polypeptide further comprises a linker sequence between at least one of the one or more additional target-binding domains and the second target-binding domain in the second chimeric polypeptide.

Embodiment H204. The method of any one of embodiments H185-H203, wherein two or more of the first target-binding domain, the second target-binding domain, and the one or more additional target-binding domains bind specifically to the same antigen.

Embodiment H205. The method of embodiment H204, wherein two or more of the first target-binding domain, the second target-binding domain, and the one or more additional target-binding domains bind specifically to the same epitope.

Embodiment H206. The method of embodiment H205, wherein two or more of the first target-binding domain, the second target-binding domain, and the one or more additional target-binding domains comprise the same amino acid sequence.

Embodiment H207. The method of embodiment H204, wherein the first target-binding domain, the second target-binding domain, and the one or more additional target-binding domains each bind specifically to the same antigen.

Embodiment H208. The method of embodiment H207, wherein the first target-binding domain, the second target-binding domain, and the one or more additional target-binding domains each bind specifically to the same epitope.

Embodiment H209. The method of embodiment H208, wherein the first target-binding domain, the second target-binding domain, and the one or more additional target-binding domains each comprise the same amino acid sequence.

Embodiment H210. The method of any one of embodiments H185-H203, wherein the first target-binding domain, the second target-binding domain, and the one or more additional target-binding domains bind specifically to different antigens.

Embodiment H211. The method of any one of embodiments H185-H210, wherein one or more of the first target-binding domain, the second target-binding domain, and the one or more target-binding domains is an antigen-binding domain.

Embodiment H212. The method of embodiment H211, wherein the first target-binding domain, the second target-binding domain, and the one or more additional target-binding domains are each an antigen-binding domain.

Embodiment H213. The method of embodiment H211 or H212, wherein the antigen-binding domain comprises a scFv.

Embodiment H214. The method of any one of embodiments H185-H213, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment H215. The method of any one of embodiments H185-H213, wherein one or more of the first target-binding domain, the second target-binding domain, and the one or more additional target-binding domains is a soluble interleukin, soluble cytokine protein, or soluble cell surface protein.

Embodiment H216. The method of embodiment H215, wherein the soluble interleukin. soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H217. The method of any one of embodiments H185-H213, wherein one or more of the first target-binding domain, the second target-binding domain, and the one or more additional target-binding domains is a soluble interleukin or cytokine receptor.

Embodiment H218. The method of embodiment H217, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment H219. The method of any one of embodiments H166-H218, wherein the first chimeric polypeptide further comprises a peptide tag at the N-terminal end or the C-terminal end of the first chimeric polypeptide.

Embodiment H220. The method of any one of embodiments H166-H218, wherein the second chimeric polypeptide further comprises a peptide tag at the N-terminal end or the C-terminal end of the second chimeric polypeptide.

Embodiment H221. The method of any one of embodiments H166-H220, wherein the linker domain is a soluble tissue factor domain.

Embodiment H222. The method of embodiment H221, wherein the soluble tissue factor domain is a soluble human tissue factor domain.

Embodiment H223. The method of embodiment H222, wherein the soluble human tissue factor domain comprises a sequence that is at least 80% identical to SEQ ID NO: 1.

Embodiment H224. The method of embodiment H223, wherein the soluble human tissue factor domain comprises a sequence that is at least 90% identical to SEQ ID NO: 1.

Embodiment H225. The method of embodiment H224, wherein the soluble human tissue factor domain comprises a sequence that is at least 95% identical to SEQ ID NO: 1.

Embodiment H226. The method of any one of embodiments H222-H225, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H227. The method of embodiment H226, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H228. The method of any one of embodiments H221-H227, wherein the soluble tissue factor domain is not capable of binding to Factor VIIa.

Embodiment H229. The method of any one of embodiments H221-H228, wherein the soluble tissue factor domain does not convert inactive Factor X into Factor Xa.

Embodiment H230. The method of any one of embodiments H221-H229, wherein the multi-chain chimeric polypeptide does not stimulate blood coagulation in a mammal.

Embodiment H231. The method of any one of embodiments H221-H230, wherein the IgG1 antibody construct comprises at least one antigen-binding domain that binds specifically to the soluble tissue factor domain.

Embodiment H232. The method of any one of embodiments H166-H220, wherein the linker domain is selected from the group consisting of: a kappa chain and a lambda chain.

Embodiment H233. The method of any one of embodiments H166-H232, wherein the IgG1 antibody construct is a monoclonal IgG1 antibody, where both antigen-binding domains in the monoclonal IgG1 antibody bind specifically to the linker domain.

Embodiment H234. The method of any one of embodiments H166-H232, wherein the IgG1 antibody construct is a bispecific IgG1 antibody, where one of the two antigen-binding domains in the bispecific IgG1 antibody binds specifically to the linker domain.

Embodiment H235. The method of any one of embodiments H166-H234, wherein the pair of affinity domains is a sushi domain from an alpha chain of human IL-15 receptor (IL15Rα) and a soluble IL-15.

Embodiment H236. The method of embodiment H235, wherein the soluble IL15 has a D8N or D8A amino acid substitution.

Embodiment H237. The method of embodiment H235 or H236, wherein the human IL15Rα is a mature full-length IL15Rα.

Embodiment H238. The method of any one of embodiments H166-H234, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment H239. The method of any one of embodiments H166-H238, wherein the first chimeric polypeptide and/or the second chimeric polypeptide further comprises a signal sequence at its N-terminal end.

Embodiment H240. The method of any one of embodiments H166-H238, wherein the first chimeric polypeptide and/or the second chimeric polypeptide lacks a signal sequence at its N-terminal end.

Embodiment H241. The method of any one of embodiments H166-H240, wherein the contacting step is performed for a period of about 2 hours to about 20 days.

Embodiment H242. The method of embodiment H241, wherein the contacting step is performed for a period of about 1 day to about 15 days.

Embodiment H243. The method of any one of embodiments H166-H242, wherein the liquid culture medium is a serum-free liquid culture medium.

Embodiment H244. The method of any one of embodiments H166-H242, wherein the liquid culture medium is a chemically-defined liquid culture medium.

Embodiment H245. The method of any one of embodiments H166-H244, wherein the liquid culture medium comprises the multi-chain chimeric polypeptide and the IgG1 antibody construct at a molar ratio of about 0.5:1 to about 2:1.

Embodiment H246. The method of embodiment H245, wherein the liquid culture medium comprises the multi-chain chimeric polypeptide and the IgG1 antibody construct at a molar ratio of about 0.8:1 to about 1.2:1.

Embodiment H247. The method of any one of embodiments H166-H246, wherein the NK cell or T cell was previously obtained from a subject.

Embodiment H248. The method of embodiment H247, wherein the method further comprises obtaining the NK cell or T cell from the subject prior to the contacting step.

Embodiment H249. The method of any one of embodiments H166-H248, wherein the NK cell or T cell has previously been genetically modified to express a chimeric antigen receptor or a recombinant T-cell receptor.

Embodiment H250. The method of any one of embodiments H166-H248, wherein the method further comprises, after the contacting step, introducing into the NK cell or the T cell a nucleic acid encoding a chimeric antigen-receptor or a recombinant T-cell receptor.

Embodiment H251. The method of any one of embodiments H166-H248, wherein the method further comprises, before the contacting step, introducing into the NK cell or the T cell a nucleic acid encoding a chimeric antigen-receptor or a recombinant T-cell receptor.

Embodiment H252. The method of any one of embodiments H166-H251, wherein the method further comprises, after the contacting step, isolating the NK cell or the T cell.

Embodiment H253. The method of any one of embodiments H166-H252, wherein after the contacting step, the NK cell or the T cell has an increased level of expression or secretion of one or more proteins selected from the group consisting of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step.

Embodiment H254. The method of any one of embodiments H166-H253, wherein the method further comprises, after the contacting step, administering the NK cell or the T cell to a subject in need thereof.

Embodiment H255. The method of embodiment H254, wherein the subject has been identified or diagnosed as having an age-related disease or condition.

Embodiment H256. The method of embodiment H255, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H257. The method of embodiment H254, wherein the subject has been identified or diagnosed as having a cancer.

Embodiment H258. The method of embodiment H257, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H259. The method of embodiment H254, wherein the subject has been diagnosed or identified as having an infectious disease.

Embodiment H260. The method of embodiment H259, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment H261. An activated NK cell or T cell produced by the method of any one of embodiments H166-H253.

Embodiment H262. A pharmaceutical composition comprising the activated NK cell or the activated T cell of embodiment H261.

Embodiment H263. A kit comprising a pharmaceutical composition comprising the activated NK cell or the activated T cell of embodiment H261.

Embodiment H264. A method of killing a cancer cell, an infected cell, or a senescent cell in a subject in need thereof, the method comprising administering to the subject a therapeutically effective amount of the activated NK cell or the activated T cell of embodiment H261 or the pharmaceutical composition of embodiment H262.

Embodiment H265. The method of embodiment H264, wherein the subject has been identified or diagnosed as having a cancer.

Embodiment H266. The method of embodiment H265, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H267. The method of embodiment H264, wherein the subject has been identified or diagnosed as having an aging-related disease or condition.

Embodiment H268. The method of embodiment H267, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Embodiment H269. A method of treating a subject in need thereof, the method comprising administering to the subject a therapeutically effective amount of the activated NK cell or the activated T cell of embodiment H261 or the pharmaceutical composition of embodiment H262.

Embodiment H270. The method of embodiment H269, wherein the subject has been identified or diagnosed as having a cancer.

Embodiment H271. The method of embodiment H270, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H272. The method of embodiment H269, wherein the subject has been identified or diagnosed as having an aging-related disease or condition.

Embodiment H273. The method of embodiment H272, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H274. The method of embodiment H269, wherein the subject has been diagnosed or identified as having an infectious disease.

Embodiment H275. The method of embodiment H274, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment H276. A kit comprising:
(1) a multi-chain chimeric polypeptide comprising:
(a) a first chimeric polypeptide comprising:
(i) a first target-binding domain;
(ii) a linker domain; and
(iii) a first domain of a pair of affinity domains;
(b) a second chimeric polypeptide comprising:
(i) a second domain of a pair of affinity domains; and
(ii) a second target-binding domain,
wherein the first chimeric polypeptide and the second chimeric polypeptide associate through the binding of the first domain and the second domain of the pair of affinity domains; and
(2) an effective amount of an IgG1 antibody that comprises at least one antigen-binding domain that binds specifically to the linker domain.

Embodiment H277. The kit of embodiment H276, wherein the first target-binding domain and the linker domain directly abut each other in the first chimeric polypeptide.

Embodiment H278. The kit of embodiment H276, wherein the first chimeric polypeptide further comprises a linker sequence between the first target-binding domain and the linker domain in the first chimeric polypeptide.

Embodiment H279. The kit of any one of embodiments H276-H278, wherein the linker domain and the first domain of the pair of affinity domains directly abut each other in the first chimeric polypeptide.

Embodiment H280. The kit of any one of embodiments H276-H278, wherein the first chimeric polypeptide further comprises a linker sequence between the linker domain and the first domain of the pair of affinity domains in the first chimeric polypeptide.

Embodiment H281. The kit of any one of embodiments H276-H280, wherein the second domain of the pair of affinity domains and the second target-binding domain directly abut each other in the second chimeric polypeptide.

Embodiment H282. The kit of any one of embodiments H276-H280, wherein the second chimeric polypeptide further comprises a linker sequence between the second domain of the pair of affinity domains and the second target-binding domain in the second chimeric polypeptide.

Embodiment H283. The kit of any one of embodiments H276-H282, wherein the first target-binding domain and the second target-binding domain bind specifically to the same antigen.

Embodiment H284. The kit of embodiment H283, wherein the first target-binding domain and the second target-binding domain bind specifically to the same epitope.

Embodiment H285. The kit of embodiment H284, wherein the first target-binding domain and the second target-binding domain comprise the same amino acid sequence.

Embodiment H286. The kit of any one of embodiments H276-H282, wherein the first target-binding domain and the second target-binding domain bind specifically to different antigens.

Embodiment H287. The kit of any one of embodiments H276-H286, wherein one or both of the first target-binding domain and the second target-binding domain is an antigen-binding domain.

Embodiment H288. The kit of embodiment H287, wherein the first target-binding domain and the second target-binding domain are each antigen-binding domains.

Embodiment H289. The kit of embodiment H287 or H288, wherein the antigen-binding domain comprises a scFv or a single domain antibody.

Embodiment H290. The kit of any one of embodiments H276-H289, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H291. The kit of any one of embodiments H276-H289, wherein one or both of the first target-binding domain and the second target-binding domain is a soluble interleukin, soluble cytokine protein, or soluble cell surface protein.

Embodiment H292. The kit of embodiment H291, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H293. The kit of any one of embodiments H276-H289, wherein one or both of the first target-binding domain and the second target-binding domain is a soluble interleukin or cytokine receptor.

Embodiment H294. The kit of embodiment H293, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment H295. The kit of any one of embodiments H276-H294, wherein the first chimeric polypeptide further comprises one or more additional target-binding domain(s), where at least one of the one or more target-binding domain(s) is positioned between the linker domain and the first domain of the pair of affinity domains.

Embodiment H296. The kit of embodiment H295, wherein the first chimeric polypeptide further comprises a linker sequence between the linker domain and the at least one of the one or more target antigen-binding domain(s), and/or a linker sequence between the at least one of the one or more target antigen-binding domain(s) and the first domain of the pair of affinity domains.

Embodiment H297. The kit of any one of embodiments H276-H294, wherein the first chimeric polypeptide further comprises one or more additional target-binding domains at the N-terminal and/or C-terminal end of the first chimeric polypeptide.

Embodiment H298. The kit of embodiment H297, wherein at least one of the one or more additional target-binding domains directly abuts the first domain of the pair of affinity domains in the first chimeric polypeptide.

Embodiment H299. The kit of embodiment H297, wherein the first chimeric polypeptide further comprises a linker sequence between the at least one of the one or more additional target-binding domains and the first domain of the pair of affinity domains.

Embodiment H300. The kit of embodiment H297, wherein the at least one of the one or more additional target-binding domains directly abuts the first target-binding domain in the first chimeric polypeptide.

Embodiment H301. The kit of embodiment H297, wherein the first chimeric polypeptide further comprises a linker sequence between the at least one of the one or more additional target-binding domains and the first target-binding domain.

Embodiment H302. The kit of embodiment H297, wherein at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide.

Embodiment H303. The kit of embodiment H302, wherein the at least one additional target-binding domain of the one or more additional target-binding domains disposed at the N-terminus directly abuts the first target-binding domain or the first domain of the pair of affinity domains in the first chimeric polypeptide.

Embodiment H304. The kit of embodiment H302, wherein the first chimeric polypeptide further comprises a linker sequence disposed between the at least one additional target-binding domain and the first target-binding domain or the first domain of the pair of affinity domains in the first chimeric polypeptide.

Embodiment H305. The kit of embodiment H302, wherein the at least one additional target-binding domain of the one or more additional target-binding domains disposed at the C-terminus directly abuts the first target-binding domain or the first domain of the pair of affinity domains in the first chimeric polypeptide.

Embodiment H306. The kit of embodiment H302, wherein the first chimeric polypeptide further comprises a linker sequence disposed between the at least one additional target-binding domain and the first target-binding domain or the first domain of the pair of affinity domains in the first chimeric polypeptide.

Embodiment H307. The kit of embodiment H302, wherein the at least one of the one or more additional target-binding domains positioned between the linker domain and the first domain of the pair of affinity domains, directly abuts the linker domain and/or the first domain of the pair of affinity domains.

Embodiment H308. The kit of embodiment H302, wherein the first chimeric polypeptide further comprises a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

Embodiment H309. The kit of any one of embodiments H276-H308, wherein the second chimeric polypeptide further comprises one or more additional target-binding domains at the N-terminal end or the C-terminal end of the second chimeric polypeptide.

Embodiment H310. The kit of embodiment H309, wherein at least one of the one or more additional target-binding domains directly abuts the second domain of the pair of affinity domains in the second chimeric polypeptide.

Embodiment H311. The kit of embodiment H309, wherein the second chimeric polypeptide further comprises a linker sequence between at least one of the one or more additional target-binding domains and the second domain of the pair of affinity domains in the second chimeric polypeptide.

Embodiment H312. The kit of embodiment H309, wherein at least one of the one or more additional target-binding domains directly abuts the second target-binding domain in the second chimeric polypeptide.

Embodiment H313. The kit of embodiment H309, wherein the second chimeric polypeptide further comprises a linker sequence between at least one of the one or more additional target-binding domains and the second target-binding domain in the second chimeric polypeptide.

Embodiment H314. The kit of any one of embodiments H295-H313, wherein two or more of the first target-binding domain, the second target-binding domain, and the one or more additional target-binding domains bind specifically to the same antigen.

Embodiment H315. The kit of embodiment H314, wherein two or more of the first target-binding domain, the second target-binding domain, and the one or more additional target-binding domains bind specifically to the same epitope.

Embodiment H316. The kit of embodiment H315, wherein two or more of the first target-binding domain, the second target-binding domain, and the one or more additional target-binding domains comprise the same amino acid sequence.

Embodiment H317. The kit of embodiment H314, wherein the first target-binding domain, the second target-binding domain, and the one or more additional target-binding domains each bind specifically to the same antigen.

Embodiment H318. The kit of embodiment H317, wherein the first target-binding domain, the second target-binding domain, and the one or more additional target-binding domains each bind specifically to the same epitope.

Embodiment H319. The kit of embodiment H318, wherein the first target-binding domain, the second target-binding domain, and the one or more additional target-binding domains each comprise the same amino acid sequence.

Embodiment H320. The kit of any one of embodiments H295-H313, wherein the first target-binding domain, the second target-binding domain, and the one or more additional target-binding domains bind specifically to different antigens.

Embodiment H321. The kit of any one of embodiments H295-H320, wherein one or more of the first target-binding domain, the second target-binding domain, and the one or more target-binding domains is an antigen-binding domain.

Embodiment H322. The kit of embodiment H321, wherein the first target-binding domain, the second target-binding domain, and the one or more additional target-binding domains are each an antigen-binding domain.

Embodiment H323. The kit of embodiment H321 or H322, wherein the antigen-binding domain comprises a scFv.

Embodiment H324. The kit of any one of embodiments H295-H323, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-β receptor III (TGF-βRIII), a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment H325. The kit of any one of embodiments H295-H323, wherein one or more of the first target-binding domain, the second target-binding domain, and the one or more additional target-binding domains is a soluble interleukin, soluble cytokine protein, or soluble cell surface protein.

Embodiment H326. The kit of embodiment H325, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H327. The kit of any one of embodiments H295-H323, wherein one or more of the first target-binding domain, the second target-binding domain, and the one or more additional target-binding domains is a soluble interleukin or cytokine receptor.

Embodiment H328. The kit of embodiment H327, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment H329. The kit of any one of embodiments H295-H328, wherein one or both of the first target-binding domain and the second target-binding domain is a ligand of a co-stimulatory molecule.

Embodiment H330. The kit of embodiment H329, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H331. The kit of any one of embodiments H276-H330, wherein the linker domain is a soluble tissue factor domain.

Embodiment H332. The kit of embodiment H331, wherein the soluble tissue factor domain is a soluble human tissue factor domain.

Embodiment H333. The kit of embodiment H332, wherein the soluble human tissue factor domain comprises a sequence that is at least 80% identical to SEQ ID NO: 1.

Embodiment H334. The kit of embodiment H333, wherein the soluble human tissue factor domain comprises a sequence that is at least 90% identical to SEQ ID NO: 1.

Embodiment H335. The kit of embodiment H334, wherein the soluble human tissue factor domain comprises a sequence that is at least 95% identical to SEQ ID NO: 1.

Embodiment H336. The kit of any one of embodiments H332-H335, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H337. The kit of embodiment H336, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H338. The kit of any one of embodiments H331-H337, wherein the soluble tissue factor domain is not capable of binding to Factor VIIa.

Embodiment H339. The kit of any one of embodiments H331-H338, wherein the soluble tissue factor domain does not convert inactive Factor X into Factor Xa.

Embodiment H340. The kit of any one of embodiments H331-H339, wherein the multi-chain chimeric polypeptide does not stimulate blood coagulation in a mammal.

Embodiment H341. The kit of any one of embodiments H331-H340, wherein the IgG1 antibody construct comprises at least one antigen-binding domain that binds specifically to the soluble tissue factor domain.

Embodiment H342. The kit of any one of embodiments H276-H330, wherein the linker domain is selected from the group consisting of: a kappa chain and a lambda chain.

Embodiment H343. The kit of any one of embodiments H276-H342, wherein the IgG1 antibody construct is a monoclonal IgG1 antibody, where both antigen-binding domains in the monoclonal IgG1 antibody bind specifically to the linker domain.

Embodiment H344. The kit of any one of embodiments H276-H342, wherein the IgG1 antibody construct is a bispecific IgG1 antibody, where one of the two antigen-binding domains in the bispecific IgG1 antibody binds specifically to the linker domain.

Embodiment H345. The kit of any one of embodiments H276-H344, wherein the pair of affinity domains is a sushi domain from an alpha chain of human IL-15 receptor (IL15Rα) and a soluble IL-15.

Embodiment H346. The kit of embodiment H345, wherein the soluble IL15 has a D8N or D8A amino acid substitution.

Embodiment H347. The kit of embodiment H345 or H346, wherein the human IL15Rα is a mature full-length IL15Rα.

Embodiment H348. The kit of any one of embodiments H276-H344, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment H349. The kit of any one of embodiments H276-H348, wherein the first chimeric polypeptide and/or the second chimeric polypeptide further comprises a signal sequence at its N-terminal end.

Embodiment H350. The kit of any one of embodiments H276-H348, wherein the first chimeric polypeptide and/or the second chimeric polypeptide lacks a signal sequence at its N-terminal end.

Embodiment H351. The method of any one of embodiments H1-H16, wherein one or both of the first target-binding domain and the second target-binding domain is a ligand of a co-stimulatory molecule.

Embodiment H352. The method of embodiment H351, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H353. The method of any one of embodiments H1-H62, wherein the single-chain chimeric polypeptide further comprises a signal sequence at its N-terminal end.

Embodiment H354. The method of any one of embodiments H1-H62, wherein the single-chain chimeric polypeptide lacks a signal sequence at its N-terminal end.

Embodiment H355. The kit of any one of embodiments H101-H162, wherein the single-chain chimeric polypeptide further comprises a signal sequence at its N-terminal end.

Embodiment H356. The kit of any one of embodiments H101-H162, wherein the single-chain chimeric polypeptide lacks a signal sequence at its N-terminal end.

Embodiment H357. The method of any one of embodiments H166-H179, wherein one or both of the first target-binding domain and the second target-binding domain is a ligand of a co-stimulatory molecule.

Embodiment H358. The method of embodiment H357, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H359. The method of any one of embodiments H185-H217, wherein one or both of the first target-binding domain and the second target-binding domain is a ligand of a co-stimulatory molecule.

Embodiment H360. The method of embodiment H359, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H361. The kit of any one of embodiments H276-H294, wherein one or both of the first target-binding domain and the second target-binding domain is a ligand of a co-stimulatory molecule.

Embodiment H362. The kit of embodiment H361 wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H363. The kit of any one of embodiments H276-H330, wherein the first chimeric polypeptide further comprises a peptide tag at the N-terminal end or the C-terminal end of the first chimeric polypeptide.

Embodiment H364. The kit of any one of embodiments H276-H328, wherein the second chimeric polypeptide further comprises a peptide tag at the N-terminal end or the C-terminal end of the second chimeric polypeptide.

Embodiment H365. A method of increasing the glucose consumption of an immune cell, the method comprising:

contacting an immune cell in a liquid culture medium comprising an effective amount of (i) a single-chain chimeric polypeptide comprising a first target-binding domain, a linker domain, and a second target-binding domain, and optionally (ii) an IgG1 antibody construct that comprises at least one antigen-binding domain that binds specifically to the linker domain, under conditions that allow for glucose consumption in the immune cell, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules.

Embodiment H366. A method of increasing the oxidative phosphorylation of an immune cell, the method comprising:

contacting an immune cell in a liquid culture medium comprising an effective amount of (i) a single-chain chimeric polypeptide comprising a first target-binding domain, a linker domain, and a second target-binding domain, and optionally (ii) an IgG1 antibody construct that comprises at least one antigen-binding domain that binds specifically to the linker domain, under conditions that allow for oxidative phosphorylation in the immune cell, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules.

Embodiment H367. A method of increasing the aerobic glycolysis of an immune cell, the method comprising:

contacting an immune cell in a liquid culture medium comprising an effective amount of (i) a single-chain chimeric polypeptide comprising a first target-binding domain, a linker domain, and a second target-binding domain, and optionally (ii) an IgG1 antibody construct that comprises at least one antigen-binding domain that binds specifically to the linker domain, under conditions that allow for aerobic glycolysis in the immune cell, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules.

Embodiment H368. A method of increasing the extracellular acidification rate (ECAR) of an immune cell, the method comprising:

contacting an immune cell in a liquid culture medium comprising an effective amount of (i) a single-chain chimeric polypeptide comprising a first target-binding domain, a linker domain, and a second target-binding domain, and optionally (ii) an IgG1 antibody construct that comprises at least one antigen-binding domain that binds specifically to the linker domain, under conditions that allow for extracellular acidification by the immune cell, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules.

Embodiment H369. A method of increasing the mitochondrial oxygen consumption rate of an immune cell, the method comprising:

contacting an immune cell in a liquid culture medium comprising an effective amount of (i) a single-chain chimeric polypeptide comprising a first target-binding domain, a linker domain, and a second target-binding domain, and optionally (ii) an IgG1 antibody construct that comprises at least one antigen-binding domain that binds specifically to the linker domain, under conditions that allow for mitochondrial oxygen consumption rate by the immune cell, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules.

Embodiment H370. The method of any one of embodiments H365-H369, wherein the liquid culture medium comprises the single-chain chimeric polypeptide and the IgG1 antibody construct.

Embodiment H371. The method of embodiment H370, wherein the IgG1 antibody construct is a monoclonal IgG1 antibody, where both of the antigen-binding domains in the monoclonal IgG1 antibody bind specifically to the linker domain.

Embodiment H372. The method of embodiment H370, wherein the IgG1 antibody construct is a bispecific IgG1 antibody, where one of the two antigen-binding domains in the bispecific IgG1 antibody binds specifically to the linker domain.

Embodiment H373. The method of any one of embodiments H365-H372, wherein the contacting step is performed for a period of about 2 hours to about 20 days.

Embodiment H374. The method of embodiment H373, wherein the contacting step is performed for a period of about 1 day to about 15 days.

Embodiment H375. The method of any one of embodiments H365-H374, wherein the liquid culture medium is a serum-free liquid culture medium.

Embodiment H376. The method of any one of embodiments H365-H374, wherein the liquid culture medium is a chemically-defined liquid culture medium.

Embodiment H377. The method of any one of embodiments H365-H374, wherein the liquid culture medium comprises serum.

Embodiment H378. The method of any one of embodiments H365-H377, wherein the liquid culture medium comprises the single-chain chimeric polypeptide and the IgG1 antibody construct at a molar ratio of about 0.5:1 to about 2:1.

Embodiment H379. The method of embodiment H378, wherein the liquid culture medium comprises the single-chain chimeric polypeptide and the IgG1 antibody construct at a molar ratio of about 0.8:1 to about 1.2:1.

Embodiment H380. The method of any one of embodiments H365-H379, wherein the first target-binding domain and the linker domain directly abut each other.

Embodiment H381. The method of any one of embodiments H365-H379, wherein the single-chain chimeric polypeptide further comprises a linker sequence between the first target-binding domain and the linker domain.

Embodiment H382. The method of any one of embodiments H365-H381, wherein the linker domain and the second target-binding domain directly abut each other.

Embodiment H383. The method of any one of embodiments H365-H381, wherein the single-chain chimeric polypeptide further comprises a linker sequence between the linker domain and the second target-binding domain.

Embodiment H384. The method of any one of embodiments H365-H379, wherein the first target-binding domain and the second target-binding domain directly abut each other.

Embodiment H385. The method of any one of embodiments H365-H379, wherein the single-chain chimeric polypeptide further comprises a linker sequence between the first target-binding domain and the second target-binding domain.

Embodiment H386. The method of embodiment H384 or H385, wherein the second target-binding domain and the linker domain directly abut each other.

Embodiment H387. The method of embodiment H384 or H385, wherein the single-chain chimeric polypeptide further comprises a linker sequence between the second target-binding domain and the linker domain.

Embodiment H388. The method of any one of embodiments H365-H387, wherein the first target-binding domain and the second target-binding domain bind specifically to the same antigen.

Embodiment H389. The method of embodiment H388, wherein the first target-binding domain and the second target-binding domain bind specifically to the same epitope.

Embodiment H390. The method of embodiment H389, wherein the first target-binding domain and the second target-binding domain comprise the same amino acid sequence.

Embodiment H391. The method of any one of embodiments H365-H387, wherein the first target-binding domain and the second target-binding domain bind specifically to different antigens.

Embodiment H392. The method of any one of embodiments H365-H391, wherein one or both of the first target-binding domain and the second target-binding domain is an antigen-binding domain.

Embodiment H393. The method of embodiment H392, wherein the first target-binding domain and the second target-binding domain are each an antigen-binding domain.

Embodiment H394. The method of embodiment H392 or H393, wherein antigen-binding domain comprises a scFv or a single domain antibody.

Embodiment H395. The method of any one of embodiments H365-H394, wherein one or both of the first target-binding domain and the second target-binding domain bind to a target selected from the group consisting of: CD16a, CD28, CD3, CD33, CD20, CD19, CD22, CD52, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H396. The method of any one of embodiments H365-H394, wherein one or both of the first target-binding domain and the second target-binding domain is a soluble interleukin, soluble cytokine protein, or soluble cell surface protein.

Embodiment H397. The method of embodiment H396, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H398. The method of any one of embodiments H365-H394, wherein one or both of the first target-binding domain and the second target-binding domain is a soluble interleukin or cytokine receptor.

Embodiment H399. The method of embodiment H398, wherein the soluble interleukin or cytokine receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment H400. The method of any one of embodiments H365-H399, wherein the linker domain is a soluble tissue factor domain.

Embodiment H401. The method of embodiment H400, wherein the soluble tissue factor domain is a soluble human tissue factor domain.

Embodiment H402. The method of embodiment H401, wherein the soluble human tissue factor domain comprises a sequence that is at least 80% identical to SEQ ID NO: 1.

Embodiment H403. The method of embodiment H402, wherein the soluble human tissue factor domain comprises a sequence that is at least 90% identical to SEQ ID NO: 1.

Embodiment H404. The method of embodiment H403, wherein the soluble human tissue factor domain comprises a sequence that is at least 95% identical to SEQ ID NO: 1.

Embodiment H405. The method of any one of embodiments H401-H404, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H406. The method of embodiment H405, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H407. The method of any one of embodiments H400-H406, wherein the soluble tissue factor domain is not capable of binding Factor VIIa.

Embodiment H408. The method of any one of embodiments H400-H407, wherein the soluble tissue factor domain does not convert inactive Factor X into Factor Xa.

Embodiment H409. The method of any one of embodiments H400-H408, wherein the single-chain chimeric polypeptide does not stimulate blood coagulation in a mammal.

Embodiment H410. The method of any one of embodiments H400-H409, wherein the IgG1 antibody construct comprises at least one antigen-binding domain that binds specifically to the soluble tissue factor domain.

Embodiment H411. The method of any one of embodiments H365-H399, wherein the linker domain is selected from the group consisting of: a kappa chain and a lambda chain.

Embodiment H412. The method of any one of embodiments H365-H411, wherein the IgG1 antibody construct is a monoclonal IgG1 antibody, where both of the antigen-binding domains in the monoclonal IgG1 antibody bind specifically to the linker domain.

Embodiment H413. The method of any one of embodiments H365-H411, wherein the IgG1 antibody construct is a bispecific IgG1 antibody, where one of the two antigen-binding domains in the bispecific IgG1 antibody binds specifically to the linker domain.

Embodiment H414. The method of any one of embodiments H365-H413, wherein the single-chain chimeric polypeptide further comprises one or more additional target-binding domains at its N- and/or C-terminus.

Embodiment H415. The method of embodiment H414, wherein the single-chain chimeric polypeptide comprises one or more additional target-binding domains at its N-terminus.

Embodiment H416. The method of embodiment H415, wherein one or more additional target-binding domains directly abuts the first target-binding domain, the second target-binding domain, or the linker domain.

Embodiment H417. The method of embodiment H416, wherein the single-chain chimeric polypeptide further comprises a linker sequence between one of the at least one additional target-binding domains and the first target-binding domain, the second target-binding domain, or the linker domain.

Embodiment H418. The method of embodiment H414, wherein the single-chain chimeric polypeptide comprises one or more additional target-binding domains at its C-terminus.

Embodiment H419. The method of embodiment H418, wherein one of the one or more additional target-binding domains directly abuts the first target-binding domain, the second target-binding domain, or the linker domain.

Embodiment H420. The method of embodiment H418, wherein the single-chain chimeric polypeptide further comprises a linker sequence between one of the at least one additional target-binding domains and the first target-binding domain, the second target-binding domain, or the linker domain.

Embodiment H421. The method of embodiment H414, wherein the single-chain chimeric polypeptide comprises one or more additional target binding domains at its N-terminus and the C-terminus.

Embodiment H422. The method of embodiment H421, wherein one of the one or more additional target-binding domains at the N-terminus directly abuts the first target-binding domain, the second target-binding domain, or the linker domain.

Embodiment H423. The method of embodiment H421, wherein the single-chain chimeric polypeptide further comprises a linker sequence between one of the one or more additional target-binding domains at the N-terminus and the first target-binding domain, the second target-binding domain, or the linker domain.

Embodiment H424. The method of embodiment H421, wherein one of the one or more additional target-binding domains at the C-terminus directly abuts the first target-binding domain, the second target-binding domain, or the linker domain.

Embodiment H425. The method of embodiment H421, wherein the single-chain chimeric polypeptide further comprises a linker sequence between one of the one or more additional target-binding domains at the C-terminus and the first target-binding domain, the second target-binding domain, or the linker domain.

Embodiment H426. The method of any one of embodiments H414-H425, wherein two or more of the first target-binding domain, the second target-binding domain, and the one or more additional target-binding domains bind specifically to the same antigen.

Embodiment H427. The method of embodiment H426, wherein two or more of the first target-binding domain, the second target-binding domain, and the one or more additional target-binding domains bind specifically to the same epitope.

Embodiment H428. The method of embodiment H427, wherein two or more of the first target-binding domain, the second target-binding domain, and the one or more additional target-binding domains comprise the same amino acid sequence.

Embodiment H429. The method of embodiment H426, wherein the first target-binding domain, the second target-binding domain, and the one or more additional target-binding domains each bind specifically to the same antigen.

Embodiment H430. The method of embodiment H429, wherein the first target-binding domain, the second target-binding domain, and the one or more additional target-binding domains each bind specifically to the same epitope.

Embodiment H431. The method of embodiment H430, wherein the first target-binding domain, the second target-binding domain, and the one or more additional target-binding domains each comprise the same amino acid sequence.

Embodiment H432. The method of any one of embodiments H414-H425, wherein the first target-binding domain, the second target-binding domain, and the one or more additional target-binding domains bind specifically to different antigens.

Embodiment H433. The method of any one of embodiments H414-H432, wherein one or more of the first target-binding domain, the second target-binding domain, and the one or more target-binding domains is an antigen-binding domain.

Embodiment H434. The method of embodiment H433, wherein the first target-binding domain, the second target-binding domain, and the one or more additional target-binding domains are each an antigen-binding domain.

Embodiment H435. The method of embodiment H433 or H434, wherein the antigen-binding domain comprises a scFv or a single domain antibody.

Embodiment H436. The method of any one of embodiments H414-H435, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H437. The method of any one of embodiments H414-H432, wherein one or more of the first target-binding domain, the second target-binding domain, and the one or more additional target-binding domains is a soluble interleukin, soluble cytokine protein, or soluble cell surface protein.

Embodiment H438. The method of embodiment H437, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H439. The method of any one of embodiments H414-H432, wherein one or more of the first target-binding domain, the second target-binding domain, and the one or more additional target-binding domains is a soluble interleukin or cytokine receptor.

Embodiment H440. The method of embodiment H439, wherein the soluble interleukin or cytokine receptor is a soluble TGF-β receptor II (TGF-βRII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment H441. The method of any one of embodiments H414-H432, wherein one or more of the first target-binding domain, the second target-binding domain, and the one or more additional target-binding domains is a ligand of a co-stimulatory molecule.

Embodiment H442. The method of embodiment H441, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H443. The method of any one of embodiments H365-H442, wherein the single-chain chimeric polypeptide further comprises a peptide tag positioned at the N-terminal end or the C-terminal end of the single-chain chimeric polypeptide.

Embodiment H444. The method of any one of embodiments H365-H443, wherein the NK cell or T cell was previously obtained from a subject.

Embodiment H445. The method of embodiment H444, wherein the method further comprises obtaining the NK cell or T cell from the subject prior to the contacting step.

Embodiment H446. The method of any one of embodiments H365-H445, wherein the immune cell has previously been genetically modified to express a chimeric antigen receptor or a recombinant T-cell receptor.

Embodiment H447. The method of any one of embodiments H365-H445, wherein the method further comprises, after the contacting step, introducing into the immune cell a nucleic acid encoding a chimeric antigen-receptor or a recombinant T-cell receptor.

Embodiment H448. The method of any one of embodiments H365-H445, wherein the method further comprises, before the contacting step, introducing into the immune cell a nucleic acid encoding a chimeric antigen-receptor or a recombinant T-cell receptor.

Embodiment H449. The method of any one of embodiments H365-H448, wherein the method further comprises, after the contacting step, isolating the immune cell.

Embodiment H450. The method of any one of embodiments H365-H449, wherein after the contacting step, the immune cell has an increased level of expression or secretion of one or more proteins selected from the group consisting of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step.

Embodiment H451. The method of any one of embodiments H365-H450, wherein the method further comprises, after the contacting step, administering the immune cell to a subject in need thereof.

Embodiment H452. The method of embodiment H451, wherein the subject has been identified or diagnosed as having an age-related disease or condition.

Embodiment H453. The method of embodiment H452, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H454. The method of embodiment H451, wherein the subject has been identified or diagnosed as having a cancer.

Embodiment H455. The method of embodiment H454, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H456. The method of embodiment H451, wherein the subject has been diagnosed or identified as having an infectious disease.

Embodiment H457. The method of embodiment H456, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment H458. An activated immune cell produced by the method of any one of embodiments H365-H450.

Embodiment H459. A pharmaceutical composition comprising the activated immune cell of embodiment H458.

Embodiment H460. A kit comprising a pharmaceutical composition comprising the activated immune cell of embodiment H458.

Embodiment H461. A method of killing a cancer cell, an infected cell, or a senescent cell in a subject in need thereof, the method comprising administering to the subject a therapeutically effective amount of the activated immune cell of embodiment H458 or the pharmaceutical composition of embodiment H459.

Embodiment H462. The method of embodiment H461, wherein the subject has been identified or diagnosed as having a cancer.

Embodiment H463. The method of embodiment H462, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H464. The method of embodiment H462, wherein the subject has been identified or diagnosed as having an aging-related disease or condition.

Embodiment H465. The method of embodiment H464, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H466. A method of treating a subject in need thereof, the method comprising administering to the subject a therapeutically effective amount of the activated immune cell of embodiment H458 or the pharmaceutical composition of embodiment H459.

Embodiment H467. The method of embodiment H466, wherein the subject has been identified or diagnosed as having a cancer.

Embodiment H468. The method of embodiment H467, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H469. The method of embodiment H466, wherein the subject has been identified or diagnosed as having an aging-related disease or condition.

Embodiment H470. The method of embodiment H469, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H471. The method of embodiment H466, wherein the subject has been diagnosed or identified as having an infectious disease.

Embodiment H472. The method of embodiment H471, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Embodiment H473. A method of increasing the glucose consumption of an immune cell, the method comprising:
  contacting an immune cell in a liquid culture medium comprising (1) an effective amount of a multi-chain chimeric polypeptide comprising:
    (a) a first chimeric polypeptide comprising:
      (i) a first target-binding domain;
      (ii) a linker domain; and
      (iii) a first domain of a pair of affinity domains;
    (b) a second chimeric polypeptide comprising:
      (i) a second domain of a pair of affinity domains; and
      (ii) a second target-binding domain,
    wherein the first chimeric polypeptide and the second chimeric polypeptide associate through the binding of the first domain and the second domain of the pair of affinity domains; and
  (2) an effective amount of an IgG1 antibody construct comprising at least one antigen-binding domain that binds specifically to the linker domain, under conditions that allow for glucose consumption in the immune cell.

Embodiment H474. A method of increasing the oxidative phosphorylation of an immune cell, the method comprising:
  contacting an immune cell in a liquid culture medium comprising (1) an effective amount of a multi-chain chimeric polypeptide comprising:
    (a) a first chimeric polypeptide comprising:
      (i) a first target-binding domain;
      (ii) a linker domain; and
      (iii) a first domain of a pair of affinity domains;
    (b) a second chimeric polypeptide comprising:
      (i) a second domain of a pair of affinity domains; and
      (ii) a second target-binding domain,
    wherein the first chimeric polypeptide and the second chimeric polypeptide associate through the binding of the first domain and the second domain of the pair of affinity domains; and
  (2) an effective amount of an IgG1 antibody construct comprising at least one antigen-binding domain that binds specifically to the linker domain, under conditions that allow for oxidative phosphorylation in the immune cell.

Embodiment H475. A method of increasing the aerobic glycolysis of an immune cell, the method comprising:
  contacting an immune cell in a liquid culture medium comprising (1) an effective amount of a multi-chain chimeric polypeptide comprising:

(a) a first chimeric polypeptide comprising:
(i) a first target-binding domain;
(ii) a linker domain; and
(iii) a first domain of a pair of affinity domains;
(b) a second chimeric polypeptide comprising:
(i) a second domain of a pair of affinity domains; and
(ii) a second target-binding domain,
wherein the first chimeric polypeptide and the second chimeric polypeptide associate through the binding of the first domain and the second domain of the pair of affinity domains; and
(2) an effective amount of an IgG1 antibody construct comprising at least one antigen-binding domain that binds specifically to the linker domain, under conditions that allow for aerobic glycolysis in the immune cell.

Embodiment H476. A method of increasing the extracellular acidification rate (ECAR) of an immune cell, the method comprising:
contacting an immune cell in a liquid culture medium comprising (1) an effective amount of a multi-chain chimeric polypeptide comprising:
(a) a first chimeric polypeptide comprising:
(i) a first target-binding domain;
(ii) a linker domain; and
(iii) a first domain of a pair of affinity domains;
(b) a second chimeric polypeptide comprising:
(i) a second domain of a pair of affinity domains; and
(ii) a second target-binding domain,
wherein the first chimeric polypeptide and the second chimeric polypeptide associate through the binding of the first domain and the second domain of the pair of affinity domains; and
(2) an effective amount of an IgG1 antibody construct comprising at least one antigen-binding domain that binds specifically to the linker domain, under conditions that allow for extracellular acidification by the immune cell.

Embodiment H477. A method of increasing the mitochondrial oxygen consumption rate of an immune cell, the method comprising:
contacting an immune cell in a liquid culture medium comprising (1) an effective amount of a multi-chain chimeric polypeptide comprising:
(a) a first chimeric polypeptide comprising:
(i) a first target-binding domain;
(ii) a linker domain; and
(iii) a first domain of a pair of affinity domains;
(b) a second chimeric polypeptide comprising:
(i) a second domain of a pair of affinity domains; and
(ii) a second target-binding domain,
wherein the first chimeric polypeptide and the second chimeric polypeptide associate through the binding of the first domain and the second domain of the pair of affinity domains; and
(2) an effective amount of an IgG1 antibody construct comprising at least one antigen-binding domain that binds specifically to the linker domain, under conditions that allow for mitochondrial oxygen consumption rate by the immune cell.

Embodiment H478. The method of any one of embodiments H473-H477, wherein the liquid culture medium comprises the single-chain chimeric polypeptide and the IgG1 antibody construct.

Embodiment H479. The method of embodiment H478, wherein the IgG1 antibody construct is a monoclonal IgG1 antibody, where both of the antigen-binding domains in the monoclonal IgG1 antibody bind specifically to the linker domain.

Embodiment H480. The method of embodiment H478, wherein the IgG1 antibody construct is a bispecific IgG1 antibody, where one of the two antigen-binding domains in the bispecific IgG1 antibody binds specifically to the linker domain.

Embodiment H481. The method of any one of embodiments H473-H480, wherein the contacting step is performed for a period of about 2 hours to about 20 days.

Embodiment H482. The method of embodiment H481, wherein the contacting step is performed for a period of about 1 day to about 15 days.

Embodiment H483. The method of any one of embodiments H473-H482, wherein the liquid culture medium is a serum-free liquid culture medium.

Embodiment H484. The method of any one of embodiments H473-H482, wherein the liquid culture medium is a chemically-defined liquid culture medium.

Embodiment H485. The method of any one of embodiments H473-H482, wherein the liquid culture medium comprises serum.

Embodiment H486. The method of any one of embodiments H473-H485, wherein the liquid culture medium comprises the single-chain chimeric polypeptide and the IgG1 antibody construct at a molar ratio of about 0.5:1 to about 2:1.

Embodiment H487. The method of embodiment H486, wherein the liquid culture medium comprises the single-chain chimeric polypeptide and the IgG1 antibody construct at a molar ratio of about 0.8:1 to about 1.2:1.

Embodiment H488. The method of any one of embodiments H473-H487, wherein the first target-binding domain and the linker domain directly abut each other in the first chimeric polypeptide.

Embodiment H489. The method of any one of embodiments H473-H487, wherein the first chimeric polypeptide further comprises a linker sequence between the first target-binding domain and the linker domain in the first chimeric polypeptide.

Embodiment H490. The method of any one of embodiments H473-H489, wherein the linker domain and the first domain of the pair of affinity domains directly abut each other in the first chimeric polypeptide.

Embodiment H491. The method of any one of embodiments H473-H489, wherein the first chimeric polypeptide further comprises a linker sequence between the linker domain and the first domain of the pair of affinity domains in the first chimeric polypeptide.

Embodiment H492. The method of any one of embodiments H473-H491, wherein the second domain of the pair of affinity domains and the second target-binding domain directly abut each other in the second chimeric polypeptide.

Embodiment H493. The method of any one of embodiments H473-H491, wherein the second chimeric polypeptide further comprises a linker sequence between the second domain of the pair of affinity domains and the second target-binding domain in the second chimeric polypeptide.

Embodiment H494. The method of any one of embodiments H473-H493, wherein the first target-binding domain and the second target-binding domain bind specifically to the same antigen.

Embodiment H495. The method of embodiment H494, wherein the first target-binding domain and the second target-binding domain bind specifically to the same epitope.

Embodiment H496. The method of embodiment H495, wherein the first target-binding domain and the second target-binding domain comprise the same amino acid sequence.

Embodiment H497. The method of any one of embodiments H473-H493, wherein the first target-binding domain and the second target-binding domain bind specifically to different antigens.

Embodiment H498. The method of any one of embodiments H473-H497, wherein one or both of the first target-binding domain and the second target-binding domain is an antigen-binding domain.

Embodiment H499. The method of embodiment H498, wherein the first target-binding domain and the second target-binding domain are each antigen-binding domains.

Embodiment H500. The method of embodiment H498 or H499, wherein the antigen-binding domain comprises a scFv or a single domain antibody.

Embodiment H501. The method of any one of embodiments H473-H500, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H502. The method of any one of embodiments H473-H497, wherein one or both of the first target-binding domain and the second target-binding domain is a soluble interleukin, soluble cytokine protein, or soluble cell surface protein.

Embodiment H503. The method of embodiment H502, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H504. The method of any one of embodiments H473-H497, wherein one or both of the first target-binding domain and the second target-binding domain is a soluble interleukin or cytokine receptor.

Embodiment H505. The method of embodiment H504, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment H506. The method of any one of embodiments H473-H505, wherein the first chimeric polypeptide further comprises one or more additional target-binding domain(s), where at least one of the one or more target-binding domain(s) is positioned between the linker domain and the first domain of the pair of affinity domains.

Embodiment H507. The method of embodiment H506, wherein the first chimeric polypeptide further comprises a linker sequence between the linker domain and the at least one of the one or more target antigen-binding domain(s), and/or a linker sequence between the at least one of the one or more target antigen-binding domain(s) and the first domain of the pair of affinity domains.

Embodiment H508. The method of any one of embodiments H473-H505, wherein the first chimeric polypeptide further comprises one or more additional target-binding domains at the N-terminal and/or C-terminal end of the first chimeric polypeptide.

Embodiment H509. The method of embodiment H508, wherein at least one of the one or more additional target-binding domains directly abuts the first domain of the pair of affinity domains in the first chimeric polypeptide.

Embodiment H510. The method of embodiment H508, wherein the first chimeric polypeptide further comprises a linker sequence between the at least one of the one or more additional target-binding domains and the first domain of the pair of affinity domains.

Embodiment H511. The method of embodiment H508, wherein the at least one of the one or more additional target-binding domains directly abuts the first target-binding domain in the first chimeric polypeptide.

Embodiment H512. The method of embodiment H508, wherein the first chimeric polypeptide further comprises a linker sequence between the at least one of the one or more additional target-binding domains and the first target-binding domain.

Embodiment H513. The method of embodiment H508, wherein at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide.

Embodiment H514. The method of embodiment H513, wherein the at least one additional target-binding domain of the one or more additional target-binding domains disposed at the N-terminus directly abuts the first target-binding domain or the first domain of the pair of affinity domains in the first chimeric polypeptide.

Embodiment H515. The method of embodiment H513, wherein the first chimeric polypeptide further comprises a linker sequence disposed between the at least one additional target-binding domain and the first target-binding domain or the first domain of the pair of affinity domains in the first chimeric polypeptide.

Embodiment H516. The method of embodiment H513, wherein the at least one additional target-binding domain of the one or more additional target-binding domains disposed at the C-terminus directly abuts the first target-binding domain or the first domain of the pair of affinity domains in the first chimeric polypeptide.

Embodiment H517. The method of embodiment H513, wherein the first chimeric polypeptide further comprises a linker sequence disposed between the at least one additional target-binding domain and the first target-binding domain or the first domain of the pair of affinity domains in the first chimeric polypeptide.

Embodiment H518. The method of embodiment H513, wherein the at least one of the one or more additional target-binding domains positioned between the linker domain and the first domain of the pair of affinity domains, directly abuts the linker domain and/or the first domain of the pair of affinity domains.

Embodiment H519. The method of embodiment H513, wherein the first chimeric polypeptide further comprises a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

Embodiment H520. The method of any one of embodiments H473-H519, wherein the second chimeric polypeptide further comprises one or more additional target-binding domains at the N-terminal end and/or the C-terminal end of the second chimeric polypeptide.

Embodiment H521. The method of embodiment H520, wherein at least one of the one or more additional target-binding domains directly abuts the second domain of the pair of affinity domains in the second chimeric polypeptide.

Embodiment H522. The method of embodiment H520, wherein the second chimeric polypeptide further comprises a linker sequence between at least one of the one or more additional target-binding domains and the second domain of the pair of affinity domains in the second chimeric polypeptide.

Embodiment H523. The method of embodiment H520, wherein at least one of the one or more additional target-binding domains directly abuts the second target-binding domain in the second chimeric polypeptide.

Embodiment H524. The method of embodiment H520, wherein the second chimeric polypeptide further comprises a linker sequence between at least one of the one or more additional target-binding domains and the second target-binding domain in the second chimeric polypeptide.

Embodiment H525. The method of any one of embodiments H506-H524, wherein two or more of the first target-binding domain, the second target-binding domain, and the one or more additional target-binding domains bind specifically to the same antigen.

Embodiment H526. The method of embodiment H525, wherein two or more of the first target-binding domain, the second target-binding domain, and the one or more additional target-binding domains bind specifically to the same epitope.

Embodiment H527. The method of embodiment H526, wherein two or more of the first target-binding domain, the second target-binding domain, and the one or more additional target-binding domains comprise the same amino acid sequence.

Embodiment H528. The method of embodiment H525, wherein the first target-binding domain, the second target-binding domain, and the one or more additional target-binding domains each bind specifically to the same antigen.

Embodiment H529. The method of embodiment H528, wherein the first target-binding domain, the second target-binding domain, and the one or more additional target-binding domains each bind specifically to the same epitope.

Embodiment H530. The method of embodiment H529, wherein the first target-binding domain, the second target-binding domain, and the one or more additional target-binding domains each comprise the same amino acid sequence.

Embodiment H531. The method of any one of embodiments H506-H524, wherein the first target-binding domain, the second target-binding domain, and the one or more additional target-binding domains bind specifically to different antigens.

Embodiment H532. The method of any one of embodiments H506-H531, wherein one or more of the first target-binding domain, the second target-binding domain, and the one or more target-binding domains is an antigen-binding domain.

Embodiment H533. The method of embodiment H532, wherein the first target-binding domain, the second target-binding domain, and the one or more additional target-binding domains are each an antigen-binding domain.

Embodiment H534. The method of embodiment H532 or H533, wherein the antigen-binding domain comprises a scFv.

Embodiment H535. The method of any one of embodiments H506-H534, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment H536. The method of any one of embodiments H506-H534, wherein one or more of the first target-binding domain, the second target-binding domain, and the one or more additional target-binding domains is a soluble interleukin, soluble cytokine protein, or soluble cell surface protein.

Embodiment H537. The method of embodiment H536, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H538. The method of any one of embodiments H506-H534, wherein one or more of the first target-binding domain, the second target-binding domain, and the one or more additional target-binding domains is a soluble interleukin or cytokine receptor.

Embodiment H539. The method of embodiment H538, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment H540. The method of any one of embodiments H473-H539, wherein the first chimeric polypeptide further comprises a peptide tag at the N-terminal end or the C-terminal end of the first chimeric polypeptide.

Embodiment H541. The method of any one of embodiments H473-H539, wherein the second chimeric polypeptide further comprises a peptide tag at the N-terminal end or the C-terminal end of the second chimeric polypeptide.

Embodiment H542. The method of any one of embodiments H473-H541, wherein the linker domain is a soluble tissue factor domain.

Embodiment H543. The method of embodiment H542, wherein the soluble tissue factor domain is a soluble human tissue factor domain.

Embodiment H544. The method of embodiment H543, wherein the soluble human tissue factor domain comprises a sequence that is at least 80% identical to SEQ ID NO: 1.

Embodiment H545. The method of embodiment H544, wherein the soluble human tissue factor domain comprises a sequence that is at least 90% identical to SEQ ID NO: 1.

Embodiment H546. The method of embodiment H545, wherein the soluble human tissue factor domain comprises a sequence that is at least 95% identical to SEQ ID NO: 1.

Embodiment H547. The method of any one of embodiments H543-H546, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H548. The method of embodiment H547, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H549. The method of any one of embodiments H542-H548, wherein the soluble tissue factor domain is not capable of binding to Factor VIIa.

Embodiment H550. The method of any one of embodiments H542-H549, wherein the soluble tissue factor domain does not convert inactive Factor X into Factor Xa.

Embodiment H551. The method of any one of embodiments H542-H550, wherein the multi-chain chimeric polypeptide does not stimulate blood coagulation in a mammal.

Embodiment H552. The method of any one of embodiments H542-H551, wherein the IgG1 antibody construct comprises at least one antigen-binding domain that binds specifically to the soluble tissue factor domain.

Embodiment H553. The method of any one of embodiments H473-H541, wherein the linker domain is selected from the group consisting of: a kappa chain and a lambda chain.

Embodiment H554. The method of any one of embodiments H473-H553, wherein the IgG1 antibody construct is a monoclonal IgG1 antibody, where both antigen-binding domains in the monoclonal IgG1 antibody bind specifically to the linker domain.

Embodiment H555. The method of any one of embodiments H473-H553, wherein the IgG1 antibody construct is a bispecific IgG1 antibody, where one of the two antigen-binding domains in the bispecific IgG1 antibody binds specifically to the linker domain.

Embodiment H556. The method of any one of embodiments H473-H555, wherein the pair of affinity domains is a sushi domain from an alpha chain of human IL-15 receptor (IL15Rα) and a soluble IL-15.

Embodiment H557. The method of embodiment H556, wherein the soluble IL15 has a D8N or D8A amino acid substitution.

Embodiment H558. The method of embodiment H556 or H557, wherein the human IL15Rα is a mature full-length IL15Rα.

Embodiment H559. The method of any one of embodiments H473-H555, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment H560. The method of any one of embodiments H473-H559, wherein the first chimeric polypeptide and/or the second chimeric polypeptide further comprises a signal sequence at its N-terminal end.

Embodiment H561. The method of any one of embodiments H473-H559, wherein the first chimeric polypeptide and/or the second chimeric polypeptide lacks a signal sequence at its N-terminal end.

Embodiment H562. The method of any one of embodiments H473-H561, wherein the immune cell was previously obtained from a subject.

Embodiment H563. The method of embodiment H562, wherein the method further comprises obtaining the immune cell from the subject prior to the contacting step.

Embodiment H564. The method of any one of embodiments H473-H563, wherein the immune cell has previously been genetically modified to express a chimeric antigen receptor or a recombinant T-cell receptor.

Embodiment H565. The method of any one of embodiments H473-H563, wherein the method further comprises, after the contacting step, introducing into the immune cell a nucleic acid encoding a chimeric antigen-receptor or a recombinant T-cell receptor.

Embodiment H566. The method of any one of embodiments H473-H563, wherein the method further comprises, before the contacting step, introducing into the immune cell a nucleic acid encoding a chimeric antigen-receptor or a recombinant T-cell receptor.

Embodiment H567. The method of any one of embodiments H473-H566, wherein the method further comprises, after the contacting step, isolating the immune cell.

Embodiment H568. The method of any one of embodiments H473-H567, wherein after the contacting step, the immune cell has an increased level of expression or secretion of one or more proteins selected from the group consisting of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step.

Embodiment H569. The method of any one of embodiments H473-H568, wherein the method further comprises, after the contacting step, administering the immune cell to a subject in need thereof.

Embodiment H570. The method of embodiment H569, wherein the subject has been identified or diagnosed as having an age-related disease or condition.

Embodiment H571. The method of embodiment H570, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H572. The method of embodiment H569, wherein the subject has been identified or diagnosed as having a cancer.

Embodiment H573. The method of embodiment H572, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H574. The method of embodiment H569, wherein the subject has been diagnosed or identified as having an infectious disease.

Embodiment H575. The method of embodiment H574, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment H576. An activated immune cell produced by the method of any one of embodiments H473-H568.

Embodiment H577. A pharmaceutical composition comprising the activated cell of embodiment H576.

Embodiment H578. A kit comprising a pharmaceutical composition comprising the activated immune cell of embodiment H261.

Embodiment H579. A method of killing a cancer cell, an infected cell, or a senescent cell in a subject in need thereof, the method comprising administering to the subject a therapeutically effective amount of the activated immune cell of embodiment H576 or the pharmaceutical composition of embodiment H577.

Embodiment H580. The method of embodiment H579, wherein the subject has been identified or diagnosed as having a cancer.

Embodiment H581. The method of embodiment H580, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H582. The method of embodiment H579, wherein the subject has been identified or diagnosed as having an aging-related disease or condition.

Embodiment H583. The method of embodiment H582, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Embodiment H584. A method of treating a subject in need thereof, the method comprising administering to the subject a therapeutically effective amount of the activated immune cell of embodiment H576 or the pharmaceutical composition of embodiment H577.

Embodiment H585. The method of embodiment H584, wherein the subject has been identified or diagnosed as having a cancer.

Embodiment H586. The method of embodiment H585, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H587. The method of embodiment H584, wherein the subject has been identified or diagnosed as having an aging-related disease or condition.

Embodiment H588. The method of embodiment H587, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H589. The method of embodiment H584, wherein the subject has been diagnosed or identified as having an infectious disease.

Embodiment H590. The method of embodiment H589, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

What is claimed is:

1. A method of promoting the activation and proliferation of a natural killer cell or a T cell, the method comprising:
contacting a natural killer cell or a T cell in a liquid culture medium comprising:
(1) an effective amount of a multi-chain chimeric polypeptide comprising:
(a) a first chimeric polypeptide comprising:
(i) a first target-binding domain;
(ii) a soluble tissue factor domain comprising a sequence that is at least 90% identical to SEQ ID NO: 1; and
(iii) a first domain of a pair of affinity domains comprising a sequence that is at least 90% identical to SEQ ID NO: 39;
(b) a second chimeric polypeptide comprising:
(i) a second domain of a pair of affinity domains comprising a sequence that is at least 90% identical to SEQ ID NO: 10; and
(ii) a second target-binding domain,
wherein the first chimeric polypeptide and the second chimeric polypeptide associate through the binding of the first domain and the second domain of the pair of affinity domains, and wherein:
(A) the first target-binding domain comprises a sequence that is at least 90% identical to SEQ ID NO: 135 and the second target-binding domain comprises a sequence that is at least 90% identical to SEQ ID NO: 124;
(B) the first target-binding domain comprises a sequence that is at least 90% identical to SEQ ID NO: 124 and the second target-binding domain comprises a sequence that is at least 90% identical to SEQ ID NO: 135; or
(C) the first target-binding domain comprises a sequence that is at least 90% identical to SEQ ID NO: 124 and the second target-binding domain comprises a sequence that is at least 90% identical to SEQ ID NO: 60; and
(2) an effective amount of an IgG1 antibody construct comprising at least one antigen-binding domain that binds specifically to the soluble tissue factor domain, under conditions that allow for the activation and proliferation of the natural killer cell or the T cell.

2. The method of claim 1, wherein the first target-binding domain and the soluble tissue factor domain directly abut each other in the first chimeric polypeptide.

3. The method of claim 1, wherein the first chimeric polypeptide further comprises a linker sequence between the first target-binding domain and the soluble tissue factor domain in the first chimeric polypeptide.

4. The method of claim 1, wherein the soluble tissue factor domain and the first domain of the pair of affinity domains directly abut each other in the first chimeric polypeptide.

5. The method of claim 1, wherein the first chimeric polypeptide further comprises a linker sequence between the soluble tissue factor domain and the first domain of the pair of affinity domains in the first chimeric polypeptide.

6. The method of claim 1, wherein the second domain of the pair of affinity domains and the second target-binding domain directly abut each other in the second chimeric polypeptide.

7. The method of claim 1, wherein the second chimeric polypeptide further comprises a linker sequence between the second domain of the pair of affinity domains and the second target-binding domain in the second chimeric polypeptide.

8. The method of claim 1, wherein the soluble tissue factor domain is a soluble human tissue factor domain.

9. The method of claim 1, wherein the soluble tissue factor domain does not stimulate blood coagulation.

10. The method of claim 1, wherein the soluble tissue factor domain does not stimulate blood coagulation.

11. The method of claim 1, wherein the first chimeric polypeptide comprises a sequence at least 90% identical to SEQ ID NO: 141, and the second chimeric polypeptide comprises a sequence at least 90% identical to SEQ ID NO: 145.

12. The method of claim 1, wherein the first chimeric polypeptide comprises a sequence at least 95% identical to SEQ ID NO: 141, and the second chimeric polypeptide comprises a sequence at least 95% identical to SEQ ID NO: 145.

13. The method of claim 1, wherein the first chimeric polypeptide comprises SEQ ID NO: 141, and the second chimeric polypeptide comprises SEQ ID NO: 145.

14. The method of claim 1, wherein the multi-chain chimeric polypeptide does not stimulate blood coagulation.

15. The method of claim 1, wherein the contacting step is performed for a period of about 2 hours to about 20 days.

16. The method of claim 1, wherein the liquid culture medium comprises the multi-chain chimeric polypeptide and the IgG1 antibody construct at a molar ratio of about 0.5:1 to about 2:1.

17. The method of claim 1, wherein the NK cell or T cell has previously been genetically modified to express a chimeric antigen receptor or a recombinant T-cell receptor.

18. The method of claim 1, wherein the method further comprises, after the contacting step, introducing into the NK cell or the T cell a nucleic acid encoding a chimeric antigen-receptor of a recombinant T-cell receptor.

19. The method of claim 1, wherein:
the first target-binding domain comprises a sequence that is at least 90% identical to SEQ ID NO: 135; and
the second target-binding domain comprises a sequence that is at least 90% identical to SEQ ID NO: 124.

20. The method of claim 1, wherein:
the first target-binding domain comprises a sequence that is at least 95% identical to SEQ ID NO: 135;
the soluble tissue factor domain comprises a sequence that is at least 95% identical to SEQ ID NO: 1;
the first domain of the pair of affinity domains comprises a sequence that is at least 95% identical to SEQ ID NO: 39;
the second domain of the pair of affinity domains comprises a sequence that is at least 95% identical to SEQ ID NO: 10; and
the second target-binding domain comprises a sequence that is at least 95% identical to SEQ ID NO: 124.

21. The method of claim 1, wherein:
the first target-binding domain comprises SEQ ID NO: 135;
the soluble tissue factor domain comprises SEQ ID NO: 1;
the first domain of the pair of affinity domains comprises SEQ ID NO: 39;
the second domain of the pair of affinity domains comprises SEQ ID NO: 10; and
the second target-binding domain comprises SEQ ID NO: 124.

22. The method of claim 1, wherein:
the first target-binding domain comprises a sequence that is at least 90% identical to SEQ ID NO: 124; and
the second target-binding domain comprises a sequence that is at least 90% identical to SEQ ID NO: 135.

23. The method of claim 1, wherein:
the first target-binding domain comprises a sequence that is at least 95% identical to SEQ ID NO: 124;
the soluble tissue factor domain comprises a sequence that is at least 95% identical to SEQ ID NO: 1;
the first domain of the pair of affinity domains comprises a sequence that is at least 95% identical to SEQ ID NO: 39;
the second domain of the pair of affinity domains comprises a sequence that is at least 95% identical to SEQ ID NO: 10; and
the second target-binding domain comprises a sequence that is at least 95% identical to SEQ ID NO: 135.

24. The method of claim 1, wherein:
the first target-binding domain comprises SEQ ID NO: 124;
the soluble tissue factor domain comprises SEQ ID NO: 1;
the first domain of the pair of affinity domains comprises SEQ ID NO: 39;
the second domain of the pair of affinity domains comprises SEQ ID NO: 10; and
the second target-binding domain comprises SEQ ID NO: 135.

25. The method of claim 1, wherein:
the first chimeric polypeptide comprises a sequence that is at least 90% identical to SEQ ID NO: 126; and
the second chimeric polypeptide comprises a sequence that is at least 90% identical to SEQ ID NO: 137.

26. The method of claim 1, wherein:
the first chimeric polypeptide comprises a sequence that is at least 95% identical to SEQ ID NO: 126; and
the second chimeric polypeptide comprises a sequence that is at least 95% identical to SEQ ID NO: 137.

27. The method of claim 1, wherein:
the first chimeric polypeptide comprises SEQ ID NO: 126; and
the second chimeric polypeptide comprises SEQ ID NO: 137.

28. The method of claim 1, wherein:
the first target-binding domain comprises a sequence that is at least 95% identical to SEQ ID NO: 124;
the soluble tissue factor domain comprises a sequence that is at least 95% identical to SEQ ID NO: 1;
the first domain of the pair of affinity domains comprises a sequence that is at least 95% identical to SEQ ID NO: 39;
the second domain of the pair of affinity domains comprises a sequence that is at least 95% identical to SEQ ID NO: 10; and
the second target-binding domain comprises a sequence that is at least 95% identical to SEQ ID NO: 60.

* * * * *

UNITED STATES PATENT AND TRADEMARK OFFICE
CERTIFICATE OF CORRECTION

| | |
|---|---|
| PATENT NO. | : 11,730,762 B2 |
| APPLICATION NO. | : 16/557822 |
| DATED | : August 22, 2023 |
| INVENTOR(S) | : Hing Wong |

It is certified that error appears in the above-identified patent and that said Letters Patent is hereby corrected as shown below:

On the Title Page

Item (71), under Applicant, Line 1, delete "Biologies," and insert -- Biologics, --.

In the Claims

Claim 10: In Column 883, Lines 28-29, delete "10. The method of claim 1, wherein the soluble tissue factor domain does not stimulate blood coagulation."

Please renumber claims 11-27 to claims 10-26 in view of the above correction.

Claim 27: In Column 884, Line 68, below "137", insert
-- 27. The method of claim 1, wherein:
    the first target-binding domain comprises a sequence that is at least 90% identical to SEQ ID NO: 124; and
    the second target-binding domain comprises a sequence that is at least 90% identical to SEQ ID NO: 60. --

Signed and Sealed this
Twenty-eighth Day of November, 2023

Katherine Kelly Vidal
*Director of the United States Patent and Trademark Office*

SEQUENCE LISTING

```
<160> NUMBER OF SEQ ID NOS: 198

<210> SEQ ID NO 1
<211> LENGTH: 219
<212> TYPE: PRT
<213> ORGANISM: Homo sapiens
<220> FEATURE:
<221> NAME/KEY: source
<223> OTHER INFORMATION: /note="soluble human tissue factor domain"

<400> SEQUENCE: 1

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
```

165                 170                 175
Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 2
<211> LENGTH: 657
<212> TYPE: DNA
<213> ORGANISM: Homo sapiens
<220> FEATURE:
<221> NAME/KEY: source
<223> OTHER INFORMATION: /note="Soluble Human Tissue Factor Domain"

<400> SEQUENCE: 2
agcggcacaa ccaacacagt cgctgcctat aacctcactt ggaagagcac caacttcaaa      60
accatcctcg aatgggaacc caaacccgtt aaccaagttt acaccgtgca gatcagcacc     120
aagtccggcg actggaagtc caaatgtttc tataccaccg acaccgagtg cgatctcacc     180
gatgagatcg tgaaagatgt gaaacagacc tacctcgccc gggtgtttag ctaccccgcc     240
ggcaatgtgg agagcactgg ttccgctggc gagcctttat acgagaacag ccccgaattt     300
accccttacc tcgagaccaa tttaggacag cccaccatcc aaagctttga gcaagttggc     360
acaaaggtga atgtgacagt ggaggacgag cggactttag tgcggcggaa caacacccttt    420 ctcagcctcc gggatgtgtt cggcaaagat ttaatctaca cactgtatta ctggaagtcc     480
tcttcctccg gcaagaagac agctaaaacc aacacaaacg agttttttaat cgacgtggat    540 aaaggcgaaa actactgttt cagcgtgcaa gctgtgatcc cctcccggac cgtgaatagg     600
aaaagcaccg atagccccgt tgagtgcatg ggccaagaaa agggcgagtt ccgggag       657

<210> SEQ ID NO 3
<211> LENGTH: 223
<212> TYPE: PRT
<213> ORGANISM: Mus musculus
<220> FEATURE:
<221> NAME/KEY: source
<223> OTHER INFORMATION: /note="Soluble Mouse Tissue Factor domain"

<400> SEQUENCE: 3

Ala Gly Ile Pro Glu Lys Ala Phe Asn Leu Thr Trp Ile Ser Thr Asp
1               5                   10                  15

Phe Lys Thr Ile Leu Glu Trp Gln Pro Lys Pro Thr Asn Tyr Thr Tyr
            20                  25                  30

Thr Val Gln Ile Ser Asp Arg Ser Arg Asn Trp Lys Asn Lys Cys Phe
        35                  40                  45

Ser Thr Thr Asp Thr Glu Cys Asp Leu Thr Asp Glu Ile Val Lys Asp
    50                  55                  60

Val Thr Trp Ala Tyr Glu Ala Lys Val Leu Ser Val Pro Arg Arg Asn
65                  70                  75                  80

Ser Val His Gly Asp Gly Asp Gln Leu Val Ile His Gly Glu Glu Pro
                85                  90                  95

Pro Phe Thr Asn Ala Pro Lys Phe Leu Pro Tyr Arg Asp Thr Asn Leu
            100                 105                 110

Gly Gln Pro Val Ile Gln Gln Phe Glu Gln Asp Gly Arg Lys Leu Asn
        115                 120                 125

Val Val Val Lys Asp Ser Leu Thr Leu Val Arg Lys Asn Gly Thr Phe
            130                 135                 140

Leu Thr Leu Arg Gln Val Phe Gly Lys Asp Leu Gly Tyr Ile Ile Thr
145                 150                 155                 160

Tyr Arg Lys Gly Ser Ser Thr Gly Lys Lys Thr Asn Ile Thr Asn Thr
                165                 170                 175

Asn Glu Phe Ser Ile Asp Val Glu Glu Gly Val Ser Tyr Cys Phe Phe
                180                 185                 190

Val Gln Ala Met Ile Phe Ser Arg Lys Thr Asn Gln Asn Ser Pro Gly
                195                 200                 205

Ser Ser Thr Val Cys Thr Glu Gln Trp Lys Ser Phe Leu Gly Glu
            210                 215                 220

<210> SEQ ID NO 4
<211> LENGTH: 224
<212> TYPE: PRT
<213> ORGANISM: Rattus rattus
<220> FEATURE:
<221> NAME/KEY: source
<223> OTHER INFORMATION: /note="Soluble rat Tissue Factor domain"

<400> SEQUENCE: 4

Ala Gly Thr Pro Pro Gly Lys Ala Phe Asn Leu Thr Trp Ile Ser Thr
1               5                   10                  15

Asp Phe Lys Thr Ile Leu Glu Trp Gln Pro Lys Pro Thr Asn Tyr Thr
                20                  25                  30

Tyr Thr Val Gln Ile Ser Asp Arg Ser Arg Asn Trp Lys Tyr Lys Cys
                35                  40                  45

Thr Gly Thr Thr Asp Thr Glu Cys Asp Leu Thr Asp Glu Ile Val Lys
            50                  55                  60

Asp Val Asn Trp Thr Tyr Glu Ala Arg Val Leu Ser Val Pro Trp Arg
65                  70                  75                  80

Asn Ser Thr His Gly Lys Glu Thr Leu Phe Gly Thr His Gly Glu Glu
                85                  90                  95

Pro Pro Phe Thr Asn Ala Arg Lys Phe Leu Pro Tyr Arg Asp Thr Lys
                100                 105                 110

Ile Gly Gln Pro Val Ile Gln Lys Tyr Glu Gln Gly Thr Lys Leu
            115                 120                 125

Lys Val Thr Val Lys Asp Ser Phe Thr Leu Val Arg Lys Asn Gly Thr
            130                 135                 140

Phe Leu Thr Leu Arg Gln Val Phe Gly Asn Asp Leu Gly Tyr Ile Leu
145                 150                 155                 160

Thr Tyr Arg Lys Asp Ser Ser Thr Gly Arg Lys Thr Asn Thr Thr His
                165                 170                 175

Thr Asn Glu Phe Leu Ile Asp Val Glu Lys Gly Val Ser Tyr Cys Phe
                180                 185                 190

Phe Ala Gln Ala Val Ile Phe Ser Arg Lys Thr Asn His Lys Ser Pro
                195                 200                 205

Glu Ser Ile Thr Lys Cys Thr Glu Gln Trp Lys Ser Val Leu Gly Glu
            210                 215                 220

<210> SEQ ID NO 5
<211> LENGTH: 219
<212> TYPE: PRT
<213> ORGANISM: Homo sapiens
<220> FEATURE:
<221> NAME/KEY: source
<223> OTHER INFORMATION: /note="Mutant Soluble Human Tissue Factor Domain"

<400> SEQUENCE: 5

```
Ser Gly Thr Thr Asn Thr Val Ala Ala Tyr Asn Leu Thr Trp Lys Ser
1               5                   10                  15

Thr Asn Phe Ala Thr Ala Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Ala Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Ala Arg Asn Asn Thr Ala Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215
```

<210> SEQ ID NO 6
<211> LENGTH: 219
<212> TYPE: PRT
<213> ORGANISM: Homo sapiens
<220> FEATURE:
<221> NAME/KEY: source
<223> OTHER INFORMATION: /note="Mutant Soluble Human Tissue Factor Domain"

<400> SEQUENCE: 6

```
Ser Gly Thr Thr Asn Thr Val Ala Ala Tyr Asn Leu Thr Trp Lys Ser
1               5                   10                  15

Thr Asn Phe Ala Thr Ala Leu Glu Trp Glu Pro Lys Pro Val Asn Gln
            20                  25                  30

Val Tyr Thr Val Gln Ile Ser Thr Lys Ser Gly Asp Ala Lys Ser Lys
        35                  40                  45

Cys Phe Tyr Thr Thr Asp Thr Glu Cys Ala Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Ala Glu Asn
                85                  90                  95

Ser Pro Glu Phe Thr Pro Tyr Leu Glu Thr Asn Leu Gly Gln Pro Thr
            100                 105                 110
```

```
Ile Gln Ser Phe Glu Gln Val Gly Thr Lys Val Asn Val Thr Val Glu
            115                 120                 125

Asp Glu Arg Thr Leu Val Ala Arg Asn Asn Thr Ala Leu Ser Leu Arg
        130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
        210                 215
```

<210> SEQ ID NO 7
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic linker sequence"

<400> SEQUENCE: 7

```
Gly Gly Gly Gly Ser Gly Gly Gly Gly Ser Gly Gly Gly Gly Ser
1               5                   10                  15
```

<210> SEQ ID NO 8
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic linker sequence"

<400> SEQUENCE: 8
ggcggtggag gatccggagg aggtggctcc ggcggcggag gatct      45

<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic linker sequence"

<400> SEQUENCE: 9

```
Gly Gly Gly Ser Gly Gly Gly Ser
1               5
```

<210> SEQ ID NO 10
<211> LENGTH: 65
<212> TYPE: PRT
<213> ORGANISM: Homo sapiens
<220> FEATURE:
<221> NAME/KEY: source
<223> OTHER INFORMATION: /note="sushi domain from an alpha chain of IL-15 receptor alpha (IL15Ralpha)"

<400> SEQUENCE: 10

```
Ile Thr Cys Pro Pro Pro Met Ser Val Glu His Ala Asp Ile Trp Val
1               5                   10                  15
```

-continued

```
Lys Ser Tyr Ser Leu Tyr Ser Arg Glu Arg Tyr Ile Cys Asn Ser Gly
         20                  25                  30

Phe Lys Arg Lys Ala Gly Thr Ser Ser Leu Thr Glu Cys Val Leu Asn
     35                  40                  45

Lys Ala Thr Asn Val Ala His Trp Thr Thr Pro Ser Leu Lys Cys Ile
 50                  55                  60

Arg
 65

<210> SEQ ID NO 11
<211> LENGTH: 195
<212> TYPE: DNA
<213> ORGANISM: Homo sapiens
<220> FEATURE:
<221> NAME/KEY: source
<223> OTHER INFORMATION: /note="sushi domain from an alpha chain of
      IL-15 receptor alpha (IL15Ralpha)"

<400> SEQUENCE: 11
attacatgcc cccctcccat gagcgtggag cacgccgaca tctgggtgaa gagctatagc        60
ctctacagcc gggagaggta tatctgtaac agcggcttca agaggaaggc cggcaccagc       120
agcctcaccg agtgcgtgct gaataaggct accaacgtgg ctcactggac aacaccctct       180
ttaaagtgca tccgg                                                       195

<210> SEQ ID NO 12
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic anti-CD3 scFv sequence"

<400> SEQUENCE: 12
cagatcgtgc tgacccaaag ccccgccatc atgagcgcta gccccggtga aaggtgacc         60 atgacatgct ccgcttccag ctccgtgtcc tacatgaact ggtatcagca gaaaagcgga       120
accagcccca aaggtggat ctacgacacc agcaagctgg cctccggagt gcccgctcat        180
ttccggggct ctggatccgg caccagctac tctttaacca tttccggcat ggaagctgaa       240
gacgctgcca cctactattg ccagcaatgg agcagcaacc ccttcacatt cggatctggc       300
accaagctcg aaatcaatcg tggaggaggt ggcagcggcg gcggtggatc cggcggagga       360
ggaagccaag ttcaactcca gcagagcggc gctgaactgg cccggcccgg cgcctccgtc       420
aagatgagct gcaaggcttc cggctataca tttactcgtt acacaatgca ttgggtcaag       480
cagaggcccg gtcaaggttt agagtggatc ggatatatca cccttcccg gggctacacc       540 aactataacc aaaagttcaa ggataaagcc actttaacca ctgacaagag ctcctccacc       600
gcctacatgc agctgtcctc tttaaccagc gaggactccg ctgtttacta ctgcgctagg       660
tattacgacg accactactg tttagactat tggggacaag gtaccacttt aaccgtcagc       720
agc                                                                    723

<210> SEQ ID NO 13
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic anti-CD28 scFv sequence"

<400> SEQUENCE: 13

```
gtccagctgc agcagagcgg acccgaactc gtgaaacccg gtgcttccgt gaaaatgtct      60
tgtaaggcca gcggatacac cttcaccctcc tatgtgatcc agtgggtcaa acagaagccc    120
```
*(note: line 2 above as printed)*

```
gtccagctgc agcagagcgg acccgaactc gtgaaacccg gtgcttccgt gaaaatgtct      60
tgtaaggcca gcggatacac cttcacctcc tatgtgatcc agtgggtcaa acagaagccc    120
ggacaaggtc tcgagtggat cggcagcatc aaccttaca  acgactatac caaatacaac    180
gagaagttta agggaaaggc tactttaacc tccgacaaaa gctccatcac agcctacatg    240
gagttcagct ctttaacatc cgaggacagc gctctgtact attgcgcccg tggggcgac     300
ggcaattact ggggacgggg cacaacactg accgtgagca gcggaggcgg aggctccggc    360
ggaggcggat ctggcggtgg cggctccgac atcgagatga cccagtcccc cgctatcatg    420
tccgcctctt taggcgagcg ggtcacaatg acttgtacag cctcctccag cgtctcctcc    480
tcctacttcc attggtacca acagaaaccc ggaagctccc ctaaactgtg catctacagc    540
accagcaatc tcgccagcgg cgtgccccct aggttttccg gaagcggaag caccagctac    600
tctttaacca tctcctccat ggaggctgag gatgccgcca cctactttg  tcaccagtac    660
caccggtccc ccaccttcgg aggcggcacc aaactggaga caaagagg              708
```

<210> SEQ ID NO 14
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic sequencing primer C186-IFNG135F"

<400> SEQUENCE: 14

```
ggtgggtata atggg                                                      15
```

<210> SEQ ID NO 15
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic sequencing primer C54-IFNG261F"

<400> SEQUENCE: 15

```
attattttat tttaaaaaat ttgtg                                           25
```

<210> SEQ ID NO 16
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic anti-CD3 scFv heavy chain variable domain sequence"

<400> SEQUENCE: 16

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60
```

-continued

```
Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115
```

<210> SEQ ID NO 17
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic anti-CD3 scFv light chain variable domain sequence"

<400> SEQUENCE: 17

```
Gln Ile Val Leu Thr Gln Ser Pro Ala Ile Met Ser Ala Ser Pro Gly
  1               5                  10                  15

Glu Lys Val Thr Met Thr Cys Ser Ala Ser Ser Val Ser Tyr Met
                 20                  25                  30

Asn Trp Tyr Gln Gln Lys Ser Gly Thr Ser Pro Lys Arg Trp Ile Tyr
             35                  40                  45

Asp Thr Ser Lys Leu Ala Ser Gly Val Pro Ala His Phe Arg Gly Ser
         50                  55                  60

Gly Ser Gly Thr Ser Tyr Ser Leu Thr Ile Ser Gly Met Glu Ala Glu
 65                  70                  75                  80

Asp Ala Ala Thr Tyr Tyr Cys Gln Gln Trp Ser Ser Asn Pro Phe Thr
                 85                  90                  95

Phe Gly Ser Gly Thr Lys Leu Glu Ile Asn Arg
            100                 105
```

<210> SEQ ID NO 18
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic anti-CD3 scFv heavy chain variable domain sequence"

<400> SEQUENCE: 18

```
caagttcagc tccagcaaag cggcgccgaa ctcgctcggc ccggcgcttc cgtgaagatg    60
tcttgtaagg cctccggcta taccttcacc cggtacacaa tgcactgggt caagcaacgg   120
cccggtcaag gtttagagtg gattggctat atcaacccct cccggggcta taccaactac   180
aaccagaagt tcaaggacaa agccacccte accaccgaca gtccagcag cacccgcttac  240 atgcagctga gctctttaac atccgaggat tccgccgtgt actactgcgc tcggtactac   300
gacgatcatt actgcctcga ttactggggc caaggtacca ccttaacagt ctcctcc     357
```

<210> SEQ ID NO 19
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic anti-CD3 scFv light chain variable domain sequence"

<400> SEQUENCE: 19

```
cagatcgtgc tgacccagtc ccccgctatt atgagcgcta gccccggtga aaaggtgact      60
atgacatgca gcgccagctc ttccgtgagc tacatgaact ggtatcagca gaagtccggc     120
accagcccta aaaggtggat ctacgacacc agcaagctgg ccagcggcgt ccccgctcac     180
tttcggggct ccggctccgg aacaagctac tctctgacca tcagcggcat ggaagccgag     240
gatgccgcta cctattactg tcagcagtgg agctccaacc ccttcacctt tggatccggc     300
accaagctcg agattaatcg t                                               321
```

<210> SEQ ID NO 20
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence: Synthetic anti-CD3 scFv sequence"

<400> SEQUENCE: 20

```
Gln Ile Val Leu Thr Gln Ser Pro Ala Ile Met Ser Ala Ser Pro Gly
 1               5                  10                  15
Glu Lys Val Thr Met Thr Cys Ser Ala Ser Ser Ser Val Ser Tyr Met
            20                  25                  30
Asn Trp Tyr Gln Gln Lys Ser Gly Thr Ser Pro Lys Arg Trp Ile Tyr
        35                  40                  45
Asp Thr Ser Lys Leu Ala Ser Gly Val Pro Ala His Phe Arg Gly Ser
    50                  55                  60
Gly Ser Gly Thr Ser Tyr Ser Leu Thr Ile Ser Gly Met Glu Ala Glu
65                  70                  75                  80
Asp Ala Ala Thr Tyr Tyr Cys Gln Gln Trp Ser Ser Asn Pro Phe Thr
                85                  90                  95
Phe Gly Ser Gly Thr Lys Leu Glu Ile Asn Arg Gly Gly Gly Gly Ser
            100                 105                 110
Gly Gly Gly Gly Ser Gly Gly Gly Ser Gln Val Gln Leu Gln Gln
        115                 120                 125
Ser Gly Ala Glu Leu Ala Arg Pro Gly Ala Ser Val Lys Met Ser Cys
130                 135                 140
Lys Ala Ser Gly Tyr Thr Phe Thr Arg Tyr Thr Met His Trp Val Lys
145                 150                 155                 160
Gln Arg Pro Gly Gln Gly Leu Glu Trp Ile Gly Tyr Ile Asn Pro Ser
                165                 170                 175
Arg Gly Tyr Thr Asn Tyr Asn Gln Lys Phe Lys Asp Lys Ala Thr Leu
            180                 185                 190
Thr Thr Asp Lys Ser Ser Ser Thr Ala Tyr Met Gln Leu Ser Ser Leu
        195                 200                 205
Thr Ser Glu Asp Ser Ala Val Tyr Tyr Cys Ala Arg Tyr Tyr Asp Asp
    210                 215                 220
His Tyr Cys Leu Asp Tyr Trp Gly Gln Gly Thr Thr Leu Thr Val Ser
225                 230                 235                 240
Ser
```

<210> SEQ ID NO 21
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic anti-CD3 scFv sequence"

<400> SEQUENCE: 21

```
cagatcgtgc tgacccagtc ccccgctatt atgagcgcta gccccggtga aaaggtgact    60
atgacatgca gcgccagctc ttccgtgagc tacatgaact ggtatcagca gaagtccggc   120
accagcccta aaaggtggat ctacgacacc agcaagctgg ccagcggcgt ccccgctcac   180
tttcggggct ccggctccgg aacaagctac tctctgacca tcagcggcat ggaagccgag   240
gatgccgcta cctattactg tcagcagtgg agctccaacc ccttcacctt tggatccggc   300
accaagctcg agattaatcg tggaggcgga ggtagcggag gaggcggatc cggcggtgga   360
ggtagccaag ttcagctcca gcaaagcggc gccgaactcg tcggcccgg cgcttccgtg    420 aagatgtctt gtaaggcctc cggctatacc ttcacccggt acacaatgca ctgggtcaag   480
caacggcccg gtcaaggttt agagtggatt ggctatatca cccctcccg gggctatacc    540 aactacaacc agaagttcaa ggacaaagcc accctcacca ccgacaagtc agcagcacc    600 gcttacatgc agctgagctc tttaacatcc gaggattccg ccgtgtacta ctgcgctcgg   660
tactacgacg atcattactg cctcgattac tggggccaag gtaccacctt aacagtctcc   720
tcc                                                                  723
```

<210> SEQ ID NO 22
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic anti-CD28 scFv heavy chain variable domain sequence"

<400> SEQUENCE: 22

```
Asp Ile Glu Met Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Phe His Trp Tyr Gln Gln Lys Pro Gly Ser Ser Pro Lys Leu Cys
        35                  40                  45

Ile Tyr Ser Thr Ser Asn Leu Ala Ser Gly Val Pro Pro Arg Phe Ser
    50                  55                  60

Gly Ser Gly Ser Thr Ser Tyr Ser Leu Thr Ile Ser Ser Met Glu Ala
65                  70                  75                  80

Glu Asp Ala Ala Thr Tyr Phe Cys His Gln Tyr His Arg Ser Pro Thr
                85                  90                  95

Phe Gly Gly Gly Thr Lys Leu Glu Thr Lys Arg
            100                 105
```

<210> SEQ ID NO 23
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic anti-CD28 scFv light chain variable domain sequence"

<400> SEQUENCE: 23

```
Val Gln Leu Gln Gln Ser Gly Pro Glu Leu Val Lys Pro Gly Ala Ser
```

```
1               5                   10                  15
Val Lys Met Ser Cys Lys Ala Ser Gly Tyr Thr Phe Thr Ser Tyr Val
                20                  25                  30

Ile Gln Trp Val Lys Gln Lys Pro Gly Gln Gly Leu Glu Trp Ile Gly
        35                  40                  45

Ser Ile Asn Pro Tyr Asn Asp Tyr Thr Lys Tyr Asn Glu Lys Phe Lys
    50                  55                  60

Gly Lys Ala Thr Leu Thr Ser Asp Lys Ser Ser Ile Thr Ala Tyr Met
65                  70                  75                  80

Glu Phe Ser Ser Leu Thr Ser Glu Asp Ser Ala Leu Tyr Tyr Cys Ala
                85                  90                  95

Arg Trp Gly Asp Gly Asn Tyr Trp Gly Arg Gly Thr Thr Leu Thr Val
                100                 105                 110

Ser Ser
```

<210> SEQ ID NO 24
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic anti-CD28 scFv heavy chain variable domain sequence"

<400> SEQUENCE: 24

```
gacatcgaga tgacacagtc ccccgctatc atgagcgcct ctttaggaga acgtgtgacc      60
atgacttgta cagcttcctc cagcgtgagc agctcctatt ccactggtta ccagcagaaa    120
cccggctcct cccctaaact gtgtatctac tccacaagca atttagctag cggcgtgcct    180
cctcgtttta gcggctccgg cagcacctct tactctttaa ccattagctc tatggaggcc    240
gaagatgccg ccacatactt ttgccatcag taccaccggt cccctacctt tggcggaggc    300
acaaagctgg agaccaagcg g                                              321
```

<210> SEQ ID NO 25
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic anti-CD28 scFv light chain variable domain sequence"

<400> SEQUENCE: 25

```
gtgcagctgc agcagtccgg acccgaactg gtcaagcccg gtgcctccgt gaaaatgtct      60
tgtaaggctt ctggctacac ctttacctcc tacgtcatcc aatgggtgaa gcagaagccc    120
ggtcaaggtc tcgagtggat cggcagcatc aatccctaca cgattacac caagtataac    180 gaaaagttta agggcaaggc cactctgaca agcgacaaga gctccattac cgcctacatg    240
gagttttcct ctttaacttc tgaggactcc gctttatact attgcgctcg ttggggcgat    300
ggcaattatt ggggccgggg aactacttta acagtgagct cc                       342
```

<210> SEQ ID NO 26
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic anti-CD28 scFv sequence"

<400> SEQUENCE: 26

```
Val Gln Leu Gln Gln Ser Gly Pro Glu Leu Val Lys Pro Gly Ala Ser
1               5                   10                  15
Val Lys Met Ser Cys Lys Ala Ser Gly Tyr Thr Phe Thr Ser Tyr Val
            20                  25                  30
Ile Gln Trp Val Lys Gln Lys Pro Gly Gln Gly Leu Glu Trp Ile Gly
        35                  40                  45
Ser Ile Asn Pro Tyr Asn Asp Tyr Thr Lys Tyr Asn Glu Lys Phe Lys
    50                  55                  60
Gly Lys Ala Thr Leu Thr Ser Asp Lys Ser Ser Ile Thr Ala Tyr Met
65                  70                  75                  80
Glu Phe Ser Ser Leu Thr Ser Glu Asp Ser Ala Leu Tyr Tyr Cys Ala
                85                  90                  95
Arg Trp Gly Asp Gly Asn Tyr Trp Gly Arg Gly Thr Thr Leu Thr Val
            100                 105                 110
Ser Ser Gly Gly Gly Gly Ser Gly Gly Gly Gly Ser Gly Gly Gly Gly
        115                 120                 125
Ser Asp Ile Glu Met Thr Gln Ser Pro Ala Ile Met Ser Ala Ser Leu
    130                 135                 140
Gly Glu Arg Val Thr Met Thr Cys Thr Ala Ser Ser Ser Val Ser Ser
145                 150                 155                 160
Ser Tyr Phe His Trp Tyr Gln Gln Lys Pro Gly Ser Ser Pro Lys Leu
                165                 170                 175
Cys Ile Tyr Ser Thr Ser Asn Leu Ala Ser Gly Val Pro Pro Arg Phe
            180                 185                 190
Ser Gly Ser Gly Ser Thr Ser Tyr Ser Leu Thr Ile Ser Ser Met Glu
        195                 200                 205
Ala Glu Asp Ala Ala Thr Tyr Phe Cys His Gln Tyr His Arg Ser Pro
    210                 215                 220
Thr Phe Gly Gly Gly Thr Lys Leu Glu Thr Lys Arg
225                 230                 235
```

<210> SEQ ID NO 27
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence: Synthetic anti-CD28 scFv sequence"

<400> SEQUENCE: 27

```
gtgcagctgc agcagtccgg acccgaactg gtcaagcccg gtgcctccgt gaaaatgtct      60
tgtaaggctt ctggctacac ctttacctcc tacgtcatcc aatgggtgaa gcagaagccc     120
ggtcaaggtc tcgagtggat cggcagcatc aatccctaca cgattacac caagtataac     180
gaaaagttta agggcaaggc cactctgaca agcgacaaga gctccattac cgcctacatg     240
gagttttcct ctttaacttc tgaggactcc gctttatact attgcgctcg ttggggcgat     300
ggcaattatt gggccggggg aactacttta acagtgagct ccggcggcgg cggaagcgga     360
ggtggaggat ctggcggtgg aggcagcgac atcgagatga cacagtcccc cgctatcatg     420
agcgcctctt taggagaacg tgtgaccatg acttgtacag cttcctccag cgtgagcagc     480
tcctatttcc actggtacca gcagaaaccc ggctcctccc ctaaactgtg tatctactcc     540
acaagcaatt tagctagcgg cgtgcctcct cgttttagcg gctccggcag cacctcttac     600
```

```
tctttaacca ttagctctat ggaggccgaa gatgccgcca catactttg ccatcagtac    660 caccggtccc ctacctttgg cggaggcaca aagctggaga ccaagcgg               708
```

<210> SEQ ID NO 28
<211> LENGTH: 133
<212> TYPE: PRT
<213> ORGANISM: Homo sapiens
<220> FEATURE:
<221> NAME/KEY: source
<223> OTHER INFORMATION: /note="Human Soluble IL-2"

<400> SEQUENCE: 28

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 29
<211> LENGTH: 133
<212> TYPE: PRT
<213> ORGANISM: Homo sapiens
<220> FEATURE:
<221> NAME/KEY: source
<223> OTHER INFORMATION: /note="Human Soluble IL-3"

<400> SEQUENCE: 29

```
Ala Pro Met Thr Gln Thr Thr Pro Leu Lys Thr Ser Trp Val Asn Cys
1               5                   10                  15

Ser Asn Met Ile Asp Glu Ile Ile Thr His Leu Lys Gln Pro Pro Leu
                20                  25                  30

Pro Leu Leu Asp Phe Asn Asn Leu Asn Gly Glu Asp Gln Asp Ile Leu
            35                  40                  45

Met Glu Asn Asn Leu Arg Arg Pro Asn Leu Glu Ala Phe Asn Arg Ala
        50                  55                  60

Val Lys Ser Leu Gln Asn Ala Ser Ala Ile Glu Ser Ile Leu Lys Asn
65                  70                  75                  80

Leu Leu Pro Cys Leu Pro Leu Ala Thr Ala Ala Pro Thr Arg His Pro
                85                  90                  95

Ile His Ile Lys Asp Gly Asp Trp Asn Glu Phe Arg Arg Lys Leu Thr
            100                 105                 110

Phe Tyr Leu Lys Thr Leu Glu Asn Ala Gln Ala Gln Gln Thr Thr Leu
        115                 120                 125

Ser Leu Ala Ile Phe
```

130

<210> SEQ ID NO 30
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic sequencing primer IFNG127F"

<400> SEQUENCE: 30
atggtatagg tgggtataat gg                                          22

<210> SEQ ID NO 31
<211> LENGTH: 79
<212> TYPE: PRT
<213> ORGANISM: Homo sapiens
<220> FEATURE:
<221> NAME/KEY: source
<223> OTHER INFORMATION: /note="Human Soluble IL-8"

<400> SEQUENCE: 31

Glu Gly Ala Val Leu Pro Arg Ser Ala Lys Glu Leu Arg Cys Gln Cys
1               5                   10                  15

Ile Lys Thr Tyr Ser Lys Pro Phe His Pro Lys Phe Ile Lys Glu Leu
            20                  25                  30

Arg Val Ile Glu Ser Gly Pro His Cys Ala Asn Thr Glu Ile Ile Val
        35                  40                  45

Lys Leu Ser Asp Gly Arg Glu Leu Cys Leu Asp Pro Lys Glu Asn Trp
    50                  55                  60

Val Gln Arg Val Val Glu Lys Phe Leu Lys Arg Ala Glu Asn Ser
65                  70                  75

<210> SEQ ID NO 32
<211> LENGTH: 160
<212> TYPE: PRT
<213> ORGANISM: Homo sapiens
<220> FEATURE:
<221> NAME/KEY: source
<223> OTHER INFORMATION: /note="Human Soluble IL-10"

<400> SEQUENCE: 32

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

```
Ile Phe Ile Asn Tyr Ile Glu Ala Tyr Met Thr Met Lys Ile Arg Asn
145                 150                 155                 160
```

<210> SEQ ID NO 33
<211> LENGTH: 306
<212> TYPE: PRT
<213> ORGANISM: Homo sapiens
<220> FEATURE:
<221> NAME/KEY: source
<223> OTHER INFORMATION: /note="Human Soluble IL-12beta (p40)"

<400> SEQUENCE: 33

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305
```

<210> SEQ ID NO 34
<211> LENGTH: 918
<212> TYPE: DNA

<213> ORGANISM: Homo sapiens
<220> FEATURE:
<221> NAME/KEY: source
<223> OTHER INFORMATION: /note="Human Soluble IL-12beta (p40)"

<400> SEQUENCE: 34

```
atttgggaac tgaagaagga cgtctacgtg gtcgaactgg actggtatcc cgatgctccc      60
ggcgaaatgg tggtgctcac ttgtgacacc cccgaagaag acggcatcac ttggaccctc     120
gatcagagca gcgaggtgct gggctccgga aagaccctca caatccaagt taaggagttc     180
ggagacgctg ccaatacac atgccacaag ggaggcgagg tgctcagcca ttccttatta     240
ttattacaca agaaggaaga cggaatctgg tccaccgaca ttttaaaaga tcagaaggag     300
cccaagaata agacctttt aaggtgtgag gccaaaaact acagcggtcg tttcacttgt     360
tggtggctga ccaccatttc caccgattta accttctccg tgaaaagcag ccggggaagc     420
tccgaccctc aaggtgtgac atgtggagcc gctaccctca gcgctgagag ggttcgtggc     480
gataacaagg aatacgagta cagcgtggag tgccaagaag atagcgcttg tcccgctgcc     540
gaagaatctt tacccattga ggtgatggtg gacgccgtgc acaaactcaa gtacgagaac     600
tacacctcct ccttctttat ccgggacatc attaagcccg atcctcctaa gaatttacag     660
ctgaagcctc tcaaaaatag ccggcaagtt gaggtctctt gggaatatcc cgacacttgg     720
agcacacccc acagctactt ctctttaacc ttttgtgtgc aagttcaagg taaaagcaag     780
cgggagaaga agaccgggt gtttaccgac aaaaccagcg ccaccgtcat ctgtcggaag     840
aacgcctcca tcagcgtgag ggctcaagat cgttattact ccagcagctg gtccgagtgg     900
gccagcgtgc cttgttcc                                                   918
```

<210> SEQ ID NO 35
<211> LENGTH: 197
<212> TYPE: PRT
<213> ORGANISM: Homo sapiens
<220> FEATURE:
<221> NAME/KEY: source
<223> OTHER INFORMATION: /note="Human Soluble IL-12alpha (p35)"

<400> SEQUENCE: 35

```
Arg Asn Leu Pro Val Ala Thr Pro Asp Pro Gly Met Phe Pro Cys Leu
1               5                  10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160
```

```
Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 36
<211> LENGTH: 591
<212> TYPE: DNA
<213> ORGANISM: Homo sapiens
<220> FEATURE:
<221> NAME/KEY: source
<223> OTHER INFORMATION: /note="Human Soluble IL-12alpha (p35)"

<400> SEQUENCE: 36
cgtaacctcc ccgtggctac ccccgatccc ggaatgttcc cttgtttaca ccacagccag      60
aatttactga gggccgtgag caacatgctg cagaaagcta ggcagacttt agaattttac     120
ccttgcacca gcgaggagat cgaccatgaa gatatcacca aggacaagac atccaccgtg     180
gaggcttgtt tacctctgga gctgacaaag aacgagtctt gtctcaactc tcgtgaaacc     240
agcttcatca caaatggctc ttgtttagct tcccggaaga cctcctttat gatggcttta     300
tgcctcagct ccatctacga ggatttaaag atgtaccaag tggagttcaa gaccatgaac     360
gccaagctgc tcatggaccc taaacggcag atcttttag accagaacat gctggctgtg     420
attgatgagc tgatgcaagc tttaaacttc aactccagag ccgtccctca gaagtcctcc     480
ctcgaggagc ccgattttta caagacaaag atcaaactgt gcattttact ccacgccttt     540
aggatccggg ccgtgaccat tgaccgggtc atgagctatt taaacgccag c              591

<210> SEQ ID NO 37
<211> LENGTH: 518
<212> TYPE: PRT
<213> ORGANISM: Homo sapiens
<220> FEATURE:
<221> NAME/KEY: source
<223> OTHER INFORMATION: /note="Human Soluble IL-12"

<400> SEQUENCE: 37

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140
```

```
Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Ser Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser
        515

<210> SEQ ID NO 38
<211> LENGTH: 1554
<212> TYPE: DNA
<213> ORGANISM: Homo sapiens
<220> FEATURE:
<221> NAME/KEY: source
```

<223> OTHER INFORMATION: /note="Human Soluble IL-12"

<400> SEQUENCE: 38

```
atttgggaac tgaagaagga cgtctacgtg gtcgaactgg actggtatcc cgatgctccc      60
ggcgaaatgg tggtgctcac ttgtgacacc cccgaagaag acggcatcac ttggaccctc     120
gatcagagca gcgaggtgct gggctccgga aagaccctca caatccaagt taaggagttc     180
ggagacgctg gccaatacac atgccacaag ggaggcgagg tgctcagcca ttccttatta     240
ttattacaca agaaggaaga cggaatctgg tccaccgaca ttttaaaaga tcagaaggag     300
cccaagaata agaccttttt aaggtgtgag gccaaaaact acagcggtcg tttcacttgt     360
tggtggctga ccaccatttc caccgattta accttctccg tgaaaagcag ccggggaagc     420
tccgaccctc aaggtgtgac atgtggagcc gctaccctca cgctgagag ggttcgtggc      480
gataacaagg aatacgagta cagcgtggag tgccaagaag atagcgcttg tcccgctgcc     540
gaagaatctt tacccattga ggtgatggtg gacgccgtgc acaaactcaa gtacgagaac     600
tacacctcct ccttctttat ccgggacatc attaagcccg atcctcctaa gaatttacag     660
ctgaagcctc tcaaaaatag ccggcaagtt gaggtctctt gggaatatcc gacacttgg      720
agcacacccc acagctactt ctcttaaccc ttttgtgtgc aagttcaagg taaaagcaag     780
cgggagaaga aagaccgggt gtttaccgac aaaaccagcg ccaccgtcat ctgtcggaag     840
aacgcctcca tcagcgtgag ggctcaagat cgttattact ccagcagctg gtccgagtgg     900
gccagcgtgc cttgttccgg cggtggagga tccggaggag gtggctccgg cggcggagga     960
tctcgtaacc tccccgtggc tacccccgat cccggaatgt tccccttgttt acaccacagc    1020
cagaatttac tgagggccgt gagcaacatg ctgcagaaag ctaggcagac tttagaattt    1080
tacccttgca ccagcgagga gatcgaccat gaagatatca ccaaggacaa gacatccacc    1140
gtggaggctt gtttacctct ggagctgaca agaacgagt cttgtctcaa ctctcgtgaa     1200
accagcttca tcacaaatgg ctcttgttta gcttcccgga agacctcctt tatgatggct    1260
ttatgcctca gctccatcta cgaggattta agatgtacc aagtggagtt caagaccatg     1320
aacgccaagc tgctcatgga ccctaaacgg cagatctttt tagaccagaa catgctggct    1380
gtgattgatg agctgatgca agctttaaac ttcaactccg agaccgtccc tcagaagtcc    1440
tccctcgagg agcccgattt ttacaagaca agatcaaac tgtgcatttt actccacgcc     1500
tttaggatcc gggccgtgac cattgaccgg gtcatgagct atttaaacgc cagc           1554
```

<210> SEQ ID NO 39
<211> LENGTH: 114
<212> TYPE: PRT
<213> ORGANISM: Homo sapiens
<220> FEATURE:
<221> NAME/KEY: source
<223> OTHER INFORMATION: /note="Human Soluble IL-15"

<400> SEQUENCE: 39

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60
```

```
Asn Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 40
<211> LENGTH: 132
<212> TYPE: PRT
<213> ORGANISM: Homo sapiens
<220> FEATURE:
<221> NAME/KEY: source
<223> OTHER INFORMATION: /note="Human Soluble IL-17"

<400> SEQUENCE: 40

Gly Ile Thr Ile Pro Arg Asn Pro Gly Cys Pro Asn Ser Glu Asp Lys
 1               5                   10                  15

Asn Phe Pro Arg Thr Val Met Val Asn Leu Asn Ile His Asn Arg Asn
                20                  25                  30

Thr Asn Thr Asn Pro Lys Arg Ser Ser Asp Tyr Tyr Asn Arg Ser Thr
            35                  40                  45

Ser Pro Trp Asn Leu His Arg Asn Glu Asp Pro Glu Arg Tyr Pro Ser
 50                  55                  60

Val Ile Trp Glu Ala Lys Cys Arg His Leu Gly Cys Ile Asn Ala Asp
 65                  70                  75                  80

Gly Asn Val Asp Tyr His Met Asn Ser Val Pro Ile Gln Gln Glu Ile
                85                  90                  95

Leu Val Leu Arg Arg Glu Pro Pro His Cys Pro Asn Ser Phe Arg Leu
                100                 105                 110

Glu Lys Ile Leu Val Ser Val Gly Cys Thr Cys Val Thr Pro Ile Val
            115                 120                 125

His His Val Ala
        130

<210> SEQ ID NO 41
<211> LENGTH: 157
<212> TYPE: PRT
<213> ORGANISM: Homo sapiens
<220> FEATURE:
<221> NAME/KEY: source
<223> OTHER INFORMATION: /note="Human Soluble IL-18"

<400> SEQUENCE: 41

Tyr Phe Gly Lys Leu Glu Ser Lys Leu Ser Val Ile Arg Asn Leu Asn
 1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
 50                  55                  60

Ser Val Lys Cys Glu Lys Ile Ser Thr Leu Ser Cys Glu Asn Lys Ile
 65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
```

```
                    100                 105                 110
Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Glu Asp Glu Leu
        130                 135                 140

Gly Asp Arg Ser Ile Met Phe Thr Val Gln Asn Glu Asp
145                 150                 155

<210> SEQ ID NO 42
<211> LENGTH: 471
<212> TYPE: DNA
<213> ORGANISM: Homo sapiens
<220> FEATURE:
<221> NAME/KEY: source
<223> OTHER INFORMATION: /note="Human Soluble IL-18"

<400> SEQUENCE: 42
tacttcggca aactggaatc caagctgagc gtgatccgga atttaaacga ccaagttctg    60
tttatcgatc aaggtaaccg gcctctgttc gaggacatga ccgactccga ttgccgggac   120 aatgccccc ggaccatctt cattatctcc atgtacaagg acagccagcc ccggggcatg    180
gctgtgacaa ttagcgtgaa gtgtgagaaa atcagcactt tatcttgtga aacaagatc    240 atctccttta aggaaatgaa ccccccgat aacatcaagg acaccaagtc cgatatcatc     300
ttcttccagc ggtccgtgcc cggtcacgat aacaagatgc agttcgaatc ctcctcctac   360
gagggctact ttttagcttg tgaaaaggag agggatttat tcaagctgat cctcaagaag   420
gaggacgagc tgggcgatcg ttccatcatg ttcaccgtcc aaaacgagga t            471

<210> SEQ ID NO 43
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic sequencing primer IFNG355R-bio"

<400> SEQUENCE: 43
caatatacta cacctcctct aactac                                          26

<210> SEQ ID NO 44
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic signal sequence"

<400> SEQUENCE: 44

Met Gly Val Lys Val Leu Phe Ala Leu Ile Cys Ile Ala Val Ala Glu
1               5                   10                  15

Ala

<210> SEQ ID NO 45
<211> LENGTH: 352
<212> TYPE: PRT
<213> ORGANISM: Homo sapiens
<220> FEATURE:
<221> NAME/KEY: source
<223> OTHER INFORMATION: /note="Human Soluble PDGF-DD"

<400> SEQUENCE: 45
```

Arg Asp Thr Ser Ala Thr Pro Gln Ser Ala Ser Ile Lys Ala Leu Arg
1               5                   10                  15

Asn Ala Asn Leu Arg Arg Asp Glu Ser Asn His Leu Thr Asp Leu Tyr
            20                  25                  30

Arg Arg Asp Glu Thr Ile Gln Val Lys Gly Asn Gly Tyr Val Gln Ser
        35                  40                  45

Pro Arg Phe Pro Asn Ser Tyr Pro Arg Asn Leu Leu Leu Thr Trp Arg
    50                  55                  60

Leu His Ser Gln Glu Asn Thr Arg Ile Gln Leu Val Phe Asp Asn Gln
65                  70                  75                  80

Phe Gly Leu Glu Glu Ala Glu Asn Asp Ile Cys Arg Tyr Asp Phe Val
                85                  90                  95

Glu Val Glu Asp Ile Ser Glu Thr Ser Thr Ile Ile Arg Gly Arg Trp
            100                 105                 110

Cys Gly His Lys Glu Val Pro Pro Arg Ile Lys Ser Arg Thr Asn Gln
        115                 120                 125

Ile Lys Ile Thr Phe Lys Ser Asp Asp Tyr Phe Val Ala Lys Pro Gly
    130                 135                 140

Phe Lys Ile Tyr Tyr Ser Leu Leu Glu Asp Phe Gln Pro Ala Ala Ala
145                 150                 155                 160

Ser Glu Thr Asn Trp Glu Ser Val Thr Ser Ser Ile Ser Gly Val Ser
                165                 170                 175

Tyr Asn Ser Pro Ser Val Thr Asp Pro Thr Leu Ile Ala Asp Ala Leu
            180                 185                 190

Asp Lys Lys Ile Ala Glu Phe Asp Thr Val Glu Asp Leu Leu Lys Tyr
        195                 200                 205

Phe Asn Pro Glu Ser Trp Gln Glu Asp Leu Glu Asn Met Tyr Leu Asp
    210                 215                 220

Thr Pro Arg Tyr Arg Gly Arg Ser Tyr His Asp Arg Lys Ser Lys Val
225                 230                 235                 240

Asp Leu Asp Arg Leu Asn Asp Asp Ala Lys Arg Tyr Ser Cys Thr Pro
                245                 250                 255

Arg Asn Tyr Ser Val Asn Ile Arg Glu Glu Leu Lys Leu Ala Asn Val
            260                 265                 270

Val Phe Phe Pro Arg Cys Leu Leu Val Gln Arg Cys Gly Gly Asn Cys
        275                 280                 285

Gly Cys Gly Thr Val Asn Trp Arg Ser Cys Thr Cys Asn Ser Gly Lys
    290                 295                 300

Thr Val Lys Lys Tyr His Glu Val Leu Gln Phe Glu Pro Gly His Ile
305                 310                 315                 320

Lys Arg Arg Gly Arg Ala Lys Thr Met Ala Leu Val Asp Ile Gln Leu
                325                 330                 335

Asp His His Glu Arg Cys Asp Cys Ile Cys Ser Ser Arg Pro Pro Arg
            340                 345                 350

<210> SEQ ID NO 46
<211> LENGTH: 248
<212> TYPE: PRT
<213> ORGANISM: Homo sapiens
<220> FEATURE:
<221> NAME/KEY: source
<223> OTHER INFORMATION: /note="Human Soluble SCF"

<400> SEQUENCE: 46

Glu Gly Ile Cys Arg Asn Arg Val Thr Asn Asn Val Lys Asp Val Thr

```
1               5                   10                  15
Lys Leu Val Ala Asn Leu Pro Lys Asp Tyr Met Ile Thr Leu Lys Tyr
                20                  25                  30

Val Pro Gly Met Asp Val Leu Pro Ser His Cys Trp Ile Ser Glu Met
                35                  40                  45

Val Val Gln Leu Ser Asp Ser Leu Thr Asp Leu Leu Asp Lys Phe Ser
 50                  55                  60

Asn Ile Ser Glu Gly Leu Ser Asn Tyr Ser Ile Ile Asp Lys Leu Val
 65                  70                  75                  80

Asn Ile Val Asp Asp Leu Val Glu Cys Val Lys Glu Asn Ser Ser Lys
                    85                  90                  95

Asp Leu Lys Lys Ser Phe Lys Ser Pro Glu Pro Arg Leu Phe Thr Pro
                100                 105                 110

Glu Glu Phe Phe Arg Ile Phe Asn Arg Ser Ile Asp Ala Phe Lys Asp
                115                 120                 125

Phe Val Val Ala Ser Glu Thr Ser Asp Cys Val Val Ser Ser Thr Leu
130                 135                 140

Ser Pro Glu Lys Asp Ser Arg Val Ser Val Thr Lys Pro Phe Met Leu
145                 150                 155                 160

Pro Pro Val Ala Ala Ser Ser Leu Arg Asn Asp Ser Ser Ser Ser Asn
                165                 170                 175

Arg Lys Ala Lys Asn Pro Pro Gly Asp Ser Ser Leu His Trp Ala Ala
                180                 185                 190

Met Ala Leu Pro Ala Leu Phe Ser Leu Ile Ile Gly Phe Ala Phe Gly
                195                 200                 205

Ala Leu Tyr Trp Lys Lys Arg Gln Pro Ser Leu Thr Arg Ala Val Glu
                210                 215                 220

Asn Ile Gln Ile Asn Glu Glu Asp Asn Glu Ile Ser Met Leu Gln Glu
225                 230                 235                 240

Lys Glu Arg Glu Phe Gln Glu Val
                245

<210> SEQ ID NO 47
<211> LENGTH: 209
<212> TYPE: PRT
<213> ORGANISM: Homo sapiens
<220> FEATURE:
<221> NAME/KEY: source
<223> OTHER INFORMATION: /note="Human Soluble FLT3L"

<400> SEQUENCE: 47

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
                20                  25                  30

Thr Val Ala Ser Asn Leu Gln Asp Glu Glu Leu Cys Gly Gly Leu Trp
                35                  40                  45

Arg Leu Val Leu Ala Gln Arg Trp Met Glu Arg Leu Lys Thr Val Ala
 50                  55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Pro Ser Cys Leu Arg Phe
                    85                  90                  95

Val Gln Thr Asn Ile Ser Arg Leu Leu Gln Glu Thr Ser Glu Gln Leu
                100                 105                 110
```

```
Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Pro Trp Ser
        130                 135                 140

Pro Arg Pro Leu Glu Ala Thr Ala Pro Thr Ala Pro Gln Pro Pro Leu
145                 150                 155                 160

Leu Leu Leu Leu Leu Leu Pro Val Gly Leu Leu Leu Ala Ala Ala
                165                 170                 175

Trp Cys Leu His Trp Gln Arg Thr Arg Arg Thr Pro Arg Pro Gly
                180                 185                 190

Glu Gln Val Pro Pro Val Pro Ser Pro Gln Asp Leu Leu Leu Val Glu
        195                 200                 205

His
```

```
<210> SEQ ID NO 48
<211> LENGTH: 360
<212> TYPE: PRT
<213> ORGANISM: Homo sapiens
<220> FEATURE:
<221> NAME/KEY: source
<223> OTHER INFORMATION: /note="Human Soluble MICA"

<400> SEQUENCE: 48

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255
```

```
Phe Thr Cys Tyr Met Glu His Ser Gly Asn His Ser Thr His Pro Val
            260                 265                 270

Pro Ser Gly Lys Val Leu Val Leu Gln Ser His Trp Gln Thr Phe His
        275                 280                 285

Val Ser Ala Val Ala Ala Ala Ile Phe Val Ile Ile Ile Phe Tyr
    290                 295                 300

Val Arg Cys Cys Lys Lys Lys Thr Ser Ala Ala Glu Gly Pro Glu Leu
305                 310                 315                 320

Val Ser Leu Gln Val Leu Asp Gln His Pro Val Gly Thr Ser Asp His
                325                 330                 335

Arg Asp Ala Thr Gln Leu Gly Phe Gln Pro Leu Met Ser Asp Leu Gly
                340                 345                 350

Ser Thr Gly Ser Thr Glu Gly Ala
        355                 360

<210> SEQ ID NO 49
<211> LENGTH: 361
<212> TYPE: PRT
<213> ORGANISM: Homo sapiens
<220> FEATURE:
<221> NAME/KEY: source
<223> OTHER INFORMATION: /note="Human Soluble MICB"

<400> SEQUENCE: 49

Ala Glu Pro His Ser Leu Arg Tyr Asn Leu Met Val Leu Ser Gln Asp
1               5                   10                  15

Glu Ser Val Gln Ser Gly Phe Leu Ala Glu Gly His Leu Asp Gly Gln
            20                  25                  30

Pro Phe Leu Arg Tyr Asp Arg Gln Lys Arg Arg Ala Lys Pro Gln Gly
        35                  40                  45

Gln Trp Ala Glu Asp Val Leu Gly Ala Lys Thr Trp Asp Thr Glu Thr
    50                  55                  60

Glu Asp Leu Thr Glu Asn Gly Gln Asp Leu Arg Arg Thr Leu Thr His
65                  70                  75                  80

Ile Lys Asp Gln Lys Gly Gly Leu His Ser Leu Gln Glu Ile Arg Val
                85                  90                  95

Cys Glu Ile His Glu Asp Ser Ser Thr Arg Gly Ser Arg His Phe Tyr
            100                 105                 110

Tyr Asp Gly Glu Leu Phe Leu Ser Gln Asn Leu Glu Thr Gln Glu Ser
        115                 120                 125

Thr Val Pro Gln Ser Ser Arg Ala Gln Thr Leu Ala Met Asn Val Thr
    130                 135                 140

Asn Phe Trp Lys Glu Asp Ala Met Lys Thr Lys Thr His Tyr Arg Ala
145                 150                 155                 160

Met Gln Ala Asp Cys Leu Gln Lys Leu Gln Arg Tyr Leu Lys Ser Gly
                165                 170                 175

Val Ala Ile Arg Arg Thr Val Pro Pro Met Val Asn Val Thr Cys Ser
            180                 185                 190

Glu Val Ser Glu Gly Asn Ile Thr Val Thr Cys Arg Ala Ser Ser Phe
        195                 200                 205

Tyr Pro Arg Asn Ile Thr Leu Thr Trp Arg Gln Asp Gly Val Ser Leu
    210                 215                 220

Ser His Asn Thr Gln Gln Trp Gly Asp Val Leu Pro Asp Gly Asn Gly
225                 230                 235                 240

Thr Tyr Gln Thr Trp Val Ala Thr Arg Ile Arg Gln Gly Glu Glu Gln
                245                 250                 255
```

Arg Phe Thr Cys Tyr Met Glu His Ser Gly Asn His Gly Thr His Pro
            260                 265                 270

Val Pro Ser Gly Lys Val Leu Val Leu Gln Ser Gln Arg Thr Asp Phe
        275                 280                 285

Pro Tyr Val Ser Ala Ala Met Pro Cys Phe Val Ile Ile Ile Ile Leu
    290                 295                 300

Cys Val Pro Cys Cys Lys Lys Thr Ser Ala Ala Glu Gly Pro Glu
305                 310                 315                 320

Leu Val Ser Leu Gln Val Leu Asp Gln His Pro Val Gly Thr Gly Asp
                325                 330                 335

His Arg Asp Ala Ala Gln Leu Gly Phe Gln Pro Leu Met Ser Ala Thr
            340                 345                 350

Gly Ser Thr Gly Ser Thr Glu Gly Ala
            355                 360

<210> SEQ ID NO 50
<211> LENGTH: 190
<212> TYPE: PRT
<213> ORGANISM: Homo sapiens
<220> FEATURE:
<221> NAME/KEY: source
<223> OTHER INFORMATION: /note="Human Soluble ULBP1"

<400> SEQUENCE: 50

Trp Val Asp Thr His Cys Leu Cys Tyr Asp Phe Ile Ile Thr Pro Lys
1               5                   10                  15

Ser Arg Pro Glu Pro Gln Trp Cys Glu Val Gln Gly Leu Val Asp Glu
            20                  25                  30

Arg Pro Phe Leu His Tyr Asp Cys Val Asn His Lys Ala Lys Ala Phe
        35                  40                  45

Ala Ser Leu Gly Lys Lys Val Asn Val Thr Lys Thr Trp Glu Glu Gln
    50                  55                  60

Thr Glu Thr Leu Arg Asp Val Val Asp Phe Leu Lys Gly Gln Leu Leu
65                  70                  75                  80

Asp Ile Gln Val Glu Asn Leu Ile Pro Ile Glu Pro Leu Thr Leu Gln
                85                  90                  95

Ala Arg Met Ser Cys Glu His Glu Ala His Gly His Gly Arg Gly Ser
            100                 105                 110

Trp Gln Phe Leu Phe Asn Gly Gln Lys Phe Leu Leu Phe Asp Ser Asn
        115                 120                 125

Asn Arg Lys Trp Thr Ala Leu His Pro Gly Ala Lys Lys Met Thr Glu
    130                 135                 140

Lys Trp Glu Lys Asn Arg Asp Val Thr Met Phe Phe Gln Lys Ile Ser
145                 150                 155                 160

Leu Gly Asp Cys Lys Met Trp Leu Glu Glu Phe Leu Met Tyr Trp Glu
                165                 170                 175

Gln Met Leu Asp Pro Thr Lys Pro Pro Ser Leu Ala Pro Gly
            180                 185                 190

<210> SEQ ID NO 51
<211> LENGTH: 191
<212> TYPE: PRT
<213> ORGANISM: Homo sapiens
<220> FEATURE:
<221> NAME/KEY: source
<223> OTHER INFORMATION: /note="Human Soluble ULBP2"

<400> SEQUENCE: 51

Gly Arg Ala Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
            20                  25                  30

Glu Lys Thr Phe Leu His Tyr Asp Cys Gly Asn Lys Thr Val Thr Pro
        35                  40                  45

Val Ser Pro Leu Gly Lys Lys Leu Asn Val Thr Thr Ala Trp Lys Ala
    50                  55                  60

Gln Asn Pro Val Leu Arg Glu Val Val Asp Ile Leu Thr Glu Gln Leu
65                  70                  75                  80

Arg Asp Ile Gln Leu Glu Asn Tyr Thr Pro Lys Glu Pro Leu Thr Leu
                85                  90                  95

Gln Ala Arg Met Ser Cys Glu Gln Lys Ala Glu Gly His Ser Ser Gly
                100                 105                 110

Ser Trp Gln Phe Ser Phe Asp Gly Gln Ile Phe Leu Leu Phe Asp Ser
            115                 120                 125

Glu Lys Arg Met Trp Thr Thr Val His Pro Gly Ala Arg Lys Met Lys
130                 135                 140

Glu Lys Trp Glu Asn Asp Lys Val Val Ala Met Ser Phe His Tyr Phe
145                 150                 155                 160

Ser Met Gly Asp Cys Ile Gly Trp Leu Glu Asp Phe Leu Met Gly Met
                165                 170                 175

Asp Ser Thr Leu Glu Pro Ser Ala Gly Ala Pro Leu Ala Met Ser
            180                 185                 190

<210> SEQ ID NO 52
<211> LENGTH: 188
<212> TYPE: PRT
<213> ORGANISM: Homo sapiens
<220> FEATURE:
<221> NAME/KEY: source
<223> OTHER INFORMATION: /note="Human Soluble ULBP3"

<400> SEQUENCE: 52

Asp Ala His Ser Leu Trp Tyr Asn Phe Thr Ile Ile His Leu Pro Arg
1               5                   10                  15

His Gly Gln Gln Trp Cys Glu Val Gln Ser Gln Val Asp Gln Lys Asn
            20                  25                  30

Phe Leu Ser Tyr Asp Cys Gly Ser Asp Lys Val Leu Ser Met Gly His
        35                  40                  45

Leu Glu Glu Gln Leu Tyr Ala Thr Asp Ala Trp Gly Lys Gln Leu Glu
    50                  55                  60

Met Leu Arg Glu Val Gly Gln Arg Leu Arg Leu Glu Leu Ala Asp Thr
65                  70                  75                  80

Glu Leu Glu Asp Phe Thr Pro Ser Gly Pro Leu Thr Leu Gln Val Arg
                85                  90                  95

Met Ser Cys Glu Cys Glu Ala Asp Gly Tyr Ile Arg Gly Ser Trp Gln
                100                 105                 110

Phe Ser Phe Asp Gly Arg Lys Phe Leu Leu Phe Asp Ser Asn Asn Arg
            115                 120                 125

Lys Trp Thr Val Val His Ala Gly Ala Arg Arg Met Lys Glu Lys Trp
        130                 135                 140

Glu Lys Asp Ser Gly Leu Thr Thr Phe Phe Lys Met Val Ser Met Arg
145                 150                 155                 160

Asp Cys Lys Ser Trp Leu Arg Asp Phe Leu Met His Arg Lys Lys Arg

```
                    165                 170                 175

Leu Glu Pro Thr Ala Pro Pro Thr Met Ala Pro Gly
            180                 185

<210> SEQ ID NO 53
<211> LENGTH: 233
<212> TYPE: PRT
<213> ORGANISM: Homo sapiens
<220> FEATURE:
<221> NAME/KEY: source
<223> OTHER INFORMATION: /note="Human Soluble ULBP4"

<400> SEQUENCE: 53

His Ser Leu Cys Phe Asn Phe Thr Ile Lys Ser Leu Ser Arg Pro Gly
1               5                   10                  15

Gln Pro Trp Cys Glu Ala Gln Val Phe Leu Asn Lys Asn Leu Phe Leu
            20                  25                  30

Gln Tyr Asn Ser Asp Asn Asn Met Val Lys Pro Leu Gly Leu Leu Gly
        35                  40                  45

Lys Lys Val Tyr Ala Thr Ser Thr Trp Gly Glu Leu Thr Gln Thr Leu
50                  55                  60

Gly Glu Val Gly Arg Asp Leu Arg Met Leu Leu Cys Asp Ile Lys Pro
65                  70                  75                  80

Gln Ile Lys Thr Ser Asp Pro Ser Thr Leu Gln Val Glu Met Phe Cys
                85                  90                  95

Gln Arg Glu Ala Glu Arg Cys Thr Gly Ala Ser Trp Gln Phe Ala Thr
            100                 105                 110

Asn Gly Glu Lys Ser Leu Leu Phe Asp Ala Met Asn Met Thr Trp Thr
        115                 120                 125

Val Ile Asn His Glu Ala Ser Lys Ile Lys Glu Thr Trp Lys Lys Asp
130                 135                 140

Arg Gly Leu Glu Lys Tyr Phe Arg Lys Leu Ser Lys Gly Asp Cys Asp
145                 150                 155                 160

His Trp Leu Arg Glu Phe Leu Gly His Trp Glu Ala Met Pro Glu Pro
                165                 170                 175

Thr Val Ser Pro Val Asn Ala Ser Asp Ile His Trp Ser Ser Ser
            180                 185                 190

Leu Pro Asp Arg Trp Ile Ile Leu Gly Ala Phe Ile Leu Leu Val Leu
        195                 200                 205

Met Gly Ile Val Leu Ile Cys Val Trp Trp Gln Asn Gly Glu Trp Gln
210                 215                 220

Ala Gly Leu Trp Pro Leu Arg Thr Ser
225                 230

<210> SEQ ID NO 54
<211> LENGTH: 193
<212> TYPE: PRT
<213> ORGANISM: Homo sapiens
<220> FEATURE:
<221> NAME/KEY: source
<223> OTHER INFORMATION: /note="Human Soluble ULBP5"

<400> SEQUENCE: 54

Gly Leu Ala Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
            20                  25                  30

Glu Lys Thr Phe Leu His Tyr Asp Cys Gly Ser Lys Thr Val Thr Pro
```

```
            35                  40                  45
Val Ser Pro Leu Gly Lys Lys Leu Asn Val Thr Thr Ala Trp Lys Ala
 50                  55                  60

Gln Asn Pro Val Leu Arg Glu Val Val Asp Ile Leu Thr Glu Gln Leu
 65                  70                  75                  80

Leu Asp Ile Gln Leu Glu Asn Tyr Ile Pro Lys Glu Pro Leu Thr Leu
                 85                  90                  95

Gln Ala Arg Met Ser Cys Glu Gln Lys Ala Glu Gly His Gly Ser Gly
            100                 105                 110

Ser Trp Gln Leu Ser Phe Asp Gly Gln Ile Phe Leu Leu Phe Asp Ser
        115                 120                 125

Glu Asn Arg Met Trp Thr Thr Val His Pro Gly Ala Arg Lys Met Lys
130                 135                 140

Glu Lys Trp Glu Asn Asp Lys Asp Met Thr Met Ser Phe His Tyr Ile
145                 150                 155                 160

Ser Met Gly Asp Cys Thr Gly Trp Leu Glu Asp Phe Leu Met Gly Met
                165                 170                 175

Asp Ser Thr Leu Glu Pro Ser Ala Gly Ala Pro Pro Thr Met Ser Ser
            180                 185                 190

Gly

<210> SEQ ID NO 55
<211> LENGTH: 193
<212> TYPE: PRT
<213> ORGANISM: Homo sapiens
<220> FEATURE:
<221> NAME/KEY: source
<223> OTHER INFORMATION: /note="Human Soluble ULBP6"

<400> SEQUENCE: 55

Arg Arg Asp Asp Pro His Ser Leu Cys Tyr Asp Ile Thr Val Ile Pro
 1               5                  10                  15

Lys Phe Arg Pro Gly Pro Arg Trp Cys Ala Val Gln Gly Gln Val Asp
                 20                  25                  30

Glu Lys Thr Phe Leu His Tyr Asp Cys Gly Asn Lys Thr Val Thr Pro
             35                  40                  45

Val Ser Pro Leu Gly Lys Lys Leu Asn Val Thr Met Ala Trp Lys Ala
 50                  55                  60

Gln Asn Pro Val Leu Arg Glu Val Val Asp Ile Leu Thr Glu Gln Leu
 65                  70                  75                  80

Leu Asp Ile Gln Leu Glu Asn Tyr Thr Pro Lys Glu Pro Leu Thr Leu
                 85                  90                  95

Gln Ala Arg Met Ser Cys Glu Gln Lys Ala Glu Gly His Ser Ser Gly
            100                 105                 110

Ser Trp Gln Phe Ser Ile Asp Gly Gln Thr Phe Leu Leu Phe Asp Ser
        115                 120                 125

Glu Lys Arg Met Trp Thr Thr Val His Pro Gly Ala Arg Lys Met Lys
130                 135                 140

Glu Lys Trp Glu Asn Asp Lys Asp Val Ala Met Ser Phe His Tyr Ile
145                 150                 155                 160

Ser Met Gly Asp Cys Ile Gly Trp Leu Glu Asp Phe Leu Met Gly Met
                165                 170                 175

Asp Ser Thr Leu Glu Pro Ser Ala Gly Ala Pro Leu Ala Met Ser Ser
            180                 185                 190

Gly
```

```
<210> SEQ ID NO 56
<211> LENGTH: 136
<212> TYPE: PRT
<213> ORGANISM: Homo sapiens
<220> FEATURE:
<221> NAME/KEY: source
<223> OTHER INFORMATION: /note="soluble TGFbetaRII receptor"

<400> SEQUENCE: 56

Ile Pro Pro His Val Gln Lys Ser Val Asn Asn Asp Met Ile Val Thr
 1               5                  10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135

<210> SEQ ID NO 57
<211> LENGTH: 408
<212> TYPE: DNA
<213> ORGANISM: Homo sapiens
<220> FEATURE:
<221> NAME/KEY: source
<223> OTHER INFORMATION: /note="soluble TGFbetaRII receptor"

<400> SEQUENCE: 57
atcccccccc atgtgcaaaa gagcgtgaac aacgatatga tcgtgaccga caacaacggc    60
gccgtgaagt ttccccagct ctgcaagttc tgcgatgtca ggttcagcac ctgcgataat   120
cagaagtcct gcatgtccaa ctgcacgatc acctccatct gcgagaagcc ccaagaagtg   180
tgcgtggccg tgtggcggaa aaatgacgag aacatcaccc tggagaccgt gtgtcacgac   240
cccaagctcc cttatcacga cttcattctg gaggacgctg cctcccccaa atgcatcatg   300
aaggagaaga agaagcccgg agagaccttc tttatgtgtt cctgtagcag cgacgagtgt   360
aacgacaaca tcatcttcag cgaagagtac aacaccagca accctgat              408

<210> SEQ ID NO 58

<400> SEQUENCE: 58

000

<210> SEQ ID NO 59

<400> SEQUENCE: 59

000
```

-continued

<210> SEQ ID NO 60
<211> LENGTH: 287
<212> TYPE: PRT
<213> ORGANISM: Homo sapiens
<220> FEATURE:
<221> NAME/KEY: source
<223> OTHER INFORMATION: /note="soluble TGFbetaRII receptor"

<400> SEQUENCE: 60

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp
        275                 280                 285
```

<210> SEQ ID NO 61
<211> LENGTH: 861
<212> TYPE: DNA
<213> ORGANISM: Homo sapiens
<220> FEATURE:
<221> NAME/KEY: source
<223> OTHER INFORMATION: /note="soluble TGFbetaRII receptor"

<400> SEQUENCE: 61

```
atcccccccc atgtgcaaaa gagcgtgaac aacgatatga tcgtgaccga caacaacggc      60
gccgtgaagt ttccccagct ctgcaagttc tgcgatgtca ggttcagcac ctgcgataat     120
```

```
cagaagtcct gcatgtccaa ctgcacgatc acctccatct gcgagaagcc ccagaagtg     180 tgcgtggccg tgtggcggaa aaatgacgag aacatcaccc tggagaccgt gtgtcacgac     240
cccaagctcc cttatcacga cttcattctg gaggacgctg cctcccccaa atgcatcatg     300
aaggagaaga agaagcccgg agagaccttc tttatgtgtt cctgtagcag cgacgagtgt     360
aacgacaaca tcatcttcag cgaagagtac aacaccagca ccctgatggg aggtggcgga     420
tccggaggtg gaggttctgg tggaggtggg agtattcctc ccacgtgca gaagagcgtg     480 aataatgaca tgatcgtgac cgataacaat ggcgccgtga atttcccca gctgtgcaaa     540 ttctgcgatg tgaggttttc cacctgcgac aaccagaagt cctgtatgag caactgcaca     600
atcacctcca tctgtgagaa gcctcaggag gtgtgcgtgg ctgtctggcg aagaatgac      660 gagaatatca ccctggaaac cgtctgccac gatcccaagc tgccctacca cgatttcatc     720
ctggaagacg ccgccagccc taagtgcatc atgaaagaga aaagaagcc tggcgagacc      780 tttttcatgt gctcctgcag cagcgacgaa tgcaacgaca atatcatctt tagcgaggaa     840
tacaatacca gcaaccccga c                                               861

<210> SEQ ID NO 62
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic signal sequence"

<400> SEQUENCE: 62

Met Lys Trp Val Thr Phe Ile Ser Leu Leu Phe Leu Phe Ser Ser Ala
1               5                   10                  15

Tyr Ser

<210> SEQ ID NO 63
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic signal sequence"

<400> SEQUENCE: 63
atgaaatggg tgacctttat ttctttactg ttcctctttta gcagcgccta ctcc          54

<210> SEQ ID NO 64
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic signal sequence"

<400> SEQUENCE: 64
atgaagtggg tcacatttat ctctttactg ttcctcttct ccagcgccta cagc           54

<210> SEQ ID NO 65
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic signal sequence"

<400> SEQUENCE: 65
atgaaatggg tgacctttat ttctttactg ttcctcttta gcagcgccta ctcc    54

<210> SEQ ID NO 66
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic signal sequence"

<400> SEQUENCE: 66

Met Lys Cys Leu Leu Tyr Leu Ala Phe Leu Phe Leu Gly Val Asn Cys
1               5                   10                  15

<210> SEQ ID NO 67
<211> LENGTH: 58
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic signal sequence"

<400> SEQUENCE: 67

Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
            20                  25                  30

Lys Ala Val Tyr Asn Phe Ala Thr Cys Gly Ile Leu Ala Leu Val Ser
        35                  40                  45

Phe Leu Phe Leu Ala Gly Arg Ser Cys Gly
    50                  55

<210> SEQ ID NO 68
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic signal sequence"

<400> SEQUENCE: 68

Met Pro Asn His Gln Ser Gly Ser Pro Thr Gly Ser Ser Asp Leu Leu
1               5                   10                  15

Leu Ser Gly Lys Lys Gln Arg Pro His Leu Ala Leu Arg Lys Arg
            20                  25                  30

Arg Arg Glu Met Arg Lys Ile Asn Arg Lys Val Arg Arg Met Asn Leu
        35                  40                  45

Ala Pro Ile Lys Glu Lys Thr Ala Trp Gln His Leu Gln Ala Leu Ile
    50                  55                  60

Ser Glu Ala Glu Glu Val Leu Lys Thr Ser Gln Thr Pro Gln Asn Ser
65                  70                  75                  80

Leu Thr Leu Phe Leu Ala Leu Leu Ser Val Leu Gly Pro Pro Val Thr
                85                  90                  95

Gly

<210> SEQ ID NO 69

```
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic signal sequence"

<400> SEQUENCE: 69

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser
            20                  25                  30

<210> SEQ ID NO 70
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic AviTag sequence"

<400> SEQUENCE: 70

Gly Leu Asn Asp Ile Phe Glu Ala Gln Lys Ile Glu Trp His Glu
1               5                   10                  15

<210> SEQ ID NO 71
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic calmodulin-tag sequence"

<400> SEQUENCE: 71

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 72
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polyglutamate tag sequence"

<400> SEQUENCE: 72

Glu Glu Glu Glu Glu Glu
1               5

<210> SEQ ID NO 73
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic E-tag sequence"

<400> SEQUENCE: 73

Gly Ala Pro Val Pro Tyr Pro Asp Pro Leu Glu Pro Arg
1               5                   10
```

```
<210> SEQ ID NO 74
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic FLAG-tag sequence"

<400> SEQUENCE: 74

Asp Tyr Lys Asp Asp Asp Asp Lys
1               5

<210> SEQ ID NO 75
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic HA-tag sequence"

<400> SEQUENCE: 75

Tyr Pro Tyr Asp Val Pro Asp Tyr Ala
1               5

<210> SEQ ID NO 76
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic his-tag sequence"

<400> SEQUENCE: 76

His His His His His
1               5

<210> SEQ ID NO 77
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic his-tag sequence"

<400> SEQUENCE: 77

His His His His His His
1               5

<210> SEQ ID NO 78
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic his-tag sequence"

<400> SEQUENCE: 78

His His His His His His His
1               5

<210> SEQ ID NO 79
<211> LENGTH: 8
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic his-tag sequence"

<400> SEQUENCE: 79

His His His His His His His His
1               5

<210> SEQ ID NO 80
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic his-tag sequence"

<400> SEQUENCE: 80

His His His His His His His His His
1               5

<210> SEQ ID NO 81
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic his-tag sequence"

<400> SEQUENCE: 81

His His His His His His His His His His
1               5                   10

<210> SEQ ID NO 82
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic myc-tag sequence"

<400> SEQUENCE: 82

Glu Gln Lys Leu Ile Ser Glu Glu Asp Leu
1               5                   10

<210> SEQ ID NO 83
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic NE-tag sequence"

<400> SEQUENCE: 83

Thr Lys Glu Asn Pro Arg Ser Asn Gln Glu Glu Ser Tyr Asp Asp Asn
1               5                   10                  15

Glu Ser

<210> SEQ ID NO 84
<211> LENGTH: 15
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic S-tag sequence"

<400> SEQUENCE: 84

Lys Glu Thr Ala Ala Ala Lys Phe Glu Arg Gln His Met Asp Ser
1               5                   10                  15

<210> SEQ ID NO 85
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic SBP-tag sequence"

<400> SEQUENCE: 85

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 86
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Softag 1 sequence"

<400> SEQUENCE: 86

Ser Leu Ala Glu Leu Leu Asn Ala Gly Leu Gly Gly Ser
1               5                   10

<210> SEQ ID NO 87
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Softag 3 sequence"

<400> SEQUENCE: 87

Thr Gln Asp Pro Ser Arg Val Gly
1               5

<210> SEQ ID NO 88
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Spot-tag sequence"

<400> SEQUENCE: 88

Pro Asp Arg Val Arg Ala Val Ser His Trp Ser Ser
1               5                   10

<210> SEQ ID NO 89
<211> LENGTH: 8
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic Strep-tag sequence"

<400> SEQUENCE: 89

Trp Ser His Pro Gln Phe Glu Lys
1               5

<210> SEQ ID NO 90
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TC tag sequence"

<400> SEQUENCE: 90

Cys Cys Pro Gly Cys Cys
1               5

<210> SEQ ID NO 91
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Ty tag sequence"

<400> SEQUENCE: 91

Glu Val His Thr Asn Gln Asp Pro Leu Asp
1               5                   10

<210> SEQ ID NO 92
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic V5 tag sequence"

<400> SEQUENCE: 92

Gly Lys Pro Ile Pro Asn Pro Leu Leu Gly Leu Asp Ser Thr
1               5                   10

<210> SEQ ID NO 93
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic VSV-tag sequence"

<400> SEQUENCE: 93

Tyr Thr Asp Ile Glu Met Asn Arg Leu Gly Lys
1               5                   10

<210> SEQ ID NO 94
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic Xpress tag sequence"

<400> SEQUENCE: 94

Asp Leu Tyr Asp Asp Asp Asp Lys
1               5

<210> SEQ ID NO 95

<400> SEQUENCE: 95

000

<210> SEQ ID NO 96
<211> LENGTH: 220
<212> TYPE: PRT
<213> ORGANISM: Homo sapiens
<220> FEATURE:
<221> NAME/KEY: source
<223> OTHER INFORMATION: /note="wildtype human IgG1 Fc region"

<400> SEQUENCE: 96

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 97
<211> LENGTH: 216
<212> TYPE: PRT
<213> ORGANISM: Homo sapiens
<220> FEATURE:
<221> NAME/KEY: source
<223> OTHER INFORMATION: /note="Wildtype Human IgG2 Fc region"

<400> SEQUENCE: 97

Ala Pro Pro Val Ala Gly Pro Ser Val Phe Leu Phe Pro Pro Lys Pro

```
            1               5                  10                 15
Lys Asp Thr Leu Met Ile Ser Arg Thr Pro Glu Val Thr Cys Val Val
            20                 25                 30

Val Asp Val Ser His Glu Asp Pro Glu Val Gln Phe Asn Trp Tyr Val
            35                 40                 45

Asp Gly Val Glu Val His Asn Ala Lys Thr Lys Pro Arg Glu Glu Gln
            50                 55                 60

Phe Asn Ser Thr Phe Arg Val Val Ser Val Leu Thr Val Val His Gln
 65                70                 75                 80

Asp Trp Leu Asn Gly Lys Glu Tyr Lys Cys Lys Val Ser Asn Lys Gly
                   85                 90                 95

Leu Pro Ala Pro Ile Glu Lys Thr Ile Ser Lys Thr Lys Gly Gln Pro
                  100                105                110

Arg Glu Pro Gln Val Tyr Thr Leu Pro Pro Ser Arg Glu Glu Met Thr
            115                120                125

Lys Asn Gln Val Ser Leu Thr Cys Leu Val Lys Gly Phe Tyr Pro Ser
            130                135                140

Asp Ile Ser Val Glu Trp Glu Ser Asn Gly Gln Pro Glu Asn Asn Tyr
145                150                155                160

Lys Thr Thr Pro Pro Met Leu Asp Ser Asp Gly Ser Phe Phe Leu Tyr
                  165                170                175

Ser Lys Leu Thr Val Asp Lys Ser Arg Trp Gln Gln Gly Asn Val Phe
                  180                185                190

Ser Cys Ser Val Met His Glu Ala Leu His Asn His Tyr Thr Gln Lys
                  195                200                205

Ser Leu Ser Leu Ser Pro Gly Lys
                  210                215

<210> SEQ ID NO 98
<211> LENGTH: 217
<212> TYPE: PRT
<213> ORGANISM: Homo sapiens
<220> FEATURE:
<221> NAME/KEY: source
<223> OTHER INFORMATION: /note="Wildtype Human IgG3 Fc"

<400> SEQUENCE: 98

Ala Pro Glu Leu Leu Gly Gly Pro Ser Val Phe Leu Phe Pro Lys Pro
 1               5                  10                 15

Pro Lys Asp Thr Leu Met Ile Ser Arg Thr Pro Glu Val Thr Cys Val
            20                 25                 30

Val Val Asp Val Ser His Glu Asp Pro Glu Val Gln Phe Lys Trp Tyr
            35                 40                 45

Val Asp Gly Val Glu Val His Asn Ala Lys Thr Lys Pro Arg Glu Glu
            50                 55                 60

Gln Tyr Asn Ser Thr Phe Arg Val Val Ser Val Leu Thr Val Leu His
 65                70                 75                 80

Gln Asp Trp Leu Asn Gly Lys Glu Tyr Lys Cys Lys Val Ser Asn Lys
                   85                 90                 95

Ala Leu Pro Ala Pro Ile Glu Lys Thr Ile Ser Lys Thr Lys Gly Gln
                  100                105                110

Pro Arg Glu Pro Gln Val Tyr Thr Leu Pro Pro Ser Arg Glu Glu Met
            115                120                125

Thr Lys Asn Gln Val Ser Leu Thr Cys Leu Val Lys Gly Phe Tyr Pro
            130                135                140
```

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215

<210> SEQ ID NO 99
<211> LENGTH: 217
<212> TYPE: PRT
<213> ORGANISM: Homo sapiens
<220> FEATURE:
<221> NAME/KEY: source
<223> OTHER INFORMATION: /note="Wildtype Human IgG4 Fc"

<400> SEQUENCE: 99

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 100
<211> LENGTH: 696
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic anti-CD3scFv/TF/anti-CD28scFv sequence"

<400> SEQUENCE: 100

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Asn Pro Phe Thr
                85                  90                  95

Phe Gly Ser Gly Thr Lys Leu Glu Ile Asn Arg Gly Gly Gly Ser
                100                 105                 110

Gly Gly Gly Gly Ser Gly Gly Gly Ser Gln Val Gln Leu Gln Gln
                115                 120                 125

Ser Gly Ala Glu Leu Ala Arg Pro Gly Ala Ser Val Lys Met Ser Cys
    130                 135                 140

Lys Ala Ser Gly Tyr Thr Phe Thr Arg Tyr Thr Met His Trp Val Lys
145                 150                 155                 160

Gln Arg Pro Gly Gln Gly Leu Glu Trp Ile Gly Tyr Ile Asn Pro Ser
                165                 170                 175

Arg Gly Tyr Thr Asn Tyr Asn Gln Lys Phe Lys Asp Lys Ala Thr Leu
                180                 185                 190

Thr Thr Asp Lys Ser Ser Ser Thr Ala Tyr Met Gln Leu Ser Ser Leu
                195                 200                 205

Thr Ser Glu Asp Ser Ala Val Tyr Tyr Cys Ala Arg Tyr Tyr Asp Asp
    210                 215                 220

His Tyr Cys Leu Asp Tyr Trp Gly Gln Gly Thr Thr Leu Thr Val Ser
225                 230                 235                 240

Ser Ser Gly Thr Thr Asn Thr Val Ala Ala Tyr Asn Leu Thr Trp Lys
                245                 250                 255

Ser Thr Asn Phe Lys Thr Ile Leu Glu Trp Glu Pro Lys Pro Val Asn
                260                 265                 270

Gln Val Tyr Thr Val Gln Ile Ser Thr Lys Ser Gly Asp Trp Lys Ser
                275                 280                 285

Lys Cys Phe Tyr Thr Thr Asp Thr Glu Cys Asp Leu Thr Asp Glu Ile
    290                 295                 300

Val Lys Asp Val Lys Gln Thr Tyr Leu Ala Arg Val Phe Ser Tyr Pro
305                 310                 315                 320

Ala Gly Asn Val Glu Ser Thr Gly Ser Ala Gly Glu Pro Leu Tyr Glu
                325                 330                 335

Asn Ser Pro Glu Phe Thr Pro Tyr Leu Glu Thr Asn Leu Gly Gln Pro
                340                 345                 350

Thr Ile Gln Ser Phe Glu Gln Val Gly Thr Lys Val Asn Val Thr Val
                355                 360                 365

Glu Asp Glu Arg Thr Leu Val Arg Arg Asn Asn Thr Phe Leu Ser Leu
    370                 375                 380

Arg Asp Val Phe Gly Lys Asp Leu Ile Tyr Thr Leu Tyr Tyr Trp Lys
385                 390                 395                 400

Ser Ser Ser Ser Gly Lys Lys Thr Ala Lys Thr Asn Thr Asn Glu Phe
                405                 410                 415
```

```
Leu Ile Asp Val Asp Lys Gly Glu Asn Tyr Cys Phe Ser Val Gln Ala
            420                 425                 430

Val Ile Pro Ser Arg Thr Val Asn Arg Lys Ser Thr Asp Ser Pro Val
            435                 440                 445

Glu Cys Met Gly Gln Glu Lys Gly Glu Phe Arg Glu Val Gln Leu Gln
            450                 455                 460

Gln Ser Gly Pro Glu Leu Val Lys Pro Gly Ala Ser Val Lys Met Ser
465                 470                 475                 480

Cys Lys Ala Ser Gly Tyr Thr Phe Thr Ser Tyr Val Ile Gln Trp Val
            485                 490                 495

Lys Gln Lys Pro Gly Gln Gly Leu Glu Trp Ile Gly Ser Ile Asn Pro
            500                 505                 510

Tyr Asn Asp Tyr Thr Lys Tyr Asn Glu Lys Phe Lys Gly Lys Ala Thr
            515                 520                 525

Leu Thr Ser Asp Lys Ser Ser Ile Thr Ala Tyr Met Glu Phe Ser Ser
            530                 535                 540

Leu Thr Ser Glu Asp Ser Ala Leu Tyr Tyr Cys Ala Arg Trp Gly Asp
545                 550                 555                 560

Gly Asn Tyr Trp Gly Arg Gly Thr Thr Leu Thr Val Ser Ser Gly Gly
            565                 570                 575

Gly Gly Ser Gly Gly Gly Ser Gly Gly Gly Ser Asp Ile Glu
            580                 585                 590

Met Thr Gln Ser Pro Ala Ile Met Ser Ala Ser Leu Gly Glu Arg Val
            595                 600                 605

Thr Met Thr Cys Thr Ala Ser Ser Ser Val Ser Ser Tyr Phe His
610                 615                 620

Trp Tyr Gln Gln Lys Pro Gly Ser Ser Pro Lys Leu Cys Ile Tyr Ser
625                 630                 635                 640

Thr Ser Asn Leu Ala Ser Gly Val Pro Pro Arg Phe Ser Gly Ser Gly
            645                 650                 655

Ser Thr Ser Tyr Ser Leu Thr Ile Ser Ser Met Glu Ala Glu Asp Ala
            660                 665                 670

Ala Thr Tyr Phe Cys His Gln Tyr His Arg Ser Pro Thr Phe Gly Gly
            675                 680                 685

Gly Thr Lys Leu Glu Thr Lys Arg
            690                 695

<210> SEQ ID NO 101
<211> LENGTH: 2088
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic anti-CD3scFv/TF/anti-CD28scFv sequence"

<400> SEQUENCE: 101
cagatcgtgc tgacccaaag ccccgccatc atgagcgcta gccccggtga gaaggtgacc      60
atgacatgct ccgcttccag ctccgtgtcc tacatgaact ggtatcagca gaaaagcgga     120
accagcccca aaggtggat ctacgacacc agcaagctgg cctccggagt gcccgctcat     180
ttccggggct ctggatccgg caccagctac tctttaacca tttccggcat ggaagctgaa     240
gacgctgcca cctactattg ccagcaatgg agcagcaacc ccttcacatt cggatctggc     300
accaagctcg aaatcaatcg tggaggaggt ggcagcggcg gcgtggatc cggcggagga     360 ggaagccaag ttcaactcca gcagagcggc gctgaactgg cccggcccgg cgcctccgtc     420
```

```
aagatgagct gcaaggcttc cggctataca tttactcgtt acacaatgca ttgggtcaag    480
cagaggcccg gtcaaggttt agagtggatc ggatatatca acccttcccg gggctacacc    540
aactataacc aaaagttcaa ggataaagcc actttaacca ctgacaagag ctcctccacc    600
gcctacatgc agctgtcctc tttaaccagc gaggactccg ctgtttacta ctgcgctagg    660
tattacgacg accactactg tttagactat tggggacaag gtaccacttt aaccgtcagc    720
agctccggca ccaccaatac cgtggccgct tataacctca catggaagag caccaacttc    780
aagacaattc tggaatggga acccaagccc gtcaatcaag tttacaccgt gcagatctcc    840
accaaatccg gagactggaa gagcaagtgc ttctacacaa cagacaccga gtgtgattta    900
accgacgaaa tcgtcaagga cgtcaagcaa acctatctgg ctcgggtctt ttcctacccc    960
gctggcaatg tcgagtccac cggctccgct ggcgagcctc tctacgagaa ttcccccgaa   1020
ttcaccccct atttagagac caatttaggc cagcctacca tccagagctt cgagcaagtt   1080
ggcaccaagg tgaacgtcac cgtcgaggat gaaaggactt tagtgcggcg gaataacaca   1140 ttttttatccc tccgggatgt gttcggcaaa gacctcatct acacactgta ctattggaag   1200
tccagctcct ccggcaaaaa gaccgctaag accaacacca cgagttttt aattgacgtg    1260 gacaaaggcg agaactactg cttcagcgtg caagccgtga tcccttctcg taccgtcaac   1320
cggaagagca cagattcccc cgttgagtgc atgggccaag aaaagggcga gttccgggag   1380
gtccagctgc agcagagcgg acccgaactc gtgaacccg gtgcttccgt gaaaatgtct    1440
tgtaaggcca gcggatacac cttcacctcc tatgtgatcc agtgggtcaa acagaagccc   1500
ggacaaggtc tcgagtggat cggcagcatc aacccttaca cgactatac caaatacaac   1560 gagaagttta agggaaaggc tactttaacc tccgacaaaa gctccatcac agcctacatg   1620
gagttcagct ctttaacatc cgaggacagc gctctgtact attgcgcccg tgggcgac    1680 ggcaattact ggggacgggg cacaacactg accgtgagca gcggaggcgg aggctccggc   1740
ggaggcggat ctggcggtgg cggctccgac atcgagatga cccagtcccc cgctatcatg   1800
tccgcctctt taggcgagcg ggtcacaatg acttgtacag cctcctccag cgtctcctcc   1860
tcctacttcc attggtacca acagaaaccc ggaagctccc ctaaactgtg catctacagc   1920
accagcaatc tcgccagcgg cgtgccccct aggttttccg gaagcggaag caccagctac   1980
tctttaacca tctcctccat ggaggctgag gatgccgcca cctactttg tcaccagtac   2040 caccggtccc ccaccttcgg aggcggcacc aaactggaga caaagagg              2088
```

<210> SEQ ID NO 102
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic anti-CD3scFv/TF/anti-CD28scFv sequence"

<400> SEQUENCE: 102

Met Lys Trp Val Thr Phe Ile Ser Leu Leu Phe Leu Phe Ser Ser Ala
1               5                   10                  15

Tyr Ser Gln Ile Val Leu Thr Gln Ser Pro Ala Ile Met Ser Ala Ser
            20                  25                  30

Pro Gly Glu Lys Val Thr Met Thr Cys Ser Ala Ser Ser Ser Val Ser
        35                  40                  45

Tyr Met Asn Trp Tyr Gln Gln Lys Ser Gly Thr Ser Pro Lys Arg Trp

```
            50                  55                  60
Ile Tyr Asp Thr Ser Lys Leu Ala Ser Gly Val Pro Ala His Phe Arg
 65                      70                  75                  80
Gly Ser Gly Ser Gly Thr Ser Tyr Ser Leu Thr Ile Ser Gly Met Glu
                     85                  90                  95
Ala Glu Asp Ala Ala Thr Tyr Tyr Cys Gln Gln Trp Ser Ser Asn Pro
                100                 105                 110
Phe Thr Phe Gly Ser Gly Thr Lys Leu Glu Ile Asn Arg Gly Gly Gly
            115                 120                 125
Gly Ser Gly Gly Gly Gly Ser Gly Gly Gly Gly Ser Gln Val Gln Leu
        130                 135                 140
Gln Gln Ser Gly Ala Glu Leu Ala Arg Pro Gly Ala Ser Val Lys Met
145                 150                 155                 160
Ser Cys Lys Ala Ser Gly Tyr Thr Phe Thr Arg Tyr Thr Met His Trp
                165                 170                 175
Val Lys Gln Arg Pro Gly Gln Gly Leu Glu Trp Ile Gly Tyr Ile Asn
                180                 185                 190
Pro Ser Arg Gly Tyr Thr Asn Tyr Asn Gln Lys Phe Lys Asp Lys Ala
                195                 200                 205
Thr Leu Thr Thr Asp Lys Ser Ser Ser Thr Ala Tyr Met Gln Leu Ser
210                 215                 220
Ser Leu Thr Ser Glu Asp Ser Ala Val Tyr Tyr Cys Ala Arg Tyr Tyr
225                 230                 235                 240
Asp Asp His Tyr Cys Leu Asp Tyr Trp Gly Gln Gly Thr Thr Leu Thr
                245                 250                 255
Val Ser Ser Gly Thr Thr Asn Thr Val Ala Ala Tyr Asn Leu Thr
                260                 265                 270
Trp Lys Ser Thr Asn Phe Lys Thr Ile Leu Glu Trp Glu Pro Lys Pro
                275                 280                 285
Val Asn Gln Val Tyr Thr Val Gln Ile Ser Thr Lys Ser Gly Asp Trp
                290                 295                 300
Lys Ser Lys Cys Phe Tyr Thr Thr Asp Thr Glu Cys Asp Leu Thr Asp
305                 310                 315                 320
Glu Ile Val Lys Asp Val Lys Gln Thr Tyr Leu Ala Arg Val Phe Ser
                325                 330                 335
Tyr Pro Ala Gly Asn Val Glu Ser Thr Gly Ser Ala Gly Glu Pro Leu
                340                 345                 350
Tyr Glu Asn Ser Pro Glu Phe Thr Pro Tyr Leu Glu Thr Asn Leu Gly
                355                 360                 365
Gln Pro Thr Ile Gln Ser Phe Glu Gln Val Gly Thr Lys Val Asn Val
                370                 375                 380
Thr Val Glu Asp Glu Arg Thr Leu Val Arg Arg Asn Asn Thr Phe Leu
385                 390                 395                 400
Ser Leu Arg Asp Val Phe Gly Lys Asp Leu Ile Tyr Thr Leu Tyr Tyr
                405                 410                 415
Trp Lys Ser Ser Ser Gly Lys Lys Thr Ala Lys Thr Asn Thr Asn
                420                 425                 430
Glu Phe Leu Ile Asp Val Asp Lys Gly Glu Asn Tyr Cys Phe Ser Val
            435                 440                 445
Gln Ala Val Ile Pro Ser Arg Thr Val Asn Arg Lys Ser Thr Asp Ser
        450                 455                 460
Pro Val Glu Cys Met Gly Gln Glu Lys Gly Glu Phe Arg Glu Val Gln
465                 470                 475                 480
```

```
Leu Gln Gln Ser Gly Pro Glu Leu Val Lys Pro Gly Ala Ser Val Lys
                485                 490                 495
Met Ser Cys Lys Ala Ser Gly Tyr Thr Phe Thr Ser Tyr Val Ile Gln
            500                 505                 510
Trp Val Lys Gln Lys Pro Gly Gln Gly Leu Glu Trp Ile Gly Ser Ile
        515                 520                 525
Asn Pro Tyr Asn Asp Tyr Thr Lys Tyr Asn Glu Lys Phe Lys Gly Lys
    530                 535                 540
Ala Thr Leu Thr Ser Asp Lys Ser Ser Ile Thr Ala Tyr Met Glu Phe
545                 550                 555                 560
Ser Ser Leu Thr Ser Glu Asp Ser Ala Leu Tyr Tyr Cys Ala Arg Trp
                565                 570                 575
Gly Asp Gly Asn Tyr Trp Gly Arg Gly Thr Thr Leu Thr Val Ser Ser
            580                 585                 590
Gly Gly Gly Gly Ser Gly Gly Gly Ser Gly Gly Gly Gly Ser Asp
        595                 600                 605
Ile Glu Met Thr Gln Ser Pro Ala Ile Met Ser Ala Ser Leu Gly Glu
    610                 615                 620
Arg Val Thr Met Thr Cys Thr Ala Ser Ser Ser Val Ser Ser Ser Tyr
625                 630                 635                 640
Phe His Trp Tyr Gln Gln Lys Pro Gly Ser Ser Pro Lys Leu Cys Ile
                645                 650                 655
Tyr Ser Thr Ser Asn Leu Ala Ser Gly Val Pro Pro Arg Phe Ser Gly
            660                 665                 670
Ser Gly Ser Thr Ser Tyr Ser Leu Thr Ile Ser Ser Met Glu Ala Glu
        675                 680                 685
Asp Ala Ala Thr Tyr Phe Cys His Gln Tyr His Arg Ser Pro Thr Phe
    690                 695                 700
Gly Gly Gly Thr Lys Leu Glu Thr Lys Arg
705                 710

<210> SEQ ID NO 103
<211> LENGTH: 2142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic anti-CD3scFv/TF/anti-CD28scFv sequence"

<400> SEQUENCE: 103
atgaagtggg tgaccttcat cagcttatta tttttattca gctccgccta ttcccagatc    60
gtgctgaccc aaagccccgc catcatgagc gctagcccg gtgagaaggt gaccatgaca    120
tgctccgctt ccagctccgt gtcctacatg aactggtatc agcagaaaag cggaaccagc   180
cccaaaaggt ggatctacga caccagcaag ctggcctccg gagtgcccgc tcatttccgg    240
ggctctggat ccggcaccag ctactcttta accatttccg gcatggaagc tgaagacgct    300
gccacctact attgccagca atggagcagc aaccccttca cattcggatc tggcaccaag    360
ctcgaaatca tcgtggagg aggtggcagc ggcggcggtg gatccggcgg aggaggaagc    420
caagttcaac tccagcagag cggcgctgaa ctggcccggc ccggcgcctc cgtcaagatg    480
agctgcaagg cttccggcta cacatttact cgttacacaa tgcattgggt caagcagagg    540
cccggtcaag gtttagagtg gatcggatat atcaaccctt cccggggcta caccaactat   600
aaccaaaagt tcaaggataa agccacttta accactgaca agagctcctc caccgcctac    660
```

```
atgcagctgt cctctttaac cagcgaggac tccgctgttt actactgcgc taggtattac    720
gacgaccact actgtttaga ctattgggga caaggtacca ctttaaccgt cagcagctcc    780
ggcaccacca ataccgtggc cgcttataac ctcacatgga agagcaccaa cttcaagaca    840
attctggaat gggaacccaa gcccgtcaat caagtttaca ccgtgcagat ctccaccaaa    900
tccggagact ggaagagcaa gtgcttctac acaacagaca ccgagtgtga tttaaccgac    960
gaaatcgtca aggacgtcaa gcaaacctat ctggctcggg tcttttccta ccccgctggc   1020
aatgtcgagt ccaccggctc cgctggcgag cctctctacg agaattcccc cgaattcacc   1080
ccttatttag agaccaattt aggccagcct accatccaga gcttcgagca agttggcacc   1140
aaggtgaacg tcaccgtcga ggatgaaagg actttagtgc ggcggaataa cacattttta   1200
tccctccggg atgtgttcgg caaagacctc atctacacac tgtactattg gaagtccagc   1260
tcctccggca aaagaccgc taagaccaac accaacgagt ttttaattga cgtggacaaa   1320
ggcgagaact actgcttcag cgtgcaagcc gtgatccctt ctcgtaccgt caaccggaag   1380
agcacagatt ccccgttga gtgcatgggc caagaaaagg gcgagttccg ggaggtccag   1440
ctgcagcaga gcggacccga actcgtgaaa cccggtgctt ccgtgaaaat gtcttgtaag   1500
gccagcggat acaccttcac ctcctatgtg atccagtggg tcaaacagaa gcccggacaa   1560
ggtctcgagt ggatcggcag catcaaccct acaacgact ataccaaata caacgagaag   1620
tttaagggaa aggctacttt aacctccgac aaaagctcca tcacagccta catggagttc   1680
agctctttaa catccgagga cagcgctctg tactattgcg cccggtgggg cgacggcaat   1740
tactggggac ggggcacaac actgaccgtg agcagcggag gcggaggctc cggcggaggc   1800
ggatctggcg gtggcggctc cgacatcgag atgacccagt cccccgctat catgtccgcc   1860
tctttaggcg agcgggtcac aatgacttgt acagcctcct ccagcgtctc ctcctcctac   1920
ttccattggt accaacagaa acccggaagc tcccctaaac tgtgcatcta cagcaccagc   1980
aatctcgcca gcggcgtgcc ccctaggttt tccggaagcg gaagcaccag ctactcttta   2040
accatctcct ccatggaggc tgaggatgcc gccacctact tttgtcacca gtaccaccgg   2100
tcccccacct tcggaggcgg caccaaactg gagacaaaga gg                     2142
```

<210> SEQ ID NO 104
<211> LENGTH: 399
<212> TYPE: DNA
<213> ORGANISM: Homo sapiens
<220> FEATURE:
<221> NAME/KEY: source
<223> OTHER INFORMATION: /note="IL-2"

<400> SEQUENCE: 104

```
gcacctactt caagttctac aaagaaaaca cagctacaac tggagcattt actgctggat     60
ttacagatga ttttgaatgg aattaataat tacaagaatc ccaaactcac caggatgctc    120
acatttaagt tttacatgcc caagaaggcc acagaactga acatcttca gtgtctagaa     180
gaagaactca aacctctgga ggaagtgcta aatttagctc aaagcaaaaa ctttcactta    240
agacccaggg acttaatcag caatatcaac gtaatagttc tggaactaaa gggatctgaa    300
acaacattca tgtgtgaata tgctgatgag acagcaacca ttgtagaatt tctgaacaga    360
tggattacct tttgtcaaag catcatctca acactaact                           399
```

<210> SEQ ID NO 105
<211> LENGTH: 399

<212> TYPE: DNA
<213> ORGANISM: Homo sapiens
<220> FEATURE:
<221> NAME/KEY: source
<223> OTHER INFORMATION: /note="IL-2"

<400> SEQUENCE: 105

```
gcccccacct cctcctccac caagaagacc cagctgcagc tggagcattt actgctggat      60
ttacagatga ttttaaacgg catcaacaac tacaagaacc ccaagctgac tcgtatgctg     120
accttcaagt tctacatgcc caagaaggcc accgagctga agcatttaca gtgtttagag     180
gaggagctga agcccctcga ggaggtgctg aatttagccc agtccaagaa tttccattta     240
aggccccggg atttaatcag caacatcaac gtgatcgttt tagagctgaa gggctccgag     300
accaccttca gtgcgagta cgccgacgag accgccacca tcgtggagtt tttaaatcgt      360
tggatcacct tctgccagtc catcatctcc actttaacc                            399
```

<210> SEQ ID NO 106
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic IL-2/TF/IL-2 sequence"

<400> SEQUENCE: 106

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Ser Gly Thr Thr Asn Thr Val Ala Ala Tyr Asn
    130                 135                 140

Leu Thr Trp Lys Ser Thr Asn Phe Lys Thr Ile Leu Glu Trp Glu Pro
145                 150                 155                 160

Lys Pro Val Asn Gln Val Tyr Thr Val Gln Ile Ser Thr Lys Ser Gly
                165                 170                 175

Asp Trp Lys Ser Lys Cys Phe Tyr Thr Thr Asp Thr Glu Cys Asp Leu
            180                 185                 190

Thr Asp Glu Ile Val Lys Asp Val Lys Gln Thr Tyr Leu Ala Arg Val
        195                 200                 205

Phe Ser Tyr Pro Ala Gly Asn Val Glu Ser Thr Gly Ser Ala Gly Glu
    210                 215                 220

Pro Leu Tyr Glu Asn Ser Pro Glu Phe Thr Pro Tyr Leu Glu Thr Asn
225                 230                 235                 240
```

Leu Gly Gln Pro Thr Ile Gln Ser Phe Glu Gln Val Gly Thr Lys Val
                    245                 250                 255

Asn Val Thr Val Glu Asp Glu Arg Thr Leu Val Arg Arg Asn Asn Thr
            260                 265                 270

Phe Leu Ser Leu Arg Asp Val Phe Gly Lys Asp Leu Ile Tyr Thr Leu
        275                 280                 285

Tyr Tyr Trp Lys Ser Ser Ser Gly Lys Lys Thr Ala Lys Thr Asn
    290                 295                 300

Thr Asn Glu Phe Leu Ile Asp Val Asp Lys Gly Glu Asn Tyr Cys Phe
305                 310                 315                 320

Ser Val Gln Ala Val Ile Pro Ser Arg Thr Val Asn Arg Lys Ser Thr
                325                 330                 335

Asp Ser Pro Val Glu Cys Met Gly Gln Glu Lys Gly Glu Phe Arg Glu
            340                 345                 350

Ala Pro Thr Ser Ser Ser Thr Lys Lys Thr Gln Leu Gln Leu Glu His
        355                 360                 365

Leu Leu Leu Asp Leu Gln Met Ile Leu Asn Gly Ile Asn Asn Tyr Lys
    370                 375                 380

Asn Pro Lys Leu Thr Arg Met Leu Thr Phe Lys Phe Tyr Met Pro Lys
385                 390                 395                 400

Lys Ala Thr Glu Leu Lys His Leu Gln Cys Leu Glu Glu Glu Leu Lys
                405                 410                 415

Pro Leu Glu Glu Val Leu Asn Leu Ala Gln Ser Lys Asn Phe His Leu
            420                 425                 430

Arg Pro Arg Asp Leu Ile Ser Asn Ile Asn Val Ile Val Leu Glu Leu
        435                 440                 445

Lys Gly Ser Glu Thr Thr Phe Met Cys Glu Tyr Ala Asp Glu Thr Ala
    450                 455                 460

Thr Ile Val Glu Phe Leu Asn Arg Trp Ile Thr Phe Cys Gln Ser Ile
465                 470                 475                 480

Ile Ser Thr Leu Thr
                485

<210> SEQ ID NO 107
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic IL-2/TF/IL-2 sequence"

<400> SEQUENCE: 107
gcccccacct cctcctccac caagaagacc cagctgcagc tggagcattt actgctggat      60
ttacagatga ttttaaacgg catcaacaac tacaagaacc ccaagctgac tcgtatgctg     120
accttcaagt tctacatgcc caagaaggcc accgagctga agcatttaca gtgtttagag     180
gaggagctga agcccctcga ggaggtgctg aatttagccc agtccaagaa tttccattta     240
aggccccggg atttaatcag caacatcaac gtgatcgttt tagagctgaa gggctccgag     300
accaccttca gtgcgagta cgccgacgag accgccacca tcgtggagtt tttaaatcgt     360
tggatcacct tctgccagtc catcatctcc actttaacca gcggcacaac caacacagtc     420
gctgcctata acctcacttg gaagagcacc aacttcaaaa ccatcctcga atgggaaccc     480
aaacccgtta accaagttta caccgtgcag atcagcacca gtccggcga ctggaagtcc     540 aaatgttttct ataccaccga caccgagtgc gatctcaccg atgagatcgt gaaagatgtg     600

```
aaacagacct acctcgcccg ggtgtttagc taccccgccg gcaatgtgga gagcactggt    660
tccgctggcg agcctttata cgagaacagc cccgaattta ccccttacct cgagaccaat    720
ttaggacagc ccaccatcca aagctttgag caagttggca caaaggtgaa tgtgacagtg    780
gaggacgagc ggactttagt gcggcggaac aacacctttc tcagcctccg ggatgtgttc    840
ggcaaagatt taatctacac actgtattac tggaagtcct cttcctccgg caagaagaca    900
gctaaaacca acacaaacga gtttttaatc gacgtggata aaggcgaaaa ctactgtttc    960
agcgtgcaag ctgtgatccc ctcccggacc gtgaatagga aaagcaccga tagccccgtt   1020
gagtgcatgg gccaagaaaa gggcgagttc cgggaggcac ctacttcaag ttctacaaag   1080
aaaacacagc tacaactgga gcatttactg ctggatttac agatgatttt gaatggaatt   1140
aataattaca gaatcccaa  actcaccagg atgctcacat ttaagtttta catgcccaag   1200
aaggccacag aactgaaaca tcttcagtgt ctagaagaag aactcaaacc tctggaggaa   1260
gtgctaaatt tagctcaaag caaaaacttt cacttaagac ccagggactt aatcagcaat   1320
atcaacgtaa tagttctgga actaagggga tctgaaacaa cattcatgtg tgaatatgct   1380
gatgagacag caaccattgt agaatttctg aacagatgga ttacctttg  tcaaagcatc   1440 atctcaacac taact                                                    1455
```

<210> SEQ ID NO 108
<211> LENGTH: 503
<212> TYPE: PRT
<213> ORGANISM: Artificial Sequence
<220> FEATURE:
<221> NAME/KEY: source
<223> OTHER INFORMATION: /note="Description of Artificial Sequence: Synthetic IL-2/TF/IL-2 sequence"

<400> SEQUENCE: 108

```
Met Lys Trp Val Thr Phe Ile Ser Leu Leu Phe Leu Phe Ser Ser Ala
1               5                   10                  15

Tyr Ser Ala Pro Thr Ser Ser Ser Thr Lys Lys Thr Gln Leu Gln Leu
            20                  25                  30

Glu His Leu Leu Leu Asp Leu Gln Met Ile Leu Asn Gly Ile Asn Asn
        35                  40                  45

Tyr Lys Asn Pro Lys Leu Thr Arg Met Leu Thr Phe Lys Phe Tyr Met
    50                  55                  60

Pro Lys Lys Ala Thr Glu Leu Lys His Leu Gln Cys Leu Glu Glu Glu
65                  70                  75                  80

Leu Lys Pro Leu Glu Glu Val Leu Asn Leu Ala Gln Ser Lys Asn Phe
                85                  90                  95

His Leu Arg Pro Arg Asp Leu Ile Ser Asn Ile Asn Val Ile Val Leu
            100                 105                 110

Glu Leu Lys Gly Ser Glu Thr Thr Phe Met Cys Glu Tyr Ala Asp Glu
        115                 120                 125

Thr Ala Thr Ile Val Glu Phe Leu Asn Arg Trp Ile Thr Phe Cys Gln
    130                 135                 140

Ser Ile Ile Ser Thr Leu Thr Ser Gly Thr Thr Asn Thr Val Ala Ala
145                 150                 155                 160

Tyr Asn Leu Thr Trp Lys Ser Thr Asn Phe Lys Thr Ile Leu Glu Trp
                165                 170                 175

Glu Pro Lys Pro Val Asn Gln Val Tyr Thr Val Gln Ile Ser Thr Lys
            180                 185                 190
```

```
Ser Gly Asp Trp Lys Ser Lys Cys Phe Tyr Thr Thr Asp Thr Glu Cys
        195                 200                 205

Asp Leu Thr Asp Glu Ile Val Lys Asp Val Lys Gln Thr Tyr Leu Ala
    210                 215                 220

Arg Val Phe Ser Tyr Pro Ala Gly Asn Val Glu Ser Thr Gly Ser Ala
225                 230                 235                 240

Gly Glu Pro Leu Tyr Glu Asn Ser Pro Glu Phe Thr Pro Tyr Leu Glu
                245                 250                 255

Thr Asn Leu Gly Gln Pro Thr Ile Gln Ser Phe Glu Gln Val Gly Thr
            260                 265                 270

Lys Val Asn Val Thr Val Glu Asp Glu Arg Thr Leu Val Arg Arg Asn
        275                 280                 285

Asn Thr Phe Leu Ser Leu Arg Asp Val Phe Gly Lys Asp Leu Ile Tyr
    290                 295                 300

Thr Leu Tyr Tyr Trp Lys Ser Ser Ser Gly Lys Lys Thr Ala Lys
305                 310                 315                 320

Thr Asn Thr Asn Glu Phe Leu Ile Asp Val Asp Lys Gly Glu Asn Tyr
                325                 330                 335

Cys Phe Ser Val Gln Ala Val Ile Pro Ser Arg Thr Val Asn Arg Lys
            340                 345                 350

Ser Thr Asp Ser Pro Val Glu Cys Met Gly Gln Glu Lys Gly Glu Phe
        355                 360                 365

Arg Glu Ala Pro Thr Ser Ser Thr Lys Lys Thr Gln Leu Gln Leu
    370                 375                 380

Glu His Leu Leu Leu Asp Leu Gln Met Ile Leu Asn Gly Ile Asn Asn
385                 390                 395                 400

Tyr Lys Asn Pro Lys Leu Thr Arg Met Leu Thr Phe Lys Phe Tyr Met
                405                 410                 415

Pro Lys Lys Ala Thr Glu Leu Lys His Leu Gln Cys Leu Glu Glu Glu
            420                 425                 430

Leu Lys Pro Leu Glu Glu Val Leu Asn Leu Ala Gln Ser Lys Asn Phe
        435                 440                 445

His Leu Arg Pro Arg Asp Leu Ile Ser Asn Ile Asn Val Ile Val Leu
    450                 455                 460

Glu Leu Lys Gly Ser Glu Thr Thr Phe Met Cys Glu Tyr Ala Asp Glu
465                 470                 475                 480

Thr Ala Thr Ile Val Glu Phe Leu Asn Arg Trp Ile Thr Phe Cys Gln
                485                 490                 495

Ser Ile Ile Ser Thr Leu Thr
            500
```

<210> SEQ ID NO 109
<211> LENGTH: 1509
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic IL-2/TF/IL-2 sequence"

<400> SEQUENCE: 109
atgaagtggg tgaccttcat cagcctgctg ttcctgttct ccagcgccta ctccgccccc      60
acctcctcct ccaccaagaa gacccagctg cagctggagc atttactgct ggatttacag     120
atgattttaa acggcatcaa caactacaag aaccccaagc tgactcgtat gctgaccttc     180
aagttctaca tgcccaagaa ggccaccgag ctgaagcatt tacagtgttt agaggaggag     240

```
ctgaagcccc tcgaggaggt gctgaattta gcccagtcca agaatttcca tttaaggccc     300
cgggatttaa tcagcaacat caacgtgatc gttttagagc tgaagggctc cgagaccacc     360
ttcatgtgcg agtacgccga cgagaccgcc accatcgtgg agttttaaa tcgttggatc      420 accttctgcc agtccatcat ctccacttta accagcggca caaccaacac agtcgctgcc     480
tataacctca cttggaagag caccaacttc aaaaccatcc tcgaatggga acccaaaccc     540
gttaaccaag tttacaccgt gcagatcagc accaagtccg cgactggaa gtccaaatgt       600 ttctatacca ccgacaccga gtgcgatctc accgatgaga tcgtgaaaga tgtgaaacag     660
acctacctcg cccgggtgtt tagctacccc gccggcaatg tggagagcac tggttccgct     720
ggcgagcctt tatacgagaa cagccccgaa tttaccccctt acctcgagac caatttagga    780
cagcccacca tccaaagctt tgagcaagtt ggcacaaagg tgaatgtgac agtggaggac     840
gagcggactt tagtgcggcg gaacaacacc tttctcagcc tccgggatgt gttcggcaaa     900
gatttaatct acacactgta ttactggaag tcctcttcct ccggcaagaa gacagctaaa     960
accaacacaa acgagttttt aatcgacgtg gataaaggcg aaaactactg tttcagcgtg    1020
caagctgtga tcccctcccg gaccgtgaat aggaaaagca ccgatagccc cgttgagtgc    1080
atgggccaag aaaagggcga gttccgggag gcacctactt caagttctac aaagaaaaca    1140
cagctacaac tggagcattt actgctggat tacagatga ttttgaatgg aattaataat       1200
tacaagaatc ccaaactcac caggatgctc acatttaagt tttacatgcc caagaaggcc    1260
acagaactga acatcttca gtgtctagaa gaagaactca aacctctgga ggaagtgcta      1320
aatttagctc aaagcaaaaa ctttcactta agacccaggg acttaatcag caatatcaac    1380
gtaatagttc tggaactaaa gggatctgaa acaacattca tgtgtgaata tgctgatgag    1440
acagcaacca ttgtagaatt tctgaacaga tggattacct tttgtcaaag catcatctca    1500
acactaact                                                             1509
```

<210> SEQ ID NO 110
<211> LENGTH: 342
<212> TYPE: DNA
<213> ORGANISM: Homo sapiens
<220> FEATURE:
<221> NAME/KEY: source
<223> OTHER INFORMATION: /note="IL-15"

<400> SEQUENCE: 110

```
aactgggtga acgtcatcag cgatttaaag aagatcgaag atttaattca gtccatgcat      60
atcgacgcca ctttatacac agaatccgac gtgcaccct cttgtaaggt gaccgccatg     120
aaatgttttt tactggagct gcaagttatc tctttagaga gcggagacgc tagcatccac    180
gacaccgtgg agaattaat cattttagcc aataactctt tatccagcaa cggcaacgtg    240
acagagtccg gctgcaagga gtgcgaagag ctggaggaga gaacatcaa ggagtttctg      300 caatcctttg tgcacattgt ccagatgttc atcaatacct cc                        342
```

<210> SEQ ID NO 111
<211> LENGTH: 342
<212> TYPE: DNA
<213> ORGANISM: Homo sapiens
<220> FEATURE:
<221> NAME/KEY: source
<223> OTHER INFORMATION: /note="IL-15"

<400> SEQUENCE: 111

-continued

```
aactgggtga acgtgatcag cgatttaaag aagatcgagg atttaatcca gagcatgcac      60
atcgacgcca ctctgtacac tgagagcgac gtgcacccta gctgcaaggt gactgccatg     120
aagtgctttt tactggagct gcaagttatc tctttagaga gcggcgatgc cagcatccac     180
gacactgtgg agaatttaat cattttagcc aacaactctt taagcagcaa cggcaacgtg     240
acagagagcg gctgcaagga gtgcgaggag ctggaggaga agaacatcaa ggagttttta     300
cagagcttcg tgcacatcgt gcagatgttc atcaacacta gc                        342
```

<210> SEQ ID NO 112
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic IL-15/TF/IL-15 sequence"

<400> SEQUENCE: 112

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Ser Gly Thr Thr Asn Thr Val Ala Ala Tyr Asn Leu Thr Trp
        115                 120                 125

Lys Ser Thr Asn Phe Lys Thr Ile Leu Glu Trp Glu Pro Lys Pro Val
    130                 135                 140

Asn Gln Val Tyr Thr Val Gln Ile Ser Thr Lys Ser Gly Asp Trp Lys
145                 150                 155                 160

Ser Lys Cys Phe Tyr Thr Thr Asp Thr Glu Cys Asp Leu Thr Asp Glu
                165                 170                 175

Ile Val Lys Asp Val Lys Gln Thr Tyr Leu Ala Arg Val Phe Ser Tyr
            180                 185                 190

Pro Ala Gly Asn Val Glu Ser Thr Gly Ser Ala Gly Glu Pro Leu Tyr
        195                 200                 205

Glu Asn Ser Pro Glu Phe Thr Pro Tyr Leu Glu Thr Asn Leu Gly Gln
    210                 215                 220

Pro Thr Ile Gln Ser Phe Glu Gln Val Gly Thr Lys Val Asn Val Thr
225                 230                 235                 240

Val Glu Asp Glu Arg Thr Leu Val Arg Arg Asn Asn Thr Phe Leu Ser
                245                 250                 255

Leu Arg Asp Val Phe Gly Lys Asp Leu Ile Tyr Thr Leu Tyr Tyr Trp
            260                 265                 270

Lys Ser Ser Ser Gly Lys Lys Thr Ala Lys Thr Asn Thr Asn Glu
        275                 280                 285

Phe Leu Ile Asp Val Asp Lys Gly Glu Asn Tyr Cys Phe Ser Val Gln
```

```
              290                 295                 300
Ala Val Ile Pro Ser Arg Thr Val Asn Arg Lys Ser Thr Asp Ser Pro
305                 310                 315                 320

Val Glu Cys Met Gly Gln Glu Lys Gly Glu Phe Arg Glu Asn Trp Val
                325                 330                 335

Asn Val Ile Ser Asp Leu Lys Lys Ile Glu Asp Leu Ile Gln Ser Met
                340                 345                 350

His Ile Asp Ala Thr Leu Tyr Thr Glu Ser Asp Val His Pro Ser Cys
                355                 360                 365

Lys Val Thr Ala Met Lys Cys Phe Leu Leu Glu Leu Gln Val Ile Ser
                370                 375                 380

Leu Glu Ser Gly Asp Ala Ser Ile His Asp Thr Val Glu Asn Leu Ile
385                 390                 395                 400

Ile Leu Ala Asn Asn Ser Leu Ser Ser Asn Gly Asn Val Thr Glu Ser
                405                 410                 415

Gly Cys Lys Glu Cys Glu Glu Leu Glu Glu Lys Asn Ile Lys Glu Phe
                420                 425                 430

Leu Gln Ser Phe Val His Ile Val Gln Met Phe Ile Asn Thr Ser
                435                 440                 445

<210> SEQ ID NO 113
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic IL-15/TF/IL-15 sequence"

<400> SEQUENCE: 113
aactgggtga acgtgatcag cgatttaaag aagatcgagg atttaatcca gagcatgcac      60
atcgacgcca ctctgtacac tgagagcgac gtgcacccta gctgcaaggt gactgccatg     120
aagtgctttt tactggagct gcaagttatc tctttagaga gcggcgatgc cagcatccac     180
gacactgtgg agaatttaat catttttagcc aacaactctt taagcagcaa cggcaacgtg     240
acagagagcg gctgcaagga gtgcgaggag ctggaggaga gaacatcaa ggagtttta     300 cagagcttcg tgcacatcgt gcagatgttc atcaacacta gcagcggcac aaccaacaca     360
gtcgctgcct ataacctcac ttggaagagc accaacttca aaaccatcct gaatgggaa     420 cccaaacccg ttaaccaagt ttacaccgtg cagatcagca ccaagtccgg cgactggaag     480
tccaaatgtt tctataccac cgacaccgag tgcgatctca ccgatgagat cgtgaaagat     540
gtgaaacaga cctacctcgc ccgggtgttt agctaccccg ccggcaatgt ggagagcact     600
ggttccgctg cgagcctttt atacgagaac agccccgaat ttaccccta cctcgagacc     660 aatttaggac agcccaccat ccaaagcttt gagcaagttg gcacaaaggt gaatgtgaca     720
gtggaggacg agcggacttt agtgcggcgg aacaacacct ttctcagcct ccgggatgtg     780
ttcggcaaag atttaatcta cactctgtat tactggaagt cctcttcctc cggcaagaag     840
acagctaaaa ccaacacaaa cgagttttta atcgacgtgg ataaaggcga aaactactgt     900
ttcagcgtgc aagctgtgat cccctcccgg accgtgaata ggaaaagcac cgatagcccc     960
gttgagtgca tgggccaaga aaagggcgag ttccgggaga actgggtgaa cgtcatcagc    1020
gatttaaaga agatcgaaga tttaattcag tccatgcata tcgacgccac tttatacaca    1080
gaatccgacg tgcacccctc ttgtaaggtg accgccatga aatgttttt actggagctg    1140
```

```
caagttatct ctttagagag cggagacgct agcatccacg acaccgtgga gaatttaatc    1200
attttagcca ataactcttt atccagcaac ggcaacgtga cagagtccgg ctgcaaggag    1260
tgcgaagagc tggaggagaa gaacatcaag gagtttctgc aatcctttgt gcacattgtc    1320
cagatgttca tcaataccctc c                                              1341
```

<210> SEQ ID NO 114
<211> LENGTH: 465
<212> TYPE: PRT
<213> ORGANISM: Artificial Sequence
<220> FEATURE:
<221> NAME/KEY: source
<223> OTHER INFORMATION: /note="Description of Artificial Sequence: Synthetic IL-15/TF/IL-15 sequence"

<400> SEQUENCE: 114

```
Met Lys Trp Val Thr Phe Ile Ser Leu Leu Phe Leu Phe Ser Ser Ala
1               5                   10                  15

Tyr Ser Asn Trp Val Asn Val Ile Ser Asp Leu Lys Lys Ile Glu Asp
            20                  25                  30

Leu Ile Gln Ser Met His Ile Asp Ala Thr Leu Tyr Thr Glu Ser Asp
        35                  40                  45

Val His Pro Ser Cys Lys Val Thr Ala Met Lys Cys Phe Leu Leu Glu
    50                  55                  60

Leu Gln Val Ile Ser Leu Glu Ser Gly Asp Ala Ser Ile His Asp Thr
65                  70                  75                  80

Val Glu Asn Leu Ile Ile Leu Ala Asn Asn Ser Leu Ser Ser Asn Gly
                85                  90                  95

Asn Val Thr Glu Ser Gly Cys Lys Glu Cys Glu Glu Leu Glu Glu Lys
            100                 105                 110

Asn Ile Lys Glu Phe Leu Gln Ser Phe Val His Ile Val Gln Met Phe
        115                 120                 125

Ile Asn Thr Ser Ser Gly Thr Thr Asn Thr Val Ala Ala Tyr Asn Leu
    130                 135                 140

Thr Trp Lys Ser Thr Asn Phe Lys Thr Ile Leu Glu Trp Glu Pro Lys
145                 150                 155                 160

Pro Val Asn Gln Val Tyr Thr Val Gln Ile Ser Thr Lys Ser Gly Asp
                165                 170                 175

Trp Lys Ser Lys Cys Phe Tyr Thr Thr Asp Thr Glu Cys Asp Leu Thr
            180                 185                 190

Asp Glu Ile Val Lys Asp Val Lys Gln Thr Tyr Leu Ala Arg Val Phe
        195                 200                 205

Ser Tyr Pro Ala Gly Asn Val Glu Ser Thr Gly Ser Ala Gly Glu Pro
    210                 215                 220

Leu Tyr Glu Asn Ser Pro Glu Phe Thr Pro Tyr Leu Glu Thr Asn Leu
225                 230                 235                 240

Gly Gln Pro Thr Ile Gln Ser Phe Glu Gln Val Gly Thr Lys Val Asn
                245                 250                 255

Val Thr Val Glu Asp Glu Arg Thr Leu Val Arg Arg Asn Asn Thr Phe
            260                 265                 270

Leu Ser Leu Arg Asp Val Phe Gly Lys Asp Leu Ile Tyr Thr Leu Tyr
        275                 280                 285

Tyr Trp Lys Ser Ser Ser Ser Gly Lys Lys Thr Ala Lys Thr Asn Thr
    290                 295                 300

Asn Glu Phe Leu Ile Asp Val Asp Lys Gly Glu Asn Tyr Cys Phe Ser
305                 310                 315                 320
```

```
Val Gln Ala Val Ile Pro Ser Arg Thr Val Asn Arg Lys Ser Thr Asp
                325                 330                 335

Ser Pro Val Glu Cys Met Gly Gln Glu Lys Gly Glu Phe Arg Glu Asn
            340                 345                 350

Trp Val Asn Val Ile Ser Asp Leu Lys Lys Ile Glu Asp Leu Ile Gln
        355                 360                 365

Ser Met His Ile Asp Ala Thr Leu Tyr Thr Glu Ser Asp Val His Pro
    370                 375                 380

Ser Cys Lys Val Thr Ala Met Lys Cys Phe Leu Leu Glu Leu Gln Val
385                 390                 395                 400

Ile Ser Leu Glu Ser Gly Asp Ala Ser Ile His Asp Thr Val Glu Asn
                405                 410                 415

Leu Ile Ile Leu Ala Asn Asn Ser Leu Ser Ser Asn Gly Asn Val Thr
            420                 425                 430

Glu Ser Gly Cys Lys Glu Cys Glu Glu Leu Glu Glu Lys Asn Ile Lys
        435                 440                 445

Glu Phe Leu Gln Ser Phe Val His Ile Val Gln Met Phe Ile Asn Thr
    450                 455                 460

Ser
465

<210> SEQ ID NO 115
<211> LENGTH: 1395
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic IL-15/TF/IL-15 sequence"

<400> SEQUENCE: 115
atgaagtggg tgaccttcat cagcctgctg ttcctgttct ccagcgccta ctccaactgg       60
gtgaacgtga tcagcgattt aaagaagatc gaggatttaa tccagagcat gcacatcgac      120
gccactctgt acactgagag cgacgtgcac cctagctgca aggtgactgc catgaagtgc      180
tttttactgg agctgcaagt tatctcttta gagagcggcg atgccagcat ccacgacact      240
gtggagaatt taatcatttt agccaacaac tctttaagca gcaacggcaa cgtgacagag      300
agcggctgca aggagtgcga ggagctggag gagaagaaca tcaaggagtt tttacagagc      360
ttcgtgcaca tcgtgcagat gttcatcaac actagcagcg gcacaaccaa cacagtcgct      420
gcctataacc tcacttggaa gagcaccaac ttcaaaacca cctcgaatg ggaacccaaa       480 cccgttaacc aagtttacac cgtgcagatc agcaccaagt ccggcgactg aagtccaaa       540 tgtttctata ccaccgacac cgagtgcgat ctcaccgatg agatcgtgaa agatgtgaaa      600
cagacctacc tcgcccgggt gtttagctac cccgccggca atgtggagag cactggttcc      660
gctggcgagc cttatacgga acagccccc gaatttaccc cttacctcga gaccaattta       720
ggacagccca ccatccaaag ctttgagcaa gttggcacaa aggtgaatgt gacagtggag      780
gacgagcgga ctttagtgcg gcggaacaac acctttctca gcctccggga tgtgttcggc      840
aaagatttaa tctacacact gtattactgg aagtcctctt cctccggcaa gagacagct      900 aaaaccaaca caaacgagtt tttaatcgac gtggataaag gcgaaaacta ctgtttcagc      960
gtgcaagctg tgatccctc ccggaccgtg aataggaaaa gcaccgatag ccccgttgag      1020
tgcatgggcc aagaaaaggg cgagttccgg gagaactggg tgaacgtcat cagcgattta    1080
```

```
aagaagatcg aagatttaat tcagtccatg catatcgacg ccactttata cacagaatcc    1140
gacgtgcacc cctcttgtaa ggtgaccgcc atgaaatgtt ttttactgga gctgcaagtt    1200
atctctttag agagcggaga cgctagcatc cacgacaccg tggagaattt aatcatttta    1260
gccaataact ctttatccag caacggcaac gtgacagagt ccggctgcaa ggagtgcgaa    1320
gagctggagg agaagaacat caaggagttt ctgcaatcct ttgtgcacat tgtccagatg    1380
ttcatcaata cctcc                                                     1395
```

<210> SEQ ID NO 116
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic IL-18/TF/IL-15:IL-12/IL-15RalphaSu sequence"

<400> SEQUENCE: 116

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65              70                  75                  80

Ile Ser Phe Lys Glu Met Asn Pro Pro Asp Asn Ile Lys Asp Thr Lys
            85                  90                  95

Ser Asp Ile Ile Phe Phe Gln Arg Ser Val Pro Gly His Asp Asn Lys
        100                 105                 110

Met Gln Phe Glu Ser Ser Ser Tyr Glu Gly Tyr Phe Leu Ala Cys Glu
    115                 120                 125

Lys Glu Arg Asp Leu Phe Lys Leu Ile Leu Lys Lys Glu Asp Glu Leu
130                 135                 140

Gly Asp Arg Ser Ile Met Phe Thr Val Gln Asn Glu Asp Ser Gly Thr
145             150                 155                 160

Thr Asn Thr Val Ala Ala Tyr Asn Leu Thr Trp Lys Ser Thr Asn Phe
            165                 170                 175

Lys Thr Ile Leu Glu Trp Glu Pro Lys Pro Val Asn Gln Val Tyr Thr
        180                 185                 190

Val Gln Ile Ser Thr Lys Ser Gly Asp Trp Lys Ser Lys Cys Phe Tyr
    195                 200                 205

Thr Thr Asp Thr Glu Cys Asp Leu Thr Asp Glu Ile Val Lys Asp Val
    210                 215                 220

Lys Gln Thr Tyr Leu Ala Arg Val Phe Ser Tyr Pro Ala Gly Asn Val
225                 230                 235                 240

Glu Ser Thr Gly Ser Ala Gly Glu Pro Leu Tyr Glu Asn Ser Pro Glu
            245                 250                 255

Phe Thr Pro Tyr Leu Glu Thr Asn Leu Gly Gln Pro Thr Ile Gln Ser
        260                 265                 270

Phe Glu Gln Val Gly Thr Lys Val Asn Val Thr Val Glu Asp Glu Arg
    275                 280                 285

Thr Leu Val Arg Arg Asn Asn Thr Phe Leu Ser Leu Arg Asp Val Phe
```

```
            290                 295                 300
Gly Lys Asp Leu Ile Tyr Thr Leu Tyr Tyr Trp Lys Ser Ser Ser Ser
305                 310                 315                 320

Gly Lys Lys Thr Ala Lys Thr Asn Thr Asn Glu Phe Leu Ile Asp Val
                325                 330                 335

Asp Lys Gly Glu Asn Tyr Cys Phe Ser Val Gln Ala Val Ile Pro Ser
                340                 345                 350

Arg Thr Val Asn Arg Lys Ser Thr Asp Ser Pro Val Glu Cys Met Gly
            355                 360                 365

Gln Glu Lys Gly Glu Phe Arg Glu Asn Trp Val Asn Val Ile Ser Asp
        370                 375                 380

Leu Lys Lys Ile Glu Asp Leu Ile Gln Ser Met His Ile Asp Ala Thr
385                 390                 395                 400

Leu Tyr Thr Glu Ser Asp Val His Pro Ser Cys Lys Val Thr Ala Met
                405                 410                 415

Lys Cys Phe Leu Leu Glu Leu Gln Val Ile Ser Leu Glu Ser Gly Asp
                420                 425                 430

Ala Ser Ile His Asp Thr Val Glu Asn Leu Ile Ile Leu Ala Asn Asn
            435                 440                 445

Ser Leu Ser Ser Asn Gly Asn Val Thr Glu Ser Gly Cys Lys Glu Cys
        450                 455                 460

Glu Glu Leu Glu Glu Lys Asn Ile Lys Glu Phe Leu Gln Ser Phe Val
465                 470                 475                 480

His Ile Val Gln Met Phe Ile Asn Thr Ser
                485                 490

<210> SEQ ID NO 117
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic IL-18/TF/IL-15:IL-12/IL-15RalphaSu sequence"

<400> SEQUENCE: 117
tacttcggca aactggaatc caagctgagc gtgatccgga atttaaacga ccaagttctg    60
tttatcgatc aaggtaaccg gcctctgttc gaggacatga ccgactccga ttgccgggac   120 aatgccccc  ggaccatctt cattatctcc atgtacaagg acagccagcc ccggggcatg   180
gctgtgacaa ttagcgtgaa gtgtgagaaa atcagcactt tatcttgtga aaacaagatc   240
atctccttta aggaaatgaa ccccccgat  aacatcaagg acaccaagtc cgatatcatc   300
ttcttccagc ggtccgtgcc cggtcacgat aacaagatgc agttcgaatc ctcctcctac   360
gagggctact ttttagcttg tgaaaaggag agggatttat tcaagctgat cctcaagaag   420
gaggacgagc tgggcgatcg ttccatcatg ttcaccgtcc aaaacgagga tagcggcaca   480
accaacacag tcgctgccta taacctcact tggaagagca ccaacttcaa aaccatcctc   540
gaatgggaac ccaaacccgt taaccaagtt tacaccgtgc agatcagcac caagtccggc   600
gactggaagt ccaaatgttt ctataccacc gacaccgagt cgatctcac  cgatgagatc   660 gtgaaagatg tgaaacagac ctacctcgcc cgggtgttta gctaccccgc cggcaatgtg   720
gagagcactg gttccgctgg cgagcctta  tacgagaaca gccccgaatt tacccttac   780 ctcgagacca atttaggaca gcccaccatc caaagctttg agcaagttgg cacaaaggtg   840
aatgtgacag tggaggacga gcggactta  gtgcggcgga caacaccttt ctcagcctc   900
```

-continued

```
cgggatgtgt tcggcaaaga tttaatctac acactgtatt actggaagtc ctcttcctcc      960
ggcaagaaga cagctaaaac caacacaaac gagttttaa tcgacgtgga taaaggcgaa     1020
aactactgtt tcagcgtgca agctgtgatc ccctcccgga ccgtgaatag aaaagcacc     1080 gatagccccg ttgagtgcat gggccaagaa aagggcgagt tccggagaa ctgggtgaac     1140 gtcatcagcg atttaaagaa gatcgaagat ttaattcagt ccatgcatat cgacgccact     1200
ttatacacag aatccgacgt gcacccctct tgtaaggtga ccgccatgaa atgttttta     1260 ctggagctgc aagttatctc tttagagagc ggagacgcta gcatccacga caccgtggag     1320
aatttaatca ttttagccaa taactcttta tccagcaacg gcaacgtgac agagtccggc     1380
tgcaaggagt gcgaagagct ggaggagaag aacatcaagg agtttctgca atcctttgtg     1440
cacattgtcc agatgttcat caatacctcc                                     1470
```

<210> SEQ ID NO 118
<211> LENGTH: 508
<212> TYPE: PRT
<213> ORGANISM: Artificial Sequence
<220> FEATURE:
<221> NAME/KEY: source
<223> OTHER INFORMATION: /note="Description of Artificial Sequence: Synthetic IL-18/TF/IL-15:IL-12/IL-15RalphaSu sequence"

<400> SEQUENCE: 118

```
Met Lys Trp Val Thr Phe Ile Ser Leu Leu Phe Leu Phe Ser Ser Ala
1               5                   10                  15

Tyr Ser Tyr Phe Gly Lys Leu Glu Ser Lys Leu Ser Val Ile Arg Asn
            20                  25                  30

Leu Asn Asp Gln Val Leu Phe Ile Asp Gln Gly Asn Arg Pro Leu Phe
        35                  40                  45

Glu Asp Met Thr Asp Ser Asp Cys Arg Asp Asn Ala Pro Arg Thr Ile
    50                  55                  60

Phe Ile Ile Ser Met Tyr Lys Asp Ser Gln Pro Arg Gly Met Ala Val
65                  70                  75                  80

Thr Ile Ser Val Lys Cys Glu Lys Ile Ser Thr Leu Ser Cys Glu Asn
                85                  90                  95

Lys Ile Ile Ser Phe Lys Glu Met Asn Pro Pro Asp Asn Ile Lys Asp
            100                 105                 110

Thr Lys Ser Asp Ile Ile Phe Phe Gln Arg Ser Val Pro Gly His Asp
        115                 120                 125

Asn Lys Met Gln Phe Glu Ser Ser Ser Tyr Glu Gly Tyr Phe Leu Ala
    130                 135                 140

Cys Glu Lys Glu Arg Asp Leu Phe Lys Leu Ile Leu Lys Lys Glu Asp
145                 150                 155                 160

Glu Leu Gly Asp Arg Ser Ile Met Phe Thr Val Gln Asn Glu Asp Ser
                165                 170                 175

Gly Thr Thr Asn Thr Val Ala Ala Tyr Asn Leu Thr Trp Lys Ser Thr
            180                 185                 190

Asn Phe Lys Thr Ile Leu Glu Trp Glu Pro Lys Pro Val Asn Gln Val
        195                 200                 205

Tyr Thr Val Gln Ile Ser Thr Lys Ser Gly Asp Trp Lys Ser Lys Cys
    210                 215                 220

Phe Tyr Thr Thr Asp Thr Glu Cys Asp Leu Thr Asp Glu Ile Val Lys
225                 230                 235                 240

Asp Val Lys Gln Thr Tyr Leu Ala Arg Val Phe Ser Tyr Pro Ala Gly
```

```
                245                 250                 255
Asn Val Glu Ser Thr Gly Ser Ala Gly Glu Pro Leu Tyr Glu Asn Ser
            260                 265                 270

Pro Glu Phe Thr Pro Tyr Leu Glu Thr Asn Leu Gly Gln Pro Thr Ile
        275                 280                 285

Gln Ser Phe Glu Gln Val Gly Thr Lys Val Asn Val Thr Val Glu Asp
    290                 295                 300

Glu Arg Thr Leu Val Arg Arg Asn Asn Thr Phe Leu Ser Leu Arg Asp
305                 310                 315                 320

Val Phe Gly Lys Asp Leu Ile Tyr Thr Leu Tyr Tyr Trp Lys Ser Ser
                325                 330                 335

Ser Ser Gly Lys Lys Thr Ala Lys Thr Asn Thr Asn Glu Phe Leu Ile
            340                 345                 350

Asp Val Asp Lys Gly Glu Asn Tyr Cys Phe Ser Val Gln Ala Val Ile
        355                 360                 365

Pro Ser Arg Thr Val Asn Arg Lys Ser Thr Asp Ser Pro Val Glu Cys
    370                 375                 380

Met Gly Gln Glu Lys Gly Glu Phe Arg Glu Asn Trp Val Asn Val Ile
385                 390                 395                 400

Ser Asp Leu Lys Lys Ile Glu Asp Leu Ile Gln Ser Met His Ile Asp
                405                 410                 415

Ala Thr Leu Tyr Thr Glu Ser Asp Val His Pro Ser Cys Lys Val Thr
            420                 425                 430

Ala Met Lys Cys Phe Leu Leu Glu Leu Gln Val Ile Ser Leu Glu Ser
        435                 440                 445

Gly Asp Ala Ser Ile His Asp Thr Val Glu Asn Leu Ile Ile Leu Ala
    450                 455                 460

Asn Asn Ser Leu Ser Ser Asn Gly Asn Val Thr Glu Ser Gly Cys Lys
465                 470                 475                 480

Glu Cys Glu Glu Leu Glu Glu Lys Asn Ile Lys Glu Phe Leu Gln Ser
                485                 490                 495

Phe Val His Ile Val Gln Met Phe Ile Asn Thr Ser
            500                 505
```

<210> SEQ ID NO 119
<211> LENGTH: 1524
<212> TYPE: DNA
<213> ORGANISM: Artificial Sequence
<220> FEATURE:
<221> NAME/KEY: source
<223> OTHER INFORMATION: /note="Description of Artificial Sequence: Synthetic IL-18/TF/IL-15:IL-12/IL-15RalphaSu sequence"

<400> SEQUENCE: 119

```
atgaagtggg tcacatttat ctctttactg ttcctcttct ccagcgccta cagctacttc      60
ggcaaactgg aatccaagct gagcgtgatc cggaatttaa acgaccaagt tctgtttatc     120
gatcaaggta accggcctct gttcgaggac atgaccgact ccgattgccg ggacaatgcc     180
ccccggacca tcttcattat ctccatgtac aaggacagcc agccccgggg catggctgtg     240
acaattagcg tgaagtgtga aaaatcagca ctttatcttg tgagaacaa gatcatctcc      300 tttaaggaaa tgaaccccccc cgataacatc aaggacacca gtccgatat catcttcttc    360 cagcggtccg tgcccggtca cgataacaag atgcagttcg aatcctcctc ctacgagggc     420
tactttttag cttgtgaaaa ggagagggat ttattcaagc tgatcctcaa gaggaggac     480 gagctgggcg atcgttccat catgttcacc gtccaaaacg aggatagcgg cacaaccaac     540
```

-continued

```
acagtcgctg cctataacct cacttggaag agcaccaact tcaaaaccat cctcgaatgg    600
gaacccaaac ccgttaacca agtttacacc gtgcagatca gcaccaagtc cggcgactgg    660
aagtccaaat gtttctatac caccgacacc gagtgcgatc tcaccgatga gatcgtgaaa    720
gatgtgaaac agacctacct cgcccgggtg tttagctacc ccgccggcaa tgtggagagc    780
actggttccg ctggcgagcc tttatacgag aacagccccg aatttacccc ttacctcgag    840
accaatttag acagcccac catccaaagc tttgagcaag ttggcacaaa ggtgaatgtg    900
acagtggagg acgagcggac tttagtgcgg cggaacaaca cctttctcag cctccgggat    960
gtgttcggca agatttaat ctacacactg tattactgga agtcctcttc ctccggcaag   1020
aagacagcta aaccaacac aaacgagttt taatcgacg tggataaagg cgaaaactac   1080
tgtttcagcg tgcaagctgt gatcccctcc cggaccgtga ataggaaaag caccgatagc   1140
cccgttgagt gcatgggcca agaaaagggc gagttccggg agaactgggt gaacgtcatc   1200
agcgatttaa agaagatcga agatttaatt cagtccatgc atatcgacgc cactttatac   1260
acagaatccg acgtgcaccc ctcttgtaag gtgaccgcca tgaaatgttt tttactggag   1320
ctgcaagtta tctctttaga gagcggagac gctagcatcc acgacaccgt ggagaattta   1380
atcattttag ccaataactc tttatccagc aacggcaacg tgacagagtc cggctgcaag   1440
gagtgcgaag agctggagga gaagaacatc aaggagtttc tgcaatcctt tgtgcacatt   1500
gtccagatgt tcatcaatac ctcc                                         1524
```

<210> SEQ ID NO 120
<211> LENGTH: 583
<212> TYPE: PRT
<213> ORGANISM: Artificial Sequence
<220> FEATURE:
<221> NAME/KEY: source
<223> OTHER INFORMATION: /note="Description of Artificial Sequence: Synthetic IL-12/IL-15RalphaSu sequence"

<400> SEQUENCE: 120

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175
```

```
Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Ile Thr Cys Pro Pro Met Ser Val Glu
        515                 520                 525

His Ala Asp Ile Trp Val Lys Ser Tyr Ser Leu Tyr Ser Arg Glu Arg
    530                 535                 540

Tyr Ile Cys Asn Ser Gly Phe Lys Arg Lys Ala Gly Thr Ser Ser Leu
545                 550                 555                 560

Thr Glu Cys Val Leu Asn Lys Ala Thr Asn Val Ala His Trp Thr Thr
                565                 570                 575

Pro Ser Leu Lys Cys Ile Arg
            580
```

<210> SEQ ID NO 121
<211> LENGTH: 1749
<212> TYPE: DNA
<213> ORGANISM: Artificial Sequence
<220> FEATURE:
<221> NAME/KEY: source
<223> OTHER INFORMATION: /note="Description of Artificial Sequence: Synthetic IL-12/IL-15RalphaSu sequence"

<400> SEQUENCE: 121

```
atttgggaac tgaagaagga cgtctacgtg gtcgaactgg actggtatcc cgatgctccc      60
ggcgaaatgg tggtgctcac ttgtgacacc cccgaagaag acggcatcac ttggacccte     120
gatcagagca gcgaggtgct gggctccgga aagaccctca caatccaagt taaggagttc     180
ggagacgctg ccaatacaca atgccacaag ggaggcgagg tgctcagcca ttccttatta     240
ttattacaca agaaggaaga cggaatctgg tccaccgaca ttttaaaaga tcagaaggag     300
cccaagaata agacctttt aaggtgtgag gccaaaaact acagcggtcg tttcacttgt     360
tggtggctga ccaccattc caccgattta accttctccg tgaaaagcag ccggggaagc     420
tccgaccctc aaggtgtgac atgtggagcc gctaccctca gcgctgagag ggttcgtggc     480
gataacaagg aatacgagta cagcgtggag tgccaagaag atagcgcttg ccccgctgcc     540
gaagaatctt acccattga ggtgatggtg gacgccgtgc acaaactcaa gtacgagaac     600
tacacctcct ccttctttat ccgggacatc attaagcccg atcctcctaa gaatttacag     660
ctgaagcctc tcaaaaatag ccggcaagtt gaggtctctt gggaatatcc cgacacttgg     720
agcacacccc acagctactt ctctttaacc ttttgtgtgc aagttcaagg taaaagcaag     780
cgggagaaga agaccgggt gtttaccgac aaaaccagcg ccaccgtcat ctgtcggaag     840
aacgcctcca tcagcgtgag ggctcaagat cgttattact ccagcagctg gtccgagtgg     900
gccagcgtgc cttgttccgg cggtggagga tccggaggag gtggctccgg cggcggagga     960
tctcgtaacc tccccgtggc tacccccgat cccggaatgt tcccttgttt acaccacagc    1020
cagaatttac tgagggccgt gagcaacatg ctgcagaaag ctaggcagac tttagaattt    1080
taccttgca ccagcgagga gatcgaccat gaagatatca ccaaggacaa gacatccacc    1140
gtggaggctt gtttacctct ggagctgaca aagaacgagt cttgtctcaa ctctcgtgaa    1200
accagcttca tcacaaatgg ctcttgttta gcttcccgga agacctcctt tatgatggct    1260
ttatgcctca gctccatcta cgaggattta aagatgtacc aagtggagtt caagaccatg    1320
aacgccaagc tgctcatgga ccctaaacgg cagatctttt tagaccagaa catgctggct    1380
gtgattgatg agctgatgca agctttaaac ttcaactccg agaccgtccc tcagaagtcc    1440
tccctcgagg agcccgattt ttacaagaca aagatcaaac tgtgcatttt actccacgcc    1500
tttaggatcc gggccgtgac cattgaccgg gtcatgagct atttaaacgc cagcattaca    1560
tgccccccctc ccatgagcgt ggagcacgcc gacatctggg tgaagagcta tagcctctac    1620
agccgggaga ggtatatctg taacagcggc ttcaagagga aggccggcac cagcagcctc    1680
accgagtgcg tgctgaataa ggctaccaac gtggctcact ggacaacacc ctctttaaag    1740
tgcatccgg                                                            1749
```

<210> SEQ ID NO 122
<211> LENGTH: 601
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic IL-12/IL-15RalphaSu sequence"

<400> SEQUENCE: 122

```
Met Lys Trp Val Thr Phe Ile Ser Leu Leu Phe Leu Phe Ser Ser Ala
1               5                   10                  15

Tyr Ser Ile Trp Glu Leu Lys Lys Asp Val Tyr Val Val Glu Leu Asp
            20                  25                  30

Trp Tyr Pro Asp Ala Pro Gly Glu Met Val Val Leu Thr Cys Asp Thr
        35                  40                  45

Pro Glu Glu Asp Gly Ile Thr Trp Thr Leu Asp Gln Ser Ser Glu Val
    50                  55                  60

Leu Gly Ser Gly Lys Thr Leu Thr Ile Gln Val Lys Glu Phe Gly Asp
65                  70                  75                  80

Ala Gly Gln Tyr Thr Cys His Lys Gly Gly Glu Val Leu Ser His Ser
                85                  90                  95

Leu Leu Leu Leu His Lys Lys Glu Asp Gly Ile Trp Ser Thr Asp Ile
            100                 105                 110

Leu Lys Asp Gln Lys Glu Pro Lys Asn Lys Thr Phe Leu Arg Cys Glu
        115                 120                 125

Ala Lys Asn Tyr Ser Gly Arg Phe Thr Cys Trp Trp Leu Thr Thr Ile
    130                 135                 140

Ser Thr Asp Leu Thr Phe Ser Val Lys Ser Ser Arg Gly Ser Ser Asp
145                 150                 155                 160

Pro Gln Gly Val Thr Cys Gly Ala Ala Thr Leu Ser Ala Glu Arg Val
                165                 170                 175

Arg Gly Asp Asn Lys Glu Tyr Glu Tyr Ser Val Glu Cys Gln Glu Asp
            180                 185                 190

Ser Ala Cys Pro Ala Ala Glu Glu Ser Leu Pro Ile Glu Val Met Val
        195                 200                 205

Asp Ala Val His Lys Leu Lys Tyr Glu Asn Tyr Thr Ser Ser Phe Phe
    210                 215                 220

Ile Arg Asp Ile Ile Lys Pro Asp Pro Pro Lys Asn Leu Gln Leu Lys
225                 230                 235                 240

Pro Leu Lys Asn Ser Arg Gln Val Glu Val Ser Trp Glu Tyr Pro Asp
                245                 250                 255

Thr Trp Ser Thr Pro His Ser Tyr Phe Ser Leu Thr Phe Cys Val Gln
            260                 265                 270

Val Gln Gly Lys Ser Lys Arg Glu Lys Lys Asp Arg Val Phe Thr Asp
        275                 280                 285

Lys Thr Ser Ala Thr Val Ile Cys Arg Lys Asn Ala Ser Ile Ser Val
    290                 295                 300

Arg Ala Gln Asp Arg Tyr Tyr Ser Ser Ser Trp Ser Glu Trp Ala Ser
305                 310                 315                 320

Val Pro Cys Ser Gly Gly Gly Ser Gly Gly Gly Ser Gly Gly
                325                 330                 335

Gly Gly Ser Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
        355                 360                 365

Leu Gln Lys Ala Arg Gln Thr Leu Glu Phe Tyr Pro Cys Thr Ser Glu
    370                 375                 380

Glu Ile Asp His Glu Asp Ile Thr Lys Asp Lys Thr Ser Thr Val Glu
385                 390                 395                 400
```

```
Ala Cys Leu Pro Leu Glu Leu Thr Lys Asn Glu Ser Cys Leu Asn Ser
                405                 410                 415

Arg Glu Thr Ser Phe Ile Thr Asn Gly Ser Cys Leu Ala Ser Arg Lys
            420                 425                 430

Thr Ser Phe Met Met Ala Leu Cys Leu Ser Ser Ile Tyr Glu Asp Leu
        435                 440                 445

Lys Met Tyr Gln Val Glu Phe Lys Thr Met Asn Ala Lys Leu Leu Met
    450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
            500                 505                 510

Cys Ile Leu Leu His Ala Phe Arg Ile Arg Ala Val Thr Ile Asp Arg
        515                 520                 525

Val Met Ser Tyr Leu Asn Ala Ser Ile Thr Cys Pro Pro Pro Met Ser
    530                 535                 540

Val Glu His Ala Asp Ile Trp Val Lys Ser Tyr Ser Leu Tyr Ser Arg
545                 550                 555                 560

Glu Arg Tyr Ile Cys Asn Ser Gly Phe Lys Arg Lys Ala Gly Thr Ser
                565                 570                 575

Ser Leu Thr Glu Cys Val Leu Asn Lys Ala Thr Asn Val Ala His Trp
            580                 585                 590

Thr Thr Pro Ser Leu Lys Cys Ile Arg
        595                 600
```

<210> SEQ ID NO 123
<211> LENGTH: 1803
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic IL-12/IL-15RalphaSu sequence"

<400> SEQUENCE: 123

```
atgaaatggg tgacctttat ttctttactg ttcctctttta gcagcgccta ctccatttgg      60
gaactgaaga aggacgtcta cgtggtcgaa ctggactggt atcccgatgc tcccggcgaa     120
atggtggtgc tcacttgtga caccccgaa gaagacggca tcacttggac cctcgatcag     180
agcagcgagg tgctgggctc cggaaagacc ctcacaatcc aagttaagga gttcggagac     240
gctggccaat acacatgcca caggggaggc gaggtgctca gccattcctt attattatta     300
cacaagaagg aagacggaat ctggtccacc gacattttaa aagatcagaa ggagcccaag     360
aataagacct ttttaaggtg tgaggccaaa aactacagcg tcgtttcac ttgttggtgg     420 ctgaccacca tttccaccga tttaaccttc tccgtgaaaa gcagccgggg aagctccgac     480
cctcaaggtg tgacatgtgg agccgctacc ctcagcgctg agagggttcg tggcgataac     540
aaggaatacg agtacagcgt ggagtgccaa gaagatagcg cttgtccgc tgccgaagaa     600 tctttaccca ttgaggtgat ggtggacgcc gtgcacaaac tcaagtacga aactacacc     660 tcctccttct ttatccggga catcattaag cccgatcctc taagaatttt acagctgaag     720
cctctcaaaa atagccggca agttgaggtc tcttgggaat atcccgacac ttggagcaca     780
ccccacagct acttctcttt aaccttttgt gtgcaagttc aaggtaaaag caagcgggag     840
```

```
aagaaagacc gggtgtttac cgacaaaacc agcgccaccg tcatctgtcg aagaacgcc      900
tccatcagcg tgagggctca agatcgttat tactccagca gctggtccga gtgggccagc      960
gtgccttgtt ccggcggtgg aggatccgga ggaggtggct ccggcggcgg aggatctcgt     1020
aacctccccg tggctacccc cgatcccgga atgttccctt gtttacacca cagccagaat     1080
ttactgaggg ccgtgagcaa catgctgcag aaagctaggc agactttaga attttaccct     1140
tgcaccagcg aggagatcga ccatgaagat atcaccaagg acaagacatc caccgtggag     1200
gcttgtttac ctctggagct gacaaagaac gagtcttgtc tcaactctcg tgaaaccagc     1260
ttcatcacaa atggctcttg tttagcttcc cggaagacct cctttatgat ggctttatgc     1320
ctcagctcca tctacgagga tttaaagatg taccaagtgg agttcaagac catgaacgcc     1380
aagctgctca ggaccctaa acggcagatc tttttagacc agaacatgct ggctgtgatt     1440
gatgagctga tgcaagcttt aaacttcaac tccgagaccg tccctcagaa gtcctccctc     1500
gaggagcccg attttacaa gacaaagatc aaactgtgca ttttactcca cgcctttagg     1560
atccgggccg tgaccattga ccgggtcatg agctatttaa acgccagcat acatgcccc     1620
cctcccatga gcgtggagca cgccgacatc tgggtgaaga gctatagcct ctacagccgg     1680
gagaggtata tctgtaacag cggcttcaag aggaaggccg gcaccagcag cctcaccgag     1740
tgcgtgctga ataaggctac caacgtggct cactggacaa caccctcttt aaagtgcatc     1800
cgg                                                                    1803

<210> SEQ ID NO 124
<211> LENGTH: 133
<212> TYPE: PRT
<213> ORGANISM: Homo sapiens
<220> FEATURE:
<221> NAME/KEY: source
<223> OTHER INFORMATION: /note="IL-21"

<400> SEQUENCE: 124

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 125
<211> LENGTH: 399
<212> TYPE: DNA
<213> ORGANISM: Homo sapiens
<220> FEATURE:
```

```
<221> NAME/KEY: source
<223> OTHER INFORMATION: /note="IL-21"

<400> SEQUENCE: 125
cagggccagg acaggcacat gatccggatg aggcagctca tcgacatcgt cgaccagctg      60
aagaactacg tgaacgacct ggtgcccgag tttctgcctg cccccgagga cgtggagacc     120
aactgcgagt ggtccgcctt ctcctgcttt cagaaggccc agctgaagtc cgccaacacc     180
ggcaacaacg agcggatcat caacgtgagc atcaagaagc tgaagcggaa gcctccctcc     240
acaaacgccg gcaggaggca aagcacaggc tgacctgcc ccagctgtga ctcctacgag      300
aagaagcccc ccaaggagtt cctggagagg ttcaagtccc tgctgcagaa gatgatccat     360
cagcacctgt cctccaggac ccacggctcc gaggactcc                            399

<210> SEQ ID NO 126
<211> LENGTH: 466
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 21t15 sequence"

<400> SEQUENCE: 126
```

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ser Gly Thr Thr Asn Thr Val Ala Ala Tyr Asn
    130                 135                 140

Leu Thr Trp Lys Ser Thr Asn Phe Lys Thr Ile Leu Glu Trp Glu Pro
145                 150                 155                 160

Lys Pro Val Asn Gln Val Tyr Thr Val Gln Ile Ser Thr Lys Ser Gly
                165                 170                 175

Asp Trp Lys Ser Lys Cys Phe Tyr Thr Thr Asp Thr Glu Cys Asp Leu
            180                 185                 190

Thr Asp Glu Ile Val Lys Asp Val Lys Gln Thr Tyr Leu Ala Arg Val
        195                 200                 205

Phe Ser Tyr Pro Ala Gly Asn Val Glu Ser Thr Gly Ser Ala Gly Glu
    210                 215                 220

Pro Leu Tyr Glu Asn Ser Pro Glu Phe Thr Pro Tyr Leu Glu Thr Asn
225                 230                 235                 240

Leu Gly Gln Pro Thr Ile Gln Ser Phe Glu Gln Val Gly Thr Lys Val
                245                 250                 255

```
Asn Val Thr Val Glu Asp Glu Arg Thr Leu Val Arg Arg Asn Asn Thr
            260                 265                 270

Phe Leu Ser Leu Arg Asp Val Phe Gly Lys Asp Leu Ile Tyr Thr Leu
        275                 280                 285

Tyr Tyr Trp Lys Ser Ser Ser Gly Lys Lys Thr Ala Lys Thr Asn
    290                 295                 300

Thr Asn Glu Phe Leu Ile Asp Val Asp Lys Gly Glu Asn Tyr Cys Phe
305                 310                 315                 320

Ser Val Gln Ala Val Ile Pro Ser Arg Thr Val Asn Arg Lys Ser Thr
                325                 330                 335

Asp Ser Pro Val Glu Cys Met Gly Gln Glu Lys Gly Glu Phe Arg Glu
            340                 345                 350

Asn Trp Val Asn Val Ile Ser Asp Leu Lys Lys Ile Glu Asp Leu Ile
        355                 360                 365

Gln Ser Met His Ile Asp Ala Thr Leu Tyr Thr Glu Ser Asp Val His
    370                 375                 380

Pro Ser Cys Lys Val Thr Ala Met Lys Cys Phe Leu Leu Glu Leu Gln
385                 390                 395                 400

Val Ile Ser Leu Glu Ser Gly Asp Ala Ser Ile His Asp Thr Val Glu
                405                 410                 415

Asn Leu Ile Ile Leu Ala Asn Asn Ser Leu Ser Ser Asn Gly Asn Val
            420                 425                 430

Thr Glu Ser Gly Cys Lys Cys Glu Glu Leu Glu Glu Lys Asn Ile
        435                 440                 445

Lys Glu Phe Leu Gln Ser Phe Val His Ile Val Gln Met Phe Ile Asn
450                 455                 460

Thr Ser
465

<210> SEQ ID NO 127
<211> LENGTH: 1398
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21t15 sequence"

<400> SEQUENCE: 127
cagggccagg acaggcacat gatccggatg aggcagctca tcgacatcgt cgaccagctg      60
aagaactacg tgaacgacct ggtgcccgag tttctgcctg cccccgagga cgtggagacc     120
aactgcgagt ggtccgcctt ctcctgcttt cagaaggccc agctgaagtc cgccaacacc     180
ggcaacaacg agcggatcat caacgtgagc atcaagaagc tgaagcggaa gcctcccctcc    240 acaaacgccg gcaggaggca gaagcacagg ctgacctgcc cagctgtga ctcctacgag      300 aagaagcccc ccaaggagtt cctggagagg ttcaagtccc tgctgcagaa gatgatccat    360
cagcacctgt cctccaggac ccacggctcc gaggactcct ccggcaccac caataccgtg    420
gccgcttata acctcacatg gaagagcacc aacttcaaga caattctgga atgggaaccc    480
aagcccgtca atcaagttta caccgtgcag atctccacca atccggaga ctggaagagc    540 aagtgcttct acacaacaga caccgagtgt gatttaaccg acgaaatcgt caaggacgtc   600
aagcaaacct atctggctcg ggtcttttcc taccccgctg gcaatgtcga gtccaccggc   660
tccgctggcg agcctctcta cgagaattcc cccgaattca ccccttattt agagaccaat   720
ttaggccagc ctaccatcca gagcttcgag caagttggca ccaaggtgaa cgtcaccgtc   780
```

```
gaggatgaaa ggactttagt gcggcggaat aacacatttt tatccctccg ggatgtgttc      840
ggcaaagacc tcatctacac actgtactat tggaagtcca gctcctccgg caaaaagacc      900
gctaagacca acaccaacga gttttttaatt gacgtggaca aaggcgagaa ctactgcttc     960
agcgtgcaag ccgtgatccc ttctcgtacc gtcaaccgga agagcacaga ttcccccgtt     1020
gagtgcatgg gccaagaaaa gggcgagttc cgggagaact gggtgaacgt catcagcgat     1080
ttaaagaaga tcgaagattt aattcagtcc atgcatatcg acgccacttt atacacagaa     1140
tccgacgtgc accccctcttg taaggtgacc gccatgaaat gttttttact ggagctgcaa     1200
gttatctctt tagagagcgg agacgctagc atccacgaca ccgtggagaa tttaatcatt     1260
ttagccaata actctttatc cagcaacggc aacgtgacag agtccggctg caaggagtgc     1320
gaagagctgg aggagaagaa catcaaggag tttctgcaat cctttgtgca cattgtccag     1380
atgttcatca atacctcc                                                    1398
```

<210> SEQ ID NO 128
<211> LENGTH: 484
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 21t15 sequence"

<400> SEQUENCE: 128

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
                20                  25                  30

Asp Ile Val Asp Gln Leu Lys Asn Tyr Val Asn Asp Leu Val Pro Glu
            35                  40                  45

Phe Leu Pro Ala Pro Glu Asp Val Glu Thr Asn Cys Glu Trp Ser Ala
        50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ser Gly Thr Thr Asn Thr Val Ala Ala
145                 150                 155                 160

Tyr Asn Leu Thr Trp Lys Ser Thr Asn Phe Lys Thr Ile Leu Glu Trp
                165                 170                 175

Glu Pro Lys Pro Val Asn Gln Val Tyr Thr Val Gln Ile Ser Thr Lys
            180                 185                 190

Ser Gly Asp Trp Lys Ser Lys Cys Phe Tyr Thr Thr Asp Thr Glu Cys
        195                 200                 205

Asp Leu Thr Asp Glu Ile Val Lys Asp Val Lys Gln Thr Tyr Leu Ala
    210                 215                 220

Arg Val Phe Ser Tyr Pro Ala Gly Asn Val Glu Ser Thr Gly Ser Ala
225                 230                 235                 240
```

```
Gly Glu Pro Leu Tyr Glu Asn Ser Pro Glu Phe Thr Pro Tyr Leu Glu
                245                 250                 255

Thr Asn Leu Gly Gln Pro Thr Ile Gln Ser Phe Glu Gln Val Gly Thr
            260                 265                 270

Lys Val Asn Val Thr Val Glu Asp Glu Arg Thr Leu Val Arg Arg Asn
        275                 280                 285

Asn Thr Phe Leu Ser Leu Arg Asp Val Phe Gly Lys Asp Leu Ile Tyr
    290                 295                 300

Thr Leu Tyr Tyr Trp Lys Ser Ser Ser Gly Lys Lys Thr Ala Lys
305                 310                 315                 320

Thr Asn Thr Asn Glu Phe Leu Ile Asp Val Asp Lys Gly Glu Asn Tyr
                325                 330                 335

Cys Phe Ser Val Gln Ala Val Ile Pro Ser Arg Thr Val Asn Arg Lys
            340                 345                 350

Ser Thr Asp Ser Pro Val Glu Cys Met Gly Gln Glu Lys Gly Glu Phe
        355                 360                 365

Arg Glu Asn Trp Val Asn Val Ile Ser Asp Leu Lys Lys Ile Glu Asp
    370                 375                 380

Leu Ile Gln Ser Met His Ile Asp Ala Thr Leu Tyr Thr Glu Ser Asp
385                 390                 395                 400

Val His Pro Ser Cys Lys Val Thr Ala Met Lys Cys Phe Leu Leu Glu
                405                 410                 415

Leu Gln Val Ile Ser Leu Glu Ser Gly Asp Ala Ser Ile His Asp Thr
            420                 425                 430

Val Glu Asn Leu Ile Ile Leu Ala Asn Asn Ser Leu Ser Ser Asn Gly
        435                 440                 445

Asn Val Thr Glu Ser Gly Cys Lys Glu Cys Glu Glu Leu Glu Glu Lys
    450                 455                 460

Asn Ile Lys Glu Phe Leu Gln Ser Phe Val His Ile Val Gln Met Phe
465                 470                 475                 480

Ile Asn Thr Ser

<210> SEQ ID NO 129
<211> LENGTH: 1452
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21t15 sequence"

<400> SEQUENCE: 129
atgaagtggg tgaccttcat cagcctgctg ttcctgttct ccagcgccta ctcccagggc      60
caggacaggc acatgatccg gatgaggcag ctcatcgaca tcgtcgacca gctgaagaac     120
tacgtgaacg acctggtgcc cgagtttctg cctgcccccg aggacgtgga gaccaactgc     180
gagtggtccg ccttctcctg ctttcagaag gcccagctga gtccgccaa caccggcaac      240 aacgagcgga tcatcaacgt gagcatcaag aagctgaagc ggaagcctcc ctccacaaac     300
gccggcagga ggcagaagca caggctgacc tgccccagct gtgactccta cgagaagaag     360
ccccccaagg agttcctgga gaggttcaag tccctgctgc agaagatgat ccatcagcac     420
ctgtcctcca ggacccacgg ctccgaggac tcctccggca ccaccaatac cgtggccgct     480
tataacctca catggaagag caccaacttc aagacaattc tggaatggga acccaagccc     540
gtcaatcaag tttacaccgt gcagatctcc accaaatccg gagactggaa gagcaagtgc     600
```

-continued

```
ttctacacaa cagacaccga gtgtgattta accgacgaaa tcgtcaagga cgtcaagcaa    660
acctatctgg ctcgggtctt ttcctacccc gctggcaatg tcgagtccac cggctccgct    720
ggcgagcctc tctacgagaa ttcccccgaa ttcacccctt atttagagac caatttaggc    780
cagcctacca tccagagctt cgagcaagtt ggcaccaagg tgaacgtcac cgtcgaggat    840
gaaaggactt tagtgcggcg gaataacaca tttttatccc tccgggatgt gttcggcaaa    900
gacctcatct acacactgta ctattggaag tccagctcct ccggcaaaaa gaccgctaag    960
accaacacca acgagttttt aattgacgtg gacaaaggcg agaactactg cttcagcgtg   1020
caagccgtga tcccttctcg taccgtcaac cggaagagca cagattcccc cgttgagtgc   1080
atgggccaag aaaagggcga gttccgggag aactgggtga acgtcatcag cgatttaaag   1140
aagatcgaag atttaattca gtccatgcat atcgacgcca ctttatacac agaatccgac   1200
gtgcacccct cttgtaaggt gaccgccatg aaatgttttt tactggagct gcaagttatc   1260
tctttagaga gcggagacgc tagcatccac gacaccgtgg agaatttaat cattttagcc   1320
aataactctt tatccagcaa cggcaacgtg acagagtccg gctgcaagga gtgcgaagag   1380
ctggaggaga agaacatcaa ggagtttctg caatcctttg tgcacattgt ccagatgttc   1440
atcaataacct cc                                                      1452
```

<210> SEQ ID NO 130
<211> LENGTH: 352
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRs sequence"

<400> SEQUENCE: 130

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

```
Lys Ser Cys Met Ser Asn Cys Ser Ile Thr Ser Ile Cys Glu Lys Pro
            195                 200                 205
Gln Glu Val Cys Val Ala Val Trp Arg Lys Asn Asp Glu Asn Ile Thr
        210                 215                 220
Leu Glu Thr Val Cys His Asp Pro Lys Leu Pro Tyr His Asp Phe Ile
225                 230                 235                 240
Leu Glu Asp Ala Ala Ser Pro Lys Cys Ile Met Lys Glu Lys Lys
                245                 250                 255
Pro Gly Glu Thr Phe Phe Met Cys Ser Cys Ser Asp Glu Cys Asn
                260                 265                 270
Asp Asn Ile Ile Phe Ser Glu Glu Tyr Asn Thr Ser Asn Pro Asp Ile
            275                 280                 285
Thr Cys Pro Pro Pro Met Ser Val Glu His Ala Asp Ile Trp Val Lys
        290                 295                 300
Ser Tyr Ser Leu Tyr Ser Arg Glu Arg Tyr Ile Cys Asn Ser Gly Phe
305                 310                 315                 320
Lys Arg Lys Ala Gly Thr Ser Ser Leu Thr Glu Cys Val Leu Asn Lys
                325                 330                 335
Ala Thr Asn Val Ala His Trp Thr Thr Pro Ser Leu Lys Cys Ile Arg
            340                 345                 350
```

```
<210> SEQ ID NO 131
<211> LENGTH: 1056
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRs sequence"

<400> SEQUENCE: 131 atccccccccc atgtgcaaaa gagcgtgaac aacgatatga tcgtgaccga caacaacggc      60
gccgtgaagt ttccccagct ctgcaagttc tgcgatgtca ggttcagcac ctgcgataat     120
cagaagtcct gcatgtccaa ctgcacgatc acctccatct gcgagaagcc caagaagtg     180
tgcgtggccg tgtggcggaa aaatgacgag aacatcaccc tggagaccgt gtgtcacgac     240
cccaagctcc cttatcacga cttcattctg gaggacgctg cctcccccaa atgcatcatg     300
aaggagaaga agaagcccgg agagaccttc tttatgtgtt cctgtagcag cgacgagtgt     360
aacgacaaca tcatcttcag cgaagagtac aacaccagca accctgatgg aggtggcgga     420
tccggaggtg gaggttctgg tggaggtggg agtattcctc cccacgtgca gaagagcgtg     480
aataatgaca tgatcgtgac cgataacaat ggcgccgtga atttccccca gctgtgcaaa     540
ttctgcgatg tgaggttttc cacctgcgac aaccagaagt cctgtatgag caactgcaca     600
atcacctcca tctgtgagaa gcctcaggag gtgtgcgtgg ctgtctggcg gaagaatgac     660
gagaatatca ccctggaaac cgtctgccac gatcccaagc tgccctacca cgatttcatc     720
ctggaagacg ccgccagccc taagtgcatc atgaaagaga aaagaagcc tggcgagacc     780
ttttcatgt gctcctgcag cagcgacgaa tgcaacgaca atatcatctt tagcgaggaa     840
tacaatacca gcaaccccga catcacgtgt cctcctccta tgtccgtgga acacgcagac     900
atctgggtca agagctacag cttgtactcc agggagcggt acatttgtaa ctctggtttc     960
aagcgtaaag ccggcacgtc cagcctgacg gagtgcgtgt tgaacaaggc cacgaatgtc    1020
gcccactgga caaccccag tctcaaatgt attaga                                1056
```

<210> SEQ ID NO 132
<211> LENGTH: 370
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRs sequence"

<400> SEQUENCE: 132

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ile Thr Cys Pro Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
        355                 360                 365
```

Ile Arg
    370

<210> SEQ ID NO 133
<211> LENGTH: 1110
<212> TYPE: DNA
<213> ORGANISM: Artificial Sequence
<220> FEATURE:
<221> NAME/KEY: source
<223> OTHER INFORMATION: /note="Description of Artificial Sequence: Synthetic TGFRs sequence"

<400> SEQUENCE: 133

| | | | | | |
|---|---|---|---|---|---|
| atgaagtggg | tgaccttcat | cagcctgctg | ttcctgttct | ccagcgccta | ctccatcccc | 60 |
| ccccatgtgc | aaaagagcgt | gaacaacgat | atgatcgtga | ccgacaacaa | cggcgccgtg | 120 |
| aagtttcccc | agctctgcaa | gttctgcgat | gtcaggttca | gcacctgcga | taatcagaag | 180 |
| tcctgcatgt | ccaactgcac | gatcacctcc | atctgcgaga | agccccaaga | agtgtgcgtg | 240 |
| gccgtgtggc | ggaaaaatga | cgagaacatc | accctggaga | ccgtgtgtca | cgaccccaag | 300 |
| ctcccttatc | acgacttcat | tctggaggac | gctgcctccc | ccaaatgcat | catgaaggag | 360 |
| aagaagaagc | ccggagagac | cttctttatg | tgttcctgta | gcagcgacga | gtgtaacgac | 420 |
| aacatcatct | tcagcgaaga | gtacaacacc | agcaaccctg | atggaggtgg | cggatccgga | 480 |
| ggtggaggtt | ctggtggagg | tgggagtatt | cctccccacg | tgcagaagag | cgtgaataat | 540 |
| gacatgatcg | tgaccgataa | caatggcgcc | gtgaaatttc | cccagctgtg | caaattctgc | 600 |
| gatgtgaggt | tttccacctg | cgacaaccag | aagtcctgta | tgagcaactg | cacaatcacc | 660 |
| tccatctgtg | agaagcctca | ggaggtgtgc | gtggctgtct | ggcggaagaa | tgacgagaat | 720 |
| atcaccctgg | aaaccgtctg | ccacgatccc | aagctgccct | accacgattt | catcctggaa | 780 |
| gacgccgcca | gccctaagtg | catcatgaaa | gagaaaaaga | agcctggcga | gaccttttc | 840 |
| atgtgctcct | gcagcagcga | cgaatgcaac | gacaatatca | tctttagcga | ggaatacaat | 900 |
| accagcaacc | ccgacatcac | cgtgcctcct | cctatgtccg | tggaacacgc | agacatctgg | 960 |
| gtcaagagct | acagcttgta | ctccagggag | cggtacattt | gtaactctgg | tttcaagcgt | 1020 |
| aaagccggca | cgtccagcct | gacggagtgc | gtgttgaaca | aggccacgaa | tgtcgcccac | 1080 |
| tggacaaccc | ccagtctcaa | atgtattaga | | | 1110 |

<210> SEQ ID NO 134
<211> LENGTH: 399
<212> TYPE: DNA
<213> ORGANISM: Homo sapiens
<220> FEATURE:
<221> NAME/KEY: source
<223> OTHER INFORMATION: /note="IL-21"

<400> SEQUENCE: 134

| | | | | | |
|---|---|---|---|---|---|
| caaggtcaag | atcgccacat | gattagaatg | cgtcaactta | tagatattgt | tgatcagctg | 60 |
| aaaaattatg | tgaatgactt | ggtccctgaa | tttctgccag | ctccagaaga | tgtagagaca | 120 |
| aactgtgagt | ggtcagcttt | ttcctgtttt | cagaaggccc | aactaaagtc | agcaaataca | 180 |
| ggaaacaatg | aaaggataat | caatgtatca | attaaaaagc | tgaagaggaa | accaccttcc | 240 |
| acaaatgcag | ggagaagaca | gaaacacaga | ctaacatgcc | cttcatgtga | ttcttatgag | 300 |
| aaaaaaccac | ccaaagaatt | cctagaaaga | ttcaaatcac | ttctccaaaa | gatgattcat | 360 |
| cagcatctgt | cctctagaac | acacggaagt | gaagattcc | | | 399 |

<210> SEQ ID NO 135
<211> LENGTH: 152
<212> TYPE: PRT
<213> ORGANISM: Homo sapiens
<220> FEATURE:
<221> NAME/KEY: source
<223> OTHER INFORMATION: /note="IL-7"

<400> SEQUENCE: 135

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150
```

<210> SEQ ID NO 136
<211> LENGTH: 456
<212> TYPE: DNA
<213> ORGANISM: Homo sapiens
<220> FEATURE:
<221> NAME/KEY: source
<223> OTHER INFORMATION: /note="IL-7"

<400> SEQUENCE: 136

```
gattgtgata ttgaaggtaa agatggcaaa caatatgaga gtgttctaat ggtcagcatc      60
gatcaattat tggacagcat gaaagaaatt ggtagcaatt gcctgaataa tgaatttaac     120
ttttttaaaa gacatatctg tgatgctaat aaggaaggta tgtttttatt ccgtgctgct     180
cgcaagttga ggcaatttct taaaatgaat agcactggtg attttgatct ccacttatta     240
aaagtttcag aaggcacaac aatactgttg aactgcactg gccaggttaa ggaagaaaa     300 ccagctgccc tgggtgaagc ccaaccaaca aagagtttgg aagaaaataa atctttaaag     360
gaacagaaaa aactgaatga cttgtgtttc ctaaagagac tattacaaga gataaaaact     420
tgttggaata aatttttgat gggcactaaa gaacac                              456
```

<210> SEQ ID NO 137
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 7s sequence"

<400> SEQUENCE: 137

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65              70                  75                  80

Lys Val Ser Glu Gly Thr Thr Ile Leu Leu Asn Cys Thr Gly Gln Val
            85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His Ile Thr Cys Pro Pro Pro Met Ser
145             150                 155                 160

Val Glu His Ala Asp Ile Trp Val Lys Ser Tyr Ser Leu Tyr Ser Arg
            165                 170                 175

Glu Arg Tyr Ile Cys Asn Ser Gly Phe Lys Arg Lys Ala Gly Thr Ser
            180                 185                 190

Ser Leu Thr Glu Cys Val Leu Asn Lys Ala Thr Asn Val Ala His Trp
        195                 200                 205

Thr Thr Pro Ser Leu Lys Cys Ile Arg
    210                 215

<210> SEQ ID NO 138
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7s sequence"

<400> SEQUENCE: 138
gattgtgata ttgaaggtaa agatggcaaa caatatgaga gtgttctaat ggtcagcatc     60
gatcaattat tggacagcat gaaagaaatt ggtagcaatt gcctgaataa tgaatttaac    120
ttttttaaaa gacatatctg tgatgctaat aaggaaggta tgttttttatt ccgtgctgct    180 cgcaagttga gcaatttcct taaaatgaat agcactggtg attttgatct ccacttatta    240
aaagtttcag aaggcacaac aatactgttg aactgcactg gccaggttaa aggaagaaaa    300
ccagctgccc tgggtgaagc ccaaccaaca aagagtttgg aagaaaataa atctttaaag    360
gaacagaaaa aactgaatga cttgtgtttc ctaaagagac tattacaaga gataaaaact    420
tgttggaata aaattttgat gggcactaaa gaacacatca cgtgccctcc ccccatgtcc    480
gtggaacacg cagacatctg ggtcaagagc tacagcttgt actccaggga gcggtacatt    540
tgtaactctg gtttcaagcg taaagccggc acgtccagcc tgacggagtg cgtgttgaac    600
aaggccacga atgtcgccca ctggacaacc cccagtctca aatgcattag a             651

<210> SEQ ID NO 139

-continued

<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7s sequence"

<400> SEQUENCE: 139

Met Gly Val Lys Val Leu Phe Ala Leu Ile Cys Ile Ala Val Ala Glu
1               5                   10                  15

Ala Asp Cys Asp Ile Glu Gly Lys Asp Gly Lys Gln Tyr Glu Ser Val
            20                  25                  30

Leu Met Val Ser Ile Asp Gln Leu Leu Asp Ser Met Lys Glu Ile Gly
        35                  40                  45

Ser Asn Cys Leu Asn Asn Glu Phe Asn Phe Phe Lys Arg His Ile Cys
    50                  55                  60

Asp Ala Asn Lys Glu Gly Met Phe Leu Phe Arg Ala Ala Arg Lys Leu
65                  70                  75                  80

Arg Gln Phe Leu Lys Met Asn Ser Thr Gly Asp Phe Asp Leu His Leu
                85                  90                  95

Leu Lys Val Ser Glu Gly Thr Thr Ile Leu Leu Asn Cys Thr Gly Gln
            100                 105                 110

Val Lys Gly Arg Lys Pro Ala Ala Leu Gly Glu Ala Gln Pro Thr Lys
        115                 120                 125

Ser Leu Glu Glu Asn Lys Ser Leu Lys Glu Gln Lys Lys Leu Asn Asp
    130                 135                 140

Leu Cys Phe Leu Lys Arg Leu Leu Gln Glu Ile Lys Thr Cys Trp Asn
145                 150                 155                 160

Lys Ile Leu Met Gly Thr Lys Glu His Ile Thr Cys Pro Pro Pro Met
                165                 170                 175

Ser Val Glu His Ala Asp Ile Trp Val Lys Ser Tyr Ser Leu Tyr Ser
            180                 185                 190

Arg Glu Arg Tyr Ile Cys Asn Ser Gly Phe Lys Arg Lys Ala Gly Thr
        195                 200                 205

Ser Ser Leu Thr Glu Cys Val Leu Asn Lys Ala Thr Asn Val Ala His
    210                 215                 220

Trp Thr Thr Pro Ser Leu Lys Cys Ile Arg
225                 230

<210> SEQ ID NO 140
<211> LENGTH: 702
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 7s sequence"

<400> SEQUENCE: 140
atgggagtga aagttctttt tgcccttatt tgtattgctg tggccgaggc cgattgtgat      60
attgaaggta agatggcaa acaatatgag agtgttctaa tggtcagcat cgatcaatta      120
ttggacagca tgaaagaaat tggtagcaat tgcctgaata atgaatttaa cttttttaaa     180
agacatatct gtgatgctaa taaggaaggt atgttttat tccgtgctgc tcgcaagttg      240
aggcaatttc ttaaaatgaa tagcactggt gattttgatc tccacttatt aaaagtttca     300
gaaggcacaa caatactgtt gaactgcact ggccaggtta aggaagaaa accagctgcc     360

```
ctgggtgaag cccaaccaac aaagagtttg aagaaaata atctttaaa ggaacagaaa      420 aaactgaatg acttgtgttt cctaaagaga ctattacaag agataaaaac ttgttggaat      480
aaaattttga tgggcactaa agaacacatc acgtgccctc cccccatgtc cgtggaacac      540
gcagacatct gggtcaagag ctacagcttg tactccaggg agcggtacat ttgtaactct      600
ggtttcaagc gtaaagccgg cacgtccagc ctgacggagt gcgtgttgaa caaggccacg      660
aatgtcgccc actggacaac ccccagtctc aaatgcatta ga                        702
```

<210> SEQ ID NO 141
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15 sequence"

<400> SEQUENCE: 141

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Leu Asn Asp Leu
        115                 120                 125

Cys Phe Leu Lys Arg Leu Leu Gln Glu Ile Lys Thr Cys Trp Asn Lys
130                 135                 140

Ile Leu Met Gly Thr Lys Glu His Ser Gly Thr Thr Asn Thr Val Ala
145                 150                 155                 160

Ala Tyr Asn Leu Thr Trp Lys Ser Thr Asn Phe Lys Thr Ile Leu Glu
                165                 170                 175

Trp Glu Pro Lys Pro Val Asn Gln Val Tyr Thr Val Gln Ile Ser Thr
            180                 185                 190

Lys Ser Gly Asp Trp Lys Ser Lys Cys Phe Tyr Thr Thr Asp Thr Glu
        195                 200                 205

Cys Asp Leu Thr Asp Glu Ile Val Lys Asp Val Lys Gln Thr Tyr Leu
    210                 215                 220

Ala Arg Val Phe Ser Tyr Pro Ala Gly Asn Val Glu Ser Thr Gly Ser
225                 230                 235                 240

Ala Gly Glu Pro Leu Tyr Glu Asn Ser Pro Glu Phe Thr Pro Tyr Leu
                245                 250                 255

Glu Thr Asn Leu Gly Gln Pro Thr Ile Gln Ser Phe Glu Gln Val Gly
            260                 265                 270

Thr Lys Val Asn Val Thr Val Glu Asp Glu Arg Thr Leu Val Arg Arg
        275                 280                 285

Asn Asn Thr Phe Leu Ser Leu Arg Asp Val Phe Gly Lys Asp Leu Ile
```

|     |     |     |     |     |     | 290 |     |     |     |     |     | 295 |     |     |     |     |     | 300 |     |
| --- | --- | --- | --- | --- | --- | --- | --- | --- | --- | --- | --- | --- | --- | --- | --- | --- | --- | --- | --- |

Tyr Thr Leu Tyr Tyr Trp Lys Ser Ser Ser Gly Lys Lys Thr Ala
305                     310                      315                       320

Lys Thr Asn Thr Asn Glu Phe Leu Ile Asp Val Asp Lys Gly Glu Asn
                        325                      330                      335

Tyr Cys Phe Ser Val Gln Ala Val Ile Pro Ser Arg Thr Val Asn Arg
                    340                      345                      350

Lys Ser Thr Asp Ser Pro Val Glu Cys Met Gly Gln Glu Lys Gly Glu
            355                      360                      365

Phe Arg Glu Asn Trp Val Asn Val Ile Ser Asp Leu Lys Lys Ile Glu
        370                      375                      380

Asp Leu Ile Gln Ser Met His Ile Asp Ala Thr Leu Tyr Thr Glu Ser
385                      390                      395                      400

Asp Val His Pro Ser Cys Lys Val Thr Ala Met Lys Cys Phe Leu Leu
                    405                      410                      415

Glu Leu Gln Val Ile Ser Leu Glu Ser Gly Asp Ala Ser Ile His Asp
                420                      425                      430

Thr Val Glu Asn Leu Ile Ile Leu Ala Asn Asn Ser Leu Ser Ser Asn
            435                      440                      445

Gly Asn Val Thr Glu Ser Gly Cys Lys Glu Cys Glu Glu Leu Glu Glu
        450                      455                      460

Lys Asn Ile Lys Glu Phe Leu Gln Ser Phe Val His Ile Val Gln Met
465                      470                      475                      480

Phe Ile Asn Thr Ser
                485

<210> SEQ ID NO 142
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15 sequence"

<400> SEQUENCE: 142

```
gattgcgaca tcgagggcaa ggacggcaag cagtacgaga gcgtgctgat ggtgtccatc    60
gaccagctgc tggacagcat gaaggagatc ggctccaact gcctcaacaa cgagttcaac   120
ttcttcaagc ggcacatctg cgacgccaac aaggagggca tgttcctgtt cagggccgcc   180
aggaaactgc ggcagttcct gaagatgaac tccaccggcg acttcgacct gcacctgctg   240
aaggtgtccg agggcaccac catcctgctg aactgcaccg acaggtgaa ggggccggaaa   300 cctgctgctc tgggagaggc ccaacccacc aagagcctgg aggagaacaa gtccctgaag   360
gagcagaaga agctgaacga cctgtgcttc ctgaagaggc tgctgcagga gatcaagacc   420
tgctggaaca agatcctgat gggcaccaag gagcatagcg gcacaaccaa cacagtcgct   480
gcctataacc tcacttggaa gagcaccaac ttcaaaacca tcctcgaatg gaacccaaa    540 cccgttaacc aagtttacac cgtgcagatc agcaccaagt ccggcgactg aagtccaaa    600 tgtttctata ccaccgacac cgagtgcgat ctcaccgatg agatcgtgaa agatgtgaaa   660
cagacctacc tcgcccgggt gtttagctac cccgccggca atgtggagag cactggttcc   720
gctggcgagc ctttatacga aacagcccc gaatttaccc cttacctcga gaccaattta    780
ggacagccca ccatccaaag ctttgagcaa gttggcacaa aggtgaatgt gacagtggag   840
gacgagcgga ctttagtgcg gcggaacaac acctttctca gcctccggga tgtgttcggc   900
```

```
aaagatttaa tctacacact gtattactgg aagtcctctt cctccggcaa gaagacagct    960
aaaaccaaca caaacgagtt tttaatcgac gtggataaag gcgaaaacta ctgtttcagc   1020
gtgcaagctg tgatcccctc ccggaccgtg aataggaaaa gcaccgatag ccccgttgag   1080
tgcatgggcc aagaaaaggg cgagttccgg gagaactggg tgaacgtcat cagcgattta   1140
aagaagatcg aagatttaat tcagtccatg catatcgacg ccactttata cacagaatcc   1200
gacgtgcacc cctcttgtaa ggtgaccgcc atgaaatgtt ttttactgga gctgcaagtt   1260
atctctttag agagcggaga cgctagcatc cacgacaccg tggagaattt aatcatttta   1320
gccaataact ctttatccag caacggcaac gtgacagagt ccggctgcaa ggagtgcgaa   1380
gagctggagg agaagaacat caaggagttt ctgcaatcct ttgtgcacat tgtccagatg   1440
ttcatcaata cctcc                                                   1455
```

<210> SEQ ID NO 143
<211> LENGTH: 503
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15 sequence"

<400> SEQUENCE: 143

```
Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
            20                  25                  30

Val Leu Met Val Ser Ile Asp Gln Leu Leu Asp Ser Met Lys Glu Ile
        35                  40                  45

Gly Ser Asn Cys Leu Asn Asn Glu Phe Asn Phe Phe Lys Arg His Ile
    50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His
                85                  90                  95

Leu Leu Lys Val Ser Glu Gly Thr Thr Ile Leu Leu Asn Cys Thr Gly
            100                 105                 110

Gln Val Lys Gly Arg Lys Pro Ala Ala Leu Gly Glu Ala Gln Pro Thr
        115                 120                 125

Lys Ser Leu Glu Glu Asn Lys Ser Leu Lys Glu Gln Lys Lys Leu Asn
    130                 135                 140

Asp Leu Cys Phe Leu Lys Arg Leu Leu Gln Glu Ile Lys Thr Cys Trp
145                 150                 155                 160

Asn Lys Ile Leu Met Gly Thr Lys Glu His Ser Gly Thr Thr Asn Thr
                165                 170                 175

Val Ala Ala Tyr Asn Leu Thr Trp Lys Ser Thr Asn Phe Lys Thr Ile
            180                 185                 190

Leu Glu Trp Glu Pro Lys Pro Val Asn Gln Val Tyr Thr Val Gln Ile
        195                 200                 205

Ser Thr Lys Ser Gly Asp Trp Lys Ser Lys Cys Phe Tyr Thr Thr Asp
    210                 215                 220

Thr Glu Cys Asp Leu Thr Asp Glu Ile Val Lys Asp Val Lys Gln Thr
225                 230                 235                 240

Tyr Leu Ala Arg Val Phe Ser Tyr Pro Ala Gly Asn Val Glu Ser Thr
```

```
            245                 250                 255
Gly Ser Ala Gly Glu Pro Leu Tyr Glu Asn Ser Pro Glu Phe Thr Pro
        260                 265                 270
Tyr Leu Glu Thr Asn Leu Gly Gln Pro Thr Ile Gln Ser Phe Glu Gln
    275                 280                 285
Val Gly Thr Lys Val Asn Val Thr Val Glu Asp Glu Arg Thr Leu Val
290                 295                 300
Arg Arg Asn Asn Thr Phe Leu Ser Leu Arg Asp Val Phe Gly Lys Asp
305                 310                 315                 320
Leu Ile Tyr Thr Leu Tyr Tyr Trp Lys Ser Ser Ser Gly Lys Lys
                325                 330                 335
Thr Ala Lys Thr Asn Thr Asn Glu Phe Leu Ile Asp Val Asp Lys Gly
            340                 345                 350
Glu Asn Tyr Cys Phe Ser Val Gln Ala Val Ile Pro Ser Arg Thr Val
        355                 360                 365
Asn Arg Lys Ser Thr Asp Ser Pro Val Glu Cys Met Gly Gln Glu Lys
    370                 375                 380
Gly Glu Phe Arg Glu Asn Trp Val Asn Val Ile Ser Asp Leu Lys Lys
385                 390                 395                 400
Ile Glu Asp Leu Ile Gln Ser Met His Ile Asp Ala Thr Leu Tyr Thr
                405                 410                 415
Glu Ser Asp Val His Pro Ser Cys Lys Val Thr Ala Met Lys Cys Phe
            420                 425                 430
Leu Leu Glu Leu Gln Val Ile Ser Leu Glu Ser Gly Asp Ala Ser Ile
        435                 440                 445
His Asp Thr Val Glu Asn Leu Ile Ile Leu Ala Asn Asn Ser Leu Ser
    450                 455                 460
Ser Asn Gly Asn Val Thr Glu Ser Gly Cys Lys Glu Cys Glu Glu Leu
465                 470                 475                 480
Glu Glu Lys Asn Ile Lys Glu Phe Leu Gln Ser Phe Val His Ile Val
                485                 490                 495
Gln Met Phe Ile Asn Thr Ser
            500

<210> SEQ ID NO 144
<211> LENGTH: 1509
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15 sequence"

<400> SEQUENCE: 144
atgaagtggg tgaccttcat cagcctgctg ttcctgttct ccagcgccta ctccgattgc      60
gacatcgagg caaggacgg caagcagtac gagagcgtgc tgatggtgtc catcgaccag     120
ctgctggaca gcatgaagga gatcggctcc aactgcctca caacgagtt caacttcttc     180 aagcggcaca tctgcgacgc caacaaggag ggcatgttcc tgttcagggc cgccaggaaa     240
ctgcggcagt tcctgaagat gaactccacc ggcgacttcg acctgcacct gctgaaggtg     300
tccgagggca ccaccatcct gctgaactgc accggacagg tgaagggccg aaacctgct      360 gctctgggag aggcccaacc caccaagagc ctggaggaga caagtccct gaaggagcag     420 aagaagctga cgacctgtg cttcctgaag aggctgctgc aggagatcaa gacctgctgg     480
aacaagatcc tgatgggcac caaggagcat agcggcacaa ccaacacagt cgctgcctat     540
```

-continued

```
aacctcactt ggaagagcac caacttcaaa accatcctcg aatgggaacc caaacccgtt      600
aaccaagttt acaccgtgca gatcagcacc aagtccggcg actggaagtc caaatgtttc      660
tataccaccg acaccgagtg cgatctcacc gatgagatcg tgaaagatgt gaaacagacc      720
tacctcgccc gggtgtttag ctaccccgcc ggcaatgtgg agagcactgg ttccgctggc      780
gagcctttat acgagaacag ccccgaattt accccttacc tcgagaccaa tttaggacag      840
cccaccatcc aaagctttga gcaagttggc acaaaggtga atgtgacagt ggaggacgag      900
cggactttag tgcggcggaa caacaccttt ctcagcctcc gggatgtgtt cggcaaagat      960
ttaatctaca cactgtatta ctggaagtcc tcttcctccg gcaagaagac agctaaaacc     1020
aacacaaacg agttttaat cgacgtggat aaaggcgaaa actactgttt cagcgtgcaa      1080
gctgtgatcc cctcccggac cgtgaatagg aaaagcaccg atagcccgt tgagtgcatg      1140 ggccaagaaa agggcgagtt ccgggagaac tgggtgaacg tcatcagcga tttaaagaag     1200
atcgaagatt taattcagtc catgcatatc gacgccactt tatacacaga atccgacgtg     1260 caccctctt gtaaggtgac cgccatgaaa tgttttttac tggagctgca agttatctct      1320
ttagagagcg gagacgctag catccacgac accgtggaga atttaatcat tttagccaat     1380
aactctttat ccagcaacgg caacgtgaca gagtccggct gcaaggagtg cgaagagctg     1440
gaggagaaga acatcaagga gtttctgcaa tcctttgtgc acattgtcca gatgttcatc     1500
aatacctcc                                                             1509
```

<210> SEQ ID NO 145
<211> LENGTH: 198
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 21s sequence"

<400> SEQUENCE: 145

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ile Thr Cys Pro Pro Met Ser Val Glu His
    130                 135                 140

Ala Asp Ile Trp Val Lys Ser Tyr Ser Leu Tyr Ser Arg Glu Arg Tyr
145                 150                 155                 160

Ile Cys Asn Ser Gly Phe Lys Arg Lys Ala Gly Thr Ser Ser Leu Thr
                165                 170                 175

```
Glu Cys Val Leu Asn Lys Ala Thr Asn Val Ala His Trp Thr Thr Pro
            180                 185                 190

Ser Leu Lys Cys Ile Arg
        195

<210> SEQ ID NO 146
<211> LENGTH: 594
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21s sequence"

<400> SEQUENCE: 146
cagggccagg acaggcacat gatccggatg aggcagctca tcgacatcgt cgaccagctg      60
aagaactacg tgaacgacct ggtgcccgag tttctgcctg cccccgagga cgtggagacc     120
aactgcgagt ggtccgcctt ctcctgcttt cagaaggccc agctgaagtc cgccaacacc     180
ggcaacaacg agcggatcat caacgtgagc atcaagaagc tgaagcggaa gcctccctcc     240
acaaacgccg gcaggaggca gaagcacagg ctgacctgcc ccagctgtga ctcctacgag     300
aagaagcccc ccaaggagtt cctggagagg ttcaagtccc tgctgcagaa gatgatccat     360
cagcacctgt cctccaggac ccacggctcc gaggactcca ttacatgccc ccctcccatg     420
agcgtggagc acgccgacat ctgggtgaag agctatagcc tctacagccg ggagaggtat     480
atctgtaaca gcggcttcaa gaggaaggcc ggcaccagca gcctcaccga gtgcgtgctg     540
aataaggcta ccaacgtggc tcactggaca acaccctctt taaagtgcat ccgg           594

<210> SEQ ID NO 147
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 21s sequence"

<400> SEQUENCE: 147

Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ile Thr Cys Pro Pro Pro Met Ser Val
```

145                 150                 155                 160
Glu His Ala Asp Ile Trp Val Lys Ser Tyr Ser Leu Tyr Ser Arg Glu
                    165                 170                 175

Arg Tyr Ile Cys Asn Ser Gly Phe Lys Arg Lys Ala Gly Thr Ser Ser
                180                 185                 190

Leu Thr Glu Cys Val Leu Asn Lys Ala Thr Asn Val Ala His Trp Thr
            195                 200                 205

Thr Pro Ser Leu Lys Cys Ile Arg
    210                 215

<210> SEQ ID NO 148
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21s sequence"

<400> SEQUENCE: 148
atgaagtggg tgaccttcat cagcctgctg ttcctgttct ccagcgccta ctcccagggc      60
caggacaggc acatgatccg gatgaggcag ctcatcgaca tcgtcgacca gctgaagaac     120
tacgtgaacg acctggtgcc cgagtttctg cctgccccg aggacgtgga gaccaactgc     180
gagtggtccg ccttctcctg ctttcagaag gcccagctga agtccgccaa caccggcaac     240
aacgagcgga tcatcaacgt gagcatcaag aagctgaagc ggaagcctcc ctccacaaac     300
gccggcagga ggcagaagca caggctgacc tgccccagct gtgactccta cgagaagaag     360
ccccccaagg agttcctgga gaggttcaag tccctgctgc agaagatgat ccatcagcac     420
ctgtcctcca ggacccacgg ctccgaggac tccattacat gccccctcc catgagcgtg     480 gagcacgccg acatctgggt gaagagctat agcctctaca gccgggagag gtatatctgt     540
aacagcggct tcaagaggaa ggccggcacc agcagcctca ccgagtgcgt gctgaataag     600
gctaccaacg tggctcactg gacaacaccc tctttaaagt gcatccgg                  648

<210> SEQ ID NO 149
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic CD16 scfv light chain variable domain sequence"

<400> SEQUENCE: 149

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn His Val
                85                  90                  95

Val Phe Gly Gly Gly Thr Lys Leu Thr Val Gly His

<210> SEQ ID NO 150
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic CD16 scfv light chain variable domain sequence"

<400> SEQUENCE: 150

```
tccgagctga cccaggaccc tgctgtgtcc gtggctctgg gccagaccgt gaggatcacc      60
tgccagggcg actccctgag gtcctactac gcctcctggt accagcagaa gcccggccag     120
gctcctgtgc tggtgatcta cggcaagaac aacaggccct ccggcatccc tgacaggttc     180
tccggatcct cctccggcaa caccgcctcc ctgaccatca caggcgctca ggccgaggac     240
gaggctgact actactgcaa ctccagggac tcctccggca accatgtggt gttcggcggc     300
ggcaccaagc tgaccgtggg ccat                                            324
```

<210> SEQ ID NO 151
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic CD16 scfv heavy chain variable domain sequence"

<400> SEQUENCE: 151

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Leu Leu Phe Asp Tyr Trp Gly Gln Gly Thr Leu
            100                 105                 110

Val Thr Val Ser Arg
        115
```

<210> SEQ ID NO 152
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic CD16 scfv heavy chain variable domain sequence"

<400> SEQUENCE: 152

```
gaggtgcagc tggtggagtc cggaggagga gtggtgaggc ctggaggctc cctgaggctg      60
agctgtgctg cctccggctt caccttcgac gactacggca tgtcctgggt gaggcaggct     120
cctggaaagg gcctggagtg ggtgtccggc atcaactgga acggcggatc caccggctac     180
```

```
gccgattccg tgaagggcag gttcaccatc agcagggaca acgccaagaa ctccctgtac      240
ctgcagatga actccctgag ggccgaggac accgccgtgt actactgcgc caggggcagg      300
tccctgctgt tcgactactg gggacagggc accctggtga ccgtgtccag g               351
```

<210> SEQ ID NO 153  
<211> LENGTH: 823  
<212> TYPE: PRT  
<213> ORGANISM: Artificial Sequence  
<220> FEATURE:  
<221> NAME/KEY: source  
<223> OTHER INFORMATION: /note="Description of Artificial Sequence: Synthetic 12s16 sequence"

<400> SEQUENCE: 153

```
Ile Trp Glu Leu Lys Lys Asp Val Tyr Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320
```

```
Ser Arg Asn Leu Pro Val Ala Thr Pro Asp Pro Gly Met Phe Pro Cys
            325                 330                 335

Leu His His Ser Gln Asn Leu Leu Arg Ala Val Ser Asn Met Leu Gln
        340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
        370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Ile Thr Cys Pro Pro Met Ser Val Glu
        515                 520                 525

His Ala Asp Ile Trp Val Lys Ser Tyr Ser Leu Tyr Ser Arg Glu Arg
        530                 535                 540

Tyr Ile Cys Asn Ser Gly Phe Lys Arg Lys Ala Gly Thr Ser Ser Leu
545                 550                 555                 560

Thr Glu Cys Val Leu Asn Lys Ala Thr Asn Val Ala His Trp Thr Thr
                565                 570                 575

Pro Ser Leu Lys Cys Ile Arg Ser Glu Leu Thr Gln Asp Pro Ala Val
            580                 585                 590

Ser Val Ala Leu Gly Gln Thr Val Arg Ile Thr Cys Gln Gly Asp Ser
        595                 600                 605

Leu Arg Ser Tyr Tyr Ala Ser Trp Tyr Gln Gln Lys Pro Gly Gln Ala
        610                 615                 620

Pro Val Leu Val Ile Tyr Gly Lys Asn Asn Arg Pro Ser Gly Ile Pro
625                 630                 635                 640

Asp Arg Phe Ser Gly Ser Ser Ser Gly Asn Thr Ala Ser Leu Thr Ile
                645                 650                 655

Thr Gly Ala Gln Ala Glu Asp Glu Ala Asp Tyr Tyr Cys Asn Ser Arg
            660                 665                 670

Asp Ser Ser Gly Asn His Val Val Phe Gly Gly Gly Thr Lys Leu Thr
        675                 680                 685

Val Gly His Gly Gly Gly Gly Ser Gly Gly Gly Gly Ser Gly Gly Gly
        690                 695                 700

Gly Ser Glu Val Gln Leu Val Glu Ser Gly Gly Val Val Arg Pro
705                 710                 715                 720

Gly Gly Ser Leu Arg Leu Ser Cys Ala Ala Ser Gly Phe Thr Phe Asp
                725                 730                 735

Asp Tyr Gly Met Ser Trp Val Arg Gln Ala Pro Gly Lys Gly Leu Glu
```

```
                    740                 745                 750
Trp Val Ser Gly Ile Asn Trp Asn Gly Gly Ser Thr Gly Tyr Ala Asp
            755                 760                 765

Ser Val Lys Gly Arg Phe Thr Ile Ser Arg Asp Asn Ala Lys Asn Ser
        770                 775                 780

Leu Tyr Leu Gln Met Asn Ser Leu Arg Ala Glu Asp Thr Ala Val Tyr
785                 790                 795                 800

Tyr Cys Ala Arg Gly Arg Ser Leu Leu Phe Asp Tyr Trp Gly Gln Gly
                805                 810                 815

Thr Leu Val Thr Val Ser Arg
            820

<210> SEQ ID NO 154
<211> LENGTH: 2469
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 12s16 sequence"

<400> SEQUENCE: 154
atttgggaac tgaagaagga cgtctacgtg gtcgaactgg actggtatcc cgatgctccc        60
ggcgaaatgg tggtgctcac ttgtgacacc cccgaagaag acggcatcac ttggaccctc       120
gatcagagca gcgaggtgct gggctccgga aagaccctca caatccaagt taaggagttc       180
ggagacgctg ccaatacac atgccacaag ggaggcgagg tgctcagcca ttccttatta       240
ttattacaca agaaggaaga cggaatctgg tccaccgaca ttttaaaaga tcagaaggag       300
cccaagaata agacctttt aaggtgtgag gccaaaaact acagcggtcg tttcacttgt       360
tggtggctga ccaccatttc caccgattta accttctccg tgaaaagcag ccggggaagc       420
tccgaccctc aaggtgtgac atgtggagcc gctaccctca gcgctgagag ggttcgtggc       480
gataacaagg aatacgagta cagcgtggag tgccaagaag atagcgcttg tcccgctgcc       540
gaagaatctt tacccattga ggtgatggtg gacgccgtgc acaaactcaa gtacgagaac       600
tacacctcct ccttctttat ccgggacatc attaagcccg atcctcctaa gaatttacag       660
ctgaagcctc tcaaaaatag ccggcaagtt gaggtctctt gggaatatcc cgacacttgg       720
agcacacccc acagctactt ctcttttaacc ttttgtgtgc aagttcaagg taaaagcaag       780
cgggagaaga agaccgggt gtttaccgac aaaaccagcg ccaccgtcat ctgtcggaag       840
aacgcctcca tcagcgtgag ggctcaagat cgttattact ccagcagctg gtccgagtgg       900
gccagcgtgc cttgttccgg cggtggagga tccggaggag gtggctccgg cggcggagga       960
tctcgtaacc tccccgtggc tacccccgat cccggaatgt tcccttgttt acaccacagc      1020
cagaatttac tgagggccgt gagcaacatg ctgcagaaag ctaggcagac tttagaattt      1080
tacccttgca ccagcgagga gatcgaccat gaagatatca ccaaggacaa gacatccacc      1140
gtggaggctt gtttacctct ggagctgaca agaacgagt cttgtctcaa ctctcgtgaa      1200
accagcttca tcacaaatgg ctcttgttta gcttcccgga agacctcctt tatgatggct      1260
ttatgcctca gctccatcta cgaggattta agatgtacc aagtggagtt caagaccatg      1320
aacgccaagc tgctcatgga ccctaaacgg cagatctttt tagaccagaa catgctggct      1380
gtgattgatg agctgatgca agctttaaac ttcaactccg agaccgtccc tcagaagtcc      1440
tccctcgagg agcccgattt ttacaagaca aagatcaaac tgtgcattt actccacgcc      1500
```

```
tttaggatcc gggccgtgac cattgaccgg gtcatgagct atttaaacgc cagcattaca   1560 tgccccctc ccatgagcgt ggagcacgcc gacatctggg tgaagagcta tagcctctac   1620
agccgggaga ggtatatctg taacagcggc ttcaaggaga aggccggcac cagcagcctc   1680
accgagtgcg tgctgaataa ggctaccaac gtggctcact ggacaacacc ctctttaaag   1740
tgcatccggt ccgagctgac ccaggaccct gctgtgtccg tggctctggg ccagaccgtg   1800
aggatcacct gccagggcga ctccctgagg tcctactacg cctcctggta ccagcagaag   1860
cccggccagg ctcctgtgct ggtgatctac ggcaagaaca acaggccctc cggcatccct   1920
gacaggttct ccggatcctc ctccggcaac accgcctccc tgaccatcac aggcgctcag   1980
gccgaggacg aggctgacta ctactgcaac tccaggggact cctccggcaa ccatgtggtg   2040
ttcggcggcg gcaccaagct gaccgtgggc catggcggcg gcggctccgg aggcggcggc   2100
agcggcggag gaggatccga ggtgcagctg gtggagtccg gaggaggagt ggtgaggcct   2160
ggaggctccc tgaggctgag ctgtgctgcc tccggcttca ccttcgacga ctacggcatg   2220
tcctgggtga ggcaggctcc tggaaagggc ctggagtggg tgtccggcat caactggaac   2280
ggcggatcca ccggctacgc cgattccgtg aagggcaggt tcaccatcag cagggacaac   2340
gccaagaact ccctgtacct gcagatgaac tccctgaggg ccgaggacac cgccgtgtac   2400
tactgcgcca ggggcaggtc cctgctgttc gactactggg gacagggcac cctggtgacc   2460
gtgtccagg                                                          2469
```

<210> SEQ ID NO 155
<211> LENGTH: 841
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 12s16 sequence"

<400> SEQUENCE: 155

```
Met Lys Trp Val Thr Phe Ile Ser Leu Leu Phe Leu Phe Ser Ser Ala
1               5                   10                  15

Tyr Ser Ile Trp Glu Leu Lys Lys Asp Val Tyr Val Val Glu Leu Asp
            20                  25                  30

Trp Tyr Pro Asp Ala Pro Gly Glu Met Val Val Leu Thr Cys Asp Thr
        35                  40                  45

Pro Glu Glu Asp Gly Ile Thr Trp Thr Leu Asp Gln Ser Ser Glu Val
    50                  55                  60

Leu Gly Ser Gly Lys Thr Leu Thr Ile Gln Val Lys Glu Phe Gly Asp
65                  70                  75                  80

Ala Gly Gln Tyr Thr Cys His Lys Gly Gly Glu Val Leu Ser His Ser
                85                  90                  95

Leu Leu Leu Leu His Lys Lys Glu Asp Gly Ile Trp Ser Thr Asp Ile
            100                 105                 110

Leu Lys Asp Gln Lys Glu Pro Lys Asn Lys Thr Phe Leu Arg Cys Glu
        115                 120                 125

Ala Lys Asn Tyr Ser Gly Arg Phe Thr Cys Trp Trp Leu Thr Thr Ile
    130                 135                 140

Ser Thr Asp Leu Thr Phe Ser Val Lys Ser Ser Arg Gly Ser Ser Asp
145                 150                 155                 160

Pro Gln Gly Val Thr Cys Gly Ala Ala Thr Leu Ser Ala Glu Arg Val
                165                 170                 175
```

```
Arg Gly Asp Asn Lys Glu Tyr Glu Tyr Ser Val Glu Cys Gln Glu Asp
            180                 185                 190

Ser Ala Cys Pro Ala Ala Glu Glu Ser Leu Pro Ile Glu Val Met Val
        195                 200                 205

Asp Ala Val His Lys Leu Lys Tyr Glu Asn Tyr Thr Ser Ser Phe Phe
    210                 215                 220

Ile Arg Asp Ile Ile Lys Pro Asp Pro Lys Asn Leu Gln Leu Lys
225                 230                 235                 240

Pro Leu Lys Asn Ser Arg Gln Val Glu Val Ser Trp Glu Tyr Pro Asp
                245                 250                 255

Thr Trp Ser Thr Pro His Ser Tyr Phe Ser Leu Thr Phe Cys Val Gln
            260                 265                 270

Val Gln Gly Lys Ser Lys Arg Glu Lys Lys Asp Arg Val Phe Thr Asp
        275                 280                 285

Lys Thr Ser Ala Thr Val Ile Cys Arg Lys Asn Ala Ser Ile Ser Val
    290                 295                 300

Arg Ala Gln Asp Arg Tyr Tyr Ser Ser Ser Trp Ser Glu Trp Ala Ser
305                 310                 315                 320

Val Pro Cys Ser Gly Gly Gly Ser Gly Gly Gly Ser Gly Gly
                325                 330                 335

Gly Gly Ser Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
            355                 360                 365

Leu Gln Lys Ala Arg Gln Thr Leu Glu Phe Tyr Pro Cys Thr Ser Glu
    370                 375                 380

Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser
                405                 410                 415

Arg Glu Thr Ser Phe Ile Thr Asn Gly Ser Cys Leu Ala Ser Arg Lys
            420                 425                 430

Thr Ser Phe Met Met Ala Leu Cys Leu Ser Ser Ile Tyr Glu Asp Leu
            435                 440                 445

Lys Met Tyr Gln Val Glu Phe Lys Thr Met Asn Ala Lys Leu Leu Met
    450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
            500                 505                 510

Cys Ile Leu Leu His Ala Phe Arg Ile Arg Ala Val Thr Ile Asp Arg
        515                 520                 525

Val Met Ser Tyr Leu Asn Ala Ser Ile Thr Cys Pro Pro Met Ser
    530                 535                 540

Val Glu His Ala Asp Ile Trp Val Lys Ser Tyr Ser Leu Tyr Ser Arg
545                 550                 555                 560

Glu Arg Tyr Ile Cys Asn Ser Gly Phe Lys Arg Lys Ala Gly Thr Ser
                565                 570                 575

Ser Leu Thr Glu Cys Val Leu Asn Lys Ala Thr Asn Val Ala His Trp
            580                 585                 590

Thr Thr Pro Ser Leu Lys Cys Ile Arg Ser Glu Leu Thr Gln Asp Pro
```

|   |   | 595 |   |   |   | 600 |   |   |   | 605 |   |
|---|---|---|---|---|---|---|---|---|---|---|---|

Ala Val Ser Val Ala Leu Gly Gln Thr Val Arg Ile Thr Cys Gln Gly
    610                  615                620

Asp Ser Leu Arg Ser Tyr Tyr Ala Ser Trp Tyr Gln Gln Lys Pro Gly
625                630                635              640

Gln Ala Pro Val Leu Val Ile Tyr Gly Lys Asn Asn Arg Pro Ser Gly
              645                650              655

Ile Pro Asp Arg Phe Ser Gly Ser Ser Ser Gly Asn Thr Ala Ser Leu
        660                665              670

Thr Ile Thr Gly Ala Gln Ala Glu Asp Glu Ala Asp Tyr Tyr Cys Asn
    675                680                685

Ser Arg Asp Ser Ser Gly Asn His Val Val Phe Gly Gly Gly Thr Lys
        690                695              700

Leu Thr Val Gly His Gly Gly Gly Gly Ser Gly Gly Gly Ser Gly
705                710              715              720

Gly Gly Gly Ser Glu Val Gln Leu Val Glu Ser Gly Gly Gly Val Val
            725                730              735

Arg Pro Gly Gly Ser Leu Arg Leu Ser Cys Ala Ala Ser Gly Phe Thr
              740                745              750

Phe Asp Asp Tyr Gly Met Ser Trp Val Arg Gln Ala Pro Gly Lys Gly
        755                760              765

Leu Glu Trp Val Ser Gly Ile Asn Trp Asn Gly Gly Ser Thr Gly Tyr
770                775              780

Ala Asp Ser Val Lys Gly Arg Phe Thr Ile Ser Arg Asp Asn Ala Lys
785                790              795              800

Asn Ser Leu Tyr Leu Gln Met Asn Ser Leu Arg Ala Glu Asp Thr Ala
            805                810              815

Val Tyr Tyr Cys Ala Arg Gly Arg Ser Leu Leu Phe Asp Tyr Trp Gly
        820                825              830

Gln Gly Thr Leu Val Thr Val Ser Arg
        835                840

<210> SEQ ID NO 156
<211> LENGTH: 2523
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 12s16 sequence"

<400> SEQUENCE: 156

```
atgaaatggg tgacctttat ttctttactg ttcctctttta gcagcgccta ctccatttgg    60
gaactgaaga aggacgtcta cgtggtcgaa ctgactggt atcccgatgc tcccggcgaa   120
atggtggtgc tcacttgtga cacccccgaa gaagacggca tcacttggac cctcgatcag   180
agcagcgagt gctgggctc cggaaagacc ctcacaatcc aagttaagga gttcggagac   240
gctggccaat acacatgcca caagggaggc gaggtgctca gccattcctt attattatta   300
cacaagaagg aagacggaat ctggtccacc gacattttaa aagatcagaa ggagcccaag   360
aataagacct ttttaaggtg tgaggccaaa aactacagcg gtcgtttcac ttgttggtgg   420
ctgaccacca tttccaccga tttaaccttc tccgtgaaaa gcagccgggg aagctccgac   480
cctcaaggtg tgcatgtgg agccgctacc ctcagcgctg agagggttcg tggcgataac   540
aaggaatacg agtacagcgt ggagtgccaa gaagatagcg cttgtccgc tgccgaagaa   600
```

```
tctttacccca ttgaggtgat ggtggacgcc gtgcacaaac tcaagtacga gaactacacc    660
tcctccttct ttatccggga catcattaag cccgatcctc ctaagaattt acagctgaag    720
cctctcaaaa atagccggca agttgaggtc tcttgggaat atcccgacac ttggagcaca    780
ccccacagct acttctcttt aaccttttgt gtgcaagttc aaggtaaaag caagcgggag    840
aagaaagacc gggtgtttac cgacaaaacc agcgccaccg tcatctgtcg gaagaacgcc    900
tccatcagcg tgagggctca agatcgttat tactccagca gctggtccga gtgggccagc    960
gtgccttgtt ccggcggtgg aggatccgga ggaggtggct ccggcggcgg aggatctcgt   1020
aacctccccg tggctacccc cgatcccgga atgttcccct gtttacacca cagccagaat   1080
ttactgaggg ccgtgagcaa catgctgcag aaagctagga agactttaga attttacccct  1140 tgcaccagcg aggagatcga ccatgaagat atcaccaagg acaagacatc caccgtggag   1200
gcttgtttac ctctggagct gacaaagaac gagtcttgtc tcaactctcg tgaaaccagc   1260
ttcatcacaa atggctcttg tttagcttcc cggaagacct cctttatgat ggctttatgc   1320
ctcagctcca tctacgagga tttaaagatg taccaagtgg agttcaagac catgaacgcc   1380
aagctgctca tggaccctaa acggcagatc ttttagacc agaacatgct ggctgtgatt    1440
gatgagctga tgcaagcttt aaacttcaac tccgagaccg tccctcagaa gtcctccctc   1500
gaggagcccg attttacaa gacaaagatc aaactgtgca ttttactcca cgcctttagg    1560
atccgggccg tgaccattga ccgggtcatg agctatttaa acgccagcat acatgcccc    1620 cctcccatga gcgtggagca cgccgacatc tgggtgaaga gctatagcct ctacagccgg   1680
gagaggtata tctgtaacag cggcttcaag aggaaggccg gcaccagcag cctcaccgag   1740
tgcgtgctga ataaggctac caacgtggct cactggacaa cccctctttt aaagtgcatc   1800
cggtccgagc tgacccagga ccctgctgtg tccgtggctc tgggccagac cgtgaggatc   1860
acctgccagg gcgactccct gaggtcctac tacgcctcct ggtaccagca gaagcccggc   1920
caggctcctg tgctggtgat ctacggcaag aacaacaggc cctccggcat ccctgacagg   1980
ttctccggat cctcctccgg caacaccgcc tccctgacca tcacaggcgc tcaggccgag   2040
gacgaggctg actactactg caactccagg gactcctccg caaccatgt ggtgttcggc    2100 ggcggcacca agctgaccgt gggccatggc ggcggcggct ccggaggcgg cggcagcggc   2160
ggaggaggat ccgaggtgca gctggtggag tccggaggag gagtggtgag gcctggaggc   2220
tccctgaggc tgagctgtgc tgcctccggc ttcaccttcg acgactacgg catgtcctgg   2280
gtgaggcagg ctcctggaaa gggcctggag tgggtgtccg gcatcaactg gaacggcgga   2340
tccaccggct acgccgattc cgtgaagggc aggttcacca tcagcaggga caacgccaag   2400
aactccctgt acctgcagat gaactccctg agggccgagg acaccgccgt gtactactgc   2460
gccaggggca ggtccctgct gttcgactac tggggacagg gcaccctggt gaccgtgtcc   2520
agg                                                                 2523
```

<210> SEQ ID NO 157
<211> LENGTH: 438
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 16s21 sequence"

<400> SEQUENCE: 157

Ser Glu Leu Thr Gln Asp Pro Ala Val Ser Val Ala Leu Gly Gln Thr

-continued

```
1               5                   10                  15
Val Arg Ile Thr Cys Gln Gly Asp Ser Leu Arg Ser Tyr Tyr Ala Ser
                20                  25                  30

Trp Tyr Gln Gln Lys Pro Gly Gln Ala Pro Val Leu Val Ile Tyr Gly
                35                  40                  45

Lys Asn Asn Arg Pro Ser Gly Ile Pro Asp Arg Phe Ser Gly Ser Ser
            50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn His Val
                85                  90                  95

Val Phe Gly Gly Gly Thr Lys Leu Thr Val Gly His Gly Gly Gly Gly
                100                 105                 110

Ser Gly Gly Gly Gly Ser Gly Gly Gly Ser Glu Val Gln Leu Val
            115                 120                 125

Glu Ser Gly Gly Gly Val Val Arg Pro Gly Gly Ser Leu Arg Leu Ser
130                 135                 140

Cys Ala Ala Ser Gly Phe Thr Phe Asp Asp Tyr Gly Met Ser Trp Val
145                 150                 155                 160

Arg Gln Ala Pro Gly Lys Gly Leu Glu Trp Val Ser Gly Ile Asn Trp
                165                 170                 175

Asn Gly Gly Ser Thr Gly Tyr Ala Asp Ser Val Lys Gly Arg Phe Thr
                180                 185                 190

Ile Ser Arg Asp Asn Ala Lys Asn Ser Leu Tyr Leu Gln Met Asn Ser
                195                 200                 205

Leu Arg Ala Glu Asp Thr Ala Val Tyr Tyr Cys Ala Arg Gly Arg Ser
210                 215                 220

Leu Leu Phe Asp Tyr Trp Gly Gln Gly Thr Leu Val Thr Val Ser Arg
225                 230                 235                 240

Ile Thr Cys Pro Pro Pro Met Ser Val Glu His Ala Asp Ile Trp Val
                245                 250                 255

Lys Ser Tyr Ser Leu Tyr Ser Arg Glu Arg Tyr Ile Cys Asn Ser Gly
                260                 265                 270

Phe Lys Arg Lys Ala Gly Thr Ser Ser Leu Thr Glu Cys Val Leu Asn
                275                 280                 285

Lys Ala Thr Asn Val Ala His Trp Thr Thr Pro Ser Leu Lys Cys Ile
                290                 295                 300

Arg Gln Gly Gln Asp Arg His Met Ile Arg Met Arg Gln Leu Ile Asp
305                 310                 315                 320

Ile Val Asp Gln Leu Lys Asn Tyr Val Asn Asp Leu Val Pro Glu Phe
                325                 330                 335

Leu Pro Ala Pro Glu Asp Val Glu Thr Asn Cys Glu Trp Ser Ala Phe
                340                 345                 350

Ser Cys Phe Gln Lys Ala Gln Leu Lys Ser Ala Asn Thr Gly Asn Asn
                355                 360                 365

Glu Arg Ile Ile Asn Val Ser Ile Lys Lys Leu Lys Arg Lys Pro Pro
370                 375                 380

Ser Thr Asn Ala Gly Arg Arg Gln Lys His Arg Leu Thr Cys Pro Ser
385                 390                 395                 400

Cys Asp Ser Tyr Glu Lys Lys Pro Pro Lys Glu Phe Leu Glu Arg Phe
                405                 410                 415

Lys Ser Leu Leu Gln Lys Met Ile His Gln His Leu Ser Ser Arg Thr
                420                 425                 430
```

His Gly Ser Glu Asp Ser
        435

<210> SEQ ID NO 158
<211> LENGTH: 1314
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 16s21 sequence"

<400> SEQUENCE: 158

```
tccgagctga cccaggaccc tgctgtgtcc gtggctctgg gccagaccgt gaggatcacc      60
tgccagggcg actccctgag gtcctactac gcctcctggt accagcagaa gcccggccag     120
gctcctgtgc tggtgatcta cggcaagaac aacaggccct ccggcatccc tgacaggttc     180
tccggatcct cctccggcaa caccgcctcc ctgaccatca caggcgctca ggccgaggac     240
gaggctgact actactgcaa ctccaggac tcctccggca accatgtggt gttcggcggc     300
ggcaccaagc tgaccgtggg ccatggcggc ggcggctccg gaggcggcgg cagcggcgga     360
ggaggatccg aggtgcagct ggtggagtcc ggaggaggag tggtgaggcc tggaggctcc     420
ctgaggctga gctgtgctgc ctccggcttc accttcgacg actacggcat gtcctgggtg     480
aggcaggctc tggaaaggg cctggagtgg gtgtccggca tcaactggaa cggcggatcc     540
accggctacg ccgattccgt gaagggcagg ttcaccatca gcagggacaa cgccaagaac     600
tccctgtacc tgcagatgaa ctccctgagg gccgaggaca ccgccgtgta ctactgcgcc     660
aggggcaggt ccctgctgtt cgactactgg ggacagggca cctggtgac cgtgtccagg     720
attacatgcc cccctcccat gagcgtggag cacgccgaca tctgggtgaa gagctatagc     780
ctctacagcc gggagaggta tatctgtaac agcggcttca agaggaaggc cggcaccagc     840
agcctcaccg agtgcgtgct gaataaggct accaacgtgg ctcactggac aaccccctct     900
ttaaagtgca tccggcaggg ccaggacagg cacatgatcc ggatgaggca gctcatcgac     960
atcgtcgacc agctgaagaa ctacgtgaac gacctggtgc ccgagtttct gcctgccccc    1020
gaggacgtgg agaccaactg cgagtggtcc gccttctcct gctttcagaa gcccagctg     1080
aagtccgcca caccggcaa caacgagcgg atcatcaacg tgagcatcaa gaagctgaag    1140
cggaagcctc cctccacaaa cgccggcagg aggcagaagc acaggctgac ctgccccagc    1200
tgtgactcct acgagaagaa gccccccaag gagttcctgg agaggttcaa gtccctgctg    1260
cagaagatga tccatcagca cctgtcctcc aggacccacg gctccgagga ctcc           1314
```

<210> SEQ ID NO 159
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 16s21 sequence"

<400> SEQUENCE: 159

Met Lys Trp Val Thr Phe Ile Ser Leu Leu Phe Leu Phe Ser Ser Ala
1               5                   10                  15

Tyr Ser Ser Glu Leu Thr Gln Asp Pro Ala Val Ser Val Ala Leu Gly
            20                  25                  30

Gln Thr Val Arg Ile Thr Cys Gln Gly Asp Ser Leu Arg Ser Tyr Tyr

-continued

```
                35                  40                  45
Ala Ser Trp Tyr Gln Gln Lys Pro Gly Gln Ala Pro Val Leu Val Ile
 50                  55                  60
Tyr Gly Lys Asn Asn Arg Pro Ser Gly Ile Pro Asp Arg Phe Ser Gly
 65                  70                  75                  80
Ser Ser Ser Gly Asn Thr Ala Ser Leu Thr Ile Thr Gly Ala Gln Ala
                 85                  90                  95
Glu Asp Glu Ala Asp Tyr Tyr Cys Asn Ser Arg Asp Ser Ser Gly Asn
                100                 105                 110
His Val Val Phe Gly Gly Gly Thr Lys Leu Thr Val Gly His Gly Gly
                115                 120                 125
Gly Gly Ser Gly Gly Gly Ser Gly Gly Gly Ser Glu Val Gln
                130                 135                 140
Leu Val Glu Ser Gly Gly Gly Val Val Arg Pro Gly Gly Ser Leu Arg
145                 150                 155                 160
Leu Ser Cys Ala Ala Ser Gly Phe Thr Phe Asp Asp Tyr Gly Met Ser
                165                 170                 175
Trp Val Arg Gln Ala Pro Gly Lys Gly Leu Glu Trp Val Ser Gly Ile
                180                 185                 190
Asn Trp Asn Gly Gly Ser Thr Gly Tyr Ala Asp Ser Val Lys Gly Arg
                195                 200                 205
Phe Thr Ile Ser Arg Asp Asn Ala Lys Asn Ser Leu Tyr Leu Gln Met
                210                 215                 220
Asn Ser Leu Arg Ala Glu Asp Thr Ala Val Tyr Tyr Cys Ala Arg Gly
225                 230                 235                 240
Arg Ser Leu Leu Phe Asp Tyr Trp Gly Gln Gly Thr Leu Val Thr Val
                245                 250                 255
Ser Arg Ile Thr Cys Pro Pro Met Ser Val Glu His Ala Asp Ile
                260                 265                 270
Trp Val Lys Ser Tyr Ser Leu Tyr Ser Arg Glu Arg Tyr Ile Cys Asn
                275                 280                 285
Ser Gly Phe Lys Arg Lys Ala Gly Thr Ser Ser Leu Thr Glu Cys Val
                290                 295                 300
Leu Asn Lys Ala Thr Asn Val Ala His Trp Thr Thr Pro Ser Leu Lys
305                 310                 315                 320
Cys Ile Arg Gln Gly Gln Asp Arg His Met Ile Arg Met Arg Gln Leu
                325                 330                 335
Ile Asp Ile Val Asp Gln Leu Lys Asn Tyr Val Asn Asp Leu Val Pro
                340                 345                 350
Glu Phe Leu Pro Ala Pro Glu Asp Val Glu Thr Asn Cys Glu Trp Ser
                355                 360                 365
Ala Phe Ser Cys Phe Gln Lys Ala Gln Leu Lys Ser Ala Asn Thr Gly
                370                 375                 380
Asn Asn Glu Arg Ile Ile Asn Val Ser Ile Lys Lys Leu Lys Arg Lys
385                 390                 395                 400
Pro Pro Ser Thr Asn Ala Gly Arg Arg Gln Lys His Arg Leu Thr Cys
                405                 410                 415
Pro Ser Cys Asp Ser Tyr Glu Lys Lys Pro Pro Lys Glu Phe Leu Glu
                420                 425                 430
Arg Phe Lys Ser Leu Leu Gln Lys Met Ile His Gln His Leu Ser Ser
                435                 440                 445
Arg Thr His Gly Ser Glu Asp Ser
450                 455
```

<210> SEQ ID NO 160
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 16s21 sequence"

<400> SEQUENCE: 160

```
atgaagtggg tgaccttcat cagcctgctg ttcctgttct ccagcgccta ctcctccgag      60
ctgacccagg accctgctgt gtccgtggct ctgggccaga ccgtgaggat cacctgccag     120
ggcgactccc tgaggtccta ctacgcctcc tggtaccagc agaagcccgg ccaggctcct     180
gtgctggtga tctacggcaa gaacaacagg ccctccggca tccctgacag gttctccgga     240
tcctcctccg gcaacaccgc ctccctgacc atcacaggcg ctcaggccga ggacgaggct     300
gactactact gcaactccag ggactcctcc ggcaaccatg tggtgttcgg cggcggcacc     360
aagctgaccg tgggccatgg cggcggcggc tccggaggcg gcggcagcgg cggaggagga     420
tccgaggtgc agctggtgga gtccggagga ggagtggtga ggcctggagg ctccctgagg     480
ctgagctgtg ctgcctccgg cttcaccttc gacgactacg gcatgtcctg ggtgaggcag     540
gctcctggaa agggcctgga gtgggtgtcc ggcatcaact ggaacggcgg atccaccggc     600
tacgccgatt ccgtgaaggg caggttcacc atcagcaggg acaacgccaa gaactccctg     660
tacctgcaga tgaactccct gaggccgag acaccgccg tgtactactg cgccaggggc     720
aggtccctgc tgttcgacta ctggggacag ggcaccctgg tgaccgtgtc caggattaca     780
tgcccccctc ccatgagcgt ggagcacgcc gacatctggg tgaagagcta tagcctctac     840
agccgggaga ggtatatctg taacagcggc ttcaagagga aggccggcac cagcagcctc     900
accgagtgcg tgctgaataa ggctaccaac gtggctcact ggacaacacc ctctttaaag     960
tgcatccggc agggccagga caggcacatg atccggatga ggcagctcat cgacatcgtc    1020
gaccagctga gaactacgt gaacgacctg gtgcccgagt ttctgcctgc ccccgaggac    1080
gtggagacca actgcgagtg gtccgccttc tcctgctttc agaaggccca gctgaagtcc    1140
gccaacaccg gcaacaacga gcggatcatc aacgtgagca tcaagaagct gaagcggaag    1200
cctccctcca aaacgccgg caggaggcag aagcacaggc tgacctgccc cagctgtgac    1260
tcctacgaga gaagccccc caaggagttc ctggagaggt tcaagtccct gctgcagaag    1320
atgatccatc agcacctgtc ctccaggacc cacggctccg aggactcc                1368
```

<210> SEQ ID NO 161
<211> LENGTH: 620
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15 sequence"

<400> SEQUENCE: 161

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

```
Ser Ile Thr Ser Ile Cys Glu Lys Pro Gln Glu Val Cys Ala Val
 50                  55                  60

Trp Arg Lys Asn Asp Glu Asn Ile Thr Leu Glu Thr Val Cys His Asp
 65                  70                  75                  80

Pro Lys Leu Pro Tyr His Asp Phe Ile Leu Glu Asp Ala Ala Ser Pro
                 85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Gly Gly Gly Ser Gly Gly Gly
        130                 135                 140

Gly Ser Gly Gly Gly Ser Ile Pro Pro His Val Gln Lys Ser Val
145                 150                 155                 160

Asn Asn Asp Met Ile Val Thr Asp Asn Gly Ala Val Lys Phe Pro
                165                 170                 175

Gln Leu Cys Lys Phe Cys Asp Val Arg Phe Ser Thr Cys Asp Asn Gln
                180                 185                 190

Lys Ser Cys Met Ser Asn Cys Ser Ile Thr Ser Ile Cys Glu Lys Pro
            195                 200                 205

Gln Glu Val Cys Val Ala Val Trp Arg Lys Asn Asp Glu Asn Ile Thr
        210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
                260                 265                 270

Asp Asn Ile Ile Phe Ser Glu Glu Tyr Asn Thr Ser Asn Pro Asp Ser
            275                 280                 285

Gly Thr Thr Asn Thr Val Ala Ala Tyr Asn Leu Thr Trp Lys Ser Thr
        290                 295                 300

Asn Phe Lys Thr Ile Leu Glu Trp Glu Pro Lys Pro Val Asn Gln Val
305                 310                 315                 320

Tyr Thr Val Gln Ile Ser Thr Lys Ser Gly Asp Trp Lys Ser Lys Cys
                325                 330                 335

Phe Tyr Thr Thr Asp Thr Glu Cys Asp Leu Thr Asp Glu Ile Val Lys
                340                 345                 350

Asp Val Lys Gln Thr Tyr Leu Ala Arg Val Phe Ser Tyr Pro Ala Gly
            355                 360                 365

Asn Val Glu Ser Thr Gly Ser Ala Gly Glu Pro Leu Tyr Glu Asn Ser
        370                 375                 380

Pro Glu Phe Thr Pro Tyr Leu Glu Thr Asn Leu Gly Gln Pro Thr Ile
385                 390                 395                 400

Gln Ser Phe Glu Gln Val Gly Thr Lys Val Asn Val Thr Val Glu Asp
                405                 410                 415

Glu Arg Thr Leu Val Arg Arg Asn Asn Thr Phe Leu Ser Leu Arg Asp
            420                 425                 430

Val Phe Gly Lys Asp Leu Ile Tyr Thr Leu Tyr Tyr Trp Lys Ser Ser
        435                 440                 445

Ser Ser Gly Lys Lys Thr Ala Lys Thr Asn Thr Asn Glu Phe Leu Ile
    450                 455                 460
```

| Asp | Val | Asp | Lys | Gly | Glu | Asn | Tyr | Cys | Phe | Ser | Val | Gln | Ala | Val | Ile |
|---|---|---|---|---|---|---|---|---|---|---|---|---|---|---|---|
| 465 | | | | 470 | | | | 475 | | | | | | | 480 |

| Pro | Ser | Arg | Thr | Val | Asn | Arg | Lys | Ser | Thr | Asp | Ser | Pro | Val | Glu | Cys |
|---|---|---|---|---|---|---|---|---|---|---|---|---|---|---|---|
| | | | | 485 | | | | | 490 | | | | | 495 | |

| Met | Gly | Gln | Glu | Lys | Gly | Glu | Phe | Arg | Glu | Asn | Trp | Val | Asn | Val | Ile |
|---|---|---|---|---|---|---|---|---|---|---|---|---|---|---|---|
| | | | 500 | | | | | 505 | | | | | 510 | | |

| Ser | Asp | Leu | Lys | Lys | Ile | Glu | Asp | Leu | Ile | Gln | Ser | Met | His | Ile | Asp |
|---|---|---|---|---|---|---|---|---|---|---|---|---|---|---|---|
| | | 515 | | | | | 520 | | | | | 525 | | | |

| Ala | Thr | Leu | Tyr | Thr | Glu | Ser | Asp | Val | His | Pro | Ser | Cys | Lys | Val | Thr |
|---|---|---|---|---|---|---|---|---|---|---|---|---|---|---|---|
| | 530 | | | | | 535 | | | | | 540 | | | | |

| Ala | Met | Lys | Cys | Phe | Leu | Leu | Glu | Leu | Gln | Val | Ile | Ser | Leu | Glu | Ser |
|---|---|---|---|---|---|---|---|---|---|---|---|---|---|---|---|
| 545 | | | | | 550 | | | | | 555 | | | | | 560 |

| Gly | Asp | Ala | Ser | Ile | His | Asp | Thr | Val | Glu | Asn | Leu | Ile | Ile | Leu | Ala |
|---|---|---|---|---|---|---|---|---|---|---|---|---|---|---|---|
| | | | | 565 | | | | | 570 | | | | | 575 | |

| Asn | Asn | Ser | Leu | Ser | Ser | Asn | Gly | Asn | Val | Thr | Glu | Ser | Gly | Cys | Lys |
|---|---|---|---|---|---|---|---|---|---|---|---|---|---|---|---|
| | | | 580 | | | | | 585 | | | | | 590 | | |

| Glu | Cys | Glu | Glu | Leu | Glu | Glu | Lys | Asn | Ile | Lys | Glu | Phe | Leu | Gln | Ser |
|---|---|---|---|---|---|---|---|---|---|---|---|---|---|---|---|
| | | 595 | | | | | 600 | | | | | 605 | | | |

| Phe | Val | His | Ile | Val | Gln | Met | Phe | Ile | Asn | Thr | Ser |
|---|---|---|---|---|---|---|---|---|---|---|---|
| 610 | | | | | 615 | | | | | 620 | |

<210> SEQ ID NO 162
<211> LENGTH: 1860
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic TGFRt15 sequence"

<400> SEQUENCE: 162

```
atccccccccc atgtgcaaaa gagcgtgaac aacgatatga tcgtgaccga caacaacggc      60
gccgtgaagt ttccccagct ctgcaagttc tgcgatgtca ggttcagcac ctgcgataat     120
cagaagtcct gcatgtccaa ctgcagcatc acctccatct gcgagaagcc caagaagtg     180
tgcgtggccg tgtggcggaa aaatgacgag aacatcaccc tggagaccgt gtgtcacgac     240
cccaagctcc cttatcacga cttcattctg gaggacgctg cctcccccaa atgcatcatg     300
aaggagaaga gaagcccggg agagaccttc tttatgtgtt cctgtagcag cgacgagtgt     360
aacgacaaca tcatcttcag cgaagagtac aacaccagca ccctgatgg aggtggcgga     420
tccggaggtg gaggttctgg tggaggtggg agtattcctc ccacgtgca gaagagcgtg     480
aataatgaca tgatcgtgac cgataacaat ggcgccgtga atttcccca gctgtgcaaa     540
ttctgcgatg tgaggttttc cacctgcgac aaccagaagt cctgtatgag caactgctcc     600
atcacctcca tctgtgagaa gcctcaggag gtgtgcgtgg ctgtctggcg gaagaatgac     660
gagaatatca ccctggaaac cgtctgccac gatcccaagc tgccctacca cgatttcatc     720
ctggaagacg ccgccagccc taagtgcatc atgaaagaga aaagaagcc tggcgagacc     780
ttttccatgt gctcctgcag cagcgacgaa tgcaacgaca tatcatctt agcgaggaa     840
tacaatacca gcaccccga cagcggcaca accaacacag tcgctgccta aacctcact     900
tggaagagca ccaacttcaa aaccatcctc gaatgggaac ccaaacccgt taaccaagtt     960
tacaccgtgc agatcagcac caagtccggc gactggaagt ccaaatgttt ctataccacc    1020
gacaccgagt cgatctcac cgatgagatc gtgaaagatg tgaaacagac ctacctcgcc    1080
cgggtgttta gctaccccgc cggcaatgtg gagagcactg gttccgctgg cgagccttta    1140
```

-continued

```
tacgagaaca gccccgaatt taccccttac ctcgagacca atttaggaca gcccaccatc   1200
caaagctttg agcaagttgg cacaaaggtg aatgtgacag tggaggacga gcggacttta   1260
gtgcggcgga acaacacctt tctcagcctc cgggatgtgt tcggcaaaga tttaatctac   1320
acactgtatt actggaagtc ctcttcctcc ggcaagaaga cagctaaaac caacacaaac   1380 gagttttttaa tcgacgtgga taaaggcgaa aactactgtt tcagcgtgca agctgtgatc   1440
ccctcccgga ccgtgaatag gaaaagcacc gatagccccg ttgagtgcat gggccaagaa   1500
aagggcgagt tccgggagaa ctgggtgaac gtcatcagcg atttaaagaa gatcgaagat   1560
ttaattcagt ccatgcatat cgacgccact ttatacacag aatccgacgt gcacccctct   1620
tgtaaggtga ccgccatgaa atgtttttta ctggagctgc aagttatctc tttagagagc   1680
ggagacgcta gcatccacga caccgtggag aatttaatca ttttagccaa taactcttta   1740
tccagcaacg gcaacgtgac agagtccggc tgcaaggagt gcgaagagct ggaggagaag   1800
aacatcaagg agtttctgca atcctttgtg cacattgtcc agatgttcat caatacctcc   1860
```

<210> SEQ ID NO 163
<211> LENGTH: 638
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15 sequence"

<400> SEQUENCE: 163

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220
```

-continued

```
Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
            245                 250                 255

Phe Ile Leu Glu Asp Ala Ala Ser Pro Lys Cys Ile Met Lys Glu Lys
        260                 265                 270

Lys Lys Pro Gly Glu Thr Phe Phe Met Cys Ser Cys Ser Ser Asp Glu
    275                 280                 285

Cys Asn Asp Asn Ile Ile Phe Ser Glu Glu Tyr Asn Thr Ser Asn Pro
290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
            325                 330                 335

Gln Val Tyr Thr Val Gln Ile Ser Thr Lys Ser Gly Asp Trp Lys Ser
        340                 345                 350

Lys Cys Phe Tyr Thr Thr Asp Thr Glu Cys Asp Leu Thr Asp Glu Ile
    355                 360                 365

Val Lys Asp Val Lys Gln Thr Tyr Leu Ala Arg Val Phe Ser Tyr Pro
370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
            405                 410                 415

Thr Ile Gln Ser Phe Glu Gln Val Gly Thr Lys Val Asn Val Thr Val
        420                 425                 430

Glu Asp Glu Arg Thr Leu Val Arg Arg Asn Asn Thr Phe Leu Ser Leu
    435                 440                 445

Arg Asp Val Phe Gly Lys Asp Leu Ile Tyr Thr Leu Tyr Tyr Trp Lys
450                 455                 460

Ser Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
            485                 490                 495

Val Ile Pro Ser Arg Thr Val Asn Arg Lys Ser Thr Asp Ser Pro Val
        500                 505                 510

Glu Cys Met Gly Gln Glu Lys Gly Glu Phe Arg Glu Asn Trp Val Asn
    515                 520                 525

Val Ile Ser Asp Leu Lys Lys Ile Glu Asp Leu Ile Gln Ser Met His
530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
            565                 570                 575

Glu Ser Gly Asp Ala Ser Ile His Asp Thr Val Glu Asn Leu Ile Ile
        580                 585                 590

Leu Ala Asn Asn Ser Leu Ser Ser Asn Gly Asn Val Thr Glu Ser Gly
    595                 600                 605

Cys Lys Glu Cys Glu Glu Leu Glu Glu Lys Asn Ile Lys Glu Phe Leu
610                 615                 620

Gln Ser Phe Val His Ile Val Gln Met Phe Ile Asn Thr Ser
625                 630                 635
```

<210> SEQ ID NO 164
<211> LENGTH: 1914
<212> TYPE: DNA
<213> ORGANISM: Artificial Sequence
<220> FEATURE:
<221> NAME/KEY: source
<223> OTHER INFORMATION: /note="Description of Artificial Sequence: Synthetic TGFRt15 sequence"

<400> SEQUENCE: 164

| | | | | | |
|---|---|---|---|---|---|
| atgaagtggg | tgaccttcat | cagcctgctg | ttcctgttct | ccagcgccta | ctccatcccc | 60 |
| ccccatgtgc | aaaagagcgt | gaacaacgat | atgatcgtga | ccgacaacaa | cggcgccgtg | 120 |
| aagtttcccc | agctctgcaa | gttctgcgat | gtcaggttca | gcacctgcga | taatcagaag | 180 |
| tcctgcatgt | ccaactgcag | catcaccctc | atctgcgaga | agccccaaga | agtgtgcgtg | 240 |
| gccgtgtggc | ggaaaaatga | cgagaacatc | acctggaga | ccgtgtgtca | cgaccccaag | 300 |
| ctcccttatc | acgacttcat | tctggaggac | gctgcctccc | ccaaatgcat | catgaaggag | 360 |
| aagaagaagc | cggagagac | cttctttatg | tgttcctgta | gcagcgacga | gtgtaacgac | 420 |
| aacatcatct | tcagcgaaga | gtacaacacc | agcaaccctg | atggaggtgg | cggatccgga | 480 |
| ggtggaggtt | ctggtggagg | tgggagtatt | cctccccacg | tgcagaagag | cgtgaataat | 540 |
| gacatgatcg | tgaccgataa | caatggcgcc | gtgaaatttc | cccagctgtg | caaattctgc | 600 |
| gatgtgaggt | tttccacctg | cgacaaccag | aagtcctgta | tgagcaactg | ctccatcacc | 660 |
| tccatctgtg | agaagcctca | ggaggtgtgc | gtggctgtct | ggcggaagaa | tgacgagaat | 720 |
| atcaccctgg | aaaccgtctg | ccacgatccc | aagctgccct | accacgattt | catcctggaa | 780 |
| gacgccgcca | gccctaagtg | catcatgaaa | gagaaaaaga | agcctggcga | gaccttttc | 840 |
| atgtgctcct | gcagcagcga | cgaatgcaac | gacaatatca | tctttagcga | ggaatacaat | 900 |
| accagcaacc | ccgacagcgg | cacaaccaac | acagtcgctg | cctataacct | cacttggaag | 960 |
| agcaccaact | tcaaaaccat | cctcgaatgg | gaacccaaac | ccgttaacca | agtttacacc | 1020 |
| gtgcagatca | gcaccaagtc | cggcgactgg | aagtccaaat | gtttctatac | caccgacacc | 1080 |
| gagtgcgatc | tcaccgatga | gatcgtgaaa | gatgtgaaac | agacctacct | cgcccgggtg | 1140 |
| tttagctacc | ccgccggcaa | tgtggagagc | actggttccg | ctggcgagcc | tttatacgag | 1200 |
| aacagccccg | aatttacccc | ttacctcgag | accaatttag | gacagcccac | catccaaagc | 1260 |
| tttgagcaag | ttggcacaaa | ggtgaatgtg | acagtggagg | acgagcggac | tttagtgcgg | 1320 |
| cggaacaaca | cctttctcag | cctccgggat | gtgttcggca | agatttaat | ctacacactg | 1380 |
| tattactgga | gtcctcttc | ctccggcaag | aagacagcta | aaaccaacac | aaacgagttt | 1440 |
| ttaatcgacg | tggataaagg | cgaaaactac | tgtttcagcg | tgcaagctgt | gatcccctcc | 1500 |
| cggaccgtga | taggaaaag | caccgatagc | cccgttgagt | gcatgggcca | agaaaagggc | 1560 |
| gagttccggg | agaactgggt | gaacgtcatc | agcgatttaa | agaagatcga | agatttaatt | 1620 |
| cagtccatgc | atatcgacgc | cactttatac | acagaatccg | acgtgcaccc | ctcttgtaag | 1680 |
| gtgaccgcca | tgaatgtttt | tttactggag | ctgcaagtta | tctctttaga | gagcggagac | 1740 |
| gctagcatcc | acgacaccgt | ggagaattta | atcattttag | ccaataactc | tttatccagc | 1800 |
| aacggcaacg | tgacagagtc | cggctgcaag | gagtgcgaag | agctggagga | agaacatc | 1860 |
| aaggagtttc | tgcaatcctt | tgtgcacatt | gtccagatgt | tcatcaatac | ctcc | 1914 |

<210> SEQ ID NO 165
<211> LENGTH: 184
<212> TYPE: PRT

<213> ORGANISM: Artificial Sequence
<220> FEATURE:
<221> NAME/KEY: source
<223> OTHER INFORMATION: /note="Description of Artificial Sequence: Synthetic CD137L sequence"

<400> SEQUENCE: 165

```
Arg Glu Gly Pro Glu Leu Ser Pro Asp Asp Pro Ala Gly Leu Leu Asp
1               5                   10                  15
Leu Arg Gln Gly Met Phe Ala Gln Leu Val Ala Gln Asn Val Leu Leu
            20                  25                  30
Ile Asp Gly Pro Leu Ser Trp Tyr Ser Asp Pro Gly Leu Ala Gly Val
        35                  40                  45
Ser Leu Thr Gly Gly Leu Ser Tyr Lys Glu Asp Thr Lys Glu Leu Val
    50                  55                  60
Val Ala Lys Ala Gly Val Tyr Tyr Val Phe Phe Gln Leu Glu Leu Arg
65                  70                  75                  80
Arg Val Val Ala Gly Glu Gly Ser Gly Ser Val Ser Leu Ala Leu His
                85                  90                  95
Leu Gln Pro Leu Arg Ser Ala Ala Gly Ala Ala Ala Leu Ala Leu Thr
            100                 105                 110
Val Asp Leu Pro Pro Ala Ser Ser Glu Ala Arg Asn Ser Ala Phe Gly
        115                 120                 125
Phe Gln Gly Arg Leu Leu His Leu Ser Ala Gly Gln Arg Leu Gly Val
    130                 135                 140
His Leu His Thr Glu Ala Arg Ala Arg His Ala Trp Gln Leu Thr Gln
145                 150                 155                 160
Gly Ala Thr Val Leu Gly Leu Phe Arg Val Thr Pro Glu Ile Pro Ala
                165                 170                 175
Gly Leu Pro Ser Pro Arg Ser Glu
            180
```

<210> SEQ ID NO 166
<211> LENGTH: 552
<212> TYPE: DNA
<213> ORGANISM: Artificial Sequence
<220> FEATURE:
<221> NAME/KEY: source
<223> OTHER INFORMATION: /note="Description of Artificial Sequence: Synthetic CD137L sequence"

<400> SEQUENCE: 166

```
cgcgagggtc ccgagctttc gcccgacgat cccgccggcc tcttggacct gcggcagggc    60
atgtttgcgc agctggtggc ccaaaatgtt ctgctgatcg atgggcccct gagctggtac   120
agtgacccag gctggcagg cgtgtccctg acgggggggcc tgagctacaa agaggacacg   180
aaggagctgg tggtggccaa ggctggagtc tactatgtct tctttcaact agagctgcgg   240
cgcgtggtgg ccggcgaggg ctcaggctcc gtttcacttg cctgcacct gcagccactg   300
cgctctgctg ctggggccgc cgccctggct ttgaccgtgg acctgccacc gcctcctcc   360
gaggctcgga actcggcctt cggttccag ggccgcttgc tgcacctgag tgccggccag   420
cgcctgggcg tccatcttca cactgaggcc agggcacgcc atgcctggca gcttacccag   480
ggcgccacag tcttgggact cttccggtg acccccgaaa tcccagccgg actcccttca   540
ccgaggtcgg aa                                                       552
```

<210> SEQ ID NO 167
<211> LENGTH: 165

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic CD137L (short version) sequence"

<400> SEQUENCE: 167
```

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile
                165

```
<210> SEQ ID NO 168
<211> LENGTH: 495
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic CD137L (short version) sequence"

<400> SEQUENCE: 168
gatcccgccg gcctcttgga cctgcggcag ggcatgtttg cgcagctggt ggcccaaaat    60
gttctgctga tcgatgggcc cctgagctgg tacagtgacc caggcctggc aggcgtgtcc   120
ctgacggggg gcctgagcta caagaggac acgaaggagc tggtggtggc caaggctgga   180
gtctactatg tcttctttca actagagctg cggcgcgtgg tggccggcga gggctcaggc   240
tccgtttcac ttgcgctgca cctgcagcca ctgcgctctg ctgctgggc cgccgccctg   300 gctttgaccg tggacctgcc acccgcctcc tccgaggctc ggaactcggc cttcggtttc   360
cagggccgct tgctgcacct gagtgccggc cagcgcctgg gcgtccatct tcacactgag   420
gccagggcac gccatgcctg gcagcttacc cagggcgcca cagtcttggg actcttccgg   480
gtgacccccg aaatc                                                   495

<210> SEQ ID NO 169
<211> LENGTH: 397
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic 21s137L sequence"

<400> SEQUENCE: 169

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ile Thr Cys Pro Pro Met Ser Val Glu His
    130                 135                 140

Ala Asp Ile Trp Val Lys Ser Tyr Ser Leu Tyr Ser Arg Glu Arg Tyr
145                 150                 155                 160

Ile Cys Asn Ser Gly Phe Lys Arg Lys Ala Gly Thr Ser Ser Leu Thr
                165                 170                 175

Glu Cys Val Leu Asn Lys Ala Thr Asn Val Ala His Trp Thr Thr Pro
            180                 185                 190

Ser Leu Lys Cys Ile Arg Gly Gly Gly Ser Gly Gly Gly Ser
        195                 200                 205

Gly Gly Gly Gly Ser Arg Glu Gly Pro Glu Leu Ser Pro Asp Asp Pro
    210                 215                 220

Ala Gly Leu Leu Asp Leu Arg Gln Gly Met Phe Ala Gln Leu Val Ala
225                 230                 235                 240

Gln Asn Val Leu Leu Ile Asp Gly Pro Leu Ser Trp Tyr Ser Asp Pro
                245                 250                 255

Gly Leu Ala Gly Val Ser Leu Thr Gly Gly Leu Ser Tyr Lys Glu Asp
            260                 265                 270

Thr Lys Glu Leu Val Val Ala Lys Ala Gly Val Tyr Tyr Val Phe Phe
        275                 280                 285

Gln Leu Glu Leu Arg Arg Val Val Ala Gly Glu Gly Ser Gly Ser Val
    290                 295                 300

Ser Leu Ala Leu His Leu Gln Pro Leu Arg Ser Ala Ala Gly Ala Ala
305                 310                 315                 320

Ala Leu Ala Leu Thr Val Asp Leu Pro Pro Ala Ser Ser Glu Ala Arg
                325                 330                 335

Asn Ser Ala Phe Gly Phe Gln Gly Arg Leu Leu His Leu Ser Ala Gly
            340                 345                 350

Gln Arg Leu Gly Val His Leu His Thr Glu Ala Arg Ala Arg His Ala
        355                 360                 365

Trp Gln Leu Thr Gln Gly Ala Thr Val Leu Gly Leu Phe Arg Val Thr
    370                 375                 380

Pro Glu Ile Pro Ala Gly Leu Pro Ser Pro Arg Ser Glu
385                 390                 395
```

<210> SEQ ID NO 170
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 21s137L sequence"

<400> SEQUENCE: 170

```
cagggccagg acaggcacat gatccggatg aggcagctca tcgacatcgt cgaccagctg      60
aagaactacg tgaacgacct ggtgcccgag tttctgcctg cccccgagga cgtggagacc     120
aactgcgagt ggtccgcctt ctcctgcttt cagaaggccc agctgaagtc cgccaacacc     180
ggcaacaacg agcggatcat caacgtgagc atcaagaagc tgaagcggaa gcctccctcc     240
acaaacgccg gcaggaggca gaagcacagg ctgacctgcc ccagctgtga ctcctacgag     300
aagaagcccc ccaaggagtt cctggagagg ttcaagtccc tgctgcagaa gatgatccat     360
cagcacctgt cctccaggac ccacggctcc gaggactcca ttacatgccc cctcccatg     420
agcgtggagc acgccgacat ctgggtgaag agctatagcc tctacagccg ggagaggtat     480
atctgtaaca gcggcttcaa gaggaaggcc ggcaccagca gcctcaccga gtgcgtgctg     540
aataaggcta ccaacgtggc tcactggaca cacccctctt taaagtgcat ccggggcggt     600
ggaggatccg gaggaggtgg ctccggcggc ggaggatctc gcgagggtcc cgagctttcg     660
cccgacgatc ccgccggcct cttggacctg cggcagggca tgtttgcgca gctggtggcc     720
caaaatgttc tgctgatcga tgggcccctg agctggtaca gtgacccagg cctggcaggc     780
gtgtccctga cggggggcct gagctacaaa gaggacacga aggagctggt ggtgccaag     840
gctggagtct actatgtctt ctttcaacta gagctgcggc gcgtggtggc cggcgagggc     900
tcaggctccg tttcacttgc gctgcacctg cagccactgc gctctgctgc tggggccgcc     960
gccctggctt tgaccgtgga cctgccaccc gcctcctccg aggctcggaa ctcggccttc    1020
ggtttccagg gccgcttgct gcacctgagt gccggccagc gcctgggcgt ccatcttcac    1080
actgaggcca gggcacgcca tgcctggcag cttacccagg cgccacagt cttgggactc    1140
ttccgggtga cccccgaaat cccagccgga ctcccttcac cgaggtcgga a              1191
```

<210> SEQ ID NO 171
<211> LENGTH: 415
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 21s137L sequence"

<400> SEQUENCE: 171

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80
```

```
Asn Glu Arg Ile Ile Asn Val Ser Ile Lys Lys Leu Lys Arg Lys Pro
                    85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
130                 135                 140

Thr His Gly Ser Glu Asp Ser Ile Thr Cys Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
            180                 185                 190

Leu Thr Glu Cys Val Leu Asn Lys Ala Thr Asn Val Ala His Trp Thr
        195                 200                 205

Thr Pro Ser Leu Lys Cys Ile Arg Gly Gly Gly Ser Gly Gly Gly
210                 215                 220

Gly Ser Gly Gly Gly Ser Arg Glu Gly Pro Glu Leu Ser Pro Asp
225                 230                 235                 240

Asp Pro Ala Gly Leu Leu Asp Leu Arg Gln Gly Met Phe Ala Gln Leu
            245                 250                 255

Val Ala Gln Asn Val Leu Leu Ile Asp Gly Pro Leu Ser Trp Tyr Ser
                260                 265                 270

Asp Pro Gly Leu Ala Gly Val Ser Leu Thr Gly Leu Ser Tyr Lys
            275                 280                 285

Glu Asp Thr Lys Glu Leu Val Val Ala Lys Ala Gly Val Tyr Tyr Val
290                 295                 300

Phe Phe Gln Leu Glu Leu Arg Arg Val Val Ala Gly Glu Gly Ser Gly
305                 310                 315                 320

Ser Val Ser Leu Ala Leu His Leu Gln Pro Leu Arg Ser Ala Ala Gly
                325                 330                 335

Ala Ala Ala Leu Ala Leu Thr Val Asp Leu Pro Pro Ala Ser Ser Glu
            340                 345                 350

Ala Arg Asn Ser Ala Phe Gly Phe Gln Gly Arg Leu Leu His Leu Ser
        355                 360                 365

Ala Gly Gln Arg Leu Gly Val His Leu His Thr Glu Ala Arg Ala Arg
370                 375                 380

His Ala Trp Gln Leu Thr Gln Gly Ala Thr Val Leu Gly Leu Phe Arg
385                 390                 395                 400

Val Thr Pro Glu Ile Pro Ala Gly Leu Pro Ser Pro Arg Ser Glu
            405                 410                 415

<210> SEQ ID NO 172
<211> LENGTH: 1245
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21s137L sequence"

<400> SEQUENCE: 172
atgaagtggg tgaccttcat cagcctgctg ttcctgttct ccagcgccta ctcccagggc      60
caggacaggc acatgatccg gatgaggcag ctcatcgaca tcgtcgacca gctgaagaac     120
```

```
tacgtgaacg acctggtgcc cgagtttctg cctgcccccg aggacgtgga gaccaactgc    180
gagtggtccg ccttctcctg ctttcagaag gcccagctga agtccgccaa caccggcaac    240
aacgagcgga tcatcaacgt gagcatcaag aagctgaagc ggaagcctcc ctccacaaac    300
gccggcagga ggcagaagca caggctgacc tgccccagct gtgactccta cgagaagaag    360
ccccccaagg agttcctgga gaggttcaag tccctgctgc agaagatgat ccatcagcac    420
ctgtcctcca ggacccacgg ctccgaggac tccattacat gccccctcc catgagcgtg    480 gagcacgccg acatctgggt gaagagctat agcctctaca gcgggagag gtatatctgt    540 aacagcggct tcaagaggaa ggccggcacc agcagcctca ccgagtgcgt gctgaataag    600
gctaccaacg tggctcactg gacaacaccc tctttaaagt gcatccgggg cggtggagga    660
tccggaggag gtggctccgg cggcggagga tctcgcgagg gtcccgagct ttcgcccgac    720
gatcccgccg gcctcttgga cctgcggcag ggcatgtttg cgcagctggt ggcccaaaat    780
gttctgctga tcgatgggcc cctgagctgg tacagtgacc caggcctggc aggcgtgtcc    840
ctgacggggg gcctgagcta caagaggac acgaaggagc tggtggtggc caaggctgga    900
gtctactatg tcttctttca actagagctg cggcgcgtgg tggccggcga gggctcaggc    960
tccgtttcac ttgcgctgca cctgcagcca ctgcgctctg ctgctggggc cgccgccctg   1020
gctttgaccg tggacctgcc acccgcctcc tccgaggctc ggaactcggc cttcggtttc   1080
cagggccgct tgctgcacct gagtgccggc cagcgcctgg gcgtccatct tcacactgag   1140
gccagggcac gccatgcctg gcagcttacc cagggcgcca cagtcttggg actcttccgg   1200 gtgaccccg aaatcccagc cggactccct tcaccgaggt cggaa                    1245
```

<210> SEQ ID NO 173
<211> LENGTH: 378
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 21s137L (short version) sequence"

<400> SEQUENCE: 173

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ile Thr Cys Pro Pro Met Ser Val Glu His
    130                 135                 140

Ala Asp Ile Trp Val Lys Ser Tyr Ser Leu Tyr Ser Arg Glu Arg Tyr

```
145                 150                 155                 160
Ile Cys Asn Ser Gly Phe Lys Arg Lys Ala Gly Thr Ser Ser Leu Thr
                165                 170                 175
Glu Cys Val Leu Asn Lys Ala Thr Asn Val Ala His Trp Thr Thr Pro
            180                 185                 190
Ser Leu Lys Cys Ile Arg Gly Gly Gly Ser Gly Gly Gly Ser
        195                 200                 205
Gly Gly Gly Gly Ser Asp Pro Ala Gly Leu Leu Asp Leu Arg Gln Gly
    210                 215                 220
Met Phe Ala Gln Leu Val Ala Gln Asn Val Leu Leu Ile Asp Gly Pro
225                 230                 235                 240
Leu Ser Trp Tyr Ser Asp Pro Gly Leu Ala Gly Val Ser Leu Thr Gly
                245                 250                 255
Gly Leu Ser Tyr Lys Glu Asp Thr Lys Glu Leu Val Val Ala Lys Ala
            260                 265                 270
Gly Val Tyr Tyr Val Phe Phe Gln Leu Glu Leu Arg Arg Val Val Ala
        275                 280                 285
Gly Glu Gly Ser Gly Ser Val Ser Leu Ala Leu His Leu Gln Pro Leu
    290                 295                 300
Arg Ser Ala Ala Gly Ala Ala Ala Leu Ala Leu Thr Val Asp Leu Pro
305                 310                 315                 320
Pro Ala Ser Ser Glu Ala Arg Asn Ser Ala Phe Gly Phe Gln Gly Arg
                325                 330                 335
Leu Leu His Leu Ser Ala Gly Gln Arg Leu Gly Val His Leu His Thr
            340                 345                 350
Glu Ala Arg Ala Arg His Ala Trp Gln Leu Thr Gln Gly Ala Thr Val
        355                 360                 365
Leu Gly Leu Phe Arg Val Thr Pro Glu Ile
    370                 375

<210> SEQ ID NO 174
<211> LENGTH: 1134
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21s137L (short version) sequence"

<400> SEQUENCE: 174
cagggccagg acaggcacat gatccggatg aggcagctca tcgacatcgt cgaccagctg      60
aagaactacg tgaacgacct ggtgcccgag tttctgcctg cccccgagga cgtggagacc     120
aactgcgagt ggtccgcctt ctcctgcttt cagaaggccc agctgaagtc cgccaacacc     180
ggcaacaacg agcggatcat caacgtgagc atcaagaagc tgaagcggaa gcctccctcc     240
acaaacgccg gcaggaggca gaagcacagg ctgacctgcc ccagctgtga ctcctacgag     300
aagaagcccc ccaaggagtt cctggagagg ttcaagtccc tgctgcagaa gatgatccat     360
cagcacctgt cctccaggac ccacggctcc gaggactcca ttacatgccc cctcccatg      420 agcgtggagc acgccgacat ctgggtgaag agctatagcc tctacagccg ggagaggtat     480
atctgtaaca gcggcttcaa gaggaaggcc ggcaccagca gcctcaccga gtgcgtgctg     540
aataaggcta ccaacgtggc tcactggaca cacccctctt taaagtgcat ccggggcggt     600
ggaggatccg gaggaggtgg ctccggcggc ggaggatctg atcccgccgg cctcttggac     660
ctgcggcagg gcatgtttgc gcagctggtg gcccaaaatg ttctgctgat cgatgggccc     720
```

```
ctgagctggt acagtgaccc aggcctggca ggcgtgtccc tgacgggggg cctgagctac    780
aaagaggaca cgaaggagct ggtggtggcc aaggctggag tctactatgt cttctttcaa    840
ctagagctgc ggcgcgtggt ggccggcgag ggctcaggct ccgtttcact tgcgctgcac    900
ctgcagccac tgcgctctgc tgctgggggcc gccgccctgg cttttgaccgt ggacctgcca    960 cccgcctcct ccgaggctcg gaactcggcc ttcggtttcc agggccgctt gctgcacctg   1020
agtgccggcc agcgcctggg cgtccatctt cacactgagg ccagggcacg ccatgcctgg   1080
cagcttaccc agggcgccac agtcttggga ctcttccggg tgaccccga aatc          1134
```

<210> SEQ ID NO 175
<211> LENGTH: 396
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 21s137L (short version) sequence"

<400> SEQUENCE: 175

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
                20                  25                  30

Asp Ile Val Asp Gln Leu Lys Asn Tyr Val Asn Asp Leu Val Pro Glu
            35                  40                  45

Phe Leu Pro Ala Pro Glu Asp Val Glu Thr Asn Cys Glu Trp Ser Ala
        50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
                100                 105                 110

Ser Cys Asp Ser Tyr Glu Lys Lys Pro Pro Lys Glu Phe Leu Glu Arg
            115                 120                 125

Phe Lys Ser Leu Leu Gln Lys Met Ile His Gln His Leu Ser Ser Arg
        130                 135                 140

Thr His Gly Ser Glu Asp Ser Ile Thr Cys Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
                180                 185                 190

Leu Thr Glu Cys Val Leu Asn Lys Ala Thr Asn Val Ala His Trp Thr
            195                 200                 205

Thr Pro Ser Leu Lys Cys Ile Arg Gly Gly Gly Ser Gly Gly
        210                 215                 220

Gly Ser Gly Gly Gly Gly Ser Asp Pro Ala Gly Leu Leu Asp Leu Arg
225                 230                 235                 240

Gln Gly Met Phe Ala Gln Leu Val Ala Gln Asn Val Leu Leu Ile Asp
                245                 250                 255

Gly Pro Leu Ser Trp Tyr Ser Asp Pro Gly Leu Ala Gly Val Ser Leu
            260                 265                 270

Thr Gly Gly Leu Ser Tyr Lys Glu Asp Thr Lys Glu Leu Val Val Ala
```

|  | | | 275 | | | 280 | | | 285 | | |
|---|---|---|---|---|---|---|---|---|---|---|---|

Lys Ala Gly Val Tyr Tyr Val Phe Phe Gln Leu Glu Leu Arg Arg Val
                290                 295                 300

Val Ala Gly Glu Gly Ser Gly Ser Val Ser Leu Ala Leu His Leu Gln
305                 310                 315                 320

Pro Leu Arg Ser Ala Ala Gly Ala Ala Ala Leu Ala Leu Thr Val Asp
                325                 330                 335

Leu Pro Pro Ala Ser Ser Glu Ala Arg Asn Ser Ala Phe Gly Phe Gln
                340                 345                 350

Gly Arg Leu Leu His Leu Ser Ala Gly Gln Arg Leu Gly Val His Leu
                355                 360                 365

His Thr Glu Ala Arg Ala Arg His Ala Trp Gln Leu Thr Gln Gly Ala
                370                 375                 380

Thr Val Leu Gly Leu Phe Arg Val Thr Pro Glu Ile
385                 390                 395

```
<210> SEQ ID NO 176
<211> LENGTH: 1188
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21s137L (short version) sequence"

<400> SEQUENCE: 176
atgaagtggg tgaccttcat cagcctgctg ttcctgttct ccagcgccta ctcccagggc      60
caggacaggc acatgatccg gatgaggcag ctcatcgaca tcgtcgacca gctgaagaac     120
tacgtgaacg acctggtgcc cgagtttctg cctgccccg aggacgtgga gaccaactgc     180
gagtggtccg ccttctcctg ctttcagaag gcccagctga gtccgccaa caccggcaac     240 aacgagcgga tcatcaacgt gagcatcaag aagctgaagc ggaagcctcc ctccacaaac    300
gccggcagga ggcagaagca caggctgacc tgccccagct gtgactccta cgagaagaag    360 cccccaagg agttcctgga gaggttcaag tccctgctgc agaagatgat ccatcagcac     420
ctgtcctcca ggacccacgg ctcccgaggac tccattacat gcccccctcc catgagcgtg    480
gagcacgccg acatctgggt gaagagctat agcctctaca gccgggagag gtatatctgt    540
aacagcggct tcaagaggaa ggccggcacc agcagcctca ccgagtgcgt gctgaataag    600
gctaccaacg tggctcactg gacaacaccc tctttaaagt gcatccgggg cggtggagga    660
tccggaggag gtggctccgg cggcggagga tctgatcccg ccggcctctt ggacctgcgg    720
cagggcatgt ttgcgcagct ggtggcccaa aatgttctgc tgatcgatgg ccccctgagc    780
tggtacagtg acccaggcct ggcaggcgtg tccctgacgg ggggcctgag ctacaaagag    840
gacacgaagg agctggtggt ggccaaggct ggagtctact atgtcttctt tcaactagag    900
ctgcggcgcg tggtggccgg cgagggctca ggctccgttt cacttgcgct gcacctgcag    960
ccactgcgct ctgctgctgg ggccgccgcc ctggctttga ccgtggacct gccacccgcc   1020
tcctccgagg ctcggaactc ggccttcggt ttccagggcc gcttgctgca cctgagtgcc   1080
ggccagcgcc tgggcgtcca tcttcacact gaggccaggg cacgccatgc ctggcagctt   1140
acccagggcg ccacagtctt gggactcttc cgggtgaccc ccgaaatc                1188

<210> SEQ ID NO 177
<211> LENGTH: 485
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic TGFRs21 sequence"

<400> SEQUENCE: 177

```
Ile Pro Pro His Val Gln Lys Ser Val Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ile
        275                 280                 285

Thr Cys Pro Pro Pro Met Ser Val Glu His Ala Asp Ile Trp Val Lys
    290                 295                 300

Ser Tyr Ser Leu Tyr Ser Arg Glu Arg Tyr Ile Cys Asn Ser Gly Phe
305                 310                 315                 320

Lys Arg Lys Ala Gly Thr Ser Ser Leu Thr Glu Cys Val Leu Asn Lys
                325                 330                 335

Ala Thr Asn Val Ala His Trp Thr Thr Pro Ser Leu Lys Cys Ile Arg
            340                 345                 350

Gln Gly Gln Asp Arg His Met Ile Arg Met Arg Gln Leu Ile Asp Ile
        355                 360                 365

Val Asp Gln Leu Lys Asn Tyr Val Asn Asp Leu Val Pro Glu Phe Leu
    370                 375                 380
```

Pro Ala Pro Glu Asp Val Glu Thr Asn Cys Glu Trp Ser Ala Phe Ser
385                 390                 395                 400

Cys Phe Gln Lys Ala Gln Leu Lys Ser Ala Asn Thr Gly Asn Asn Glu
            405                 410                 415

Arg Ile Ile Asn Val Ser Ile Lys Lys Leu Lys Arg Lys Pro Pro Ser
        420                 425                 430

Thr Asn Ala Gly Arg Arg Gln Lys His Arg Leu Thr Cys Pro Ser Cys
        435                 440                 445

Asp Ser Tyr Glu Lys Lys Pro Pro Lys Glu Phe Leu Glu Arg Phe Lys
        450                 455                 460

Ser Leu Leu Gln Lys Met Ile His Gln His Leu Ser Ser Arg Thr His
465                 470                 475                 480

Gly Ser Glu Asp Ser
            485

<210> SEQ ID NO 178
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRs21 sequence"

<400> SEQUENCE: 178

| | |
|---|---|
| atcccccccc atgtgcaaaa gagcgtgaac aacgatatga tcgtgaccga caacaacggc | 60 |
| gccgtgaagt ttccccagct ctgcaagttc tgcgatgtca ggttcagcac ctgcgataat | 120 |
| cagaagtcct gcatgtccaa ctgcagcatc acctccatct gcgagaagcc caagaagtg | 180 |
| tgcgtggccg tgtggcggaa aaatgacgag aacatcaccc tggagaccgt gtgtcacgac | 240 |
| cccaagctcc cttatcacga cttcattctg gaggacgctg cctcccccaa atgcatcatg | 300 |
| aaggagaaga agaagcccgg agagaccttc tttatgtgtt cctgtagcag cgacgagtgt | 360 |
| aacgacaaca tcatcttcag cgaagagtac aacaccagca accctgatgg aggtggcgga | 420 |
| tccggaggtg gaggttctgg tggaggtggg agtattcctc ccacgtgca gaagagcgtg | 480 |
| aataatgaca tgatcgtgac cgataacaat ggcgccgtga atttcccca gctgtgcaaa | 540 |
| ttctgcgatg tgaggttttc cacctgcgac aaccagaagt cctgtatgag caactgctcc | 600 |
| atcacctcca tctgtgagaa gcctcaggag gtgtgcgtgg ctgtctggcg gaagaatgac | 660 |
| gagaatatca ccctggaaac cgtctgccac gatcccaagc tgccctacca cgatttcatc | 720 |
| ctggaagacg ccgccagccc taagtgcatc atgaaagaga aaaagaagcc tggcgagacc | 780 |
| tttttcatgt gctcctgcag cagcgacgaa tgcaacgaca tatcatctt tagcgaggaa | 840 |
| tacaatacca gcaaccccga cattacatgc ccccctccca tgagcgtgga gcacgccgac | 900 |
| atctgggtga gagctatag cctctacagc cgggagaggt atatctgtaa cagcggcttc | 960 |
| aagaggaagg ccggcaccag cagcctcacc gagtgcgtgc tgaataaggc taccaacgtg | 1020 |
| gctcactgga caacaccctc tttaaagtgc atccggcagg ccaggacag gcacatgatc | 1080 |
| cggatgaggc agctcatcga catcgtcgac cagctgaaga actacgtgaa cgacctggtg | 1140 |
| cccgagtttc tgcctgcccc cgaggacgtg agaccaact gcgagtggtc cgccttctcc | 1200 |
| tgctttcaga aggcccagct gaagtccgcc aacaccggca caacgagcg atcatcaac | 1260 |
| gtgagcatca agaagctgaa gcggaagcct ccctccacaa cgccggcag gaggcagaag | 1320 |
| cacaggctga cctgccccag ctgtgactcc tacgagaaga gccccccaa ggagttcctg | 1380 |

```
gagaggttca gtccctgct gcagaagatg atccatcagc acctgtcctc caggacccac   1440
ggctccgagg actcc                                                   1455
```

<210> SEQ ID NO 179
<211> LENGTH: 503
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRs21 sequence"

<400> SEQUENCE: 179

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ile Thr Cys Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335
```

```
Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
        355                 360                 365

Ile Arg Gln Gly Gln Asp Arg His Met Ile Arg Met Arg Gln Leu Ile
    370                 375                 380

Asp Ile Val Asp Gln Leu Lys Asn Tyr Val Asn Asp Leu Val Pro Glu
385                 390                 395                 400

Phe Leu Pro Ala Pro Glu Asp Val Glu Thr Asn Cys Glu Trp Ser Ala
                405                 410                 415

Phe Ser Cys Phe Gln Lys Ala Gln Leu Lys Ser Ala Asn Thr Gly Asn
                420                 425                 430

Asn Glu Arg Ile Ile Asn Val Ser Ile Lys Lys Leu Lys Arg Lys Pro
            435                 440                 445

Pro Ser Thr Asn Ala Gly Arg Arg Gln Lys His Arg Leu Thr Cys Pro
        450                 455                 460

Ser Cys Asp Ser Tyr Glu Lys Lys Pro Pro Lys Glu Phe Leu Glu Arg
465                 470                 475                 480

Phe Lys Ser Leu Leu Gln Lys Met Ile His Gln His Leu Ser Ser Arg
                485                 490                 495

Thr His Gly Ser Glu Asp Ser
            500
```

<210> SEQ ID NO 180
<211> LENGTH: 1509
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRs21 sequence"

<400> SEQUENCE: 180

```
atgaagtggg tgaccttcat cagcctgctg ttcctgttct ccagcgccta ctccatcccc     60
ccccatgtgc aaaagagcgt gaacaacgat atgatcgtga ccgacaacaa cggcgccgtg    120
aagtttcccc agctctgcaa gttctgcgat gtcaggttca gcacctgcga taatcagaag    180
tcctgcatgt ccaactgcag catcacctcc atctgcgaga agcccaagaa agtgtgcgtg    240
gccgtgtggc ggaaaaatga cgagaacatc accctggaga ccgtgtgtca cgaccccaag    300
ctcccttatc acgacttcat tctggaggac gctgcctccc ccaaatgcat catgaaggag    360
aagaagaagc ccggagagac cttctttatg tgttcctgta gcagcgacga gtgtaacgac    420
aacatcatct tcagcgaaga gtacaacacc agcaaccctg atggaggtgg cggatccgga    480
ggtggaggtt ctggtggagg tgggagtatt cctccccacg tgcagaagag cgtgaataat    540
gacatgatcg tgaccgataa caatggcgcc gtgaaatttc cccagctgtg caaattctgc    600
gatgtgaggt tttccacctg cgacaaccag aagtcctgta tgagcaactg ctccatcacc    660
tccatctgtg agaagcctca ggaggtgtgc gtggctgtct ggcggaagaa tgacgagaat    720
atcaccctgg aaaccgtctg ccacgatccc aagctgccct accacgattt catcctggaa    780
gacgccgcca gccctaagtg catcatgaaa gagaaaaaga gcctggcga gaccttttc    840 atgtgctcct gcagcagcga cgaatgcaac gacaatatca tctttagcga ggaatacaat    900
accagcaacc ccgacattac atgccccccct cccatgagcg tggagcacgc cgacatctgg    960
gtgaagagct atagcctcta cagccgggag aggtatatct gtaacagcgg cttcaagagg   1020
```

-continued

```
aaggccggca ccagcagcct caccgagtgc gtgctgaata aggctaccaa cgtggctcac    1080
tggacaacac cctctttaaa gtgcatccgg cagggccagg acaggcacat gatccggatg    1140
aggcagctca tcgacatcgt cgaccagctg aagaactacg tgaacgacct ggtgcccgag    1200
tttctgcctg cccccgagga cgtggagacc aactgcgagt ggtccgcctt ctcctgcttt    1260
cagaaggccc agctgaagtc cgccaacacc ggcaacaacg agcggatcat caacgtgagc    1320
atcaagaagc tgaagcggaa gcctccctcc acaaacgccg gcaggaggca gaagcacagg    1380
ctgacctgcc ccagctgtga ctcctacgag aagaagcccc caaggagtt cctggagagg     1440 ttcaagtccc tgctgcagaa gatgatccat cagcacctgt cctccaggac ccacggctcc    1500
gaggactcc                                                            1509
```

<210> SEQ ID NO 181
<211> LENGTH: 592
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRs16 sequence"

<400> SEQUENCE: 181

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255
```

```
Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ile
            275                 280                 285

Thr Cys Pro Pro Pro Met Ser Val Glu His Ala Asp Ile Trp Val Lys
            290                 295                 300

Ser Tyr Ser Leu Tyr Ser Arg Glu Arg Tyr Ile Cys Asn Ser Gly Phe
305                 310                 315                 320

Lys Arg Lys Ala Gly Thr Ser Ser Leu Thr Glu Cys Val Leu Asn Lys
            325                 330                 335

Ala Thr Asn Val Ala His Trp Thr Thr Pro Ser Leu Lys Cys Ile Arg
            340                 345                 350

Ser Glu Leu Thr Gln Asp Pro Ala Val Ser Val Ala Leu Gly Gln Thr
            355                 360                 365

Val Arg Ile Thr Cys Gln Gly Asp Ser Leu Arg Ser Tyr Tyr Ala Ser
            370                 375                 380

Trp Tyr Gln Gln Lys Pro Gly Gln Ala Pro Val Leu Val Ile Tyr Gly
385                 390                 395                 400

Lys Asn Asn Arg Pro Ser Gly Ile Pro Asp Arg Phe Ser Gly Ser Ser
            405                 410                 415

Ser Gly Asn Thr Ala Ser Leu Thr Ile Thr Gly Ala Gln Ala Glu Asp
            420                 425                 430

Glu Ala Asp Tyr Tyr Cys Asn Ser Arg Asp Ser Ser Gly Asn His Val
            435                 440                 445

Val Phe Gly Gly Gly Thr Lys Leu Thr Val Gly His Gly Gly Gly Gly
            450                 455                 460

Ser Gly Gly Gly Gly Ser Gly Gly Gly Ser Glu Val Gln Leu Val
465                 470                 475                 480

Glu Ser Gly Gly Gly Val Val Arg Pro Gly Gly Ser Leu Arg Leu Ser
            485                 490                 495

Cys Ala Ala Ser Gly Phe Thr Phe Asp Asp Tyr Gly Met Ser Trp Val
            500                 505                 510

Arg Gln Ala Pro Gly Lys Gly Leu Glu Trp Val Ser Gly Ile Asn Trp
            515                 520                 525

Asn Gly Gly Ser Thr Gly Tyr Ala Asp Ser Val Lys Gly Arg Phe Thr
            530                 535                 540

Ile Ser Arg Asp Asn Ala Lys Asn Ser Leu Tyr Leu Gln Met Asn Ser
545                 550                 555                 560

Leu Arg Ala Glu Asp Thr Ala Val Tyr Tyr Cys Ala Arg Gly Arg Ser
            565                 570                 575

Leu Leu Phe Asp Tyr Trp Gly Gln Gly Thr Leu Val Thr Val Ser Arg
            580                 585                 590

<210> SEQ ID NO 182
<211> LENGTH: 1776
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRs16 sequence"

<400> SEQUENCE: 182
atcccccccc atgtgcaaaa gagcgtgaac aacgatatga tcgtgaccga caacaacggc      60
gccgtgaagt ttccccagct ctgcaagttc tgcgatgtca ggttcagcac ctgcgataat     120
```

```
cagaagtcct gcatgtccaa ctgcagcatc acctccatct gcgagaagcc ccaagaagtg    180
tgcgtggccg tgtggcggaa aaatgacgag aacatcaccc tggagaccgt gtgtcacgac    240
cccaagctcc cttatcacga cttcattctg gaggacgctg cctcccccaa atgcatcatg    300
aaggagaaga gaagcccgg agagaccttc tttatgtgtt cctgtagcag cgacgagtgt    360
aacgacaaca tcatcttcag cgaagagtac aacaccagca ccctgatgg aggtggcgga    420
tccggaggtg gaggttctgg tggaggtggg agtattcctc cccacgtgca gaagagcgtg    480
aataatgaca tgatcgtgac cgataacaat ggcgccgtga aatttcccca gctgtgcaaa    540
ttctgcgatg tgaggttttc cacctgcgac aaccagaagt cctgtatgag caactgctcc    600
atcacctcca tctgtgagaa gcctcaggag gtgtgcgtgg ctgtctggcg aagaatgac    660
gagaatatca ccctggaaac cgtctgccac gatcccaagc tgccctacca cgatttcatc    720
ctggaagacg ccgccagccc taagtgcatc atgaaagaga aaagaagcc tggcgagacc    780
ttttccatgt gctcctgcag cagcgacgaa tgcaacgaca atatcatctt agcgaggaa    840
tacaatacca gcaaccccga cattacatgc ccccctccca tgagcgtgga gcacgccgac    900
atctgggtga agagctatag cctctacagc cgggagaggt atatctgtaa cagcggcttc    960
aagaggaagg ccggcaccag cagcctcacc gagtgcgtgc tgaataaggc taccaacgtg    1020
gctcactgga caaccaccctc tttaaagtgc atccggtccg agctgaccca ggaccctgct    1080
gtgtccgtgc tctgggcca accgtgagg atcacctgcc agggcgactc cctgaggtcc    1140
tactacgcct cctggtacca gcagaagccc ggccaggctc ctgtgctggt gatctacggc    1200
aagaacaaca ggccctccgg catccctgac aggttctccg atcctcctc cggcaacacc    1260
gcctccctga ccatcacagg cgctcaggcc gaggacgagg ctgactacta ctgcaactcc    1320
agggactcct ccggcaacca tgtggtgttc ggcggcggca ccaagctgac cgtgggccat    1380
ggcggcggcg gctccggagg cggcggcagc ggcggaggag gatccgaggt gcagctggtg    1440
gagtccggag gaggagtggt gaggcctgga ggctccctga gctgagctg tgctgcctcc    1500
ggcttcacct tcgacgacta cggcatgtcc tgggtgaggc aggctcctgg aaagggcctg    1560
gagtgggtgt ccggcatcaa ctggaacggc gatccaccg gctacgccga ttccgtgaag    1620
ggcaggttca ccatcagcag ggacaacgcc aagaactccc tgtacctgca gatgaactcc    1680
ctgagggccg aggacaccgc cgtgtactac tgcgccaggg gcaggtccct gctgttcgac    1740
tactggggac agggcaccct ggtgaccgtg tccagg                              1776
```

<210> SEQ ID NO 183
<211> LENGTH: 610
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRs16 sequence"

<400> SEQUENCE: 183

Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

```
Asn Cys Ser Ile Thr Ser Ile Cys Glu Lys Pro Gln Glu Val Cys Val
 65                  70                  75                  80

Ala Val Trp Arg Lys Asn Asp Glu Asn Ile Thr Leu Glu Thr Val Cys
                 85                  90                  95

His Asp Pro Lys Leu Pro Tyr His Asp Phe Ile Leu Glu Asp Ala Ala
                100                 105                 110

Ser Pro Lys Cys Ile Met Lys Glu Lys Lys Pro Gly Glu Thr Phe
                115                 120                 125

Phe Met Cys Ser Cys Ser Ser Asp Glu Cys Asn Asp Asn Ile Ile Phe
            130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
                180                 185                 190

Phe Pro Gln Leu Cys Lys Phe Cys Asp Val Arg Phe Ser Thr Cys Asp
            195                 200                 205

Asn Gln Lys Ser Cys Met Ser Asn Cys Ser Ile Thr Ser Ile Cys Glu
210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
                260                 265                 270

Lys Lys Pro Gly Glu Thr Phe Phe Met Cys Ser Cys Ser Ser Asp Glu
275                 280                 285

Cys Asn Asp Asn Ile Ile Phe Ser Glu Glu Tyr Asn Thr Ser Asn Pro
290                 295                 300

Asp Ile Thr Cys Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
                340                 345                 350

Asn Lys Ala Thr Asn Val Ala His Trp Thr Thr Pro Ser Leu Lys Cys
                355                 360                 365

Ile Arg Ser Glu Leu Thr Gln Asp Pro Ala Val Ser Val Ala Leu Gly
                370                 375                 380

Gln Thr Val Arg Ile Thr Cys Gln Gly Asp Ser Leu Arg Ser Tyr Tyr
385                 390                 395                 400

Ala Ser Trp Tyr Gln Gln Lys Pro Gly Gln Ala Pro Val Leu Val Ile
                405                 410                 415

Tyr Gly Lys Asn Asn Arg Pro Ser Gly Ile Pro Asp Arg Phe Ser Gly
                420                 425                 430

Ser Ser Ser Gly Asn Thr Ala Ser Leu Thr Ile Thr Gly Ala Gln Ala
                435                 440                 445

Glu Asp Glu Ala Asp Tyr Tyr Cys Asn Ser Arg Asp Ser Ser Gly Asn
                450                 455                 460

His Val Val Phe Gly Gly Gly Thr Lys Leu Thr Val Gly His Gly Gly
465                 470                 475                 480
```

```
Gly Gly Ser Gly Gly Gly Gly Ser Gly Gly Gly Ser Glu Val Gln
            485                 490                 495

Leu Val Glu Ser Gly Gly Val Val Arg Pro Gly Ser Leu Arg
        500                 505                 510

Leu Ser Cys Ala Ala Ser Gly Phe Thr Phe Asp Asp Tyr Gly Met Ser
            515                 520                 525

Trp Val Arg Gln Ala Pro Gly Lys Gly Leu Glu Trp Val Ser Gly Ile
530                 535                 540

Asn Trp Asn Gly Gly Ser Thr Gly Tyr Ala Asp Ser Val Lys Gly Arg
545                 550                 555                 560

Phe Thr Ile Ser Arg Asp Asn Ala Lys Asn Ser Leu Tyr Leu Gln Met
                565                 570                 575

Asn Ser Leu Arg Ala Glu Asp Thr Ala Val Tyr Tyr Cys Ala Arg Gly
            580                 585                 590

Arg Ser Leu Leu Phe Asp Tyr Trp Gly Gln Gly Thr Leu Val Thr Val
        595                 600                 605

Ser Arg
    610

<210> SEQ ID NO 184
<211> LENGTH: 1830
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRs16 sequence"

<400> SEQUENCE: 184
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcag catcacctcc atctgcgaga agccccaaga agtgtgcgtg     240
gccgtgtggc ggaaaaatga cgagaacatc accctggaga ccgtgtgtca cgaccccaag     300
ctcccttatc acgacttcat tctggaggac gctgcctccc ccaaatgcat catgaaggag     360
aagaagaagc ccggagagac cttctttatg tgttcctgta gcagcgacga gtgtaacgac     420
aacatcatct tcagcgaaga gtacaacacc agcaaccctg atggaggtgg cggatccgga     480
ggtggaggtt ctggtggagg tgggagtatt cctccccacg tgcagaagag cgtgaataat     540
gacatgatcg tgaccgataa caatggcgcc gtgaaatttc cccagctgtg caaattctgc     600
gatgtgaggt tttccaccct cgacaaccag aagtcctgta tgagcaactg ctccatcacc     660
tccatctgtg agaagcctca ggaggtgtgc gtggctgtct ggcggaagaa tgacgagaat     720
atcaccctgg aaaccgtctg ccacgatccc aagctgccct accacgattt catcctggaa     780
gacgccgcca gccctaagtg catcatgaaa gagaaaaaga gcctggcga dccttttttc     840 atgtgctcct gcagcagcga cgaatgcaac gacaatatca tctttagcga ggaatacaat     900
accagcaacc ccgacattac atgcccccct cccatgagcg tggagcacgc cgacatctgg     960
gtgaagagct atagcctcta cagccgggag aggtatatct gtaacagcgg cttcaagagg    1020
aaggccggca ccagcagcct caccgagtgc gtgctgaata aggctaccaa cgtggctcac    1080
tggacaacac cctcttttaaa gtgcatccgg tccgagctga cccaggaccc tgctgtgtcc    1140
gtggctctgg gccagaccgt gaggatcacc tgccagggcg actccctgag gtcctactac    1200
```

-continued

```
gcctcctggt accagcagaa gcccggccag gctcctgtgc tggtgatcta cggcaagaac    1260
aacaggccct ccggcatccc tgacaggttc tccggatcct cctccggcaa caccgcctcc    1320
ctgaccatca caggcgctca ggccgaggac gaggctgact actactgcaa ctccagggac    1380
tcctccggca accatgtggt gttcggcggc ggcaccaagc tgaccgtggg ccatggcggc    1440
ggcggctccg gaggcggcgg cagcggcgga ggaggatccg aggtgcagct ggtggagtcc    1500
ggaggaggag tggtgaggcc tggaggctcc ctgaggctga gctgtgctgc ctccggcttc    1560
accttcgacg actacggcat gtcctgggtg aggcaggctc ctggaaaggg cctggagtgg    1620
gtgtccggca tcaactggaa cggcggatcc accggctacg ccgattccgt gaagggcagg    1680
ttcaccatca gcagggacaa cgccaagaac tccctgtacc tgcagatgaa ctccctgagg    1740
gccgaggaca ccgccgtgta ctactgcgcc aggggcaggt ccctgctgtt cgactactgg    1800
ggacagggca ccctggtgac cgtgtccagg                                     1830
```

<210> SEQ ID NO 185
<211> LENGTH: 551
<212> TYPE: PRT
<213> ORGANISM: Artificial Sequence
<220> FEATURE:
<221> NAME/KEY: source
<223> OTHER INFORMATION: /note="Description of Artificial Sequence:
   Synthetic TGFRs137L sequence"

<400> SEQUENCE: 185

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240
```

```
Leu Glu Asp Ala Ala Ser Pro Lys Cys Ile Met Lys Glu Lys Lys
            245                 250                 255
Pro Gly Glu Thr Phe Phe Met Cys Ser Cys Ser Ser Asp Glu Cys Asn
        260                 265                 270
Asp Asn Ile Ile Phe Ser Glu Glu Tyr Asn Thr Ser Asn Pro Asp Ile
            275                 280                 285
Thr Cys Pro Pro Met Ser Val Glu His Ala Asp Ile Trp Val Lys
        290                 295                 300
Ser Tyr Ser Leu Tyr Ser Arg Glu Arg Tyr Ile Cys Asn Ser Gly Phe
305                 310                 315                 320
Lys Arg Lys Ala Gly Thr Ser Ser Leu Thr Glu Cys Val Leu Asn Lys
            325                 330                 335
Ala Thr Asn Val Ala His Trp Thr Thr Pro Ser Leu Lys Cys Ile Arg
            340                 345                 350
Gly Gly Gly Gly Ser Gly Gly Gly Ser Gly Gly Gly Ser Arg
        355                 360                 365
Glu Gly Pro Glu Leu Ser Pro Asp Asp Pro Ala Gly Leu Leu Asp Leu
        370                 375                 380
Arg Gln Gly Met Phe Ala Gln Leu Val Ala Gln Asn Val Leu Leu Ile
385                 390                 395                 400
Asp Gly Pro Leu Ser Trp Tyr Ser Asp Pro Gly Leu Ala Gly Val Ser
                405                 410                 415
Leu Thr Gly Gly Leu Ser Tyr Lys Glu Asp Thr Lys Glu Leu Val Val
            420                 425                 430
Ala Lys Ala Gly Val Tyr Tyr Val Phe Phe Gln Leu Glu Leu Arg Arg
        435                 440                 445
Val Val Ala Gly Glu Gly Ser Gly Ser Val Ser Leu Ala Leu His Leu
450                 455                 460
Gln Pro Leu Arg Ser Ala Ala Gly Ala Ala Ala Leu Ala Leu Thr Val
465                 470                 475                 480
Asp Leu Pro Pro Ala Ser Ser Glu Ala Arg Asn Ser Ala Phe Gly Phe
                485                 490                 495
Gln Gly Arg Leu Leu His Leu Ser Ala Gly Gln Arg Leu Gly Val His
            500                 505                 510
Leu His Thr Glu Ala Arg Ala Arg His Ala Trp Gln Leu Thr Gln Gly
            515                 520                 525
Ala Thr Val Leu Gly Leu Phe Arg Val Thr Pro Glu Ile Pro Ala Gly
        530                 535                 540
Leu Pro Ser Pro Arg Ser Glu
545                 550

<210> SEQ ID NO 186
<211> LENGTH: 1653
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRs137L sequence"

<400> SEQUENCE: 186 atccccccc  atgtgcaaaa  gagcgtgaac  aacgatatga  tcgtgaccga  caacaacggc    60
gccgtgaagt  ttccccagct  ctgcaagttc  tgcgatgtca  ggttcagcac  ctgcgataat   120
cagaagtcct  gcatgtccaa  ctgcagcatc  acctccatct  gcgagaagcc  ccaagaagtg   180
tgcgtggccg  tgtggcggaa  aaatgacgag  aacatcaccc  tggagaccgt  gtgtcacgac   240
```

-continued

```
cccaagctcc cttatcacga cttcattctg gaggacgctg cctcccccaa atgcatcatg      300
aaggagaaga agaagcccgg agagaccttc tttatgtgtt cctgtagcag cgacgagtgt      360
aacgacaaca tcatcttcag cgaagagtac aacaccagca accctgatgg aggtggcgga      420
tccggaggtg gaggttctgg tggaggtggg agtattcctc cccacgtgca gaagagcgtg      480
aataatgaca tgatcgtgac cgataacaat ggcgccgtga aatttcccca gctgtgcaaa      540
ttctgcgatg tgaggttttc cacctgcgac aaccagaagt cctgtatgag caactgctcc      600
atcacctcca tctgtgagaa gcctcaggag gtgtgcgtgg ctgtctggcg gaagaatgac      660
gagaatatca ccctggaaac cgtctgccac gatcccaagc tgccctacca cgatttcatc      720
ctggaagacg ccgccagccc taagtgcatc atgaaagaga aaagaagcc tggcgagacc       780 ttttcatgt gctcctgcag cagcgacgaa tgcaacgaca atatcatctt tagcgaggaa      840
tacaatacca gcaaccccga cattacatgc cccctccca tgagcgtgga gcacgccgac       900
atctgggtga agagctatag cctctacagc cgggagaggt atatctgtaa cagcggcttc      960
aagaggaagg ccggcaccag cagcctcacc gagtgcgtgc tgaataaggc taccaacgtg    1020
gctcactgga caacaccctc tttaaagtgc atccggggcg gtggaggatc cggaggaggt    1080
ggctccggcg gcggaggatc tcgcgagggt cccgagcttt cgcccgacga tcccgccggc    1140
ctcttggacc tgcggcaggg catgtttgcg cagctggtgg cccaaaatgt tctgctgatc    1200
gatgggcccc tgagctggta cagtgaccca ggcctggcag gcgtgtccct gacgggggc     1260 ctgagctaca aagaggacac gaaggagctg gtggtggcca aggctggagt ctactatgtc    1320 ttcttcaac tagagctgcg gcgcgtggtg gccggcgagg gctcaggctc cgtttcactt     1380
gcgctgcacc tgcagccact gcgctctgct gctgggggccg ccgccctggc tttgaccgtg    1440
gacctgccac ccgcctcctc cgaggctcgg aactcggcct tcggtttcca gggccgcttg    1500
ctgcacctga gtgccggcca gcgcctgggc gtccatcttc acactgaggc cagggcacgc    1560
catgcctggc agcttaccca gggcgccaca gtcttggac tcttccgggt gaccccgaa      1620 atcccagccg gactcccttc accgaggtcg gaa                                  1653
```

<210> SEQ ID NO 187
<211> LENGTH: 569
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRs137L sequence"

<400> SEQUENCE: 187

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95
```

-continued

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
        115                 120                 125

Phe Met Cys Ser Cys Ser Ser Asp Glu Cys Asn Asp Asn Ile Ile Phe
130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
            195                 200                 205

Asn Gln Lys Ser Cys Met Ser Asn Cys Ser Ile Thr Ser Ile Cys Glu
            210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
            275                 280                 285

Cys Asn Asp Asn Ile Ile Phe Ser Glu Glu Tyr Asn Thr Ser Asn Pro
290                 295                 300

Asp Ile Thr Cys Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
            355                 360                 365

Ile Arg Gly Gly Gly Gly Ser Gly Gly Gly Gly Ser Gly Gly Gly Gly
370                 375                 380

Ser Arg Glu Gly Pro Glu Leu Ser Pro Asp Asp Pro Ala Gly Leu Leu
385                 390                 395                 400

Asp Leu Arg Gln Gly Met Phe Ala Gln Leu Val Ala Gln Asn Val Leu
            405                 410                 415

Leu Ile Asp Gly Pro Leu Ser Trp Tyr Ser Asp Pro Gly Leu Ala Gly
            420                 425                 430

Val Ser Leu Thr Gly Gly Leu Ser Tyr Lys Glu Asp Thr Lys Glu Leu
            435                 440                 445

Val Val Ala Lys Ala Gly Val Tyr Tyr Val Phe Phe Gln Leu Glu Leu
            450                 455                 460

Arg Arg Val Val Ala Gly Glu Gly Ser Gly Ser Val Ser Leu Ala Leu
465                 470                 475                 480

His Leu Gln Pro Leu Arg Ser Ala Ala Gly Ala Ala Leu Ala Leu
            485                 490                 495

Thr Val Asp Leu Pro Pro Ala Ser Ser Glu Ala Arg Asn Ser Ala Phe
            500                 505                 510

Gly Phe Gln Gly Arg Leu Leu His Leu Ser Ala Gly Gln Arg Leu Gly 515                 520                 525
Val His Leu His Thr Glu Ala Arg Ala Arg His Ala Trp Gln Leu Thr
        530                 535                 540

Gln Gly Ala Thr Val Leu Gly Leu Phe Arg Val Thr Pro Glu Ile Pro
545                 550                 555                 560

Ala Gly Leu Pro Ser Pro Arg Ser Glu
                565

<210> SEQ ID NO 188
<211> LENGTH: 1707
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRs137L sequence"

<400> SEQUENCE: 188

| | | | | | |
|---|---|---|---|---|---|
| atgaagtggg | tgaccttcat | cagcctgctg | ttcctgttct | ccagcgccta | ctccatcccc | 60 |
| ccccatgtgc | aaaagagcgt | gaacaacgat | atgatcgtga | ccgacaacaa | cggcgccgtg | 120 |
| aagtttcccc | agctctgcaa | gttctgcgat | gtcaggttca | gcacctgcga | taatcagaag | 180 |
| tcctgcatgt | ccaactgcag | catcaccctc | atctgcgaga | agccccaaga | agtgtgcgtg | 240 |
| gccgtgtggc | ggaaaaatga | cgagaacatc | accctggaga | ccgtgtgtca | cgaccccaag | 300 |
| ctcccttatc | acgacttcat | tctggaggac | gctgcctccc | ccaaatgcat | catgaaggag | 360 |
| aagaagaagc | cggagagac | cttctttatg | tgttcctgta | gcagcgacga | gtgtaacgac | 420 |
| aacatcatct | tcagcgaaga | gtacaacacc | agcaaccctg | atggaggtgg | cggatccgga | 480 |
| ggtggaggtt | ctggtggagg | tgggagtatt | cctccccacg | tgcagaagag | cgtgaataat | 540 |
| gacatgatcg | tgaccgataa | caatggcgcc | gtgaaatttc | cccagctgtg | caaattctgc | 600 |
| gatgtgaggt | tttccacctg | cgacaaccag | aagtcctgta | tgagcaactg | ctccatcacc | 660 |
| tccatctgtg | agaagcctca | ggaggtgtgc | gtggctgtct | ggcggaagaa | tgacgagaat | 720 |
| atcaccctgg | aaaccgtctg | ccacgatccc | aagctgccct | accacgattt | catcctggaa | 780 |
| gacgccgcca | gccctaagtg | catcatgaaa | gagaaaaaga | gcctggcga | accttttttc | 840 |
| atgtgctcct | gcagcagcga | cgaatgcaac | gacaatatca | tctttagcga | ggaatacaat | 900 |
| accagcaacc | ccgacattac | atgccccct | cccatgagcg | tggagcacgc | cgacatctgg | 960 |
| gtgaagagct | atagcctcta | cagccgggag | aggtatatct | gtaacagcgg | cttcaagagg | 1020 |
| aaggccggca | ccagcagcct | caccgagtgc | gtgctgaata | aggctaccaa | cgtggctcac | 1080 |
| tggacaacac | cctctttaaa | gtgcatccgg | ggcggtggag | gatccggagg | aggtggctcc | 1140 |
| ggcggcggag | gatctcgcga | gggtcccgag | ctttcgcccg | acgatcccgc | cggcctcttg | 1200 |
| gacctgcggc | agggcatgtt | tgcgcagctg | gtggcccaaa | atgttctgct | gatcgatggg | 1260 |
| cccctgagct | ggtacagtga | cccaggcctg | caggcgtgt | ccctgacggg | ggcctgagc | 1320 |
| tacaaagagg | acacgaagga | gctggtggtg | gccaaggctg | gagtctacta | tgtcttcttt | 1380 |
| caactagagc | tgcggcgcgt | ggtggccggc | gagggctcag | gctccgtttc | acttgcgctg | 1440 |
| cacctgcagc | cactgcgctc | tgctgctggg | gccgccgccc | tggctttgac | cgtggacctg | 1500 |
| ccacccgcct | cctccgaggc | tcggaactcg | gccttcggtt | tccagggccg | cttgctgcac | 1560 |
| ctgagtgccg | gccagcgcct | gggcgtccat | cttcacactg | aggccagggc | acgccatgcc | 1620 |
| tggcagctta | cccagggcgc | cacagtcttg | ggactcttcc | gggtgacccc | cgaaatccca | 1680 | gccggactcc cttcaccgag gtcggaa 1707

<210> SEQ ID NO 189
<211> LENGTH: 720
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 18s sequence"

<400> SEQUENCE: 189

| | | | | | |
|---|---|---|---|---|---|
| atgaagtggg | tcacatttat | ctctttactg | ttcctcttct | ccagcgccta | cagctacttc | 60 |
| ggcaaactgg | aatccaagct | gagcgtgatc | cggaatttaa | acgaccaagt | tctgtttatc | 120 |
| gatcaaggta | accggcctct | gttcgaggac | atgaccgact | ccgattgccg | ggacaatgcc | 180 |
| ccccggacca | tcttcattat | ctccatgtac | aaggacagcc | agccccgggg | catggctgtg | 240 |
| acaattagcg | tgaagtgtga | gaaaatcagc | actttatctt | gtgagaacaa | gatcatctcc | 300 |
| tttaaggaaa | tgaaccccccc | cgataacatc | aaggacacca | agtccgatat | catcttcttc | 360 |
| cagcggtccg | tgcccggtca | cgataacaag | atgcagttcg | aatcctcctc | ctacgagggc | 420 |
| tacttttttag | cttgtgaaaa | ggagagggat | ttattcaagc | tgatcctcaa | gaaggaggac | 480 |
| gagctgggcg | atcgttccat | catgttcacc | gtccaaaacg | aggatattac | atgccccccct | 540 |
| cccatgagcg | tggagcacgc | cgacatctgg | gtgaagagct | atagcctcta | cagccgggag | 600 |
| aggtatatct | gtaacagcgg | cttcaagagg | aaggccggca | ccagcagcct | caccgagtgc | 660 |
| gtgctgaata | aggctaccaa | cgtggctcac | tggacaacac | cctctttaaa | gtgcatccgg | 720 |

<210> SEQ ID NO 190
<211> LENGTH: 2607
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 12t15 sequence"

<400> SEQUENCE: 190

| | | | | | |
|---|---|---|---|---|---|
| atgaaatggg | tgacctttat | ttctttactg | ttcctcttta | gcagcgccta | ctccatttgg | 60 |
| gaactgaaga | aggacgtcta | cgtggtcgaa | ctggactggt | atcccgatgc | tcccggcgaa | 120 |
| atggtggtgc | tcacttgtga | cacccccgaa | gaagacggca | tcacttggac | cctcgatcag | 180 |
| agcagcgagg | tgctgggctc | cggaaagacc | ctcacaatcc | aagttaagga | gttcggagac | 240 |
| gctggccaat | acacatgcca | caagggaggc | gaggtgctca | gccattcctt | attattatta | 300 |
| cacaagaagg | aagacggaat | ctggtccacc | gacatttttaa | aagatcagaa | ggagcccaag | 360 |
| aataagacct | ttttaaggtg | tgaggccaaa | aactacagcg | gtcgtttcac | ttgttggtgg | 420 |
| ctgaccacca | tttccaccga | tttaaccttc | tccgtgaaaa | gcagccgggg | aagctccgac | 480 |
| cctcaaggtg | tgacatgtgg | agccgctacc | ctcagcgctg | agagggttcg | tggcgataac | 540 |
| aaggaatacg | agtacagcgt | ggagtgccaa | gaagatagcg | cttgtcccgc | tgccgaagaa | 600 |
| tctttaccca | ttgaggtgat | ggtggacgcc | gtgcacaaac | tcaagtacga | gaactacacc | 660 |
| tcctccttct | ttatccggga | catcattaag | cccgatcctc | ctaagaattt | acagctgaag | 720 |
| cctctcaaaa | atagccggca | agttgaggtc | tcttgggaat | atcccgacac | ttggagcaca | 780 |
| ccccacagct | acttctcttt | aacctttttgt | gtgcaagttc | aaggtaaaag | caagcgggag | 840 |
| aagaaagacc | gggtgtttac | cgacaaaacc | agcgccaccg | tcatctgtcg | gaagaacgcc | 900 |

```
tccatcagcg tgagggctca agatcgttat tactccagca gctggtccga gtgggccagc    960
gtgccttgtt ccggcggtgg aggatccgga ggaggtggct ccggcggcgg aggatctcgt   1020
aacctccccg tggctacccc cgatcccgga atgttccctt gtttacacca cagccagaat   1080
ttactgaggg ccgtgagcaa catgctgcag aaagctaggc agactttaga attttaccct   1140
tgcaccagcg aggagatcga ccatgaagat atcaccaagg acaagacatc caccgtggag   1200
gcttgtttac ctctggagct gacaaagaac gagtcttgtc tcaactctcg tgaaaccagc   1260
ttcatcacaa atggctcttg tttagcttcc cggaagacct cctttatgat ggctttatgc   1320
ctcagctcca tctacgagga tttaaagatg taccaagtgg agttcaagac catgaacgcc   1380
aagctgctca tggaccctaa acggcagatc ttttagacc agaacatgct ggctgtgatt   1440
gatgagctga tgcaagcttt aaacttcaac tccgagaccg tccctcagaa gtcctccctc   1500
gaggagcccg attttacaa gacaaagatc aaactgtgca ttttactcca cgcctttagg   1560
atccgggccg tgaccattga ccgggtcatg agctatttaa cgccagcag cggcacaacc   1620 aacacagtcg ctgcctataa cctcacttgg aagagcacca acttcaaaac catcctcgaa   1680
tgggaaccca aaccgttaa ccaagtttac ccgtgcaga tcagcaccaa gtccggcgac   1740
tggaagtcca atgtttcta taccaccgac accgagtgcg atctcaccga tgagatcgtg   1800
aaagatgtga acagaccta cctcgcccgg gtgtttagct accccgccgg caatgtggag   1860
agcactggtt ccgctggcga gcctttatac gagaacagcc ccgaatttac cccttacctc   1920
gagaccaatt taggacagcc caccatccaa agctttgagc aagttggcac aaaggtgaat   1980
gtgacagtgg aggacgagcg gactttagtg cggcggaaca caccttttct cagcctccgg   2040
gatgtgttcg gcaaagattt aatctacaca ctgtattact ggaagtcctc ttcctccggc   2100
aagaagacag ctaaaaccaa cacaaacgag tttttaatcg acgtggataa aggcgaaaac   2160
tactgtttca gcgtgcaagc tgtgatcccc tcccggaccg tgaataggaa agcaccgat    2220 agccccgttg agtgcatggg ccaagaaaag ggcgagttcc gggagaactg ggtgaacgtc   2280
atcagcgatt taagaagat cgaagattta attcagtcca tgcatatcga cgccacttta   2340
tacacagaat ccgacgtgca cccctcttgt aaggtgaccg ccatgaaatg ttttttactg   2400
gagctgcaag ttatctcttt agagagcgga gacgctagca tccacgacac cgtggagaat   2460
ttaatcattt tagccaataa ctctttatcc agcaacggca acgtgacaga gtccggctgc   2520
aaggagtgcg aagagctgga ggagaagaac atcaaggagt ttctgcaatc ctttgtgcac   2580
attgtccaga tgttcatcaa tacctcc                                      2607
```

<210> SEQ ID NO 191
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 18s sequence"

<400> SEQUENCE: 191

```
Met Lys Trp Val Thr Phe Ile Ser Leu Leu Phe Leu Phe Ser Ser Ala
1               5                   10                  15

Tyr Ser Tyr Phe Gly Lys Leu Glu Ser Lys Leu Ser Val Ile Arg Asn
            20                  25                  30

Leu Asn Asp Gln Val Leu Phe Ile Asp Gln Gly Asn Arg Pro Leu Phe
        35                  40                  45
```

```
Glu Asp Met Thr Asp Ser Asp Cys Arg Asp Asn Ala Pro Arg Thr Ile
 50                  55                  60

Phe Ile Ile Ser Met Tyr Lys Asp Ser Gln Pro Arg Gly Met Ala Val
 65                  70                  75                  80

Thr Ile Ser Val Lys Cys Glu Lys Ile Ser Thr Leu Ser Cys Glu Asn
                 85                  90                  95

Lys Ile Ile Ser Phe Lys Glu Met Asn Pro Pro Asp Asn Ile Lys Asp
                100                 105                 110

Thr Lys Ser Asp Ile Ile Phe Phe Gln Arg Ser Val Pro Gly His Asp
            115                 120                 125

Asn Lys Met Gln Phe Glu Ser Ser Ser Tyr Glu Gly Tyr Phe Leu Ala
130                 135                 140

Cys Glu Lys Glu Arg Asp Leu Phe Lys Leu Ile Leu Lys Lys Glu Asp
145                 150                 155                 160

Glu Leu Gly Asp Arg Ser Ile Met Phe Thr Val Gln Asn Glu Asp Ile
                165                 170                 175

Thr Cys Pro Pro Pro Met Ser Val Glu His Ala Asp Ile Trp Val Lys
                180                 185                 190

Ser Tyr Ser Leu Tyr Ser Arg Glu Arg Tyr Ile Cys Asn Ser Gly Phe
            195                 200                 205

Lys Arg Lys Ala Gly Thr Ser Ser Leu Thr Glu Cys Val Leu Asn Lys
210                 215                 220

Ala Thr Asn Val Ala His Trp Thr Thr Pro Ser Leu Lys Cys Ile Arg
225                 230                 235                 240

<210> SEQ ID NO 192
<211> LENGTH: 869
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 12t15 sequence"

<400> SEQUENCE: 192

Met Lys Trp Val Thr Phe Ile Ser Leu Leu Phe Leu Phe Ser Ser Ala
  1               5                  10                  15

Tyr Ser Ile Trp Glu Leu Lys Lys Asp Val Tyr Val Val Glu Leu Asp
                 20                  25                  30

Trp Tyr Pro Asp Ala Pro Gly Glu Met Val Val Leu Thr Cys Asp Thr
             35                  40                  45

Pro Glu Glu Asp Gly Ile Thr Trp Thr Leu Asp Gln Ser Ser Glu Val
 50                  55                  60

Leu Gly Ser Gly Lys Thr Leu Thr Ile Gln Val Lys Glu Phe Gly Asp
 65                  70                  75                  80

Ala Gly Gln Tyr Thr Cys His Lys Gly Gly Glu Val Leu Ser His Ser
                 85                  90                  95

Leu Leu Leu Leu His Lys Lys Glu Asp Gly Ile Trp Ser Thr Asp Ile
                100                 105                 110

Leu Lys Asp Gln Lys Glu Pro Lys Asn Lys Thr Phe Leu Arg Cys Glu
            115                 120                 125

Ala Lys Asn Tyr Ser Gly Arg Phe Thr Cys Trp Trp Leu Thr Thr Ile
130                 135                 140

Ser Thr Asp Leu Thr Phe Ser Val Lys Ser Ser Arg Gly Ser Ser Asp
145                 150                 155                 160
```

```
Pro Gln Gly Val Thr Cys Gly Ala Ala Thr Leu Ser Ala Glu Arg Val
            165                 170                 175

Arg Gly Asp Asn Lys Glu Tyr Glu Tyr Ser Val Glu Cys Gln Glu Asp
            180                 185                 190

Ser Ala Cys Pro Ala Ala Glu Glu Ser Leu Pro Ile Glu Val Met Val
            195                 200                 205

Asp Ala Val His Lys Leu Lys Tyr Glu Asn Tyr Thr Ser Ser Phe Phe
            210                 215                 220

Ile Arg Asp Ile Ile Lys Pro Asp Pro Lys Asn Leu Gln Leu Lys
225                 230                 235                 240

Pro Leu Lys Asn Ser Arg Gln Val Glu Val Ser Trp Glu Tyr Pro Asp
            245                 250                 255

Thr Trp Ser Thr Pro His Ser Tyr Phe Ser Leu Thr Phe Cys Val Gln
            260                 265                 270

Val Gln Gly Lys Ser Lys Arg Glu Lys Lys Asp Arg Val Phe Thr Asp
            275                 280                 285

Lys Thr Ser Ala Thr Val Ile Cys Arg Lys Asn Ala Ser Ile Ser Val
            290                 295                 300

Arg Ala Gln Asp Arg Tyr Tyr Ser Ser Ser Trp Ser Glu Trp Ala Ser
305                 310                 315                 320

Val Pro Cys Ser Gly Gly Gly Ser Gly Gly Gly Ser Gly Gly
            325                 330                 335

Gly Gly Ser Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
            355                 360                 365

Leu Gln Lys Ala Arg Gln Thr Leu Glu Phe Tyr Pro Cys Thr Ser Glu
            370                 375                 380

Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser
            405                 410                 415

Arg Glu Thr Ser Phe Ile Thr Asn Gly Ser Cys Leu Ala Ser Arg Lys
            420                 425                 430

Thr Ser Phe Met Met Ala Leu Cys Leu Ser Ser Ile Tyr Glu Asp Leu
            435                 440                 445

Lys Met Tyr Gln Val Glu Phe Lys Thr Met Asn Ala Lys Leu Leu Met
            450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
            485                 490                 495

Lys Ser Ser Leu Glu Glu Pro Asp Phe Tyr Lys Thr Lys Ile Lys Leu
            500                 505                 510

Cys Ile Leu Leu His Ala Phe Arg Ile Arg Ala Val Thr Ile Asp Arg
            515                 520                 525

Val Met Ser Tyr Leu Asn Ala Ser Ser Gly Thr Thr Asn Thr Val Ala
            530                 535                 540

Ala Tyr Asn Leu Thr Trp Lys Ser Thr Asn Phe Lys Thr Ile Leu Glu
545                 550                 555                 560

Trp Glu Pro Lys Pro Val Asn Gln Val Tyr Thr Val Gln Ile Ser Thr
            565                 570                 575

Lys Ser Gly Asp Trp Lys Ser Lys Cys Phe Tyr Thr Thr Asp Thr Glu
```

| | | | | | | | | | | | |
|---|---|---|---|---|---|---|---|---|---|---|---|
| | | | 580 | | | | 585 | | | | 590 |
| Cys | Asp | Leu | Thr | Asp | Glu | Ile | Val | Lys | Asp | Val | Lys | Gln | Thr | Tyr | Leu |
| | | | 595 | | | | | 600 | | | | 605 | | | |
| Ala | Arg | Val | Phe | Ser | Tyr | Pro | Ala | Gly | Asn | Val | Glu | Ser | Thr | Gly | Ser |
| | | 610 | | | | | 615 | | | | | 620 | | | |

Cys Asp Leu Thr Asp Glu Ile Val Lys Asp Val Lys Gln Thr Tyr Leu
            595                 600                 605

Ala Arg Val Phe Ser Tyr Pro Ala Gly Asn Val Glu Ser Thr Gly Ser
        610                 615                     620

Ala Gly Glu Pro Leu Tyr Glu Asn Ser Pro Glu Phe Thr Pro Tyr Leu
625                 630                 635                 640

Glu Thr Asn Leu Gly Gln Pro Thr Ile Gln Ser Phe Glu Gln Val Gly
                645                 650                 655

Thr Lys Val Asn Val Thr Val Glu Asp Glu Arg Thr Leu Val Arg Arg
            660                 665                 670

Asn Asn Thr Phe Leu Ser Leu Arg Asp Val Phe Gly Lys Asp Leu Ile
            675                 680                 685

Tyr Thr Leu Tyr Tyr Trp Lys Ser Ser Ser Gly Lys Lys Thr Ala
            690                 695                 700

Lys Thr Asn Thr Asn Glu Phe Leu Ile Asp Val Asp Lys Gly Glu Asn
705                 710                 715                 720

Tyr Cys Phe Ser Val Gln Ala Val Ile Pro Ser Arg Thr Val Asn Arg
                725                 730                 735

Lys Ser Thr Asp Ser Pro Val Glu Cys Met Gly Gln Glu Lys Gly Glu
                740                 745                 750

Phe Arg Glu Asn Trp Val Asn Val Ile Ser Asp Leu Lys Lys Ile Glu
            755                 760                 765

Asp Leu Ile Gln Ser Met His Ile Asp Ala Thr Leu Tyr Thr Glu Ser
770                 775                 780

Asp Val His Pro Ser Cys Lys Val Thr Ala Met Lys Cys Phe Leu Leu
785                 790                 795                 800

Glu Leu Gln Val Ile Ser Leu Glu Ser Gly Asp Ala Ser Ile His Asp
                805                 810                 815

Thr Val Glu Asn Leu Ile Ile Leu Ala Asn Asn Ser Leu Ser Ser Asn
                820                 825                 830

Gly Asn Val Thr Glu Ser Gly Cys Lys Glu Cys Glu Glu Leu Glu Glu
                835                 840                 845

Lys Asn Ile Lys Glu Phe Leu Gln Ser Phe Val His Ile Val Gln Met
        850                 855                 860

Phe Ile Asn Thr Ser
865

<210> SEQ ID NO 193
<211> LENGTH: 1452
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic IL-21/TF mutant/IL-15 construct sequence"

<400> SEQUENCE: 193
atgaagtggg tgaccttcat cagcctgctg ttcctgttct ccagcgccta ctcccagggc     60
caggacaggc acatgatccg gatgaggcag ctcatcgaca tcgtcgacca gctgaagaac    120
tacgtgaacg acctggtgcc cgagtttctg cctgccccg aggacgtgga gaccaactgc    180
gagtggtccg ccttctcctg ctttcagaag gcccagctga agtccgccaa caccggcaac    240
aacgagcgga tcatcaacgt gagcatcaag aagctgaagc ggaagcctcc ctccacaaac    300
gccggcagga ggcagaagca caggctgacc tgccccagct gtgactccta cgagaagaag    360

```
cccccccaagg agttcctgga gaggttcaag tccctgctgc agaagatgat ccatcagcac    420
ctgtcctcca ggacccacgg ctccgaggac tcctccggca ccaccaatac cgtggccgct    480
tataacctca catggaagag caccaacttc gcgacagctc tggaatggga acccaagccc    540
gtcaatcaag tttacaccgt gcagatctcc accaaatccg gagactggaa gagcaagtgc    600
ttctacacaa cagacaccga gtgtgcttta accgacgaaa tcgtcaagga cgtcaagcaa    660
acctatctgg ctcgggtctt ttcctacccc gctggcaatg tcgagtccac cggctccgct    720
ggcgagcctc tctacgagaa ttccccgaa ttcacccctt atttagagac caatttaggc    780
cagcctacca tccagagctt cgagcaagtt ggcaccaagg tgaacgtcac cgtcgaggat    840
gaaaggactt tagtggcgcg aataacaca gctttatccc tccgggatgt gttcggcaaa    900
gacctcatct acacactgta ctattggaag tccagctcct ccggcaaaaa gaccgctaag    960
accaacacca acgagttttt aattgacgtg gacaaaggcg agaactactg cttcagcgtg   1020
caagccgtga tcccttctcg taccgtcaac cggaagagca cagattcccc cgttgagtgc   1080
atgggccaag aaaagggcga gttccgggag aactgggtga cgtcatcag cgatttaaag   1140 aagatcgaag atttaattca gtccatgcat atcgacgcca ctttatacac agaatccgac   1200
gtgcacccct cttgtaaggt gaccgccatg aaatgttttt tactggagct gcaagttatc   1260
tctttagaga gcggagacgc tagcatccac gacaccgtgg agaatttaat catttttagcc   1320 aataactctt tatccagcaa cggcaacgtg acagagtccg gctgcaagga gtgcgaagag   1380
ctggaggaga agaacatcaa ggagtttctg caatcctttg tgcacattgt ccagatgttc   1440 atcaataccct cc                                                      1452
```

<210> SEQ ID NO 194
<211> LENGTH: 484
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic IL-21/TF mutant/IL-15 construct sequence"

<400> SEQUENCE: 194

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
                20                  25                  30

Asp Ile Val Asp Gln Leu Lys Asn Tyr Val Asn Asp Leu Val Pro Glu
            35                  40                  45

Phe Leu Pro Ala Pro Glu Asp Val Glu Thr Asn Cys Glu Trp Ser Ala
        50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ser Gly Thr Thr Asn Thr Val Ala Ala
```

```
                145                 150                 155                 160
Tyr Asn Leu Thr Trp Lys Ser Thr Asn Phe Ala Thr Ala Leu Glu Trp
                    165                 170                 175
Glu Pro Lys Pro Val Asn Gln Val Tyr Thr Val Gln Ile Ser Thr Lys
                180                 185                 190
Ser Gly Asp Trp Lys Ser Lys Cys Phe Tyr Thr Thr Asp Thr Glu Cys
            195                 200                 205
Ala Leu Thr Asp Glu Ile Val Lys Asp Val Lys Gln Thr Tyr Leu Ala
        210                 215                 220
Arg Val Phe Ser Tyr Pro Ala Gly Asn Val Glu Ser Thr Gly Ser Ala
225                 230                 235                 240
Gly Glu Pro Leu Tyr Glu Asn Ser Pro Glu Phe Thr Pro Tyr Leu Glu
                245                 250                 255
Thr Asn Leu Gly Gln Pro Thr Ile Gln Ser Phe Glu Gln Val Gly Thr
                    260                 265                 270
Lys Val Asn Val Thr Val Glu Asp Glu Arg Thr Leu Val Ala Arg Asn
                275                 280                 285
Asn Thr Ala Leu Ser Leu Arg Asp Val Phe Gly Lys Asp Leu Ile Tyr
            290                 295                 300
Thr Leu Tyr Tyr Trp Lys Ser Ser Ser Gly Lys Lys Thr Ala Lys
305                 310                 315                 320
Thr Asn Thr Asn Glu Phe Leu Ile Asp Val Asp Lys Gly Glu Asn Tyr
                    325                 330                 335
Cys Phe Ser Val Gln Ala Val Ile Pro Ser Arg Thr Val Asn Arg Lys
                340                 345                 350
Ser Thr Asp Ser Pro Val Glu Cys Met Gly Gln Glu Lys Gly Glu Phe
            355                 360                 365
Arg Glu Asn Trp Val Asn Val Ile Ser Asp Leu Lys Lys Ile Glu Asp
        370                 375                 380
Leu Ile Gln Ser Met His Ile Asp Ala Thr Leu Tyr Thr Glu Ser Asp
385                 390                 395                 400
Val His Pro Ser Cys Lys Val Thr Ala Met Lys Cys Phe Leu Leu Glu
                405                 410                 415
Leu Gln Val Ile Ser Leu Glu Ser Gly Asp Ala Ser Ile His Asp Thr
                    420                 425                 430
Val Glu Asn Leu Ile Ile Leu Ala Asn Asn Ser Leu Ser Ser Asn Gly
                435                 440                 445
Asn Val Thr Glu Ser Gly Cys Lys Glu Cys Glu Glu Leu Glu Glu Lys
            450                 455                 460
Asn Ile Lys Glu Phe Leu Gln Ser Phe Val His Ile Val Gln Met Phe
465                 470                 475                 480
Ile Asn Thr Ser
```

<210> SEQ ID NO 195
<211> LENGTH: 2142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic alphaCD28scFv/TF/alphaCD3scFv sequence"

<400> SEQUENCE: 195

```
atgaaatggg tcaccttcat ctctttactg ttttttattta gcagcgccta cagcgtgcag    60
ctgcagcagt ccggacccga actggtcaag cccggtgcct ccgtgaaaat gtcttgtaag   120
```

```
gcttctggct acacctttac ctcctacgtc atccaatggg tgaagcagaa gcccggtcaa      180
ggtctcgagt ggatcggcag catcaatccc tacaacgatt acaccaagta taacgaaaag      240
tttaagggca aggccactct gacaagcgac aagagctcca ttaccgccta catggagttt      300
tcctctttaa cttctgagga ctccgcttta tactattgcg ctcgttgggg cgatggcaat      360
tattggggcc ggggaactac tttaacagtg agctccggcg gcggcggaag cggaggtgga      420
ggatctggcg gtgaggcag cgacatcgag atgacacagt cccccgctat catgagcgcc      480
tctttaggag aacgtgtgac catgacttgt acagcttcct ccagcgtgag cagctcctat      540
ttccactggt accagcagaa acccggctcc tcccctaaac tgtgtatcta ctccacaagc      600
aatttagcta gcggcgtgcc tcctcgtttt agcggctccg gcagcaccct ttactcttta      660
accattagct ctatggaggc cgaagatgcc gccacatact tttgccatca gtaccaccgg      720
tcccctacct ttggcggagg cacaaagctg agaccaagc ggagcggcac caccaacaca      780
gtggccgcct acaatctgac ttggaaatcc accaacttca agaccatcct cgagtgggag      840
cccaagcccg ttaatcaagt ttataccgtg cagatttcca ccaagagcgg cgactggaaa      900
tccaagtgct ctataccac agacaccgag tgcgatctca ccgacgagat cgtcaaagac      960
gtgaagcaga catatttagc tagggtgttc tcctacccg ctggaaacgt ggagagcacc     1020
ggatccgctg gagagccttt atacgagaac tcccccgaat tcaccccta tctgaaaacc     1080 aatttaggcc agcccaccat ccagagcttc gaacaagttg gcacaaaggt gaacgtcacc     1140
gtcgaagatg agaggacttt agtgcggagg aacaatacat ttttatcctt acgtgacgtc     1200
ttcggcaagg atttaatcta cacactgtat tactggaagt ctagctcctc cggcaagaag     1260
accgccaaga ccaataccaa cgaatttta attgacgtgg acaagggcga gaactactgc     1320
ttctccgtgc aagctgtgat cccctccgg acagtgaacc ggaagtccac cgactccccc     1380
gtggagtgca tgggccaaga gaagggagag tttcgtgagc agatcgtgct gacccagtcc     1440
cccgctatta tgagcgctag ccccggtgaa aaggtgacta tgcatgcag cgccagctct     1500 tccgtgagct acatgaactg gtatcagcag aagtccggca ccagccctaa aggtggatc     1560 tacgacacca gcaagctggc cagcggcgtc cccgctcact ttcggggctc cggctccgga     1620
acaagctact ctctgaccat cagcggcatg gaagccgagg atgccgctac ctattactgt     1680
cagcagtgga gctccaaccc cttcacctt ggatccggca ccaagctcga gattaatcgt     1740
ggaggcggag gtagcggagg aggcggatcc ggcggtggag gtagccaagt tcagctccag     1800
caaagcggcc ccgaactcgc tcggcccggc gcttccgtga agatgtcttg taaggcctcc     1860 ggctataccct tcacccggta cacaatgcac tgggtcaagc aacggcccgg tcaaggttta     1920
gagtggattg gctatatcaa ccctcccgg ggctatacca actacaacca gaagttcaag     1980
gacaaagcca ccctcaccac cgacaagtcc agcagcaccg cttacatgca gctgagctct     2040
ttaacatccg aggattccgc cgtgtactac tgcgctcggt actacgacga tcattactgc     2100
ctcgattact ggggccaagg taccacctta acagtctcct cc                         2142
```

<210> SEQ ID NO 196
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic alphaCD28scFv/TF/alphaCD3scFv sequence"

```
<400> SEQUENCE: 196

Met Lys Trp Val Thr Phe Ile Ser Leu Leu Phe Leu Phe Ser Ser Ala
1               5                   10                  15

Tyr Ser Val Gln Leu Gln Gln Ser Gly Pro Glu Leu Val Lys Pro Gly
            20                  25                  30

Ala Ser Val Lys Met Ser Cys Lys Ala Ser Gly Tyr Thr Phe Thr Ser
        35                  40                  45

Tyr Val Ile Gln Trp Val Lys Gln Lys Pro Gly Gln Gly Leu Glu Trp
    50                  55                  60

Ile Gly Ser Ile Asn Pro Tyr Asn Asp Tyr Thr Lys Tyr Asn Glu Lys
65                  70                  75                  80

Phe Lys Gly Lys Ala Thr Leu Thr Ser Asp Lys Ser Ser Ile Thr Ala
                85                  90                  95

Tyr Met Glu Phe Ser Ser Leu Thr Ser Glu Asp Ser Ala Leu Tyr Tyr
            100                 105                 110

Cys Ala Arg Trp Gly Asp Gly Asn Tyr Trp Gly Arg Gly Thr Thr Leu
        115                 120                 125

Thr Val Ser Ser Gly Gly Gly Ser Gly Gly Gly Gly Ser Gly Gly
    130                 135                 140

Gly Gly Ser Asp Ile Glu Met Thr Gln Ser Pro Ala Ile Met Ser Ala
145                 150                 155                 160

Ser Leu Gly Glu Arg Val Thr Met Thr Cys Thr Ala Ser Ser Ser Val
                165                 170                 175

Ser Ser Ser Tyr Phe His Trp Tyr Gln Gln Lys Pro Gly Ser Ser Pro
            180                 185                 190

Lys Leu Cys Ile Tyr Ser Thr Ser Asn Leu Ala Ser Gly Val Pro Pro
        195                 200                 205

Arg Phe Ser Gly Ser Gly Ser Thr Ser Tyr Ser Leu Thr Ile Ser Ser
    210                 215                 220

Met Glu Ala Glu Asp Ala Ala Thr Tyr Phe Cys His Gln Tyr His Arg
225                 230                 235                 240

Ser Pro Thr Phe Gly Gly Gly Thr Lys Leu Glu Thr Lys Arg Ser Gly
                245                 250                 255

Thr Thr Asn Thr Val Ala Ala Tyr Asn Leu Thr Trp Lys Ser Thr Asn
            260                 265                 270

Phe Lys Thr Ile Leu Glu Trp Glu Pro Lys Pro Val Asn Gln Val Tyr
        275                 280                 285

Thr Val Gln Ile Ser Thr Lys Ser Gly Asp Trp Lys Ser Lys Cys Phe
    290                 295                 300

Tyr Thr Thr Asp Thr Glu Cys Asp Leu Thr Asp Glu Ile Val Lys Asp
305                 310                 315                 320

Val Lys Gln Thr Tyr Leu Ala Arg Val Phe Ser Tyr Pro Ala Gly Asn
                325                 330                 335

Val Glu Ser Thr Gly Ser Ala Gly Glu Pro Leu Tyr Glu Asn Ser Pro
            340                 345                 350

Glu Phe Thr Pro Tyr Leu Glu Thr Asn Leu Gly Gln Pro Thr Ile Gln
        355                 360                 365

Ser Phe Glu Gln Val Gly Thr Lys Val Asn Val Thr Val Glu Asp Glu
    370                 375                 380

Arg Thr Leu Val Arg Arg Asn Asn Thr Phe Leu Ser Leu Arg Asp Val
385                 390                 395                 400

Phe Gly Lys Asp Leu Ile Tyr Thr Leu Tyr Tyr Trp Lys Ser Ser Ser
                405                 410                 415
```

Ser Gly Lys Lys Thr Ala Lys Thr Asn Thr Asn Glu Phe Leu Ile Asp
            420                 425                 430

Val Asp Lys Gly Glu Asn Tyr Cys Phe Ser Val Gln Ala Val Ile Pro
            435                 440                 445

Ser Arg Thr Val Asn Arg Lys Ser Thr Asp Ser Pro Val Glu Cys Met
    450                 455                 460

Gly Gln Glu Lys Gly Glu Phe Arg Glu Gln Ile Val Leu Thr Gln Ser
465                 470                 475                 480

Pro Ala Ile Met Ser Ala Ser Pro Gly Glu Lys Val Thr Met Thr Cys
                485                 490                 495

Ser Ala Ser Ser Ser Val Ser Tyr Met Asn Trp Tyr Gln Gln Lys Ser
            500                 505                 510

Gly Thr Ser Pro Lys Arg Trp Ile Tyr Asp Thr Ser Lys Leu Ala Ser
        515                 520                 525

Gly Val Pro Ala His Phe Arg Gly Ser Gly Ser Gly Thr Ser Tyr Ser
    530                 535                 540

Leu Thr Ile Ser Gly Met Glu Ala Glu Asp Ala Ala Thr Tyr Tyr Cys
545                 550                 555                 560

Gln Gln Trp Ser Ser Asn Pro Phe Thr Phe Gly Ser Gly Thr Lys Leu
                565                 570                 575

Glu Ile Asn Arg Gly Gly Gly Gly Ser Gly Gly Gly Gly Ser Gly Gly
            580                 585                 590

Gly Gly Ser Gln Val Gln Leu Gln Gln Ser Gly Ala Glu Leu Ala Arg
        595                 600                 605

Pro Gly Ala Ser Val Lys Met Ser Cys Lys Ala Ser Gly Tyr Thr Phe
    610                 615                 620

Thr Arg Tyr Thr Met His Trp Val Lys Gln Arg Pro Gly Gln Gly Leu
625                 630                 635                 640

Glu Trp Ile Gly Tyr Ile Asn Pro Ser Arg Gly Tyr Thr Asn Tyr Asn
                645                 650                 655

Gln Lys Phe Lys Asp Lys Ala Thr Leu Thr Thr Asp Lys Ser Ser Ser
            660                 665                 670

Thr Ala Tyr Met Gln Leu Ser Ser Leu Thr Ser Glu Asp Ser Ala Val
        675                 680                 685

Tyr Tyr Cys Ala Arg Tyr Tyr Asp Asp His Tyr Cys Leu Asp Tyr Trp
    690                 695                 700

Gly Gln Gly Thr Thr Leu Thr Val Ser Ser
705                 710

<210> SEQ ID NO 197
<211> LENGTH: 456
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic IL-7 sequence"

<400> SEQUENCE: 197
gattgcgaca tcgagggcaa ggacggcaag cagtacgaga gcgtgctgat ggtgtccatc      60
gaccagctgc tggacagcat gaaggagatc ggctccaact gcctcaacaa cgagttcaac     120
ttcttcaagc ggcacatctg cgacgccaac aaggagggca tgttcctgtt cagggccgcc     180
aggaaactgc ggcagttcct gaagatgaac tccaccggcg acttcgacct gcacctgctg     240
aaggtgtccg agggcaccac catcctgctg aactgcaccg gacaggtgaa gggccggaaa     300

```
cctgctgctc tgggagaggc ccaacccacc aagagcctgg aggagaacaa gtccctgaag      360
gagcagaaga agctgaacga cctgtgcttc ctgaagaggc tgctgcagga gatcaagacc      420
tgctggaaca agatcctgat gggcaccaag gagcat                                456

<210> SEQ ID NO 198
<211> LENGTH: 861
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFbetaRII receptor sequence"

<400> SEQUENCE: 198 atccccccc  atgtgcaaaa gagcgtgaac aacgatatga tcgtgaccga caacaacggc        60
gccgtgaagt tcccccagct ctgcaagttc tgcgatgtca ggttcagcac ctgcgataat       120
cagaagtcct gcatgtccaa ctgcagcatc acctccatct gcgagaagcc caagaagtg       180 tgcgtggccg tgtggcggaa aaatgacgag aacatcaccc tggagaccgt gtgtcacgac       240
cccaagctcc cttatcacga cttcattctg gaggacgctg cctcccccaa atgcatcatg       300
aaggagaaga agaagcccgg agagaccttc tttatgtgtt cctgtagcag cgacgagtgt      360
aacgacaaca tcatcttcag cgaagagtac aacaccagca accctgatgg aggtggcgga       420
tccggaggtg gaggttctgg tggaggtggg agtattcctc cccacgtgca gaagagcgtg      480
aataatgaca tgatcgtgac cgataacaat ggcgccgtga aatttcccca gctgtgcaaa      540
ttctgcgatg tgaggttttc cacctgcgac aaccagaagt cctgtatgag caactgctcc      600
atcacctcca tctgtgagaa gcctcaggag gtgtgcgtgg ctgtctggcg gaagaatgac      660
gagaatatca ccctggaaac cgtctgccac gatcccaagc tgccctacca cgatttcatc      720
ctggaagacg ccgccagccc taagtgcatc atgaaagaga aaagaagcc tggcgagacc       780 tttttcatgt gctcctgcag cagcgacgaa tgcaacgaca atatcatctt tagcgaggaa      840
tacaatacca gcaaccccga c                                                861
```